US012559492B2

(12) United States Patent
Nasveschuk et al.

(10) Patent No.: US 12,559,492 B2
(45) Date of Patent: Feb. 24, 2026

(54) BRAF DEGRADERS

(71) Applicant: C4 Therapeutics, Inc., Watertown, MA (US)

(72) Inventors: Christopher G. Nasveschuk, Stoneham, MA (US); Martin Duplessis, Somerville, MA (US); Mark E. Fitzgerald, Newton, MA (US); Victoria Garza, San Antonio, TX (US); Andrew Charles Good, Watertown, MA (US); Katrina L. Jackson, Weston, MA (US); Yanke Liang, Belmont, MA (US); Moses Moustakim, Cambridge, MA (US); Morgan Welzel O'Shea, Waltham, MA (US); Gesine Kerstin Veits, Somerville, MA (US); Jeremy L. Yap, Sudbury, MA (US); Robert T. Yu, Arlington, MA (US); Cosimo Dolente, Allschwil (CH); David Stephen Hewings, Basel (CH); Daniel Hunziker, Mohlin (CH); Bernd Kuhn, Reinach (CH); Piergiorgio Francesco Tommaso Pettazzoni, Regensdorf (CH); Fabienne Ricklin, Hombourg (FR); Claus Riemer, Freiburg (DE); Juergen Wichmann, Steinen (DE)

(73) Assignee: C4 Therapeutics, Inc., Watertown, MA (US)

( * ) Notice: Subject to any disclaimer, the term of this patent is extended or adjusted under 35 U.S.C. 154(b) by 585 days.

(21) Appl. No.: 18/084,380

(22) Filed: Dec. 19, 2022

(65) Prior Publication Data

US 2023/0145336 A1 May 11, 2023

Related U.S. Application Data

(63) Continuation of application No. PCT/EP2021/066524, filed on Jun. 18, 2021.

(60) Provisional application No. 63/136,574, filed on Jan. 12, 2021, provisional application No. 63/041,335, filed on Jun. 19, 2020.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC ...... C07D 471/04; C07D 519/00; A61P 35/00
See application file for complete search history.

(56) References Cited

U.S. PATENT DOCUMENTS

| | | | |
|---|---|---|---|
| 6,306,663 | B1 | 10/2001 | Kenten et al. |
| 9,750,816 | B2 | 9/2017 | Bradner et al. |
| 9,821,068 | B2 | 11/2017 | Bradner et al. |
| 10,646,575 | B2 | 5/2020 | Phillips et al. |
| 10,660,968 | B2 | 5/2020 | Phillips et al. |
| 10,723,717 | B2 | 7/2020 | Crew et al. |
| 10,849,982 | B2 | 12/2020 | Phillips et al. |
| 10,899,768 | B2 | 1/2021 | Bradner et al. |
| 10,905,768 | B1 | 2/2021 | Phillips et al. |
| 11,173,211 | B2 | 11/2021 | Crew et al. |
| 11,185,592 | B2 | 11/2021 | Phillips et al. |
| 11,220,515 | B2 | 1/2022 | Crews et al. |
| 11,254,672 | B2 | 2/2022 | Norcross et al. |
| 11,401,256 | B2 | 8/2022 | Norcross et al. |
| 11,407,732 | B1 | 8/2022 | Henderson et al. |
| 11,459,335 | B2 | 10/2022 | Phillips et al. |
| 11,578,075 | B2 | 2/2023 | Bradner et al. |
| 11,584,748 | B2 | 2/2023 | Nasveschuk et al. |
| 11,623,929 | B2 | 4/2023 | Nasveschuk et al. |
| 11,623,932 | B2 | 4/2023 | Mainolfi et al. |
| 2019/0233433 | A1 | 8/2019 | Crews et al. |
| 2020/0207733 | A1 | 7/2020 | Norcross et al. |
| 2020/0207783 | A1 | 7/2020 | Norcross et al. |
| 2021/0009559 | A1 | 1/2021 | Henderson et al. |
| 2021/0198256 | A1 | 7/2021 | Nasveschuk et al. |
| 2022/0098194 | A1 | 3/2022 | Nasveschuk et al. |
| 2022/0251061 | A1 | 8/2022 | Phillips et al. |
| 2022/0289738 | A1 | 9/2022 | Norcross et al. |
| 2022/0313826 | A1 | 10/2022 | Phillips et al. |
| 2022/0313827 | A1 | 10/2022 | Phillips et al. |
| 2022/0372016 | A1 | 11/2022 | Phillips et al. |
| 2023/0014124 | A1 | 1/2023 | Phillips et al. |
| 2023/0019060 | A1 | 1/2023 | Nasveschuk et al. |
| 2023/0060334 | A1 | 3/2023 | Nasveschuk et al. |

(Continued)

FOREIGN PATENT DOCUMENTS

| | | | |
|---|---|---|---|
| WO | WO 2007/002325 | A1 | 1/2007 |
| WO | WO 2007/002433 | A1 | 1/2007 |

(Continued)

OTHER PUBLICATIONS

Bartlett, et al. "The evolution of thalidomide and its IMiD derivatives as anticancer agents," Nat Rev Cancer, 4(4):314-322, Apr. 1, 2004.
Berndsen et al. "New insights into ubiquitin E3 ligase mechanism," Nat. Struct. Mol. Biol. Nature America, Inc. 21:4, 301-307, Apr. 4, 2014.
Bondeson et al. "Catalytic in vivo protein knockdown by small-molecule PROTACs" Nature Chemical Biology, 11:611-617, Jun. 10, 2015.
C4 Therapeutics Presentation Phillips—"Small Molecule Driven Targeted Protein Degradation", ChemBio in the Hub 47, Cambridge, MA, 47 pages, Oct. 22, 2018.

(Continued)

*Primary Examiner* — Joseph K Mckane
*Assistant Examiner* — Anna Grace Kuckla
(74) *Attorney, Agent, or Firm* — Knowles Intellectual Property Strategies, LLC

(57) ABSTRACT

Present invention provides compounds that cause specifically the degradation of BRAF. The present compounds are useful for the treatment of various cancers.

23 Claims, 2 Drawing Sheets

(56) References Cited

U.S. PATENT DOCUMENTS

2023/0082430 A1 3/2023 Henderson et al.
2023/0095223 A1 3/2023 Phillips et al.
2023/0110648 A1 4/2023 Nasveschuk et al.

FOREIGN PATENT DOCUMENTS

WO WO 2008/079903 A1 7/2008
WO WO 2008/079906 A1 7/2008
WO WO 2010/104945 A1 9/2010
WO WO 2010/104973 A1 9/2010
WO WO 2010/129567 A1 11/2010
WO WO 2010/129570 A1 11/2010
WO WO 2011/079133 A2 6/2011
WO WO 2012/109075 A1 8/2012
WO WO 2012/118492 A1 9/2012
WO WO 2012/138809 A1 10/2012
WO WO 2014/194127 A1 12/2014
WO WO 2015/150472 A2 10/2015
WO WO 2015/160845 A2 10/2015
WO WO 2016/083956 A1 6/2016
WO WO 2016/149668 A1 9/2016
WO WO 2016/191296 A1 12/2016
WO WO 2016/191303 A1 12/2016
WO WO 2016/197032 A1 12/2016
WO WO 2016/197114 A1 12/2016
WO WO 2017/007612 A1 1/2017
WO WO 2017/024317 A2 2/2017
WO WO 2017/024319 A1 2/2017
WO WO 2017/066193 A1 4/2017
WO WO 2017/197046 A1 11/2017
WO WO 2018/053354 A1 3/2018
WO WO 2018/071606 A1 4/2018
WO WO 2018/098280 A1 5/2018
WO WO 2018/102067 A2 6/2018
WO WO 2018/102725 A1 6/2018
WO WO 2018/118598 A1 6/2018
WO WO 2018/119357 A1 6/2018
WO WO 2018/119441 A1 6/2018
WO WO 2018/119448 A1 6/2018
WO WO 2018/134254 A1 7/2018
WO WO 2018/140809 A1 8/2018
WO WO 2018/144649 A1 8/2018
WO WO 2018/148443 A1 8/2018
WO WO 2019/060742 A1 3/2019
WO WO 2019/084462 A1 5/2019
WO WO 2019/140380 A1 7/2019
WO WO 2019/148055 A1 8/2019
WO WO 2019/199816 A1 10/2019
WO WO 2020/016243 A1 1/2020
WO WO-2020051564 A1 * 3/2020 ........... C07D 471/04
WO WO 2020/176983 A1 9/2020
WO WO 2021/011634 A1 1/2021
WO WO 2022/047145 A1 3/2022

OTHER PUBLICATIONS

C4 Therapeutics Presentation Fisher—"Targeted Protein Degradation", Targeted Protein Degradation Summit, Boston, MA, 39 pages, Oct. 24-25, 2018.

C4 Therapeutics Presentation Fisher—"Degrader Drugs: From cellular activity to in vivo pharmacology Discovery on Target," Boston, MA, 21 pages, Sep. 18, 2019.

C4 Therapeutics Presentation Nasveschuk—"Degrader Drug Space: What Rules?" HT-ADME Conference Cambridge, MA, 20 pages, Jun. 20, 2019.

Chamberlain et al. "Structure of the human cereblon-DDB1-lenalidomide complex reveals basis for responsiveness to thalidomide analogs" Nature Structural and Molecule Biology, Nature American, Inc., 21(9):803-809, Aug. 10, 2014.

Chao Zhang et al. "RAF inhibitors that evade paradoxical MAPK pathway activation" Nature, vol. 526, pp. 583-586, Oct. 14, 2015.

Corson et al. "Design and applications of bifunctional small molecules: Why two heads are better than one" ACS Chemical Biology 3(11), 677-692, Oct. 24, 2008.

Fischer et al. "Structure of the DDB1-CRBN E3 ubiquitin ligase in complex with thalidomide" Nature, Macmillan Publisher Limited, 512:49-53, Jul. 16, 2014.

Fischer et al. "The Molecular Basis of $CRL4^{DDB2/CSA}$ Ubiquitin Ligase Architecture, Targeting, and Activation," Cell, 147:1024-1039, Nov. 23, 2011.

International Search Report and Written Opinion for PCT/EP2021/066524 dated, 10 pages, Jul. 7, 2021.

Ross A. Okimoto et al. "Preclinical efficacy of a RAF inhibitor that evades paradoxical MAPK pathway activation in protein kinase BRAF-mutant lung cancer" Proceedings of the National Academy of Sciences of the United States of America 113(47), 13456-13461, Nov. 9, 2016.

Nobumichi Ohoka et al. "Development of a potent small-molecule degrader against oncogenic $BRAF^{V600E}$ protein that evades paradoxical MAPK activation" Cancer Science, 113:2828-2838. DOI: 10.1111/cas.15401, May 17, 2022.

C. S. A. Tutuka et al. "PLX8394, a new generation BRAF inhibitor, selectively inhibits BRAF in colonic adenocarcinoma cells and prevents paradoxical MAPK pathway activation" Molecular Cancer, 16:112, Jun. 28, 2017.

Xiao-Ran, Han et al. "Discovery of selective small molecule degraders of BRAF-V600E," Journal of Medicinal Chemistry, vol. 63, No. 8, 23, pp. 4069-4080, Mar. 30, 2020.

Zhan Yao et al. "RAF inhibitor PLX8394 selectively disrupts BRAF dimers and RAS-independent BRAF-mutant-driven signaling" Nat. Med. 25, 284-291, DOI: 10.1038/s41591-018-0274-5, Dec. 17, 2018.

U.S. Appl. No. 18/100,992, Nasveschuk et al., filed Jan. 24, 2023.
U.S. Appl. No. 18/105,735, Henderson et al., filed Feb. 3, 2023.
U.S. Appl. No. 18/106,893, Proia et al., filed Feb. 7, 2023.
U.S. Appl. No. 18/117,978, Nasveschuk et al., filed Mar. 6, 2023.
U.S. Appl. No. 18/134,971, Nasveschuk et al., filed Apr. 14, 2023.
U.S. Appl. No. 18/134,985, Nasveschuk et al., filed Apr. 14, 2023.
U.S. Appl. No. 18/134,990, Nasveschuk et al., filed Apr. 14, 2023.
U.S. Appl. No. 18/144,800, Nasveschuk et al., filed May 8, 2023.
U.S. Appl. No. 17/878,753, Norcross et al., filed Aug. 1, 2022.
U.S. Appl. No. 17/959,144, Phillips et al., filed Oct. 3, 2022.
U.S. Appl. No. 17/965,569, Nasveschuk et al., filed Oct. 13, 2022.
U.S. Appl. No. 18/079,815, Phillips et al., filed Dec. 12, 2022.

* cited by examiner

BRAF DEGRADERS

CROSS-REFERENCE TO RELATED APPLICATIONS

This application is a continuation of International Application No. PCT/EP2021/066524 filed in the European Receiving Office on Jun. 18, 2021, which claims the benefit of European Patent Application No. 20180967.0, filed on Jun. 19, 2020; U.S. Provisional Application No. 63/041,335, filed on Jun. 19, 2020, and U.S. Provisional Application No. 63/136,574, filed on Jan. 12, 2021. The entirety of each of these applications is incorporated by reference for all purposes.

FIELD OF THE INVENTION

The present invention provides compounds that selectively cause the degradation of BRAF, via the ubiquitination of the BRAF protein and subsequent proteasomal degradation. The present compounds are useful for the treatment of various cancers.

BACKGROUND OF THE INVENTION

BRAF is a serine/threonine protein kinase which is a member of the signal transduction protein kinases.

BRAF V600E/K mutations are often observed in a variety of human tumors including melanoma for example unresectable or metastatic melanoma, thyroid cancer, colorectal cancer, lung cancer and others. Despite the evident therapeutic benefits exerted by available BRAF inhibitors in the clinic in many of these indications, the duration of the antitumor response to these drugs is limited by the acquisition of drug resistance.

The BRAF protein presents a mechanism for signaling propagation that requires protein homo-dimerization (BRAF-BRAF) or hetero-dimerization with other RAF proteins (BRAF-RAF1 or BRAF-ARAF). When BRAF is mutated, as observed in oncological indications with BRAF V600E/K substitution, BRAF signaling becomes independent from the generation of homo and/or heterodimers. In this context, the kinase becomes hyperactivated as a monomeric protein and drives cellular proliferative signals.

Because currently available inhibitors only block BRAF activity in its monomeric form and are ineffective on BRAF homo or heterodimers, it is not surprising that many BRAF-resistance inducing mechanisms act by restoring RAF homo and heterodimerization mediated signaling.

Targeted protein degradation is an emerging mode of action, which induces target ubiquitination by recruiting an E3 ligase thus promoting proteasome-mediated disruption of the engaged target.

The degradation of BRAF through targeted degradation may offer advantages over conventional inhibition since it eliminates scaffolding activities of BRAF V600E/K and particularly, induces BRAF protein elimination. This activity may prevent the dimerization-mediated mechanisms of resistance.

In agreement with this theory, literature reports demonstrated that BRAF protein abrogation may represent a strategy to delay the onset of resistance acquisition as well as potentially targeting tumors that acquired resistance to available inhibitors. This observation offers novel therapeutic opportunities in the treatment of BRAF V600E/K mutated tumors like melanoma, colorectal cancer, and lung cancer.

WO2018/119448, WO2019/199816 and WO2020/051564 disclose BRAF degraders.

SUMMARY OF THE INVENTION

The present invention provides compounds that specifically degrade mutant BRAF, including but not limited to BRAF presenting with the mutation V600E, via the targeted ubiquitination of the BRAF protein and subsequent proteasomal degradation. The present compounds bind to the ubiquitously expressed E3 ligase protein cereblon (CRBN) and alter the substrate specificity of the CRBN E3 ubiquitin ligase complex, resulting in the recruitment and ubiquitination of mutant BRAF, such as for example BRAF V600E. The present compounds are also binders of WT BRAF, RAF1 and ARAF, however more effective targeted degradation is triggered by these compounds for mutant BRAF, such as for example BRAF V600E.

(I)

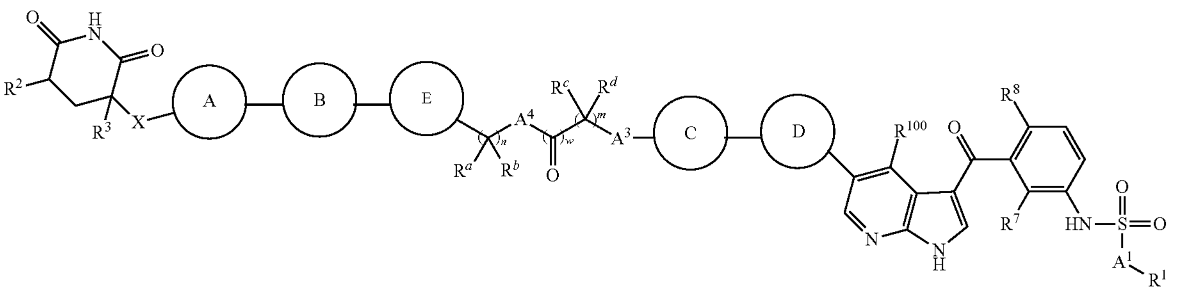

(II)

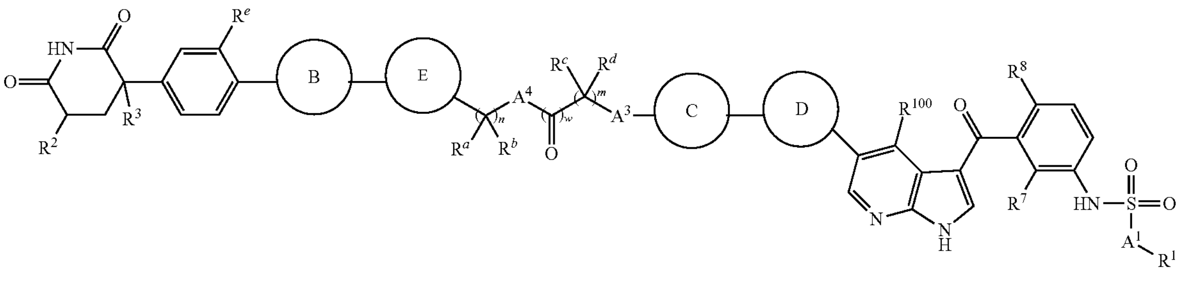

-continued
(III)
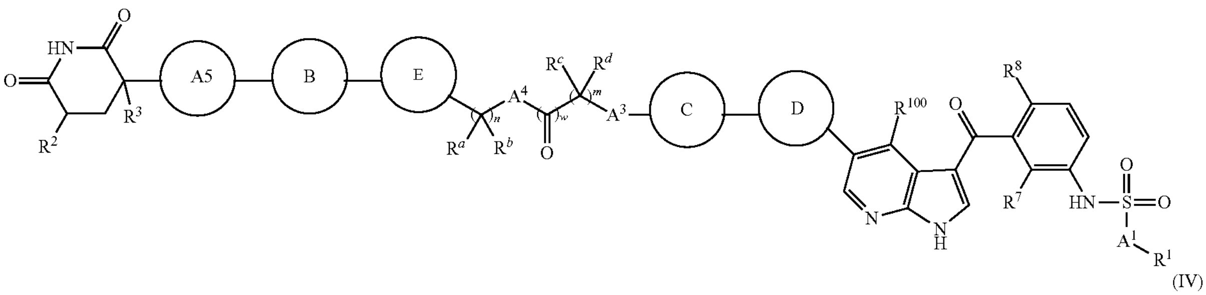
(IV)
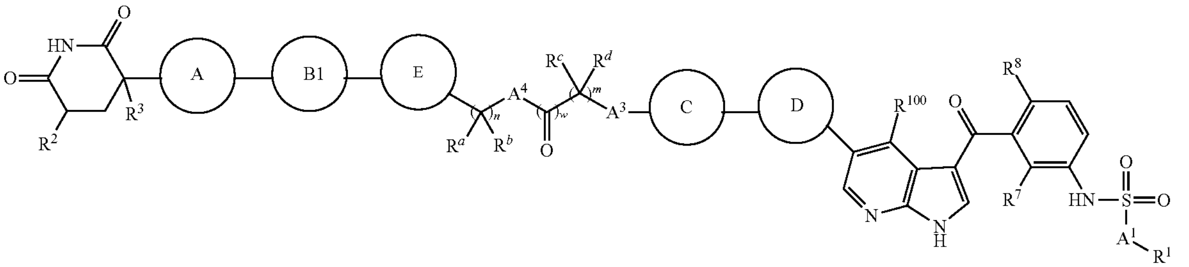
(V)
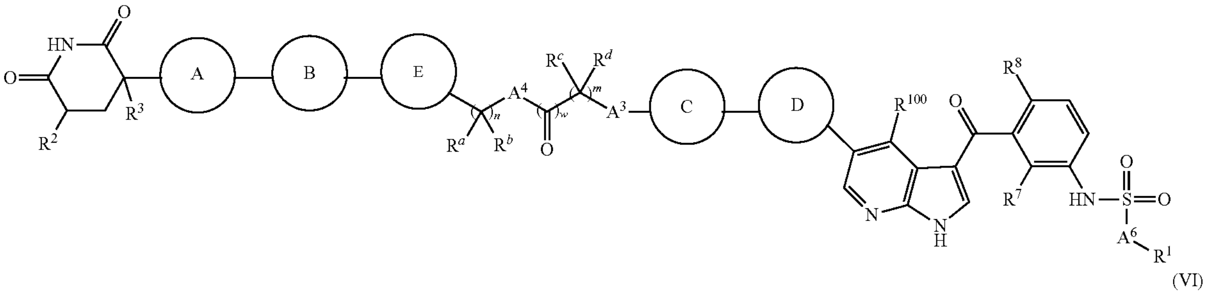
(VI)
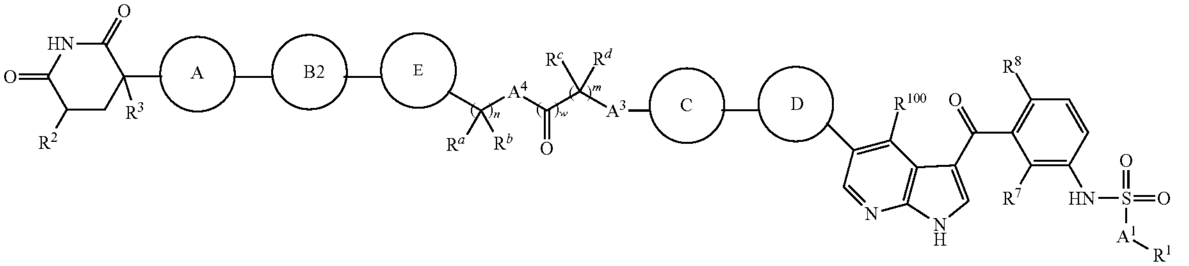
(VII)
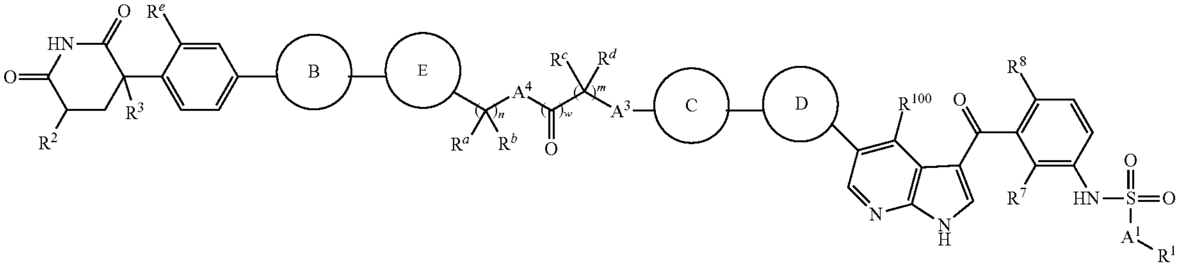
wherein the substituents and variables are as described below and in the claims.

In certain embodiments the compound of formula I is of formula:

(I-A)

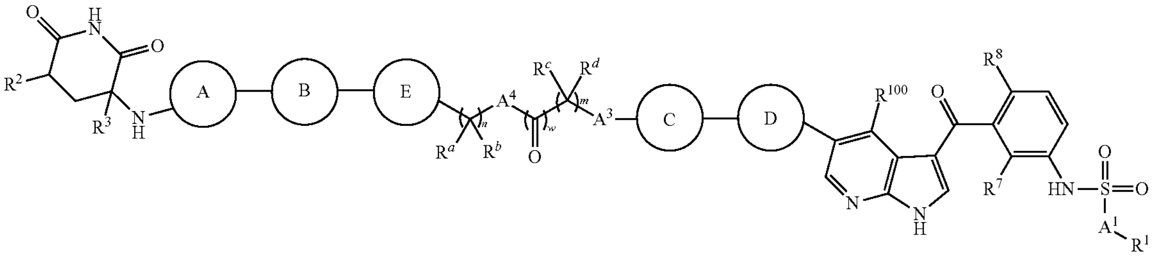

(I-B)

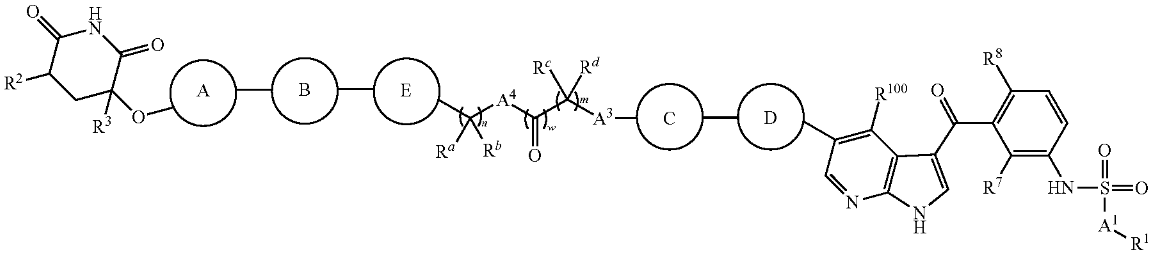

or a pharmaceutically acceptable salt thereof, wherein the substituents and variables are as described below and in the claims.

In certain embodiments the compound of formula II is of formula:

(II-A)

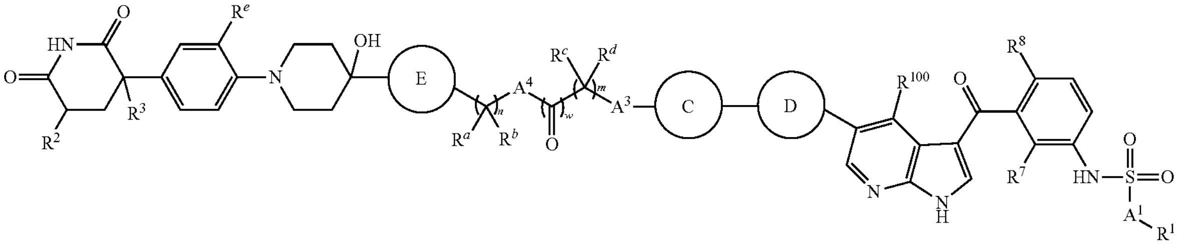

or a pharmaceutically acceptable salt thereof, wherein the substituents and variables are as described below and in the claims.

In certain embodiments the compound of formula III is of formula:

(III-A)

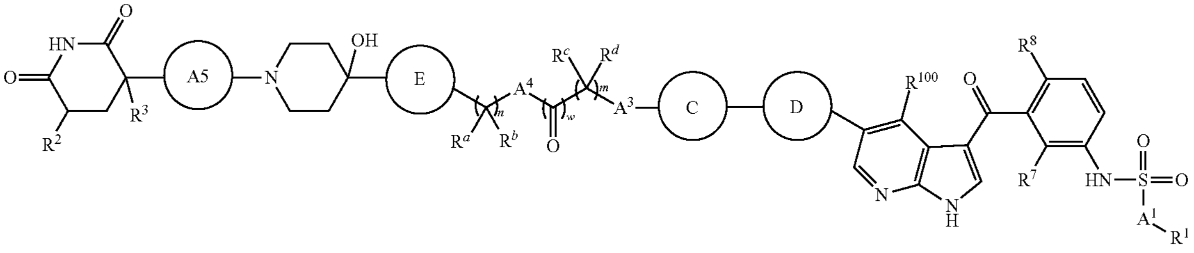

or a pharmaceutically acceptable salt thereof, wherein the substituents and variables are as described below and in the claims.

In certain embodiments the compound of formula IV is of formula:

(IV-A)

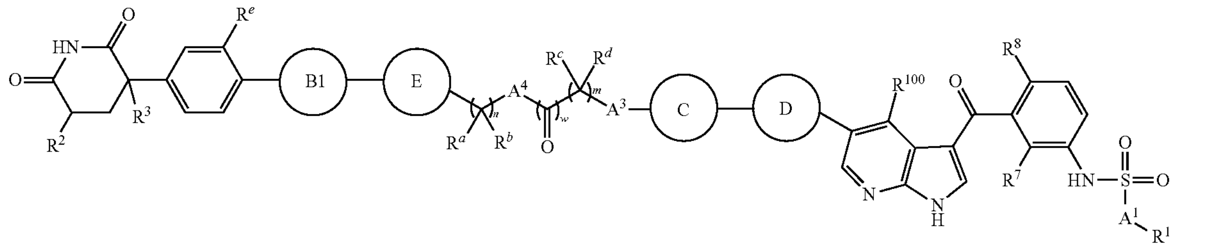

or a pharmaceutically acceptable salt thereof, wherein the substituents and variables are as described below and in the claims.

In certain embodiments the compound of formula V is of formula:

(V-A)

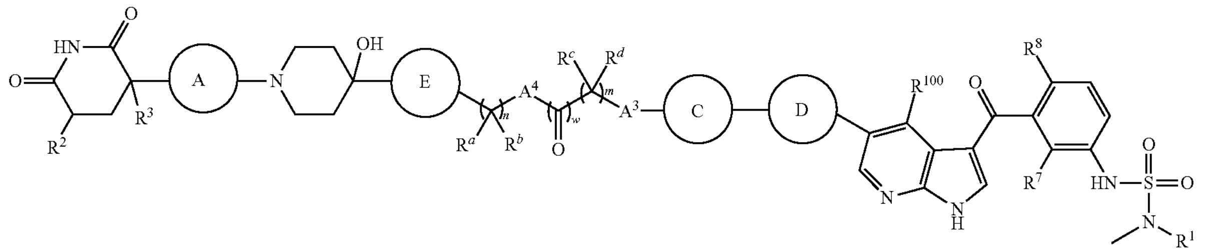

or a pharmaceutically acceptable salt thereof, wherein the substituents and variables are as described below and in the claims.

The present compounds are useful for the therapeutic and/or prophylactic treatment of cancer.

DETAILED DESCRIPTION OF THE INVENTION

Figure 1:
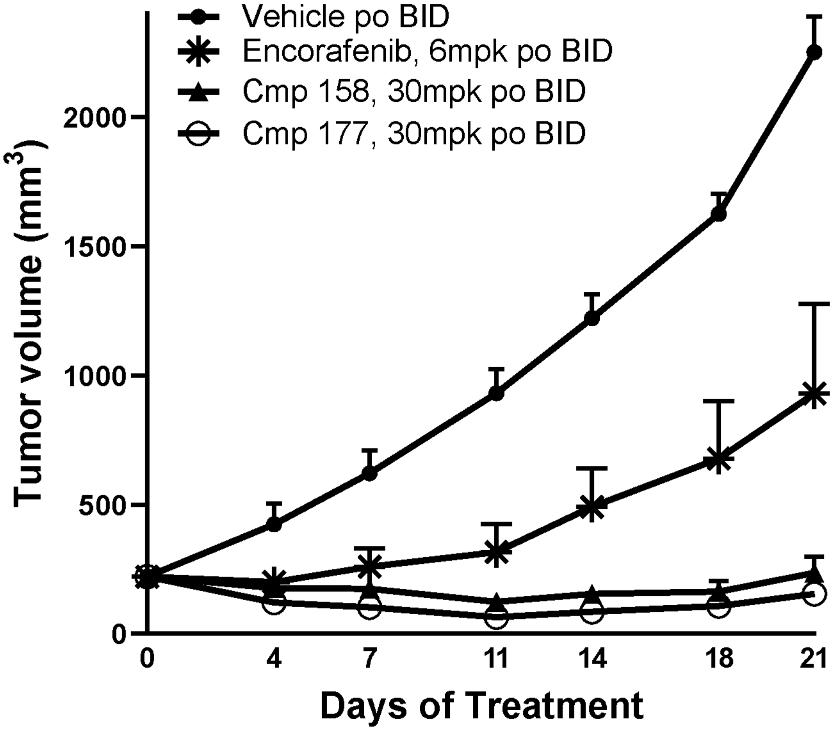
FIG. 1 is a graph comparing tumor volume with no treatment, treatment of 6 mg/kg of encorafenib p.o. twice a day, treatment of 30 mg/kg of Compound 158 p.o. twice a day, and treatment of 30 mg/kg of Compound 177 p.o. twice a day. The y-axis is tumor volume measured in $mm^3$ and the x-axis is days of treatment.

The present invention provides a compound of formula I, formula II, formula III, formula IV, formula V, formula VI, or formula VII, or a pharmaceutically acceptable salt thereof, the preparation of the above mentioned compounds, medicaments containing them and their manufacture as well as the use of the above mentioned compounds in the therapeutic and/or prophylactic treatment of cancer.

The following definitions of the general terms used in the present description apply irrespectively of whether the terms in question appear alone or in combination with other terms.

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl (2-methyl-propyl), 1,2-dimethyl-propyl and the like. Specific groups are methyl and ethyl.

The term "$C_{1-6}$-alkylsulfonyl", alone or in combination with other groups, stands for a group of formula R'—$SO_2$—, wherein the R' is a $C_{1-6}$-alkyl as defined herein. Particular $C_{1-6}$-alkylsulfonyl group are methylsulfonyl, ethylsulfonyl, propylsulfonyl, butyl sulfonyl. More particular group is methyl sulfonyl.

The term "cyano", alone or in combination with other groups, denotes the group —C≡N.

The term "$C_{3-8}$-cycloalkyl" denotes a monovalent saturated monocyclic or bicyclic hydrocarbon group of 3 to 8 ring carbon atoms. Bicyclic means a ring system consisting of two saturated carbocycles having one or two carbon atoms in common. Examples of monocyclic $C_{3-8}$-cycloalkyl are cyclopropyl, cyclobutanyl, cyclopentyl, cyclohexyl and cycloheptyl. An example of bicyclic $C_{3-8}$-cycloalkyl is spiro [3.3]heptanyl. More particular monocyclic $C_{3-8}$-cycloalkyl groups are cyclopentyl and cyclohexyl.

The term "$C_{3-8}$-cycloalkylsulfonyl", alone or in combination with other groups, stands for a group of formula R'—$SO_2$—, wherein the R' is a $C_{3-8}$-cycloalkyl as defined herein. Particular $C_{3-8}$-alkyl sulfonyl group are cyclopropylsulfonyl, cyclopentylsulfonyl and cyclohexylsulfonyl.

The term "halo-$C_{1-6}$-alkyl" denotes an $C_{1-6}$-alkyl group wherein at least one of the hydrogen atoms of the $C_{1-6}$-alkyl group has been replaced by the same or different halogen atoms. The term "perhalo-$C_{1-6}$-alkyl" denotes an —$C_{1-6}$-alkyl group where all hydrogen atoms of the alkyl group have been replaced by the same or different halogen atoms. Examples of halo-$C_{1-6}$-alkyl include fluoromethyl, difluoromethyl, trifluoromethyl, fluoroethyl, difluoroethyl and trifluoroethyl. Particular halo-$C_{1-6}$-alkyl groups include trifluoromethyl and difluoroethyl. More particular halo-$C_{1-6}$-alkyl groups are difluoromethyl and trifluoromethyl.

The term "halogen", alone or in combination with other groups, denotes chloro (Cl), iodo (I), fluoro (F) and bromo (Br). Specific group is F.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon which is optionally substituted with oxo. Bicyclic means consisting of two cycles having one or two ring atoms in common. The heterocycloalkyl is preferably a monovalent saturated or partly unsaturated monocyclic ring system of 4 to 6 ring atoms, comprising 1 or 2 ring heteroatoms selected from N, O and S (4- to 6-membered heterocycloalkyl). Examples of monocyclic saturated heterocycloalkyl include 4,5-dihydro-oxazolyl, oxetanyl, azetidinyl, pyrrolidinyl, 2-oxo-pyrrolidin-4-yl, 3-oxo-morpholin-6-yl, tetrahydrofuranyl, tetrahydrothiophenyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, and oxazepanyl. Examples of bicyclic saturated heterocycloalkyl include oxabicyclo[2.2.1]heptanyl, oxaspiro[3.3]heptanyl, 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, and 3-thia-9-aza-bicyclo[3.3.1]nonyl. Examples for partly unsaturated heterocycloalkyl include dihydrofuryl, imidazolinyl, dihydro-oxazolyl, tetrahydro-pyridinyl and dihydropyranyl. Heterocyclyl is preferably azetidinyl, morpholinyl, pyrrolidinyl, piperazinyl, oxetanyl, 2-oxo-pyrrolidin-4-yl, or 3-oxo-morpholin-6-yl. Particular heterocycloalkyl is pyrrolidinyl.

The term "hydroxy", alone or in combination with other groups, denotes the group —OH.

The term "sulfonyl", alone or in combination with other groups, denotes the group —$SO_2$—.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "a pharmaceutically acceptable salt" refers to a salt that is suitable for use in contact with the tissues of humans and animals. Examples of suitable salts with inorganic and organic acids include, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid.

The term "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

The term "inhibitor" denotes a compound which competes with, reduces or prevents the binding of a particular ligand to particular receptor or which reduces or prevents the function of a particular protein.

The term "aromatic" denotes the conventional idea of aromaticity as defined in the literature, in particular in IUPAC.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

All separate embodiments may be combined.

E1: One embodiment of the invention relates to a compound of formula I, formula II, formula III, formula IV, formula V, formula VI, or formula VII, or a pharmaceutically acceptable salt thereof, (I)
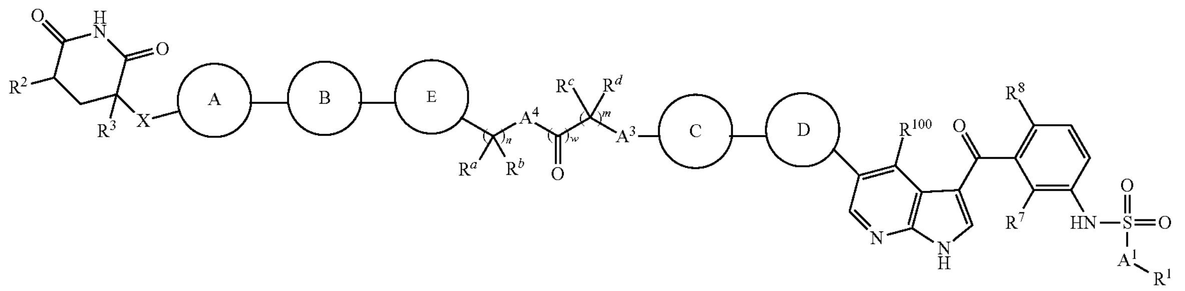
(II)
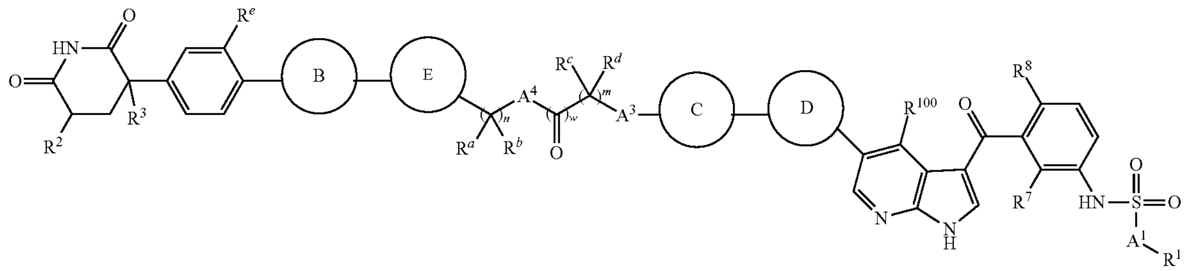
(III)
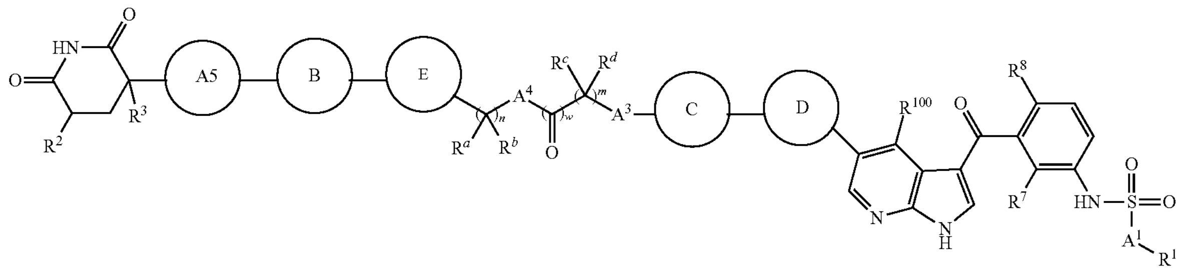
(IV)
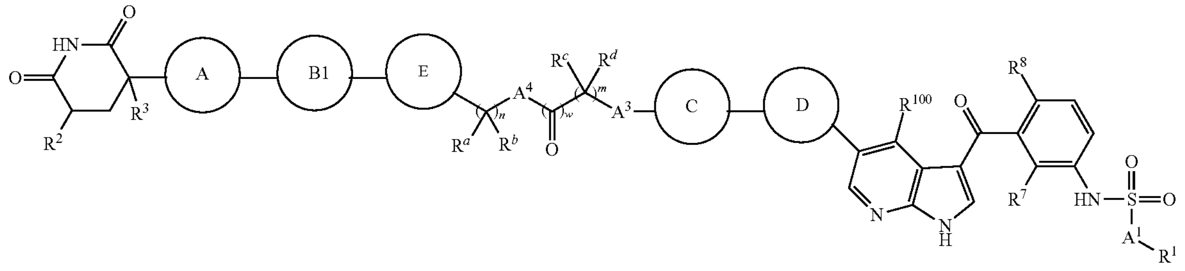
(V)
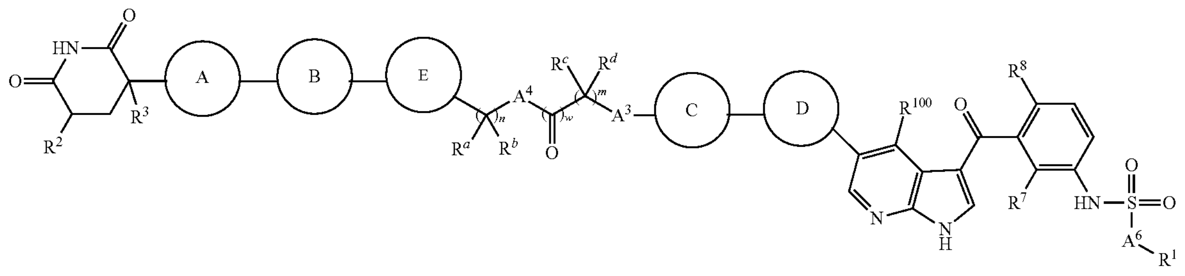

-continued (VI)

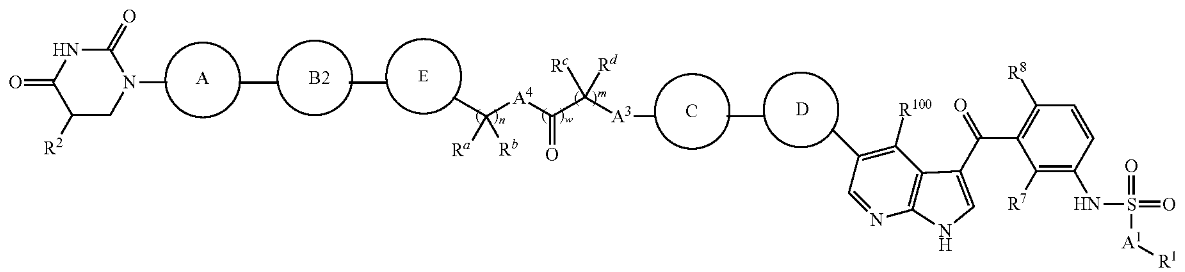

(VII)

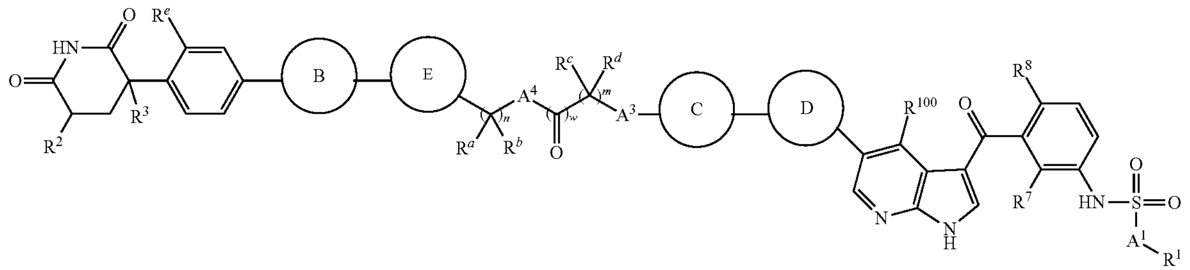

wherein $R^2$ and $R^3$ are independently selected from
- i) H, and
- ii) $C_{1-6}$-alkyl;

or $R^2$ and $R^3$ together form $—CH_2—$;

X is selected from
- i) $—CH_2—$
- ii) $—NR^4—$, and
- iii) —O—;

$R^4$ is selected from
- i) H, and
- ii) $C_{1-6}$-alkyl;

A is selected from the ring systems F, G, H, I, BA, BB, BC, BD and BE;

A5 is selected from the ring systems H, I, BA, BB, and BC;

F

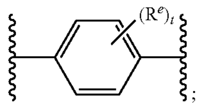

G

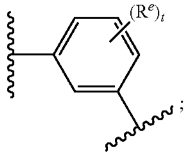

H

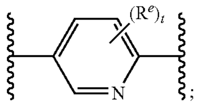

I

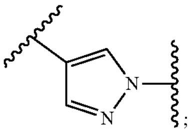

-continued

BA

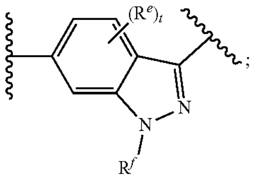

BB

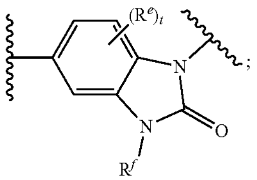

BC

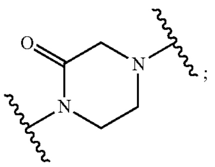

BD

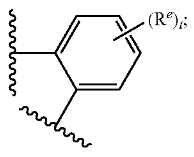

$R^e$ is independently selected from
- i) halogen,
- ii) cyano, and
- iii) $C_{1-6}$-alkyl;

t is selected from
- i) 0,
- ii) 1, and
- iii) 2;

$R^f$ is independently selected from i) H, ii) $C_{3-8}$-cycloalkyl, and iii) $C_{1-6}$-alkyl;

B is absent or selected from the ring systems AA, AB, AD, AE, AF, AG, AH, AI, AJ, AK, AL and AR;

AA

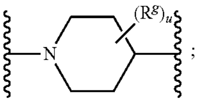

AB

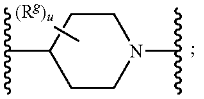

AD

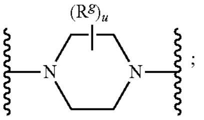

AL

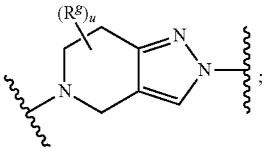

AE

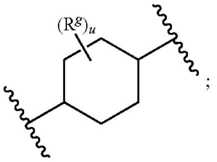

AF

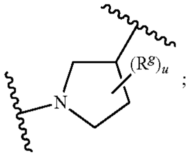

AG

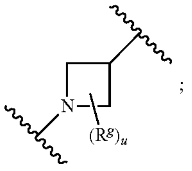

AH

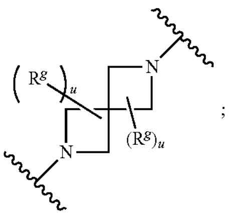

AI

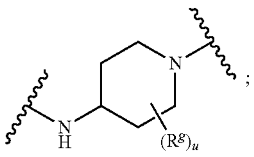

-continued

AJ

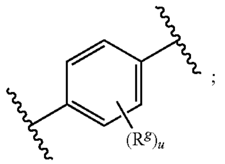

AK

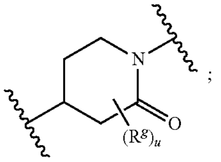

AR

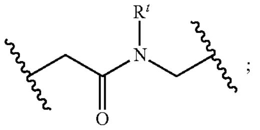

B1 is selected from the ring systems AA, AB, AE, AF, AG, AH, AI, AJ, AK, AL and AR;

B2 is selected from the ring systems AA, AB, AD, AE, AF, AG, AH, AI, AJ, AK, and AL;

$R^g$ is independently selected from i) halogen, ii) hydroxy, and iii) $C_{1-6}$-alkyl;

$R^t$ is independently selected from i) H, ii) $C_{3-8}$-cycloalkyl, and iii) $C_{1-6}$-alkyl;

u is independently selected from i) 0, ii) 1, and iii) 2;

E is absent or selected from the ring systems AM, AN, AO, AP and AQ;

AM

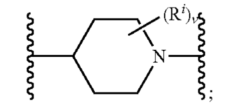

AN

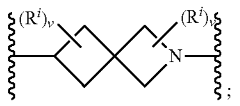

AO

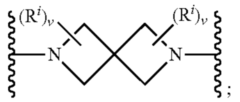

AP

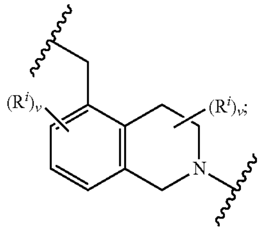

-continued

AQ

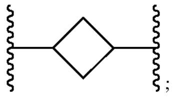

$R^i$ is independently selected from
i) halogen,
ii) hydroxy,
iii) $C_{3-8}$-cycloalkyl, and
iv) $C_{1-6}$-alkyl;

v is independently selected from
i) 0,
ii) 1, and
iii) 2;

m and n are independently selected from
i) 0,
ii) 1,
iii) 2, and
iv) 3;

$R^a$, $R^b$, $R^c$ and $R^d$ are independently selected from
i) H, and
ii) $C_{1-6}$-alkyl;

$A^4$ is selected from
i) a bond, and
ii) —$NR^{101}$—;

$R^{101}$ is selected from
i) H, and
ii) $C_{1-6}$-alkyl;

w is selected from
i) 0, and
ii) 1;

$A^3$ is selected from
i) a bond,
ii) —O—,
iii) —$NR^{200}$—, and
iv)

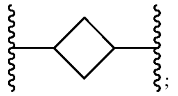 [SMILES: *C1CC(*)C1]

$R^{200}$ is selected from
i) H, and
ii) $C_{1-6}$-alkyl;

C is selected from the ring systems J, K, O, R, T, EA, EB, EC, ED, EF, EG, JA, KA, OA, P, PA, S, U, V and JAA;

J

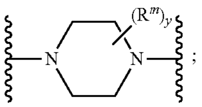

K

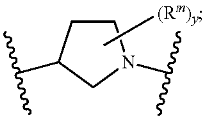

O

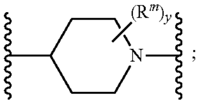

-continued

R

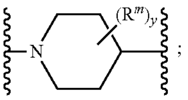

T

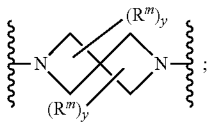

EA

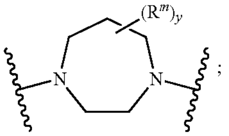

EB

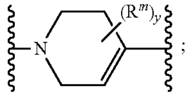

EC

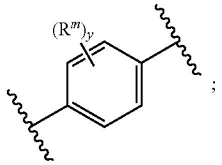

ED

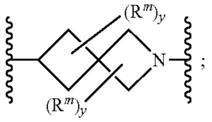

EF

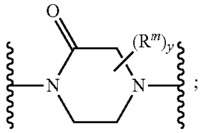

EG

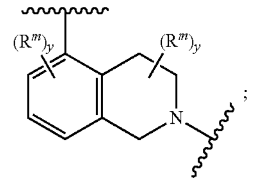

JA

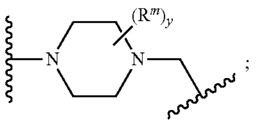

KA

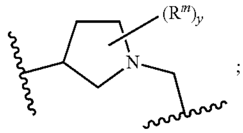

OA

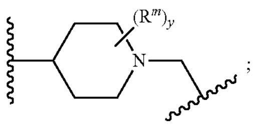

-continued

P

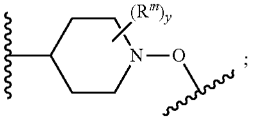

PA

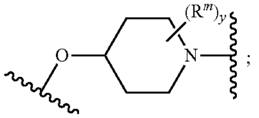

S

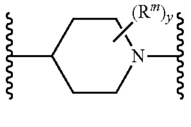

S

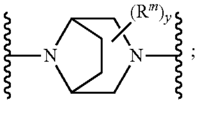

U

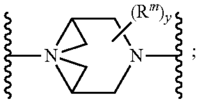

V

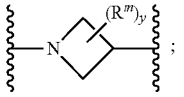

JAA

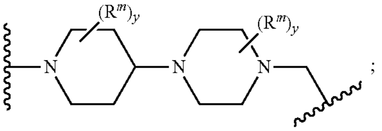

$R^m$ is independently selected from
i) halogen,
ii) hydroxy,
iii) $C_{3-8}$-cycloalkyl, and
iv) $C_{1-6}$-alkyl;
y is independently selected from
i) 0,
ii) 1, and
iii) 2;
D is selected from the ring systems W, X, Y, Q, Z and CA;

W

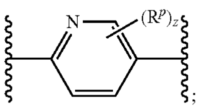

X

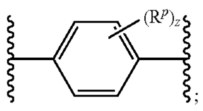

Y

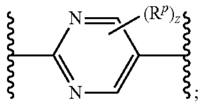

-continued

Q

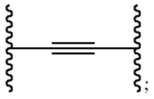

Z

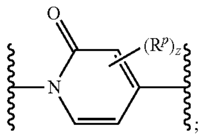

CA

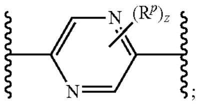

$R^p$ is independently selected from
i) halogen,
ii) $C_{3-8}$-cycloalkyl,
iii) halo-$C_{1-6}$-alkyl,
iv) $C_{1-6}$-alkyl,
v) cyano,
vi) $C_{1-6}$-alkylsulfonyl, and
vii) $C_{3-8}$-cycloalkylsulfonyl;
z is independently selected from
i) 0,
ii) 1, and
iii) 2;
$R^{100}$ is selected from
i) H,
ii) halogen, and
iii) $C_{1-6}$-alkyl;
$R^7$ and $R^8$ are independently selected from
i) H,
ii) $C_{1-6}$-alkyl, and
iii) halogen;
$A^1$ is selected from
i) —$NR^5$—, and
ii) —$CHR^6$—;
$A^6$ is selected from
i) —N(alkyl)-, and
ii) —$CHR^6$—;
$R^5$ is selected from
i) H, and
ii) $C_{1-6}$-alkyl;
or $R^1$ and $R^5$ together with the nitrogen atom to which they are attached form a heterocycloalkyl optionally substituted by $R^{14}$, $R^{15}$ and $R^{16}$;
$R^6$ is selected from
i) H, and
ii) $C_{1-6}$-alkyl;
or $R^1$ and $R^6$ together with the carbon atom to which they are attached form a cycloalkyl optionally substituted by $R^{14}$, $R^{15}$ and $R^{16}$;
$R^{14}$, $R^{15}$ and $R^{16}$ are independently selected from
i) $C_{1-6}$-alkyl, and
ii) halogen;
$R^1$ is selected from
i) $C_{1-6}$-alkyl, and
ii) $C_{3-8}$-cycloalkyl.

E2: A certain embodiment of the invention relates to the compound of formula I, formula II, formula III, formula IV, formula V, formula VI, or formula VII as described herein, or a pharmaceutically acceptable salt thereof, wherein $R^2$ and $R^3$ are H.

E3: A certain embodiment of the invention relates to the compound of formula I, formula II, formula III, formula IV, formula V, or formula VII as described herein, or a pharmaceutically acceptable salt thereof, wherein $R^2$ and $R^3$ together form —$CH_2$—.

E4: A certain embodiment of the invention relates to the compound of formula I as described herein, or a pharmaceutically acceptable salt thereof, wherein X is —$NR^4$—.

E5: A certain embodiment of the invention relates to the compound of formula I, formula IV, formula V, or formula VI as described herein, or a pharmaceutically acceptable salt thereof, wherein A is the ring system F.

E6: A certain embodiment of the invention relates to the compound of formula I, formula II, formula III, formula IV, formula V, formula VI, or formula VII as described herein, or a pharmaceutically acceptable salt thereof, wherein $R^e$ is halogen.

E7: A certain embodiment of the invention relates to the compound of formula I, formula II, formula III, formula IV, formula V, formula VI, or formula VII as described herein, or a pharmaceutically acceptable salt thereof, wherein t is 1.

E8: A certain embodiment of the invention relates to the compound of formula I, formula II, formula III, formula IV, formula V, formula VI, or formula VII as described herein, or a pharmaceutically acceptable salt thereof, wherein $R^f$ is $C_{1-6}$-alkyl.

E9: A certain embodiment of the invention relates to the compound of formula I, formula II, formula III, formula V, or formula VII as described herein, or a pharmaceutically acceptable salt thereof, wherein B is selected from the ring systems AA and AB.

E10: A certain embodiment of the invention relates to the compound of formula I, formula II, formula III, formula V, or formula VII as described herein, or a pharmaceutically acceptable salt thereof, wherein B is selected from the ring systems AA.

E11: A certain embodiment of the invention relates to the compound of formula I, formula II, formula III, formula IV, formula V, formula VI, or formula VII as described herein, or a pharmaceutically acceptable salt thereof, wherein $R^g$ is hydroxy.

E12: A certain embodiment of the invention relates to the compound of formula I, formula II, formula III, formula IV, formula V, formula VI, or formula VII as described herein, or a pharmaceutically acceptable salt thereof, wherein $R^g$ is phosphate.

E13: A certain embodiment of the invention relates to the compound of formula I, formula II, formula III, formula IV, formula V, formula VI, or formula VII as described herein, or a pharmaceutically acceptable salt thereof, wherein u is 1.

E14: A certain embodiment of the invention relates to the compound of formula I, formula II, formula III, formula IV, formula V, formula VI, or formula VII as described herein, or a pharmaceutically acceptable salt thereof, wherein R' is hydroxy.

E15: A certain embodiment of the invention relates to the compound of formula I, formula II, formula III, formula IV, formula V, formula VI, or formula VII as described herein, or a pharmaceutically acceptable salt thereof, wherein E is absent.

E16: A certain embodiment of the invention relates to the compound of formula I, formula II, formula III, formula IV, formula V, formula VI, or formula VII as described herein, or a pharmaceutically acceptable salt thereof, wherein v is selected from i) 0, and
ii) 1.

E17: A certain embodiment of the invention relates to the compound of formula I, formula II, formula III, formula IV, formula V, formula VI, or formula VII as described herein, or a pharmaceutically acceptable salt thereof, wherein m is selected from i) 0,
ii) 1, and
iii) 3.

E18: A certain embodiment of the invention relates to the compound of formula I, formula II, formula III, formula IV, formula V, formula VI, or formula VII as described herein, or a pharmaceutically acceptable salt thereof, wherein m is 0.

E19: A certain embodiment of the invention relates to the compound of formula I, formula II, formula III, formula IV, formula V, formula VI, or formula VII as described herein, or a pharmaceutically acceptable salt thereof, wherein n is selected from i) 0,
ii) 1,
iii) 2, and
iv) 3.

E20: A certain embodiment of the invention relates to the compound of formula I, formula II, formula III, formula IV, formula V, formula VI, or formula VII as described herein, or a pharmaceutically acceptable salt thereof, wherein n is 0.

E21: A certain embodiment of the invention relates to the compound of formula I, formula II, formula III, formula IV, formula V, formula VI, or formula VII as described herein, or a pharmaceutically acceptable salt thereof, wherein $R^a$ and $R^b$ are selected from i) H, and
ii) $C_{1-6}$-alkyl.

E22: A certain embodiment of the invention relates to the compound of formula I, formula II, formula III, formula IV, formula V, formula VI, or formula VII as described herein, or a pharmaceutically acceptable salt thereof, wherein $R^a$ and $R^b$ are H.

E23: A certain embodiment of the invention relates to the compound formula I, formula II, formula III, formula IV, formula V, formula VI, or formula VII as described herein, or a pharmaceutically acceptable salt thereof, wherein $R^c$ and $R^d$ are H.

E24: A certain embodiment of the invention relates to the compound of formula I, formula II, formula III, formula IV, formula V, formula VI, or formula VII as described herein, or a pharmaceutically acceptable salt thereof, wherein $R^m$ is hydroxy.

E25: A certain embodiment of the invention relates to the compound of formula I, formula II, formula III, formula IV, formula V, formula VI, or formula VII as described herein, or a pharmaceutically acceptable salt thereof, wherein y is selected from i) 0, and
ii) 1.

E26: A certain embodiment of the invention relates to the compound of formula I, formula II, formula III, formula IV, formula V, formula VI, or formula VII as described herein, or a pharmaceutically acceptable salt thereof, wherein $R^p$ is selected from i) halogen,
ii) halo-$C_{1-6}$-alkyl,
iii) $C_{1-6}$-alkyl,
iv) cyano, and
v) $C_{1-6}$-alkyl sulfonyl.

E27: A certain embodiment of the invention relates to the compound of formula I, formula II, formula III, formula IV, formula V, formula VI, or formula VII as described herein, or a pharmaceutically acceptable salt thereof, wherein $R^5$ is $C_{1-6}$-alkyl.

E28: A certain embodiment of the invention relates to the compound of formula I, formula II, formula III, formula IV, formula VI, or formula VII as described herein, or a pharmaceutically acceptable salt thereof, wherein $R^{14}$ is halogen.

E29: A certain embodiment of the invention relates to the compound of formula I, formula II, formula III, formula IV, formula V, formula VI, or formula VII as described herein, or a pharmaceutically acceptable salt thereof, wherein $R^7$ and $R^8$ are halogen.

E30: A certain embodiment of the invention relates to the compound of formula I, formula II, formula III, formula IV, formula V, formula VI, or formula VII as described herein, or a pharmaceutically acceptable salt thereof, wherein $R^{100}$ is H.

E31: A certain embodiment of the invention relates to the compound of formula I, formula II, formula III, formula IV, formula V, formula VI, or formula VII as described herein, or a pharmaceutically acceptable salt thereof, wherein z is 0.

E32: A certain embodiment of the invention relates to the compound of formula I, formula II, formula III, formula IV, formula V, formula VI, or formula VII as described herein, or a pharmaceutically acceptable salt thereof, wherein y is 0.

E33: A certain embodiment of the invention relates to the compound of formula I, formula II, formula III, formula IV, formula V, formula VI, or formula VII as described herein, or a pharmaceutically acceptable salt thereof, wherein w is 1.

E34: A certain embodiment of the invention relates to the compound of formula I, formula II, formula III, formula IV, formula V, formula VI, or formula VII as described herein, or a pharmaceutically acceptable salt thereof, wherein C is the ring system J.

E35: A certain embodiment of the invention relates to the compound of formula I, formula II, formula III, formula IV, formula V, formula VI, or formula VII as described herein, or a pharmaceutically acceptable salt thereof, wherein D is the ring system W.

E36: A certain embodiment of the invention relates to the compound of formula I, formula II, formula III, formula IV, formula V, formula VI, or formula VII as described herein, or a pharmaceutically acceptable salt thereof, wherein $A^4$ is a bond.

E37: A certain embodiment of the invention relates to the compound of formula I, formula II, formula III, formula IV, formula V, formula VI, or formula VII as described herein, or a pharmaceutically acceptable salt thereof, wherein $A^3$ is a bond.

E38: A certain embodiment of the invention relates to the compound of formula I, formula II, formula III, formula IV, formula V, formula VI, or formula VII as described herein, or a pharmaceutically acceptable salt thereof, wherein $A^1$ is —$NR^5$—.

E39: A certain embodiment of the invention relates to the compound of formula I, formula II, formula III, formula IV, formula V, formula VI, or formula VII as described herein, or a pharmaceutically acceptable salt thereof, which is selected from the group consisting of N-[3-[5-[2-[4-[2-[4-[4-[(2,6-dioxo-3-piperidyl)amino]phenyl]-1-piperidyl]acetyl]piperazin-1-yl]pyrimidin-5-yl]-1H-pyrrolo[2,3-b]pyridine-3-carbonyl]-2,4-difluoro-phenyl]propane-1-sulfonamide;

N-[3-[5-[2-[4-[2-[4-[4-[(2,6-dioxo-3-piperidyl)oxy]phenyl]-1-piperidyl]acetyl]piperazin-1-yl]pyrimidin-5-yl]-1H-pyrrolo[2,3-b]pyridine-3-carbonyl]-2,4-difluoro-phenyl]propane-1-sulfonamide;

N-[3-[5-[2-[4-[2-[4-[4-[(2,6-dioxo-3-piperidyl)amino]phenyl]-1-piperidyl]acetyl]piperazin-1-yl]-3-pyridyl]-1H-pyrrolo[2,3-b]pyridine-3-carbonyl]-2,4-difluoro-phenyl]propane-1-sulfonamide;

N-[3-[5-[2-[4-[2-[4-[4-[(2,6-dioxo-3-piperidyl)amino]phenyl]-1-piperidyl]acetyl]piperazin-1-yl]-3-pyridyl]-1H-pyrrolo[2,3-b]pyridine-3-carbonyl]-2,4-difluoro-phenyl]butane-2-sulfonamide;

N-[3-[5-[2-[4-[2-[4-[4-[(2,6-dioxo-3-piperidyl)amino]phenyl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide;

N-[3-[5-[2-[4-[2-[4-[4-[(2,6-dioxo-3-piperidyl)amino]-2-fluoro-phenyl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide;

N-[3-[5-[2-[4-[2-[4-[4-[(2,6-dioxo-3-piperidyl)oxy]phenyl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide;

N-[3-[5-[2-[4-[2-[4-[4-(2,6-dioxo-3-piperidyl)phenyl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide;

N-[3-[5-[2-[4-[2-[4-[4-(2,6-dioxo-3-piperidyl)-2-fluoro-phenyl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide;

N-[3-[5-[2-[4-[2-[4-[4-(2,4-dioxohexahydropyrimidin-1-yl)-1-methyl-indazol-6-yl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide;

N-[3-[5-[2-[4-[2-[4-[4-[(2,6-dioxo-3-piperidyl)amino]phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide;

N-[3-[5-[2-[4-[2-[4-[4-[(2,6-dioxo-3-piperidyl)amino]-2-fluoro-phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide;

N-[3-[5-[2-[4-[2-[4-[4-[(2,6-dioxo-3-piperidyl)oxy]phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide;

N-[3-[5-[2-[4-[2-[4-[4-(2,6-dioxo-3-piperidyl)phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide N-[3-[5-[2-[4-[2-[4-[4-(2,6-dioxo-3-piperidyl)-2-fluoro-phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide;

N-[3-[5-[6-[4-[2-[4-[4-[(2,6-dioxo-3-piperidyl)amino]phenyl]-1-piperidyl]acetyl]piperazin-1-yl]-3-pyridyl]-1H-pyrrolo[2,3-b]pyridine-3-carbonyl]-2,4-difluoro-phenyl]pyrrolidine-1-sulfonamide;

(3R)—N-[3-[5-[4-[4-[2-[4-[4-[(2,6-dioxo-3-piperidyl)amino]phenyl]-1-piperidyl]acetyl]piperazin-1-yl]phenyl]-1H-pyrrolo[2,3-b]pyridine-3-carbonyl]-2,4-difluoro-phenyl]-3-fluoro-pyrrolidine-1-sulfonamide;

5-[2-[4-[2-[4-[4-[(2,6-dioxo-3-piperidyl)amino]phenyl]-1-piperidyl]acetyl]piperazin-1-yl]pyrimidin-5-yl]-3-

[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]piperazin-1-yl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]-2-fluoro-phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]-2-pyridyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)-methyl-amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]-1-piperidyl]cyclobutanecarbonyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-(2,4-dioxohexahydropyrimidin-1-yl)phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[[(3S)-2,6-dioxo-3-piperidyl]amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[[(3R)-2,6-dioxo-3-piperidyl]amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

3-(2,6-dioxo-3-piperidyl)-6-[1-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl]-1-methyl-indazole;

3-(2,6-dioxo-3-piperidyl)-6-[[1-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl]amino]-1-methyl-indazole;

5-[2-[4-[2-[4-[4-[(2,6-dioxo-3-piperidyl)amino]-3-fluoro-phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]-3,3-difluoro-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(2,6-dioxo-3-piperidyl)amino]phenyl]-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,4-dioxohexahydropyrimidin-1-yl)methyl]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

1-(2,6-dioxo-3-piperidyl)-5-[1-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl]-3-methyl-2-oxo-benzimidazole;

3-(2,4-dioxohexahydropyrimidin-1-yl)-6-[1-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl]-1-methyl-indazole;

5-[2-[4-[2-[4-[4-[(2,6-dioxo-3-piperidyl)amino]phenyl]cyclohexyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]cyclohexyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-(2,6-dioxo-3-piperidyl)-3-oxo-piperazin-1-yl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(2,6-dioxo-3-piperidyl)amino]phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-(difluoromethyl)-4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[2-cyano-4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)oxy]-2,6-difluoro-phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(2,6-dioxo-3-piperidyl)amino]-2-fluoro-phenyl]-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

1-(2,6-dioxo-3-piperidyl)-5-[4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-1-piperidyl]-3-methyl-2-oxo-benzimidazole;

5-[2-[4-[2-[1-[4-(2,4-dioxohexahydropyrimidin-1-yl)-2-fluoro-phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(2,6-dioxo-3-piperidyl)amino]-2,6-difluoro-phenyl]-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]-2,6-difluoro-phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

3-(2,6-dioxo-3-piperidyl)-6-[4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-1-piperidyl]-1-methyl-indazole;

5-[2-[4-[2-[1-[4-[(2,6-dioxo-3-piperidyl)amino]-2-fluoro-phenyl]pyrrolidin-3-yl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(2,6-dioxo-3-piperidyl)amino]phenyl]-2,6-diazaspiro[3.3]heptan-6-yl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-(2,6-dioxo-3-piperidyl)-3-oxo-piperazin-1-yl]phenyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(2,6-dioxo-3-piperidyl)amino]-2-fluoro-phenyl]-3-hydroxy-pyrrolidin-3-yl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(2,6-dioxo-3-piperidyl)amino]-2-fluoro-phenyl]azetidin-3-yl]cyclobutanecarbonyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(2,6-dioxo-3-piperidyl)amino]-2-fluoro-phenyl]azetidin-3-yl]cyclobutanecarbonyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[(4S)-4-[4-[(2,6-dioxo-3-piperidyl)amino]phenyl]-3,3-difluoro-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[(4R)-4-[4-[(2,6-dioxo-3-piperidyl)amino]phenyl]-3,3-difluoro-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

3-(2,4-dioxohexahydropyrimidin-1-yl)-6-[4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-1-piperidyl]-1-methyl-indazole;

5-[2-[4-[2-[1-[5-[(2,6-dioxo-3-piperidyl)amino]-2-pyridyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[5-[(2,6-dioxo-3-piperidyl)amino]-3-fluoro-2-pyridyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(2,6-dioxo-3-piperidyl)amino]-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(2,6-dioxo-3-piperidyl)amino]phenyl]-4-piperidyl]-2,2-difluoro-acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

3-(2,4-dioxohexahydropyrimidin-1-yl)-6-[1-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-3,3-difluoro-4-piperidyl]-1-methyl-indazole;

5-[2-[4-[2-[1-[4-[(2,6-dioxo-3-piperidyl)amino]phenyl]-1-piperidyl]acetyl]-4-piperidyl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(2,6-dioxo-3-piperidyl)amino]phenyl]-1-piperidyl]acetyl]-1,4-diazepan-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(2,6-dioxo-3-piperidyl)amino]phenyl]-1-piperidyl]acetyl]-2,6-diazaspiro[3.3]heptan-6-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-4-methyl-1H-pyrrolo[2,3-b]pyridine;

5-[2-[4-[2-[1-[4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-4-fluoro-1H-pyrrolo[2,3-b]pyridine;

5-[6-[4-[2-[4-[4-[(2,6-dioxo-3-piperidyl)oxy]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[4-[4-[(2,6-dioxo-3-piperidyl)amino]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[4-[4-[(2,6-dioxo-3-piperidyl)amino]phenyl]piperazin-1-yl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[5-[(2,6-dioxo-3-piperidyl)amino]isoindolin-2-yl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[4-[4-[(2,4-dioxo-3-azabicyclo[3.1.1]heptan-1-yl)amino]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[4-[4-(2,6-dioxo-3-piperidyl)phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[4-[4-[[(3 S)-2,6-dioxo-3-piperidyl]oxy]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[4-[4-[[(3R)-2,6-dioxo-3-piperidyl]oxy]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

3-(2,6-dioxo-3-piperidyl)-6-[[1-[2-[4-[5-[3-[3-[[ethyl(methyl)sulfamoyl]amino]-2,6-difluoro-benzoyl]-1H-pyrrolo[2,3-b]pyridin-5-yl]-2-pyridyl]piperazin-1-yl]-2-oxo-ethyl]-4-piperidyl]amino]-1-methyl-indazole;

5-[6-[4-[2-[1-[4-[(2,6-dioxo-3-piperidyl)amino]phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[(4R)-4-[2[(2,6-dioxo-3-piperidyl)amino]phenyl]-3,3-difluoro-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[1-[5-[(2,6-dioxo-3-piperidyl)amino]-2-pyridyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[1-[5-[(2,6-dioxo-3-piperidyl)amino]-3-fluoro-2-pyridyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[2-[2-[4-[4-[(2,6-dioxo-3-piperidyl)amino]phenyl]-1-piperidyl]acetyl]-2,6-diazaspiro[3.3]heptan-6-yl]-3-pyridyl]-3-[3-[[ethyl(methyl)sulfamoyl]amino]-2,6-difluoro-benzoyl]-1H-pyrrolo[2,3-b]pyridine;

5-[5-cyano-6-[4-[2-[4-[4-[(2,6-dioxo-3-piperidyl)amino]phenyl]-1-piperidyl]acetyl]piperazin-1-yl]-3-pyridyl]-

3-[3-[[ethyl(methyl)sulfamoyl]amino]-2,6-difluoro-benzoyl]-1H-pyrrolo[2,3-b]pyridine;

5-[4-[4-[2-[4-[4-[(2,6-dioxo-3-piperidyl)oxy]phenyl]-1-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[4-[4-[2-[4-[4-[(2,6-dioxo-3-piperidyl)amino]phenyl]-1-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[4-[4-[2-[4-[4-[(2,6-dioxo-3-piperidyl)amino]pyrazol-1-yl]-1-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[4-[4-[2-[1-[4-[(2,6-dioxo-3-piperidyl)amino]phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[4-[4-[2-[1-[4-[(2,6-dioxo-3-piperidyl)amino]-2-fluoro-phenyl]-3-hydroxy-pyrrolidin-3-yl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[4-[4-[2-[1-[5-[(2,6-dioxo-3-piperidyl)amino]-2-pyridyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[4-[4-[2-[1-[5-[(2,6-dioxo-3-piperidyl)amino]-3-fluoro-2-pyridyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[4-[1-[2-[4-[4-[(2,6-dioxo-3-piperidyl)amino]phenyl]-1-piperidyl]acetyl]-4-piperidyl]phenyl]-3-[3-[[ethyl(methyl)sulfamoyl]amino]-2,6-difluoro-benzoyl]-1H-pyrrolo[2,3-b]pyridine;

5-[4-[1-[2-[1-[4-[(2,6-dioxo-3-piperidyl)amino]phenyl]-4-piperidyl]acetyl]-3,6-dihydro-2H-pyridin-4-yl]phenyl]-3-[3-[[ethyl(methyl)sulfamoyl]amino]-2,6-difluoro-benzoyl]-1H-pyrrolo[2,3-b]pyridine;

5-[4-[4-[2-[4-[4-[(2,6-dioxo-3-piperidyl)amino]phenyl]-1-piperidyl]acetyl]piperazin-1-yl]-3,5-difluoro-phenyl]-3-[3-[[ethyl(methyl)sulfamoyl]amino]-2,6-difluoro-benzoyl]-1H-pyrrolo[2,3-b]pyridine;

5-[4-[[4-[2-[4-[4-[(2,6-dioxo-3-piperidyl)amino]phenyl]-1-piperidyl]-2-oxo-ethyl]piperazin-1-yl]methyl]phenyl]-3-[3-[[ethyl(methyl)sulfamoyl]amino]-2,6-difluoro-benzoyl]-1H-pyrrolo[2,3-b]pyridine;

5-[4-[[4-[2-[4-[4-[(2,6-dioxo-3-piperidyl)amino]phenyl]piperazin-1-yl]acetyl]piperazin-1-yl]methyl]phenyl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[4-[4-[(2,6-dioxo-3-piperidyl)amino]-2-fluoro-phenyl]-1-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[1-[4-[(2,6-dioxo-3-piperidyl)amino]-2-fluoro-phenyl]-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[1-[4-[(2,6-dioxo-3-piperidyl)amino]phenyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[4-[4-[(2,6-dioxo-3-piperidyl)amino]phenyl]-3,3-difluoro-1-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[1-[4-[(2,6-dioxo-3-piperidyl)amino]-2-fluoro-phenyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[1-[4-[(2,6-dioxo-3-piperidyl)amino]-2-fluoro-phenyl]-3-hydroxy-pyrrolidin-3-yl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[1-[2-chloro-4-[(2,6-dioxo-3-piperidyl)amino]phenyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[1-[4-[(2,6-dioxo-3-piperidyl)amino]-3-fluoro-2-pyridyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[1-[5-[(2,6-dioxo-3-piperidyl)amino]-2-pyridyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[1-[4-[(2,6-dioxo-3-piperidyl)amino]-2-(trifluoromethyl)phenyl]-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[6-[4-[2-[4-[4-[(2,6-dioxo-3-piperidyl)amino]phenyl]-1-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[6-[4-[2-[4-[4-[(2,6-dioxo-3-piperidyl)oxy]phenyl]-1-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[6-[4-[2-[1-[4-[(2,6-dioxo-3-piperidyl)amino]phenyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[6-[4-[2-[4-[4-[(2,6-dioxo-3-piperidyl)amino]phenyl]-3,3-difluoro-1-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[6-[4-[2-[1-[4-[(2,6-dioxo-3-piperidyl)amino]-2-fluoro-phenyl]-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[6-[4-[2-[1-[5-[(2,6-dioxo-3-piperidyl)amino]-2-pyridyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[6-[4-[2-[1-[4-[(2,6-dioxo-3-piperidyl)amino]-2-fluoro-phenyl]-3-hydroxy-pyrrolidin-3-yl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[6-[4-[2-[1-[4-[(2,6-dioxo-3-piperidyl)amino]-3-fluoro-2-pyridyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[4-[4-[2-[1-[4-[(2,6-dioxo-3-piperidyl)amino]phenyl]-4-hydroxy-4-piperidyl]acetyl]piperazin-1-yl]phenyl]-3-[3-[[ethyl(methyl)sulfamoyl]amino]-2-fluoro-benzoyl]-1H-pyrrolo[2,3-b]pyridine;

5-[4-[4-[2-[1-[5-[(2,6-dioxo-3-piperidyl)amino]-2-pyridyl]-4-hydroxy-4-piperidyl]acetyl]piperazin-1-yl]phenyl]-3-[3-[[ethyl(methyl)sulfamoyl]amino]-2-fluoro-benzoyl]-1H-pyrrolo[2,3-b]pyridine;

5-[4-[4-[2-[1-[4-[(2,6-dioxo-3-piperidyl)amino]-2-fluoro-phenyl]-3-hydroxy-pyrrolidin-3-yl]acetyl]piperazin-1-yl]phenyl]-3-[3-[[ethyl(methyl)sulfamoyl]amino]-2-fluoro-benzoyl]-1H-pyrrolo[2,3-b]pyridine;

5-[4-[4-[2-[1-[4-[(2,6-dioxo-3-piperidyl)amino]-2-fluoro-phenyl]-4-hydroxy-4-piperidyl]acetyl]piperazin-1-yl]phenyl]-3-[3-[[ethyl(methyl)sulfamoyl]amino]-2-fluoro-benzoyl]-1H-pyrrolo[2,3-b]pyridine;

5-[4-[4-[2-[1-[4-[(2,6-dioxo-3-piperidyl)amino]-3-fluoro-2-pyridyl]-4-hydroxy-4-piperidyl]acetyl]piperazin-1-yl]phenyl]-3-[3-[[ethyl(methyl)sulfamoyl]amino]-2-fluoro-benzoyl]-1H-pyrrolo[2,3-b]pyridine;

3-[2-chloro-3-[[ethyl(methyl)sulfamoyl]amino]-6-fluoro-benzoyl]-5-[2-[4-[2-[4-[4-[(2,6-dioxo-3-piperidyl)amino]phenyl]-1-piperidyl]acetyl]piperazin-1-yl]pyrimidin-5-yl]-1H-pyrrolo[2,3-b]pyridine;

3-[2-bromo-3-[[ethyl(methyl)sulfamoyl]amino]benzoyl]-5-[6-[4-[2-[4-[4-[(2,6-dioxo-3-piperidyl)amino]phenyl]-1-piperidyl]acetyl]piperazin-1-yl]-3-pyridyl]-1H-pyrrolo[2,3-b]pyridine;

5-[2-[4-[2-[4-[4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-6-fluoro-2-methyl-benzoyl]-1H-pyrrolo[2,3-b]pyridine;

5-[4-[1-[2-[1-[4-[(2,6-dioxo-3-piperidyl)amino]-2-fluoro-phenyl]-1-piperidyl]acetyl]-4-piperidyl]ethynyl]-3-[3-[[ethyl(methyl)sulfamoyl]amino]-2,6-difluoro-benzoyl]-1H-pyrrolo[2,3-b]pyridine;

5-[4-[1-[2-[1-[4-[(2,6-dioxo-3-piperidyl)amino]-2-fluoro-phenyl]-4-hydroxy-4-piperidyl]acetyl]-4-piperidyl]-3-fluoro-phenyl]-3-[3-[[ethyl(methyl)sulfamoyl]amino]-2,6-difluoro-benzoyl]-1H-pyrrolo[2,3-b]pyridine;

5-[2-[4-[4-[4-[4-[(2,6-dioxo-3-piperidyl)amino]phenyl]-1-piperidyl]piperidine-1-carbonyl]phenyl]ethynyl]-3-[3-[[ethyl(methyl)sulfamoyl]amino]-2,6-difluoro-benzoyl]-1H-pyrrolo[2,3-b]pyridine;

5-[2-[4-[4-[4-[(2,6-dioxo-3-piperidyl)amino]phenyl]piperidine-1-carbonyl]-1-piperidyl]pyrimidin-5-yl]-3-[3-[[ethyl(methyl)sulfamoyl]amino]-2,6-difluoro-benzoyl]-1H-pyrrolo[2,3-b]pyridine;

N-[1-[4-[(2,6-dioxo-3-piperidyl)amino]-2-fluoro-phenyl]-4-piperidyl]-1-[5-[3-[3-[[ethyl(methyl)sulfamoyl]amino]-2,6-difluoro-benzoyl]-1H-pyrrolo[2,3-b]pyridin-5-yl]pyrimidin-2-yl]piperidine-4-carboxamide;

5-[2-[(3R)-3-[4-[4-[(2,6-dioxo-3-piperidyl)amino]phenyl]piperidine-1-carbonyl]pyrrolidin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[(3 S)-3-[4-[4-[(2,6-dioxo-3-piperidyl)amino]phenyl]piperidine-1-carbonyl]pyrrolidin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[(3 S)-3-[2-[4-[4-[(2,6-dioxo-3-piperidyl)amino]phenyl]-1-piperidyl]-2-oxo-ethyl]pyrrolidin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[6-[4-[4-[(2,6-dioxo-3-piperidyl)amino]phenyl]piperidine-1-carbonyl]-2-azaspiro[3.3]heptan-2-yl]pyrimidin-5-yl]-3-[3-[[ethyl(methyl)sulfamoyl]amino]-2,6-difluoro-benzoyl]-1H-pyrrolo[2,3-b]pyridine;

5-[2-[6-[2-[4-[4-[(2,6-dioxo-3-piperidyl)amino]phenyl]-1-piperidyl]-2-oxo-ethyl]-2-azaspiro[3.3]heptan-2-yl]pyrimidin-5-yl]-3-[3-[[ethyl(methyl)sulfamoyl]amino]-2,6-difluoro-benzoyl]-1H-pyrrolo[2,3-b]pyridine;

N-[1-[4-[(2,6-dioxo-3-piperidyl)amino]-2-fluoro-phenyl]-4-piperidyl]-2-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]acetamide;

1-[4-[(2,6-dioxo-3-piperidyl)amino]-2-fluoro-phenyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]-N-methyl-piperidine-4-carboxamide;

1-[4-[(2,6-dioxo-3-piperidyl)amino]-2-fluoro-phenyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]piperidine-4-carboxamide;

4-[4-[(2,6-dioxo-3-piperidyl)amino]phenyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]piperidine-1-carboxamide;

N-[1-[4-[(2,6-dioxo-3-piperidyl)amino]-2-fluoro-phenyl]-4-piperidyl]-4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazine-1-carboxamide;

N-[1-[4-[(2,6-dioxo-3-piperidyl)amino]phenyl]-4-piperidyl]-4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazine-1-carboxamide;

N-[1-[4-[(2,6-dioxo-3-piperidyl)amino]-2-fluoro-phenyl]-4-piperidyl]-4-[5-[3-[3-[[ethyl(methyl)sulfamoyl]amino]-2,6-difluoro-benzoyl]-1H-pyrrolo[2,3-b]pyridin-5-yl]-2-pyridyl]piperazine-1-carboxamide;

N-[1-[4-[(2,6-dioxo-3-piperidyl)amino]-2-fluoro-phenyl]-4-piperidyl]-4-[5-[3-[3-[[ethyl(methyl)sulfamoyl]amino]-2-fluoro-benzoyl]-1H-pyrrolo[2,3-b]pyridin-5-yl]pyrimidin-2-yl]piperazine-1-carboxamide;

5-[2-[4-[2-[4-[4-[(2,6-dioxo-3-piperidyl)amino]phenyl]-1-hydroxy-cyclohexyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[2-[4-[4-[(2,6-dioxo-3-piperidyl)amino]phenyl]-1-piperidyl]ethyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[4-[4-[(2,6-dioxo-3-piperidyl)oxy]phenyl]-1-piperidyl]ethyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]-1-hydroxy-cyclohexyl]ethyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]-2-oxo-1-piperidyl]ethyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[2-[4-[4-[(2,6-dioxo-3-piperidyl)oxy]phenyl]-1-piperidyl]ethyl]-3-oxo-piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[1-[4-[(2,6-dioxo-3-piperidyl)amino]phenyl]-4-piperidyl]ethyl]-3-oxo-piperazin-1-yl]-3-pyridyl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]-1-piperidyl]ethyl]-4-hydroxy-1-piperidyl]pyrimidin-5-yl]-3-[3-[[ethyl(methyl)sulfamoyl]amino]-2,6-difluoro-benzoyl]-1H-pyrrolo[2,3-b]pyridine;

5-[[4-[4-[(2,6-dioxo-3-piperidyl)amino]phenyl]-1-piperidyl]methyl]-2-[5-[3-[3-[[ethyl(methyl)sulfamoyl]amino]-2,6-difluoro-benzoyl]-1H-pyrrolo[2,3-b]pyridin-5-yl]pyrimidin-2-yl]-3,4-dihydro-1H-isoquinoline;

5-[2-[6-[4-[4-[(2,6-dioxo-3-piperidyl)amino]phenyl]-1-piperidyl]-2-azaspiro[3.3]heptan-2-yl]pyrimidin-5-yl]-3-[3-[[ethyl(methyl)sulfamoyl]amino]-2,6-difluoro-benzoyl]-1H-pyrrolo[2,3-b]pyridine;

5-[4-[(2,6-dioxo-3-piperidyl)amino]phenyl]-2[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]-6,7-dihydro-4H-pyrazolo[4,3-c]pyridine;

5-[2-[4-[4-[4-[4-[(2,6-dioxo-3-piperidyl)amino]phenyl]-1-piperidyl]pyrazol-1-yl]-1-piperidyl]pyrimidin-5-yl]-3-[3-[[ethyl(methyl)sulfamoyl]amino]-2,6-difluoro-benzoyl]-1H-pyrrolo[2,3-b]pyridine;

N-[1-[4-[(2,6-dioxo-3-piperidyl)amino]-2-fluoro-phenyl]-4-piperidyl]-4-[5-[3-[3-[[ethyl(methyl)sulfamoyl]amino]-2-fluoro-benzoyl]-1H-pyrrolo[2,3-b]pyridin-5-yl]-2-pyridyl]piperazine-1-carboxamide;

3-[2-chloro-3-[[ethyl(methyl)sulfamoyl]amino]-6-fluoro-benzoyl]-5-[4-[4-[2-[1-[4-[(2,6-dioxo-3-piperidyl)amino]-2-fluoro-phenyl]-4-hydroxy-4-piperidyl]acetyl]piperazin-1-yl]phenyl]-1H-pyrrolo[2,3-b]pyridine;

5-[6-[4-[2-[1-[2-chloro-4-[(2,6-dioxo-3-piperidyl)amino]phenyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[2-[4-[2-[1-[2-chloro-4-[(2,6-dioxo-3-piperidyl)amino]phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[2-[1-[4-(2,6-dioxo-3-piperidyl)-2-fluoro-phenyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[6-[4-[2-[1-[4-(2,6-dioxo-3-piperidyl)-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

6-[4-[(2,6-dioxo-3-piperidyl)amino]phenyl]-2-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]-5,7-dihydro-4H-pyrazolo[3,4-c]pyridine;

5-[2-[4-[2-[1-[4-(2,6-dioxo-3-piperidyl)-2-fluoro-phenyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

3-(2,4-dioxohexahydropyrimidin-1-yl)-6-[4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-hydroxy-1-piperidyl]-1-methyl-indazole;

5-[6-[4-[2-[1-[4-(2,4-dioxohexahydropyrimidin-1-yl)-2-fluoro-phenyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[2-[4-[2-[1-[4-(2,4-dioxohexahydropyrimidin-1-yl)-2-fluoro-phenyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[1-[4-[[(3 S)-2,6-dioxo-3-piperidyl]amino]-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-(2,4-dioxohexahydropyrimidin-1-yl)-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[2-[1-[4-(2,4-dioxohexahydropyrimidin-1-yl)-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[4-[4-[2-[1-[4-(2,4-dioxohexahydropyrimidin-1-yl)-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

3[2-chloro-3-[[ethyl(methyl)sulfamoyl]amino]-6-fluoro-benzoyl]-5[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-1H-pyrrolo[2,3-b]pyridine;

5-[6-[4-[2-[4-[4-(2,6-dioxo-3-piperidyl)-3-oxo-piperazin-1-yl]-3,3-difluoro-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[4-[4-[2-[4-[4-(2,6-dioxo-3-piperidyl)-3-oxo-piperazin-1-yl]-3,3-difluoro-1-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[2-[4-[2-[4-[4-(2,6-dioxo-3-piperidyl)-3-oxo-piperazin-1-yl]-3,3-difluoro-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[[(3R)-2,6-dioxo-3-piperidyl]amino]-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[4-[4-[2-[1-[4-(2,6-dioxo-3-piperidyl)-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[6-[4-[2-[1-[4-[[(3 S)-2,6-dioxo-3-piperidyl]amino]-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[4-[4-[2-[1-[4-[[(3R)-2,6-dioxo-3-piperidyl]amino]-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[4-[4-[2-[1-[4-[[(3S)-2,6-dioxo-3-piperidyl]amino]-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[3-chloro-4[4-[2-[1-[4-[(2,6-dioxo-3-piperidyl)amino]-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[1-[1-[2-[1-[4-[(2,6-dioxo-3-piperidyl)amino]-2-fluoro-phenyl]-4-hydroxy-4-piperidyl]acetyl]-4-piperidyl]-2-oxo-4-pyridyl]-3-[3-[[ethyl(methyl)sulfamoyl]amino]-2,6-difluoro-benzoyl]-1H-pyrrolo[2,3-b]pyridine;

5-[2-[4-[1-[4-[4-[(2,6-dioxo-3-piperidyl)amino]-2-fluoro-phenyl]-4-piperidyl]methoxy]-1-piperidyl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[2-[1-[4-[(2,6-dioxo-3-piperidyl)amino]-3-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[4-[4-[2-[1-[4-[(2,6-dioxo-3-piperidyl)amino]-3-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

3-[6-chloro-3-[[ethyl(methyl)sulfamoyl]amino]-2-fluoro-benzoyl]-5-[2-[4-[2-[1-[4-[(2,6-dioxo-3-piperidyl)amino]-2-fluoro-phenyl]-4-hydroxy-4-piperidyl]acetyl]piperazin-1-yl]pyrimidin-5-yl]-1H-pyrrolo[2,3-b]pyridine;

5-[5-cyano-6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[5-[4-[2-[1-[4-[(2,6-dioxo-3-piperidyl)amino]-2-fluoro-phenyl]-4-hydroxy-4-piperidyl]acetyl]piperazin-1-yl]pyrazin-2-yl]-3-[3-[[ethyl(methyl)sulfamoyl]amino]-2,6-difluoro-benzoyl]-1H-pyrrolo[2,3-b]pyridine;

5-[6-[4-[2-[1-[4-[(2,6-dioxo-3-piperidyl)amino]-2-fluoro-phenyl]-4-hydroxy-4-piperidyl]acetyl]piperazin-1-yl]-5-fluoro-3-pyridyl]-3-[3-[[ethyl(methyl)sulfamoyl]amino]-2,6-difluoro-benzoyl]-1H-pyrrolo[2,3-b]pyridine;

5-[4-[4-[2-[1-[4-[(2,6-dioxo-3-piperidyl)amino]-2-fluoro-phenyl]-4-hydroxy-4-piperidyl]acetyl]piperazin-1-yl]-2-methyl-phenyl]-3-[3-[[ethyl(methyl)sulfamoyl]amino]-2,6-difluoro-benzoyl]-1H-pyrrolo[2,3-b]pyridine;

(3R)—N-[3-[5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-1H-pyrrolo[2,3-b]pyridine-3-carbonyl]-2,4-difluoro-phenyl]-3-fluoro-pyrrolidine-1-sulfonamide;

(3R)—N-[3-[5-[4-[4-[2-[1-[4-[(2,6-dioxo-3-piperidyl)amino]-2-fluoro-phenyl]-4-hydroxy-4-piperidyl]acetyl]piperazin-1-yl]phenyl]-1H-pyrrolo[2,3-b]pyridine-3-carbonyl]-2,4-difluoro-phenyl]-3-fluoro-pyrrolidine-1-sulfonamide;

5-[4-[4-[2-[1-[4-[(2,6-dioxo-3-piperidyl)amino]-2-fluoro-phenyl]-4-hydroxy-4-piperidyl]acetyl]piperazin-1-yl]-3-methyl-phenyl]-3-[3-[[ethyl(methyl)sulfamoyl]amino]-2,6-difluoro-benzoyl]-1H-pyrrolo[2,3-b]pyridine;

3-(2,4-dioxohexahydropyrimidin-1-yl)-6-[4-[2-[4-[5-[3-[3-[[ethyl(methyl)sulfamoyl]amino]-2,6-difluoro-benzoyl]-1H-pyrrolo[2,3-b]pyridin-5-yl]-2-pyridyl]piperazin-1-yl]-2-oxo-ethyl]-4-hydroxy-1-piperidyl]-1-methyl-indazole;

5-[6-[4-[2-[1-[4-(2,4-dioxohexahydropyrimidin-1-yl)-2-fluoro-phenyl]-4-hydroxy-4-piperidyl]acetyl]piperazin-1-yl]-5-fluoro-3-pyridyl]-3-[3-[[ethyl(methyl)sulfamoyl]amino]-2,6-difluoro-benzoyl]-1H-pyrrolo[2,3-b]pyridine;

5-[4-[4-[2-[1-[4-[(2,6-dioxo-3-piperidyl) amino]-2-fluoro-phenyl]-4-hydroxy-4-piperidyl]acetyl]piperazin-1-yl]-3,5-difluoro-phenyl]-3-[3-[[ethyl(methyl)sulfamoyl]amino]-2,6-difluoro-benzoyl]-1H-pyrrolo[2,3-b]pyridine;

5-[2-[6-[1-[4-[(2,6-dioxo-3-piperidyl)amino]-2-fluoro-phenyl]-4-piperidyl]-6-hydroxy-2-azaspiro[3.3]heptan-2-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[2-[1-[2-(difluoromethyl)-4-[(2,6-dioxo-3-piperidyl)amino]phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[4-[4-[2-[1-[4-[(2,6-dioxo-3-piperidyl)amino]-2-fluoro-phenyl]-4-hydroxy-4-piperidyl]acetyl]piperazin-1-yl]-3-fluoro-phenyl]-3-[3-[[ethyl(methyl)sulfamoyl]amino]-2,6-difluoro-benzoyl]-1H-pyrrolo[2,3-b]pyridine;

5-[2-[6-[1-[4-[(2,6-dioxo-3-piperidyl)amino]-2-fluoro-phenyl]-4-piperidyl]-2-azaspiro[3.3]heptan-2-yl]pyrimidin-5-yl]-3-[3-[[ethyl(methyl)sulfamoyl]amino]-2,6-difluoro-benzoyl]-1H-pyrrolo[2,3-b]pyridine;

5-[3-(difluoromethyl)-4-[4-[2-[1-[4-[(2,6-dioxo-3-piperidyl)amino]-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

3-[6-chloro-3-[[ethyl(methyl)sulfamoyl]amino]-2-fluoro-benzoyl]-5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-1H-pyrrolo[2,3-b]pyridine;

3-(2,4-dioxohexahydropyrimidin-1-yl)-6-[4-[2-[4-[4-[3-[3-[[ethyl(methyl)sulfamoyl]amino]-2,6-difluoro-benzoyl]-1H-pyrrolo[2,3-b]pyridin-5-yl]phenyl]piperazin-1-yl]-2-oxo-ethyl]-4-hydroxy-1-piperidyl]-1-methyl-indazole;

5-[2-[2-[1-[4-[(2,6-dioxo-3-piperidyl)amino]-2-fluoro-phenyl]-4-piperidyl]-2,6-diazaspiro[3.3]heptan-6-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[2-(difluoromethyl)-4-[(2,6-dioxo-3-piperidyl)amino]phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[2-[1-[4-(2,6-dioxo-3-piperidyl)-2-fluoro-phenyl]-4-hydroxy-4-piperidyl]acetyl]piperazin-1-yl]-5-fluoro-3-pyridyl]-3-[3-[[ethyl(methyl)sulfamoyl]amino]-2,6-difluoro-benzoyl]-1H-pyrrolo[2,3-b]pyridine;

5-[2-[4-[2-[1-[2-chloro-4-[[(3S)-2,6-dioxo-3-piperidyl]amino]phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-3-[3-[[ethyl(methyl)sulfamoyl]amino]-2,5-difluoro-benzoyl]-1H-pyrrolo[2,3-b]pyridine;

5-[6-[4-[2-[1-[2-chloro-4-[[(3S)-2,6-dioxo-3-piperidyl]amino]phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[2-[4-[2-[1-[2-chloro-4-[[(3R)-2,6-dioxo-3-piperidyl]amino]phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[4-[4-[2-[1-[4-[(2,6-dioxo-3-piperidyl)amino]-2-fluoro-phenyl]-4-hydroxy-4-piperidyl]acetyl]piperazin-1-yl]-2-fluoro-phenyl]-3-[3-[[ethyl(methyl)sulfamoyl]amino]-2,6-difluoro-benzoyl]-1H-pyrrolo[2,3-b]pyridine;

5-[6-[4-[2-[1-[4-[(2,6-dioxo-3-piperidyl)amino]-2-fluoro-phenyl]-4-hydroxy-4-piperidyl]acetyl]piperazin-1-yl]-5-methyl sulfonyl-3-pyridyl]-3-[3-[[ethyl(methyl)sulfamoyl]amino]-2,6-difluoro-benzoyl]-1H-pyrrolo[2,3-b]pyridine;

5-[4-[4-[2-[1-[4-[(2,6-dioxo-3-piperidyl)amino]-2-fluoro-phenyl]-4-hydroxy-4-piperidyl]acetyl]piperazin-1-yl]-3-(trifluoromethyl)phenyl]-3-[3-[[ethyl(methyl)sulfamoyl]amino]-2,6-difluoro-benzoyl]-1H-pyrrolo[2,3-b]pyridine;

5-[2-[4-[2-[1-[2-chloro-4-(2,4-dioxohexahydropyrimidin-1-yl)phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[2-[1-[2-chloro-4-(2,4-dioxohexahydropyrimidin-1-yl)phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[1-[2-chloro-4-(2,4-dioxohexahydropyrimidin-1-yl)-5-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[2-[4-[2-[1-[2-chloro-4-(2,4-dioxohexahydropyrimidin-1-yl)-5-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

3[3-[[cyclopropyl(methyl)sulfamoyl]amino]-2,6-difluoro-benzoyl]-5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-1H-pyrrolo[2,3-b]pyridine;

5-[6-[4-[2-[1-[2,5-dichloro-4-(2,4-dioxohexahydropyrimidin-1-yl)phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[1-[5-chloro-4-(2,4-dioxohexahydropyrimidin-1-yl)-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[1-[4-(2,4-dioxohexahydropyrimidin-1-yl)-2,5-difluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[4-[4-[2-[1-[4-[(2,6-dioxo-3-piperidyl)amino]-2-fluoro-phenyl]-4-hydroxy-4-piperidyl]acetyl]piperazin-1-yl]-2,5-difluoro-phenyl]-3-[3-[[ethyl(methyl)sulfamoyl]amino]-2,6-difluoro-benzoyl]-1H-pyrrolo[2,3-b]pyridine;

5-[6-[4-[2-[4-[4-[(2,6-dioxo-3-piperidyl)oxy]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[4-[4-[4-[(2,6-dioxo-3-piperidyl)oxy]phenyl]-1-piperidyl]butanoyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[4-[4-[(2,6-dioxo-3-piperidyl)oxy]phenyl]-1-piperidyl]-2-oxo-ethyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[4-[[4-[4-[4-[(2,6-dioxo-3-piperidyl)oxy]phenyl]piperazine-1-carbonyl]piperazin-1-yl]methyl]phenyl]-3-[3-[[ethyl(methyl)sulfamoyl]amino]-2,6-difluoro-benzoyl]-1H-pyrrolo[2,3-b]pyridine;

5-[6-[4-[4-[4-[4-[(2,6-dioxo-3-piperidyl)oxy]phenyl]-1-piperidyl]-4-oxo-butyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)oxy]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[[4-[2-[4-[4-[(2,6-dioxo-3-piperidyl)amino]phenyl]-1-piperidyl]acetyl]piperazin-1-yl]methyl]-3-pyridyl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[[4-[2-[4-[4-[(2,6-dioxo-3-piperidyl)amino]phenyl]piperazin-1-yl]acetyl]piperazin-1-yl]methyl]-3-pyridyl]-3-[3-[[ethyl(methyl)sulfamoyl]amino]-2,6-difluoro-benzoyl]-1H-pyrrolo[2,3-b]pyridine;

5-[4-[[4-[1-[2-[4-[4-[(2,6-dioxo-3-piperidyl)amino]phenyl]-1-piperidyl]acetyl]-4-piperidyl]piperazin-1-yl]methyl]phenyl]-3-[3-[[ethyl(methyl)sulfamoyl]amino]-2,6-difluoro-benzoyl]-1H-pyrrolo[2,3-b]pyridine;

5-[4-[4-[4-[4-[4-[(2,6-dioxo-3-piperidyl)oxy]phenyl]-1-piperidyl]butanoyl]piperazin-1-yl]phenyl]-3-[3-[[ethyl(methyl)sulfamoyl]amino]-2,6-difluoro-benzoyl]-1H-pyrrolo[2,3-b]pyridine;

5-[4-[4-[4-[4-[4-[(2,6-dioxo-3-piperidyl)amino]phenyl]piperazin-1-yl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[4-[4-[4-[(2,6-dioxo-3-piperidyl)amino]phenyl]-1-piperidyl]butanoyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[2-[4-[4-[4-[4-[(2,6-dioxo-3-piperidyl)amino]phenyl]-1-piperidyl]butanoyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[4-[[3-[4-[4-[(2,6-dioxo-3-piperidyl)oxy]phenyl]piperazine-1-carbonyl]pyrrolidin-1-yl]methyl]phenyl]-3-

[3-[[ethyl(methyl)sulfamoyl]amino]-2,6-difluoro-benzoyl]-1H-pyrrolo[2,3-b]pyridine;

5-[4-[[3-[4-[4-[(2,6-dioxo-3-piperidyl)oxy]phenyl]piperidine-1-carbonyl]pyrrolidin-1-yl]methyl]phenyl]-3-[3-[[ethyl(methyl)sulfamoyl]amino]-2,6-difluoro-benzoyl]-1H-pyrrolo[2,3-b]pyridine;

5-[4-[[4-[2-[4-[4-[(2,6-dioxo-3-piperidyl)amino]phenyl]-1-piperidyl]-2-oxo-ethyl]piperazin-1-yl]methyl]phenyl]-3-[3-[[ethyl(methyl)sulfamoyl]amino]-2,6-difluoro-benzoyl]-1H-pyrrolo[2,3-b]pyridine 2,2,2-trifluoroacetic acid;

5-[4-[[4-[2-[4-[4-[(2,6-dioxo-3-piperidyl)oxy]phenyl]-1-piperidyl]acetyl]piperazin-1-yl]methyl]phenyl]-3-[3-[[ethyl(methyl)sulfamoyl]amino]-2,6-difluoro-benzoyl]-1H-pyrrolo[2,3-b]pyridine;

5-[4-[[4-[2-[4-[4-[(2,6-dioxo-3-piperidyl)amino]phenyl]-1-piperidyl]acetyl]piperazin-1-yl]methyl]phenyl]-3-[3-[[ethyl(methyl)sulfamoyl]amino]-2,6-difluoro-benzoyl]-1H-pyrrolo[2,3-b]pyridine;

5-[4-[[4-[2-[4-[3-[(2,6-dioxo-3-piperidyl)amino]phenyl]piperazin-1-yl]acetyl]piperazin-1-yl]methyl]phenyl]-3-[3-[[ethyl(methyl)sulfamoyl]amino]-2,6-difluoro-benzoyl]-1H-pyrrolo[2,3-b]pyridine 2,2,2-trifluoroacetic acid;

5-[4-[[4-[2-[4-[3-[(2,6-dioxo-3-piperidyl)amino]phenyl]piperazin-1-yl]acetyl]piperazin-1-yl]methyl]phenyl]-3-[3-[[ethyl(methyl)sulfamoyl]amino]-2,6-difluoro-benzoyl]-1H-pyrrolo[2,3-b]pyridine 2,2,2-trifluoroacetic acid;

5-[4-[[4-[4-[4-[4-[(2,6-dioxo-3-piperidyl)amino]phenyl]-1-piperidyl]butanoyl]piperazin-1-yl]methyl]phenyl]-3-[3-[[ethyl(methyl)sulfamoyl]amino]-2,6-difluoro-benzoyl]-1H-pyrrolo[2,3-b]pyridine 2,2,2-trifluoroacetic acid;

N-[1-[[4-[3-[2,6-difluoro-3-(pyrrolidin-1-ylsulfonylamino)benzoyl]-1H-pyrrolo[2,3-b]pyridin-5-yl]phenyl]methyl]-4-piperidyl]-4-[4-[(2,6-dioxo-3-piperidyl)oxy]phenyl]piperidine-1-carboxamide formic acid;

N-[3-[5-[6-[4-[2-[4-[4-[(2,6-dioxo-3-piperidyl)oxy]phenyl]-1-piperidyl]acetyl]piperazin-1-yl]-3-pyridyl]-1H-pyrrolo[2,3-b]pyridine-3-carbonyl]-2,4-difluoro-phenyl]butane-2-sulfonamide;

5-[4-[[1-[2-[4-[4-[(2,6-dioxo-3-piperidyl)oxy]phenyl]-1-piperidyl]acetyl]-4-piperidyl]oxy]phenyl]-3-[3-[[ethyl(methyl)sulfamoyl]amino]-2,6-difluoro-benzoyl]-1H-pyrrolo[2,3-b]pyridine;

5-[4-[[1-[2-[4-[4-[(2,6-dioxo-3-piperidyl)amino]phenyl]-1-piperidyl]acetyl]-4-piperidyl]oxy]phenyl]-3-[3-[[ethyl(methyl)sulfamoyl]amino]-2,6-difluoro-benzoyl]-1H-pyrrolo[2,3-b]pyridine;

N-[3-[5-[6-[4-[2-[4-[4-[(2,6-dioxo-3-piperidyl)oxy]phenyl]-1-piperidyl]acetyl]piperazin-1-yl]-3-pyridyl]-1H-pyrrolo[2,3-b]pyridine-3-carbonyl]-2,4-difluoro-phenyl]cyclohexanesulfonamide;

N-[3-[5-[6-[4-[2-[4-[4-[(2,6-dioxo-3-piperidyl)amino]phenyl]-1-piperidyl]acetyl]piperazin-1-yl]-3-pyridyl]-1H-pyrrolo[2,3-b]pyridine-3-carbonyl]-2,4-difluoro-phenyl]cyclohexanesulfonamide;

4-[4-[(2,6-dioxo-3-piperidyl)amino]phenyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]piperidine-1-carboxamide formic acid;

5-[6-[4-[3-[4-[4-[(2,6-dioxo-3-piperidyl)oxy]phenyl]-1-piperidyl]propanoyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[4-[4-[2-[4-[4-[(2,6-dioxo-3-piperidyl)amino]phenyl]-1-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[6-[[4-[2-[5-[(2,6-dioxo-3-piperidyl)amino]isoindolin-2-yl]acetyl]piperazin-1-yl]methyl]-3-pyridyl]-3-[3-[[ethyl(methyl)sulfamoyl]amino]-2,6-difluoro-benzoyl]-1H-pyrrolo[2,3-b]pyridine;

2-[4-[(2,6-dioxo-3-piperidyl)amino]phenyl]-N-[2-[4-[5-[3-[3-[[ethyl(methyl)sulfamoyl]amino]-2,6-difluoro-benzoyl]-1H-pyrrolo[2,3-b]pyridin-5-yl]-2-pyridyl]piperazin-1-yl]-2-oxo-ethyl]-N-methyl-acetamide;

4-[5-[(2,6-dioxo-3-piperidyl)amino]-2-pyridyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]piperidine-1-carboxamide formic acid;

4-[4-[(2,6-dioxo-3-piperidyl)amino]phenyl]-N-[1-[5-[3-[3-[[ethyl(methyl)sulfamoyl]amino]-2,6-difluoro-benzoyl]-1H-pyrrolo[2,3-b]pyridin-5-yl]-2-pyridyl]-4-piperidyl]piperidine-1-carboxamide formic acid;

4-[4-[(2,6-dioxo-3-piperidyl)oxy]phenyl]-N-[1-[5-[3-[3-[[ethyl(methyl)sulfamoyl]amino]-2,6-difluoro-benzoyl]-1H-pyrrolo[2,3-b]pyridin-5-yl]-2-pyridyl]-4-piperidyl]piperidine-1-carboxamide formic acid;

5-[2-[1-[2-[4-[4-[(2,6-dioxo-3-piperidyl)amino]phenyl]-1-piperidyl]acetyl]-4-piperidyl]ethynyl]-3-[3-[[ethyl(methyl)sulfamoyl]amino]-2,6-difluoro-benzoyl]-1H-pyrrolo[2,3-b]pyridine;

5-[6-[4-[2-[4-[5-[(2,6-dioxo-3-piperidyl)oxy]-2-pyridyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

N-[3-[5-[4-[4-[2-[4-[4-[(2,6-dioxo-3-piperidyl)amino]phenyl]-1-piperidyl]acetyl]piperazin-1-yl]phenyl]-1H-pyrrolo[2,3-b]pyridine-3-carbonyl]-2,4-difluoro-phenyl]pyrrolidine-1-sulfonamide;

5-[6-[1-[2-[4-[4-[(2,6-dioxo-3-piperidyl)amino]phenyl]-1-piperidyl]acetyl]-4-piperidyl]-3-pyridyl]-3-[3-[[ethyl(methyl)sulfamoyl]amino]-2,6-difluoro-benzoyl]-1H-pyrrolo[2,3-b]pyridine;

N-[3-[5-[4-[4-[2-[4[4-[(2,6-dioxo-3-piperidyl)oxy]phenyl]-1-piperidyl]acetyl]piperazin-1-yl]phenyl]-1H-pyrrolo[2,3-b]pyridine-3-carbonyl]-2,4-difluoro-phenyl]pyrrolidine-1-sulfonamide;

N-[3-[5-[4-[4-[2-[4-[4-[(2,6-dioxo-3-piperidyl)amino]phenyl]piperazin-1-yl]acetyl]piperazin-1-yl]phenyl]-1H-pyrrolo[2,3-b]pyridine-3-carbonyl]-2,4-difluoro-phenyl]pyrrolidine-1-sulfonamide;

N-[3-[5-[4-[4-[2-[4-[4-[(2,6-dioxo-3-piperidyl)amino]phenyl]-1-piperidyl]acetyl]piperazin-1-yl]phenyl]-1H-pyrrolo[2,3-b]pyridine-3-carbonyl]-2,4-difluoro-phenyl]cyclopentanesulfonamide;

N-[1-[[4-[3-[2,6-difluoro-3-(pyrrolidin-1-ylsulfonylamino)benzoyl]-1H-pyrrolo[2,3-b]pyridin-5-yl]phenyl]methyl]-4-piperidyl]-4-[4-[(2,6-dioxo-3-piperidyl)amino]phenyl]piperidine-1-carboxamide formic acid;

5-[2-[4-[2-[4-[4-[(2,6-dioxo-3-piperidyl)amino]phenyl]-1-piperidyl]-2-methyl-propanoyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

2-[4-[5-[(2,6-dioxo-3-piperidyl)amino]-2-pyridyl]-1-piperidyl]-N-[1-[4-[3-[3-[[ethyl(methyl)sulfamoyl]amino]-2,6-difluoro-benzoyl]-1H-pyrrolo[2,3-b]pyridin-5-yl]phenyl]-4-piperidyl]acetamide formic acid;

2-[4-[5-[(2,6-dioxo-3-piperidyl)amino]-2-pyridyl]-1-piperidyl]-N-[1-[5-[3-[3-[[ethyl(methyl)sulfamoyl]

amino]-2,6-difluoro-benzoyl]-1H-pyrrolo[2,3-b]pyridin-5-yl]-2-pyridyl]-4-piperidyl]acetamide formic acid;

2-[4-[5-[(2,6-dioxo-3-piperidyl)amino]-2-pyridyl]-1-piperidyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]flacetamide formic acid;

2-[4-[4-[(2,6-dioxo-3-piperidyl)oxy]phenyl]-1-piperidyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]acetamide formic acid;

2-[4-[5-[(2,6-dioxo-3-piperidyl)oxy]-2-pyridyl]-1-piperidyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]acetamide formic acid;

2-[4-[4-[(2,6-dioxo-3-piperidyl)oxy]phenyl]-1-piperidyl]-N-[1-[5-[3-[3-[[ethyl(methyl)sulfamoyl]amino]-2,6-difluoro-benzoyl]-1H-pyrrolo[2,3-b]pyridin-5-yl]-2-pyridyl]-4-piperidyl]acetamide formic acid;

2-[4-[4-[(2,6-dioxo-3-piperidyl)amino]phenyl]-1-piperidyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]acetamide formic acid;

2-[4-[4-[(2,6-dioxo-3-piperidyl)oxy]phenyl]-1-piperidyl]-N-[1-[4-[3-[3-[[ethyl(methyl)sulfamoyl]amino]-2,6-difluoro-benzoyl]-1H-pyrrolo[2,3-b]pyridin-5-yl]phenyl]-4-piperidyl]acetamide formic acid;

2-[4-[5-[(2,6-dioxo-3-piperidyl)oxy]-2-pyridyl]-1-piperidyl]-N-[1-[4-[3-[3-[[ethyl(methyl)sulfamoyl]amino]-2,6-difluoro-benzoyl]-1H-pyrrolo[2,3-b]pyridin-5-yl]phenyl]-4-piperidyl]acetamide formic acid;

2-[4-[5-[(2,6-dioxo-3-piperidyl)oxy]-2-pyridyl]-1-piperidyl]-N-[1-[5-[3-[3-[[ethyl(methyl)sulfamoyl]amino]-2,6-difluoro-benzoyl]-1H-pyrrolo[2,3-b]pyridin-5-yl]-2-pyridyl]-4-piperidyl]acetamide formic acid;

2-[4-[4-[(2,6-dioxo-3-piperidyl)amino]phenyl]-1-piperidyl]-N-[1-[5-[3-[3-[[ethyl(methyl)sulfamoyl]amino]-2,6-difluoro-benzoyl]-1H-pyrrolo[2,3-b]pyridin-5-yl]-2-pyridyl]-4-piperidyl]acetamide formic acid;

2-[4-[4-[(2,6-dioxo-3-piperidyl)amino]phenyl]-1-piperidyl]-N-[1-[4-[3-[3-[[ethyl(methyl)sulfamoyl]amino]-2,6-difluoro-benzoyl]-1H-pyrrolo[2,3-b]pyridin-5-yl]phenyl]-4-piperidyl]acetamide formic acid;

5-[2-[4-[2-[4-[5-[(2,6-dioxo-3-piperidyl)oxy]-2-pyridyl]piperazin-1-yl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[5-[(2,6-dioxo-3-piperidyl)amino]-2-pyridyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)-methyl-amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

3-[3-[[ethyl(methyl)sulfamoyl]amino]-2,6-difluoro-benzoyl]-5-[6-[rac-(1R,5S)-8-[2-[4-[4-[(2,6-dioxo-3-piperidyl)amino]phenyl]-1-piperidyl]acetyl]-3,8-diazabicyclo[3.2.1]octan-3-yl]-3-pyridyl]-1H-pyrrolo[2,3-b]pyridine;

N-[3-[5-[6-[4-[2-[4-[4-[(2,6-dioxo-3-piperidyl)amino]phenyl]piperazin-1-yl]acetyl]piperazin-1-yl]-3-pyridyl]-1H-pyrrolo[2,3-b]pyridine-3-carbonyl]-2,4-difluoro-phenyl]pyrrolidine-1-sulfonamide;

rac-(3R)—N-[3-[5-[4-[4-[2-[4-[4-[(2,6-dioxo-3-piperidyl)amino]phenyl]piperazin-1-yl]acetyl]piperazin-1-yl]phenyl]-1H-pyrrolo[2,3-b]pyridine-3-carbonyl]-2,4-difluoro-phenyl]-3-fluoro-pyrrolidine-1-sulfonamide;

5-[6-[2-[2-[4-[4-[(2,6-dioxo-3-piperidyl)amino]phenyl]piperazin-1-yl]acetyl]-2,6-diazaspiro[3.3]heptan-6-yl]-3-pyridyl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]pyrazol-1-yl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[4-[4-[4-(2,6-dioxo-3-piperidyl)phenyl]-1-piperidyl]butanoyl]piperazin-1-yl]-3-pyridyl]-3-[3-[[ethyl(methyl)sulfamoyl]amino]-2,6-difluoro-benzoyl]-1H-pyrrolo[2,3-b]pyridine;

N-[2,4-difluoro-3-[5-[6-[rac-(1S,5R)-9-[2-[4-[4-[(2,6-dioxo-3-piperidyl)amino]phenyl]-1-piperidyl]acetyl]-3,9-diazabicyclo[3.3.1]nonan-3-yl]-3-pyridyl]-1H-pyrrolo[2,3-b]pyridine-3-carbonyl]phenyl]pyrrolidine-1-sulfonamide;

N-[3-[5-[4-[4-[2-[4-[4-(2,6-dioxo-3-piperidyl)phenyl]-1-piperidyl]acetyl]piperazin-1-yl]phenyl]-1H-pyrrolo[2,3-b]pyridine-3-carbonyl]-2,4-difluoro-phenyl]pyrrolidine-1-sulfonamide;

N-[2-[4-[4-[(2,6-dioxo-3-piperidyl)amino]phenyl]-1-piperidyl]ethyl]-4-[2-[3-[3-[[ethyl(methyl)sulfamoyl]amino]-2,6-difluoro-benzoyl]-1H-pyrrolo[2,3-b]pyridin-5-yl]ethynyl]benzamide;

5-[2-[4-[2-[4-[4-[(2,4-dioxo-3-azabicyclo[3.1.1]heptan-1-yl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine formic acid;

N-[3-[5-[4-[4-[2-[4-[3-(2,4-dioxohexahydropyrimidin-1-yl)phenyl]-1-piperidyl]acetyl]piperazin-1-yl]phenyl]-1H-pyrrolo[2,3-b]pyridine-3-carbonyl]-2,4-difluoro-phenyl]pyrrolidine-1-sulfonamide;

N-[3-[5-[4-[1-[4-[4-[4-[(2,6-dioxo-3-piperidyl)amino]phenyl]-1-piperidyl]butanoyl]azetidin-3-yl]phenyl]-1H-pyrrolo[2,3-b]pyridine-3-carbonyl]-2,4-difluoro-phenyl]pyrrolidine-1-sulfonamide;

5-[2-[4-[[2-[4-[5-[(2,6-dioxo-3-piperidyl)amino]-2-pyridyl]-1-piperidyl]-2-oxo-ethyl]-methyl-amino]-1-piperidyl]pyrimidin-5-yl]-3-[3-[[ethyl(methyl)sulfamoyl]amino]-2,6-difluoro-benzoyl]-1H-pyrrolo[2,3-b]pyridine formic acid;

5-[2-[4-[2-[4-[4-(2,4-dioxohexahydropyrimidin-1-yl)phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

2-[4-[5-[(2,6-dioxo-3-piperidyl)amino]-2-pyridyl]-1-piperidyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]-N-methyl-acetamide formic acid;

5-[2-[4-[[2-[4-[5-[(2,6-dioxo-3-piperidyl)amino]-2-pyridyl]-1-piperidyl]-2-oxo-ethyl]amino]-1-piperidyl]pyrimidin-5-yl]-3-[3-[[ethyl(methyl)sulfamoyl]amino]-2,6-difluoro-benzoyl]-1H-pyrrolo[2,3-b]pyridine formic acid;

5-[2-[4-[4-[4-[(2,6-dioxo-3-piperidyl)amino]phenyl]piperidine-1-carbonyl]-1-piperidyl]pyrimidin-5-yl]-3-[3-

[[ethyl(methyl)sulfamoyl]amino]-2,6-difluoro-benzoyl]-1H-pyrrolo[2,3-b]pyridine;

2-[4-[5-[(2,6-dioxo-3-piperidyl)amino]-2-pyridyl]-1-piperidyl]-N-[1-[5-[3-[3-[[ethyl(methyl)sulfamoyl]amino]-2,6-difluoro-benzoyl]-1H-pyrrolo[2,3-b]pyridin-5-yl]-2-pyridyl]-4-piperidyl]-N-methyl-acetamide; hydrochloride;

5-[4-[4-[[2-[4-[5-[(2,6-dioxo-3-piperidyl)amino]-2-pyridyl]-1-piperidyl]-2-oxo-ethyl]amino]-1-piperidyl]phenyl]-3-[3-[[ethyl(methyl)sulfamoyl]amino]-2,6-difluoro-benzoyl]-1H-pyrrolo[2,3-b]pyridine hydrochloride;

5-[4-[4-[[2-[4-[5-[(2,6-dioxo-3-piperidyl)oxy]-2-pyridyl]-1-piperidyl]-2-oxo-ethyl]amino]-1-piperidyl]phenyl]-3-[3-[[ethyl(methyl)sulfamoyl]amino]-2,6-difluoro-benzoyl]-1H-pyrrolo[2,3-b]pyridine hydrochloride;

5-[4-[4-[[2-[4-[4-[(2,6-dioxo-3-piperidyl)amino]phenyl]-1-piperidyl]-2-oxo-ethyl]amino]-1-piperidyl]phenyl]-3-[3-[[ethyl(methyl)sulfamoyl]amino]-2,6-difluoro-benzoyl]-1H-pyrrolo[2,3-b]pyridine hydrochloride;

5-[4-[4-[[2-[4-[4-[(2,6-dioxo-3-piperidyl)oxy]phenyl]-1-piperidyl]-2-oxo-ethyl]amino]-1-piperidyl]phenyl]-3-[3-[[ethyl(methyl)sulfamoyl]amino]-2,6-difluoro-benzoyl]-1H-pyrrolo[2,3-b]pyridine hydrochloride;

5-[2-[4-[[2-[4-[4-[(2,6-dioxo-3-piperidyl)amino]phenyl]-1-piperidyl]-2-oxo-ethyl]amino]-1-piperidyl]pyrimidin-5-yl]-3-[3-[[ethyl(methyl)sulfamoyl]amino]-2,6-difluoro-benzoyl]-1H-pyrrolo[2,3-b]pyridine hydrochloride;

5-[6-[4-[[2-[4-[5-[(2,6-dioxo-3-piperidyl)amino]-2-pyridyl]-1-piperidyl]-2-oxo-ethyl]-methyl-amino]-1-piperidyl]-3-pyridyl]-3-[3-[[ethyl(methyl)sulfamoyl]amino]-2,6-difluoro-benzoyl]-1H-pyrrolo[2,3-b]pyridine hydrochloride;

5-[2-[4-[[2-[4-[4-[(2,6-dioxo-3-piperidyl)oxy]phenyl]-1-piperidyl]-2-oxo-ethyl]amino]-1-piperidyl]pyrimidin-5-yl]-3-[3-[[ethyl(methyl)sulfamoyl]amino]-2,6-difluoro-benzoyl]-1H-pyrrolo[2,3-b]pyridine formic acid;

5-[2-[4-[2-[4-[4-[[(3R)-2,6-dioxo-3-piperidyl]amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[2-[4-[4-(2,4-dioxohexahydropyrimidin-1-yl)phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

N-[3-[[1-[5-[3-[2,6-difluoro-3-(pyrrolidin-1-ylsulfonylamino)benzoyl]-1H-pyrrolo[2,3-b]pyridin-5-yl]-2-pyridyl]-4-piperidyl]oxy]cyclobutyl]-2-[4-[(2,6-dioxo-3-piperidyl)amino]phenyl]acetamide;

5-[6-[4-[[2-[4-[5-[(2,6-dioxo-3-piperidyl)oxy]-2-pyridyl]-1-piperidyl]-2-oxo-ethyl]amino]-1-piperidyl]-3-pyridyl]-3-[3-[[ethyl(methyl)sulfamoyl]amino]-2,6-difluoro-benzoyl]-1H-pyrrolo[2,3-b]pyridine formic acid;

N-[3-[5-[6-[4-[3-[4-[4-[(2,6-dioxo-3-piperidyl)amino]phenyl]-1-piperidyl]cyclobutanecarbonyl]piperazin-1-yl]-3-pyridyl]-1H-pyrrolo[2,3-b]pyridine-3-carbonyl]-2,4-difluoro-phenyl]propane-2-sulfonamide;

N-[3-[5-[6-[4-[2-[4-[4-(2,4-dioxohexahydropyrimidin-1-yl)phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide;

5-[6-[4-[[2-[4-[5-[(2,6-dioxo-3-piperidyl)oxy]phenyl]-1-piperidyl]-2-oxo-ethyl]amino]-1-piperidyl]-3-pyridyl]-3-[3-[[ethyl(methyl)sulfamoyl]amino]-2,6-difluoro-benzoyl]-1H-pyrrolo[2,3-b]pyridine formic acid;

5-[6-[4-[[2-[4-[4-[(2,6-dioxo-3-piperidyl)amino]phenyl]-1-piperidyl]-2-oxo-ethyl]amino]-1-piperidyl]-3-pyridyl]-3-[3-[[ethyl(methyl)sulfamoyl]amino]-2,6-difluoro-benzoyl]-1H-pyrrolo[2,3-b]pyridine formic acid;

5-[2-[4-[2-[4-[4-[[(3S)-2,6-dioxo-3-piperidyl]amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]-1-piperidyl]-2-oxo-ethyl]-1-piperidyl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-(2,4-dioxohexahydropyrimidin-1-yl)phenyl]-1-piperidyl]-2-oxo-ethyl]-1-piperidyl]pyrimidin-5-yl]-3-[3-[[ethyl(methyl)sulfamoyl]amino]-2,6-difluoro-benzoyl]-1H-pyrrolo[2,3-b]pyridine;

rac-(3R)—N-[3-[5-[6-[2-[2-[4-[4-[(2,6-dioxo-3-piperidyl)oxy]phenyl]-1-piperidyl]acetyl]-2,6-diazaspiro[3.3]heptan-6-yl]-3-pyridyl]-1H-pyrrolo[2,3-b]pyridine-3-carbonyl]-2,4-difluoro-phenyl]-3-fluoro-pyrrolidine-1-sulfonamide;

N-[3-[5-[4-[2-[2-[4-[4-[(2,6-dioxo-3-piperidyl)oxy]phenyl]-1-piperidyl]acetyl]-2,6-diazaspiro[3.3]heptan-6-yl]phenyl]-1H-pyrrolo[2,3-b]pyridine-3-carbonyl]-2,4-difluoro-phenyl]pyrrolidine-1-sulfonamide;

N-[3-[5-[4-[2-[2-[4-[4-[(2,4-dioxo-3-azabicyclo[3.1.1]heptan-1-yl)amino]phenyl]-1-piperidyl]acetyl]-2,6-diazaspiro[3.3]heptan-6-yl]phenyl]-1H-pyrrolo[2,3-b]pyridine-3-carbonyl]-2,4-difluoro-phenyl]pyrrolidine-1-sulfonamide;

N-[3-[5-[2-[2-[2-[4-[4-(2,6-dioxo-3-piperidyl)phenyl]-1-piperidyl]acetyl]-2,6-diazaspiro[3.3]heptan-6-yl]pyrimidin-5-yl]-1H-pyrrolo[2,3-b]pyridine-3-carbonyl]-2,4-difluoro-phenyl]pyrrolidine-1-sulfonamide;

N-[3-[5-[2-[2-[2-[4-[4-[(2,6-dioxo-3-piperidyl)oxy]phenyl]-1-piperidyl]acetyl]-2,6-diazaspiro[3.3]heptan-6-yl]pyrimidin-5-yl]-1H-pyrrolo[2,3-b]pyridine-3-carbonyl]-2,4-difluoro-phenyl]pyrrolidine-1-sulfonamide;

N-[3-[5-[2-[2-[2-[4-[4-[(2,6-dioxo-3-piperidyl)amino]phenyl]-1-piperidyl]acetyl]-2,6-diazaspiro[3.3]heptan-6-yl]pyrimidin-5-yl]-1H-pyrrolo[2,3-b]pyridine-3-carbonyl]-2,4-difluoro-phenyl]pyrrolidine-1-sulfonamide;

5-[6-[4-[2-[4-[4-[[(3S)-2,6-dioxo-3-piperidyl]oxy]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[4-[4-[[(3R)-2,6-dioxo-3-piperidyl]oxy]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

N-[1-[4-[(2,6-dioxo-3-piperidyl)amino]-2-fluoro-phenyl]-4-piperidyl]-4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazine-1-carboxamide;2,2,2-trifluoroacetic acid;

5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[4-[4-[2-[1-[4-[(2,6-dioxo-3-piperidyl)amino]-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[2-[4-[2-[1-[4-(2,6-dioxo-3-piperidyl)-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine; and 5-[2-[4-[2-[1-[4-[[(3R)-2,6-dioxo-3-piperidyl]amino]-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine.

E40: A certain embodiment of the invention relates to the compound of formula I, formula II, formula III, formula IV, formula V, formula VI, or formula VII as described herein, or a pharmaceutically acceptable salt thereof, which is selected from the group consisting of 5-[2-[4-[2-[1-[4-((3R)2,6-dioxo-3-piperidyl)-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(3 S)-2,6-dioxo-3-piperidyl]-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(3R)-3-deuterio-2,6-dioxo-3-piperidyl]-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(3 S)-3-deuterio-2,6-dioxo-3-piperidyl]-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine; and

[1-[4-(2,6-dioxo-3-piperidyl)-2-fluoro-phenyl]-4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl] dihydrogen phosphate.

E41: A certain embodiment of the invention relates to the compound of formula I, formula II, formula III, formula IV, formula V, formula VI, or formula VII as described herein, or a pharmaceutically acceptable salt thereof, for use as therapeutically active substance.

E42: A certain embodiment of the invention relates to a pharmaceutical composition comprising the compound of formula I, formula II, formula III, formula IV, formula V, formula VI, or formula VII as described herein, or a pharmaceutically acceptable salt thereof, and a pharmaceutically acceptable auxiliary substance.

E43: A certain embodiment of the invention relates to the compound of formula I, formula II, formula III, formula IV, formula V, formula VI, or formula VII as described herein, or a pharmaceutically acceptable salt thereof, for the use in the therapeutic and/or prophylactic treatment of cancer, more particularly melanoma, colorectal cancer and lung cancer.

E44: A certain embodiment of the invention relates to the use of compound of formula I, formula II, formula III, formula IV, formula V, formula VI, or formula VII as described herein, or a pharmaceutically acceptable salt thereof, for the treatment and/or prophilaxy of cancer, melanoma, colorectal cancer and lung cancer.

E45: A certain embodiment of the invention relates to the compound formula I, formula II, formula III, formula IV, formula V, formula VI, or formula VII as described herein, or a pharmaceutically acceptable salt thereof, for the manufacture of a medicament for the therapeutic and/or prophylactic treatment of cancer, melanoma, colorectal cancer and lung cancer.

E46: A certain embodiment of the invention relates to a method for the therapeutic and/or prophylactic treatment cancer, melanoma, colorectal cancer and lung cancer, by administering the compound of formula I, formula II, formula III, formula IV, formula V, formula VI, or formula VII as described herein, or a pharmaceutically acceptable salt thereof, to a patient.

E47: The invention includes all substituents in its corresponding deuterated form, wherever applicable, of the compounds of formula I, formula II, formula III, formula IV, formula V, formula VI, or formula VII.

E48: A certain embodiment of the invention relates to a prodrug of the compound of formula I, formula II, formula III, formula IV, formula V, formula VI, or formula VII as described herein, wherein the compound of the invention may be derivatised, at one or more functional groups to provide derivatives which are capable of conversion back to the parent compound in vivo. In a particular embodiment the compound of formula I, formula II, formula III, formula IV, formula V, formula VI, or formula VII as described herein, is a prodrug wherein a hydroxy group was derivatised to a phosphate group.

E49: The invention includes all optical isomers, i.e. diastereoisomers, diastereomeric mixtures, racemic mixtures, all their corresponding enantiomers and/or tautomers as well as their solvates, wherever applicable, of the compounds of formula I, formula II, formula III, formula IV, formula V, formula VI, or formula VII.

E50: A certain embodiment of the invention relates to compound:
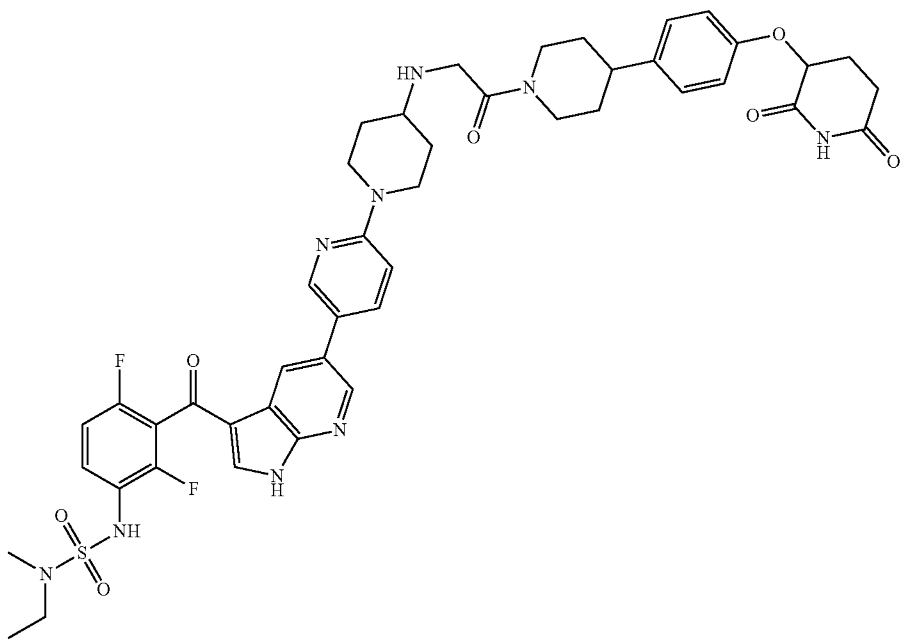 [SMILES: CCN(C)S(=O)(=O)Nc1ccc(F)c(C(=O)c2c[nH]c3ncc(-c4ccc(N5CCC(NCC(=O)N6CCC(c7ccc(OC8CCC(=O)NC8=O)cc7)CC6)CC5)nc4)cc23)c1F]
or a pharmaceutically acceptable salt thereof.
E51: A certain embodiment of the invention relates to compound:
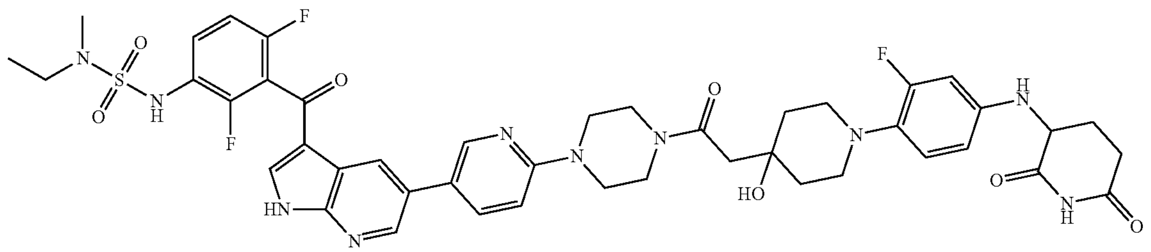 [SMILES: CCN(C)S(=O)(=O)Nc1ccc(F)c(C(=O)c2c[nH]c3ncc(-c4ccc(N5CCN(C(=O)CC6(O)CCN(c7ccc(NC8CCC(=O)NC8=O)cc7F)CC6)CC5)nc4)cc23)c1F]
or a pharmaceutically acceptable salt thereof.
E52: A certain embodiment of the invention relates to compound:
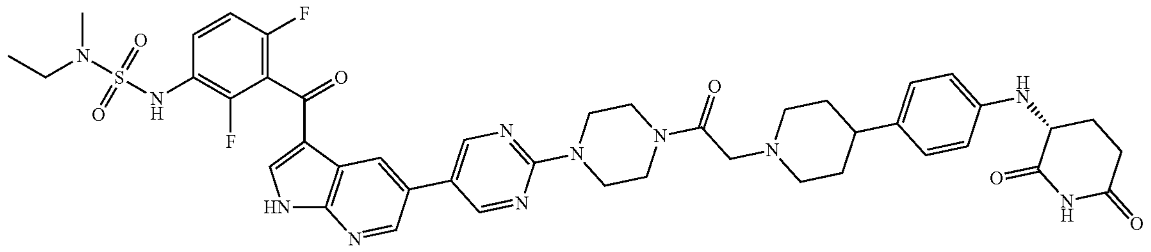
or a pharmaceutically acceptable salt thereof.

E53: A certain embodiment of the invention relates to compound:
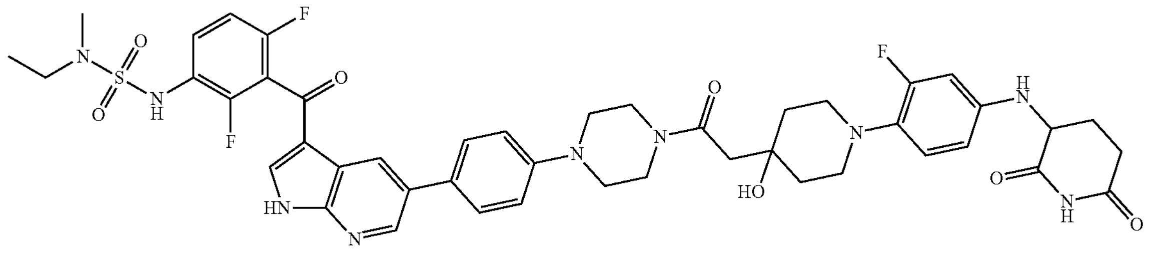 [SMILES: CCN(C)S(=O)(=O)Nc1ccc(F)c(C(=O)c2c[nH]c3ncc(-c4ccc(N5CCN(C(=O)CC6(O)CCN(c7ccc(NC8CCC(=O)NC8=O)cc7F)CC6)CC5)cc4)cc23)c1F]
or a pharmaceutically acceptable salt thereof.
E54: A certain embodiment of the invention relates to compound:
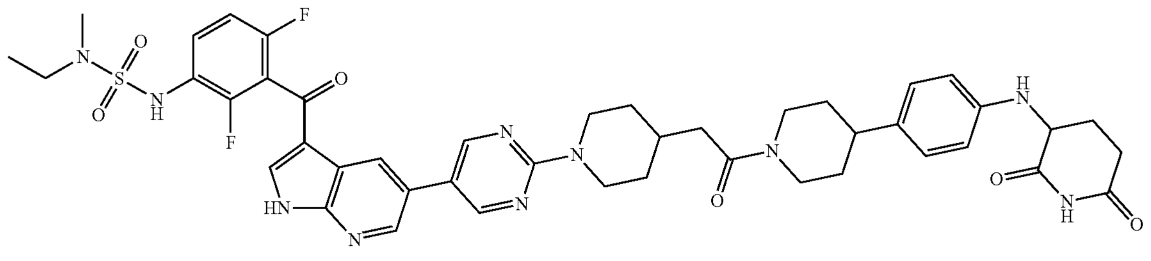 [SMILES: CCN(C)S(=O)(=O)Nc1ccc(F)c(C(=O)c2c[nH]c3ncc(-c4cnc(N5CCC(CC(=O)N6CCC(c7ccc(NC8CCC(=O)NC8=O)cc7)CC6)CC5)nc4)cc23)c1F]
or a pharmaceutically acceptable salt thereof.
E55: A certain embodiment of the invention relates to compound:
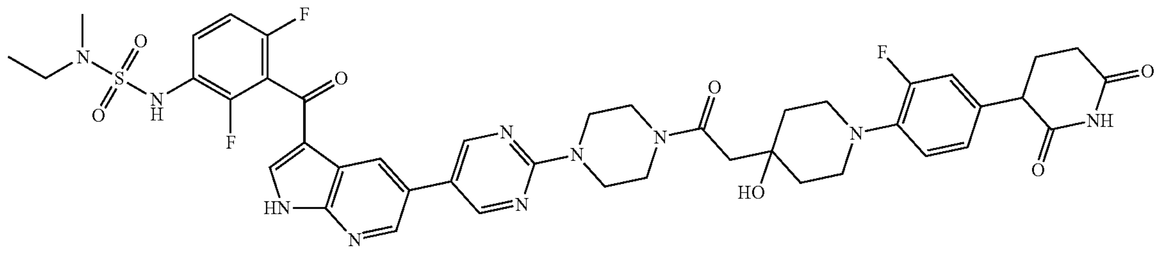 [SMILES: CCN(C)S(=O)(=O)Nc1ccc(F)c(C(=O)c2c[nH]c3ncc(-c4cnc(N5CCN(C(=O)CC6(O)CCN(c7ccc(C8CCC(=O)NC8=O)cc7F)CC6)CC5)nc4)cc23)c1F]
or a pharmaceutically acceptable salt thereof. compound:

E56: A certain embodiment of the invention relates to
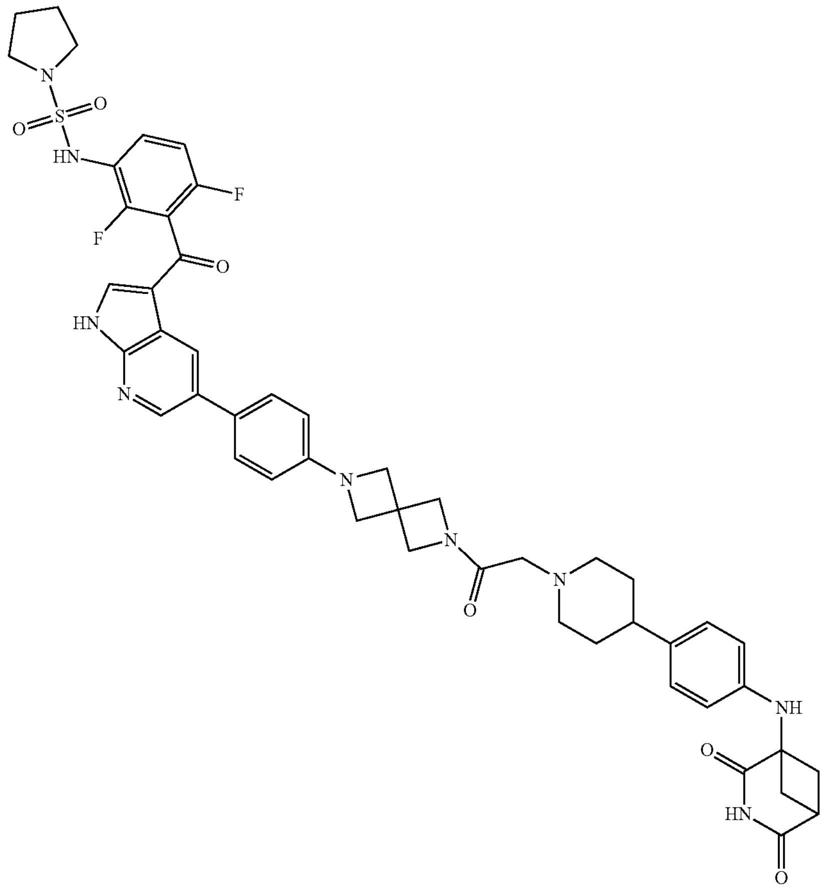 [SMILES: O=C(c1c(F)ccc(NS(=O)(=O)N2CCCC2)c1F)c1c[nH]c2ncc(-c3ccc(N4CC5(CN(C(=O)CN6CCC(c7ccc(NC89CC(C8)C(=O)NC9=O)cc7)CC6)C5)C4)cc3)cc12]
or a pharmaceutically acceptable salt thereof.
E57: A certain embodiment of the invention relates to compound:
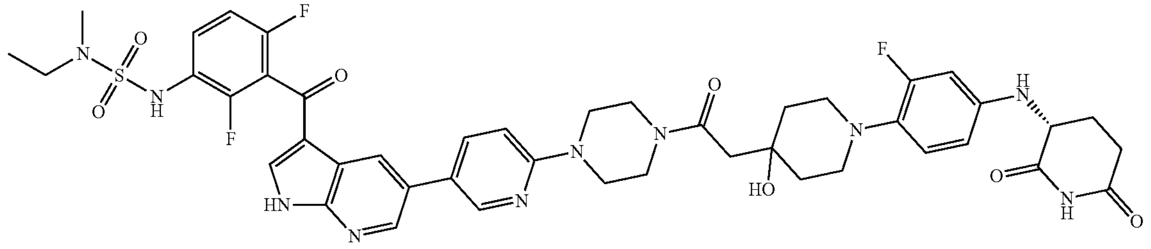 [SMILES: CCN(C)S(=O)(=O)Nc1ccc(F)c(C(=O)c2c[nH]c3ncc(-c4ccc(N5CCN(C(=O)CC6(O)CCN(c7ccc(N[C@@H]8CCC(=O)NC8=O)cc7F)CC6)CC5)nc4)cc23)c1F]
or a pharmaceutically acceptable salt thereof.

E58: A certain embodiment of the invention relates to compound:
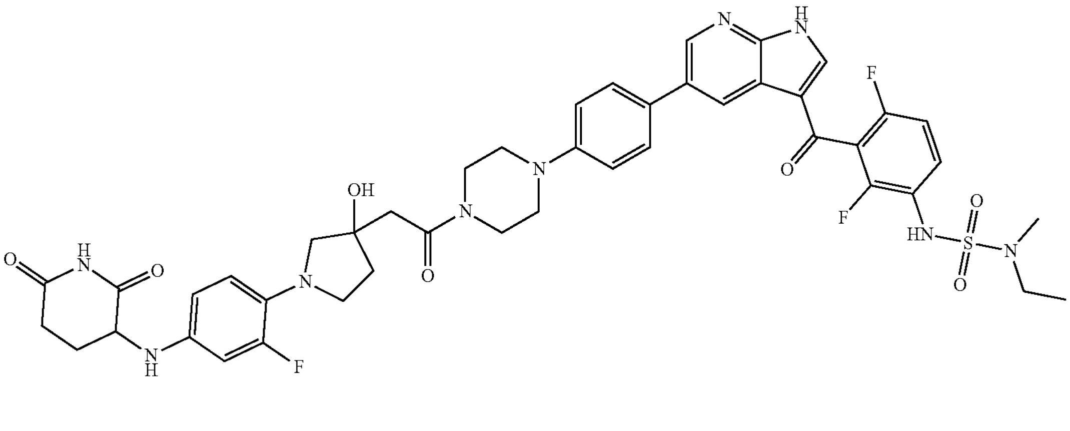 [SMILES: CCN(C)S(=O)(=O)Nc1ccc(F)c(C(=O)c2c[nH]c3ncc(-c4ccc(N5CCN(C(=O)CC6(O)CCN(c7ccc(NC8CCC(=O)NC8=O)cc7F)C6)CC5)cc4)cc23)c1F]
or a pharmaceutically acceptable salt thereof.
E59: A certain embodiment of the invention relates to compound:
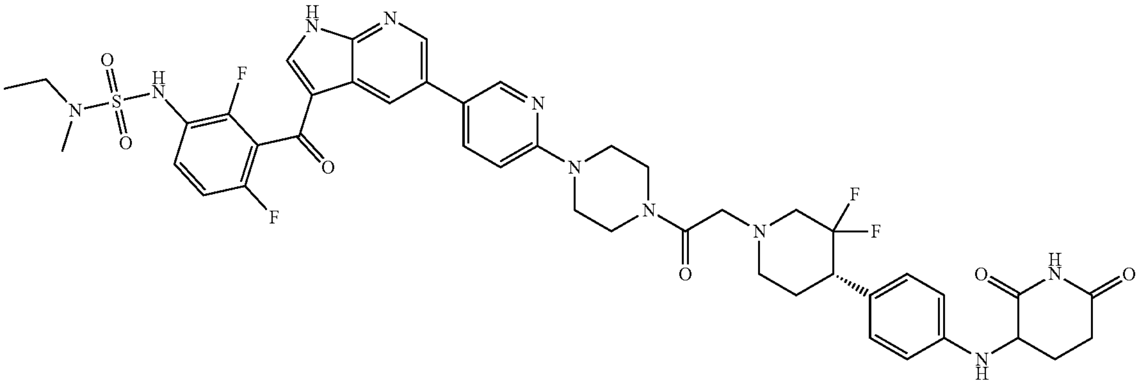 [SMILES: CCN(C)S(=O)(=O)Nc1ccc(F)c(C(=O)c2c[nH]c3ncc(-c4ccc(N5CCN(C(=O)CN6CC[C@@H](c7ccc(NC8CCC(=O)NC8=O)cc7)C(F)(F)C6)CC5)nc4)cc23)c1F]
or a pharmaceutically acceptable salt thereof.
E60: A certain embodiment of the invention relates to compound:
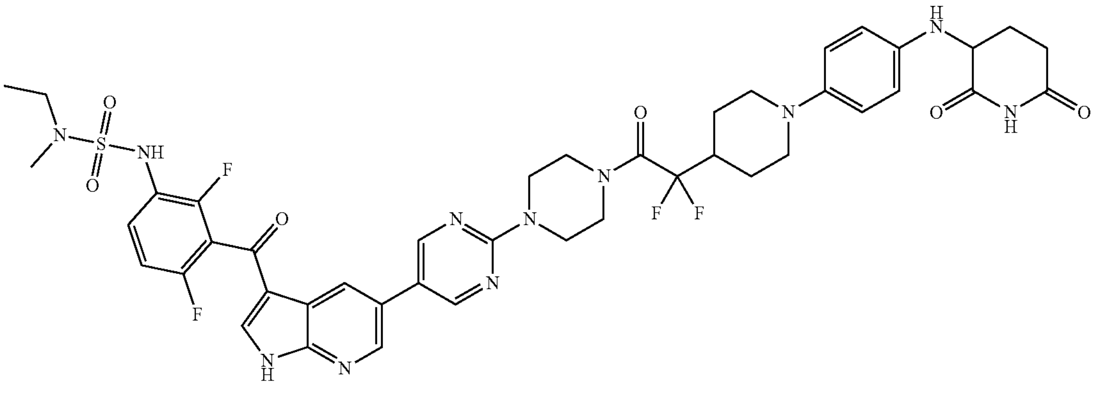 [SMILES: CCN(C)S(=O)(=O)Nc1ccc(F)c(C(=O)c2c[nH]c3ncc(-c4cnc(N5CCN(C(=O)C(F)(F)C6CCN(c7ccc(NC8CCC(=O)NC8=O)cc7)CC6)CC5)nc4)cc23)c1F]
or a pharmaceutically acceptable salt thereof.

Additional embodiments of the present invention include:
E61: A certain embodiment of the invention relates to compound:
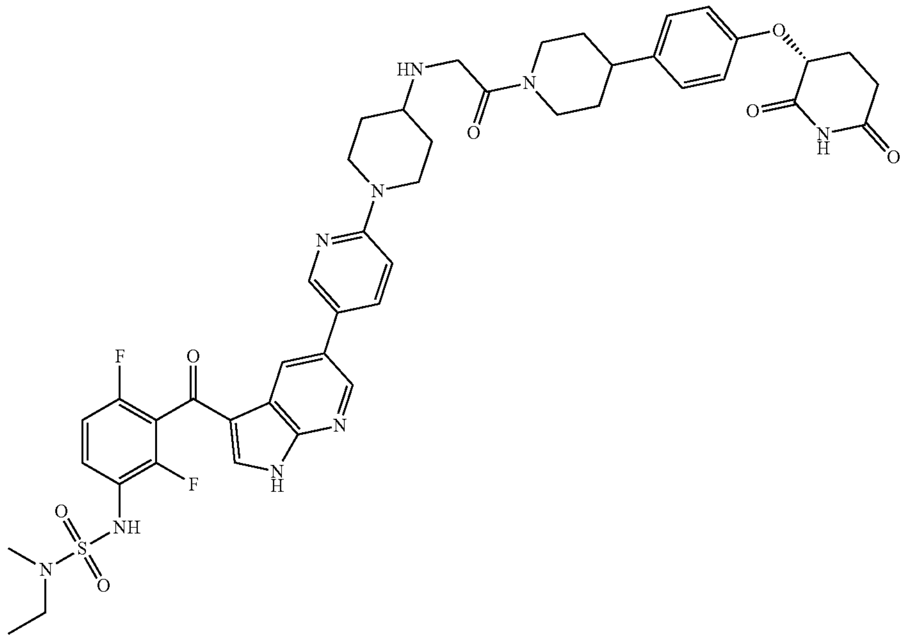
or
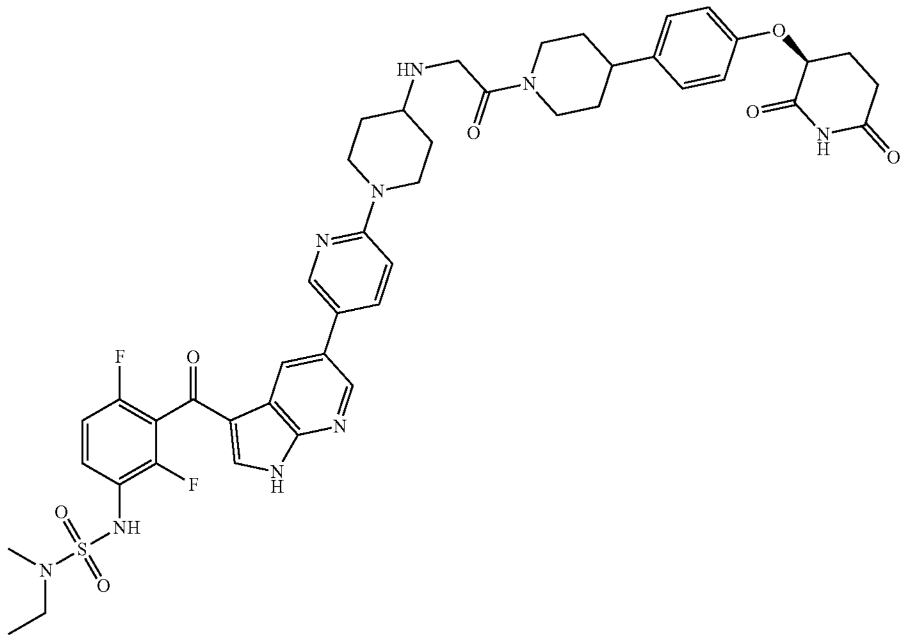
or a pharmaceutically acceptable salt thereof.

E62: A certain embodiment of the invention relates to compound:
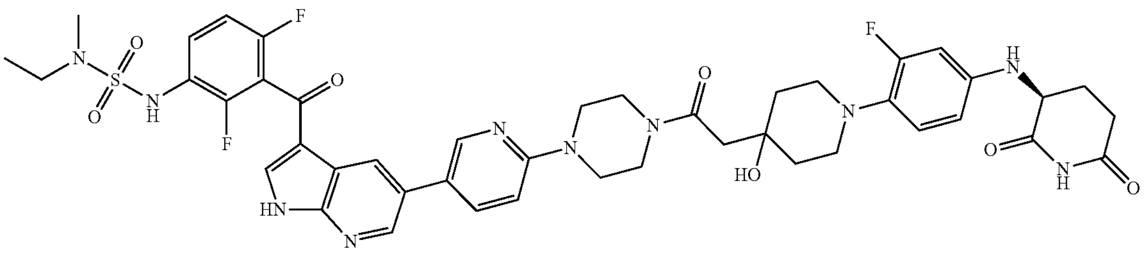
or
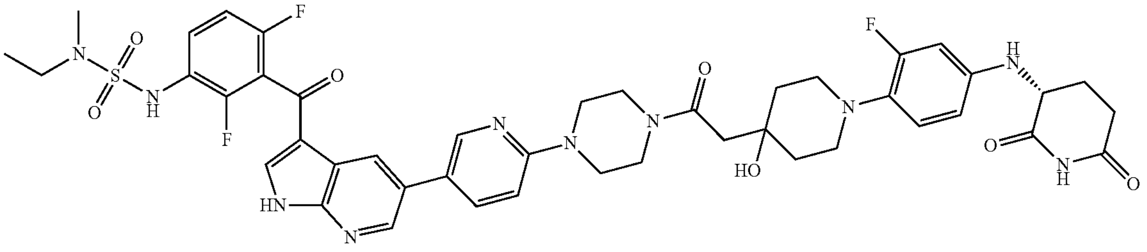
or a pharmaceutically acceptable salt thereof.
E63: A certain embodiment of the invention relates to compound:
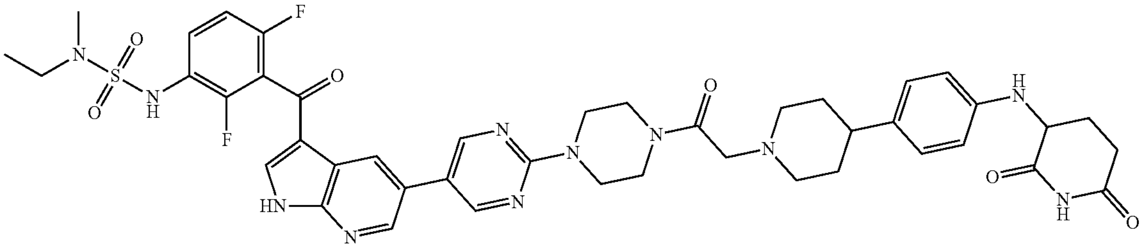
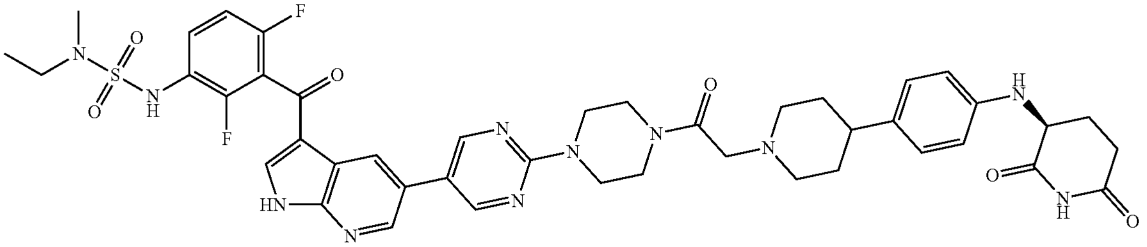
or
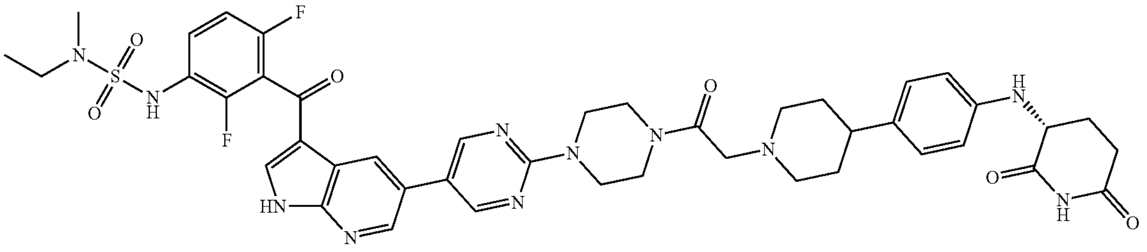
or a pharmaceutically acceptable salt thereof.

E64: A certain embodiment of the invention relates to compound:
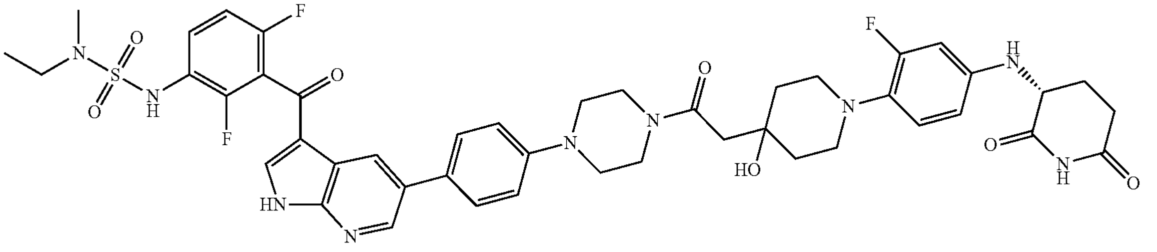
or
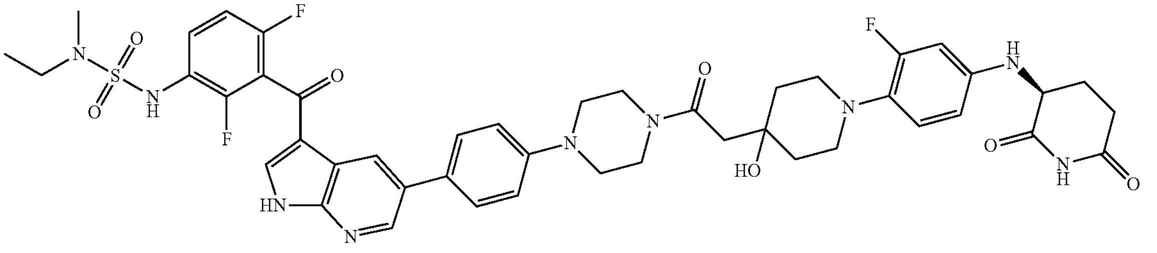
or a pharmaceutically acceptable salt thereof.
E65: A certain embodiment of the invention relates to compound:
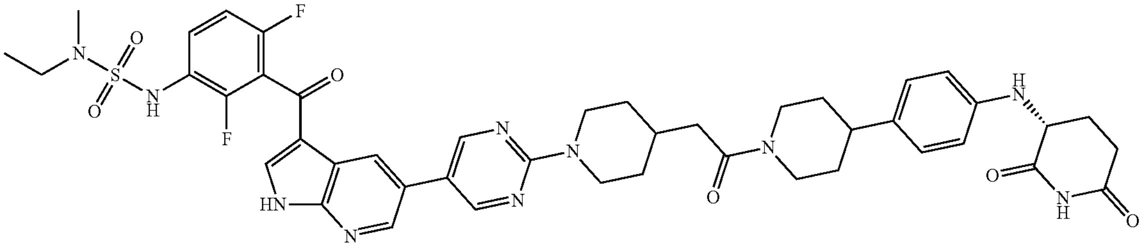
or
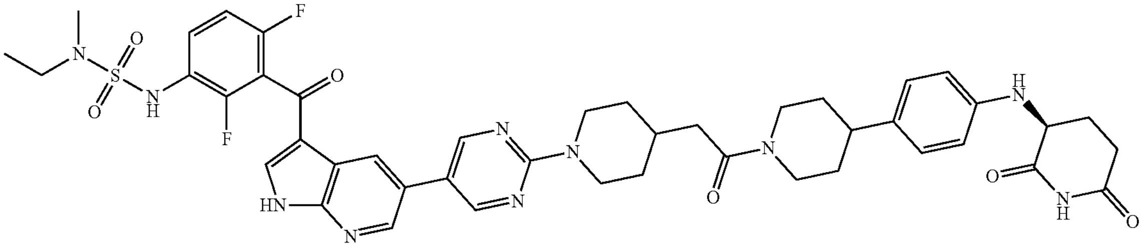
or a pharmaceutically acceptable salt thereof.

E66: A certain embodiment of the invention relates to compound:
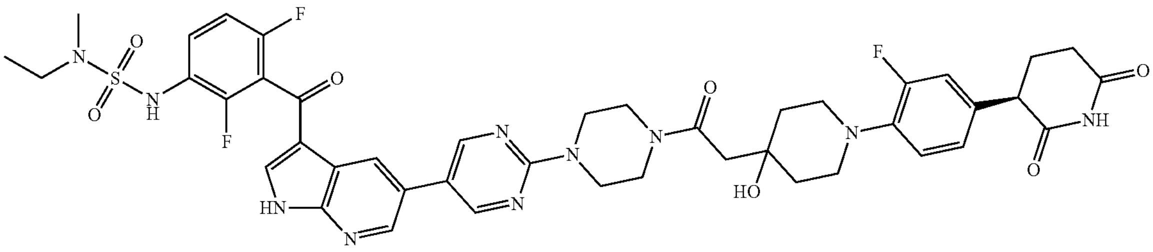
or
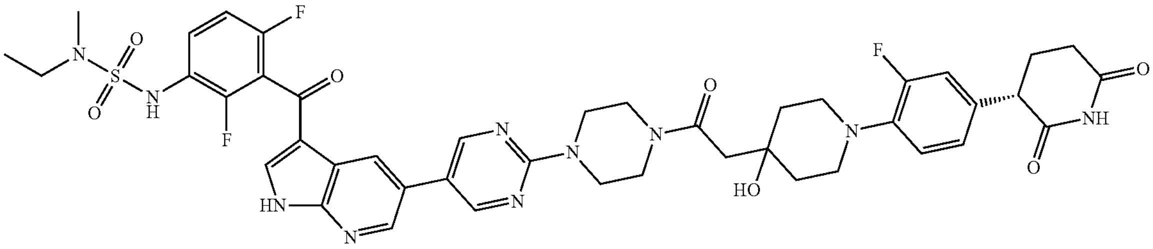
or a pharmaceutically acceptable salt thereof.
E67: A certain embodiment of the invention relates to compound:
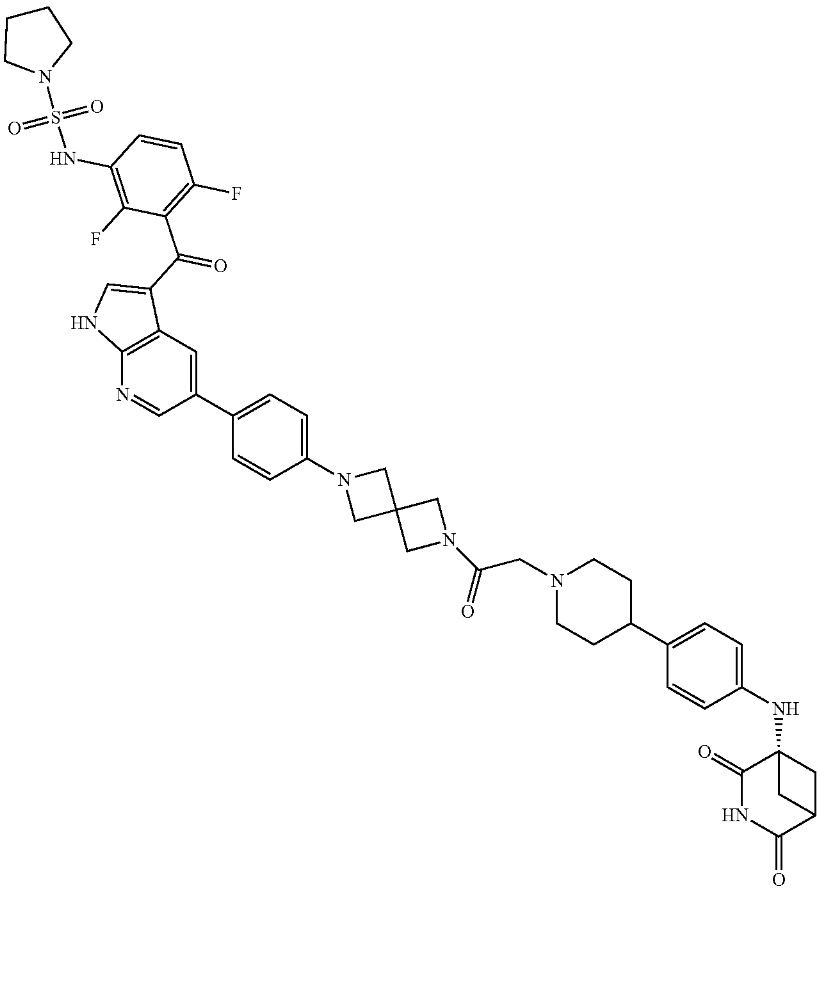
or -continued
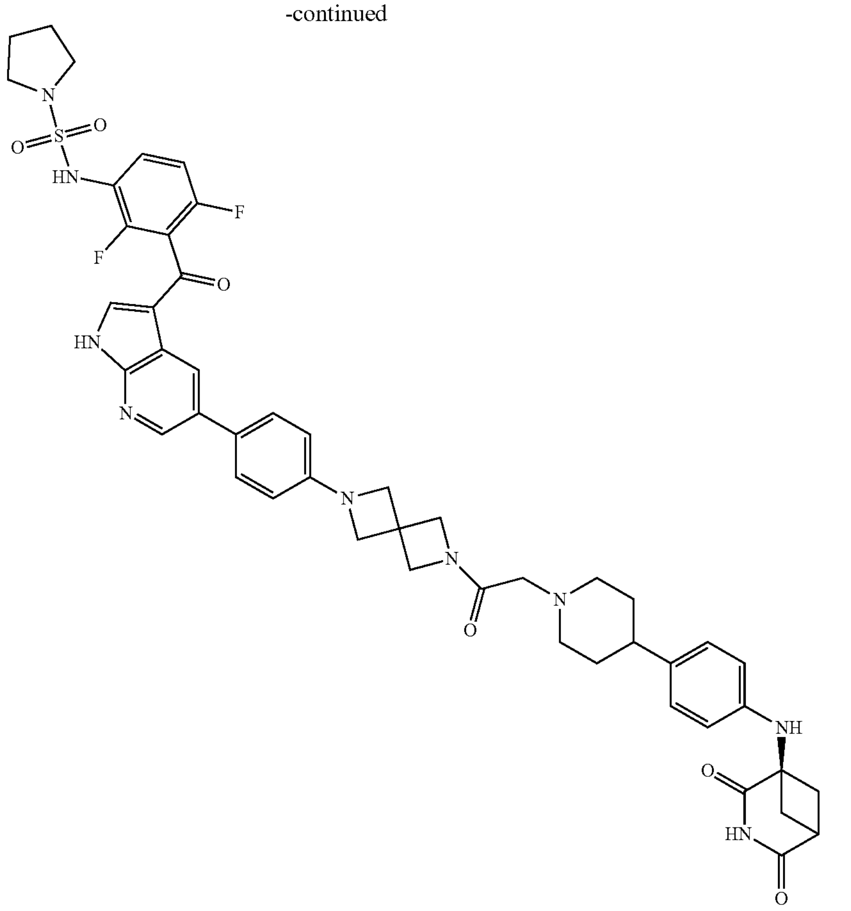
or a pharmaceutically acceptable salt thereof.
E68: A certain embodiment of the invention relates to compound:
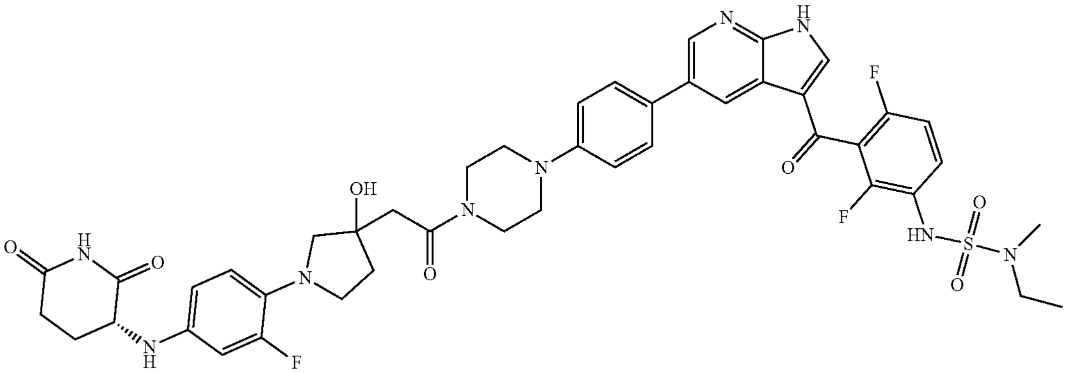
or -continued
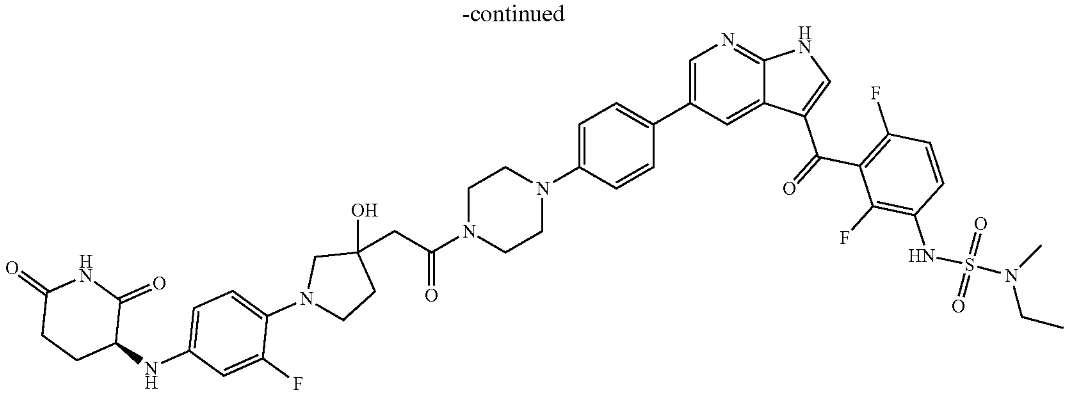
or a pharmaceutically acceptable salt thereof.
E69: A certain embodiment of the invention relates to compound:
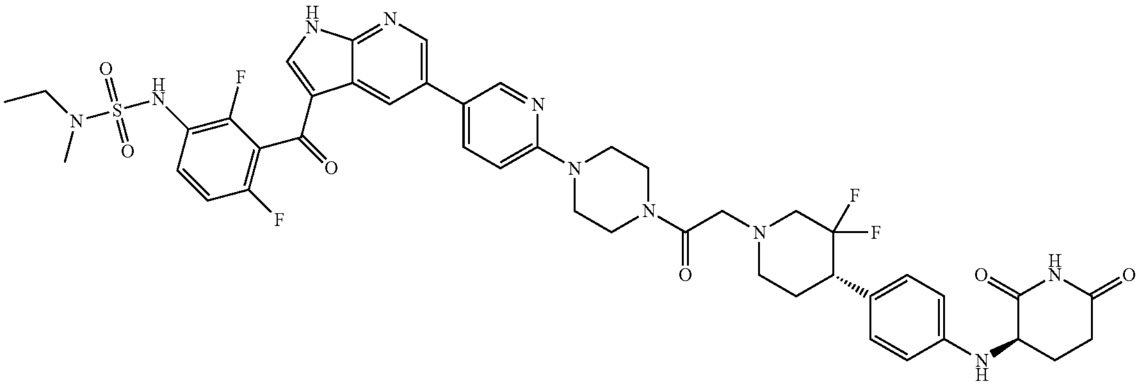
or
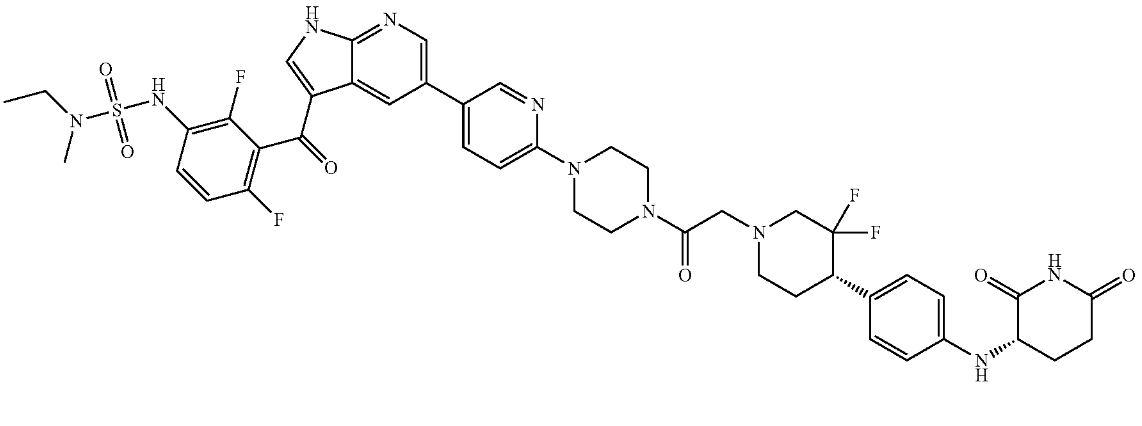
or a pharmaceutically acceptable salt thereof.

E70: A certain embodiment of the invention relates to compound:
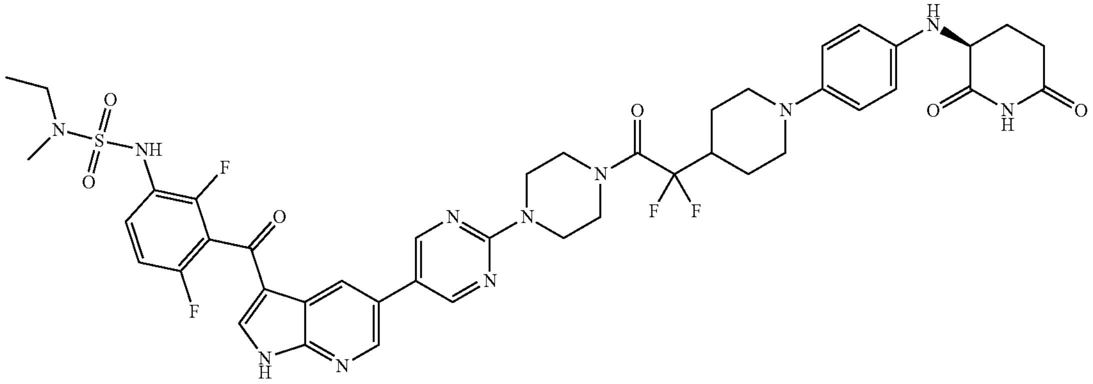
or
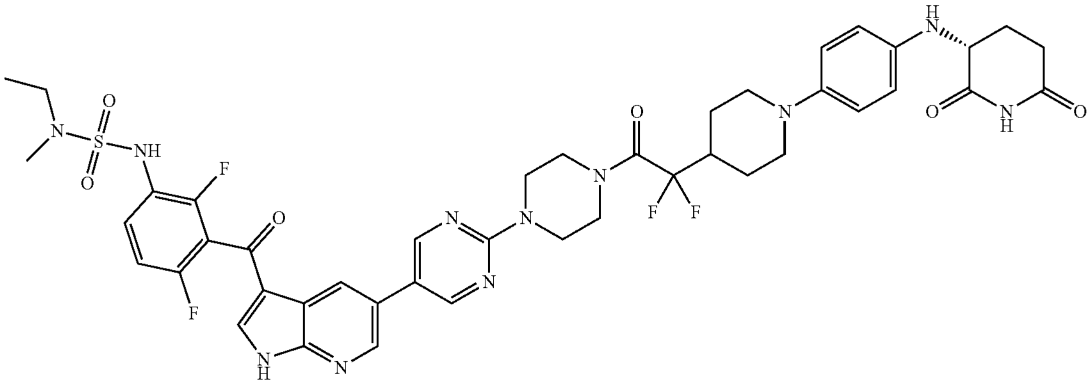
or a pharmaceutically acceptable salt thereof.
E71: In certain embodiments A5 is selected from the ring systems H, BA, BB, and BC.
E72: In an alternative embodiment the compound of Formula II is selected from:
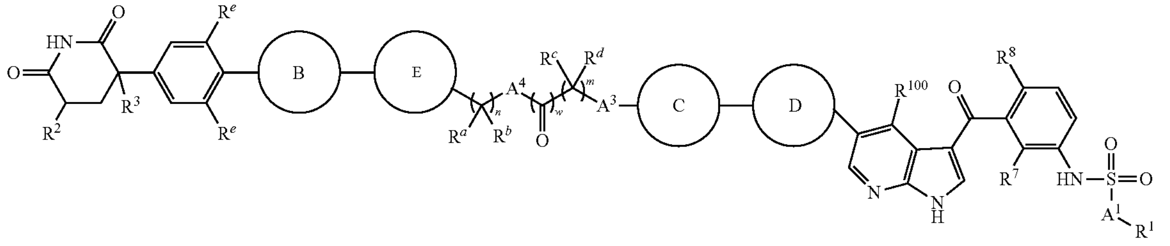
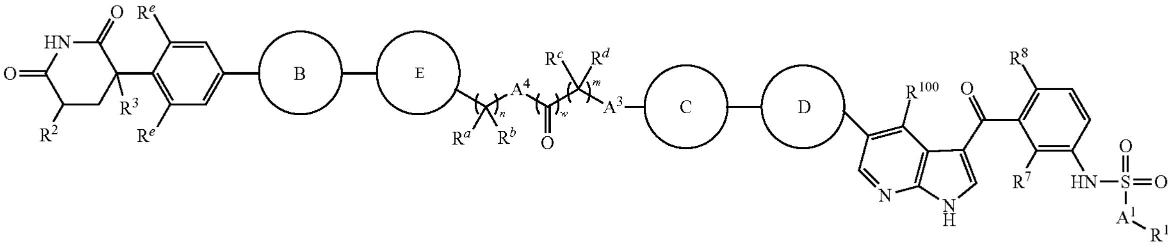

-continued

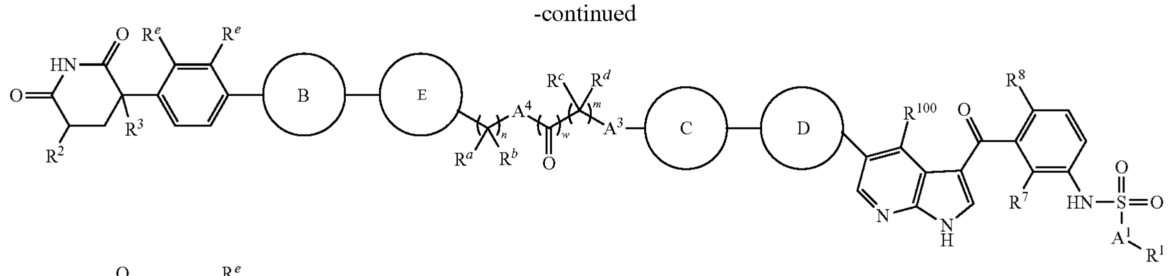

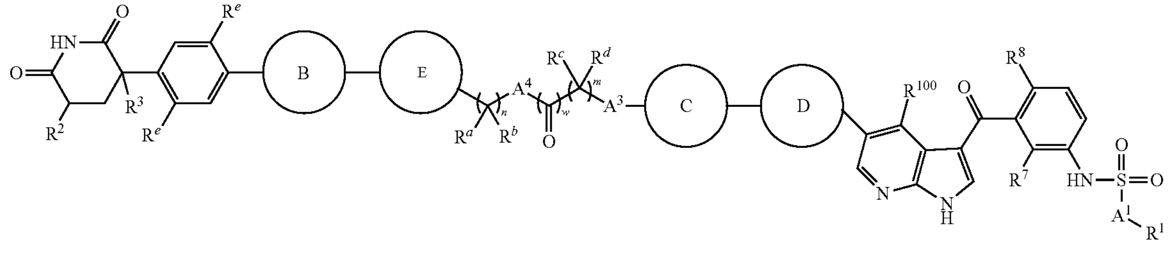

or a pharmaceutically acceptable salt thereof.

The compounds of formula I, formula II, formula III, formula IV, formula V, formula VI, or formula VII may contain one or more asymmetric centers and can therefore occur as racemates, mixtures of enantiomers, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

Compounds of formula I, formula II, formula III, formula IV, formula V, formula VI, and formula VII can be prepared according to the following processes. As described in the following general schemes 1 to 7 and using method known to the person skilled in the art.

Methods of Treatment

A compound of as described herein, or a pharmaceutically acceptable salt thereof, can be used in an effective amount to treat a patient with a BRAF mediated disorder. For example, in certain embodiments a compound described herein or a pharmaceutically acceptable salt thereof is used in the therapeutic and/or prophylactic treatment of cancer, more particularly non-small cell lung cancer (NSCLC), colorectal cancer (CRC), melanoma for example late-stage melanoma, thyroid cancer for example papillary thyroid cancer, leukemia for example hairy cell leukemia, or histiocytosis for example Langerhan's cell histiocytosis.

One aspect of the present invention provides a compound as described herein, or a pharmaceutically acceptable salt thereof for use in the treatment or prevention of a cancer in a patient in need thereof; wherein the cancer cell is mediated by BRAF or wherein there is a need of BRAF inhibition for the treatment or prevention of cancer.

In certain embodiments the BRAF mediated cancer is relapsed and/or refractory melanoma.

In certain embodiments the BRAF mediated cancer is relapsed and/or refractory non-small cell lung cancer.

In certain embodiments the BRAF mediated cancer is melanoma and the BRAF has a V600E mutation.

Additional non-limiting examples of BRAF mediated cancers include thyroid gland anaplastic carcinoma, thyroid gland follicular carcinoma, pilocytic astrocytoma, Erdheim-Chester disease, pleomorphic xanthoastrocytoma, ganglioglioma, B-cell lymphoma for example mature b-cell lymphoma, b-cell leukemia for example mature b-cell leukemia, malignant solid tumor, cutaneous melanoma, multiple myeloma, glioma, pancreatic carcinoma, breast carcinoma, ovarian carcinoma, colorectal adenocarcinoma, non-Hodgkin lymphoma, poorly differentiated thyroid gland carcinoma, gastric carcinoma, squamous cell lung carcinoma, thyroid gland adenocarcinoma, cholangiocarcinoma, bladder carcinoma, malignant glioma, lymphoma, head and/or neck carcinoma for example head and neck squamous cell carcinoma, esophageal carcinoma, gastrointestinal stromal tumor, anaplastic pleomorphic xanthoastrocytoma, histiocytic and/or dendritic cell neoplasm, colon carcinoma, mucosal melanoma, non-squamous non-small cell lung carcinoma, urothelial carcinoma, pancreatic ductal adenocarcinoma, neuroblastoma, pancreatic adenocarcinoma, malignant salivary gland neoplasm, adenocarcinoma of the gastroesophageal junction, esophageal squamous cell carcinoma, germ cell tumor, sarcoma for example soft tissue sarcoma and histiocytic sarcoma, renal cell carcinoma, histiocytosis, papillary craniopharyngioma, anaplastic ganglioglioma, small intestinal adenocarcinoma, colon adenocarcinoma, solid neoplasm, skin squamous cell carcinoma, malignant central nervous system neoplasm, endometrial carcinoma, bile duct carcinoma, primary brain neoplasm, rectal carcinoma, biliary tract carcinoma, malignant hepatobiliary neoplasm, hepatobiliary neoplasm, glioblastoma, malignant uterine neoplasm, malignant peripheral nerve sheath tumor, thymic carcinoma, malignant female reproductive system neoplasm, small cell lung carcinoma, B-cell non Hodgkin lymphoma, hepatocellular carcinoma, gallbladder carcinoma, gastric adenocarcinoma, prostate carcinoma, squamous cell carcinoma, cervical squamous sell carcinoma, cervical carcinoma, nasal cavity and/or paranasal sinus carcinoma, lip and/or oral cavity carcinoma, nasopharyngeal carcinoma, oropharyngeal carcinoma, acute myeloid leukemia, myelodysplastic syndrome, ameloblastoma, bronchogenic carcinoma, chronic lymphocytic leukemia, chronic myelomonocytic leukemia, embryonal rhabdomyosarcoma, Hodgkin lymphoma, juvenile xanthogranuloma, malignant laryngeal neoplasm, metastatic malignant neoplasm in the brain, neurofibroma, neurofibromatosis, optic nerve glioma, rhabdoid tumor, schwannoma, and splenic diffuse red pulp small B-cell lymphoma.

In one aspect a method of treating a patient with a BRAF mediated cancer, for example a V600 mutant which was previously treated with a MEK inhibitor is provided that includes administering an effective amount of one of the compounds described herein or a pharmaceutically acceptable salt thereof. In another aspect a method of treating a patient with a BRAF mediated cancer, for example a V600 mutant which was previously treated with a BRAF kinase inhibitor is provided that includes administering an effective amount of one of the compounds described herein or a pharmaceutically acceptable salt thereof. In yet another aspect a method of treating a patient with a BRAF mediated cancer, for example a V600 mutant which was previously treated with a BRAF kinase inhibitor and MEK inhibitor is provided that includes administering an effective amount of one of the compounds described herein or a pharmaceutically acceptable salt thereof.

In certain embodiments, the method comprises administering an effective amount of the active compound or its salt as described herein, optionally including a pharmaceutically acceptable excipient, carrier, or adjuvant (i.e., a pharmaceutically acceptable composition), or optionally in combination or alternation with another bioactive agent or combination of agents, to a patient in need thereof.

In one aspect, the present invention provides a method for treating or lessening the severity of a disease, condition, or disorder wherein BRAF is implicated in the disease state. In certain embodiments the BRAF protein is mutated. Non-limiting examples of mutant BRAF proteins include V600E, V600K, V600D, V600R, V600M, K601E, K601N, K601T, L597Q, L597V, G469A, G469V, G469R, G464V, D287H, V459L, G466V, G466E, G466A, S467L, G469E, N581S, N581I, D594N, D594G, D594A, D594H, F595L, F468C, G596S, V600X, R575K, H568D, and G596D.

In certain embodiments the BRAF protein has a solvent front mutation.

In certain embodiments the BRAF protein has a gatekeeping mutation.

In certain embodiments the BRAF protein has an activating mutation.

In certain embodiments the BRAF protein has an exon 15 mutation, codon 600 missense, BRAF fusion, codon 469 missense, codon 594 missense, amplifying mutation, KIAA1549 fusion, codon 581 missense, codon 597 missense, codon 464 missense, or codon 596 missense.

In certain embodiments the BRAF protein has a V600 mutation, for example the BRAF protein may be V600E mutant BRAF. In certain embodiments the BRAF protein has a K601 mutation. In certain embodiments the BRAF protein has a L597 mutation. In certain embodiments the BRAF protein has a G469 mutation. In certain embodiments the BRAF protein has a G464 mutation. In certain embodiments the BRAF protein has a D287 mutation. In certain embodiments the BRAF protein has a V459 mutation. In certain embodiments the BRAF protein has a G466 mutation. In certain embodiments the BRAF protein has a S467 mutation. In certain embodiments the BRAF protein has a G469 mutation. In certain embodiments the BRAF protein has a N581 mutation. In certain embodiments the BRAF protein has a D594 mutation. In certain embodiments the BRAF protein has a F595 mutation. In certain embodiments the BRAF protein has a G596 mutation.

In certain embodiments an effective amount of the compound is administered to a host described herein is used to treat a disorder with a MAPK reactivation-mediated resistance mechanism. Non-limiting examples of MAPK reactivation mediated resistance mechanisms include: BRAF amplification, CRAF overexpression, BRAF splice variation or truncation, NRAS mutation, MEK1 mutation, MEK2 mutation, or IGFIR overexpression.

In one aspect of the invention a compound is provided that selectively degrades mutant BRAF versus wildtype BRAF. For example, the compound may exhibit a DC50 of at least about 2 to 1, at least about 5 to 1, at least about 10 to 1, at least about 100 to 1, at least about 250 to 1, at least about 500 to 1, at least about 750 to 1, at least about 1,000 to 1, at least about 2,000 to 1, at least about 3,000 to 1, at least about 4,000 to 1, at least about 5,000 to 1, or at least about 10,000 to 1.

In one aspect of the invention a method is provided to treat a MEK and/or BRAF inhibitor resistant cancer comprising administering a compound described herein, or a pharmaceutically acceptable salt, thereof to a patient. In certain embodiments the cancer is resistant to treatment with a MEK inhibitor. In certain embodiments the cancer is resistant to treatment with a BRAF inhibitor. In certain embodiments the cancer is resistant to treatment with a MEK and BRAF inhibitor. In certain embodiments the resistance was acquired during treatment (e.g. a compound described herein is administered as a second- or third-line treatment). In other embodiments the cancer is inherently resistant (e.g. a compound described herein is administered as a first-line treatment).

In certain embodiments the cancer is resistant to treatment with encorafenib.

In certain embodiments the cancer is resistant to treatment with binimetinib.

In certain embodiments the cancer is resistant to treatment with dabrafenib.

In certain embodiments the cancer is resistant to treatment with trametinib.

In certain embodiments the cancer is resistant to treatment with cetuximab, dasatinib, imatinib, panitumumab, pembrolizumab, sunitinib, trametinib, astrametinib, cobimetinib, and/or vemurafenib.

In certain embodiments a compound described herein, or a pharmaceutically acceptable salt thereof, is used to treat a refractory cancer. In certain embodiments a compound described herein, or a pharmaceutically acceptable salt thereof, is used to treat a relapsed cancer.

In one aspect a compound described herein is used in the treatment of a cancer, for example melanoma, that has acquired resistance to BRAF ligands by mutation of NRAS for example NRAS Q61K, for example melanoma that is resistant to treatment with encorafenib.

In another aspect of the invention a compound described herein, or a pharmaceutically acceptable salt thereof, is administered in combination with an additional therapeutic agent, radiation, and/or surgery.

In certain embodiments a compound described herein, or a pharmaceutically acceptable salt thereof, is administered in combination with a MEK and/or BRAF inhibitor to a patient in need thereof. In certain embodiments a compound described herein, or a pharmaceutically acceptable salt thereof, is administered in combination with a MEK inhibitor to a patient in need thereof. In certain embodiments a compound described herein, or a pharmaceutically acceptable salt thereof, is administered in combination with a BRAF inhibitor to a patient in need thereof. In certain embodiments a compound described herein, or a pharmaceutically acceptable salt thereof, is administered in combination with a BRAF and MEK inhibitor to a patient in need thereof.

Non-limiting examples of MEK inhibitors include astrametinib, cobimetinib, and binimetinib.

In certain embodiments a compound described herein, or a pharmaceutically acceptable salt thereof, is used in combination with encorafenib.

In certain embodiments a compound described herein, or a pharmaceutically acceptable salt thereof, is used in combination with binimetinib.

In certain embodiments a compound described herein, or a pharmaceutically acceptable salt thereof, is used in combination with dabrafenib.

In certain embodiments a compound described herein, or a pharmaceutically acceptable salt thereof, is used in combination with trametinib.

In certain embodiments a compound described herein, or a pharmaceutically acceptable salt thereof, is used in combination with cetuximab, dasatinib, imatinib, panitumumab, pembrolizumab, sunitinib, astrametinib, cobimetinib, and/or vemurafenib.

In certain embodiments a compound described herein, or a pharmaceutically acceptable salt thereof, is administered in an orally bioavailable form.

Approved small molecule inhibitors of BRAF V600E, for example vemurafenib, dabrafenib, and encorafenib, block the constitutive activation of the MAPK pathway by the mutant BRAF monomer. However, BRAF inhibition with these molecules can lead to an alternative activation pathway known as paradoxical activation. Under these conditions BRAF inhibitors bind and inhibit BRAF V600E, but this inhibited form can form a dimer with other RAF proteins, including both wild type BRAF and BRAF mutants, activating the second molecule for signaling. This BRAF driven paradoxical activation activates, rather than inhibits, the MAPK pathway. By degrading instead of simply binding the BRAF protein a compound described herein avoids paradoxical activation.

In certain embodiments a compound described herein is administered to a patient and significantly less paradoxical RAF activation occurs.

In certain embodiments a compound described herein exhibits deeper and/or more sustained inhibition of BRAF via degradation than non-degrading ligands such as encorafenib, dabrafenib, and trametinib.

Pharmaceutical Compositions

A compound as described herein can be administered as the neat chemical, but is more typically administered as a pharmaceutical composition, that includes an effective amount for a patient, typically a human, in need of such treatment for any of the disorders described herein. Accordingly, the disclosure provides pharmaceutical compositions comprising an effective amount of compound or pharmaceutically acceptable salt together with at least one pharmaceutically acceptable carrier for any of the uses described herein. The pharmaceutical composition may contain a compound or salt as the only active agent, or, in an alternative embodiment, the compound and at least one additional active agent.

In general, the compositions of the disclosure will be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compositions of the disclosure for a given disease.

In certain embodiments the compound is administered as a pharmaceutically acceptable salt. Non-limiting examples of pharmaceutically acceptable salts include: acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemi sulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

Thus, the composition of the disclosure can be administered as a pharmaceutical formulation including one suitable for oral (including buccal and sub-lingual), rectal, nasal, topical, transdermal, pulmonary, vaginal or parenteral (including intramuscular, intra-arterial, intrathecal, subcutaneous and intravenous), injections, inhalation or spray, intra-aortal, intracranial, subdermal, intraperitioneal, subcutaneous, or by other means of administration containing conventional pharmaceutically acceptable carriers. A typical manner of administration is oral, topical or intravenous, using a convenient daily dosage regimen which can be adjusted according to the degree of affliction.

Depending on the intended mode of administration, the pharmaceutical compositions can be in the form of solid, semi-solid or liquid dosage forms, such as, for example, tablets, suppositories, pills, capsules, powders, liquids, syrup, suspensions, creams, ointments, lotions, paste, gel, spray, aerosol, foam, or oil, injection or infusion solution, a transdermal patch, a subcutaneous patch, an inhalation formulation, in a medical device, suppository, buccal, or sublingual formulation, parenteral formulation, or an ophthalmic solution, or the like, preferably in unit dosage form suitable for single administration of a precise dosage.

Some dosage forms, such as tablets and capsules, are subdivided into suitably sized unit doses containing appropriate quantities of the active components, e.g., an effective amount to achieve the desired purpose. The compositions will include an effective amount of the selected drug in combination with a pharmaceutically acceptable carrier and, in addition, can include other pharmaceutical agents, adjuvants, diluents, buffers, and the like.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to adjuvants, binders, buffering agents, coloring agents, diluents, disintegrants, excipients, emulsifiers, flavorants, gels, glidents, lubricants, preservatives, stabilizers, surfactants, solubilizer, tableting agents, wetting agents or solidifying material.

Some carriers may be listed in more than one class, for example vegetable oil may be used as a lubricant in some formulations and a diluent in others.

Exemplary pharmaceutically acceptable carriers include sugars, starches, celluloses, powdered tragacanth, malt, gelatin; talc, petroleum jelly, lanoline, polyethylene glycols, alcohols, transdermal enhancers and vegetable oils. Optional active agents may be included in a pharmaceutical composition, which do not substantially interfere with the activity of the compound of the present invention.

Some excipients include, but are not limited, to liquids such as water, saline, glycerol, polyethylene glycol, hyaluronic acid, ethanol, and the like. The compound can be provided, for example, in the form of a solid, a liquid, spray dried material, a microparticle, nanoparticle, controlled release system, etc., as desired according to the goal of the therapy. Suitable excipients for non-liquid formulations are also known to those of skill in the art. A thorough discussion of pharmaceutically acceptable excipients and salts is available in Remington's Pharmaceutical Sciences, 18th Edition (Easton, Pennsylvania: Mack Publishing Company, 1990).

Additionally, auxiliary substances, such as wetting or emulsifying agents, biological buffering substances, surfactants, and the like, can be present in such vehicles. A biological buffer can be any solution which is pharmacologically acceptable, and which provides the formulation with the desired pH, i.e., a pH in the physiologically acceptable range. Examples of buffer solutions include saline, phosphate buffered saline, Tris buffered saline, Hank's buffered saline, and the like.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

In yet another embodiment provided is the use of permeation enhancer excipients including polymers such as: polycations (chitosan and its quaternary ammonium derivatives, poly-L-arginine, aminoted gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

In certain embodiments the excipient is selected from butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

The pharmaceutical compositions/combinations can be formulated for oral administration. For oral administration, the composition will generally take the form of a tablet, capsule, a softgel capsule or can be an aqueous or nonaqueous solution, suspension or syrup. Tablets and capsules are typical oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Typically, sterile injectable suspensions are formulated according to techniques known in the art using suitable carriers, dispersing or wetting agents and suspending agents. The sterile injectable formulation can also be a sterile injectable solution or a suspension in a acceptably nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as a continuous infusion system. A formulation provided by the disclosure can be administered using a syringe, injector, pump, or any other device recognized in the art for parenteral administration.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, typical methods of preparation are vacuum-drying and freeze-drying techniques which yield a powder of the active ingredient plus any additional desired ingredient from a previously sterile-filtered solution thereof.

Alternatively, the pharmaceutical compositions of the disclosure can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

The pharmaceutical compositions of the disclosure can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, propellants such as fluorocarbons or nitrogen, and/or other conventional solubilizing or dispersing agents.

Formulations for buccal administration include tablets, lozenges, gels and the like. Alternatively, buccal administration can be effected using a transmucosal delivery system as known to those skilled in the art. The compounds of the disclosure can also be delivered through the skin or mucosal tissue using conventional transdermal drug delivery systems, i.e., transdermal "patches" wherein the agent is typically contained within a laminoted structure that serves as a drug delivery device to be affixed to the body surface. In such a structure, the drug composition is typically contained in a layer, or "reservoir," underlying an upper backing layer. The laminoted device can contain a single reservoir, or it can contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like.

Alternatively, the drug-containing reservoir and skin contact adhesive are present as separate and distinct layers, with the adhesive underlying the reservoir which, in this case, can be either a polymeric matrix as described above, or it can be a liquid or gel reservoir, or can take some other form. The backing layer in these laminotes, which serves as the upper surface of the device, functions as the primary structural element of the laminoted structure and provides the device with much of its flexibility. The material selected for the backing layer should be substantially impermeable to the active agent and any other materials that are present.

The compositions of the disclosure can be formulated for aerosol administration, particularly to the respiratory tract and including intranasal administration. The compound may, for example generally have a small particle size for example of the order of 5 microns or less. Such a particle size can be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol can conveniently also contain a surfactant such as lecithin. The dose of drug can be controlled by a metered valve.

Alternatively, the active ingredients can be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges of e.g., gelatin or blister packs from which the powder can be administered by means of an inhaler.

In certain embodiments, the pharmaceutical composition is suitable for topical application to the skin using a mode of administration and defined above.

In certain embodiments, the pharmaceutical composition is suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound.

In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Dosing

Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compositions of the disclosure for a given disease.

In some embodiments, compounds disclosed herein or used as described are administered once a day (QD), twice a day (BID), or three times a day (TID). In some embodiments, compounds disclosed herein or used as described are administered at least once a day for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least 35 days, at least 45 days, at least 60 days, at least 75 days, at least 90 days, at least 120 days, at least 150 days, at least 180 days, or longer.

In certain embodiments the compound of the present invention is administered once a day, twice a day, three times a day, or four times a day.

In certain embodiments the compound of the present invention is administered orally once a day. In certain embodiments the compound of the present invention is administered orally twice a day. In certain embodiments the compound of the present invention is administered orally three times a day. In certain embodiments the compound of the present invention is administered orally four times a day.

In certain embodiments the compound of the present invention is administered intravenously once a day. In certain embodiments the compound of the present invention is administered intravenously twice a day. In certain embodiments the compound of the present invention is administered intravenously three times a day. In certain embodiments the compound of the present invention is administered intravenously four times a day.

In some embodiments the compound of the present invention is administered with a treatment holiday in between treatment cycles. For example, the compound may have a treatment holiday of 1 day, 2 days, 3 days, 4 days, 5 days, 6 days, 7 days, 8 days, 9 days, 10 days, 11 days, 12 days, 13 days, or 14 days per treatment cycle.

In some embodiments a loading dose is administered to begin treatment. For example, the compound may be administered at least about 1.5×, at least about 2×, at least about 2.5×, at least about 3×, at least about 3.5×, at least about 4×, at least about 4.5×, at least about 5×, at least about 5.5×, at least about 6×, at least about 6.5×, at least about 7×, at least about 7.5×, at least about 8×, at least about 8.5×, at least about 9×, at least about 9.5×, or at least about 10× higher dose on the first day of treatment than the remaining days of treatment in the treatment cycle. Additional exemplary loading doses include at least about 1.5×, at least about 2×, at least about 2.5×, at least about 3×, at least about 3.5×, at least about 4×, at least about 4.5×, at least about 5×, at least about 5.5×, at least about 6×, at least about 6.5×, at least about 7×, at least about 7.5×, at least about 8×, at least about 8.5×, at least about 9×, at least about 9.5×, or at least about 10× higher dose on the first 2, 3, 4, 5, 6, 7, 8, 9, or 10 days of treatment than the remaining days of treatment in the treatment cycle.

In certain embodiments the a compound described herein is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least about 0.1, 0.5, 1, 2, 3, 4, 5, 6, 7, 8, 9, 10, 11, 12, 13, 14, 15, 20, 25, 50, 100, 200, 250, 300, 400, 500, 600, 700, or 750 mg of active compound, or its salt.

In certain embodiments the dose ranges from about 0.01-100 mg/kg of patient bodyweight, for example at least about 0.01 mg/kg, at least about 0.05 mg/kg, at least about 0.1 mg/kg, at least about 0.5 mg/kg, at least about 1 mg/kg, at least about 1.5 mg/kg, at least about 2 mg/kg, at least about 2.5 mg/kg, at least about 3 mg/kg, at least about 3.5 mg/kg, at least about 4 mg/kg, at least about 4.5 mg/kg, at least about 5 mg/kg, at least about 10 mg/kg, at least about 15 mg/kg, at least about 20 mg/kg, at least about 25 mg/kg, at least about 30 mg/kg, at least about 35 mg/kg, at least about 40 mg/kg, at least about 45 mg/kg, at least about 50 mg/kg, at least about 55 mg/kg, at least about 60 mg/kg, at least about 65 mg/kg, at least about 70 mg/kg, at least about 75 mg/kg, at least about 80 mg/kg, at least about 85 mg/kg, at least about 90 mg/kg, at least about 95 mg/kg, or at least about 100 mg/kg.

Embodiments of the Present Invention

1. A compound of formula I, or a pharmaceutically acceptable salt thereof, (I)

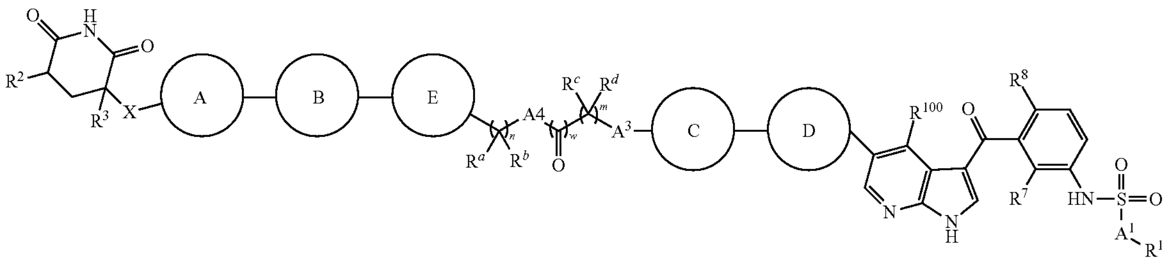

wherein $R^2$ and $R^3$ are independently selected from i) H, and ii) $C_{1-6}$-alkyl;

or $R^2$ and $R^3$ together form —$CH_2$—;

X is selected from i) —$CH_2$—, ii) —$NR^4$—, and iii) —O—;

$R^4$ is selected from i) H, and ii) $C_{1-6}$-alkyl;

A is selected from the ring systems F, G, H, I, BA, BB, BC, BD and BE;

F

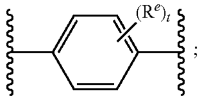

G

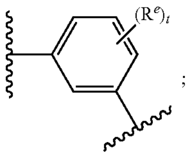

H

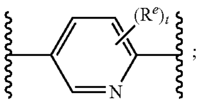

I

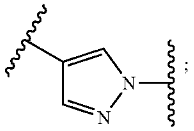

BA

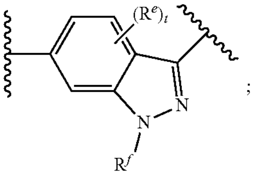

-continued

BB

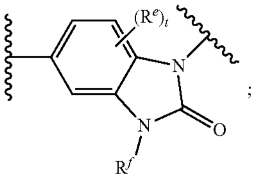

BC

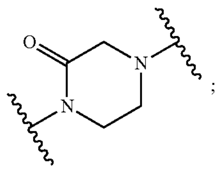

BD

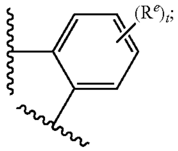

$R^e$ is independently selected from i) halogen, ii) cyano, and iii) $C_{1-6}$-alkyl;

t is selected from i) 0, ii) 1, and iii) 2;

$R^f$ is independently selected from i) H, ii) $C_{3-8}$-cycloalkyl, and iii) $C_{1-6}$-alkyl;

B is absent or selected from the ring systems AA, AB, AD, AE, AF, AG, AH, AI, AJ, AK, AL and AR;

AA

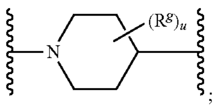

-continued
AB
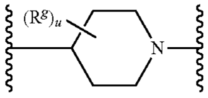
;
AD
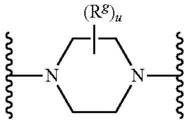
;
AL
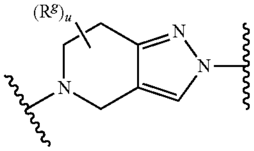
;
AE
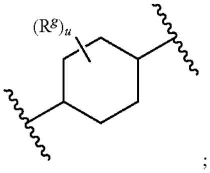
;
AF
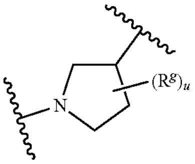
;
AG
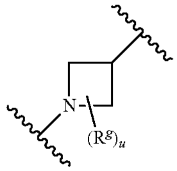
;
AH
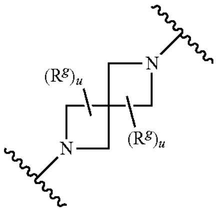
;
AI
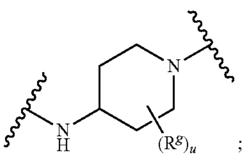
;
AJ
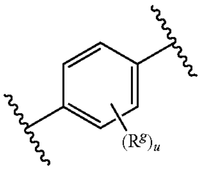
;
-continued
AK
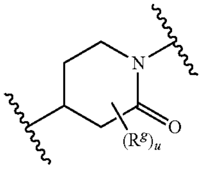
;
AR
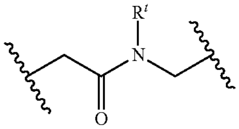
;
$R^g$ is independently selected from
- i) halogen,
- ii) hydroxy, and
- iii) $C_{1-6}$-alkyl;
$R^t$ is independently selected from
- i) H,
- ii) $C_{3-8}$-cycloalkyl, and
- iii) $C_{1-6}$-alkyl;
u is independently selected from
- i) 0,
- ii) 1, and
- iii) 2;
E is absent or selected from the ring systems AM, AN, AO, AP and AQ;
AM
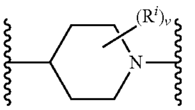
;
AN
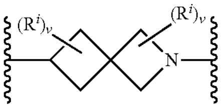
;
AO
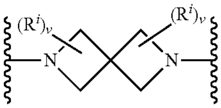
;
AP
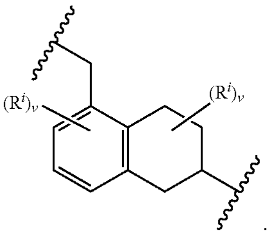
;
AQ
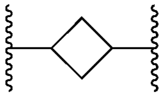
;

$R^i$ is independently selected from
i) halogen,
ii) hydroxy,
iii) $C_{3-8}$-cycloalkyl, and
iv) $C_{1-6}$-alkyl;
v is independently selected from
i) 0,
ii) 1, and
iii) 2;
m and n are independently selected from
i) 0,
ii) 1,
iii) 2, and
iv) 3;
$R^a$, $R^b$, $R^c$ and $R^d$ are independently selected from
i) H, and
ii) $C_{1-6}$-alkyl;
$A^4$ is selected from
i) a bond, and
ii) —$NR^{101}$—;
$R^{101}$ is selected from
i) H, and
ii) $C_{1-6}$-alkyl;
w is selected from
i) 0, and
ii) 1;
$A^3$ is selected from
i) a bond,
ii) —O—,
iii) —$NR^{200}$—, and
iv)

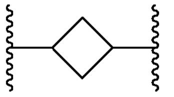
;

$R^{200}$ is selected from
i) H, and
ii) $C_{1-6}$-alkyl;
C is selected from the ring systems J, K, O, R, T, EA, EB, EC, ED, EF, EG, JA, KA, OA, P, PA, S, U, V and JAA;

J

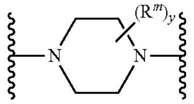
;

K

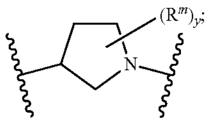

O

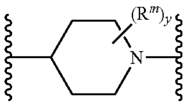
;

R

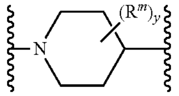
;

-continued

T

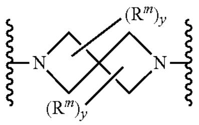
;

EA

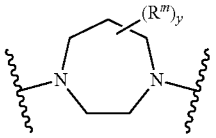
;

EB

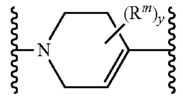
;

EC

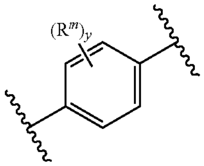
;

ED

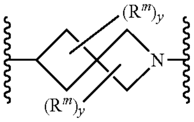
;

EF

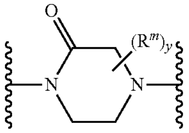
;

EG

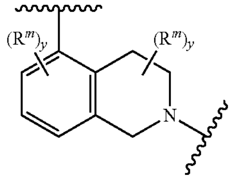
;

JA

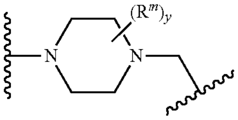
;

KA

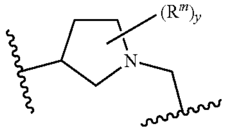
;

OA

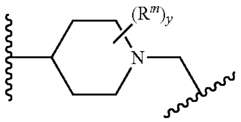
;

P

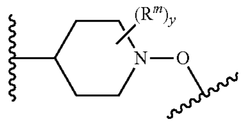
;

-continued

PA

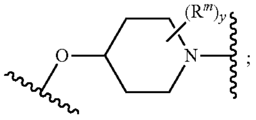

S

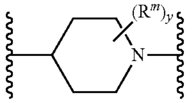

S

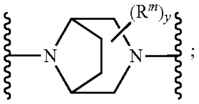

U

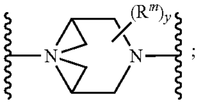

V

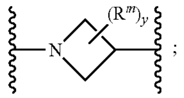

JAA

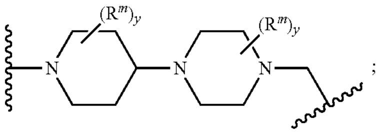

$R^m$ independently selected from
i) halogen,
ii) hydroxy,
iii) $C_{3-8}$-cycloalkyl, and
iv) $C_{1-6}$-alkyl;
y is independently selected from
i) 0,
ii) 1, and
iii) 2;
D is selected from the ring systems W, X, Y, Q, Z and CA;

W

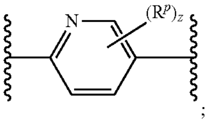

X

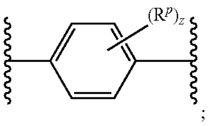

Y

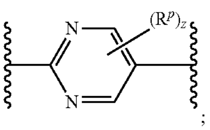

Q

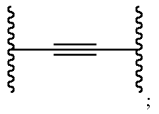

-continued

Z

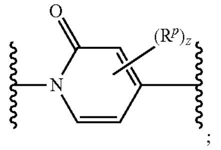

CA

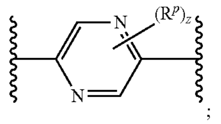

$R^p$ is independently selected from
i) halogen,
ii) $C_{3-8}$-cycloalkyl,
iii) halo-$C_{1-6}$-alkyl,
iv) $C_{1-6}$-alkyl,
v) cyano,
vi) $C_{1-6}$-alkylsulfonyl, and
vii) $C_{3-8}$-cycloalkylsulfonyl;
z is independently selected from
i) 0,
ii) 1, and
iii) 2;
$R^{100}$ is selected from
i) H,
ii) halogen, and
iii) $C_{1-6}$-alkyl;
$R^7$ and $R^8$ are independently selected from
i) H,
ii) $C_{1-6}$-alkyl, and
iii) halogen;
$A^1$ is selected from
i) —$NR^5$—, and
ii) —$CHR^6$—;
$R^5$ is selected from
i) H, and
ii) $C_{1-6}$-alkyl;
or $R^1$ and $R^5$ together with the nitrogen atom to which they are attached form a heterocycloalkyl optionally substituted by $R^{14}$, $R^{15}$ and $R^{16}$;
$R^6$ is selected from
i) H, and
ii) $C_{1-6}$-alkyl;
or $R^1$ and $R^6$ together with the carbon atom to which they are attached form a cycloalkyl optionally substituted by $R^{14}$, $R^{15}$ and $R^{16}$;
$R^{14}$, $R^{15}$ and $R^{16}$ are independently selected from
i) $C_{1-6}$-alkyl, and
ii) halogen;
$R^1$ is selected from
i) $C_{1-6}$-alkyl, and
ii) $C_{3-8}$-cycloalkyl.

2. A compound according to embodiment 1, or a pharmaceutically acceptable salt thereof, wherein $R^2$ is —$CR^3$—.

3. A compound according to any one of embodiments 1 to 2, or a pharmaceutically acceptable salt thereof, wherein $R^2$ and $R^3$ are H.

4. A compound according to any one of embodiments 1 to 3, or a pharmaceutically acceptable salt thereof, wherein $R^2$ and $R^3$ together form —$CH_2$—.

5. A compound according to any one of embodiments 1 to 4, or a pharmaceutically acceptable salt thereof, wherein X is —$NR^4$—.

6. A compound according to any one of embodiments 1 to 5, or a pharmaceutically acceptable salt thereof, wherein A is the ring system F.

7. A compound according to any one of embodiments 1 to 6, or a pharmaceutically acceptable salt thereof, wherein $R^e$ is halogen.

8. A compound according to any one of embodiments 1 to 7, or a pharmaceutically acceptable salt thereof, wherein t is 1.

9. A compound according to any one of embodiments 1 to 8, or a pharmaceutically acceptable salt thereof, wherein $R^f$ is $C_{1-6}$-alkyl.

10. A compound according to any one of embodiments 1 to 9, or a pharmaceutically acceptable salt thereof, wherein B is selected from the ring systems AA and AB.

11. A compound according to any one of embodiments 1 to 10, or a pharmaceutically acceptable salt thereof, wherein B is selected from the ring system AA.

12. A compound according to any one of embodiments 1 to 11, or a pharmaceutically acceptable salt thereof, wherein $R^g$ is hydroxy.

13. A compound according to any one of embodiments 1 to 12, or a pharmaceutically acceptable salt thereof, wherein u is 1.

14. A compound according to any one of embodiments 1 to 13, or a pharmaceutically acceptable salt thereof, wherein $R^i$ is hydroxy.

15. A compound according to any one of embodiments 1 to 14, or a pharmaceutically acceptable salt thereof, wherein E is absent.

16. A compound according to any one of embodiments 1 to 15, or a pharmaceutically acceptable salt thereof, wherein v is selected from i) 0, and ii) 1.

17. A compound according to any one of embodiments 1 to 16, or a pharmaceutically acceptable salt thereof, wherein m is selected from i) 0, ii) 1, and iii) 3.

18. A compound according to any one of embodiments 1 to 17, or a pharmaceutically acceptable salt thereof, wherein m is 0.

19. A compound according to any one of embodiments 1 to 18, or a pharmaceutically acceptable salt thereof, wherein n is selected from i) 0, ii) 1, iii) 2, and iv) 3.

20. A compound according to any one of embodiments 1 to 19, or a pharmaceutically acceptable salt thereof, wherein n is 0.

21. A compound according to any one of embodiments 1 to 20, or a pharmaceutically acceptable salt thereof, wherein $R^a$ and $R^b$ are selected from i) H, and ii) $C_{1-6}$-alkyl.

22. A compound according to any one of embodiments 1 to 21, or a pharmaceutically acceptable salt thereof, wherein $R^a$ and $R^b$ are H.

23. A compound according to any one of embodiments 1 to 22, or a pharmaceutically acceptable salt thereof, wherein $R^c$ and $R^d$ are H.

24. A compound according to any one of embodiments 1 to 23, or a pharmaceutically acceptable salt thereof, wherein $R^m$ is hydroxy.

25. A compound according to any one of embodiments 1 to 24, or a pharmaceutically acceptable salt thereof, wherein y is selected from i) 0, and ii) 1.

26. A compound according to any one of embodiments 1 to 25, or a pharmaceutically acceptable salt thereof, wherein $R^p$ is selected from i) halogen, ii) halo-$C_{1-6}$-alkyl, iii) $C_{1-6}$-alkyl, iv) cyano, and v) $C_{1-6}$-alkyl sulfonyl.

27. A compound according to any one of embodiments 1 to 26, or a pharmaceutically acceptable salt thereof, wherein $R^5$ is $C_{1-6}$-alkyl.

28. A compound according to any one of embodiments 1 to 27, or a pharmaceutically acceptable salt thereof, wherein $R^{14}$ is halogen.

29. A compound according to any one of embodiments 1 to 28, or a pharmaceutically acceptable salt thereof, wherein $R^7$ and $R^8$ are halogen.

30. A compound according to any one of embodiments 1 to 29, or a pharmaceutically acceptable salt thereof, wherein $R^{100}$ is H.

31. A compound according to any one of embodiments 1 to 30, or a pharmaceutically acceptable salt thereof, wherein z is 0.

32. A compound according to any one of embodiments 1 to 31, or a pharmaceutically acceptable salt thereof, wherein y is 0.

33. A compound according to any one of embodiments 1 to 32, or a pharmaceutically acceptable salt thereof, wherein w is 1.

34. A compound according to any one of embodiments 1 to 33, or a pharmaceutically acceptable salt thereof, wherein C is the ring system J.

35. A compound according to any one of embodiments 1 to 34, or a pharmaceutically acceptable salt thereof, wherein D is the ring system W.

36. A compound according to any one of embodiments 1 to 35, or a pharmaceutically acceptable salt thereof, wherein $A^4$ is a bond.

37. A compound according to any one of embodiments 1 to 36, or a pharmaceutically acceptable salt thereof, wherein $A^3$ is a bond or —$NR^5$—.

38. A compound according to any one of embodiments 1 to 37, or a pharmaceutically acceptable salt thereof, wherein $A^1$ is —$NR^5$—.

39. A compound according to any one of embodiments 1 to 38, or a pharmaceutically acceptable salt thereof, selected from N-[3-[5-[2-[4-[2-[4-[4-[(2,6-dioxo-3-piperidyl)amino]phenyl]-1-piperidyl]acetyl]piperazin-1-yl]pyrimidin-5-yl]-1H-pyrrolo[2,3-b]pyridine-3-carbonyl]-2,4-difluoro-phenyl]propane-1-sulfonamide;

N-[3-[5-[2-[4-[2-[4-[4-[(2,6-dioxo-3-piperidyl)oxy]phenyl]-1-piperidyl]acetyl]piperazin-1-yl]pyrimidin-5-yl]-1H-pyrrolo[2,3-b]pyridine-3-carbonyl]-2,4-difluoro-phenyl]propane-1-sulfonamide;

N-[3-[5-[6-[4-[2-[4-[4-[(2,6-dioxo-3-piperidyl)amino]phenyl]-1-piperidyl]acetyl]piperazin-1-yl]-3-pyridyl]-1H-pyrrolo[2,3-b]pyridine-3-carbonyl]-2,4-difluoro-phenyl]propane-1-sulfonamide;

N-[3-[5-[6-[4-[2-[4-[4-[(2,6-dioxo-3-piperidyl)amino]phenyl]-1-piperidyl]acetyl]piperazin-1-yl]-3-pyridyl]-1H-pyrrolo[2,3-b]pyridine-3-carbonyl]-2,4-difluoro-phenyl]butane-2-sulfonamide;

N-[3-[5-[2-[4-[2-[4-[4-[(2,6-dioxo-3-piperidyl)amino]phenyl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide;

N-[3-[5-[2-[4-[2-[4-[4-[(2,6-dioxo-3-piperidyl)amino]-2-fluoro-phenyl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide;

N-[3-[5-[2-[4-[2-[4-[4-[(2,6-dioxo-3-piperidyl)oxy]phenyl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide;

N-[3-[5-[2-[4-[2-[4-[4-(2,6-dioxo-3-piperidyl)phenyl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide;

N-[3-[5-[2-[4-[2-[4-[4-(2,6-dioxo-3-piperidyl)-2-fluoro-phenyl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide;

N-[3-[5-[2-[4-[2-[4-[3-(2,4-dioxohexahydropyrimidin-1-yl)-1-methyl-indazol-6-yl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide;

N-[3-[5-[6-[4-[2-[4-[4-[(2,6-dioxo-3-piperidyl)amino]phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide;

N-[3-[5-[2-[4-[2-[4-[4-[(2,6-dioxo-3-piperidyl)amino]-2-fluoro-phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide;

N-[3-[5-[6-[4-[2-[4-[4-[(2,6-dioxo-3-piperidyl)oxy]phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide;

N-[3-[5-[6-[4-[2-[4-[4-(2,6-dioxo-3-piperidyl)phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide N-[3-[5-[6-[4-[2-[4-[4-(2,6-dioxo-3-piperidyl)-2-fluoro-phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide;

N-[3-[5-[2-[4-[2-[4-[4-[(2,6-dioxo-3-piperidyl)amino]phenyl]-1-piperidyl]acetyl]piperazin-1-yl]-3-pyridyl]-1H-pyrrolo[2,3-b]pyridine-3-carbonyl]-2,4-difluoro-phenyl]pyrrolidine-1-sulfonamide;

(3R)—N-[3-[5-[4-[4-[2-[4-[4-[(2,6-dioxo-3-piperidyl)amino]phenyl]-1-piperidyl]acetyl]piperazin-1-yl]phenyl]-1H-pyrrolo[2,3-b]pyridine-3-carbonyl]-2,4-difluoro-phenyl]-3-fluoro-pyrrolidine-1-sulfonamide;

5-[2-[4-[2-[4-[4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]piperazin-1-yl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]-2-fluoro-phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[5-[(2,6-dioxo-3-piperidyl)amino]-2-pyridyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)-methyl-amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[3-[4-[4-[(2,6-dioxo-3-piperidyl)amino]phenyl]-1-piperidyl]cyclobutanecarbonyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-(2,4-dioxohexahydropyrimidin-1-yl)phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[[(3 S)-2,6-dioxo-3-piperidyl]amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[[(3R)-2,6-dioxo-3-piperidyl]amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

3-(2,6-dioxo-3-piperidyl)-6-[1-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl]-1-methyl-indazole;

3-(2,6-dioxo-3-piperidyl)-6-[[1-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl]amino]-1-methyl-indazole;

5-[2-[4-[2-[4-[4-[(2,6-dioxo-3-piperidyl)amino]-3-fluoro-phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]-3,3-difluoro-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(2,6-dioxo-3-piperidyl)amino]phenyl]-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,4-dioxohexahydropyrimidin-1-yl)methyl]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

1-(2,6-dioxo-3-piperidyl)-5-[1-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl]-3-methyl-2-oxo-benzimidazole;

3-(2,4-dioxohexahydropyrimidin-1-yl)-6-[1-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl]-1-methyl-indazole;

5-[2-[4-[2-[4-[4-[(2,6-dioxo-3-piperidyl)amino]phenyl]cyclohexyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]cyclohexyl]acetyl]piperazin-1-yl]pyrimidin-5-yl]-3-[3-

[[ethyl(methyl)sulfamoyl]amino]-2,6-difluoro-benzoyl]-1H-pyrrolo[2,3-b]pyridine;

5-[2-[4-[2-[4-[4-(2,6-dioxo-3-piperidyl)-3-oxo-piperazin-1-yl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(2,6-dioxo-3-piperidyl)amino]phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-(difluoromethyl)-4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[2-cyano-4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)oxy]-2,6-difluoro-phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(2,6-dioxo-3-piperidyl)amino]-2-fluoro-phenyl]-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

1-(2,6-dioxo-3-piperidyl)-5-[4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-1-piperidyl]-3-methyl-2-oxo-benzimidazole;

5-[2-[4-[2-[4-[4-(2,4-dioxohexahydropyrimidin-1-yl)-2-fluoro-phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(2,6-dioxo-3-piperidyl)amino]-2,6-difluoro-phenyl]-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]-2,6-difluoro-phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

3-(2,6-dioxo-3-piperidyl)-6-[4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-1-piperidyl]-1-methyl-indazole;

5-[2-[4-[2-[1-[4-[(2,6-dioxo-3-piperidyl)amino]-2-fluoro-phenyl]pyrrolidin-3-yl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[2-[4-[(2,6-dioxo-3-piperidyl)amino]phenyl]-2,6-diazaspiro[3.3]heptan-6-yl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-(2,6-dioxo-3-piperidyl)-3-oxo-piperazin-1-yl]phenyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(2,6-dioxo-3-piperidyl)amino]-2-fluoro-phenyl]-3-hydroxy-pyrrolidin-3-yl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[3-[1-[4-[(2,6-dioxo-3-piperidyl)amino]-2-fluoro-phenyl]azetidin-3-yl]cyclobutanecarbonyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[3-[1-[4-[(2,6-dioxo-3-piperidyl)amino]-2-fluoro-phenyl]azetidin-3-yl]cyclobutanecarbonyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[(4S)-4-[4-[(2,6-dioxo-3-piperidyl)amino]phenyl]-3,3-difluoro-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[(4R)-4-[4-[(2,6-dioxo-3-piperidyl)amino]phenyl]-3,3-difluoro-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

3-(2,4-dioxohexahydropyrimidin-1-yl)-6-[4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-1-piperidyl]-1-methyl-indazole;

5-[2-[4-[2-[1-[5-[(2,6-dioxo-3-piperidyl)amino]-2-pyridyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[5-[(2,6-dioxo-3-piperidyl)amino]-3-fluoro-2-pyridyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(2,6-dioxo-3-piperidyl)amino]-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[(2,6-dioxo-3-piperidyl)amino]phenyl]-4-piperidyl]-2,2-difluoro-acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

3-(2,4-dioxohexahydropyrimidin-1-yl)-6-[1-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-3,3-difluoro-4-piperidyl]-1-methyl-indazole;

5-[2-[1-[2-[4-[4-[(2,6-dioxo-3-piperidyl)amino]phenyl]-1-piperidyl]acetyl]-4-piperidyl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]-1-piperidyl]acetyl]-1,4-diazepan-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[2-[2-[4-[4-[(2,6-dioxo-3-piperidyl)amino]phenyl]-1-piperidyl]acetyl]-2,6-diazaspiro[3.3]heptan-6-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-4-methyl-1H-pyrrolo[2,3-b]pyridine;

5-[2-[4-[2-[4-[4-[(2,6-dioxo-3-piperidyl)amino]phenyl]-1-piperidyl]acetyl]piperazin-1-yl]pyrimidin-5-yl]-3-

[3-[[ethyl(methyl)sulfamoyl]amino]-2,6-difluoro-benzoyl]-4-fluoro-1H-pyrrolo[2,3-b]pyridine;

5-[6-[4-[2-[4-[4-[(2,6-dioxo-3-piperidyl)oxy]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[4-[4-[(2,6-dioxo-3-piperidyl)amino]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[4-[4-[(2,6-dioxo-3-piperidyl)amino]phenyl]piperazin-1-yl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[5-[(2,6-dioxo-3-piperidyl)amino]isoindolin-2-yl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[4-[4-[(2,4-dioxo-3-azabicyclo[3.1.1]heptan-1-yl)amino]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[4-[4-(2,6-dioxo-3-piperidyl)phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[4-[4-[[(3 S)-2,6-dioxo-3-piperidyl]oxy]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[4-[4-[[(3R)-2,6-dioxo-3-piperidyl]oxy]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

3-(2,6-dioxo-3-piperidyl)-6-[[1-[2-[4-[5-[3-[3-[[ethyl(methyl)sulfamoyl]amino]-2,6-difluoro-benzoyl]-1H-pyrrolo[2,3-b]pyridin-5-yl]-2-pyridyl]piperazin-1-yl]-2-oxo-ethyl]-4-piperidyl]amino]-1-methyl-indazole;

5-[6-[4-[2-[1-[4-[(2,6-dioxo-3-piperidyl)amino]phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[(4R)-4-[4-[(2,6-dioxo-3-piperidyl)amino]phenyl]-3,3-difluoro-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[1-[5-[(2,6-dioxo-3-piperidyl)amino]-2-pyridyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[1-[5-[(2,6-dioxo-3-piperidyl)amino]-3-fluoro-2-pyridyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[2-[2-[4-[4-[(2,6-dioxo-3-piperidyl)amino]phenyl]-1-piperidyl]acetyl]-2,6-diazaspiro[3.3]heptan-6-yl]-3-pyridyl]-3-[3-[[ethyl(methyl)sulfamoyl]amino]-2,6-difluoro-benzoyl]-1H-pyrrolo[2,3-b]pyridine;

5-[5-cyano-6-[4-[2-[4-[4-[(2,6-dioxo-3-piperidyl)amino]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[4-[4-[2-[4-[4-[(2,6-dioxo-3-piperidyl)oxy]phenyl]-1-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[4-[4-[2-[4-[4-[(2,6-dioxo-3-piperidyl)amino]phenyl]-1-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[4-[4-[2-[4-[4-[(2,6-dioxo-3-piperidyl)amino]pyrazol-1-yl]-1-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[4-[4-[2-[1-[4-[(2,6-dioxo-3-piperidyl)amino]phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[4-[4-[2-[1-[4-[(2,6-dioxo-3-piperidyl)amino]-2-fluoro-phenyl]-3-hydroxy-pyrrolidin-3-yl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[4-[4-[2-[1-[5-[(2,6-dioxo-3-piperidyl)amino]-2-pyridyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[4-[4-[2-[1-[5-[(2,6-dioxo-3-piperidyl)amino]-3-fluoro-2-pyridyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[4-[1-[2-[4-[4-[(2,6-dioxo-3-piperidyl)amino]phenyl]-1-piperidyl]acetyl]-4-piperidyl]phenyl]-3-[3-[[ethyl(methyl)sulfamoyl]amino]-2,6-difluoro-benzoyl]-1H-pyrrolo[2,3-b]pyridine;

5-[4-[1-[2-[1-[4-[(2,6-dioxo-3-piperidyl)amino]phenyl]-4-piperidyl]acetyl]-3,6-dihydro-2H-pyridin-4-yl]phenyl]-3-[3-[[ethyl(methyl)sulfamoyl]amino]-2,6-difluoro-benzoyl]-1H-pyrrolo[2,3-b]pyridine;

5-[4-[4-[2-[4-[4-[(2,6-dioxo-3-piperidyl)amino]phenyl]-1-piperidyl]acetyl]piperazin-1-yl]-3,5-difluoro-phenyl]-3-[3-[[ethyl(methyl)sulfamoyl]amino]-2,6-difluoro-benzoyl]-1H-pyrrolo[2,3-b]pyridine;

5-[4-[[4-[2-[4-[4-[(2,6-dioxo-3-piperidyl)amino]phenyl]-1-piperidyl]-2-oxo-ethyl]piperazin-1-yl]methyl]phenyl]-3-[3-[[ethyl(methyl)sulfamoyl]amino]-2,6-difluoro-benzoyl]-1H-pyrrolo[2,3-b]pyridine;

5-[4-[[4-[2-[4-[4-[(2,6-dioxo-3-piperidyl)amino]phenyl]piperazin-1-yl]acetyl]piperazin-1-yl]methyl]phenyl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[4-[4-[(2,6-dioxo-3-piperidyl)amino]-2-fluoro-phenyl]-1-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[1-[4-[(2,6-dioxo-3-piperidyl)amino]-2-fluoro-phenyl]-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[1-[4-[(2,6-dioxo-3-piperidyl)amino]phenyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[4-[4-[(2,6-dioxo-3-piperidyl)amino]phenyl]-3,3-difluoro-1-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[1-[4-[(2,6-dioxo-3-piperidyl)amino]-2-fluoro-phenyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[1-[4-[(2,6-dioxo-3-piperidyl)amino]-2-fluoro-phenyl]-3-hydroxy-pyrrolidin-3-yl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[1-[2-chloro-4-[(2,6-dioxo-3-piperidyl)amino]phenyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[1-[5-[(2,6-dioxo-3-piperidyl)amino]-3-fluoro-2-pyridyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[1-[5-[(2,6-dioxo-3-piperidyl)amino]-2-pyridyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[1-[4-[(2,6-dioxo-3-piperidyl)amino]-2-(trifluoromethyl)phenyl]-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[6-[4-[2-[4-[4-[(2,6-dioxo-3-piperidyl)amino]phenyl]-1-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[6-[4-[2-[4-[4-[(2,6-dioxo-3-piperidyl)oxy]phenyl]-1-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[6-[4-[2-[1-[4-[(2,6-dioxo-3-piperidyl)amino]phenyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[6-[4-[2-[4-[4-[(2,6-dioxo-3-piperidyl)amino]phenyl]-3,3-difluoro-1-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[6-[4-[2-[1-[4-[(2,6-dioxo-3-piperidyl)amino]-2-fluoro-phenyl]-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[6-[4-[2-[1-[5-[(2,6-dioxo-3-piperidyl)amino]-2-pyridyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[6-[4-[2-[1-[4-[(2,6-dioxo-3-piperidyl)amino]-2-fluoro-phenyl]-3-hydroxy-pyrrolidin-3-yl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[6-[4-[2-[1-[5-[(2,6-dioxo-3-piperidyl)amino]-3-fluoro-2-pyridyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[4-[4-[2-[1-[4-[(2,6-dioxo-3-piperidyl)amino]phenyl]-4-hydroxy-4-piperidyl]acetyl]piperazin-1-yl]phenyl]-3-[3-[[ethyl(methyl)sulfamoyl]amino]-2-fluoro-benzoyl]-1H-pyrrolo[2,3-b]pyridine;

5-[4-[4-[2-[1-[5-[(2,6-dioxo-3-piperidyl)amino]-2-pyridyl]-4-hydroxy-4-piperidyl]acetyl]piperazin-1-yl]phenyl]-3-[3-[[ethyl(methyl)sulfamoyl]amino]-2-fluoro-benzoyl]-1H-pyrrolo[2,3-b]pyridine;

5-[4-[4-[2-[1-[4-[(2,6-dioxo-3-piperidyl)amino]-2-fluoro-phenyl]-3-hydroxy-pyrrolidin-3-yl]acetyl]piperazin-1-yl]phenyl]-3-[3-[[ethyl(methyl)sulfamoyl]amino]-2-fluoro-benzoyl]-1H-pyrrolo[2,3-b]pyridine;

5-[4-[4-[2-[1-[4-[(2,6-dioxo-3-piperidyl)amino]-2-fluoro-phenyl]-4-hydroxy-4-piperidyl]acetyl]piperazin-1-yl]phenyl]-3-[3-[[ethyl(methyl)sulfamoyl]amino]-2-fluoro-benzoyl]-1H-pyrrolo[2,3-b]pyridine;

5-[4-[4-[2-[1-[5-[(2,6-dioxo-3-piperidyl)amino]-3-fluoro-2-pyridyl]-4-hydroxy-4-piperidyl]acetyl]piperazin-1-yl]phenyl]-3-[3-[[ethyl(methyl)sulfamoyl]amino]-2-fluoro-benzoyl]-1H-pyrrolo[2,3-b]pyridine;

3-[2-chloro-3-[[ethyl(methyl)sulfamoyl]amino]-6-fluoro-benzoyl]-5-[2-[4-[2-[4-[4-[(2,6-dioxo-3-piperidyl)amino]phenyl]-1-piperidyl]acetyl]piperazin-1-yl]pyrimidin-5-yl]-1H-pyrrolo[2,3-b]pyridine;

3-[2-bromo-3-[[ethyl(methyl)sulfamoyl]amino]benzoyl]-5-[6-[4-[2-[4-[4-[(2,6-dioxo-3-piperidyl)amino]phenyl]-1-piperidyl]acetyl]piperazin-1-yl]-3-pyridyl]-1H-pyrrolo[2,3-b]pyridine;

5-[2-[4-[2-[4-[4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-6-fluoro-2-methyl-benzoyl]-1H-pyrrolo[2,3-b]pyridine;

5-[4-[1-[2-[1-[4-[(2,6-dioxo-3-piperidyl)amino]-2-fluoro-phenyl]-1-piperidyl]acetyl]-4-piperidyl]ethynyl]-3-[3-[[ethyl(methyl)sulfamoyl]amino]-2,6-difluoro-benzoyl]-1H-pyrrolo[2,3-b]pyridine;

5-[4-[1-[2-[1-[4-[(2,6-dioxo-3-piperidyl)amino]-2-fluoro-phenyl]-4-hydroxy-4-piperidyl]acetyl]-4-piperidyl]-3-fluoro-phenyl]-3-[3-[[ethyl(methyl)sulfamoyl]amino]-2,6-difluoro-benzoyl]-1H-pyrrolo[2,3-b]pyridine;

5-[2-[4-[4-[4-[4-[(2,6-dioxo-3-piperidyl)amino]phenyl]-1-piperidyl]piperidine-1-carbonyl]phenyl]ethynyl]-3-[3-[[ethyl(methyl)sulfamoyl]amino]-2,6-difluoro-benzoyl]-1H-pyrrolo[2,3-b]pyridine;

5-[2-[4-[4-[4-[(2,6-dioxo-3-piperidyl)amino]phenyl]piperidine-1-carbonyl]-1-piperidyl]pyrimidin-5-yl]-3-[3-[[ethyl(methyl)sulfamoyl]amino]-2,6-difluoro-benzoyl]-1H-pyrrolo[2,3-b]pyridine;

N-[1-[4-[(2,6-dioxo-3-piperidyl)amino]-2-fluoro-phenyl]-4-piperidyl]-1-[5-[3-[3-[[ethyl(methyl)sulfamoyl]amino]-2,6-difluoro-benzoyl]-1H-pyrrolo[2,3-b]pyridin-5-yl]pyrimidin-2-yl]piperidine-4-carboxamide;

5-[2-[(3R)-3-[4-[4-[(2,6-dioxo-3-piperidyl)amino]phenyl]piperidine-1-carbonyl]pyrrolidin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[(3S)-3-[4-[4-[(2,6-dioxo-3-piperidyl)amino]phenyl]piperidine-1-carbonyl]pyrrolidin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[(3 S)-3-[2-[4-[4-[(2,6-dioxo-3-piperidyl)amino]phenyl]-1-piperidyl]-2-oxo-ethyl]pyrrolidin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[6-[4-[4-[(2,6-dioxo-3-piperidyl)amino]phenyl]piperidine-1-carbonyl]-2-azaspiro[3.3]heptan-2-yl]pyrimidin-5-yl]-3-[3-[[ethyl(methyl)sulfamoyl]amino]-2,6-difluoro-benzoyl]-1H-pyrrolo[2,3-b]pyridine;

5-[2-[6-[2-[4-[4-[(2,6-dioxo-3-piperidyl)amino]phenyl]-1-piperidyl]-2-oxo-ethyl]-2-azaspiro[3.3]heptan-2-yl]

pyrimidin-5-yl]-3-[3-[[ethyl(methyl)sulfamoyl]amino]-2,6-difluoro-benzoyl]-1H-pyrrolo[2,3-b]pyridine;

N-[1-[4-[(2,6-dioxo-3-piperidyl)amino]-2-fluoro-phenyl]-4-piperidyl]-2-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]acetamide;

1-[4-[(2,6-dioxo-3-piperidyl)amino]-2-fluoro-phenyl]-2-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]-N-methyl-piperidine-4-carboxamide;

1-[4-[(2,6-dioxo-3-piperidyl)amino]-2-fluoro-phenyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]piperidine-4-carboxamide;

4-[4-[(2,6-dioxo-3-piperidyl)amino]phenyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]piperidine-1-carboxamide;

N-[1-[4-[(2,6-dioxo-3-piperidyl)amino]-2-fluoro-phenyl]-4-piperidyl]-4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazine-1-carboxamide;

N-[1-[4-[(2,6-dioxo-3-piperidyl)amino]phenyl]-4-piperidyl]-4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazine-1-carboxamide;

N-[1-[4-[(2,6-dioxo-3-piperidyl)amino]-2-fluoro-phenyl]-4-piperidyl]-4-[5-[3-[3-[[ethyl(methyl)sulfamoyl]amino]-2,6-difluoro-benzoyl]-1H-pyrrolo[2,3-b]pyridin-5-yl]-2-pyridyl]piperazine-1-carboxamide;

N-[1-[4-[(2,6-dioxo-3-piperidyl)amino]-2-fluoro-phenyl]-4-piperidyl]-4-[5-[3-[3-[[ethyl(methyl)sulfamoyl]amino]-2-fluoro-benzoyl]-1H-pyrrolo[2,3-b]pyridin-5-yl]pyrimidin-2-yl]piperazine-1-carboxamide;

5-[2-[4-[2-[4-[4-[(2,6-dioxo-3-piperidyl)amino]phenyl]-1-hydroxy-cyclohexyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[2-[4-[4-[(2,6-dioxo-3-piperidyl)amino]phenyl]-1-piperidyl]ethyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[4-[4-[(2,6-dioxo-3-piperidyl)oxy]phenyl]-1-piperidyl]ethyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]-1-hydroxy-cyclohexyl]ethyl]piperazin-1-yl]pyrimidin-5-yl]-3[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]-2-oxo-1-piperidyl]ethyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[2-[4-[4-[(2,6-dioxo-3-piperidyl)oxy]phenyl]-1-piperidyl]ethyl]-3-oxo-piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[1-[4-[(2,6-dioxo-3-piperidyl)amino]phenyl]-4-piperidyl]ethyl]-3-oxo-piperazin-1-yl]-3-pyridyl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]-1-piperidyl]ethyl]-4-hydroxy-1-piperidyl]pyrimidin-5-yl]-3-[3-[[ethyl(methyl)sulfamoyl]amino]-2,6-difluoro-benzoyl]-1H-pyrrolo[2,3-b]pyridine;

5-[[4-[4-[(2,6-dioxo-3-piperidyl)amino]phenyl]-1-piperidyl]methyl]-2-[5-[3-[3-[[ethyl(methyl)sulfamoyl]amino]-2,6-difluoro-benzoyl]-1H-pyrrolo[2,3-b]pyridin-5-yl]pyrimidin-2-yl]-3,4-dihydro-1H-isoquinoline;

5-[2-[6-[4-[4-[(2,6-dioxo-3-piperidyl)amino]phenyl]-1-piperidyl]-2-azaspiro[3.3]heptan-2-yl]pyrimidin-5-yl]-3-[3-[[ethyl(methyl)sulfamoyl]amino]-2,6-difluoro-benzoyl]-1H-pyrrolo[2,3-b]pyridine;

5-[4-[(2,6-dioxo-3-piperidyl)amino]phenyl]-2-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]-6,7-dihydro-4H-pyrazolo[4,3-c]pyridine;

5-[2-[4-[4-[4-[4-[(2,6-dioxo-3-piperidyl)amino]phenyl]-1-piperidyl]pyrazol-1-yl]-1-piperidyl]pyrimidin-5-yl]-3-[3-[[ethyl(methyl)sulfamoyl]amino]-2,6-difluoro-benzoyl]-1H-pyrrolo[2,3-b]pyridine;

N-[1-[4-[(2,6-dioxo-3-piperidyl)amino]-2-fluoro-phenyl]-4-piperidyl]-4-[5-[3-[3-[[ethyl(methyl)sulfamoyl]amino]-2-fluoro-benzoyl]-1H-pyrrolo[2,3-b]pyridin-5-yl]-2-pyridyl]piperazine-1-carboxamide;

3[2-chloro-3-[[ethyl(methyl)sulfamoyl]amino]-6-fluoro-benzoyl]-5-[4-[4-[2-[1-[4-[(2,6-dioxo-3-piperidyl)amino]-2-fluoro-phenyl]-4-hydroxy-4-piperidyl]acetyl]piperazin-1-yl]phenyl]-1H-pyrrolo[2,3-b]pyridine;

5-[6-[4-[2-[1-[2-chloro-4-[(2,6-dioxo-3-piperidyl)amino]phenyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[2-[4-[2-[1-[2-chloro-4-[(2,6-dioxo-3-piperidyl)amino]phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[2-[1-[4-(2,6-dioxo-3-piperidyl)-2-fluoro-phenyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[6-[4-[2-[1-[4-(2,6-dioxo-3-piperidyl)-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

6-[4-[(2,6-dioxo-3-piperidyl)amino]phenyl]-2-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]-5,7-dihydro-4H-pyrazolo[3,4-c]pyridine;

5-[2-[4-[2-[1-[4-(2,6-dioxo-3-piperidyl)-2-fluoro-phenyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

3-(2,4-dioxohexahydropyrimidin-1-yl)-6-[4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-hydroxy-1-piperidyl]-1-methyl-indazole;

5-[6-[4-[2-[1-[4-(2,4-dioxohexahydropyrimidin-1-yl)-2-fluoro-phenyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine;

5-[2-[4-[2-[1-[4-(2,4-dioxohexahydropyrimidin-1-yl)-2-fluoro-phenyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine;

5-[2-[4-[2-[1-[4-[[(3S)-2,6-dioxo-3-piperidyl]amino]-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-(2,4-dioxohexahydropyrimidin-1-yl)-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[2-[1-[4-(2,4-dioxohexahydropyrimidin-1-yl)-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[4-[4-[2-[1-[4-(2,4-dioxohexahydropyrimidin-1-yl)-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

3-[2-chloro-3-[[ethyl(methyl)sulfamoyl]amino]-6-fluoro-benzoyl]-5-[6-[4-[2-[1[4-[(2,6-dioxo-3-piperidyl)amino]-2-fluoro-phenyl]-4-hydroxy-4-piperidyl]acetyl]piperazin-1-yl]-3-pyridyl]-1H-pyrrolo[2,3-b]pyridine;

5-[6-[4-[2-[4-[4-(2,6-dioxo-3-piperidyl)-3-oxo-piperazin-1-yl]-3,3-difluoro-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[4-[4-[2-[4-[4-(2,6-dioxo-3-piperidyl)-3-oxo-piperazin-1-yl]-3,3-difluoro-1-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[2-[4-[2-[4-[4-(2,6-dioxo-3-piperidyl)-3-oxo-piperazin-1-yl]-3,3-difluoro-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[4-[[(3R)-2,6-dioxo-3-piperidyl]amino]-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[4-[4-[2-[1-[4-(2,6-dioxo-3-piperidyl)-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[6-[4-[2-[1-[4-[[(3 S)-2,6-dioxo-3-piperidyl]amino]-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[4-[4-[2-[1-[4-[[(3R)-2,6-dioxo-3-piperidyl]amino]-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[4-[4-[2-[1-[4-[[(3 S)-2,6-dioxo-3-piperidyl]amino]-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[3-chloro-4-[4-[2-[1-[4-[(2,6-dioxo-3-piperidyl)amino]-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[1-[1-[2-[1-[4-[(2,6-dioxo-3-piperidyl)amino]-2-fluoro-phenyl]-4-hydroxy-4-piperidyl]acetyl]-4-piperidyl]-2-oxo-4-pyridyl]-3-[3-[[ethyl(methyl)sulfamoyl]amino]-2,6-difluoro-benzoyl]-1H-pyrrolo[2,3-b]pyridine;

5-[2-[4-[[1-[4-[(2,6-dioxo-3-piperidyl)amino]-2-fluoro-phenyl]-4-piperidyl]methoxy]-1-piperidyl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[2-[1-[4-[(2,6-dioxo-3-piperidyl)amino]-3-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[4-[4-[2-[1-[4-[(2,6-dioxo-3-piperidyl)amino]-3-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

3-[6-chloro-3-[[ethyl(methyl)sulfamoyl]amino]-2-fluoro-benzoyl]-5-[2-[4-[2-[1-[4-[(2,6-dioxo-3-piperidyl)amino]-2-fluoro-phenyl]-4-hydroxy-4-piperidyl]acetyl]piperazin-1-yl]pyrimidin-5-yl]-1H-pyrrolo[2,3-b]pyridine;

5-[5-cyano-6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[5-[4-[2-[1-[4-[(2,6-dioxo-3-piperidyl)amino]-2-fluoro-phenyl]-4-hydroxy-4-piperidyl]acetyl]piperazin-1-yl]pyrazin-2-yl]-3-[3-[[ethyl(methyl)sulfamoyl]amino]-2,6-difluoro-benzoyl]-1H-pyrrolo[2,3-b]pyridine;

5-[6-[4-[2-[1-[4-[(2,6-dioxo-3-piperidyl)amino]-2-fluoro-phenyl]-4-hydroxy-4-piperidyl]acetyl]piperazin-1-yl]-5-fluoro-3-pyridyl]-3-[3-[[ethyl(methyl)sulfamoyl]amino]-2,6-difluoro-benzoyl]-1H-pyrrolo[2,3-b]pyridine;

5-[4-[4-[2-[1-[4-[(2,6-dioxo-3-piperidyl)amino]-2-fluoro-phenyl]-4-hydroxy-4-piperidyl]acetyl]piperazin-1-yl]-2-methyl-phenyl]-3-[3-[[ethyl(methyl)sulfamoyl]amino]-2,6-difluoro-benzoyl]-1H-pyrrolo[2,3-b]pyridine;

(3R)—N-[3-[5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-1H-pyrrolo[2,3-b]pyridine-3-carbonyl]-2,4-difluoro-phenyl]-3-fluoro-pyrrolidine-1-sulfonamide;

(3R)—N-[3-[5-[4-[4-[2-[1-[4-[(2,6-dioxo-3-piperidyl)amino]-2-fluoro-phenyl]-4-hydroxy-4-piperidyl]acetyl]piperazin-1-yl]phenyl]-1H-pyrrolo[2,3-b]pyridine-3-carbonyl]-2,4-difluoro-phenyl]-3-fluoro-pyrrolidine-1-sulfonamide;

5-[4-[4-[2-[1-[4-[(2,6-dioxo-3-piperidyl)amino]-2-fluoro-phenyl]-4-hydroxy-4-piperidyl]acetyl]piperazin-1-yl]-3-methyl-phenyl]-3-[3-[[ethyl(methyl)sulfamoyl]amino]-2,6-difluoro-benzoyl]-1H-pyrrolo[2,3-b]pyridine;

3-(2,4-dioxohexahydropyrimidin-1-yl)-6-[4-[2-[4-[5-[3-[3-[[ethyl(methyl)sulfamoyl]amino]-2,6-difluoro-benzoyl]-1H-pyrrolo[2,3-b]pyridin-5-yl]-2-pyridyl]piperazin-1-yl]-2-oxo-ethyl]-4-hydroxy-1-piperidyl]-1-methyl-indazole;

5-[6-[4-[2-[1-[4-(2,4-dioxohexahydropyrimidin-1-yl)-2-fluoro-phenyl]-4-hydroxy-4-piperidyl]acetyl]piperazin-1-yl]-5-fluoro-3-pyridyl]-3-[3-[[ethyl(methyl)sulfamoyl]amino]-2,6-difluoro-benzoyl]-1H-pyrrolo[2,3-b]pyridine;

5-[4-[4-[2-[1-[4-[(2,6-dioxo-3-piperidyl) amino]-2-fluoro-phenyl]-4-hydroxy-4-piperidyl]acetyl]piperazin-1-yl]-3,5-difluoro-phenyl]-3-[3-[[ethyl(methyl)sulfamoyl]amino]-2,6-difluoro-benzoyl]-1H-pyrrolo[2,3-b]pyridine;

5-[2-[6-[1-[4-[(2,6-dioxo-3-piperidyl)amino]-2-fluoro-phenyl]-4-piperidyl]-6-hydroxy-2-azaspiro[3.3]heptan-2-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[2-[1-[2-(difluoromethyl)-4-[(2,6-dioxo-3-piperidyl)amino]phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[4-[4-[2-[1-[4-[(2,6-dioxo-3-piperidyl)amino]-2-fluoro-phenyl]-4-hydroxy-4-piperidyl]acetyl]piperazin-1-yl]-3-fluoro-phenyl]-3-[3-[[ethyl(methyl)sulfamoyl]amino]-2,6-difluoro-benzoyl]-1H-pyrrolo[2,3-b]pyridine;

5-[2-[6-[1-[4-[(2,6-dioxo-3-piperidyl)amino]-2-fluoro-phenyl]-4-piperidyl]-2-azaspiro[3.3]heptan-2-yl]pyrimidin-5-yl]-3-[3-[[ethyl(methyl)sulfamoyl]amino]-2,6-difluoro-benzoyl]-1H-pyrrolo[2,3-b]pyridine;

5-[3-(difluoromethyl)-4-[4-[2-[1-[4-[(2,6-dioxo-3-piperidyl)amino]-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

3-[6-chloro-3-[[ethyl(methyl)sulfamoyl]amino]-2-fluoro-benzoyl]-5-[6-[4-[2-[2-[4-[(2,6-dioxo-3-piperidyl)amino]-2-fluoro-phenyl]-4-hydroxy-4-piperidyl]acetyl]piperazin-1-yl]-3-pyridyl]-1H-pyrrolo[2,3-b]pyridine;

3-(2,4-dioxohexahydropyrimidin-1-yl)-6-[4-[2-[4-[4-[3-[3-[[ethyl(methyl)sulfamoyl]amino]-2,6-difluoro-benzoyl]-1H-pyrrolo[2,3-b]pyridin-5-yl]phenyl]piperazin-1-yl]-2-oxo-ethyl]-4-hydroxy-1-piperidyl]-1-methyl-indazole;

5-[2-[2-[1-[4-[(2,6-dioxo-3-piperidyl)amino]-2-fluoro-phenyl]-4-piperidyl]-2,6-diazaspiro[3.3]heptan-6-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[1-[2-(difluoromethyl)-4-[(2,6-dioxo-3-piperidyl)amino]phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[2-[1-[4-(2,6-dioxo-3-piperidyl)-2-fluoro-phenyl]-4-hydroxy-4-piperidyl]acetyl]piperazin-1-yl]-5-fluoro-3-pyridyl]-3-[3-[[ethyl(methyl)sulfamoyl]amino]-2,6-difluoro-benzoyl]-1H-pyrrolo[2,3-b]pyridine;

5-[2-[4-[2-[1-[2-chloro-4-[[(3S)-2,6-dioxo-3-piperidyl]amino]phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-3-[3-[[ethyl(methyl)sulfamoyl]amino]-2,5-difluoro-benzoyl]-1H-pyrrolo[2,3-b]pyridine;

5-[6-[4-[2-[1-[2-chloro-4-[[(3 S)-2,6-dioxo-3-piperidyl]amino]phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[2-[4-[2-[1-[2-chloro-4-[[(3R)-2,6-dioxo-3-piperidyl]amino]phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[4-[4-[2-[1-[4-[(2,6-dioxo-3-piperidyl)amino]-2-fluoro-phenyl]-4-hydroxy-4-piperidyl]acetyl]piperazin-1-yl]-2-fluoro-phenyl]-3-[3-[[ethyl(methyl)sulfamoyl]amino]-2,6-difluoro-benzoyl]-1H-pyrrolo[2,3-b]pyridine;

5-[6-[4-[2-[1-[4-[(2,6-dioxo-3-piperidyl)amino]-2-fluoro-phenyl]-4-hydroxy-4-piperidyl]acetyl]piperazin-1-yl]-5-methylsulfonyl-3-pyridyl]-3-[3-[[ethyl(methyl)sulfamoyl]amino]-2,6-difluoro-benzoyl]-1H-pyrrolo[2,3-b]pyridine;

5-[4-[4-[2-[1-[4-[(2,6-dioxo-3-piperidyl)amino]-2-fluoro-phenyl]-4-hydroxy-4-piperidyl]acetyl]piperazin-1-yl]-3-(trifluoromethyl)phenyl]-3-[3-[[ethyl(methyl)sulfamoyl]amino]-2,6-difluoro-benzoyl]-1H-pyrrolo[2,3-b]pyridine;

5-[2-[4-[2-[1-[2-chloro-4-(2,4-dioxohexahydropyrimidin-1-yl)phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[2-[1-[2-chloro-4-(2,4-dioxohexahydropyrimidin-1-yl)phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[1-[2-chloro-4-(2,4-dioxohexahydropyrimidin-1-yl)-5-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[2-[4-[2-[1-[2-chloro-4-(2,4-dioxohexahydropyrimidin-1-yl)-5-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

3-[3-[[cyclopropyl(methyl)sulfamoyl]amino]-2,6-difluoro-benzoyl]-5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-1H-pyrrolo[2,3-b]pyridine;

5-[6-[4-[2-[1-[2,5-dichloro-4-(2,4-dioxohexahydropyrimidin-1-yl)phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[1-[5-chloro-4-(2,4-dioxohexahydropyrimidin-1-yl)-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[1-[4-(2,4-dioxohexahydropyrimidin-1-yl)-2,5-difluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[4-[4-[2-[1-[4-[(2,6-dioxo-3-piperidyl)amino]-2-fluoro-phenyl]-4-hydroxy-4-piperidyl]acetyl]piperazin-1-yl]-2,5-difluoro-phenyl]-3-[3-[[ethyl(methyl)sulfamoyl]amino]-2,6-difluoro-benzoyl]-1H-pyrrolo[2,3-b]pyridine;

5-[6-[4-[2-[4-[4-[(2,6-dioxo-3-piperidyl)oxy]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[4-[4-[4-[(2,6-dioxo-3-piperidyl)oxy]phenyl]-1-piperidyl]butanoyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[4-[4-[(2,6-dioxo-3-piperidyl)oxy]phenyl]-1-piperidyl]-2-oxo-ethyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[4-[[4-[4-[4-[(2,6-dioxo-3-piperidyl)oxy]phenyl]piperazine-1-carbonyl]piperazin-1-yl]methyl]phenyl]-3-[3-[[ethyl(methyl)sulfamoyl]amino]-2,6-difluoro-benzoyl]-1H-pyrrolo[2,3-b]pyridine;

5-[6-[4-[4-[4-[4-[(2,6-dioxo-3-piperidyl)oxy]phenyl]-1-piperidyl]-4-oxo-butyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)oxy]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[[4-[2-[4-[4-[(2,6-dioxo-3-piperidyl)amino]phenyl]-1-piperidyl]acetyl]piperazin-1-yl]methyl]-3-pyridyl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[[4-[2-[4-[4-[(2,6-dioxo-3-piperidyl)amino]phenyl]piperazin-1-yl]acetyl]piperazin-1-yl]methyl]-3-pyridyl]-3-[3-[[ethyl(methyl)sulfamoyl]amino]-2,6-difluoro-benzoyl]-1H-pyrrolo[2,3-b]pyridine;

5-[4-[[4-[1-[2-[4-[4-[(2,6-dioxo-3-piperidyl)amino]phenyl]-1-piperidyl]acetyl]-4-piperidyl]piperazin-1-yl]methyl]phenyl]-3-[3-[[ethyl(methyl)sulfamoyl]amino]-2,6-difluoro-benzoyl]-1H-pyrrolo[2,3-b]pyridine;

5-[4-[4-[4-[4-[4-[(2,6-dioxo-3-piperidyl)oxy]phenyl]-1-piperidyl]butanoyl]piperazin-1-yl]phenyl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]piperazin-1-yl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[4-[4-[4-[(2,6-dioxo-3-piperidyl)amino]phenyl]-1-piperidyl]butanoyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[2-[4-[4-[4-[4-[(2,6-dioxo-3-piperidyl)amino]phenyl]-1-piperidyl]butanoyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[4-[[3-[4-[4-[(2,6-dioxo-3-piperidyl)oxy]phenyl]piperazine-1-carbonyl]pyrrolidin-1-yl]methyl]phenyl]-3-[3-[[ethyl(methyl)sulfamoyl]amino]-2,6-difluoro-benzoyl]-1H-pyrrolo[2,3-b]pyridine;

5-[4-[[3-[4-[4-[(2,6-dioxo-3-piperidyl)oxy]phenyl]piperidine-1-carbonyl]pyrrolidin-1-yl]methyl]phenyl]-3-

[3-[[ethyl(methyl)sulfamoyl]amino]-2,6-difluoro-benzoyl]-1H-pyrrolo[2,3-b]pyridine;

5-[6-[[4-[2-[4-[4-[(2,6-dioxo-3-piperidyl)amino]phenyl]-1-piperidyl]-2-oxo-ethyl]piperazin-1-yl]methyl]phenyl]-3-[3-[[ethyl(methyl)sulfamoyl]amino]-2,6-difluoro-benzoyl]-1H-pyrrolo[2,3-b]pyridine 2,2,2-trifluoroacetic acid;

5-[6-[[4-[2-[4-[4-[(2,6-dioxo-3-piperidyl)oxy]phenyl]-1-piperidyl]acetyl]piperazin-1-yl]methyl]phenyl]-3-[3-[[ethyl(methyl)sulfamoyl]amino]-2,6-difluoro-benzoyl]-1H-pyrrolo[2,3-b]pyridine;

5-[6-[[4-[2-[4-[4-[(2,6-dioxo-3-piperidyl)amino]phenyl]-1-piperidyl]acetyl]piperazin-1-yl]methyl]phenyl]-3-[3-[[ethyl(methyl)sulfamoyl]amino]-2,6-difluoro-benzoyl]-1H-pyrrolo[2,3-b]pyridine;

5-[6-[[4-[2-[4-[4-[(2,6-dioxo-3-piperidyl)amino]phenyl]piperazin-1-yl]acetyl]piperazin-1-yl]methyl]phenyl]-3-[3-[[ethyl(methyl)sulfamoyl]amino]-2,6-difluoro-benzoyl]-1H-pyrrolo[2,3-b]pyridine 2,2,2-trifluoroacetic acid;

5-[6-[[4-[2-[4-[3-[(2,6-dioxo-3-piperidyl)amino]phenyl]piperazin-1-yl]acetyl]piperazin-1-yl]methyl]phenyl]-3-[3-[[ethyl(methyl)sulfamoyl]amino]-2,6-difluoro-benzoyl]-1H-pyrrolo[2,3-b]pyridine 2,2,2-trifluoroacetic acid;

5-[6-[[4-[2-[4-[4-[(2,6-dioxo-3-piperidyl)amino]phenyl]-1-piperidyl]butanoyl]piperazin-1-yl]methyl]phenyl]-3-[3-[[ethyl(methyl)sulfamoyl]amino]-2,6-difluoro-benzoyl]-1H-pyrrolo[2,3-b]pyridine 2,2,2-trifluoroacetic acid;

N-[1-[[4-[3-[2,6-difluoro-3-(pyrrolidin-1-ylsulfonylamino)benzoyl]-1H-pyrrolo[2,3-b]pyridin-5-yl]phenyl]methyl]-4-piperidyl]-4-[4-[(2,6-dioxo-3-piperidyl)oxy]phenyl]piperidine-1-carboxamide formic acid;

N-[3-[5-[6-[4-[4-[4-[4-[(2,6-dioxo-3-piperidyl)oxy]phenyl]-1-piperidyl]acetyl]piperazin-1-yl]-3-pyridyl]-1H-pyrrolo[2,3-b]pyridine-3-carbonyl]-2,4-difluoro-phenyl]butane-2-sulfonamide;

5-[4-[[1-[2-[4-[4-[(2,6-dioxo-3-piperidyl)oxy]phenyl]-1-piperidyl]acetyl]-4-piperidyl]oxy]phenyl]-3-[3-[[ethyl(methyl)sulfamoyl]amino]-2,6-difluoro-benzoyl]-1H-pyrrolo[2,3-b]pyridine;

5-[4-[[1-[2-[4-[4-[(2,6-dioxo-3-piperidyl)amino]phenyl]-1-piperidyl]acetyl]-4-piperidyl]oxy]phenyl]-3-[3-[[ethyl(methyl)sulfamoyl]amino]-2,6-difluoro-benzoyl]-1H-pyrrolo[2,3-b]pyridine;

N-[3-[5-[6-[4-[2-[4-[4-[(2,6-dioxo-3-piperidyl)oxy]phenyl]-1-piperidyl]acetyl]piperazin-1-yl]-3-pyridyl]-1H-pyrrolo[2,3-b]pyridine-3-carbonyl]-2,4-difluoro-phenyl]cyclohexanesulfonamide;

N-[3-[5-[6-[4-[2-[4-[4-[(2,6-dioxo-3-piperidyl)amino]phenyl]-1-piperidyl]acetyl]piperazin-1-yl]-3-pyridyl]-1H-pyrrolo[2,3-b]pyridine-3-carbonyl]-2,4-difluoro-phenyl]cyclohexanesulfonamide;

4-[4-[(2,6-dioxo-3-piperidyl)amino]phenyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]piperidine-1-carboxamide formic acid;

5-[6-[4-[3-[4-[4-[(2,6-dioxo-3-piperidyl)oxy]phenyl]-1-piperidyl]propanoyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[4-[4-[2-[4-[4-[(2,6-dioxo-3-piperidyl)amino]phenyl]-1-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[6-[[4-[2-[5-[(2,6-dioxo-3-piperidyl)amino]isoindolin-2-yl]acetyl]piperazin-1-yl]methyl]-3-pyridyl]-3-[3-[[ethyl(methyl)sulfamoyl]amino]-2,6-difluoro-benzoyl]-1H-pyrrolo[2,3-b]pyridine;

2-[4-[(2,6-dioxo-3-piperidyl)amino]phenyl]-N-[2-[4-[5-[3-[3-[[ethyl(methyl)sulfamoyl]amino]-2,6-difluoro-benzoyl]-1H-pyrrolo[2,3-b]pyridin-5-yl]-2-pyridyl]piperazin-1-yl]-2-oxo-ethyl]-N-methyl-acetamide;

4-[5-[(2,6-dioxo-3-piperidyl)amino]-2-pyridyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]piperidine-1-carboxamide formic acid;

4-[4-[(2,6-dioxo-3-piperidyl)amino]phenyl]-N-[1-[5-[3-[3-[[ethyl(methyl)sulfamoyl]amino]-2,6-difluoro-benzoyl]-1H-pyrrolo[2,3-b]pyridin-5-yl]-2-pyridyl]-4-piperidyl]piperidine-1-carboxamide formic acid;

4-[4-[(2,6-dioxo-3-piperidyl)oxy]phenyl]-N-[1-[5-[3-[3-[[ethyl(methyl)sulfamoyl]amino]-2,6-difluoro-benzoyl]-1H-pyrrolo[2,3-b]pyridin-5-yl]-2-pyridyl]-4-piperidyl]piperidine-1-carboxamide formic acid;

5-[2-[1-[2-[4-[4-[(2,6-dioxo-3-piperidyl)amino]phenyl]-1-piperidyl]acetyl]-4-piperidyl]ethynyl]-3-[3-[[ethyl(methyl)sulfamoyl]amino]-2,6-difluoro-benzoyl]-1H-pyrrolo[2,3-b]pyridine;

5-[6-[4-[2-[4-[5-[(2,6-dioxo-3-piperidyl)oxy]-2-pyridyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

N-[3-[5-[4-[4-[2-[4-[4-[(2,6-dioxo-3-piperidyl)amino]phenyl]-1-piperidyl]acetyl]piperazin-1-yl]phenyl]-1H-pyrrolo[2,3-b]pyridine-3-carbonyl]-2,4-difluoro-phenyl]pyrrolidine-1-sulfonamide;

5-[6-[1-[2-[4-[4-[(2,6-dioxo-3-piperidyl)amino]phenyl]-1-piperidyl]acetyl]-4-piperidyl]-3-pyridyl]-3-[3-[[ethyl(methyl)sulfamoyl]amino]-2,6-difluoro-benzoyl]-1H-pyrrolo[2,3-b]pyridine;

N-[3-[5-[4-[4-[2-[4-[4-[(2,6-dioxo-3-piperidyl)oxy]phenyl]-1-piperidyl]acetyl]piperazin-1-yl]phenyl]-1H-pyrrolo[2,3-b]pyridine-3-carbonyl]-2,4-difluoro-phenyl]pyrrolidine-1-sulfonamide;

N-[3-[5-[4-[4-[2-[4-[4-[(2,6-dioxo-3-piperidyl)amino]phenyl]piperazin-1-yl]acetyl]piperazin-1-yl]phenyl]-1H-pyrrolo[2,3-b]pyridine-3-carbonyl]-2,4-difluoro-phenyl]pyrrolidine-1-sulfonamide;

N-[3-[5-[4-[4-[2-[4-[4-[(2,6-dioxo-3-piperidyl)amino]phenyl]-1-piperidyl]acetyl]piperazin-1-yl]phenyl]-1H-pyrrolo[2,3-b]pyridine-3-carbonyl]-2,4-difluoro-phenyl]cyclopentanesulfonamide;

N-[1-[[4-[3-[2,6-difluoro-3-(pyrrolidin-1-ylsulfonylamino)benzoyl]-1H-pyrrolo[2,3-b]pyridin-5-yl]phenyl]methyl]-4-piperidyl]-4-[4-[(2,6-dioxo-3-piperidyl)amino]phenyl]piperidine-1-carboxamide formic acid;

5-[2-[4-[2-[4-[4-[(2,6-dioxo-3-piperidyl)amino]phenyl]-1-piperidyl]-2-methyl-propanoyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

2-[4-[5-[(2,6-dioxo-3-piperidyl)amino]-2-pyridyl]-1-piperidyl]-N-[1-[4-[3-[3-[[ethyl(methyl)sulfamoyl]amino]-2,6-difluoro-benzoyl]-1H-pyrrolo[2,3-b]pyridin-5-yl]phenyl]-4-piperidyl]acetamide formic acid;

2-[4-[5-[(2,6-dioxo-3-piperidyl)amino]-2-pyridyl]-1-piperidyl]-N-[1-[4-[3-[3-[[ethyl(methyl)sulfamoyl]amino]-2,6-difluoro-benzoyl]-1H-pyrrolo[2,3-b]pyridin-5-yl]-2-pyridyl]-4-piperidyl]acetamide formic acid;

2-[4-[5-[(2,6-dioxo-3-piperidyl)amino]-2-pyridyl]-1-piperidyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]acetamide formic acid;

2-[4-[4-[(2,6-dioxo-3-piperidyl)oxy]phenyl]-1-piperidyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]acetamide formic acid;

2-[4-[5-[(2,6-dioxo-3-piperidyl)oxy]-2-pyridyl]-1-piperidyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]acetamide formic acid;

2-[4-[4-[(2,6-dioxo-3-piperidyl)oxy]phenyl]-1-piperidyl]-N-[1-[5-[3-[3-[[ethyl(methyl)sulfamoyl]amino]-2,6-difluoro-benzoyl]-1H-pyrrolo[2,3-b]pyridin-5-yl]-2-pyridyl]-4-piperidyl]acetamide formic acid;

2-[4-[4-[(2,6-dioxo-3-piperidyl)amino]phenyl]-1-piperidyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]acetamide formic acid;

2-[4-[4-[(2,6-dioxo-3-piperidyl)oxy]phenyl]-1-piperidyl]-N-[1-[4-[3-[3-[[ethyl(methyl)sulfamoyl]amino]-2,6-difluoro-benzoyl]-1H-pyrrolo[2,3-b]pyridin-5-yl]phenyl]-4-piperidyl]acetamide formic acid;

2-[4-[5-[(2,6-dioxo-3-piperidyl)oxy]-2-pyridyl]-1-piperidyl]-N-[1-[5-[3-[3-[[ethyl(methyl)sulfamoyl]amino]-2,6-difluoro-benzoyl]-1H-pyrrolo[2,3-b]pyridin-5-yl]phenyl]-4-piperidyl]acetamide formic acid;

2-[4-[5-[(2,6-dioxo-3-piperidyl)oxy]-2-pyridyl]-1-piperidyl]-N-[1-[5-[3-[3-[[ethyl(methyl)sulfamoyl]amino]-2,6-difluoro-benzoyl]-1H-pyrrolo[2,3-b]pyridin-5-yl]-2-pyridyl]-4-piperidyl]acetamide formic acid;

2-[4-[4-[(2,6-dioxo-3-piperidyl)amino]phenyl]-1-piperidyl]-N-[1-[5-[3-[3-[[ethyl(methyl)sulfamoyl]amino]-2,6-difluoro-benzoyl]-1H-pyrrolo[2,3-b]pyridin-5-yl]-2-pyridyl]-4-piperidyl]acetamide formic acid;

2-[4-[4-[(2,6-dioxo-3-piperidyl)amino]phenyl]-1-piperidyl]-N-[1-[4-[3-[3-[[ethyl(methyl)sulfamoyl]amino]-2,6-difluoro-benzoyl]-1H-pyrrolo[2,3-b]pyridin-5-yl]phenyl]-4-piperidyl]acetamide formic acid;

5-[2-[4-[2-[4-[5-[(2,6-dioxo-3-piperidyl)oxy]-2-pyridyl]piperazin-1-yl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[5-[(2,6-dioxo-3-piperidyl)amino]-2-pyridyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)-methyl-amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

3-[3-[[ethyl(methyl)sulfamoyl]amino]-2,6-difluoro-benzoyl]-5-[6-[rac-(1R,5S)-8-[2-[4-[4-[(2,6-dioxo-3-piperidyl)amino]phenyl]-1-piperidyl]acetyl]-3,8-diazabicyclo[3.2.1]octan-3-yl]-3-pyridyl]-1H-pyrrolo[2,3-b]pyridine;

N-[3-[5-[6-[4-[2-[4-[4-[(2,6-dioxo-3-piperidyl)amino]phenyl]piperazin-1-yl]acetyl]piperazin-1-yl]-3- pyridyl]-1H-pyrrolo[2,3-b]pyridine-3-carbonyl]-2,4-difluoro-phenyl]pyrrolidine-1-sulfonamide;

rac-(3R)—N-[3-[5-[4-[4-[2-[4-[4-[(2,6-dioxo-3-piperidyl)amino]phenyl]piperazin-1-yl]acetyl]piperazin-1-yl]phenyl]-1H-pyrrolo[2,3-b]pyridine-3-carbonyl]-2,4-difluoro-phenyl]-3-fluoro-pyrrolidine-1-sulfonamide;

5-[6-[2-[2-[4-[4-[(2,6-dioxo-3-piperidyl)amino]phenyl]piperazin-1-yl]acetyl]-2,6-diazaspiro[3.3]heptan-6-yl]-3-pyridyl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]pyrazol-1-yl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[4-[4-[4-(2,6-dioxo-3-piperidyl)phenyl]-1-piperidyl]butanoyl]piperazin-1-yl]-3-pyridyl]-3-[3-[[ethyl(methyl)sulfamoyl]amino]-2,6-difluoro-benzoyl]-1H-pyrrolo[2,3-b]pyridine;

N-[2,4-difluoro-3-[5-[6-[rac-(1 S,5R)-9-[2-[4-[4-[(2,6-dioxo-3-piperidyl)amino]phenyl]-1-piperidyl]acetyl]-3,9-diazabicyclo[3.3.1]nonan-3-yl]-3-pyridyl]-1H-pyrrolo[2,3-b]pyridine-3-carbonyl]phenyl]pyrrolidine-1-sulfonamide;

N-[3-[5-[4-[4-[2-[4-[4-(2,6-dioxo-3-piperidyl)phenyl]-1-piperidyl]acetyl]piperazin-1-yl]phenyl]-1H-pyrrolo[2,3-b]pyridine-3-carbonyl]-2,4-difluoro-phenyl]pyrrolidine-1-sulfonamide;

N-[2-[4-[4-[(2,6-dioxo-3-piperidyl)amino]phenyl]-1-piperidyl]ethyl]-4-[2-[3-[3-[[ethyl(methyl)sulfamoyl]amino]-2,6-difluoro-benzoyl]-1H-pyrrolo[2,3-b]pyridin-5-yl]ethynyl]benzamide;

5-[2-[4-[2-[4-[4-[(2,4-dioxo-3-azabicyclo[3.1.1]heptan-1-yl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine formic acid;

N-[3-[5-[4-[4-[2-[4-[3-(2,4-dioxohexahydropyrimidin-1-yl)phenyl]-1-piperidyl]acetyl]piperazin-1-yl]phenyl]-1H-pyrrolo[2,3-b]pyridine-3-carbonyl]-2,4-difluoro-phenyl]pyrrolidine-1-sulfonamide;

N-[3-[5-[4-[1-[4-[4-[4-[(2,6-dioxo-3-piperidyl)amino]phenyl]-1-piperidyl]butanoyl]azetidin-3-yl]phenyl]-1H-pyrrolo[2,3-b]pyridine-3-carbonyl]-2,4-difluoro-phenyl]pyrrolidine-1-sulfonamide;

5-[2-[4-[[2-[4-[5-[(2,6-dioxo-3-piperidyl)amino]-2-pyridyl]-1-piperidyl]-2-oxo-ethyl]-methyl-amino]-1-piperidyl]pyrimidin-5-yl]-3-[3-[[ethyl(methyl)sulfamoyl]amino]-2,6-difluoro-benzoyl]-1H-pyrrolo[2,3-b]pyridine formic acid;

5-[2-[4-[2-[4-[4-(2,4-dioxohexahydropyrimidin-1-yl)phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

2-[4-[5-[(2,6-dioxo-3-piperidyl)amino]-2-pyridyl]-1-piperidyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]-N-methyl-acetamide formic acid;

5-[2-[4-[[2-[4-[5-[(2,6-dioxo-3-piperidyl)amino]-2-pyridyl]-1-piperidyl]-2-oxo-ethyl]amino]-1-piperidyl]pyrimidin-5-yl]-3-[3-[[ethyl(methyl)sulfamoyl]amino]-2,6-difluoro-benzoyl]-1H-pyrrolo[2,3-b]pyridine formic acid;

5-[2-[4-[4-[4-[(2,6-dioxo-3-piperidyl)amino]phenyl]piperidine-1-carbonyl]-1-piperidyl]pyrimidin-5-yl]-3-[3-[[ethyl(methyl)sulfamoyl]amino]-2,6-difluoro-benzoyl]-1H-pyrrolo[2,3-b]pyridine;

2-[4-[5-[(2,6-dioxo-3-piperidyl)amino]-2-pyridyl]-1-piperidyl]-N-[1-[5-[3-[3-[[ethyl(methyl)sulfamoyl]amino]-2,6-difluoro-benzoyl]-1H-pyrrolo[2,3-b]pyridin-5-yl]-2-pyridyl]-4-piperidyl]-N-methyl-acetamide; hydrochloride;

5-[4-[4-[[2-[4-[5-[(2,6-dioxo-3-piperidyl)amino]-2-pyridyl]-1-piperidyl]-2-oxo-ethyl]amino]-1-piperidyl]phenyl]-3-[3-[[ethyl(methyl)sulfamoyl]amino]-2,6-difluoro-benzoyl]-1H-pyrrolo[2,3-b]pyridine hydrochloride;

5-[4-[4-[[2-[4-[5-[(2,6-dioxo-3-piperidyl)oxy]-2-pyridyl]-1-piperidyl]-2-oxo-ethyl]amino]-1-piperidyl]phenyl]-3-[3-[[ethyl(methyl)sulfamoyl]amino]-2,6-difluoro-benzoyl]-1H-pyrrolo[2,3-b]pyridine hydrochloride;

5-[4-[4-[[2-[4-[4-[(2,6-dioxo-3-piperidyl)amino]phenyl]-1-piperidyl]-2-oxo-ethyl]amino]-1-piperidyl]phenyl]-3-[3-[[ethyl(methyl)sulfamoyl]amino]-2,6-difluoro-benzoyl]-1H-pyrrolo[2,3-b]pyridine hydrochloride;

5-[4-[4-[[2-[4-[4-[(2,6-dioxo-3-piperidyl)oxy]phenyl]-1-piperidyl]-2-oxo-ethyl]amino]-1-piperidyl]phenyl]-3-[3-[[ethyl(methyl)sulfamoyl]amino]-2,6-difluoro-benzoyl]-1H-pyrrolo[2,3-b]pyridine hydrochloride;

5-[2-[4-[[2-[4-[4-[(2,6-dioxo-3-piperidyl)amino]phenyl]-1-piperidyl]-2-oxo-ethyl]amino]-1-piperidyl]pyrimidin-5-yl]-3-[3-[[ethyl(methyl)sulfamoyl]amino]-2,6-difluoro-benzoyl]-1H-pyrrolo[2,3-b]pyridine hydrochloride;

5-[6-[4-[[2-[4-[4-[(2,6-dioxo-3-piperidyl)amino]-2-pyridyl]-1-piperidyl]-2-oxo-ethyl]-methyl-amino]-1-piperidyl]-3-pyridyl]-3-[3-[[ethyl(methyl)sulfamoyl]amino]-2,6-difluoro-benzoyl]-1H-pyrrolo[2,3-b]pyridine hydrochloride;

5-[2-[4-[[2-[4-[4-[(2,6-dioxo-3-piperidyl)oxy]phenyl]-1-piperidyl]-2-oxo-ethyl]amino]-1-piperidyl]pyrimidin-5-yl]-3-[3-[[ethyl(methyl)sulfamoyl]amino]-2,6-difluoro-benzoyl]-1H-pyrrolo[2,3-b]pyridine formic acid;

5-[2-[4-[2-[4-[4-[[(3R)-2,6-dioxo-3-piperidyl]amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[6-[4-[2-[4-[4-(2,4-dioxohexahydropyrimidin-1-yl)phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

N-[3-[[1-[5-[3-[2,6-difluoro-3-(pyrrolidin-1-ylsulfonylamino)benzoyl]-1H-pyrrolo[2,3-b]pyridin-5-yl]-2-pyridyl]-4-piperidyl]oxy]cyclobutyl]-2-[4-[(2,6-dioxo-3-piperidyl)amino]phenyl]acetamide;

5-[6-[4-[[2-[4-[5-[(2,6-dioxo-3-piperidyl)oxy]-2-pyridyl]-1-piperidyl]-2-oxo-ethyl]amino]-1-piperidyl]-3-pyridyl]-3-[3-[[ethyl(methyl)sulfamoyl]amino]-2,6-difluoro-benzoyl]-1H-pyrrolo[2,3-b]pyridine formic acid;

N-[3-[5-[6-[4-[3-[4-[4-[(2,6-dioxo-3-piperidyl)amino]phenyl]-1-piperidyl]cyclobutanecarbonyl]piperazin-1-yl]-3-pyridyl]-1H-pyrrolo[2,3-b]pyridine-3-carbonyl]-2,4-difluoro-phenyl]propane-2-sulfonamide;

N-[3-[5-[6-[4-[3-[4-[4-(2,4-dioxohexahydropyrimidin-1-yl)phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide;

5-[6-[4-[[2-[4-[4-[(2,6-dioxo-3-piperidyl)oxy]phenyl]-1-piperidyl]-2-oxo-ethyl]amino]-1-piperidyl]-3-pyridyl]-3-[3-[[ethyl(methyl)sulfamoyl]amino]-2,6-difluoro-benzoyl]-1H-pyrrolo[2,3-b]pyridine formic acid;

5-[6-[4-[[2-[4-[4-[(2,6-dioxo-3-piperidyl)amino]phenyl]-1-piperidyl]-2-oxo-ethyl]amino]-1-piperidyl]-3-pyridyl]-3-[3-[[ethyl(methyl)sulfamoyl]amino]-2,6-difluoro-benzoyl]-1H-pyrrolo[2,3-b]pyridine formic acid;

5-[2-[4-[2-[4-[4-[[(3 S)-2,6-dioxo-3-piperidyl]amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-[(2,6-dioxo-3-piperidyl)amino]phenyl]-1-piperidyl]-2-oxo-ethyl]-1-piperidyl]pyrimidin-5-yl]-3-[3-[[ethyl(methyl)sulfamoyl]amino]-2,6-difluoro-benzoyl]-1H-pyrrolo[2,3-b]pyridine;

5-[2-[4-[2-[4-[4-(2,4-dioxohexahydropyrimidin-1-yl)phenyl]-1-piperidyl]-2-oxo-ethyl]-1-piperidyl]pyrimidin-5-yl]-3-[3-[[ethyl(methyl)sulfamoyl]amino]-2,6-difluoro-benzoyl]-1H-pyrrolo[2,3-b]pyridine;

rac-(3R)—N-[3-[5-[6-[2-[2-[4-[4-[(2,6-dioxo-3-piperidyl)oxy]phenyl]-1-piperidyl]acetyl]-2,6-diazaspiro[3.3]heptan-6-yl]-3-pyridyl]-1H-pyrrolo[2,3-b]pyridine-3-carbonyl]-2,4-difluoro-phenyl]-3-fluoro-pyrrolidine-1-sulfonamide;

N-[3-[5-[4-[2-[2-[4-[4-[(2,6-dioxo-3-piperidyl)oxy]phenyl]-1-piperidyl]acetyl]-2,6-diazaspiro[3.3]heptan-6-yl]phenyl]-1H-pyrrolo[2,3-b]pyridine-3-carbonyl]-2,4-difluoro-phenyl]pyrrolidine-1-sulfonamide;

N-[3-[5-[4-[2-[2-[4-[4-[(2,4-dioxo-3-azabicyclo[3.1.1]heptan-1-yl)amino]phenyl]-1-piperidyl]acetyl]-2,6-diazaspiro[3.3]heptan-6-yl]phenyl]-1H-pyrrolo[2,3-b]pyridine-3-carbonyl]-2,4-difluoro-phenyl]pyrrolidine-1-sulfonamide;

N-[3-[5-[2-[2-[2-[4-[4-(2,6-dioxo-3-piperidyl)phenyl]-1-piperidyl]acetyl]-2,6-diazaspiro[3.3]heptan-6-yl]pyrimidin-5-yl]-1H-pyrrolo[2,3-b]pyridine-3-carbonyl]-2,4-difluoro-phenyl]pyrrolidine-1-sulfonamide;

N-[3-[5-[2-[2-[2-[4-[4-[(2,6-dioxo-3-piperidyl)oxy]phenyl]-1-piperidyl]acetyl]-2,6-diazaspiro[3.3]heptan-6-yl]pyrimidin-5-yl]-1H-pyrrolo[2,3-b]pyridine-3-carbonyl]-2,4-difluoro-phenyl]pyrrolidine-1-sulfonamide;

N-[3-[5-[2-[2-[2-[4-[4-[(2,6-dioxo-3-piperidyl)amino]phenyl]-1-piperidyl]acetyl]-2,6-diazaspiro[3.3]heptan-6-yl]pyrimidin-5-yl]-1H-pyrrolo[2,3-b]pyridine-3-carbonyl]-2,4-difluoro-phenyl]pyrrolidine-1-sulfonamide;

5-[6-[4-[2-[4-[4-[[(3 S)-2,6-dioxo-3-piperidyl]oxy]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[6-[4-[2-[4-[4-[[(3R)-2,6-dioxo-3-piperidyl]oxy]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

N-[1-[4-[(2,6-dioxo-3-piperidyl)amino]-2-fluoro-phenyl]-4-piperidyl]-4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazine-1-carboxamide;2,2,2-trifluoroacetic acid;

5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine;

5-[4-[4-[2-[1-[4-[(2,6-dioxo-3-piperidyl)amino]-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine;

5-[2-[4-[2-[1-[4-(2,6-dioxo-3-pi p eri dyl)-2-fluoro-phenyl]-4-hy droxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine; and 5-[6-[4-[2-[1-[4-[[(3R)-2,6-dioxo-3-piperidyl]amino]-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine.

40. A compound according to any one of embodiments 1 to 39, or a pharmaceutically acceptable salt thereof, for use as therapeutically active substance.

41. A pharmaceutical composition comprising a compound according to any one of embodiments 1 to 39, or a pharmaceutically acceptable salt thereof, and a pharmaceutically acceptable carrier.

42. The use of a compound according to any one of embodiments 1 to 39, or a pharmaceutically acceptable salt thereof, for the therapeutic and/or prophylactic treatment of cancer.

43. A compound according to any one of embodiments 1 to 39, or a pharmaceutically acceptable salt thereof, for use in the therapeutic and/or prophylactic treatment of cancer.

44. The use of a compound according to any one of embodiments 1 to 39, or a pharmaceutically acceptable salt thereof, for the preparation of a medicament for the therapeutic and/or prophylactic treatment of cancer.

45. A method for the preparation of a medicament for the therapeutic and/or prophylactic treatment of cancer, which method comprises administering an effective amount of a compound according to any one of embodiments 1 to 39, or a pharmaceutically acceptable salt thereof.

46. A method for the therapeutic and/or prophylactic treatment of cancer, which method comprises administering an effective amount of a compound according to any one of embodiments 1 to 39, or a pharmaceutically acceptable salt thereof, to a patient in need thereof.

47. The invention as hereinbefore described.

General Scheme for Synthesis of Degraders Via Acid Amine Coupling Reaction:

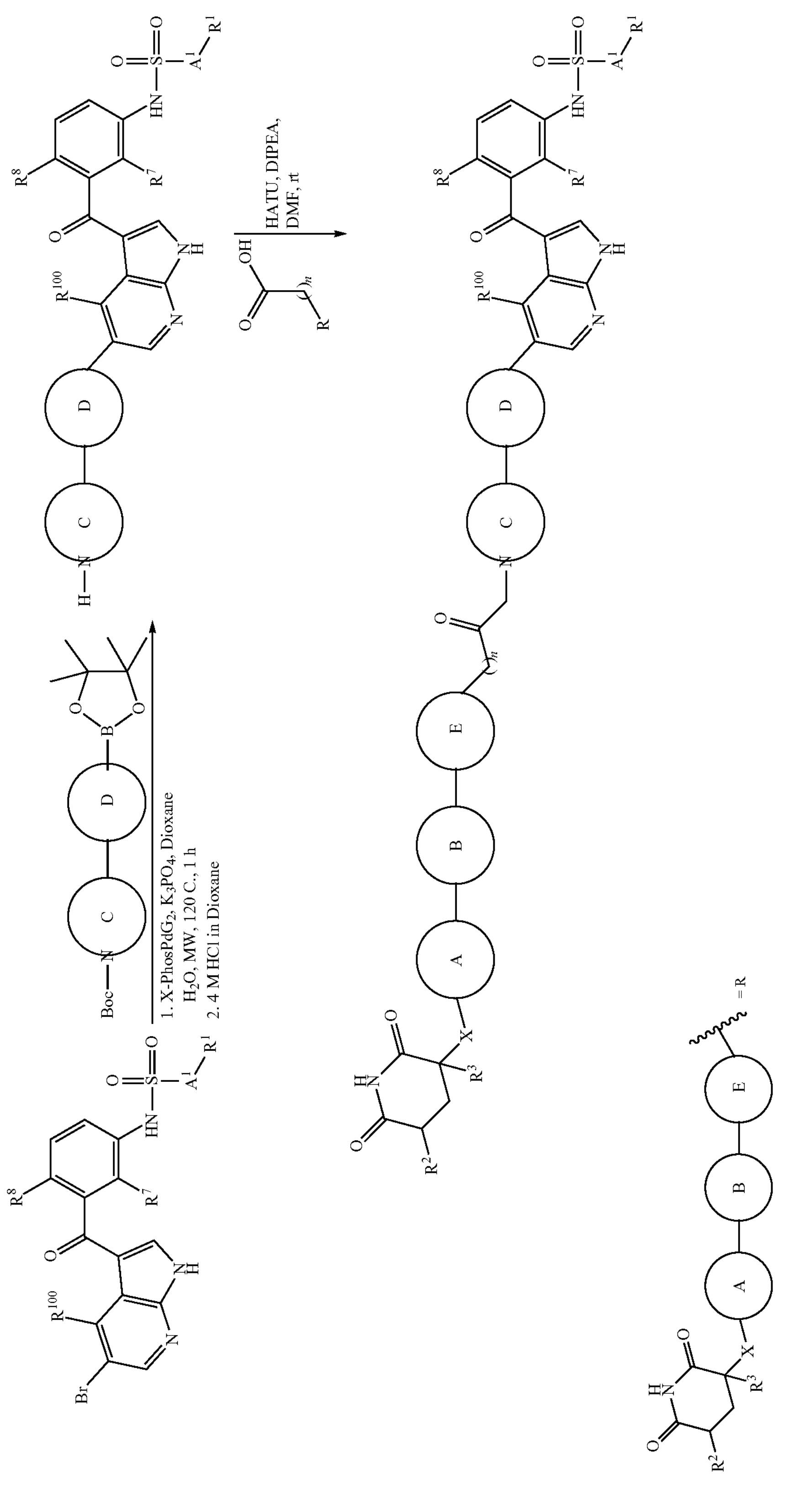
1. X-PhosPdG2, K3PO4, Dioxane
H2O, MW, 120 C., 1 h
2. 4 M HCl in Dioxane
HATU, DIPEA,
DMF, rt Examples of Targeting Ligands Synthesized:
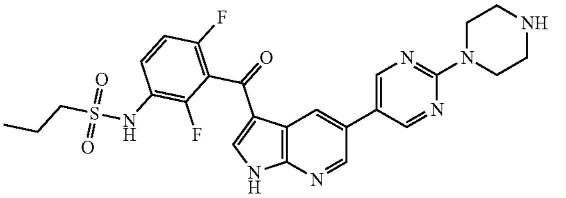
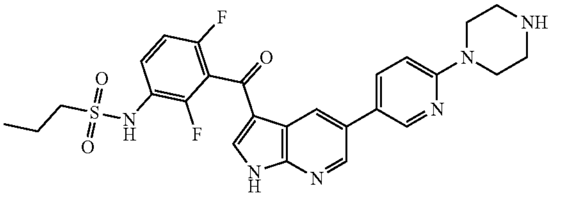
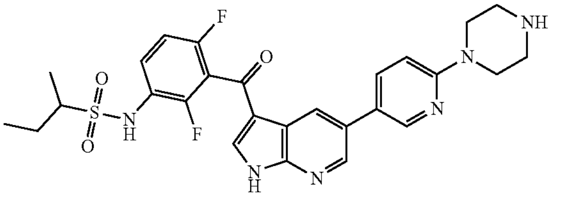
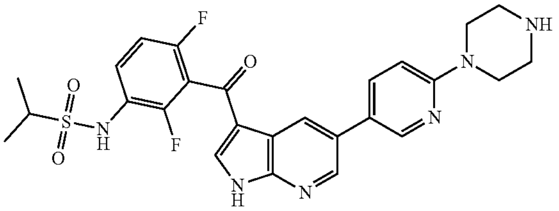
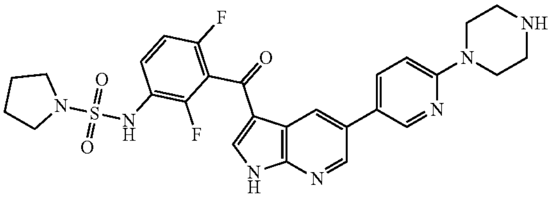
Chiral
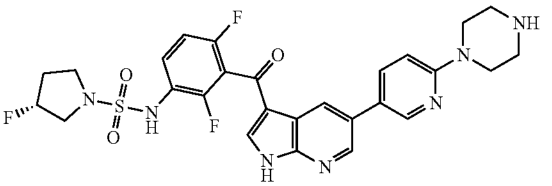
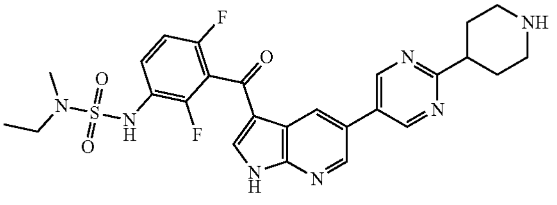
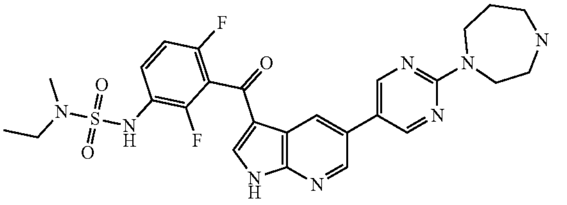
-continued
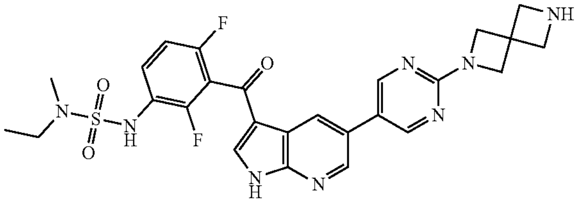
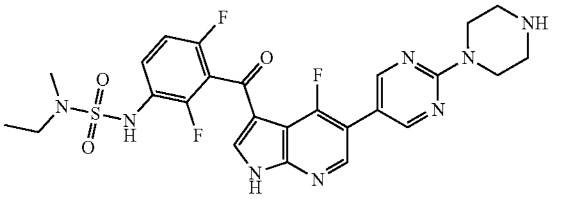
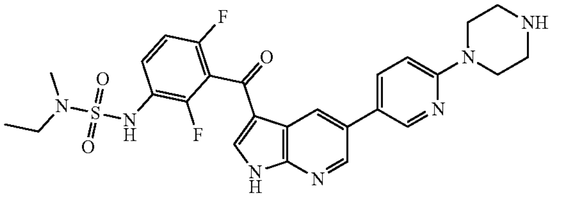
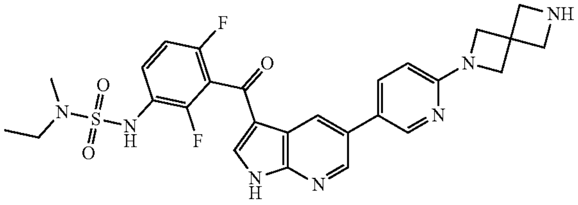
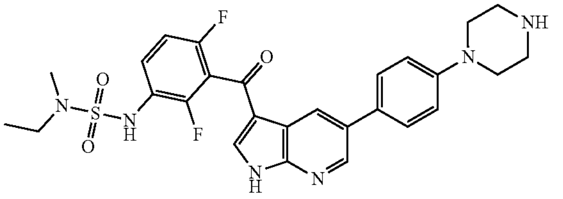
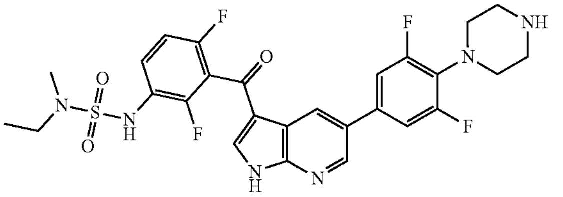
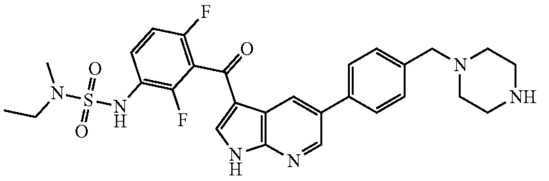
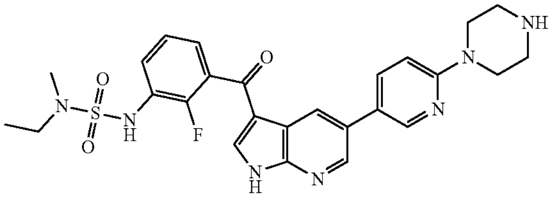

-continued
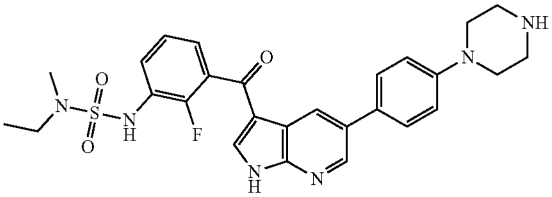
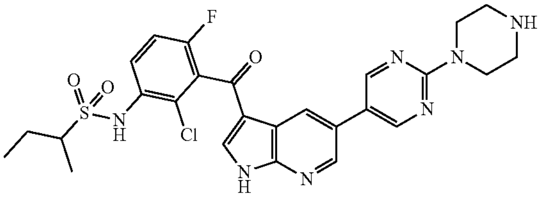
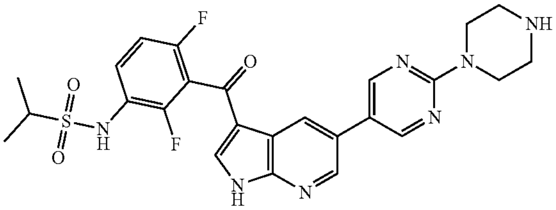
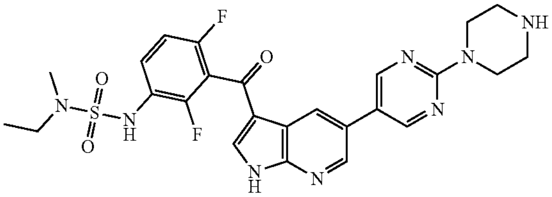
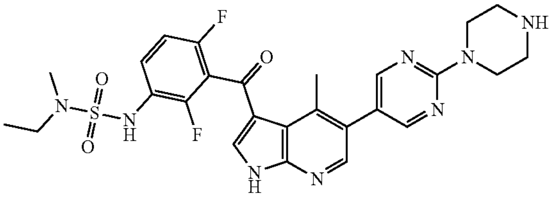
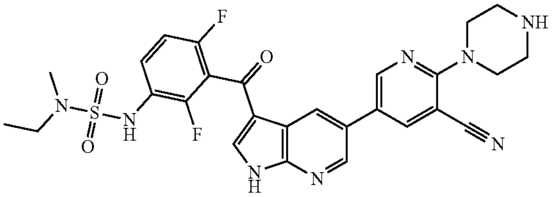
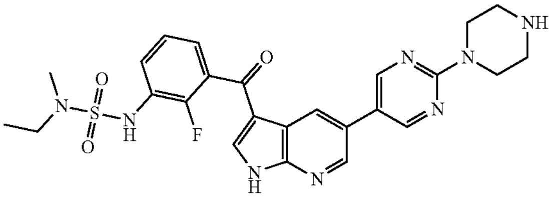
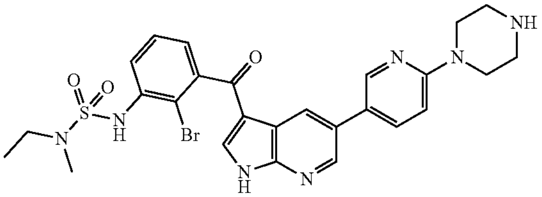
Examples of CRBN Ligands Synthesized:
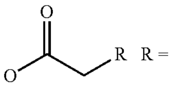
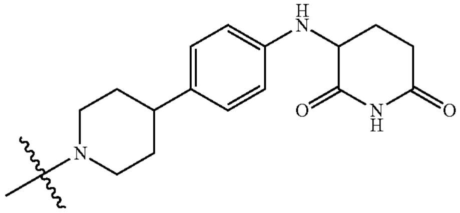
Chiral
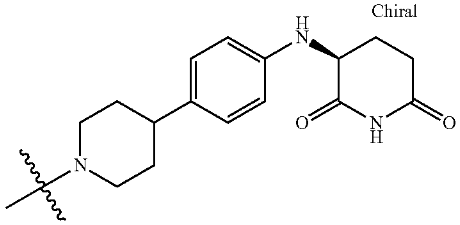
Chiral
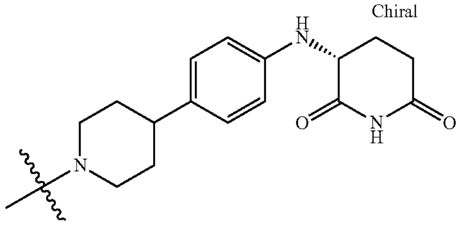
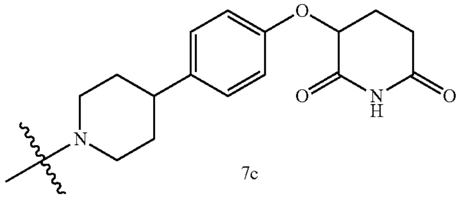
7c
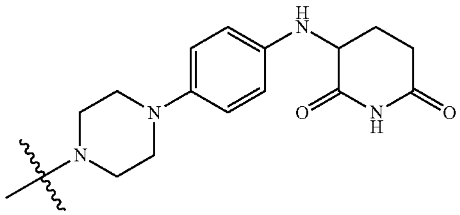
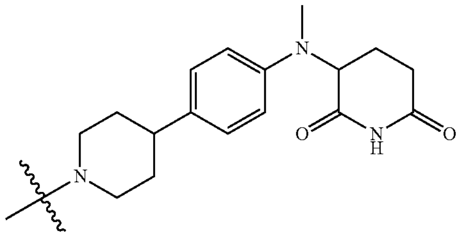
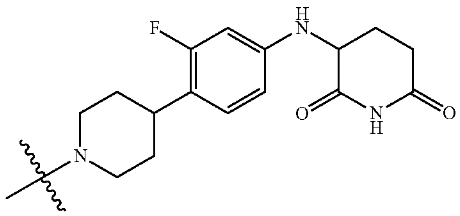

-continued
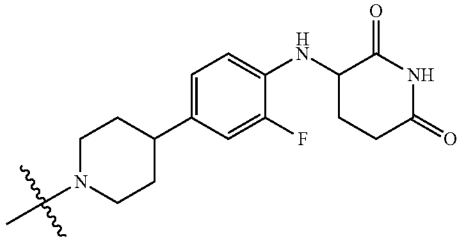
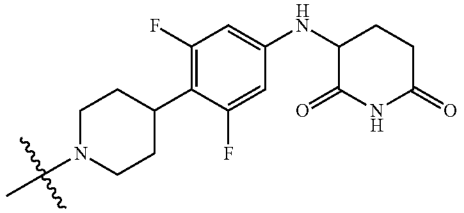
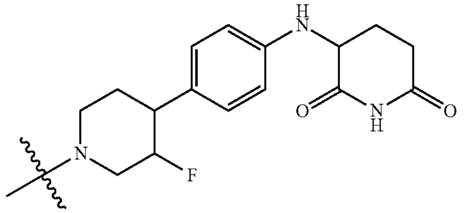
4j
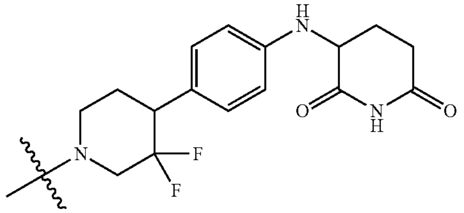
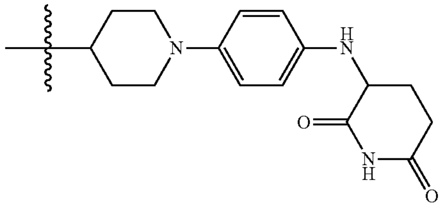
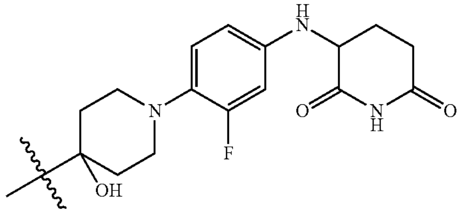
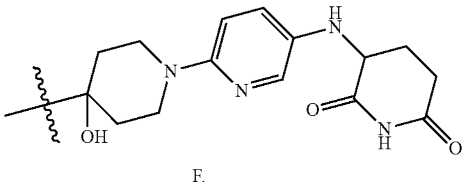
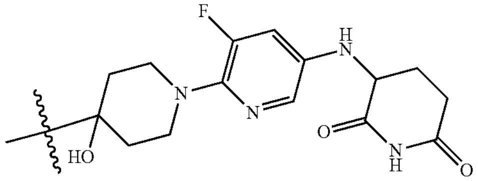
-continued
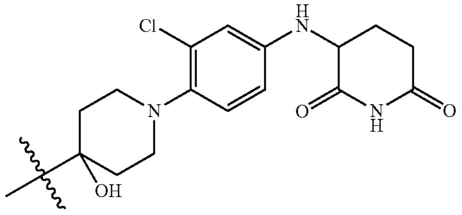
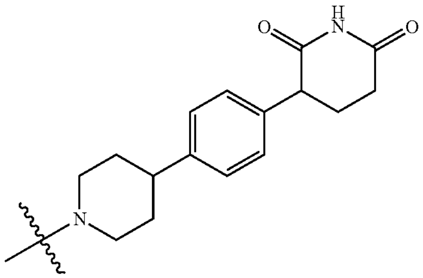
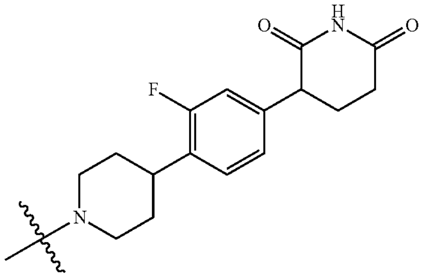
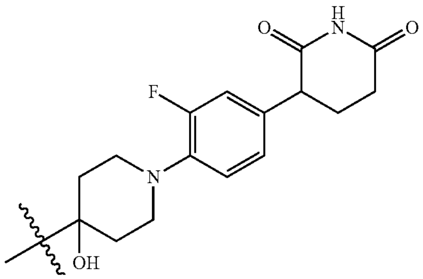
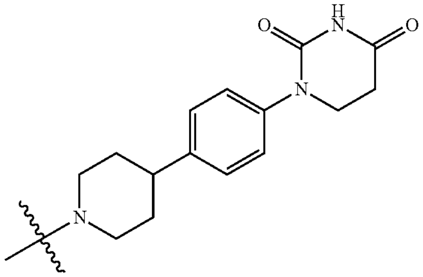
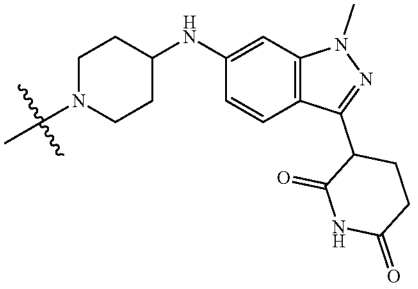

-continued
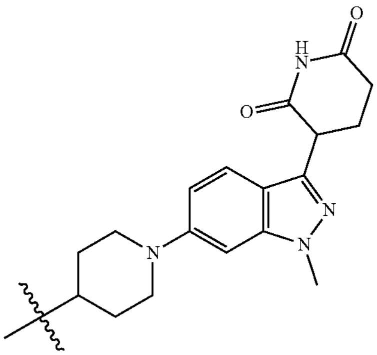
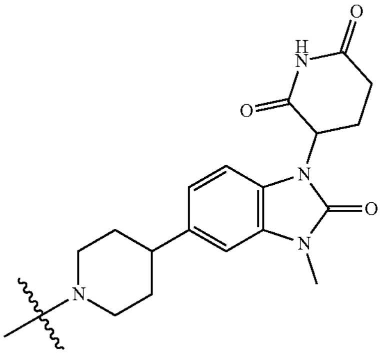
4e
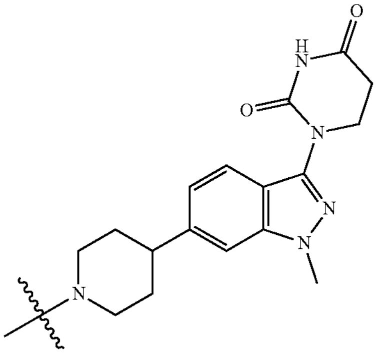
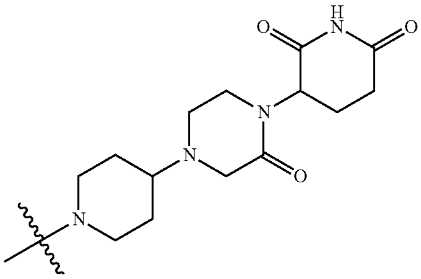
Chiral
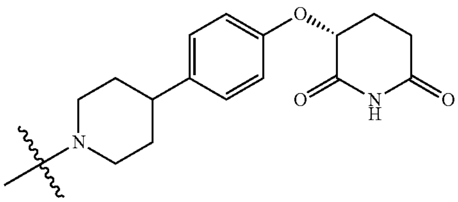
-continued
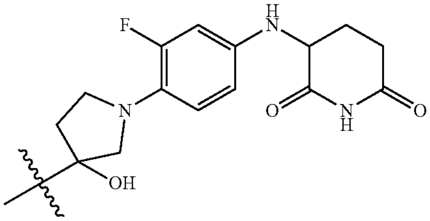
Chiral
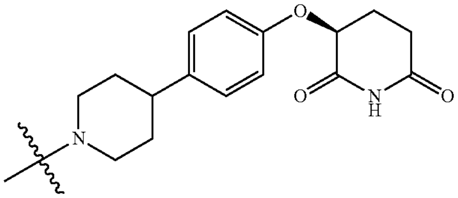
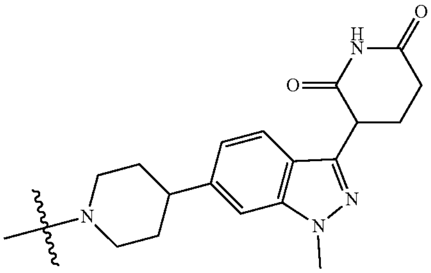
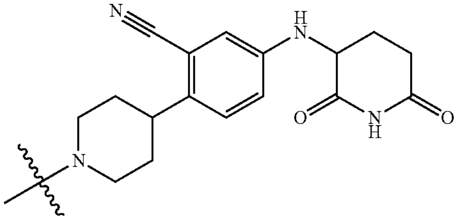
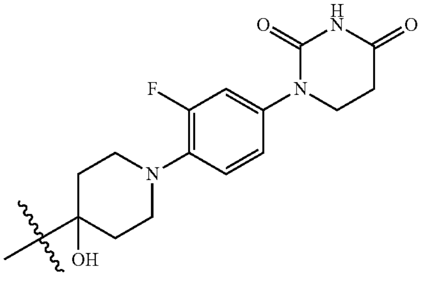
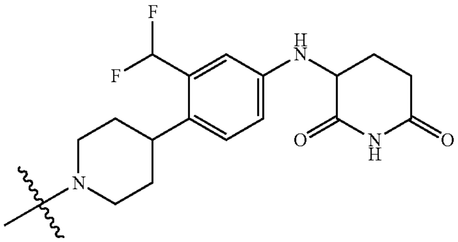

-continued
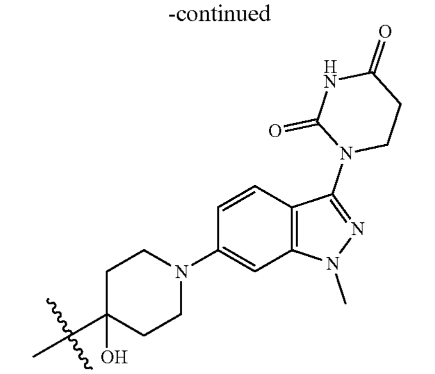
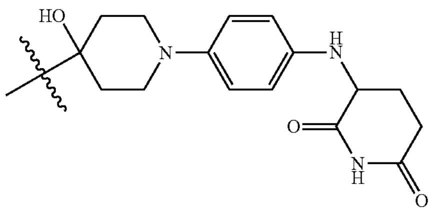
-continued
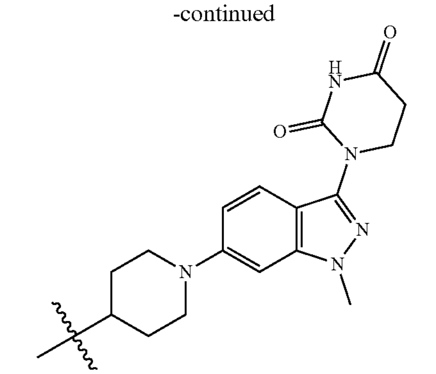
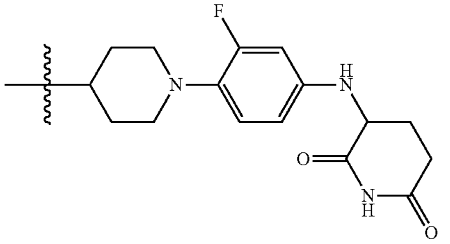
Compounds of formula I, formula II, formula III, formula IV, formula V, formula VI, and formula VII can be prepared according to the following processes. The processes are described in more detail with the following general schemes 1 to 7.
Scheme 1
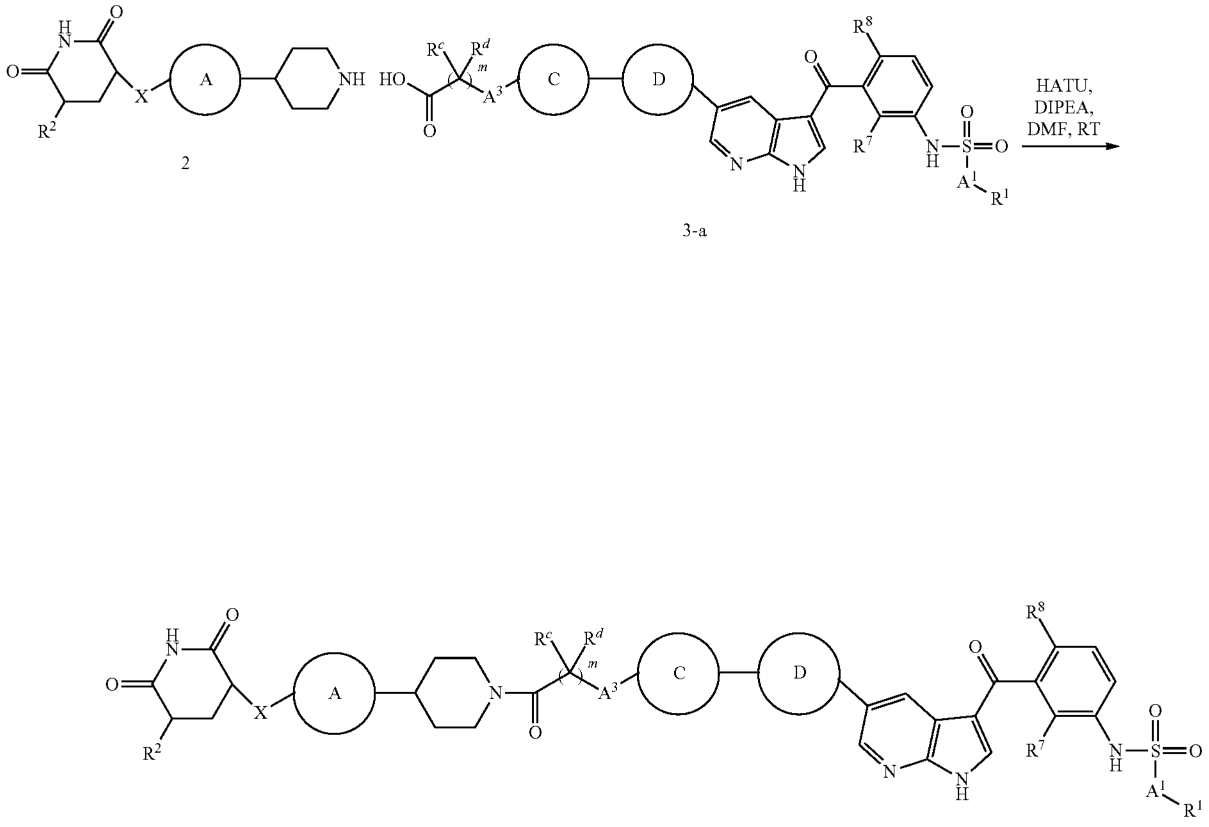
2
3-a
1-a Compounds of the present invention of formula 1-a can be prepared by amide coupling of an appropriately substituted amine of intermediate formula 2 with an appropriately substituted acid of intermediate formula 3-a in a solvent such as N,N-dimethylformamide, a base such as Hunig's Base and a coupling reagent such as HATU. Scheme 1 is hereinafter further illustrated by the general procedure VIII.

Scheme 2

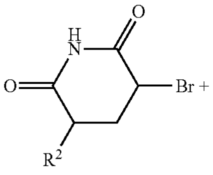

4

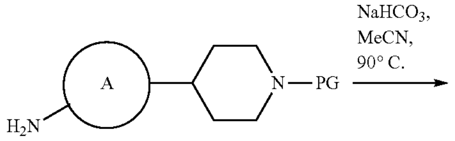

5

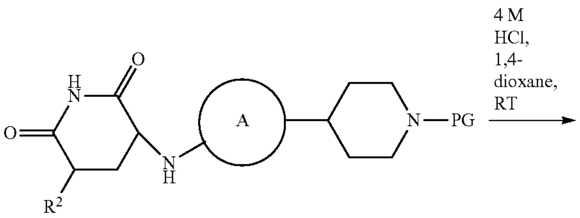

6

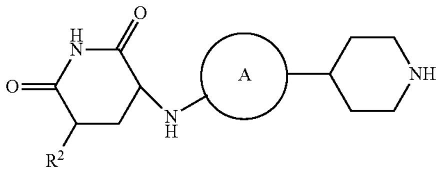

2-a

Compounds of intermediate formula 6 can be prepared by thermal condensation of an appropriately substituted aniline derivative of intermediate formula 5 with bromo-glutarimide of intermediate formula 4 in a solvent such as acetonitrile and a base such as sodium hydrogen carbonate. Aniline derivatives of intermediate formula 5 are either commercially available or can be prepared by methods known in the art or described hereinafter. Compounds of intermediate formula 2-a can be obtained by deprotection with an acid such as hydrogen chloride in a solvent such as 1,4-dioxane or tetrahydrofuran. Scheme 2 is hereinafter further illustrated by the general procedure I.

Scheme 3

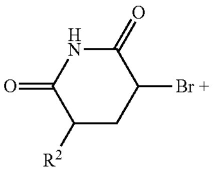

5

-continued

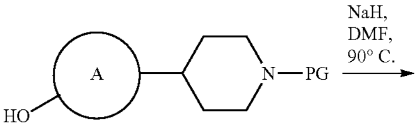

7

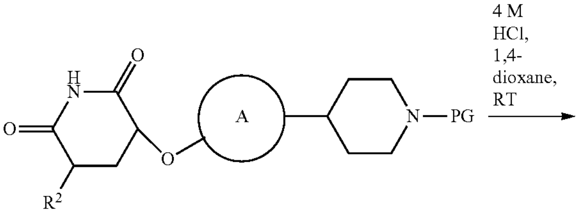

8

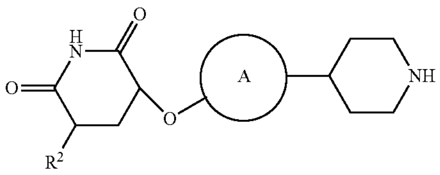

2-b

Compounds of intermediate formula 8 can be prepared by thermal condensation of an appropriately substituted phenol derivative of intermediate formula 7 with bromo-glutarimide of intermediate formula 5 in a solvent such as N,N-dimethylformamide and a base such as sodium hydride. Phenol derivatives of intermediate formula 7 are either commercially available or can be prepared by methods known in the art or described hereinafter. Compounds of intermediate formula 2-b can be obtained by deprotection with an acid such as hydrogen chloride in a solvent such as 1,4-dioxane or tetrahydrofuran. Scheme 3 is hereinafter further illustrated by the general procedure II.

Scheme 4

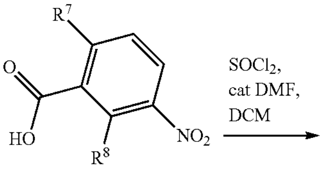

9

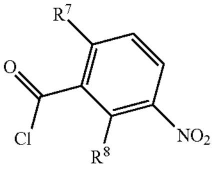

10

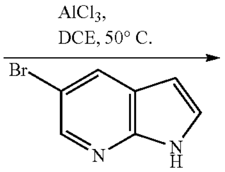

11

-continued

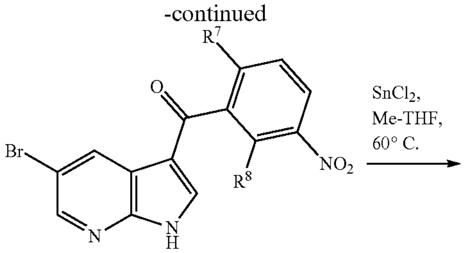

12

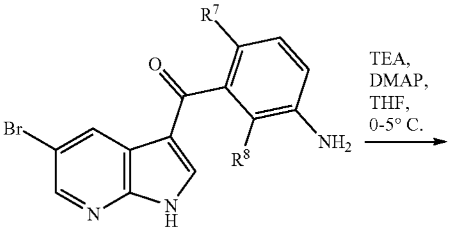

13

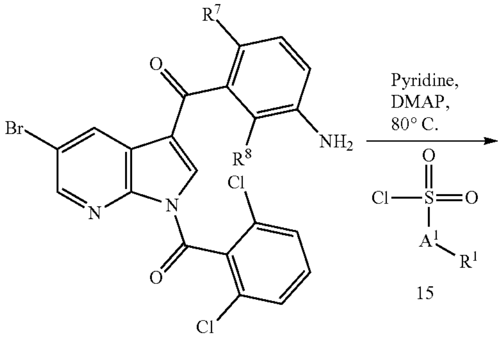

15

14

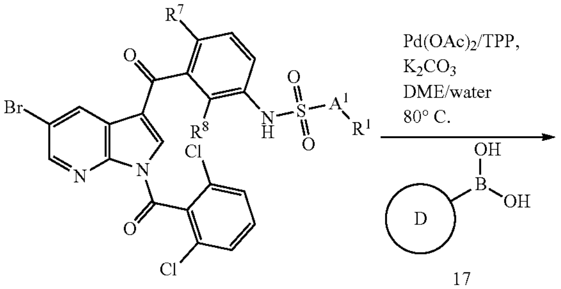

17

16

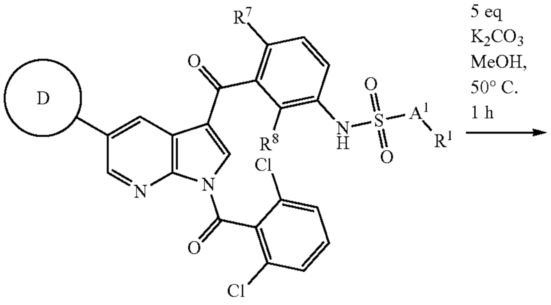

18

-continued

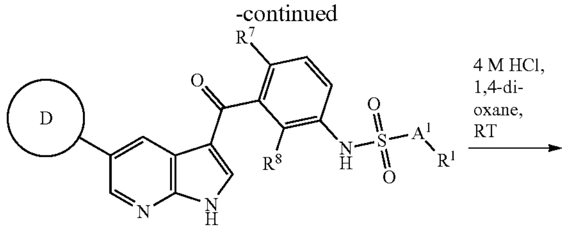

19

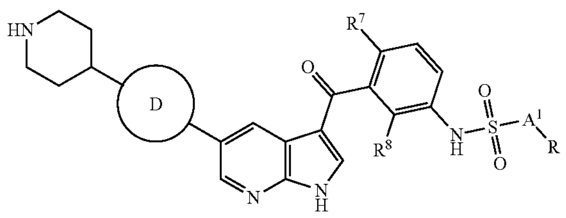

3-b

Intermediates of intermediate formula 3-b can be prepared as described hereinafter: Treatment of an acid intermediate of intermediate formula 9 in a solvent such as dichloromethane and thionyl chloride in the presence of a catalytical amount of N,N-dimethylformamide gives an acid chloride intermediate of intermediate formula 10. Ketone compounds of intermediate formula 12 can be obtained by Friedel Craft's acylation of an intermediate of 11 with an acid chloride intermediate of intermediate formula 10 in a solvent such as 1,2-dichloroethane at 50° C. Ketone intermediates of intermediate formula 12 can be reduced to anilino intermediates of intermediate formula 13 in a solvent such as methyltetrahydrofuran and tin(II) chloride at 60° C. Anilino intermediates of intermediate formula 13 are protected by acylation with 2,5-dichlorobenzoyl chloride in tetrahydrofuran at 0-5° C. using Huenig's Base and a catalytical amount of DMAP. Treatment of a protected intermediate of intermediate formula 14 with a sulfamoyl- or sulfonyl-chloride intermediate of intermediate formula 15 in a solvent such as pyridine at 80° C. gives rise to compounds of intermediate formula 16. Cross coupling of an intermediate of intermediate formula 16 with a boronic acid of intermediate formula 17 in the presence of a palladium catalyst, e.g. formed in situ from palladium acetate and triphenylphosphine, and an inorganic base such as potassium carbonate gives an intermediate of intermediate formula 18. Further deprotection with potassium carbonate in methanol at 50° C. gives an intermediate of intermediate formula 19. Protecting group deprotections can be done by methods known in the art to give intermediates of intermediate formula 3-b. Generally speaking, the sequence of steps used to synthesize the compounds of intermediate formula 3-b can also be modified in certain cases.

Scheme 5

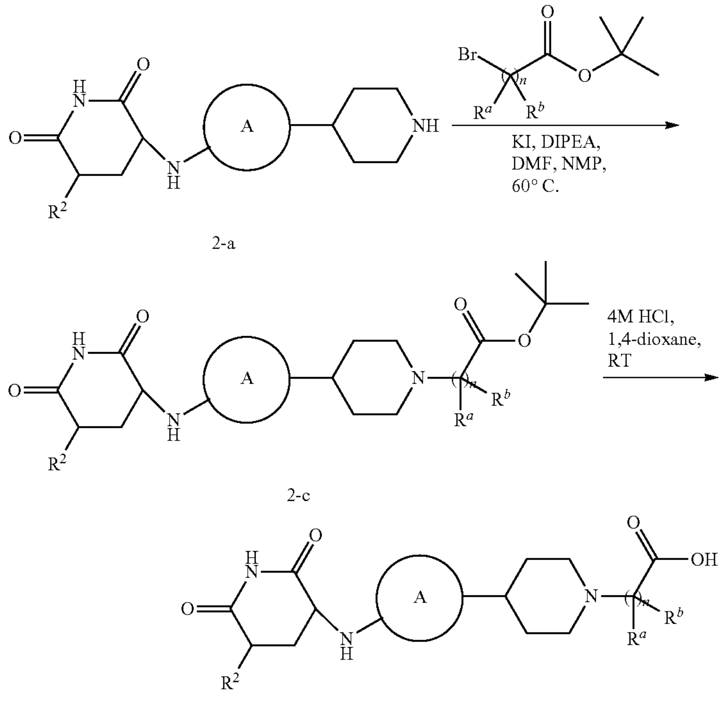

2-a 2-c 2-d

Compounds of intermediate formula 2-c can be prepared from compounds of intermediate formula 2-a by thermal condensation of an alkyl halogenide in a solvent such as N-methylpyrrolidone or N,N-dimethylformamide using potassium iodide and a base such as Hunig's Base. Compounds of intermediate formula 2-d can be obtained by deprotection with an acid such as hydrogen chloride in a solvent such as 1,4-dioxane or tetrahydrofuran. Scheme 5 is hereinafter further illustrated by the general procedure IV.

Scheme 6

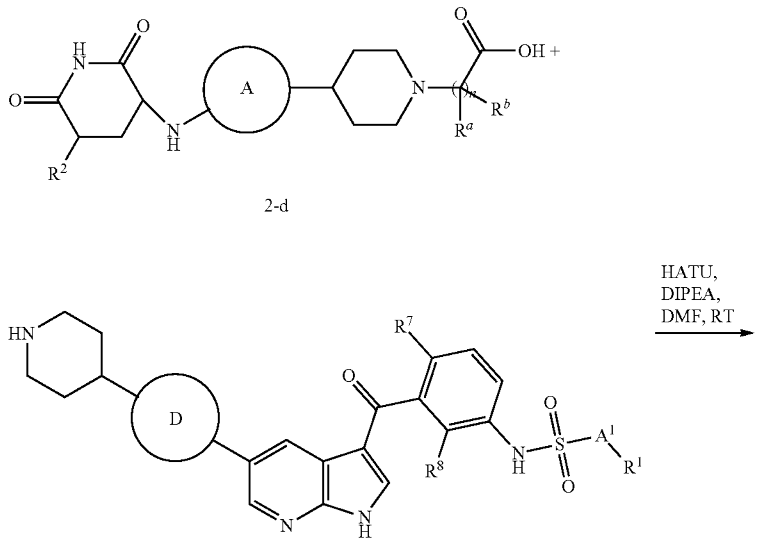

2-d 3-b

-continued

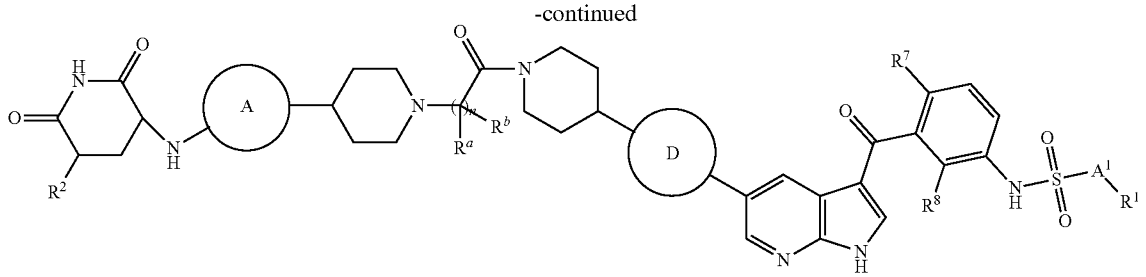

1-b

Compounds of the present invention of formula 1-b can be prepared by amide coupling of an appropriately substituted amine of formula 2-d with an appropriately substituted acid of intermediate formula 3-b in a solvent such as N,N-dimethylformamide, a base such as Hunig's Base and a coupling reagent such as HATU. Scheme 6 is hereinafter further illustrated by the general procedure 8.

Scheme 7

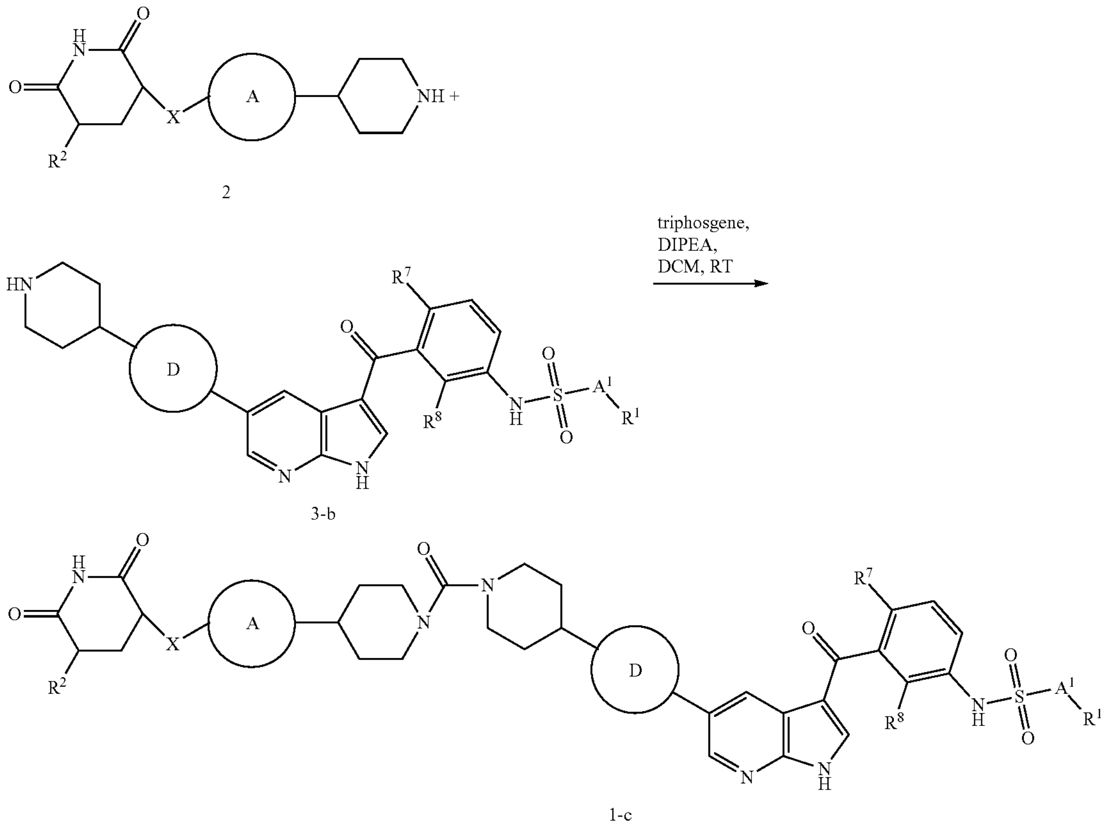

2

3-b 1-c

Compounds of the present invention of formula 1-c can be prepared by treatment of an appropriately substituted amine of intermediate formula 2 with an appropriately substituted amine of intermediate formula 3-b in dichloromethane and a base such as Hunig's Base at room temperature. Generally speaking, the sequence of steps used to synthesize the compounds of intermediate formula 1-c can also be modified in certain cases.

Generally speaking, the sequence of steps used to synthesize the compounds of formula I, formula II, formula III, formula IV, formula V, formula VI, and formula VII can also be modified in certain cases.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I, formula II, formula III, formula IV, formula V, formula VI, and formula VII can be separated using chiral HPLC. Racemic mixtures of chiral synthetic intermediates may also be separated using chiral HPLC.

Salts of Compounds of Formula I, Formula II, Formula III, Formula IV, Formula V, Formula VI, or Formula VII In cases where the compounds of formula I, formula II, formula III, formula IV, formula V, formula VI, or formula VII are basic they may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. A specific salt is the fumarate. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

Insofar as their preparation is not described in the examples, the compounds of formula I, formula II, formula III, formula IV, formula V, formula VI, and formula VII as well as all intermediate products can be prepared according to analogous methods or according to the methods set forth herein. Starting materials are commercially available, known in the art or can be prepared by methods known in the art or in analogy thereto.

It will be appreciated that the compounds of general formula I, formula II, formula III, formula IV, formula V, formula VI, and formula VII in this invention may be derivatised at functional groups to provide derivatives which are capable of conversion back to the parent compound in vivo.

Pharmacological Tests

The compounds of formula I, formula II, formula III, formula IV, formula V, formula VI, and formula VII and their pharmaceutically acceptable salts possess valuable pharmacological properties. The compounds were investigated in accordance with the test given hereinafter.

Materials

DMEM no-phenol red medium supplemented with L-glutamine was purchased from (Corning). Fetal bovine serum (FBS) was purchased from Gibco (Grand Island, NY, USA). Nano-Glo® HiBiT Lytic Assay Buffer & Reagents were purchased from Promega (Madison, WI, USA). A375 (harboring BRAF homozygous V600E mutation) was purchased from ATCC. A375.10 cell line was generated from A375 cell line from ATCC by knocking-in a HiBiT tag at the N-terminal of $BRAF^{V600E}$ protein via CRISPR technology. Cell culture flasks and 384-well black flat-bottom polystyrene TC-treated microplates were acquired from Corning (Corning, NY, USA).

HiBiT Cellular $BRAFv^{600E}$ Degradation Assay

Prior to the assay, the A375.10 cell line is maintained in DMEM no-phenol red medium supplemented with 10% fetal bovine serum (FBS). Following compound treatment, $BRAF^{V600E}$ degradation was determined based on quantification of HiBiT luminescence signal by lysing the cells followed by addition of Nano-Glo® HiBiT Lytic Assay Reagents. The luminescence signal detected correlates with the total $BRAF^{V600E}$ protein level in cells. Briefly, test compounds were added to the 384-well plate from a top concentration of 10 μM with 11 half log dilutions of compound, plated in duplicate. Then, 30 uL of a suspension of A375.10 cell lines was dispensed into columns 1-24 of the 384-well plates at a cell density of 7500 cells per well. The plates were kept at 37° C. with 5% CO2 for the duration of the assay (6 or 24 hr). After the desired incubation time with compound, 30 uL of Nano-Glo® HiBiT Lytic Buffer containing LgBiT protein (diluted 1:100) and luminescence substrate (diluted 1:50) were added to the cells in columns 1-23 of the assay plate. The plate was the incubated for 30 min on the bench at room temperature. Finally, HiBiT luminescence signal was acquired on EnVision™ Multilabel Reader (PerkinElmer, Santa Clara, CA, USA).

Quantification of luminescence responses measured in the presence of compound were normalized to a high signal/no degradation control (untreated cells+lytic detection reagent) and a low signal/full degradation control (untreated cells, no lytic detection reagent). Data were analyzed with a 4-parameter logistic fit to generate sigmoidal dose-response curves. The DC50 is the concentration of compound at which exactly 50% of the total cellular $BRAF^{V600E}$ has been degraded. The Emax, or maximum effect of each compound, represents the amount of residual protein remaining in the cell following compound treatment.

TABLE 1

| | $DC_{50}$ value | |
|---|---|---|
| Ex. | HiBit 24 h DC50 [nM] | HiBit 24 h Emax [%] |
| 1 | 0.79 | 7.81 |
| 2 | 12.23 | 7.81 |
| 3 | 3.04 | 9.60 |
| A29 | 3.05 | 10.89 |
| 5 | 3.94 | 8.80 |
| 6 | 5.59 | 7.96 |
| 7 | 12.55 | 10.31 |
| 8 | 4.67 | 2.37 |
| 9 | 10.68 | 3.41 |
| 10 | 4.45 | 8.46 |
| 11 | 5.08 | 7.97 |
| 12 | 9.73 | 8.03 |
| 13 | 20.88 | 9.56 |
| 14 | 8.56 | 3.41 |
| 15 | 9.59 | 2.65 |
| A72 | 4.47 | 16.13 |
| A75 | 4.46 | 16.16 |
| 18 | 2.85 | 7.93 |
| 19 | 8.57 | 11.26 |
| A54 | 3.94 | 9.71 |
| 21 | 7.10 | 11.87 |
| 22 | 19.36 | 18.02 |
| A78 | 8.93 | 15.44 |
| 24 | 5.59 | 7.88 |
| 25 | 3.63 | 6.36 |
| 26 | 4.55 | 7.00 |
| 27 | 2.09 | 10.81 |
| 28 | 5.81 | 11.97 |
| 29 | 2.76 | 7.67 |

TABLE 1-continued

| DC$_{50}$ value | | |
|---|---|---|
| Ex. | HiBit 24 h DC50 [nM] | HiBit 24 h Emax [%] |
| 30 | 4.27 | 7.84 |
| 31 | 30.02 | 21.16 |
| 32 | 35.02 | 10.63 |
| 33 | 2.51 | 19.18 |
| 34 | 2.52 | 8.14 |
| 35 | 24.96 | 23.10 |
| 36 | 21.03 | 16.12 |
| 37 | 17.25 | 9.14 |
| 38 | 4.44 | 13.41 |
| 39 | 10.22 | 8.74 |
| 40 | 11.68 | 8.42 |
| 41 | 24.51 | 9.48 |
| 42 | 3.41 | 11.49 |
| 43 | 22.07 | 35.21 |
| 44 | 41.28 | 13.24 |
| 45 | 23.65 | 14.24 |
| 46 | 9.10 | 7.88 |
| 47 | 5.38 | 19.29 |
| 48 | 22.98 | 14.99 |
| 49 | 24.92 | 17.54 |
| 50 | 4.57 | 7.42 |
| 51 | 5.51 | 6.09 |
| 52 | 6.44 | 7.57 |
| 53 | 13.29 | 6.35 |
| 54 | 4.72 | 6.94 |
| 55 | 4.61 | 6.57 |
| 56 | 5.12 | 14.27 |
| 57 | 10.10 | 18.16 |
| 58 | 4.25 | 9.42 |
| 59 | 2.41 | 8.84 |
| 60 | 16.60 | 16.00 |
| 61 | 3.75 | 7.83 |
| A46 | 7.44 | 10.75 |
| 63 | 40.17 | 11.84 |
| 64 | 7.21 | 9.33 |
| 65 | 9.97 | 3.79 |
| 66 | 3.06 | 8.10 |
| A7 | 16.81 | 12.94 |
| A8 | 8.18 | 9.42 |
| A11 | 6.71 | 11.57 |
| A37 | 14.64 | 20.65 |
| A47 | 3.86 | 10.66 |
| A82 | 7.65 | 9.60 |
| 73 | 12.29 | 8.05 |
| 74 | 32.53 | 9.07 |
| 75 | 6.26 | 11.57 |
| 76 | 7.81 | 14.24 |
| 77 | 3.49 | 9.19 |
| 78 | 9.89 | 23.28 |
| 79 | 2.13 | 9.51 |
| 80 | 2.97 | 9.93 |
| A76 | 14.91 | 16.87 |
| 82 | 7.57 | 7.60 |
| A14 | 10.62 | 9.74 |
| 84 | 3.14 | 9.62 |
| A80 | 27.52 | 21.60 |
| 86 | 4.29 | 11.83 |
| 87 | 13.26 | 9.64 |
| 88 | 15.69 | 22.21 |
| 89 | 1.40 | 8.60 |
| 90 | 2.13 | 7.44 |
| A44 | 10.40 | 9.52 |
| 92 | 22.93 | 4.78 |
| 93 | 23.79 | 8.31 |
| 94 | 21.20 | 12.76 |
| 95 | 30.40 | 12.78 |
| 96 | 9.43 | 8.26 |
| 97 | 6.62 | 7.94 |
| 98 | 4.67 | 7.42 |
| 99 | 9.55 | 13.22 |
| 100 | 9.52 | 6.76 |
| 101 | 3.38 | 10.16 |
| 102 | 6.88 | 8.28 |

TABLE 1-continued

| DC$_{50}$ value | | |
|---|---|---|
| Ex. | HiBit 24 h DC50 [nM] | HiBit 24 h Emax [%] |
| 103 | 3.04 | 8.98 |
| 104 | 3.37 | 10.79 |
| 105 | 42.25 | 36.90 |
| 106 | 34.84 | 11.46 |
| 107 | 3.08 | 7.97 |
| 108 | 5.60 | 11.44 |
| 109 | 5.49 | 10.79 |
| 110 | 4.47 | 7.75 |
| 111 | 9.66 | 15.63 |
| 112 | 6.46 | 10.78 |
| 113 | 26.27 | 27.68 |
| 114 | 2.29 | 10.88 |
| 115 | 5.13 | 12.18 |
| 116 | 5.32 | 13.36 |
| 117 | 23.07 | 25.27 |
| 118 | 27.19 | 13.39 |
| 119 | 8.71 | 10.53 |
| 120 | 2.87 | 9.99 |
| 121 | 2.30 | 4.98 |
| A114 | 8.83 | 7.68 |
| 123 | 46.42 | 11.68 |
| 124 | 22.11 | 12.98 |
| 125 | 36.08 | 11.01 |
| A83 | 6.97 | 8.89 |
| 127 | 13.18 | 7.62 |
| 128 | 20.90 | 14.61 |
| 129 | 5.11 | 13.78 |
| 130 | 9.73 | 12.88 |
| 131 | 27.08 | 21.19 |
| 132 | 18.16 | 12.01 |
| 133 | 14.69 | 11.38 |
| 134 | 18.87 | 10.99 |
| 135 | 3.94 | 10.23 |
| 136 | 3.26 | 7.37 |
| 137 | 6.93 | 19.33 |
| 138 | 10.48 | 7.71 |
| 139 | 6.89 | 9.49 |
| 140 | 15.22 | 8.77 |
| 141 | 2.84 | 7.91 |
| 142 | 6.94 | 11.70 |
| 143 | 4.04 | 11.52 |
| 144 | 16.08 | 15.62 |
| 145 | 18.93 | 29.51 |
| 146 | 14.37 | 9.32 |
| 147 | 17.16 | 14.62 |
| 148 | 19.80 | 13.93 |
| 149 | 9.25 | 10.57 |
| 150 | 32.82 | 13.32 |
| 151 | 1.85 | 6.38 |
| 152 | 16.60 | 11.89 |
| 153 | 38.16 | 28.82 |
| 154 | 2.94 | 8.25 |
| 155 | 6.33 | 10.94 |
| 156 | 6.82 | 9.35 |
| 157 | 6.19 | 8.52 |
| 158 | 2.73 | 9.38 |
| 158c | 1.99 | 7.84 |
| 158d | 204.83 | 11.60 |
| 158e | 10.81 | 11.72 |
| 159 | 3.51 | 6.33 |
| 160 | 3.12 | 6.70 |
| 161 | 14.55 | 8.46 |
| 162 | 2.09 | 7.81 |
| 163 | 4.52 | 9.67 |
| 164 | 2.31 | 10.20 |
| 165 | 6.27 | 10.78 |
| 166 | 2.82 | 8.90 |
| 167 | 7.05 | 9.37 |
| 168 | 3.00 | 10.24 |
| 169 | 2.82 | 7.34 |
| 170 | 4.59 | 10.51 |
| 171 | 5.87 | 7.61 |
| 172 | 4.67 | 6.28 |

TABLE 1-continued

| DC50 value | | |
|---|---|---|
| Ex. | HiBit 24 h DC50 [nM] | HiBit 24 h Emax [%] |
| 173 | 6.37 | 7.19 |
| 174 | 2.39 | 9.44 |
| 175 | 7.12 | 9.59 |
| 176 | 5.84 | 9.54 |
| 177 | 3.65 | 9.99 |
| 178 | 2.71 | 9.65 |
| 179 | 5.91 | 8.35 |
| 180 | 4.62 | 8.93 |
| 181 | 11.49 | 13.50 |
| 182 | 17.91 | 7.70 |
| 183 | 1.94 | 8.35 |
| 184 | 3.54 | 9.04 |
| 185 | 6.48 | 7.43 |
| 186 | 5.45 | 8.35 |
| 187 | 3.60 | 7.80 |
| 188 | 4.50 | 5.98 |
| 189 | 58.35 | 14.86 |
| 190 | 2.72 | 7.07 |
| 191 | 3.89 | 7.76 |
| 192 | 13.85 | 8.18 |
| 193 | 1.70 | 7.39 |
| 194 | 4.50 | 8.29 |
| 195 | 6.23 | 7.60 |
| 196 | 1.14 | 6.81 |
| 197 | 7.36 | 8.11 |
| 198 | 2.42 | 6.19 |
| 199 | 28.30 | 7.17 |
| 200 | 5.38 | 6.13 |
| 201 | 4.19 | 6.67 |
| 202 | 2.10 | 7.44 |
| 203 | 2.28 | 5.13 |
| 204 | 3.80 | 8.60 |
| 205 | 2.34 | 6.63 |
| 206 | 2.28 | 6.90 |
| 207 | 1.23 | 6.98 |
| 208 | 1.73 | 7.34 |
| 209 | 0.76 | 5.52 |
| 210 | 7.69 | 7.60 |
| 211 | 11.35 | 9.30 |
| 212 | 32.78 | 7.02 |
| 213 | 0.42 | 6.06 |
| 214 | 0.65 | 5.48 |
| 215 | 2.71 | 7.87 |
| 216 | 1.33 | 7.40 |
| 217 | 62.20 | 21.00 |
| 218 | 4.10 | 6.24 |
| 219 | 1.65 | 6.11 |
| 220 | 1.45 | 7.62 |
| 221 | 5.65 | 9.12 |
| A1 | 17.00 | 13 |
| A2 | 66.00 | 22 |
| A3 | 46.00 | 19 |
| A4 | 83.00 | 31 |
| A5 | 104.00 | 34 |
| A6 | 15.00 | 13 |
| A9 | 30.00 | 14 |
| A10 | 3.00 | 8 |
| A12 | 74.00 | 24 |
| A13 | 91.00 | 23 |
| A15 | 24.00 | 14 |
| A16 | 8.00 | 11 |
| A17 | 44.00 | 14 |
| A18 | 42.00 | 15 |
| A19 | 84.00 | 19 |
| A20 | 138.00 | 24 |
| A21 | 21.00 | 13 |
| A22 | 77.00 | 20 |
| A23 | 19.00 | 13 |
| A24 | 30.00 | 13 |
| A25 | 101.00 | 18 |
| A26 | 166.00 | 19 |
| A27 | 104.00 | 30 |
| A28 | 12.00 | 14 |

TABLE 1-continued

| DC50 value | | |
|---|---|---|
| Ex. | HiBit 24 h DC50 [nM] | HiBit 24 h Emax [%] |
| A30 | 53.00 | 13 |
| A31 | 15.00 | 12 |
| A32 | 39.00 | 15 |
| A33 | 34.00 | 13 |
| A34 | 79.00 | 25 |
| A35 | 54.00 | 21 |
| A36 | 3.00 | 10 |
| A38 | 47.00 | 20 |
| A39 | 35.00 | 18 |
| A40 | 8.00 | 17 |
| A41 | 7.00 | 31 |
| A42 | 173.00 | 33 |
| A43 | 57.00 | 32 |
| A45 | 65.00 | 21 |
| A48 | 5.00 | 12 |
| A49 | 17.00 | 11 |
| A50 | 15.00 | 12 |
| A51 | 4.00 | 14 |
| A52 | 10.00 | 12 |
| A53 | 27.00 | 22 |
| A55 | 97.00 | 26 |
| A56 | 20.00 | 11 |
| A57 | 33.00 | 13 |
| A58 | 43.00 | 13 |
| A59 | 60.00 | 13 |
| A60 | 275.00 | 24 |
| A61 | 40.00 | 16 |
| A62 | 8.00 | 18 |
| A63 | 20.00 | 19 |
| A64 | 67.00 | 13 |
| A65 | 151.00 | 18 |
| A66 | 17.00 | 13 |
| A67 | 7.00 | 11 |
| A68 | 50.00 | 11 |
| A69 | 7.00 | 12 |
| A70 | 19.00 | 18 |
| A71 | 28.00 | 23 |
| A73 | 6.00 | 19 |
| A74 | 7.00 | 19 |
| A77 | 47.00 | 31 |
| A79 | 60.00 | 22 |
| A81 | 49.00 | 13 |
| A84 | 11.00 | 11 |
| A85 | 16.00 | 11 |
| A86 | 32.00 | 23 |
| A87 | 6.00 | 7 |
| A88 | 52.00 | 26 |
| A89 | 73.00 | 12 |
| A90 | 31.00 | 20 |
| A91 | 5.00 | 8 |
| A92 | 8.00 | 7 |
| A93 | 16.00 | 14 |
| A94 | 13.00 | 8 |
| A95 | 11.00 | 7 |
| A96 | 18.00 | 9 |
| A97 | 84.00 | 12 |
| A98 | 12.00 | 12 |
| A99 | 32.00 | 9 |
| A100 | 10.00 | 11 |
| A101 | 20.00 | 19 |
| A102 | 33.00 | 12 |
| A103 | 4.00 | 6 |
| A104 | 10.00 | 7 |
| A105 | 24.00 | 30 |
| A106 | 197.00 | 22 |
| A107 | 12.00 | 12 |
| A108 | 14.00 | 8 |
| A109 | 44.00 | 13 |
| A110 | 13.00 | 13 |
| A111 | 4.00 | 7 |
| A112 | 15.00 | 15 |
| A113 | 53.00 | 33 |
| A115 | 204.00 | 15 |

TABLE 1-continued

| DC$_{50}$ value | | |
|---|---|---|
| Ex. | HiBit 24 h DC50 [nM] | HiBit 24 h Emax [%] |
| A116 | 26.00 | 8 |
| A117 | 192.00 | 24 |
| A118 | 29.00 | 11 |
| A119 | 47.00 | 12 |
| A120 | 8.00 | 8 |
| A121 | 12.00 | 8 |
| A122 | 32.00 | 9 |
| A123 | 10.00 | 8 |

Pharmaceutical Compositions

The compounds of formula I, formula II, formula III, formula IV, formula V, formula VI, and formula VII and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I, formula II, formula III, formula IV, formula V, formula VI, and formula VII and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I, formula II, formula III, formula IV, formula V, formula VI, or formula VII or a pharmaceutically acceptable salt thereof and a therapeutically inert carrier are also provided by the present invention, as is a process for their production, which comprises bringing one or more compounds of formula I, formula II, formula III, formula IV, formula V, formula VI, or formula VII and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I, formula II, formula III, formula IV, formula V, formula VI, or formula VII or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I, formula II, formula III, formula IV, formula V, formula VI, or formula VII. Examples of compositions according to the invention are:

Example A

Tablets of the following composition are manufactured in the usual manner:

TABLE 2

| possible tablet composition | | | | |
|---|---|---|---|---|
| | mg/tablet | | | |
| ingredient | 5 | 25 | 100 | 500 |
| Compound of formula I, formula II, formula III, formula IV, formula V, formula VI, or formula VII | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 3

| possible capsule ingredient composition | | | | |
|---|---|---|---|---|
| | mg/capsule | | | |
| ingredient | 5 | 25 | 100 | 500 |
| Compound of formula I, formula II, formula III, formula IV, formula V, formula VI, or formula VII | 5 | 25 | 100 | 500 |
| Hydrous Lactose | 159 | 123 | 148 | — |
| Corn Starch | 25 | 35 | 40 | 70 |
| Talc | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula I, formula II, formula III, formula IV, formula V, formula VI, or formula VII, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 4

| possible soft gelatin capsule ingredient composition | |
|---|---|
| ingredient | mg/capsule |
| Compound of formula I, formula II, formula III, formula IV, formula V, formula VI, or formula VII | 5 |
| Yellow wax | 8 |
| Hydrogenated Soya bean oil | 8 |
| Partially hydrogenated plant oils | 34 |
| Soya bean oil | 110 |
| Total | 165 |

TABLE 5

| possible soft gelatin capsule composition | |
|---|---|
| ingredient | mg/capsule |
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I, formula II, formula III, formula IV, formula V, formula VI, or formula VII is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 6

| possible suppository composition | |
|---|---|
| ingredient | mg/supp. |
| Compound of formula I, formula II, formula III, formula IV, formula V, formula VI, or formula VII | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I, formula II, formula III, formula IV, formula V, formula VI, or formula VII is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 7

| possible injection solution composition | |
|---|---|
| ingredient | mg/injection solution. |
| Compound of formula I, formula II, formula III, formula IV, formula V, formula VI, or formula VII | 3 |
| Polyethylene Glycol 400 | 150 |
| acetic acid | q.s. ad pH 5.0 |
| water for injection solutions | ad 1.0 ml |

Manufacturing Procedure

The compound of formula I, formula II, formula III, formula IV, formula V, formula VI, or formula VII is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8

| possible sachet composition | |
|---|---|
| ingredient | mg/sachet |
| Compound of formula I, formula II, formula III, formula IV, formula V, formula VI, or formula VII | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I, formula II, formula III, formula IV, formula V, formula VI, or formula VII is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

Abbreviations

ACN=acetonitrile; Boc=tert-butyloxycarbonyl; dba=dibenzylideneacetone; COMU=(1-Cyano-2-ethoxy-2-oxoethylidenaminooxy)dimethylamino-morpholino-carbenium hexafluorophosphat, 1-[(1-(Cyan-2-ethoxy-2-oxoethylidenaminooxy)-dimethylamino-morpholino)]-uronium-hexafluorophosphat; DAST=Diethylaminosulfur trifluoride; dba=Dibenzylideneacetone; DBU=1,8-Diazabicyclo[5.4.0]undec-7-ene; DCM=dichloromethane; DIPEA=diisopropylethylamin; DMAP=4-Dimethylaminopyridine; DMF=dimethylformamide; DMSO=dimethyl sulfoxide; dppf=1,1'-Bis(diphenylphosphino)ferrocene; ESI=electrospray ionization; EtOAc=ethyl acetate; Ex.=example; HATU= hexafluorophosphate azabenzotriazole tetramethyl uronium; HPLC=high performance liquid chromatogaphy; IPA= isopropanol; LC-MS=liquid chromatography coupled with mass spectrometry; MS=mass spectrometry; MTBE=methyl tert-butyl ether; NBS=N-Bromosuccinimide; NMR=nuclear magnetic resonance; pin=pinacolato; rt=room temperature; SFC=supercritical fluid chromatography; TEA= triethylamine; Tf=triflate; TFA=trifluoroacetic acid; THF= tetrahydrofuran; TLC=thin layer chromatography; UPLC=ultra performance liquid chromatography.

General Procedure for Amide Coupling:

Procedure A: To a stirred solution of acid (1 eq.) and amine (1 eq.) in N, N-Dimethylformamide (4 mL/mmol) was added N,N-Diisopropylethylamine (4 eq.) at room temperature under nitrogen, followed by the addition of HATU (1.1 eq.) at same temperature. The reaction mixture was stirred at room temperature for 12 h. The progress of the reaction was monitored by LCMS. After completion, the reaction mixture was diluted with water and extracted with 10% Isopropanol in Dichloromethane. Combined orgonic layers were dried over sodium sulphate, filtered and concentrated under reduced pressure to afford crude compound. The crude compound was purified by preparative-HPLC (Mobile phase: 10 mM $NH_4OAc$ in $H_2O$/Acetonitrile or 10 mM Formic acid in $H_2O$\Acetonitrile) and fractions were lyophilized to afford the target compound.

Procedure B: To a stirred solution of acid (1 eq.) and amine (1 eq.) in N,N-Dimethylformamide, was added N,N-Diisopropylethylamine (4 eq.) and COMU (1.1 eq.) at room temperature under nitrogen atmosphere. The reaction mixture was stirred at room temperature for 6 h. The progress of the reaction was monitored by LCMS. After completion, the reaction mixture was diluted with water (10 mL) and extracted with 10% Isopropanol in Dichloromethane (3×20 mL). Combined organic layers were dried over sodium sulphate, filtered and concentrated under reduced pressure to afford crude. The desired product was purified from crude by preparative HPLC (10 mM Ammonium acetate in water: Acetonitrile or 10 mM Formic acid in $H_2O$\Acetonitrile) and fractions were lyophilized to afford target compound.

Procedure C: To a stirred solution of acid (1 eq.) and amine (1 eq.) in N,N-Dimethylformamide was added Triethylamine (4 eq.) at room temperature under nitrogen, followed by the addition of T3P (1.1 eq.) at the same temperature. The reaction mixture was stirred at room temperature for 2 h. The progress of the reaction was monitored by LCMS. After completion, the reaction mixture was diluted with water and extracted with 10% Isopropanol in Dichloromethane. Combined organic layers were dried over sodium sulphate, filtered and concentrated under reduced pressure to afford crude compound. The crude compound was purified by preparative-HPLC (Mobile phase: 10 mM $NH_4OAc$ in $H_2O$/Acetonitrile or 10 mM Formic acid in $H_2O$/Acetonitrile) and fractions were lyophilized to get the target compound.

Procedure D: To a stirred solution of acid (1 eq.) and amine (1 eq.) in N,N-Dimethylformamide was added N,N-Diisopropylethylamine (4 eq.) at room temperature under nitrogen, followed by the addition of PyBOP (1.1 eq.) at same temperature. The reaction mixture was stirred at room temperature for 12 h. The progress of the reaction was monitored by LCMS. After completion, the reaction mixture was diluted with water and extracted with 10% Isopropanol in Dichloromethane. Combined organic layers were dried over sodium sulphate, filtered and concentrated under reduced pressure to afford crude compound. The crude compound was purified by preparative-HPLC (Mobile phase: 10 mM $NH_4OAc$ in $H_2O$\Acetonitrile or 10 mM Formic acid in $H_2O$/Acetonitrile) and fractions were lyophilized to get the target compound.

Synthesis of Building Blocks

Intermediates Synthesis

Scheme I

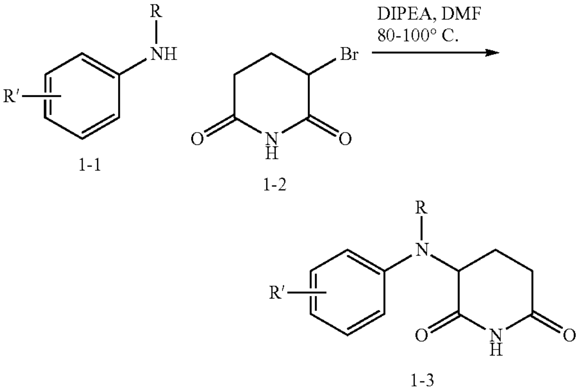

1-1

1-2

1-3

R = H, $CH_3$

General Procedure for the Reaction According to Scheme I

To a mixture of 1-1 (1 mmol) and 1-2 (2 mmol) in 1,4-dioxane (3 mL) was added N,N-Diisopropylethylamine (2 mmol). The resulting solution was heated in a sealed tube at 70-110° C. for 24 hours to produce 1-3. Reaction mixture was then cooled to room temperature, diluted with water and extracted with Ethyl acetate. The combined Ethyl acetate extract was washed with brine, dried over anhydrous sodium sulphate and concentrated under reduced pressure. The residue was purified by column chromatography (silica, gradient: 0-3% methanol in dichloromethane) to afford 1-3.

Intermediate tert-butyl 4-(4-((2,6-dioxopiperidin-3-yl)amino)phenyl)piperidine-1-carboxylate

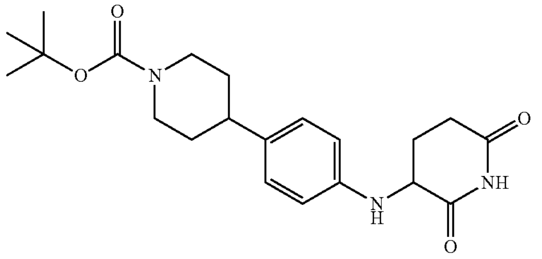 [SMILES: CC(C)(C)OC(=O)N1CCC(c2ccc(NC3CCC(=O)NC3=O)cc2)CC1]

tert-butyl 4-(4-((2,6-dioxopiperidin-3-yl)amino)phenyl) piperidine-1-carboxylate was synthesized from tert-Butyl 4-(4-aminophenyl)-1-piperidinecarboxylate (CAS #170011-57-1) following general procedure (N,N-diisopropylethyl-amine/Dioxane). Yield-45%; $^1$H NMR (400 MHz, DMSO-d6) δ 10.75 (s, 1H), 6.94 (d, J=8.16 Hz, 2H), 6.60 (d, J=7.88 Hz, 2H), 5.64 (d, J=6.96 Hz, 1H), 4.28-4.24 (m, 1H), 4.07-4.00 (m, 2H), 2.79-2.64 (m, 4H), 2.53-2.48 (m, 2H), 2.11-2.05 (m, 1H), 1.89-1.81 (m, 1H), 1.71-1.64 (m, 2H), 1.40-1.34 (m, 10H); LCMS (ES+): 386.3 $[M+H]^+$.

Intermediate tert-butyl 4-(4-((2,6-dioxopiperidin-3-yl)amino)phenyl)piperazine-1-carboxylate

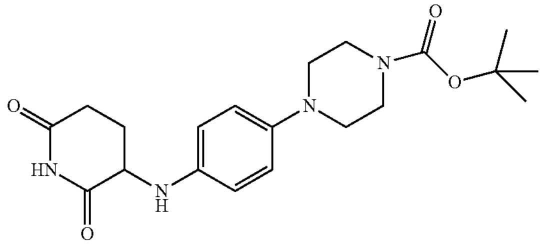 [SMILES: CC(C)(C)OC(=O)N1CCN(c2ccc(NC3CCC(=O)NC3=O)cc2)CC1]

Tert-butyl 4-(4-((2,6-dioxopiperidin-3-yl)amino)phenyl) piperazine-1-carboxylate was synthesized following general procedure (DIPEA/DMF). Yield-50%; LCMS(ES+): 389.2 $[M+H]^+$.

Intermediate 3-((6-(piperidin-4-yl)pyridin-3-yl) amino)piperidine-2,6-dione hydrochloride

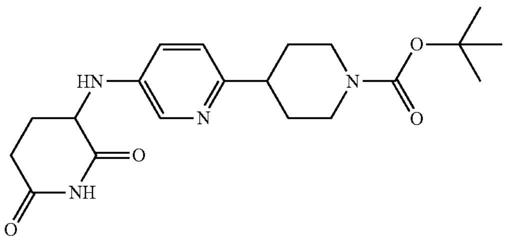 [SMILES: CC(C)(C)OC(=O)N1CCC(c2ccc(NC3CCC(=O)NC3=O)cn2)CC1]

Tert-butyl 4-(5-((2,6-dioxopiperidin-3-yl)amino)pyridin-2-yl)piperidine-1-carboxylate was synthesized from tert-butyl 4-(5-aminopyridin-2-yl)piperidine-1-carboxylate (CAS #885693-48-1) following the general procedure: Yield: 14%, LCMS (ESI+): 389.2 $[M+H]^+$.

Scheme II

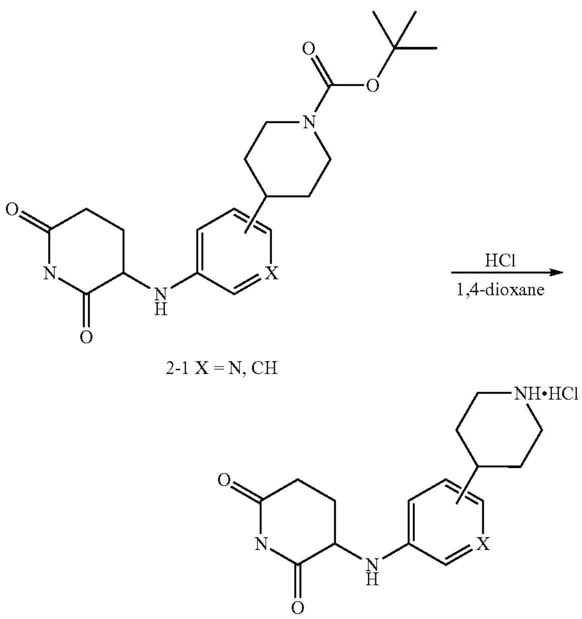

2-1 X = N, CH 2-2 X = N, CH

General Procedure for the Reaction According to Scheme II

To 2-1 dissolved in methanol (0.1 M) at room temperature was added hydrogen chloride (4M in 1,4-dioxane, 5 equiv.) and the reaction mixture was heated at 40° C. for 2 hours. The volatiles were evaporated under reduced pressure to afford 2-2.

Intermediate 3-((4-(piperidin-4-yl)phenyl)amino) piperidine-2,6-dione hydrochloride

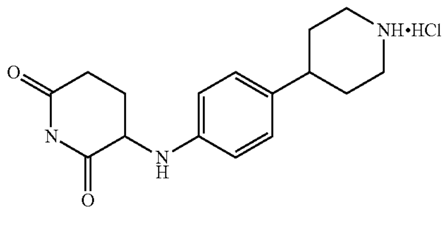

3-((4-(piperidin-4-yl)phenyl)amino)piperidine-2,6-dione hydrochloride was synthesized from tert-butyl 4-(4-((2,6-dioxopiperidin-3-yl)amino)phenyl)piperidine-1-carboxylate following general procedure. Yield-88%; $^1$H NMR (400 MHz, DMSO-d6) δ 10.80 (s, 1H), 8.84 (brs, 1H), 8.77 (brs, 1H), 6.95 (d, J=8.44 Hz, 2H), 6.66 (d, J=8.48 Hz, 2H), 4.29 (dd, J=11.4, 4.72 Hz, 1H), 3.35-3.29 (m, 2H), 2.99-2.91 (m, 2H), 2.71-2.53 (m, 3H), 2.10-2.05 (m, 1H), 1.89-1.71 (m, 5H); LCMS (ES+): 288.2 $[M+H]^+$.

Intermediate 3-((4-(piperazin-1-yl)phenyl)amino) piperidine-2,6-dione hydrochloride

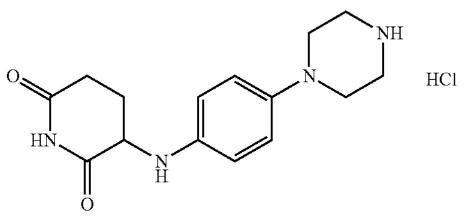 [SMILES: O=C1CCC(Nc2ccc(N3CCNCC3)cc2)C(=O)N1 ; Cl]

3-((4-(piperazin-1-yl)phenyl)amino)piperidine-2,6-dione hydrochloride was synthesized following general procedure (Boc-deprotection). Yield—92%; $^{1}$H NMR (400 MHz, MeOD) δ 7.38 (d, 8.52 Hz, 2H), 7.21 (d, J=8.6 Hz, 2H), 4.71-4.65 (m, 1H), 3.53 (brs, 4H), 3.40 (brs, 4H), 2.74-2.66 (m, 2H), 2.04 (brs, 2H); LCMS (ES+): 289.1 $[M+H]^{+}$.

Intermediate 3-((6-(piperidin-4-yl)pyridin-3-yl) amino)piperidine-2,6-dione hydrochloride

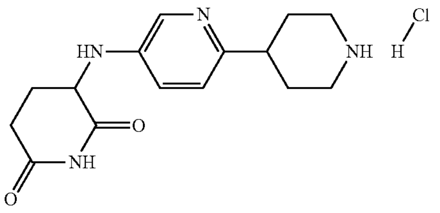

3-((6-(piperidin-4-yl)pyridin-3-yl)amino)piperidine-2,6-dione hydrochloride was synthesized from tert-butyl 4-(5-((2,6-dioxopiperidin-3-yl)amino)pyridin-2-yl)piperidine-1-carboxylate following the general procedure. Yield: 83%, LCMS (ESI+): 289.0 $[M+H]^{+}$.

Synthesis of Intermediate tert-butyl 4-[4-[[(35)-2,6-dioxo-3-piperidyl]amino]phenyl]piperidine-1-carboxylate and tert-butyl 4-[4[[(3R)-2,6-dioxo-3-piperidyl]amino]phenyl]piperidine-1-carboxylate by chiral SFC separation

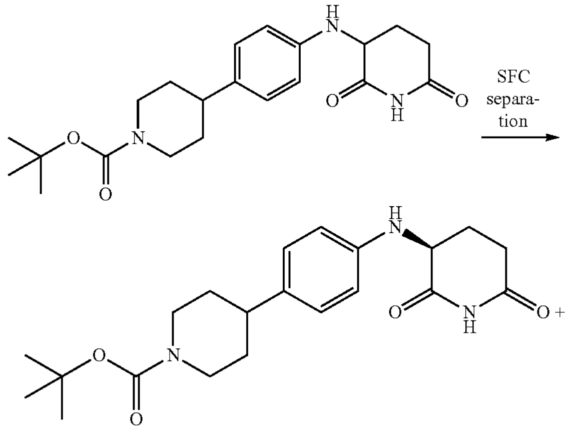

-continued

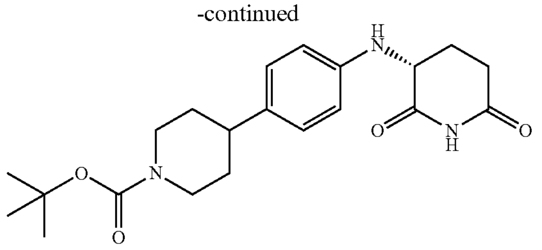

Separation of tert-butyl 4-[4-[(2,6-dioxo-3-piperidyl) amino]phenyl]piperidine-1-carboxylate (4 g, 10.32 mmol) by chiral SFC afforded two sets of fractions.

The following preparative scale SFC method was used to separate the enantiomers:

Column: Chiralpak ID (250×21 mm) 5 um

Flow: 35 g/min

Mobile Phase: 45% CO2+55% Isopropyl alcohol

ABPR: 100 bar

Temperature: 35° C.

The earlier eluting fractions were lyophilized to afford tert-butyl 4-[4-[[(3S)-2,6-dioxo-3-piperidyl]amino]phenyl] piperidine-1-carboxylate (1.44 g, 3.70 mmol, 35.88% yield, 99.66% enantiomeric excess, Chiral SFC Rt=4.31 min). $^{1}$H NMR (400 MHz, DMSO-D6) δ 10.77 (s, 1H), 6.94 (d, J=8.1 Hz, 2H), 6.60 (d, J=8.2 Hz, 2H), 5.68-5.66 (m, 1H), 4.29-4.23 (m, 1H), 4.05-4.02 (m, 2H), 2.78-2.54 (m, 5H), 2.11-2.07 (m, 1H), 1.89-1.83 (m, 1H), 1.69-1.66 (m, 2H), 1.40-1.36 (m 11H).

The later fractions were lyophilized to afford tert-butyl 4-[4-[[(3R)-2,6-dioxo-3-piperidyl]amino]phenyl]piperidine-1-carboxylate (1.56 g, 3.95 mmol, 38.24% yield, 98.06% enantiomeric excess, Chiral SFC Rt=5.96 min). $^{1}$H NMR (400 MHz, DMSO-D6) δ 10.77 (s, 1H), 6.94 (d, J=8.2 Hz, 2H), 6.60 (d, J=8.3 Hz, 2H), 5.68-5.66 (m, 1H), 4.29-4.23 (m, 1H), 4.05-4.02 (m, 2H), 2.78-2.58 (m, 5H), 2.11-2.07 (m, 1H), 1.87-1.83 (m, 1H), 1.70-1.67 (m, 2H), 1.40-1.35 (m 11H).

Synthesis of 2-[4-[4-[[(3S)-2,6-dioxo-3-piperidyl] amino]phenyl]-1-piperidyl]acetic acid trifluoroacetic acid salt and 2-[4-[4-[[(3R)-2,6-dioxo-3-piperidyl] amino]phenyl]-1-piperidyl]acetic acid trifluoroacetic acid salt Tert-butyl 2-[4-[4-[(2,6-dioxo-3-piperidyl)amino] phenyl]-1-piperidyl]acetate

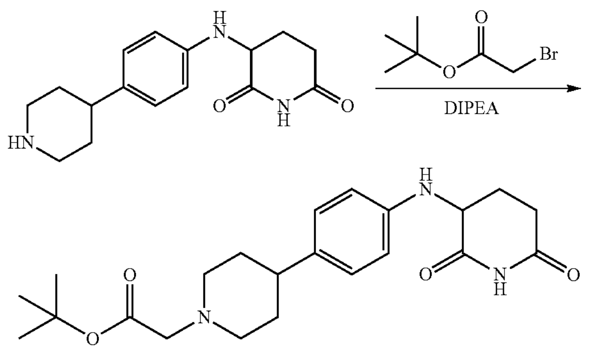

To a stirred solution of 3-[4-(4-piperidyl)anilino]piperidine-2,6-dione (2.0 g, 6.96 mmol) in DMF (20 mL) was added triethyl amine (3.52 g, 34.80 mmol, 4.85 mL) followed by tert-butyl 2-bromoacetate (1.49 g, 7.66 mmol, 1.12 mL) and stirred the reaction mixture at rt for 16 h. Water (75 mL) was added and the product was extracted with ethyl acetate (3×150 mL). The combined organic layers were dried over sodium sulphate, filtered and concentrated under reduced pressure. The residue was purified by silica gel chromatography using 30% ethyl acetate-petroleum ether as eluent to give tert-butyl 2-[4-[4-[(2,6-dioxo-3-piperidyl)amino]phenyl]-1-piperidyl]acetate (1.40 g, 3.36 mmol, 48.33% yield) as a green solid.

SFC separation conditions to obtain tert-butyl (S)-2-[4-[4-[(2,6-dioxo-3-piperidyl)amino]phenyl]-1-piperidyl]acetate and tert-butyl (R)-2-[4-[4-[(2,6-dioxo-3-piperidyl)amino]phenyl]-1-piperidyl]

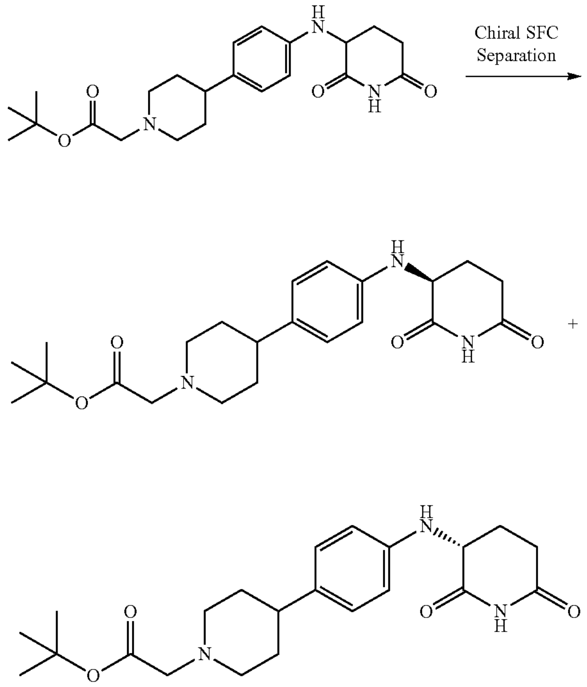

The racemic intermediate tert-butyl 2-[4-[4-[(2,6-dioxo-3-piperidyl)amino]phenyl]-1-piperidyl]acetate (1.40 g, 3.36 mmol) was resolved using chiral SFC method using Chiralcel OD-H column (250 mm×30 mm; 5 micron) eluting with 40% isopropyl alcohol/$CO_2$ (Flow Rate: 3 ml/min; Outlet Pressure: 100 bar). The first eluting set of fractions was evaporated under reduced pressure to afford tert-butyl (S)-2-[4-[4-[(2,6-dioxo-3-piperidyl)amino]phenyl]-1-piperidyl]acetate (500 mg, 36% yield, Rt=3.36 min, 96.22% purity, >99% enantiomeric excess). The second set of fractions was evaporated under reduced pressure to afford 500 mg of tert-butyl (R)-2-[4-[4-[(2,6-dioxo-3-piperidyl)amino]phenyl]-1-piperidyl]acetate (500 mg, 36% yield, Rt=4.84 min., purity 96.22%, 99.04% enantiomeric excess). LCMS First eluted (m/z: 402.4 $[M+H]^+$), LCMS Second eluted (m/z: 402.2 $[M+H]^+$).

2-[4-[4-[[(3S)-2,6-dioxo-3-piperidyl]amino]phenyl]-1-piperidyl]acetic acid trifluoroacetic acid salt

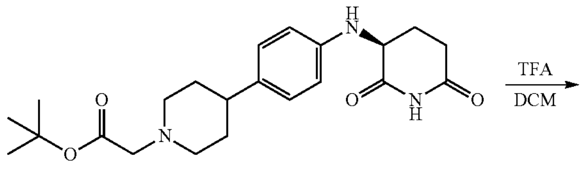

tert-butyl (S)-2-(4-(4-((2,6-dioxopiperidin-3-yl)amino)phenyl)piperidin-1-yl)acetate

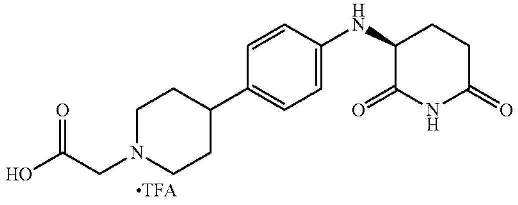

Tert-butyl 2-[4-[4-[[(3S)-2,6-dioxo-3-piperidyl]amino]phenyl]-1-piperidyl]acetate (500 mg, 1.25 mmol) was dissolved in dichloromethane (5 mL) and trifluoroacetic acid (12.26 g, 107.51 mmol, 8 mL) was added dropwise at 0° C. and the reaction was stirred at room temperature for 3 h. After completion of the reaction, reaction mixture was concentrated. The material was triturated with a methanol: MTBE mixture (1:4), solid was collected and the volatiles were evaporated under reduced pressure to give 2-[4-[4-[[(3S)-2,6-dioxo-3-piperidyl]amino]phenyl]-1-piperidyl]acetic acid trifluoroacetic acid salt (600 mg, 1.24 mmol, 99.6% yield) as an off white solid. LCMS (ESI+): 346.1 $[M+H]^+$ 2-[4-[4-[[(3R)-2,6-dioxo-3-piperidyl]amino]phenyl]-1-piperidyl]acetic acid:trifluoroacetic acid salt

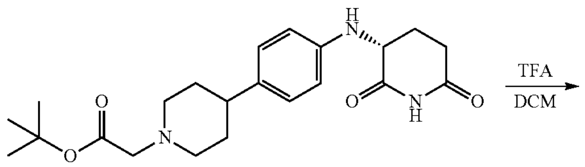

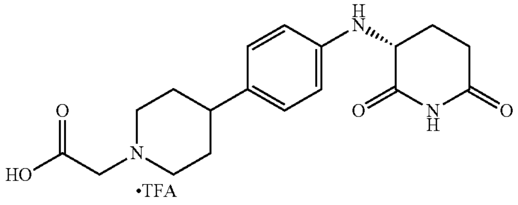

Tert-butyl 2-[4-[4-[[(3R)-2,6-dioxo-3-piperidyl]amino]phenyl]-1-piperidyl]acetate (500.00 mg, 1.25 mmol) was treated in a way similar to 2-[4-[4-[[(3 S)-2,6-dioxo-3-piperidyl]amino]phenyl]-1-piperidyl]acetic acid trifluoroacetic acid salt to yield 2-[4-[4-[[(3R)-2,6-dioxo-3-piperidyl]amino]phenyl]-1-piperidyl]acetic acid trifluoroacetic acid salt (600 mg, 1.24 mmol, 99.63% yield) as an off white solid. LCMS (ESI+): 346.1 $[M+H]^+$ Synthesis of Intermediate 3-(3-Fluoro-4-piperidin-4-yl-phenylamino)-piperidine-2,6-dione hydrochloride

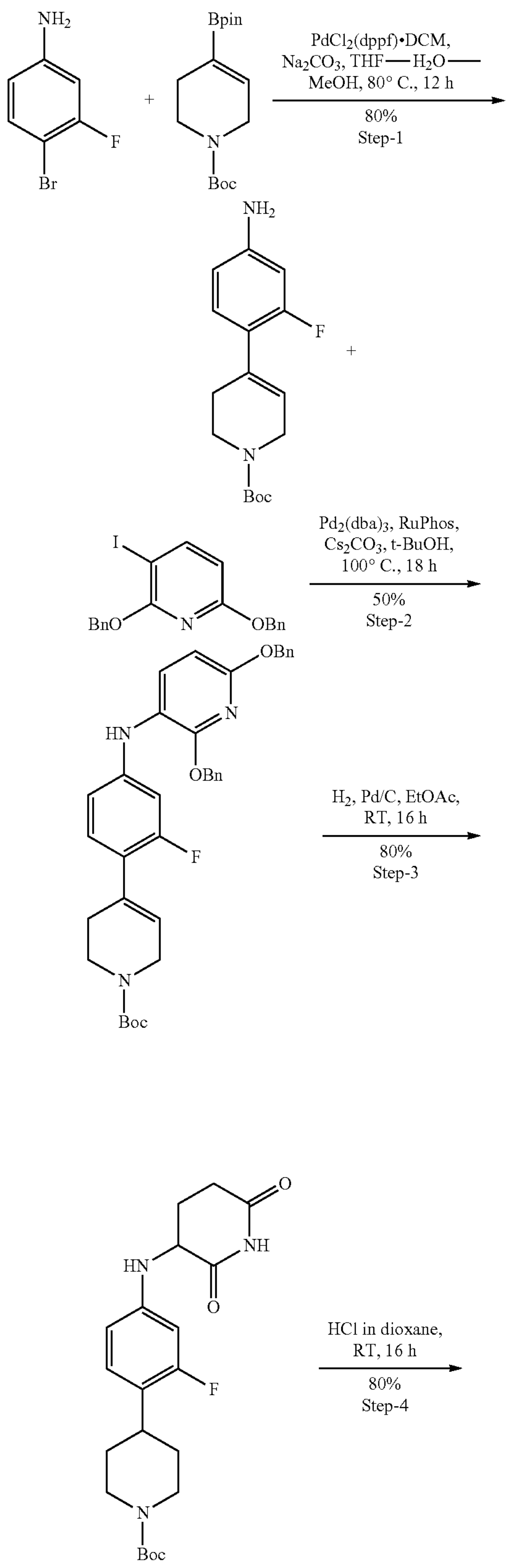

-continued

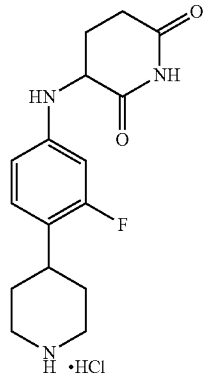 [SMILES: O=C1CCC(Nc2ccc(C3CCNCC3)c(F)c2)C(=O)N1 ; Cl]

Step 1: Preparation of 4-(4-Amino-2-fluoro-phenyl)-3,6-dihydro-2H-pyridine-1-carboxylic acid tert-butyl ester Sodium carbonate (6.14 g, 57.89 mmol, 2.43 mL) was added to a stirred solution of 4-bromo-3-fluoro-aniline (5.00 g, 26.3 mmol) and tert-butyl 4-(4,4,5,5-tetramethyl-1,3,2-dioxaborolan-2-yl)-3,6-dihydro-2H-pyridine-1-carboxylate (8.95 g, 29.0 mmol) in water (12 mL), THF (60 mL) and methanol (24 mL) and the flask was thoroughly purged with argon. $PdCl_2$(dppf)·dichloromethane (430 mg, 526 μmol) was added and the reaction mixture was degassed with nitrogen and then heated at 80° C. for 12 h. The reaction mixture was diluted with ethyl acetate, filtered through a short pad of celite and washed with ethyl acetate. The combined organic extracts were washed with water and brine, dried over anhydrous sodium sulphate, filtered and concentrated under reduced pressure. The residue was purified by column chromatography (15% ethyl acetate-hexane) to get tert-butyl 4-(4-amino-2-fluoro-phenyl)-3,6-dihydro-2H-pyridine-1-carboxylate (6.1 g, 20.9 mmol, 79% yield) as pale yellow solid. LCMS (ESI+): 293 $[M+H]^+$ Step 2: Preparation of 4-[4-(2,6-Bis-benzyloxy-pyridin-3-ylamino)-2-fluoro-phenyl]-3,6-dihydro-2H-pyridine-1-carboxylic acid tert-butyl ester Cesium carbonate (19.73 g, 60.54 mmol) was added to a stirred solution of tert-butyl 4-(4-amino-2-fluoro-phenyl)-3,6-dihydro-2H-pyridine-1-carboxylate (5.9 g, 20.2 mmol) and 2,6-dibenzyloxy-3-iodo-pyridine (9.26 g, 22.2 mmol) in t-BuOH (60 mL) The resulting mixture was degassed with argon and $Pd_2(dba)_3$ (924 mg, 1.01 mmol), RuPhos (942 mg, 2.02 mmol) were added under inert atmosphere. The resulting mixture was heated at 100° C. for 18 h. The reaction mixture was diluted with ethyl acetate, filtered through a short pad of celite and washed with ethyl acetate. The combined organic extracts were washed with water and brine, dried over anhydrous sodium sulphate, filtered and concentrated under reduced pressure. The residue was purified by column chromatography (15% ethyl acetate-hexane) to get tert-butyl 4-[4-[(2,6-dibenzyloxy-3-pyridyl)amino]-2-fluoro-phenyl]-3,6-dihydro-2H-pyridine-1-carboxylate (5.9 g, 10.1 mmol, 50% yield) as pale yellow solid. LCMS (ES+): 582 $[M+H]^+$ Step 3: Preparation of 4-[4-(2,6-Dioxo-piperidin-3-ylamino)-2-fluoro-phenyl]-piperidine-1-carboxylic acid tert-butyl ester 10% Pd—C (50% wet, 4.6 g) was added to a stirred nitrogen-degassed solution of tert-butyl 4-[4-[(2,6-dibenzyloxy-3-pyridyl)amino]-2-fluoro-phenyl]-3,6-dihydro-2H-pyridine-1-carboxylate (4.6 g, 7.91 mmol) in ethyl acetate (40 mL). The resulting mixture was stirred at ambient temperature under hydrogen balloon pressure for 20 h. The reaction mixture was filtered through a small pad of celite and washed with ethyl acetate. The combined filtrate was evaporated under reduced pressure and purified by column chromatography (40% ethyl acetate in hexane) to afford tert-butyl 4-[4-[(2,6-dioxo-3-piperidyl)amino]-2-fluoro-phenyl]piperidine-1-carboxylate (2.6 g, 6.41 mmol, 81% yield) as a blue solid. LCMS (ES+): 406 $[M+H]^+$

Step 4: Preparation of 3-(3-Fluoro-4-piperidin-4-yl-phenylamino)-piperidine-2,6-dione hydrochloride Dioxane-HCl (4M, 30 mL, 130 mmol) was added to tert-butyl 4-[4-[(2,6-dioxo-3-piperidyl)amino]-2-fluoro-phenyl]piperidine-1-carboxylate (1.3 g, 3.21 mmol) at 10° C. the resulting mixture was warmed to ambient temperature and stirred for 16 h. The reaction mixture was concentrated under reduced pressure, triturated with ether and lyophilized to yield 3-[3-fluoro-4-(4-piperidyl)anilino]piperidine-2,6-dione (840 mg, 2.73 mmol, 85.25% yield) as green solid. LCMS (ES+): 306 $[M+H]^+$. $^1$H NMR (400 MHz, DMSO-D6) d 10.79 (s, 1H), 9.00 (br s, 1H), 8.85-8.83 (m, 1H), 6.96-6.91 (m, 1H), 6.50-6.45 (m, 2H), 4.34-4.30 (m, 1H), 3.32-3.29 (m, 2H), 2.98-2.93 (m, 3H), 2.77-2.69 (m, 1H), 2.60-2.56 (m, 1H), 2.08-2.05 (m, 1H), 1.92-1.81 (m, 5H).

Intermediate Synthesis of 3-(2-Fluoro-4-piperidin-4-yl-phenylamino)-piperidine-2,6-dione hydrochloride

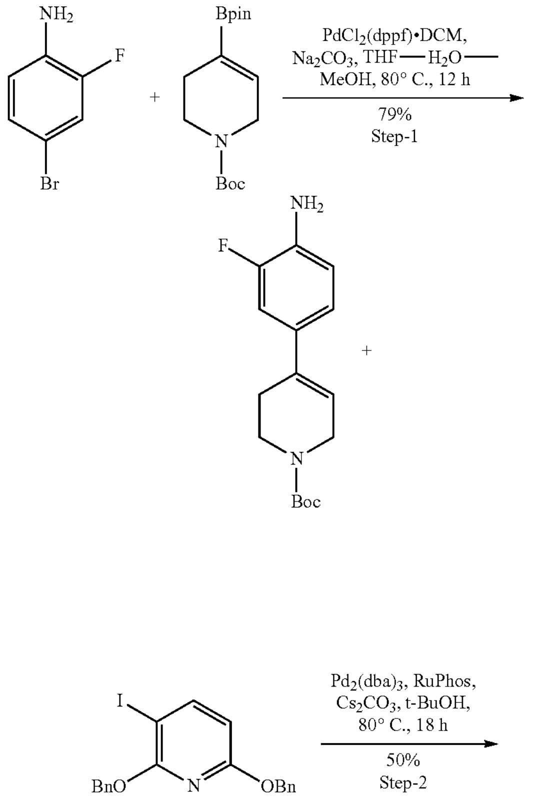

-continued

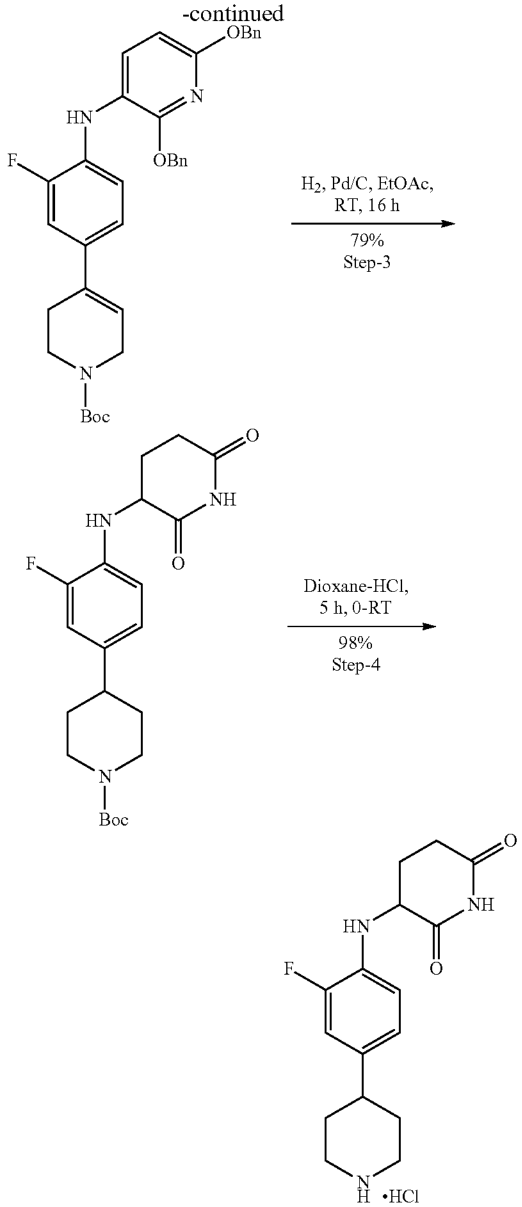

Step 1: Preparation of 4-(4-Amino-3-fluoro-phenyl)-3,6-dihydro-2H-pyridine-1-carboxylic acid tert-butyl ester Sodium carbonate (6.14 g, 57.89 mmol) was added to a stirred solution of 4-bromo-2-fluoro-aniline (5.00 g, 26.3 mmol) and tert-butyl 4-(4,4,5,5-tetramethyl-1,3,2-dioxaborolan-2-yl)-3,6-dihydro-2H-pyridine-1-carboxylate (8.95 g, 29.0 mmol) in water (12 mL), THF (60 mL) and methanol (24 mL). The resulting mixture was degassed with argon and PdCl$_2$(dppf)·dichloromethane (430 mg, 526 μmol) was added under inert atmosphere. The resulting mixture was heated at 80° C. for 12 h. The reaction mixture was diluted with ethyl acetate, filtered through a short pad of celite and washed with ethyl acetate. The combined organic extracts were washed with water, brine, dried over anhydrous sodium sulphate, filtered and concentrated under reduced pressure. The residue was purified by column chromatography (15% ethyl acetate-hexane) to yield tert-butyl 4-(4-amino-3- fluoro-phenyl)-3,6-dihydro-2H-pyridine-1-carboxylate (6.1 g, 20.9 mmol, 79% yield) as pale yellow solid. LCMS (ES+): 293 $[M+H]^+$ Step 2: Preparation of 4-[4-(2,6-Bis-benzyloxy-pyridin-3-ylamino)-3-fluoro-phenyl]-3,6-dihydro-2H-pyridine-1-carboxylic acid tert-butyl ester Cesium carbonate (19.73 g, 60.54 mmol) was added to a stirred solution of tert-butyl 4-(4-amino-3-fluoro-phenyl)-3,6-dihydro-2H-pyridine-1-carboxylate (5.9 g, 20.2 mmol) and 2,6-dibenzyloxy-3-iodo-pyridine (9.26 g, 22.2 mmol) in t-BuOH (60 mL). The resulting mixture was degassed with argon and $Pd_2(dba)_3$ (924 mg, 1.01 mmol) and RuPhos (942 mg, 2.02 mmol) were added under inert atmosphere. The resulting mixture was heated at 100° C. for 18 h. The reaction mixture was diluted with ethyl acetate, filtered through a short pad of celite and washed with ethyl acetate. The combined organic extracts were washed with water, brine, dried over anhydrous sodium sulphate, filtered and concentrated under reduced pressure. The residue was purified by column chromatography (10% ethyl acetate-hexane) to yield tert-butyl 4-[4-[(2,6-dibenzyloxy-3-pyridyl)amino]-3-fluoro-phenyl]-3,6-dihydro-2H-pyridine-1-carboxylate (5.9 g, 10.1 mmol, 50% yield) as pale yellow solid. LCMS (ES+): 582 $[M+H]^+$ Step 3: Preparation of 4-[4-(2,6-Dioxo-piperidin-3-ylamino)-3-fluoro-phenyl]-piperidine-1-carboxylic acid tert-butyl ester 10% Pd—C (50% wet, 4.6 g) was added to a stirred degassed solution of tert-butyl 4-[4-[(2,6-dibenzyloxy-3-pyridyl)amino]-3-fluoro-phenyl]-3,6-dihydro-2H-pyridine-1-carboxylate (4.6 g, 7.91 mmol) in ethyl acetate (40 mL). The resulting mixture was stirred at ambient temperature under hydrogen balloon pressure for 20 h. The reaction mixture was filtered through a short pad of celite and washed with ethyl acetate. The combined filtrate was evaporated under reduced pressure and purified by column chromatography (40% ethyl acetate-hexane) to yield tert-butyl 4-[4-[(2,6-dioxo-3-piperidyl)amino]-3-fluoro-phenyl]piperidine-1-carboxylate (2.6 g, 6.41 mmol, 81% yield) as a blue solid. LCMS (ES+): 406 $[M+H]^+$ Step 4: Preparation of 3-(2-Fluoro-4-piperidin-4-yl-phenylamino)piperidine-2,6-dione hydrochloride Dioxane HCl (4M, 10 mL, 40 mmol) was added to tert-butyl 4-[4-[(2,6-dioxo-3-piperidyl)amino]-3-fluoro-phenyl]piperidine-1-carboxylate (1.3 g, 3.21 mmol) at 10° C. The resulting mixture was warmed to ambient temperature and stirred for 16 h. The reaction mixture was concentrated under reduced pressure, triturated with ether and lyophilized to yield 3-[2-fluoro-4-(4-piperidyl)anilino]piperidine-2,6-dione hydrochloride (840 mg, 2.73 mmol, 85% yield) as a green solid. LCMS (ES+): 306 $[M+H]^+$. $^1$H NMR (400 MHz, DMSO-D6) d 10.82 (s, 1H), 8.85 (br s, 1H), 8.69-8.68 (m, 1H), 6.92-6.89 (m, 1H), 6.83-6.77 (m, 2H), 4.40-4.36 (m, 2H), 3.37-3.31 (m, 2H), 2.98-2.90 (m, 2H), 2.76-2.71 (m, 2H), 2.58-2.56 (m, 1H), 2.05-1.73 (m, 6H).

Intermediate: Synthesis of 1-(6-bromo-1-methyl-indazol-3-yl)hexahydropyrimidine-2,4-dione

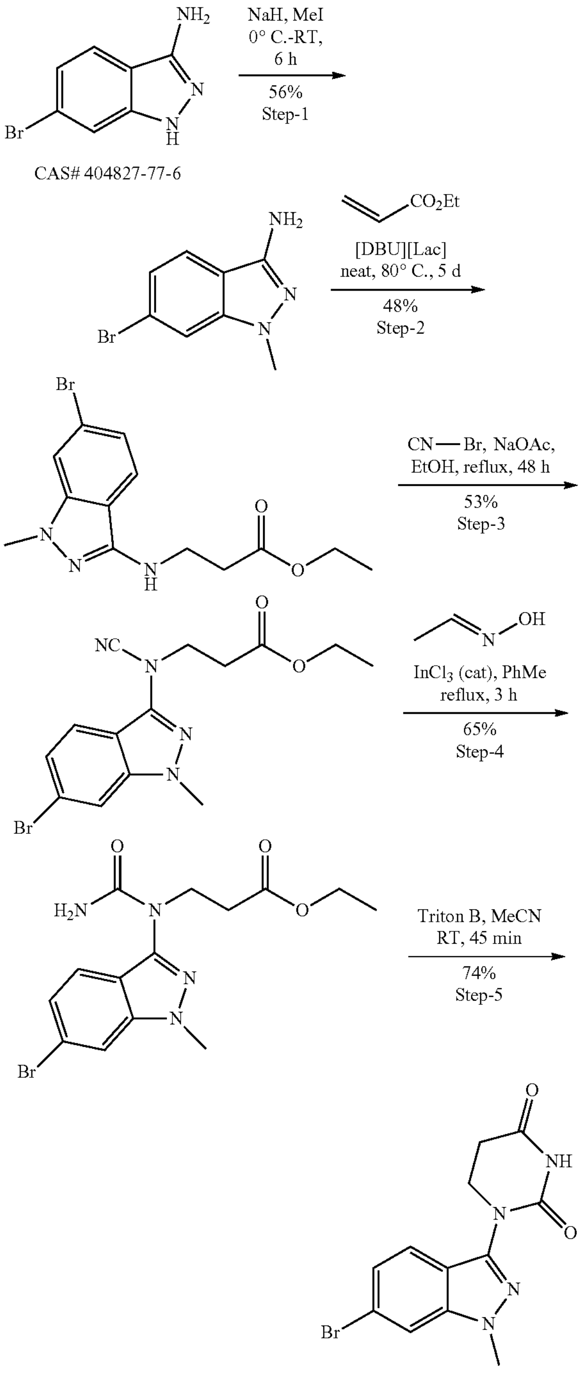

Step 1: Preparation of 6-bromo-1-methyl-indazol-3-amine

Sodium hydride (60% in oil 2.38 g, 59.4 mmol) was added portion wise at 0° C. to a stirred solution of 6-bromo-1H-indazol-3-amine (7 g, 33.0 mmol, 439 µL) in DMF (150 mL) and the mixture was stirred for 40 min. Iodomethane (5.15 g, 36.3 mmol, 2.26 mL) was added drop-wise under cooling and the resulting mixture was warmed to ambient temperature and stirred for 16 h. The reaction mixture was quenched with saturated ammonium chloride solution and extracted with ethyl acetate. The combined organic extracts were washed with water, brine, dried over anhydrous sodium sulphate, filtered and concentrated under reduced pressure. The residue was purified by silica gel chromatography (50% ethyl acetate-hexane) to yield 6-bromo-1-methyl-indazol-3-amine (4.2 g, 18.6 mmol, 56% yield). LCMS (ES+): 227 $[M+H]^+$ Step 2: Preparation of ethyl 3-[(6-bromo-1-methyl-indazol-3-yl)amino]propanoate Ethyl acrylate (14.0 g, 139 mmol) was added in 5 portions (2.8 g each) over 5 days to a mixture of 6-bromo-1-methyl-indazol-3-amine (4.2 g, 18.6 mmol), [DBU][Lac] (prepared by mixing equimolar mixture of DBU and lactic acid with stirring for 16 h at ambient temperature, 2.09 g, 14.9 mmol) at 80° C. After completion, the reaction mixture was quenched with sodium hypochlorite (30% aq, 5 mL) and diluted with ethyl acetate. The combined organics were washed with water, brine, dried over anhydrous sodium sulphate, filtered and concentrated under reduced pressure. The residue was purified by silica gel chromatography (50% ethyl acetate-hexane) to yield ethyl 3-[(6-bromo-1-methyl-indazol-3-yl)amino]propanoate (2.9 g, 8.89 mmol, 48% yield). LCMS (ESI+): 327 $[M+H]^+$ Step 3: Preparation of ethyl 3-[(6-bromo-1-methyl-indazol-3-yl)-cyano-amino]propanoate Anhydrous sodium acetate (1.46 g, 17.8 mmol), followed by cyanogen bromide (1.41 g, 13.3 mmol) were added to a stirred solution of ethyl 3-[(6-bromo-1-methyl-indazol-3-yl)amino]propanoate (2.9 g, 8.89 mmol) in ethanol (40 mL) at ambient temperature. The resulting mixture was heated to reflux for 48 h. The reaction mixture was concentrated under reduced pressure and diluted with ethyl acetate. The combined organics were washed with water, brine, dried over anhydrous sodium sulphate, filtered and concentrated under reduced pressure. The residue was purified by column chromatography (45% ethyl acetate-hexane) to yield ethyl 3-[(6-bromo-1-methyl-indazol-3-yl)-cyano-amino]propanoate (1.65 g, 4.70 mmol, 53% yield). LCMS (ES+): 352 $[M+H]^+$ Step 4: Preparation of ethyl 3-[(6-bromo-1-methyl-indazol-3-yl)-carbamoyl-amino]propanoate (1E)-Acetaldehyde oxime (1.01 g, 17.1 mmol), followed by indium (III) chloride (126 mg, 569 μmol) were added to a stirred solution of ethyl 3-[(6-bromo-1-methyl-indazol-3-yl)-cyano-amino]propanoate (2 g, 5.69 mmol) in toluene (60 mL) at ambient temperature. The resulting mixture was heated to reflux for 1 h. The reaction mixture was diluted with ethyl acetate, washed with water and brine. The organics were dried over anhydrous sodium sulphate, filtered and concentrated under reduced pressure. The residue was purified by column chromatography (60% ethyl acetate-hexane) to yield ethyl 3-[(6-bromo-1-methyl-indazol-3-yl)-carbamoyl-amino]propanoate (1.4 g, 3.79 mmol, 67% yield). LCMS (ES+): 370 $[M+H]^+$ Step 5: Preparation of 1-(6-bromo-1-methyl-indazol-3-yl)hexahydropyrimidine-2,4-dione Triton-B (40% in methanol, 2.4 mL, 5.69 mmol) was added drop-wise to a stirred solution of ethyl 3-[(6-bromo-1-methyl-indazol-3-yl)-carbamoyl-amino]propanoate (1.40 g, 3.79 mmol) in MeCN (70 mL) at ambient temperature. The resulting mixture was stirred at ambient temperature for 45 minutes. The reaction mixture was concentrated under vacuum and diluted with ethyl acetate. The organic layer was washed with water, brine, dried over anhydrous sodium sulphate, filtered and concentrated under reduced pressure. The residue was purified by column chromatography (30% ethyl acetate-hexane) to yield 1-(6-bromo-1-methyl-indazol-3-yl)hexahydropyrimidine-2,4-dione (910 mg, 2.81 mmol, 74% yield) as white solid. LCMS (ES+): 324 $[M+H]^+$. $^1H$ NMR (400 MHz, DMSO-D6) d 10.60 (s, 1H), 7.97 (s, 1H), 7.61 (d, J=8.6 Hz, 1H), 7.26-7.23 (m, 1H), 3.98 (s, 3H), 3.93 (t, J=6.6 Hz, 2H), 2.76 (t, J=6.6 Hz, 2H).

Preparation of 1-(1-methyl-6-(piperidin-4-yl)-1H-indazol-3-yl)dihydropyrimidine-2,4(1H,3H)-dione hydrochloride Step 1: tert-butyl 4-[4-(2,4-dioxohexahydropyrimidin-1-yl)-1-methyl-indazol-6-yl]-3,6-dihydro-2H-pyridine-1-carboxylate

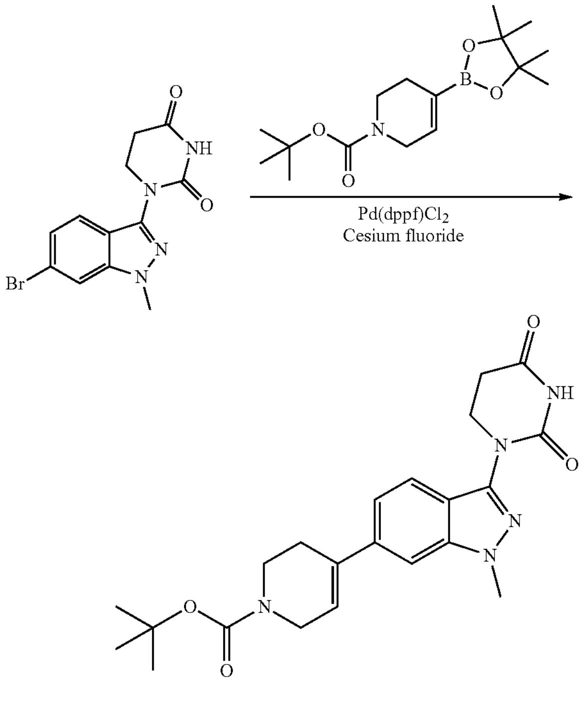

A solution of 1-(6-bromo-1-methyl-indazol-3-yl)hexahydropyrimidine-2,4-dione (1.25 g, 3.87 mmol) and tert-butyl 4-(4,4,5,5-tetramethyl-1,3,2-dioxaborolan-2-yl)-3,6-dihydro-2H-pyridine-1-carboxylate (2.39 g, 7.74 mmol) was bubbled with $N_2$ for 10 min. Then, cesium fluoride (1.18 g, 7.74 mmol) and Pd(dppf)$Cl_2$ (566 mg, 774 μmol) were added and the mixture was stirred at 85° C. for 2 h. The mixture was cooled to ambient temperature, diluted with ethyl acetate and filtered through Celite/silica gel. After washing with ethyl acetate, the filtrate was diluted with water and layers were separated, and the organic layer was washed with brine, dried over sodium sulphate, filtered, and concentrated. The residue was purified by normal phase chromatography (5-100% ethyl acetate in Hexanes) to afford tert-butyl 4-[3-(2,4-dioxohexahydropyrimidin-1-yl)-1-methyl-indazol-6-yl]-3,6-dihydro-2H-pyridine-1-carboxylate (1.04 g, 2.44 mmol, 63% yield). LCMS (ESI+): 426.3 $[M+H]^+$ Step 2: tert-butyl 4-[3-(2,4-dioxohexahydropyrimidin-1-yl)-1-methyl-indazol-6-yl]piperidine-1-carboxylate

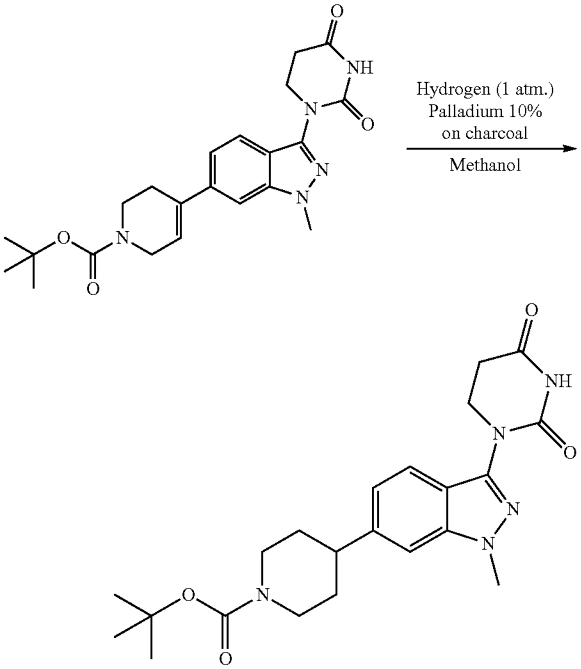

Palladium (10% on carbon, Type 487, dry, 1.08 g, 1.02 mmol) was added to a solution of tert-butyl 4-[3-(2,4-dioxohexahydropyrimidin-1-yl)-1-methyl-indazol-6-yl]-3,6-dihydro-2H-pyridine-1-carboxylate (1.44 g, 3.38 mmol) in methanol (30 mL) and the mixture was stirred at ambient temperature under a hydrogen balloon atmosphere. After 24 h, the reaction mixture was filtered through a pad of celite, washed with a mixture of dichloromethane/methanol (1:1), and concentrated in vacuo to yield tert-butyl 4-[3-(2,4-dioxohexahydropyrimidin-1-yl)-1-methyl-indazol-6-yl]piperidine-1-carboxylate (1.42 g, 3.32 mmol, 98% yield). LCMS (ESI+): 372.3 $[M\text{-tert-butyl}+H]^+$.

Step 3: 1-(1-methyl-6-(piperidin-4-yl)-1H-indazol-3-yl)dihydropyrimidine-2,4(1H,3H)-dione hydrochloride

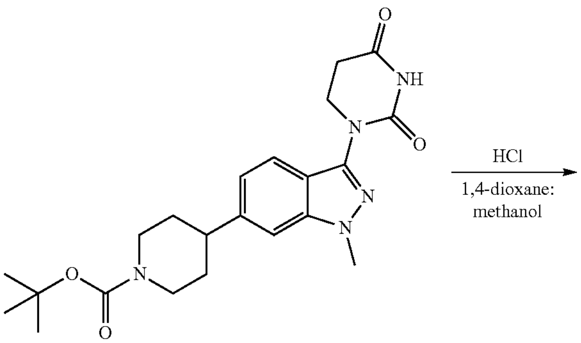

-continued

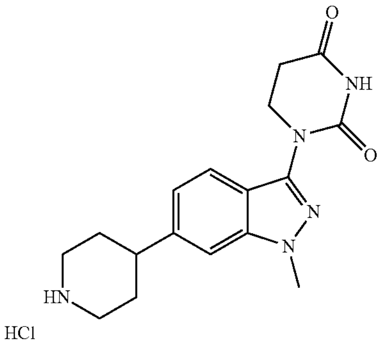

1-(1-methyl-6-(piperidin-4-yl)-1H-indazol-3-yl)dihydropyrimidine-2,4(1H,3H)-dione hydrochloride was obtained in quantitative yield from tert-butyl 4-[3-(2,4-dioxohexahydropyrimidin-1-yl)-1-methyl-indazol-6-yl]-3,6-dihydro-2H-pyridine-1-carboxylate using the general method B for tert-butoxycarbonyl protecting group deprotection. LCMS (ESI+): 328.1 $[M+H]^+$.

Synthesis of intermediate 5-[4-(4-piperidyl)anilino]-3-azabicyclo[3.1.1]heptane-2,4-dione hydrochloride

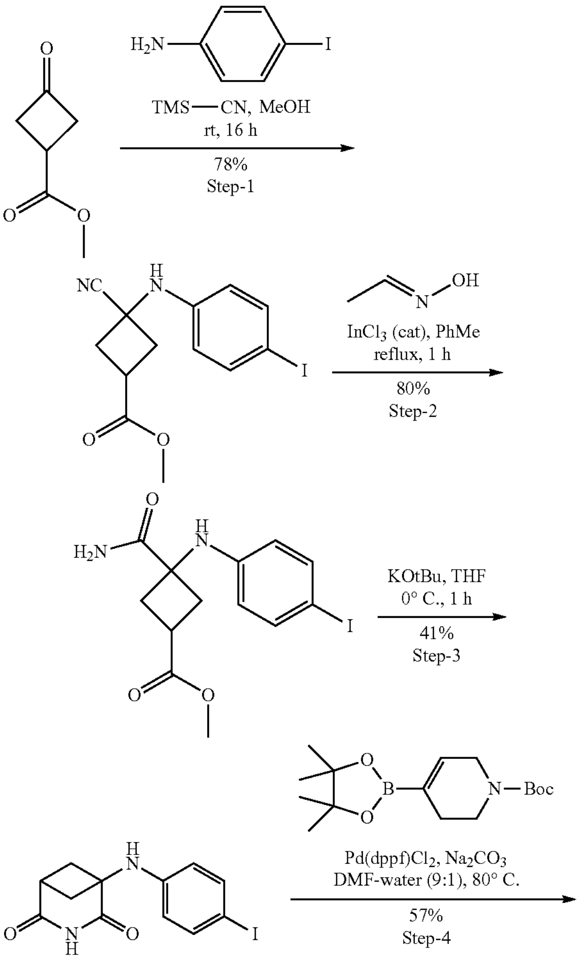

-continued

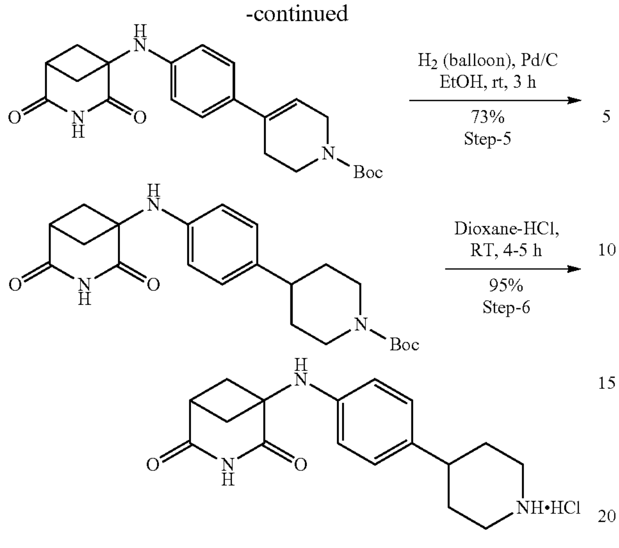

Step 1: Preparation of 3-Cyano-3-(4-iodo-phenylamino)-cyclobutane carboxylic acid methyl ester 4-Iodoaniline (13.2 g, 60.1 mmol) followed by trimethylsilyl cyanide (10.8 g, 109 mmol, 13.7 mL) were added to a stirred solution of methyl 3-oxocyclobutanecarboxylate (7 g, 54.6 mmol) in methanol (270 mL). The resulting mixture was stirred at ambient temperature for 16 h. The reaction mixture was concentrated under reduced pressure and the residue was purified by silica gel chromatography (5-10% ethyl acetate-hexane) to afford methyl 3-cyano-3-(4-iodoanilino)cyclobutanecarboxylate (15.2 g, 42.7 mmol, 78% yield) as an off-white solid. LCMS (ESI+): 357 $[M+H]^+$ Step 2: Preparation of 3-Carbamoyl-3-(4-iodo-phenylamino)-cyclobutane carboxylic acid methyl ester Acetaldehyde oxime (4.98 g, 84.2 mmol), followed by indium chloride (62.1 mg, 281 μmol) were added to a stirred solution of methyl 3-cyano-3-(4-iodoanilino) cyclobutanecarboxylate (10 g, 28.1 mmol) in toluene (120 mL) at ambient temperature. The resulting mixture was heated to reflux for 1 h. After completion, the reaction mixture was cooled to ambient temperature and the precipitate thus formed was filtered, washed with toluene:ether (1:1) and dried to yield methyl 3-carbamoyl-3-(4-iodoanilino) cyclobutanecarboxylate (8.4 g, 22.5 mmol, 80% yield). It was used in the next step without further purification. LCMS (ESI+): 375 $[M+H]^+$ Step 3: Preparation of 1-(4-Iodo-phenylamino)-3-aza-bicyclo[3.1.1]heptane-2,4-dione Potassium tert-butoxide (4.62 g, 41.2 mmol) was added at 0° C. to a stirred solution of methyl 3-[2-amino-1-(4-iodoanilino)-2-oxo-ethyl]cyclobutanecarboxylate (8 g, 20.6 mmol) in THF (150 mL), and the reaction mixture was stirred for 1 h at 0° C. The reaction mixture was neutralized with 1M citric acid solution and adjusted to pH-6 and extracted with ethyl acetate. The combined organic layers were dried over sodium sulfate, filtered and concentrated under reduced pressure. The residue mass was purified by column chromatography (40% ethyl acetate/hexane) to afford 5-(4-iodoanilino)-3-azabicyclo[3.1.1]heptane-2,4-dione (2.9 g, 8.48 mmol, 41% yield). LCMS (ESI+): 343 $[M+H]^+$ Step 4: Preparation of 4-[4-(2,4-Dioxo-3-aza-bicyclo[3.1.1]hept-1-ylamino)-phenyl]-3,6-dihydro-2H-pyridine1-carboxylic acid tert-butyl ester Sodium carbonate (1.98 g, 18.7 mmol) was added to a stirred solution of 5-(4-iodoanilino)-3-azabicyclo[3.1.1]heptane-2,4-dione (2.9 g, 8.48 mmol) and tert-butyl 4-(4,4,5,5-tetramethyl-1,3,2-dioxaborolan-2-yl)-3,6-dihydro-2H-pyridine-1-carboxylate (5.24 g, 17.0 mmol) in DMF (32 mL) and water (8 mL) and the reaction was degassed with argon. $Pd(dppf)Cl_2$ (692 mg, 848 μmol) was added under inert atmosphere. The resulting mixture was heated at 80° C. for 16 h. The reaction mixture was diluted with ethyl acetate and filtered through a short pad of celite. The filtrate was washed with water, brine, dried over anhydrous sodium sulphate, filtered and concentrated under reduced pressure. The residue was purified by column chromatography (5-10% ethyl acetate-hexane) to yield tert-butyl 4-[4-[(2,4-dioxo-3-azabicyclo[3.1.1]heptan-5-yl)amino]phenyl]-3,6-dihydro-2H-pyridine-1-carboxylate (1.91 g, 4.81 mmol, 57% yield). LCMS (ES+): 398 $[M+H]^+$ Step 5: Preparation of 4-[4-(2,4-Dioxo-3-aza-bicyclo[3.1.1]hept-1-ylamino)-phenyl]-piperidine-1-carboxylic acid tert-butyl ester 10% Pd—C (50% wet, 1 g) was added to a degassed solution of tert-butyl 4-[4-[(2,4-dioxo-3-azabicyclo[3.1.1]heptan-5-yl)amino]phenyl]-3,6-dihydro-2H-pyridine-1-carboxylate (1.91 g, 4.81 mmol) in ethanol (20 mL). The resulting mixture was stirred at ambient temperature under a hydrogen balloon atmosphere for 3 h. After completion, the reaction mixture was filtered through a short pad of celite, washed with ethyl acetate and concentrated under reduced pressure. The residue was purified by silica gel chromatography (60-70% ethyl acetate-hexane) to yield tert-butyl 4-[4-[(2,4-dioxo-3-azabicyclo[3.1.1]heptan-5-yl)amino]phenyl]piperidine-1-carboxylate (1.4 g, 3.50 mmol, 73% yield). LCMS (ES+): 400 $[M+H^+]$ Step 6: Preparation of 5-(4-Piperidin-4-yl-phenylamino)-3-aza-bicyclo [3.1.1]heptane-2,4-dione hydrochloride Dioxane HCl (4M, 15 mL, 60 mmol) was added to tert-butyl 4-[4-[(2,4-dioxo-3-azabicyclo[3.1.1]heptan-5-yl)amino]phenyl]piperidine-1-carboxylate (1.4 g, 3.50 mmol) at 10° C. The resulting mixture was warmed to ambient temperature and stirred for 5 h. The reaction mixture was concentrated under reduced pressure, triturated with ether and lyophilized to yield 5-[4-(4-piperidyl)anilino]-3-azabicyclo[3.1.1]heptane-2,4-dione hydrochloride (1.08 g, 3.34 mmol, 95% yield) as an off white solid. LCMS (ES+): 300 $[M+H]^+$, $^1$H-NMR (400 MHz, DMSO-D6) d 10.72 (s, 1H), 8.95 (br s, 1H), 8.81-8.79 (m, 1H), 6.90 (d, J=8.2 Hz, 2H), 6.44 (d, J=8.16 Hz, 2H), 3.32-3.29 (m, 2H), 2.95-2.91 (m, 3H), 2.73-2.62 (m, 3H), 2.49 (br m, 2H), 1.85-1.72 (m, 4H).

Synthesis of 3-[3-(difluoromethyl)-4-(4-piperidyl) anilino]piperidine-2,6-dione hydrochloride

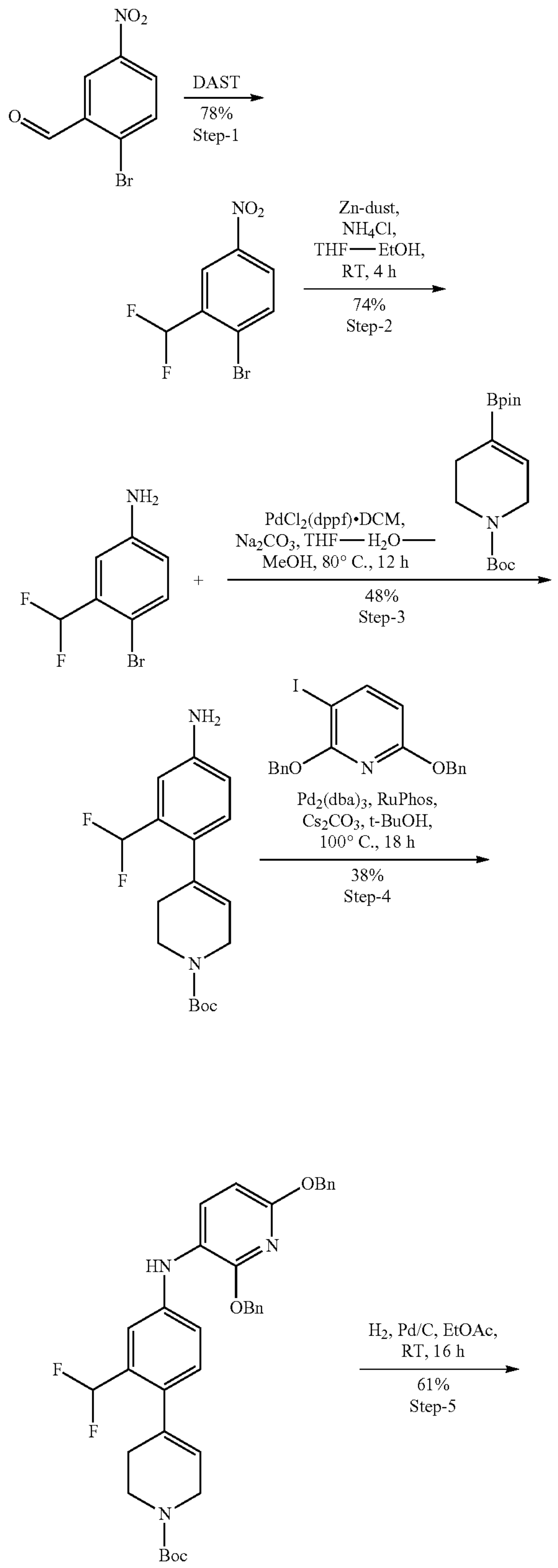

-continued

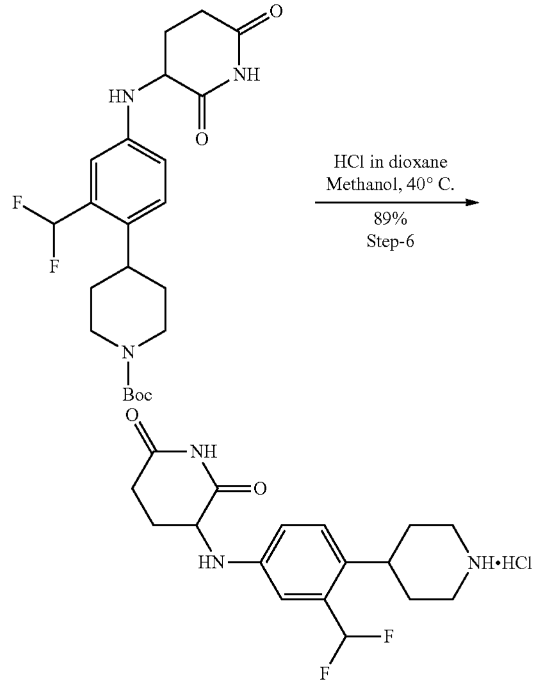

Step 1: Synthesis of 1-Bromo-2-difluoromethyl-4-nitro-benzene

DAST (24.13 mL, 182.60 mmol) was added to a stirred solution of 2-bromo-5-nitro-benzaldehyde (7 g, 30.4 mmol) in dichloromethane (350 mL) at 0° C. and the resulting reaction mixture was stirred at ambient temperature for 16 h. After completion, the reaction mixture was basified with 10% $NaHCO_3$ solution and extracted with dichloromethane. The combined organic extracts were washed with water, brine, dried over sodium sulphate, filtered and concentrated under reduced pressure. The residue was purified by column chromatography (10% ethyl acetate/hexane) to afford 1-bromo-2-(difluoromethyl)-4-nitro-benzene (6 g, 23.8 mmol, 78% yield).

Step 2: Synthesis of 4-Bromo-3-difluoromethyl-phenylamine

Ammonium chloride (12.7 g, 238 mmol) and zinc (15.6 g, 238 mmol) were added to a stirred solution of 1-bromo-2-(difluoromethyl)-4-nitro-benzene (6.0 g, 23.8 mmol) in THF (70 mL) and ethanol (70 mL) at ambient temperature. The resulting mixture was stirred at ambient temperature for 4 h. After completion, reaction mixture was filtered through a short pad of celite and washed with ethanol. The filtrate was concentrated under reduced pressure and the residue purified by column chromatography (40% ethyl acetate-hexane) to afford 4-bromo-3-(difluoromethyl) aniline (3.95 g, 17.8 mmol, 75% yield). LCMS (ES+): 221 $[M+H]^+$.

Step 3: Synthesis of 4-(4-Amino-2-difluoromethyl-phenyl)-3,6-dihydro-2H-pyridine-1-carboxylic acid tert-butyl ester Sodium carbonate (3.06 g, 28.82 mmol) was added to a stirred solution of 4-bromo-3-(difluoromethyl)aniline (3.2 g, 14.4 mmol) and tert-butyl 4-methyl-3,6-dihydro-2H-pyridine-1-carboxylate (3.08 g, 15.9 mmol) in THF (20 mL), methanol (10 mL) and water (10 mL) and the mixture was thoroughly purged with argon. $PdCl_2$(dppf)·dichloromethane (2.35 g, 2.88 mmol) was added under inert atmosphere. Resulting mixture was heated at 80° C. for 12 h. After completion, the reaction mixture was diluted with ethyl acetate, filtered through a short pad of celite and washed with ethyl acetate. The combined organic part was washed with water, brine, dried over anhydrous sodium sulphate, filtered and concentrated under reduced pressure. The residue was purified by column chromatography (20% ethyl acetate-hexane) to afford tert-butyl 4-[4-amino-2-(difluoromethyl)phenyl]-3,6-dihydro-2H-pyridine-1-carboxylate (2.24 g, 6.91 mmol, 48% yield). LCMS (ES+): 325 $[M+H]^+$.

Step 4: Synthesis of 4-[4-(2,6-Bis-benzyloxy-pyridin-3-ylamino)-2-difluoromethyl-phenyl]-3,6-dihydro-2H pyridine-1-carboxylic acid tert-butyl ester Cesium carbonate (5.12 g, 15.72 mmol) was added to a stirred solution of tert-butyl 4-[4-amino-2-(difluoromethyl) phenyl]-3,6-dihydro-2H-pyridine-1-carboxylate (1.7 g, 5.24 mmol) and 2,6-dibenzyloxy-3-iodo-pyridine (2.41 g, 5.77 mmol) in tert Butanol (40 mL). The resulting mixture was degassed with argon and $Pd_2(dba)_3$ (96 mg, 1.05 mmol), RuPhos (978 mg, 2.10 mmol) were added under inert atmosphere. The resulting mixture was heated at 100° C. for 18 h. After completion, the reaction mixture was diluted with ethyl acetate, filtered through a short pad of celite and washed with ethyl acetate. The filtrate was washed with water, brine, dried over anhydrous sodium sulphate, filtered and concentrated under reduced pressure. The residue was purified by column chromatography (25% ethyl acetate-hexane) to afford tert-butyl 4-[4-[(2,6-dibenzyloxy-3-pyridyl)amino]-2-(difluoromethyl)phenyl]-3,6-dihydro-2H-pyridine-1-carboxylate (1.23 g, 2.00 mmol, 38% yield). LCMS (ES+): 614 $[M+H]^+$.

Step 5

Synthesis of 4-[2-Difluoromethyl-4-(2,6-dioxo-piperidin-3-ylamino)-phenyl]-piperidine-1-carboxylic acid tert-butyl ester 10% Pd—C (50% wet, 2 g) was added to a degassed solution of tert-butyl 4-[4-[(2,6-dibenzyloxy-3-pyridyl) amino]-2-(difluoromethyl)phenyl]-3,6-dihydro-2H-pyridine-1-carboxylate (2 g, 3.26 mmol) in ethyl acetate (15 mL). The resulting mixture was stirred at ambient temperature under a hydrogen balloon atmosphere for 16 h. After completion, the reaction mixture was filtered through a short pad of celite, washed with ethyl acetate and concentrated under reduced pressure. The residue was purified by silica gel chromatography (60% ethyl acetate in hexane) to afford tert-butyl 4-[2-(difluoromethyl)-4-[(2,6-dioxo-3-piperidyl) amino]phenyl]piperidine-1-carboxylate (880 mg, 1.99 mmol, 61% yield) as a light blue solid. LCMS (ES+): 438 $[M+H]^+$. $^1H$ NMR (400 MHz, DMSO-d6) d 10.77 (s, 1H), 7.26-6.98 (m, 2H), 6.81 (s, 1H), 6.77 (d, J=8.8 Hz, 1H), 6.03 (d, J=7.8 Hz, 1H), 4.34 (bs, 1H), 4.06-4.03 (m, 2H), 2.90-2.70 (m, 4H), 2.60-2.56 (m, 1H), 2.09-2.06 (m, 1H), 1.91-1.87 (m, 1H), 1.61-1.59 (m, 2H), 1.51-1.46 (m, 2H), 1.41 (s, 9H).

Step 6: Synthesis of 3-[3-(difluoromethyl)-4-(4-piperidyl)anilino]piperidine-2,6-dione hydrochloride tert-Butyl 4-[2-(difluoromethyl)-4-[(2,6-dioxo-3-piperidyl)amino]phenyl]piperidine-1-carboxylate (191 mg, 436.59 µmol) was dissolved in a methanol (3 mL) and hydrogen chloride solution (4.0M in 1,4-dioxane, 1.09 mL) was added. The reaction mixture was heated at 40° C. for 4 h, and the reaction was complete. The volatiles were evaporated under reduce pressure. The material was submitted to high vacuum, frozen to −78° C. and thawed to afford 3-[3-(difluoromethyl)-4-(4-piperidyl)anilino]piperidine-2,6-dione hydrochloride (145 mg, 388 µmol, 89% yield) as a dense off-white solid. Rt=0.954 min., LCMS (ESI+): 338.3 $[M+H]^+$.

Synthesis of 5-[(2,6-dioxo-3-piperidyl)amino]-2-(4-piperidyl)benzonitrile hydrochloride

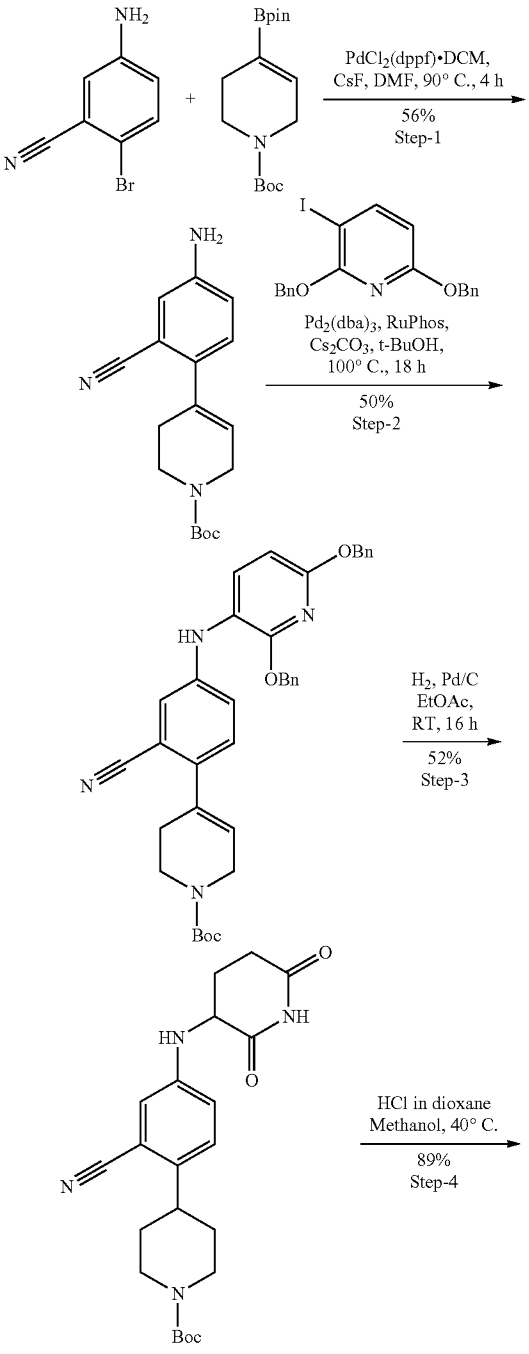

-continued

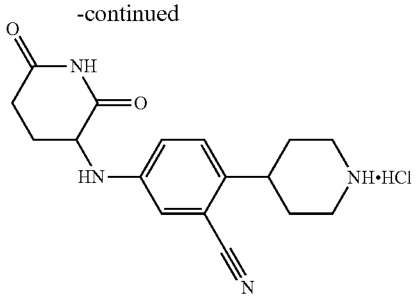

Step 1: Synthesis of 4-(4-Amino-2-cyano-phenyl)-3,6-dihydro-2H-pyridine-1-carboxylic acid tert-butyl ester To a stirred solution of 5-amino-2-bromo-benzonitrile (5 g, 25.38 mmol) and tert-butyl 4-(4,4,5,5-tetramethyl-1,3,2-dioxaborolan-2-yl)-3,6-dihydro-2H-pyridine-1-carboxylate (11.77 g, 38.06 mmol) in DMF (60 mL) was added cesium fluoride (7.71 g, 50.75 mmol, 1.87 mL) and the reaction mixture was degassed with argon. $PdCl_2$(dppf)·dichloromethane (4.14 g, 5.08 mmol) was added under inert atmosphere. Resulting mixture was heated at 90° C. for 16 h. After completion, reaction mixture was diluted with ethyl acetate, filtered through a short pad of celite and washed with ethyl acetate. Combined organic part was washed with water, brine, dried over anhydrous sodium sulphate, filtered and concentrated under reduced pressure. Crude mass was purified by column chromatography (20% ethyl acetate-hexane) to afford tert-butyl 4-(4-amino-2-cyano-phenyl)-3,6-dihydro-2H-pyridine-1-carboxylate (4.3 g, 14.36 mmol, 56.60% yield). LCMS (ES+): 300 $[M+H]^+$.

Step 2: Synthesis of 4-[4-(2,6-Bis-benzyloxy-pyridin-3-ylamino)-2-cyano-phenyl]-3,6-dihydro-2H-pyridine-1-carboxylic acid tert-butyl ester To a stirred solution of tert-butyl 4-(4-amino-2-cyano-phenyl)-3,6-dihydro-2H-pyridine-1-carboxylate (3 g, 10.02 mmol) and 2,6-dibenzyloxy-3-iodo-pyridine (4.60 g, 11.02 mmol) in t-BuOH (50 mL), cesium carbonate (9.80 g, 30.06 mmol) was added. Resulting mixture was degassed with argon and $Pd_2(dba)_3$ (458.83 mg, 501.06 RuPhos (467.62 mg, 1.00 mmol) were added under inert atmosphere. Resulting mixture was heated at 100° C. for 18 h. The reaction mixture was diluted with ethyl acetate, filtered through a short pad of celite and washed with ethyl acetate. Combined organic part was washed with water, brine, dried over anhydrous sodium sulphate, filtered and concentrated under reduced pressure. Crude mass was purified by column chromatography (25% ethyl acetate-hexane) to afford tert-butyl 4-[2-cyano-4-[(2,6-dibenzyloxy-3-pyridyl)amino]phenyl]-3,6-dihydro-2H-pyridine-1-carboxylate (3 g, 5.10 mmol, 50.85% yield) LCMS (ES+): 589 $[M+H]^+$.

Step 3: Synthesis of 4-[2-Cyano-4-(2,6-dioxo-piperidin-3-ylamino)-phenyl]-piperidine-1-carboxylic acid tert-butyl ester To a degassed solution of tert-butyl 4-[2-cyano-4-[(2,6-dibenzyloxy-3-pyridyl)amino]phenyl]-3,6-dihydro-2H-pyridine-1-carboxylate (3 g, 5.10 mmol) in ethyl acetate (60 mL), 10% Pd—C (50% wet, 3 g) was added. Resulting mixture was stirred at ambient temperature under hydrogen at balloon pressure for 16 h. The reaction mixture was filtered through a short pad of celite, washed with ethyl acetate and concentrated under reduced pressure. The crude mass was purified by silica gel column chromatography (60% ethyl acetate in hexane) to afford tert-butyl 4-[2-cyano-4-[(2,6-dioxo-3-piperidyl)amino]phenyl]piperidine-1-carboxylate (1.1 g, 2.65 mmol, 52.07% yield) as pale green solid. LCMS (ES+): 413 $[M+H]^+$. $^1H$ NMR (400 MHz, DMSO-d6) d 10.81 (s, 1H), 7.20 (d, J=8.5 Hz, 1H), 6.96 (t, J=8.7 Hz, 2H), 6.26 (d, J=7.9 Hz, 1H), 4.43-4.37 (m, 1H), 4.09-4.06 (m, 2H), 2.87-2.69 (m, 4H), 2.60-2.55 (m, 1H), 2.10-2.06 (m, 1H), 1.92-1.87 (m, 1H), 1.70-1.67 (m, 2H), 1.57-1.46 (m, 2H), 1.41 (s, 9H).

Step 4: Synthesis of 5[(2,6-dioxo-3-piperidyl)amino]-2-(4-piperidyl)benzonitrile hydrochloride Tert-butyl 4-[2-cyano-4-[(2,6-dioxo-3-piperidyl)amino]phenyl]piperidine-1-carboxylate (120 mg, 290.92 μmol) was dissolved in methanol mixture (3 mL) mL) and Hydrogen chloride solution 4.0M in 1,4-dioxane (4 M, 727.31 μL) was added. The reaction mixture was heated at 40° C. for 4 hours, and the reaction was complete. The volatiles were evaporated under reduce pressure. The material was submitted to high vacuum, frozen to −78° C. and thawed to afford 5-[(2,6-dioxo-3-piperidyl)amino]-2-(4-piperidyl)benzonitrile hydrochloride (107 mg, 277.51 μmol, 95% yield) as a dense solid. LCMS (ESI+): 313.2 $[M+H]^+$.

Synthesis of 4-[3-(2,4-dioxohexahydropyrimidin-1-yl)-1-methyl-indazol-6-yl]-3,3-difluoro-piperidine hydrochloride Step 1: Tert-butyl 3,3-difluoro-4-(trifluoromethylsulfonyloxy)-2,6-dihydropyridine-1-carboxylate

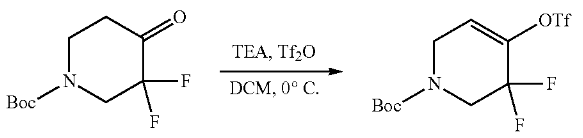 [SMILES: CC(C)(C)OC(=O)N1CCC(=O)C(F)(F)C1 ; "DCM, 0° C." ; "TEA, Tf2O" ; CC(C)(C)OC(=O)N1CC=C(OS(=O)(=O)C(F)(F)F)C(F)(F)C1]

N,N-diethylethanamine (3.23 g, 31.9 mmol, 4.44 mL), followed by trifluoromethylsulfonic anhydride (4.50 g, 15.9 mmol, 2.68 mL) were added drop-wise to a stirred solution of tert-butyl 3,3-difluoro-4-oxo-piperidine-1-carboxylate (2.5 g, 10.6 mmol) in dichloromethane (25 mL) at 0° C. The reaction was stirred at ambient temperature for 16 h. Then, the reaction was quenched with aqueous $NaHCO_3$, and extracted with dichloromethane, washed with brine, dried over sodium sulphate, and concentrated. The residue was purified by silica gel chromatography (100% hexanes to 4:1 hexanes:ethyl acetate) to yield tert-butyl 3,3-difluoro-4-(trifluoromethylsulfonyloxy)-2,6-dihydropyridine-1-carboxylate (1.2 g, 2.29 mmol, 21% yield). $^1H$ NMR (400 MHz, Methanol-d4) δ 6.59 (s, 1H), 4.29 (q, J=4.3 Hz, 2H), 4.04 (t, J=11.0 Hz, 2H), 1.51 (s, 9H).

Step 2: 1-[1-methyl-6-(4,4,5,5-tetramethyl-1,3,2-dioxaborolan-2-yl)indazol-3-yl]hexahydropyrimidine-2,4-dione

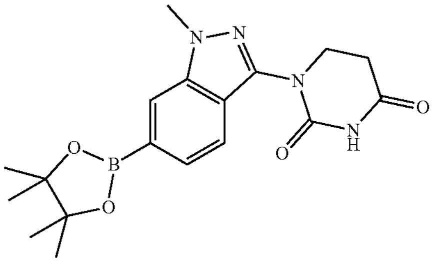 [SMILES: Cn1nc(N2CCC(=O)NC2=O)c2ccc(B3OC(C)(C)C(C)(C)O3)cc21]

Potassium acetate (911 mg, 9.28 mmol) and Pd(dppf)$Cl_2$ (113 mg, 155 mol) were added to a solution of 1-(6-bromo-1-methyl-indazol-3-yl)hexahydropyrimidine-2,4-dione (1.0 g, 3.09 mmol) and bis(pinacolato)diboron (1.18 g, 4.64 mmol) in 1,4-dioxane (15 mL). The mixture was stirred at 85° C. under a nitrogen atmosphere for 16 h. The mixture was cooled to ambient temperature and filtered through a pad of silica gel. The filter cake was washed with ethyl acetate and the filtrate was concentrated under reduced pressure. The residue was purified by silica gel chromatography (100% hexanes to 100% ethyl acetate) to yield 1-[1-methyl-6-(4,4,5,5-tetramethyl-1,3,2-dioxaborolan-2-yl)indazol-3-yl]hexahydropyrimidine-2,4-dione (1.1 g, 2.97 mmol, 96% yield). LCMS (ESI+): 371 $[M+H]^+$.

Step 3: tert-Butyl 4-(3-(2,4-dioxotetrahydropyrimidin-1(2H)-yl)-1-methyl-1H-indazol-6-yl)-3,3-difluoro-3,6-dihydropyridine-1(2H)-carboxylate

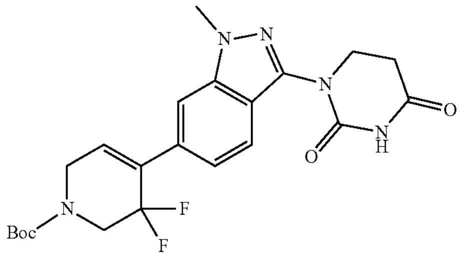 [SMILES: Cn1nc(N2CCC(=O)NC2=O)c2ccc(C3=CCN(C(=O)OC(C)(C)C)CC3(F)F)cc21]

Sodium carbonate (485 mg, 4.57 mmol) was added to a solution of 1-[1-methyl-6-(4,4,5,5-tetramethyl-1,3,2-dioxaborolan-2-yl)indazol-3-yl]hexahydropyrimidine-2,4-dione (677 mg, 1.83 mmol) and tert-butyl 3,3-difluoro-4-(trifluoromethylsulfonyloxy)-2,6-dihydropyridine-1-carboxylate (560 mg, 1.52 mmol) in 1,4-dioxane (10 mL) and water (2.5 mL) and the solvent was sparged with $N_2$ gas for 10 min. 1,1'-Bis(Diphenylphosphino)ferrocenepalladium (II) dichloride (111 mg, 152 μmol) was added and the reaction mixture was stirred at 55° C. for 2 h. Then, the reaction mixture was cooled and diluted with water/ethyl acetate. After extraction, organic layer was washed with brine, dried over sodium sulphate, and concentrated. The residue was purified by silica gel chromatography (100% hexanes to 100% ethyl acetate) to give tert-butyl 4-[3-(2,4-dioxohexahydropyrimidin-1-yl)-1-methyl-indazol-6-yl]-3,3-difluoro-2,6-dihydropyridine-1-carboxylate (480 mg, 1.04 mmol, 68% yield). LCMS (ESI+): 462.2 $[M+H]^+$.

Step 4: tert-butyl 4-[3-(2,4-dioxohexahydropyrimidin-1-yl)-1-methyl-indazol-6-yl]-3,3-difluoro-piperidine-1-carboxylate

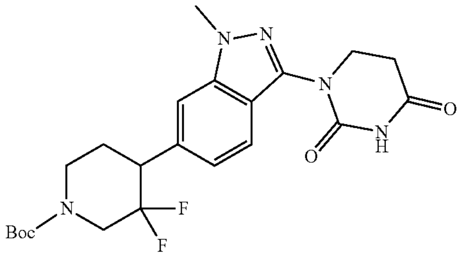 [SMILES: Cn1nc(N2CCC(=O)NC2=O)c2ccc(C3CCN(C(=O)OC(C)(C)C)CC3(F)F)cc21]

Palladium, 10% on carbon (Type 487, dry, 331 mg, 311 μmol) was added to a solution of tert-butyl 4-[3-(2,4-dioxohexahydropyrimidin-1-yl)-1-methyl-indazol-6-yl]-3,3-difluoro-2,6-dihydropyridine-1-carboxylate (478 mg, 1.04 mmol) in methanol (10.3 mL) and the mixture was stirred at ambient temperature under a hydrogen balloon atmosphere. After 24 h, the hydrogen balloon was removed and the mixture was diluted with dichloromethane (20 mL) and the slurry was stirred for additional 24 h. Then, the mixture was filtered through a pad of celite, washed using a solution of dichloromethane/methanol (3:1), and concentrated to afford tert-butyl 4-[3-(2,4-dioxohexahydropyrimidin-1-yl)-1-methyl-indazol-6-yl]-3,3-difluoro-piperidine-1-carboxylate (450 mg, 94% yield). LCMS (ESI+): 408.2 $[M\text{-tert-butyl}+H]^+$.

Step 5: 4-[3-(2,4-dioxohexahydropyrimidin-1-yl)-1-methyl-indazol-6-yl]-3,3-difluoro-piperidine hydrochloride

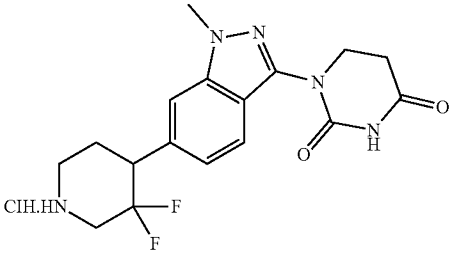

4-[3-(2,4-dioxohexahydropyrimidin-1-yl)-1-methyl-indazol-6-yl]-3,3-difluoro-piperidine hydrochloride was obtained in quantitative yield from tert-butyl 4-[3-(2,4-dioxohexahydropyrimidin-1-yl)-1-methyl-indazol-6-yl]-3,3-difluoro-piperidine-1-carboxylate using General method B for the removal of the tert-butoxycarbonyl group. LCMS (ESI+): 354.2 $[M+H]^+$.

Synthesis of tert-butyl 3,3-difluoro-4-(4-nitrophenyl)piperidine-1-carboxylate, isomer 1 and tert-butyl 3,3-difluoro-4-(4-nitrophenyl)piperidine-1-carboxylate, isomer 2

Step 1: Synthesis of tert-butyl 4-(4-nitrophenyl)-3-oxo-piperidine-1-carboxylate

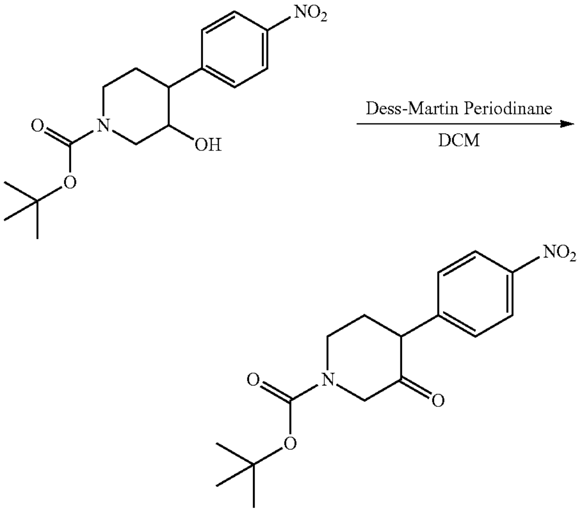

tert-Butyl 3-hydroxy-4-(4-nitrophenyl)piperidine-1-carboxylate (19.5 g, 60.5 mmol) (CAS #1232788-17-8) was dissolved in dichloromethane (200 mL) and cooled to 0° C. Dess-Martin Periodinane (38.5 g, 90.7 mmol) was added portion-wise. The reaction solution was stirred at that temperature for 2 h and stirring was continued while the temperature gradually climbed up to ambient temperature. Dichloromethane (100 mL) was added, followed by Dess-Martin Periodinane (8.3 g, 19.6 mmol) at 16° C. and the reaction was stirred for 17 h. The reaction solution was cooled back down to 4° C. Saturated $NaHCO_3$ solution (250 mL) was carefully added, followed by sodium thiosulfate pentahydrate (13.8 g, 48.4 mmol) dissolved in 175 mL of water. The mixture was diluted with dichloromethane (150 mL). The resulting precipitate was removed by filtration and the cake was washed with dichloromethane (75 mL×3). The filtrate was separated into layers and the organic layer was dried over sodium sulphate, filtered and concentrated to afford tert-butyl 4-(4-nitrophenyl)-3-oxo-piperidine-1-carboxylate (19.4 g, 60.5 mmol, quantitative yield). LCMS (ESI+): 354.1 $[M+Na]^+$/221.0 $[M-Boc+H]^+$.

Step 2: Synthesis of tert-butyl 3,3-difluoro-4-(4-nitrophenyl)piperidine-1-carboxylate

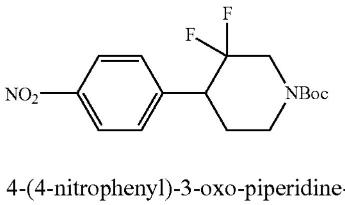

tert-Butyl 4-(4-nitrophenyl)-3-oxo-piperidine-1-carboxylate (3.78 g, 11.8 mmol) was dissolved in dichloromethane (40 mL) and the solution was cooled to 0° C. DAST (3.80 g, 23.6 mmol, 3.12 mL) was added slowly via a syringe. The reaction mixture was warmed slowly to room temperature while it was stirred overnight. The reaction solution was cooled to −1.3° C. and saturated aqueous $NaHCO_3$ (100 mL) was added carefully via an addition funnel (exothermic). Internal temperature was maintained below 18° C. during the addition. The reaction mixture was diluted with ethyl acetate (80 mL) and warmed up to ambient temperature. The layers were separated and the aqueous layer was washed with ethyl acetate (80 mL). The combined organics were washed with aqueous 18% NaCl solution and concentrated. The residue was purified by silica gel chromatography (gradient: 10-30% ethyl acetate in hexanes to afford tert-butyl 3,3-difluoro-4-(4-nitrophenyl)piperidine-1-carboxylate (2.50 g, 62% yield) LCMS (ESI+): 280.2 $[M-t-Bu+H]^+$/ 243.1 $[M-Boc+H]^+$.

Step 3: Chiral separation to obtain tert-butyl 3,3-difluoro-4-(4-nitrophenyl)piperidine-1-carboxylate, isomer 1 and tert-butyl 3,3-difluoro-4-(4-nitrophenyl)piperidine-1-carboxylate, isomer 2

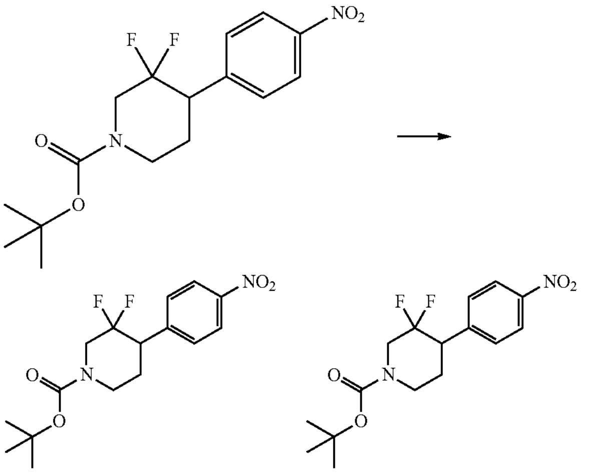

Isomer 1 Isomer 2

Racemic tert-butyl 3,3-difluoro-4-(4-nitrophenyl)piperidine-1-carboxylate (2.49 g) was subjected to a Chiral SFC separation, under the following conditions:

Column: ChiralPak IC-H 21×250 mm

Mobile Phase: 10% 2-propanol in carbon dioxide.

Flow rate: 70 mL/min

Detection: 220 nm UV

Pressure: 100 bar

The first eluting set of fractions was evaporated under reduced pressure to afford tert-butyl 3,3-difluoro-4-(4-nitrophenyl)piperidine-1-carboxylate, isomer 1 (800 mg, 32% yield, Rt=1.74 min, >99% enantiomeric excess) LCMS (ES+): 280.2 $[M-tBu+H]^+$/243.1 $[M-Boc+H]^+$.

The second eluting set of fractions was evaporated under reduced pressure to afford afford tert-butyl 3,3-difluoro-4-(4-nitrophenyl)piperidine-1-carboxylate, isomer 2 (800 mg, 32% yield, Rt=2.31 min., 99.6% enantiomeric excess). LCMS (ES+): 280.2 $[M-t-Bu+H]^+$/243.1 $[M-Boc+H]^+$.

The enantiomeric excess of the purified enantiomers was determined using the following analytical SFC method.

Column: ChiralPak IC-H 4.6×100 mm

Mobile phase: 10% iso-propanol in carbon dioxide

Flow rate: 4 mL/min

Pressure: 100 bar

Synthesis of 3-[4-[3,3-difluoro-4-piperidyl]anilino]piperidine-2,6-dione dihydrochloride, isomer 1

Step 1: Tert-butyl-4-(4-aminophenyl)-3,3-difluoro-piperidine-1-carboxylate, isomer 1

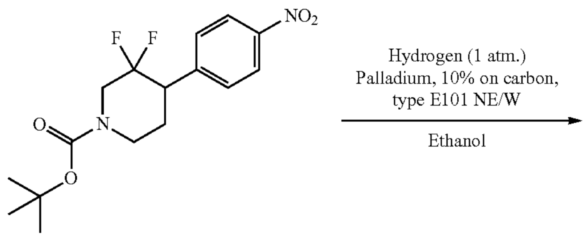

Isomer 1

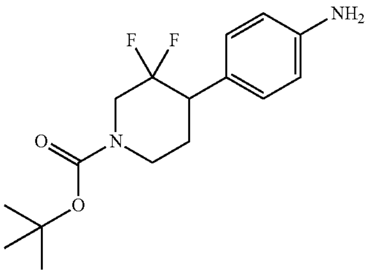

Isomer 1 tert-Butyl 3,3-difluoro-4-(4-nitrophenyl)piperidine-1-carboxylate, isomer 1 (0.8 g, 2.34 mmol) was dissolved in ethanol (12 mL) and the solution was degassed with nitrogen. Palladium, 10% on carbon, type E101 NOW (125 mg, 1.17 mmol) was then added. After degassing again with nitrogen couple, the reaction mixture was stirred under a hydrogen balloon atmosphere for 16 h. The reaction mixture was filtered through a pad of celite, washed with ethyl acetate (12 mL×3) and the filtrate was concentrated to yield tert-butyl-4-(4-aminophenyl)-3,3-difluoro-piperidine-1-carboxylate, isomer 1 (722 mg, 98% yield). LCMS (ESI+): 257 $[M-tBu+H]^+$

Step 2: tert-butyl (4S)-4-[4-[(2,6-dioxo-3-piperidyl)amino]phenyl]-3,3-difluoro-piperidine-1-carboxylate, isomer 1

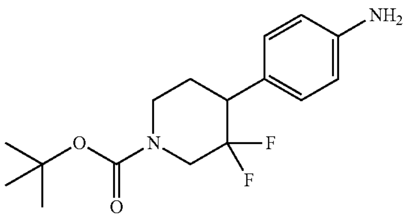

Isomer 1

+

-continued

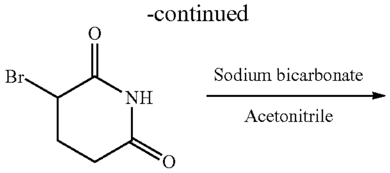

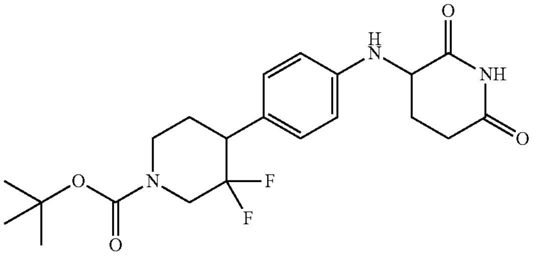

Isomer 1

Acetonitrile (3.5 mL) was added to tert-Butyl 4-(4-aminophenyl)-3,3-difluoro-piperidine-1-carboxylate, isomer 1 (520 mg, 1.66 mmol), 3-bromopiperidine-2,6-dione (478 mg, 2.49 mmol) and $NaHCO_3$ (418 mg, 4.98 mmol) in a vial. The reaction mixture was heated to 70° C. for 45 h. 3-bromopiperidine-2,6-dione (92 mg, 0.28 equiv) and $NaHCO_3$ (110 mg, 0.78 equiv) were added and heating was continued for a further 72 h, at which point, the reaction was cooled to ambient temperature and water (18 mL) was slowly added. The mixture was stirred for 4 h, then the precipitate was collected by filtration, washing with water (10 mL×3), then with 9:1 hexane:ethyl acetate (5 mL×3). The filter cake was dried under vacuum to afford tert-butyl 4-[4-[(2,6-dioxo-3-piperidyl)amino]phenyl]-3,3-difluoro-piperidine-1-carboxylate, isomer 1 (577 mg, 78% yield) as a green solid. LCMS (ESI+): 446 $[M+Na]^+$

Step 3: 3-[4-[3,3-difluoro-4-piperidyl]anilino]piperidine-2,6-dione dihydrochloride, isomer 1

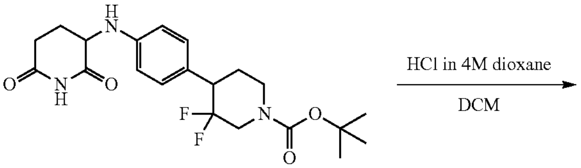

Isomer 1

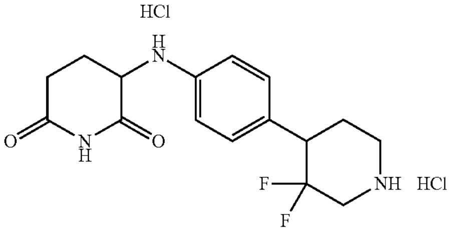

Isomer 1

Tert-butyl 4-[4-[(2,6-dioxo-3-piperidyl)amino]phenyl]-3,3-difluoro-piperidine-1-carboxylate, isomer 1 (300 mg, 709 μmol), was dissolved in dichloromethane (3.4 mL), and hydrogen chloride (4M in 1,4-dioxane, 850 μL, 3.4 mmol) was added under stirring. After 1 hour, the reaction mixture was concentrated to afford 3-[4-[3,3-difluoro-4-piperidyl]

anilino]piperidine-2,6-dione dihydrochloride, isomer 1 in quantitative yield. LCMS (ESI+): 324 $[M+H]^+$.

Synthesis of 3-[4-[3,3-difluoro-4-piperidyl]anilino]piperidine-2,6-dione dihydrochloride, isomer 2

Step 1: Synthesis of tert-butyl-4-(4-aminophenyl)-3,3-difluoro-piperidine-1-carboxylate, isomer 2

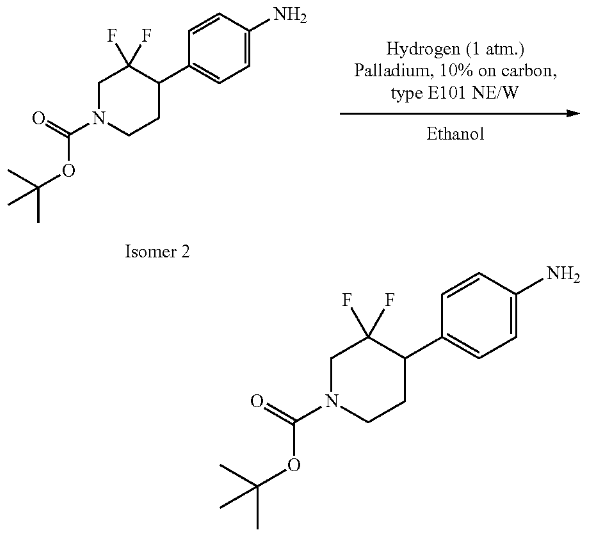

Isomer 2

Isomer 2

Tert-butyl 3,3-difluoro-4-(4-nitrophenyl)piperidine-1-carboxylate, isomer 2 (800 mg, 2.34 mmol) was dissolved in Ethanol (12 mL). The solution was evacuated and backfilled with nitrogen couple times. Palladium, 10% on carbon, type E101 NE/W (124.35 mg, 1.17 mmol) was then added. After evacuated and backfilled with nitrogen couple more times, the reaction mixture was subjected to hydrogenation ($H_2$ balloon) at ambient temperature for 16 hours. The reaction mixture was filtered through a pad of Celite, washing with ethyl acetate (12 mL×3). The filtrate was concentrated in vacuo and further dried under vacuum to yield a semi-solid (oily) upon standing; tert-butyl-4-(4-aminophenyl)-3,3-difluoro-piperidine-1-carboxylate, isomer 2 (724 mg, 94% yield). LCMS (ESI+): 257.1 $[M\text{-}tBu+H]^+$

Step 2: Synthesis of 4-[4-[(2,6-dioxo-3-piperidyl)amino]phenyl]-3,3-difluoro-piperidine-1-carboxylate, isomer 2

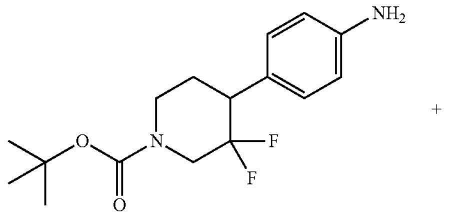

Isomer 2

-continued

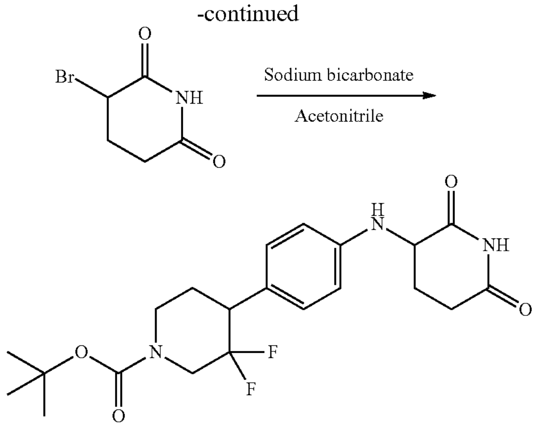

Isomer 2

To a vial was added tert-butyl 4-(4-aminophenyl)-3,3-difluoro-piperidine-1-carboxylate, isomer 2 (721.54 mg, 2.31 mmol), 3-bromopiperidine-2,6-dione (665.32 mg, 3.47 mmol), and Sodium bicarbonate (582.19 mg, 6.93 mmol, 269.53 Added Acetonitrile (5 mL). Reaction mixture was warmed to 70° C. (block temperature) overnight. After 48 hours, added additional amount of 3-bromopiperidine-2,6-dione (129 mg, 0.28 equiv), NaHCO3 (129 mg, 0.66 equiv). After another 72 hours, cooled to ambient temperature. Water (25 mL) was added slowly. Stirred at ambient temperature for couple hours. Reaction mixture was filtered to collect solid. Washed with water (12 mL×3), 9:1 hexane: ethyl acetate (5 mL×2), and dried under vacuum to afford tert-butyl 4-[4-[(2,6-dioxo-3-piperidyl)amino]phenyl]-3,3-difluoro-piperidine-1-carboxylate, isomer 2 (838 mg, 81.4% yield) as a green solid. LCMS (ESI+): 446.4 $[M+Na]^+$

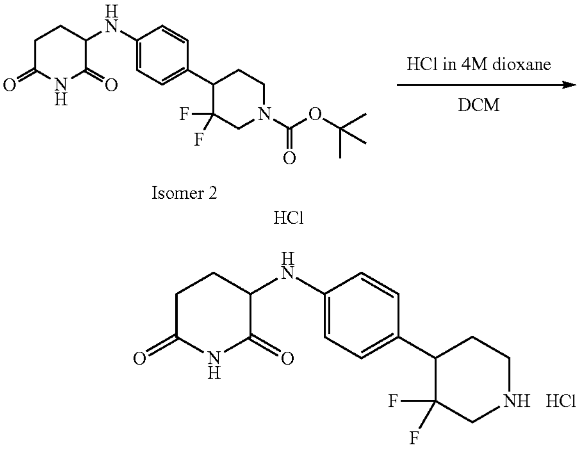

Isomer 2

Isomer 2

Tert-butyl 4-[4-[(2,6-dioxo-3-piperidyl)amino]phenyl]-3,3-difluoro-piperidine-1-carboxylate, isomer 2 (300 mg, 708.5 µmol), was dissolved in Dichloromethane (3.4 mL), and hydrogen chloride (4M in 1,4-dioxane, 850 µL, 3.4 mmol) was added under stirring. After 1 hour, the reaction mixture was evaporated to dryness under reduced pressure to afford 3-[4-[3,3-difluoro-4-piperidyl]anilino]piperidine-2,6-dione dihydrochloride, isomer 2 in quantitative yield. LCMS (ESI+): 324.1 $[M+H]^+$ Synthesis of 2-[1-[4-[(2,6-dioxo-3-piperidyl)amino]-2-(trifluoromethyl)phenyl]-4-hydroxy-4-piperidyl] acetic acid Step 1: tert-butyl 2-[4-hydroxy-1-[4-nitro-2-(trifluoromethyl)phenyl]-4-piperidyl]acetate

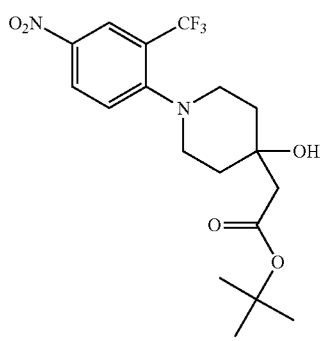 [SMILES: CC(C)(C)OC(=O)CC1(O)CCN(c2ccc([N+](=O)[O-])cc2C(F)(F)F)CC1]

Lithium diisopropylamide (0.7 M in THF, 54 mL, 37.82 mmol) was added dropwise over a period of 10 min to a stirred solution of tert-butyl acetate (1.76 g, 15.1 mmol, 2.04 mL) in dry THF (40 ml) at −78° C. The reaction mixture was stirred for 1 h. 1-[4-nitro-2-(trifluoromethyl)phenyl]piperidin-4-one (4.36 g, 15.1 mmol) dissolved in THF (20 ml) was added slowly. The reaction was stirred for 1 h at −78° C. The reaction was quenched with aqueous ammonium chloride solution at −78° C. and the mixture was warmed to ambient temperature and extracted with ethyl acetate. The organic layer was washed with brine and concentrated to afford a residue which was used without further purification. LCMS (ESI−): 403.1 $[M-H]^-$.

Step 2: tert-butyl 2-[1-[4-amino-2-(trifluoromethyl) phenyl]-4-hydroxy-4-piperidyl]acetate

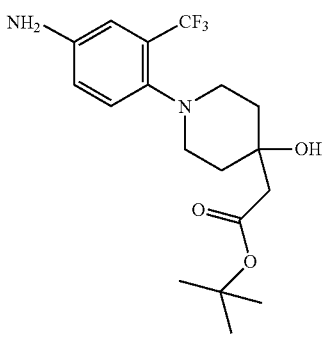 [SMILES: CC(C)(C)OC(=O)CC1(O)CCN(c2ccc(N)cc2C(F)(F)F)CC1]

A stirred solution of tert-butyl 2-[4-hydroxy-1-[4-nitro-2-(trifluoromethyl)phenyl]-4-piperidyl]acetate (2 g, 4.95 mmol) in a ethyl acetate (40 mL) was purged with nitrogen for 5 min. Pd/C, 10% ON DRY BASIS (1.05 g, 9.89 mmol) was added to the reaction mixture. The reaction mixture was placed under a hydrogen atmosphere (balloon). The reaction mixture was stirred for 4 h. The reaction mixture was filtered through a celite bed by flushing with a dichloromethane: ethyl acetate mixture (1:1, 500 mL). The filtrate was concentrated under reduced pressure to afford brownish solid was dissolved in dichloromethane (20 mL) and dry packed on silica under reduced pressure. The compound was purified by silica gel (230-400 mesh) column chromatography using a ethyl acetate:petroleum ether. The pure fractions were combined and concentrated under reduced pressure to afford pure reddish-brown solid tert-butyl 2-[1-[4-amino-2-(trifluoromethyl)phenyl]-4-hydroxy-4-piperidyl]acetate (1.1 g, 1.96 mmol, 40% yield). LCMS (ES+): 375.2 $[M+H]^+$.

Step 3: tert-butyl 2-[1-[4-[(2,6-dioxo-3-piperidyl) amino]-2-(trifluoromethyl)phenyl]-4-hydroxy-4-piperidyl]acetate

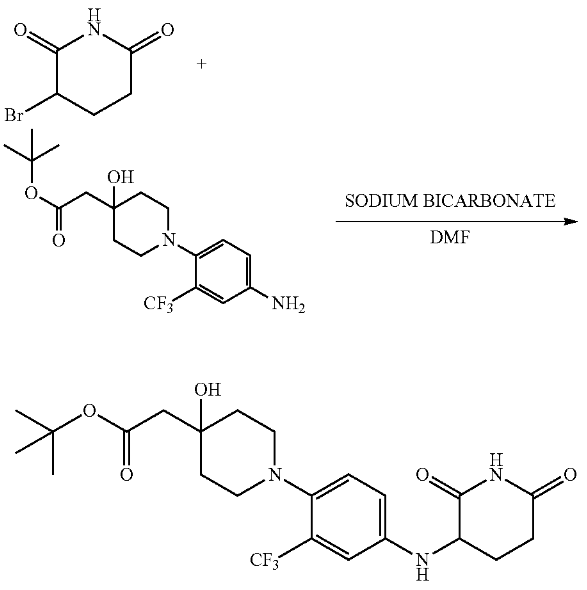

To a stirred solution of tert-butyl 2-[1-[4-amino-2-(trifluoromethyl)phenyl]-4-hydroxy-4-piperidyl]acetate (1.1 g, 2.94 mmol) and 3-bromopiperidine-2,6-dione (846.21 mg, 4.41 mmol) in DMF (10 mL) was added sodium bicarbonate (740.45 mg, 8.81 mmol) at room temperature, after 10 min the temperature of the reaction was raised to 60° C. and continued the reaction about 12 hr. The reaction mixture was diluted with Ice-Cold water (20 mL) and extracted by ethyl acetate (2*100 mL), washed with brine (10 mL), dried over anhydrous $Na_2SO_4$, filtered and concentrated under reduced pressure. The crude product was purified using silica gel chromatography using a 10% to 100% Ethyl acetate in Petroleum ether eluent gradient. The pure fractions were combined and concentrated under reduced pressure to afford tert-butyl 2-[1-[4-[(2,6-dioxo-3-piperidyl)amino]-2-(trifluoromethyl)phenyl]-4-hydroxy-4-piperidyl]acetate (300 mg, 468.45 μmol, 16% yield) as a brownish-green solid. LCMS (ESI+): 486.2 $[M+H]^+$.

Step 4: Synthesis of 2-[1-[4-[(2,6-dioxo-3-piperidyl)amino]-2-(trifluoromethyl)phenyl]-4-hydroxy-4-piperidyl]acetic acid

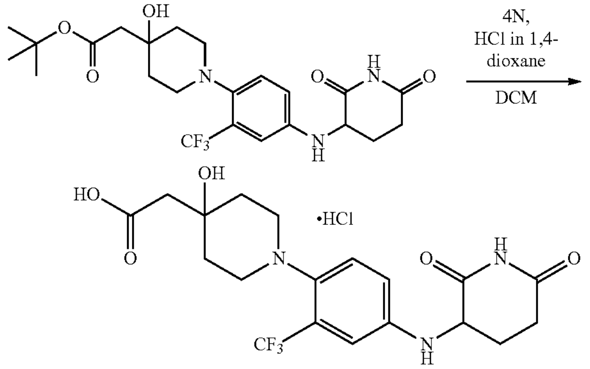

To a stirred solution of tert-butyl 2-[1-[4-[(2,6-dioxo-3-piperidyl)amino]-2-(trifluoromethyl)phenyl]-4-hydroxy-4-piperidyl]acetate (620 mg, 1.28 mmol) in dichloromethane (3 mL) was added hydrogen chloride (4M in 1,4-dioxane, 0.32 mL, 6.39 mmol) dropwise at 0° C. under nitrogen atmosphere, it was stirred for 6 h at room temperature. The reaction mixture was distilled under vacuum and triturated with diethyl ether, decanted the diethyl ether then dried to afford 2-[1-[4-[(2,6-dioxo-3-piperidyl)amino]-2-(trifluoromethyl)phenyl]-4-hydroxy-4-piperidyl]acetic acid (345 mg, 661 μmol, 52% yield) as a green colored solid. LCMS (ES+): 430.1 $[M+H]^+$.

General Procedure for the Alkylation of Intermediates with Tert-Butyl 2-Bromoacetate

Synthesis of tert-butyl 2-[4-[4-[(2,6-dioxo-3-piperidyl)amino]phenyl]-1-piperidyl]acetate

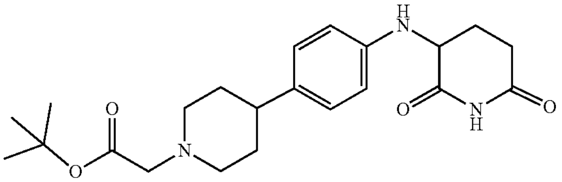 [SMILES: CC(C)(C)OC(=O)CN1CCC(c2ccc(NC3CCC(=O)NC3=O)cc2)CC1]

3-[4-(4-piperidyl)anilino]piperidine-2,6-dione hydrochloride (1 g, 3.09 mmol) was dissolved in N,N-dimethylacetamide (15 mL) and N,N-diisopropylethylamine (1.60 g, 12.4 mmol, 2.15 mL) was added. The mixture was cooled to 0° C., and tert-butyl 2-bromoacetate (663 mg, 3.40 mmol, 498 μL) was added. The mixture was stirred at 0° C. for 4 h. The reaction was diluted with ethyl acetate and washed with saturated sodium bicarbonate and brine. The organic layer was concentrated and purified by silica gel chromatography (0-10% Methanol in dichloromethane) to yield tert-butyl 2-[4-[4-[(2,6-dioxo-3-piperidyl)amino]phenyl]-1-piperidyl]acetate (0.84 g, 2.09 mmol, 68% yield) as a white solid. LCMS (ESI+): 402.2 $[M+H]^+$ The following compounds were synthesized using General procedure, as that used for the synthesis of tert-butyl 2-[4-[4-[(2,6-dioxo-3-piperidyl)amino]phenyl]-1-piperidyl]acetate from 3-[4-(4-piperidyl)anilino]piperidine-2,6-dione hydrochloride.

| Starting material | Product | LCMS (ESI+) m/z | % Yield |
|---|---|---|---|
| 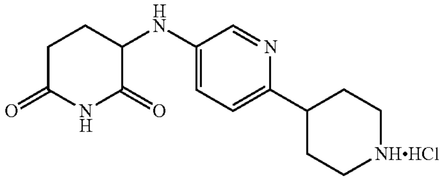 3-((6-(piperidin-4-yl)pyridin-3-yl)amino)piperidine-2,6-dione hydrochloride | 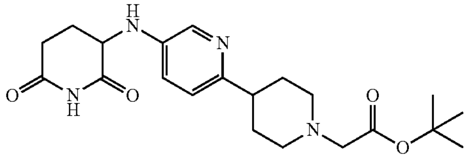 [SMILES: CC(C)(C)OC(=O)CN1CCC(c2ccc(NC3CCC(=O)NC3=O)cn2)CC1] tert-butyl 2-(4-(5-((2,6-dioxopiperidin-3-yl)amino)pyridin-2-yl)piperidin-1-yl)acetate | 347.2 [M − tBu + H] | 73% |
| 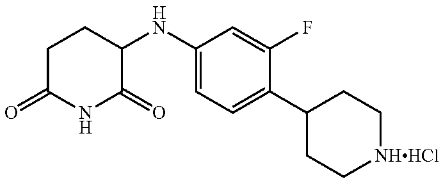 3-((3-fluoro-4-(piperidin-4-yl)phenyl)amino)piperidine-2,6-dione hydrochloride | 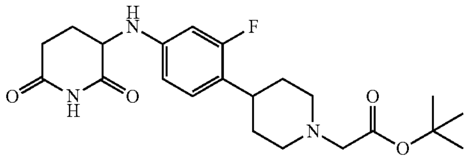 [SMILES: CC(C)(C)OC(=O)CN1CCC(c2ccc(NC3CCC(=O)NC3=O)cc2F)CC1] tert-butyl 2-(4-(4-((2,6-dioxopiperidin-3-yl)amino)-2-fluorophenyl)piperidin-1-yl)acetate | 420.2 [M + H] | 72% |

-continued

| Starting material | Product | LCMS (ESI+) m/z | % Yield |
| --- | --- | --- | --- |
| 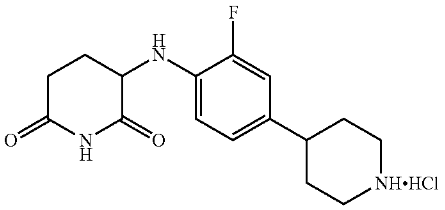 3-((2-fluoro-4-(piperidin-4-yl)phenyl)amino)piperidine-2,6-dione hydrochloride | 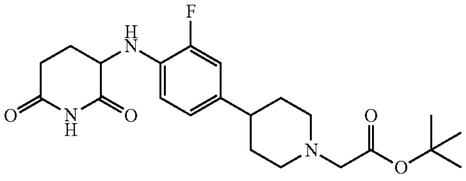 [SMILES: CC(C)(C)OC(=O)CN1CCC(c2ccc(NC3CCC(=O)NC3=O)c(F)c2)CC1] tert-butyl 2-(4-(4-((2,6-dioxopiperidin-3-yl)amino)-3-fluorophenyl)piperidin-1-yl)acetate | 420.2 [M + H] | 65% |
| 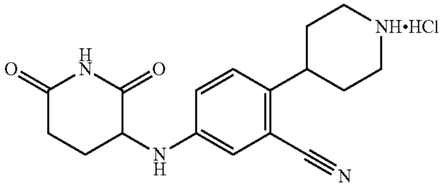 5-((2,6-dioxopiperidin-3-yl)amino)-2-(piperidin-4-yl)benzonitrile hydrochloride | 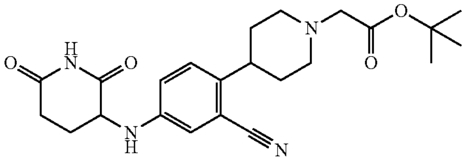 [SMILES: CC(C)(C)OC(=O)CN1CCC(c2ccc(NC3CCC(=O)NC3=O)cc2C#N)CC1] tert-butyl 2-(4-(2-cyano-4-((2,6-dioxopiperidin-3-yl)amino) phenyl)piperidin-1-yl)acetate | 427 [M + H] | 82% |
| 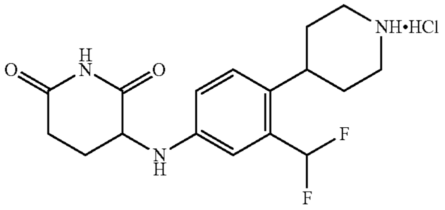 3-((3-(difluoromethyl)-4-(piperidin-4-yl)phenyl)amino)piperidine-2,6-dione hydrochloride | 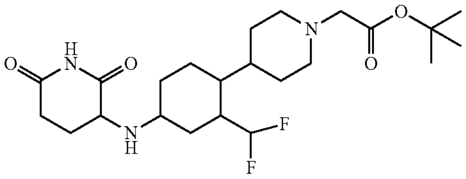 tert-butyl 2-(4-(2-(difluoromethyl)-4-((2,6-dioxopiperidin-3-yl)amino)phenyl)piperidin-1-yl)acetate | 452.2 [M + H] | 68% |
| 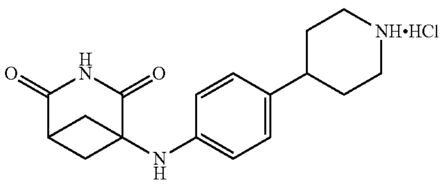 1-((4-(piperidin-4-yl)phenyl)amino)-3-azabicyclo[3.1.1]heptane-2,4-dione hydrochloride | 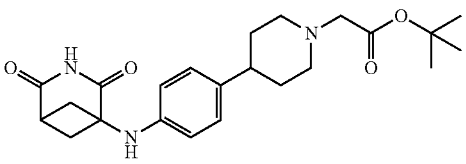 [SMILES: CC(C)(C)OC(=O)CN1CCC(c2ccc(NC34CC(C3)C(=O)NC4=O)cc2)CC1] tert-Butyl 2-(4-(4-((2,4-dioxo-3-azabicyclo[3.1.1]heptan-1-yl)amino)phenyl)piperidin-1-yl)acetate | 414.51 [M + H] | 57% |

-continued

| Starting material | Product | LCMS (ESI+) m/z | % Yield |
|---|---|---|---|
| 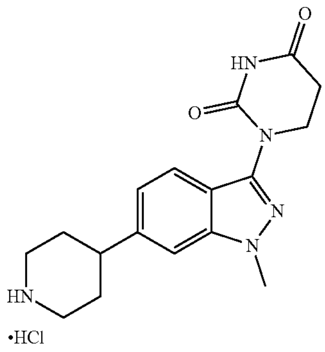 1-(1-methyl-6-(piperidin-4-yl)-1H-indazol-3-yl)dihydropyrimidine-2,4(1H,3H)-dione hydrochloride | 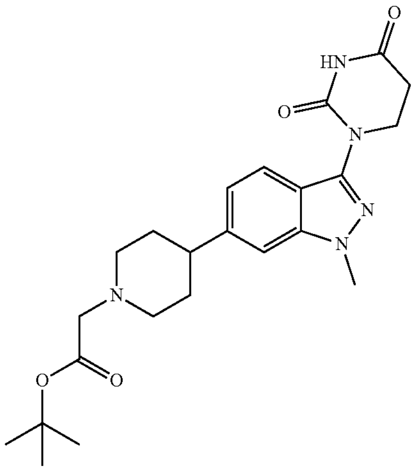 [SMILES: Cn1nc(N2CCC(=O)NC2=O)c2ccc(C3CCN(CC(=O)OC(C)(C)C)CC3)cc21] tert-butyl 2-(4-(3-(2,4-dioxotetrahydropyrimidin-1(2H)-yl)-1-methyl-1H-indazol-6-yl)piperidin-1-yl)acetate | 442.3 [M + H] | 75% |
| 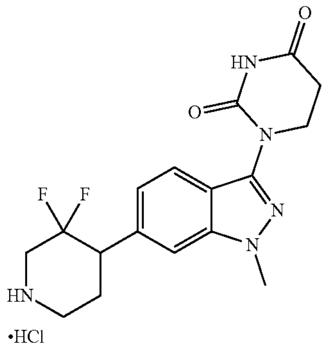 1-(6-(3,3-difluoropiperidin-4-yl)-1-methyl-1H-indazol-3-yl)dihydropyrimidine-2,4(1H,3H)-dione hydrochloride | 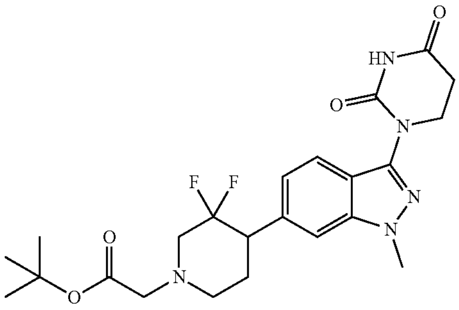 [SMILES: Cn1nc(N2CCC(=O)NC2=O)c2ccc(C3CCN(CC(=O)OC(C)(C)C)CC3(F)F)cc21] tert-butyl 2-(4-(3-(2,4-dioxotetrahydropyrimidin-1(2H)-yl)-1-methyl-1H-indazol-6-yl)-3,3-difluoropiperidin-1-yl)acetate | 478.5 [M + H] | 47% |
| 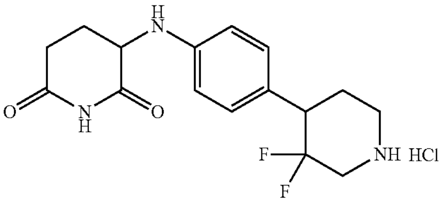 Isomer 1 3-[4-[3,3-difluoro-4-piperidyl]anilino]piperidine-2,6-dione dihydrochloride, isomer 1 | 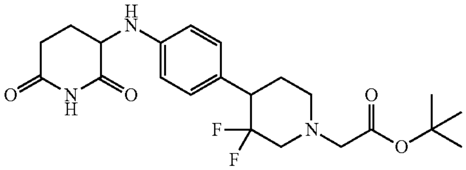 Isomer 1 tert-butyl 2-(4-(4-((2,6-dioxopiperidin-3-yl)amino)phenyl)-3,3-difluoropiperidin-1-yl)acetate, isomer 1 | 438.2 [M + H] | 84% |

-continued

| Starting material | Product | LCMS (ESI+) m/z | % Yield |
|---|---|---|---|
| 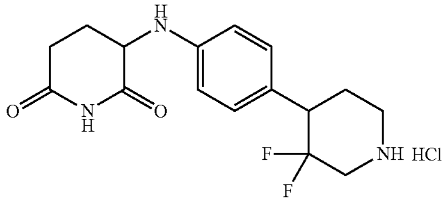 Isomer 2 3-[4-[3,3-difluoro-4-piperidyl]anilino]piperidine-2,6-dione dihydrochloride, isomer 2 | 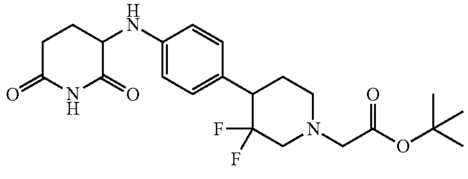 Isomer 2 tert-butyl 2-(4-(4-((2,6-dioxopiperidin-3-yl)amino)phenyl)-3,3-difluoropiperidin-1-yl)acetate, isomer 2 | 438.2 [M + H] | 87% |

General Procedure for the Tert-Butyl Ester Cleavage of Intermediates: 2-[4-[4-[(2,6-dioxo-3-piperidyl)amino]phenyl]-1-piperidyl]acetic acid, trifluoroacetic acid salt

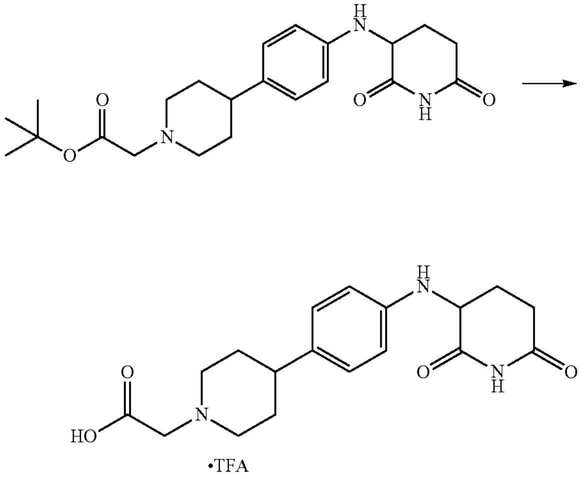

tert-Butyl 2-[4-[4-[(2,6-dioxo-3-piperidyl)amino]phenyl]-1-piperidyl]acetate was dissolved in dichloromethane (5 mL) and TFA (1.61 mL, 20.9 mmol) was added. The reaction mixture was heated at 40° C. for 4 h, and the reaction was complete. The volatiles were evaporated under reduce pressure. The material was frozen to −78° C., submitted to high vacuum, and thawed to afford a dense solid. The solid was re-dissolved in methanol:dicloromethane (1:4), MTBE was added dropwise, until a precipitate formed. The suspension was submitted to sonication, and the solid was filtered under suction. The green solid was collected by filtration to afford 2-[4-[4-[(2,6-dioxo-3-piperidyl)amino]phenyl]-1-piperidyl]acetic acid, trifluoroacetic acid salt (0.95 g, 2.07 mmol, 97% yield). LCMS (ESI+): 346.4 $[M+H]^+$.

The following intermediates were synthesized from the appropriate starting materials using general procedure for 2-[4-[4-[(2,6-dioxo-3-piperidyl)amino]phenyl]-1-piperidyl]acetic acid, trifluoroacetic acid salt synthesis.

| Starting material | Product | Yield | LCMS (ESI+) m/z |
|---|---|---|---|
| 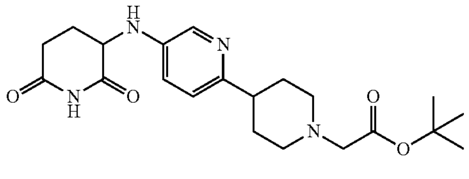 [SMILES: CC(C)(C)OC(=O)CN1CCC(c2ccc(NC3CCC(=O)NC3=O)cn2)CC1] tert-butyl 2-(4-(5-((2,6-dioxopiperidin-3-yl)amino)pyridin-2-yl)piperidin-1-yl)acetate | 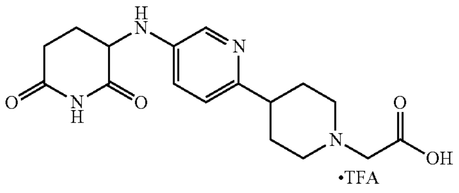 [SMILES: O=C(O)CN1CCC(c2ccc(NC3CCC(=O)NC3=O)cn2)CC1] 2-(4-(5-((2,6-dioxopiperidin-3-yl)amino)pyridin-2-yl)piperidin-1-yl)acetic acid | 72% | 347.2 [M + H] |

-continued

| Starting material | Product | Yield | LCMS (ESI+) m/z |
|---|---|---|---|
| 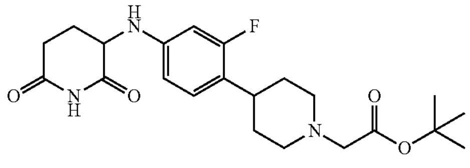 [SMILES: CC(C)(C)OC(=O)CN1CCC(c2ccc(NC3CCC(=O)NC3=O)cc2F)CC1] tert-butyl 2-(4-(4-((2,6-dioxopiperidin-3-yl)amino)-2-fluorophenyl)piperidin-1-yl)acetate | 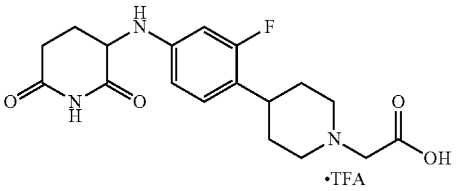 [SMILES: O=C(O)CN1CCC(c2ccc(NC3CCC(=O)NC3=O)cc2F)CC1] 2-(4-(5-((2,6-dioxopiperidin-3-yl)amino)pyridin-2-yl)piperidin-1-yl)acetic acid | >98% | 364.2 [M + H] |
| 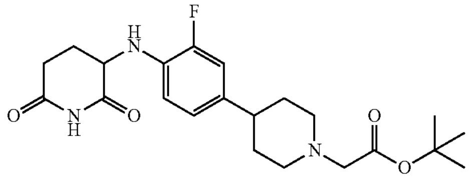 [SMILES: CC(C)(C)OC(=O)CN1CCC(c2ccc(NC3CCC(=O)NC3=O)c(F)c2)CC1] tert-butyl 2-(4-(4-((2,6-dioxopiperidin-3-yl)amino)-3-fluorophenyl)piperidin-1-yl)acetate | 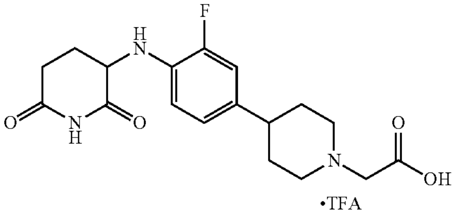 [SMILES: O=C(O)CN1CCC(c2ccc(NC3CCC(=O)NC3=O)c(F)c2)CC1] 2-(4-(4-((2,6-dioxopiperidin-3-yl)amino)-3-fluorophenyl)piperidin-1-yl)acetic acid | >98% | 364.5 [M + H] |
| 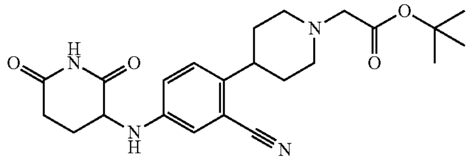 [SMILES: CC(C)(C)OC(=O)CN1CCC(c2ccc(NC3CCC(=O)NC3=O)cc2C#N)CC1] tert-butyl 2-(4-(2-cyano-4-((2,6-dioxopiperidin-3-yl)amino)phenyl)piperidin-1-yl)acetate | 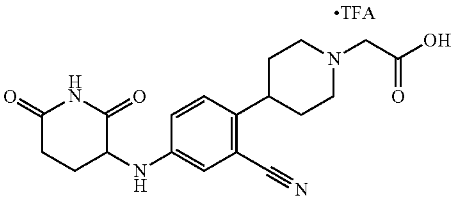 [SMILES: N#Cc1cc(NC2CCC(=O)NC2=O)ccc1C1CCN(CC(=O)O)CC1] 2-(4-(2-cyano-4-((2,6-dioxopiperidin-3-yl)amino)phenyl)piperidin-1-yl)acetic acid | >98% | 371.2 [M + H] |
| 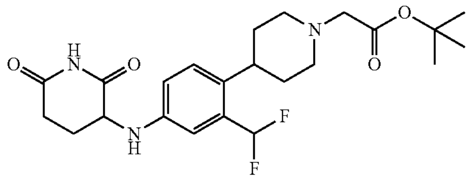 tert-butyl 2-(4-(2-(difluoromethyl)-4-((2,6-dioxopiperidin-3-yl)amino)phenyl)piperidin-1-yl)acetate | 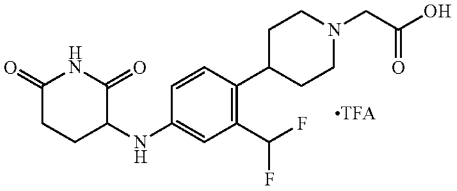 [SMILES: O=C(O)CN1CCC(c2ccc(NC3CCC(=O)NC3=O)cc2C(F)F)CC1] 2-(4-(2-(difluoromethyl)-4-((2,6-dioxopiperidin-3-yl)amino)phenyl)piperidin-1-yl)acetic acid | 94% | 369.2 [M + H] |

-continued

| Starting material | Product | Yield | LCMS (ESI+) m/z |
|---|---|---|---|
| 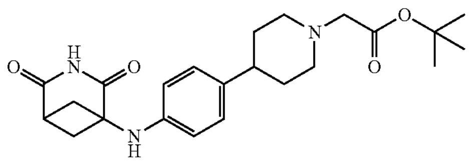 [SMILES: CC(C)(C)OC(=O)CN1CCC(c2ccc(NC34CC(C3)C(=O)NC4=O)cc2)CC1] tert-butyl 2-(4-(4-((2,4-dioxo-3-azabicyclo[3.1.1]heptan-1-yl)amino)phenyl)piperidin-1-yl)acetate | 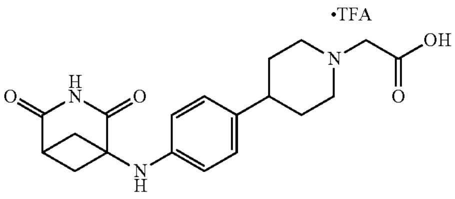 [SMILES: O=C(O)CN1CCC(c2ccc(NC34CC(C3)C(=O)NC4=O)cc2)CC1] 2-(4-(4-((2,4-dioxo-3-azabicyclo[3.1.1]heptan-1-yl)amino)phenyl)piperidin-1-yl)acetic acid | 73% | 358.1 [M + H] |
| 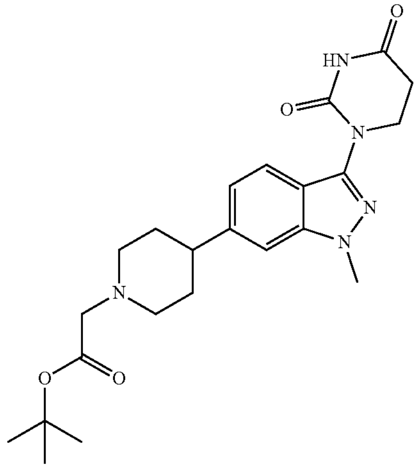 [SMILES: Cn1nc(N2CCC(=O)NC2=O)c2ccc(C3CCN(CC(=O)OC(C)(C)C)CC3)cc21] tert-butyl 2-(4-(3-(2,4-dioxotetrahydropyrimidin-1(2H)-yl)-1-methyl-1H-indazol-6-yl)piperidin-1-yl)acetate | 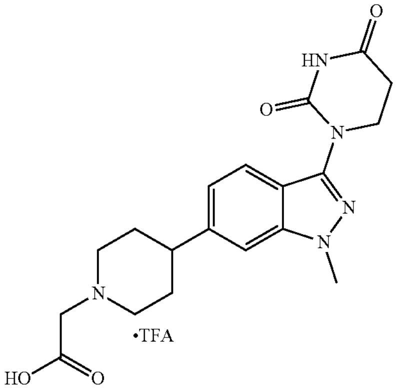 [SMILES: Cn1nc(N2CCC(=O)NC2=O)c2ccc(C3CCN(CC(=O)O)CC3)cc21] 2-(4-(3-(2,4-dioxotetrahydropyrimidin-1(2H)-yl)-1-methyl-1H-indazol-6-yl)piperidin-1-yl)acetic acid | 82% | 386.1 [M + H] |

General Procedure for tert-butyl ester deprotection: Synthesis of 2-[4-[4-[(2,6-dioxo-3-piperidyl)amino]phenyl]-1-piperidyl]acetic acid hydrochloride

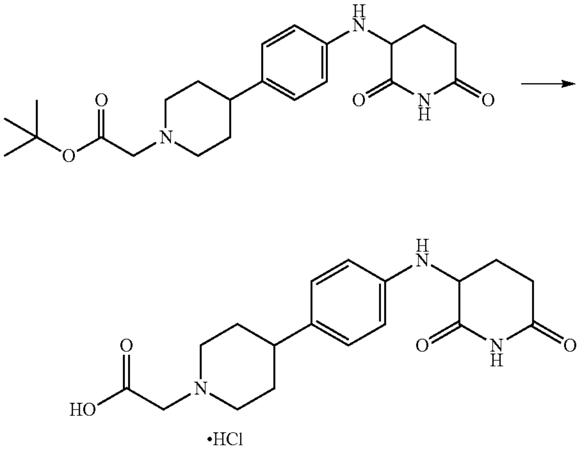

tert-Butyl 2-[4-[4-[(2,6-dioxo-3-piperidyl)amino]phenyl]-1-piperidyl]acetate (228 mg, 568 μmol) was dissolved in dichloromethane (2 mL) and 4M hydrochloric acid in 1,4-dioxane (8 mmol, 2 mL) was added. The resulting mixture was stirred at room temperature for 4 h. The reaction mixture was concentrated under reduced pressure and the residue was triturated with diethyl ether and then filtered to afford 2-[4-[4-[(2,6-dioxo-3-piperidyl)amino]phenyl]-1-piperidyl]acetic acid hydrochloride (210 mg, 428 μmol) as grey solid. LCMS (ES+): 345 $[M+H]^+$.

The following intermediates were synthesized from the appropriate starting materials using the above General procedure for 2-[4-[4-[(2,6-dioxo-3-piperidyl)amino]phenyl]-1-piperidyl]acetic acid hydrochloride synthesis

| Starting material | Intermediate | % Yield | LCMS (ESI+) m/z |
|---|---|---|---|
| 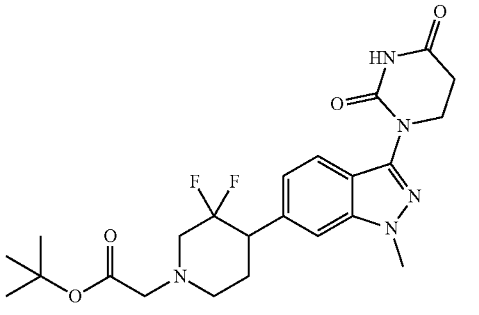 [SMILES: Cn1nc(N2CCC(=O)NC2=O)c2ccc(C3CCN(CC(=O)OC(C)(C)C)CC3(F)F)cc21]<br>tert-butyl 2-(4-(3-(2,4-dioxotetrahydropyrimidin-1(2H)-yl)-1-methyl-1H-indazol-6-yl)-3,3-difluoropiperidin-1-yl)acetate | 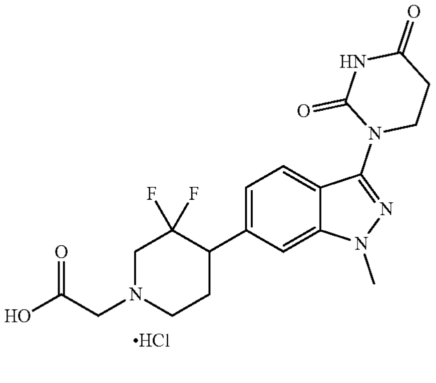 [SMILES: Cn1nc(N2CCC(=O)NC2=O)c2ccc(C3CCN(CC(=O)O)CC3(F)F)cc21 ; Cl]<br>2-(4-(3-(2,4-dioxotetrahydropyrimidin-1(2H)-yl)-1-methyl-1H-indazol-6-yl)-3,3-difluoropiperidin-1-yl)acetic acid hydrochloride | 90% | |
| 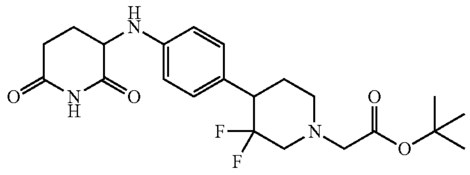<br>Isomer 1<br>tert-butyl 2-(4-(4-((2,6-dioxopiperidin-3-yl)amino)phenyl)-3,3-difluoropiperidin-1-yl)acetate, isomer 1 | 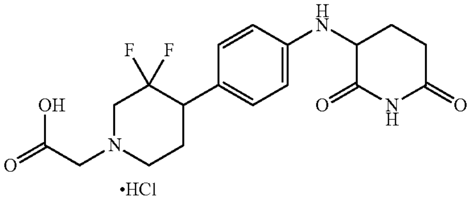<br>Isomer 1 | >98% | 382.2 [M + H] |
| 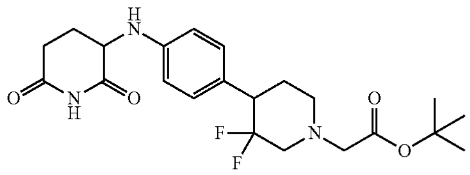<br>Isomer 2<br>tert-butyl 2-(4-(4-((2,6-dioxopiperidin-3-yl)amino)phenyl)-3,3-difluoropiperidin-1-yl)acetate, isomer 2 | 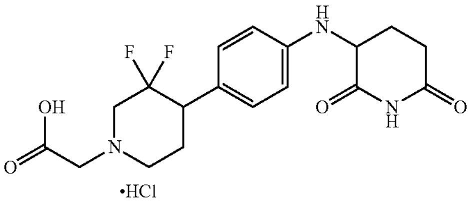<br>Isomer 2 | >98% | 382.2 [M + H] |

Synthesis of (3S)-3-[4-(4-piperidyl)phenoxy]piperidine-2,6-dione hydrochloride and (3R)-3-[4-(4-piperidyl)phenoxy]piperidine-2,6-dione hydrochloride

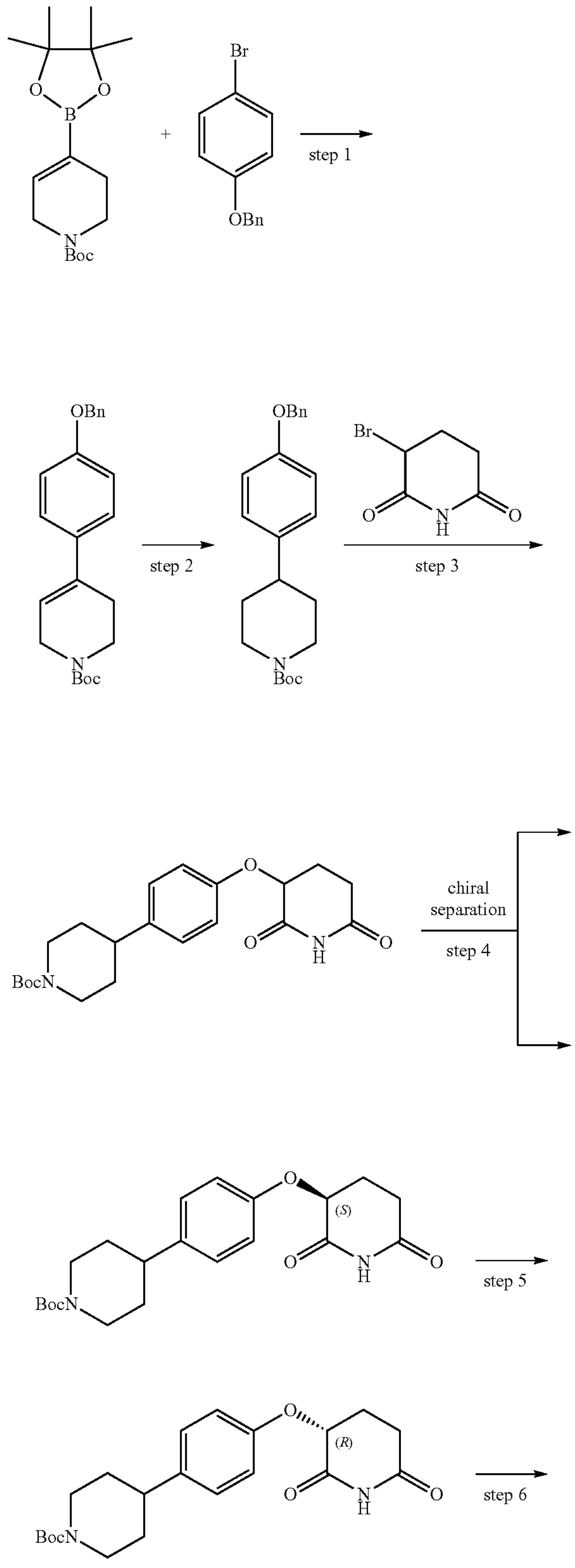

-continued

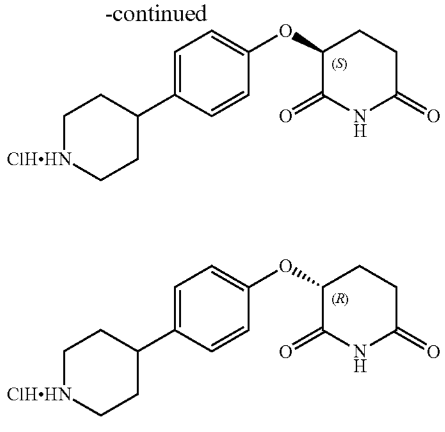

Step 1: Preparation of tert-butyl 4-(4-benzyloxyphenyl)-3,6-dihydro-2H-pyridine-1-carboxylate To a stirred solution of 1-benzyloxy-4-bromo-benzene (10 g, 38.00 mmol) and tert-butyl 4-(4,4,5,5-tetramethyl-1,3,2-dioxaborolan-2-yl)-3,6-dihydro-2H-pyridine-1-carboxylate (12.93 g, 41.80 mmol) in acetonitrile (100 mL) and water (100 mL) was added sodium carbonate (10.07 g, 95.01 mmol) and thoroughly purged with argon. $Pd(PPh_3)_4$ (2.19 g, 1.90 mmol) was added under inert atmosphere. Resulting mixture was heated at 100° C. for 16 h. After, reaction mixture was diluted with ethyl acetate, filtered through a short pad of celite and washed with ethyl acetate. Combined organic part was washed with water and brine, dried over anhydrous sodium sulphate, filtered and concentrated under reduced pressure. Crude mass was purified by column chromatography (15% ethyl acetate-hexane) to get tert-butyl 4-(4-benzyloxyphenyl)-3,6-dihydro-2H-pyridine-1-carboxylate (8 g, 21.89 mmol, 57.60% yield). LCMS (ES+): 366 $[M+H]^+$.

Step 2: Preparation of tert-butyl 4-(4-hydroxyphenyl)piperidine-1-carboxylate

To a degassed solution of tert-butyl 4-(4-benzyloxyphenyl)-3,6-dihydro-2H-pyridine-1-carboxylate (8 g, 21.89 mmol) in ethanol (100 mL) 10% Pd—C (50% wet, 8 g) was added. Resulting mixture was stirred at room temperature under hydrogen balloon pressure for 16 h. After completion, the reaction mixture was filtered through a short pad of celite, washed with ethyl acetate and concentrated under reduced pressure. Crude mass was purified by combiflash chromatography (55% ethyl acetate in hexane) to get tert-butyl 4-(4-hydroxyphenyl)piperidine-1-carboxylate (4.85 g, 17.49 mmol, 79.88% yield). LCMS (ES+): 278 $[M+H]^+$.

Step 3: Preparation of tert-butyl 4-[4-[(2,6-dioxo-3-piperidyl)oxy]phenyl]piperidine-1-carboxylate To a stirred solution of tert-butyl 4-(4-hydroxyphenyl)piperidine-1-carboxylate (4.5 g, 16.22 mmol) in THF (60 mL), Sodium hydride (60% dispersion in mineral oil (1.55 g, 38.85 mmol) was added portion wise at 0° C. and stirred for 40 min. A solution of 3-bromopiperidine-2,6-dione (6.23 g, 32.45 mmol) in THF was added drop wise added at 0° C. Resulting mixture was warmed to room temperature over a period of 2 h and stirred for 16 h. After completion, reaction mixture was quenched with saturated ammonium chloride solution and extracted with ethyl acetate, washed with water and brine. Organic layer was dried over anhydrous sodium sulphate, filtered and concentrated under reduced pressure. Crude mass was purified by combiflash chromatography (50% ethyl acetate-hexane) to get tert-butyl 4-[4-[(2,6-dioxo-3-piperidyl)oxy]phenyl]piperidine-1-carboxylate (3.4 g, 8.75 mmol, 53.95% yield). LCMS (ES+): 389 $[M+H]^+$.

Step 4: Preparation of tert-butyl 4-[4-[[(3S)-2,6-dioxo-3-piperidyl]oxy]phenyl]piperidine-1-carboxylate and tert-butyl 4-[4-[[(3R)-2,6-dioxo-3-piperidyl]oxy]phenyl]piperidine-1-carboxylate Chiral separation of tert-butyl 4-[4-[(2,6-dioxo-3-piperidyl)oxy]phenyl]piperidine-1-carboxylate (2.5 g, 6.44 mmol) by SFC afforded tert-butyl 4-[4-[[(3S)-2,6-dioxo-3-piperidyl]oxy]phenyl]piperidine-1-carboxylate (850 mg, 2.16 mmol, 33.57% yield, 98.74% purity) [as 1st eluent in chiral prep separation by SFC] and tert-butyl 4-[4-[[(3R)-2,6-dioxo-3-piperidyl]oxy]phenyl]piperidine-1-carboxylate (870 mg, 2.21 mmol, 34.35% yield, 98.71% purity) [as 2nd eluent in chiral prep separation by SFC] after lyophilization.

Following method was used to separate the enantiomers by SFC:

Column: Chiralpak IA (250×20 mm) 5 μm

Flow: 25 mL/min

Mobile Phase: 45% $CO_2$+55% Isopropyl alcohol

ABPR: 100 bar

Temperature: 35° C.

[Both the structures are tentative and actual stereochemistry was not known].

S-Isomer $^1$H NMR (400 MHz, DMSO-D6) δ 10.91 (s, 1H), 7.14 (d, J=8.4 Hz, 2H), 6.93 (d, J=8.4 Hz, 2H), 5.16-5.12 (m, 1H), 4.06-4.04 (m, 2H), 2.78-2.57 (m, 5H), 2.17-2.09 (m, 2H), 1.73-1.70 (m, 2H), 1.48-1.41 (m, 11H).

R-Isomer $^1$H NMR (400 MHz, DMSO-D6) δ 10.91 (s, 1H), 7.14 (d, J=8.4 Hz, 2H), 6.92 (d, J=8.4 Hz, 2H), 5.16-5.12 (m, 1H), 4.07-4.04 (m, 2H), 2.78-2.57 (m, 5H), 2.17-2.08 (m, 2H), 1.72-1.70 (m, 2H), 1.48-1.40 (m, 11H).

Step 5: Preparation of (35)-3-[4-(4-piperidyl)phenoxy]piperidine-2,6-dione hydrochloride Hydrogen chloride (2M in diethyl ether, 5 mL, 10 mmol) was added to tert-butyl 4-[4-[[(3S)-2,6-dioxo-3-piperidyl]oxy]phenyl]piperidine-1-carboxylate (200 mg, 514.86 μmol) at 10° C. Resulting mixture was warmed to room temperature and stirred for 16 h. After completion, reaction mixture was concentrated under reduced pressure, triturated with ether and lyophilized to get (3S)-3-[4-(4-piperidyl)phenoxy]piperidine-2,6-dione (130 mg, 393.76 μmol, 76.48% yield, hydrochloric acid salt) as white solid. $^1$H NMR (400 MHz, DMSO-D6) δ 10.92 (s, 1H), 8.67-8.65 (m, 1H), 8.42 (bs, 1H), 7.13 (d, J=8.3 Hz, 2H), 6.97 (d, J=8.4 Hz, 2H), 5.18-5.14 (m, 1H), 3.37-3.30 (m, 1H), 2.99-2.96 (m, 2H), 2.78-2.58 (m, 3H), 2.20-2.09 (m, 2H), 1.92-1.89 (m, 2H), 1.80-1.70 (m, 2H).

Step 6: Preparation of (3R)-3-[4-(4-piperidyl)phenoxy]piperidine-2,6-dione hydrochloride Hydrogen chloride (2M in diethyl ether, 10 mL, 20 mmol) was added to tert-butyl 4-[4-[[(3R)-2,6-dioxo-3-piperidyl]oxy]phenyl]piperidine-1-carboxylate (200 mg, 514.86 μmol) at 10° C. Resulting mixture was warmed to room temperature and stirred for 16 h. After completion, reaction mixture was concentrated under reduced pressure, triturated with ether and lyophilized to get (3R)-3-[4-(4-piperidyl)phenoxy]piperidine-2,6-dione (120 mg, 367.72 μmol, 71.42% yield, hydrochloric acid salt) as white salt. $^1$H NMR (400 MHz, DMSO-D6) δ 10.92 (s, 1H), 8.74 (bs, 1H), 8.55 (bs, 1H), 7.13 (d, J=8.4 Hz, 2H), 6.97 (d, J=8.4 Hz, 2H), 5.19-5.14 (m, 1H), 3.36-3.32 (m, 1H), 2.98-2.95 (m, 2H), 2.81-2.58 (m, 3H), 2.18-2.10 (m, 2H), 1.91-1.76 (m, 4H).

Synthesis of 2-[4-[4-[(2,6-dioxo-3-piperidyl)oxy]phenyl]-1-piperidyl]acetic acid

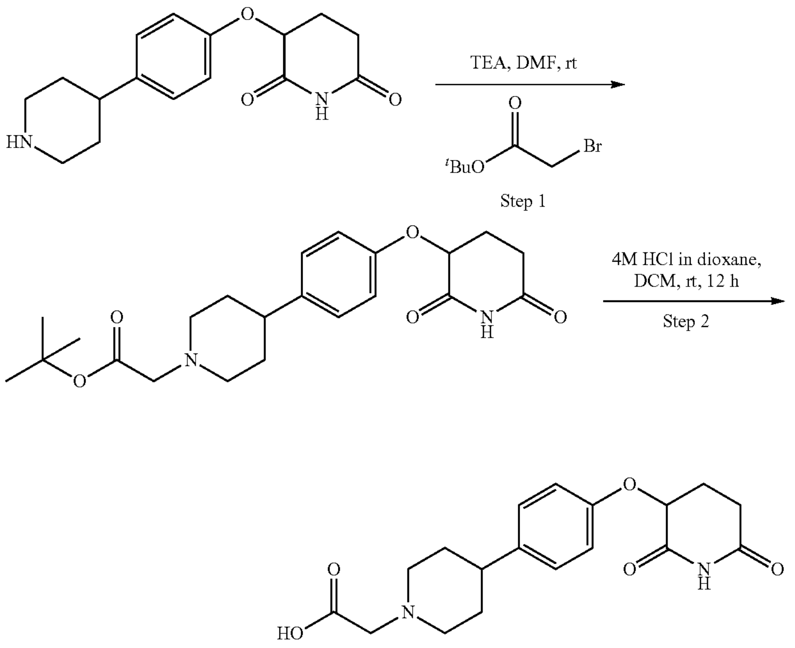

Step 1: To a stirred solution of 3-[4-(4-piperidyl)phenoxy]piperidine-2,6-dione (500 mg, 1.73 mmol) and triethyl amine (526.41 mg, 5.20 mmol, 725.08 μL) in N,N-Dimethylformamide (5 mL) was added tert-butyl 2-bromoacetate (338.24 mg, 1.73 mmol, 254.31 μL), and stirred at room temperature for 14 h. After completion of reaction, the reaction mixture was diluted with water (30 mL) and extracted with ethyl acetate (2×25 mL). The organic layer was washed with brine solution (20 mL), dried over sodium sulphate and concentrated under reduced pressure to get tert-butyl 2-[4-[4-[(2,6-dioxo-3-piperidyl)oxy]phenyl]-1-piperidyl]acetate (400 mg, 944.14 μmol, 54.45% yield).

Step 2: To a solution of tert-butyl 2-[4-[4-[(2,6-dioxo-3-piperidyl)oxy]phenyl]-1-piperidyl]acetate (400 mg, 993.83 μmol) in dichloromethane (3 mL) was added 4 M HCl in 1,4 dioxane (993.83 μmol, 2 mL) at 0° C. and stirred at room temperature for 6 h. The reaction mixture was concentrated under reduced pressure to get crude which was triturated with petroleum ether to afford 2-[4-[4-[(2,6-dioxo-3-piperidyl)oxy]phenyl]-1-piperidyl]acetic acid (360 mg, 921.54 μmol, 92.73% yield) as off white solid. LCMS (ESI+): 347.1 $[M+H]^+$.

Synthesis of 2-[4-[4-[[(3S)-2,6-dioxo-3-piperidyl]oxy]phenyl]-1-piperidyl]acetic acid

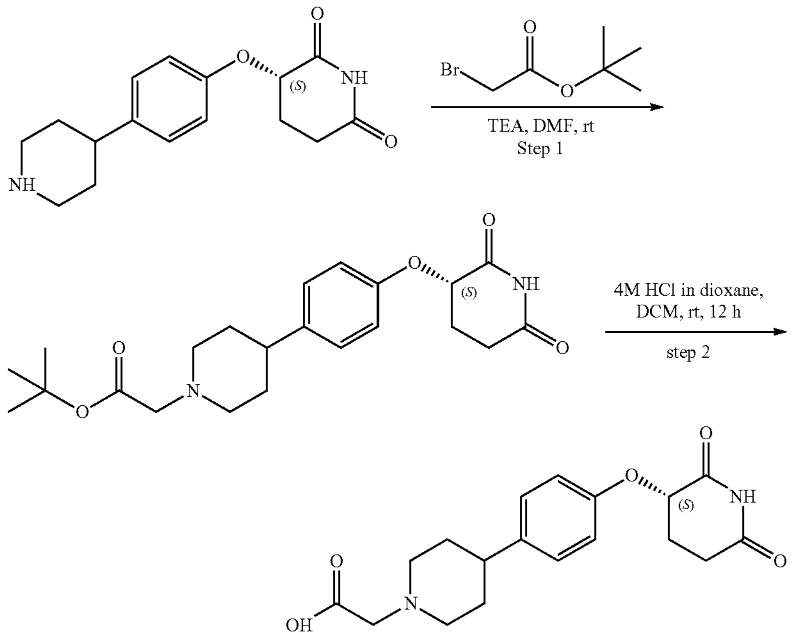

Step 1: To a stirred solution of (3S)-3-[4-(4-piperidyl)phenoxy]piperidine-2,6-dione (52.55 mg, 182.24 μmol) in DMF (1 mL) was added Triethylamine (55.32 mg, 546.73 μmol, 76.20 uL) at room temperature followed by tert-butyl 2-bromoacetate (39.10 mg, 200.47 μmol, 29.40 uL) and the resulting reaction mixture was stirred at 25° C. for 12 h. After completion, the reaction mixture was diluted with water (3 mL) and extracted with ethyl acetate (3×5 mL). The combined organic layers were dried over sodium sulphate and concentrated under reduced pressure. The obtained crude was purified by mass directed Prep HPLC using [Mobile phase A: 10 mM ammonium acetate in water, Mobile phase B: ACN, Wave length: 215, Column: Sunfire C18 OBD (19 mmx 100 mm; 5 micron)] to give tert-butyl 2-[4-[4-[[(3S)-2,6-dioxo-3-piperidyl]oxy]phenyl]-1-piperidyl]acetate (31 mg, 76.14 μmol, 41.78% yield) as white solid. LCMS (ESI+): 403.3 $[M+H]^+$.

Step 2: To a stirred solution of tert-butyl 2-[4-[4-[[(3S)-2,6-dioxo-3-piperidyl]oxy]phenyl]-1-piperidyl]acetate (31 mg, 77.02 μmol) in DCM (1 mL) was added TFA (740.00 mg, 6.49 mmol, 0.5 mL) at 0° C. and the resulting reaction mixture was stirred for 3 h at room temperature. Reaction mixture was concentrated under reduced pressure. The residue obtained was co-distilled with toluene (2×20 mL), dried under reduced pressure to afford 2-[4-[4-[[(3S)-2,6-dioxo-3-piperidyl]oxy]phenyl]-1-piperidyl]acetic acid (30 mg, 63.39 μmol, 82.31% yield, trifluoroacetic acid salt) as pale yellow solid. LCMS (ESI+): 347.2 $[M+H]^+$. $^1H$ NMR (400 MHz, DMSO-$d_6$): δ 10.93 (s, 1H), 9.76 (bs, 1H), 8.21 (bs, 1H), 7.16 (d, J=7.60 Hz, 2H), 6.96 (d, J=8.40 Hz, 2H), 5.19-5.15 (m, 1H), 4.16 (bs, 2H), 3.60-3.59 (m, 2H), 3.16-3.14 (m, 2H), 2.74-2.72 (m, 2H), 2.75-2.60 (m, 3H), 2.25-2.05 (m, 2H), 2.05-1.95 (m, 2H).

Synthesis of 2-[4-[4-[[(3R)-2,6-dioxo-3-piperidyl]oxy]phenyl]-1-piperidyl]acetic acid

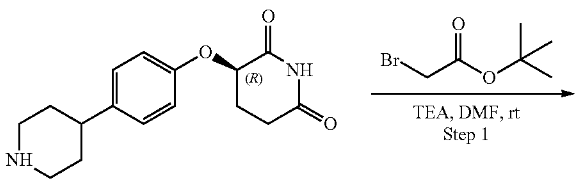

-continued

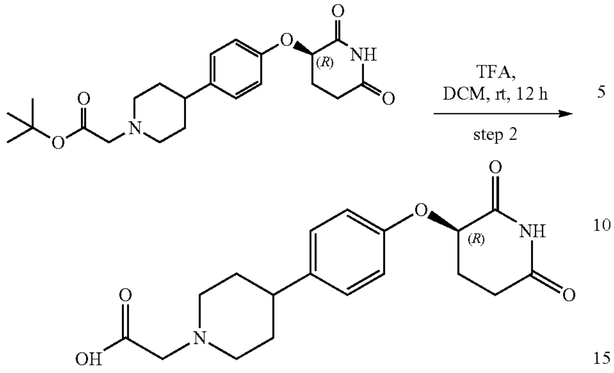

Step 1: To a stirred solution of (3R)-3-[4-(4-piperidyl)phenoxy]piperidine-2,6-dione (50 mg, 173.41 μmol) in N,N-Dimethylformamide (1 mL) was added triethylamine (52.64 mg, 520.22 μmol, 72.51 μL) at room temperature followed by tert-butyl 2-bromoacetate (37.21 mg, 190.75 μmol, 27.97 μL) and the resulting reaction mixture was stirred at 25° C. for 12 h. After completion, the reaction mixture was diluted with water (3 mL) and extracted with ethyl acetate (3×5 mL). The combined organic layers were dried over sodium sulphate, concentrated under reduced pressure. The crude product obtained was purified by mass directed Prep HPLC using [Mobile phase A: 10 mM ammonium acetate in water, Mobile phase: acetonitrile, Wavelength: 215 nm, Column: Sunfire C18 OBD (19 mm×100 mm; 5 micron)] to afford tert-butyl 2-[4-[4-[[(3R)-2,6-dioxo-3-piperidyl]oxy]phenyl]-1-piperidyl]acetate (30 mg, 73.79 μmol, 42.55% yield) as white solid. LCMS (ESI+): 403.3 $[M+H]^+$.

Step 2: To a stirred solution of tert-butyl 2-[4-[4-[[(3R)-2,6-dioxo-3-piperidyl]oxy]phenyl]-1-piperidyl]acetate (30 mg, 74.54 μmol) in Dichloromethane (1 mL) was added TFA (740.00 mg, 6.49 mmol, 0.5 mL) at 0° C. and the resulting reaction mixture was stirred for 3 h at room temperature. Reaction mixture was concentrated under reduced pressure. The residue obtained was co-distilled with toluene (2×20 mL), dried under reduced pressure to afford 2-[4-[4-[[(3R)-2,6-dioxo-3-piperidyl]oxy]phenyl]-1-piperidyl]acetic acid (30 mg, 60.07 μmol, 80.59% yield, trifluoroacetic acid salt) as pale yellow solid. LCMS (ESI+): 347.3 $[M+H]^+$.

Synthesis of 3-[N-methyl-4-(4-piperidyl)anilino]piperidine-2,6-dione

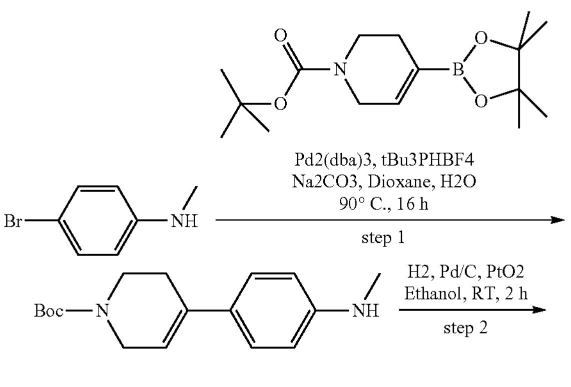

-continued

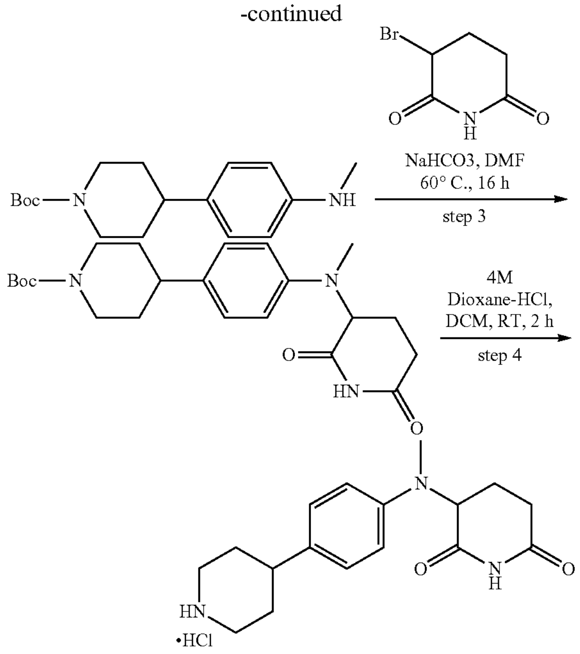

Step 1: Preparation of 4-(4-Methylamino-phenyl)-3,6-dihydro-2H-pyridine-1-carboxylic acid tert-butyl ester A stirred solution of 4-bromo-N-methyl-aniline 1 (9 g, 48.37 mmol), sodium carbonate (15.38 g, 145.12 mmol, 6.08 mL) and tert-butyl 4-(4,4,5,5-tetramethyl-1,3,2-dioxaborolan-2-yl)-3,6-dihydro-2H-pyridine-1-carboxylate 2 (13.46 g, 43.54 mmol) in 1,4-dioxane (10 mL) and Water (2 mL) was purged with argon for 20 minutes followed by the addition of tri-tert-butylphosphonium tetrafluoroborate (2.81 g, 9.67 mmol) and $Pd_2(dba)_3$ (4.43 g, 4.84 mmol). The reaction mixture was heated for 14 hours at 90° C. Reaction mixture was cooled, concentrated under reduced pressure to afford the crude product. The crude product thus obtained was purified by flash chromatography using 0%-10% ethyl acetate-hexane to afford tert-butyl 4-[4-(methyl amino)phenyl]-3,6-dihydro-2H-pyridine-1-carboxylate (8.4 g, 29.13 mmol, 60.21% yield) as light yellow solid. LCMS (ES+): 289.2 $[M+H]^+$.

Step 2: Preparation of 4-(4-Methylamino-phenyl)-piperidine-1-carboxylic acid tert-butyl ester A stirred solution of tert-butyl 4-[4-(methylamino)phenyl]-3,6-dihydro-2H-pyridine-1-carboxylate (8.4 g, 29.13 mmol) in Ethanol (80 mL) was degassed with argon for 20 minutes. Palladium on carbon (3.10 g, 2.91 mmol, 10% purity) and $PtO_2$ (330.72 mg, 1.46 mmol) were added to the reaction mixture and was stirred at room temperature under hydrogen balloon for 2 hours. The reaction mixture was filtered through celite bed, filtrate was concentrated to afford tert-butyl 4-[4-(methylamino)phenyl]piperidine-1-carboxylate 4 (8.3 g, 28.58 mmol, 98.12% yield) as white solid. LCMS (ES+): 291.2 $[M+H]^+$.

Step 3: Preparation of 4-{4-[(2,6-Dioxo-piperidin-3-yl)-methyl-amino]-phenyl}-piperidine-1-carboxylic acid tert-butyl ester To the stirred solution of tert-butyl 4-[4-(methylamino)phenyl]piperidine-1-carboxylate 4 (3.4 g, 11.71 mmol) in DMF (40 mL) was added 3-bromopiperidine-2,6-dione 5 (3.37 g, 17.56 mmol) and Sodium hydrogen carbonate (1.97 g, 23.42 mmol, 910.73 uL). The reaction mixture was heated at 60° C. for 16 hours. The reaction mixture was cooled to 0° C. and diluted with ethyl acetate. Organic part was washed with ice cold water, brine, dried over sodium sulfate, filtered and concentrated under reduced pressure. Crude material was purified by column chromatography (eluting at 0%-1% methanol in dichloromethane) to afford tert-butyl 4-[4-[(2,6-dioxo-3-piperidyl)-methyl-amino]phenyl]piperidine-1-carboxylate 6 (2.2 g, 5.48 mmol, 46.80% yield) as off white solid. LCMS (ES+): 402.2 $[M+H]^+$.

Step 4: Preparation of 3-[Methyl-(4-piperidin-4-yl-phenyl)-amino]-piperidine-2,6-dione hydrochloride To the stirred solution of tert-butyl 4-[4-[(2,6-dioxo-3-piperidyl)-methyl-amino]phenyl]piperidine-1-carboxylate (12.2 g, 30.39 mmol) in DCM (50 mL) was added 4M Hydrogen chloride in 1,4-dioxane (5.23 mmol, 30 mL) at 0° C. It was stirred at room temperature for 1 hour. Reaction mixture was concentrated under reduced pressure, washed with ethyl acetate and was lyophilized to afford 3-[N-methyl-4-(4-piperidyl)anilino]piperidine-2,6-dione (10.8 g, 30.19 mmol, 99.36% yield) as an off white solid. $^1H$ NMR (400 MHz, DMSO-d6) δ 10.76 (s, 1H), 8.99 (br s, 1H), 8.82 (br s, 1H), 7.02 (d, J=8.56 Hz, 2H), 6.77 (d, J=8.68 Hz, 2H), 4.84 (dd, J=12.6, 4.88 Hz, 1H), 3.32-3.29 (m, 2H), 2.98-2.77 (m, 3H), 2.71-2.66 (m, 4H), 2.56 (m, 1H), 2.34-2.23 (m, 1H), 1.89-1.75 (m, 5H). LCMS (ES+): 302.3 $[M+H]^+$.

Synthesis of 2-[4-[4-[(2,6-dioxo-3-piperidyl)amino]-2,6-difluoro-phenyl]-1-piperidyl]acetic acid

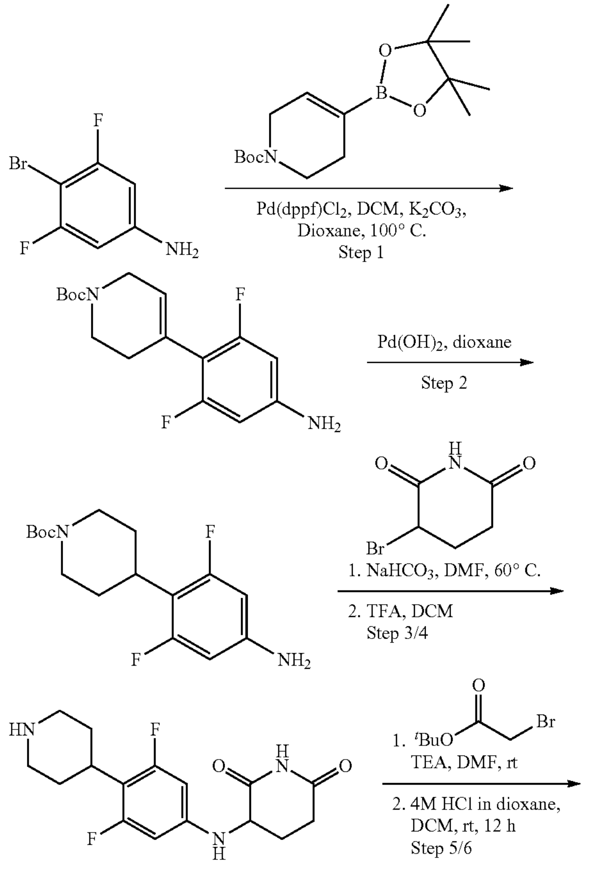

-continued

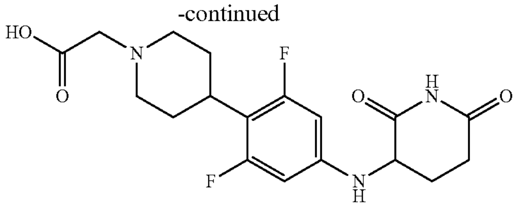

Step 1: To a stirred solution of 4-bromo-3,5-difluoro-aniline (2.49 g, 11.96 mmol) in THF (20 mL), Methanol (5 mL) and Water (5 mL) was added tert-butyl 4-(4,4,5,5-tetramethyl-1,3,2-dioxaborolan-2-yl)-3,6-dihydro-2H-pyridine-1-carboxylate (5.55 g, 17.94 mmol) and degassed with $N_2$ for 20 minutes. Pd(dppf)$Cl_2$·dichloromethane (0.98 g, 1.20 mmol), Sodium carbonate (3.80 g, 35.89 mmol, 1.50 mL) were added to the reaction mixture and heated at 100° C. for 12 h. After completion, the reaction mixture was filtered and concentrated under reduced pressure to get crude which was purified by column chromatography on silica gel eluted with 20% ethyl acetate in petroleum ether to yield tert-butyl 4-(4-amino-2,6-difluoro-phenyl)-3,6-dihydro-2H-pyridine-1-carboxylate (3 g, 7.06 mmol, 58.99% yield) as off white solid. LCMS (ESI+): 255.1 $[M-56+H]^+$.

Step 2: A solution of tert-butyl 4-(4-amino-2,6-difluoro-phenyl)-3,6-dihydro-2H-pyridine-1-carboxylate (2.1 g, 6.77 mmol) in 1,4-Dioxane (25 mL) was degassed with $N_2$ for 15 min. $Pd(OH)_2$ (2.1 g, 14.95 mmol) was added to the reaction mixture and stirred under $H_2$ balloon pressure for 24 h. After completion, the reaction mixture was filtered through celite and concentrated under reduced pressure to get tert-butyl 4-(4-amino-2,6-difluoro-phenyl)piperidine-1-carboxylate (2 g, 5.51 mmol, 81.38% yield) as off white solid. LCMS (ESI+): 257.1 $[M-56+H]^+$.

Step 3: To a stirred solution of tert-butyl 4-(4-amino-2,6-difluoro-phenyl)piperidine-1-carboxylate (500 mg, 1.60 mmol) in N,N-Dimethylformamide (20 mL) were added Sodium bicarbonate (807 mg, 9.61 mmol, 373.61 μL) and 3-bromopiperidine-2,6-dione (923 mg, 4.81 mmol). The reaction mixture was stirred at 60° C. for 16 h. After completion, the reaction mixture was diluted with ice water (20 mL) and extracted with ethyl acetate (2×50 mL). The combined organic layers were dried over anhydrous sodium sulphate, filtered and concentrated under reduced pressure to get crude which was purified by column chromatography on silica gel eluted with 50% ethyl acetate in petroleum ether to yield tert-butyl 4-[4-[(2,6-dioxo-3-piperidyl)amino]-2,6-difluoro-phenyl]piperidine-1-carboxylate (460 mg, 380.21 μmol, 23.75% yield) as an oily liquid. LCMS (ESI+): 368.1 $[M-56+1]^+$.

Step 4: To a stirred solution of tert-butyl 4-[4-[(2,6-dioxo-3-piperidyl)amino]-2,6-difluoro-phenyl]piperidine-1-carboxylate (460 mg, 1.09 mmol) in Dichloromethane (10 mL) was added Hydrogen chloride (4M in 1,4-dioxane, 4.00 g, 109.71 mmol, 5 mL) at 0° C. and the reaction mixture was stirred at room temperature for 12 h. The reaction mixture was concentrated under reduced pressure to get crude which was triturated with diethyl ether to afford 3-[3,5-difluoro-4-(4-piperidyl)anilino]piperidine-2,6-dione (100 mg, 255.53 μmol, 23.52% yield) as off white solid. LCMS (ESI+): 324.1 $[M+H]^{30}$.

Step 5: To a stirred solution of 3-[3,5-difluoro-4-(4-piperidyl)anilino]piperidine-2,6-dione (300 mg, 927.82 μmol) in N,N-Dimethylformamide (5 mL) were added TEA (470 mg, 4.64 mmol, 647.38 μL) and tert-butyl 2-bromoacetate (200 mg, 1.03 mmol, 150.38 μL) at 0° C. and the reaction mixture was stirred at room temperature for 12 h. The reaction mixture was diluted with ice water (30 mL) and extracted with ethyl acetate (2×50 mL). The combined organic layers were dried over anhydrous sodium sulphate, filtered and evaporated under reduced pressure to get tert-butyl 2-[4-[4-[(2,6-dioxo-3-piperidyl)amino]-2,6-difluoro-phenyl]-1-piperidyl]acetate (310 mg, 666.09 μmol, 71.79% yield) as off white solid. LCMS (ESI+): 438.1 $[M+H]^+$.

Step 6: To a stirred solution of tert-butyl 2-[4-[4-[(2,6-dioxo-3-piperidyl)amino]-2,6-difluoro-phenyl]-1-piperidyl] acetate (250 mg, 571.46 μmol) in Dichloromethane (10 mL) was added Hydrogen chloride solution (4M in 1,4-dioxane, 4.00 g, 109.71 mmol, 5 mL) at 0° C. and the reaction mixture was stirred at room temperature for 12 h. The reaction mixture was concentrated under reduced pressure to get crude which was triturated with diethyl ether to afford 2-[4-[4-[(2,6-dioxo-3-piperidyl)amino]-2,6-difluoro-phenyl]-1-piperidyl]acetic acid (200 mg, 459.51 μmol, 80.41% yield) as off white solid. LCMS (ESI+): 382.1 $[M+H]^+$.

Synthesis of 2-[1-[4-[(2,6-dioxo-3-piperidyl)amino]-2-fluoro-phenyl]-4-piperidyl]acetic acid

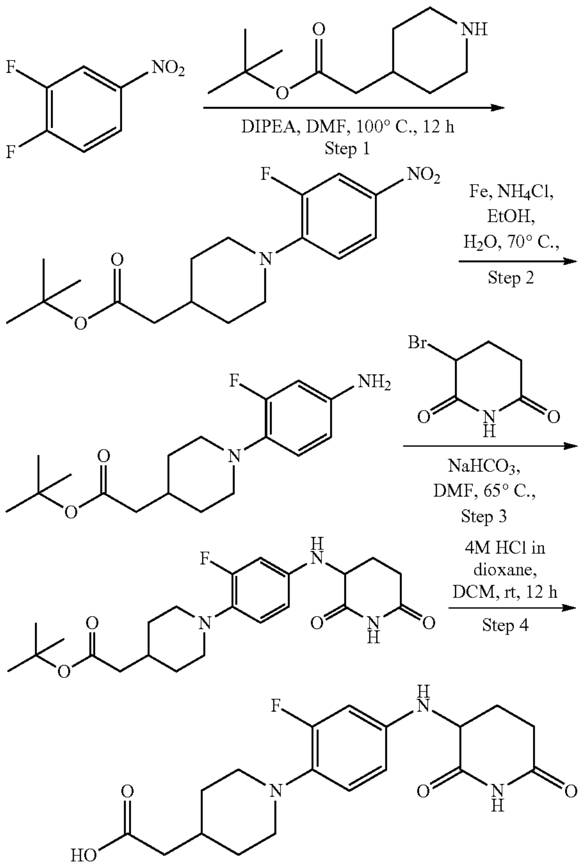

Step 1: To a stirred solution of 1,2-difluoro-4-nitro-benzene (1.5 g, 9.43 mmol, 1.04 mL) and tert-butyl 2-(4-piperidyl)acetate (1.88 g, 9.43 mmol) in N,N-Dimethylformamide (15 mL) was added N,N-Diisopropylethylamine (6.09 g, 47.14 mmol, 8.21 mL) the reaction mixture was heated at 100° C. for 12 h. After completion, the reaction mixture was added to ice water, then solid was obtained. The solid was filtered, washed with cold water and dried under reduced pressure to get tert-butyl 2-[1-(2-fluoro-4-nitro-phenyl)-4-piperidyl]acetate (2.7 g, 5.67 mmol, 60.09% yield) as off white solid. LCMS (ESI+): 339.1 $[M+H]^+$.

Step 2: To a stirred solution of tert-butyl 2-[1-(2-fluoro-4-nitro-phenyl)-4-piperidyl]acetate (2.7 g, 7.98 mmol) in Water (10 mL) and Ethanol (25 mL) were added Iron powder (2.23 g, 39.90 mmol, 283.47 μL) and Ammonium Chloride (2.13 g, 39.90 mmol, 1.39 mL) at room temperature under nitrogen atmosphere. Then stirred the reaction at 70° C. for 5 h. After completion, the reaction mixture was cooled to room temperature, diluted with water (50 mL) and extracted with ethyl acetate (3×70 mL), The combined organic layers were washed with brine solution (100 mL), dried over sodium sulphate, filtered and concentrated under reduced pressure. The crude compound was purified by silica gel column chromatography with 40-50% ethyl acetate in petroleum ether as a eluent to afford tert-butyl 2[1-(4-amino-2-fluoro-phenyl)-4-piperidyl]acetate (2.5 g, 5.27 mmol, 66.04% yield) as a yellow solid. LCMS (ESI+): 309.1 $[M+H]^+$.

Step 3: To a stirred solution of tert-butyl 2-[1-(4-amino-2-fluoro-phenyl)-4-piperidyl]acetate (1.5 g, 4.86 mmol) in N,N-Dimethylformamide (20 mL) were added Sodium bicarbonate (1.23 g, 14.59 mmol, 567.51 μL) and 3-bromopiperidine-2,6-dione (2.1 g, 10.94 mmol). The reaction mixture was stirred at 70° C. for 16 h. The reaction mixture was diluted with ice water (20 mL) and extracted with ethyl acetate (2×50 mL). The combined organic layers were dried over anhydrous sodium sulfate, filtered and concentrated under reduced pressure to get crude which was purified by column chromatography on silica gel eluted with 50% ethyl acetate in petroleum ether to yield tert-butyl 2-[1-[4-[(2,6-dioxo-3-piperidyl)amino]-2-fluoro-phenyl]-4-piperidyl]acetate (900 mg, 2.10 mmol, 43.23% yield) as off white solid. LCMS (ESI+): 420.2 $[M+H]^+$.

Step 4: To a stirred solution of tert-butyl 2-[1-[4-[(2,6-dioxo-3-piperidyl)amino]-2-fluoro-phenyl]-4-piperidyl]acetate (950 mg, 2.26 mmol) in Dichloromethane (10 mL) was added Hydrogen chloride solution (4M in 1,4-dioxane, 1.60 g, 43.88 mmol, 2 mL) at 0° C. and the reaction mixture was stirred at room temperature for 12 h. The reaction mixture was concentrated under reduced pressure to get crude which was triturated with diethyl ether to afford 2-[1-[4-[(2,6-dioxo-3-piperidyl)amino]-2-fluoro-phenyl]-4-piperidyl]acetic acid (800 mg, 1.56 mmol, 68.91% yield) as off white solid. LCMS (ESI+): 364.2 $[M+H]^+$.

Synthesis of 1-[4-[(2,6-dioxo-3-piperidyl)amino]-2-fluoro-phenyl]piperidine-4-carboxylic acid

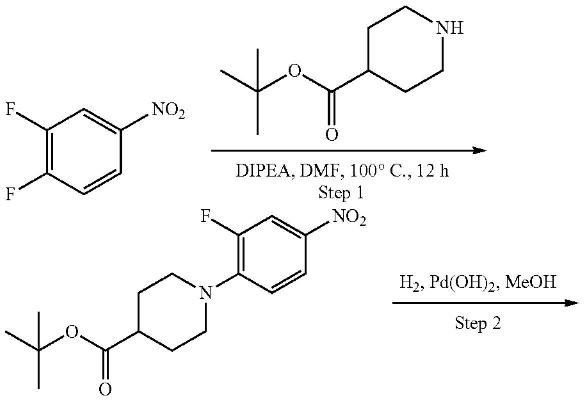

-continued

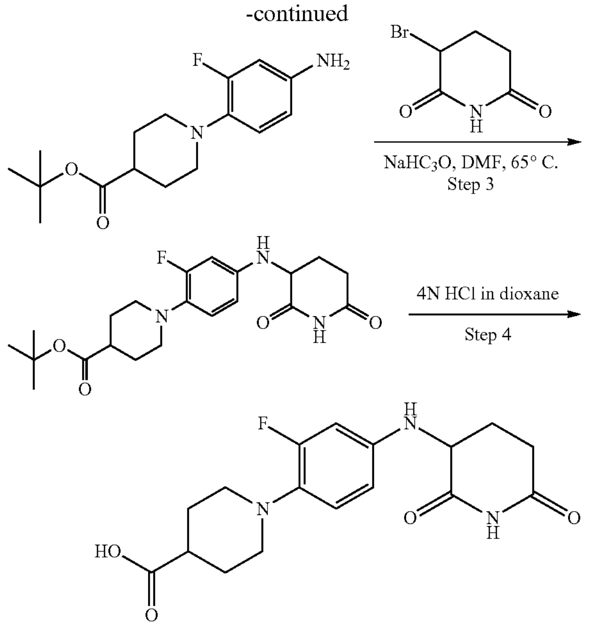

Step 1: To a stirred solution of 1,2-difluoro-4-nitrobenzene (2 g, 12.57 mmol, 1.39 mL), tert-butyl piperidine-4-carboxylate (2.79 g, 15.09 mmol) in Dimethyl sulfoxide (20 mL) was added N,N-Diisopropylethylamine (8.12 g, 62.86 mmol, 10.95 mL). The reaction mixture was heated to 120° C. for 12 h. After completion, the reaction mixture was diluted with water (20 mL) and extracted with ethyl acetate (2×50 mL). The combined organic layers were dried over sodium sulphate, filtered and concentrated under vacuum to get crude. The crude compound was purified by silica gel column chromatography using 20-30% ethyl acetate in petroleum ether to get tert-butyl 1-(2-fluoro-4-nitro-phenyl) piperidine-4-carboxylate (2.7 g, 8.24 mmol, 65.55% yield) as a brown solid. LCMS (ESI+): 325.1 $[M+H]^+$ Step 2: To a stirred solution of tert-butyl 1-(2-fluoro-4-nitro-phenyl)piperidine-4-carboxylate (2.7 g, 8.32 mmol) in Methanol (30 mL) was added Palladium hydroxide on carbon (20 wt. %, 50% water, 1.17 g, 8.32 mmol). The reaction mixture was stirred at room temperature under hydrogen balloon (1 atm) for 12 h. After completion, the reaction mixture was filtered through celite, filtrate was concentrated under vacuum to get tert-butyl 1-(4-amino-2-fluoro-phenyl)piperidine-4-carboxylate (2.5 g, 6.71 mmol, 80.60% yield) as a brown liquid. LCMS (ESI+): 295.0 $[M+H]^+$ Step 3: To a stirred solution of tert-butyl 1-(4-amino-2-fluoro-phenyl)piperidine-4-carboxylate (1 g, 3.40 mmol), 3-bromopiperidine-2,6-dione (652.29 mg, 3.40 mmol) in N,N-Dimethyl formamide (20 mL) was added Sodium bicarbonate (285.38 mg, 3.40 mmol, 132.12 μL). The reaction mixture was heated to 70° C. for 12 h. After completion, the reaction mixture was diluted with water (30 mL) and extracted with ethyl acetate (2×100 mL). The combined organic layers were dried over sodium sulphate, filtered and concentrated under vacuum to get crude. The crude compound was purified by silica gel column chromatography using 40-50% ethyl acetate in pet-ether to afford tert-butyl 1-[4-[(2,6-dioxo-3-piperidyl)amino]-2-fluoro-phenyl]piperidine-4-carboxylate (1 g, 1.68 mmol, 49.37% yield) as a brown solid. LCMS (ESI+): 405.9 $[M+H]^+$ Step 4: To a stirred solution of tert-butyl 1-[4-[(2,6-dioxo-3-piperidyl)amino]-2-fluoro-phenyl]piperidine-4-carboxylate (1 g, 2.47 mmol) in Dichloromethane (20 mL) at 0° C. was added Hydrogen chloride solution (4M in 1,4-dioxane, 89.92 mg, 2.47 mmol, 112.41 μL). The reaction mixture was stirred at room temperature for 12 h. After completion, the reaction mixture was concentrated under vacuum to get 1-[4-[(2,6-dioxo-3-piperidyl)amino]-2-fluoro-phenyl]piperidine-4-carboxylic acid (900 mg, 2.33 mmol, 94.58% yield) as colourless solid. LCMS (ESI+): 350.1 $[M+H]^+$.

Synthesis of CRBN building block 2-[1-[4-[(2,6-dioxo-3-piperidyl)amino]phenyl]-4-hydroxy-4-piperidyl]acetic acid

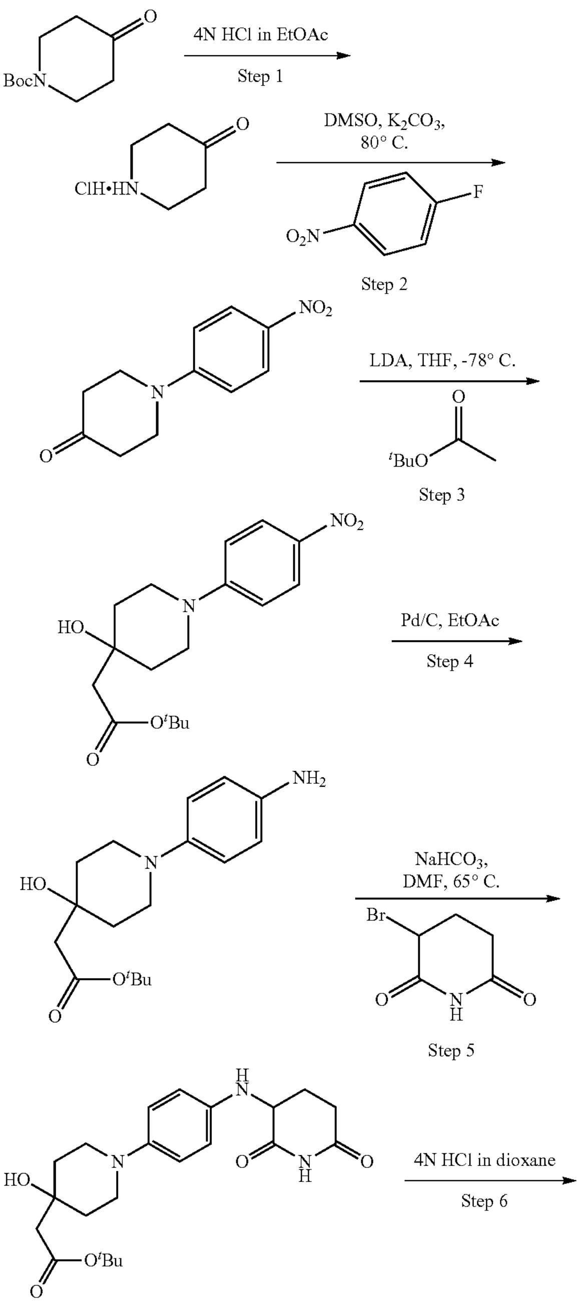

-continued

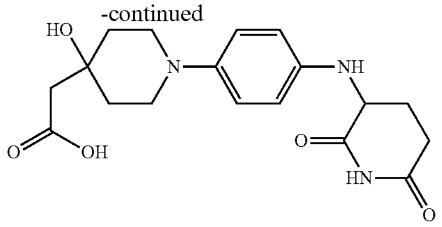

Step 1: To a stirred solution of tert-butyl 4-oxopiperidine-1-carboxylate (15 g, 75.28 mmol) in ethyl acetate (50 mL), was added 4 N HCl in ethyl acetate (40.00 g, 1.10 mol, 50 mL) at 5° C. The reaction mixture was stirred at room temperature for 6 h. After completion, the reaction mixture was completely concentrated under reduced pressure to afford crude piperidin-4-one (10.5 g, 69.69 mmol, 92.58% yield) as a brown solid. $^1$H-NMR (400 MHz, DMSO-$d_6$): δ 3.39 (t, J=8.80 Hz, 4H), 2.59 (t, J=8.40 Hz, 4H).

Step 2: To a solution of piperidin-4-one (10.5 g, 77.44 mmol) in DMSO (50 mL) were added 4-nitroaniline (11.77 g, 85.18 mmol) and DIPEA (20.02 g, 154.88 mmol, 26.98 mL) and heated at 110° C. for 14 h. The reaction mixture was diluted with ethyl acetate (500 mL), washed with cold water (150 mL). The organic layer was washed with brine solution (150 mL), dried over sodium sulphate and concentrated under reduced pressure to get crude, which was purified by column chromatography on silica gel eluted with 40% ethyl acetate in petroleum ether to afford 1-(4-nitrophenyl)piperidin-4-one (14.1 g, 64.03 mmol, 82.68% yield) as a brown solid. LCMS (ESI+): 221.1 [M+H]$^+$.

Step 3: To a stirred solution of tert-butyl acetate (6.33 g, 54.49 mmol, 7.33 mL) in THF (100 mL) was added (diisopropylamino)lithium (9.73 g, 90.82 mmol, 46 mL) at −78° C. in 0.5 h. After 1 h stirring at −78° C. then solution of 1-(4-nitrophenyl)piperidin-4-one (10 g, 45.41 mmol) in THF (200 mL) was added to the reaction mixture at −78° C. within 0.5 h. After addition, the reaction temperature raised to −10° C. for 2 h. After consumption of starting material, the reaction was quenched with a saturated ammonium chloride solution (25 mL). The reaction mixture was diluted with ethyl acetate (500 mL), washed with cold water (150 mL). The organic layer was washed with brine solution (150 mL), dried over sodium sulphate and concentrated under reduced pressure to get crude, which was purified by column chromatography on silica gel eluted with 30% ethyl acetate in petroleum ether to afford t-butyl 2-[4-hydroxy-1-(4-nitrophenyl)-4-piperidyl]acetate (7 g, 20.35 mmol, 44.82% yield) as a pale yellow solid. LCMS (ESI+): 337.2 [M+H]$^+$.

Step 4: To a stirred solution of tert-butyl 2-[4-hydroxy-1-(4-nitrophenyl)-4-piperidyl]acetate (7 g, 20.81 mmol) in ethyl acetate (70 mL) was added 10% palladium on carbon wet (3 g, 28.19 mmol) at room temperature under nitrogen. Reaction stirred under $H_2$ bladder (~1 atm) for 16 h at room temperature. After 16 h, the reaction mixture was filtered through celite bed to remove catalyst with ethyl acetate (100 mL) washing. The filtrate concentrated under reduced pressure to afford tert-butyl 2-[1-(4-aminophenyl)-4-hydroxy-4-piperidyl]acetate (5.8 g, 17.87 mmol, 85.86% yield) as an off white solid. LCMS (ESI+): 307.20 [M+H]$^+$.

Step 5: To a stirred solution of tert-butyl 2-[1-(4-aminophenyl)-4-hydroxy-4-piperidyl]acetate (4 g, 13.05 mmol) in N, N-Dimethylformamide (40 mL) was added sodium; hydrogen carbonate (3.29 g, 39.16 mmol, 1.52 mL) followed by 3-bromopiperidine-2,6-dione (3.76 g, 19.58 mmol) at room temperature. The resulted reaction mixture stirred for 16 h at 65° C. After 16 h, the reaction was quenched by adding ice cold water (25 mL). The reaction mixture was diluted with ethyl acetate (2×100 mL), washed with cold water (50 mL). The organic layer was washed with brine solution (100 mL), dried over sodium sulphate and concentrated under reduced pressure to get crude, which was purified by column chromatography on silica gel eluted with 80% ethyl acetate in petroleum ether to afford tert-butyl 2-[1-[4-[(2,6-dioxo-3-piperidyl)amino]phenyl]-4-hydroxy-4-piperidyl]acetate (3.3 g, 7.90 mmol, 60.55% yield) as green solid. LCMS (ESI+): 418.2 [M+H]$^+$.

Step 6: To stirred solution of tert-butyl 2-[1-[4-[(2,6-dioxo-3-piperidyl)amino]phenyl]-4-hydroxy-4-piperidyl] acetate (3.3 g, 7.90 mmol) in 1,4-Dioxane (3.3 mL) was added Hydrogen chloride solution 4.0 M in 1,4-dioxane (2.64 g, 72.41 mmol, 3.3 mL) at 0° C. The resulting reaction mixture stirred for 16 h at room temperature. After completion, the reaction mixture was completely concentrated under reduced pressure to afford 2-[1-[4-[(2,6-dioxo-3-piperidyl)amino]phenyl]-4-hydroxy-4-piperidyl]acetic acid (3.3 g, 7.53 mmol, 95.28% yield) as pale blue solid. LCMS (ESI+): 362.2 [M+H]$^+$.

Synthesis of 2-[1-[4-[(2,6-dioxo-3-piperidyl)amino]-2-fluoro-phenyl]-4-hydroxy-4-piperidyl]acetic acid

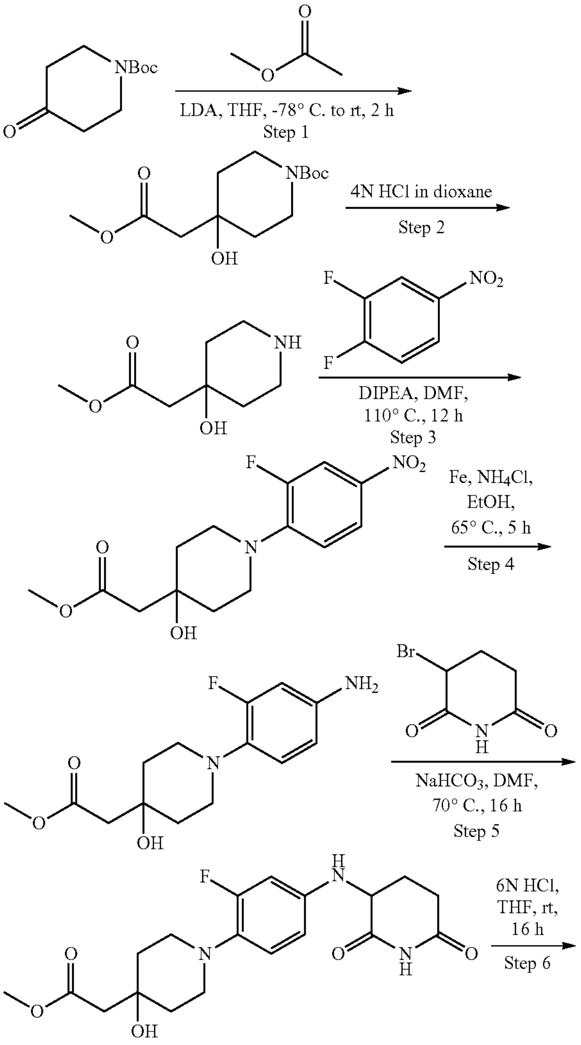

-continued

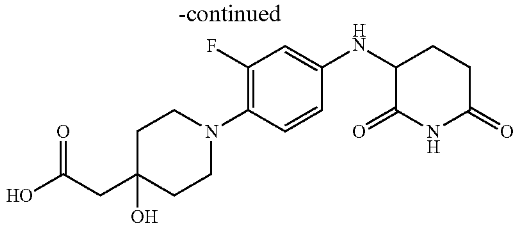

Step 1: To a stirred solution of methyl acetate (4.46 g, 60.23 mmol, 4.78 mL) in dry THF (200 mL), was added Lithium diisopropylamide (10.75 g, 100.38 mmol, 50.19 mL) dropwise under nitrogen atmosphere at −78° C. Reaction mixture was stirred at −78° C. for 30 minutes and then tert-butyl 4-oxopiperidine-1-carboxylate (10 g, 50.19 mmol) in THF (50 mL) solution was added dropwise −78° C. and stirred reaction mixture at room temperature for 2 h. After completion, the reaction mixture was quenched with saturated ammonium chloride solution (250 mL) at 0° C. and extracted with ethyl acetate (3x200 mL). Combined organic layers dried over sodium sulphate, filtered and concentrated. The crude compound was purified by column chromatography (60-120 silica gel) by using 40-50% ethyl acetate in petroleum ether as eluent to afford tert-butyl 4-hydroxy-4-(2-methoxy-2-oxo-ethyl)piperidine-1-carboxylate (5.6 g, 16.75 mmol, 33.37% yield) as yellow liquid. LCMS (ESI+): 174.1 $[M-100+H]^+$.

Step 2: To a stirred solution of tert-butyl 4-hydroxy-4-(2-methoxy-2-oxo-ethyl)piperidine-1-carboxylate (5.5 g, 20.12 mmol) in Dichloromethane (70 mL), was added Hydrogen chloride solution (4M in 1,4-dioxane, 1.10 mol, 50 mL) at 5° C. The reaction mixture was stirred at room temperature for 12 h. After completion, the reaction mixture was concentrated under reduced pressure to afford crude methyl 2-(4-hydroxy-4-piperidyl)acetate (5.5 g, 26.23 mmol) as light yellow gummy liquid. LCMS (ESI+): 174.1 $[M+H]^+$ Step 3: Methyl 2-(4-hydroxy-4-piperidyl)acetate (5.5 g, 31.75 mmol) in DMSO (70 mL) was taken in a sealed tube and added N-ethyl-N-isopropyl-propan-2-amine (14.36 g, 111.14 mmol, 19.36 mL) and 1,2-difluoro-4-nitro-benzene (6.06 g, 38.10 mmol, 4.21 mL) at room temperature. The reaction mixture was stirred at 100° C. for 12 h. After completion, the reaction mixture was diluted with water (70 mL), extracted with ethyl acetate (3x100 mL). Combined organic layers dried over sodium sulphate, filtered and concentrated under reduced pressure to afford crude. Desired product was purified by column chromatography (60-120 silica gel), by using 40-50% ethyl acetate in petroleum ether as eluent to afford methyl 2-[1-(2-fluoro-4-nitro-phenyl)-4-hydroxy-4-piperidyl]acetate (2.7 g, 7.95 mmol, 25.04% yield) as yellow gummy liquid. LCMS (ESI+): 313.1 $[M+H]^+$ Step 4: To a stirred solution of methyl 2-[1-(2-fluoro-4-nitro-phenyl)-4-hydroxy-4-piperidyl]acetate (6.1 g, 19.53 mmol) in Ethanol (200 mL) and Water (36 mL), were added Iron powder (5.45 g, 97.66 mmol) and Ammonium Chloride (3.13 g, 58.60 mmol) at room temperature. The reaction mixture was stirred at 75° C. for 5 h. After completion, the reaction mixture was filtered through celite pad, concentrated under reduced pressure, diluted with water (50 mL) and extracted with ethyl acetate (3x70 mL). Combined organic layers dried over sodium sulphate, filtered and concentrated under reduced pressure to afford crude methyl 2-[1-(4-amino-2-fluoro-phenyl)-4-hydroxy-4-piperidyl]acetate (5.5 g, 19.48 mmol, 99.74% yield) as a light brown liquid. $^1$H-NMR (400 MHz, DMSO-$d_6$): δ 6.75-6.80 (m, 1H), 6.27-6.34 (m, 2H), 4.93 (s, 2H), 4.53 (s, 1H), 3.59 (s, 3H), 2.77-2.89 (m, 4H), 2.50 (s, 2H), 1.75-1.78 (m, 4H).

Step 5: Methyl 2-[1-(4-amino-2-fluoro-phenyl)-4-hydroxy-4-piperidyl]acetate (5.5 g, 19.48 mmol) was taken in a sealed tube and dissolved in N,N-dimethylformamide (70 mL), and added sodium bicarbonate (4.91 g, 58.45 mmol, 2.27 mL) and 3-bromopiperidine-2,6-dione (6.24 g, 48.71 mmol) at room temperature. The reaction mixture was stirred at 75° C. for 16 h. After completion, the reaction mixture was filtered through celite pad, concentrated under reduced pressure, diluted with water (100 mL) and extracted with ethyl acetate (3x150 mL). Combined organic layers dried over sodium sulphate, filtered and concentrated under reduced pressure to afford crude. Desired product was purified by column chromatography (60-120 silica gel), by using 80-90% ethyl acetate in petroleum ether as eluent to afford product. The product was washed sequentially with diethyl ether and ethyl acetate to afford methyl 2-[1-[4-[(2,6-dioxo-3-piperidyl)amino]-2-fluoro-phenyl]-4-hydroxy-4-piperidyl]acetate (3.8 g, 8.82 mmol, 45.27% yield) as a light green solid. LCMS (ESI+): 394.0 $[M+H]^+$ Step 6: To a stirred solution of methyl 2-[1-[4-[(2,6-dioxo-3-piperidyl)amino]-2-fluoro-phenyl]-4-hydroxy-4-piperidyl]acetate (3.8 g, 9.66 mmol) in THF (20 mL), was added 6N HCl aqueous solution (1.14 mmol, 80 mL) at 5° C. The reaction mixture was stirred at room temperature for 16 h. After completion, the reaction mixture was concentrated under reduced pressure to afford crude. Crude was washed sequentially with diethyl ether and acetonitrile to afford 2-[1-[4-[(2,6-dioxo-3-piperidyl)amino]-2-fluoro-phenyl]-4-hydroxy-4-piperidyl]acetic acid (4 g, 8.42 mmol, 87.16% yield) as a yellow solid. LCMS (ESI+): 380.1 $[M+H]^+$ Synthesis of (S)-2-(1-(4-((2,6-dioxopiperidin-3-yl)amino)-2-fluorophenyl)-4-hydroxypiperidin-4-yl)acetic acid hydrochloride and (R)-2-(1-(4-((2,6-dioxopiperidin-3-yl)amino)-2-fluorophenyl)-4-hydroxypiperidin-4-yl)acetic acid hydrochloride (arbitrarily assigned)

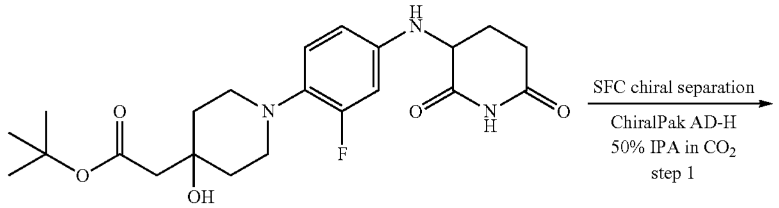

racemate

-continued

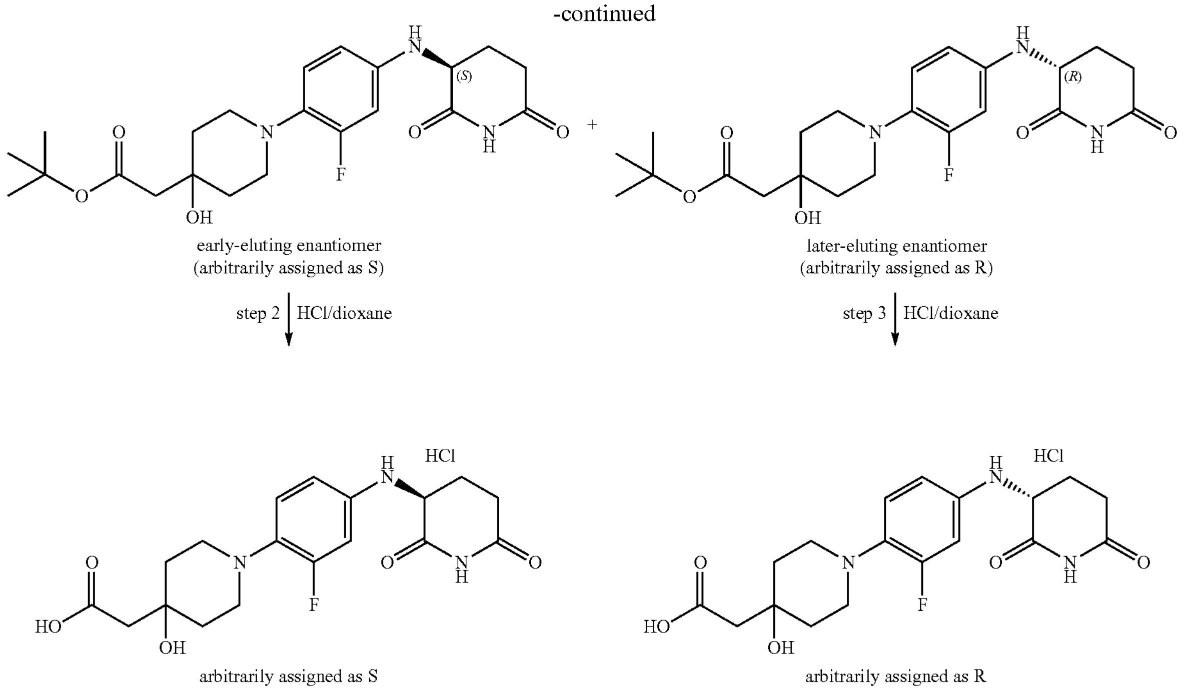

Racemic tert-butyl 2-(1-(4-((2,6-dioxopiperidin-3-yl)amino)-2-fluorophenyl)-4-hydroxypiperidin-4-yl)acetate was synthesized in the same fashion as the above mentioned methyl 2-[1-[4-[(2,6-dioxo-3-piperidyl)amino]-2-fluoro-phenyl]-4-hydroxy-4-piperidyl]acetate, using 1-Benzyl-4-piperidone (CAS: 3612-20-2) and tert-Butyl acetate (CAS: 540-88-5) as starting materials. Yield: 40% over 5 steps. LCMS (ESI+): 436.2 $[M+H]^+$.

Step 1: Chiral Separation

Racemate tert-butyl 2-(1-(4-((2,6-dioxopiperidin-3-yl)amino)-2-fluorophenyl)-4-hydroxypiperidin-4-yl)acetate (5.3 g, 12.1 mmol) was dissolved in a mixed solution of 2-propanol (110 mL) and dichloromethane (30 mL). The racemic solution (2.5 mL/injection) was separated by preparative chiral SFC using ChiralPak AD-H column (21×250 mm), eluting with 50% 2-propanol in $CO_2$ (flow rate: 70 mL/min). The separation afforded 2.47 g of the early-eluting enantiomer (>99% e.e.) and 2.56 g of the later-eluting enantiomer (97.5% e.e.) as faint-greenish solids. Early-eluting enantiomer: $^1$H NMR (400 MHz, Chloroform-d) δ 7.93 (s, 1H), 6.87 (d, J=10.0 Hz, 1H), 6.40-6.30 (m, 2H), 4.55-4.50 (m, 1H), 3.93 (d, J=12.2 Hz, 1H), 3.69 (s, 1H), 3.01-2.95 (m, 4H), 2.81 (dt, J=18.1, 3.8 Hz, 1H), 2.68 (ddd, J=18.2, 13.3, 5.1 Hz, 1H), 2.46 (dtd, J=13.1, 4.9, 2.7 Hz, 1H), 2.39-2.34 (m, 2H), 1.83 (qd, J=13.3, 4.7 Hz, 1H), 1.75-1.70 (m, 4H), 1.41 (s, 9H). LCMS (ESI+): 436.265 $[M+H]^+$ Later-eluting enantiomer: $^1$H NMR (400 MHz, Chloroform-d) δ 7.96 (s, 1H), 6.86 (s, 1H), 6.40-6.30 (m, 2H), 4.55-4.50 (m, 1H), 3.93 (d, J=12.1 Hz, 1H), 3.70 (s, 1H), 3.01-2.95 (s, 4H), 2.85-2.75 (m, 1H), 2.68 (ddd, J=18.1, 13.3, 5.1 Hz, 1H), 2.54-2.40 (m, 1H), 2.37 (s, 2H), 1.91-1.76 (m, 1H), 1.75-1.70 (m, 4H), 1.41 (s, 9H). LCMS (ESI+): 436.3 $[M+H]^+$ Step 2: The separated enantiomer, tert-butyl 2-[1-[4-[[(3S)-2,6-dioxo-3-piperidyl]amino]-2-fluoro-phenyl]-4-hydroxy-4-piperidyl]acetate (2.40 g, 5.51 mmol) was dissolved in dichloromethane (40 mL). The substrate solution was added in a portion wise fashion to a stirring solution of 4M hydrogen chloride in 1,4-dioxane (4 M, 21.53 mL) at ambient temperature. The gel-like mixture was stirred at ambient temperature. After 20 h, the gel like material was concentrated in vacuo and was further azeotroped with toluene (80 mL) to obtain 2.23 g (97% yield) of desired product, (S)-2-(1-(4-((2,6-dioxopiperidin-3-yl)amino)-2-fluorophenyl)-4-hydroxypiperidin-4-yl)acetic acid hydrochloride (arbitrarily assigned), as a faint-greenish (almost off-white) solid. $^1$H NMR (400 MHz, Methanol-$d_4$) δ 7.40 (t, J=8.9 Hz, 1H), 6.62 (dd, J=14.9, 2.6 Hz, 1H), 6.61-6.53 (m, 1H), 4.31 (dd, J=12.1, 5.0 Hz, 1H), 3.88 (td, J=12.8, 2.9 Hz, 2H), 3.50-3.40 (m, 2H), 2.73 (ddd, J=17.9, 12.5, 5.4 Hz, 1H), 2.63 (ddd, J=17.9, 5.0, 3.2 Hz, 1H), 2.51 (s, 2H), 2.24-2.12 (m, 3H), 2.05-1.97 (m, 2H), 1.90 (qd, J=12.6, 4.9 Hz, 1H). LCMS (ESI+): 380.2 $[M+H]^+$.

Step 3: The separated enantiomer, tert-butyl 2-[1-[4-[[(3R)-2,6-dioxo-3-piperidyl]amino]-2-fluoro-phenyl]-4-hydroxy-4-piperidyl]acetate (2.50 g, 5.74 mmol) was dissolved in dichloromethane (40 mL). The substrate solution was added in a portion wise fashion to a stirring solution of 4M hydrogen chloride in 1,4-dioxane (4 M, 21.53 mL) at room temperature. The gel-like mixture was stirred at room temperature. After 20 h, the gel like material was concentrated in vacuo and was further azeotroped with toluene (80 mL) to obtain 2.23 g (94% yield) of desired product, (R)-2-(1-(4-((2,6-dioxopiperidin-3-yl)amino)-2-fluorophenyl)-4-hydroxypiperidin-4-yl)acetic acid hydrochloride (arbitrarily assigned), as a faint-greenish (almost off-white) solid. $^1$H NMR (400 MHz, Methanol-$d_4$) δ 7.39 (t, J=8.9 Hz, 1H), 6.62 (dd, J=14.9, 2.6 Hz, 1H), 6.61-6.53 (m, 1H), 4.31 (dd, J=12.1, 5.0 Hz, 1H), 3.88 (td, J=12.8, 2.9 Hz, 2H), 3.50-3.41 (m, 2H), 2.73 (ddd, J=17.9, 12.5, 5.4 Hz, 1H), 2.63 (ddd, J=17.9, 5.0, 3.2 Hz, 1H), 2.51 (s, 2H), 2.24-2.16 (m, 1H), 2.21-2.12 (m, 2H), 2.05-1.77 (m, 3H). LCMS (ESI+): 380.1 $[M+H]^+$.

Synthesis of 2-[1-[5-[(2,6-dioxo-3-piperidyl)amino]-2-pyridyl]-4-hydroxy-4-piperidyl]acetic acid

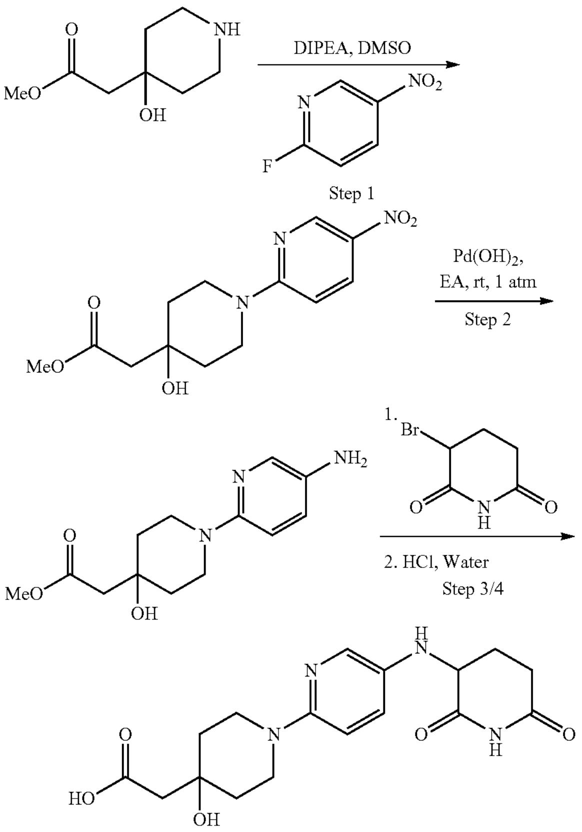

Step 1: To the stirred solution of methyl 2-(4-hydroxy-4-piperidyl)acetate (2.5 g, 11.92 mmol) and 2-fluoro-5-nitro-pyridine (1.78 g, 12.52 mmol) in DMSO (10 mL) in a seal tube was added N-ethyl-N-isopropyl-propan-2-amine (7.71 g, 59.62 mmol, 10.38 mL) and heated at 80° C. for 16 hours. After completion, reaction mixture was diluted with water (100 mL) and extracted with ethyl acetate (3x50 mL). Combined organic phases were washed with brine, dried over anhydrous sodium sulphate, filtered and concentrated under reduced pressure to afford crude residue which was purified by flash silica-gel (60-120 mesh) column chromatography with 1:1 Ethyl acetate:petroleum ether to afford methyl 2-[4-hydroxy-1-(5-nitro-2-pyridyl)-4-piperidyl]acetate (3.3 g, 10.28 mmol, 86.20% yield) as a yellow brown solid. LCMS (ESI+): 296.0 $[M+H]^+$.

Step 2: A stirred solution of methyl 2-[4-hydroxy-1-(5-nitro-2-pyridyl)-4-piperidyl]acetate (3.0 g, 10.16 mmol) in ethyl acetate (100 mL) was degassed with nitrogen and Palladium hydroxide on carbon (20 wt. %, 50% water, 713.37 mg, 5.08 mmol) was added slowly. The reaction mixture was stirred at room temperature under hydrogen atmosphere using hydrogen bladder for 6 hours. After completion, reaction mixture was purged with nitrogen for few minutes and filtered through a pad of celite, washing with ethyl acetate (50 mL). The filtrate was concentrated under reduced pressure to afford methyl 2-[1-(5-amino-2-pyridyl)-4-hydroxy-4-piperidyl]acetate (2.9 g, 8.39 mmol, 82.63% yield) as a dark brown thick syrup. LCMS (ESI+): 266 $[M+H]^+$.

Step 3: To the solution of methyl 2[1-(5-amino-2-pyridyl)-4-hydroxy-4-piperidyl]acetate (2.9 g, 10.93 mmol) and 3-bromopiperidine-2,6-dione (3.15 g, 16.40 mmol) in N,N-Dimethylformamide (20 mL) was added sodium bicarbonate (2.30 g, 27.33 mmol) and heated at 70° C. for 16 hours. After completion, excess solvent was distilled out under reduced pressure and crude product obtained was purified by reverse phase column (120 g) using 0.1% $HCO_2H$ in water and acetonitrile as eluents to afford methyl 2-[1-[5-[(2,6-dioxo-3-piperidyl)amino]-2-pyridyl]-4-hydroxy-4-piperidyl]acetate (3.5 g, 5.91 mmol, 54.04% yield) as a brown purple solid. LCMS (ESI+): 377.2 $[M+H]^+$.

Step 4: To a suspension of methyl 2-[1-[5-[(2,6-dioxo-3-piperidyl)amino]-2-pyridyl]-4-hydroxy-4-piperidyl]acetate (3.2 g, 8.50 mmol) in tetrahydrofuran (10.0 mL) was added 8N HCl in water (8.50 mmol, 10.0 mL) at 0° C. The reaction mixture was warmed to room temperature and stirred for 24 hours. After completion, the reaction mixture was concentrated under reduced pressure and the resulting crude product was washed with diethyl ether (3x20 mL), dried to afford 2-[1-[5-[(2,6-dioxo-3-piperidyl)amino]-2-pyridyl]-4-hydroxy-4-piperidyl]acetic acid (3.0 g, 89% yield) as a light brown solid. LCMS (ESI+): 363.2 $[M+H]^+$.

Synthesis of 2-[1-[5-[(2,6-dioxo-3-piperidyl)amino]-3-fluoro-2-pyridyl]-4-hydroxy-4-piperidyl]acetic acid

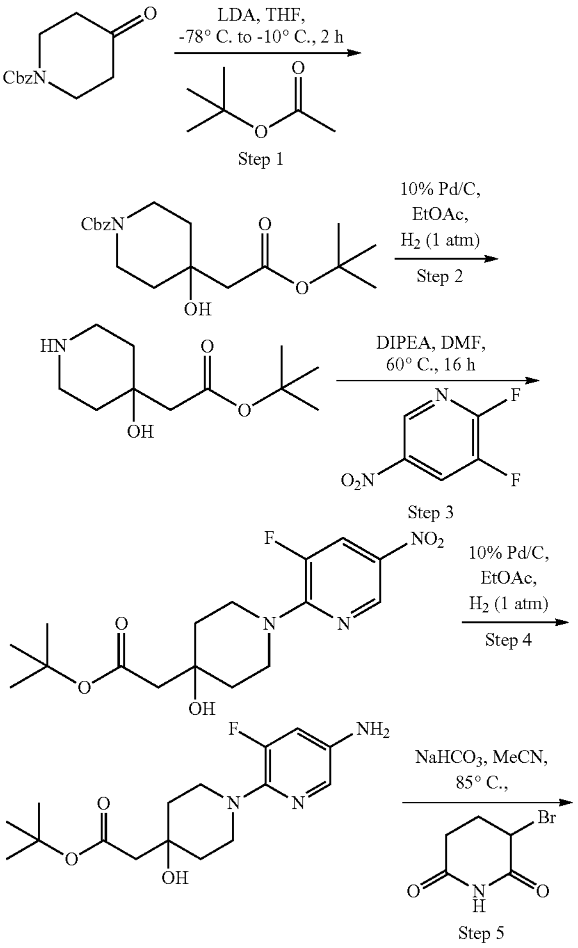

-continued

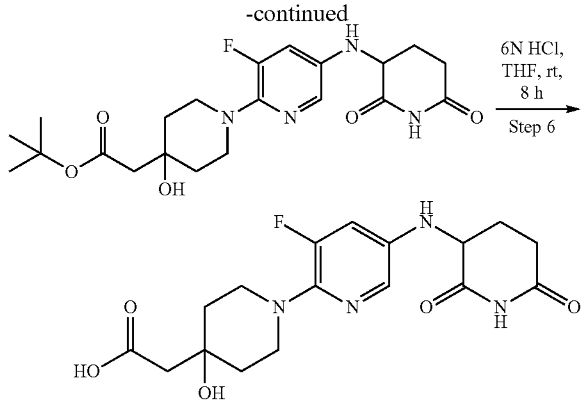

Step 1: To stirred solution of tert-butyl acetate (11.95 g, 102.89 mmol, 13.85 mL) in THF (150 mL) was added lithium diisopropylamide (18.37 g, 171.48 mmol) at −78° C. and continued the reaction for 1 h at the same temperature. To this, solution of benzyl 4-oxopiperidine-1-carboxylate (20 g, 85.74 mmol, 17.09 mL) in THF (150 mL) was added to reaction mixture at −78° C. and reaction temperature raised to −10° C. in 2 h. After completion, reaction mixture was quenched with a saturated aqueous ammonium chloride solution (250 mL) and extracted with Ethyl acetate (2×250 mL). Combined organic layer washed with brine solution (1×250 mL), dried over sodium sulphate and concentrated under reduced pressure. Crude compound was purified by column chromatography using 60-120 silica gel and Ethyl acetate in petroleum ether as eluent. Product eluted between 20-25% of Ethyl acetate in petroleum ether. After getting pure fractions concentrated under reduced pressure got title compound benzyl 4-(2-tert-butoxy-2-oxo-ethyl)-4-hydroxy-piperidine-1-carboxylate (24 g, 68.61 mmol, 80.02% yield) as pale-yellow oil. LCMS (ESI+): 292.0 $[M-56-H]^+$.

Step 2: To stirred solution of benzyl 4-(2-tert-butoxy-2-oxo-ethyl)-4-hydroxy-piperidine-1-carboxylate (24 g, 68.69 mmol) in Ethyl acetate (250 mL) was added 10% Palladium on carbon (7.2 g, 67.66 mmol) at room temperature under nitrogen. Reaction stirred under $H_2$ bladder (~1 atm) for 16 h at room temperature. After completion, reaction mixture filtered through celite bed and washed with ethyl acetate (250 mL). Clear filtrate concentrated under reduced pressure afford tert-butyl 2-(4-hydroxy-4-piperidyl)acetate (12.4 g, 47.46 mmol, 69.10% yield) as an off white solid. LCMS (ESI+): 216.1 $[M+H]^+$.

Step 3: To stirred solution of tert-butyl 2-(4-hydroxy-4-piperidyl)acetate (6.40 g, 29.74 mmol) in N,N-Dimethylformamide (25 mL) was added N-ethyl-N-isopropyl-propan-2-amine (10.98 g, 84.97 mmol, 14.80 mL) and 2-chloro-3-fluoro-5-nitro-pyridine (5 g, 28.32 mmol) at room temperature. Then reaction mixture temperature heated to 60° C. and maintained for 16 h at same temperature. After completion, the reaction mixture diluted with water (250 mL) and extracted by ethyl acetate (2×250 mL). Combined organic layer washed with brine solution (250 mL) and dried over sodium sulphate and after filtration concentrated under reduced pressure to get crude. Crude compound was purified by column chromatography using 60-120 silica gel eluted between 18-20% of Ethyl acetate in petroleum ether to get tert-butyl 2-[1-(3-fluoro-5-nitro-2-pyridyl)-4-hydroxy-4-piperidyl]acetate (9.6 g, 26.34 mmol, 93.00% yield) as a yellow solid. LCMS (ESI+): 300.0 $[M-56+H]^+$ Step 4: To stirred solution of tert-butyl 2-[1-(3-fluoro-5-nitro-2-pyridyl)-4-hydroxy-4-piperidyl]acetate (10.5 g, 29.55 mmol) in Ethyl acetate (200 mL) was added 10% Palladium on carbon (2.10 g, 19.74 mmol) at room temperature under nitrogen. Reaction stirred under $H_2$ bladder (~1 atm) for 5 h at room temperature. After completion, reaction mixture was filtered through celite bed and washed with ethyl acetate (200 mL) and concentrated under reduced pressure afford tert-butyl 2-[1-(5-amino-3-fluoro-2-pyridyl)-4-hydroxy-4-piperidyl]acetate (8 g, 24.32 mmol, 82.30% yield) as a pale brown solid. LCMS (ESI+): 268.0 $[M-56-H]^+$.

Step 5: To stirred solution of tert-butyl 2-[1-(5-amino-3-fluoro-2-pyridyl)-4-hydroxy-4-piperidyl]acetate (8 g, 24.59 mmol) in N,N-Dimethylformamide (80 mL) was added sodium hydrogen carbonate (6.20 g, 73.76 mmol, 2.87 mL) and 3-bromopiperidine-2,6-dione (9.44 g, 49.17 mmol) at room temperature. Reaction stirred for 16 h at 70° C. After completion, the reaction mixture was diluted with water (500 mL) and extracted by ethyl acetate (2×500 mL). The combined organic layer washed with brine solution (500 mL), dried over sodium sulphate and concentrated under reduced pressure. Crude compound was purified by column chromatography using 60-120 silica gel eluted between 80-95% of Ethyl acetate in petroleum ether to afford tert-butyl 2-[1-[5-[(2,6-dioxo-3-piperidyl)amino]-3-fluoro-2-pyridyl]-4-hydroxy-4-piperidyl]acetate (9.0 g, 16.97 mmol, 69.02% yield) as a pale blue solid. LCMS (ESI+): 437.0 $[M+H]^+$.

Step 6: To stirred solution of tert-butyl 2-[1-[5-[(2,6-dioxo-3-piperidyl)amino]-3-fluoro-2-pyridyl]-4-hydroxy-4-piperidyl]acetate (9 g, 20.62 mmol) in 1,4-dioxane (10 mL) was added hydrogen chloride solution (4M in 1,4-dioxane, 1.97 mol, 90 mL) at room temperature. Reaction stirred for 16 h at room temperature. After completion, the reaction mixture was concentrated under reduced pressure get crude. Crude compound was triturated with diethyl ether (100 mL) to get 2-[1-[5-[(2,6-dioxo-3-piperidyl)amino]-3-fluoro-2-pyridyl]-4-hydroxy-4-piperidyl]acetic acid (8.0 g, 19.19 mmol, 93.08% yield) as a pale blue solid. LCMS (ESI+): 381.0 $[M+H]^+$.

Synthesis of 2-[1-[2-chloro-4-[(2,6-dioxo-3-piperidyl)amino]phenyl]-4-hydroxy-4-piperidyl]acetic acid

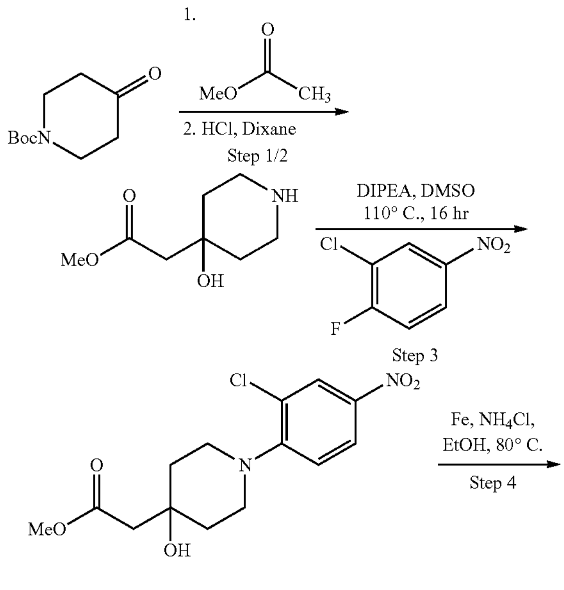

-continued

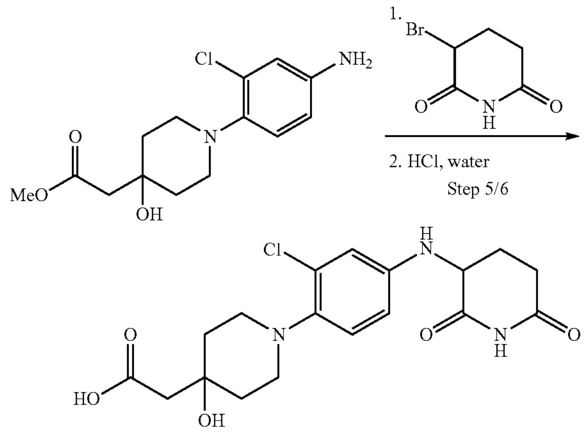

Step 1: Into a 500 mL three-necked round-bottomed flask containing a well-stirred solution of methyl acetate (6.69 g, 90.34 mmol, 7.17 mL) in THF (100 mL) was added (diisopropylamino)lithium (16.13 g, 150.57 mmol) under nitrogen atmosphere at −78° C. and the resulting mixture was stirred for 1 hour. To this, tert-butyl 4-oxopiperidine-1-carboxylate (15 g, 75.28 mmol) in THF (100 mL) was added dropwise at −78° C. and allowed to stir at room temperature for 2 hours. After completion, the reaction mixture was quenched with saturated ammonium chloride solution (100 mL) and the aqueous phase was extracted with ethyl acetate (3×100 mL). Combined organic phases were washed with brine, dried over sodium sulphate, filtered, and concentrated under reduced pressure. The crude residue was purified by flash silica-gel (230-400 mesh) column with 3:7 ethyl acetate: petroleum ether to afford tert-butyl 4-hydroxy-4-(2-methoxy-2-oxo-ethyl)piperidine-1-carboxylate (15.2 g, 53.94 mmol, 71.65% yield) as a yellow gummy liquid. LCMS (ESI+): 174 $[M+H-100]^+$ Step 2: To the solution of tert-butyl 4-hydroxy-4-(2-methoxy-2-oxo-ethyl)piperidine-1-carboxylate (4.0 g, 14.63 mmol) in 1,4-dioxane (10 mL) was added hydrogen chloride (4M in 1,4-dioxane, 2.67 g, 73.17 mmol, 3.33 mL) at 0° C. and allowed to stir at room temperature for 4 hours. After completion, solvent was removed under reduced pressure and the obtained product was triturated with diethyl ether (3×30 mL) to afford methyl 2-(4-hydroxy-4-piperidyl)acetate (3.0 g, 14.25 mmol, 97.38% yield). LCMS (ESI+): 174.1 $[M+H]^+$ Step 3: To the solution of methyl 2-(4-hydroxy-4-piperidyl)acetate (2.45 g, 14.14 mmol) and 2-chloro-1-fluoro-4-nitro-benzene (2.73 g, 15.56 mmol) in DMSO was added N,N-diisopropylethylamine (9.14 g, 70.72 mmol, 12.32 mL) and stirred at 110° C. for 16 h. After completion, the reaction mixture was diluted with water (50 mL) and extracted with Ethyl acetate (3×60 mL). The combined organic phase was washed with brine solution (30 mL), dried over anhydrous sodium sulphate, filtered and concentrated under reduced pressure to get the crude residue, which was purified by flash silica-gel (230-400 mesh) column with 4:6 Ethyl acetate/petroleum ether to afford methyl 2-[1-(2-chloro-4-nitro-phenyl)-4-hydroxy-4-piperidyl]acetate (3.2 g, 9.67 mmol, 68.33% yield) as yellow solid. LCMS (ESI+): 329.0 $[M+H]^+$.

Step 4: To a stirred solution of methyl 2-[1-(2-chloro-4-nitro-phenyl)-4-hydroxy-4-piperidyl]acetate (2.8 g, 8.52 mmol) in ethanol (20 mL) and water (8 mL) was added Iron powder (2.38 g, 42.59 mmol) and ammonium chloride (2.28 g, 42.59 mmol) and heated at 70-80° C. for 6 hours. After completion, reaction mixture was filtered through a pad of celite, washing with ethyl acetate (100 mL). Combined organic layer was concentrated under reduced pressure. The crude product was diluted with Ethyl acetate (100 mL), washed with water (50 mL), followed by brine. The organic layer was dried over sodium sulphate, filtered and concentrated under reduced pressure. The crude product was purified by silica-gel chromatography (60-120 mesh) by eluting at 50% ethyl acetate/petroleum ether to afford methyl 2[1-(4-amino-2-chloro-phenyl)-4-hydroxy-4-piperidyl]acetate (1.7 g, 5.54 mmol, 65.07% yield) as yellow semi solid. LCMS (ESI+): 298.9 $[M+H]^+$.

Step 5: To the solution of methyl 2-[1-(4-amino-2-chloro-phenyl)-4-hydroxy-4-piperidyl]acetate (1.7 g, 5.69 mmol) and 3-bromopiperidine-2,6-dione (1.64 g, 8.54 mmol) in N,N-Dimethylformamide (20 mL) was added sodium bicarbonate (1.20 g, 14.23 mmol) and heated at 70° C. for 16 hours. After completion. excess solvent was distilled out. Crude product was purified by 120 g C-18 reverse phase column using 0.1% formic acid in water and acetonitrile to afford methyl 2-[1-[2-chloro-4-[(2,6-dioxo-3-piperidyl)amino]phenyl]-4-hydroxy-4-piperidyl]acetate (2.1 g, 3.45 mmol, 60.72% yield) as dark purple solid. LCMS (ESI+): 410 $[M+H]^+$.

Step 6: To the solution of methyl 2-[1-[2-chloro-4-[(2,6-dioxo-3-piperidyl)amino]phenyl]-4-hydroxy-4-piperidyl] acetate (2.1 g, 5.12 mmol) in THF (10 mL) was added aqueous HCl (6N, 219.41 mmol, 10 mL) slowly and stirred at room temperature for 48 hours. After completion, excess solvent was distilled out and obtained crude was co-distilled with toluene (2×50 mL). The semisolid obtain was triturated with diethyl ether and dried under vacuum to afford crude 2-[1-[2-chloro-4-[(2,6-dioxo-3-piperidyl)amino]phenyl]-4-hydroxy-4-piperidyl]acetic acid (1.1 g, 1.53 mmol, 29.80% yield) as light brown solid. LCMS (ESI+): 396.0 $[M+H]^+$.

Synthesis of 2-[1-[4-[(2,6-dioxo-3-piperidyl)amino]-2-fluoro-phenyl]-3-hydroxy-pyrrolidin-3-yl]acetic acid

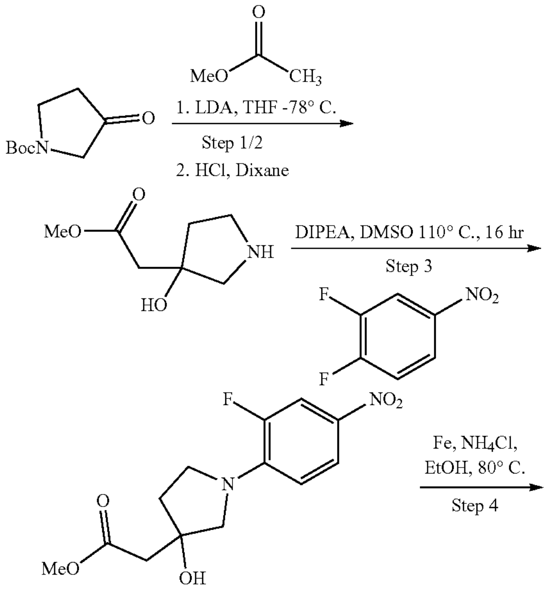

-continued

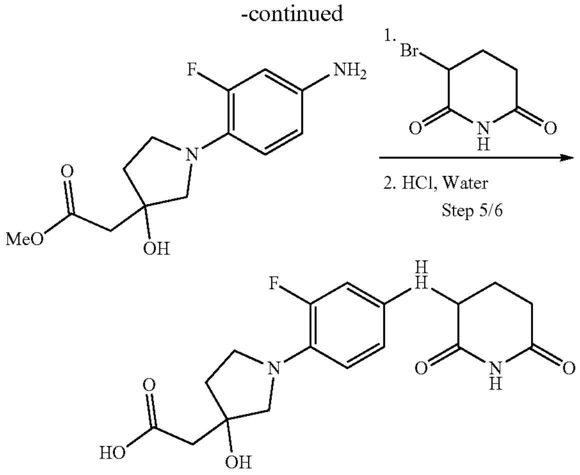

Step 1: To a stirred solution of methyl acetate (4.80 g, 64.79 mmol, 5.14 mL) in THF (100 mL) was added lithium diisopropylamide solution 2.0 M in THF (8.68 g, 80.98 mmol, 50 mL) at −78° C. under nitrogen. The reaction mixture was stirred at same temperature for 1 h and added solution of tert-butyl 3-oxopyrrolidine-1-carboxylate (10 g, 53.99 mmol) in THF (100 mL) at −78° C. The reaction mixture was stirred at same temperature for 2 h. After completion, the reaction mixture was quenched with saturated ammonium chloride solution (250 mL) and extracted with ethyl acetate (2×200 mL). The combined organic layers were dried over sodium sulphate, filtered and concentrated under reduced pressure. The crude compound was purified by silica gel column chromatography with 30-35% ethyl acetate in petroleum ether as a eluent to afford tert-butyl 3-hydroxy-3-(2-methoxy-2-oxo-ethyl)pyrrolidine-1-carboxylate (10.20 g, 36.19 mmol, 67.03% yield) as a pale yellow oil. LCMS (ESI+): 160.1 $[M-100+H]^+$ Step 2: To a stirred solution of tert-butyl 3-hydroxy-3-(2-methoxy-2-oxo-ethyl)pyrrolidine-1-carboxylate (10.20 g, 39.34 mmol) in DCM (50 mL) was added hydrogen chloride solution 4.0M in 1,4-dioxane (16.00 g, 438.83 mmol, 20.0 mL) at 0-5° C. under nitrogen. The reaction mixture was stirred at room temperature for 6 h. After completion, the reaction mixture was concentrated under reduced pressure and washed with diethyl ether (2×100 mL) to afford methyl 2-(3-hydroxypyrrolidin-3-yl)acetate (7.1 g, 35.93 mmol, 91.33% yield) as a light brownish gummy liquid, which was carried forward without further purification. LCMS (ESI+): 160.1 $[M+H]^+$.

Step 3: A solution of methyl 2-(3-hydroxypyrrolidin-3-yl)acetate (7.10 g, 36.29 mmol, HCl salt) in DMF (70 mL) was taken in a sealed tube and added N,N-Diisopropylethylamine (23.74 g, 183.72 mmol, 32.0 mL) and 1,2-difluoro-4-nitro-benzene (3, 6.50 g, 40.86 mmol, 4.51 mL) at room temperature. The reaction mixture was heated to 110° C. for 12 h. After completion, water (100 mL) was added to the reaction mixture and extracted with ethyl acetate (2×200 mL). The combined organic layers were dried over sodium sulphate, filtered and concentrated under reduced pressure to afford methyl 2-[1-(2-fluoro-4-nitro-phenyl)-3-hydroxy-pyrrolidin-3-yl]acetate (11.0 g, 19.18 mmol, 52.84% yield) as a light brownish gummy liquid, which was carried forward without further purification. LCMS (ESI+): 299.1 $[M+H]^+$.

Step 4: To a stirred solution of methyl 2-[1-(2-fluoro-4-nitro-phenyl)-3-hydroxy-pyrrolidin-3-yl]acetate (11 g, 36.88 mmol) in Ethanol (80 mL) and Water (30 mL) mixture was added Iron powder (11 g, 196.97 mmol, 1.40 mL), Ammonium Chloride (4.0 g, 74.78 mmol) at room temperature. The reaction mixture was heated to 85° C. for 3 h. After completion, the reaction mixture was filtered through celite and filtrate was extracted with ethyl acetate (2×300 mL). The combined organic layers were dried over sodium sulphate, filtered and concentrated under reduced pressure to afford methyl 2-[1-(4-amino-2-fluoro-phenyl)-3-hydroxy-pyrrolidin-3-yl]acetate (8 g, 24.45 mmol, 66.30% yield) as a brownish gummy liquid, which was carried forward without further purification. LCMS (ESI+): 269.0 $[M+H]^+$.

Step 5: A solution of methyl 2-[1-(4-amino-2-fluoro-phenyl)-3-hydroxy-pyrrolidin-3-yl]acetate (4 g, 14.91 mmol) in DMF (50 mL) was taken in a sealed tube and added Sodium bicarbonate (3.80 g, 45.23 mmol, 1.76 mL) and 3-bromopiperidine-2,6-dione (7.20 g, 37.50 mmol) at room temperature. The reaction mixture was heated to 70° C. for 12 h. After completion, water (100 mL) was added to the reaction mixture and extracted with ethyl acetate (2×200 mL). The combined organic layers were dried over sodium sulphate, filtered and concentrated under reduced pressure. The crude compound was purified by silica gel column chromatography with 90% ethyl acetate in petroleum ether as a eluent to afford methyl 2-[1-[4-[(2,6-dioxo-3-piperidyl)amino]-2-fluoro-phenyl]-3-hydroxy-pyrrolidin-3-yl]acetate (3.0 g, 7.43 mmol, 49.85% yield) as a light green solid. LCMS (ESI+): 380.0 $[M+H]^+$.

Step 6: To a stirred solution of methyl 2-[1-[4-[(2,6-dioxo-3-piperidyl)amino]-2-fluoro-phenyl]-3-hydroxy-pyrrolidin-3-yl]acetate (2.0 g, 5.27 mmol) in THF (10 mL) was added Hydrogen chloride solution 6.0 M in Water (5.27 mmol, 20 mL) at 0-5° C. The reaction mixture was stirred at room temperature for 12 h. After completion, the reaction mixture was concentrated under reduced pressure and washed with diethyl ether (2×50 mL) to afford 2-[1-[4-[(2,6-dioxo-3-piperidyl)amino]-2-fluoro-phenyl]-3-hydroxy-pyrrolidin-3-yl]acetic acid (2.1 g, 3.76 mmol, 71.38% yield) as a dark grey colour solid, which was carried forward without further purification. LCMS (ESI+): 365.9 $[M+H]^+$.

Synthesis of 2-[4-[4-(2,6-dioxo-3-piperidyl)-3-oxo-piperazin-1-yl]-1-piperidyl]acetic acid

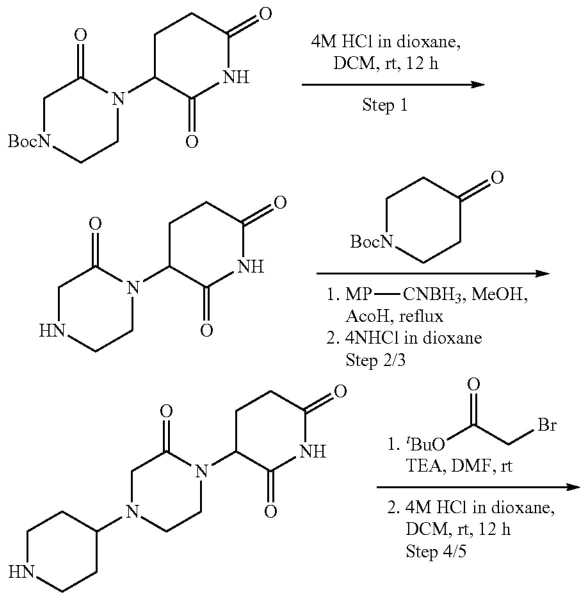

-continued

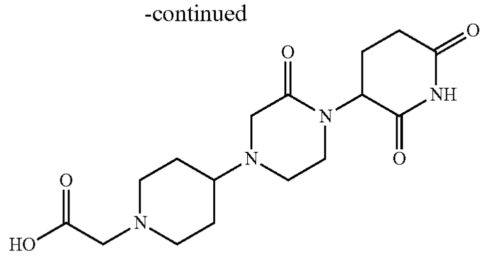

Step 1: To a stirred solution of tert-butyl 4-(2,6-dioxo-3-piperidyl)-3-oxo-piperazine-1-carboxylate (500 mg, 1.61 mmol) in Dichloromethane (10 mL) was added Hydrogen chloride (4M in 1,4-dioxane, 2.00 g, 54.85 mmol, 2.5 mL) at 0-5° C. under nitrogen. The reaction mixture was stirred at room temperature for 3 h. After completion, the reaction mixture was concentrated under reduced pressure to afford 3-(2-oxopiperazin-1-yl)piperidine-2,6-dione (395 mg, 1.59 mmol, 99.01% yield) as a grey solid, which was carried forward without further purification. LCMS (ESI+): 212.1 $[M+H]^+$.

Step 2: To a stirred solution of 3-(2-oxopiperazin-1-yl) piperidine-2,6-dione (280 mg, 1.33 mmol) in Methanol (5 mL) was added tert-butyl 4-oxopiperidine-1-carboxylate (374.96 mg, 1.59 mmol) at room temperature, followed by the addition of Acetic acid (79.61 mg, 1.33 mmol, 75.82 μL) and MP-Cyanoborohydride (280 mg, 1.33 mmol) at same temperature. The reaction mixture was heated to 70° C. for 5 h. After completion, the reaction mixture was filtered, and concentrated under reduced pressure. The crude compound was washed with diethyl ether to afford a tert-butyl 4-[4-(2,6-dioxo-3-piperidyl)-3-oxo-piperazin-1-yl]piperidine-1-carboxylate (200 mg, 448.20 μmol, 33.81% yield) as off-white solid. LCMS (ESI+): 339.3 $[M-56+H]^+$.

Step 3: To a stirred solution of tert-butyl 4-[4-(2,6-dioxo-3-piperidyl)-3-oxo-piperazin-1-yl]piperidine-1-carboxylate (200 mg, 507.02 μmol) in Dichloromethane (5 mL) was added Hydrogen chloride (4M in 1,4-dioxane, 1.60 g, 43.88 mmol, 2 mL) at 0-5° C. under nitrogen. The reaction mixture was stirred at room temperature for 1 h. After completion, the reaction mixture was concentrated under reduced pressure to afford 3-[2-oxo-4-(4-piperidyl)piperazin-1-yl]piperidine-2,6-dione (175 mg, 506.26 μmol, 99.85% yield) as a pale yellow solid, which was carried forward without further purification. LCMS (ESI+): 295.2 $[M+H]^+$.

Step 4: A solution of 3-[2-oxo-4-(4-piperidyl)piperazin-1-yl]piperidine-2,6-dione (180 mg, 544.12 μmol) in N,N-Dimethylformamide (5 mL) was taken in a multi neck round bottom flask and added Triethylamine (275.30 mg, 2.72 mmol, 379.20 μL) at room temperature under nitrogen, followed by the addition of tert-butyl 2-bromoacetate (116.75 mg, 598.53 μmol, 87.78 μL) at same temperature. The reaction mixture was stirred at room temperature for 16 h. After completion, the reaction mixture was concentrated under reduced pressure. The crude compound was washed with diethyl ether to afford a tert-butyl 2-[4-[4-(2,6-dioxo-3-piperidyl)-3-oxo-piperazin-1-yl]-1-piperidyl]acetate (250 mg, 502.46 μmol, 92.34% yield) as off-white solid. LCMS (ESI+): 353.3 $[M-56+H]^+$.

Step 5: To a stirred solution of tert-butyl 2-[4-[4-(2,6-dioxo-3-piperidyl)-3-oxo-piperazin-1-yl]-1-piperidyl]acetate (250 mg, 612.01 mol) in dichloromethane (10 mL) was added hydrogen chloride solution (4M in 1,4-dioxane, 223.14 mg, 6.12 mmol, 278.93 μL) at 0-5° C. under nitrogen. The reaction mixture was stirred at room temperature for 16 h. After completion, the reaction mixture was concentrated under reduced pressure and washed with diethyl ether to afford 2-[4-[4-(2,6-dioxo-3-piperidyl)-3-oxo-piperazin-1-yl]-1-piperidyl]acetic acid (200 mg, 354.90 mol, 57.99% yield) as a pale grey solid. LCMS (ESI+): 353.1 $[M+H]^{30}$.

Synthesis of 2-(4-(4-(2,6-dioxopiperidin-3-yl)-3-oxopiperazin-1-yl)-3,3-difluoropiperidin-1-yl)acetic acid

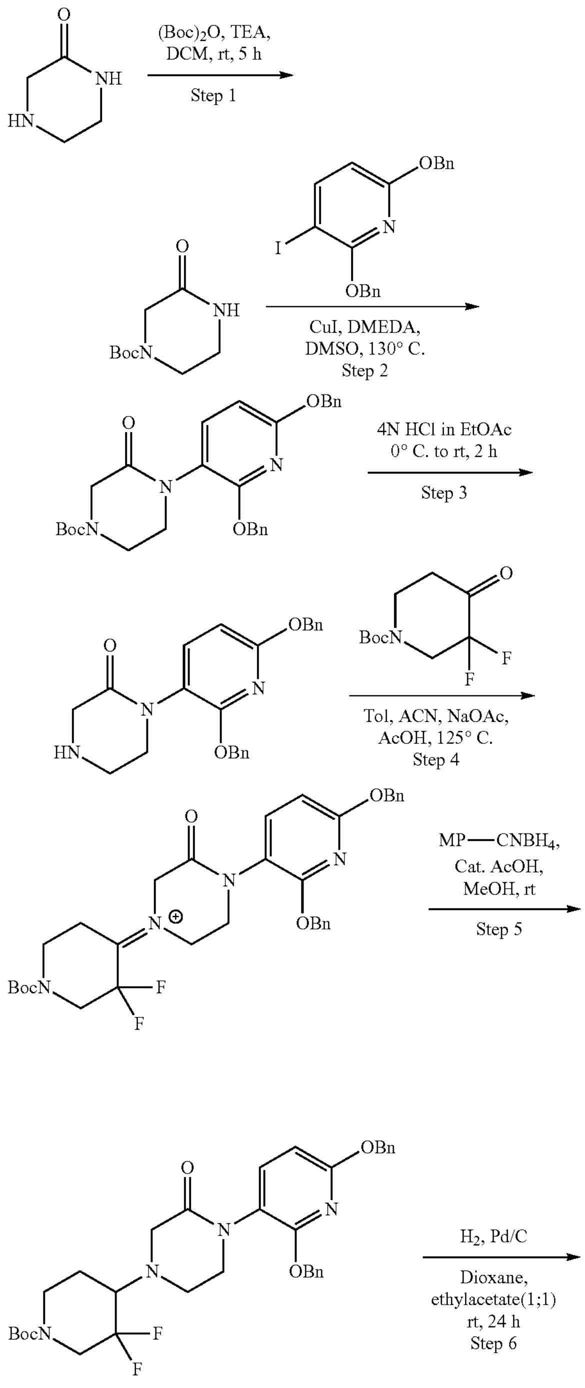

-continued

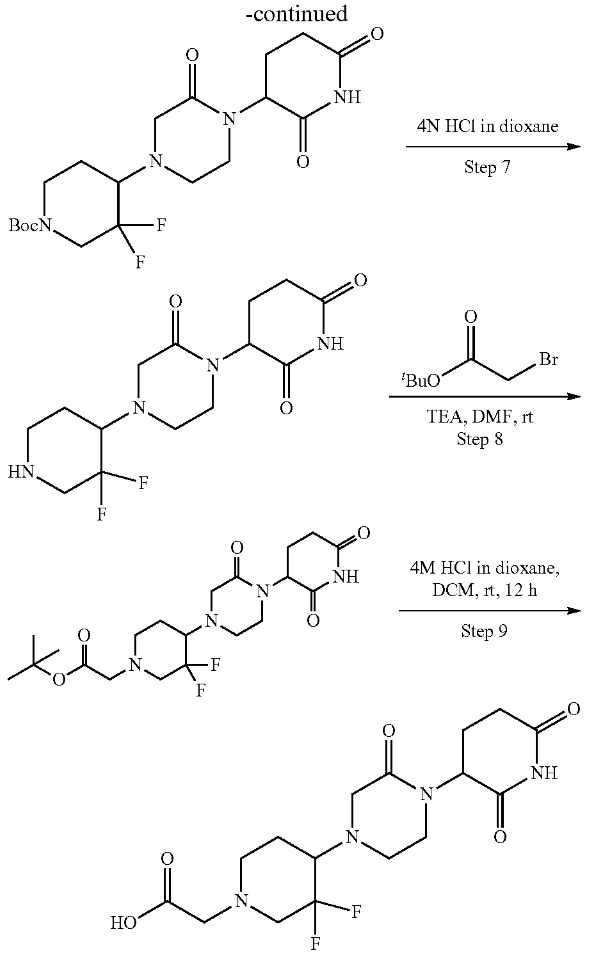

Step 1: To a stirred solution of piperazin-2-one (3 g, 29.96 mmol) in Dichloromethane (30 mL) were added Triethylamine (9.10 g, 89.89 mmol, 12.53 mL), di-tert-butyl dicarbonate (44.95 mmol) at 0° C. The reaction mixture was stirred at room temperature for 12 h. After completion, The reaction mixture was diluted with water (30 mL) and extracted with ethyl acetate (2×100 mL). The combined organic layers were dried over sodium sulphate, filtered and concentrated under vacuum to get crude tert-butyl 3-oxopiperazine-1-carboxylate (5 g, 24.97 mmol, 83.33% yield) as an off white solid. LCMS (ESI+): 145.1 $[M+H-56]^+$.

Step 2: A solution of tert-butyl 3-oxopiperazine-1-carboxylate (2.5 g, 12.49 mmol), 2,6-dibenzyloxy-3-iodo-pyridine (5.21 g, 12.49 mmol) in 1,4-dioxane (100 mL) was taken in a sealed tube and added Cesium carbonate (12.20 g, 37.46 mmol) at room temperature. The reaction mixture was degassed for 20 minutes, and L-Proline (718.72 mg, 6.24 mmol, 528.47 μL) and Copper (I) iodide (1.19 g, 6.24 mmol, 211.55 μL) were added. The reaction mixture was heated to 120° C. for 16 h. After completion, the reaction mixture was diluted with water (50 mL) and extracted with ethyl acetate (2×100 mL). The combined organic layers were dried over sodium sulphate, filtered and concentrated under vacuum. The crude compound was purified by silica gel column chromatography eluted with 40-50% ethylacetate in pet-ether to get tert-butyl 4-(2,6-dibenzyloxy-3-pyridyl)-3-oxo-piperazine-1-carboxylate (2.5 g, 5.06 mmol, 40.49% yield) as a brown solid. LCMS (ESI−): 488.2 $[M-H]^-$.

Step 3: To a stirred solution of tert-butyl 4-(2,6-dibenzyloxy-3-pyridyl)-3-oxo-piperazine-1-carboxylate (2.5 g, 5.11 mmol) in 1,4-Dioxane (20 mL) at 0° C. was added 1M Hydrogen chloride solution in ethyl acetate (232.74 μL, 5.11 mmol). The reaction mixture was stirred at room temperature for 2 h. The reaction mixture was concentrated under nitrogen atmosphere to get crude 1-(2,6-dibenzyloxy-3-pyridyl)piperazin-2-one (2.2 g, 4.96 mmol, 97.11% yield) as a brown solid. LCMS (ESI+): 390.1 $[M+H]^+$.

Step 4: To a stirred solution of 1-(2,6-dibenzyloxy-3-pyridyl)piperazin-2-one (2.5 g, 6.42 mmol), tert-butyl 3,3-difluoro-4-oxo-piperidine-1-carboxylate (2.27 g, 9.63 mmol) in toluene (20 mL), Acetonitrile (2 mL) were added anhydrous sodium acetate, (526.61 mg, 6.42 mmol, 344.19 acetic acid (385.50 mg, 6.42 mmol, 367.14 The reaction mixture was heated to 125° C. for 2 h. After completion, the reaction mixture was diluted with water (20 mL) and extracted with ethyl acetate (2×50 mL). The combined organic layers were dried over sodium sulphate, filtered and concentrated under vacuum to get crude tert-butyl (4E)-4-[4-(2,6-dibenzyloxy-3-pyridyl)-3-oxo-piperazin-1-ium-1-ylidene]-3,3-difluoro-piperidine-1-carboxylate (4 g, 4.15 mmol, 64.60% yield) as a brown liquid. LCMS (ESI+): 608.3 $[M+H]^+$ Step 5: To a stirred solution of tert-butyl (4E)-4-[4-(2,6-dibenzyloxy-3-pyridyl)-3-oxo-piperazin-1-ium-1-ylidene]-3,3-difluoro-piperidine-1-carboxylate (1.6 g, 2.63 mmol) in methanol (20 mL) at 0° C. were added MP-Cyanoborohydride (3 g, 2.63 mmol), acetic acid (158.12 mg, 2.63 mmol, 150.59 The reaction mixture was stirred at room temperature for 48 h. After completion, the reaction mixture was diluted with water (30 mL) and extracted with ethyl acetate (2×50 mL). The combined organic layers were dried over sodium sulphate, filtered and concentrated under vacuum to get crude. The crude compound was purified by silica gel column chromatography eluted with 40-50% ethyl acetate in pet-ether to get tert-butyl 4-[4-(2,6-dibenzyloxy-3-pyridyl)-3-oxo-piperazin-1-yl]-3,3-difluoro-piperidine-1-carboxylate (1.6 g, 2.37 mmol, 89.85% yield) as brown liquid. LCMS (ESI−): 607.3 $[M-H]^-$ Step 6: To a stirred solution of tert-butyl 4-[4-(2,6-dibenzyloxy-3-pyridyl)-3-oxo-piperazin-1-yl]-3,3-difluoro-piperidine-1-carboxylate (1.6 g, 2.63 mmol) in ethyl acetate (10 mL), 1,4-dioxane (10 mL) was added 10% Palladium on carbon (279.74 mg, 2.63 mmol). The reaction mixture was subjected to hydrogenation under 1 atm pressure and stirred at room temperature for 48 h. After completion, the reaction mixture was filtered through celite, filtrate was concentrated under vacuum to get crude 3-[4-(3,3-difluoro-4-piperidyl)-2-oxo-piperazin-1-yl]piperidine-2,6-dione (700 mg, 2.12 mmol, 80.61% yield) as colorless solid. LCMS (ESI+): 374.8 $[M+H-56]^+$.

Step 7: To a stirred solution of tert-butyl 4-[4-(2,6-dioxo-3-piperidyl)-3-oxo-piperazin-1-yl]-3,3-difluoro-piperidine-1-carboxylate (700 mg, 1.63 mmol) in 1,4-dioxane (7 mL) was added 4.0 M hydrogen chloride solution in 1,4-dioxane (74.12 μL, 1.63 mmol) at 0° C. The reaction mixture was stirred at room temperature for 2 h. After completion, the reaction mixture was concentrated under vacuum to get crude 3-[4-(3,3-difluoro-4-piperidyl)-2-oxo-piperazin-1-yl]piperidine-2,6-dione (600 mg, 1.55 mmol, 95.56% yield) as colorless solid. LCMS (ESI+): 331.1 $[M+H]^+$ Step 8: To a stirred solution of 3-[4-(3,3-difluoro-4-piperidyl)-2-oxo-piperazin-1-yl]piperidine-2,6-dione (700 mg, 2.12 mmol) in N,N-dimethylformamide (7 mL) were added triethylamine (643.29 mg, 6.36 mmol, 886.08 μL), tert-butyl bromoacetate (620.01 mg, 3.18 mmol, 466.17 μL) at 0° C. The reaction mixture stirred at room temperature for 12 h. After completion, the reaction mixture was diluted with water (10 mL) and extracted with ethyl acetate (2×30 mL). The combined organic layers were dried over sodium sulphate, filtered and concentrated under vacuum to get crude tert-butyl 2-[4-[4-(2,6-dioxo-3-piperidyl)-3-oxo-piperazin-1-yl]-3,3-difluoro-1-piperidyl]acetate (500 mg, 978.69 μmol, 46.18% yield) as brown solid. LCMS (ESI+): 445.2 $[M+H]^+$.

Step 9: To a stirred solution of tert-butyl 2-[4-[4-(2,6-dioxo-3-piperidyl)-3-oxo-piperazin-1-yl]-3,3-difluoro-1-piperidyl]acetate (500 mg, 1.12 mmol) in Dichloromethane (5 mL) at 0° C. was added hydrogen chloride solution in 1,4-dioxane (4 M, 2.81 mL, 11.24 mmol). The reaction mixture was stirred at room temperature for 12 h. The reaction mixture was concentrated under vacuum to get crude 2-[4-[4-(2,6-dioxo-3-piperidyl)-3-oxo-piperazin-1-yl]-3,3-difluoro-1-piperidyl]acetic acid (400 mg, 837.99 μmol, 74.49% yield) as brown solid. LCMS (ESI+): 389.2 $[M+H]^+$ Synthesis of 2-[4-[4-(2,6-dioxo-3-piperidyl)phenyl]-1-piperidyl]acetic acid

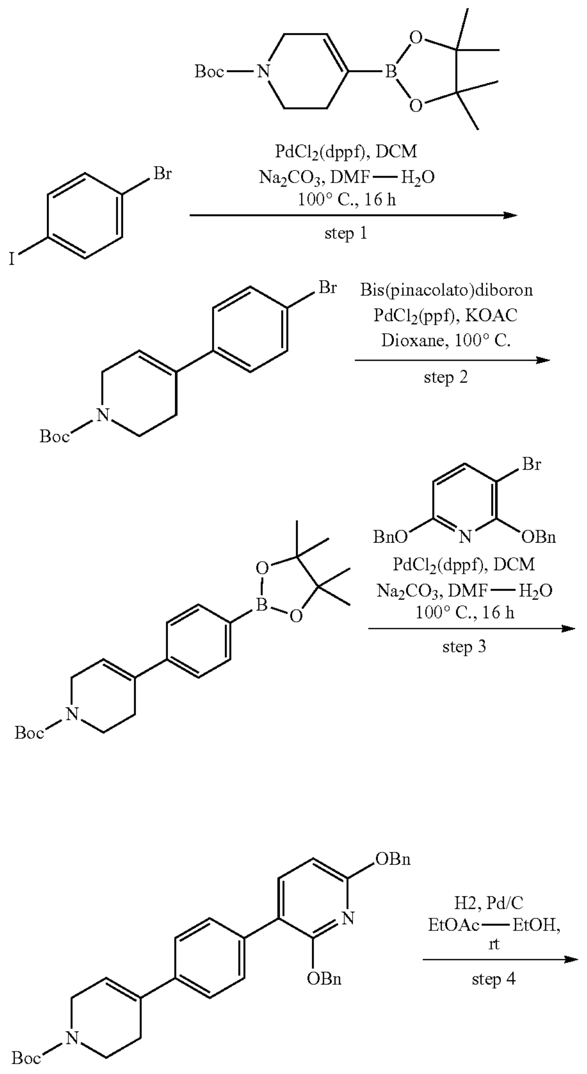

-continued

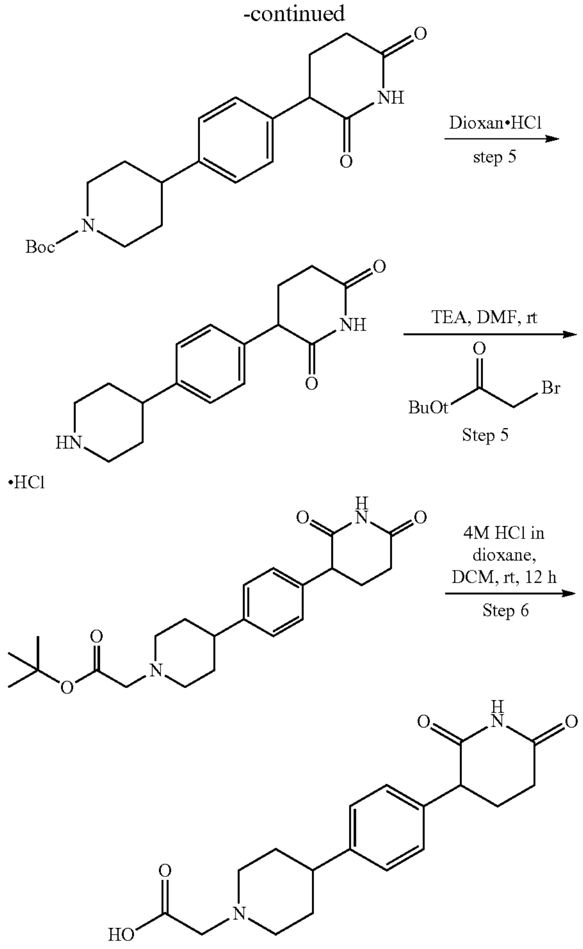

Step 1: Preparation of 4-(4-Bromo-phenyl)-3,6-dihydro-2H-pyridine-1-carboxylic acid tert-butyl ester To the stirred solution of 1-bromo-4-iodo-benzene (30 g, 106.04 mmol), Sodium carbonate (28.10 g, 265.11 mmol, 11.11 mL) and tert-butyl 4-(4,4,5,5-tetramethyl-1,3,2-dioxaborolan-2-yl)-3,6-dihydro-2H-pyridine-1-carboxylate (32.79 g, 106.04 mmol) in water (50 mL) and DMF (300 mL) was purged with argon for 20 minutes followed by the addition of [1, F-Bis(diphenylphosphino)ferrocene]dichloropalladium(II), complex with dichloromethane (8.66 g, 10.60 mmol) and the reaction mixture was allowed to stir for 14 hours at 90° C. Reaction mixture was cooled, concentrated under reduced pressure to afford the crude product. Crude product thus obtained was purified by flash chromatography using 0%-10% ethyl acetate-hexane to afford tert-butyl 4-(4-bromophenyl)-3,6-dihydro-2H-pyridine-1-carboxylate (31 g, 91.65 mmol, 86.43% yield) as a colorless liquid. $^1H$ NMR (400 MHz, DMSO-d6) δ 7.52 (d, J=8.32 Hz, 2H), 7.38 (d, J=8.32 Hz, 2H), 6.19 (br s, 1H), 3.98 (br s, 2H), 3.52 (t, J=5.24 Hz, 2H), 2.43 (br s, 2H), 1.42 (s, 9H).

Step 2: Preparation of 4-[4-(4,4,5,5-Tetramethyl-[1,3,2]dioxaborolan-2-yl)-phenyl]-3,6-dihydro-2H-pyridine-1-carboxylic acid tert-butyl ester To the stirred solution of tert-butyl 4-(4-bromophenyl)-3,6-dihydro-2H-pyridine-1-carboxylate (31 g, 91.65 mmol), Potassium acetate (22.49 g, 229.13 mmol, 14.32 mL) and bis(pinacolato)diboron (34.91 g, 137.48 mmol) in 1,4-dioxane (200 mL) was purged with argon for 20 minutes, followed by the addition of [1,1'-Bis(diphenylphosphino) ferrocene]dichloropalladium(II), complex with dichloromethane (7.48 g, 9.17 mmol) and the reaction mixture was allowed to stir for 14 hours at 90° C. Reaction mixture was cooled, filtered through celite bed concentrated under reduced pressure to afford the crude tert-butyl 4-[4-(4,4,5,5-tetramethyl-1,3,2-dioxaborolan-2-yl)phenyl]-3,6-dihydro-2H-pyridine-1-carboxylate (31 g, 80.46 mmol, 87.79% yield) as a light brown gum which was used in the next step without purification.

Step 3: Preparation of 4-[4-(2,6-Bis-benzyloxy-pyridin-3-yl)-phenyl]-3,6-dihydro-2H-pyridine-1-carboxylic acid tert-butyl ester A stirred solution of tert-butyl 4-[4-(4,4,5,5-tetramethyl-1,3,2-dioxaborolan-2-yl)phenyl]-3,6-dihydro-2H-pyridine-1-carboxylate (31 g, 80.46 mmol), sodium carbonate (21.32 g, 201.14 mmol, 8.43 mL) and 2,6-dibenzyloxy-3-bromo-pyridine (20.85 g, 56.32 mmol) in DMF (300 mL) and Water (50 mL) was purged with argon for 20 minutes followed by the addition of [1,1'-Bis(diphenylphosphino)ferrocene]dichloropalladium(II), complex with dichloromethane (6.57 g, 8.05 mmol) and the reaction mixture was allowed to stir for 14 hours at 90° C. Reaction mixture was cooled, concentrated under reduced pressure to afford the crude product. Crude product thus obtained was purified by flash chromatography using 0%-10% ethyl acetate-hexane to afford tert-butyl 4-[4-(2,6-dibenzyloxy-3-pyridyl)phenyl]-3,6-dihydro-2H-pyridine-1-carboxylate (23 g, 41.92 mmol, 52.10% yield) as a light yellow solid. $^{1}$H NMR (400 MHz, DMSO-d6) δ 7.75 (d, J=8.12 Hz, 1H), 7.56-7.53 (m, 2H), 7.48-7.27 (m, 12H), 6.55 (d, J=8.12 Hz, 1H), 6.19 (br s, 1H), 5.41-5.37 (m, 4H), 4.00 (s, 2H), 3.53 (m, 2H), 2.49 (m, 2H), 1.42 (s, 9H).

Step 4: Preparation of 4-[4-(2,6-Dioxo-piperidin-3-yl)-phenyl]-piperidine-1-carboxylic acid tert-butyl ester A stirred suspension of tert-butyl 4-[4-(2,6-dibenzyloxy-3-pyridyl)phenyl]-3,6-dihydro-2H-pyridine-1-carboxylate (23 g, 41.92 mmol) in Ethanol (80 mL) was degassed with nitrogen, Palladium, 10% on carbon, Type 487, dry (4.46 g, 4.19 mmol, 10% purity) and $PtO_2$ (475.95 mg, 2.10 mmol) as added and stirred reaction mixture at room temperature under Hydrogen balloon for 2 hours. Reaction mixture was filtered through celite bed, filtrate was concentrated to afford tert-butyl 4-[4-(2,6-dioxo-3 piperidyl)phenyl]piperidine-1-carboxylate (13 g, 34.90 mmol, 83.26% yield) as white solid. LCMS (ES+): 373.4 [M+H]$^{+}$.

Step 5: Preparation of 3-(4-Piperidin-4-yl-phenyl)-piperidine-2,6-dione hydrochloride To a stirred solution of tert-butyl 4-[4-(2,6-dioxo-3-piperidyl)phenyl]piperidine-1-carboxylate (12 g, 32.22 mmol) in 1,4-dioxane (100 mL) was added 4N Dioxane in HCl (15 mL). Reaction mixture was stirred at room temperature for 2 hours. Volatiles were removed under reduced pressure and residual solid was triturated with diethyl ether and dried under vacuum to afford 3-[4-(4-piperidyl)phenyl]piperidine-2,6-dione (10.80 g, 39.66 mmol, 123.08% yield) as an off-white solid. $^{1}$H NMR (400 MHz, DMSO-d6) δ 10.82 (s, 1H), 8.91 (br s, 1H), 8.78 (br s, 1H), 7.18 (s, 4H), 3.83 (dd, J=11.52, 4.96 Hz, 1H), 3.36-3.33 (m, 2H), 3.02-2.93 (m, 2H), 2.85-2.79 (m, 1H), 2.69-2.62 (m, 1H), 2.49-2.46 (m, 1H), 2.20-2.15 (m, 1H), 2.05-1.99 (m, 1H), 1.93-1.80 (m, 4H); LCMS (ES+): 273.15 [M+H]$^{+}$ Step 6: To a stirred solution of 3-[4-(4-piperidyl)phenyl] piperidine-2,6-dione (250 mg, 809.58 μmol) in N, N-Dimethylformamide (3.0 mL) was taken in a sealed tube and added triethylamine (435.60 mg, 4.30 mmol, 0.60 mL) at room temperature under nitrogen, followed by the addition of tert-butyl 2-bromoacetate (180 mg, 922.82 μmol, 135.34 μL) at same temperature. The reaction mixture was stirred at room temperature for 12 h. Water was added to the reaction mixture and extracted with ethyl acetate (2×50 mL). The combined organic layers were dried over sodium sulphate, filtered and concentrated under reduced pressure to afford tert-butyl 2-[4-[4-(2,6-dioxo-3-piperidyl)phenyl]-1-piperidyl]acetate (240 mg, 580.06 μmol, 71.65% yield) as off-white solid. LCMS (ESI+): 387.1 [M+H]$^{+}$.

Step 7: To a stirred solution of tert-butyl 2-[4-[4-(2,6-dioxo-3-piperidyl)phenyl]-1-piperidyl]acetate (240 mg, 620.98 μmol) in dichloromethane (3.0 mL) was added 4M hydrogen chloride in 1,4-dioxane (10.0 mL) at 0-5° C. under nitrogen. The reaction mixture was stirred at room temperature for 1 h. Reaction mixture was concentrated under reduced pressure to afford 2-[4-[4-(2,6-dioxo-3-piperidyl) phenyl]-1-piperidyl]acetic acid (205 mg, 542.06 μmol, 87.29% yield) as an off-white solid. LCMS (ESI+): 331.1 [M+H]$^{+}$.

Synthesis of 2-[4-[4-(2,6-dioxo-3-piperidyl)-2-fluoro-phenyl]-1-piperidyl]acetic acid

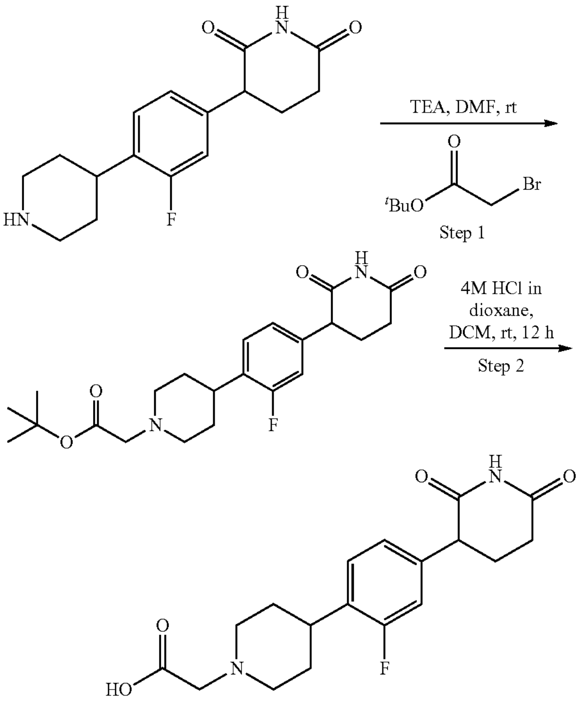

Step 1: To a stirred solution of 3-[3-fluoro-4-(4-piperidyl) phenyl]piperidine-2,6-dione (200 mg, 688.87 μmol) in N,N-Dimethylformamide (4 mL) were added triethylamine (69.71 mg, 688.87 μmol, 96.01 μL) and tert-butyl 2-bromoacetate (134.37 mg, 688.87 μmol, 101.03 μL), and stirred at room temperature for 14 h. The reaction mixture was diluted with ethyl acetate (60 mL), washed with water (20 mL) and brine (20 mL). The organic layer was dried over sodium sulphate and concentrated under reduced pressure to afford tert-butyl 2-[4-[4-(2,6-dioxo-3-piperidyl)-2-fluoro-phenyl]-1-piperidyl]acetate (230 mg, 437.85 μmol, 63.56% yield) as light brown solid. LCMS (ESI+): 405.2 $[M+H]^+$.

Step 2: To a stirred solution of tert-butyl 2-[4-[4-(2,6-dioxo-3-piperidyl)-2-fluoro-phenyl]-1-piperidyl]acetate (230 mg, 568.64 μmol) in Dichloromethane (2 mL) was added 4M HCl in 1,4 Dioxane (1.0 mL) and stirred at room temperature for 4 h. The reaction mixture was concentrated under reduced pressure to get 2-[4-[4-(2,6-dioxo-3-piperidyl)-2-fluoro-phenyl]-1-piperidyl]acetic acid (210 mg, 534.78 μmol, 94.05% yield) as light brown solid. LCMS (ESI+): 349.2 $[M+H]^+$.

Synthesis of 2-[1-[4-(2,6-dioxo-3-piperidyl)-2-fluoro-phenyl]-4-hydroxy-4-piperidyl]acetic acid

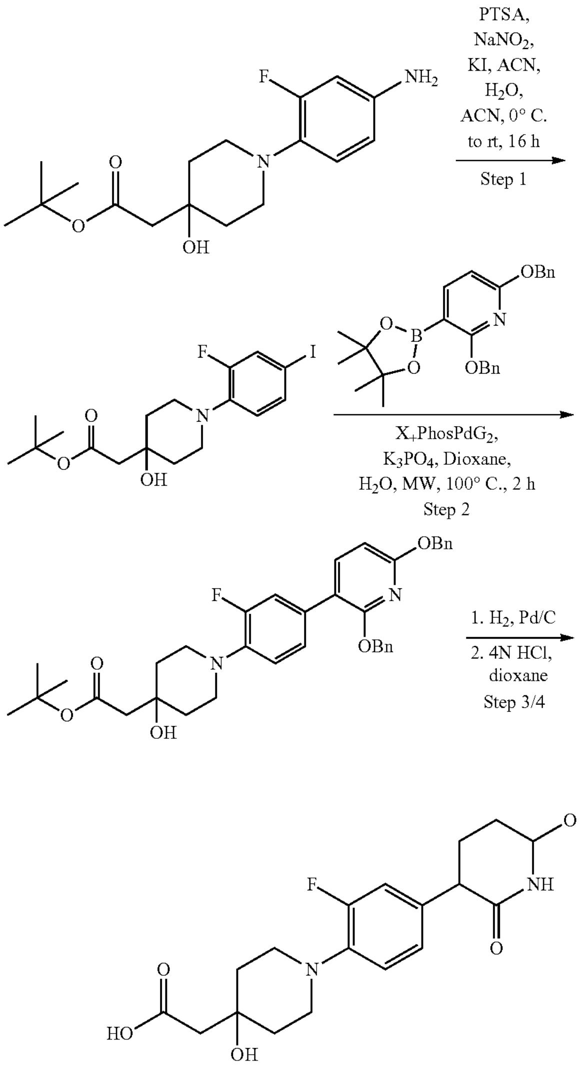

-continued

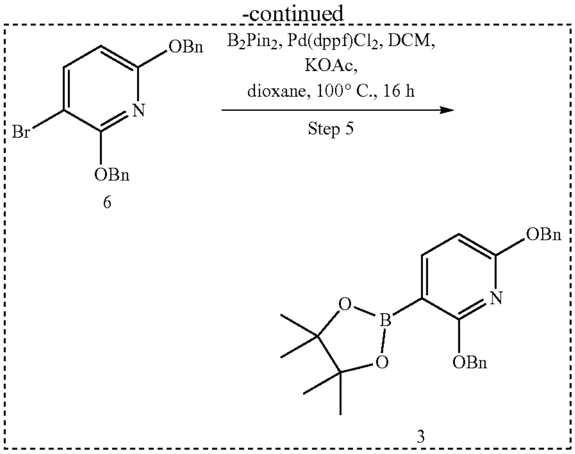

6
3

Step 1: To a stirred solution of tert-butyl 2-[1-(4-amino-2-fluoro-phenyl)-4-hydroxy-4-piperidyl]acetate (3.0 g, 9.25 mmol) in Acetonitrile (30 mL) and Water (10 mL) mixture was added p-Toluene sulfonic acid monohydrate (5.50 g, 28.91 mmol, 4.44 mL) at 0-5° C., followed by the addition of Sodium Nitrite (1.30 g, 18.84 mmol, 599.08 μL) in water (10 mL) at same temperature. The reaction mixture was stirred at 0-5° C. for 1 h, then added Potassium iodide (3.50 g, 21.08 mmol, 1.12 mL) in water (10 mL) at same temperature. The reaction mixture was stirred at room temperature for 16 h. After completion, water (100 mL) was added to the reaction mixture and extracted with ethyl acetate (2×200 mL). The combined organic layers were washed with 10% sodium bisulfite solution (3×100 mL), dried over sodium sulphate, filtered and concentrated under reduced pressure. The crude compound was purified by silica gel column chromatography with 20% ethyl acetate in petroleum ether as a eluent to afford tert-butyl 2-[1-(2-fluoro-4-iodo-phenyl)-4-hydroxy-4-piperidyl]acetate (2.40 g, 4.91 mmol, 53.06% yield) as a yellow solid. LCMS (ESI+): 436.0 $[M+H]^+$.

Step 2: A solution of tert-butyl 2-[1-(2-fluoro-4-iodo-phenyl)-4-hydroxy-4-piperidyl]acetate (1.0 g, 2.30 mmol) in 1,4-dioxane (12 mL) and water (3 mL) mixture was taken in a microwave vial and added 2,6-dibenzyloxy-3-(4,4,5,5-tetramethyl-1,3,2-dioxaborolan-2-yl)pyridine (2.20 g, 5.27 mmol), Potassium phosphate tribasic anhydrous (1.50 g, 7.07 mmol) at room temperature under nitrogen atmosphere. The reaction mixture was degassed with nitrogen for 10 minutes, then added XPhosPdG2 (190 mg, 241.48 μmol) at same temperature. The reaction mixture was irradiated under microwave at 100° C. for 2 h. After completion, the reaction mixture was filtered through celite. Water (50 mL) was added to the filtrate and extracted with ethyl acetate (2×100 mL). The combined organic layers were dried over sodium sulphate, filtered and concentrated under reduced pressure. The crude compound was purified by silica gel column chromatography with 40% ethyl acetate in petroleum ether as a eluent to afford tert-butyl 2-[1-[4-(2,6-dibenzyloxy-3-pyridyl)-2-fluoro-phenyl]-4-hydroxy-4-piperidyl]acetate (1.30 g, 1.63 mmol, 70.88% yield) as a pale yellowish gummy liquid. LCMS (ESI+): 599.3 $[M+H]^+$.

Step 3: To a stirred solution of tert-butyl 2-[1-[4-(2,6-dibenzyloxy-3-pyridyl)-2-fluoro-phenyl]-4-hydroxy-4-piperidyl]acetate (1.3 g, 2.17 mmol) in Ethanol (20 mL) was charged 10% Palladium on carbon (700 mg, 6.58 mmol) saturated with hydrogen by bubbling hydrogen gas through for 10 minutes and then subjected to hydrogenation (1 atm)

at room temperature for 16 h. After completion, the reaction mixture was purged with nitrogen, catalyst was removed by filtration through a celite pad. The filtrate was concentrated under reduced pressure. The crude compound was purified by silica gel column chromatography with 80-90% ethyl acetate in petroleum ether as a eluent to afford tert-butyl 2-[1-[4-(2,6-dioxo-3-piperidyl)-2-fluoro-phenyl]-4-hydroxy-4-piperidyl]acetate (500 mg, 1.15 mmol, 53.06% yield) as an off-white solid. LCMS (ESI+): 421.1 $[M+H]^+$.

Step 4: To a stirred solution of tert-butyl 2-[1-[4-(2,6-dioxo-3-piperidyl)-2-fluoro-phenyl]-4-hydroxy-4-piperidyl] acetate (500 mg, 1.19 mmol) in 1,4-Dioxane (2.0 mL) was added 4M Hydrogen chloride solution in 1,4-dioxane (6.0 mL) at 0-5° C. under nitrogen. The reaction mixture was stirred at room temperature for 16 h. After completion, the reaction mixture was concentrated under reduced pressure and washed with diethyl ether (2×30 mL) to afford 2-[1-[4-(2,6-dioxo-3-piperidyl)-2-fluoro-phenyl]-4-hydroxy-4-piperidyl]acetic acid (495 mg, 1.19 mmol, 99.70% yield) as an off-white solid. LCMS (ESI+): 365.0 $[M+H]^+$. $^1$HNMR (400 MHz, DMSO-$d_6$): δ 10.86 (s, 1H), 7.28 (s, 1H), 7.14 (d, J=13.60 Hz, 1H), 7.04 (d, J=8.00 Hz, 1H), 4.80 (bs, 1H), 3.86 (dd, J=4.80, 11.80 Hz, 1H), 3.3-3.1 (m, 2H), 2.62-2.69 (m, 1H), 2.49 (s, 2H), 2.20-2.26 (m, 1H), 1.95-2.03 (m, 3H), 1.72-1.82 (m, 2H).

Step 5: A solution of 2,6-dibenzyloxy-3-bromo-pyridine (2.0 g, 5.40 mmol) in 1,4-Dioxane (20 mL) was taken in a sealed tube and added 4,4,5,5-tetramethyl-2-(4,4,5,5-tetramethyl-1,3,2-dioxaborolan-2-yl)-1,3,2-dioxaborolane (1.80 g, 7.09 mmol), Potassium Acetate (1.60 g, 16.30 mmol, 1.02 mL) at room temperature under nitrogen atmosphere. The reaction mixture was degassed with nitrogen for 15 minutes, then added $Pd(dppf)Cl_2 \cdot CH_2Cl_2$ (450 mg, 551.04 μmol) at same temperature. The reaction mixture was heated to 100° C. for 16 h. After completion, the reaction mixture was filtered through Celite and filtrate was extracted with ethyl acetate (2×100 mL). The combined organic layers were dried over sodium sulphate, filtered and concentrated under reduced pressure. The crude compound was purified by silica gel column chromatography with 80% ethyl acetate in petroleum ether as a eluent to afford 2,6-dibenzyloxy-3-(4,4,5,5-tetramethyl-1,3,2-dioxaborolan-2-yl)pyridine (2.20 g, 2.32 mmol, 42.94% yield) as a yellowish gummy liquid. LCMS (ESI+): 418.1 $[M+H]^+$.

Synthesis of 1-[4-(4-piperidyl)phenyl]hexahydropyrimidine-2,4-dione; hydrochloride

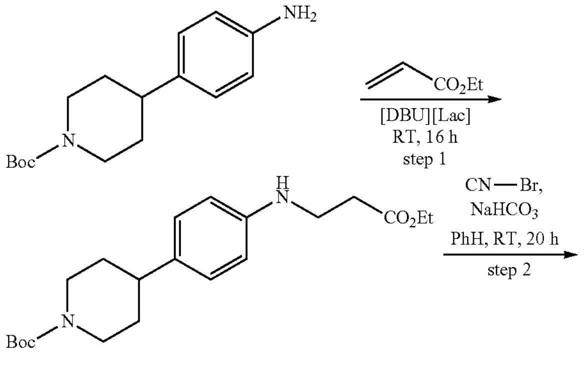

-continued

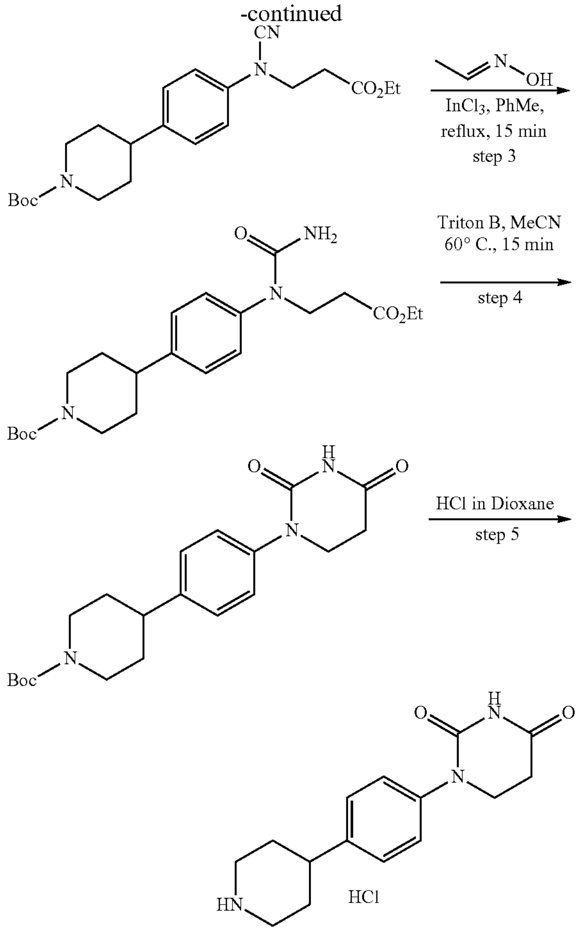

Step-1: Preparation of tert-butyl 4-[4-[(3-ethoxy-3-oxo-propyl)amino]phenyl]piperidine-1-carboxylate A mixture of tert-butyl 4-(4-aminophenyl)piperidine-1-carboxylate (16 g, 57.89 mmol), DBU-Lactic acid (10.28 g, 34.74 mmol) (ionic liquid) and ethyl acrylate 2 (7.53 g, 75.26 mmol, 8.02 mL) was stirred at 90° C. for 3 hours. The reaction mixture was cooled to room temperature, diluted with EtOAc and water. Layers were separated, organic layer was dried over sodium sulphate, concentrated to get crude which was purified by flash chromatography using 5-10% EtOAc-Hexane to afford tert-butyl 4-[4-[(3-ethoxy-3-oxo-propyl)amino]phenyl]piperidine-1-carboxylate (12.5 g, 33.20 mmol, 57.35% yield) as a gummy yellow liquid. LCMS (ES+): 377.2 $[M+H]^+$.

Step-2: Preparation of tert-butyl 4-[4-[cyano-(3-ethoxy-3-oxo-propyl)amino]phenyl]piperidine-1-carboxylate To the stirred solution of tert-butyl 4-[4-[(3-ethoxy-3-oxo-propyl)amino]phenyl]piperidine-1-carboxylate (15 g, 39.84 mmol) in Benzene (100 mL). Cyanogen bromide (6.75 g, 63.75 mmol, 3.34 mL) and sodium bicarbonate (5.36 g, 63.75 mmol, 2.48 mL) were added simultaneously and stirred for 24 hours at room temperature. The reaction mixture was diluted with ethyl acetate (500 mL). Organic phase was washed with water, dried over sodium sulphate and concentrated under vacuum. The crude residue was purified by column chromatography using (0%-20%) Ethyl acetate/hexane to afford tert-butyl 4-[4-[cyano-(3-ethoxy-3-oxo-propyl)amino]phenyl]piperidine-1-carboxylate (12.5 g, 31.13 mmol, 78.14% yield) as a semi solid. LCMS (ES+): 402.2 [M+H]+.

Step-3: Preparation of tert-butyl 4-[4-[carbamoyl-(3-ethoxy-3-oxo-propyl)amino]phenyl]piperidine-1-carboxylate A stirred mixture solution of tert-butyl 4-[4-[cyano-(3-ethoxy-3-oxo-propyl)amino]phenyl]piperidine-1-carboxylate (12.5 g, 31.13 mmol), trichloroindigane (2.07 g, 9.34 mmol) and (1Z)-acetaldehyde oxime (5.52 g, 93.40 mmol) in Toluene (100 mL) was refluxed for 1 hour. Reaction mixture was concentrated under vacuum pump and washed with pentane to obtain tert-butyl 4-[4-[carbamoyl-(3-ethoxy-3-oxo-propyl)amino]phenyl]piperidine-1-carboxylate (12 g, 28.60 mmol, 91.88% yield) as a gummy liquid, which was used in next step without further purification. LCMS (ES+): 420.6 [M+H]+.

Step-4: Preparation of tert-butyl 4-[4-(2,4-dioxo-hexahydropyrimidin-1-yl)phenyl]piperidine-1-carboxylate A stirred Solution of tert-butyl 4-[4-[carbamoyl-(3-ethoxy-3-oxo-propyl)amino]phenyl]piperidine-1-carboxylate (12 g, 28.60 mmol) in acetonitrile (120 mL) was heated at 60° C. followed by the addition of Triton B (40% in methanol, 17.94 g, 42.91 mmol, 19.50 mL) and stirred at 60° C. for 15 minutes. The reaction mixture was evaporated and the crude residue was purified by column chromatography to afford tert-butyl 4-[4-(2,4-dioxohexahydropyrimidin-1-yl)phenyl]piperidine-1-carboxylate (8 g, 21.42 mmol, 74.89% yield) as white solid. LCMS (ES+): 374.5 [M+H]+.

Step-5: Preparation of 1-[4-(4-piperidyl)phenyl]hexahydropyrimidine-2,4-dione;hydrochloride To a stirred suspension of tert-butyl 4-[4-(2,4-dioxohexahydropyrimidin-1-yl)phenyl]piperidine-1-carboxylate (13.50 g, 36.15 mmol) in 1,4-Dioxane (40 mL) was added hydrogen chloride (4M in 1,4-Dioxane, 50 mL, 200 mmol) at 0° C. and the reaction mixture was stirred for 3 hours at room temperature. Volatiles were removed under vacuum to afford 1-[4-(4-piperidyl)phenyl]hexahydropyrimidine-2,4-dione hydrochloride (11.1 g, 35.53 mmol, 98.28% yield) as white solid. $^1$H NMR (400 MHz, DMSO-d6) δ 10.34 (s, 1H), 8.99 (br s, 1H), 8.87 (br s, 1H), 7.30-7.22 (m, 4H), 3.76 (t, J=6.58 Hz, 2H), 3.38-3.31 (m, 2H), 3.05-2.91 (m, 2H), 2.88-2.80 (m, 1H), 2.69 (t, J=6.58 Hz, 2H), 1.94-1.80 (m, 4H). LCMS (ES+): 274.4 [M+H]+.

Synthesis of 2-[1-[4-(2,4-dioxohexahydropyrimidin-1-yl)-2-fluoro-phenyl]-4-hydroxy-4-piperidyl]acetic acid

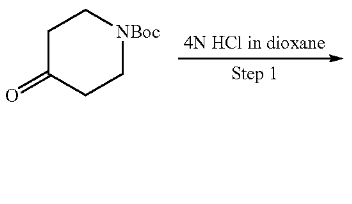

-continued

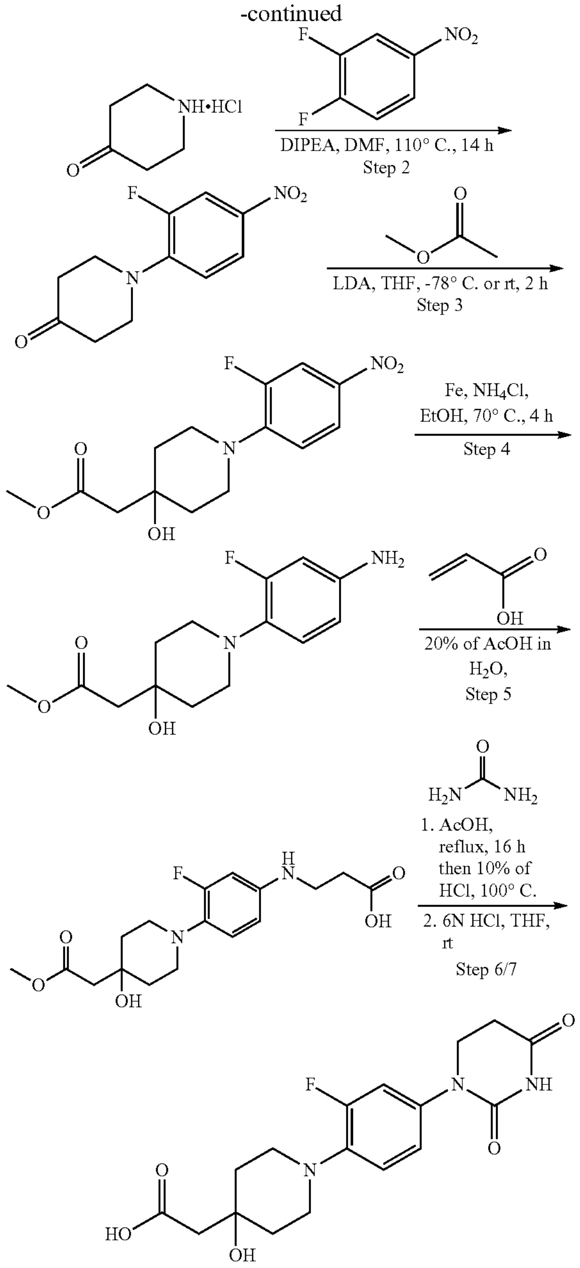

Step 1: Piperidin-4-one; hydrochloride

To a solution of tert-butyl 4-oxopiperidine-1-carboxylate (10 g, 50.19 mmol) in 1,4 Dioxane (100 mL) was added Hydrogen chloride (4M in 1,4-dioxane, 50.00 mL) at 0° C. and stirred at room temperature for 6 h. After completion, the reaction mixture was concentrated under reduced pressure to get piperidin-4-one hydrochloride (7.0 g, 49.04 mmol, 97.72% yield, 95% purity) as an off-white solid. Desired product was confirmed by $^1$HNMR. $^1$H NMR (400 MHz, DMSO-$d_6$): δ 9.75 (s, 2H), 3.39 (t, J=8.40 Hz, 4H), 2.60 (t, J=8.80 Hz, 4H).

Step 2: To a solution of piperidin-4-one hydrochloride (7.0 g, 70.61 mmol) in N, N-Dimethylformamide (30 mL) was added 1,2-difluoro-4-nitro-benzene (11.23 g, 70.61 mmol, 7.80 mL) and N,N-Diisopropylethylamine (36.50 g, 282.46 mmol, 49.20 mL). The reaction was heated at 110° C. for 14 h at which time it was cooled, diluted with ethyl acetate (500 mL) and washed with cold water (150 mL). The organic layer was washed with brine solution (150 mL), dried over sodium sulphate and concentrated under reduced pressure to get crude. The crude compound was purified by column chromatography on silica gel eluted with 40% ethyl acetate in petroleum ether to afford 1-(2-fluoro-4-nitro-phenyl)piperidin-4-one (9 g, 37.40 mmol, 52.97% yield) as a brown solid. LCMS (ESI+): 238.9 $[M+H]^+$.

Step 3: To a stirred solution of methyl acetate (3.36 g, 45.34 mmol, 3.60 mL) in THF (300 mL) was added LDA (2M in THF, 37.78 mL) at −78° C. slowly for 20 minutes. The reaction mixture was stirred at same temperature for 1 h. 1-(2-fluoro-4-nitro-phenyl)piperidin-4-one (9 g, 37.78 mmol) in THF (60 ml) was added to the reaction mixture at −78° C. and stirred at same reaction condition for 2 h. The reaction mixture was slowly brought to −40° C. After completion of the reaction, the reaction mixture was quenched with $NH_4Cl$ solution (100 ml) and extracted with ethyl acetate (600 ml). The organic layer was washed with water (150 mL), brine (150 mL), dried over sodium sulphate and concentrated under reduced pressure. The crude compound was purified by column chromatography on silica gel eluted with 50% ethyl acetate in petroleum ether to afford methyl 2-[1-(2-fluoro-4-nitro-phenyl)-4-hydroxy-4-piperidyl]acetate (6.5 g, 20.11 mmol, 53.22% yield) as a brown sticky solid. LCMS (ESI+): 313.1 $[M+H]^+$.

Step 4: To a solution of methyl 2-[1-(2-fluoro-4-nitro-phenyl)-4-hydroxy-4-piperidyl]acetate (6.5 g, 20.81 mmol) in Ethanol (10 mL), Water (2 mL) were added Iron powder (5.81 g, 104.07 mmol, 739.47 Ammonium Chloride (3.34 g, 62.44 mmol, 2.18 mL). The reaction was stirred at 70° C. for 4 h. After completion of the reaction, the reaction mixture was filtered through celite and washed with ethyl acetate (200 mL). The filtrate was washed with water (80 mL), $NaHCO_3$ solution (60 mL) and brine (60 mL). The organic layer was dried over sodium sulphate and concentrated under reduced pressure to get crude, which was purified by column chromatography on silica gel eluted with 70% ethyl acetate in petroleum ether to afford methyl 2-[1-(4-amino-2-fluoro-phenyl)-4-hydroxy-4-piperidyl]acetate (5.6 g, 16.86 mmol, 81.01% yield) as a brown sticky solid. LCMS (ESI+): 283.1 $[M+H]^+$.

Step 5: To a solution of methyl 2[1-(4-amino-2-fluoro-phenyl)-4-hydroxy-4-piperidyl]acetate (3.0 g, 10.63 mmol) in Acetic acid (6 mL), Water (24 mL) was added Acrylic acid (918.91 mg, 12.75 mmol, 875.15 μL) and the reaction was heated at 100° C. for 14 h. The reaction mixture was concentrated under reduced pressure to get crude which was diluted with ethyl acetate (60 mL). The organic layer was dried over sodium sulphate and concentrated under reduced pressure to get crude 3-[3-fluoro-4-[4-hydroxy-4-(2-methoxy-2-oxo-ethyl)-1-piperidyl]anilino]propanoic acid (2.5 g, 2.71 mmol, 25.55% yield), which was taken to next step without purification. LCMS (ESI+): 355.1 $[M+H]^+$.

Step 6: To a solution of 3-[3-fluoro-4-[4-hydroxy-4-(2-methoxy-2-oxo-ethyl)-1-piperidyl]anilino]propanoic acid (2.0 g, 5.64 mmol) in acetic acid (15 mL) was added urea (677.88 mg, 11.29 mmol, 505.88 μL) and the reaction was heated at 110° C. in sealed tube for 14 h. After completion, 2N HCl solution (10 mL) was added to the reaction mixture and it was heated at 100° C. for 1 h. The reaction mixture was concentrated under reduced pressure to get crude, which was diluted with ethyl acetate (100 mL), washed with $NaHCO_3$ solution (30 mL), water (30 mL) and brine solution (30 mL). The organic layer was dried over sodium sulphate and concentrated under reduced pressure to get crude which was purified by column chromatography on silica gel eluted with 60% ethyl petroleum ether to afford methyl 2-[1-[4-(2,4-dioxohexahydropyrimidin-1-yl)-2-fluoro-phenyl]-4-hydroxy-4-piperidyl]acetate (680 mg, 1.70 mmol, 30.17% yield) as a light brown solid. LCMS (ESI+): 379.8 $[M+H]^+$.

Step 7: To a solution of methyl 2-[1-[4-(2,4-dioxohexahydropyrimidin-1-yl)-2-fluoro-phenyl]-4-hydroxy-4-piperidyl]acetate (120 mg, 316.30 μmol) in THF (2 mL) was added 6N HCl (3 mL) and the reaction was stirred at room temperature for 14 h. The reaction mixture was concentrated under reduced pressure to get 2-[1-[4-(2,4-dioxohexahydropyrimidin-1-yl)-2-fluoro-phenyl]-4-hydroxy-4-piperidyl]acetic acid (100 mg, 194.12 μmol, 61.37% yield) as brown sticky solid. LCMS (ESI+): 366.1 $[M+H]^+$.

Synthesis of 2-[4-[3-(2,6-dioxo-3-piperidyl)-1-methyl-indazol-6-yl]-1-piperidyl]acetic acid

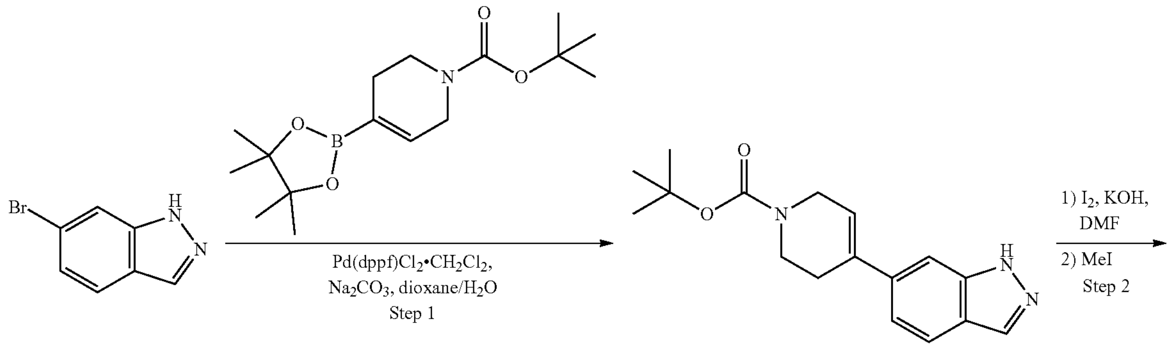

-continued
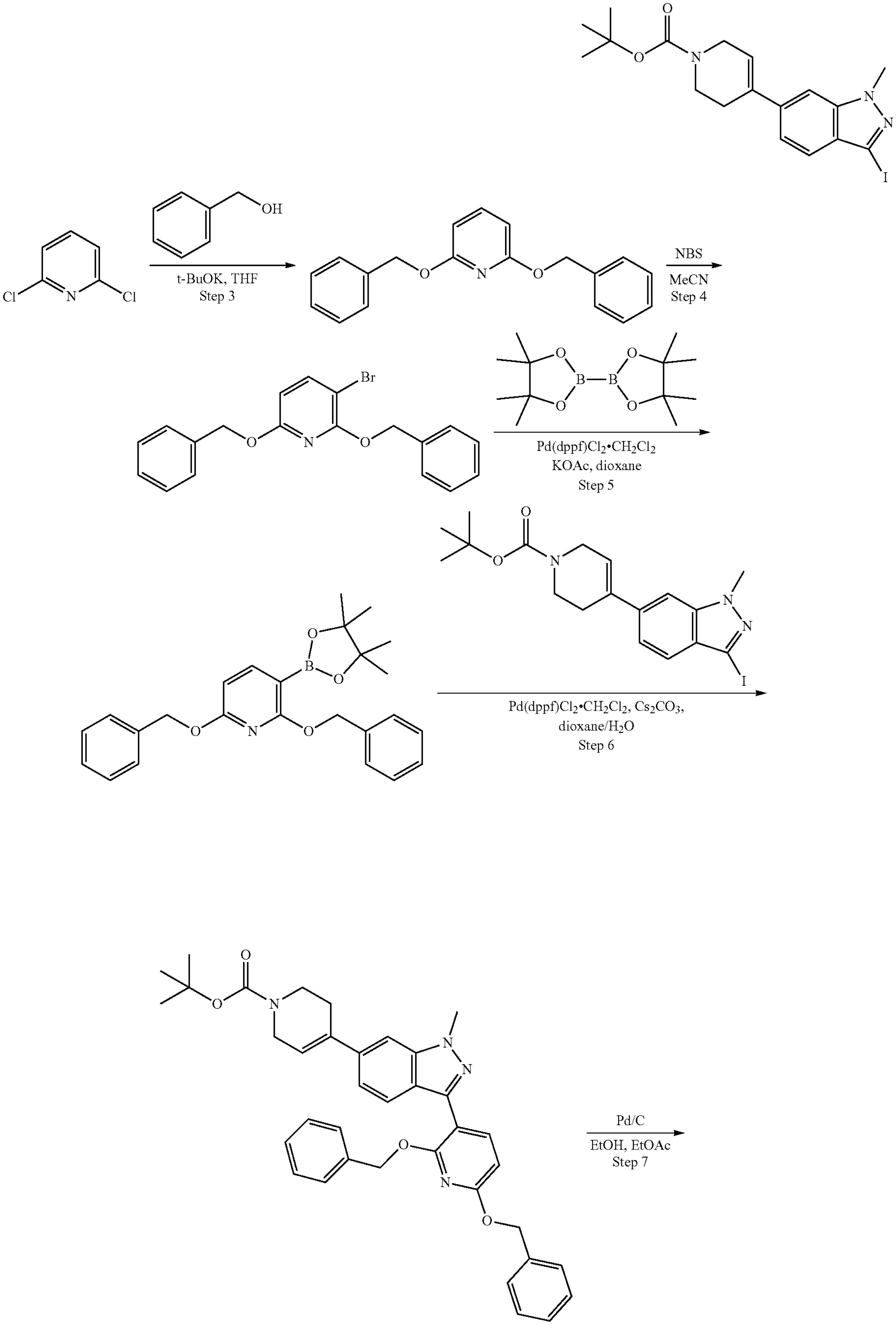

-continued

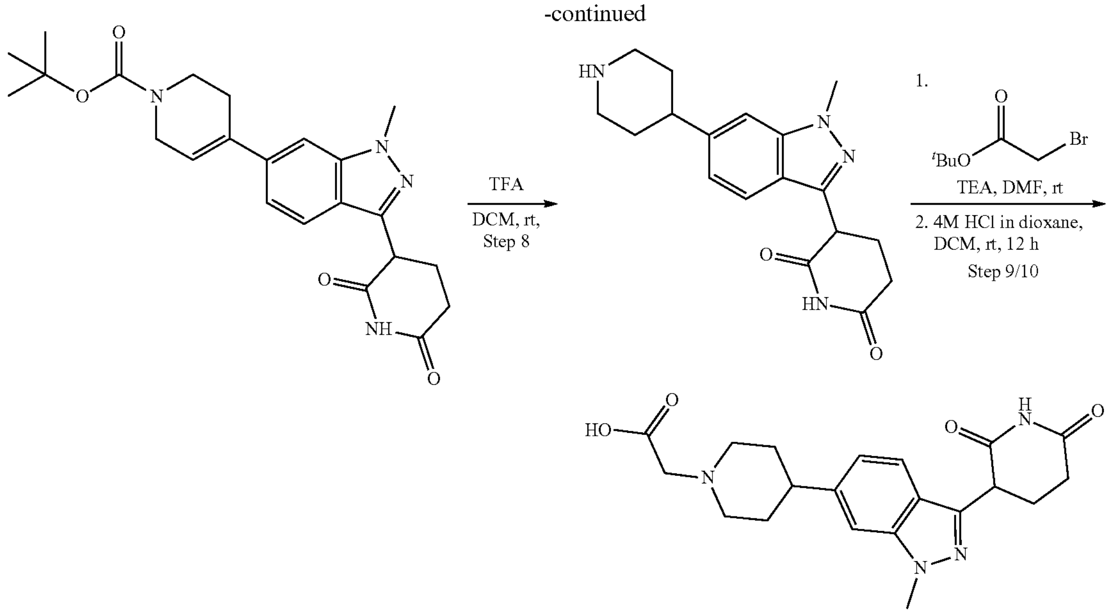

Step 1: tert-butyl 4-(1H-indazol-6-yl)-3,6-dihydropyridine-1(2H)-carboxylate

A mixture of 6-bromo-1H-indazole (57.0 g, 289 mmol), tert-butyl 4-(4,4,5,5-tetramethyl-1,3,2-dioxaborolan-2-yl)-3,6-dihydropyridine-1(2H)-carboxylate (134 g, 433 mmol), Pd(dppf)$Cl_2$·$CH_2Cl_2$ (12.0 g, 14.6 mmol) and $Na_2CO_3$ (100 g, 943 mmol) in dioxane (480 mL) and $H_2O$ (120 mL) was stirred at 105° C. for 12 h. The mixture was filtered through a pad of Celite and washed with ethyl acetate (500 mL). The filtrate was washed with brine (3×150 mL), dried over sodium sulphate, filtered and concentrated under reduced pressure. The residue was purified by silica gel chromatography (0~30% ethyl acetate/petroleum ether) to afford tert-butyl 4-(1H-indazol-6-yl)-3,6-dihydropyridine-1(2H)-carboxylate (80.0 g, 239 mmol, 83% yield) as yellow oil.

LCMS (ES+): 300.1 $[M+H]^+$

Step 2: tert-butyl 4-(3-iodo-1-methyl-1H-indazol-6-yl)-3,6-dihydropyridine-1(2H)-carboxylate To a solution of tert-butyl 4-(1H-indazol-6-yl)-3,6-dihydropyridine-1(2H)-carboxylate (75.0 g, 224 mmol) in DMF (700 mL) was added KOH (37.7 g, 672 mmol) and $I_2$ (85.3 g, 336 mmol, 67.7 mL). The mixture was stirred at 25° C. for 12 h and was cooled to 0° C. Mel (44.6 g, 314 mmol, 19.6 mL) was then added. The resulting mixture was stirred at 25° C. for 1 h. The mixture was poured into water (1500 mL) and extracted with ethyl acetate (3×500 mL). The combined organic phase was washed by brine (3×500 mL) and dried over sodium sulphate, filtered and concentrated under vacuum to give a residue, which was purified by silica gel chromatography (0~8% ethyl acetate/petroleum ether) to obtain tert-butyl 4-(3 odo-1-methyl-1H-indazol-6-yl)-3,6-dihydropyridine-1(2H)-carboxylate (23.0 g, 52.3 mmol, 23% yield) as a yellow oil. LCMS (ES+): 440.1 $[M+H]^+$.

Step 3: 2,6-bis(benzyloxy)pyridine

To a solution of t-BuOK (190 g, 1.69 mol) in THF (1.00 L) was added phenylmethanol (73.4 g, 679 mmol, 70.6 mL) at 0° C. 2,6-Dichloropyridine (50.0 g, 338 mmol) was added to the mixture at 25° C. and stirred at 75° C. for 12 h. The reaction was quenched with sat. aq. $NH_4Cl$ (200 mL) at 0° C., diluted with ethyl acetate (200 mL), and extracted with ethyl acetate (3×200 mL). The combined organic layers were washed with brine (500 mL), dried over sodium sulphate, filtered, and concentrated under reduced pressure to give a residue. The residue was triturated with petroleum ether (150 mL) to afford 2,6-bis(benzyloxy)pyridine (84.0 g, 85% yield) as a yellow solid. LCMS (ES+): 292.2 $[M+H]^+$ Step 4: 2,6-bis(benzyloxy)-3-bromopyridine To a solution of 2,6-bis(benzyloxy)pyridine (34.0 g, 116 mmol) in MeCN (100 mL) was added a solution of NBS (21.0 g, 118 mmol, 1.01 eq) in MeCN (200 mL) at 40° C. and the reaction mixture was stirred at 85° C. for 12 h. The reaction mixture was concentrated under reduced pressure, diluted with water (500 mL), and extracted with ethyl acetate (3×300 mL). The combined organic layers were washed with brine (200 mL), dried over sodium sulphate, filtered and concentrated. The residue was triturated with petroleum ether (60 ml) to afford 2,6-bis(benzyloxy)-3-bromopyridine (27.7 g, 64% yield). LCMS (ES+): 371.9 $[M+H]^+$ Step 5: 2,6-bis(benzyloxy)-3-(4,4,5,5-tetramethyl-1,3,2-dioxaborolan-2-yl)pyridine To a solution of 2,6-bis(benzyloxy)-3-bromopyridine (52.4 g, 139 mmol) in dioxane (500 mL) was added 4,4,4',4',5,5,5',5'-octamethyl-2,2'-bi(1,3,2-dioxaborolane) (37.1 g, 146 mmol), KOAc (41.0 g, 418 mmol) and Pd(dppf) $Cl_2$·$CH_2Cl_2$ (5.69 g, 6.97 mmol). The reaction mixture was stirred at 105° C. for 12 h. The reaction mixture was filtered through a pad of Celite. The filtrate was diluted with water (500 mL) and extracted with ethyl acetate (2×500 mL). The extracts were washed with brine (400 mL), dried over sodium sulphate, filtered and concentrated. The residue was purified by silica gel chromatography (0100% ethyl acetate/petroleum ether) to afford 2,6-bis(benzyloxy)-3-(4,4,5,5- tetramethyl-1,3,2-dioxaborolan-2-yl)pyridine (35.0 g, 60.1% yield) as yellow oil. LCMS (ES+): 418.3 $[M+H]^+$ Step 6: tert-butyl 4-(3-(2,6-bis(benzyloxy)pyridin-3-yl)-1-methyl-1H-indazol-6-yl)-3,6-dihydropyridine-1(2H)-carboxylate To a solution of 2,6-bis(benzyloxy)-3-(4,4,5,5-tetramethyl-1,3,2-dioxaborolan-2-yl)pyridine (20.0 g, 45.53 mmol), tert-butyl 4-(1H-indazol-6-yl)-3,6-dihydropyridine-1(2H)-carboxylate (26.6 g, 63.7 mmol) and $Cs_2CO_3$ (44.5 g, 136 mmol) in dioxane (200 mL) and $H_2O$ (40 mL) was added $Pd(dppf)Cl_2CH_2Cl_2$ (3.72 g, 4.55 mmol, 0.10 eq). The reaction mixture was stirred at 100° C. for 2 h. The reaction mixture was filtered through a pad of Celite, and the filtrate was washed with brine (60 mL×3 mL), dried over sodium sulphate, filtered and concentrated. The residue was purified by silica gel chromatography (0100% ethyl acetate/petroleum ether) to obtain tert-butyl 4-(3-(2,6-bis(benzyloxy)pyridin-3-yl)-1-methyl-1H-indazol-6-yl)-3,6-dihydropyridine-1(2H)-carboxylate (20.0 g, 73% yield) as yellow oil. LCMS (ES+): 603.3 $[M+H]^+$ Step 7: tert-butyl 4-(3-(2,6-dioxopiperidin-3-yl)-1-methyl-1H-indazol-6-yl)piperidine-1-carboxylate To a solution of tert-butyl 4-(3-(2,6-bis(benzyloxy)pyridin-3-yl)-1-methyl-1H-indazol-6-yl)-3,6-dihydropyridine-1(2H)-carboxylate (18.0 g, 29.8 mmol, 1.00 eq) in EtOH (270 mL) and EtOAc (270 mL) was added Pd/C (4.00 g, 10% purity) under $N_2$ atmosphere. The suspension was degassed and purged with $H_2$ 3 times. The mixture was stirred under $H_2$ (15 psi) at 30° C. for 24 h. The reaction mixture was filtered through a pad of Celite and the filtrate was concentrated. The residue was purified by silica gel chromatography (ethyl acetate/petroleum ether) to afford tert-butyl 4-(3-(2,6-dioxopiperidin-3-yl)-1-methyl-1H-indazol-6-yl)piperidine-1-carboxylate (5.3 g, 41% yield) as a white solid. LCMS (ES+): 427.2 $[M+H]^+$ Step 8: 3-[1-methyl-6-(4-piperidyl)indazol-3-yl]piperidine-2,6-dione Into a 25 mL single neck round bottom flask containing a well-stirred solution of tert-butyl 4-[3-(2,6-dioxo-3-piperidyl)-1-methyl-indazol-6-yl]piperidine-1-carboxylate (500 mg, 1.17 mmol) in anhydrous DCM (5 mL) was added TFA (668.35 mg, 5.86 mmol, 451.59 μL) at 0° C. After stirring at room temperature for 3 h, the reaction mixture was concentrated under reduced pressure. The residue was azeotroped with toluene (2×15 mL) and triturated with diethylether (20 mL) to afford 3-[1-methyl-6-(4-piperidyl)indazol-3-yl]piperidine-2,6-dione (500 mg, 1.12 mmol, 95% yield, trifluoroacetic acid salt) as an off-white solid. LCMS (ESI+): 326.9 $[M+H]^+$ Step 9: To a stirred solution of 3-[1-methyl-6-(4-piperidyl)indazol-3-yl]piperidine-2,6-dione (230 mg, 704.67 μmol) in N, N-Dimethylformamide (4 mL) was added Triethylamine (213.92 mg, 2.11 mmol, 294.65 μL) followed by tert-Butyl bromoacetate (151.19 mg, 775.14 μmol, 113.68 μL) at room temperature and the resulting reaction mixture was stirred at room temperature for 12 h. After completion, water was added and extracted with 5% Methanol-Dichloromethane (2×30 mL). The combined organic layers were washed with ice cold water (2×30 mL), dried over anhydrous sodium sulphate, filtered and filtrate was evaporated under reduced pressure to get the desired crude compound tert-butyl 2-[4-[3-(2,6-dioxo-3-piperidyl)-1-methyl-indazol-6-yl]-1-piperidyl]acetate (260 mg, 576.44 μmol, 81.80% yield) as off white solid. LCMS (ESI+): 441.4 $[M+H]^+$.

Step 10: To a stirred solution of tert-butyl 2-[4-[3-(2,6-dioxo-3-piperidyl)-1-methyl-indazol-6-yl]-1-piperidyl]acetate (260 mg, 590.19 μmol) in Dichloromethane (5 mL) was added Hydrogen chloride solution (4.0 M in dioxane, 590.19 μmol, 4 mL) at 0° C. and the resulting reaction mixture was stirred for 12 h at room temperature. The reaction mixture was concentrated under reduced pressure. The residue obtained was co-distilled with toluene (2×20 mL) and triturated with diethyl ether (2×5 mL), dried under reduced pressure to afford 2-[4-[3-(2,6-dioxo-3-piperidyl)-1-methyl-indazol-6-yl]-1-piperidyl]aceti c acid (230 mg, 545.86 μmol, 92.49% yield, hydrochloric acid salt) as off white solid. LCMS (ESI+): 385.3 $[M+H]^+$.

Synthesis of 2-[4-[[3-(2,6-dioxo-3-piperidyl)-1-methyl-indazol-6-yl]amino]-1-piperidyl]acetic acid

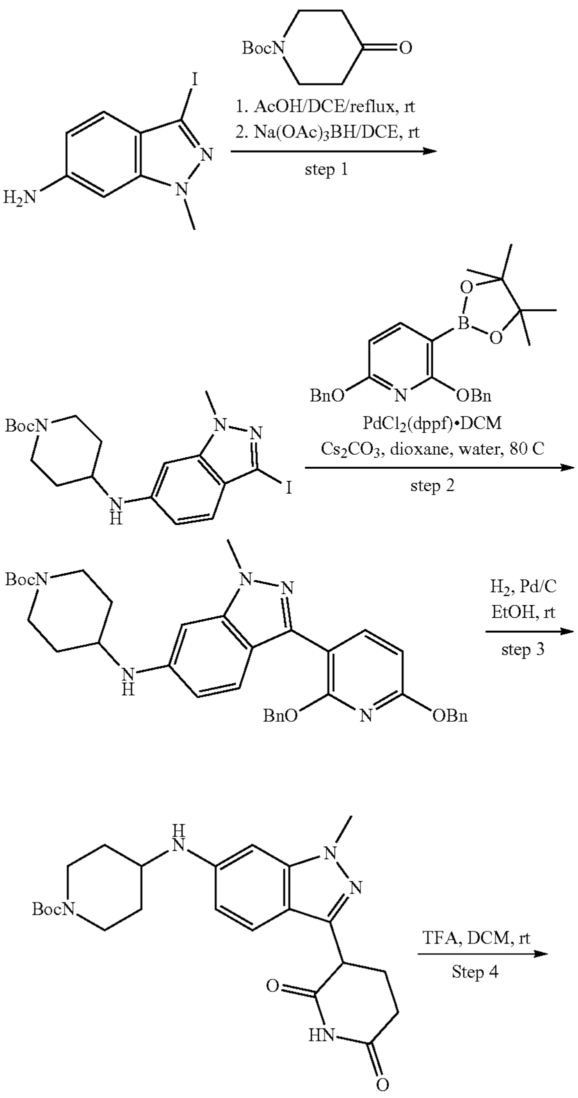

-continued

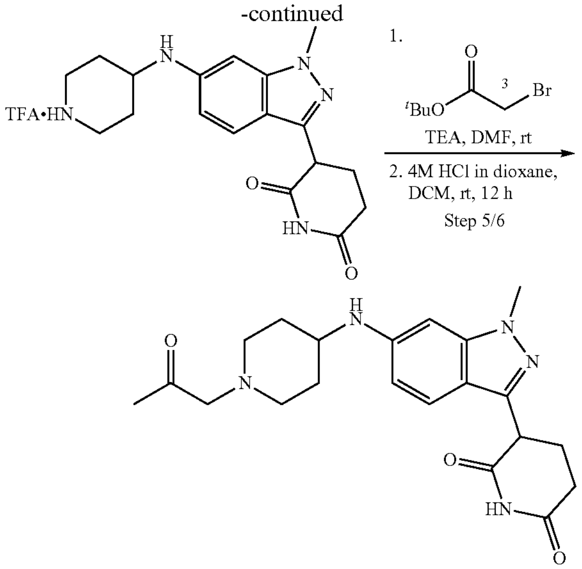

Step 1: A mixture of tert-butyl 4-oxopiperidine-1-carboxylate (790 mg, 3.96 mmol) and 3-iodo-1-methyl-indazol-6-amine (900 mg, 3.30 mmol) in DCE (15 mL) was warmed at 80° C. in presence of acetic acid (0.2 mL, 3.30 mmol) for 4 hr in a sealed vial. The reaction mixture was subsequently cooled at room temperature and triacetoxyborohydride (1.4 g, 6.60 mmol) was added in portions at 0° C. and stirred for further 3 hr at room temperature. After consumption of starting material, DCM (25 mL) was added to the reaction mixture and neutralized by saturated sodium bicarbonate solution. The mixed organic portion was washed with water/brine. After separation of the organic layer, it was dried over sodium sulphate and evaporated. The crude mass was purified by column chromatography to obtain desire solid product as yellow solid tert-butyl 4-[(3-iodo-1-methyl-indazol-6-yl) amino]piperidine-1-carboxylate (1 g, 2.19 mmol, 66.41% yield). LCMS (ES+): 457.1 $[M+H]^+$.

Step 2: To a mixture of tert-butyl 4-[(3-iodo-1-methyl-indazol-6-yl)amino]piperidine-1-carboxylate (1.3 g, 2.85 mmol) and 2,6-dibenzyloxy-3-(4,4,5,5-tetramethyl-1,3,2-dioxaborolan-2-yl)pyridine (2.14 g, 5.13 mmol) in dioxane-water (12 mL, 4:1, v/v), Cesium carbonate (2.78 g, 8.55 mmol) was added and the reaction mixture was thoroughly degassed with $N_2$ followed by the addition of Pd(dppf) Cl2·DCM (140 mg, 170.93 μmol). After the addition was complete, the reaction mixture was then heated at 80° C. for 12 hr. After completion of reaction, the reaction mixture was filtered through celite bed and washed with 10% MeOH in DCM (30 mL). The filtrate was collected and evaporated. The crude material was purified by column chromatography to afford desired tert-butyl 4-[[3-(2,6-dibenzyloxy-3-pyridyl)-1-methyl-indazol-6-yl]amino]piperidine-1-carboxylate (850 mg, 48.14% yield) LCMS (ES+): 620.2$[M+H]^+$.

Step 3: The stirred solution of tert-butyl 4-[[3-(2,6-dibenzyloxy-3-pyridyl)-1-methyl-indazol-6-yl]amino]piperidine-1-carboxylate (850 mg, 1.37 mmol) in Ethanol (40 mL) was hydrogenated in presence of Pd/C (100 mg, 10% by weight) at 1 atm pressure. After completion, solution was filtered through celite bed and washed with 10% MeOH in DCM (40 mL). Filtrate was evaporated and the crude material was purified by column chromatography to obtain desired white solid product tert-butyl 4-[[3-(2,6-dioxo-3-piperidyl)-1-methyl-indazol-6-yl]amino]piperidine-1-carboxylate (320 mg, 52.46% yield). LCMS (ES+): 442.1$[M+H]^+$.

Step 4: To a stirred solution of tert-butyl 4-[[3-(2,6-dioxo-3-piperidyl)-1-methyl-indazol-6-yl]amino]piperidine-1-carboxylate (250 mg, 566.22 μmol) in Dichloromethane (5 mL) was added Trifluoroacetic acid (2.96 g, 25.96 mmol, 2 mL) at 0° C. and the resulting reaction mixture was stirred for 12 h at room temperature. After completion, the reaction mixture was concentrated under reduced pressure. The residue obtained was co-distilled with toluene (2×20 mL), dried under reduced pressure to afford 3-[2-(azetidin-3-yl)ethyl]-6-[2-cyano-3-[[ethyl(methyl)sulfamoyl]amino]-6-fluoro-phenoxy]-4-oxo-quinazoline (800 mg, 1.27 mmol, 98.97% yield) as a white sticky solid. LCMS (ESI+): 342.3 $[M+H]^+$.

Step 5: To a stirred solution of 3-[1-methyl-6-(4-piperidylamino)indazol-3-yl]piperidine-2,6-dione (260.68 mg, 763.54 μmol) in N, N-Dimethylformamide (5 mL) was added Triethylamine (231.79 mg, 2.29 mmol, 319.27 μL) at room temperature followed by tert-butyl 2-bromoacetate (148.93 mg, 763.54 μmol, 111.98 μL) was added and the resulting reaction mixture was stirred at room temperature for 12 h. The reaction mixture was quenched with water (100 mL) and extracted with ethyl acetate (3×100 mL), The combined organic layers were dried over sodium sulphate and concentrated under reduced pressure to give crude product, which was used without purification. LCMS (ESI+): 456.3 $[M+H]^+$.

Step 6: To a stirred solution of tert-butyl 2-[4-[[3-(2,6-dioxo-3-piperidyl)-1-methyl-indazol-6-yl]amino]-1-piperidyl]acetate (220 mg, 482.93 μmol) in Dichloromethane (5 mL) was added Trifluoroacetic acid (2.96 g, 25.96 mmol, 2 mL) at 0° C. and the resulting reaction mixture was stirred for 3 h at room temperature. The reaction mixture was concentrated under reduced pressure. The residue obtained was co-distilled with toluene (2×20 mL), dried under reduced pressure to afford 2-[4-[[3-(2,6-dioxo-3-piperidyl)-1-methyl-indazol-6-yl]amino]-1-piperidyl]acetic acid (230 mg, 391.16 μmol, 81.00% yield) as white sticky solid which was directly used without further purification. LCMS (ESI+): 400.4 $[M+H]^+$.

Synthesis of 2-[1-[3-(2,6-dioxo-3-piperidyl)-1-methyl-indazol-6-yl]-4-piperidyl]acetic acid

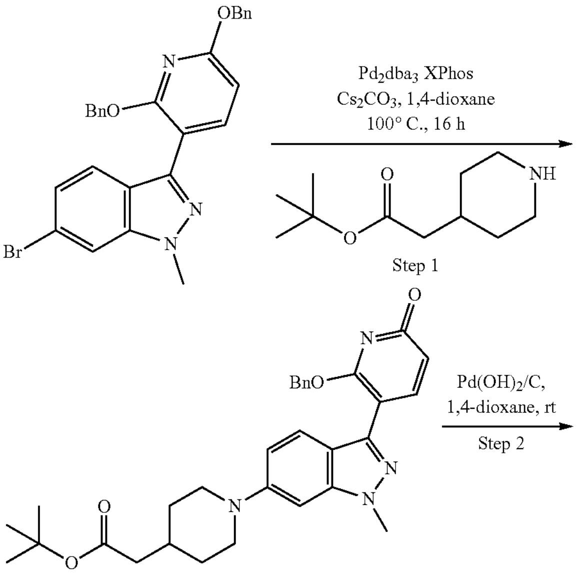

-continued

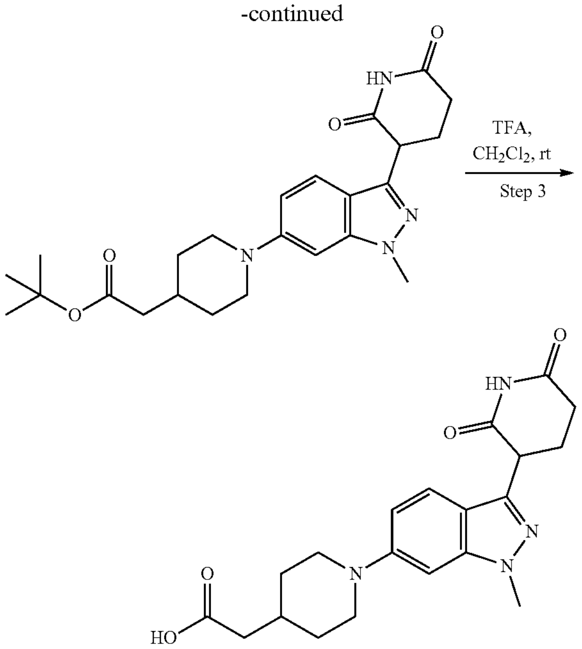

Step 1: A stirred solution of tert-butyl 2-(4-piperidyl) acetate (50 mg, 250.89 μmol) and 6-bromo-3-(2,6-dibenzyloxy-3-pyridyl)-1-methyl-indazole (125.54 mg, 250.89 μmol) in 1,4-dioxane (3 mL) was degassed for 5 minutes, followed by addition of $Cs_2CO_3$ (97.6 mg, 250.89 μmol). Then, XPhos (9.1 mg, 250.89 μmol) was added, followed by the addition of Tris(dibenzylideneacetone)dipalladium(0) (9.5 mg, 250.89 μmol). The reaction mixture was stirred for 16 h at 100° C. The reaction mixture was diluted with ethyl acetate (20 mL), washed with cold water (5 mL). The organic layer was washed with brine solution (5 mL), dried over sodium sulphate and concentrated under reduced pressure to get crude, which was purified by column chromatography on silica gel eluted with 30% ethyl acetate in petroleum ether to afford tert-butyl 2-[1-[3-(2,6-dibenzyloxy-3-pyridyl)-1-methyl-indazol-6-yl]-4-piperidyl]acetate (40 mg, 46.54 μmol, 18.55% yield) as yellow solid. LCMS (ESI+): 619.3 $[M+H]^+$.

Step 2: To a stirred solution of tert-butyl 2-[1-[3-(2,6-dibenzyloxy-3-pyridyl)-1-methyl-indazol-6-yl]-4-piperidyl] acetate (500 mg, 808.06 μmol) in 1,4-dioxane (20 mL) was added palladium hydroxide on carbon, 20 wt. % and 50% water (226.97 mg, 1.62 mmol) at 25° C. The reaction mixture was stirred for 16 h at 25° C. under hydrogen balloon pressure. After completion, the reaction mixture was filtered through celite bed and washed with 1,4-dioxane (150 mL). The filtrate was concentrated under reduced pressure to yield a crude residue. The residue was washed with diethyl ether (20 mL) to get tert-butyl 2-[1-[3-(2,6-dioxo-3-piperidyl)-1-methyl-indazol-6-yl]-4-piperidyl]acetate (400 mg, 573.85 μmol, 71.02% yield) as brown solid. LCMS (ESI+): 441.2 $[M+H]^+$.

Step 3: To a stirred solution of tert-butyl 2-[1-[3-(2,6-dioxo-3-piperidyl)-1-methyl-indazol-6-yl]-4-piperidyl]acetate (300 mg, 680.99 μmol) in Dichloromethane (5 mL) was added trifluoroacetic acid (388.24 mg, 3.40 mmol, 262.33 μL) at 0° C. Total reaction mixture was stirred for 2 h at 25° C. After completion of reaction, the reaction mixture was concentrated under reduced pressure to yield crude. The crude was washed with diethyl ether (20 mL) to afford 2-[1-[3-(2,6-dioxo-3-piperidyl)-1-methyl-indazol-6-yl]-4-piperidyl]acetic acid (220 mg, 353.09 μmol, 51.85% yield) as light pink solid.

Synthesis of 2-(4-(1-(2,6-dioxopiperidin-3-yl)-3-methyl-2-oxo-2,3-dihydro-1H-benzo[d]imidazol-5-yl)piperidin-1-yl)acetic acid

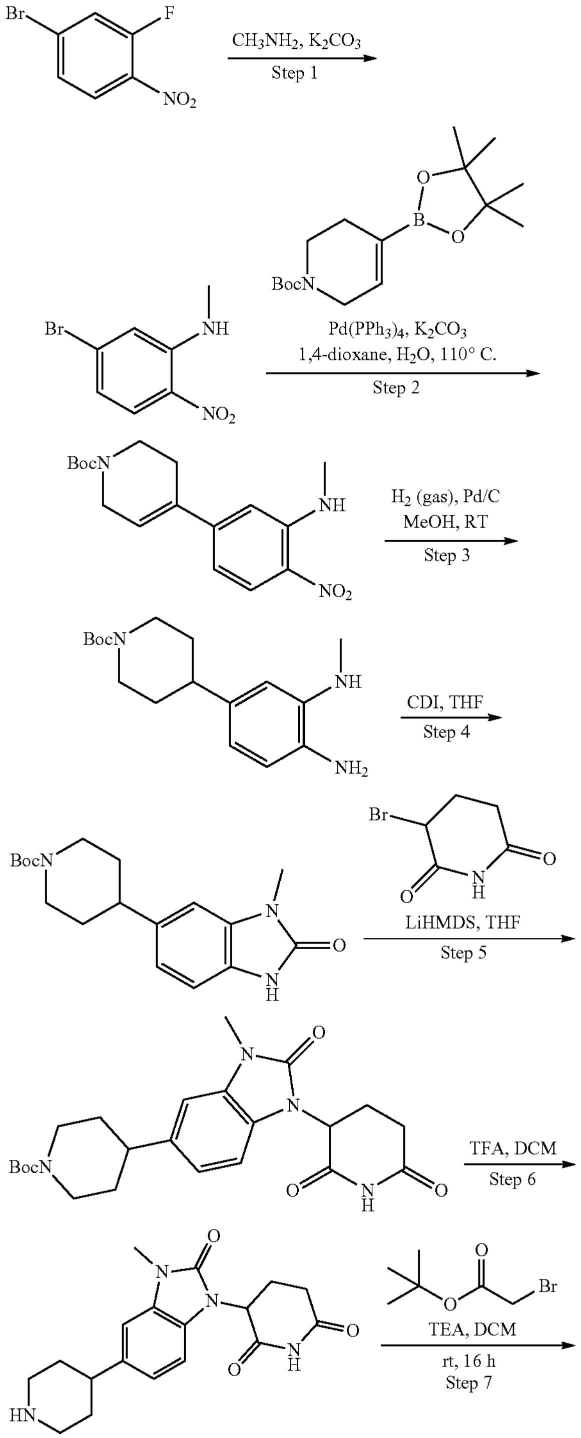

-continued

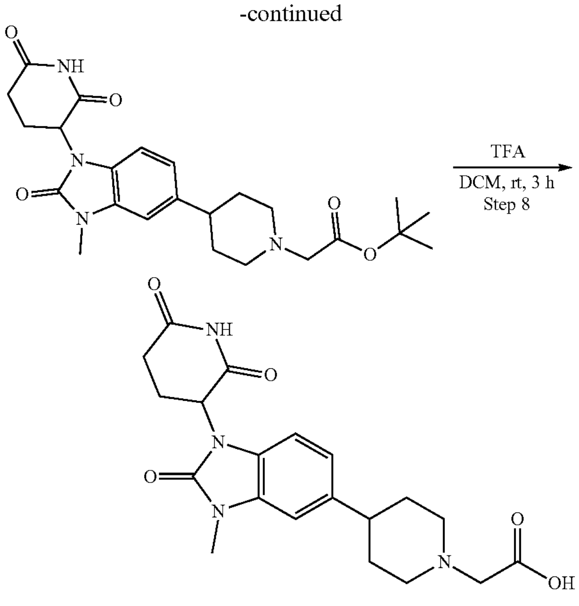

Step 1: 5-bromo-N-methyl-2-nitroaniline

To a stirred solution of 4-bromo-2-fluoro-1-nitrobenzene (300 g, 1.36 mol) in DCM (3 L) were added $K_2CO_3$ (0.94 Kg, 6.8 mol) and methylamine (2M in THF) (2.04 L, 4.09 mol) at room temperature and stirred for 16 h. Two batches of the reaction were combined. After completion of reaction, the reaction mixture was diluted with water (3.0 L) and extracted with DCM (2×2.5 L). The combined organic layer was washed with saturated sodium bicarbonate solution (2×1.5 L) and brine (2×1.5 L). The organic layer was dried over sodium sulphate, filtered and solvent removed under reduced pressure to obtain 5-bromo-N-methyl-2-nitroaniline (600 g, 95% yield) as a yellow solid. LCMS (ES+): 231.1 $[M+H]^+$ Step 2: tert-butyl 4-(3-(methylamino)-4-nitrophenyl)-3,6-dihydropyridine-1(2H)-carboxylate To a stirred solution of 5-bromo-N-methyl-2-nitroaniline (75.0 g, 0.326 mol) in 1,4-dioxane (1.2 L) and water (0.3 L) was added $K_2CO_3$ (270.3 g, 1.956 mol) and the mixture was stirred for 5 min. tert-Butyl 4-(4,4,5,5-tetramethyl-1,3,2-dioxaborolan-2-yl)-3,6-dihydropyridine-1(2H)-carboxylate (151.0 g, 0.489 mol) was added to the reaction mixture under nitrogen atmosphere and the reaction mixture was purged with nitrogen for 10 min. Palladium(0) tetrakis (triphenylphosphine) (37.66 g, 0.032 mol) was added to the reaction under nitrogen atmosphere. After purging with nitrogen for 10 min, the reaction was stirred at 110° C. for 4 h. Two batches of the reaction were combined. The reaction mixture was cooled to room temperature and filtered through celite. The filtrate was diluted with water (1.5 L) and extracted with ethyl acetate (2×500 mL). The combined organic layer was washed with brine, dried over sodium sulphate, filtered and solvent removed under reduced pressure. The residue was purified by silica gel chromatography (0-20% EtOAc in petroleum ether as an eluent) to obtain tert-butyl 4-(3-(methyl amino)-4-nitrophenyl)-3,6-dihydropyridine-1(2H)-carboxylate (150 g, 69% yield) as a red solid. LCMS (ES+): 334.3 $[M+H]^+$ Step 3: tert-butyl 4-(4-amino-3-(methylamino)phenyl)piperidine-1-carboxylate A solution of tert-butyl 4-(3-(methyl ami no)-4-nitrophenyl)-3,6-dihydropyridine-1(2H)-carboxylate (50 g, 0.149 mol) in methanol (1 L) in a Parr-shaker flask was degassed. Palladium on carbon (10%, wet) (25.0 g) was added and the reaction mixture was put under an atmosphere of hydrogen (70-75 psi). Four batches were combined. After 8 h, the reaction mixture was filtered through Celite, washing with methanol. The filtrate was evaporated under reduced pressure and the residue purified by silica gel chromatography (0-20% ethyl acetate and petroleum ether as an eluent) to obtain tert-butyl 4-(4-amino-3-(methylamino)phenyl)piperidine-1-carboxylate (120.0 g, 65% yield) as dark brown solid. LCMS (ES−): 304.2 $[M-H]^-$ Step 4: tert-butyl 4-(3-methyl-2-oxo-2,3-dihydro-1H-benzo[d]imidazol-5-yl)piperidine-1-carboxylate To a stirred solution of tert-butyl 4-(4-amino-3-(methylamino)phenyl)piperidine-1-carboxylate (60 g, 0.196 mol) in THF (900 mL) at 0° C. was added CDI (33.45 g, 0.206 mol) and the reaction mixture was stirred at room temperature overnight. Two batches were combined. The solvent was removed under reduced pressure. The residue was triturated with MTBE and filtered to afford tert-butyl 4-(3-methyl-2-oxo-2,3-dihydro-1H-benzo[d]imidazol-5-yl)piperidine-1-carboxylate (88.0 g, 67.5% yield) as an off-white solid. LCMS (ES+): 332.3 $[M+H]^+$ Step 5: tert-butyl 4-(1-(2,6-dioxopiperidin-3-yl)-3-methyl-2-oxo-2,3-dihydro-1H-benzo[d]imidazol-5-yl)piperidine-1-carboxylate To an ice cold stirred solution of tert-butyl 4-(3-methyl-2-oxo-2,3-dihydro-1H-benzo[d]imidazol-5-yl)piperidine-1-carboxylate (44 g, 0.133 mol) in anhydrous THF (900 mL) at 0° C. was added 1 M LiHMDS (403 ml, 0.387 mol). The reaction mixture was stirred for 10 min before adding 3-bromopiperidine-2,6-dione (43.34 g, 0.225 mol). After addition, the reaction mixture was stirred at 70-75° C. for 16 h. Two batches were combined. The reaction mixture was cooled to 0° C. and quenched by slow addition of aqueous 1N HCl (620 mL). The mixture was diluted with EtOAc (1 L) and the layers separated. The organic layer was washed with 0.5 N HCl (1.4 L), water (2×1.5 L) and brine (1.5 L). The combined organic layer was dried over sodium sulphate, filtered and concentrated under reduced pressure. The residue was purified by silica gel chromatography (20-50% EtOAc in Petroleum ether) to obtain tert-butyl 4-(1-(2,6-dioxopi peri din-3-yl)-3-methyl-2-oxo-2,3-dihydro-1H-b enzo[d]imidazol-5-yl)piperidine-1-carboxylate (51.0 g, 43.4% yield) as a grey off-white solid. LCMS (ES−): 441.1 $[M-H]^-$ Step 6: 3-(3-methyl-2-oxo-5-(piperidin-4-yl)-2,3-dihydro-1H-benzo yl)piperidine-2,6-dione To a stirred solution of tert-butyl 4-(1-(2,6-dioxopiperidin-3-yl)-3-methyl-2-oxo-2,3-dihydro-1H-benzo[d]imidazol-5-yl)piperidine-1-carboxylate (25.5 g, 0.057 moles) in DCM (250 mL) at 0° C. was added TFA (87.2 ml) via dropwise addition. The reaction mixture was stirred at room temperature for 4 h. Two batches were combined. The volatiles were evaporated under reduced pressure and azeotroped twice with toluene. The residue was triturated with diethyl ether and dried under reduced pressure to obtain 3-(3-methyl-2-oxo-5-(piperidin-4-yl)-2,3-dihydro-1H-benzo[d]imidazol-1-yl)piperidine-2,6-dione (26 g, 43.12 mmol, trifluoroacetic acid salt) as an off white solid. LCMS (ES+): 343.3 $[M+H]^+$ Step 7: tert-butyl 2-[4-[1-(2,6-dioxo-3-piperidyl)-3-methyl-2-oxo-benzimidazol-5-yl]-1-piperidyl]acetate Into a 50 mL round bottom flask containing a well-stirred solution of 3-[3-methyl-2-oxo-5-(4-piperidyl)benzo[d]imidazol-1-yl]piperidine-2,6-dione (500 mg, 733.98 μmol) in DMF (5 mL) was added triethylamine (371.36 mg, 3.67 mmol, 511.51 μL). The mixture was cooled to 0° C., and tert-butyl bromoacetate (186.12 mg, 954.18 μmol, 139.94 μL) was added. The reaction mixture was stirred at ambient temperature for 16 h. The reaction was quenched with water (15 mL) and the precipitate was collected by filtration, washed with water (15 mL), and dried under reduced pressure to afford tert-butyl 2-[4-[1-(2,6-dioxo-3-piperidyl)-3-methyl-2-oxo-benzimidazol-5-yl]-1-piperidyl]acetate (270 mg, 560.54 μmol, 76% yield) as a pink solid. LCMS (ES+): 456.9 $[M+H]^+$ Step 8: 2-(4-(1-(2,6-dioxopiperidin-3-yl)-3-methyl-2-oxo-2,3-dihydro-1H-benzo[d]imidazol-5-yl)piperidin-1-yl)acetic acid Into a 25 mL round bottom flask containing a well-stirred solution of tert-butyl 2-[4-[1-(2,6-dioxo-3-piperidyl)-3-methyl-2-oxo-benzimidazol-5-yl]-1-piperidyl]acetate (300 mg, 657.13 μmol) in DCM (3 mL) was added TFA (224.78 mg, 1.97 mmol, 151.88 μL) dropwise at 0° C. The reaction mixture was stirred at room temperature for 3 h. The volatiles were removed under reduced pressure and the residue was triturated with diethyl ether (2×10 mL) to yield 2-(4-(1-(2,6-dioxopiperidin-3-yl)-3-methyl-2-oxo-2,3-dihydro-1H-benzo[d]imidazol-5-yl)piperidin-1-yl)acetic acid (280 mg, 622.34 μmol, 95% yield) as a light brown solid. LCMS (ES+): 401.3 $[M+H]^+$ Synthesis of (3-amino-2,6-difluorophenyl)(5-bromo-1H-pyrrolo[2,3-b]pyridin-3-yl)methanone

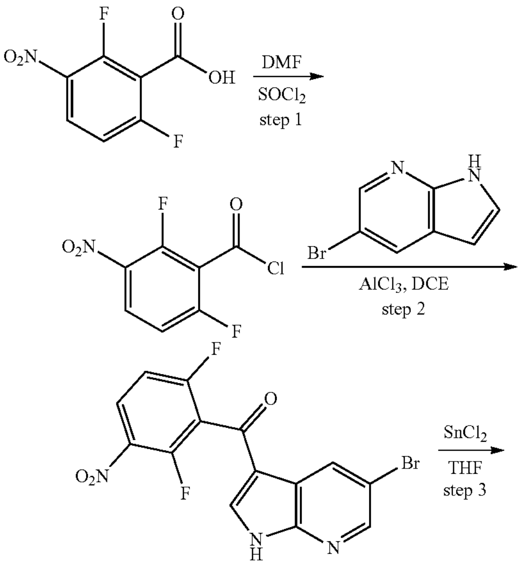

-continued

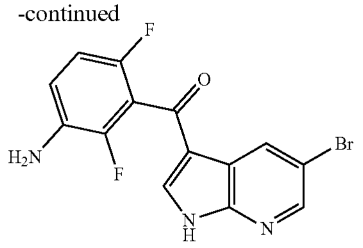

Step 1: To a solution of 2,6-difluoro-3-nitrobenzoic acid (230 g, 1.13 mol, 1.00 eq) in $SOCl_2$ (1.04 kg, 8.72 mol, 632 mL, 7.70 eq) was added dropwise DMF (8.28 g, 113 mmol, 8.71 mL, 0.10 eq). The mixture was stirred at 75° C. for 8 h. The reaction mixture was concentrated under vacuum to give 2,6-difluoro-3-nitrobenzoyl chloride (245 g, crude) as yellow oil.

Step 2: To a solution of 5-bromo-1H-pyrrolo[2,3-b]pyridine (177 g, 902 mmol, 1.00 eq) in DCE (1.10 L) was added $AlCl_3$ (481 g, 3.61 mol, 197 mL, 4.00 eq), and drop-wise 2,6-difluoro-3-nitrobenzoyl chloride (200 g, 902 mmol, 1.00 eq) in DCE (600 mL), the mixture was stirred at 50° C. for 4 h. Water (6.00 L) was poured into the reaction mixture and filtered, the filter cake was triturated with petroleum ether/ethyl acetate=5/1 (4.00 L) at 15° C. for 30 min. The slurry was filtered and the filter cake was dried over vacuum oven to give (5-bromo-1H-pyrrolo[2,3-b]pyridin-3-yl)(2,6-difluoro-3-nitrophenyl)methanone (350 g, crude) as a yellow solid.

Step 3: To a solution of (5-bromo-1H-pyrrolo[2,3-b]pyridin-3-yl)(2,6-difluoro-3-nitrophenyl)methanone (200 g, 523 mmol, 1.00 eq) in THF (2.00 L) was added $SnCl_2 \cdot 2H_2O$ (354 g, 1.57 mol, 3.00 eq), the mixture was stirred at 90° C. for 3 h. The reaction mixture was poured into 20% $K_2CO_3$ aqueous solution (9.00 L) and extracted with ethyl acetate (3×5.00 L). The combined organic layer was washed with brine (5.00 L), dried over sodium sulphate, filtered and concentrated. The crude residue was triturated with ethyl acetate (1.50 L) at 25° C. for 1 h, then filtered, the filter cake dissolve in DMSO (400 mL), then added dropwise to water (1.50 L) at 25° C., filtered, the filter cake was triturated with water (1.50 L) at 25° C. for 3 hr, filtered, the filter cake dry for 8 hours at 50° C. in the drying oven and grind again to give (3-amino-2,6-difluorophenyl)(5-bromo-1H-pyrrolo[2,3-b]pyridin-3-yl)methanone (100 g, 53.1% yield) as yellow solid. $^1H$ NMR (400 MHz, DMSO): δ 12.62-13.43 (m, 1H), 8.55 (br d, J=1.22 Hz, 1H), 8.49 (d, J=2.20 Hz, 1H), 8.14 (s, 1H), 6.85-7.00 (m, 2H), 5.21 (s, 2H).

Example 1

N-[3-[5-[2-[4-[2-[4-[4-[(2,6-dioxo-3-piperidyl) amino]phenyl]-1-piperidyl]acetyl]piperazin-1-yl] pyrimidin-5-yl]-1H-pyrrolo[2,3-b]pyridine-3-carbonyl]-2,4-difluoro-phenyl]propane-1-sulfonamide

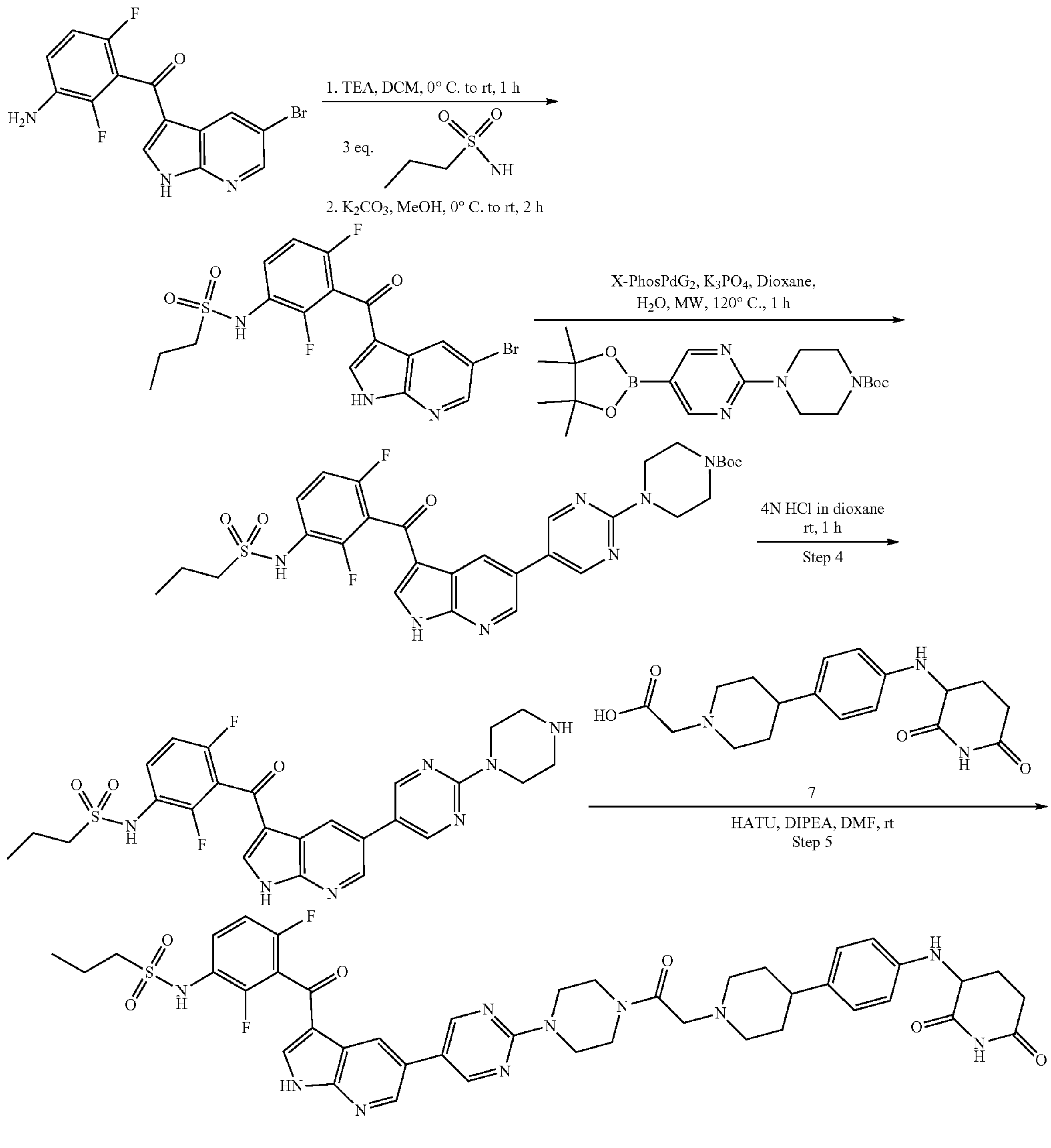

Step 1/2: To a stirred solution of (3-amino-2,6-difluoro-phenyl)-(5-bromo-1H-pyrrolo[2,3-b]pyridin-3-yl)methanone (600 mg, 1.70 mmol) in DCM (10 mL) at 0° C. were added triethylamine (862.09 mg, 8.52 mmol, 1.19 mL), DMAP (10.41 mg, 85.20 μmol) and propane-1-sulfonyl chloride (728.95 mg, 5.11 mmol, 573.98 μL). The reaction mixture was stirred at room temperature for 30 minutes. The reaction mixture was diluted with water (10 mL) and extracted with ethyl acetate (2×30 mL). The combined organic layers were dried over sodium sulphate, filtered and concentrated under vacuum to afford N-[3-(5-bromo-1-propyl sulfonyl-pyrrolo[2,3-b]pyridine-3-carbonyl)-2,4-difluoro-phenyl]-N-propyl sulfonyl-propane-1-sulfonamide (600 mg, 662.13 μmol, 38.86% yield) as brown liquid. This intermediate was taken forward for selective deprotection of sulfonamide by using methanol (10 mL) and $K_2CO_3$ (246.96 mg, 1.79 mmol) at room temperature for 2 h. After completion, the reaction mixture was diluted with water (10 mL) and extracted with ethyl acetate (2×30 mL). The combined organic layers were dried over sodium sulphate, filtered and concentrated under vacuum. The crude was purified by silica gel column compound eluted with 30% ethyl acetate in petroleum ether to get N-[3-(5-bromo-1H-pyrrolo[2,3-b]pyridine-3-carbonyl)-2,4-difluoro-phenyl]propane-1-sulfonamide (200 mg, 353.50 μmol, 39.51% yield) as brown solid. LCMS (ESI+): 458.0 [M+H]$^+$.

Step 3: A solution of N-[3-(5-bromo-1H-pyrrolo[2,3-b]pyridine-3-carbonyl)-2,4-difluoro-phenyl]propane-1-sulfonamide (100 mg, 218.21 μmol) in dioxane (2 mL) and, water (0.5 mL) was taken in a microwave vial and added tert-butyl 4-[5-(4,4,5,5-tetramethyl-1,3,2-dioxaborolan-2-yl)pyrimidin-2-yl]piperazine-1-carboxylate (93.68 mg, 240.03 μmol) mixture was taken in a microwave vial and added and potassium phosphate tribasic anhydrous (46.32 mg, 218.21 μmol) at room temperature under nitrogen. The reaction mixture was degassed with nitrogen for 10 min, then added XPhosPdG2 (171.69 mg, 218.21 μmol) at same temperature. The reaction mixture was irradiated under microwave at 120° C. for 1 h. After completion, reaction mixture was diluted with water (30 mL) and extracted with ethyl acetate (3×50 mL). The combined organic layers were dried over sodium sulphate, filtered and concentrated under reduced pressure to get crude product. The obtained crude product was further purified by silica gel column chromatography with 50% ethyl acetate in petroleum ether as a eluent to afford tert-butyl 4-[5-[3-[2,6-difluoro-3-(propyl sulfonylamino)benzoyl]-1H-pyrrolo[2,3-b]pyridin-5-yl]pyrimidin-2-yl]piperazine-1-carboxylate (50 mg, 39.74 μmol, 18.21% yield) as brown solid. LCMS (ESI+): 642.2 [M+H]$^+$.

Step 4: To a stirred solution of tert-butyl 4-[5-[3-[2,6-difluoro-3-(propylsulfonylamino)benzoyl]-1H-pyrrolo[2,3-b]pyridin-5-yl]pyrimidin-2-yl]piperazine-1-carboxylate (50 mg, 77.92 μmol) in DCM (2 mL) at 0° C. was added 4 M HCl solution in 1,4-dioxane (2.84 mg, 77.92 μmol, 3.55 μL). The reaction mixture was stirred at room temperature for 1 h. The reaction mixture was concentrated under reduced pressure to get crude product N-[2,4-difluoro-3-[5-(2-piperazin-1-ylpyrimidin-5-yl)-1H-pyrrolo[2,3-b]pyridine-3-carbonyl]phenyl]propane-1-sulfonamide (45 mg, 53.72 μmol, 68.94% yield) as pale yellow solid. LCMS (ESI+): 542.2 [M+H]$^+$.

Step 5: Target compound was prepared via PyBOP mediated acid-amine coupling reaction (procedure D). Amide coupling was carried out using N-[2,4-difluoro-3-[5-(2-piperazin-1-ylpyrimidin-5-yl)-1H-pyrrolo[2,3-b]pyridine-3-carbonyl]phenyl]propane-1-sulfonamide (45 mg, 83.09 μmol), 2-[4-[4-[(2,6-dioxo-3-piperidyl)amino]phenyl]-1-piperidyl]acetic acid (28.70 mg, 83.09 μmol) and PyBOP (64.86 mg, 124.64 and N,N-Diisopropylethylamine 53.69 mg, 415.46 μmol, 72.36 μL) to afford N-[3-[5-[2-[4-[2-[4-[4-[(2,6-dioxo-3-piperidyl)amino]phenyl]-1-piperidyl]acetyl]piperazin-1-yl]pyrimidin-5-yl]-1H-pyrrolo[2,3-b]pyridine-3-carbonyl]-2,4-difluoro-phenyl]propane-1-sulfonamide (5 mg, 5.52 μmol, 6.64% yield) as pale green solid. LCMS (ESI+): 869.2 [M+H]$^{30}$. $^1$H NMR (400 MHz, DMSO-d6): δ 13.00 (s, 1H), 10.77 (s, 1H), 8.81 (s, 2H), 8.68 (s, 1H), 8.23 (s, 1H), 8.59 (s, 1H), 7.59 (q, J=8.92 Hz, 1H), 7.28 (t, J=8.72 Hz, 1H), 6.96 (d, J=8.28 Hz, 2H), 6.61 (d, J=8.32 Hz, 2H), 5.65 (d, J=7.44 Hz, 1H), 4.29-4.23 (m, 1H), 3.89-3.59 (m, 8H), 3.12 (t, J=7.72 Hz, 3H), 2.96 (d, J=10.16 Hz, 2H), 2.78-2.67 (m, 3H), 2.37-2.31 (m, 1H), 2.15-2.09 (m, 3H), 1.91-1.81 (m, 4H), 1.77-1.59 (m, 4H), 0.97 (t, J=7.44 Hz, 3H).

Example 2

N-[3-[5-[2-[4-[2-[4-[4-[(2,6-dioxo-3-piperidyl)oxy]phenyl]-1-piperidyl]acetyl]piperazin-1-yl]pyrimidin-5-yl]-1H-pyrrolo[2,3-b]pyridine-3-carbonyl]-2,4-difluoro-phenyl]propane-1-sulfonamide

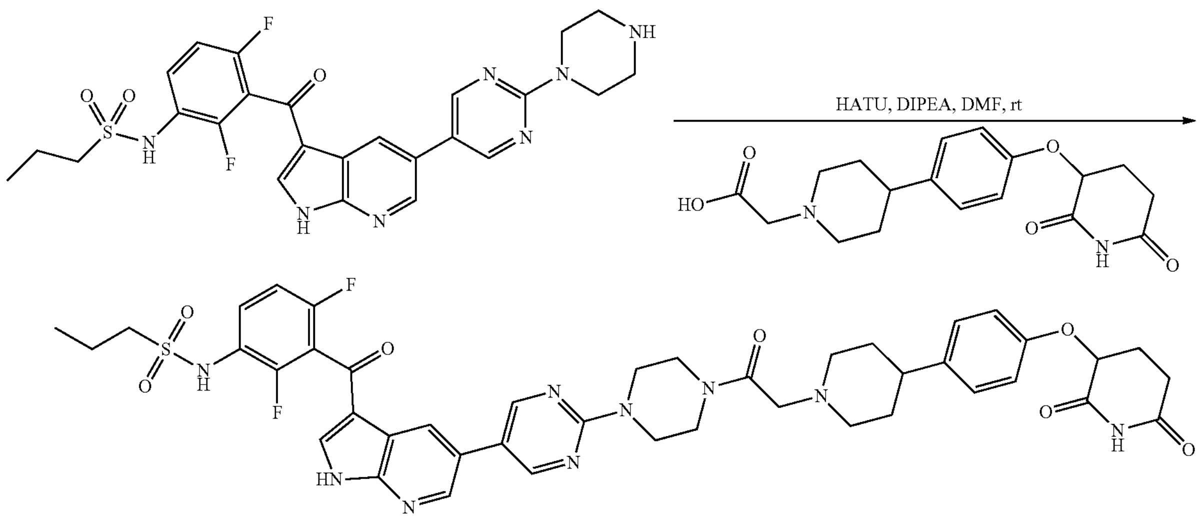

Target compound was prepared via HATU mediated acid-amine coupling reaction (procedure A). Amide coupling was carried out using a solution of N-[2,4-difluoro-3-[5-(2-piperazin-1-ylpyrimidin-5-yl)-1H-pyrrolo[2,3-b]pyridine-3-carbonyl]phenyl]propane-1-sulfonamide (25 mg, 46.16 μmol), 2-[4-[4-[(2,6-dioxo-3-piperidyl)oxy]phenyl]-1-piperidyl]acetic acid (15.99 mg, 46.16 μmol), HATU (26.33 mg, 69.24 μmol), and N,N-Diisopropylethylamine (29.83 mg, 230.81 μmol, 40.20 μL) to afford N-[3-[5-[2-[4-[2-[4-[4-[(2,6-dioxo-3-piperidyl)oxy]phenyl]-1-piperidyl]acetyl]piperazin-1-yl]pyrimidin-5-yl]-1H-pyrrolo[2,3-b]pyridine-3-carbonyl]-2,4-difluoro-phenyl]propane-1-sulfonamide (4 mg, 4.50 μmol, 9.76% yield) as off white solid. LCMS (ESI+): 870.2 [M+H]$^+$. $^1$H NMR (400 MHz, DMSO-$d_6$): δ 13.00 (s, 1H), 10.91 (s, 1H), 8.82 (s, 2H), 8.68 (s, 1H), 8.60 (s, 1H), 8.23 (s, 1H), 7.62-7.56 (m, 1H), 7.28 (t, J=7.60 Hz, 1H), 7.17 (d, J=8.80 Hz, 2H), 6.94 (d, J=8.80 Hz, 2H), 5.17-5.13 (m, 1H), 3.90-3.60 (m, 8H), 3.33-3.25 (m, 2H), 3.13 (t, J=2.00 Hz, 2H), 2.98 (d, J=10.80 Hz, 2H), 2.76-2.62 (m, 4H), 2.19-2.12 (m, 4H), 1.78-1.63 (m, 6H), 0.97 (t, J=7.60 Hz, 3H).

Example 3

N-[3-[5-[6-[4-[2-[4-[4-[(2,6-dioxo-3-piperidyl) amino]phenyl]-1-piperidyl]acetyl]piperazin-1-yl]-3-pyridyl]-1H-pyrrolo[2,3-b]pyridine-3-carbonyl]-2,4-difluoro-phenyl]propane-1-sulfonamide

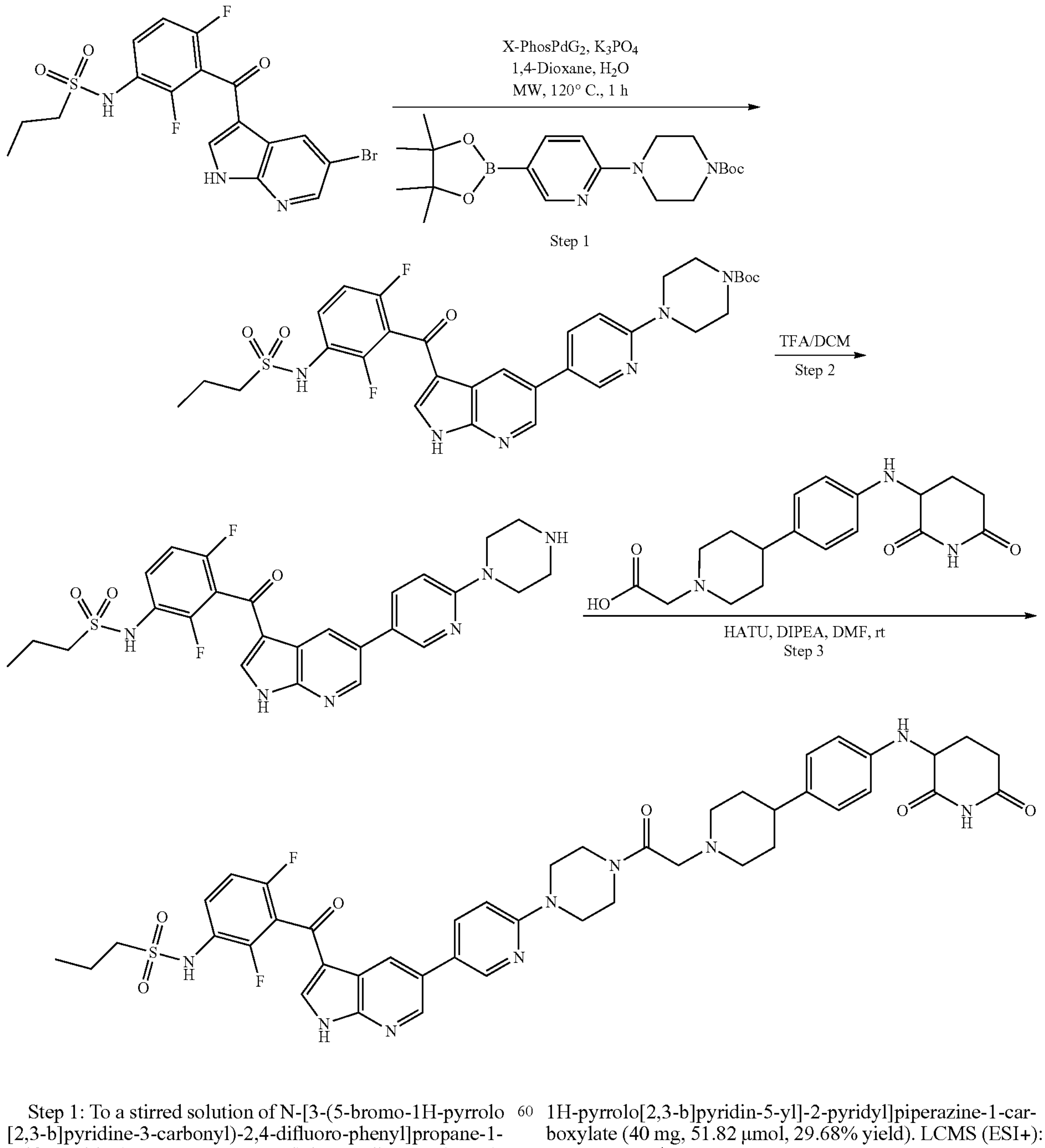

Step 1: To a stirred solution of N-[3-(5-bromo-1H-pyrrolo[2,3-b]pyridine-3-carbonyl)-2,4-difluoro-phenyl]propane-1-sulfonamide (80 mg, 174.57 μmol) in 1,4-dioxane (2 mL), water (0.5 mL) were added tert-butyl 4-[5-(4,4,5,5-tetramethyl-1,3,2-dioxaborolan-2-yl)-2-pyridyl]piperazine-1-carboxylate (74.75 mg, 192.02 μmol) and potassium phosphate tribasic anhydrous (37.05 mg, 174.57 μmol). The reaction mixture was degassed for 20 minutes and Xphos Pd G2 (6.87 mg, 8.73 μmol) was added. The reaction mixture was irradiated under microwave at 120° C. for 1 h. The reaction mixture was diluted with water (5 mL) and extracted with ethyl acetate (2×20 mL). The combined organic layers were dried over sodium sulphate, filtered and concentrated under vacuum to get crude product. The crude was purified by silica gel column chromatography compound eluted with 50% ethyl acetate in petroleum ether to afford tert-butyl 4-[5-[3-[2,6-difluoro-3-(propyl sulfonyl amino)benzoyl]-1H-pyrrolo[2,3-b]pyridin-5-yl]-2-pyridyl]piperazine-1-carboxylate (40 mg, 51.82 μmol, 29.68% yield). LCMS (ESI+): 641.2 $[M+H]^+$.

Step 2: To a stirred solution of tert-butyl 4-[5-[3-[2,6-difluoro-3-(propyl sulfonylamino)benzoyl]-1H-pyrrolo[2,3-b]pyridin-5-yl]-2-pyridyl]piperazine-1-carboxylate (40 mg, 62.43 μmol) in DCM (2 mL) at 0° C. was added Trifluoroacetic acid (7.12 mg, 62.43 μmol, 4.81 The reaction mixture was stirred at room temperature for 1 h. The reaction mixture was evaporated to get N-[2,4-difluoro-3-[5-(6-piperazin-1-yl-3-pyridyl)-1H-pyrrolo[2,3-b]pyridine-3-carbonyl]phenyl]propane-1-sulfonamide (40 mg, 51.94 μmol, 83.19% yield, trifluoroacetic acid salt) as brown gummy compound. LCMS (ESI+): 541.3 $[M+H]^+$.

Step 3: Target compound was prepared via PyBOP mediated acid-amine coupling reaction (procedure D). Amide coupling was carried out using N-[2,4-difluoro-3-[5-(6-piperazin-1-yl-3-pyridyl)-1H-pyrrolo[2,3-b]pyridine-3-carbonyl]phenyl]propane-1-sulfonamide (30 mg, 55.50 μmol), 2-[4-[4-[(2,6-dioxo-3-piperidyl)amino]phenyl]-1-piperidyl] acetic acid (19.17 mg, 55.50 μmol), PyBOP (43.32 mg, 83.24 μmol) and DIPEA (35.86 mg, 277.48 μmol, 48.33 μL) to afford N-[3-[5-[6-[4-[2-[4-[4-[(2,6-dioxo-3-piperidyl) amino]phenyl]-1-piperidyl]acetyl]piperazin-1-yl]-3-pyridyl]-1H-pyrrolo[2,3-b]pyridine-3-carbonyl]-2,4-difluoro-phenyl]propane-1-sulfonamide (5 mg, 5.59 μmol, 10.07% yield) as pale green colour solid. LCMS (ESI+): 868.3 $[M+H]^+$. $^1H$ NMR (400 MHz, DMSO-$d_6$): δ 13.00 (s, 1H), 10.92 (s, 1H), 8.68 (s, 1H), 8.54 (s, 2H), 8.19 (s, 1H), 7.99-7.97 (m, 1H), 7.62-7.56 (m, 1H), 7.28 (t, J=8.00 Hz, 1H), 7.04 (d, J=8.80 Hz, 1H), 6.96 (d, J=8.80 Hz, 2H), 6.61 (d, J=8.80 Hz, 2H), 5.66 (d, J=7.60 Hz, 1H), 4.35-4.26 (m, 1H), 3.74-3.60 (m, 8H), 3.34-3.23 (m, 2H), 3.14-3.10 (m, 2H), 2.95 (d, J=10.80 Hz, 2H), 2.74-2.56 (m, 3H), 2.33-2.33 (m, 1H), 2.14-2.08 (m, 2H), 1.84-1.60 (m, 8H), 0.97 (t, J=7.60 Hz, 3H).

Examples 5-10

General Scheme for Synthesis of Isopropyl-Sulfonamide Degraders with Pyrimidinylpiperazine Unit

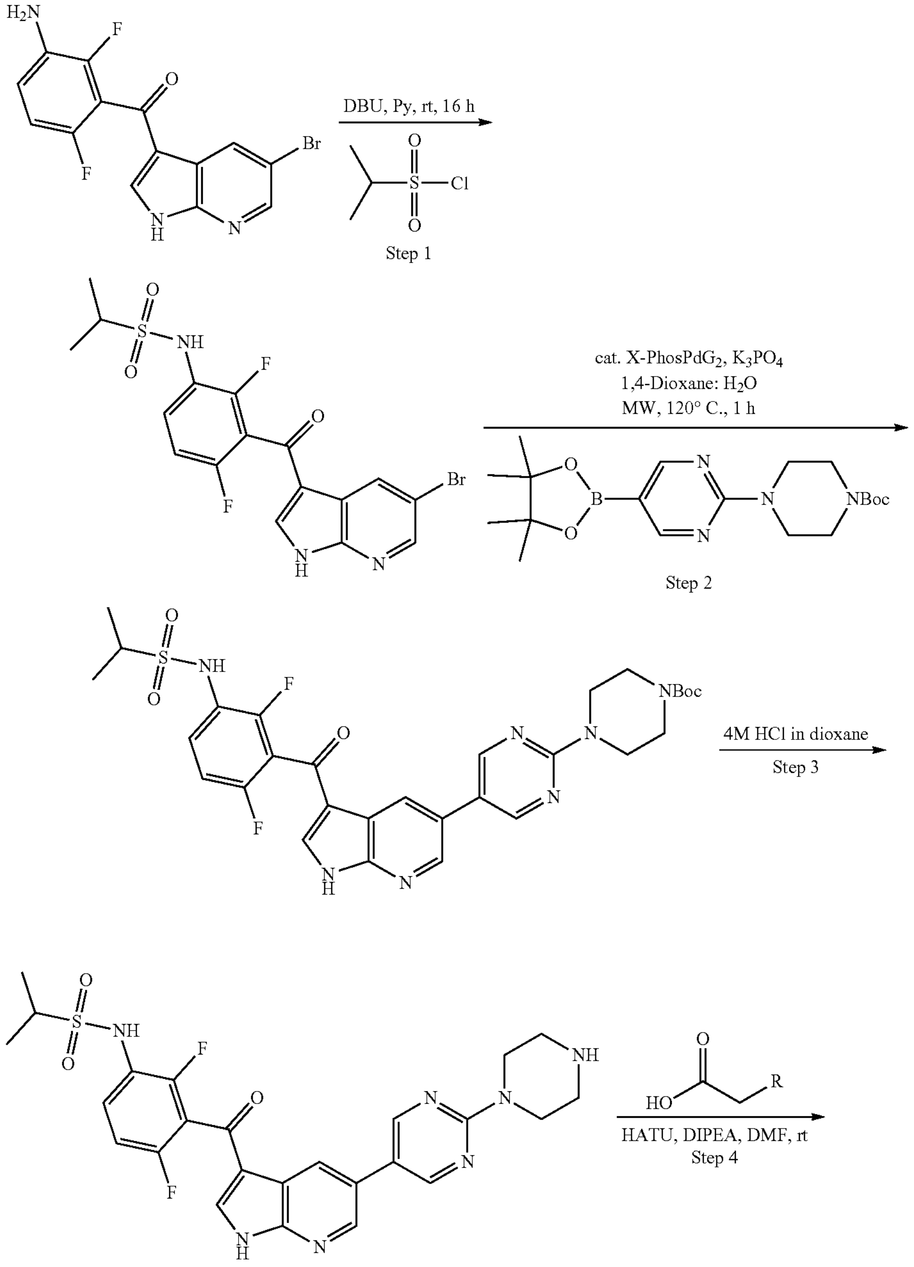

-continued

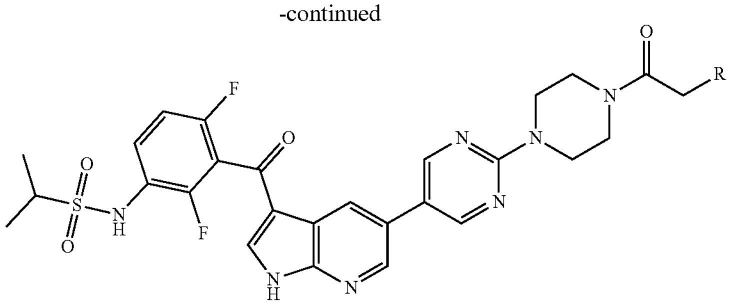

Examples 5-10

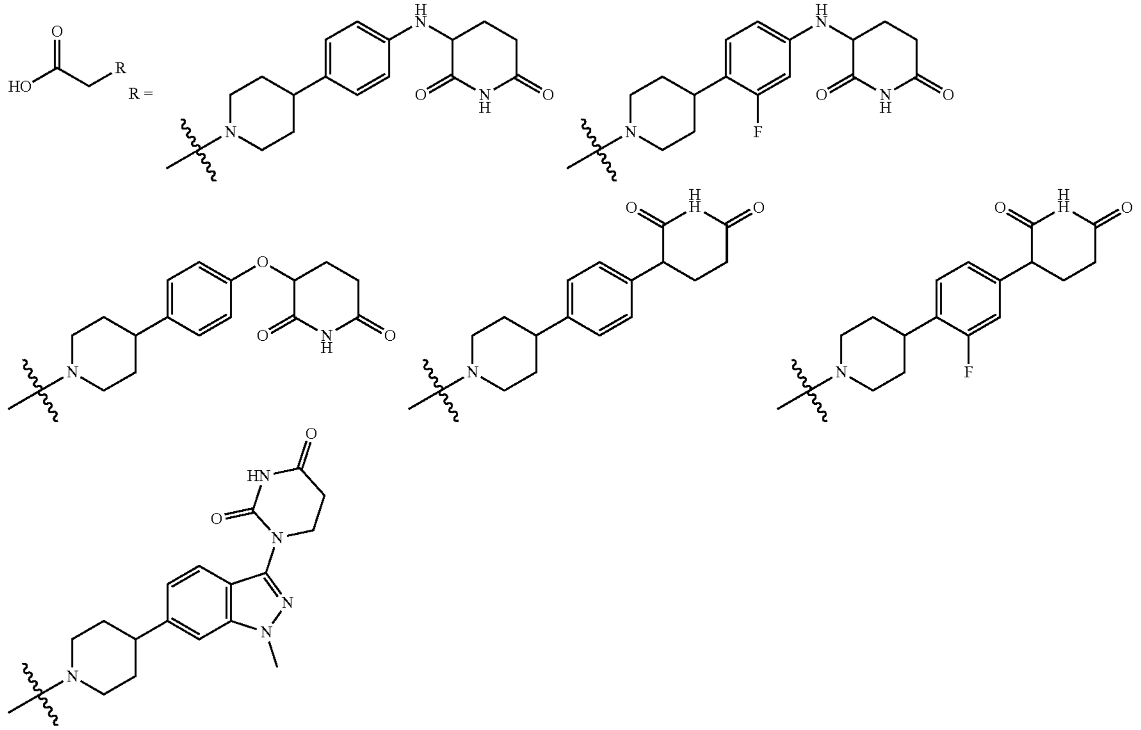

Synthesis of intermediate: N-[2,4-difluoro-3-[5-(6-piperazin-1-yl-3-pyridyl)-1H-pyrrolo[2,3-b]pyridine-3-carbonyl]phenyl]propane-2-sulfonamide Step 1: To a stirred solution of (3-amino-2,6-difluoro-phenyl)-(5-bromo-1H-pyrrolo[2,3-b]pyridin-3-yl)methanone (2.50 g, 7.10 mmol) in N,N-Dimethylformamide (25 mL) was added DBU at room temperature and continued stirring for 15 min at same temperature. Then reaction mixture was cooled to 0-5° C. with ice bath was added propane-2-sulfonyl chloride (5.06 g, 35.50 mmol, 3.99 mL) slowly to the reaction mixture and stirred at room temperature for 16 h. After completion, the reaction mixture was diluted with water (30 mL) and extracted with ethyl acetate (2×50 mL). The combined organic layers were washed with water, brine, dried over sodium sulphate and concentrated under reduced pressure. The crude product purified by silica gel column chromatography by using acetone in petroleum ether used as an eluent (0-50%) to afford N-[3-(5-bromo-1H-pyrrolo[2,3-b]pyridine-3-carbonyl)-2,4-difluoro-phenyl]propane-2-sulfonamide (1.5 g, 3.03 mmol, 42.64% yield) as pale yellow solid. LCMS (ESI+): 458.0 $[M+H]^+$.

Step 2: To a stirred solution of N-[3-(5-bromo-1H-pyrrolo[2,3-b]pyridine-3-carbonyl)-2,4-difluoro-phenyl]propane-2-sulfonamide (600.00 mg, 1.31 mmol) in 1,4-dioxane (12 mL) and water (3 mL) mixture was taken in a microwave vial and added tert-butyl 4-[5-(4,4,5,5,-tetramethyl-1,3,2-dioxaborolan-2-yl)-2-pyridyl]piperazine-1-carboxylate (560.65 mg, 1.44 mmol) and $K_3PO_4$ (833.73 mg, 3.93 mmol) at room temperature under nitrogen. The reaction mixture was degassed with nitrogen for 10 min, then added XPhos Pd G2 (51.51 mg, 65.46 μmol) at same temperature. The reaction mixture was heated to 120° C. for 1 h in microwave. After completion, reaction mixture was diluted with water (30 mL) product extracted by Ethyl acetate (3×50 mL). The combined organic layers were dried over sodium sulphate, filtered and concentrated under reduced pressure to get crude product. The obtained crude product was further purified by by silica gel column chromatography with 80% ethyl acetate in petroleum ether as a eluent to afford tert-tert-butyl 4-[5-[3-[2,6-difluoro-3-(isopropylsulfonylamino)benzoyl]-1H-pyrrolo[2,3-b]pyridin-5-yl]-2-pyridyl]piperazine-1-carboxylate (400 mg, 494.71 μmol, 37.79% yield) isolated by filtration. LCMS (ESI+): 642.2 $[M+H]^+$.

Step 3: To a stirred solution of tert-butyl 4-[5-[3-[2,6-difluoro-3-(isopropylsulfonylamino)benzoyl]-1H-pyrrolo[2,3-b]pyridin-5-yl]-2-pyridyl]piperazine-1-carboxylate (400.00 mg, 624.32 μmol) in 1,4-dioxane (2 mL) was added 4M HCl in 1,4-dioxane (3.20 g, 87.77 mmol, 4 mL) at 0-5° C. under nitrogen. The reaction mixture was stirred at room temperature for 3 h. After complete conversion of starting material, the reaction mixture was concentrated under reduced pressure to afford N-[2,4-difluoro-3-[5-(6-piperazin-1-yl-3-pyridyl)-1H-pyrrolo[2,3-b]pyridine-3-carbonyl]phenyl]propane-2-sulfonamide (400 mg, 595.24 μmol, 95.34% yield, hydrochloric acid salt) as a pale yellow solid. LCMS (ESI+): 543.0 $[M+H]^+$.

Example 5

N-[3-[5-[2-[4-[2-[4-[4-[(2,6-dioxo-3-piperidyl)amino]phenyl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide

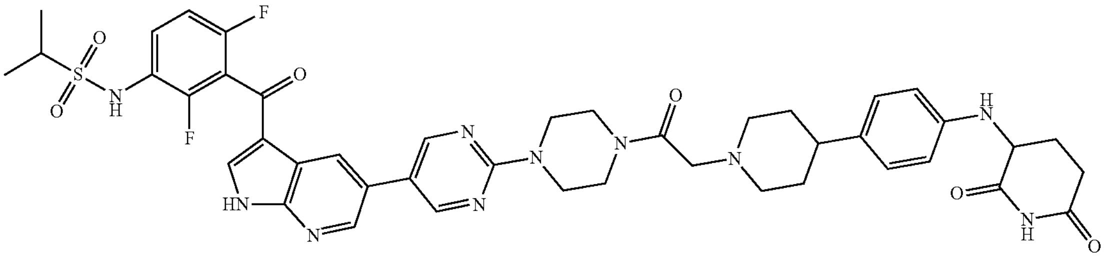 [SMILES: CC(C)S(=O)(=O)Nc1ccc(F)c(C(=O)c2c[nH]c3ncc(-c4cnc(N5CCN(C(=O)CN6CCC(c7ccc(NC8CCC(=O)NC8=O)cc7)CC6)CC5)nc4)cc23)c1F]

Target compound was prepared via HATU mediated acid-amine coupling reaction (procedure A). Amide coupling was carried out using N-[2,4-difluoro-3-[5-(2-piperazin-1-ylpyrimidin-5-yl)-1H-pyrrolo[2,3-b]pyridine-3-carbonyl]phenyl]propane-2-sulfonamide (30 mg, 51.90 μmol), 2-[4-[4-[(2,6-dioxo-3-piperidyl)amino]phenyl]-1-piperidyl]acetic acid (19.82 mg, 51.90 μmol), N,N-diisopropylethylamine (40.25 mg, 311.40 μmol, 54.24 μL) and HATU (23.68 mg, 62.28 μmol) to afford N-[3-[5-[2-[4-[2-[4-[4-[(2,6-dioxo-3-piperidyl)amino]phenyl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide (7.20 mg, 7.84 μmol, 15.10% yield) as green solid. LCMS (ESI+): 869.2 $[M+H]^+$. $^1H$ NMR (400 MHz, DMSO-$d_6$): δ 13.01 (s, 1H), 10.76 (s, 1H), 9.75 (s, 1H), 8.83 (s, 2H), 8.68 (s, 1H), 8.58 (s, 1H), 8.21 (s, 1H), 7.64-7.58 (m, 1H), 7.28 (t, J=8.40 Hz, 1H), 6.97 (d, J=8.40 Hz, 2H), 6.61 (d, J=8.40 Hz, 2H), 5.65 (d, J=7.60 Hz, 1H), 4.28-4.25 (m, 1H), 3.89-3.60 (m, 8H), 3.33-2.98 (m, 5H), 2.98-2.95 (m, 2H), 2.74-2.70 (m, 2H), 2.12-2.09 (m, 2H), 1.73-1.59 (m, 5H), 1.28 (d, J=6.80 Hz, 6H).

Example 6

N-[3-[5-[2-[4-[2-[4-[4-[(2,6-dioxo-3-piperidyl)amino]-2-fluoro-phenyl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide

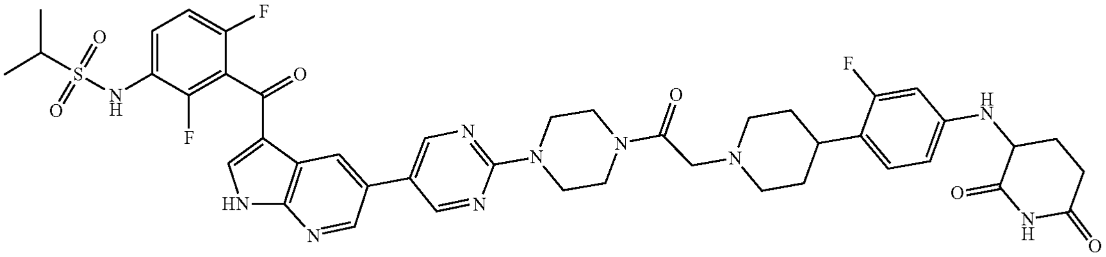 [SMILES: CC(C)S(=O)(=O)Nc1ccc(F)c(C(=O)c2c[nH]c3ncc(-c4cnc(N5CCN(C(=O)CN6CCC(c7ccc(NC8CCC(=O)NC8=O)cc7F)CC6)CC5)nc4)cc23)c1F]

Target compound was prepared via HATU mediated acid-amine coupling reaction (procedure A). Amide coupling was carried out using N-[2,4-difluoro-3-[5-(2-piperazin-1-ylpyrimidin-5-yl)-1H-pyrrolo[2,3-b]pyridine-3-carbonyl]phenyl]propane-2-sulfonamide (30 mg, 55.39 μmol), 2-[4-[4-[(2,6-dioxo-3-piperidyl)amino]-2-fluoro-phenyl]-1-piperidyl]acetic acid (22.15 mg, 55.39 μmol, hydrochloric acid salt), N,N-diisopropylethylamine (42.95 mg, 332.37 μmol, 57.89 μL) and HATU (25.28 mg, 66.47 μmol) to afford N-[3-[5-[2-[4-[2-[4-[4-[(2,6-dioxo-3-piperidyl)amino]-2-fluoro-phenyl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide (6.5 mg, 7.12 μmol, 12.85% yield) as green solid. LCMS (ESI+): 887.2 $[M+H]^+$. $^1H$ NMR (400 MHz, DMSO-$d_6$): δ 13.01 (s, 1H), 10.78 (s, 1H), 9.75 (s, 1H), 8.81 (s, 2H), 8.68 (s, 1H), 8.58 (s, 1H), 8.22 (s, 1H), 7.64-7.58 (m, 1H), 7.30-7.26 (m, 1H), 7.01 (t, J=8.40 Hz, 1H), 6.48-6.47 (m, 2H), 4.32-4.29 (m, 1H), 3.90-3.60 (m, 8H), 3.33-3.27 (m, 4H), 2.97 (s, 2H), 2.73-2.52 (m, 5H), 2.11-2.06 (m, 3H), 1.88-1.68 (m, 4H), 1.29 (d, J=6.80 Hz, 6H).

Example 7

N-[3-[5-[2-[4-[2-[4-[4-[(2,6-dioxo-3-piperidyl)oxy]phenyl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide

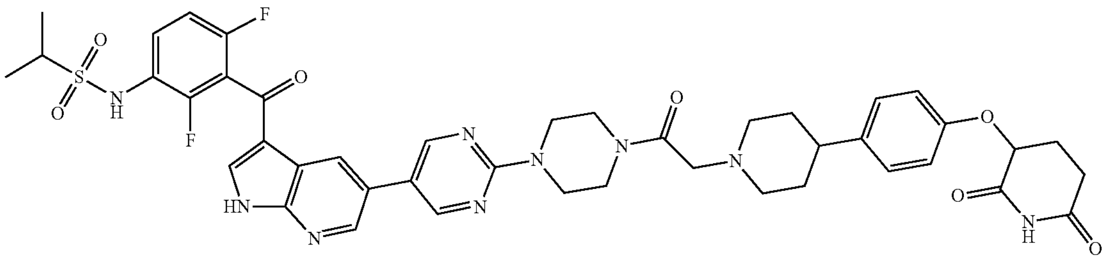 [SMILES: CC(C)S(=O)(=O)Nc1ccc(F)c(C(=O)c2c[nH]c3ncc(-c4cnc(N5CCN(C(=O)CN6CCC(c7ccc(OC8CCC(=O)NC8=O)cc7)CC6)CC5)nc4)cc23)c1F]

Target compound was prepared via HATU mediated acid-amine coupling reaction (procedure A). Amide coupling was carried out using N-[2,4-difluoro-3-[5-(2-piperazin-1-ylpyrimidin-5-yl)-1H-pyrrolo[2,3-b]pyridine-3-carbonyl]phenyl]propane-2-sulfonamide (30 mg, 51.90 μmol), 2-[4-[4-[(2,6-dioxo-3-piperidyl)oxy]phenyl]-1-piperidyl]acetic acid (19.87 mg, 51.90 μmol), HATU (23.68 mg, 62.28 μmol) and N,N-diisopropylethylamine to afford N-[3-[5-[2-[4-[2-[4-[4-[(2,6-dioxo-3-piperidyl)oxy]phenyl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide (16.0 mg, 16.41 μmol, 31.62% yield) as pale yellow solid. LCMS (ESI+): 870.2 $[M+H]^+$. $^1H$ NMR (400 MHz, DMSO-$d_6$): δ 13.01 (s, 1H), 10.91 (s, 1H), 9.81 (s, 1H), 8.81 (s, 2H), 8.68 (s, 1H), 8.58 (s, 1H), 8.22 (s, 1H), 7.63-7.58 (m, 1H), 7.28 (t, J=9.20 Hz, 1H), 7.17 (d, J=8.80 Hz, 2H), 6.94 (d, J=8.40 Hz, 2H), 5.17-5.13 (m, 1H), 3.67 (d, J=109.20 Hz, 8H), 3.33-2.90 (m, 3H), 2.74-0.69 (m, 3H), 2.57-2.53 (m, 2H), 2.20-2.10 (m, 4H), 1.76-1.75 (m, 4H), 1.29 (d, J=6.80 Hz, 6H).

Example 8

N-[3-[5-[2-[4-[2-[4-[4-(2,6-dioxo-3-piperidyl)phenyl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide

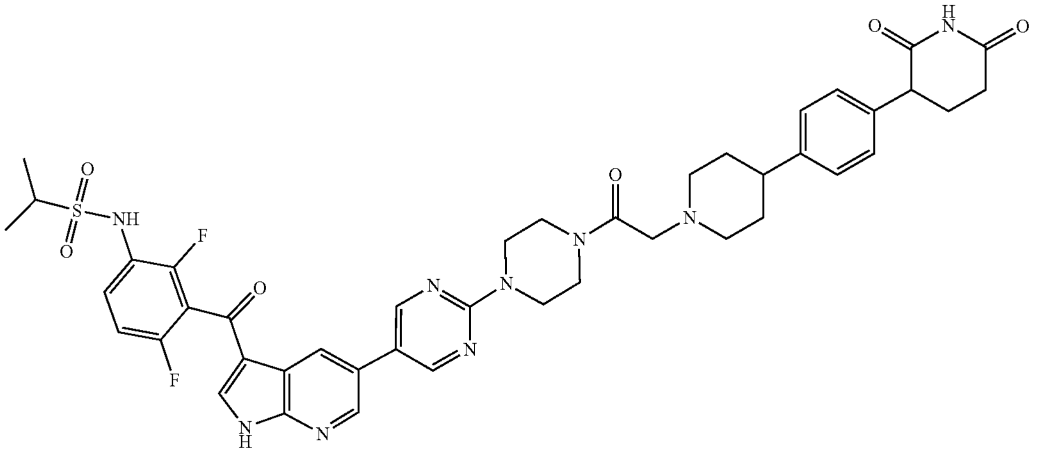 [SMILES: CC(C)S(=O)(=O)Nc1ccc(F)c(C(=O)c2c[nH]c3ncc(-c4cnc(N5CCN(C(=O)CN6CCC(c7ccc(C8CCC(=O)NC8=O)cc7)CC6)CC5)nc4)cc23)c1F]

Target compound was prepared via HATU mediated acid-amine coupling reaction (procedure A). Amide coupling was carried out using N-[2,4-difluoro-3-[5-(2-piperazin-1-ylpyrimidin-5-yl)-1H-pyrrolo[2,3-b]pyridine-3-carbonyl]phenyl]propane-2-sulfonamide (30 mg, 55.39 μmol), 2-[4-[4-(2,6-dioxo-3-piperidyl)phenyl]-1-piperidyl]acetic acid (20.32 mg, 55.39 μmol), HATU (25.28 mg, 66.47 μmol) and N,N-diisopropylethylamine (42.95 mg, 332.37 μmol, 57.89 μL) to afford N-[3-[5-[2-[4-[2-[4-[4-(2,6-dioxo-3-piperidyl)phenyl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide (8.0 mg, 9.08μ, 16.38% yield) as a green solid. LCMS (ESI+): 855.2 $[M+H]^+$. $^1H$ NMR (400 MHz, DMSO-$d_6$): δ 12.87 (s, 1H), 10.75 (s, 1H), 9.69 (s, 1H), 8.74 (s, 2H), 8.61 (s, 1H), 8.49 (s, 1H), 8.13 (s, 1H), 7.56-7.50 (m, 1H), 7.20-7.06 (m, 5H), 3.82-3.52 (m, 8H), 3.15-3.26 (m, 5H), 2.92-2.89 (m, 2H), 2.61-2.58 (m, 6H), 2.07 (t, J=11.24 Hz, 2H), 1.97-1.93 (m, 1H), 1.71-1.58 (m, 5H), 1.20 (d, J=6.28 Hz, 2H).

Example 9

N-[3-[5-[2-[4-[2-[4-[4-(2,6-dioxo-3-piperidyl)-2-fluoro-phenyl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide

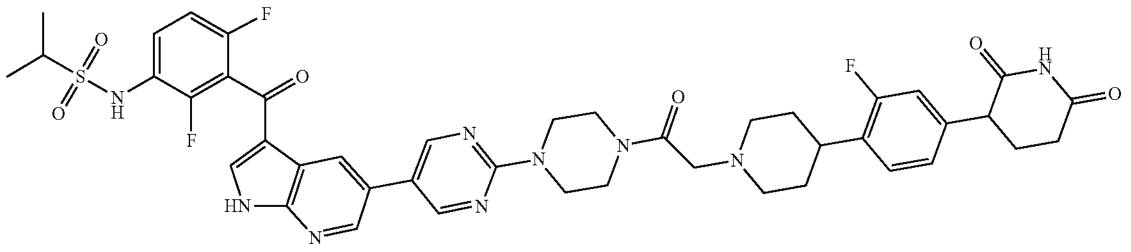 [SMILES: CC(C)S(=O)(=O)Nc1ccc(F)c(C(=O)c2c[nH]c3ncc(-c4cnc(N5CCN(C(=O)CN6CCC(c7ccc(C8CCC(=O)NC8=O)cc7F)CC6)CC5)nc4)cc23)c1F]

Target compound was prepared via HATU mediated acid-amine coupling reaction (procedure A). Amide coupling was carried out using N-[2,4-difluoro-3-[5-(2-piperazin-1-ylpyrimidin-5-yl)-1H-pyrrolo[2,3-b]pyridine-3-carbonyl]phenyl]propane-2-sulfonamide (30 mg, 55.39 μmol), 2-[4-[4-(2,6-dioxo-3-piperidyl)-2-fluoro-phenyl]-1-piperidyl]acetic acid (21.32 mg, 55.39 μmol), HATU (25.28 mg, 66.47 μmol) and N,N-diisopropylethylamine (42.95 mg, 332.37 μmol, 57.89 μL) to afford N-[3-[5-[2-[4-[2-[4-[4-(2,6-dioxo-3-piperidyl)-2-fluoro-phenyl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide (11.50 mg, 13.10 μmol, 23.65% yield) as pale yellow solid. LCMS (ESI+): 872.2 $[M+H]^+$. $^1H$ NMR (400 MHz, DMSO-d6): δ 13.01 (s, 1H), 10.84 (s, 1H), 9.75 (s, 1H), 8.81 (s, 2H), 8.68 (s, 1H), 8.57 (s, 1H), 8.22 (s, 1H), 7.64-7.58 (m, 1H), 7.33-7.26 (m, 2H), 7.06-7.02 (m, 2H), 3.86-3.38 (m, 9H), 3.33-3.27 (m, 4H), 3.00 (d, J=8.40 Hz, 2H), 2.69-2.62 (m, 3H), 2.24-2.18 (m, 3H), 1.29 (s, 4H), 1.26 (d, J=14.80 Hz, 6H).

Example 10

N-[3-[5-[2-[4-[2-[4-[3-(2,4-dioxohexahydropyrimidin-1-yl)-1-methyl-indazol-6-yl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide

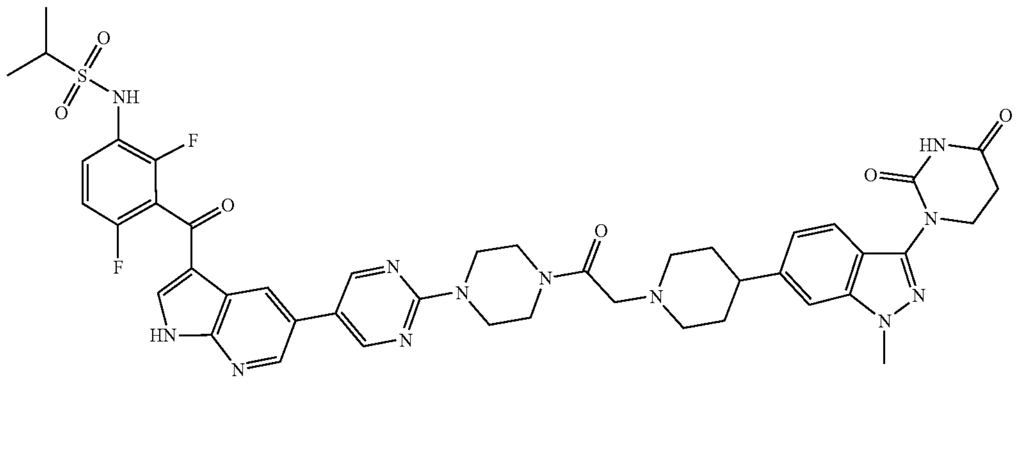 [SMILES: CC(C)S(=O)(=O)Nc1ccc(F)c(C(=O)c2c[nH]c3ncc(-c4cnc(N5CCN(C(=O)CN6CCC(c7ccc8c(N9CCC(=O)NC9=O)nn(C)c8c7)CC6)CC5)nc4)cc23)c1F]

Target compound was prepared via HATU mediated acid-amine coupling reaction (procedure A). Amide coupling was carried out using N-[2,4-difluoro-3-[5-(2-piperazin-1-ylpyrimidin-5-yl)-1H-pyrrolo[2,3-b]pyridine-3-carbonyl]phenyl]propane-2-sulfonamide (100 mg, 173.00 μmol), 2-[4-[3-(2,4-dioxohexahydropyrimidin-1-yl)-1-methyl-indazol-6-yl]-1-piperidyl]acetic acid (73.34 mg, 173.85 μmol), N,N-diisopropylethylamine (134.15 mg, 1.04 mmol, 180.80 μL) and HATU (79.35 mg, 207.60 μmol) to afford N-[3-[5-[2-[4-[2-[4-[3-(2,4-dioxohexahydropyrimidin-1-yl)-1-methyl-indazol-6-yl]-1-piperidyl]acetyl]piperazin-1-yl]pyrimidin-5-yl]-1H-pyrrolo[2,3-b]pyridine-3-carbonyl]-2,4-difluoro-phenyl]propane-2-sulfonamide (24 mg, 25.69 μmol, 14.85% yield) as off-white solid. LCMS (ESI+): 909.0 $[M+H]^+$. $^1H$ NMR (400 MHz, DMSO-$d_6$): δ 13.01 (s, 1H), 10.55 (s, 1H), 9.76 (s, 2H), 8.82 (s, 2H), 8.69 (s, 1H), 8.58 (s, 1H), 8.22 (s, 1H), 7.64-7.55 (m, 2H), 7.46 (s, 1H), 7.29 (t, J=8.00 Hz, 1H), 7.06 (d, J=8.80 Hz, 1H), 3.89 (s, 3H), 3.83-3.37 (m, 10H), 3.30-3.32 (m, 3H), 3.03-3.02 (m, 2H), 2.68 (t, J=2.00 Hz, 2H), 2.34-2.08 (m, 2H), 1.83-1.76 (m, 4H), 1.26 (d, J=14.40 Hz, 6H).

Examples 11-15

General Scheme for Synthesis of isopropyl-sulfonamide Degraders with Pyridinyl-piperazine Unit

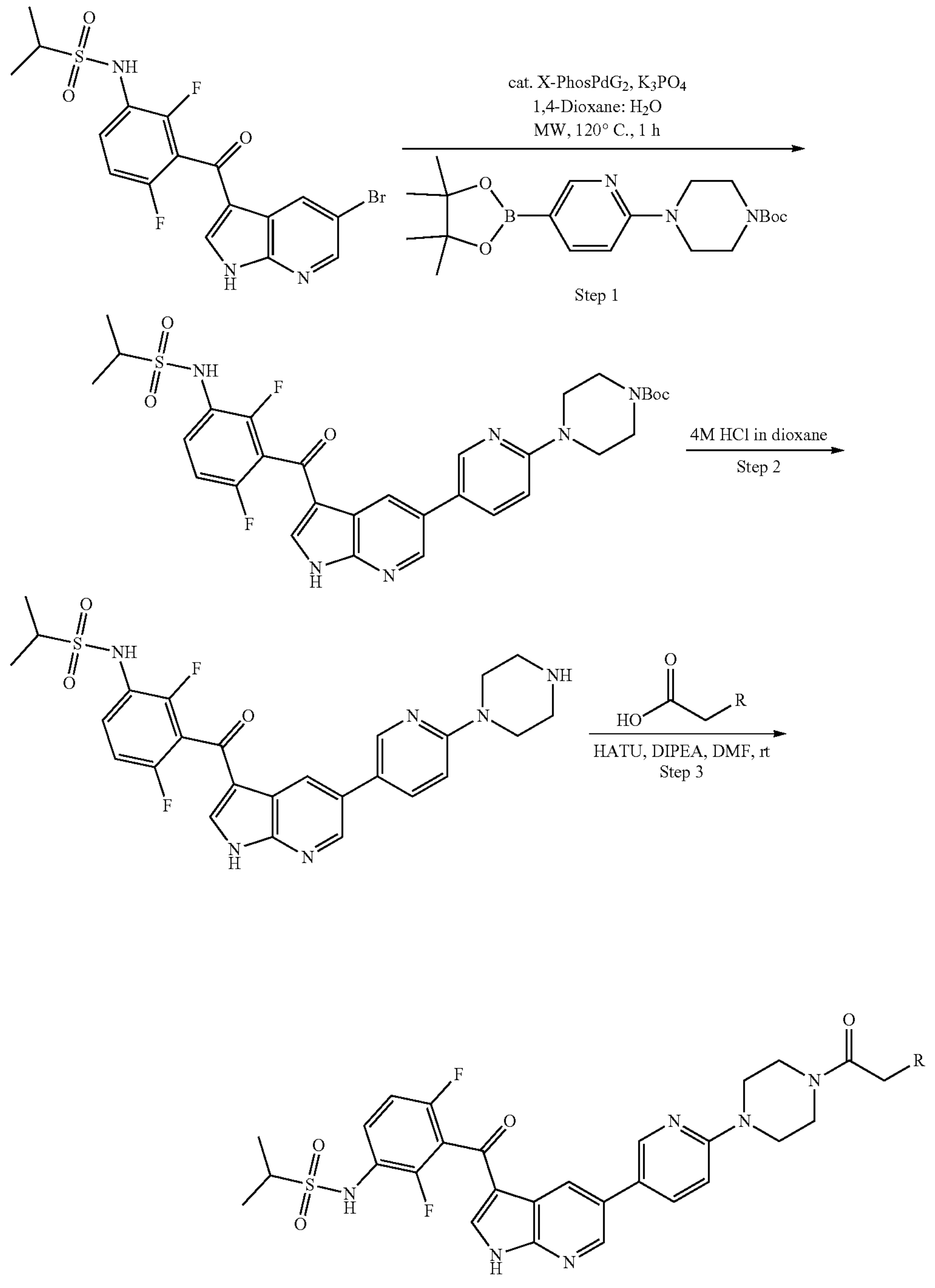

-continued

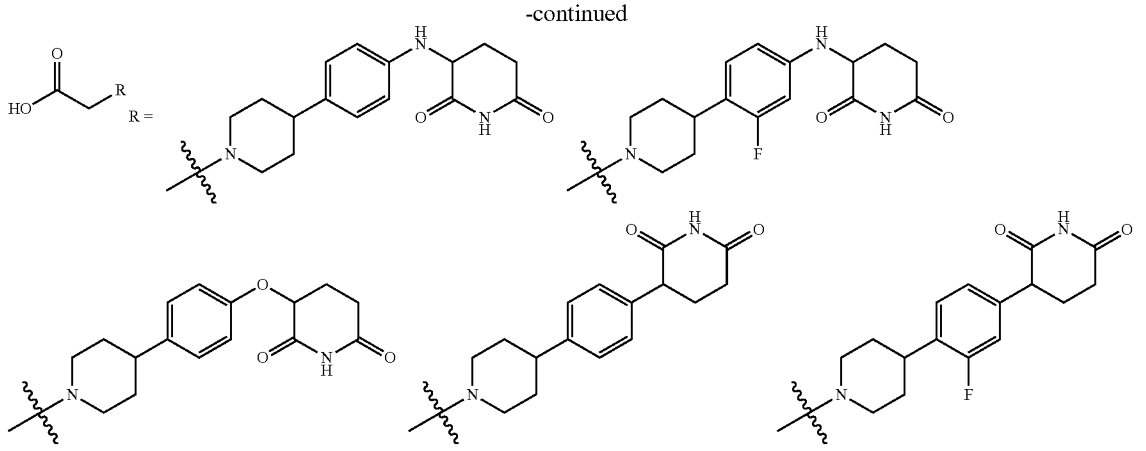

Synthesis of intermediate: N-[2,4-difluoro-3-[5-(6-piperazin-1-yl-3-pyridyl)-1H-pyrrolo[2,3-b]pyridine-3-carbonyl]phenyl]propane-2-sulfonamide Step 1: To a solution of N-[3-(5-bromo-1H-pyrrolo[2,3-b]pyridine-3-carbonyl)-2,4-difluoro-phenyl]propane-2-sulfonamide (600.00 mg, 1.31 mmol) in 1,4-dioxane (12 mL), water (3 mL) mixture was taken in a microwave vial and added tert-butyl 4-[5-(4,4,5,5-tetramethyl-1,3,2-dioxaborolan-2-yl)-2-pyridyl]piperazine-1-carboxylate (560.65 mg, 1.44 mmol), $K_3PO_4$ (833.73 mg, 3.93 mmol) at room temperature under nitrogen. The reaction mixture was degassed with nitrogen for 10 min, then added XPhos Pd G2 (51.51 mg, 65.46 μmol) at same temperature. The reaction mixture was heated to 120° C. for 1 h in microwave. Reaction diluted with water (30 mL) product extracted by ethyl acetate (3×50 mL). Ethyl acetate layer dried over sodium sulphate and concentrated under reduced pressure to get crude product. The crude product purified by silica gel column chromatography by using acetone in petroleum ether used as an eluent (0-50%) to afford tert-butyl 4-[5-[3-[2,6-difluoro-3-(isopropylsulfonylamino)benzoyl]-1H-pyrrolo[2,3-b]pyridin-5-yl]-2-pyridyl]piperazine-1-carboxylate (400 mg, 494.71 μmol, 37.79% yield). LCMS (ESI+): 641.2 $[M+]^+$.

Step 2: To a stirred solution of tert-butyl 4-[5-[3-[2,6-difluoro-3-(isopropylsulfonylamino)benzoyl]-1H-pyrrolo[2,3-b]pyridin-5-yl]-2-pyridyl]piperazine-1-carboxylate (400.00 mg, 624.32 μmol) in 1,4-dioxane (2 mL) was added hydrogen chloride 4M in 1,4-dioxane, 99% (3.20 g, 87.77 mmol, 4 mL) at 0-5° C. under nitrogen. The reaction mixture was stirred at room temperature for 3 h. After completion, the reaction mixture was concentrated under reduced pressure to afford N-[2,4-difluoro-3-[5-(6-piperazin-1-yl-3-pyridyl)-1H-pyrrolo[2,3]pyridine-3-carbonyl]phenyl]propane-2-sulfonamide (400 mg, 595.24 μmol, 95.34% yield, hydrochloric acid salt) as a pale yellow solid. LCMS (ESI+): 541.1 $[M+H]^+$.

Example 11

N-[3-[5-[6-[4-[2-[4-[4-[(2,6-dioxo-3-piperidyl)amino]phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide

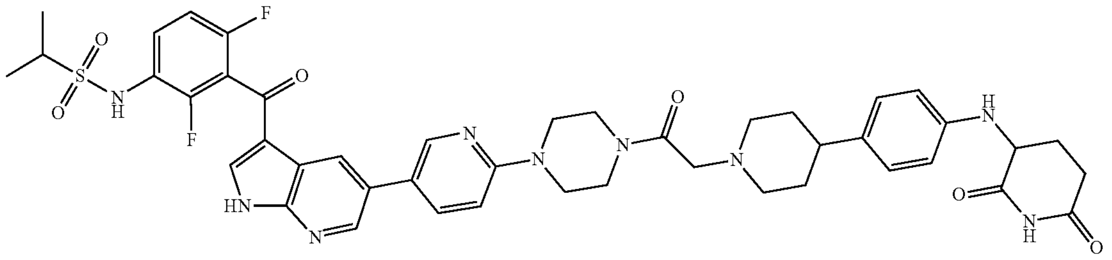 [SMILES: CC(C)S(=O)(=O)Nc1ccc(F)c(C(=O)c2c[nH]c3ncc(-c4ccc(N5CCN(C(=O)CN6CCC(c7ccc(NC8CCC(=O)NC8=O)cc7)CC6)CC5)nc4)cc23)c1F]

Target compound was prepared via HATU mediated acid-amine coupling reaction (procedure A). Amide coupling was carried out using N-[2,4-difluoro-3-[5-(6-piperazin-1-yl-3-pyridyl)-1H-pyrrolo[2,3]pyridine-3-carbonyl]phenyl]propane-2-sulfonamide (30 mg, 51.99 μmol), 2-[4-[3-[(2,6-dioxo-3-piperidyl)amino]phenyl]-1-piperidyl]acetic acid (19.85 mg, 51.99 μmol), N,N-diisopropylethylamine (40.31 mg, 311.93 μmol, 54.33 μL) and HATU (23.72 mg, 62.39 μmol) to afford N-[3-[5-[6-[4-[2-[4-[4-[(2,6-dioxo-3-piperidyl)amino]phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide (11.50 mg, 12.47 μmol, 23.99% yield) as green solid. LCMS (ESI+): 868.3 $[M+H]^+$. $^1H$ NMR (400 MHz, DMSO-d6): δ 13.00 (s, 1H), 10.76 (s, 1H), 8.68 (s, 1H), 8.52 (s, 2H), 8.19 (s, 1H), 7.99-7.96 (m, 1H), 7.62-7.58 (m, 1H), 7.27 (t, J=8.40 Hz, 1H), 7.04 (d, J=8.80 Hz, 1H), 6.96 (d, J=8.40 Hz, 2H), 6.61 (d, J=8.80 Hz, 2H), 5.65 (d, J=7.60 Hz, 1H), 4.20-4.32 (m, 1H), 3.74-3.60 (m, 8H), 3.33-3.23 (m, 3H), 2.96-2.93 (m, 2H), 2.74-2.67 (m, 2H), 2.59-2.52 (m, 3H), 2.14-2.08 (m, 3H), 1.76-1.57 (m, 4H), 1.28 (d, J=6.80 Hz, 6H).

Example 12

N-[3-[5-[6-[4-[2-[4-[4-[(2,6-dioxo-3-piperidyl) amino]-2-fluoro-phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide

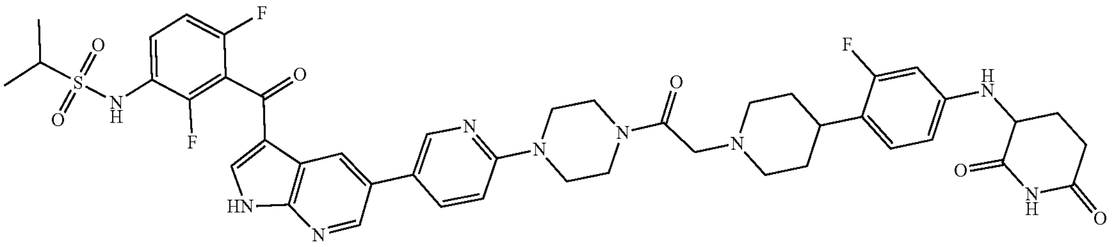 [SMILES: CC(C)S(=O)(=O)Nc1ccc(F)c(C(=O)c2c[nH]c3ncc(-c4ccc(N5CCN(C(=O)CN6CCC(c7ccc(NC8CCC(=O)NC8=O)cc7F)CC6)CC5)nc4)cc23)c1F]

Target compound was prepared via HATU mediated acid-amine coupling reaction (procedure A). Amide coupling was carried out using N-[2,4-difluoro-3-[5-(6-piperazin-1-yl-3-pyridyl)-1H-pyrrolo[2,3-b]pyridine-3-carbonyl]phenyl]propane-2-sulfonamide (30 mg, 55.50 μmol), 2-[4-[3-[(2,6-dioxo-3-piperidyl)amino]-2-fluoro-phenyl]-1-piperidyl] acetic acid (22.19 mg, 55.50 μmol), N,N-diisopropylethylamine (43.03 mg, 332.97 μmol, 58.00 μL) and HATU (25.32 mg, 66.59 μmol) to afford N-[3-[5-[6-[4-[2-[4-[4-[(2,6-dioxo-3-piperidyl)amino]-2-fluoro-phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide (8.0 mg, 8.73 μmol, 15.74% yield) as green solid. LCMS (ESI+): 886.3 $[M+H]^+$. $^1H$ NMR (400 MHz, DMSO-$d_6$): δ 12.97 (s, 1H), 10.78 (s, 1H), 9.75 (s, 1H), 8.68 (s, 1H), 8.53 (s, 2H), 8.19 (s, 1H), 7.99-7.99 (m, 1H), 7.64-7.58 (m, 1H), 7.30-7.26 (m, 1H), 7.05-6.98 (m, 2H), 6.47-6.43 (m, 2H), 6.01 (d, J=7.60 Hz, 1H), 4.32-4.29 (m, 1H), 3.73-3.60 (m, 9H), 3.34 (m, 2H), 2.98 (m, 2H), 2.74-2.58 (m, 3H), 2.11-2.06 (m, 2H), 1.92-1.76 (m, 6H), 1.28 (d, J=6.80 Hz, 6H).

Example 13

N-[3-[5-[6-[4-[2-[4-[4-[(2,6-dioxo-3-piperidyl)oxy] phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide

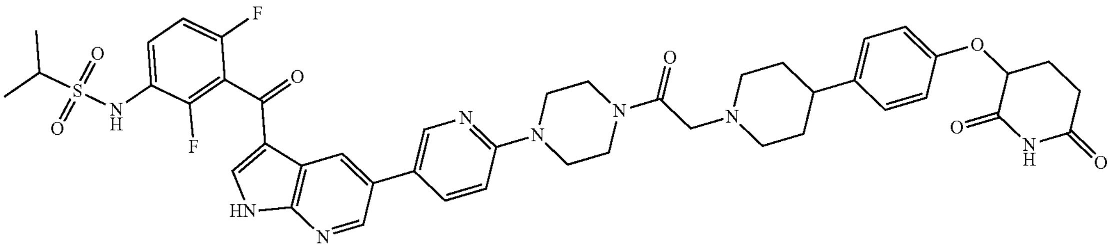 [SMILES: CC(C)S(=O)(=O)Nc1ccc(F)c(C(=O)c2c[nH]c3ncc(-c4ccc(N5CCN(C(=O)CN6CCC(c7ccc(OC8CCC(=O)NC8=O)cc7)CC6)CC5)nc4)cc23)c1F]

Target compound was prepared via HATU mediated acid-amine coupling reaction (procedure A). Amide coupling was carried out using N-[2,4-difluoro-3-[5-(6-piperazin-1-yl-3-pyridyl)-1H-pyrrolo[2,3-b]pyridine-3-carbonyl]phenyl]propane-2-sulfonamide (28.06 mg, 51.90 μmol), 2-[4-[3-[(2,6-dioxo-3-piperidyl)oxy]phenyl]-1-piperidyl]acetic acid (21.86 mg, 57.09 μmol), N,N-diisopropylethylamine (40.25 mg, 311.40 μmol, 54.24 μL) and HATU (23.68 mg, 62.28 μmol to afford N-[3-[5-[6-[4-[2-[4-[4-[(2,6-dioxo-3-piperidyl)oxy]phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide (2.90 mg, 3.25 μmol, 6.25% yield) as pale yellow solid. LCMS (ESI+): 869.2 $[M+H]^+$. $^1H$ NMR (400 MHz, DMSO-$d_6$): δ 12.97 (s, 1H), 10.92 (s, 1H), 9.77 (s, 1H), 8.68 (s, 1H), 8.53 (s, 2H), 8.20 (s, 1H), 8.00-7.97 (m, 1H), 7.64-7.58 (m, 1H), 7.28-7.30 (m, 1H), 7.26 (d, J=1.20 Hz, 2H), 7.17 (d, J=8.40 Hz, 1H), 7.04 (d, J=8.80 Hz, 2H), 5.17-5.13 (m, 1H), 3.74-3.39 (m, 8H), 3.30-3.25 (m, 2H), 2.97-2.71 (m, 3H), 2.68-2.60 (m, 3H), 2.19-2.10 (m, 4H), 1.76-1.75 (m, 4H), 1.28 (d, J=6.80 Hz, 6H).

Example 14

N-[3-[5-[6-[4-[2-[4-[4-(2,6-dioxo-3-piperidyl)phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide

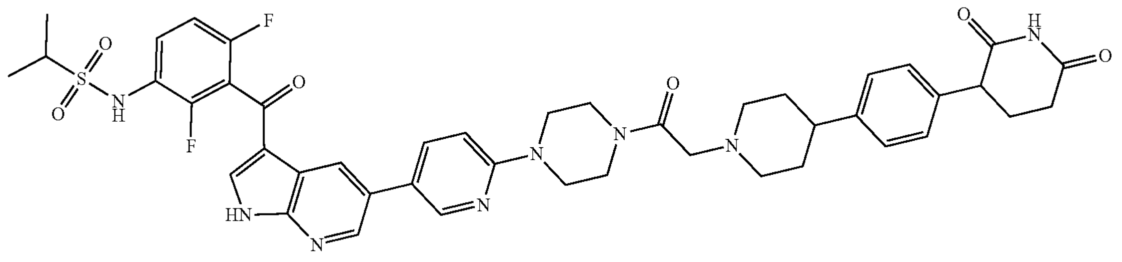 [SMILES: CC(C)S(=O)(=O)Nc1ccc(F)c(C(=O)c2c[nH]c3ncc(-c4ccc(N5CCN(C(=O)CN6CCC(c7ccc(C8CCC(=O)NC8=O)cc7)CC6)CC5)nc4)cc23)c1F]

Target compound was prepared via HATU mediated acid-amine coupling reaction (procedure A). Amide coupling was carried out using N-[2,4-difluoro-3-[5-(6-piperazin-1-yl-3-pyridyl)-1H-pyrrolo[2,3-b]pyridine-3-carbonyl]phenyl]propane-2-sulfonamide (30.00 mg, 55.50 μmol), 2-[4-[4-(2,6-dioxo-3-piperidyl)phenyl]-1-piperidyl]acetic acid (20.36 mg, 55.50 μmol), N,N-diisopropylethylamine (43.03 mg, 332.97 μmol, 58.00 μL) and HATU (25.32 mg, 66.59 μmol) to afford N-[3-[5-[6-[4-[2-[4-[4-(2,6-dioxo-3-piperidyl)phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide (8.60 mg, 9.89 μmol, 17.83% yield) as pale yellow solid. LCMS (ESI+): 853.0 $[M+H]^+$; $^1H$ NMR (400 MHz, DMSO-$d_6$): δ 10.81 (s, 1H), 8.66 (s, 1H), 8.51 (s, 2H), 8.13 (s, 1H), 7.98-7.95 (m, 1H), 7.58-7.54 (m, 1H), 7.23-7.13 (m, 5H), 7.03 (d, J=8.80 Hz, 1H), 3.83-3.60 (m, 7H), 3.33-3.20 (m, 6H), 3.18-3.16 (m, 2H), 2.65-2.61 (m, 2H), 2.17-2.12 (m, 3H), 2.04-2.00 (m, 1H), 1.87 (s, 1H), 1.79-1.65 (m, 4H), 1.24 (d, J=6.80 Hz, 6H).

Example 15

N-[3-[5-[6-[4-[2-[4-[4-(2,6-dioxo-3-piperidyl)-2-fluoro-phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide

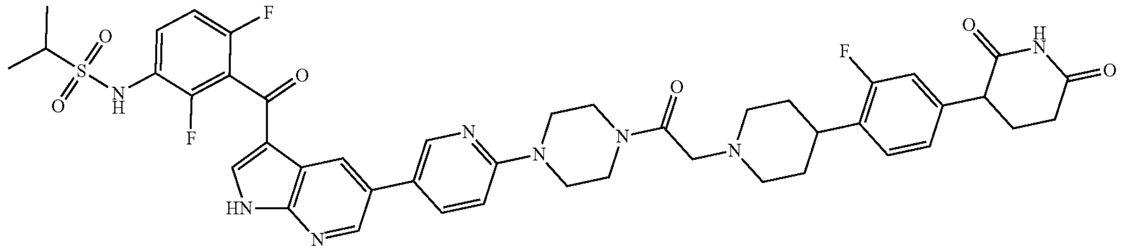 [SMILES: CC(C)S(=O)(=O)Nc1ccc(F)c(C(=O)c2c[nH]c3ncc(-c4ccc(N5CCN(C(=O)CN6CCC(c7ccc(C8CCC(=O)NC8=O)cc7F)CC6)CC5)nc4)cc23)c1F]

Target compound was prepared via HATU mediated acid-amine coupling reaction (procedure A). Amide coupling was carried out using N-[2,4-difluoro-3-[5-(6-piperazin-1-yl-3-pyridyl)-1H-pyrrolo[2,3-b]pyridine-3-carbonyl]phenyl]propane-2-sulfonamide (30.0 mg, 55.50 μmol), 2-[4-[4-(2,6-dioxo-3-piperidyl)-2-fluoro-phenyl]-1-piperidyl]acetic acid (21.36 mg, 55.50 μmol), N,N-diisopropylethylamine (43.03 mg, 332.97 μmol, 58.00 μL) and HATU (25.32 mg, 66.59 μmol) to afford N-[3-[5-[6-[4-[2-[4-[4-(2,6-dioxo-3-piperidyl)-2-fluoro-phenyl]-1-piperidyl]acetyl]piperazin-1-yl]-3-pyridyl]-1H-pyrrolo[2,3-b]pyridine-3-carbonyl]-2,4-difluoro-phenyl]propane-2-sulfonamide (9.50 mg, 10.89 μmol, 19.63% yield) as pale yellow solid. LCMS (ESI+): 871.3 $[M+H]^+$. $^1H$ NMR (400 MHz, DMSO-$d_6$): δ 13.03 (s, 1H), 10.84 (s, 1H), 8.68 (s, 1H), 8.60 (s, 2H), 8.52 (s, 1H), 7.99-7.96 (m, 1H), 7.64-7.58 (m, 1H), 7.32-7.24 (m, 2H), 7.32-7.24 (m, 3H), 3.87-3.60 (m, 9H), 3.33-3.25 (m, 4H), 3.00-2.90 (m, 2H), 2.62-2.66 (m, 3H), 2.24-2.14 (m, 3H), 2.04-1.99 (m, 1H), 1.73 (s, 4H), 1.28 (d, J=6.80 Hz, 6H).

Example 18-61
General Scheme for Synthesis of
N-Ethyl(Methyl)Sulfamoyl Degraders with
Pyrimidinylpiperazine Spacer Unit
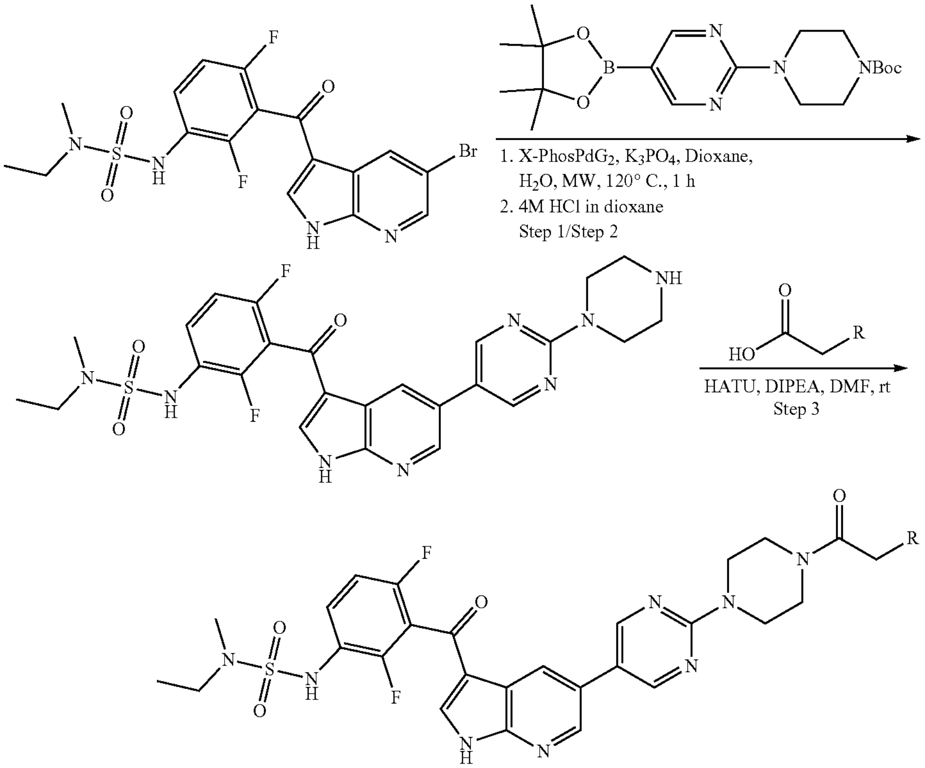
R (selected examples) =
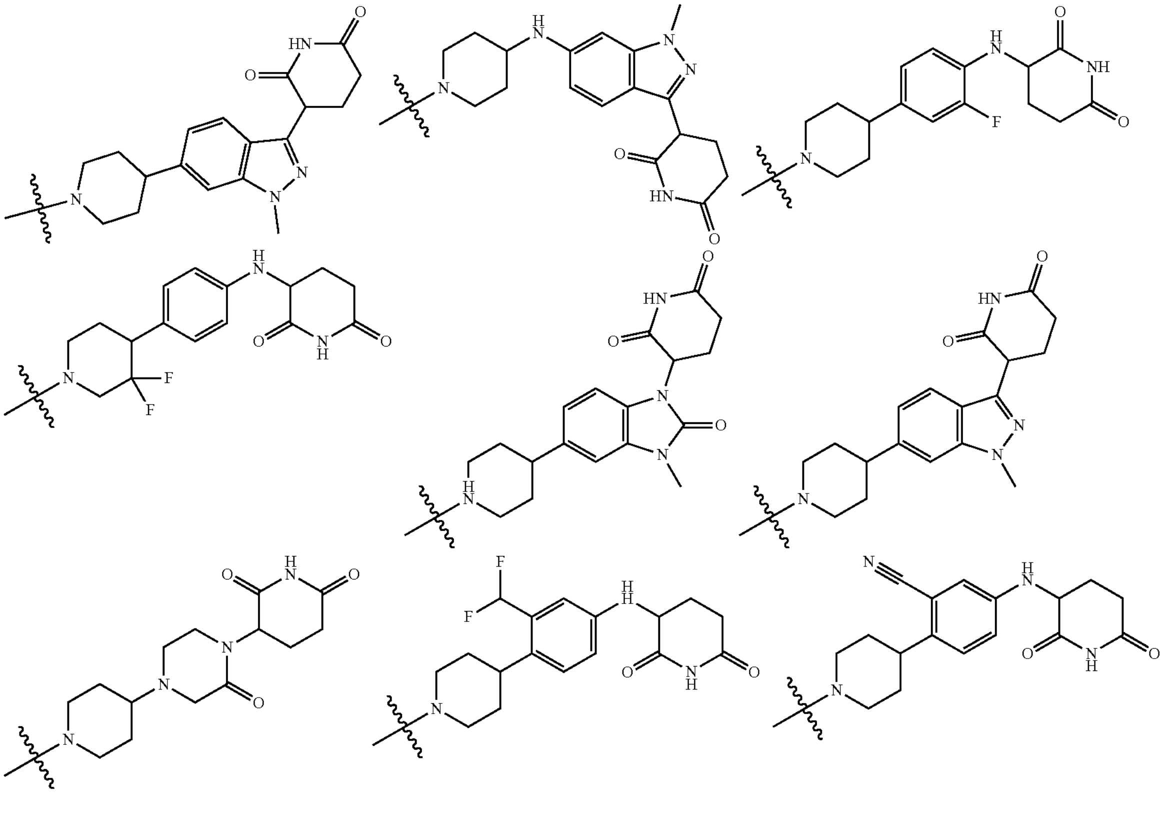

-continued

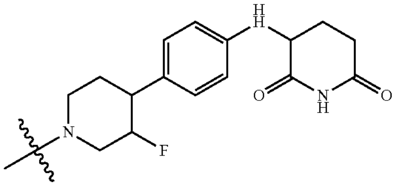

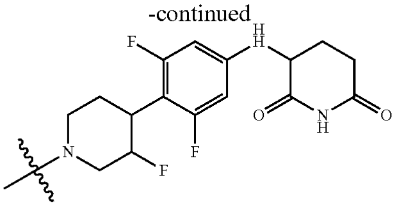

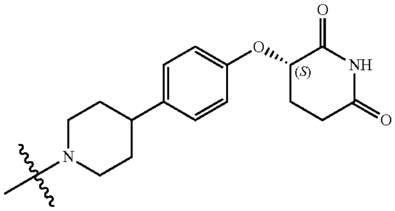

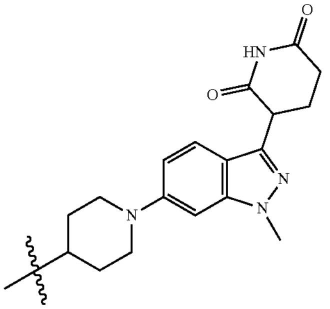

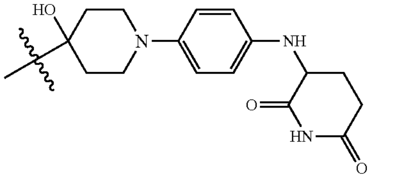

Synthesis of intermediate: 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine Step 1: A solution of 5-bromo-3-[3-[[ethyl(methyl)sulfamoyl]amino]-2,6-difluoro-benzoyl]-1H-pyrrolo[2,3-b]pyridine (1.0 g, 2.11 mmol) in 1,4-Dioxane (8.0 mL) and Water (2.0 mL) was taken in a microwave vial and added tert-butyl 4-[5-(4,4,5,5-tetramethyl-1,3,2-dioxaborolan-2-yl)pyrimidin-2-yl]piperazine-1-carboxylate (910 mg, 2.33 mmol), Potassium phosphate tribasic anhydrous (1.4 g, 6.60 mmol) at room temperature under nitrogen. The reaction mixture was degassed with nitrogen for 10 min, then added XPhos Pd G2 (85 mg, 108.03 μmol) at same temperature. The reaction mixture was irradiated under microwave at 120° C. for 1 h. After completion, water was added to the reaction mixture and extracted with ethyl acetate (2×200 mL). The combined organic layers were dried over sodium sulphate, filtered and concentrated under reduced pressure. The crude compound was purified by silica gel column chromatography with 80% ethyl acetate in petroleum ether as a eluent to afford tert-butyl 4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazine-1-carboxylate (1.0 g, 1.41 mmol, 66.56% yield) as a yellow solid. LCMS (ESI+): 656.8 $[M+H]^+$.

Step 2: To a stirred solution of tert-butyl 4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazine-1-carboxylate (1.0 g, 1.52 mmol) in 1,4-Dioxane (3.0 mL) was added 4M Hydrogen chloride in 1,4-dioxane (560.00 mg, 15.36 mmol, 0.70 mL) at 0-5° C. under nitrogen. The reaction mixture was stirred at room temperature for 5 h. After completion, the reaction mixture was concentrated under reduced pressure to afford 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (910 mg, 1.47 mmol, 96.24% yield, hydrochloric acid salt) as a yellow solid. LCMS (ESI+): 557.4 $[M+H]^+$. $^1H$ NMR (400 MHz, DMSO-$d_6$): δ 13.10 (s, 1H), 9.72 (s, 1H), 9.42 (s, 1H), 8.85 (s, 2H), 8.68 (d, J=2.00 Hz, 1H), 8.59 (s, 1H), 8.13 (s, 1H), 7.60-7.54 (m, 1H), 7.29-7.24 (m, 2H), 7.18-7.12 (m, 1H), 4.05 (t, J=5.20 Hz, 4H), 3.19 (s, 4H), 3.11 (q, J=7.20 Hz, 2H), 2.72 (s, 3H), 1.03 (t, J=6.80 Hz, 3H).

Example 18

5-[2-[4-[2-[4-[4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

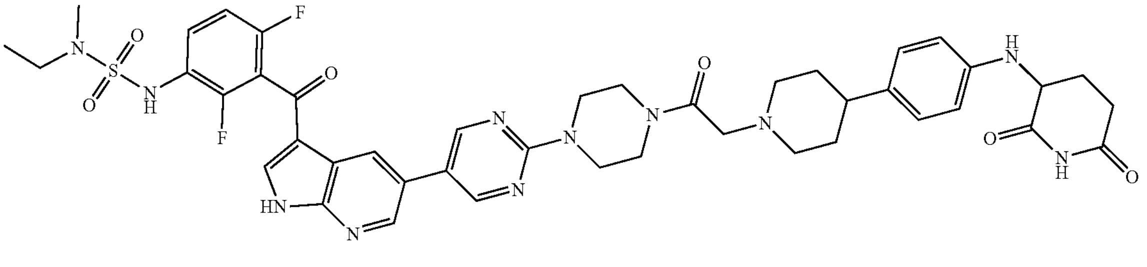 [SMILES: CCN(C)S(=O)(=O)Nc1ccc(F)c(C(=O)c2c[nH]c3ncc(-c4cnc(N5CCN(C(=O)CN6CCC(c7ccc(NC8CCC(=O)NC8=O)cc7)CC6)CC5)nc4)cc23)c1F]

To a stirred solution of 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (600 mg, 1.01 mmol) in DMF (10 mL) was added 2-[4-[4-[(2,6-dioxo-3-piperidyl)amino]phenyl]-1-piperidyl]acetic acid (390 mg, 1.02 mmol) and N,N-Diisopropylethylamine (1.48 g, 11.48 mmol, 2.0 mL) at room temperature under nitrogen, followed by the addition of HATU (470 mg, 1.24 mmol) at same temperature. The reaction mixture was stirred at room temperature for 12 h. After completion, the reaction mixture was concentrated under reduced pressure. The crude compound was purified by preparative-HPLC (Mobile phase: 10 mM $NH_4OAc$ in $H_2O$\ACN:$H_2O$ (90:10) and fractions were lyophilized to afford 5-[2-[4-[2-[4-[4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (349.84 mg, 383.02 μmol, 37.86% yield) as a green solid. LCMS (ESI+): 884.3 $[M+H]^+$. $^1H$ NMR (400 MHz, DMSO-$d_6$): δ 10.77 (s, 1H), 9.71 (s, 1H), 8.81 (s, 2H), 8.68 (d, J=2.00 Hz, 1H), 8.57 (s, 1H), 8.15 (s, 1H), 7.61-7.55 (m, 1H), 7.27 (t, J=8.40 Hz, 1H), 6.97 (d, J=8.40 Hz, 2H), 6.61 (d, J=8.80 Hz, 2H), 5.66 (d, J=7.60 Hz, 1H), 4.28-4.25 (m, 1H), 3.89-3.82 (m, 4H), 3.71 (s, 2H), 3.59 (s, 2H), 3.24 (s, 2H), 3.11 (q, J=7.20 Hz, 2H), 2.96 (d, J=10.40 Hz, 2H), 2.78-2.62 (m, 1H), 2.73 (s, 3H), 2.60-2.55 (m, 2H), 2.40-2.15 (m, 1H), 2.11-2.07 (m, 3H), 1.91-1.84 (m, 1H), 1.83-1.57 (m, 4H), 1.02 (t, J=7.20 Hz, 3H).

Example 19

5-[2-[4-[2-[4-[4-[(2,6-dioxo-3-piperidyl)amino]phenyl]piperazin-1-yl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

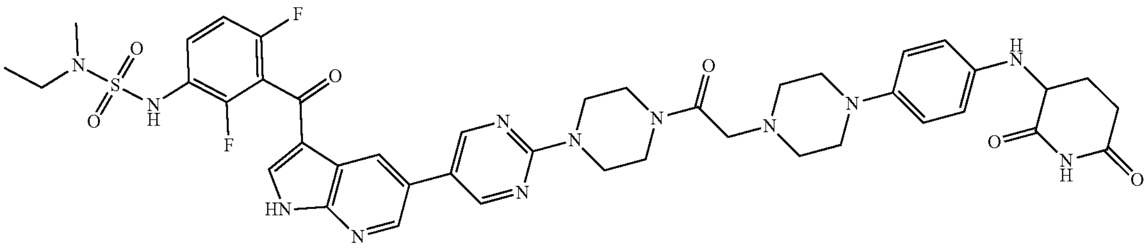 [SMILES: CCN(C)S(=O)(=O)Nc1ccc(F)c(C(=O)c2c[nH]c3ncc(-c4cnc(N5CCN(C(=O)CN6CCN(c7ccc(NC8CCC(=O)NC8=O)cc7)CC6)CC5)nc4)cc23)c1F]

2-[4-[4-[(2,6-dioxo-3-piperidyl)amino]phenyl]piperazin-1-yl]acetic acid (169.39 mg, 246.04 tri-TFA salt) was dissolved in DMF (1.5 mL) and DIPEA (212.00 mg, 1.64 mmol, 285.71 uL) was added, followed by HATU (74.84 mg, 196.84 μmol). The mixture was stirred at room temperature for 10 min, and 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (110 mg, 164.03 trifluoroacetic acid salt) was added. The mixture was stirred at room temperature overnight. The mixture was purified by reverse-phase chromatography on 100 g C18 column (5%-100% acetonitrile in water with 0.1% TFA as modifier). The product fractions were neutralized with saturated sodium bicarbonate and extracted with EtOAc, followed by flash column chromatography on silica gel (0-15% MeOH in DCM) to give 5-[2-[4-[2-[4-[4-[(2,6-dioxo-3-piperidyl)amino]phenyl]piperazin-1-yl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (65.5 mg, 70.31 μmol, 42.87% yield) as an off-white solid. LCMS (ESI+): 885.2 $[M+H]^+$. $^1H$ NMR (400 MHz, DMSO-$d_6$): δ 12.99 (s, 1H), 10.74 (s, 1H), 9.71 (s, 1H), 8.80 (s, 2H), 8.68 (d, J=2.2 Hz, 1H), 8.56 (s, 1H), 8.14 (s, 1H), 7.58 (td, J=9.0, 5.9 Hz, 1H), 7.36-7.19 (m, 1H), 6.86-6.71 (m, 2H), 6.70-6.54 (m, 2H), 5.38 (d, J=7.3 Hz, 1H), 4.20 (ddd, J=11.6, 7.1, 4.7 Hz, 1H), 3.97-3.76 (m, 4H), 3.76-3.67 (m, 2H), 3.67-3.53 (m, 2H), 3.27 (s, 2H), 3.11 (q, J=7.1 Hz, 2H), 3.04-2.87 (m, 4H), 2.82-2.66 (m, 4H), 2.65-2.54 (m, 4H), 2.11 (dq, J=12.5, 4.3, 3.9 Hz, 1H), 1.84 (qd, J=11.9, 4.7 Hz, 1H), 1.02 (t, J=7.1 Hz, 3H).

Example 21

5-[2-[4-[2-[4-[5-[(2,6-dioxo-3-piperidyl)amino]-2-pyridyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

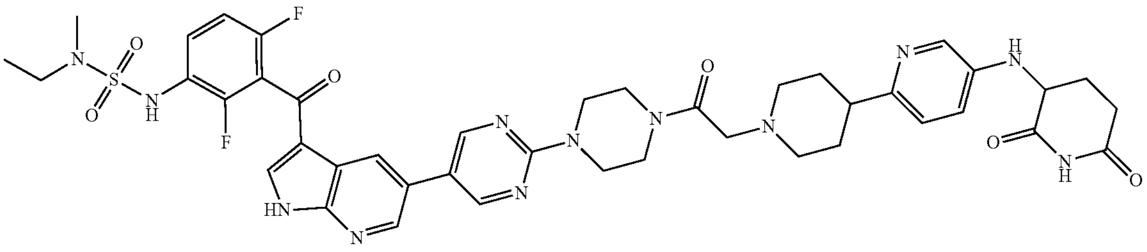 [SMILES: CCN(C)S(=O)(=O)Nc1ccc(F)c(C(=O)c2c[nH]c3ncc(-c4cnc(N5CCN(C(=O)CN6CCC(c7ccc(NC8CCC(=O)NC8=O)cn7)CC6)CC5)nc4)cc23)c1F]

2-[4-[5-[(2,6-dioxo-3-piperidyl)amino]-2-pyridyl]-1-piperidyl]acetic acid (82.39 mg, 178.94 trifluoroacetic acid salt) was dissolved in DMF (1.5 mL) and DIPEA (154.18 mg, 1.19 mmol, 207.78 uL) was added, followed by HATU (54.43 mg, 143.15 μmol). The mixture was stirred at room temperature for 10 min, and 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (80 mg, 119.29 μmol, trifluoroacetic acid salt) was added. The mixture was stirred at room temperature overnight. The mixture was purified by reverse-phase chromatography on 100 g C18 column (5%-100% acetonitrile in water with 0.1% TFA as modifier). The product fractions were neutralized with saturated sodium bicarbonate and extracted with EtOAc, followed by flash column chromatography on silica gel (0-15% MeOH in DCM) to give 5-[2-[4-[2-[4-[5-[(2,6-dioxo-3-piperidyl)amino]-2-pyridyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (65 mg, 69.78

μmol, 58.49% yield) as an off-white solid. LCMS (ESI+): 885.3 $[M+H]^+$. $^1H$ NMR (400 MHz, DMSO-$d_6$) δ 12.98 (s, 1H), 10.77 (s, 1H), 9.68 (s, 1H), 8.79 (s, 2H), 8.71-8.63 (m, 1H), 8.55 (s, 1H), 8.12 (s, 1H), 7.96 (d, J=2.2 Hz, 1H), 7.56 (td, J=8.9, 5.8 Hz, 1H), 7.26 (t, J=8.6 Hz, 1H), 6.97 (s, 2H), 5.91 (d, J=7.8 Hz, 1H), 4.32 (ddd, J=12.2, 7.7, 4.9 Hz, 1H), 3.89-3.84 (m, 2H), 3.82-3.78 (m, 2H), 3.72-3.68 (m, 2H), 3.60-3.56 (m, 2H), 3.10 (q, J=7.1 Hz, 2H), 2.98-2.94 (m, 1H), 2.71 (s, 3H), 2.70-2.63 (m, 1H), 2.61-2.52 (m, 2H), 2.29-2.04 (m, 3H), 1.89 (tt, J=12.1, 6.3 Hz, 1H), 1.83-1.66 (m, 4H), 1.00 (t, J=7.1 Hz, 3H).

Example 22

5-[2-[4-[2-[4-[4-[(2,6-dioxo-3-piperidyl)-methyl-amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

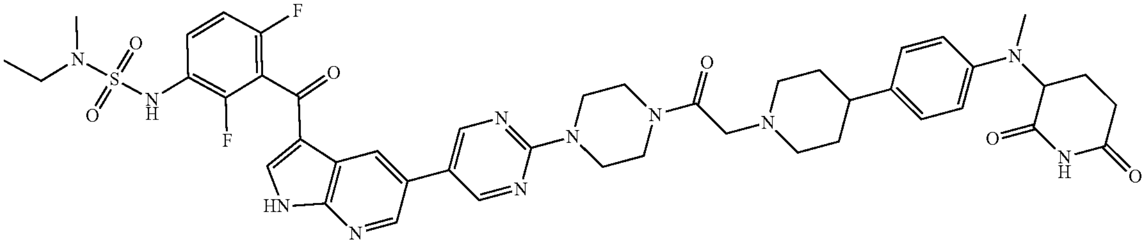 [SMILES: CCN(C)S(=O)(=O)Nc1ccc(F)c(C(=O)c2c[nH]c3ncc(-c4cnc(N5CCN(C(=O)CN6CCC(c7ccc(N(C)C8CCC(=O)NC8=O)cc7)CC6)CC5)nc4)cc23)c1F]

2-[4-[4-[(2,6-dioxo-3-piperidyl)-methyl-amino]phenyl]-1-piperidyl]acetic acid (105.12 mg, 178.94 μmol, bis-TFA salt) was dissolved in DMF (1.5 mL) and DIPEA (154.18 mg, 1.19 mmol, 207.78 uL) was added, followed by HATU (54.43 mg, 143.15 μmol). The mixture was stirred at room temperature for 10 min, and 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (80 mg, 119.29 μmol, trifluoroacetic acid salt) was added. The mixture was stirred at room temperature overnight. The mixture was purified by reverse-phase chromatography on 100 g C18 column (5%-100% acetonitrile in water with 0.1% TFA as modifier). The product fractions were neutralized with saturated sodium bicarbonate and extracted with EtOAc, followed by flash column chromatography on silica gel (0-15% MeOH in DCM) to give 5-[2-[4-[2-[4-[4-[(2,6-dioxo-3-piperidyl)-methyl-amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (58.4 mg, 61.78 μmol, 51.79% yield) as an off-white solid. LCMS (ESI+): 898.3 $[M+H]^+$. $^1H$ NMR (400 MHz, DMSO-$d_6$): δ 13.00 (s, 1H), 10.76 (s, 1H), 9.70 (s, 1H), 8.81 (s, 2H), 8.68 (d, J=2.2 Hz, 1H), 8.57 (s, 1H), 8.14 (s, 1H), 7.59 (td, J=9.0, 5.9 Hz, 1H), 7.32-7.23 (m, 1H), 7.06 (d, J=8.3 Hz, 2H), 6.75 (d, J=8.4 Hz, 2H), 4.83 (dd, J=12.6, 5.0 Hz, 1H), 3.92-3.86 (m, 2H), 3.85-3.81 (m, 2H), 3.73-3.68 (m, 2H), 3.63-3.59 (m, 2H), 3.12 (q, J=7.1 Hz, 3H), 3.04-2.93 (m, 1H), 2.84 (ddd, J=17.8, 13.3, 5.2 Hz, 1H), 2.74 (s, 3H), 2.71 (s, 3H), 2.56 (s, 1H), 2.41 (s, 1H), 2.35-2.21 (m, 2H), 1.91-1.82 (m, 1H), 1.80-1.57 (m, 4H), 1.30-1.18 (m, 3H), 1.03 (t, J=7.1 Hz, 3H).

Example 24

5-[2-[4-[2-[4-[4-(2,4-dioxohexahydropyrimidin-1-yl)phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

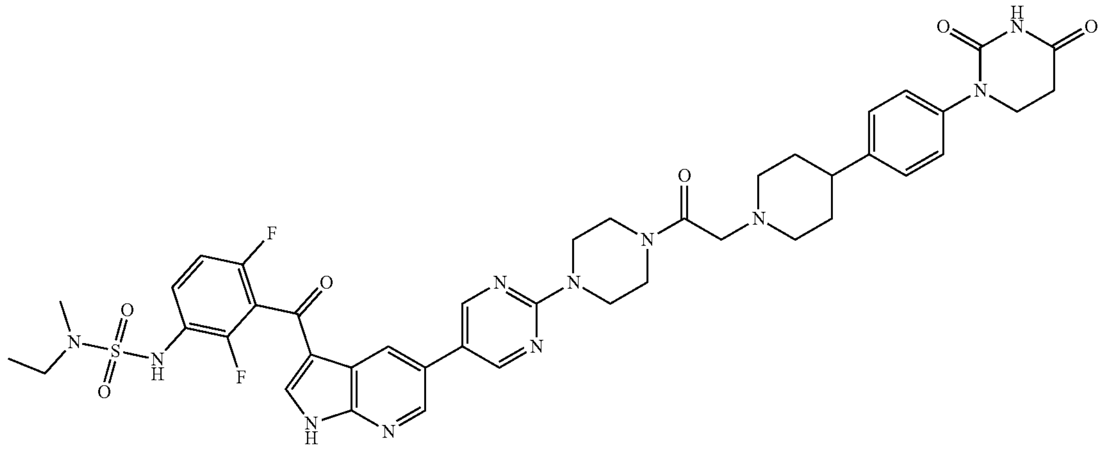 [SMILES: CCN(C)S(=O)(=O)Nc1ccc(F)c(C(=O)c2c[nH]c3ncc(-c4cnc(N5CCN(C(=O)CN6CCC(c7ccc(N8CCC(=O)NC8=O)cc7)CC6)CC5)nc4)cc23)c1F]

Target compound was prepared via procedure B, by modifying the amide coupling with 2-[4-[4-(2,4-dioxohexahydropyrimidin-1-yl)phenyl]-1-piperidyl]acetic acid (70.04 mg, 179.67 μmol), 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (100 mg, 179.67 μmol) and 1.5 of DIPEA and 1.5 eq of COMU. The crude material was purified by reverse phase column chromatography (MeCN & Water (0.01% TFA). The product elutes around 40%. The product was free based in saturated bicarbonateonate solution in EtOAc. The material was then purified by MeOH and DCM (0-30% MeOH) to afford 5-[2-[4-[2-[4-[4-(2,4-dioxohexahydropyrimidin-1-yl)phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (63.5 mg, 71.5 μmol, 39% yield) as off-white solid. LCMS (ESI+): 870.1 $[M+H]^+$. $^1H$ NMR (400 MHz, DMSO-$d_6$): δ 12.92 (s, 1H), 10.25 (s, 1H), 9.62 (s, 1H), 8.74 (s, 2H), 8.61 (d, J=2.2 Hz, 1H), 8.50 (s, 1H), 8.07 (s, 1H), 7.56-7.46 (m, 1H), 7.25-7.14 (m, 5H), 3.85-3.79 (m, 2H), 3.77-3.73 (m, 2H), 3.70 (t, J=6.7 Hz, 1H), 3.68-3.63 (m, 3H), 3.55-3.51 (m, 2H), 3.20-3.16 (m, 2H), 3.04 (q, J=7.2 Hz, 2H), 2.93-2.88 (m, 2H), 2.68-2.59 (m, 5H), 2.11-2.07 (m, 2H), 1.79-1.51 (m, 2H), 0.95 (t, J=7.1 Hz, 3H).

Example 25

5-[2-[4-[2-[4-[4-[[(3S)-2,6-dioxo-3-piperidyl]amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

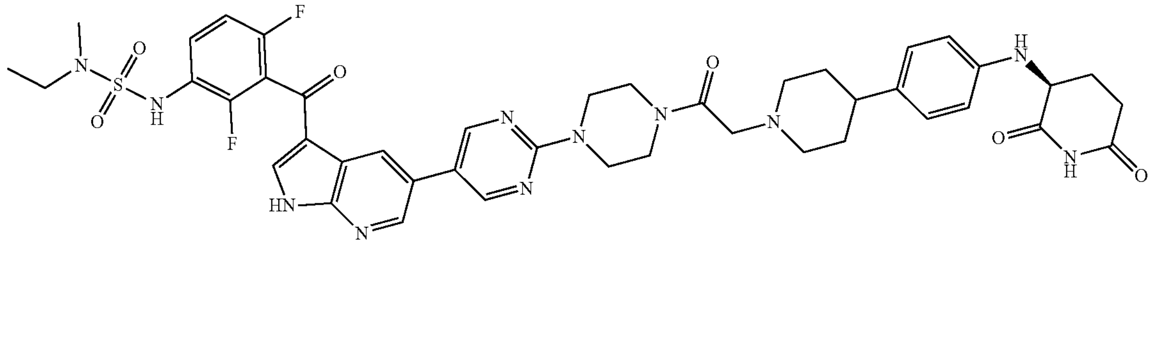 [SMILES: CCN(C)S(=O)(=O)Nc1ccc(F)c(C(=O)c2c[nH]c3ncc(-c4cnc(N5CCN(C(=O)CN6CCC(c7ccc(N[C@H]8CCC(=O)NC8=O)cc7)CC6)CC5)nc4)cc23)c1F]

target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (300 mg, 539.00 μmol), 2-[4-[4-[[(3S)-2,6-dioxo-3-piperidyl]amino]phenyl]-1-piperidyl] acetic acid (186.17 mg, 539.00 μmol), N,N-Diisopropylethylamine (278.65 mg, 2.16 mmol, 375.54 μL) and HATU (204.94 mg, 539.00 μmol) to afford 5-[2-[4-[2-[4-[4-[[(3S)-2,6-dioxo-3-piperidyl]amino]phenyl]-1-piperidyl]acetyl]piperazin-1-yl]pyrimidin-5-yl]-3-[3-[[ethyl (methyl)sulfamoyl]amino]-2,6-difluoro-benzoyl]-1H-pyrrolo[2,3-b]pyridine (150 mg, 167.60 μmol, 31.10% yield) as off white solid. LCMS (ESI+): 884.2 $[M+H]^+$. $^1H$ NMR (400 MHz, DMSO-$d_6$): δ 13.00 (s, 1H), 10.77 (s, 1H), 9.78 (s, 1H), 8.81 (s, 2H), 8.68 (d, J=2.40 Hz, 1H), 8.57 (s, 1H), 8.14 (s, 1H), 7.55-7.60 (m, 1H), 7.26 (t, J=8.40 Hz, 1H), 6.97 (d, J=8.40 Hz, 2H), 6.61 (d, J=8.80 Hz, 2H), 5.66 (d, J=7.60 Hz, 1H), 4.21-4.31 (m, 1H), 3.89 (s, 2H), 3.82 (s, 2H), 3.72 (s, 2H), 3.59 (s, 2H), 3.23 (s, 2H), 3.11 (q, J=6.80 Hz, 2H), 2.96 (d, J=10.80 Hz, 2H), 2.61-2.78 (m, 2H), 2.74 (s, 3H), 2.41-2.55 (m, 1H), 2.09-2.14 (m, 3H), 1.81-1.91 (m, 1H), 1.57-1.73 (m, 4H), 1.02 (t, J=6.80 Hz, 3H).

Example 26

5-[2-[4-[2-[4-[4-[[(3R)-2,6-dioxo-3-piperidyl]amino] phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

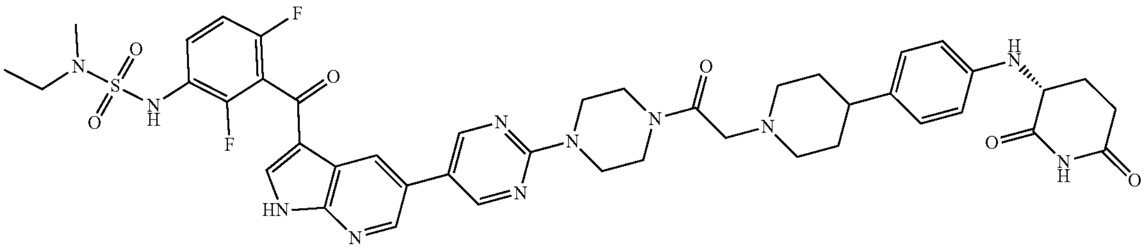 [SMILES: CCN(C)S(=O)(=O)Nc1ccc(F)c(C(=O)c2c[nH]c3ncc(-c4cnc(N5CCN(C(=O)CN6CCC(c7ccc(N[C@@H]8CCC(=O)NC8=O)cc7)CC6)CC5)nc4)cc23)c1F]

Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (50 mg, 89.83 μmol), 2-[4-[4-[[(3R)-2,6-dioxo-3-piperidyl]amino]phenyl]-1-piperidyl]acetic acid (31.03 mg, 89.83 μmol), N,N-Diisopropylethylamine (46.44 mg, 359.33 μmol, 62.59 μL) and HATU (34.16 mg, 89.83 μmol) to afford 5-[2-[4-[2-[4-[4-[[(3R)-2,6-dioxo-3-piperidyl]amino]phenyl]-1-piperidyl]acetyl]piperazin-1-yl] pyrimidin-5-yl]-3-[3-[[ethyl(methyl)sulfamoyl]amino]-2,6-difluoro-benzoyl]-1H-pyrrolo[2,3-b]pyridine (15 mg, 15.50 μmol, 17.25% yield) as off white solid. LCMS (ESI+): 884.1 $[M+H]^+$. $^1H$ NMR (400 MHz, DMSO-$d_6$): δ 13.01 (d, J=2.80 Hz, 1H), 10.79 (s, 1H), 9.71 (s, 1H), 8.84 (s, 2H), 8.69 (d, J=2.00 Hz, 1H), 8.59 (s, 1H), 8.16 (d, J=2.40 Hz, 1H), 7.56-7.62 (m, 1H), 7.29 (dd, J=7.60, 13.00 Hz, 1H), 6.99 (d, J=5.60 Hz, 2H), 6.66 (d, J=8.40 Hz, 2H), 5.76 (d, J=7.60 Hz, 1H), 4.20-4.33 (m, 2H), 3.94 (s, 2H), 3.89 (s, 2H), 3.70 (s, 2H), 3.56 (s, 4H), 3.12 (q, J=7.20 Hz, 2H), 3.01-3.10 (m, 1H), 2.72-2.81 (m, 2H), 2.74 (s, 3H), 2.61-2.68 (m, 2H), 2.46-2.55 (m, 2H), 2.06-2.15 (m, 1H), 1.86-2.01 (m, 4H), 1.03 (t, J=7.20 Hz, 3H).

Example 27

3-(2,6-dioxo-3-piperidyl)-6-[1-[2-[4-[5-[3-[3-[[ethyl (methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl]-1-methyl-indazole

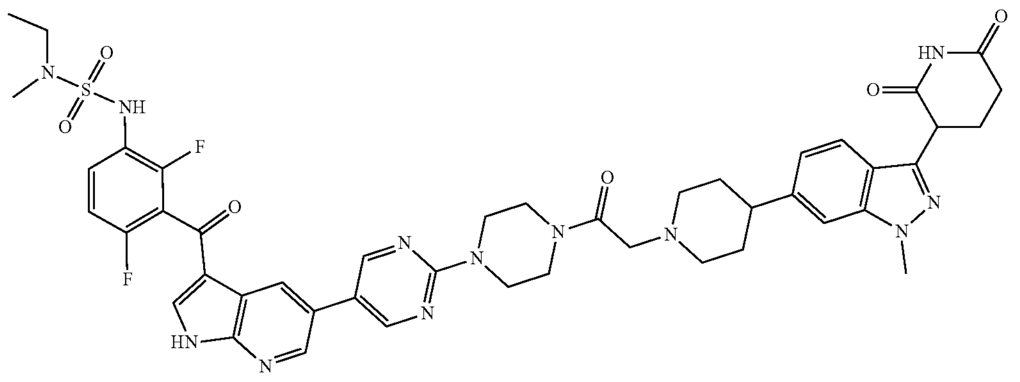 [SMILES: CCN(C)S(=O)(=O)Nc1ccc(F)c(C(=O)c2c[nH]c3ncc(-c4cnc(N5CCN(C(=O)CN6CCC(c7ccc8c(C9CCC(=O)NC9=O)nn(C)c8c7)CC6)CC5)nc4)cc23)c1F]

Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (20 mg, 33.72 μmol), 2-[4-[3-(2,6-dioxo-3-piperidyl)-1-methyl-indazol-6-yl]-1-piperidyl] acetic acid (15 mg, 35.64 μmol), HATU (16 mg, 42.08 μmol) and N,N-Diisopropylethylamine (371.00 mg, 2.87 mmol, 0.50 mL) to afford 3-(2,6-dioxo-3-piperidyl)-6-[1-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl]-1-methyl-indazole (4.75 mg, 5.12 μmol, 15.19% yield) as off-white solid. LCMS (ESI+): 923.3 $[M+H]^+$. $^1$H NMR (400 MHz, DMSO-d6): δ 12.93 (s, 1H), 10.81 (s, 1H), 9.65 (s, 1H), 8.74 (s, 2H), 8.61 (d, J=2.00 Hz, 1H), 8.50 (s, 1H), 8.07 (s, 1H), 7.48-7.55 (m, 2H), 7.38 (s, 1H), 7.20 (t, J=8.40 Hz, 1H), 6.98 (d, J=8.40 Hz, 1H), 4.24-4.27 (m, 1H), 3.90 (s, 3H), 3.84 (s, 2H), 3.75 (s, 2H), 3.67 (s, 2H), 3.53 (s, 2H), 3.26 (s, 2H), 3.04 (q, J=6.80 Hz, 2H), 2.95 (d, J=12.00 Hz, 2H), 2.65 (s, 3H), 2.32-2.52 (m, 3H), 2.05-2.26 (m, 4H), 1.68-1.84 (m, 4H), 0.95 (t, J=6.80 Hz, 3H).

Example 28

3-(2,6-dioxo-3-piperidyl)-6-[[1-[2-[4-[5-[3-[3-[[ethyl (methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl]amino]-1-methyl-indazole

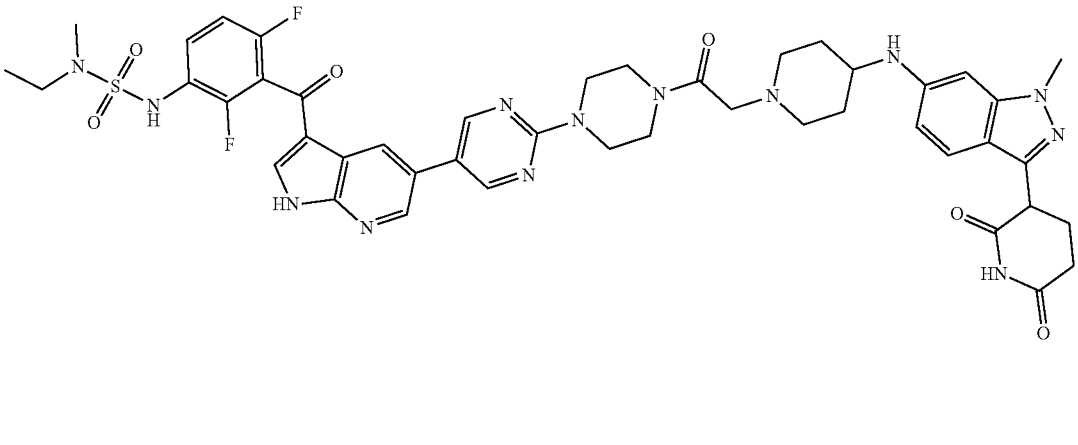 [SMILES: CCN(C)S(=O)(=O)Nc1ccc(F)c(C(=O)c2c[nH]c3ncc(-c4cnc(N5CCN(C(=O)CN6CCC(Nc7ccc8c(C9CCC(=O)NC9=O)nn(C)c8c7)CC6)CC5)nc4)cc23)c1F]

Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (20 mg, 33.72 μmol, hydrochloric acid salt), 2[4-[[3-(2,6-dioxo-3-piperidyl)-1-methyl-indazol-6-yl]amino]-1-piperidyl]acetic acid (18 mg, 35.06 μmol, trifluoroacetic acid salt), N, N-Diisopropylethylamine (371.00 mg, 2.87 mmol, 0.50 mL) and HATU (16 mg, 42.08 μmol) to yield 3-(2,6-dioxo-3-piperidyl)-6-[[1-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl]amino]-1-methyl-indazole (7.90 mg, 8.35 μmol, 24.76% yield) as off-white solid. LCMS (ESI+): 938.2 $[M+H]^+$. $^1H$ NMR (400 MHz, DMSO-$d_6$): δ 13.02 (s, 1H), 10.75 (s, 1H), 9.74 (s, 1H), 8.74 (s, 2H), 8.61 (s, 1H), 8.50 (s, 1H), 8.07 (s, 1H), 7.47-7.53 (m, 1H), 7.25 (d, J=8.80 Hz, 1H), 7.16-7.20 (m, 1H), 6.45 (d, J=10.00 Hz, 1H), 6.32 (s, 1H), 5.70 (d, J=8.00 Hz, 1H), 4.14-4.02 (m, 1H), 3.81 (s, 2H), 3.74 (s, 3H), 3.78-3.70 (m, 1H), 3.65 (s, 2H), 3.62 (s, 2H), 3.16 (s, 2H), 3.03 (q, J=7.20 Hz, 2H), 2.80 (d, J=10.80 Hz, 2H), 2.65 (s, 3H), 2.45-2.55 (m, 3H), 2.19-2.23 (m, 2H), 2.07-2.16 (m, 2H), 1.92-1.83 (m, 2H), 1.45-1.25 (m, 2H), 0.95 (t, J=7.2 Hz, 3H).

Example 29

5-[2-[4-[2-[4-[4-[(2,6-dioxo-3-piperidyl)amino]-3-fluoro-phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

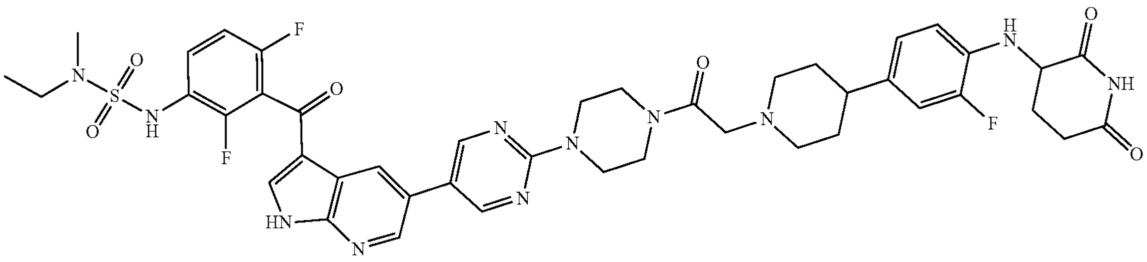 [SMILES: CCN(C)S(=O)(=O)Nc1ccc(F)c(C(=O)c2c[nH]c3ncc(-c4cnc(N5CCN(C(=O)CN6CCC(c7ccc(NC8CCC(=O)NC8=O)c(F)c7)CC6)CC5)nc4)cc23)c1F]

target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (20 mg, 33.72 μmol, hydrochloric acid salt), 2-[4-[4-[(2,6-dioxo-3-piperidyl)amino]-3-fluoro-phenyl]-1-piperidyl]acetic acid (14 mg, 35.01 μmol), N,N-Diisopropylethylamine (371.00 mg, 2.87 mmol, 0.50 mL) at and HATU (16 mg, 42.08 μmol) to afford 5-[2-[4-[2-[4-[4-[(2,6-dioxo-3-piperidyl)amino]-3-fluoro-phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (7.15 mg, 7.91 μmol, 23.46% yield) as off-white solid. LCMS (ESI+): 902.2 $[M+H]^+$. $^1H$ NMR (400 MHz, DMSO-$d_6$): δ 13.01 (s, 1H), 10.82 (s, 1H), 9.72 (s, 1H), 8.81 (s, 2H), 8.68 (d, J=2.40 Hz, 1H), 8.58 (s, 1H), 8.15 (s, 1H), 7.55-7.61 (m, 1H), 7.25-7.30 (m, 1H), 6.94-6.97 (m, 1H), 6.85-6.90 (m, 1H), 6.80-6.87 (m, 1H), 5.38-5.41 (m, 1H), 4.31-4.41 (m, 1H), 3.85-3.90 (m, 2H), 3.78-3.83 (m, 2H), 3.70-3.76 (m, 2H), 3.58-3.65 (m, 2H), 3.21-3.31 (m, 2H), 3.11 (q, J=6.80 Hz, 2H), 2.96 (d, J=10.40 Hz, 2H), 2.61-2.76 (m, 1H), 2.75 (s, 3H), 2.58-2.50 (m, 1H), 2.31-2.45 (m, 1H), 2.01-2.16 (m, 4H), 1.75-1.72 (m, 2H), 1.65-1.55 (m, 2H), 1.02 (t, J=7.2 Hz, 3H).

Example 30

5-[2-[4-[2-[4-[4-[(2,6-dioxo-3-piperidyl)amino]phenyl]-3,3-difluoro-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

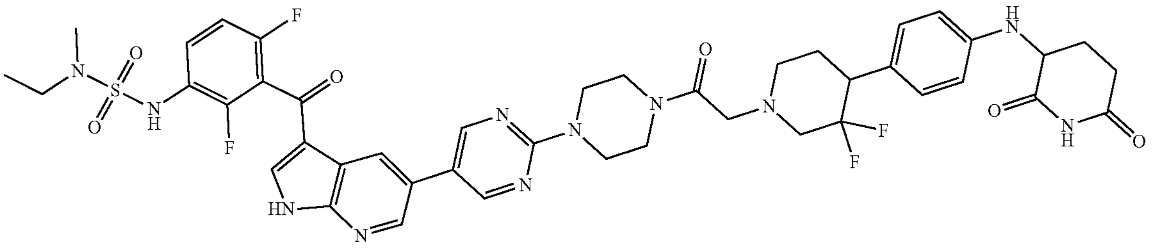 [SMILES: CCN(C)S(=O)(=O)Nc1ccc(F)c(C(=O)c2c[nH]c3ncc(-c4cnc(N5CCN(C(=O)CN6CCC(c7ccc(NC8CCC(=O)NC8=O)cc7)C(F)(F)C6)CC5)nc4)cc23)c1F]

target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (20 mg, 33.72 μmol, hydrochloric acid salt), 2-[4-[4-[(2,6-dioxo-3-piperidyl)amino]phenyl]-3,3-difluoro-1-piperidyl]acetic acid (15 mg, 35.90 μmol), N,N-Diisopropylethylamine (371.00 mg, 2.87 mmol, 0.50 mL) and HATU (15.39 mg, 40.47 μmol) to afford 5-[2-[4-[2-[4-[4-[(2,6-dioxo-3-piperidyl)amino]phenyl]-3,3-difluoro-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (10.37 mg, 10.47 μmol, 31.05% yield) as a green solid. LCMS (ESI+): 920.2 $[M+H]^+$. $^1H$ NMR (400 MHz, DMSO-$d_6$): δ 12.94 (s, 1H), 10.79 (s, 1H), 9.67 (s, 1H), 8.88 (s, 2H), 8.69 (d, J=2.00 Hz, 1H), 8.56-8.60 (m, 1H), 8.15 (s, 1H), 7.56-7.62 (m, 1H), 7.26-7.30 (m, 1H), 7.02 (d, J=8.40 Hz, 2H), 6.64 (d, J=8.80 Hz, 2H), 5.82 (d, J=7.20 Hz, 1H), 4.26-4.36 (m, 1H), 3.80-3.90 (m, 4H), 3.51-3.72 (m, 4H), 3.39-3.46 (m, 2H), 3.06-3.18 (m, 3H), 2.80-2.95 (m, 2H), 2.50-2.78 (m, 3H), 2.65 (s, 3H), 2.30-2.42 (m, 1H), 1.95-2.15 (m, 2H), 1.80-1.91 (m, 1H), 1.65-1.80 (m, 1H), 1.02 (t, J=7.20 Hz, 3H).

Example 31

5-[2-[4-[2-[1-[4-[(2,6-dioxo-3-piperidyl)amino]phenyl]-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

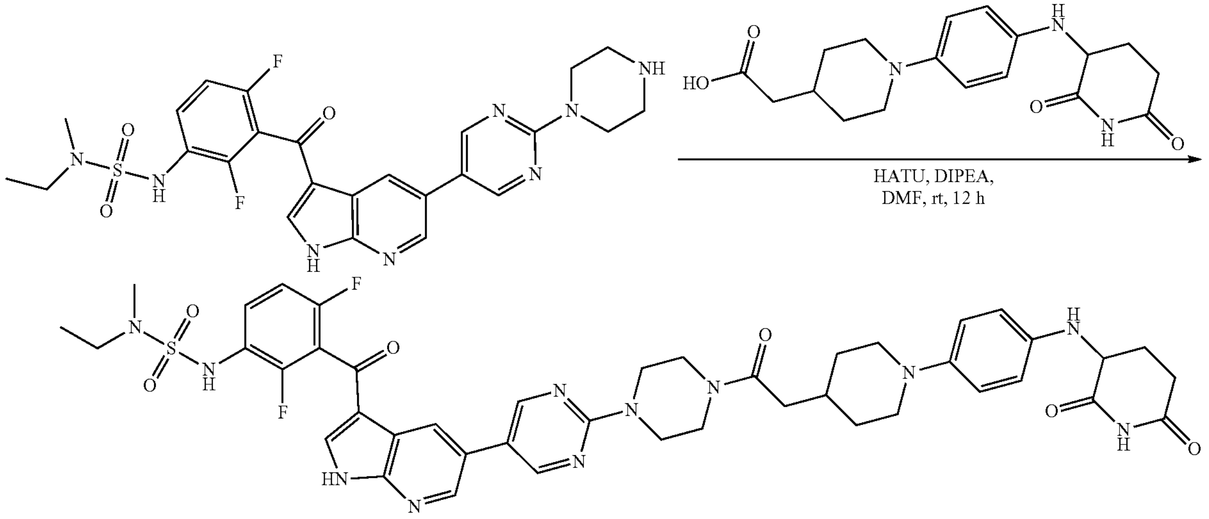

Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (80 mg, 143.73 μmol), 2-[1-[4-[(2,6-dioxo-3-piperidyl)amino]phenyl]-4-piperidyl]acetic acid (49.64 mg, 143.73 μmol), N,N-Diisopropylethylamine (74.31 mg, 574.93 μmol, 100.14 μL) and HATU (54.65 mg, 143.73 μmol) to afford 5-[2-[4-[2-[1-[4-[(2,6-dioxo-3-piperidyl)amino]phenyl]-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (25.49 mg, 27.54 μmol, 19.16% yield) as off white solid. LCMS (ESI+): 884.1 $[M+H]^+$. $^1H$ NMR (400 MHz, DMSO-$d_6$): δ 12.95 (s, 1H), 0.76 (s, 1H), 9.71 (s, 1H), 8.81 (s, 2H), 8.68 (d, J=2.40 Hz, 1H), 8.57 (s, 1H), 8.15 (s, 1H), 7.55-7.61 (m, 1H), 7.27 (dd, J=1.20, 12.40 Hz, 1H), 6.76 (d, J=8.80 Hz, 2H), 6.60 (d, J=8.80 Hz, 2H), 5.37 (d, J=7.20 Hz, 1H), 4.15-4.25 (m, 1H), 3.75-3.90 (m, 4H), 3.55-3.65 (m, 4H), 3.35-3.53 (m, 2H), 3.06-3.12 (m, 2H), 2.65-2.80 (m, 3H), 2.73 (s, 3H), 2.30-2.61 (m, 5H), 2.08-2.13 (m, 1H), 1.76-1.86 (m, 4H), 1.25-1.40 (m, 2H), 1.02 (t, J=7.20 Hz, 1H).

Example 32

5-[2-[4-[2-[4-[4-[(2,4-dioxohexahydropyrimidin-1-yl)methyl]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

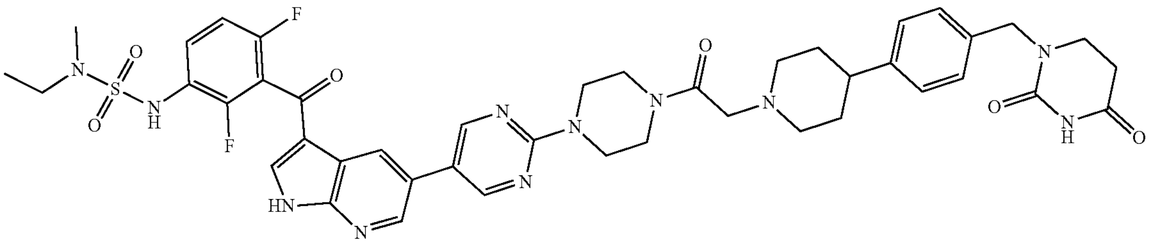 [SMILES: CCN(C)S(=O)(=O)Nc1ccc(F)c(C(=O)c2c[nH]c3ncc(-c4cnc(N5CCN(C(=O)CN6CCC(c7ccc(CN8CCC(=O)NC8=O)cc7)CC6)CC5)nc4)cc23)c1F]

Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (90 mg, 161.70 μmol), 2-[4-[4-[(2,4-dioxohexahydropyrimidin-1-yl)methyl]phenyl]-1-piperidyl]acetic acid (55.85 mg, 161.70 μmol), N, N-Diisopropylethylamine (83.59 mg, 646.80 μmol, 112.66 μL) and HATU (61.48 mg, 161.70 μmol) to afford 5-[2-[4-[2-[4-[4-[(2,4-dioxohexahydropyrimidin-1-yl)methyl]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (34.5 mg, 38.32 μmol, 23.70% yield) as an off white solid. LCMS (ESI+): 882.1 $[M+H]^+$. $^1H$ NMR (400 MHz, DMSO-$d_6$): δ 12.95 (s, 1H), 10.19 (s, 1H), 9.72 (s, 1H), 8.81 (s, 2H), 8.68 (d, J=2.40 Hz, 1H), 8.57 (s, 1H), 8.15 (s, 1H), 7.55-7.61 (m, 1H), 7.20-7.30 (m, 5H), 4.47 (s, 2H), 3.90 (s, 2H), 3.82 (s, 2H), 3.72 (s, 2H), 3.59 (s, 2H), 3.26-3.36 (m, 4H), 3.11 (q, J=7.20 Hz, 2H), 3.10 (d, J=7.20 Hz, 2H), 2.73 (s, 3H), 2.45-2.56 (m, 1H), 2.08-2.19 (m, 2H), 1.61-1.78 (m, 4H), 1.02 (t, J=7.20 Hz, 3H).

Example 33

1-(2,6-dioxo-3-piperidyl)-5-[1-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl]-3-methyl-2-oxo-benzimidazole

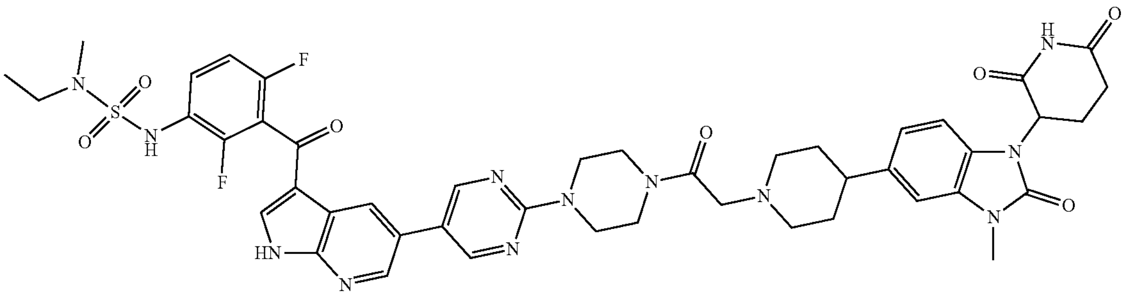 [SMILES: CCN(C)S(=O)(=O)Nc1ccc(F)c(C(=O)c2c[nH]c3ncc(-c4cnc(N5CCN(C(=O)CN6CCC(c7ccc8c(c7)n(C)c(=O)n8C7CCC(=O)NC7=O)CC6)CC5)nc4)cc23)c1F]

target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (90 mg, 161.70 μmol), 2-[4-[1-(2,6-dioxo-3-piperidyl)-3-methyl-2-oxo-benzimidazol-5-yl]-1-piperidyl]acetic acid (64.75 mg, 161.70 μmol), HATU (61.48 mg, 161.70 μmol) and DIPEA (83.59 mg, 646.80 μmol, 112.66 μL) to afford 1-(2,6-dioxo-3-piperidyl)-5-[1-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl]-3-methyl-2-oxo-benzimidazole (32 mg, 32.03 μmol, 19.81% yield) as an off white solid. LCMS (ESI+): 937.1 $[M+H]^+$. $^1H$ NMR (400 MHz, DMSO-$d_6$): δ 13.01 (s, 1H), 11.09 (s, 1H), 9.72 (s, 1H), 8.82 (s, 2H), 8.69 (d, J=2.00 Hz, 1H), 8.58 (s, 1H), 8.15 (s, 1H), 7.56-7.62 (m, 1H), 7.26-7.30 (m, 1H), 7.10 (s, 1H), 7.02 (d, J=8.00 Hz, 2H), 6.94 (d, J=7.60 Hz, 2H), 5.31-5.36 (m, 1H), 3.91 (s, 2H), 3.83 (s, 2H), 3.72 (s, 2H), 3.61 (s, 2H), 3.34-3.50 (m, 1H), 3.4 (s, 3H), 3.13 (q, J=7.20 Hz, 2H), 3.09-3.02 (m, 2H), 2.80-3.00 (m, 2H), 2.73 (s, 3H), 2.57-2.72 (m, 2H), 2.10-2.31 (m, 1H), 1.95-2.05 (m, 1H), 1.65-1.86 (m, 4H), 1.02 (t, J=7.20 Hz, 3H).

Example 34

3-(2,4-dioxohexahydropyrimidin-1-yl)-6-[1-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl]-1-methyl-indazole

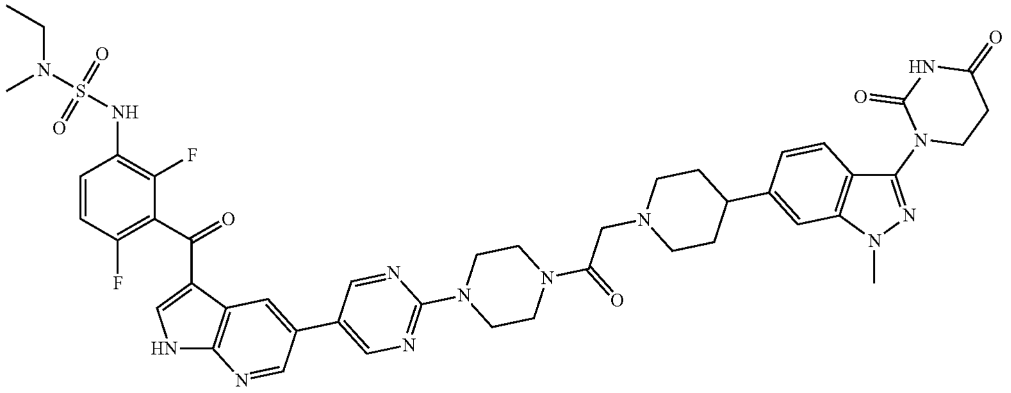 [SMILES: CCN(C)S(=O)(=O)Nc1ccc(F)c(C(=O)c2c[nH]c3ncc(-c4cnc(N5CCN(C(=O)CN6CCC(c7ccc8c(N9CCC(=O)NC9=O)nn(C)c8c7)CC6)CC5)nc4)cc23)c1F]

target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (0.1 g, 168.62 μmol, hydrochloric acid salt), 2-[4-[3-(2,4-dioxohexahydropyrimidin-1-yl)-1-methyl-indazol-6-yl]-1-piperidyl]acetic acid (64.99 mg, 154.05 μmol, hydrochloric acid salt), N-ethyl-N-isopropyl-propan-2-amine (87.17 mg, 674.48 μmol, 117.48 μL) and HATU (64.11 mg, 168.62 μmol) to afford 3-(2,4-dioxohexahydropyrimidin-1-yl)-6-[1-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl]-1-methyl-indazole (55 mg, 58.60 μmol, 34.75% yield) as an off white solid. LCMS (ESI+): 923.7 $[M+H]^+$. $^1H$ NMR (400 MHz, DMSO-$d_6$): δ 12.98 (s, 1H), 10.54 (s, 1H), 9.70 (s, 1H), 8.81 (s, 2H), 8.68 (d, J=2.00 Hz, 1H), 8.58 (s, 1H), 8.14 (s, 1H), 7.55-7.61 (m, 2H), 7.45 (s, 1H), 7.27 (t, J=8.40 Hz, 1H), 7.06 (d, J=8.40 Hz, 1H), 3.97 (s, 3H), 3.88-3.92 (m, 3H), 3.82 (s, 2H), 3.74 (s, 2H), 3.60 (s, 2H), 3.30 (s, 2H), 3.11 (q, J=6.80 Hz, 2H), 3.02 (d, J=9.60 Hz, 2H), 2.67-2.77 (m, 2H), 2.73 (s, 3H), 2.45-2.65 (m, 2H), 2.17-2.30 (m, 2H), 1.71-1.91 (m, 4H), 1.02 (t, J=7.20 Hz, 3H).

Examples 35 AND 36
Example 35
5-[2-[4-[2-[4-[4-[(2,6-dioxo-3-piperidyl)amino]phenyl]cyclohexyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine
Example 36
5-[2-[4-[2-[4-[4-[(2,6-dioxo-3-piperidyl)amino]phenyl]cyclohexyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine
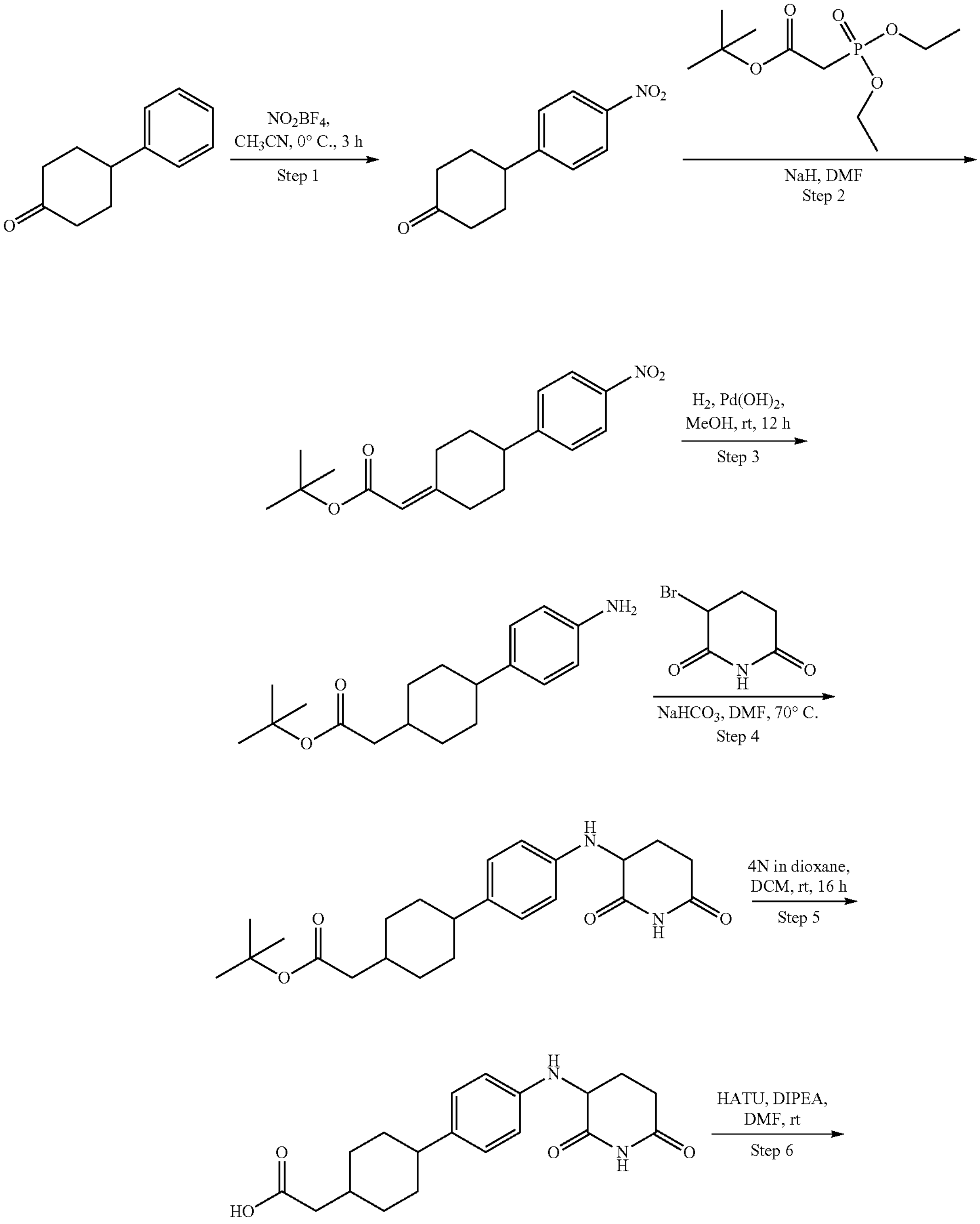

-continued

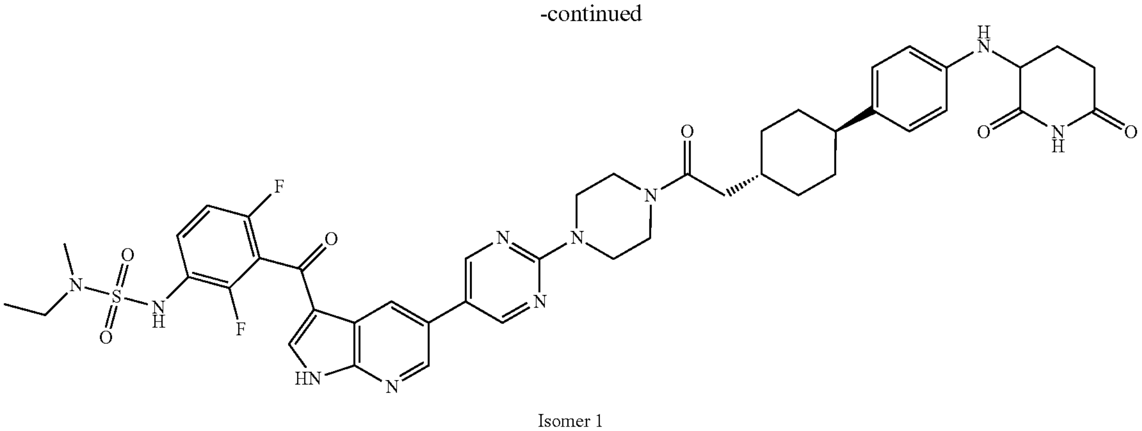

+

Isomer 1

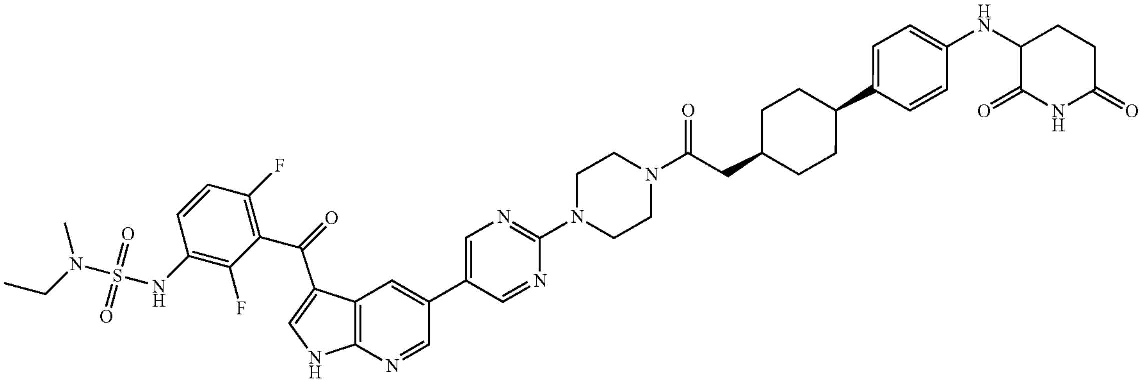

Isomer 2

Step 1: To a stirred solution of 4-phenylcyclohexanone (10 g, 2.87 mmol) in Acetonitrile (100 mL), was added nitronium tetrafluoroborate (10.67 g, 80.35 mmol) portion wise at −5° C. The reaction mixture was stirred at 0° C. for 3 h. After completion, the reaction mixture was diluted with cold water (100 mL) and extracted with ethyl acetate (3×150 mL). Combined organic layers were dried over sodium sulphate, filtered and concentrated. Crude compound was purified by column chromatography (60-120 silica gel) using 25-30% ethyl acetate in petroleum ether as eluent to afford 4-(4-nitrophenyl)cyclohexanone (3.8 g, 17.33 mmol, 30.20% yield) as green solid. Desired product was confirmed by $^1$H NMR. $^1$H NMR (400 MHz, DMSO-$d_6$): δ 8.22 (d, J=8.80 Hz, 2H), 7.44 (d, J=8.80 Hz, 2H), 3.14-3.21 (m, 1H), 2.57-2.59 (m, 4H), 2.25-2.31 (m, 2H), 1.94-2.05 (m, 2H).

Step 2: To a stirred solution of tert-butyl 2-diethoxyphosphorylacetate (1.15 g, 4.56 mmol, 1.08 mL) in N, N-Dimethylformamide (15 mL), was added Sodium hydride (60% in mineral oil, 0.35 g, 14.58 mmol) at 0° C. Reaction mixture was stirred at 0° C. for 15 minutes. To this, 4-(4-nitrophenyl) cyclohexanone (1 g, 4.56 mmol) in DMF (15 mL) solution was added by dropwise at 0° C. and continued the reaction at the same temperature for 2 h. After completion, reaction mixture was quenched with 1.5 N HCl solution (30 mL) at 0° C. and extracted with ethyl acetate. Combined organic layers dried over sodium sulphate, filtered and concentrated. Desired crude was purified by column chromatography (60-120 silica gel) by using 15-20% ethyl acetate in petroleum ether as eluent to afford tert-butyl 2-[4-(4-nitrophenyl) cyclohexylidene]acetate (0.9 g, 1.79 mmol, 39.22% yield) as a yellow liquid. LCMS (ESI+): 260.1 $[M-56-H]^+$.

Step 3: To a stirred solution of tert-butyl 2-[4-(4-nitrophenyl)cyclohexylidene]acetate (0.9 g, 2.84 mmol) in Methanol (10 mL) and Ethyl Acetate (10 mL), was charged 20% $Pd(OH)_2$ (597.35 mg, 4.25 mmol), and subjected for hydrogenation (1 atm) at room temperature for 16 h. After completion, the reaction mixture was purged with nitrogen and catalyst was removed by filtration through celite pad. The filtrate was concentrated under reduced pressure to afford crude, which was purified by column chromatography (60-120 silica gel) by using 40-50% ethyl acetate in petroleum ether as eluent to afford tert-butyl 2-[4-(4-aminophenyl)cyclohexyl]acetate (0.41 g, 1.01 mmol, 35.67% yield) as light yellow liquid. LCMS (ESI+): 234.0 $[M-56+H]^+$.

Step 4: A solution of tert-butyl 2-[4-(4-aminophenyl) cyclohexyl]acetate (0.35 g, 1.21 mmol) in DMF (15 mL) was taken in a sealed tube, and added $NaHCO_3$ (304.78 mg, 3.63 mmol, 141.10 μL) and 3-bromopiperidine-2,6-dione (464.42 mg, 2.42 mmol) at room temperature. Reaction mixture was stirred at 70° C. for 16 h. After completion, the reaction mixture diluted with water (30 mL) and extracted with ethyl acetate (3×50 mL). Combined organic layers washed with cold water (3×30 mL), dried over sodium sulphate, filtered and concentrated to afford crude. Crude compound was purified by column chromatography (60-120 silica gel) by using 55-60% ethyl acetate in petroleum ether as eluent to afford tert-butyl 2-[4-[4-[(2,6-dioxo-3-piperidyl) amino]phenyl]cyclohexyl]acetate (0.3 g, 645.23 μmol, 53.35% yield) as green solid. LCMS (ESI+): 401.3 $[M+H]^+$.

Step 5: To a stirred solution of tert-butyl 2-[4-[4-[(2,6-dioxo-3-piperidyl)amino]phenyl]cyclohexyl]acetate (0.17 g, 424.46 μmol) in DCM (10 mL), was added Hydrogen chloride solution (4 M in 1,4-dioxane, 1.60 g, 43.88 mmol, 2 mL) at 5° C. The reaction mixture was stirred at room temperature for 16 h. After completion, the reaction mixture was completely concentrated under reduced pressure to afford crude 2-[4-[4-[(2,6-dioxo-3-piperidyl)amino]phenyl] cyclohexyl]acetic acid (0.14 g, 232.68 μmol, 54.82% yield) as a light brown solid. LCMS (ESI+): 345.0 $[M+H]^+$.

Step 6: Target compound was prepared via HATU mediated acid-amine coupling reaction (procedure A). Amide coupling was carried out using 2-[4-[4-[(2,6-dioxo-3-piperidyl)amino]phenyl]cyclohexyl]acetic acid (63.58 mg, 166.93 μmol), N-ethyl-N-isopropyl-propan-2-amine (98.07 mg, 758.79 μmol, 132.17 HATU (57.70 mg, 151.76 μmol) and 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (0.09 g, 151.76 μmol) afford crude. The crude compound was purified by preparative-HPLC (10 mM Ammonium acetate:Acetonitrile) and fractions were lyophilized to afford 5-[2-[4-[2-[4-[4-[(2,6-dioxo-3-piperidyl) amino]phenyl]cyclohexyl]acetyl]piperazin-1-yl]pyrimidin-5-yl]-3-[3-[[ethyl(methyl)sulfamoyl]amino]-2,6-difluoro-benzoyl]-1H-pyrrolo[2,3]pyridine (10.67 mg, 11.82 μmol, 7.79% yield) as an off white solid and 5-[2-[4-[2-[4-[4-[(2,6-dioxo-3-piperidyl)amino]phenyl]cyclohexyl]acetyl]piperazin-1-yl]pyrimidin-5-yl]-3-[3-[[ethyl(methyl)sulfamoyl] amino]-2,6-difluoro-benzoyl]-1H-pyrrolo[2,3-b]pyridine (7.32 mg, 8.20 μmol, 5.40% yield) as an off white solid.

Data for isomer 1: LCMS (ESI+): 883.7 $[M+H]^+$. $^1H$ NMR (400 MHz, DMSO-$d_6$): δ 13.01 (s, 1H), 10.77 (s, 1H), 9.71 (s, 1H), 8.81 (s, 2H), 8.68 (d, J=2.40 Hz, 1H), 8.57 (s, 1H), 8.14 (d, J=2.80 Hz, 1H), 7.57-7.62 (m, 1H), 7.20-7.30 (m, 1H), 6.95 (d, J=8.40 Hz, 2H), 6.60 (d, J=8.40 Hz, 2H), 5.62 (d, J=7.20 Hz, 1H), 4.21-4.31 (m, 1H), 3.86-3.81 (m, 4H), 3.58-3.62 (m, 4H), 3.12 (q, J=6.80 Hz, 2H), 2.74 (s, 3H), 2.65-2.81 (m, 1H), 2.61-2.61 (m, 2H), 2.25-2.35 (m, 2H), 2.13-2.05 (m, 1H), 1.91-1.71 (m, 6H), 1.45-1.35 (m, 2H), 1.03-1.14 (m, 2H), 1.03 (t, J=7.20 Hz, 3H).

Data for isomer 2: LCMS (ESI+): 883.8 $[M+H]^+$. $^1H$ NMR (400 MHz, DMSO-$d_6$): δ 13.01 (s, 1H), 10.78 (s, 1H), 9.72 (s, 1H), 8.81 (s, 2H), 8.68 (d, J=2.00 Hz, 1H), 8.58 (s, 1H), 8.15 (s, 1H), 7.55-7.62 (m, 1H), 7.26-7.30 (m, 1H), 7.02 (d, J=8.40 Hz, 2H), 6.62 (d, J=8.80 Hz, 2H), 5.63 (s, 1H), 4.21-4.27 (m, 1H), 3.86-3.81 (m, 4H), 3.61-3.66 (m, 4H), 3.11 (q, J=7.20 Hz, 2H), 2.55-2.80 (m, 3H), 2.73 (s, 3H), 2.31-2.23 (m, 1H), 2.10-2.14 (m, 1H), 1.77-1.91 (m, 3H), 1.51-1.64 (m, 6H), 1.39-1.47 (m, 1H), 1.06-1.13 (m, 1H), 1.03 (t, J=7.20 Hz, 3H).

Note: relative configurations around cyclohexyl moieties were arbitrarily assigned to differentiate two diastereomers and to generate distinct registration numbers.

Example 37

5-[2-[4-[2-[4-[4-(2,6-dioxo-3-piperidyl)-3-oxo-piperazin-1-yl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

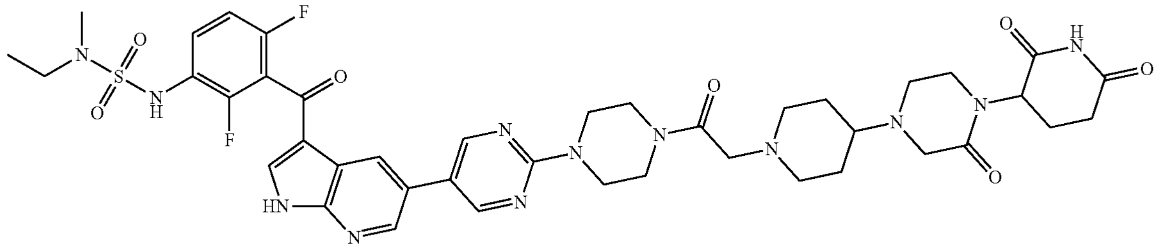 [SMILES: CCN(C)S(=O)(=O)Nc1ccc(F)c(C(=O)c2c[nH]c3ncc(-c4cnc(N5CCN(C(=O)CN6CCC(N7CCN(C8CCC(=O)NC8=O)C(=O)C7)CC6)CC5)nc4)cc23)c1F]

target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (80 mg, 134.90 μmol), DIPEA (87.17 mg, 674.48 μmol, 117.48 μL), 2-[4-[4-(2,6-dioxo-3-piperidyl)-3-oxo-piperazin-1-yl]-1-piperidyl]acetic acid (57.70 mg, 148.39 μmol) and HATU (61.55 mg, 161.88 μmol) to afford 5-[2-[4-[2-[4-[4-(2,6-dioxo-3-piperidyl)-3-oxo-piperazin-1-yl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (22.63 mg, 23.04 μmol, 17.08% yield) as off-white solid. LCMS (ESI+): 891.0 $[M+H]^+$. $^1H$ NMR (400 MHz, DMSO-$d_6$): δ 12.99 (s, 1H), 10.85 (s, 1H), 9.75 (s, 1H), 8.83 (s, 2H), 8.68 (d, J=2.40 Hz, 1H), 8.57 (s, 1H), 8.14 (s, 1H), 7.55-7.60 (m, 1H), 7.27 (t, J=8.40 Hz, 1H), 4.95 (m, 1H), 3.86 (s, 2H), 3.81 (s, 2H), 3.68 (s, 2H), 3.58 (s, 2H), 3.05-3.40 (m, 8H), 2.92-2.85 (m, 2H), 2.81-2.55 (m, 3H), 2.73 (s, 3H), 2.42-2.12 (m, 3H), 2.03 (t, J=12.80 Hz, 2H), 1.75-1.60 (m, 3H), 1.45-1.31 (m, 2H), 1.02 (t, J=6.80 Hz, 3H).

Example 38

5-[2-[4-[2-[1-[4-[(2,6-dioxo-3-piperidyl)amino]phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

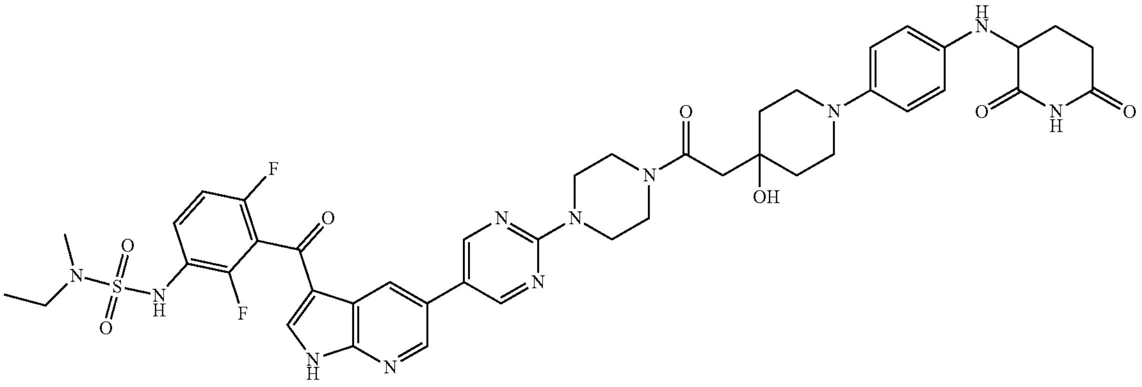 [SMILES: CCN(C)S(=O)(=O)Nc1ccc(F)c(C(=O)c2c[nH]c3ncc(-c4cnc(N5CCN(C(=O)CC6(O)CCN(c7ccc(NC8CCC(=O)NC8=O)cc7)CC6)CC5)nc4)cc23)c1F]

Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (250 mg, 372.80 μmol), 2-[1-[4-[(2,6-dioxo-3-piperidyl)amino]phenyl]-4-hydroxy-4-piperidyl]acetic acid (161.67 mg, 406.36 μmol), HATU (142.34 mg, 374.35 μmol) and N,N-diisopropylethylamine (240.90 mg, 1.86 mmol, 324.66 μL) to afford 5-[2-[4-[2-[1-[4-[(2,6-dioxo-3-piperidyl)amino]phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (116 mg, 122.06 μmol, 32.74% yield) as a grey solid. LCMS (ESI+): 900.4 $[M+H]^+$. $^1H$ NMR (400 MHz, DMSO-$d_6$): δ 13.01 (s, 1H), 10.79 (s, 1H), 9.71 (s, 1H), 8.75 (s, 2H), 8.68 (s, 1H), 8.68 (s, 1H), 8.58 (s, 1H), 8.15-8.14 (m, 1H), 7.62-7.56 (m, 1H), 7.30-7.26 (m, 1H), 6.73-6.66 (m, 3H), 5.40 (s, 1H), 4.35 (s, 1H), 3.88-3.43 (m, 8H), 3.12 (q, J=6.80 Hz, 3H), 2.74-2.67 (m, 6H), 1.88-1.84 (m, 1H), 1.76-1.75 (m, 5H), 1.03 (t, J=7.20 Hz, 3H).

Example 39

5-[2-[4-[2-[4-[2-(difluoromethyl)-4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

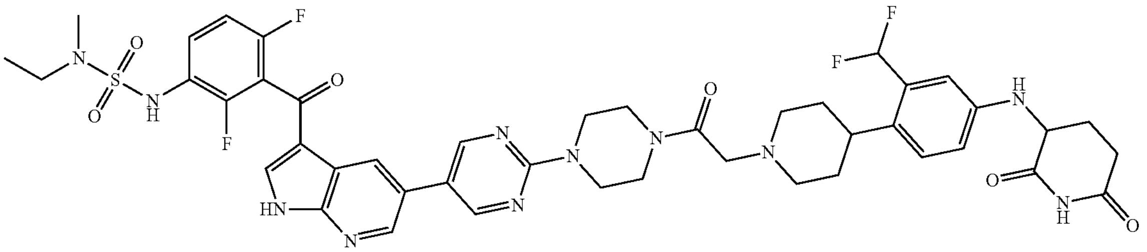 [SMILES: CCN(C)S(=O)(=O)Nc1ccc(F)c(C(=O)c2c[nH]c3ncc(-c4cnc(N5CCN(C(=O)CN6CCC(c7ccc(NC8CCC(=O)NC8=O)cc7C(F)F)CC6)CC5)nc4)cc23)c1F]

target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (100 mg, 179.67 μmol), 2-[4-[2-(difluoromethyl)-4-[(2,6-dioxo-3-piperidyl)amino]phenyl]-1-piperidyl]acetic acid (71.04 mg, 179.67 μmop, HATU (68.31 mg, 179.67 μmol) and DIPEA (92.88 mg, 718.67 μmol, 125.18 μL) to afford 5-[2-[4-[2-[4-[2-(difluoromethyl)-4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (30 mg, 29.28 μmol, 16.30% yield) as an off white solid. LCMS (ESI+): 934.1 $[M+H]^+$. $^1H$ NMR (400 MHz, DMSO-$d_6$): δ 13.01 (s, 1H), 10.79 (s, 1H), 9.70 (s, 1H), 8.83 (s, 2H), 8.69 (d, J=2.00 Hz, 1H), 8.59 (s, 1H), 8.15 (d, J=4.80 Hz, 1H), 7.56-7.61 (m, 1H), 7.28 (t, J=8.00 Hz, 1H), 7.00-7.17 (m, 2H), 6.84 (d, J=7.20 Hz, 2H), 6.10 (d, J=7.60 Hz, 1H), 4.37-4.29 (m, 1H), 3.94 (s, 2H), 3.87 (s, 2H), 3.60-3.67 (m, 4H), 3.12 (q, J=6.80 Hz, 2H), 2.93-2.91 (m, 2H), 2.65-2.80 (m, 2H), 2.74 (s, 3H), 2.40-2.57 (m, 3H), 2.55-2.62 (m, 2H), 2.00-2.09 (m, 1H), 1.80-2.00 (m, 3H), 1.80-1.69 (m, 2H), 1.03 (t, J=7.20 Hz, 3H).

Example 40

5-[2-[4-[2-[4-[2-cyano-4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

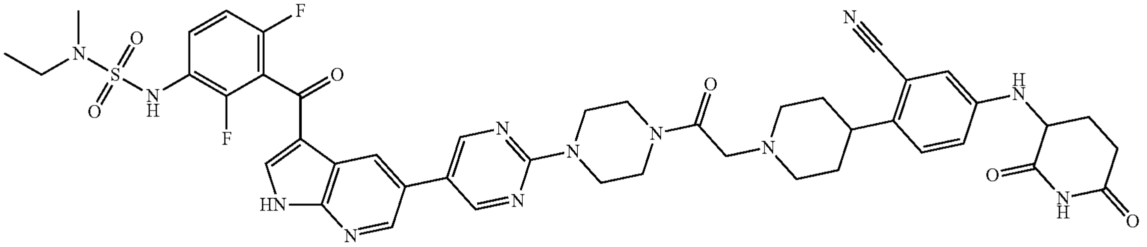 [SMILES: CCN(C)S(=O)(=O)Nc1ccc(F)c(C(=O)c2c[nH]c3ncc(-c4cnc(N5CCN(C(=O)CN6CCC(c7ccc(NC8CCC(=O)NC8=O)cc7C#N)CC6)CC5)nc4)cc23)c1F]

target compound was prepared via COMU mediated acid-amine coupling reaction (procedure B). Amide coupling was carried out using 2-[4-[2-cyano-4-[(2,6-dioxo-3-piperidyl)amino]phenyl]-1-piperidyl]acetic acid (56.26 mg, 138.27 μmol), N-ethyl-N-isopropyl-propan-2-amine (108.97 mg, 843.10 μmol, 146.85 COMU (72.21 mg, 168.62 μmol) and 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (0.1 g, 168.62 μmol) to afford 5-[2-[4-[2-[4-[2-cyano-4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (30.92 mg, 33.76 μmol, 20.02% yield) as a blue solid. LCMS (ESI+): 907.2 $[M-H]^+$. $^1H$ NMR (400 MHz, DMSO-$d_6$): δ 13.02 (s, 1H), 10.83 (s, 1H), 9.71 (s, 1H), 9.60 (s, 1H), 8.84 (s, 1H), 8.69 (d, J=2.40 Hz, 1H), 8.60 (s, 1H), 8.16 (d, J=2.80 Hz, 1H), 7.57-7.62 (m, 1H), 7.28 (t, J=8.40 Hz, 1H), 7.19 (d, J=9.60 Hz, 1H), 7.03 (s, 2H), 6.37 (d, J=7.60 Hz, 1H), 4.43-4.40 (m, 1H), 3.95 (s, 2H), 3.89 (s, 2H), 3.50-3.69 (m, 6H), 3.31-3.02 (m, 3H), 3.12 (q, J=7.20 Hz, 2H), 2.62-2.81 (m, 2H), 2.50-2.61 (m, 2H), 2.74 (s, 3H), 2.07-2.34 (m, 3H), 1.87-1.96 (m, 3H), 1.03 (t, J=7.20 Hz, 3H).

Example 41

5-[2-[4-[2-[4-[4-[(2,6-dioxo-3-piperidyl)oxy]-2,6-difluoro-phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

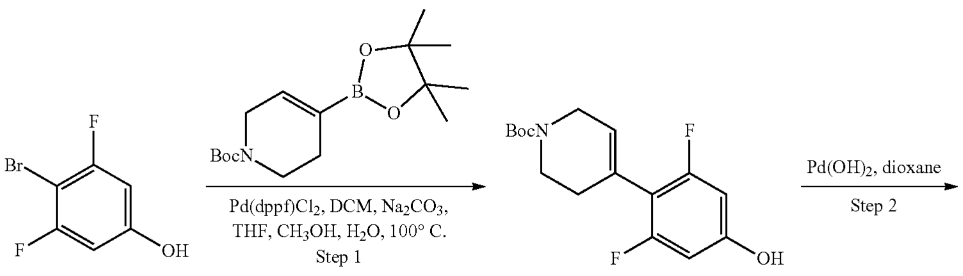

-continued

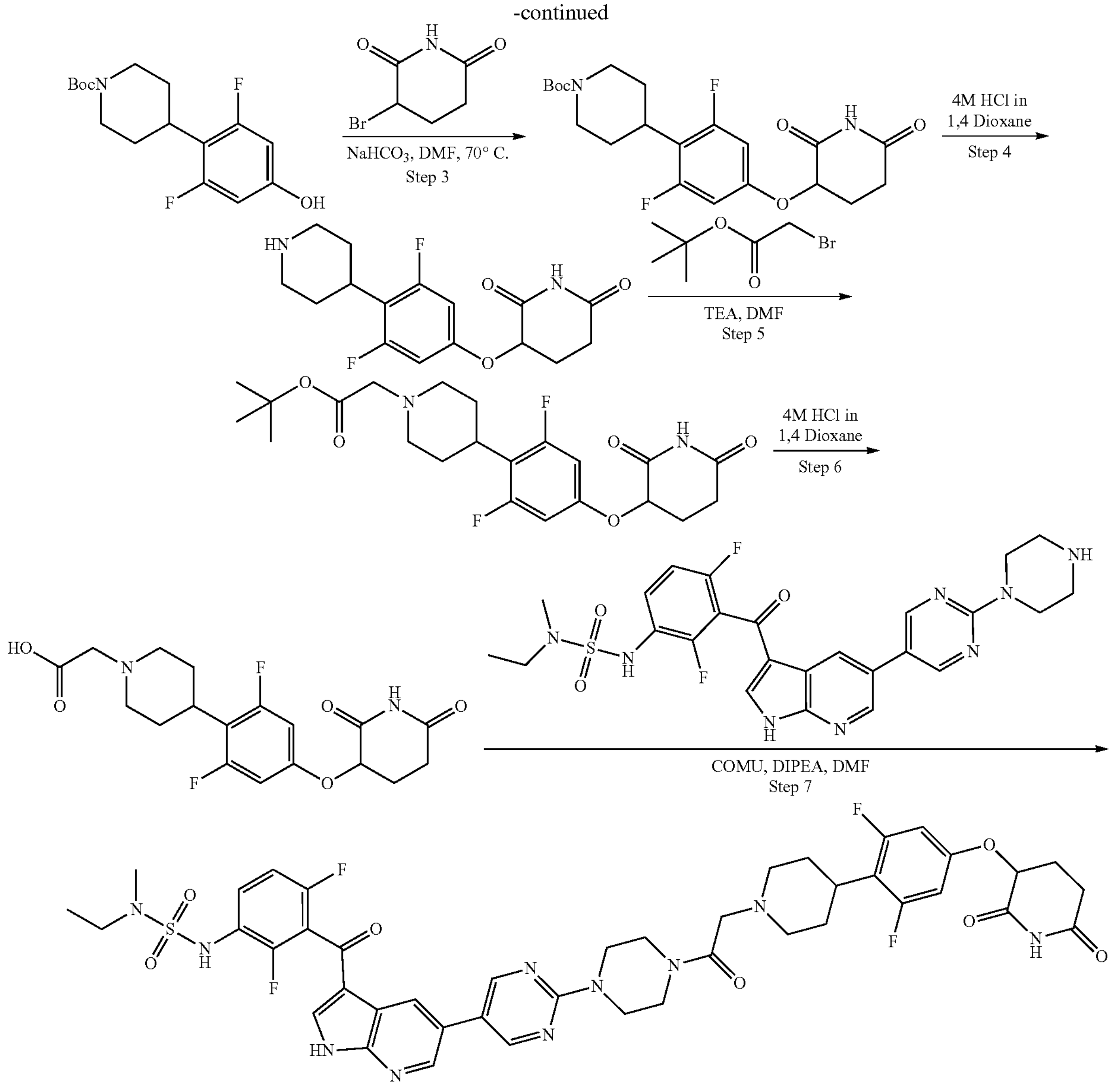

Step 1: To a stirred solution of 4-bromo-3,5-difluoro-phenol (2.5 g, 11.96 mmol) in THF (20 mL) Methanol (5 mL) and Water (5 mL) was added tert-butyl 4-(4,4,5,5-tetramethyl-1,3,2-dioxaborolan-2-yl)-3,6-dihydro-2H-pyridine-1-carboxylate (5.55 g, 17.94 mmol) and degassed with $N_2$ for 20 minutes. Pd(dppf)$Cl_2$·Dichloromethane (0.98 g, 1.20 mmol), Sodium carbonate (3.80 g, 35.89 mmol, 1.50 mL) were added to the reaction mixture and heated at 100° C. for 12 h. The reaction mixture was filtered and concentrated under reduced pressure to get crude which was purified by column chromatography on silica gel eluted with 20% ethyl acetate in petroleum ether to yield tert-butyl 4-(2,6-difluoro-4-hydroxy-phenyl)-3,6-dihydro-2H-pyridine-1-carboxylate (3.0 g, 8.09 mmol, 67.67% yield) as an off white solid. LCMS (ESI−): 310.1 $[M-H]^-$.

Step 2: To a solution of tert-butyl 4-(2,6-difluoro-4-hydroxy-phenyl)-3,6-dihydro-2H-pyridine-1-carboxylate (3.0 g, 9.64 mmol) in 1,4-Dioxane (60 mL) was degassed with $N_2$ for 15 minutes. Pd$(OH)_2$ (3.00 g, 21.36 mmol) was added to the reaction mixture and stirred under $H_2$ balloon pressure (1 atm) for 36 h at room temperature. After completion, the reaction mixture was filtered through celite and concentrated under reduced pressure to get tert-butyl 4-(2,6-difluoro-4-hydroxy-phenyl)piperidine-1-carboxylate (3.0 g, 8.90 mmol, 92.40% yield) as an off white solid. LCMS (ESI−): 312.1 $[M-H]^-$.

Step 3: To a stirred solution of tert-butyl 4-(2,6-difluoro-4-hydroxy-phenyl)piperidine-1-carboxylate (3 g, 9.57 mmol) in Acetonitrile (40 mL) was added 3-bromopiperidine-2,6-dione (3.68 g, 19.15 mmol), Cesium carbonate (7.80 g, 23.94 mmol) and tetrabutylammonium bromide (3.12 g, 9.68 mmol) at 0° C. The reaction mixture was stirred at room temperature for 48 h. The reaction mixture was diluted with water (20 mL) and extracted with ethyl acetate (2×100 mL). The combined organic layers were dried over anhydrous sodium sulphate, filtered and evaporated under reduced pressure to get crude which was purified by column chromatography on silica gel eluted with 30% ethyl acetate in pet-ether to yield tert-butyl 4-[4-[(2,6-dioxo-3-piperidyl)

oxy]-2,6-difluoro-phenyl]piperidine-1-carboxylate (2.2 g, 4.41 mmol, 46.02% yield) as an off white solid. LCMS (ESI+): 422.9 $[M+H]^+$.

Step 4: To a stirred solution of tert-butyl 4-[4-[(2,6-dioxo-3-piperidyl)oxy]-2,6-difluoro-phenyl]piperidine-1-carboxylate (2.2 g, 5.18 mmol) in Dichloromethane (20 mL) was added Hydrogen chloride solution (4 M in 1,4-dioxane, 8.00 g, 219.42 mmol, 10 mL) at 0° C. and the reaction mixture was stirred at room temperature for 12 h. After completion, the reaction mixture was concentrated under reduced pressure to get crude which was triturated with diethyl ether to afford 3-[3,5-difluoro-4-(4-piperidyl)phenoxy]piperidine-2,6-dione (1.5 g, 4.07 mmol, 78.61% yield) as an off white solid. LCMS (ESI+): 325.1 $[M+H]^+$.

Step 5: To a solution of 3-[3,5-difluoro-4-(4-piperidyl) phenoxy]piperidine-2,6-dione (1.5 g, 4.63 mmol) in N, N-Dimethylformamide (15 mL) was added Triethylamine (1.87 g, 18.50 mmol, 2.58 mL) and tert-butyl 2-bromoacetate (1.08 g, 5.55 mmol, 813.95 μL) under nitrogen atmosphere and stirred the reaction mixture at room temperature for 14 h. After completion, ice water was added to the reaction mixture and solid was filtered through Buchner funnel. Solid was dried under reduced pressure to get tert-butyl 2-[4-[4-[(2,6-dioxo-3-piperidyl)oxy]-2,6-difluoro-phenyl]-1-piperidyl]acetate (1.4 g, 3.10 mmol, 67.00% yield), which was used for next step without purification. LCMS (ESI+): 439.3 $[M+H]^+$.

Step 6: To a solution tert-butyl 2-[4-[4-[(2,6-dioxo-3-piperidyl)oxy]-2,6-difluoro-phenyl]-1-piperidyl]acetate (1.4 g, 3.19 mmol) in Dichloromethane (15 mL) was added 4 N HCl in dioxane (3.19 mmol) at 0° C. and stirred at room temperature for 4 h. The reaction mixture was concentrated under reduced pressure to get crude which was triturated with diethyl ether to afford 2-[4-[4-[(2,6-dioxo-3-piperidyl) oxy]-2,6-difluoro-phenyl]-1-piperidyl]acetic acid (1.4 g, 2.73 mmol, 85.41% yield) as white solid. LCMS (ESI+): 383.1 $[M+H]^+$.

Step 7: target compound was prepared via COMU mediated acid-amine coupling reaction (procedure B). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (100 mg, 179.67 μmol), 2-[4-[4-[(2,6-dioxo-3-piperidyl)oxy]-2,6-difluoro-phenyl]-1-piperidyl]acetic acid (68.70 mg, 179.67 μmol), N, N-Diisopropylethylamine (92.88 mg, 718.67 μmol, 125.18 μL) and COMU (76.95 mg, 179.67 μmol) to afford 5-[2-[4-[2-[4-[4-[(2,6-dioxo-3-piperidyl)oxy]-2,6-difluoro-phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (28 mg, 27.48 μmol, 15.30% yield) as an off white solid. LCMS (ESI+): 921.1 $[M+H]^+$. $^1H$ NMR (400 MHz, DMSO-$d_6$): δ 13.02 (d, J=3.20 Hz, 1H), 11.01 (s, 1H), 9.71 (s, 1H), 8.84 (s, 2H), 8.69 (d, J=2.00 Hz, 1H), 8.60 (s, 1H), 8.16 (d, J=2.80 Hz, 1H), 7.59 (dd, J=3.20, 9.00 Hz, 1H), 7.29 (t, J=8.00 Hz, 1H), 6.85 (d, J=10.80 Hz, 2H), 5.29 (dd, J=5.60, 10.80 Hz, 1H), 4.38 (s, 2H), 3.94 (s, 2H), 3.89 (s, 2H), 3.69 (s, 2H), 3.55-3.61 (m, 4H), 3.09-3.20 (m, 4H), 2.74 (s, 3H), 2.55-2.70 (m, 3H), 2.34-2.45 (m, 2H), 2.10-2.26 (m, 2H), 1.92 (d, J=12.00 Hz, 2H), 1.03 (t, J=7.20 Hz, 3H).

Example 42

5-[2-[4-[2-[1-[4-[(2,6-dioxo-3-piperidyl)amino]-2-fluoro-phenyl]-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

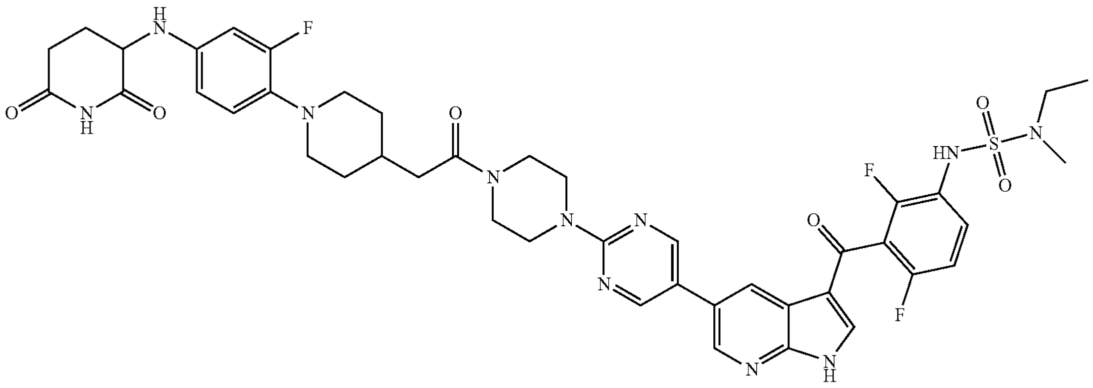 [SMILES: CCN(C)S(=O)(=O)Nc1ccc(F)c(C(=O)c2c[nH]c3ncc(-c4cnc(N5CCN(C(=O)CC6CCN(c7ccc(NC8CCC(=O)NC8=O)cc7F)CC6)CC5)nc4)cc23)c1F]

Initially 2-[1-[4-[(2,6-dioxo-3-piperidyl)amino]-2-fluoro-phenyl]-4-piperidyl]acetic acid (60 mg, 125.68 μmol, trifluoroacetic acid salt) was brought up in DMF (1 mL) and added DIPEA (52.30 mg, 404.69 μmol, 70.49 uL) followed by HATU (53.86 mg, 141.64 μmol). After 5 minutes added a solution of 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (60 mg, 101.17 μmol, hydrochloric acid salt) and DIPEA (52.30 mg, 404.69 μmol, 70.49 uL) in DMF (1 mL). The reaction was stirred overnight before adding 5 drops of sat. bicarb solution and 5 drops of water with continued stirring to cleave uronium adduct. Purified directly by RP isco 0-75% ACN/water w TFA to give 5-[2-[4-[2-[1-[4-[(2,6-dioxo-3-piperidyl)amino]-2-fluoro-phenyl]-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (50 mg, 46.75 μmol, 46.21% yield, trifluoroacetic acid salt) as an off white solid after lyophilization. LCMS (ESI+): 902.8 $[M+H]^+$. $^1H$ NMR (400 MHz, DMSO-$d_6$): δ 12.93 (d, J=3.3 Hz, 1H), 10.75 (s, 1H), 9.62 (s, 1H), 8.74 (s, 2H), 8.61 (d, J=2.3 Hz, 1H), 8.50 (s, 1H), 8.07 (d, J=3.2 Hz, 1H), 7.51 (td, J=9.0, 5.9 Hz, 1H), 7.21 (td, J=8.8, 1.5 Hz, 1H), 6.51 (d, J=33.1 Hz, 3H), 4.91-3.86 (m, 9H), 3.77 (dd, J=24.4, 5.9 Hz, 4H), 3.56 (t, J=5.4 Hz, 3H), 3.04 (q, J=7.1 Hz, 2H), 2.70-2.58 (m, 2H), 2.66 (s, 3H), 2.55-2.46 (m, 2H), 2.34 (m, 2H), 2.07-1.73 (m, 4H), 1.51 (s, 2H), 0.95 (t, J=7.1 Hz, 2H).

Example 43
1-(2,6-dioxo-3-piperidyl)-5-[4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-1-piperidyl]-3-methyl-2-oxo-benzimidazole
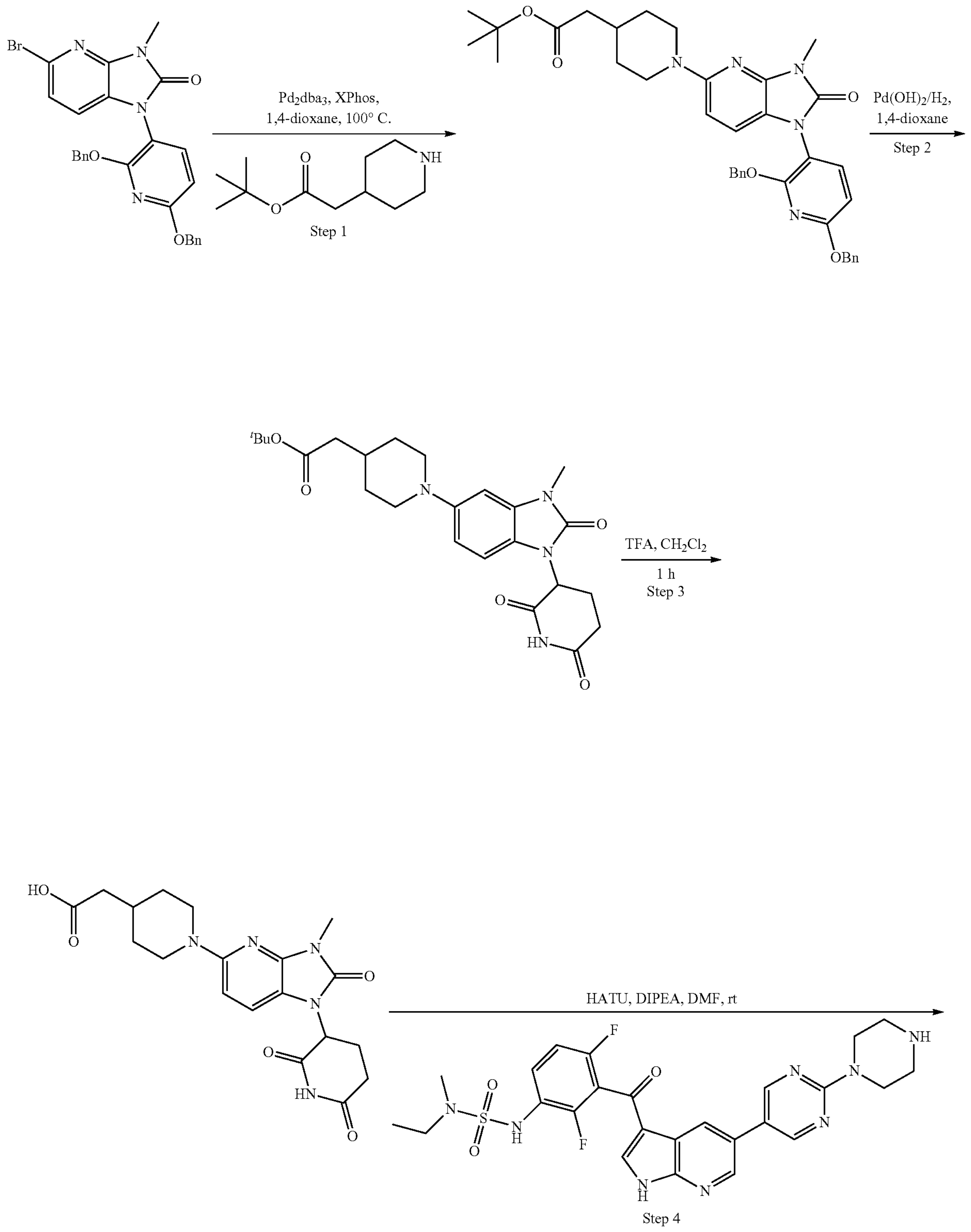

-continued

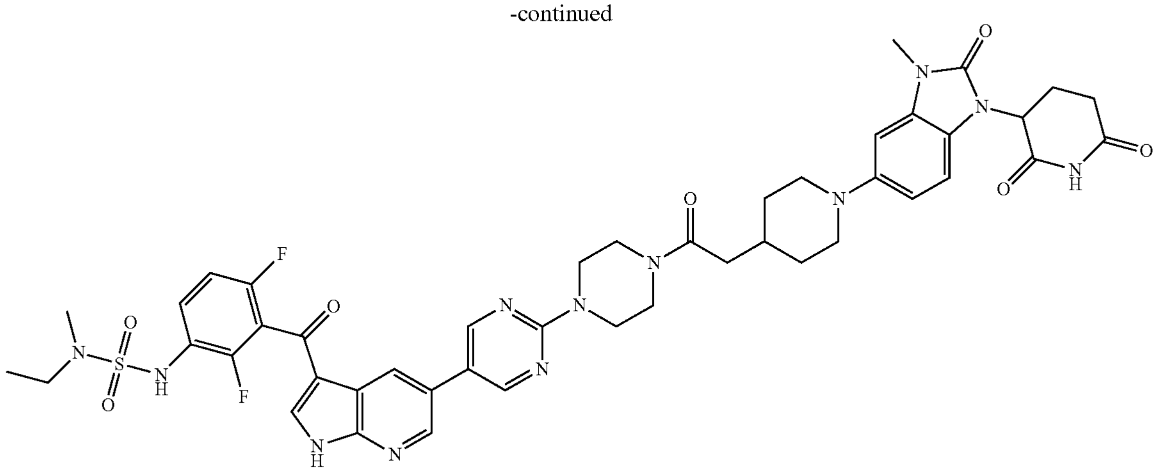

Step 1: To a stirred solution of tert-butyl 2-(4-piperidyl) acetate (192.97 mg, 968.27 μmol) and 5-bromo-1-(2,6-dibenzyloxy-3-pyridyl)-3-methyl-benzimidazol-2-one (500 mg, 968.27 μmol) were in 1,4-dioxane (7 mL) was added $Cs_2CO_3$ (946.44 mg, 2.90 mmol). The reaction mixture was degassed with nitrogen for 10 min, followed by addition of X-Phos (92.32 mg, 193.65 μmol) and $Pd_2dba_3$ (88.67 mg, 96.83 μmol). The reaction mixture was stirred for 16 h at 100° C. After completion of reaction, diluted with water (50 mL) and extracted with ethyl acetate (2×30 mL). The combined organic layers were dried over anhydrous sodium sulphate and concentrated under reduced pressure to yield crude. The crude was purified by silica gel column chromatography by using 50% petroleum ether/ethyl acetate as eluent system to afford tert-butyl 2-[1-[1-(2,6-dibenzyloxy-3-pyridyl)-3-methyl-2-oxo-benzimidazol-5-yl]-4-piperidyl] acetate (500 mg, 771.94 μmol, 79.72% yield) as gummy liquid. LCMS (ESI+): 635.3 $[M+H]^+$.

Step 2: To a stirred solution of tert-butyl 2-[1-[1-(2,6-dibenzyloxy-3-pyridyl)-3-methyl-2-oxo-benzimidazol-5-yl]-4-piperidyl]acetate (200 mg, 315.08 μmol) in 1,4 dioxane (10 mL) was added Palladium hydroxide on carbon, 20 wt. (132.74 mg, 945.24 μmol) at 25° C. The reaction mixture was stirred for 16 h at 25° C. under $H_2$ balloon pressure. After completion of reaction, filtered through celite bed and washed with 1,4-dioxane (50 mL) and Dichloromethane (50 mL). The filtrate was concentrated to yield crude. The crude was washed with diethyl ether (20 mL) to afford tert-butyl 2-[1-[1-(2,6-dioxo-3-piperidyl)-3-methyl-2-oxo-benzimidazol-5-yl]-4-piperidyl]acetate (110 mg, 219.26 μmol, 69.59% yield) as white solid. LCMS (ESI+): 457.3 $[M+H]^+$.

Step 3: To a stirred solution of tert-butyl 2-[1-[1-(2,6-dioxo-3-piperidyl)-3-methyl-2-oxo-benzimidazol-5-yl]-4-piperidyl]acetate (110 mg, 240.95 μmol) in Dichloromethane (2 mL) was added TFA (82.42 mg, 722.84 μmol, 55.69 μL) at 0° C. The reaction mixture was stirred for 2 h at 25° C. After completion of reaction, reaction mixture was concentrated under reduced pressure to yield crude. The crude was washed with diethyl ether (20 mL) to yield 2-[1-[1-(2,6-dioxo-3-piperidyl)-3-methyl-2-oxo-benzimidazol-5-yl]-4-piperidyl]acetic acid (110 mg, 221.75 μmol, 92.03% yield, formic acid salt) as an off white solid. LCMS (ESI+): 401.0 $[M+H]^+$.

Step 4: Target compound was prepared via HATU mediated acid-amine coupling reaction (procedure A). Amide coupling was carried out using 2-[1-[1-(2,6-dioxo-3-piperidyl)-3-methyl-2-oxo-benzimidazol-5-yl]-4-piperidyl] acetic acid (120 mg, 233.26 μmol), 3-[3-[[ethyl(methyl) sulfamoyl]amino]-2,6-difluoro-benzoyl]-5-(2-piperazin-1-ylpyrimidin-5-yl)-1H-pyrrolo[2,3-b]pyridine (156.43 mg, 233.26 μmol), HATU (133.04 mg, 349.89 μmol) and N,N-diisopropylethylamine (90.44 mg, 699.78 μmol, 121.89 μL) to afford 1-(2,6-dioxo-3-piperidyl)-5-[4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-1-piperidyl]-3-methyl-2-oxo-benzimidazole (50 mg, 47.01 μmol, 20.15% yield) as a light pink solid. LCMS (ESI+): 939.2 $[M+H]^+$. $^1H$ NMR (400 MHz, DMSO-$d_6$): δ 13.01 (s, 1H), 11.14 (s, 1H), 9.71 (s, 1H), 8.82 (s, 1H), 8.69 (s, 1H), 8.59 (s, 1H), 8.15 (s, 1H), 7.62-7.56 (m, 2H), 7.31-7.24 (m, 3H), 5.44-5.39 (m, 1H), 3.90-3.70 (m, 8H), 3.63-3.39 (m, 8H), 3.12 (q, J=6.80 Hz, 3H), 3.03-2.95 (m, 2H), 2.74 (s, 3H), 2.71-2.51 (m, 2H), 2.19-2.03 (m, 4H), 1.66 (s, 2H), 1.03 (t, J=7.20 Hz, 3H).

Example 44

5-[2-[4-[2-[4-[4-(2,4-dioxohexahydropyrimidin-1-yl)-2-fluoro-phenyl]-1-piperidyl]acetyl]piperazin-1-yl]pyrimidin-5-yl]-3-[3-[[ethyl(methyl)sulfamoyl] amino]-2,6-difluoro-benzoyl]-1H-pyrrolo[2,3-b] pyridine

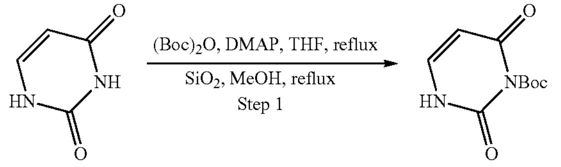

-continued
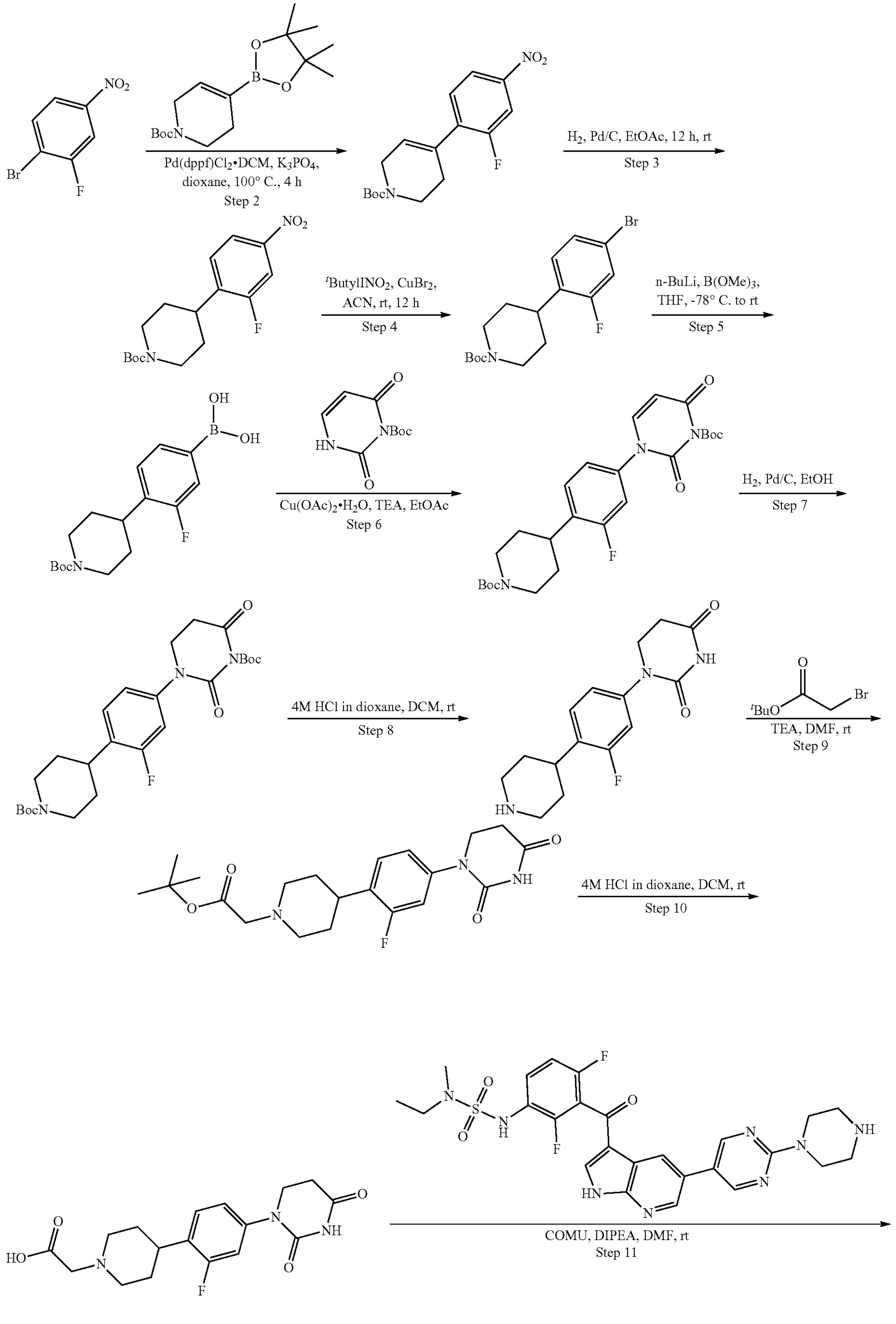

-continued

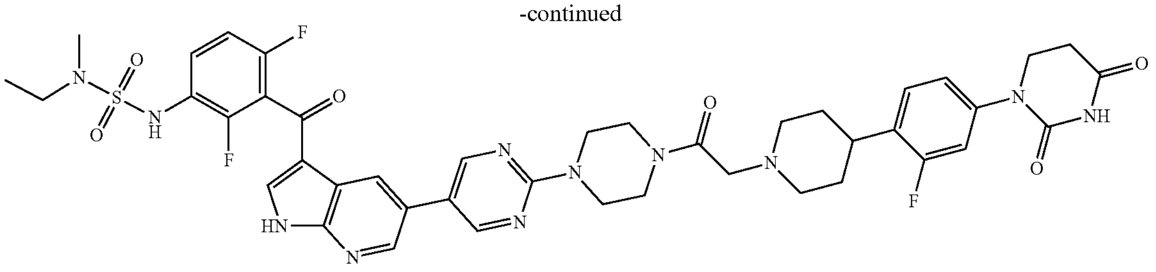

Step 1: To a solution of 1H-pyrimidine-2,4-dione (4.0 g, 35.69 mmol) in Tetrahydrofuran (40 mL) were added DMAP (435.98 mg, 3.57 mmol), tert-butoxycarbonyl tert-butyl carbonate (19.47 g, 89.22 mmol, 20.47 mL) and heated at reflux for 2 h. After formation of di-Boc intermediate, the reaction mixture was cooled to 40° C., Silica gel (2.0 g, 35.69 mmol), Methanol (10 mL) were added to the reaction mixture and heated at reflux for 1 h. The reaction mixture was concentrated under reduced pressure to get crude which was crystalized by ethyl acetate and petroleum ether to afford tert-butyl 2,4-dioxo-1H-pyrimidine-3-carboxylate (3.8 g, 15.22 mmol, 42.65% yield) as off white solid. LCMS (ESI): 211.2 $[M-H]^+$.

Step 2: To a solution of 1-bromo-2-fluoro-4-nitro-benzene (5.0 g, 22.73 mmol) in 1,4 Dioxane (40 mL) was added tert-butyl 4-(4,4,5,5-tetramethyl-1,3,2-dioxaborolan-2-yl)-3,6-dihydro-2H-pyridine-1-carboxylate (7.03 g, 22.73 mmol) and degassed with $N_2$ for 20 minutes. Potassium phosphate tribasic anhydrous (12.06 g, 56.82 mmol), $Pd(dppf)Cl_2$.Dichloromethane (1.86 g, 2.27 mmol) were added to the reaction mixture and heated at 100° C. for 4 h. The reaction mixture was filtered and concentrated under reduced pressure to get crude which was purified by column chromatography on silica gel eluted with 15% ethyl acetate in petroleum ether to yield tert-butyl 4-(2-fluoro-4-nitro-phenyl)-3,6-dihydro-2H-pyridine-1-carboxylate (5.7 g, 16.59 mmol, 72.98% yield) as an off white solid. LCMS (ESI): 321.2 $[M-H]^+$.

Step 3: A solution of tert-butyl 4-(2-fluoro-4-nitro-phenyl)-3,6-dihydro-2H-pyridine-1-carboxylate (5.7 g, 17.68 mmol) in Ethyl acetate (150 mL) was degassed with $N_2$ for 15 minutes. 10% Palladium on carbon (2.0 g, 17.68 mmol) was added to the reaction mixture and stirred under $H_2$ balloon pressure for 14 h. After completion, the reaction mixture was filtered through celite and concentrated under reduced pressure to get tert-butyl 4-(4-amino-2-fluoro-phenyl)piperidine-1-carboxylate (4.6 g, 13.60 mmol, 76.88% yield) as brown solid. LCMS (ESI+): 239.5 $[M+H-56]^+$.

Step 4: To a cooled solution of tert-butyl nitrite (2.10 g, 20.38 mmol, 2.42 mL), copper dibromide (4.55 g, 20.38 mmol, 966.59 μL) in Acetonitrile (10 mL) at 0° C. was added a solution of tert-butyl 4-(4-amino-2-fluoro-phenyl) piperidine-1-carboxylate (4.0 g, 13.59 mmol) in Acetonitrile (20 mL) and allow to stir the reaction mixture at room temperature for 2 h. After completion, the reaction mixture was diluted with water (20 mL), extracted with ethyl acetate (100 mL). The organic layer was washed with $NaHCO_3$ solution (40 mL), brine (40 mL), dried over sodium sulphate and concentrated under reduced pressure to get crude which was purified by column chromatography on silica gel eluted with 10% ethyl acetate in petroleum ether to afford tert-butyl 4-(4-bromo-2-fluoro-phenyl)piperidine-1-carboxylate (1.7 g, 3.08 mmol, 22.70% yield) as a light brown sticky solid. LCMS (ESI+): 302.0 $[M+H-56]^+$.

Step 5: To a cooled solution of tert-butyl 4-(4-bromo-2-fluoro-phenyl)piperidine-1-carboxylate (1.7 g, 4.75 mmol) in THF (20 mL) at −78° C. was added n-BuLi (1.6 M in hexane, 7.12 mmol) and stirred for 30 minutes at the same temperature. trimethyl borate (739.66 mg, 7.12 mmol, 808.37 μL) was added to the reaction mixture at −78° C. and stirred for 1 h. The reaction mixture was warmed to room temperature for 2 h. The reaction mixture was quenched with $NH_4Cl$ solution (40 mL), extracted with ethyl acetate (120 mL). The organic layer was washed with water (50 mL), brine (50 mL), dried over sodium sulphate and concentrated under reduced pressure to get crude [4-(1-tert-butoxycarbonyl-4-piperidyl)-3-fluoro-phenyl]boronic acid (1.4 g, 2.25 mmol, 47.47% yield) which was used in next step without further purification. LCMS (ESI+): 268.0 $[M+H-56]^+$.

Step 6: To a mixture of [4-(1-tert-butoxycarbonyl-4-piperidyl)-3-fluoro-phenyl]boronic acid (1.4 g, 4.33 mmol), tert-butyl 2,4-dioxo-1H-pyrimidine-3-carboxylate (919.29 mg, 4.33 mmol) in Ethyl acetate (25 mL) were added Triethylamine (1.32 g, 13.00 mmol, 1.81 mL), copper diacetate (157.37 mg, 866.43 μmol) and purged with oxygen. The reaction mixture was stirred under oxygen balloon for 26 h. The reaction mixture was diluted with ethyl acetate (80 mL), washed with water (30 mL), $NH_4Cl$ solution (30 mL) and $NH_4OH$ solution (30 mL). The organic layer was dried over sodium sulphate and concentrated under reduced pressure to get crude which was purified by column chromatography on silica gel eluted with 30% ethyl acetate in petroleum ether to afford tert-butyl 3-[4-(1-tert-butoxycarbonyl-4-piperidyl)-3-fluoro-phenyl]-2,6-dioxo-pyrimidine-1-carboxylate (1.06 g, 1.71 mmol, 39.49% yield) as light brown sticky solid. LCMS (ESI+): 334.1 $[M+H-56]^+$.

Step 7: To a solution of tert-butyl 3-[4-(1-tert-butoxycarbonyl-4-piperidyl)-3-fluoro-phenyl]-2,6-dioxo-pyrimidine-1-carboxylate (1.1 g, 2.25 mmol) in Ethanol (20 mL) was added 10% Palladium on carbon (400 mg, 2.25 mmol) and stirred under $H_2$ balloon pressure for 16 h. The reaction mixture was filtered through celite and concentrated under reduced pressure to get tert-butyl 3-[4-(1-tert-butoxycarbonyl-4-piperidyl)-3-fluoro-phenyl]-2,6-dioxo-hexahydropyrimidine-1-carboxylate (850 mg, 1.47 mmol, 65.41% yield) as a light brown sticky solid. LCMS (ESI+): 336.1 $[M+H-56]^+$.

Step 8: To a cooled solution of tert-butyl 3-[4-(1-tert-butoxycarbonyl-4-piperidyl)-3-fluoro-phenyl]-2,6-dioxo-hexahydropyrimidine-1-carboxylate (850.00 mg, 1.73 mmol) in Dichloromethane (6 mL) at 0° C. was added Trifluoroacetic acid (2.22 g, 19.47 mmol, 1.5 mL) and stirred at room temperature for 4 h. The reaction mixture was concentrated under reduced pressure to get crude which was triturated with diethyl ether to afford 1-[3-fluoro-4-(4-piperidyl)phenyl]hexahydropyrimidine-2,4-dione (760 mg, 1.69 mmol, 97.59% yield) as a brown sticky solid. LCMS (ESI+): 292.1 $[M+H]^+$.

Step 9: To a solution of 1-[3-fluoro-4-(4-piperidyl)phenyl]hexahydropyrimidine-2,4-dione (755.23 mg, 2.59 mmol), Triethylamine (1.05 g, 10.37 mmol, 1.45 mL) in N,N-Dimethylformamide (4 mL) was added tert-butyl 2-bromoacetate (505.66 mg, 2.59 mmol, 380.20 μL) and stirred at room temperature for 14 h. The reaction mixture was diluted with water (30 mL) and extracted with ethyl acetate (50 mL). The organic layer was washed with brine solution (20 mL), dried over sodium sulphate and concentrated under reduced pressure to get tert-butyl 2-[4-[4-(2,4-dioxohexahydropyrimidin-1-yl)-2-fluoro-phenyl]-1-piperidyl]acetate (620 mg, 1.36 mmol, 52.50% yield) as a light brown solid. LCMS (ESI+): 406.3 $[M+H]^+$.

Step 10: To a solution of tert-butyl 2-[4-[4-(2,4-dioxohexahydropyrimidin-1-yl)-2-fluoro-phenyl]-1-piperidyl]acetate (650 mg, 1.60 mmol) in Dichloromethane (5 mL) was added 4 M HCl in 1,4-Dioxane (1.60 mmol, 4 mL) at 0° C. and stirred at room temperature for 6 h. After completion, the reaction mixture was concentrated under reduced pressure to get crude which was triturated with petroleum ether to afford 2-[4-[4-(2,4-dioxohexahydropyrimidin-1-yl)-2-fluoro-phenyl]-1-piperidyl]acetic acid (550 mg, 1.57 mmol, 97.79% yield) as off white solid. LCMS (ESI+): 350.1 $[M+H]^+$.

Step 11: Target compound was prepared via COMU mediated acid-amine coupling reaction (procedure B). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (90 mg, 161.70 μmol), 2-[4-[4-(2,4-dioxohexahydropyrimidin-1-yl)-2-fluoro-phenyl]-1-piperidyl]acetic acid (56.49 mg, 161.70 μmol), N, N-Diisopropylethylamine (83.59 mg, 646.80 μmol, 112.66 μL) and COMU (69.25 mg, 161.70 μmol) to afford 5-[2-[4-[2-[4-[4-(2,4-dioxohexahydropyrimidin-1-yl)-2-fluoro-phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (26 mg, 27.72 μmol, 17.14% yield) as off white solid. LCMS (ESI+): 888.0 $[M+H]^+$. $^1H$ NMR (400 MHz, DMSO-$d_6$): δ 13.01 (s, 1H), 10.42 (s, 1H), 9.70 (s, 1H), 8.82 (s, 2H), 8.69 (d, J=2.00 Hz, 1H), 8.58 (s, 1H), 8.15 (s, 1H), 7.55-7.61 (m, 1H), 7.19-7.39 (m, 4H), 3.90 (s, 2H), 3.83 (s, 2H), 3.78-3.81 (m, 2H), 3.70 (s, 2H), 3.62 (s, 2H), 3.12 (q, J=7.20 Hz, 2H), 2.98-2.75 (m, 3H), 2.47-2.55 (m, 1H), 2.32-2.10 (m, 2H), 2.67-2.75 (m, 3H), 2.74 (s, 3H), 1.63-1.85 (m, 3H), 1.03 (t, J=7.20 Hz, 3H).

Example 45

5-[2-[4-[2-[1-[4-[(2,6-dioxo-3-piperidyl)amino]-2,6-difluoro-phenyl]-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

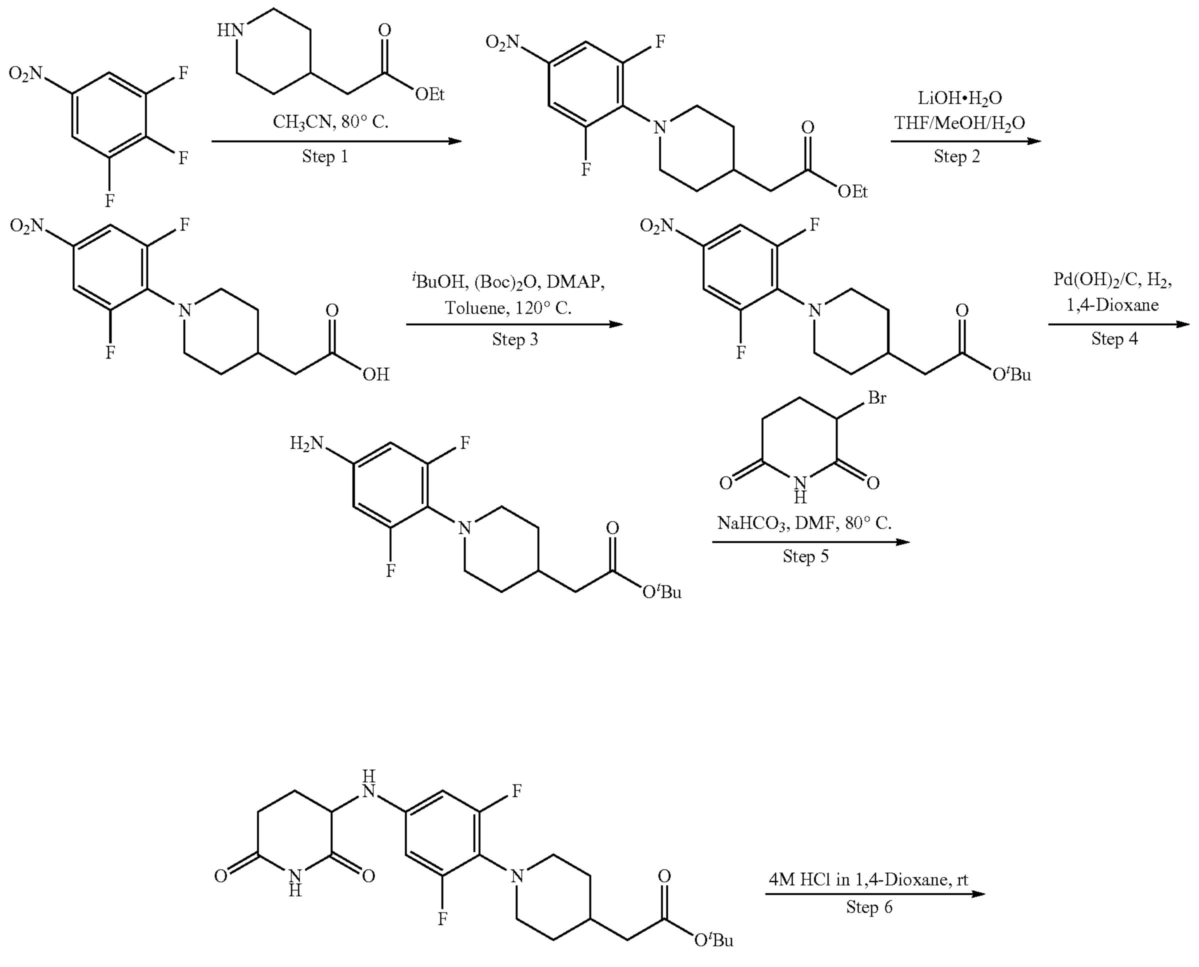

-continued

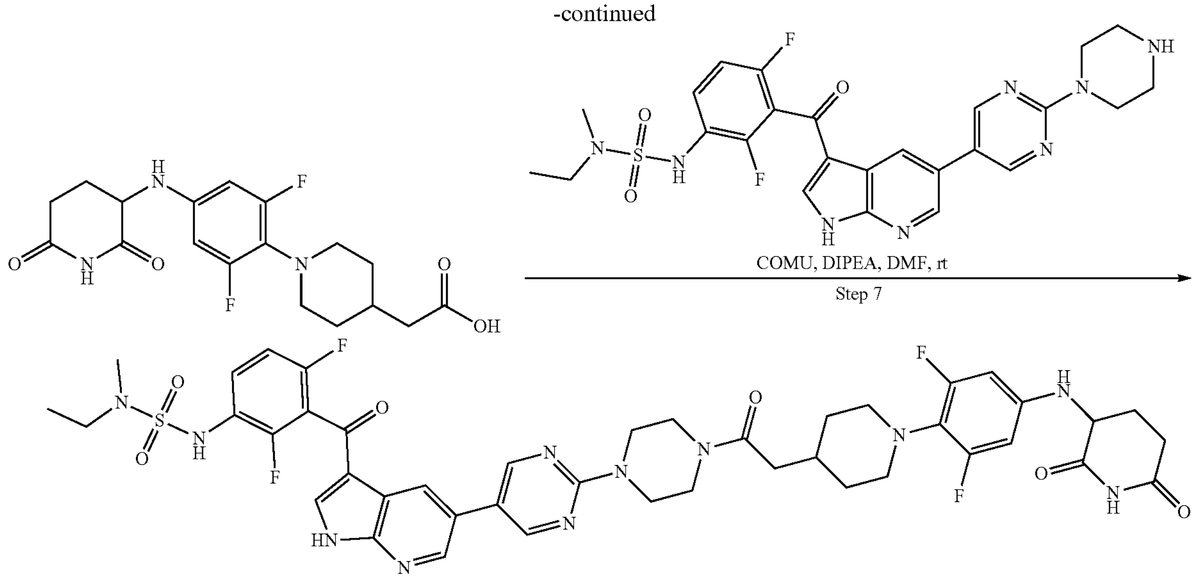

Step 1: A mixture of 1,2,3-trifluoro-5-nitro-benzene (517.06 mg, 2.92 mmol) and ethyl 2-(4-piperidyl)acetate (0.5 g, 2.92 mmol) in acetonitrile (8.0 mL) was heated at 80° C. for 12 h. Reaction was cooled to room temperature and concentrated under reduced pressure. The resulting crude residue was dissolved in ethyl acetate (50 mL), washed with water (2×50 mL), dried over sodium sulphate, filtered and concentrated under reduced pressure. The crude product was purified by silica gel column chromatography using 10% ethyl acetate in petroleum ether as an eluent to afford ethyl 2-[1-(2,6-difluoro-4-nitro-phenyl)-4-piperidyl]acetate (620 mg, 1.88 mmol, 64.37% yield) as an off-white solid. LCMS (ESI+): 328.9 $[M+H]^+$.

Step 2: To a stirred solution of ethyl 2-[1-(2,6-difluoro-4-nitro-phenyl)-4-piperidyl]acetate (620 mg, 1.89 mmol) in tetrahydrofuran (3.0 mL)/water (3.0 mL)/methanol (3.0 mL) was added Lithium hydroxide monohydrate (237.74 mg, 5.67 mmol, 157.44 μL) at room temperature. The reaction mixture was stirred at room temperature for 4 h. Reaction mixture was acidified to pH ~3 using 1.5 N aqueous HCl solution, resulting solid was filtered and dried to afford 2-[1-(2,6-difluoro-4-nitro-phenyl)-4-piperidyl]acetic acid (530 mg, 1.76 mmol, 93.29% yield) as a yellow solid. LCMS (ESI+): 300.9 $[M+H]^+$.

Step 3: To a stirred solution of 2-[1-(2,6-difluoro-4-nitro-phenyl)-4-piperidyl]acetic acid (480 mg, 1.60 mmol) in Toluene (3 mL)/t-butanol (2 mL) were added di-tert-butyl dicarbonate (201.25 mg, 922.14 μmol, 211.62 μL) followed by 4-(Dimethylamino)pyridine (195.30 mg, 1.60 mmol) at room temperature under nitrogen atmosphere. The reaction mixture was heated at 110° C. for 12 h. Reaction mixture was cooled to room temperature, quenched with aqueous sodium bicarbonate solution and extracted with ethyl acetate (2×30 mL). Combined organic layers were washed with 1.5 N aqueous HCl solution (2×30 mL), dried over sodium sulphate, filtered and concentrated under reduced pressure. The crude product was purified by silica gel column chromatography using 5% ethyl acetate in petroleum ether as an eluent to afford tert-butyl 2-[1-(2,6-difluoro-4-nitro-phenyl)-4-piperidyl]acetate (275 mg, 748.22 μmol, 46.80% yield) as a yellow solid. LCMS (ESI+): 357.2 $[M+H]^+$.

Step 4: To a stirred solution of tert-butyl 2-[1-(2,6-difluoro-4-nitro-phenyl)-4-piperidyl]acetate (800 mg, 2.24 mmol) in 1,4-Dioxane (10 mL) was added Palladium hydroxide on carbon (300 mg, 2.14 mmol) at room temperature. The reaction mixture was stirred under hydrogen pressure (1 atm) at room temperature for 12 h. Reaction was filtered through celite bed, washed with ethyl acetate (10 mL) and the resulting filtrate was concentrated under reduced pressure to afford tert-butyl 2-[1-(4-amino-2,6-difluoro-phenyl)-4-piperidyl]acetate (750 mg, 1.61 mmol, 71.57% yield) as a pale yellow semisolid. LCMS (ESI+): 327.1 $[M+H]^+$.

Step 5: To a stirred solution of tert-butyl 2-[1-(4-amino-2,6-difluoro-phenyl)-4-piperidyl]acetate (750 mg, 2.30 mmol) in N,N-dimethylformamide (5.0 mL) were added 3-bromopiperidine-2,6-dione (1.32 g, 6.89 mmol) followed by added Sodium bicarbonate (579.12 mg, 6.89 mmol, 268.11 uL) at room temperature under nitrogen atmosphere. The reaction mixture was heated at 80° C. for 48 h. Reaction mixture was cooled to room temperature, added to water (30 ml) and extracted with ethyl acetate (2×30 mL). The combined organic layers were washed with brine (30 mL), dried over sodium sulphate, filtered and concentrated under reduced pressure. The crude product was purified by silica gel column chromatography using 40% ethyl acetate in petroleum ether as an eluent to afford tert-butyl 2-[1-[4-[(2,6-dioxo-3-piperidyl)amino]-2,6-difluoro-phenyl]-4-piperidyl]acetate (280 mg, 562.01 μmol, 24.46% yield) as a brown semi solid. LCMS (ESI+): 438.2 $[M+H]^+$.

Step 6: To a stirred solution of tert-butyl 2-[1[4-[(2,6-dioxo-3-piperidyl)amino]-2,6-difluoro-phenyl]-4-piperidyl] acetate (280 mg, 640.03 μmol) in dichloromethane (5.0 mL) was added Hydrogen chloride solution, 4 M in 1,4-dioxane (640.03 μmol, 10 mL) at 0° C. The reaction mixture was warmed to room temperature and stirred for 12 h. Reaction mixture was concentrated under reduced pressure, resulting residue was triturated with diethyl ether (2×5 mL) and dried to afford 2-[1-[4-[(2,6-dioxo-3-piperidyl)amino]-2,6-difluoro-phenyl]-4-piperidyl]acetic acid (250 mg, 460.77 μmol, 71.99% yield, hydrochloric acid salt) as a brown solid. LCMS (ESI+): 382.2 $[M+H]^+$.

Step 7: Target compound was prepared via COMU mediated acid-amine coupling reaction (procedure B). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (300 mg, 505.86 μmol, hydrochloric acid salt), 2-[1-[4-[(2,6-dioxo-3-piperidyl)amino]-2,6-difluoro-phenyl]-4-piperidyl]acetic acid (192.92 mg, 461.72 μmol, hydrochloric acid salt), N,N-disopropylethylamine (326.90 mg, 2.53 mmol, 440.56 μL) and COMU (259.97 mg, 607.03 μmol) to afford 5-[2-[4-[2-

[1-[4-[(2,6-dioxo-3-piperidyl)amino]-2,6-difluoro-phenyl]-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (95.7 mg, 101.97 μmol, 20.16% yield) as an off-white solid. LCMS (ESI+): 920.3 $[M+H]^+$. $^1H$ NMR (400 MHz, DMSO-$d_6$): δ 12.80 (s, 1H), 10.81 (s, 1H), 8.80 (s, 1H), 8.67 (d, J=2.40 Hz, 1H), 8.56 (s, 1H), 8.10 (s, 1H), 7.58-7.52 (m, 1H), 7.20-7.16 (m, 1H), 6.32 (d, J=12.40 Hz, 2H), 6.23 (d, J=8.40 Hz, 1H), 4.32-3.86 (m, 1H), 3.81-3.09 (m, 4H), 3.05-2.95 (m, 4H), 3.15 (q, J=7.20 Hz, 2H), 3.05-2.95 (m, 4H), 2.74 (s, 3H), 2.36-2.33 (m, 4H), 1.90-1.85 (m, 3H), 1.84-1.71 (m, 4H), 1.35-1.31 (m, 2H), 1.02 (t, J=7.20 Hz, 3H).

Example 46

5-[2-[4-[2-[4-[4-[(2,6-dioxo-3-piperidyl)amino]-2,6-difluoro-phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

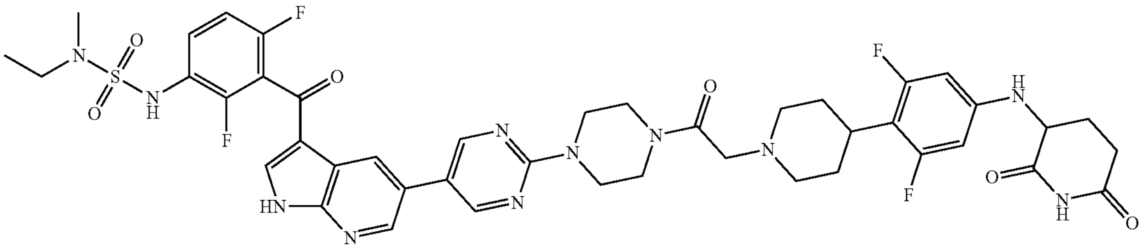 [SMILES: CCN(C)S(=O)(=O)Nc1ccc(F)c(C(=O)c2c[nH]c3ncc(-c4cnc(N5CCN(C(=O)CN6CCC(c7c(F)cc(NC8CCC(=O)NC8=O)cc7F)CC6)CC5)nc4)cc23)c1F]

target compound was prepared via COMU mediated acid-amine coupling reaction (procedure B). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (90 mg, 161.70 μmol), 2-[4-[4-[(2,6-dioxo-3-piperidyl)amino]-2,6-difluoro-phenyl]-1-piperidyl]acetic acid (61.67 mg, 161.70 μmol), DIPEA (83.59 mg, 646.80 μmol, 112.66 and COMU (69.25 mg, 161.70 μmol) to afford 5-[2-[4-[2-[4-[4-[(2,6-dioxo-3-piperidyl)amino]-2,6-difluoro-phenyl]-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (20 mg, 21.39 μmol, 13.23% yield) as an off white solid. LCMS (ESI+): 920.0 $[M+H]^+$. $^1H$ NMR (400 MHz, DMSO-$d_6$): δ 10.82 (s, 1H), 8.81 (s, 2H), 8.67 (d, J=2.00 Hz, 1H), 8.56 (s, 1H), 8.09 (s, 1H), 7.51-7.57 (m, 1H), 7.14 (t, J=8.80 Hz, 1H), 6.09-6.35 (m, 3H), 4.40-4.32 (m, 1H), 3.89 (s, 2H), 3.82 (s, 2H), 3.71 (s, 2H), 3.59 (s, 2H), 3.33 (s, 2H), 3.06 (q, J=7.20 Hz, 2H), 2.95 (d, J=10.40 Hz, 2H), 2.68-2.75 (m, 2H), 2.66 (s, 3H), 2.52-2.60 (m, 1H), 1.85-2.10 (m, 6H), 1.60 (d, J=10.40 Hz, 2H), 1.01 (t, J=7.20 Hz, 3H).

Example 47

3-(2,6-dioxo-3-piperidyl)-6-[4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-1-piperidyl]-1-methyl-indazole

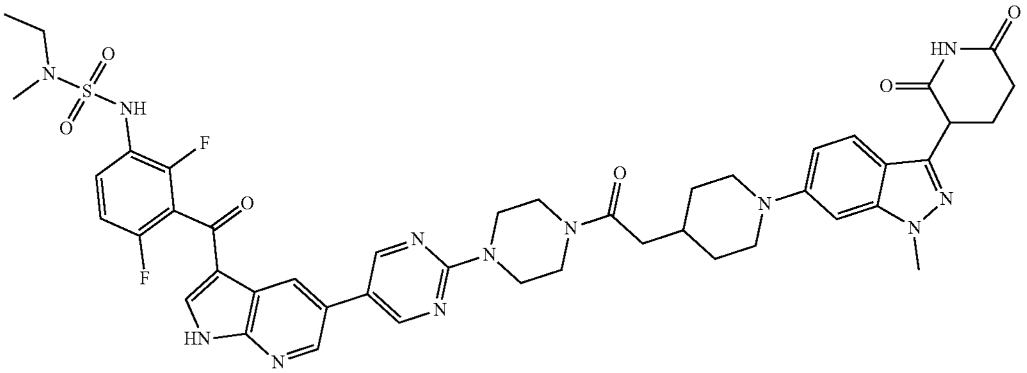 [SMILES: CCN(C)S(=O)(=O)Nc1ccc(F)c(C(=O)c2c[nH]c3ncc(-c4cnc(N5CCN(C(=O)CC6CCN(c7ccc8c(C9CCC(=O)NC9=O)nn(C)c8c7)CC6)CC5)nc4)cc23)c1F]

Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (223.33 mg, 376.57 μmol). 2-[1-[3-(2,6-dioxo-3-piperidyl)-1-methyl-indazol-6-yl]-4-piperidyl] acetic acid (200 mg, 401.24 μmol, trifluoroacetic acid salt), N,N-diisopropylethylamine and HATU (228.85 mg, 601.86 to afford 3-(2,6-dioxo-3-piperidyl)-6-[4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-1-piperidyl]-1-methyl-indazole (73 mg, 65.69 μmol, 16.37% yield) as an off white solid. LCMS (ESI+): 909.0 $[M+H]^+$. $^1H$ NMR (400 MHz, DMSO-$d_6$): δ 13.02 (s, 1H), 10.89 (s, 1H), 9.72 (s, 1H), 8.83 (s, 2H), 8.69 (s, 1H), 8.58 (s, 1H), 8.16 (s, 1H), 7.62-7.56 (m, 2H), 7.31-7.26 (m, 1H), 7.02 (t, J=51.20 Hz, 1H), 7.22-6.96 (m, 2H), 4.30-3.76 (m, 15H), 3.63 (m, 4H), 3.12 (q, J=7.20 Hz, 2H), 2.73 (s, 3H), 2.70-2.63 (m, 4H), 2.19-2.14 (m, 1H), 1.90-1.49 (m, 2H), 1.02 (t, J=7.20 Hz, 3H).

Example 48

5-[2-[4-[2-[1-[4-[(2,6-dioxo-3-piperidyl)amino]-2-fluoro-phenyl]pyrrolidin-3-yl]acetyl]piperazin-1-yl] pyrimidin-5-yl]-3-[3-[[ethyl(methyl)sulfamoyl] amino]-2,6-difluoro-benzoyl]-1H-pyrrolo[2,3-b] pyridine

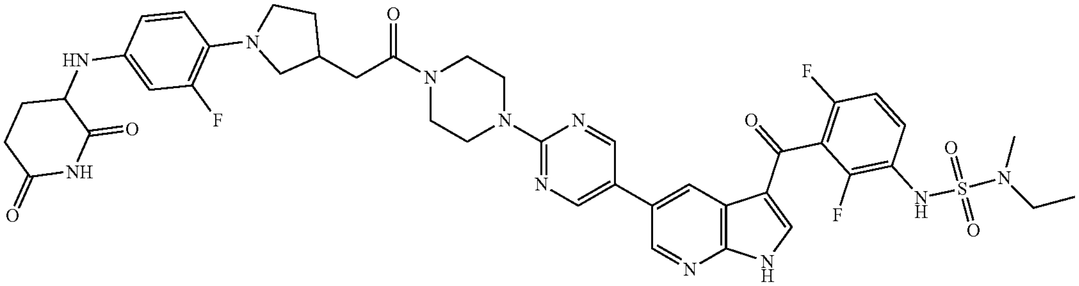 [SMILES: CCN(C)S(=O)(=O)Nc1ccc(F)c(C(=O)c2c[nH]c3ncc(-c4cnc(N5CCN(C(=O)CC6CCN(c7ccc(NC8CCC(=O)NC8=O)cc7F)C6)CC5)nc4)cc23)c1F]

Brought tert-butyl 2-pyrrolidin-3-ylacetate (368.92 mg, 1.99 mmol) and 1,2-difluoro-4-nitro-benzene (288.00 mg, 1.81 mmol, 200 uL) up in $CH_3CN$ (5.51 mL) and added TEA (238.14 mg, 2.35 mmol, 328.01 uL) before heating to 90° C. overnight. After cooling, the reaction was concentrated and purified by normal phase chromatography (0-60% EA/hx) to give tert-butyl 2-[1-(2-fluoro-4-nitro-phenyl)pyrrolidin-3-yl]acetate (430 mg, 1.26 mmol, 69.57% yield) as a yellow solid. LCMS (ES+)=325.3 $[M+H]^+$

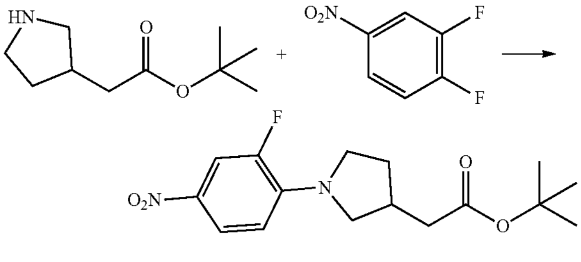

Brought tert-butyl 2-[1-(2-fluoro-4-nitro-phenyl)pyrrolidin-3-yl]acetate (420 mg, 1.29 mmol) up in Ethanol (10.22 mL)/Water (2.56 mL) and added Iron powder (289.26 mg, 5.18 mmol, 36.80 uL) and Ammonium Chloride (207.80 mg, 3.88 mmol, 135.82 uL). The vial was sealed and was heated to 80° C. overnight. The reaction was cooled and diluted with EtOH before filtering through celite. The filtrate was concentrated, and partitioned between EtOAc and sat. bicarb solution. The organic layer was dried over sodium sulfate and concentrated before purifying by flash chromatography (0-100% EtOAC/Hx) to give tert-butyl 2-[1-(4-amino-2-fluoro-phenyl)pyrrolidin-3-yl]acetate (385 mg, 1.18 mmol, 90.90% yield) as a yellow solid. LCMS (ES+): 295.3 $[M+H]^+$

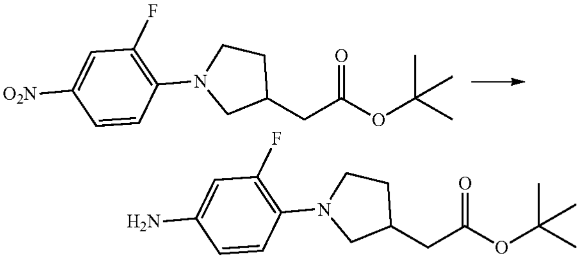

Brought 3-bromopiperidine-2,6-dione (502.26 mg, 2.62 mmol) and tert-butyl 2-[1-(4-amino-2-fluoro-phenyl)pyrrolidin-3-yl]acetate (385 mg, 1.31 mmol) up in DMF (6.42 mL) and added Sodium bicarbonate (252.71 mg, 3.01 mmol, 116.99 uL) before heating the reaction in a sealed vial at 75° C. overnight. The reaction was cooled to room temperature before being partitioned between EtOAc and water. The organic layer was washed w/ 5% Aq LiCl solution (x2) before drying over sodium sulfate and concentrating to an oil. The crude material was purified by flash chromatography (0-15% MeOH/DCM) to give tert-butyl 2-[1-[4-[(2,6-dioxo-3-piperidyl)amino]-2-fluoro-phenyl]pyrrolidin-3-yl] acetate (180 mg, 412.86 μmol, 31.57% yield) as a beige/brown solid. LCMS (ES+): 406.5 $[M+H]^+$

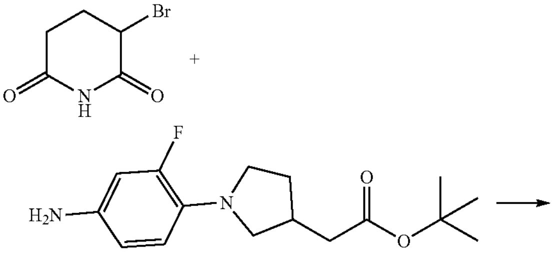

-continued

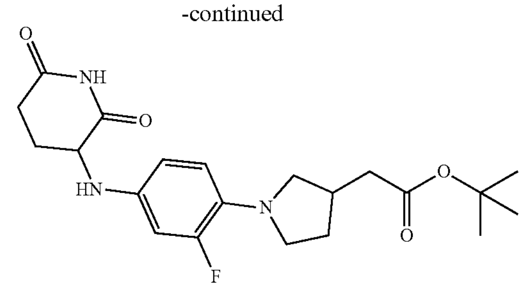

Brought tert-butyl 2-[1-[4-[(2,6-dioxo-3-piperidyl) amino]-2-fluoro-phenyl]pyrrolidin-3-yl]acetate (178 mg, 439.01 μmol) up in TFA (740.00 mg, 6.49 mmol, 0.5 mL)/DCM (2 mL) and stirred at room temperature for 6 hours. The reaction was concentrated from toluene (3×) to give crude 2-[1-[4-[(2,6-dioxo-3-piperidyl)amino]-2-fluoro-phenyl]pyrrolidin-3-yl]acetic acid (200 mg, 410.03 μmol, 93.40% yield, trifluoroacetic acid salt) as a dark solid, which was carried forward without further purification. LCMS (ES+): 350.3 $[M+H]^+$

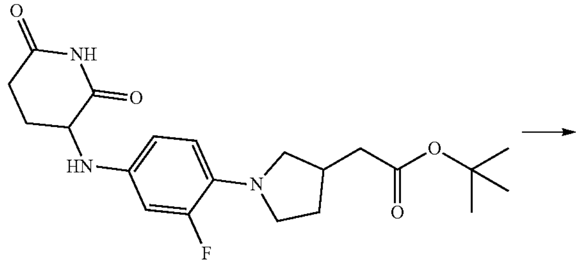

-continued

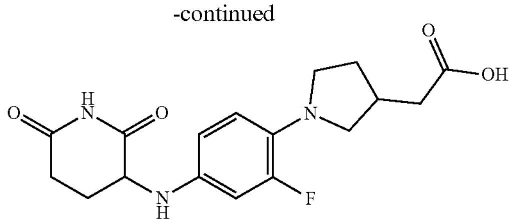

Brought 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (84.23 mg, 133.80 μmol, bis-HCl salt) and 2-[1-[4-[(2,6-dioxo-3-piperidyl)amino]-2-fluoro-phenyl]pyrrolidin-3-yl]acetic acid (62 mg, 133.80 trifluoro-acetic acid salt) up in DMF (1.22 mL) and added DIPEA (86.46 mg, 669.00 μmol, 116.52 uL) before cooling reaction to 0° C. To the reaction was added 3-[chloro-(2-oxooxazolidin-3-yl)phosphoryl]oxazolidin-2-one (35.76 mg, 140.49 μmol) in one portion and the resulting mixture gradually warmed to room temperature overnight. The crude reaction was loaded directly onto RP isco (0-100% ACN/water w TFA) to give 5-[2-[4-[2-[1-[4-[(2,6-dioxo-3-piperidyl) amino]-2-fluoro-phenyl]pyrrolidin-3-yl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (10 mg, 10.70 nmol, 8.00% yield) as an off-white solid after lyophilization. LCMS (ES+): 445.2 $[M/2+H]^+$, 888.9 $[M+H]^+$. $^1H$ NMR (400 MHz, DMSO-$d_6$): δ 12.92 (d, J=3.3 Hz, 1H), 10.68 (s, 1H), 9.62 (s, 1H), 8.73 (s, 2H), 8.60 (d, J=2.2 Hz, 1H), 8.49 (s, 1H), 8.06 (d, J=3.1 Hz, 1H), 7.51 (td, J=9.0, 5.9 Hz, 1H), 7.20 (td, J=8.7, 1.5 Hz, 1H), 6.53 (dd, J=10.2, 8.7 Hz, 1H), 6.45 (dd, J=15.9, 2.6 Hz, 1H), 6.33 (dd, J=8.7, 2.5 Hz, 1H), 5.46 (d, J=7.5 Hz, 1H), 4.13 (ddd, J=11.9, 7.5, 4.8 Hz, 1H), 3.81-3.72 (m, 4H), 3.57-3.50 (m, 4H), 3.14-3.00 (m, 3H), 2.84-2.78 (m, 1H), 2.66 (s, 3H), 2.64-2.58 (m, 1H), 2.55-2.48 (m, 3H), 2.28-2.24 (m, 1H), 2.07-1.98 (m, 2H), 1.83-1.69 (m, 1H), 1.59-1.44 (m, 1H), 0.95 (t, J=7.1 Hz, 3H).

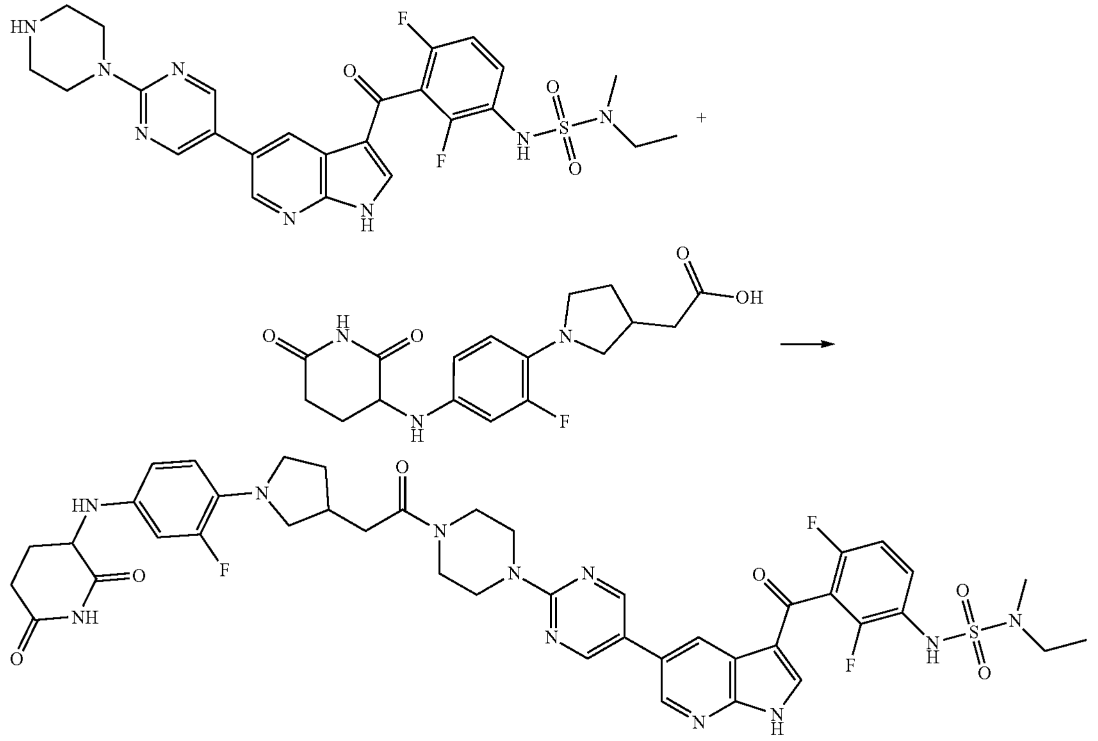

Example 49
5-[2-[4-[2-[2-[4-[(2,6-dioxo-3-piperidyl)amino]phenyl]-2,6-diazaspiro[3.3]heptan-6-yl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine
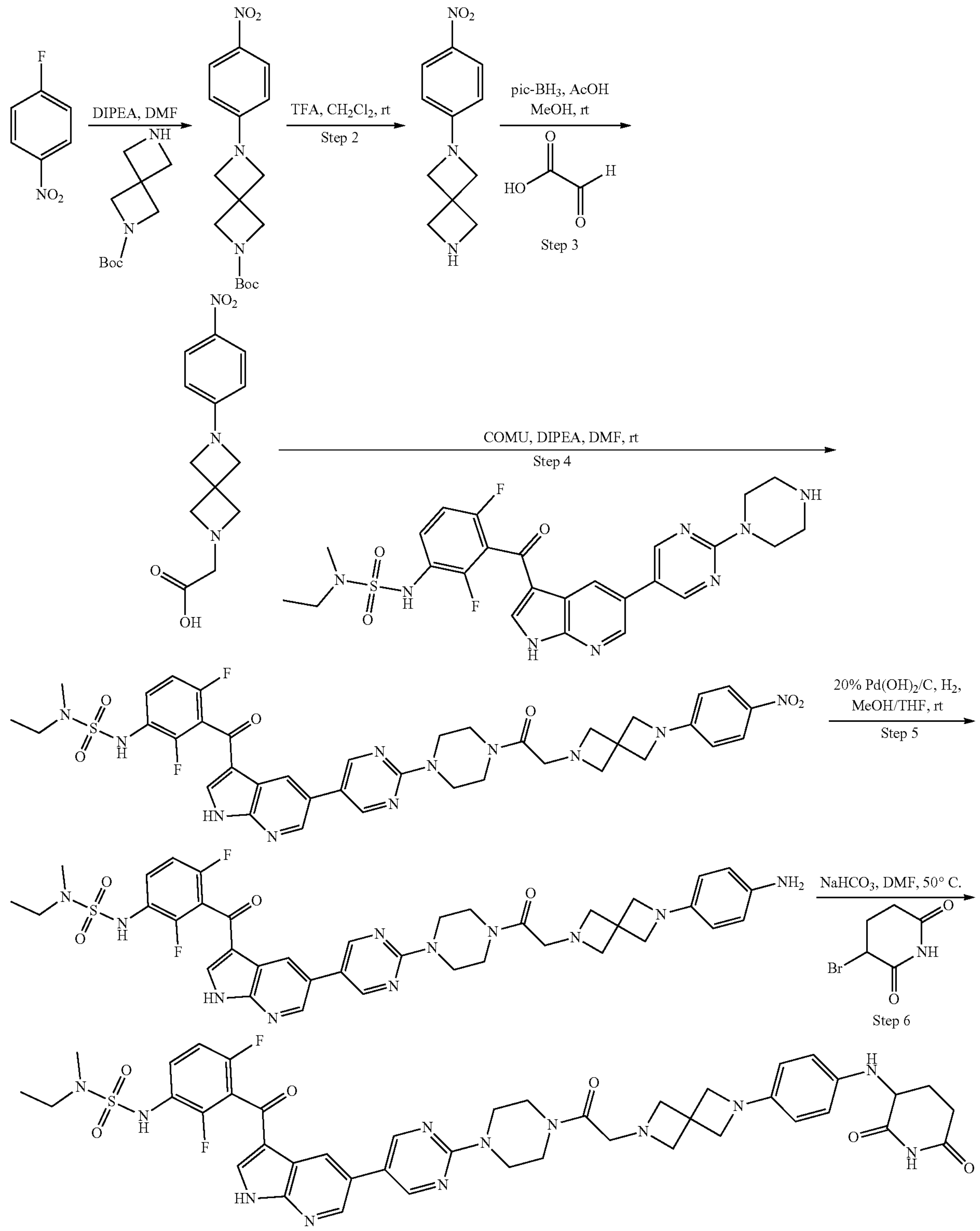

Step 1: A stirred solution of 1-fluoro-4-nitro-benzene (1.5 g, 10.63 mmol, 1.13 mL) and tert-butyl 2,6-diazaspiro[3.3] heptane-2-carboxylate (2.99 g, 12.76 mmol, hydrochloric acid salt) in N,N-Dimethylformamide (10 mL). The mixture was taken in a dried pressure tube, and N,N-Diisopropylethylamine (6.83 g, 52.82 mmol, 9.2 mL) was added and the reaction mixture was heated at 110° C. for 16 hours. Reaction mixture was cooled to room temperature and quenched with water (20 mL). The resulting precipitate was filtered using Buchner funnel and solid was washed with petroleum ether (20 mL) and dried to get tert-butyl 6-(4-nitrophenyl)-2,6-diazaspiro[3.3]heptane-2-carboxylate (2.9 g, 8.49 mmol, 79.90% yield) as a yellow solid. LCMS (ESI+): 320.2 $[M+H]^+$.

Step 2: To a solution of tert-butyl 6-(4-nitrophenyl)-2,6-diazaspiro[3.3]heptane-2-carboxylate (420 mg, 1.32 mmol) in dichloromethane (5.0 mL) was added trifluoroacetic acid (1.51 g, 13.20 mmol, 1.02 mL) at 0° C. The reaction mixture was warmed to room temperature and stirred for 2 hours. After completion, reaction mixture was concentrated under reduced pressure, to the resulting crude compound was added aqueous $NaHCO_3$ solution (15 mL) and extracted with dichloromethane (2×20 mL). Combined organics were washed with brine (20 mL), dried over sodium sulphate, filtered and concentrated under reduced pressure to afford 2-(4-nitrophenyl)-2,6-diazaspiro[3.3]heptane (320 mg, 1.27 mmol, 95.86% yield) as a yellow solid. Crude compound was directly used for next step without further purification. LCMS (ESI+): 219.9 $[M+H]^+$.

Step 3: A mixture of 2-(4-nitrophenyl)-2,6-diazaspiro[3.3] heptane (330 mg, 1.51 mmol), oxaldehydic acid (558.97 mg, 7.55 mmol, 417.14 μL), 2-picoline borane complex (242.26 mg, 2.27 mmol) and acetic acid (453.38 mg, 7.55 mmol, 431.79 μL) in methanol (8.0 mL) was stirred at room temperature for 18 hours under nitrogen. After completion, reaction mixture was added to water (20 mL), resulting solid was filtered, washed with diethyl ether (10 mL) and dried to afford 2-[2-(4-nitrophenyl)-2,6-diazaspiro[3.3]heptan-6-yl] acetic acid (180 mg, 609.57 μmol, 40.37% yield) as a light yellow solid. Crude compound was directly used for next step without purification. LCMS (ESI+): 278.1 $[M+H]^+$.

Step 4: To a mixture of 3-[3-[[ethyl(methyl)sulfamoyl] amino]-2,6-difluoro-benzoyl]-5-(2-piperazin-1-ylpyrimidin-5-yl)-1H-pyrrolo[2,3-b]pyridine (265 mg, 395.16 μmol, trifluoroacetic acid salt) and 2-[2-(4-nitrophenyl)-2,6-diazaspiro[3.3]heptan-6-yl]acetic acid (109.57 mg, 395.17 μmol) in N,N-Dimethylformamide (4.0 mL) were added COMU (169.24 mg, 395.16 μmol) followed by N,N-Diisopropylethylamine (51.07 mg, 395.16 μmol, 68.83 μL) at room temperature under nitrogen atmosphere. The reaction mixture was stirred at room temperature for 12 hours. After completion, reaction mixture was added to water (5 mL) and extracted with dichloromethane (2×10 mL). Combined organics were washed with brine (10 mL), dried over sodium sulphate, filtered and concentrated under reduced pressure. The crude product was purified by flash silica gel chromatography (50 g silica; 0-10% methanol in dichloromethane) to afford 3-[3-[[ethyl(methyl)sulfamoyl]amino]-2,6-difluoro-benzoyl]-5-[2-[4-[2-[2-(4-nitrophenyl)-2,6-diazaspiro[3.3]heptan-6-yl]acetyl]piperazin-1-yl]pyrimidin-5-yl]-1H-pyrrolo[2,3-b]pyridine (160 mg, 141.82 μmol, 35.89% yield) as a light yellow solid. LCMS (ESI+): 816.3 $[M+H]^+$.

Step 5: A mixture of 3-[3-[[ethyl(methyl)sulfamoyl] amino]-2,6-difluoro-benzoyl]-5-[2-[4-[2-[2-(4-nitrophenyl)-2,6-diazaspiro[3.3]heptan-6-yl]acetyl]piperazin-1-yl] pyrimidin-5-yl]-1H-pyrrolo[2,3-b]pyridine (1.0 g, 1.23 mmol) and Palladium hydroxide on carbon, 20 wt. % 50% water (344.27 mg, 2.45 mmol) in THF (50 mL)/Methanol (50 mL) was stirred at room temperature under hydrogen pressure (1 atm) for 12 hours. After completion, the reaction mixture was filtered through celite bed, washed with methanol (150 mL), resulting filtrate was concentrated under reduced pressure to get the crude product 5-[2-[4-[2-[2-(4-aminophenyl)-2,6-diazaspiro[3.3]heptan-6-yl]acetyl]piperazin-1-yl]pyrimidin-5-yl]-3-[3-[[ethyl(methyl)sulfamoyl] amino]-2,6-difluoro-benzoyl]-1H-pyrrolo[2,3-b]pyridine (0.8 g, 669.84 μmol, 54.65% yield) as a light brown semi solid. LCMS (ESI+): 786.2 $[M+H]^+$.

Step 6: To a solution of 5-[2-[4-[2-[2-(4-aminophenyl)-2,6-diazaspiro[3.3]heptan-6-yl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (0.8 g, 1.02 mmol) in N,N-Dimethylformamide (8 mL) was added sodium bicarbonate (427.61 mg, 5.09 mmol) and 3-bromopiperidine-2,6-dione (195.46 mg, 1.02 mmol) at room temperature under nitrogen. The resulting solution was heated to 50° C. for 16 hours. After completion, resulting solution was diluted with water (10 ml), extracted with Dichloromethane:Methanol (9:1) (2×30 mL). The separated organic layer was concentrated under reduced pressure. The crude product was purified by mass-directed preparative HPLC [Mobile-phase A: 0.1% Ammonium acetate in water, Mobile-phase B: Acetonitrile] to get the 5-[2-[4-[2-[2-[4-[(2,6-dioxo-3-piperidyl)amino]phenyl]-2,6-diazaspiro[3.3] heptan-6-yl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (18.49 mg, 19.50 μmol, 1.92% yield) as a brown solid. LCMS (ESI+): 897.0 $[M+H]^+$. $^1H$ NMR (400 MHz, DMSO-$d_6$): δ 10.74 (s, 1H), 8.80 (bs, 3H), 8.67 (d, J=2.40 Hz, 1H), 8.56 (s, 1H), 8.11 (s, 1H), 7.57-7.53 (m, 1H), 7.22-7.18 (m, 1H), 6.60 (d, J=8.80 Hz, 2H), 6.29 (d, J=8.80 Hz, 2H), 5.21-5.19 (m, 1H), 4.16-4.13 (m, 1H), 3.86-3.70 (m, 8H), 3.60-3.56 (m, 4H), 3.42-3.34 (m, 4H), 3.08 (q, J=7.20 Hz, 2H), 2.72 (s, 3H), 2.69-2.68 (m, 2H), 2.60-2.58 (m, 2H), 2.11-2.08 (m, 1H), 1.83-1.76 (m, 1H), 1.02 (t, J=6.80 Hz, 3H).

Example 50

5-[2-[4-[2-[4-[4-(2,6-dioxo-3-piperidyl)-3-oxo-piperazin-1-yl]phenyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

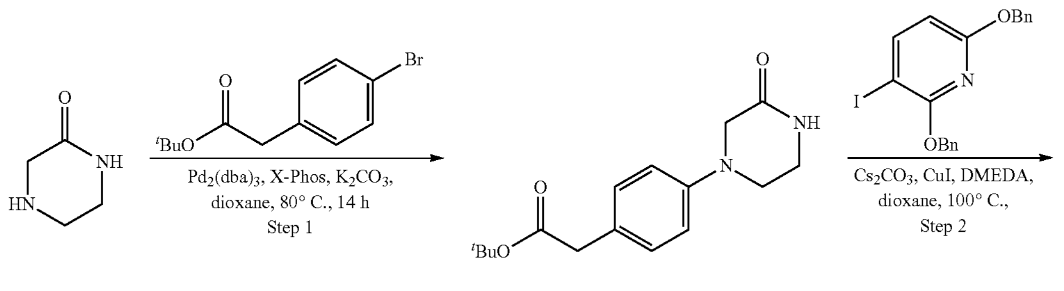

-continued

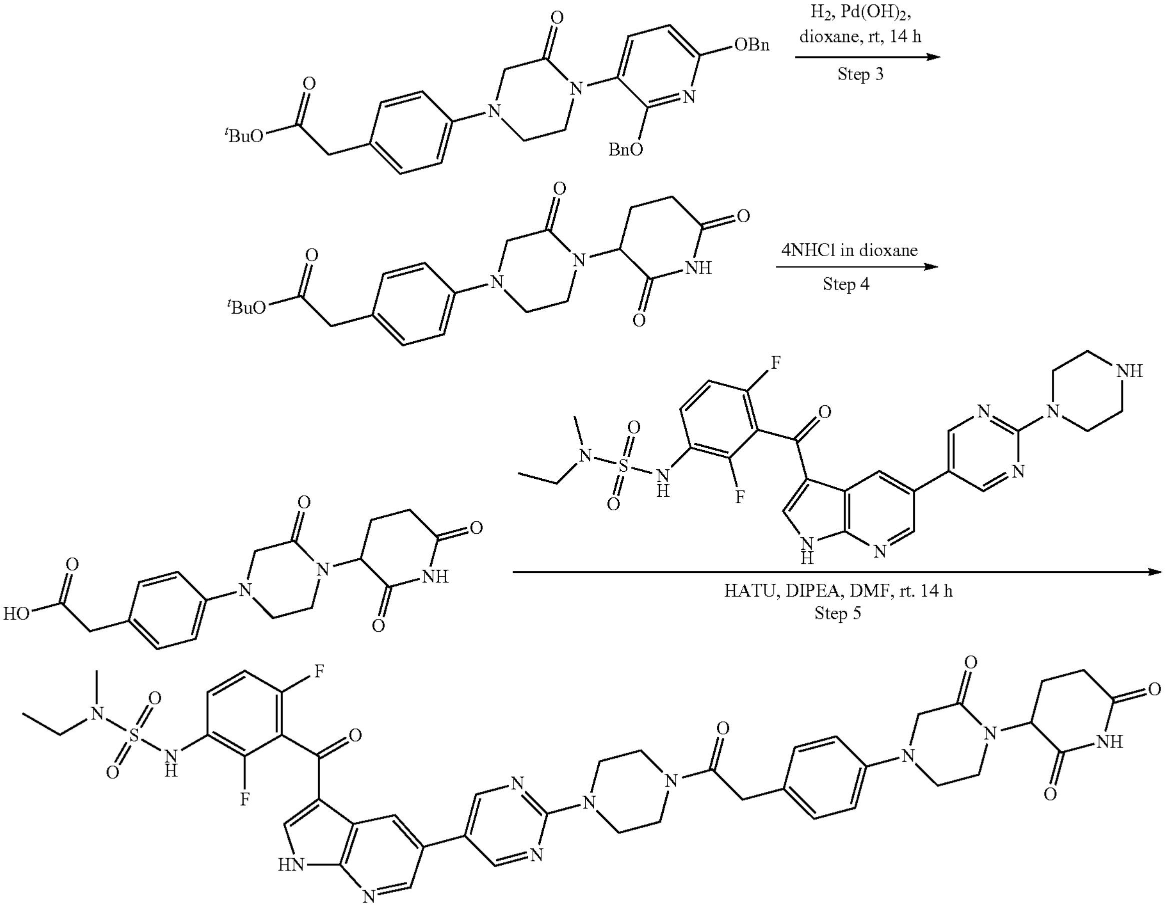

Step 1: A mixture of piperazin-2-one (2.0 g, 19.98 mmol), tert-butyl 2-(4-bromophenyl)acetate (4.87 g, 17.98 mmol) and Potassium carbonate (8.28 g, 59.93 mmol, 3.62 mL) in 1,4-Dioxane (6 mL) was degassed with $N_2$ for 10 minutes. Tris(dibenzylideneacetone)dipalladium(0) (1.83 g, 2.00 mmol), 2-Dicyclohexylphosphino-2',4',6'-triisopropyl-1,1'-biphenyl (952.30 mg, 2.00 mmol) were added to the reaction mixture and heated at 100° C. for 14 h. Upon completion, the reaction mixture was filtered and concentrated under reduced pressure to get crude which was purified by column chromatography on silica gel eluted with 4% MeOH in dichloromethane to afford tert-butyl 2-[4-(3-oxopiperazin-1-yl)phenyl]acetate (1.1 g, 3.26 mmol, 16.31% yield) as light brown solid. LCMS (ESI+): 291.1 $[M+H]^+$.

Step 2: A mixture of tert-butyl 2-[4-(3-oxopiperazin-1-yl)phenyl]acetate (1.1 g, 3.79 mmol), 2,6-dibenzyloxy-3-iodo-pyridine (1.58 g, 3.79 mmol) and Cesium carbonate (3.70 g, 11.37 mmol) in 1,4-Dioxane (20 mL) was degassed with Nitrogen for 10 minutes. Copper (I) iodide (144.30 mg, 757.69 μmol, 25.68 μL), N, N'-dimethylethane-1,2-diamine (66.79 mg, 757.69 μmol, 81.65 μL) were added to the reaction mixture and stirred at 100° C. for 14 h. The reaction mixture was filtered and concentrated under reduced pressure to get crude, which was purified by column chromatography on silica gel, eluted with 70% ethyl acetate in petroleum ether to afford tert-butyl 2-[4-[4-(2,6-dibenzyloxy-3-pyridyl)-3-oxo-piperazin-1-yl]phenyl]acetate (800 mg, 800.44 μmol, 21.13% yield) as a light brown solid. LCMS (ESI+): 580.3 $[M+H]^+$.

Step 3: A solution of tert-butyl 2-[4-[4-(2,6-dibenzyloxy-3-pyridyl)-3-oxo-piperazin-1-yl]phenyl]acetate (800 mg, 1.38 mmol) in 1,4-Dioxane (12 mL) was degassed for 10 minutes, Palladium hydroxide on carbon (20 wt. % 50% water, 193.81 mg, 1.38 mmol) was added to the reaction mixture and stirred under $H_2$ balloon pressure (1 atm) for 14 h. The reaction mixture was filtered through celite and concentrated under reduced pressure to get crude which was purified by column chromatography on silica gel eluted with ethyl acetate to afford tert-butyl 2-[4-[4-(2,6-dioxo-3-piperidyl)-3-oxo-piperazin-1-yl]phenyl]acetate (170 mg, 359.94 μmol, 26.08% yield) as a brown sticky solid. LCMS (ESI+): 402.2 $[M+H]^+$.

Step 4: To a solution of tert-butyl 2-[4-[4-(2,6-dioxo-3-piperidyl)-3-oxo-piperazin-1-yl]phenyl]acetate (170 mg, 423.46 μmol) in Dichloromethane (2 mL) was added 4 M HCl in 1,4-dioxane (423.46 μmol, 3 mL) at 0° C. and stirred at room temperature for 6 h. The reaction mixture was concentrated under reduced pressure to get crude which was triturated with petroleum ether to afford 2-[4-[4-(2,6-dioxo-3-piperidyl)-3-oxo-piperazin-1-yl]phenyl]acetic acid (150 mg, 235.72 μmol, 55.67% yield) as an off white solid. LCMS (ESI+): 346.0 $[M+H]^+$.

Step 5: Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (220 mg, 395.27 μmol), 2-[4-[4-(2,6-dioxo-3-piperidyl)-3-oxo-piperazin-1- yl]phenyl]acetic acid (150.16 mg, 434.79 μmol), N,N-Diisopropylethylamine (204.34 mg, 1.58 mmol, 275.39 μL) and HATU (150.29 mg, 395.27 μmol) to afford 5-[2-[4-[2-[4-[4-(2,6-dioxo-3-piperidyl)-3-oxo-piperazin-1-yl]phenyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (44 mg, 45.52 μmol, 11.52% yield) as an off white solid. LCMS (ESI+): 884.2 $[M+H]^+$. $^1H$ NMR (400 MHz, DMSO-$d_6$): δ 12.99 (s, 1H), 10.90 (s, 1H), 9.72 (s, 1H), 8.79 (s, 2H), 8.67 (d, J=2.40 Hz, 1H), 8.56 (s, 1H), 8.14 (s, 1H), 7.55-7.61 (m, 1H), 7.27 (t, J=8.80 Hz, 1H), 7.16 (d, J=8.80 Hz, 2H), 6.92 (d, J=8.80 Hz, 2H), 5.05-5.15 (m, 1H), 3.84 (d, J=5.20 Hz, 1H), 3.70-3.79 (m, 8H), 3.58-3.65 (m, 4H), 3.36-3.55 (m, 3H), 3.11 (q, J=7.20 Hz, 2H), 2.70-2.75 (m, 1H), 2.73 (s, 3H), 2.35-2.55 (m, 2H), 1.81-1.90 (m, 1H), 1.02 (t, J=7.20 Hz, 3H).

Example 51

5-[2-[4-[2-[1-[4-[(2,6-dioxo-3-piperidyl)amino]-2-fluoro-phenyl]-3-hydroxy-pyrrolidin-3-yl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine -continued

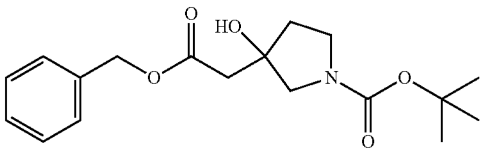

To a solution of tert-butyl 3-(2-benzyloxy-2-oxo-ethyl)-3-hydroxy-pyrrolidine-1-carboxylate (2.24 g, 6.68 mmol) in DCM (96 mL) was added TFA (64 mL). The resulting mixture stirred at room temperature for 1 hr. The reaction was concentrated, and excess solvent was removed by azeotroping with toluene to give the product benzyl 2-(3-hydroxypyrrolidin-3-yl)acetate (2.35 g, 6.39 mmol, 95.70% yield), which was carried forward without further purification. LCMS (ES+): 236.2 $[M+H]^+$

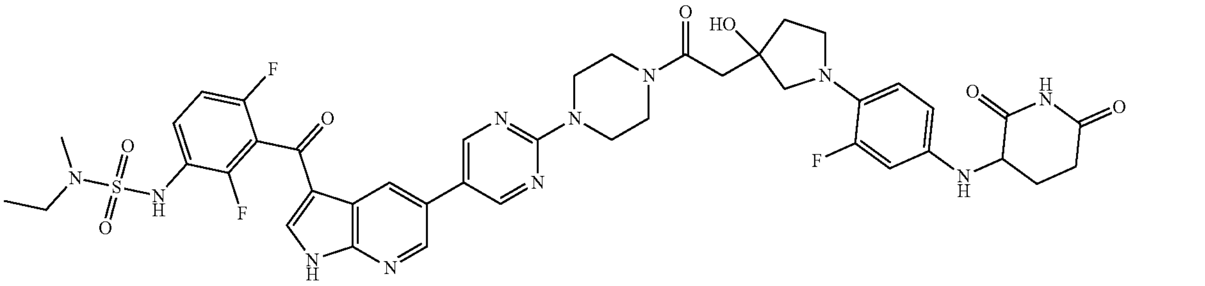 [SMILES: CCN(C)S(=O)(=O)Nc1ccc(F)c(C(=O)c2c[nH]c3ncc(-c4cnc(N5CCN(C(=O)CC6(O)CCN(c7ccc(NC8CCC(=O)NC8=O)cc7F)C6)CC5)nc4)cc23)c1F]

To a solution of (diisopropylamino)lithium (2 M, 9.72 mL) in THF (30 mL) at −78° C. was added benzyl acetate (3.16 g, 21.06 mmol, 2.98 mL). The resulting mixture stirred at this temperature for 15 minutes. A solution of tert-butyl 3-oxopyrrolidine-1-carboxylate (3 g, 16.20 mmol) in THF (9.6 mL) was added dropwise, and the reaction warmed to room temperature before stirring for 1 hr. To the reaction mixture was added sat. aq. Ammonium chloride and water. The mixture was extracted with ethyl acetate, and the combined organic layers were dried with anhydrous sodium sulphate. The crude mixture was concentrated and purified by column chromatography (silica, gradient: 20-100% ethyl acetate in hexanes) to afford the product tert-butyl 3-(2-benzyloxy-2-oxo-ethyl)-3-hydroxy-pyrrolidine-1-carboxylate (2.24 g, 6.34 mmol, 39.17% yield). LCMS (ES+): 358.3 $[M+N]^+$

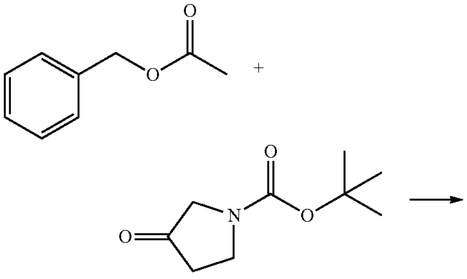

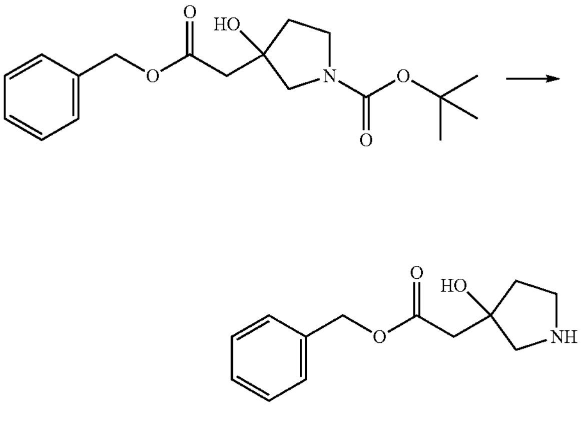

To a mixture of 1,2-difluoro-4-nitro-benzene (527.42 mg, 3.32 mmol, 366.26 uL) and benzyl 2-(3-hydroxypyrrolidin-3-yl)acetate (0.78 g, 3.32 mmol) in MeCN (10.5 mL) with Triethylamine (1.01 g, 9.95 mmol, 1.39 mL). The mixture was heated to 80° C. for 6 hr. After cooling, the reaction was concentrated. The crude material was purified by column chromatography (silica, gradient: 15-60% ethyl acetate in hexanes) to afford the product benzyl 2-[1-(2-fluoro-4-nitro-phenyl)-3-hydroxy-pyrrolidin-3-yl]acetate (706 mg, 1.79 mmol, 54.04% yield). LCMS (ES+): 375.3 $[M+H]^+$

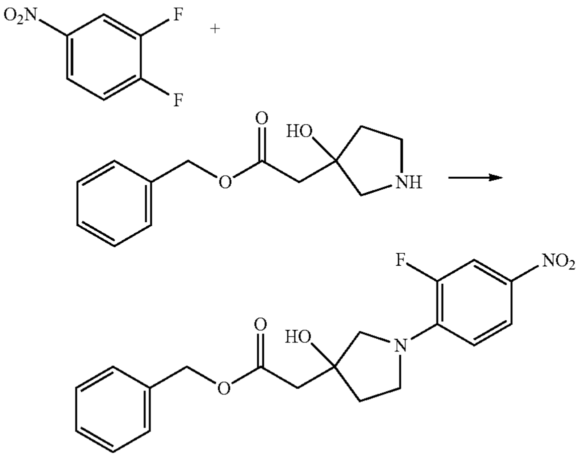

To a solution of benzyl 2-[1-(2-fluoro-4-nitro-phenyl)-3-hydroxy-pyrrolidin-3-yl]acetate (1.05 g, 2.80 mmol) in water (2.9 mL) and EtOH (11.6 mL), was added Iron powder (789.43 mg, 14.14 mmol, 100.44 uL) and Ammonium Chloride (312.07 mg, 5.83 mmol, 203.96 uL). The resulting mixture stirred at 50° C. for 4 hr. The crude reaction was cooled to room temperature and filtered through a pad of celite, washing with ethyl acetate. The filtrate was dried with anhydrous sodium sulphate and concentrated to afford the product benzyl 2-[1-(4-amino-2-fluoro-phenyl)-3-hydroxy-pyrrolidin-3-yl]acetate (919 mg, 2.54 mmol, 90.39% yield), which was carried forward without further purification. LCMS (ES+): 344.9 $[M+H]^+$

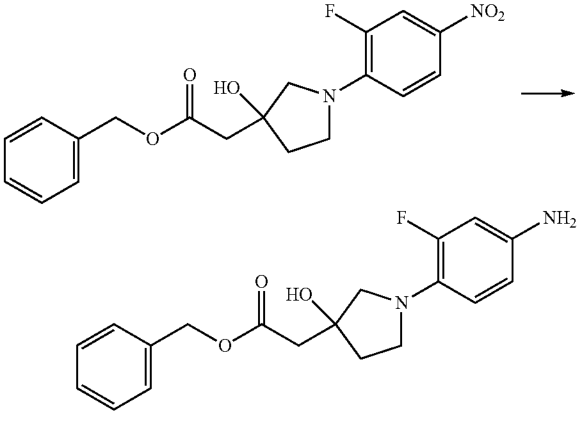

To a mixture of 3-bromopiperidine-2,6-dione (1.64 g, 8.55 mmol) and benzyl 2-[1-(4-amino-2-fluoro-phenyl)-3-hydroxy-pyrrolidin-3-yl]acetate (1.84 g, 5.34 mmol) in DMF (13 mL) was added Sodium bicarbonate (1.35 g, 16.03 mmol, 623.39 uL). The mixture was heated to 80° C. overnight. After cooling, the reaction was diluted with water and extracted with ethyl acetate. The combined organic layers were dried with anhydrous sodium sulphate and concentrated. The crude material was then purified by column chromatography (silica, gradient: 40-100% ethyl acetate in hexanes) to give the product benzyl 2-[1[4-[(2,6-dioxo-3-piperidyl)amino]-2-fluoro-phenyl]-3-hydroxy-pyrrolidin-3-yl]acetate (2.2 g, 4.59 mmol, 85.88% yield). LCMS (ES+): 455.9 $[M+H]^+$

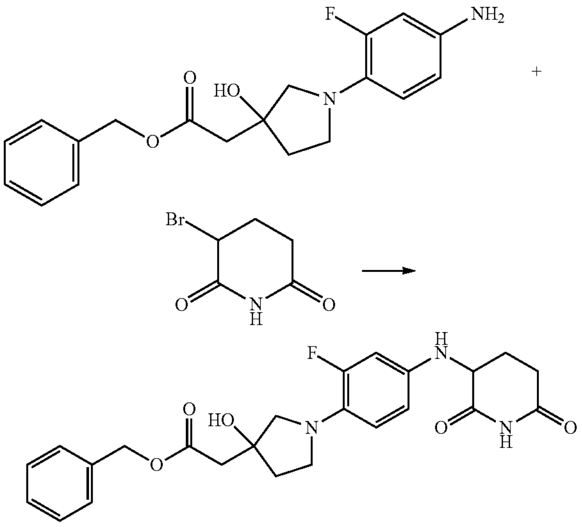

To a solution of benzyl 2-[1-[4-[(2,6-dioxo-3-piperidyl) amino]-2-fluoro-phenyl]-3-hydroxy-pyrrolidin-3-yl]acetate (2.2 g, 4.83 mmol) in ethanol (18 mL) was added Palladium, 10% on carbon, Type 487, dry (514.02 mg, 4.83 mmol). The vessel was purged with hydrogen gas for 10 minutes before the reaction stirred at room temperature for 3 hr under an atmosphere of hydrogen. The crude reaction mixture was then filtered through a pad of celite before being concentrated. The crude material was then purified by column chromatography (silica, gradient: 0-50% acetonitrile in water with 0.1% trifluoroacetic acid) to afford the product 2-[1-[4-[(2,6-dioxo-3-piperidyl)amino]-2-fluoro-phenyl]-3-hydroxy-pyrrolidin-3-yl]acetic acid (1.37 g, 2.71 mmol, 56.21% yield) as a purple solid after lyophilization. LCMS (ES+): 366.2 $[M+H]^+$

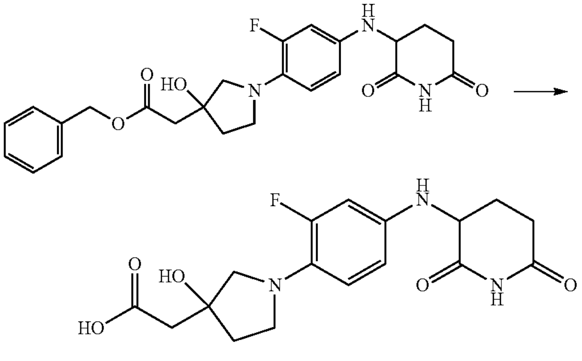

To a mixture of 2-[1-[4-[(2,6-dioxo-3-piperidyl)amino]-2-fluoro-phenyl]-3-hydroxy-pyrrolidin-3-yl]acetic acid (72.21 mg, 197.63 μmol) and 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (100 mg, 179.67 μmol) in DMF (1.6 mL) at 0° C. was added COMU (115.42 mg, 269.50 μmol) and N,N-Diisopropylethylamine (34.83 mg, 269.50 μmol, 46.94 uL). The resulting mixture stirred at 0° C. for 30 min before warming to room temperature and stirring for 2 hr. The reaction mixture was then purified directly by column chromatography (silica, gradient: 10-70% acetonitrile in water with 0.1% trifluoroacetic acid). The fractions containing product were slightly concentrated under vacuum and neutralized with saturated sodium bicarbonate. The aqueous material was extracted with ethyl acetate, and the combined organic layers were dried with anhydrous sodium sulphate. The organic layers were concentrated, and the impure residue was purified by column chromatography (silica, gradient: 0-25% methanol in dichloromethane) to afford the product 5-[2-[4-[2-[1-[4-[(2,6-dioxo-3-piperidyl)amino]-2-fluoro-phenyl]-3-hydroxy-pyrrolidin-3-yl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (28.07 mg, 29.50 μmol, 16.42% yield). LCMS (ES+): 904.8 $[M+H]^+$. $^1$H NMR (400 MHz, DMSO-d6): δ 13.00 (d, J=3.2 Hz, 1H), 10.75 (s, 1H), 9.70 (s, 1H), 8.81 (s, 2H), 8.68 (d, J=2.2 Hz, 1H), 8.57 (s, 1H), 8.14 (d, J=3.3 Hz, 1H), 7.59 (td, J=9.1, 5.9 Hz, 1H), 7.28 (t, J=8.9 Hz, 1H), 6.62-6.49 (m, 2H), 6.44-6.38 (m, 1H), 5.51 (d, J=7.4 Hz, 1H), 4.98 (s, 1H), 4.21 (dt, J=11.7, 6.0 Hz, 1H), 3.85 (d, J=19.1 Hz, 4H), 3.72-3.60 (m, 4H), 3.48-3.40 (m, 1H), 3.15 (d, J=7.0 Hz, 2H), 3.11 (t, J=7.2 Hz, 2H), 3.02 (td, J=6.6, 3.8 Hz, 2H), 2.79 (s, 2H), 2.70 (s, 2H), 2.16-2.05 (m, 1H), 2.04-1.91 (m, 2H), 1.78-1.69 (m, 2H), 1.24 (s, 1H), 1.03 (t, J=7.1 Hz, 3H).

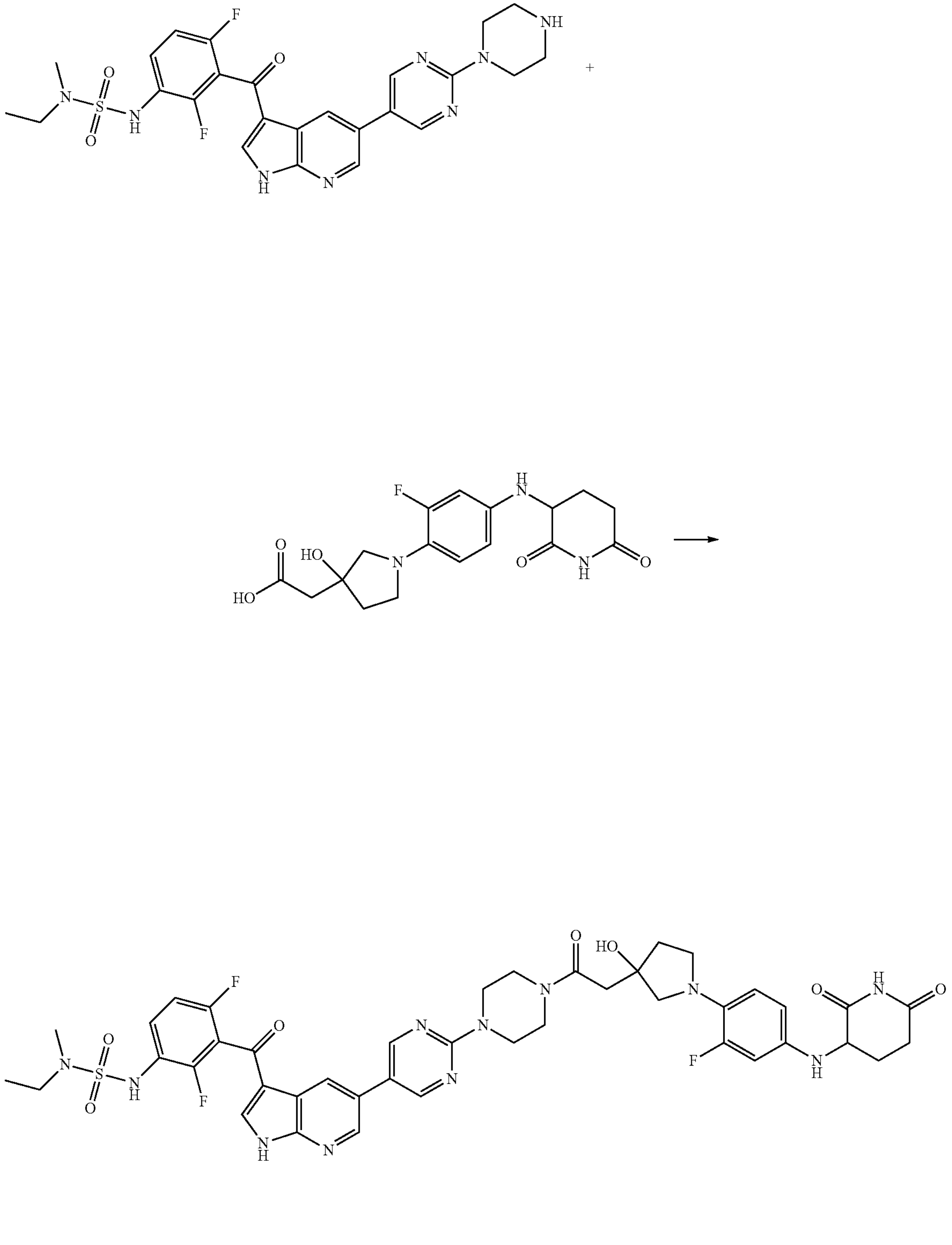

Preparation of intermediates: (1r,3r)-3-(3-(4-((2,6-dioxopiperidin-3-yl)amino)-2-fluorophenyl)azetidin-1-yl)cyclobutane-1-carboxylic acid and (1s,3s)-3-(3-(4-((2,6-dioxopiperidin-3-yl)amino)-2-fluorophenyl)azetidin-1-yl)cyclobutane-1-carboxylic acid

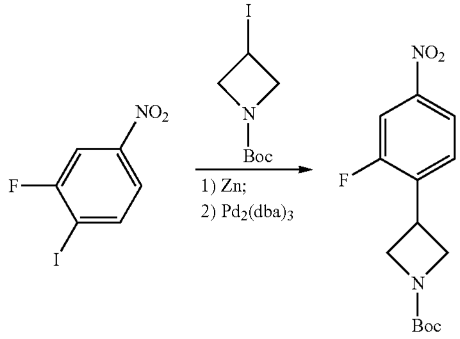 [SMILES: O=[N+]([O-])c1ccc(I)c(F)c1 ; CC(C)(C)OC(=O)N1CC(I)C1 ; CC(C)(C)OC(=O)N1CC(c2ccc([N+](=O)[O-])cc2F)C1]

1,2-dibromoethane (5.60 g, 29.8 mmol, 2.25 mL, 0.188 eq) was added to a stirred Zn powder (19.7 g, 301 mmol, 1.90 eq) in THF (49.0 mL) under $N_2$ atmosphere. The resulting mixture was stirred at 80° C. for 10 mins before cooling to room temperature. A solution of TMSCl (2.57 g, 23.6 mmol, 3.00 mL, 1.49e-1 eq) in THF (18.0 mL) at 25° C. was added, and the resulting mixture stirred for 4 mins at that temperature. Then a solution of tert-butyl 3-iodoazetidine-1-carboxylate (45.0 g, 158 mmol, 1.00 eq) in THF (102 mL) was added and stirred for 15 mins. The reaction mixture was stirred at 25° C. for 2 hrs then tris(2-furyl)phosphane (2.17 g, 9.37 mmol, 5.89e-2 eq) and $Pd_2(dba)_3$ (2.33 g, 2.54 mmol, 0.016 eq) were added, followed by the addition of a solution of 2-fluoro-1-iodo-4-nitrobenzene (43.9 g, 164 mmol, 1.03 eq) in THF (216 mL). The resulting mixture was stirred at 50° C. for 8 hrs. The reaction mixture was diluted with ethyl acetate (300 mL) and $H_2O$ (500 mL) was added. The separated organic phase was dried over sodium sulphate, filtered and concentrated under reduced pressure to give a residue, which was purified by flash silica gel chromatography (petroleum ether/ethyl acetate=10/1, $R_f$=0.1) to give tert-butyl 3-(2-fluoro-4-nitrophenyl)azetidine-1-carboxylate (22.0 g, 74.2 mmol, 46.7% yield) as a yellow oil.

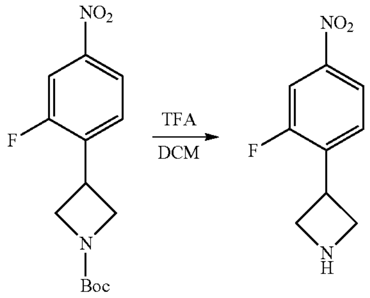 [SMILES: CC(C)(C)OC(=O)N1CC(c2ccc([N+](=O)[O-])cc2F)C1 ; O=[N+]([O-])c1ccc(C2CNC2)c(F)c1]

A mixture of tert-butyl 3-(2-fluoro-4-nitrophenyl)azetidine-1-carboxylate (10.0 g, 33.7 mmol, 1.00 eq) and TFA (19.2 g, 168 mmol, 12.4 mL, 5.00 eq) in DCM (50.0 mL) was stirred at 25° C. for 2 hrs. The reaction mixture was concentrated to give 3-(2-fluoro-4-nitrophenyl)azetidine (10.0 g, crude, trifluoroacetic acid salt) as a yellow oil.

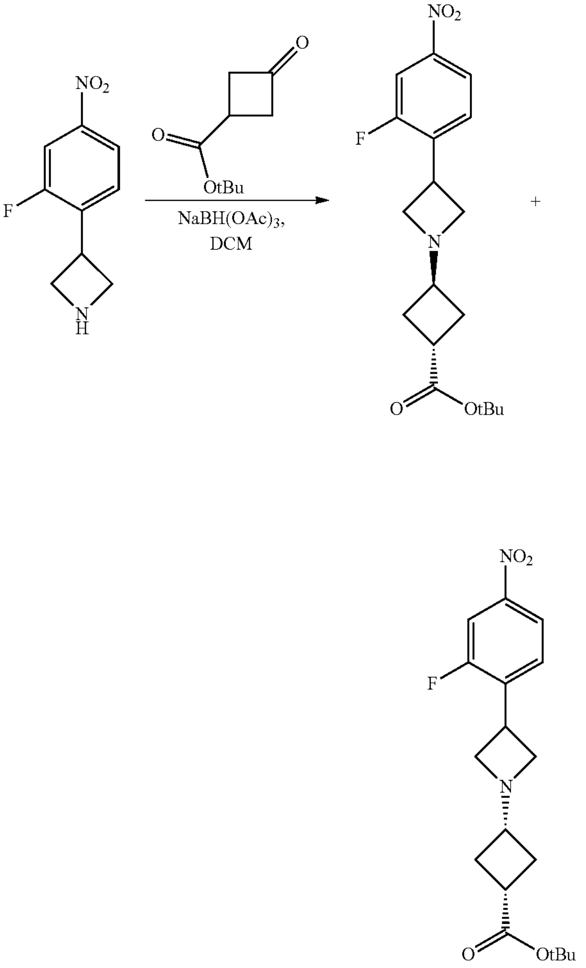

To a solution of 3-(2-fluoro-4-nitrophenyl)azetidine (10.0 g, 32.2 mmol, 1.00 eq, trifluoroacetic acid salt) in DCM (120 mL) was added AcOH (3.48 g, 57.9 mmol, 3.31 mL, 1.80 eq) and tert-butyl 3-oxocyclobutane-1-carboxylate (8 g, 47.00 mmol, 1.46 eq). The resulting mixture was stirred at 25° C. for 15 mins. $NaBH(OAc)_3$ (24.6 g, 116 mmol, 3.60 eq) was added. The reaction mixture was stirred at 30° C. for 6 hrs. The reaction mixture was diluted with DCM (200 mL) and $H_2O$ (300 mL), basified to pH-6 with sat. aq. $NaHCO_3$. The separated organic layer was dried over sodium sulphate, filtered and concentrated to give a residue, which was purified by flash silica gel chromatography (petroleum ether/ethyl acetate=0/1) to give tert-butyl (1r,3r)-3-(3-(2-fluoro-4-nitrophenyl)azetidin-1-yl)cyclobutane-1-carboxylate (5.00 g, 14.2 mmol, 98.3% yield) confirmed by $^1$HNMR and NOE as a yellow oil. tert-butyl (1s,3s)-3-(3-(2-fluoro-4-nitrophenyl)azetidin-1-yl)cyclobutane-1-carboxylate (6.00 g, 17.1 mmol, 96.5% yield) confirmed by $^1$H NMR and NOE was obtained as a yellow oil. LCMS (ES+): 351.1 $[M+H]^+$ LCMS: Rt=0.777 min cis-diastereomer $^1$H NMR δ 8.03 (dd, J=2.1, 8.4 Hz, 1H), 7.88 (dd, J=2.3, 9.7 Hz, 1H), 7.56 (t, J=7.9 Hz, 1H), 3.93 (t, J=7.6 Hz, 1H), 3.66-3.65 (m, 1H), 3.73 (t, J=7.6 Hz, 2H), 3.26 (t, J=7.3 Hz, 2H), 3.17-3.08 (m, 1H), 2.74-2.59 (m, 1H), 2.26-2.18 (m, 2H), 2.16-2.07 (m, 2H), 1.44 (s, 9H).

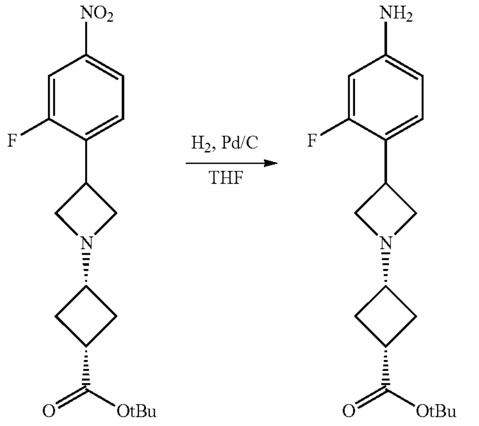 [SMILES: CC(C)(C)OC(=O)[C@H]1C[C@@H](N2CC(c3ccc([N+](=O)[O-])cc3F)C2)C1 ; CC(C)(C)OC(=O)[C@H]1C[C@@H](N2CC(c3ccc(N)cc3F)C2)C1 ; "THF"]

A mixture of tert-butyl (1s,3s)-3-(3-(2-fluoro-4-nitrophenyl)azetidin-1-yl)cyclobutane-1-carboxylate (8.00 g, 24.8 mmol, 1.00 eq) and Pd/C (600 mg, 14.2 mmol, 10% purity, 1.00 eq) in THF (20.0 mL), then the mixture stirred at 25° C. for 2 hrs under $H_2$ (15 psi) atmosphere. The reaction mixture was filtered through a celite pad and the filtrate was concentrated under reduced pressure to give tert-butyl (1s,3s)-3-(3-(4-amino-2-fluorophenyl)azetidin-1-yl)cyclobutane-1-carboxylate (7.80 g, 24.3 mmol, 98.0% yield) as a yellow oil.

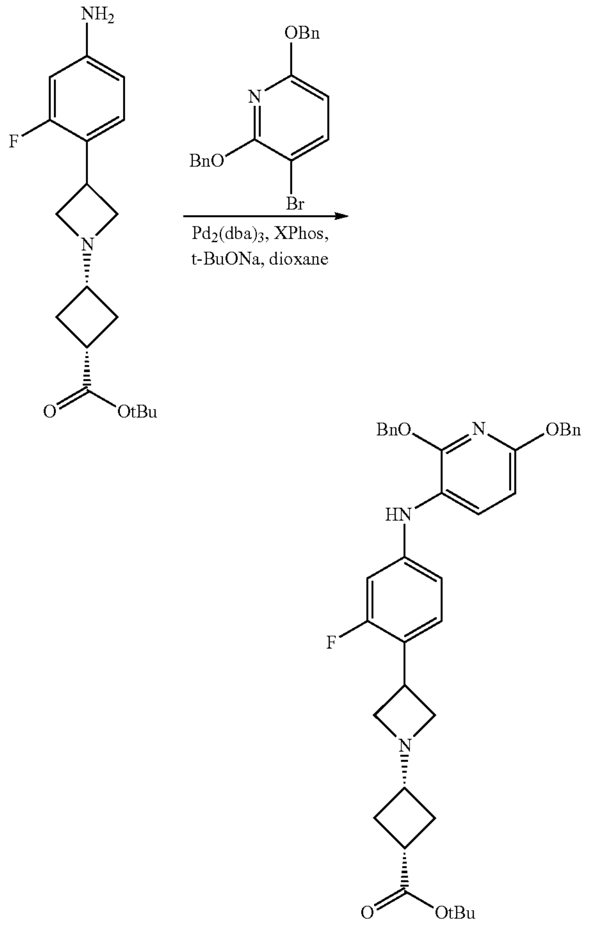

A mixture of tert-butyl (1S, 3S)-3-(3-(4-amino-2-fluorophenyl)azetidin-1-yl)cyclobutane-1-carboxylate (20.5 mmol, 1.00 eq), 2,6-bis(benzyloxy)-3-bromopyridine (22.6 mmol, 1.10 eq), $Pd_2(dba)_3$ (600 mg, 655 μmol, 5.25e-2 eq), XPhos (600 mg, 1.26 mmol, 0.1 eq) and t-BuONa (28.6 mmol, 1.40 eq) in 1,4-dioxane (70.0 mL) was stirred at 100° C. for 8 hrs under $N_2$ atmosphere. The reaction mixture was diluted with ethyl acetate (100 mL), washed with $H_2O$ (200 mL). The combined organic layers were dried over sodium sulphate, filtered and concentrated under reduced pressure to give a residue, which was purified by column chromatography ($SiO_2$, petroleum ether/ethyl acetate=50/1 to 5/1) to give tert-butyl (1s,3s)-3-(3-(4-((2,6-bis(benzyloxy)pyridin-3-yl)amino)-2-fluorophenyl)azetidin-1-yl)cyclobutane-1-carboxylate (6.30 g, 10.3 mmol, 50.9% yield) as a yellow oil. LCMS (ES+): 610.3 $[M+H]^+$

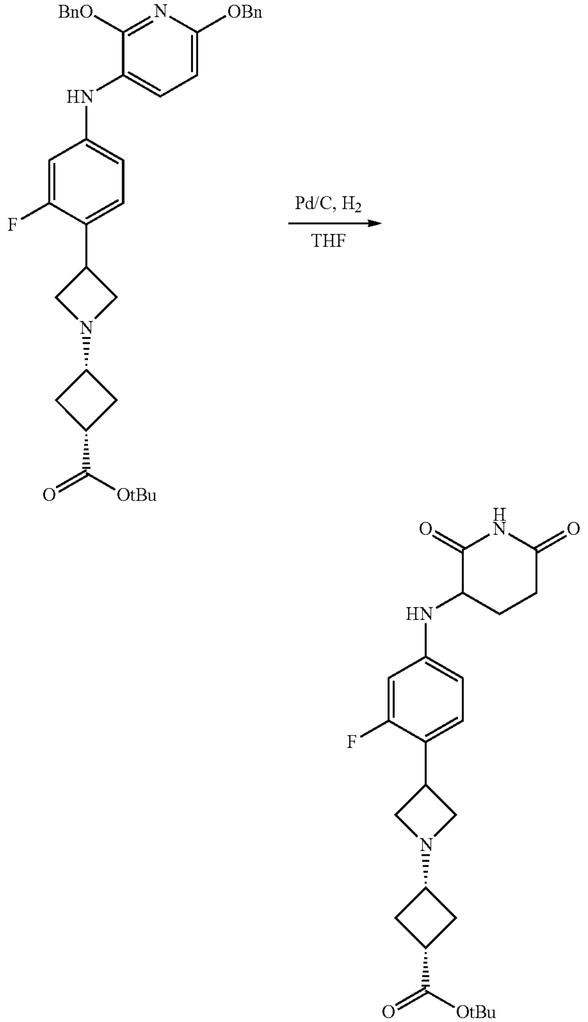

A mixture of tert-butyl (1s,3s)-3-(3-(4-((2,6-bis(benzyl oxy)pyridin-3-yl)amino)-2-fluorophenyl)azetidin-1-yl)cyclobutane-1-carboxylate (10.1 mmol, 1.00 eq) and Pd/C (600 mg, 656 μmol, 10.0% purity, 0.100 eq) in THF (40.0 mL) was stirred at 25° C. for 24 hrs under $H_2$ (50 psi) atmosphere. The reaction mixture was filtered and the filtrate was concentrated to give a residue, which was purified by column chromatography ($SiO_2$, petroleum ether/ethyl acetate=10/1 to dichloromethane/methanol=10/1) to give tert-butyl (1s,3s)-3-(3-(4-((2,6-dioxopiperidin-3-yl)amino)-2-fluorophenyl)azetidin-1-yl)cyclobutane-1-carboxylate (2.20 g, 5.10 mmol, 51.8 yield) as a blue oil. LCMS (ES+): 493.4 $[M+H]^+$

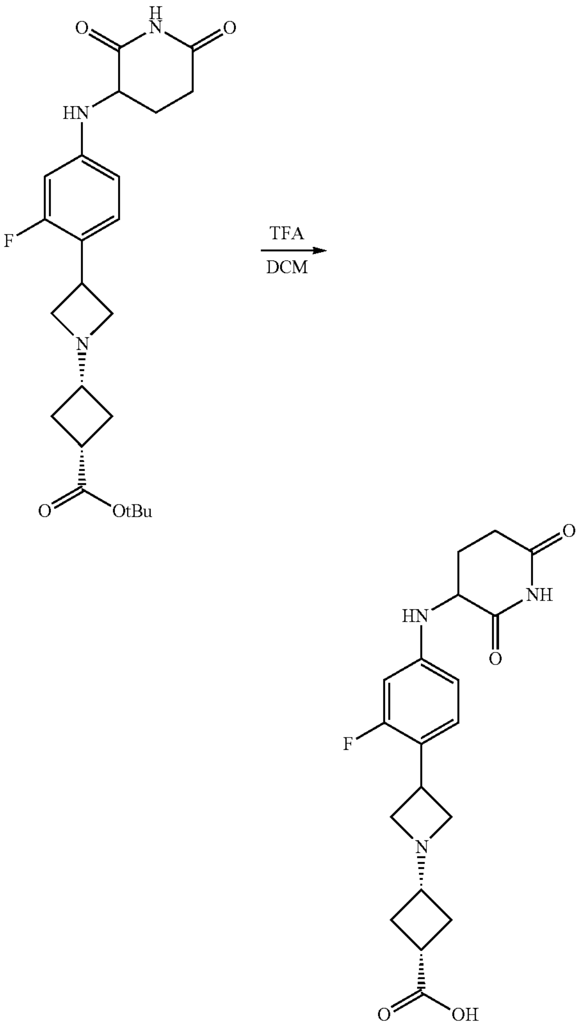

A mixture of tert-butyl (1s,3s)-3-(3-(4-((2,6-dioxopiperidin-3-yl)amino)-2-fluorophenyl)azetidin-1-yl)cyclobutane-1-carboxylate (5.1 mmol, 1.00 eq) and TFA (15.4 g, 135 mmol, 10.0 mL, 29.1 eq) in DCM (10.0 mL) was stirred at 25° C. for 2 hrs. The reaction mixture was diluted with $H_2O$ (50 mL), washed with dichloromethane (100 mL). The separated organic layer was discarded, the aqueous was lyophilized and further purified by reversed-phase-HPLC (HPLC:EW20037-26-plcl, 0.1% TFA condition) to give (1s,3s)-3-(3-(4-((2,6-dioxopiperidin-3-yl)amino)-2-fluorophenyl)azetidin-1-yl)cyclobutane-1-carboxylic acid (1.35 g, 3.60 mmol, 70.54% yield).

$^1H$ NMR (400 MHz, DMSO): δ 12.83-12.11 (m, 1H), 10.80 (s, 1H), 10.73-10.55 (m, 1H), 10.44-10.23 (m, 1H), 7.17 (br t, J=8.4 Hz, 1H), 6.58-6.46 (m, 2H), 6.41-6.14 (m, 1H), 4.37 (br dd, J=4.7, 11.6 Hz, 2H), 4.28-3.86 (m, 5H), 2.87 (quin, J=8.7 Hz, 1H), 2.80-2.68 (m, 1H), 2.58 (td, J=3.8, 17.6 Hz, 1H), 2.46 (br s, 2H), 2.22 (br d, J=9.2 Hz, 2H), 2.12-2.01 (m, 1H), 1.88 (dq, J=4.5, 12.3 Hz, 1H).

Note: the trans-diastereomer was prepared with the same manner described above.

Example 52

5-[2-[4-[3-[1-[4-[(2,6-dioxo-3-piperidyl)amino]-2-fluoro-phenyl]azetidin-3-yl]cyclobutanecarbonyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

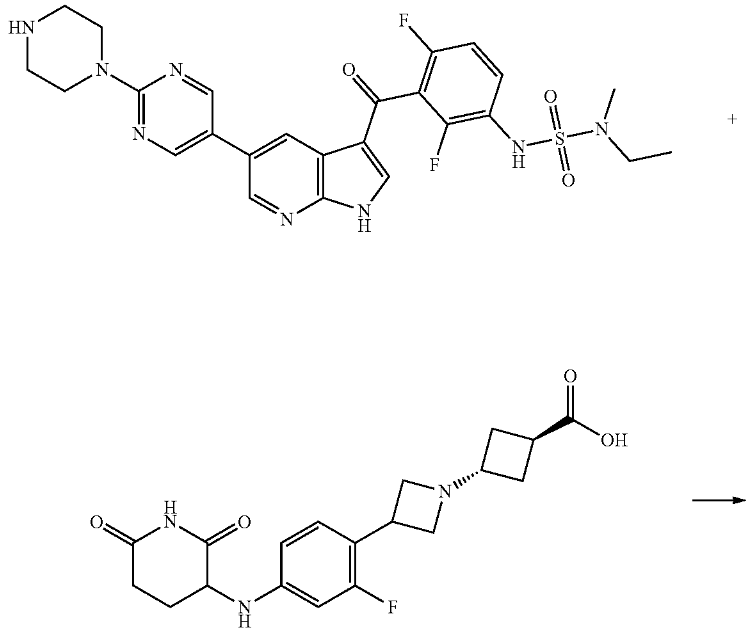

-continued

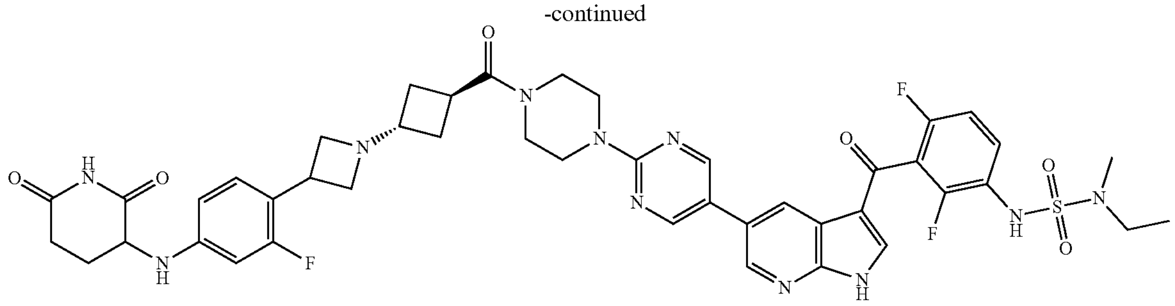

Prepared according to (General procedure A). Isolated 5-[2-[4-[3-[1-[4-[(2,6-dioxo-3-piperidyl)amino]-2-fluoro-phenyl]azetidin-3-yl]cyclobutanecarbonyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (55 mg, 50.83 μmol, 32.00% yield, trifluoroacetic acid salt) after lyophilization as an off-white solid. LCMS (ES+): 458.2 [M/2+H]$^+$, 914.8 [M+H]$^+$; $^1$H NMR (400 MHz, DMSO-d$_6$): δ 13.01 (d, J=3.3 Hz, 1H), 10.81 (d, J=2.8 Hz, 1H), 10.54 (m, 0.6H), 10.21 (s, 0.4H), 9.70 (s, 1H), 8.81 (s, 2H), 8.68 (d, J=2.1 Hz, 1H), 8.58 (s, 1H), 8.14 (d, J=3.1 Hz, 1H), 7.59 (td, J=9.0, 5.9 Hz, 1H), 7.33-7.16 (m, 2H), 6.61-6.47 (m, 2H), 4.46-4.41 (m, ~10H contains water), 4.44-4.32 (m, 2H), 4.35-4.21 (m, 1H), 4.21-4.02 (m, 2H), 3.89-3.79 (m, 4H), 3.67-3.58 (m, 2H), 3.54-3.42 (m, 3H), 3.12 (q, J=7.1 Hz, 2H), 2.82-2.69 (m, 1H), 2.74 (s, 3H), 2.59 (dt, J=17.5, 4.3 Hz, 1H), 2.41-2.33 (m, 2H), 2.09 (m, 4.2 Hz, 1H), 1.97-1.83 (m, 1H), 1.03 (t, J=7.1 Hz, 3H).

Example 53

5-[2-[4-[3-[1-[4[(2,6-dioxo-3-piperidyl)amino]-2-fluoro-phenyl]azetidin-3-yl]cyclobutanecarbonyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

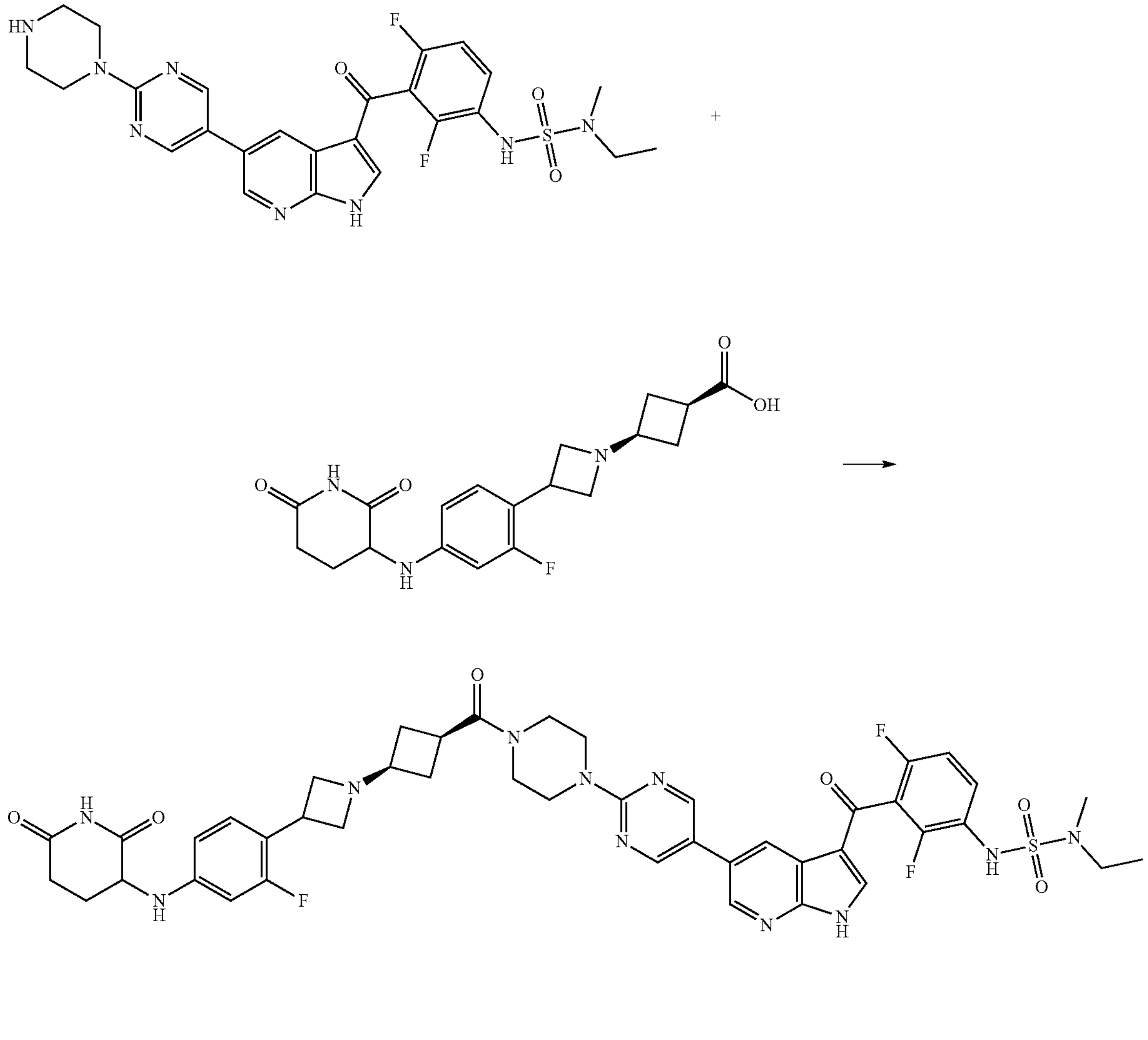 [SMILES: CCN(C)S(=O)(=O)Nc1ccc(F)c(C(=O)c2c[nH]c3ncc(-c4cnc(N5CCNCC5)nc4)cc23)c1F ; "+" ; O=C1CCC(Nc2ccc(C3CN([C@H]4C[C@@H](C(=O)O)C4)C3)c(F)c2)C(=O)N1 ; CCN(C)S(=O)(=O)Nc1ccc(F)c(C(=O)c2c[nH]c3ncc(-c4cnc(N5CCN(C(=O)[C@H]6C[C@@H](N7CC(c8ccc(NC9CCC(=O)NC9=O)cc8F)C7)C6)CC5)nc4)cc23)c1F]

Brought 3-[1-[4-[(2,6-dioxo-3-piperidyl)amino]-2-fluoro-phenyl]azetidin-3-yl]cyclobutanecarboxylic acid (77.75 mg, 158.85 trifluoroacetic acid salt) up in DMF (1 mL) and added DIPEA (102.65 mg, 794.27 μmol, 138.34 uL) before cooling to 0° C. and adding HATU (66.44 mg, 174.74 μmol). After 5-10 minutes, added solid 3-[3-[[ethyl (methyl)sulfamoyl]amino]-2,6-difluoro-benzoyl]-5-(2-piperazin-1-ylpyrimidin-5-yl)-1H-pyrrolo[2,3-b]pyridine (100 mg, 158.85 μmol, hydrochloric acid salt) in one portion. Let warm to room temperature and continued stirring overnight. Loaded the crude reaction mixture onto RP isco (0-100% ACN/water w TFA) to afford 5-[2-[4-[3-[1-[4-[(2,6-dioxo-3-piperidyl)amino]-2-fluoro-phenyl]azetidin-3-yl]cyclobutanecarbonyl]piperazin-1-yl]pyrimidin-5-yl]-3-[3-[[ethyl (methyl)sulfamoyl]amino]-2,6-difluoro-benzoyl]-1H-pyrrolo[2,3-b]pyridine (90 mg, 83.17 μmol, 52.36% yield, trifluoroacetic acid salt) as an off-white solid after lyophilization. LCMS (ES+): 458.1 $[M/2+H]^+$, 914.9 $[M+H]^+$.

$^1H$ NMR (400 MHz, DMSO-$d_6$): δ 12.96-12.90 (m, 1H), 10.73 (s, 1H), 9.62 (s, 1H), 8.74 (d, J=1.2 Hz, 2H), 8.61 (d, J=2.2 Hz, 1H), 8.51 (s, 1H), 8.07 (d, J=3.1 Hz, 1H), 7.51 (td, J=9.0, 5.9 Hz, 1H), 7.21 (td, J=8.8, 1.6 Hz, 1H), 7.18-7.06 (m, 1H), 6.53-6.45 (m, 1H), 6.49-6.40 (m, 1H), 4.35-4.26 (m, 2H), 4.19-4.01 (m, 2H), 4.01-3.82 (m, 2H), 3.76 (h, J=4.0, 3.2 Hz, 4H), 3.57-3.49 (m, 2H), 3.47 (s, 1H), 3.47-3.38 (m, 2H), 3.24-3.13 (m, 1H), 3.05 (q, J=7.1 Hz, 2H), 2.74-2.61 (m, 1H), 2.66 (s, 3H), 2.57-2.46 (m, 1H), 2.25-2.21 (m, 2H), 2.05-1.96 (m, 1H), 1.90-1.74 (m, 1H), 0.95 (t, J=7.1 Hz, 3H).

Example 54

5-[2-[4-[2-[(4S)-4-[4-[(2,6-dioxo-3-piperidyl)amino] phenyl]-3,3-difluoro-1-piperidyl]acetyl]piperazin-1-yl]pyrimidin-5-yl]-3-[3-[[ethyl(methyl)sulfamoyl] amino]-2,6-difluoro-benzoyl]-1H-pyrrolo[2,3-b] pyridine

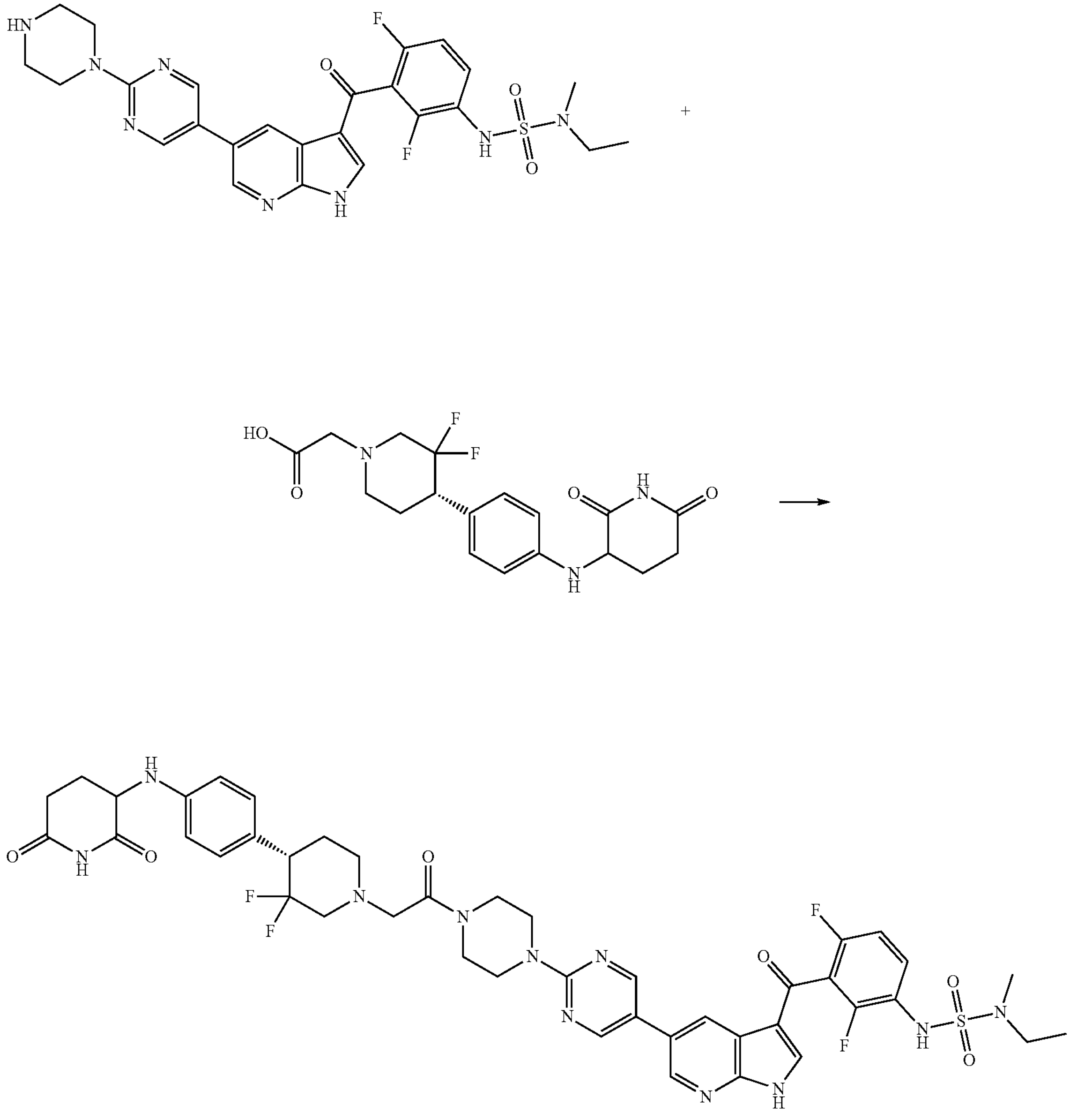

Brought 2-[(4S)-4-[4-[(2,6-dioxo-3-piperidyl)amino]phenyl]-3,3-difluoro-1-piperidyl]acetic acid (125 mg, 205.11 μmol, trifluoroacetic acid salt) up in NMP and added DIPEA (159.06 mg, 1.23 mmol, 214.36 uL) before cooling to 0° C. in an ice bath. HATU (89.69 mg, 235.88 μmol) was added, and the reaction stirred for 5 minutes before adding 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (129.12 mg, 205.11 mol, hydrochloric acid salt). The reaction was gradually warmed to room temperature overnight. After 16 hours, the crude reaction was loaded directly onto RP isco 0-60% ACN/water w Formic acid. Isolated 5-[2-[4-[2-[(4S)-4-[4-[(2,6-dioxo-3-piperidyl)amino]phenyl]-3,3-difluoro-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (80 mg, 78.68 μmol, 38.36% yield, formic acid salt) as an off-white solid after lyophilization. LCMS (ES+): 461.2 $[M/2+H]^+$, 920.8 $[M+H]^+$. $^1$H NMR (400 MHz, DMSO-$d_6$): δ 12.92 (d, J=3.3 Hz, 1H), 10.70 (s, 1H), 9.62 (s, 1H), 8.74 (s, 2H), 8.61 (d, J=2.2 Hz, 1H), 8.50 (s, 1H), 8.09-8.04 (m, 1H), 7.51 (td, J=9.0, 5.9 Hz, 1H), 7.21 (td, J=8.8, 1.5 Hz, 1H), 6.95 (d, J=8.2 Hz, 2H), 6.57 (d, J=8.4 Hz, 2H), 5.74 (d, J=7.5 Hz, 1H), 4.23 (dd, J=11.1, 5.6 Hz, 1H), 3.84-3.71 (m, 4H), 3.62-3.56 (m, 2H), 3.56-3.52 (m, 2H), 3.34 (d, J=13.3 Hz, 2H), 3.11 (s, 1H), 3.04 (q, J=7.1 Hz, 2H), 2.90 (s, 1H), 2.87 (s, 1H), 2.74-2.61 (m, 1H), 2.66 (s, 3H), 2.59-2.46 (m, 1H), 2.33 (s, 1H), 2.09-1.93 (m, 2H), 1.80 (qd, J=12.2, 4.7 Hz, 1H), 1.70-1.66 (m, 1H), 0.95 (t, J=7.1 Hz, 3H).

Example 55

5-[2-[4-[2-[(4R)-4-[4-[(2,6-dioxo-3-piperidyl)amino]phenyl]-3,3-difluoro-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

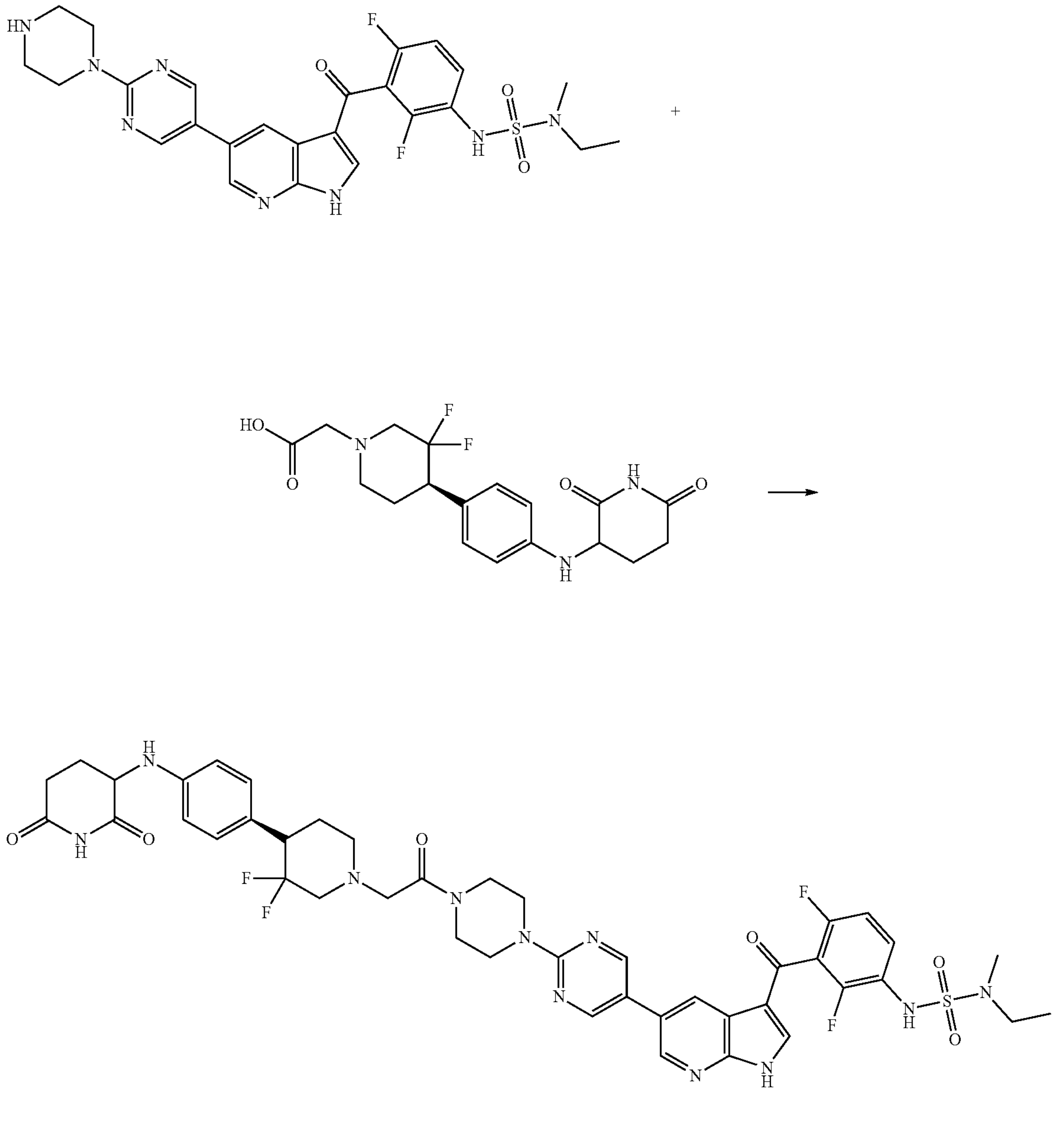

Brought 2-[(4R)-4-[4-[(2,6-dioxo-3-piperidyl)amino]phenyl]-3,3-difluoro-1-piperidyl]acetic acid (125 mg, 205.11 μmol, trifluoroacetic acid salt) up in NMP (1.84 mL) and added DIPEA (159.06 mg, 1.23 mmol, 214.36 uL) before cooling to 0° C. in an ice bath. Added HATU (89.69 mg, 235.88 μmol) and stirred for 5 minutes before adding 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (114.16 mg, 181.35 μmol, hydrochloric acid salt) as a solid. Let gradually warm to room temperature overnight. After 16 hours, loaded crude reaction directly onto RP isco 0-60% ACN/water w Formic acid. Isolated 5-[2-[4-[2-[(4R)-4-[4-[(2,6-dioxo-3-piperidyl)amino]phenyl]-3,3-difluoro-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (62 mg, 60.98 μmol, 29.73% yield, formic acid salt) as an off-white solid after lyophilization. LCMS (ES+): 461.3 $[M/2+H]^+$, 920.8 $[M+H]^+$. $^1H$ NMR (400 MHz, DMSO-$d_6$): δ 13.00 (d, J=3.3 Hz, 1H), 10.77 (s, 1H), 9.70 (s, 1H), 8.82 (s, 2H), 8.69 (d, J=2.2 Hz, 1H), 8.58 (s, 1H), 8.14 (d, J=3.1 Hz, 1H), 7.59 (td, J=9.0, 5.9 Hz, 1H), 7.28 (td, J=8.8, 1.5 Hz, 1H), 7.03 (d, J=8.3 Hz, 2H), 6.64 (d, J=8.3 Hz, 2H), 5.81 (s, 1H), 4.34-4.26 (m, 1H), 3.92-3.88 (m, 2H), 3.86-3.80 (m, 2H), 3.69-3.64 (m, 2H), 3.64-3.59 (m, 2H), 3.38 (s, 4H), 3.19 (s, 1H), 3.12 (q, J=7.1 Hz, 2H), 3.00-2.96 (m, 2H), 2.81-2.68 (m, 1H), 2.74 (s, 3H), 2.64-2.54 (m, 1H), 2.15-2.06 (m, 1H), 1.89 (tt, J=11.9, 6.1 Hz, 1H), 1.76 (s, 1H), 1.03 (t, J=7.1 Hz, 3H).

Example 56

3-(2,4-dioxohexahydropyrimidin-1-yl)-6-[4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-1-piperidyl]-1-methyl-indazole

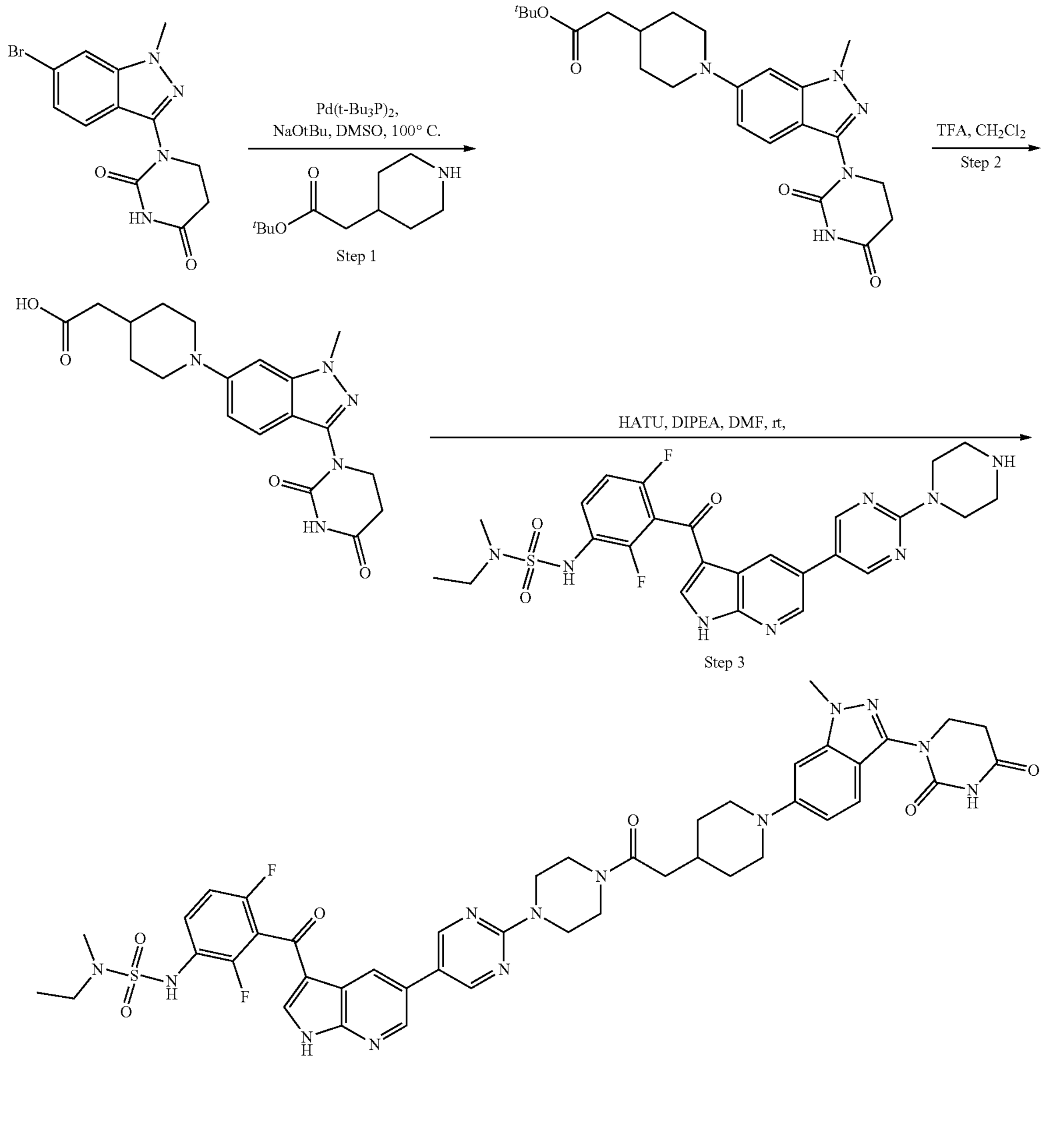

Step 1: To a stirred solution of tert-butyl 2-(4-piperidyl) acetate (308.36 mg, 1.31 mmol) and 1-(6-bromo-1-methyl-indazol-3-yl)hexahydropyrimidine-2,4-dione (500 mg, 1.55 mmol) were in DMSO (15 mL) was added Sodium tert-butoxide (446.08 mg, 4.64 mmol). The reaction mixture was degassed with nitrogen for 10 minutes, followed by Bis(tri-tert-butylphosphine) palladium (0) (316.30 mg, 618.92 μmol). The reaction mixture was stirred for 16 hours at 100° C. After completion of reaction, diluted with water (50 mL) and extracted with ethyl acetate (2×30 mL). The combined organic layers were dried over anhydrous sodium sulphate and concentrated under reduced pressure to yield crude. The crude was purified by silica gel column chromatography by using 50% ethyl acetate/petroleum ether as eluent system to afford tert-butyl 2-[1-[3-(2,4-dioxohexahydropyrimidin-1-yl)-1-methyl-indazol-6-yl]-4-piperidyl]acetate (260 mg, 435.77 μmol, 28.16% yield) as orange solid. LCMS (ESI): 442.2 [M+H]$^+$.

Step 2: To a stirred solution of tert-butyl 2[1-[3-(2,4-dioxohexahydropyrimidin-1-yl)-1-methyl-indazol-6-yl]-4-piperidyl]acetate (260 mg, 588.87 μmol) in Dichloromethane (4 mL) was added TFA (67.14 mg, 588.87 μmol, 45.37 μL) at 0° C. The reaction mixture was stirred for 2 hours at 25° C. After completion, the reaction mixture was concentrated under reduced pressure to yield crude. The crude was washed with diethyl ether (20 mL) to afford 3-[1-[3-(2,4-dioxohexahydropyrimidin-1-yl)-1-methyl-indazol-6-yl]-4-piperidyl]acetic acid (220 mg, 370.02 μmol, 62.83% yield) as off white solid. LCMS (ESI+): 386.0 [M+H]$^+$.

Step 3: Target compound was prepared via T3P mediated acid-amine coupling reaction (procedure C). Amide coupling was carried out using 2[1-[3-(2,4-dioxohexahydropyrimidin-1-yl)-1-methyl-indazol-6-yl]-4-piperidyl]acetic acid (180 mg, 360.40 μmol), 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (200.60 mg, 338.25 μmol), T3P (137.61 mg, 432.49 μmol) and N,N-diisopropylethylamine (139.74 mg, 1.08 mmol, 188.32 μL) to afford 3-(2,4-dioxohexahydropyrimidin-1-yl)-6-[4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-1-piperidyl]-1-methyl-indazole (57 mg, 55.18 μmol, 15.31% yield) as light pink solid. LCMS (ESI+): 924.0 [M+H]$^+$. $^1$H NMR (400 MHz, DMSO-d$_6$): δ 10.50 (s, 1H), 8.82 (s, 2H), 8.67 (s, 1H), 8.55 (s, 1H), 8.37 (s, 1H), 8.09 (s, 1H), 7.58-7.52 (m, 1H), 7.44 (d, J=8.80 Hz, 1H), 7.19 (t, J=8.00 Hz, 1H), 6.91 (dd, J=2.00, 9.20 Hz, 1H), 6.82 (s, 1H), 3.91-3.86 (m, 10H), 3.62-3.17 (m, 4H), 3.08 (q, J=7.20 Hz, 3H), 2.80-2.72 (m, 4H), 2.69 (s, 3H), 2.39 (d, J=6.40 Hz, 2H), 1.95-1.81 (m, 3H), 1.38-0.00 (m, 2H), 1.01 (t, J=7.20 Hz, 3H).

Example 57

5-[2-[4-[2-[1-[5-[(2,6-dioxo-3-piperidyl)amino]-2-pyridyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

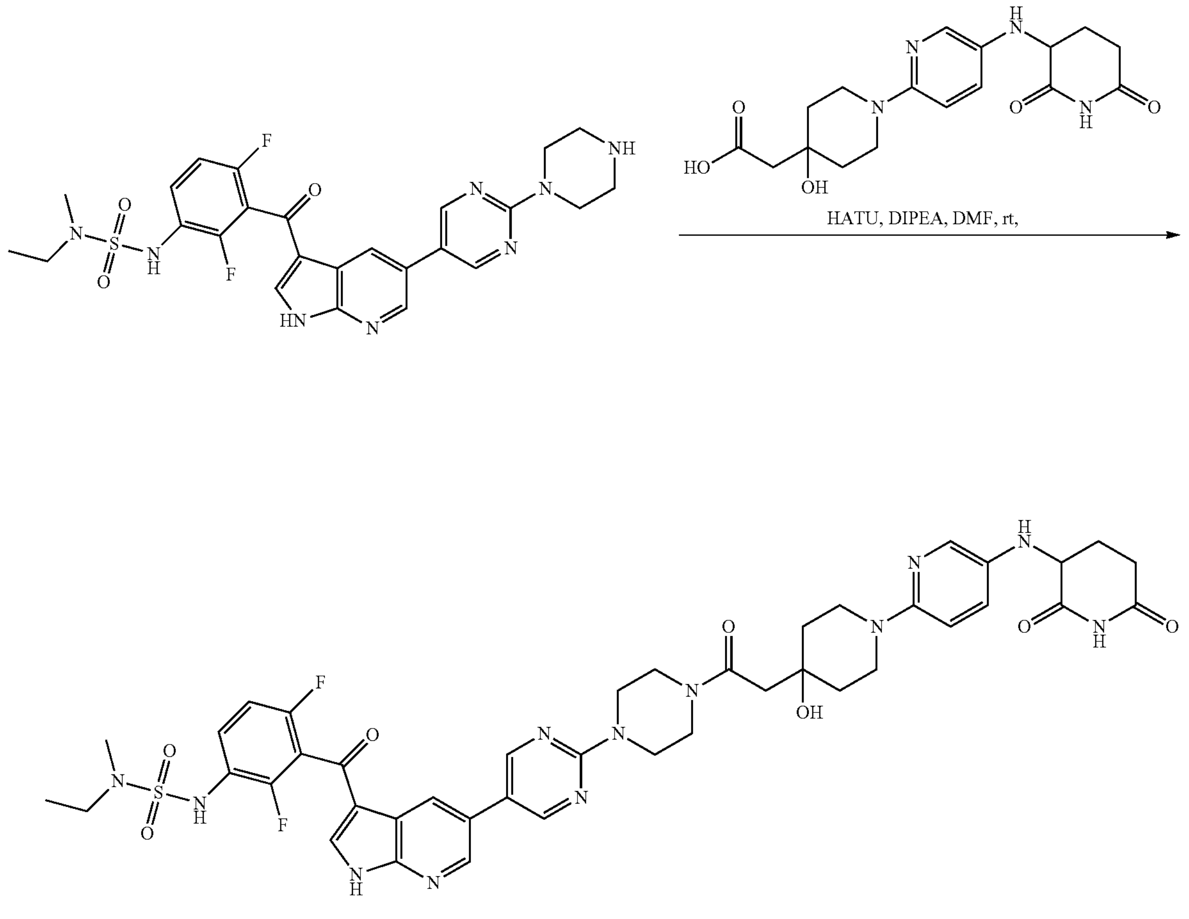

Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (500 mg, 843.10 μmol, hydrochloric acid salt), 2-[1-[5-[(2,6-dioxo-3-piperidyl)amino]-2-pyridyl]-4-hydroxy-4-piperidyl]acetic acid (403.52 mg, 1.01 mmol, hydrochloric acid salt), DMF (4.5 mL), HATU (480.86 mg, 1.26 mmol) and N,N-Diisopropylethylamine (544.81 mg, 4.22 mmol, 734.25 μL) to afford 5-[2-[4-[2-[1-[5-[(2,6-dioxo-3-piperidyl)amino]-2-pyridyl]-4-hydroxy-4-piperidyl]acetyl]piperazin-1-yl]pyrimidin-5-yl]-3-[3-[[ethyl (methyl)sulfamoyl]amino]-2,6-difluoro-benzoyl]-1H-pyrrolo[2,3-b]pyridine (148.5 mg, 153.27 μmol, 18.18% yield, Formate salt) as an off-white solid. LCMS (ESI+): 900.9 $[M+H]^+$. $^1H$ NMR (400 MHz, DMSO-d6): δ 13.01 (s, 1H), 10.87 (s, 1H), 9.71 (s, 1H), 8.83 (d, J=10.00 Hz, 2H), 8.68 (d, J=2.40 Hz, 1H), 8.58 (s, 1H), 8.15 (d, J=2.80 Hz, 1H), 7.62-7.56 (m, 2H), 7.37-7.26 (m, 3H), 6.30-6.15 (m, 1H), 5.20-5.00 (m, 1H), 4.52-4.45 (m, 1H), 3.84-3.65 (m, 6H), 3.64-3.37 (m, 4H), 3.54-3.41 (m, 2H), 3.12 (q, J=7.20 Hz, 2H), 2.74 (s, 3H), 2.70-2.61 (m, 4H), 2.12-2.08 (m, 1H), 1.96-1.93 (m, 1H), 1.85-1.65 (m, 4H), 1.03 (t, J=7.20 Hz, 3H).

Example 58

5-[2-[4-[2-[1-[5-[(2,6-dioxo-3-piperidyl)amino]-3-fluoro-2-pyridyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

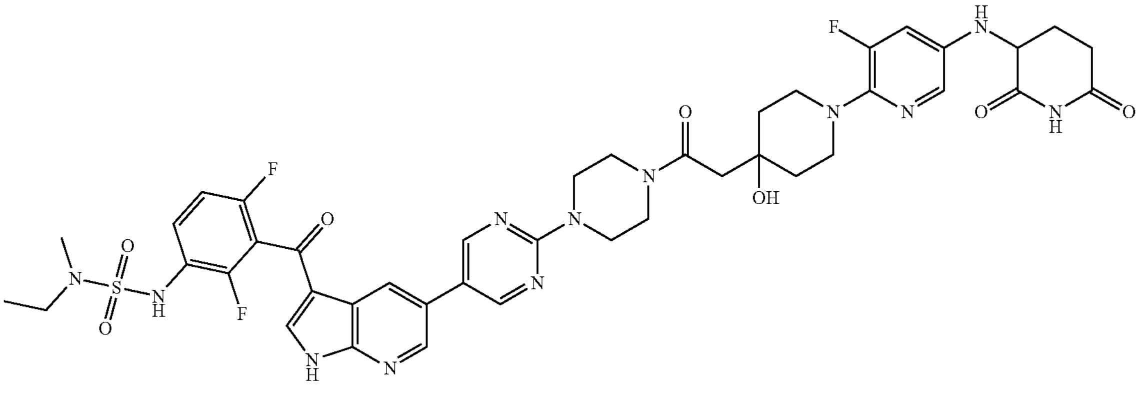 [SMILES: CCN(C)S(=O)(=O)Nc1ccc(F)c(C(=O)c2c[nH]c3ncc(-c4cnc(N5CCN(C(=O)CC6(O)CCN(c7ncc(NC8CCC(=O)NC8=O)cc7F)CC6)CC5)nc4)cc23)c1F]

Target compound was prepared via procedure B, by modifying the amide coupling 2-[1-[5-[(2,6-dioxo-3-piperidyl)amino]-3-fluoro-2-pyridyl]-4-hydroxy-4-piperidyl] acetic acid (50 mg, 131.45 μmol), 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (73.16 mg, 131.45 μmol), 6.0 eq of DIPEA and 1.3 eq of COMU. The crude material was purified by reverse phase column chromatography (MeCN & Water (0.01% TFA)). The product was free based in sat. bicarbonate solution in EtOAc. The material was then purified by MeOH and DCM (0-30% MeOH) to afford 5-[2-[4-[2-[1-[5-[(2,6-dioxo-3-piperidyl)amino]-3-fluoro-2-pyridyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b] pyridine (45.0 mg, 47.5 μmol, 36% yield) as off-white solid. LCMS (ESI+): 919.3 $[M+H]^+$. $^1H$ NMR (400 MHz, DMSO-d6): δ 10.80 (s, 1H), 8.80 (s, 2H), 8.67 (s, 1H), 8.13 (s, 1H), 7.57 (s, 2H), 7.03-6.94 (m, 1H), 5.88 (d, J=7.8 Hz, 1H), 4.90 (s, 1H), 4.31-4.25 (m, 1H), 3.89-3.80 (m, 4H), 3.75-3.60 (m, 4H), 3.16-3.04 (m, 4H), 2.79-2.66 (m, 4H), 2.61-2.57 (m, 3H), 2.13-2.08 (m, 1H), 1.96-1.82 (m, 1H), 1.77-1.63 (m, 4H), 1.02 (t, J=7.1 Hz, 4H).

Example 59

5-[2-[4-[2-[1-[4-[(2,6-dioxo-3-piperidyl)amino]-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

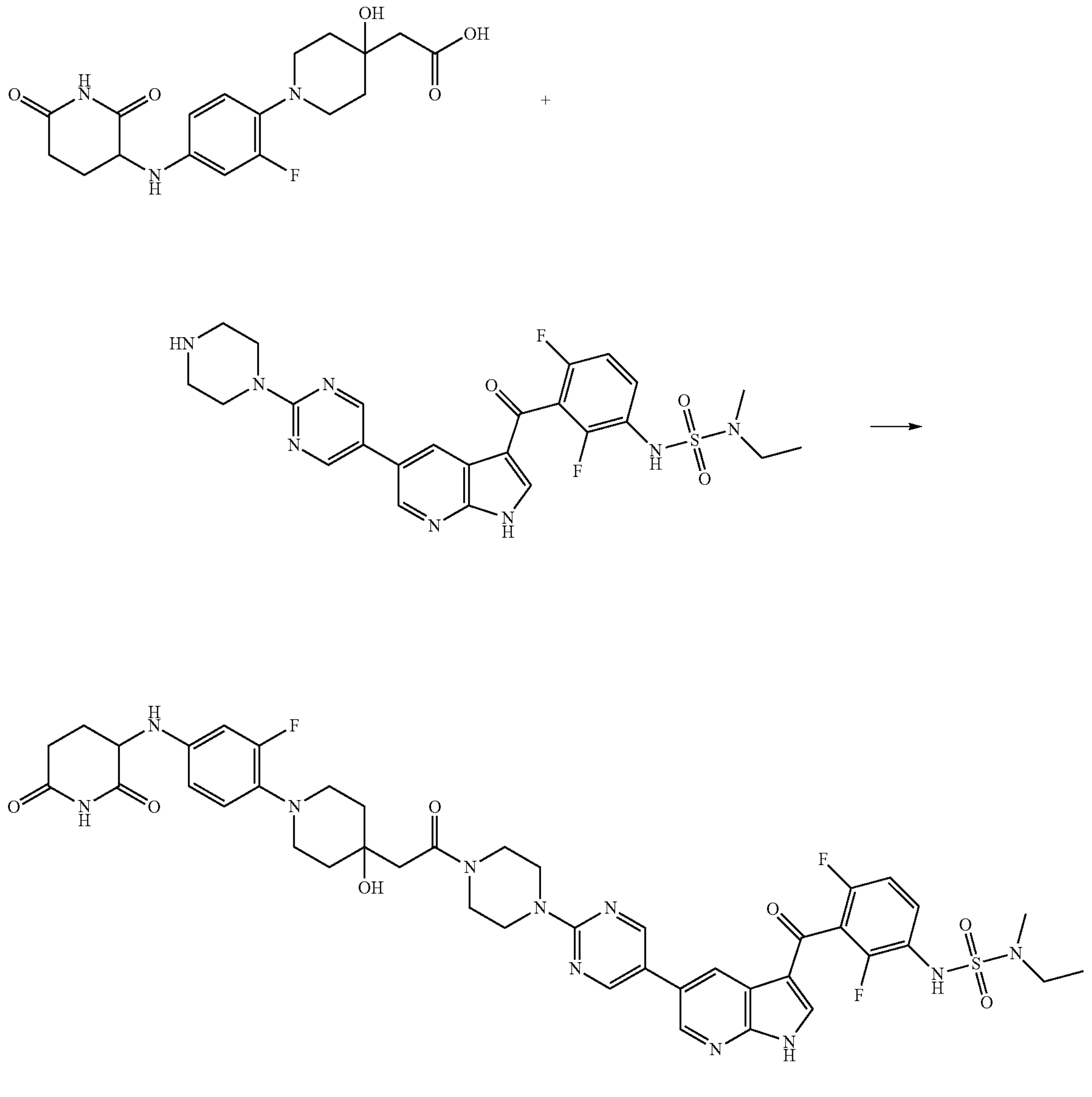

Brought 2-[1-[4-[(2,6-dioxo-3-piperidyl)amino]-2-fluoro-phenyl]-4-hydroxy-4-piperidyl]acetic acid (102.63 mg, 208 trifluoroacetic acid salt) up in DMF (3 mL) and added DIPEA (161.29 mg, 1.25 mmol, 217.37 uL) before cooling reaction to 0° C. and adding PyBOP (124.48 mg, 239.20 μmol). After 10-15 minutes, added 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (130.94 mg, 208.00 μmol, hydrochloric acid salt) and let the reaction warm to room temperature over 4 hours. Purified reaction mixture directly by RP isco (0-100% ACN/water w/ formic acid) to give 5-[2-[4-[2-[1-[4-[(2,6-dioxo-3-piperidyl)amino]-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (60 mg, 59.75 μmol, 28.73% yield, formic acid salt) as an off-white solid after lyophilization. LCMS (ES+): 460.3 $[M/2+H]^+$, 918.7 $[M+H]^+$. $^1H$ NMR (400 MHz, DMSO-$d_6$): δ 12.99 (s, 1H), 10.77 (s, 1H), 8.81 (s, 2H), 8.68 (d, J=2.3 Hz, 1H), 8.57 (s, 1H), 8.15 (d, J=16.1 Hz, 1H), 7.58 (td, J=9.0, 5.9 Hz, 1H), 7.26 (t, J=8.7 Hz, 1H), 6.87 (t, J=9.3 Hz, 1H), 6.51 (dd, J=15.0, 2.6 Hz, 1H), 6.42 (dd, J=8.6, 2.5 Hz, 1H), 5.77 (d, J=7.6 Hz, 1H), 4.86 (s, 1H), 4.25 (dt, J=11.9, 6.6 Hz, 1H), 3.88 (s, 2H), 3.83 (s, 2H), 3.70 (s, 2H), 3.65 (d, J=5.4 Hz, 2H), 3.11 (q, J=7.1 Hz, 2H), 2.90 (dt, J=18.4, 10.6 Hz, 4H), 2.80-2.67 (m, 1H), 2.73 (s, 3H), 2.60 (s, 3H), 2.08 (s, 3H), 1.91-1.79 (m, 1H), 1.77 (d, J=9.4 Hz, 2H), 1.69 (d, J=12.6 Hz, 2H), 1.02 (td, J=7.2, 3.9 Hz, 4H).

Example 60
5-[2-[4-[2-[1-[4-[(2,6-dioxo-3-piperidyl)amino]phenyl]-4-piperidyl]-2,2-difluoro-acetyl]piperazin-1-yl] pyrimidin-5-yl]-3-[3-[[ethyl(methyl)sulfamoyl] amino]-2,6-difluoro-benzoyl]-1H-pyrrolo[2,3-b] pyridine
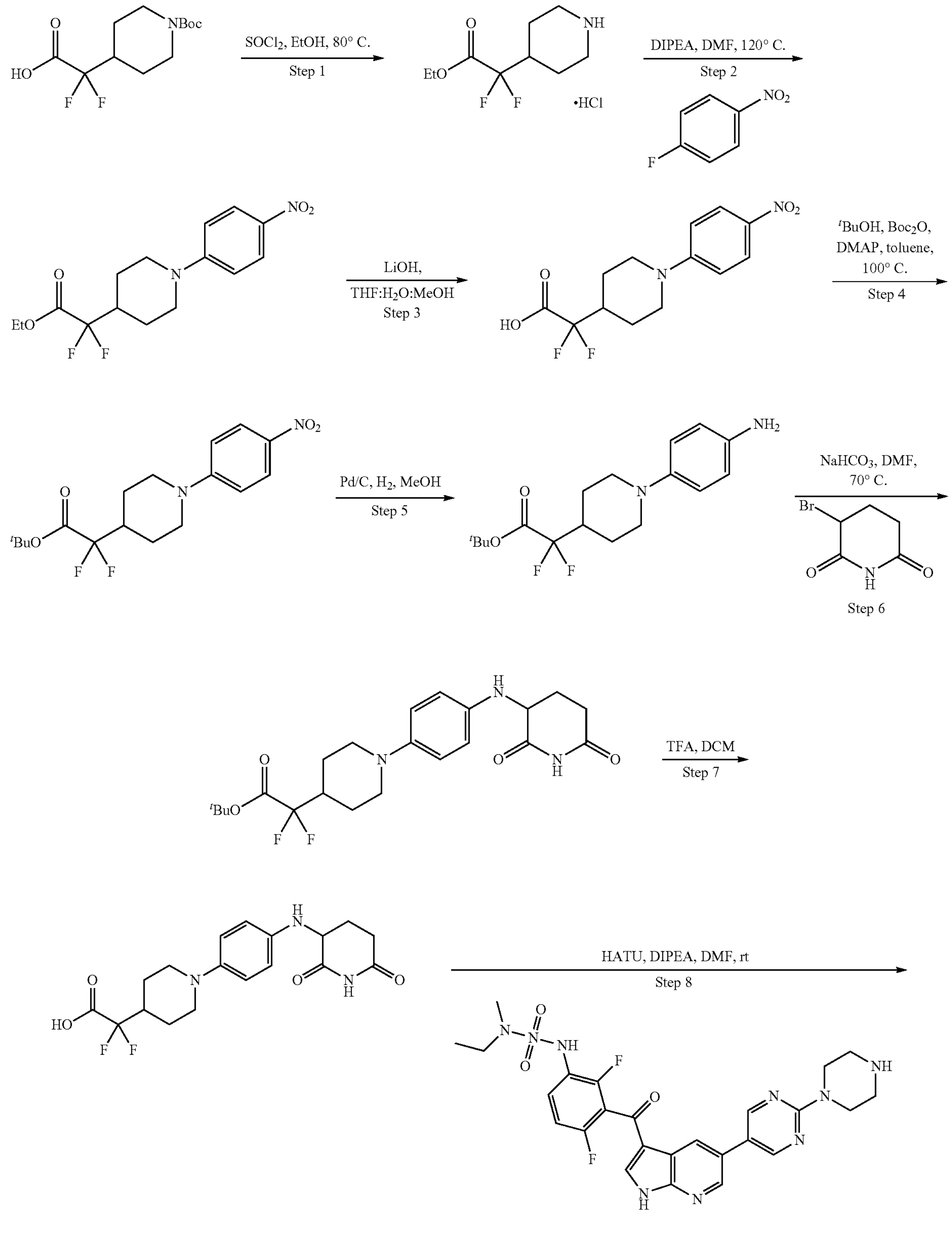

-continued

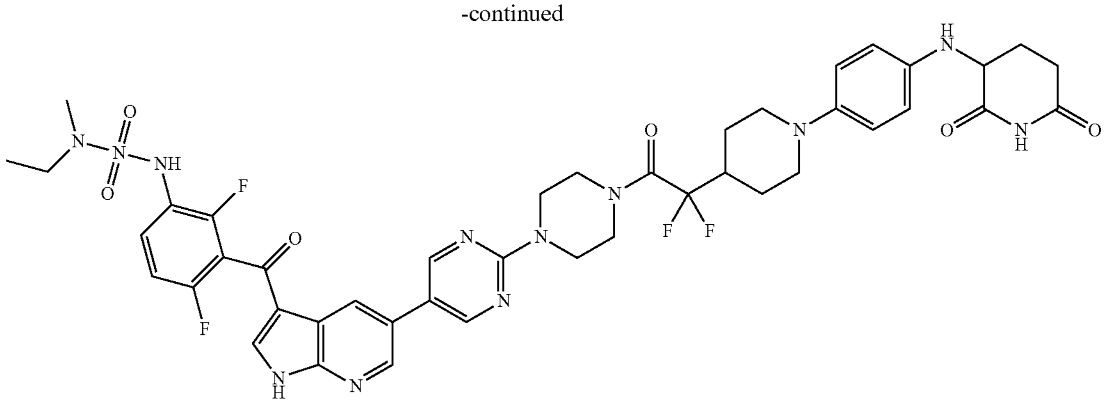

Step 1: To a stirred solution of 2-(1-tert-butoxycarbonyl-4-piperidyl)-2,2-difluoro-acetic acid (1.0 g, 3.58 mmol) in Ethanol (10 mL) was added thionyl chloride (468.59 mg, 3.94 mmol) at 0° C. The resulting mixture was stirred for 3 h at 70° C. The reaction mixture was concentrated under reduced pressure to afford ethyl 2,2-difluoro-2-(4-piperidyl) acetate (0.78 g, 2.88 mmol, 80.46% yield) as white solid. LCMS (ESI+): 208.1 $[M+H]^+$.

Step 2: To a stirred solution of ethyl 2,2-difluoro-2-(4-piperidyl)acetate (780 mg, 3.20 mmol) in N,N-Dimethylformamide (10 mL) were added N,N-Diisopropylethylamine (2.07 g, 16.00 mmol, 2.79 mL) and 1-fluoro-4-nitro-benzene (496.82 mg, 3.52 mmol, 373.55 μL) at room temperature. The resulting mixture was stirred for 16 h at 120° C. After completion, water was added to the reaction mixture and extracted with ethyl acetate (2×100 mL). Combined organic layers were dried over sodium sulphate and concentrated under reduced pressure to get crude ethyl 2,2-difluoro-2-[1-(4-nitrophenyl)-4-piperidyl]acetate (1.1 g, 2.42 mmol, 75.68% yield) as pale brown solid, which was used without further purification. LCMS (ESI+): 329.1 $[M+H]^+$.

Step 3: To a stirred solution of ethyl 2,2-difluoro-2-[1-(4-nitrophenyl)-4-piperidyl]acetate (1.1 g, 3.35 mmol) in mixture of THF (20 mL), Water (10 mL), Methanol (5 mL) was added lithium hydroxide hydrate (702.99 mg, 16.75 mmol, 465.56 μL) at room temperature. The resulting mixture was stirred for 2 h at room temperature. After completion, water was added to the reaction mixture and impurities washed with ethyl acetate (2×100 mL). Then aq. layer adjusted to pH 2-3 by adding saturated citric acid solution, then product extracted by Ethyl acetate (2×100 mL). Combined organic layers were dried over sodium sulphate and concentrated under reduced pressure to afford 2,2-difluoro-2-[1-(4-nitrophenyl)-4-piperidyl]acetic acid (0.77 g, 2.34 mmol, 69.80% yield) as brown solid, which was used without further purification. LCMS (ESI+): 301.0 $[M+H]^+$.

Step 4: To a stirred solution of 2,2-difluoro-2-[1-(4-nitrophenyl)-4-piperidyl]acetic acid (0.77 g, 2.56 mmol) in Toluene (8 mL) was added tert-butyl alcohol (2.28 g, 30.77 mmol, 2.90 mL), Di-tert-butyl dicarbonate (1.12 g, 5.13 mmol, 1.18 mL) and DMAP (31.33 mg, 256.45 μmol) at room temperature. The resulting mixture was stirred at 110° C. for 16 h. After completion, water (50 mL) was added to the reaction mixture and extracted with ethyl acetate (3×50 mL). The organic layer was dried over anhydrous sodium sulphate, filtered and evaporated under reduced pressure to get the desired crude product. The crude product was purified by silica gel column chromatography by using ethyl acetate in petroleum ether used as eluent (0-10%) to afford tert-butyl 2,2-difluoro-2-[1-(4-nitrophenyl)-4-piperidyl]acetate (620 mg, 1.63 mmol, 63.57% yield) as yellow solid. LCMS (ESI+): 357.0 $[M+H]^+$.

Step 5: To a stirred solution of tert-butyl 2,2-difluoro-2-[1-(4-nitrophenyl)-4-piperidyl]acetate (620 mg, 1.74 mmol), 10% Palladium on carbon wet (310 mg, 2.91 mmol) in methanol (15 mL) was saturated with hydrogen by bubbling Hydrogen gas through for 10 minutes and then subjected to hydrogenation (1 atm) at room temperature. After 16 hours, the reaction mixture was purged with nitrogen, the catalyst was removed by filtration through celite, and the filtrate was evaporated under reduced pressure to get crude. The crude product was purified by silica gel column chromatography using ethyl acetate in petroleum ether as eluents to afford 2-[1-(4-aminophenyl)-4-piperidyl]-2,2-difluoro-acetate (450 mg, 1.32 mmol, 75.60% yield) as pale blue solid. LCMS (ESI+): 327.2 $[M+H]^+$.

Step 6: To a stirred solution of tert-butyl 2-[1-(4-aminophenyl)-4-piperidyl]-2,2-difluoro-acetate (450 mg, 1.38 mmol) in N,N-Dimethylformamide (4 mL) was added sodium hydrogen carbonate (347.47 mg, 4.14 mmol, 160.87 μL) and 3-bromopiperidine-2,6-dione (529.47 mg, 2.76 mmol) at room temperature. The resulted mixture was stirred at 70° C. for 16 hours. After completion, water (50 mL) was added to the reaction mixture and extracted with ethyl acetate (3×50 mL) dried over anhydrous sodium sulphate, filtered and filtrate was evaporated under reduced pressure to get the desired crude product. The crude product was further purified by column silica gel chromatography using 40-50% ethyl acetate in petroleum ether as eluents to afford tert-butyl 2-[1-[4-[(2,6-dioxo-3-piperidyl)amino]phenyl]-4-piperidyl]-2,2-difluoro-acetate (470 mg, 775.03 μmol, 56.21% yield) as pale blue solid. LCMS (ESI+): 438.2 $[M+H]^+$.

Step 7: To a stirred solution of tert-butyl 2-[1-[4-[(2,6-dioxo-3-piperidyl)amino]phenyl]-4-piperidyl]-2,2-difluoro-acetate (470 mg, 1.07 mmol) in 1,4-Dioxane (2 mL) was added hydrogen chloride solution 4.0M in 1,4-dioxane (4.00 g, 109.71 mmol, 5 mL) at 0° C. The reaction mixture was stirred at room temperature for 16 hours. The reaction mixture was concentrated under reduced pressure to afford 2-[1-[4-[(2,6-dioxo-3-piperidyl)amino]phenyl]-4-piperidyl]-2,2-difluoro-acetic acid (450 mg, 968.21 μmol, 90.12% yield) as pale brown solid. LCMS (ESI+): 381.8 $[M+H]^+$.

Step 8: Target compound was prepared via HATU mediated acid-amine coupling reaction (procedure A). Amide coupling was carried out using 2-[1-[4-[(2,6-dioxo-3-piperidyl)amino]phenyl]-4-piperidyl]-2,2-difluoro-acetic acid (440 mg, 1.05 mmol), 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (562.06 mg, 947.74 μmol), HATU (480.48 mg, 1.26 mmol) and N,N-diisopropylethylamine (816.58 mg, 6.32 mmol, 1.10 mL) to afford 5-[2-[4-[2-[1-[4-[(2,6-dioxo-3-piperidyl)amino]phenyl]-4-piperidyl]-2,2-difluoro-acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (105 mg, 102.30 μmol, 9.71% yield) as blue solid. LCMS (ESI+): 920.2 $[M+H]^+$. $^1H$ NMR (400 MHz, DMSO-$d_6$): δ 13.05 (s, 1H), 10.77 (s, 1H), 9.72 (s, 1H), 8.83 (s, 1H), 8.69-8.68 (m, 1H), 8.58 (m, 1H), 8.16-8.14 (m, 1H), 7.61-7.55 (m, 1H), 7.31-7.26 (m, 1H), 6.78 (d, J=8.80 Hz, 2H), 6.61 (d, J=9.20 Hz, 2H), 5.42 (d, J=7.20 Hz, 1H), 4.39-4.18 (m, 1H), 3.90-3.71 (m, 8H), 3.50-3.47 (m, 3H), 3.11 (q, J=7.20 Hz, 2H), 2.73 (s, 3H), 2.67-2.51 (m, 5H), 2.34-2.33 (m, 1H), 1.86-1.83 (m, 3H), 1.59-1.51 (m, 2H), 1.02 (t, J=7.20 Hz, 3H).

Example 61

3-(2,4-dioxohexahydropyrimidin-1-yl)-6-[1-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-3,3-difluoro-4-piperidyl]-1-methyl-indazole

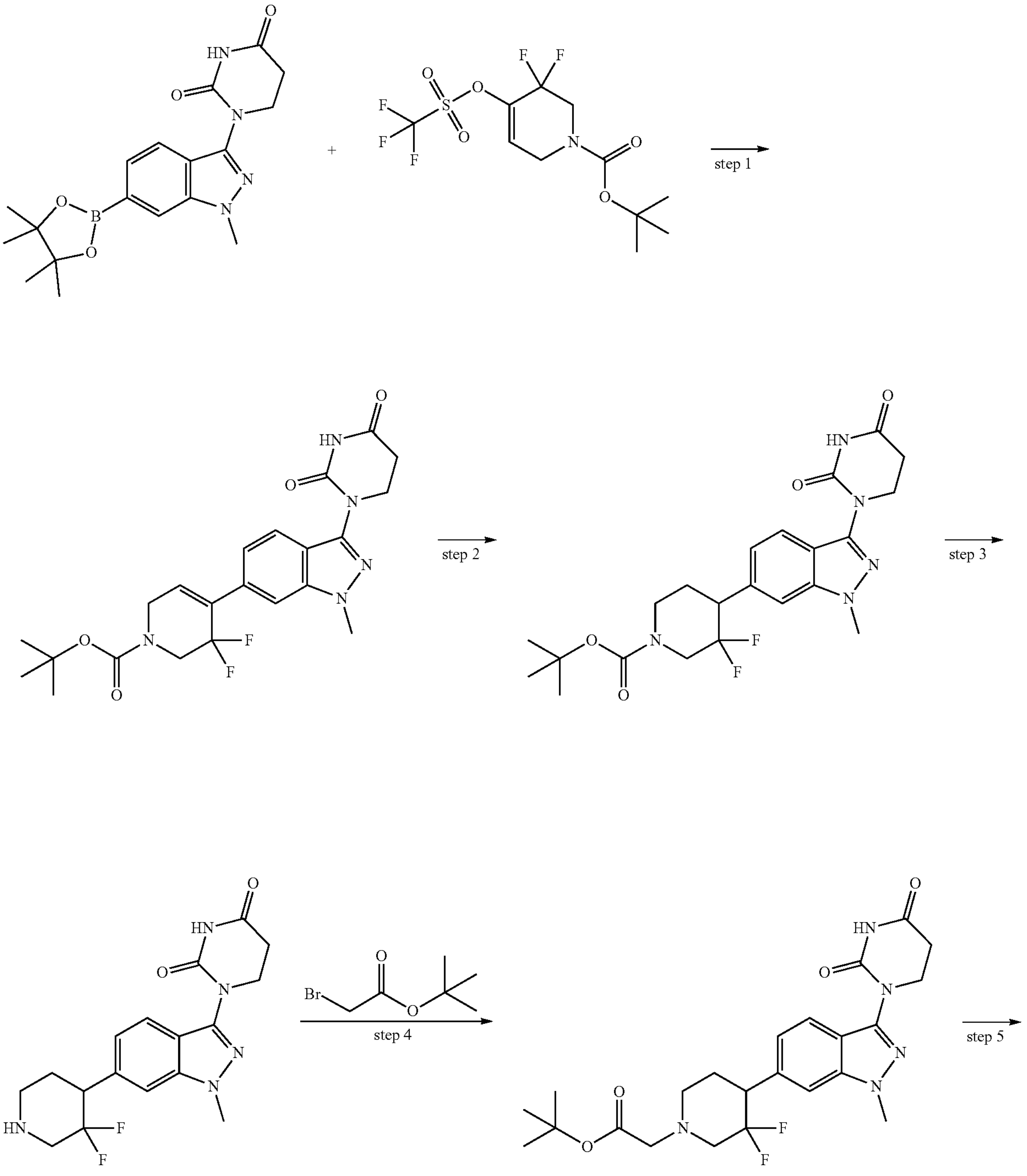

-continued

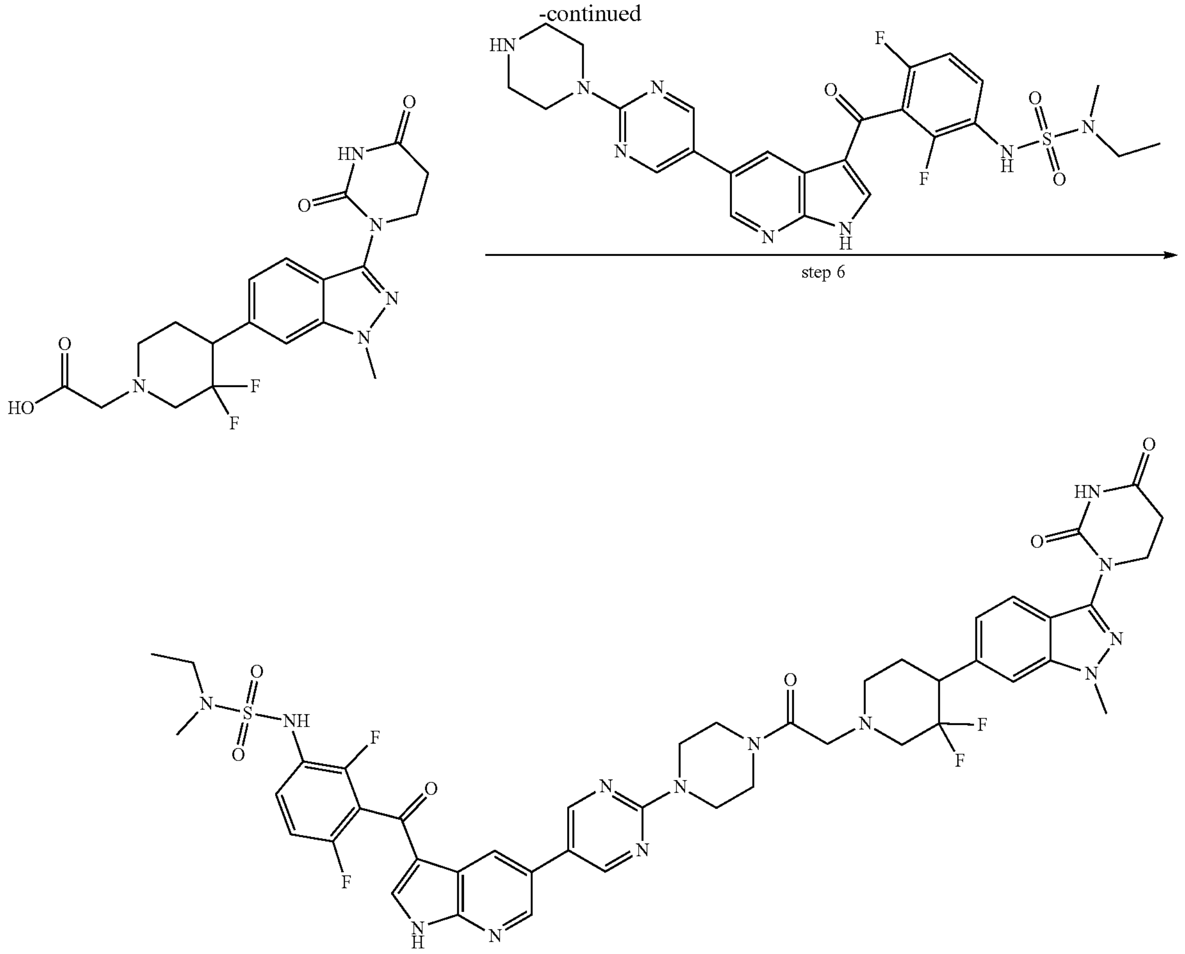

Step 1: To a solution of 1-[1-methyl-6-(4,4,5,5-tetramethyl-1,3,2-dioxaborolan-2-yl)indazol-3-yl]hexahydropyrimidine-2,4-dione (320 mg, 864.37 μmol) and tert-butyl 3,3-difluoro-4-(trifluoromethylsulfonyloxy)-2,6-dihydropyridine-1-carboxylate (264.56 mg, 720.31 μmol) in 1,4-dioxane (3.39 mL) and Water (846.27 uL) was added sodium carbonate (229.04 mg, 2.16 mmol, 90.53 uL) and the solvent was purged with $N_2$ gas for 10 minutes. Then, cyclopentyl (diphenyl)phosphane;dichloropalladium;iron (52.65 mg, 72.03 μmol) was added and stirred at 55° C. for 2 hours. Finally, the reaction mixture was cooled and diluted with water/EA. After extraction, organic layer was washed with brine, dried over sodium sulphate, and concentrated. The crude mixture was purified by ISCO column (100% HEX to 100% EA) to give tert-butyl 4-[3-(2,4-dioxohexahydropyrimidin-1-yl)-1-methyl-indazol-6-yl]-3,3-difluoro-2,6-dihydropyridine-1-carboxylate (242 mg, 498.20 μmol, 69.16% yield) as an off-white solid. LCMS (ES+): 462.9 $[M+H]^+$ Step 2: To a solution of tert-butyl 4-[3-(2,4-dioxohexahydropyrimidin-1-yl)-1-methyl-indazol-6-yl]-3,3-difluoro-2,6-dihydropyridine-1-carboxylate (242 mg, 524.42 μmol) in Ethanol (120 mL) was added Palladium, 10% on carbon, Type 487, dry (167.43 mg, 157.33 μmol, 10% purity) and the mixture was stirred at room temperature with $H_2$ balloon installed. After 24 hours, hydrogen balloon was detached, and the mixture was diluted with DCM (20 mL) and the slurry was stirred for additional 24 hours. Then, the mixture was filtered through a pad of celite, washed using a solution of DCM/MeOH (3:1), and concentrated in vacuo. The crude mixture of tert-butyl 4-[3-(2,4-dioxohexahydropyrimidin-1-yl)-1-methyl-indazol-6-yl]-3,3-difluoro-piperidine-1-carboxylate (230 mg, 446.62 μmol, 85.17% yield) was used for the next step without further purification. LCMS (ES+): 486.4 $[M+Na]^+$ Step 3: Brought tert-butyl 4-[3-(2,4-dioxohexahydropyrimidin-1-yl)-1-methyl-indazol-6-yl]-3,3-difluoro-piperidine-1-carboxylate (230 mg, 496.25 μmol) up in 1,4-dioxane (10 mL) and added Hydrochloric acid in 1,4-dioxane (4 M, 6 ml). The reaction stirred overnight at room temperature before concentrating to a crude solid. LCMS (ES+): 364.1 $[M+H]^+$ Step 4: Brought 1-[6-(3,3-difluoro-4-piperidyl)-1-methyl-indazol-3-yl]hexahydropyrimidine-2,4-dione (198.31 mg, 496 μmol, hydrochloric acid salt) up in NMP (4.44 mL) and added DIPEA (320.52 mg, 2.48 mmol, 431.97 uL) followed by tert-butyl 2-bromoacetate (111.26 mg, 570.40 μmol, 83.65 uL). The reaction mixture was purified by RP isco (0-100% ACN/water w formic acid), and pure fractions were partitioned between EtOAc and saturated bicarbonate solution. The organic layer was dried over sodium sulphate and concentrated to afford tert-butyl 2-[4-[3-(2,4-dioxohexahydropyrimidin-1-yl)-1-methyl-indazol-6-yl]-3,3-difluoro-1-piperidyl]acetate (270 mg, 537.17 μmol, 108.30% yield) as a white solid. LCMS (ES+): 478.5 $[M+H]^+$ Step 5: Brought tert-butyl 2-[4-[3-(2,4-dioxohexahydropyrimidin-1-yl)-1-methyl-indazol-6-yl]-3,3-difluoro-1-piperidyl]acetate (250 mg, 523.56 μmol) up in DCM (1 mL) and added TFA (740.00 mg, 6.49 mmol, 500 uL) before stirring overnight at room temperature. The reaction was concentrated from toluene (3×) to give 2-[4-[3-(2,4-dioxohexahydropyrimidin-1-yl)-1-methyl-indazol-6-yl]-3,3-difluoro-1-piperidyl]acetic acid (275 mg, 487.93 μmol, 93.20% yield, trifluoroacetic acid salt) as a solid. LCMS (ES+): 422.3 $[M+H]^+$ Step 6: Brought 2-[4-[3-(2,4-dioxohexahydropyrimidin-1-yl)-1-methyl-indazol-6-yl]-3,3-difluoro-1-piperidyl]acetic acid (275 mg, 513.62 trifluoroacetic acid salt) up in DMF (2.21 mL) and added DIPEA (265.52 mg, 2.05 mmol, 357.85 uL) after cooling to 0° C. Stirred at reduced temp for 20-30 minutes and then added 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (215.55 mg, 342.41 μmol, hydrochloric acid salt) in one portion. The reaction gradually warmed to room temperature overnight and loaded crude mixture onto RP isco (0-100% ACN/water w formic acid) to give slightly impure product after lyophilization. Neutralized formic acid salt and repurified by normal phase isco (0-20% MeOH/DCM) to give 3-(2,4-dioxohexahydropyrimidin-1-yl)-6-[1-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-3,3-difluoro-4-piperidyl]-1-methyl-indazole (170 mg, 170.01 μmol, 49.65% yield) as a white solid. LCMS (ES+): 481.3 $[M/2+H]^+$, 960.8 $[M+H]^+$. $^1H$ NMR (400 MHz, DMSO-$d_6$): δ 13.00 (s, 1H), 10.55 (s, 1H), 8.82 (s, 2H), 8.69 (d, J=2.2 Hz, 1H), 8.58 (s, 1H), 8.15 (d, J=7.4 Hz, 2H), 7.64-7.52 (m, 3H), 7.34-7.22 (m, 2H), 7.11 (d, J=8.6 Hz, 2H), 6.53 (s, 1H), 4.00 (s, 3H), 3.95-3.78 (m, 4H), 3.76-3.55 (m, 4H), 3.54-3.38 (m, 2H), 3.12 (q, J=7.1 Hz, 2H), 3.05 (d, J=10.8 Hz, 1H), 2.76 (t, J=6.7 Hz, 2H), 2.73 (s, 3H), 2.70 (m, 1H), 2.35-2.21 (m, 2H), 1.88 (d, J=12.8 Hz, 1H), 1.03 (t, J=7.1 Hz, 3H).

Example 63

5-[2-[4-[2-[4-[4-[(2,6-dioxo-3-piperidyl)amino]phenyl]-1-piperidyl]acetyl]-1,4-diazepan-1-yl]pyrimidin-5-yl]-3-[3-[[ethyl(methyl)sulfamoyl]amino]-2,6-difluoro-benzoyl]-1H-pyrrolo[2,3-b]pyridine

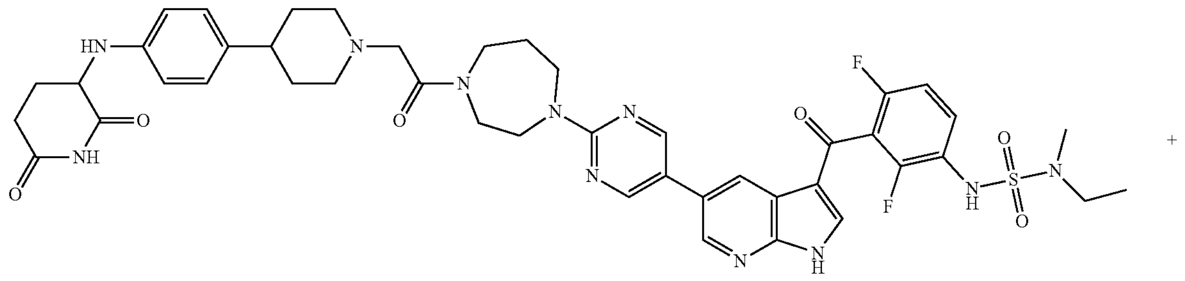

Step 1

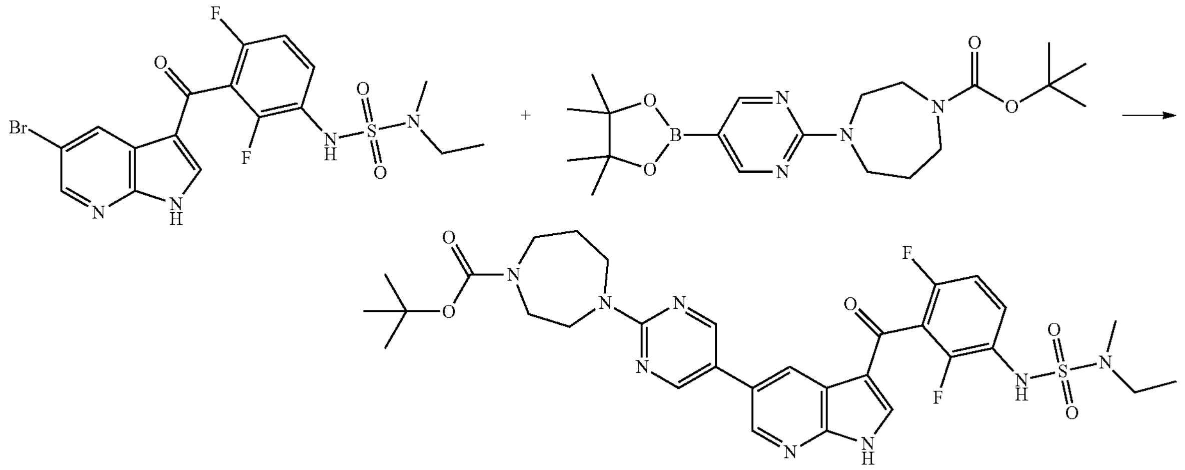

A solution of 5-bromo-3-[3-[[ethyl(methyl)sulfamoyl]amino]-2,6-difluoro-benzoyl]-1H-pyrrolo[2,3-b]pyridine (750 mg, 1.58 mmol) in a mixture of 1,4-Dioxane (8.45 mL) and Water (2.11 mL) was taken up in a microwave vial and added tert-butyl 4-[5-(4,4,5,5-tetramethyl-1,3,2-dioxaborolan-2-yl)pyrimidin-2-yl]-1,4-diazepane-1-carboxylate (832.90 mg, 2.06 mmol), Potassium phosphate tribasic anhydrous (1.05 g, 4.95 mmol) at room temperature under nitrogen. The reaction mixture was degassed with nitrogen for 10 minutes, then added XPhos Pd G2 (63.75 mg, 81.02 μmol) at same temperature. The reaction mixture was heated to 120° C. for 1 hour in microwave. After completion, water was added to the reaction mixture and extracted with ethyl acetate (2×200 mL). The combined organic layers were dried over sodium sulphate, filtered and concentrated under reduced pressure. The crude compound was purified by silica gel column chromatography (0-15% MeOH/DCM) to afford tert-butyl 4-[5-[3-[3-[[ethyl(methyl)sulfamoyl]amino]-2,6-difluoro-benzoyl]-1H-pyrrolo[2,3-b]pyridin-5-yl]pyrimidin-2-yl]-1,4-diazepane-1-carboxylate (550 mg, 779.00 μmol, 49.16% yield) as a yellow solid. LCMS (ES+): 671.7 $[M+H]^+$ Step 2

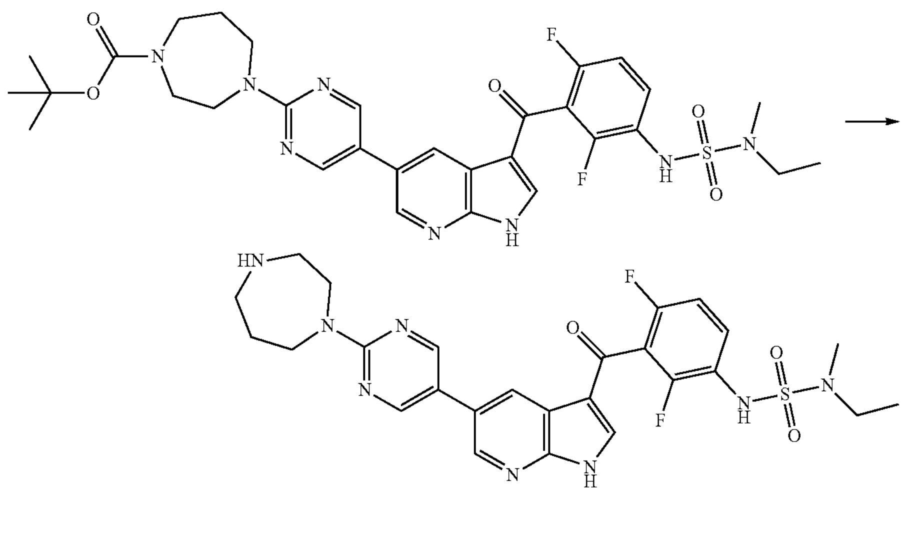

Brought tert-butyl 4-[5-[3-[3-[[ethyl(methyl)sulfamoyl]amino]-2,6-difluoro-benzoyl]-1H-pyrrolo[2,3-b]pyridin-5-yl]pyrimidin-2-yl]-1,4-diazepane-1-carboxylate (550 mg, 820.00 μmol) up in DCM (3 mL)/TFA (1.48 g, 12.98 mmol, 1 mL) and stirred at room temperature for 1 hour. Concentrated from toluene (3×) to dark, amorphous solid 5-[2-(1,4-diazepan-1-yl)pyrimidin-5-yl]-3-[3-[[ethyl(methyl)sulfamoyl]amino]-2,6-difluoro-benzoyl]-1H-pyrrolo[2,3-b]pyridine (95% purity, trifluoroacetic acid salt), which was carried forward without further purification. LCMS (ES+): 571.7 $[M+H]^+$ Step 3

Followed general procedure B. Isolated 5-[2-[4-[2-[4-[4-[(2,6-dioxo-3-piperidyl)amino]phenyl]-1-piperidyl]acetyl]-1,4-diazepan-1-yl]pyrimidin-5-yl]-3-[3-[[ethyl(methyl)sulfamoyl]amino]-2,6-difluoro-benzoyl]-1H-pyrrolo[2,3-b]pyridine (30 mg, 28.46 μmol, 22.92% yield, trifluoroacetic acid salt) as an off white solid after lyophilization. LCMS (ES+): 450.3 $[M/2+H]^+$, 898.9 $[M+H]^+$ $^1$H NMR (400 MHz, DMSO-$d_6$): δ13.06-12.96 (m, 1H), 10.78 (s, 1H), 9.69 (s, 1H), 9.43 (s, 1H), 8.80 (d, J=16.5 Hz, 2H), 8.67 (dd, J=10.0, 2.2 Hz, 1H), 8.60 (d, J=18.4 Hz, 1H), 8.14 (d, J=3.0 Hz, 1H), 7.58 (td, J=9.0, 5.8 Hz, 1H), 7.28 (t, J=8.7 Hz, 1H), 6.90 (dd, J=8.5, 3.8 Hz, 2H), 6.60 (d, J=8.2 Hz, 2H), 4.41-3.75 (m, 7H), 3.72-3.36 (m, 6H), 3.12 (q,

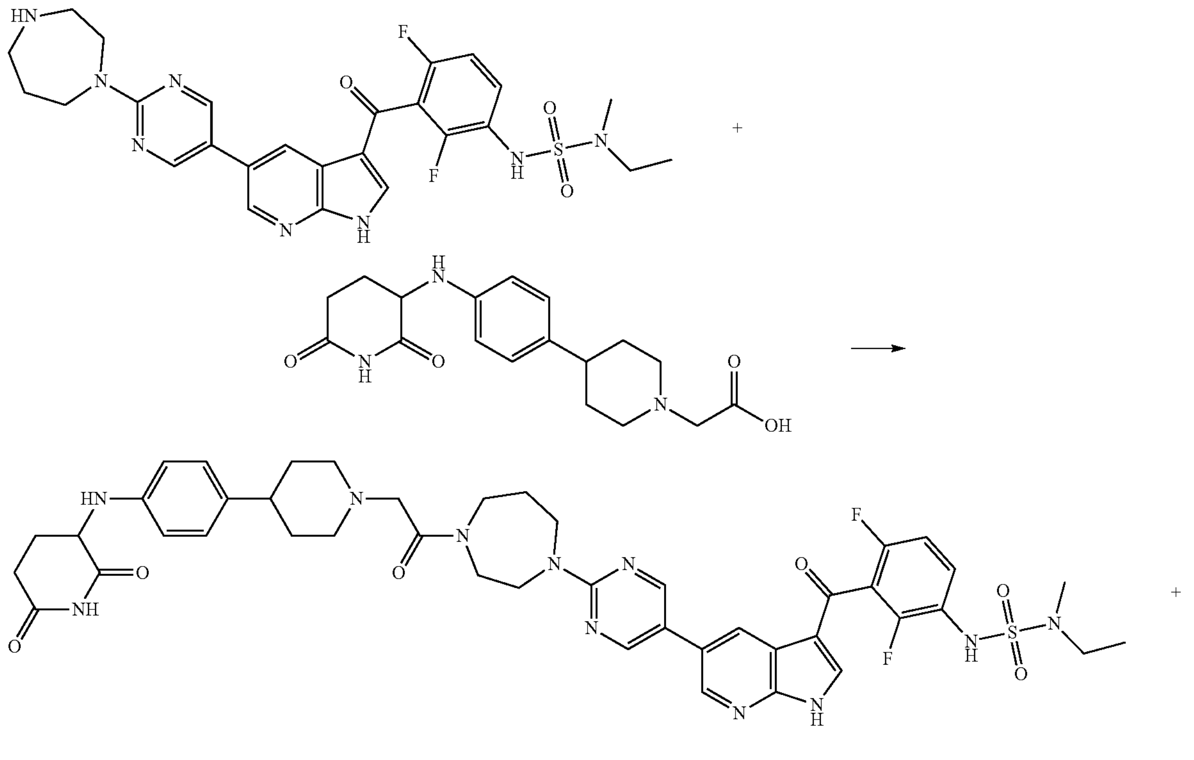

J=7.1 Hz, 2H), 3.06-2.91 (m, 2H), 2.74 (s, 4H), 2.66-2.56 (m, 2H), 2.13-2.02 (m, 1H), 1.99-1.76 (m, 5H), 1.03 (t, J=7.1 Hz, 3H).
Example 64
5-[2-[2-[2-[4-[4-[(2,6-dioxo-3-piperidyl)amino]phenyl]-1-piperidyl]acetyl]-2,6-diazaspiro[3.3]heptan-6-yl]pyrimidin-5-yl]-3-[3-[[ethyl(methyl)sulfamoyl]amino]-2,6-difluoro-benzoyl]-1H-pyrrolo[2,3-b]pyridine
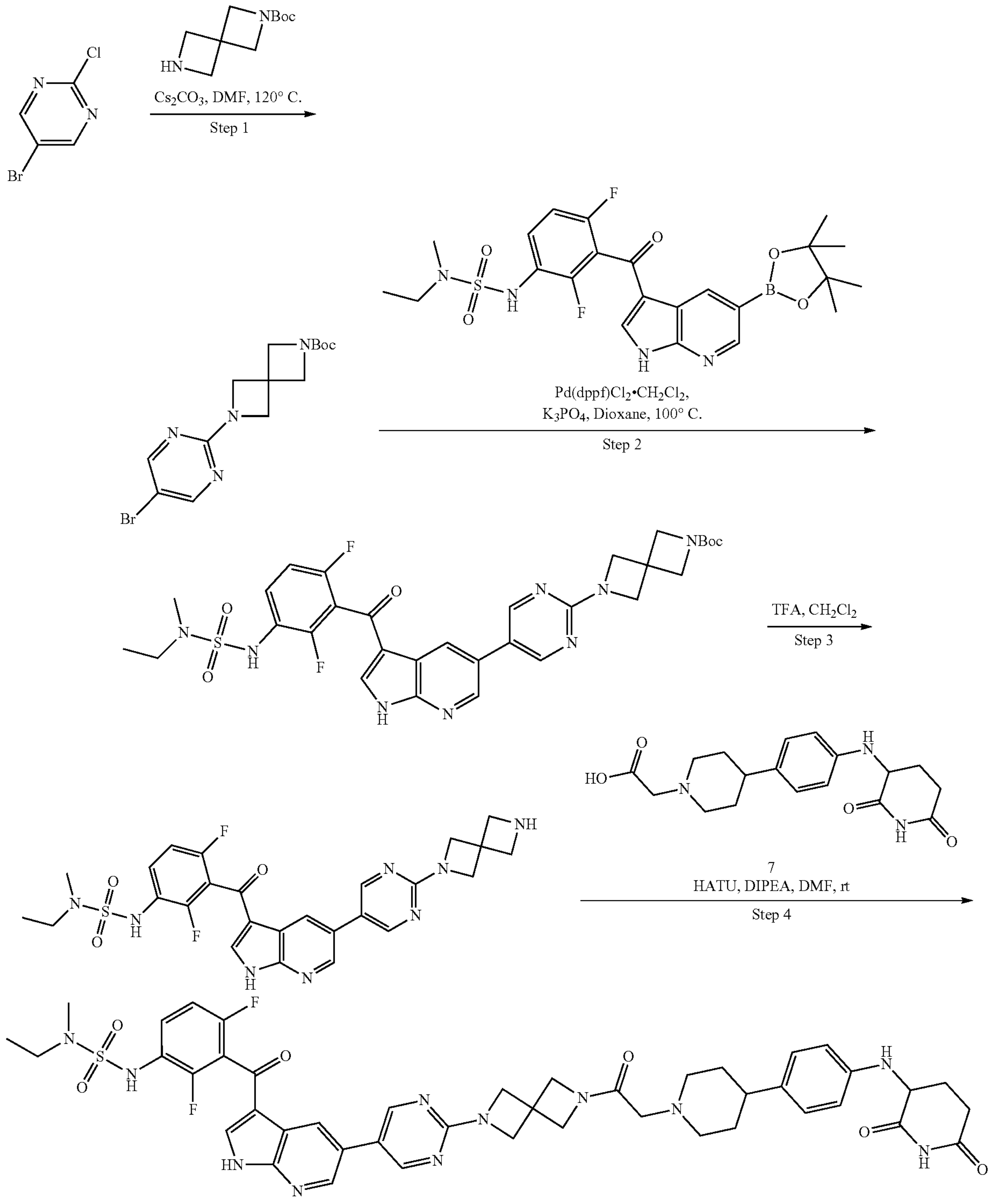

Step 1: To a stirred solution of 5-bromo-2-chloro-pyrimidine (400 mg, 2.07 mmol) in N, N-dimethylformamide (5 mL) were added tert-butyl 2,6-diazaspiro[3.3]heptane-2-carboxylate (409.99 mg, 2.07 mmol) followed by $Cs_2CO_3$ (1.35 g, 4.14 mmol) at room temperature under nitrogen atmosphere. The reaction mixture was heated at 120° C. for 12 hours. Reaction mixture was added to water, resulting solid was filtered and dried to afford tert-butyl 6-(5-bromopyrimidin-2-yl)-2,6-diazaspiro[3.3]heptane-2-carboxylate (580 mg, 1.61 mmol, 77.91% yield) as a pale brown solid. LCMS (ESI+): 355.1 $[M+H]^+$.

Step 2: A mixture of tert-butyl 6-(5-bromopyrimidin-2-yl)-2,6-diazaspiro[3.3]heptane-2-carboxylate (100 mg, 281.51 μmol), 3-[3-[[ethyl(methyl)sulfamoyl]amino]-2,6-difluoro-benzoyl]-5-(4,4,5,5-tetramethyl-1,3,2-dioxaborolan-2-yl)-1H-pyrrolo[2,3-b]pyridine (219.73 mg, 422.26 μmol) and Sodium carbonate (89.51 mg, 844.52 μmol, 35.38 μL) in 1,4-Dioxane (3 mL)/water (0.2 mL) was purged with nitrogen gas for 15 minutes followed by the addition of $Pd(dppf)Cl_2$.Dichloromethane (22.99 mg, 28.15 μmol). The reaction mixture was heated at 100° C. for 12 hours. Reaction mixture was cooled to room temperature and diluted with ethyl acetate (30 mL) and washed with water (2×30 mL). The combined organic layers were washed with brine (30 mL), dried over sodium sulphate, filtered and concentrated under reduced pressure. The crude product was purified by silica gel column chromatography with 5% methanol in dichloromethane as an eluent to afford tert-butyl 6-[5-[3-[3-[[ethyl(methyl)sulfamoyl]amino]-2,6-difluoro-benzoyl]-1H-pyrrolo[2,3-b]pyridin-5-yl]pyrimidin-2-yl]-2,6-diazaspiro[3.3]heptane-2-carboxylate (110 mg, 125.82 μmol, 44.70% yield) as a brown solid. LCMS (ESI+): 669.1 $[M+H]^+$.

Step 3: To a stirred solution of tert-butyl 6-[5-[3-[3-[[ethyl(methyl)sulfamoyl]amino]-2,6-difluoro-benzoyl]-1H-pyrrolo[2,3-b]pyridin-5-yl]pyrimidin-2-yl]-2,6-diazaspiro[3.3]heptane-2-carboxylate (200 mg, 299.08 μmol) in dichloromethane (5 mL) was added TFA (1.41 g, 12.33 mmol, 949.70 μL) at 0° C. The reaction mixture was warmed to room temperature and stirred for 2 hours. Reaction mixture was concentrated under reduced pressure, the resulting crude product was triturated with diethyl ether (20 mL) and dried to afford 5-[2-(2,6-diazaspiro[3.3]heptan-2-yl)pyrimidin-5-yl]-3-[3-[[ethyl(methyl)sulfamoyl]amino]-2,6-difluoro-benzoyl]-1H-pyrrolo[2,3-b]pyridine (200 mg, 222.38 μmol, 74.35% yield) as a yellow solid. LCMS (ESI+): 569.1 $[M+H]^+$.

Step 4: Target compound was prepared via HATU mediated acid-amine coupling reaction (procedure A). Amide coupling was carried out using 5-[2-(2,6-diazaspiro[3.3]heptan-2-yl)pyrimidin-5-yl]-3-[3-[[ethyl(methyl)sulfamoyl]amino]-2,6-difluoro-benzoyl]-1H-pyrrolo[2,3-b]pyridine (100 mg, 175.87 μmol), 2-[4-[4-[(2,6-dioxo-3-piperidyl)amino]phenyl]-1-piperidyl]acetic acid (60.74 mg, 175.87 μmol), HATU (80.25 mg, 211.05 μmol) followed by) and N,N-Diisopropylethylamine (113.65 mg, 879.36 μmol, 153.17 μL) to afford 5-[2-[2-[2-[4-[4-[(2,6-dioxo-3-piperidyl)amino]phenyl]-1-piperidyl]acetyl]-2,6-diazaspiro[3.3]heptan-6-yl]pyrimidin-5-yl]-3-[3-[[ethyl(methyl)sulfamoyl]amino]-2,6-difluoro-benzoyl]-1H-pyrrolo[2,3-b]pyridine (27.67 mg, 28.48 μmol, 16.20% yield) as an off-white solid. LCMS (ESI+): 897.0 $[M+H]^+$. $^1H$ NMR (400 MHz, DMSO-$d_6$): δ 13.01 (s, 1H), 10.78 (s, 1H), 9.72 (s, 1H), 8.77 (d, J=6.80 Hz, 2H), 8.66 (d, J=2.40 Hz, 1H), 8.55 (s, 1H), 8.15 (s, 1H), 7.61-7.55 (m, 1H), 7.28 (t, J=7.60 Hz, 1H), 6.97 (d, J=8.40 Hz, 2H), 6.62 (d, J=8.40 Hz, 2H), 5.66 (d, J=7.60 Hz, 1H), 4.46 (s, 2H), 4.25 (m, 5H), 4.12 (m, 2H), 3.11 (q, J=7.20 Hz, 2H), 3.02 (m, 2H), 2.74 (m, 3H), 2.73 (s, 3H), 2.70 (m, 2H), 2.10 (m, 2H), 0.92 (m, 2H), 1.67 (m, 4H), 1.02 (t, J=7.20 Hz, 3H).

Example 65

5-[2-[4-[2-[4-[4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-4-methyl-1H-pyrrolo[2,3-b]pyridine

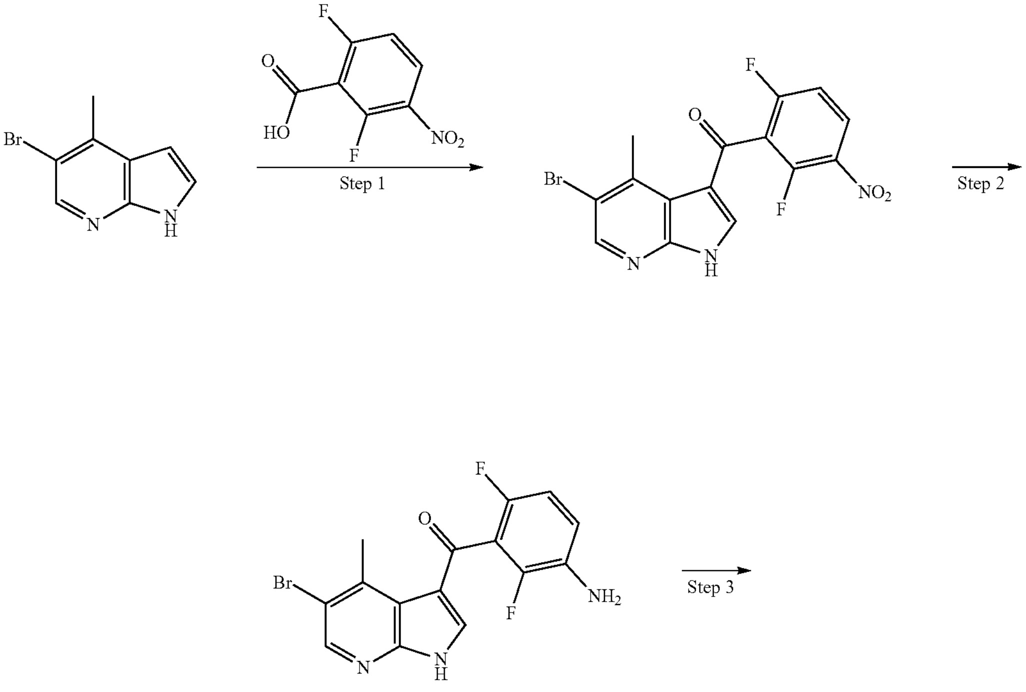

-continued
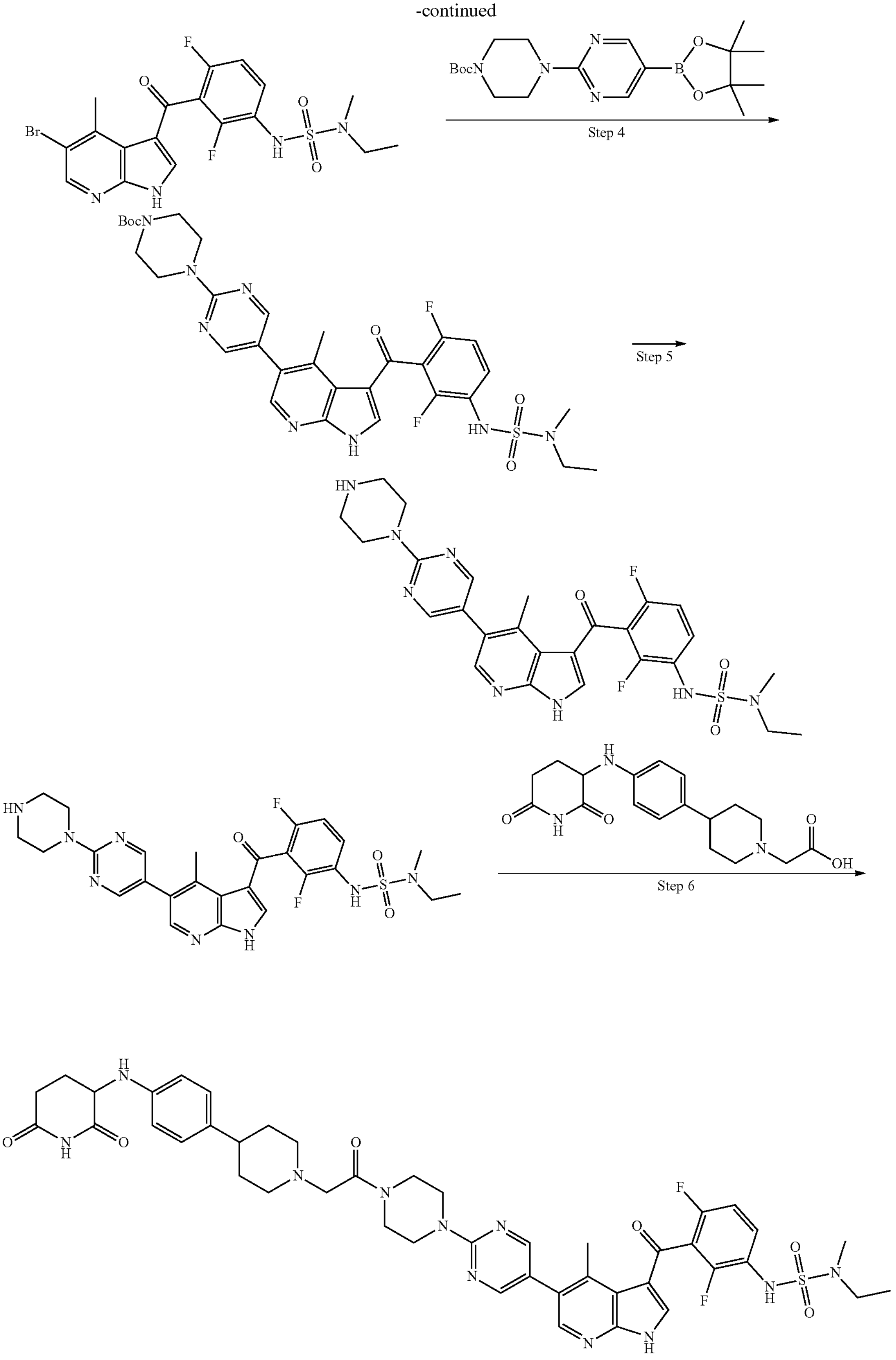

Step 1: To a stirred solution of 5-bromo-4-methyl-1H-pyrrolo[2,3-b]pyridine (700 mg, 3.32 mmol) in DCE (16.22 mL) was added Aluminum chloride, anhydrous (1.77 g, 13.27 mmol, 725.07 uL) at 0-5° C. under nitrogen, followed by the addition of above acid chloride in DCE (16.22 mL) at same temperature. The reaction mixture was stirred at room temperature for 30 minutes and then heated 50° C. for 12 hours. After completion, the reaction mixture was cooled to 0-5° C. and added cold water (500 mL). The reaction mixture was extracted with ethyl acetate (3×300 mL). The combined organic layers were dried over sodium sulphate, filtered and concentrated under reduced pressure. The crude compound was purified by silica gel column chromatography with 80% ethyl acetate in petroleum ether as a eluent to afford (5-bromo-4-methyl-1H-pyrrolo[2,3-b]pyridin-3-yl)-(2,6-difluoro-3-nitro-phenyl)methanone (1 g, 2.40 mmol, 72.30% yield) as a brown solid. LCMS (ESI+): 398.1 $[M+H]^+$ Step 2: Brought (5-bromo-4-methyl-1H-pyrrolo[2,3-b]pyridin-3-yl)-(2,6-difluoro-3-nitro-phenyl)methanone (1.3 g, 3.28 mmol) up in Ethanol (25.88 mL)/Water (6.47 mL) and added Iron powder (916.32 mg, 16.41 mmol, 116.58 uL) followed by Ammonium Chloride (526.62 mg, 9.84 mmol, 344.20 uL). The reaction was heated to 80° C. for 12 hours before cooling and filtering over celite, rinsing with EtOH, followed by ACN and DCM. The filtrate was concentrated and partitioned between EtOAc and ammonium chloride solution. The organic layer was washed with brine and concentrated to an orange solid, (3-amino-2,6-difluoro-phenyl)-(5-bromo-4-methyl-1H-pyrrolo[2,3-b]pyridin-3-yl) methanone (1.0 g, 2.59 mmol, 79.06% yield), which was used without further purification. LCMS (ESI+): 367.4 $[M+H]^+$ Step 3: Brought (3-amino-2,6-difluoro-phenyl)-(5-bromo-4-methyl-1H-pyrrolo[2,3-b]pyridin-3-yl)methanone (450 mg, 1.23 mmol) up in Pyridine (2.92 g, 36.87 mmol, 2.98 mL) at 0° C. and added N-ethyl-N-methyl-sulfamoyl chloride (387.42 mg, 2.46 mmol, 302.67 uL) followed by DMAP (30.03 mg, 245.79 μmol). The reaction warmed to room temperature and stirred for 1 night. Added N-ethyl-N-methyl-sulfamoyl chloride (387.42 mg, 2.46 mmol, 302.67 uL) and continued stirring for 3 nights. The reaction was concentrated and the crude residue was purified by isco 10-100% EtOAc/Hex to give 5-bromo-3-[3-[[ethyl(methyl)sulfamoyl]amino]-2,6-difluoro-benzoyl]-4-methyl-1H-pyrrolo[2,3-b]pyridine (75 mg, 146.21 μmol, 11.90% yield) as a beige solid. LCMS (ESI+): 489.3 $[M+H]^+$ Step 4: A solution of 5-bromo-3-[3-[[ethyl(methyl)sulfamoyl]amino]-2,6-difluoro-benzoyl]-4-methyl-1H-pyrrolo[2,3-b]pyridine (52 mg, 106.71 μmol) in a mixture of 1,4-Dioxane (623.82 uL) and Water (155.96 uL) was taken up in a microwave vial and added tert-butyl 4-[5-(4,4,5,5-tetramethyl-1,3,2-dioxaborolan-2-yl)pyrimidin-2-yl]piperazine-1-carboxylate (54.14 mg, 138.72 μmol), Potassium phosphate tribasic anhydrous (70.71 mg, 333.09 μmol) at room temperature under nitrogen. The reaction mixture was degassed with nitrogen for 10 minutes, then added XPhos Pd G2 (4.29 mg, 5.46 μmol) at same temperature. The reaction mixture was heated to 120° C. for 1 hour in a microwave. After completion, water was added to the reaction mixture and extracted with ethyl acetate (2×200 mL). The combined organic layers were dried over sodium sulphate, filtered and concentrated under reduced pressure. The crude compound was purified by silica gel column chromatography with 80% ethyl acetate in petroleum ether as a eluent to afford tert-butyl 4-[5-[3-[3-[[ethyl(methyl)sulfamoyl]amino]-2,6-difluoro-benzoyl]-4-methyl-1H-pyrrolo[2,3-b]pyridin-5-yl]pyrimidin-2-yl]piperazine-1-carboxylate (55 mg, 77.90 μmol, 73.00% yield) as a yellow solid. LCMS (ESI+): 671.7 $[M+H]^+$ Step 5: Brought tert-butyl 4-[5-[3-[3-[[ethyl(methyl)sulfamoyl]amino]-2,6-difluoro-benzoyl]-4-methyl-1H-pyrrolo[2,3-b]pyridin-5-yl]pyrimidin-2-yl]piperazine-1-carboxylate (55 mg, 82.00 μmol) up in 1,4-Dioxane (3 mL) and added Hydrogen chloride solution 4.0M in 1,4-dioxane (2.40 g, 65.82 mmol, 3 mL). The reaction stirred at room temperature for 6 hours before being concentrated to afford 3-[3-[[ethyl(methyl)sulfamoyl]amino]-2,6-difluoro-benzoyl]-4-methyl-5-(2-piperazin-1-ylpyrimidin-5-yl)-1H-pyrrolo[2,3-b]pyridine (48 mg, 75.11 μmol, 91.60% yield, hydrochloric acid salt) as an off-white solid. LCMS (ESI+): 571.5 $[M+H]^+$ Step 6: Brought 2-[4-[4-[(2,6-dioxo-3-piperidyl)amino]phenyl]-1-piperidyl]acetic acid (39.96 mg, 86.97 μmol, trifluoroacetic acid salt) up in DMF (1 mL) and added DIPEA (40.87 mg, 316.27 μmol, 55.09 uL) followed by HATU (60.13 mg, 158.14 μmol). After 5 minutes added a solution of DIPEA (40.87 mg, 316.27 μmol, 55.09 uL) and 3-[3-[[ethyl(methyl)sulfamoyl]amino]-2,6-difluoro-benzoyl]-4-methyl-5-(2-piperazin-1-ylpyrimidin-5-yl)-1H-pyrrolo[2,3-b]pyridine (48 mg, 79.07 μmol, hydrochloric acid salt) in DMF (1 mL). After stirring one night added 5 drops of sat bicarb solution and 5 drops of water to break up uronium adducts. Purified by RP isco 0-75% ACN/water w TFA to give the TFA salt of 5-[2-[4-[2-[4-[4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-4-methyl-1H-pyrrolo[2,3-b]pyridine (50 mg, 46.94 μmol, 59.36% yield, trifluoroacetic acid salt) as a solid after lyophilization. LCMS (ESI+): 450.2 $[M/2+H]^+$/898.8 $[M+H]^+$. $^1$H NMR (400 MHz, DMSO-d6): δ 12.86 (d, J=3.4 Hz, 1H), 10.70 (d, J=2.2 Hz, 1H), 9.60 (s, 1H), 9.44 (s, 1H), 8.46 (s, 2H), 8.16 (s, 1H), 7.93 (d, J=3.3 Hz, 1H), 7.49 (td, J=9.0, 5.9 Hz, 1H), 7.18 (td, J=8.8, 1.5 Hz, 1H), 6.91 (d, J=8.3 Hz, 2H), 6.59 (dd, J=8.4, 5.7 Hz, 2H), 4.46-3.41 (m, 16H), 3.05 (q, J=7.1 Hz, 3H), 2.76 (s, 3H), 2.68-2.51 (m, 3H), 2.67 (s, 3H), 2.11-1.72 (m, 6H), 0.96 (t, J=7.1 Hz, 3H).

Example 66
5-[2-[4-[2-[4-[4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-4-fluoro-1H-pyrrolo[2,3-b]pyridine
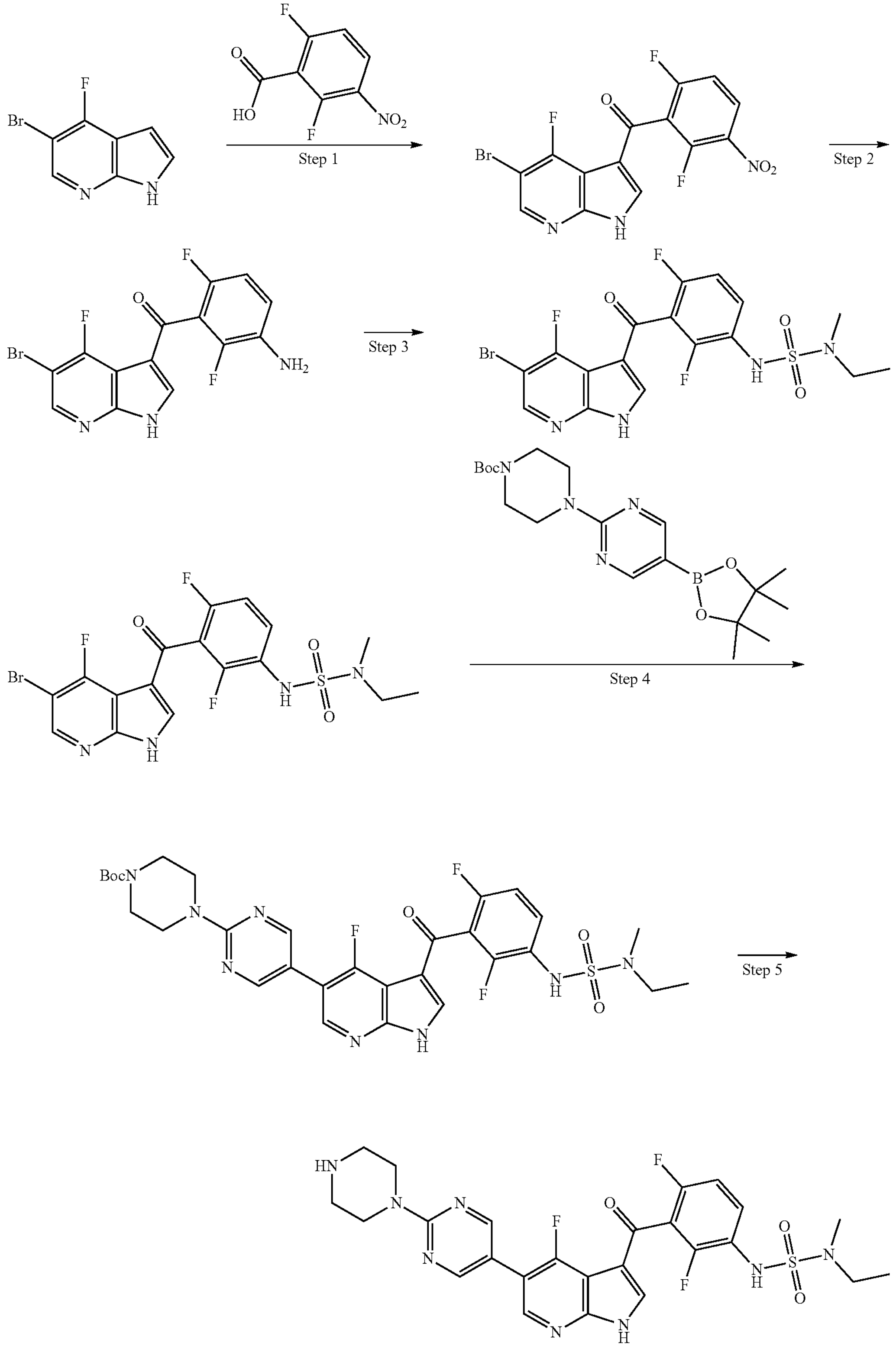

-continued

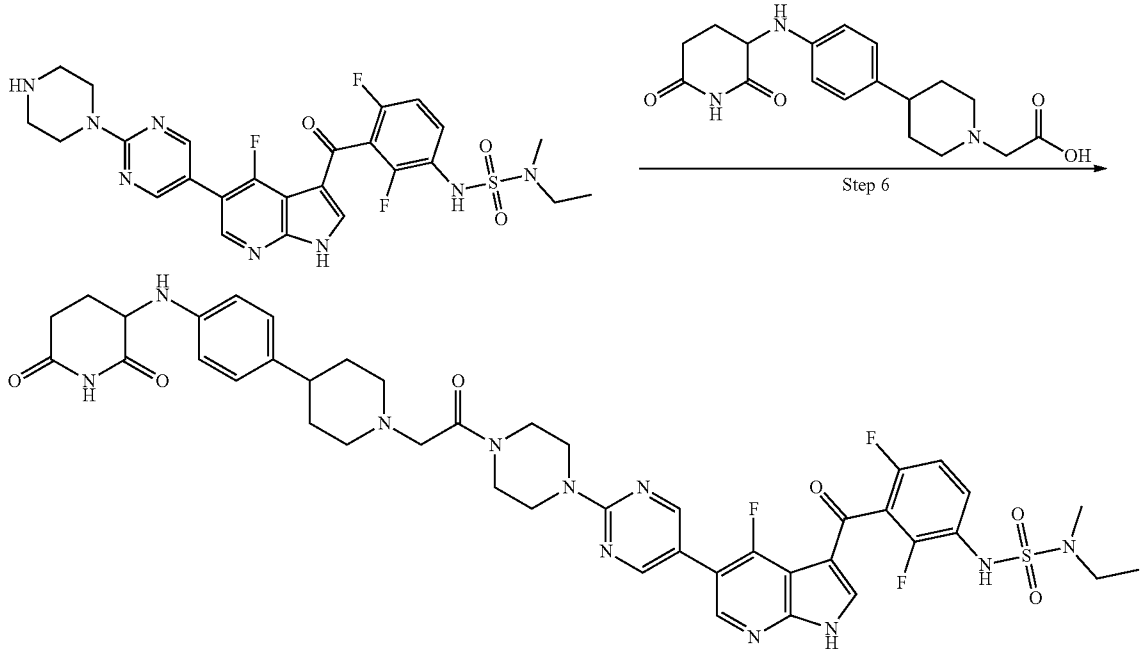

Step 1: To a stirred solution of 5-bromo-4-fluoro-1H-pyrrolo[2,3-b]pyridine (1 g, 4.65 mmol) in DCE (17.06 mL) was added Aluminum chloride, Anhydrous (2.48 g, 18.61 mmol, 1.02 mL) 0-5° C. under nitrogen, followed by the addition of above acid chloride in DCE (17.06 mL) at same temperature. The reaction mixture was stirred at room temperature for 30 minutes and then heated 50° C. for 12 hours. After completion, the reaction mixture was cooled to 0-5° C. and added cold water (500 mL). Some solid precipitated and was found to be product (683 mg). The remaining reaction mixture was extracted with ethyl acetate (3×300 mL). The combined organic layers were dried over sodium sulphate, filtered and concentrated under reduced pressure. The crude compound was purified by silica gel column chromatography with 80% ethyl acetate in petroleum ether as a eluent to afford (5-bromo-4-fluoro-1H-pyrrolo[2,3-b]pyridin-3-yl)-(2,6-difluoro-3-nitro-phenyl) methanone (1.05 g, 2.49 mmol, 53.60% yield) as a brown solid. LCMS (ESI+): 402.0 [M+H]$^+$ Step 2: Brought (5-bromo-4-fluoro-1H-pyrrolo[2,3-b] pyridin-3-yl)-(2,6-difluoro-3-nitro-phenyl)methanone (683 mg, 1.71 mmol) up in Ethanol (16.88 mL)/Water (4.22 mL) and added Iron powder (476.65 mg, 8.54 mmol, 60.64 uL) followed by Ammonium Chloride (273.94 mg, 5.12 mmol, 179.04 uL) before heating to 80° C. for 6 hours. The reaction was cooled and filtered over celite, rinsing with EtOH, ACN and DCM. The filtrate was concentrated before partitioning between EtOAc and sat bicarb solution. The organic layer was washed with brine before drying over sodium sulphate and concentrating to afford (3-amino-2,6-difluoro-phenyl)-(5-bromo-4-fluoro-1H-pyrrolo[2,3-b]pyridin-3-yl)methanone (630 mg, 1.62 mmol, 94.73% yield), as a dark orange/brown solid which was used without further purification. LCMS (ESI+): 372.2 [M+H]$^+$ Step 3: Brought (3-amino-2,6-difluoro-phenyl)-(5-bromo-4-fluoro-1H-pyrrolo[2,3-b]pyridin-3-yl)methanone (630 mg, 1.70 mmol) up in DCM (13.01 mL) and added pyridine (2.69 g, 34.04 mmol, 2.75 mL) followed by N-ethyl-N-methyl-sulfamoyl chloride (1.61 g, 10.21 mmol, 1.26 mL) before heating to 60° C. in a sealed vial for 3 days. Cooled reaction and purified by isco 15-100% EA/hex to give 5-bromo-3-[3-[[ethyl(methyl)sulfamoyl]amino]-2,6-difluoro-benzoyl]-4-fluoro-1H-pyrrolo[2,3-b]pyridine (100 mg, 193.37 μmol, 11.36% yield) as a dark solid. LCMS (ESI+): 493.2 [M+H]$^+$ Step 4: A solution of 5-bromo-3-[3-[[ethyl(methyl)sulfamoyl]amino]-2,6-difluoro-benzoyl]-4-fluoro-1H-pyrrolo[2,3-b]pyridine (70 mg, 142.48 μmol) in a mixture of 1,4-Dioxane (1.14 mL) and Water (284.97 uL) was taken up in a microwave vial and added tert-butyl 4-[5-(4,4,5,5-tetramethyl-1,3,2-dioxaborolan-2-yl)pyrimidin-2-yl]piperazine-1-carboxylate (66.73 mg, 170.98 μmol), Potassium phosphate tribasic anhydrous (94.41 mg, 444.78 μmol) at room temperature under nitrogen. The reaction mixture was degassed with nitrogen for 10 minutes, then added XPhos Pd G2 (5.73 mg, 7.29 μmol) at same temperature. The reaction mixture was heated to 120° C. for 1 hour in microwave. After completion, water was added to the reaction mixture and extracted with ethyl acetate (2×200 mL). The combined organic layers were dried over sodium sulphate, filtered and concentrated under reduced pressure. The crude compound was purified by silica gel column chromatography with 80% ethyl acetate in petroleum ether as a eluent to afford tert-butyl 4-[5-[3-[3-[[ethyl(methyl)sulfamoyl]amino]-2,6-difluoro-benzoyl]-4-fluoro-1H-pyrrolo[2,3-b]pyridin-5-yl]pyrimidin-2-yl]piperazine-1-carboxylate (35 mg, 49.28 μmol, 34.59% yield) as a yellow solid. LCMS (ESI+): 675.3 [M+H]$^+$ Step 5: Brought tert-butyl 4-[5-[3-[3-[[ethyl(methyl)sulfamoyl]amino]-2,6-difluoro-benzoyl]-4-fluoro-1H-pyrrolo [2,3-b]pyridin-5-yl]pyrimidin-2-yl]piperazine-1-carboxylate (35 mg, 51.88 μmol) up in DCM (2 mL) and added TFA (740.00 mg, 6.49 mmol, 500 uL). Stirred overnight before concentrating from toluene (2×) to give crude 3-[3-[[ethyl (methyl)sulfamoyl]amino]-2,6-difluoro-benzoyl]-4-fluoro-5-(2-piperazin-1-ylpyrimidin-5-yl)-1H-pyrrolo[2,3-b]pyridine (30 mg, 43.57 μmol, 83.98% yield, trifluoroacetic acid salt) as an oil. LCMS (ESI+): 575.8 [M+H]$^+$ Step 6: Brought 2-[4-[4-[(2,6-dioxo-3-piperidyl)amino]phenyl]-1-piperidyl]acetic acid (25.02 mg, 54.46 μmol, trifluoroacetic acid salt) up in DMF (1 mL) and added DIPEA (22.52 mg, 174.27 μmol, 30.35 uL) followed by HATU (24.85 mg, 65.35 μmol) at 0° C. The reaction stirred for 5-10 minutes and added a solution of 3-[3-[[ethyl(methyl)sulfamoyl]amino]-2,6-difluoro-benzoyl]-4-fluoro-5-(2-piperazin-1-ylpyrimidin-5-yl)-1H-pyrrolo[2,3-b]pyridine (30 mg, 43.57 μmol, trifluoroacetic acid salt) and DIPEA (22.52 mg, 174.27 μmol, 30.35 uL) in DMF (1 mL) dropwise. The reaction warm to room temperature gradually and continued stirring overnight. Loaded crude reaction directly onto RP isco 0-70% ACN/water w TFA to give 5-[2-[4-[2-[4-[4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2,6-difluoro-benzoyl]-4-fluoro-1H-pyrrolo[2,3-b]pyridine (25 mg, 23.38 μmol, 53.66% yield, trifluoroacetic acid salt) as an off-white solid after lyophilization. LCMS (ESI+): 452.1 $[M/2+H]^+$/902.9 $[M+H]^+$, $^1H$ NMR (400 MHz, DMSO-d6): δ 13.21 (d, J=2.7 Hz, 1H), 10.71 (s, 1H), 9.60 (s, 1H), 9.43 (br 1H), 8.62 (d, J=1.2 Hz, 2H), 8.46 (d, J=9.3 Hz, 1H), 8.13 (d, J=3.2 Hz, 1H), 7.50 (td, J=9.0, 5.9 Hz, 2H), 7.18 (td, J=8.8, 1.6 Hz, 2H), 6.91 (d, J=8.3 Hz, 2H), 6.59 (dd, J=8.4, 5.9 Hz, 2H), 4.32 (d, J=4.8 Hz, 2H), 4.22 (dd, J=11.3, 5.0 Hz, 1H), 3.84 (ddd, J=22.5, 6.8, 3.7 Hz, 3H), 3.62 (t, J=5.2 Hz, 1H), 3.56-3.41 (m, 3H), 3.26 (s, 1H), 3.03 (q, J=7.1 Hz, 3H), 2.75-2.54 (m, 2H), 2.67 (s, 3H), 2.11-1.69 (m, 7H), 0.95 (t, J=7.1 Hz, 3H).

Examples 73-80

Synthesis of Intermediate 3-[3-[[ethyl(methyl)sulfamoyl]amino]-2,6-difluoro-benzoyl]-5-(6-piperazin-1-yl-3-pyridyl)-1H-pyrrolo[2,3-b]pyridine

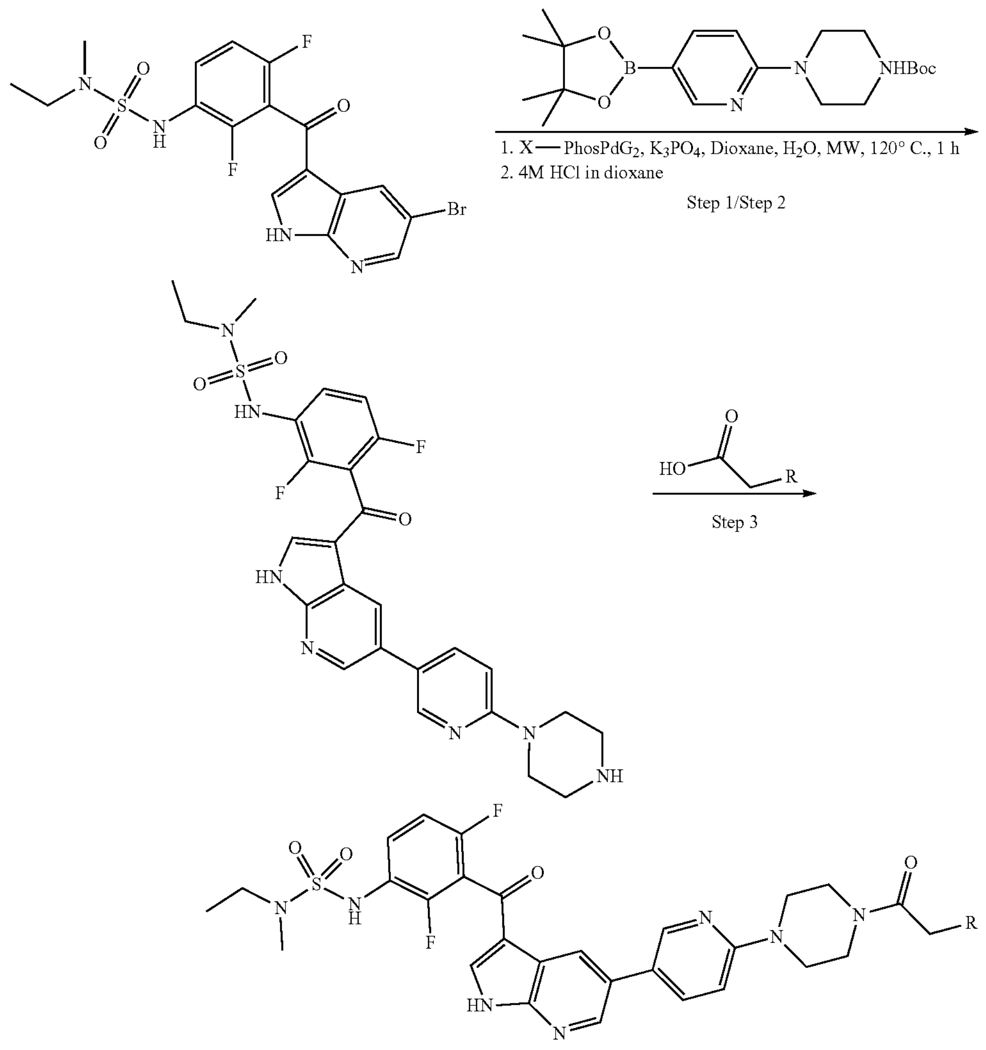

Step 1: A solution of 5-bromo-3-[3-[[ethyl(methyl)sulfamoyl]amino]-2,6-difluoro-benzoyl]-1H-pyrrolo[2,3-b]pyridine (1.0 g, 2.11 mmol) in a mixture of 1,4-Dioxane (8.0 mL) and Water (2.0 mL) was taken up in a microwave vial and added tert-butyl 4-[5-(4,4,5,5-tetramethyl-1,3,2-dioxaborolan-2-yl)-2-pyridyl]piperazine-1-carboxylate (905 mg, 2.32 mmol), Potassium phosphate (1.4 g, 6.60 mmol) at room temperature under nitrogen. The reaction mixture was degassed with nitrogen for 10 minutes, then added XPhos Pd G2 (85 mg, 108.03 μmol) at same temperature. The reaction mixture was irradiated under microwave at 120° C. for 1 hours. After completion, water was added to the reaction mixture and extracted with ethyl acetate (2×200 mL). The combined organic layers were dried over sodium sulphate, filtered and concentrated under reduced pressure. The crude compound was purified by silica gel column chromatography with 70% ethyl acetate in petroleum ether as a eluent to afford tert-butyl 4-[5-[3-[3-[[ethyl(methyl)sulfamoyl]amino]-2,6-difluoro-benzoyl]-1H-pyrrolo[2,3-b]pyridin-5-yl]-2-pyridyl]piperazine-1-carboxylate (1.1 g, 1.51 mmol, 71.70% yield) as a yellow solid. LCMS (ESI+): 656.4 $[M+H]^+$.

Step 2: To a stirred solution of tert-butyl 4-[5-[3-[3-[[ethyl(methyl)sulfamoyl]amino]-2,6-difluoro-benzoyl]-1H-pyrrolo[2,3-b]pyridin-5-yl]-2-pyridyl]piperazine-1-carboxylate (1.1 g, 1.68 mmol) in 1,4-Dioxane (3.0 mL) was added Hydrogen chloride solution (4M in 1,4-dioxane, 15.36 mmol, 0.70 mL) at 0-5° C. under nitrogen. The reaction mixture was stirred at room temperature for 5 hours. After completion, the reaction mixture was concentrated under reduced pressure to afford 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (980 mg, 1.40 mmol, 83.58% yield) as a yellow solid. LCMS (ESI+): 556.4 $[M+H]^+$.

Example 73

5-[6-[4-[2-[4-[4-[[(3S)-2,6-dioxo-3-piperidyl]oxy]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine

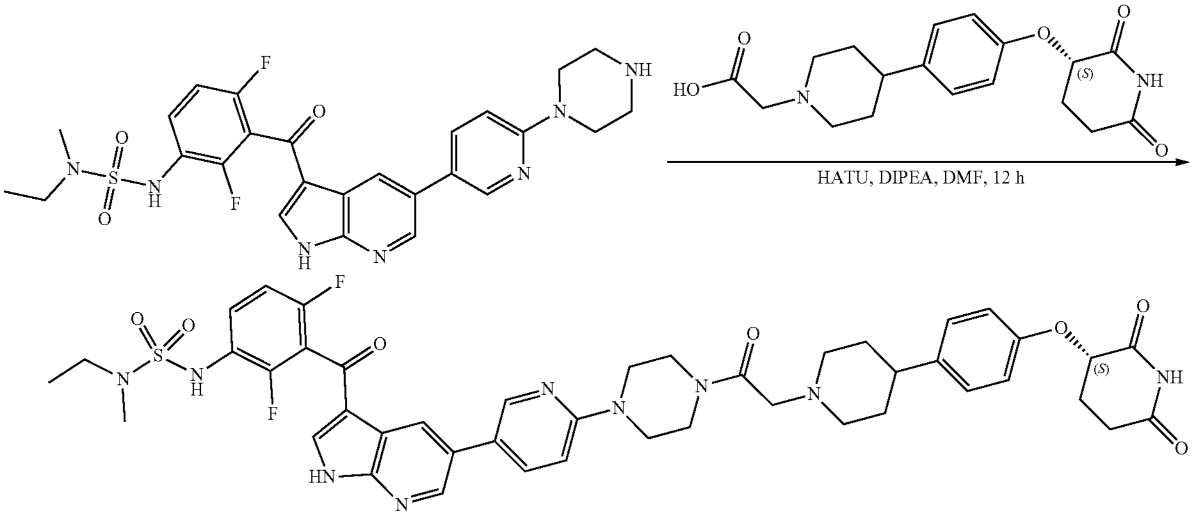

To a stirred solution of 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (25 mg, 45.00 μmol) in DMF (0.5 mL) was added 2-[4-[4-[[(3 S)-2,6-dioxo-3-piperidyl]oxy]phenyl]-1-piperidyl]acetic acid (15.59 mg, 45.00 μmol) and DIPEA (29.08 mg, 224.98 μmol, 39.19 μL) at room temperature under nitrogen, followed by the addition of HATU (20.53 mg, 54.00 μmol) at same temperature. The reaction mixture was stirred at room temperature for 16 hours. After completion, the reaction mixture was diluted with water (1.0 mL), extracted with ethyl acetate (3×1.5 mL). The combined organics were removed under Genevac at 50° C. (1 bar pressure) for 3 hours. The obtained crude product was purified by mass-directed preparative HPLC [Mobile-phase A: 10 mM ammonium acetate in $H_2O$, Mobile-phase B: ACN, Wave length: 215 nm, Column: Sunfire C18 OBD (19 mm×100 mm; 5 micron)] to afford 5-[6-[4-[2-[4-[4-[[(3 S)-2,6-dioxo-3-piperidyl]oxy]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine (2.86 mg, 3.05 μmol, 6.78% yield) as off-white solid. LCMS (ESI+): 884.4 $[M+H]^+$. $^1H$ NMR (400 MHz, DMSO-$d_6$): δ 12.97 (s, 1H), 10.92 (s, 1H), 9.75 (bs, 1H), 8.68 (s, 1H), 8.67-8.52 (m, 2H), 8.13 (s, 1H), 8.03-7.95 (m, 1H), 7.58-7.57 (m, 1H), 7.29-7.26 (m, 1H), 7.16 (d, J=8.40 Hz, 2H), 7.04 (d, J=8.40 Hz, 1H), 6.94 (d, J=8.40 Hz, 2H), 5.19-5.12 (m, 1H), 3.80-3.55 (m, 9H), 3.15-3.05 (m, 3H), 2.95-2.85 (m, 2H), 2.72 (s, 3H), 2.70-2.60 (m, 2H), 2.60-2.50 (m, 2H), 2.25-2.05 (m, 4H), 1.95-1.65 (m, 3H), 1.10 (t, J=7.20 Hz, 3H).

Example 74

5-[6-[4-[2-[4-[4-[[(3R)-2,6-dioxo-3-piperidyl]oxy] phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine

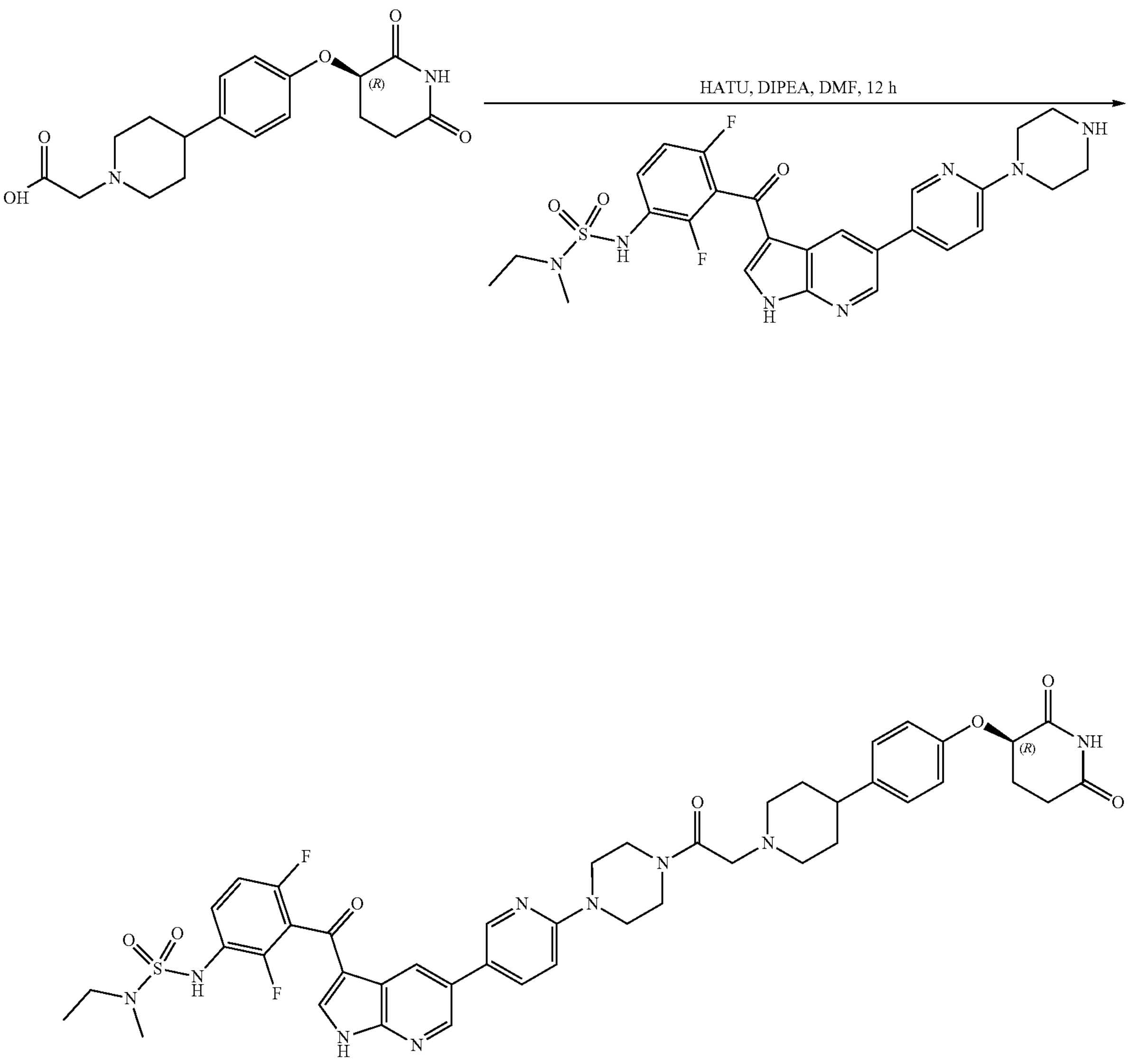

To a stirred solution of 3-[3-[[ethyl(methyl)sulfamoyl] amino]-2,6-difluoro-benzoyl]-5-(6-piperazin-1-yl-3-pyridyl)-1H-pyrrolo[2,3-b]pyridine (25 mg, 45.00 μmol) in N,N-Dimethylformamide (0.5 mL) was added 2-[4-[4-[[(3R)-2,6-dioxo-3-piperidyl]oxy]phenyl]-1-piperidyl]acetic acid (15.59 mg, 45.00 μmol) and N,N-Diisopropylethylamine (29.08 mg, 224.98 μmol, 39.19 μL) at room temperature under nitrogen, followed by the addition of HATU (20.53 mg, 54.00 μmol) at same temperature. The reaction mixture was stirred at room temperature for 16 hours. After completion, the reaction mixture was diluted with water (1.0 mL), extracted with ethyl acetate (3×1.5 mL). The combined organics were removed under Genevac at 50° C. (1 bar pressure) for 3 hours. The obtained crude product was purified by mass-directed preparative HPLC [Mobile-phase A: 10 mM ammonium acetate in water, Mobile-phase B: Acetonitrile, Column: Sunfire C18 OBD (19 mm×100 mm; 5 micron)] to give 5-[6-[4-[2-[4-[4-[[(3R)-2,6-dioxo-3-piperidyl]oxy]phenyl]-1-piperidyl] acetyl]piperazin-1-yl]-3-pyridyl]-3-[3-[[ethyl(methyl)sulfamoyl]amino]-2,6-difluoro-benzoyl]-1H-pyrrolo[2,3-b] pyridine (4.22 mg, 4.46 μmol, 9.91% yield) as off-white solid. LCMS (ESI+): 884.4 $[M+H]^+$. $^1H$ NMR (400 MHz, DMSO-$d_6$): δ 12.88 (s, 1H), 10.91 (s, 1H), 9.75 (s, 1H), 8.67 (s, 1H), 8.52-8.52 (m, 2H), 8.12 (s, 1H), 8.00-7.95 (m, 1H), 7.58-7.51 (m, 1H), 7.28-7.20 (m, 1H), 7.16 (d, J=8.40 Hz, 2H), 7.05-7.02 (m, 1H), 6.93 (d, J=8.40 Hz, 2H), 5.15-5.12 (m, 1H), 3.74-3.60 (m, 8H), 3.24 (s, 2H), 3.11-3.09 (m, 2H), 2.97-2.95 (m, 2H), 2.72 (s, 3H), 2.67-2.61 (m, 3H), 2.16-2.10 (m, 4H), 1.76-1.64 (m, 4H), 1.02 (t, J=6.80 Hz, 3H).

Example 75

3-(2,6-dioxo-3-piperidyl)-6-[[1-[2-[4-[5-[3-[3-[[ethyl (methyl)sulfamoyl]amino]-2,6-difluoro-benzoyl]-1H-pyrrolo[2,3-b]pyridin-5-yl]-2-pyridyl]piperazin-1-yl]-2-oxo-ethyl]-4-piperidyl]amino]-1-methyl-indazole

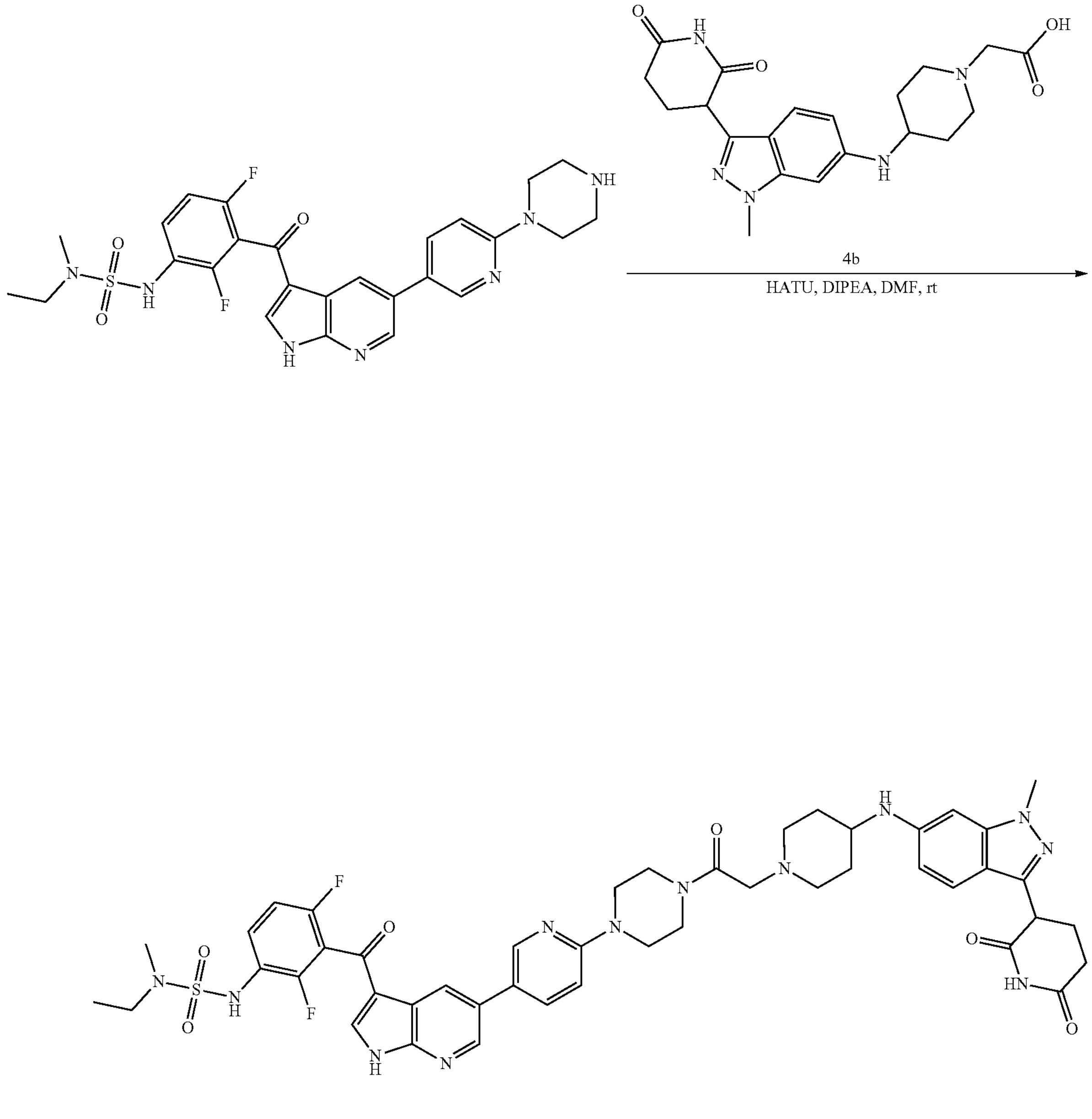

Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (20 mg, 33.78 μmol), 2-[4-[[3-(2,6-dioxo-3-piperidyl)-1-methyl-indazol-6-yl]amino]-1-piperidyl]acetic acid (18 mg, 35.06 μmol), N,N-Diisopropylethylamine (371.00 mg, 2.87 mmol, 0.50 mL) and HATU (16 mg, 42.08 μmol) to afford 3-(2,6-dioxo-3-piperidyl)-6-[[1-[2-[4-[5-[3-[3-[[ethyl(methyl)sulfamoyl] amino]-2,6-difluoro-benzoyl]-1H-pyrrolo[2,3-b]pyridin-5-yl]-2-pyridyl]piperazin-1-yl]-2-oxo-ethyl]-4-piperidyl] amino]-1-methyl-indazole (9.80 mg, 10.21 μmol, 30.23% yield) as a light brown solid. LCMS (ESI+): 937.3 $[M+H]^+$. $^1H$ NMR (400 MHz, DMSO-$d_6$): δ 12.96 (s, 1H), 10.82 (s, 1H), 9.80 (s, 1H), 8.67 (s, 1H), 8.52 (s, 2H), 8.10 (s, 1H), 7.98 (d, J=8.40 Hz, 1H), 7.60-7.50 (m, 1H), 7.31 (d, J=8.80 Hz, 1H), 7.26-7.20 (m, 1H), 7.03 (d, J=8.80 Hz, 1H), 6.52 (d, J=8.80 Hz, 1H), 6.39 (s, 1H), 5.77 (d, J=8.00 Hz, 1H), 4.16-4.19 (m, 1H), 3.81 (s, 3H), 3.74 (s, 2H), 3.56-3.65 (m, 6H), 3.23 (s, 2H), 3.08 (q, J=6.80 Hz, 2H), 2.86 (d, J=10.00 Hz, 2H), 2.69 (s, 3H), 2.55-2.65 (m, 3H), 2.22-2.31 (m, 4H), 1.96-1.85 (m, 2H), 1.49-1.35 (m, 2H), 1.01 (t, J=6.80 Hz, 3H).

Example 76

5-[6-[4-[2-[1-[4-[(2,6-dioxo-3-piperidyl)amino]phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine

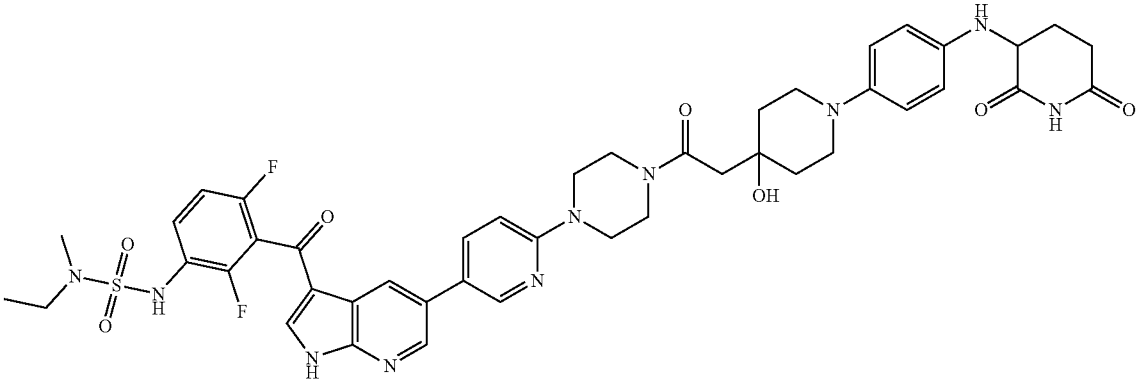

Target compound was prepared via procedure D, by modifying the amide coupling 2-[1-[4-[(2,6-dioxo-3-piperidyl)amino]phenyl]-4-hydroxy-4-piperidyl]acetic acid (25 mg, 69.18 μmol), 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (32.03 mg, 57.65 μmol) and 6.0 of DIPEA. The crude material was purified by reverse phase column chromatography (MeCN & Water (0.01% TFA)). The product was free based in sat. bicarbonate solution in EtOAc. The material was then purified by MeOH and DCM (0-30% MeOH) to afford 5-[6-[4-[2-[1-[4-[(2,6-dioxo-3-piperidyl)amino]phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine (5.4 mg, 5.8 μmol, 10% yield) as off-white solid. LCMS (ESI+): 899.3 $[M+H]^+$. $^1H$ NMR (400 MHz, DMSO-d6): δ 12.95 (s, 1H), 10.75 (s, 1H), 9.70 (s, 1H), 8.68 (d, J=2.2 Hz, 1H), 8.55-8.50 (m, 1H), 8.11 (s, 1H), 7.98 (dd, J=8.8, 2.6 Hz, 1H), 7.58 (td, J=9.0, 5.8 Hz, 1H), 7.31-7.23 (m, 1H), 7.01 (d, J=8.9 Hz, 1H), 6.77 (d, J=8.5 Hz, 2H), 6.61 (d, J=8.5 Hz, 2H), 5.34 (d, J=7.2 Hz, 1H), 4.85 (s, 1H), 4.19 (ddd, J=11.6, 7.2, 4.8 Hz, 1H), 3.80-3.44 (m, 8H), 3.16-3.06 (m, 4H), 2.92 (t, J=10.4 Hz, 2H), 2.80-2.67 (m, 4H), 2.64-2.54 (m, 3H), 2.17-2.06 (m, 1H), 1.90-1.77 (m, 1H), 1.77-1.64 (m, 4H), 1.02 (t, J=7.1 Hz, 3H).

Example 77

5-[6-[4-[2-[(4R)-4-[4-[(2,6-dioxo-3-piperidyl)amino]phenyl]-3,3-difluoro-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine

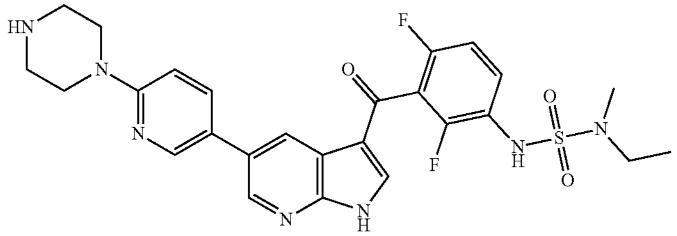

+

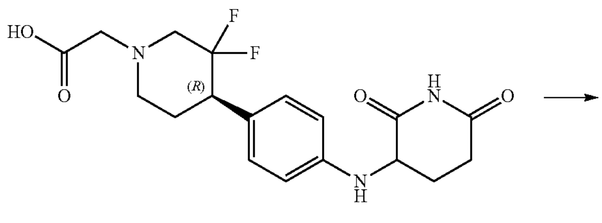

-continued

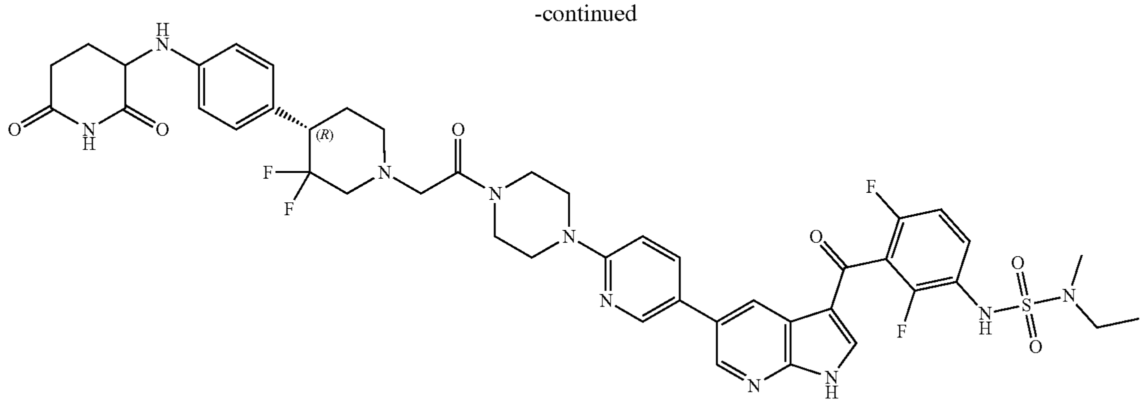

Target compound was prepared via HATU mediated acid-amine coupling reaction (procedure A). Isolated 5-[6-[4-[2-[(4R)-4-[4-[(2,6-dioxo-3-piperidyl)amino]phenyl]-3,3-difluoro-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine (50 mg, 49.22 μmol, 24.00% yield, formic acid salt) as an off-white solid after lyophilization. LCMS (ESI+): 460.9[M/2+H]$^+$, 919.9 [M+H]$^+$. $^1$H NMR (400 MHz, DMSO-$d_6$): δ 12.87 (s, 1H), 10.70 (s, 1H), 8.60 (d, J=2.3 Hz, 1H), 8.45 (d, J=2.6 Hz, 2H), 8.04 (s, 1H), 7.90 (dd, J=8.9, 2.6 Hz, 1H), 7.50 (td, J=9.0, 5.9 Hz, 1H), 7.18 (td, J=8.8, 1.6 Hz, 1H), 6.95 (dd, J=8.7, 7.0 Hz, 3H), 6.56 (d, J=8.4 Hz, 2H), 5.73 (d, J=7.5 Hz, 1H), 4.22 (ddd, J=11.9, 7.5, 4.8 Hz, 1H), 3.65-3.47 (m, 8H), 3.40-3.26 (m, 2H), 3.10 (t, J=9.7 Hz, 1H), 3.05 (d, J=7.2 Hz, 1H), 3.01 (d, J=7.1 Hz, 1H), 2.93-2.74 (m, 2H), 2.74-2.60 (m, 1H), 2.65 (s, 4H), 2.60-2.45 (m, 2H), 2.32 (t, J=11.4 Hz, 1H), 2.09-1.88 (m, 2H), 1.80 (qd, J=12.2, 4.7 Hz, 1H), 1.70-1.63 (m, 1H), 0.95 (t, J=7.1 Hz, 3H).

Example 78

5-[6-[4-[2-[1-[5-[(2,6-dioxo-3-piperidyl)amino]-2-pyridyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine

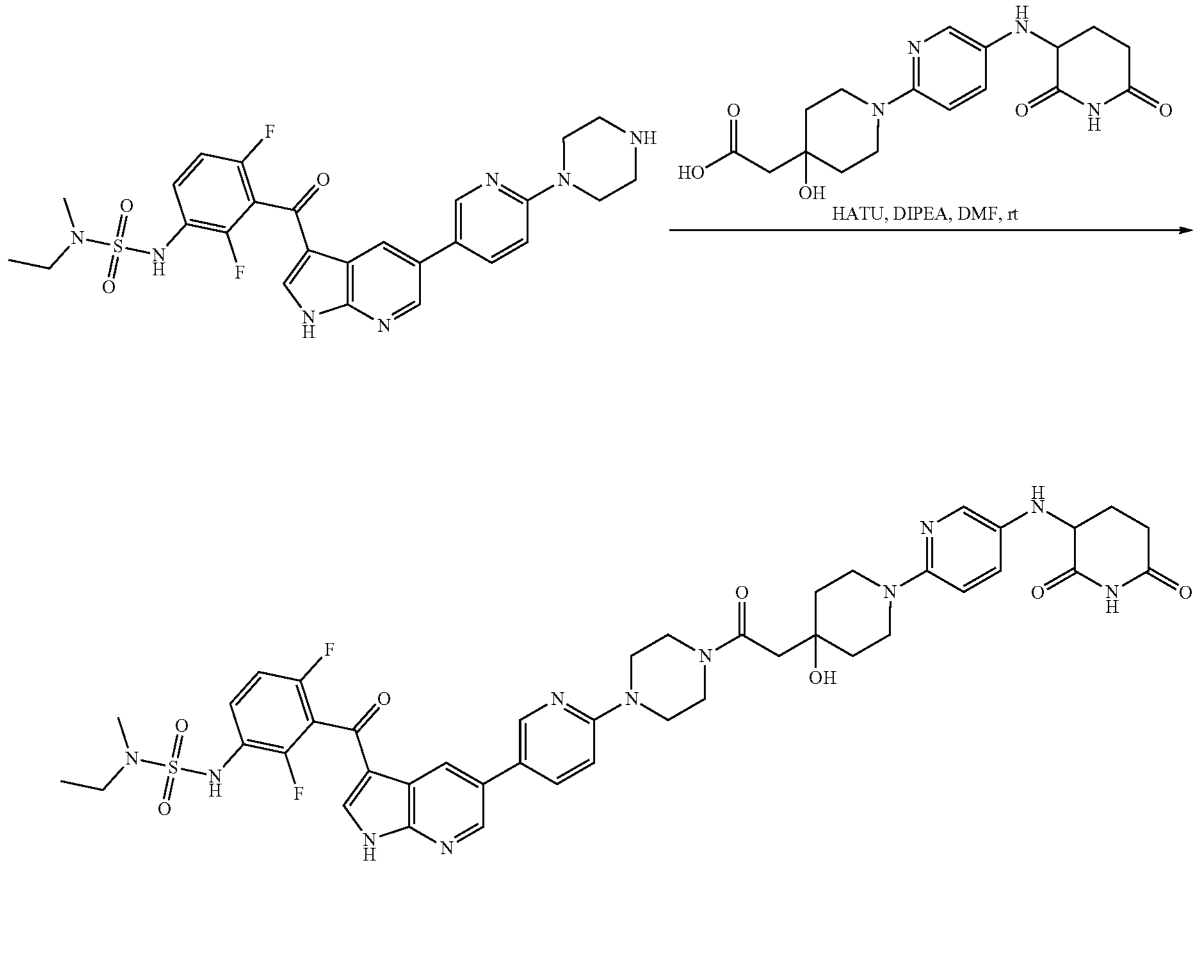

Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (500 mg, 844.51 μmol, hydrochloric acid salt), 2-[1-[5-[(2,6-dioxo-3-piperidyl)amino]-2-pyridyl]-4-hydroxy-4-piperidyl]acetic acid (404.19 mg, 1.01 mmol, hydrochloric acid salt), HATU (481.66 mg, 1.27 mmol) and N,N-Diisopropylethylamine (545.72 mg, 4.22 mmol, 735.47 μL) to afford 5-[6-[4-[2-[1-[5-[(2,6-dioxo-3-piperidyl)amino]-2-pyridyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine (206 mg, 214.13 μmol, 25.36% yield) as an off-white solid. LCMS (ESI+): 900.3 $[M+H]^+$. $^1H$ NMR (400 MHz, DMSO-$d_6$): δ 12.98 (s, 1H), 10.85 (s, 1H), 8.68 (d, J=2.40 Hz, 1H), 8.55-8.52 (m, 2H), 8.14-8.13 (m, 1H), 7.99 (dd, J=2.40, 8.80 Hz, 1H), 7.61-7.55 (m, 1H), 7.55-7.30 (m, 2H), 7.28 (t, J=9.20 Hz, 1H), 7.03-7.01 (m, 1H), 5.06 (m, 1H), 4.31-4.30 (m, 1H), 3.70-3.35 (m, 11H), 3.11 (q, J=7.20 Hz, 1H), 2.73 (s, 3H), 2.73-2.69 (m, 1H), 2.69-2.68 (m, 3H), 2.50-2.35 (m, 2H), 2.13-2.08 (m, 1H), 1.95-1.89 (m, 1H), 1.58-1.80 (m, 4H), 1.02 (t, J=7.20 Hz, 3H).

Example 79

5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine Target compound was prepared via COMU mediated acid-amine coupling reaction (procedure B). Amide coupling was carried out using 2-[1-[4-[(2,6-dioxo-3-piperidyl)amino]-2-fluoro-phenyl]-4-hydroxy-4-piperidyl]acetic acid (1.05 g, 2.53 mmol), 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (1.5 g, 2.53 mmol), N-ethyl-N-isopropyl-propan-2-amine (1.64 g, 12.67 mmol, 2.21 mL) and COMU (1.19 g, 2.79 mmol). The desired product was purified by reverse phase column chromatography (10 mM ammonium acetate in water:Acetonitrile) and fractions were lyophilized to afford 5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine (1.1 g, 1.19 mmol, 46.98% yield) as off white solid. LCMS (ESI+): 917.4 $[M+H]^+$. $^1H$ NMR (400 MHz, DMSO-$d_6$): δ 12.97 (d, J=3.20 Hz, 1H), 10.78 (s, 1H), 9.72 (s, 1H), 8.68 (d, J=2.00 Hz, 1H), 8.53-8.52 (m, 2H), 8.13 (d, J=2.80 Hz, 1H), 7.98 (dd, J=2.80, 8.60 Hz, 1H), 7.56-7.62 (m, 1H), 7.26-7.31 (m, 1H), 7.02 (d, J=8.80 Hz, 1H), 6.86 (t, J=9.60 Hz, 1H), 6.40-6.55 (m, 2H), 5.78 (d, J=7.60 Hz, 1H), 4.87 (s, 1H), 4.21-4.31 (m, 1H), 3.55-3.75 (m, 8H), 3.11 (q, J=7.20 Hz, 2H), 2.87-2.92 (m, 4H), 2.62-2.76 (m, 2H), 2.73 (s, 3H), 2.55-2.61 (m, 2H), 2.07-2.11 (m, 1H), 1.67-1.87 (m, 5H), 1.02 (t, J=7.20 Hz, 3H).

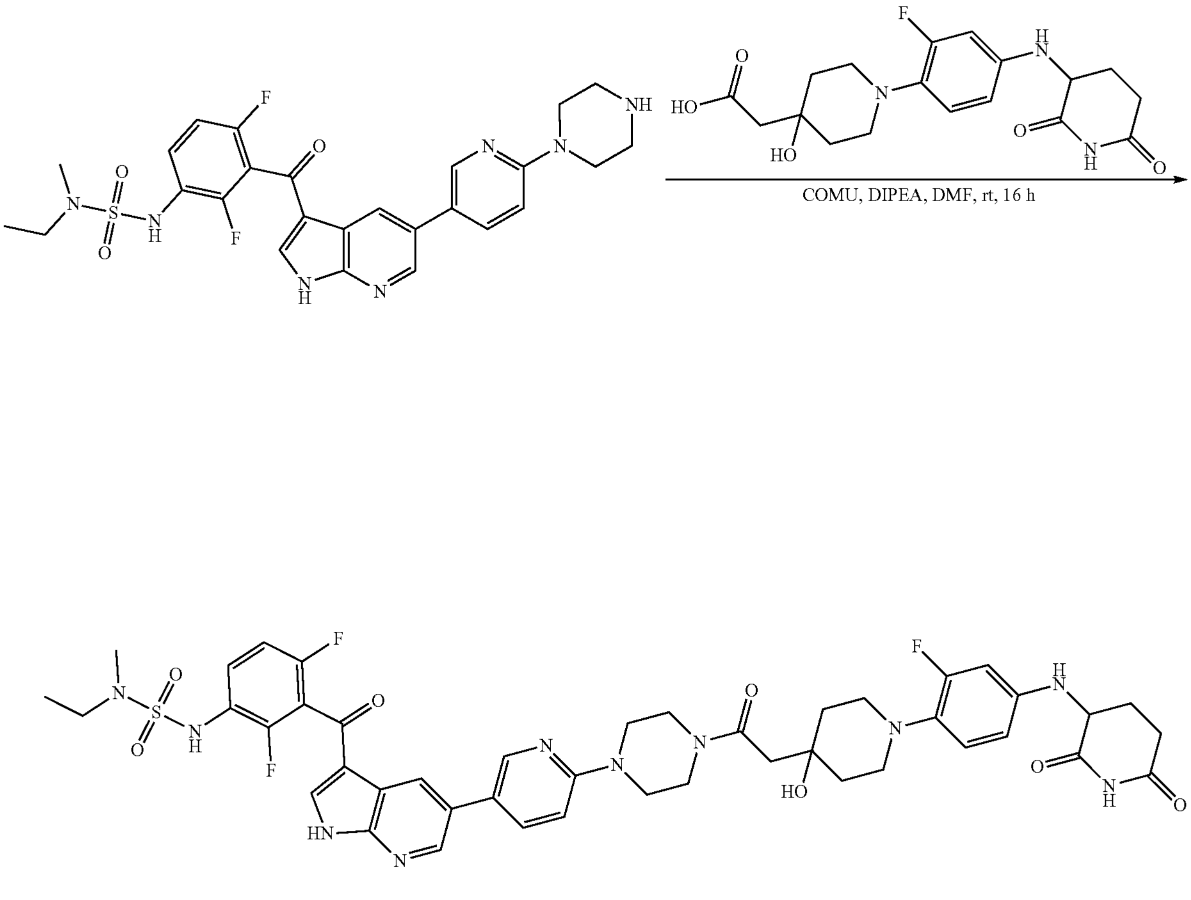

Example 80

5-[6-[4-[2-[1-[5-[(2,6-dioxo-3-piperidyl)amino]-3-fluoro-2-pyridyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine

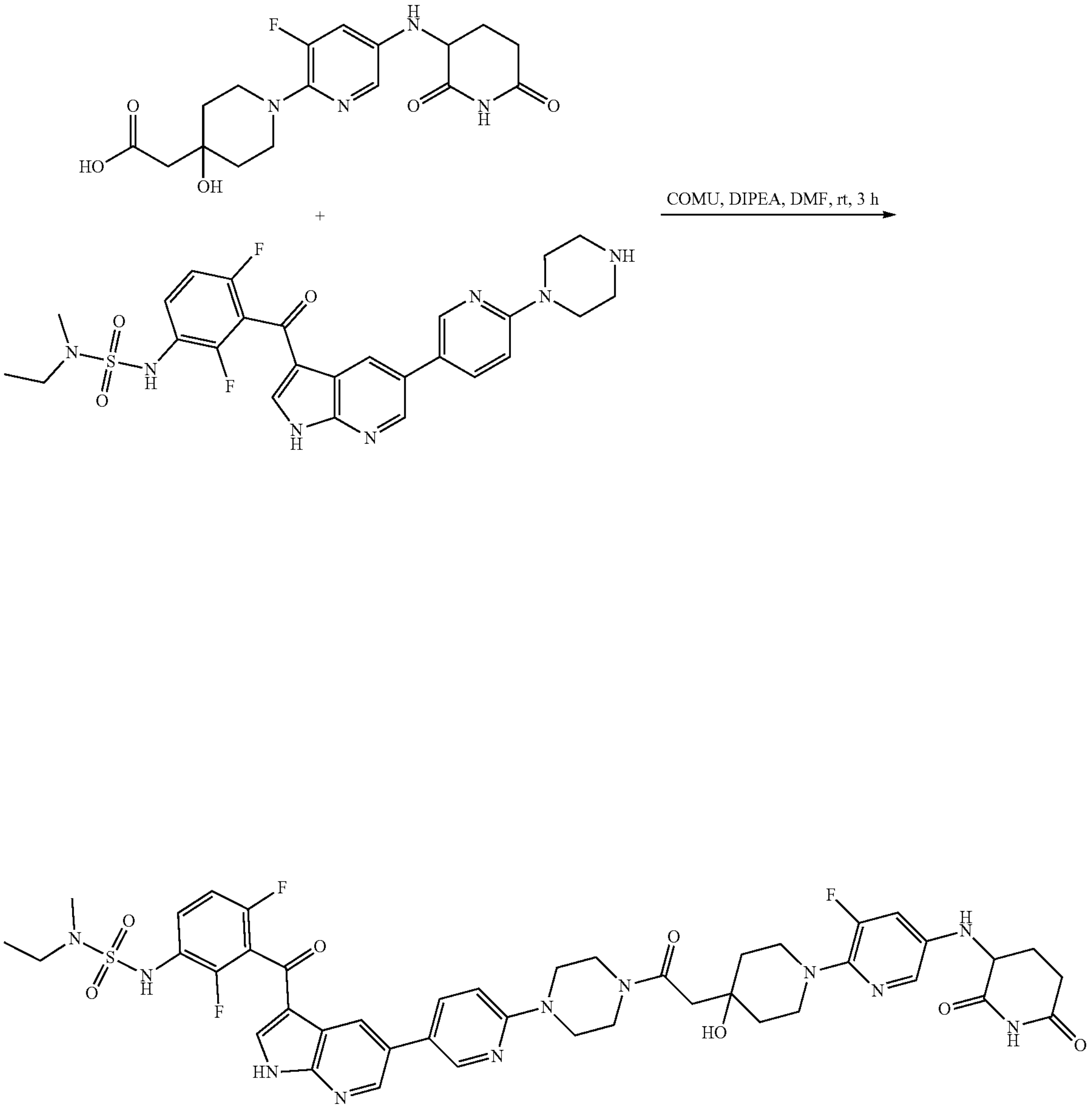

Target compound was prepared via COMU mediated acid-amine coupling reaction (procedure B). Amide coupling was carried out using 2-[1-[5-[(2,6-dioxo-3-piperidyl)amino]-3-fluoro-2-pyridyl]-4-hydroxy-4-piperidyl]acetic acid (1, 292.59 mg, 701.95 μmol, hydrochloric acid salt) in DMF (6 mL), N-ethyl-N-isopropyl-propan-2-amine (418.71 mg, 3.24 mmol, 564.29 μL), COMU (300.62 mg, 701.95 μmol) and 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (2, 300 mg, 539.96 μmol, hydrochloric acid salt) to afford 5-[6-[4-[2-[1-[5-[(2,6-dioxo-3-piperidyl)amino]-3-fluoro-2-pyridyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine (115.38 mg, 123.44 μmol, 22.86% yield) as pale brown solid. LCMS (ESI+): 918.3 $[M+H]^+$. $^1H$ NMR (400 MHz, DMSO-d6): δ 12.97 (s, 1H), 10.82 (s, 1H), 9.72 (s, 1H), 8.68 (dd, J=2.40, 4.80 Hz, 1H), 8.52 (d, J=2.40 Hz, 2H), 8.13 (d, J=2.80 Hz, 1H), 7.98 (dd, J=2.40, 9.00 Hz, 1H), 7.60-7.56 (m, 2H), 7.30-7.26 (m, 1H), 7.03-6.97 (m, 2H), 5.89 (d, J=7.60 Hz, 1H), 4.91 (s, 1H), 4.31-4.28 (m, 1H), 3.70-3.59 (m, 7H), 3.34-3.25 (m, 2H), 3.12-3.07 (m, 3H), 2.71 (s, 3H), 2.70-2.68 (m, 2H), 2.59-2.51 (m, 3H), 2.12-2.09 (m, 1H), 2.00-1.86 (m, 1H), 1.75-1.65 (m, 5H), 1.02 (t, J=7.20 Hz, 3H).

Example 82
5-[5-cyano-6-[4-[2-[4-[4-[(2,6-dioxo-3-piperidyl)amino]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine
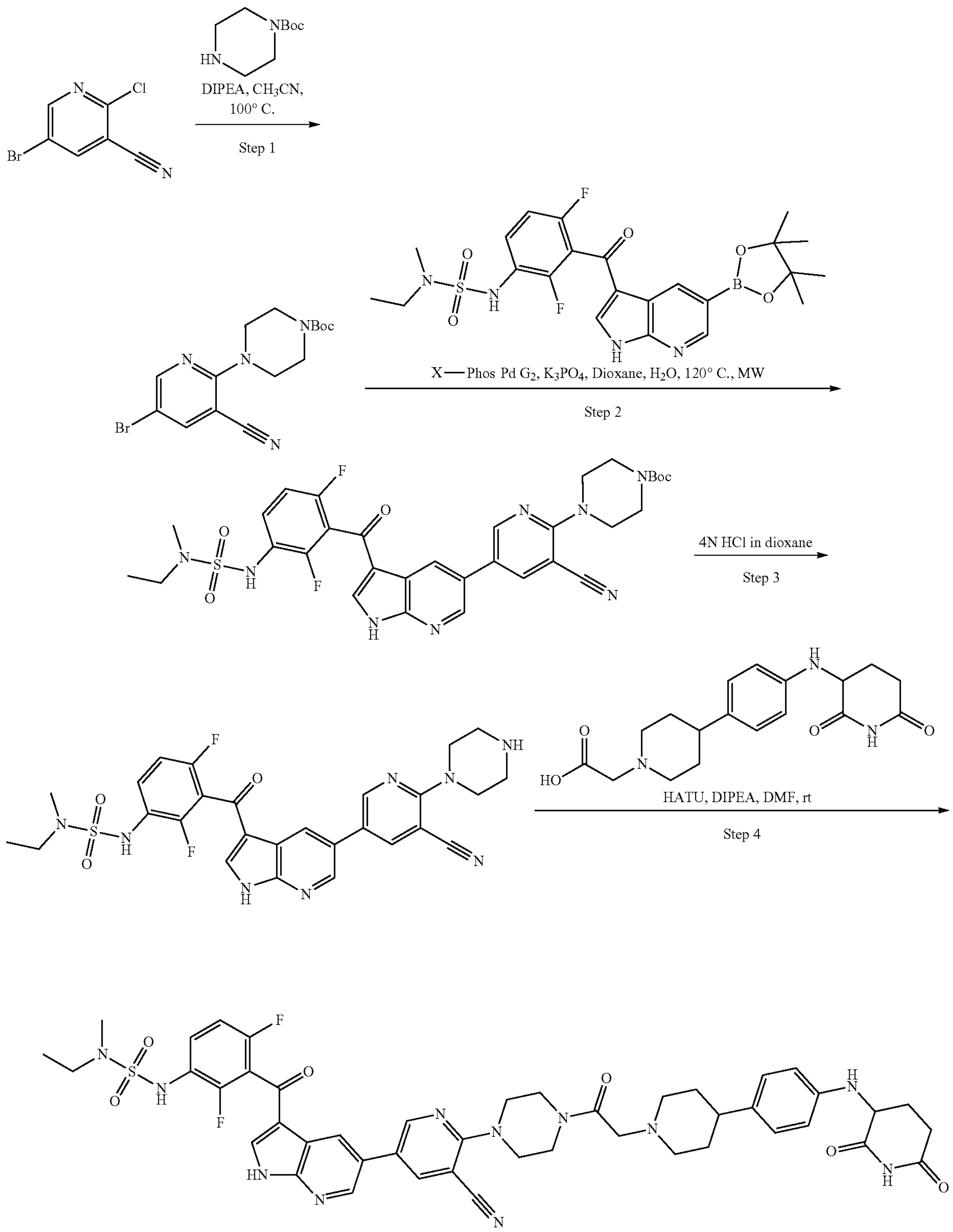

Step 1: To a stirred solution of 5-bromo-2-chloro-pyridine-3-carbonitrile (2 g, 9.20 mmol) and tert-butyl piperazine-1-carboxylate (1.71 g, 9.20 mmol) in acetonitrile (25 mL) was added N, N-diisopropylethylamine (1.19 g, 9.20 mmol, 1.60 mL) at room temperature under nitrogen atmosphere. The reaction mixture was heated at 100° C. for 16 hours. Reaction mixture was cooled room temperature, diluted with ice water (20 mL) and extracted with ethyl acetate (2×50 mL). The combined organic layers were dried over sodium sulphate, filtered and concentrated under reduced pressure. The crude product was purified by silica gel column chromatography with 5% ethyl acetate in petroleum ether as an eluent to afford tert-butyl 4-(5-bromo-3-cyano-2-pyridyl)piperazine-1-carboxylate (3.0 g, 7.76 mmol, 84.38% yield) as an off-white solid. LCMS (ESI+): 267.8 $[M-100+H]^+$.

Step 2: A mixture of tert-butyl 4-(5-bromo-3-cyano-2-pyridyl)piperazine-1-carboxylate (300 mg, 816.90 μmol), 3-[3-[[ethyl(methyl)sulfamoyl]amino]-2,6-difluoro-benzoyl]-5-(4,4,5,5-tetramethyl-1,3,2-dioxaborolan-2-yl)-1H-pyrrolo[2,3-b]pyridine (640 mg, 1.23 mmol) and Potassium phosphate tribasic anhydrous (521 mg, 2.45 mmol) in 1,4-dioxane (3 mL)/water (1 mL) was purged with nitrogen gas for 20 minutes followed by the addition of Xphos Pd G2 (65 mg, 82.72 μmol) at room temperature. The reaction mixture was irradiated in a microwave at 100° C. for 1 hour. Reaction mixture was filtered through celite pad and washed with dichloromethane and the resulting filtrate was concentrated under reduced pressure. The crude product was purified by silica gel column chromatography with 5% methanol in dichloromethane as an eluent to afford tert-butyl 4-[3-cyano-5-[3-[3-[[ethyl(methyl)sulfamoyl]amino]-2,6-difluoro-benzoyl]-1H-pyrrolo[2,3-b]pyridin-5-yl]-2-pyridyl]piperazine-1-carboxylate (450 mg, 515.63 μmol, 63.12% yield) as a brown solid. LCMS (ESI+): 678.9 $[M+H]^+$.

Step 3: To a stirred solution of tert-butyl 4-[3-cyano-5-[3-[3-[[ethyl(methyl)sulfamoyl]amino]-2,6-difluoro-benzoyl]-1H-pyrrolo[2,3-b]pyridin-5-yl]-2-pyridyl]piperazine-1-carboxylate (450 mg, 661.06 μmol) in dichloromethane (3 mL) was added Hydrogen chloride solution 4.0 M in 1,4-dioxane (1.60 g, 43.88 mmol, 2 mL) at 0° C. The reaction mixture was stirred at room temperature for 5 hours. Reaction mixture was concentrated under reduced pressure and triturated with diethyl ether to afford 5-(5-cyano-6-piperazin-1-yl-3-pyridyl)-3-[3-[[ethyl(methyl)sulfamoyl]amino]-2,6-difluoro-benzoyl]-1H-pyrrolo[2,3-b]pyridine (400 mg, 466.72 μmol, 70.60% yield) as a brown semi solid. LCMS (ESI+): 581.2 $[M+H]^+$.

Step 4: Target compound was prepared via HATU mediated acid-amine coupling reaction (procedure A). Amide coupling was carried out using 5-(5-cyano-6-piperazin-1-yl-3-pyridyl)-3-[3-[[ethyl(methyl)sulfamoyl]amino]-2,6-difluoro-benzoyl]-1H-pyrrolo[2,3-b]pyridine (100 mg, 172.23 μmol), 2-[4-[4-[(2,6-dioxo-3-piperidyl)amino]phenyl]-1-piperidyl]acetic acid (60 mg, 173.72 μmol), HATU (99 mg, 260.37 μmol) and N,N-diisopropylethylamine (225 mg, 1.74 mmol, 303.23 μL) to afford 5-[5-cyano-6-[4-[2-[4-[4-[(2,6-dioxo-3-piperidyl)amino]phenyl]-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine (23.39 mg, 23.74 μmol, 13.78% yield) as an off-white solid. LCMS (ESI+): 908.3 $[M+H]^+$. $^1H$ NMR (400 MHz, DMSO-$d_6$): δ 13.02 (s, 1H), 10.79 (s, 1H), 9.70 (s, 1H), 9.51 (s, 1H), 8.86 (d, J=2.40 Hz, 1H), 8.75 (d, J=2.00 Hz, 1H), 8.70 (s, 1H), 8.62 (d, J=2.40 Hz, 1H), 8.17 (d, J=3.20 Hz, 1H), 7.56-8.16 (m, 1H), 7.26-7.31 (m, 1H), 7.21 (m, 1H), 7.08-7.10 (m, 2H), 6.75 (m, 2H), 4.48 (m, 1H), 4.38 (m, 1H), 4.29 (m, 1H), 3.71-3.77 (m, 7H), 3.33-3.53 (m, 3H), 3.13 (q, J=7.20 Hz, 2H), 2.72 (s, 3H), 2.68-2.71 (m, 2H), 2.61 (m, 2H), 2.09-2.33 (m, 1H), 1.86-2.09 (m, 5H), 1.03 (t, J=6.80 Hz, 3H).

Example 83-90

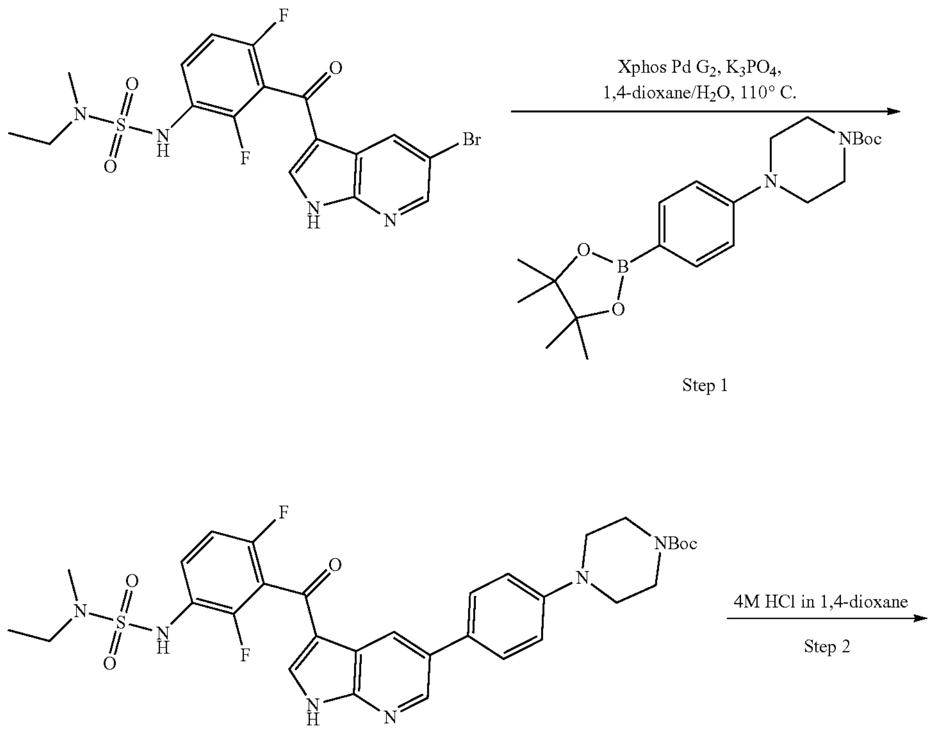

-continued

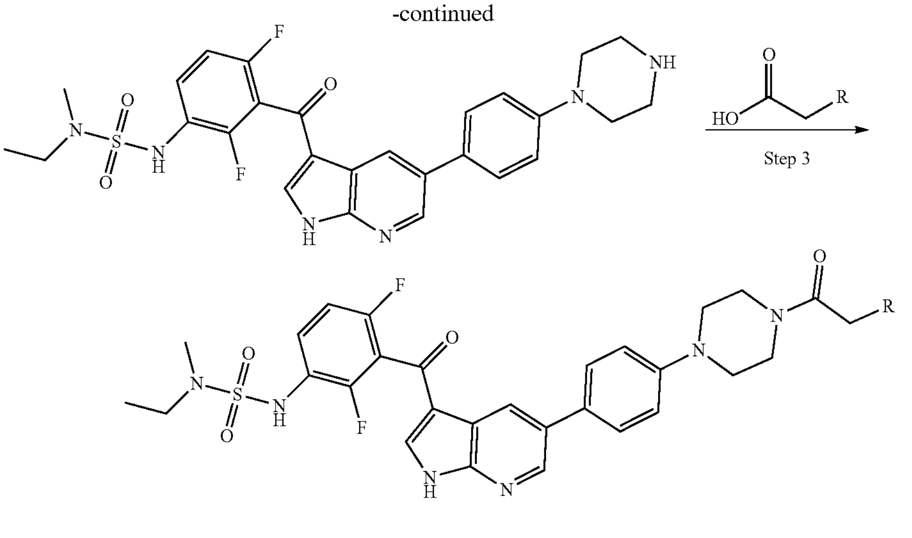

Synthesis of intermediate 3-[3-[[ethyl(methyl)sulfamoyl]amino]-2,6-difluoro-benzoyl]-5-(4-piperazin-1-ylphenyl)-1H-pyrrolo[2,3-b]pyridine Step 1: A mixture of 5-bromo-3-[3-[[ethyl(methyl)sulfamoyl]amino]-2,6-difluoro-benzoyl]-1H-pyrrolo[2,3-b]pyridine (1.0 g, 2.11 mmol), tert-butyl 4-[4-(4,4,5,5-tetramethyl-1,3,2-dioxaborolan-2-yl)phenyl]piperazine-1-carboxylate (984.53 mg, 2.54 mmol) and $K_3PO_4$ (1.35 g, 6.34 mmol) in 1,4-Dioxane (9.0 mL)/Water (1.0 mL) was purged with nitrogen gas for 10 minutes followed by the addition of XPhos Pd G2 (166.24 mg, 211.29 μmol) at room temperature. The reaction mixture was irradiated under microwave at 110° C. for 90 minutes. Reaction mixture was diluted with water (30 mL), extracted with ethyl acetate (3×30 mL). Combined organic layers were dried over sodium sulphate, filtered and concentrated under reduced pressure. The crude product was purified by silica gel column chromatography with 30% ethyl acetate in petroleum ether as an eluent to afford tert-butyl 4-[4-[3-[3-[[ethyl(methyl)sulfamoyl]amino]-2,6-difluoro-benzoyl]-1H-pyrrolo[2,3-b]pyridin-5-yl]phenyl]piperazine-1-carboxylate (666 mg, 691.81 μmol, 32.74% yield) as an off-white solid. LCMS (ESI+): 655.3 $[M+H]^+$.

Step 2: To a stirred solution of tert-butyl 4-[4-[3-[3-[[ethyl(methyl)sulfamoyl]amino]-2,6-difluoro-benzoyl]-1H-pyrrolo[2,3-b]pyridin-5-yl]phenyl]piperazine-1-carboxylate (666 mg, 1.02 mmol) in 1,4-Dioxane (4.0 mL) was added Hydrogen chloride solution 4.0 M in 1,4-dioxane (185.44 mg, 5.09 mmol, 231.80 μL) at 5° C. The reaction mixture was warmed to room temperature and stirred for 4 hours. The reaction mixture was concentrated under reduced pressure, triturated with diethyl ether (20 mL) and dried to afford 3-[3-[[ethyl(methyl)sulfamoyl]amino]-2,6-difluoro-benzoyl]-5-(4-piperazin-1-ylphenyl)-1H-pyrrolo[2,3-b]pyridine (524 mg, 765.96 μmol, 75.30% yield, hydrochloric acid salt) as an off-white solid. LCMS (ESI+): 555.2 $[M+H]^+$.

Example 84

5-[4-[4-[2-[4-[4-[(2,6-dioxo-3-piperidyl)amino]phenyl]-1-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine

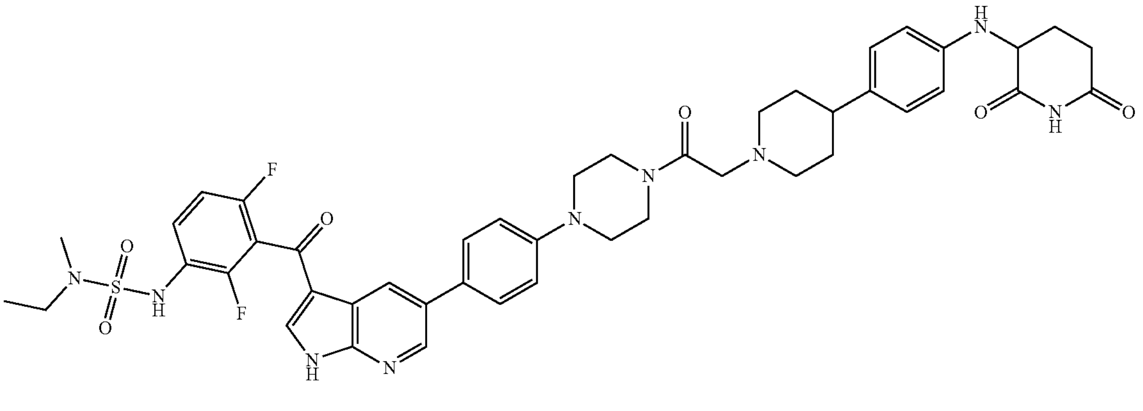

Target compound was prepared via procedure B, by modifying the amide coupling to use 3-[3-[[ethyl(methyl)sulfamoyl]amino]-2,6-difluoro-benzoyl]-5-(4-piperazin-1-ylphenyl)-1H-pyrrolo[2,3-b]pyridine (233.41 mg, 420.85 μmol), 2-[4-[4-[(2,6-dioxo-3-piperidyl)amino]phenyl]-1-piperidyl]acetic acid (193.34 mg, 420.85 μmol) and 1.5 eq of DIPEA. The crude material was purified by reverse phase column chromatography (MeCN & Water (0.01% TFA)). The product elutes around 40%. The product was free based in sat. bicarbonate solution in EtOAc. The material was then purified by MeOH and DCM (0-30% MeOH) to afford 5-[4-[4-[2-[4-[4-[(2,6-dioxo-3-piperidyl)amino]phenyl]-1-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine (118 mg, 131.11 μmol, 31% yield) as off-white solid. LCMS (ESI+): 882.2 $[M+H]^+$. $^1H$ NMR (400 MHz, DMSO-d6): δ 12.85 (s, 1H), 10.69 (s, 1H), 9.64 (s, 1H), 8.59 (d, J=2.2 Hz, 1H), 8.50-8.45 (m, 1H), 8.03 (s, 1H), 7.68-7.42 (m, 3H), 7.25-7.16 (m, 1H), 7.05 (d, J=8.5 Hz, 2H), 6.89 (d, J=8.2 Hz, 2H), 6.54 (d, J=8.3 Hz, 2H), 5.58 (d, J=7.5 Hz, 1H), 4.18 (ddd, J=11.9, 7.4, 4.8 Hz, 1H), 3.77-3.52 (m, 4H), 3.25-3.07 (m, 6H), 3.03 (q, J=7.1 Hz, 2H), 2.88 (d, J=10.5 Hz, 2H), 2.73-2.59 (m, 4H), 2.54-2.47 (m, 1H), 2.32-2.19 (m, OH), 2.08-1.97 (m, 3H), 1.85-1.71 (m, 1H), 1.64 (d, J=13.1 Hz, 2H), 1.58-1.48 (m, 2H), 0.94 (t, J=7.1 Hz, 3H).

Example 86

5-[4-[4-[2-[1-[4-[(2,6-dioxo-3-piperidyl)amino]phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine

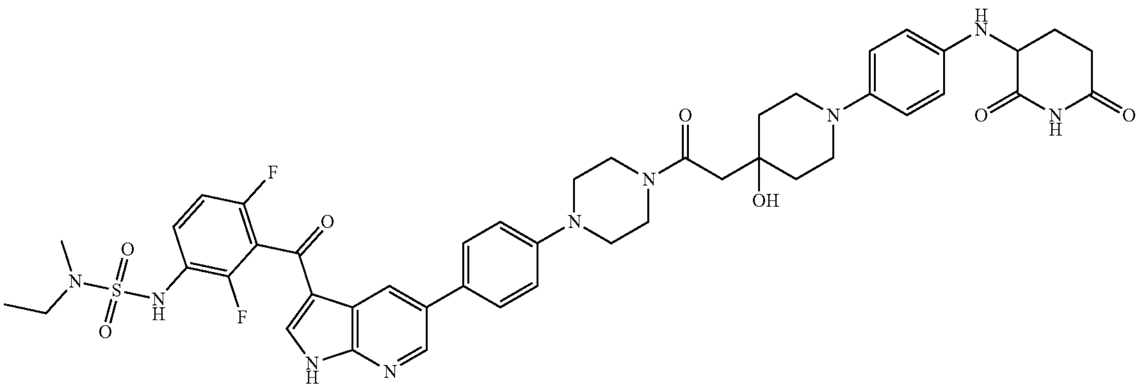 [SMILES: CCN(C)S(=O)(=O)Nc1ccc(F)c(C(=O)c2c[nH]c3ncc(-c4ccc(N5CCN(C(=O)CC6(O)CCN(c7ccc(NC8CCC(=O)NC8=O)cc7)CC6)CC5)nc4)cc23)c1F]

Target compound was prepared via procedure D, by modifying the amide coupling 2-[1-[4-[(2,6-dioxo-3-piperidyl)amino]phenyl]-4-hydroxy-4-piperidyl]acetic acid (40 mg, 110.68 μmol), 3-[3-[[ethyl(methyl)sulfamoyl]amino]-2,6-difluoro-benzoyl]-5-(4-piperazin-1-ylphenyl)-1H-pyrrolo[2,3-b]pyridine (61.39 mg, 110.68 μmol) and 6.0 eq of DIPEA. The crude material was purified by reverse phase column chromatography (MeCN & Water (0.01% TFA)). The product elutes around 40%. The product was free based in sat. bicarbonate solution in EtOAc. The material was then purified by MeOH and DCM (0-30% MeOH) to afford 5-[4-[4-[2-[1-[4-[(2,6-dioxo-3-piperidyl)amino]phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine (15.2 mg, 16.08 μmol, 15% yield) as off-white solid. LCMS (ESI+): 898.3 $[M+H]^+$. $^1H$ NMR (400 MHz, DMSO-d6): δ 12.84 (s, 1H), 10.67 (s, 1H), 9.62 (s, 1H), 8.59 (d, J=2.3 Hz, 1H), 8.47 (s, 1H), 8.02 (s, 1H), 7.59-7.46 (m, 3H), 7.25-7.15 (m, 1H), 7.04 (d, 2H), 6.70 (d, 2H), 6.57-6.49 (m, 2H), 5.26 (d, J=7.2 Hz, 1H), 4.77 (s, 1H), 4.11 (ddd, J=11.6, 7.2, 4.8 Hz, 1H), 3.70-3.58 (m, 4H), 3.23-3.11 (m, 4H), 3.09-2.99 (m, 4H), 2.85 (t, J=10.4 Hz, 2H), 2.72-2.59 (m, 4H), 2.53-2.48 (m, 3H), 2.10-1.98 (m, 1H), 1.72-1.55 (m, 4H), 0.95 (t, J=7.1 Hz, 3H).

Example 87

5-[4-[4-[2-[1-[4-[(2,6-dioxo-3-piperidyl)amino]-2-fluoro-phenyl]-3-hydroxy-pyrrolidin-3-yl]acetyl]piperazin-1-yl]phenyl]-3-[3-[[ethyl(methyl)sulfamoyl]amino]-2,6-difluoro-benzoyl]-1H-pyrrolo[2,3-b]pyridine

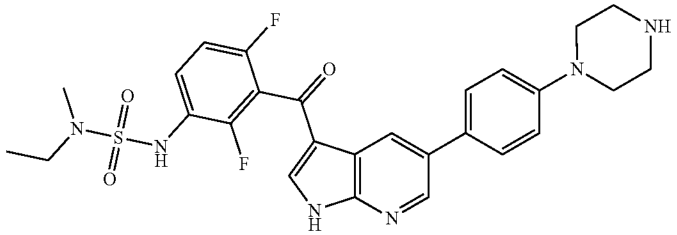

+

-continued

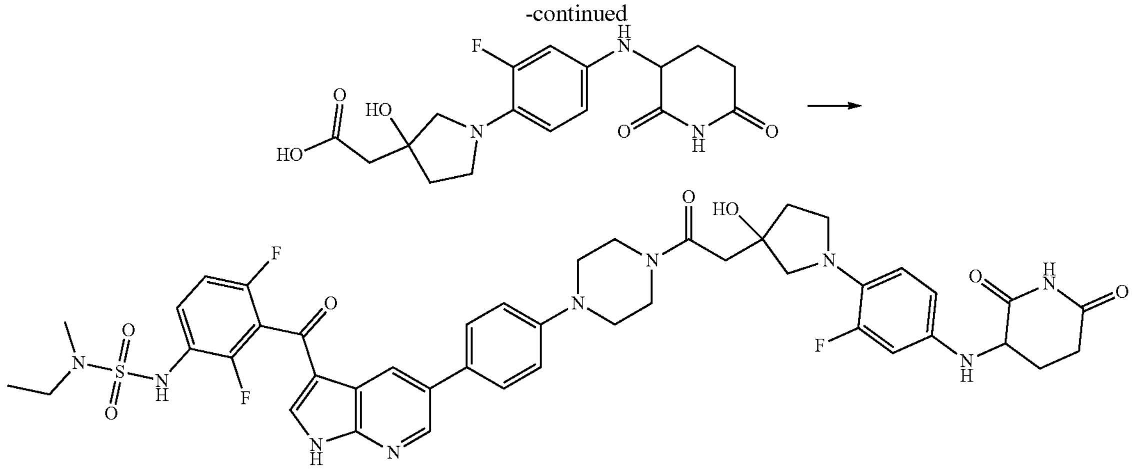

To a solution of 2-[1-[4-[(2,6-dioxo-3-piperidyl)amino]-2-fluoro-phenyl]-3-hydroxy-pyrrolidin-3-yl]acetic acid (38.03 mg, 79.34 μmol) in DMF (0.4 mL) at 0° C. was added HATU (68.56 mg, 180.31 μmol) and N,N-Diisopropylethylamine (13.98 mg, 108.18 μmol, 18.84 uL). The resulting solution was stirred at this temperature for 30 minutes before adding 3-[3-[[ethyl(methyl)sulfamoyl]amino]-2,6-difluoro-benzoyl]-5-(4-piperazin-1-ylphenyl)-1H-pyrrolo[2,3-b]pyridine (40 mg, 72.12 μmol). The resulting mixture stirred at the same temperature for 2 hours. The crude reaction mixture was directly purified by column chromatography (silica, gradient: column chromatography 20-70% acetonitrile in water with 0.1% formic acid) to afford the product 5-[4-[4-[2-[1-[4-[(2,6-dioxo-3-piperidyl)amino]-2-fluoro-phenyl]-3-hydroxy-pyrrolidin-3-yl]acetyl]piperazin-1-yl]phenyl]-3-[3-[[ethyl(methyl)sulfamoyl]amino]-2,6-difluoro-benzoyl]-1H-pyrrolo[2,3-b]pyridine (21 mg, 20.82 μmol, 28.87% yield). LCMS (ES+): 902.6 $[M+H]^+$. $^1H$ NMR (400 MHz, DMSO-d6): δ 12.84 (s, 1H), 10.68 (s, 1H), 9.62 (s, 1H), 8.59 (d, J=2.3 Hz, 1H), 8.47 (s, 1H), 8.02 (s, 1H), 7.56 (d, J=8.5 Hz, 3H), 7.53-7.46 (m, 1H), 7.20 (t, J=8.9 Hz, 1H), 7.04 (d, J=8.7 Hz, 3H), 6.56-6.41 (m, 3H), 6.34 (d, J=9.0 Hz, 2H), 5.43 (d, J=7.5 Hz, 1H), 4.91 (s, 1H), 4.14 (d, J=11.5 Hz, 1H), 3.63 (s, 6H), 3.36 (d, J=9.6 Hz, 1H), 3.05 (m, 5H), 2.71 (s, 3H), 2.01 (d, J=4.9 Hz, 1H), 1.89 (q, J=7.9 Hz, 3H), 1.76 (d, J=7.1 Hz, 1H), 1.17 (s, 1H), 0.95 (d, J=7.1 Hz, 3H).

Example 88

5-[4-[4-[2-[1-[5-[(2,6-dioxo-3-piperidyl)amino]-2-pyridyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine

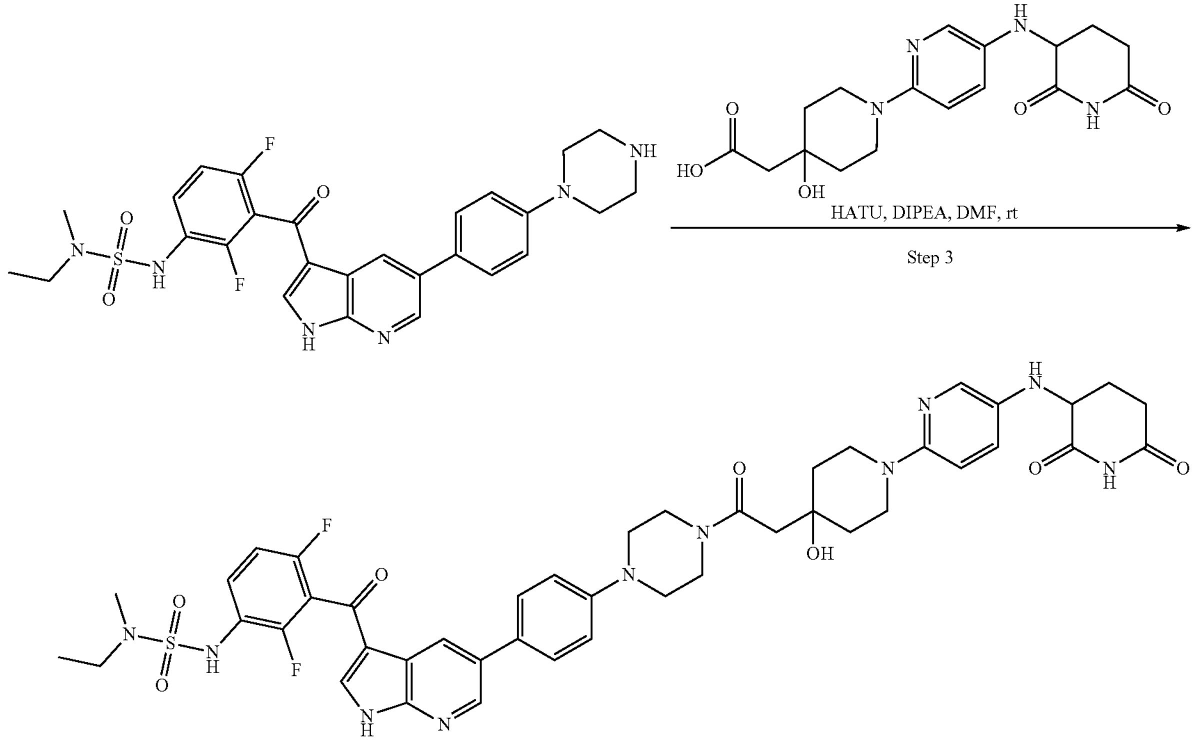

Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(4-piperazin-1-ylphenyl)-1H-pyrrolo[2,3-b]pyridine (520 mg, 879.76 μmol, hydrochloric acid salt), 2-[1-[5-[(2,6-dioxo-3-piperidyl)amino]-2-pyridyl]-4-hydroxy-4-piperidyl]acetic acid (421.06 mg, 1.06 mmol, hydrochloric acid salt), HATU (501.77 mg, 1.32 mmol) and N,N-Diisopropylethylamine (568.50 mg, 4.40 mmol, 766.17 μL) to afford 5-[4-[4-[2-[1-[5-[(2,6-dioxo-3-piperidyl)amino]-2-pyridyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3b]pyridine (175 mg, 180.02 μmol, 20.46% yield, formic acid salt) as an off-white solid. LCMS (ESI+): 899.4 $[M+H]^+$. $^1H$ NMR (400 MHz, DMSO-$d_6$): δ 12.94 (s, 1H), 10.88 (s, 1H), 9.73 (s, 1H), 8.67 (d, J=2.00 Hz, 1H), 8.56 (s, 1H), 8.12-8.11 (m, 1H), 7.63-7.55 (m, 3H), 7.43-7.28 (m, 3H), 7.26-7.11 (m, 2H), 6.21 (m, 1H), 5.10 (m, 1H), 4.38-4.32 (m, 1H), 3.73-3.69 (m, 6H), 3.27-3.22 (m, 5H), 3.11 (q, J=7.20 Hz, 2H), 2.73 (s, 3H), 2.71-2.62 (m, 3H), 2.50-2.42 (m, 1H), 2.11-2.08 (m, 1H), 1.80-1.60 (m, 4H), 1.02 (t, J=7.20 Hz, 3H).

Example 89

5-[4-[4-[2-[1-[4-[(2,6-dioxo-3-piperidyl)amino]-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine (Compound 89)

Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(4-piperazin-1-ylphenyl)-1H-pyrrolo[2,3-b]pyridine (280 mg, 473.72 μmol), 2-[1-[4-[(2,6-dioxo-3-piperidyl)amino]-2-fluoro-phenyl]-4-hydroxy-4-piperidyl]acetic acid (216.69 mg, 521.09 μmol), N,N-Diisopropylethylamine (244.89 mg, 1.89 mmol, 330.04 μL) and HATU (180.12 mg, 473.72 μmol) to afford 5-[4-[4-[2-[1-[4-[(2,6-dioxo-3-piperidyl)amino]-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine (55 mg, 54.71 μmol, 11.55% yield) as off white solid. LCMS (ESI): 914.3 $[M+H]^+$. $^1H$ NMR (400 MHz, DMSO-$d_6$): δ 12.90 (s, 1H), 10.78 (s, 1H), 9.70 (s, 1H), 8.67 (s, 1H), 8.54 (s, 1H), 8.10 (s, 1H), 7.55-7.64 (m, 3H), 7.27 (t, J=9.20 Hz, 1H), 7.12 (d, J=8.80 Hz, 2H), 6.86 (t, J=9.60 Hz, 1H), 6.48-6.52 (m, 2H), 5.78 (d, J=7.60 Hz, 1H), 4.87 (s, 1H), 4.21-4.31 (m, 1H), 3.65-3.75 (m, 4H), 3.23-3.33 (m, 4H), 3.11 (q, J=7.20 Hz, 2H), 2.83-2.95 (m, 4H), 2.65-2.79 (m, 1H), 2.73 (s, 3H), 2.55-2.61 (m, 3H), 2.02-2.08 (m, 1H), 1.66-1.85 (m, 5H), 1.02 (t, J=7.20 Hz, 3H).

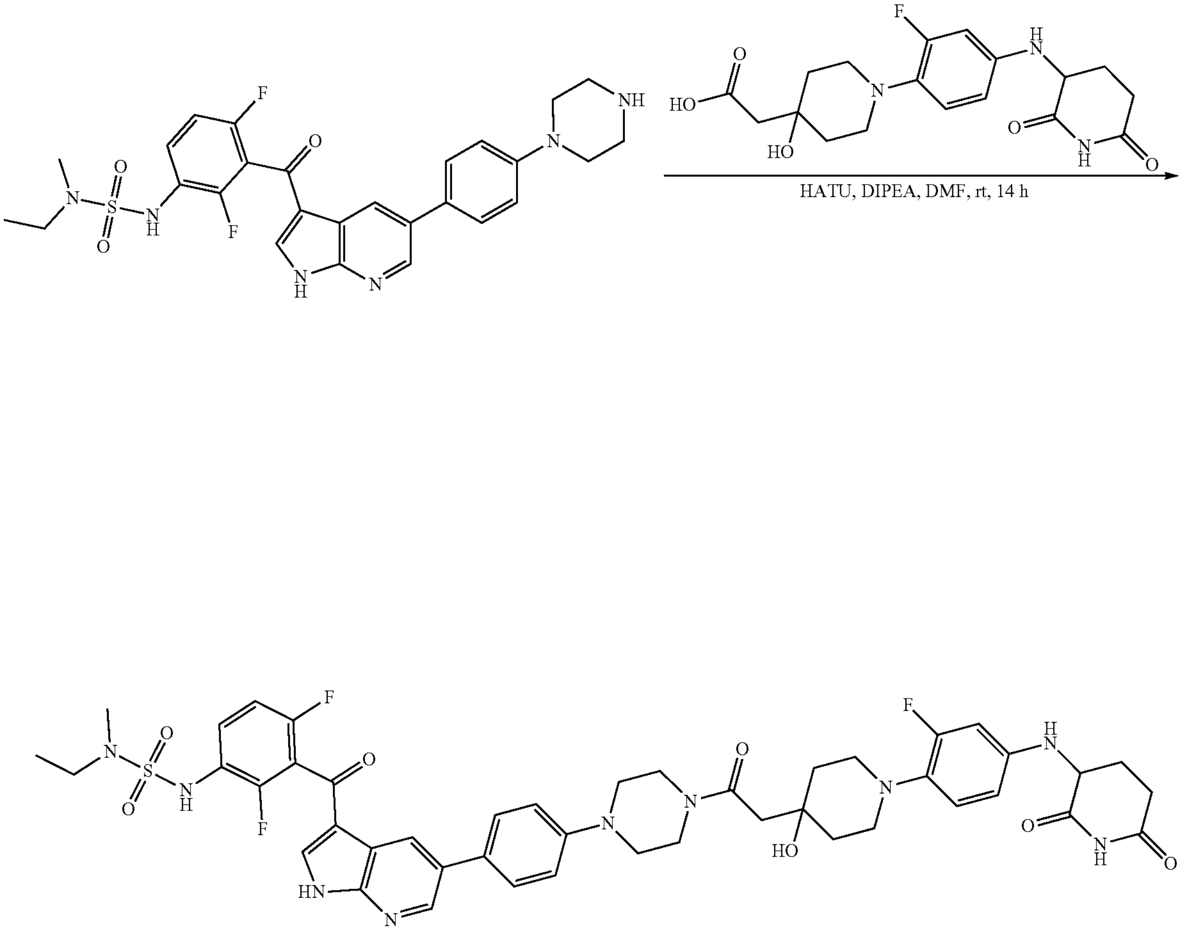

Example 90

5-[4-[4-[2-[1-[5-[(2,6-dioxo-3-piperidyl)amino]-3-fluoro-2-pyridyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine

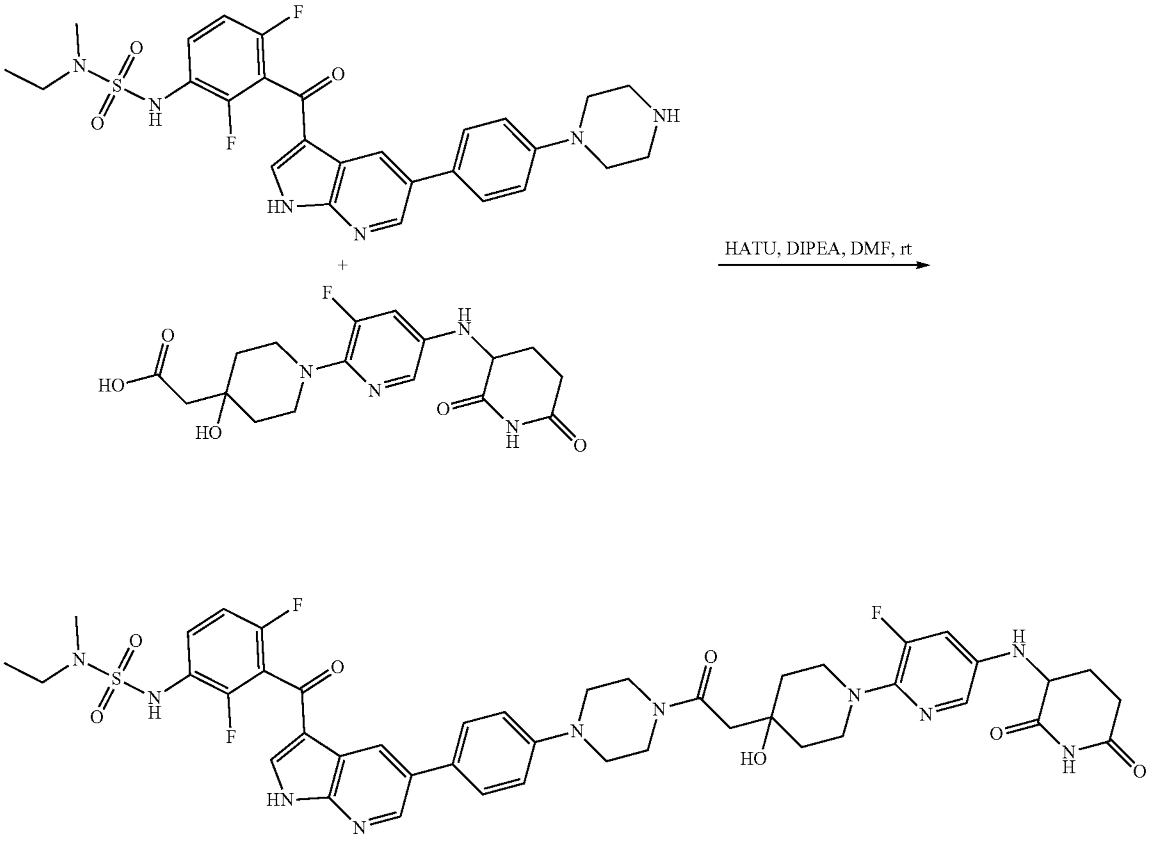

Target compound was prepared via HATU mediated acid-amine coupling reaction (procedure A). Amide coupling was carried out using 2-[1-[5-[(2,6-dioxo-3-piperidyl)amino]-3-fluoro-2-pyridyl]-4-hydroxy-4-piperidyl]acetic acid (246.90 mg, 649.10 μmop, HATU (246.81 mg, 649.10 μmol), DIPEA (349.55 mg, 2.70 mmol, 471.09 μL) and 3-[3-[[ethyl(methyl)sulfamoyl]amino]-2,6-difluoro-benzoyl]-5-(4-piperazin-1-ylphenyl)-1H-pyrrolo[2,3-b]pyridine (300.0 mg, 540.92 μmol) to afford 5-[4-[4-[2-[1-[5-[(2,6-dioxo-3-piperidyl)amino]-3-fluoro-2-pyridyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine (80.0 mg, 86.72 μmol, 16.03% yield) as off white solid. LCMS (ESI+): 915.2 $[M+H]^+$. $^1H$ NMR (400 MHz, DMSO-$d_6$): δ 12.92 (s, 1H), 10.81 (s, 1H), 9.71 (s, 1H), 8.67 (s, 1H), 8.55 (bs, 1H), 8.10 (s, 1H), 7.64-7.55 (m, 4H), 7.30-7.26 (m, 1H), 7.12 (d, J=8.80 Hz, 2H), 6.99 (dd, J=2.00, 14.80 Hz, 1H), 5.89-5.87 (m, 1H), 4.90 (s, 1H), 4.31-4.26 (m, 1H), 3.74-3.69 (m, 4H), 3.28-3.25 (m, 6H), 3.12-3.10 (m, 4H), 2.73 (s, 3H), 2.72-2.62 (m, 1H), 2.58-2.53 (m, 3H), 2.13-2.09 (m, 1H), 1.90-1.72 (m, 1H), 1.75-1.65 (m, 4H), 1.02 (t, J=7.20 Hz, 3H).

Example 92

5-[4-[1-[2-[1-[4-[(2,6-dioxo-3-piperidyl)amino]phenyl]-4-piperidyl]acetyl]-3,6-dihydro-2H-pyridin-4-yl]phenyl]-3-[3-[[ethyl(methyl)sulfamoyl]amino]-2,6-difluoro-benzoyl]-1H-pyrrolo[2,3-b]pyridine

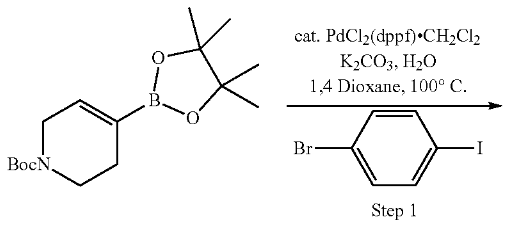

-continued

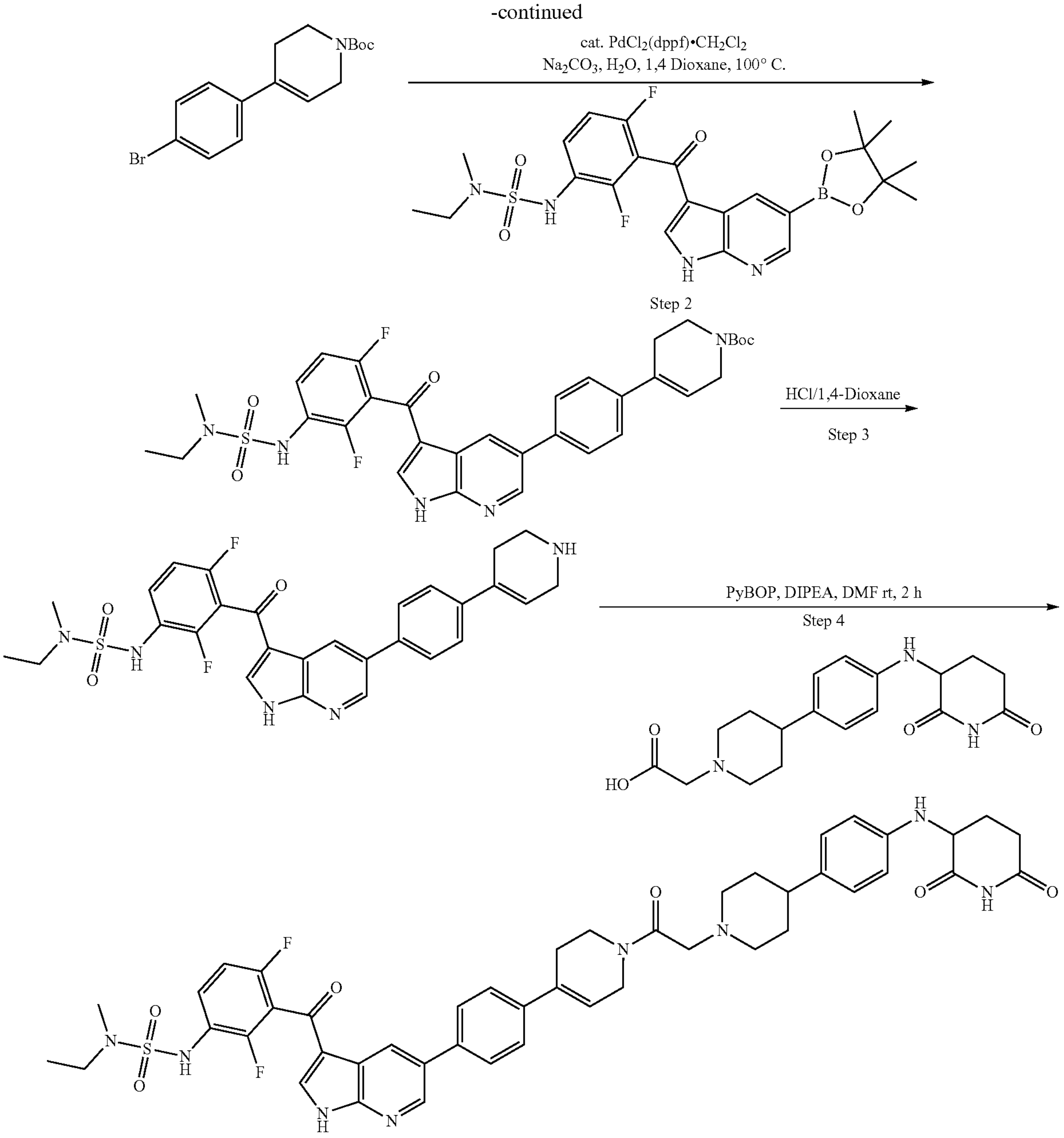

Step 1: To a stirred solution of 1-bromo-4-iodo-benzene (1 g, 3.53 mmol) and tert-butyl 4-(4,4,5,5-tetramethyl-1,3,2-dioxaborolan-2-yl)-3,6-dihydro-2H-pyridine-1-carboxylate (1.20 g, 3.89 mmol) in Water (3 mL) and 1,4-dioxane (10 mL). The reaction mixture was degassed with nitrogen for 10 minutes, followed by addition of Potassium carbonate (1.47 g, 10.60 mmol, 639.99 μL) and Pd(dppf)$Cl_2$ (288.66 mg, 353.48 μmol). The reaction mixture was stirred for 16 hours at 100° C. After completion of reaction, the reaction mixture was diluted with water (100 mL) and compound extracted in ethyl acetate (2×75 mL). The combined organic layers were dried over anhydrous sodium sulphate and concentrated under reduced pressure to get crude. The crude was purified by silica gel column chromatography on 0-30% ethyl acetate/petroleum ether as eluent system to afford tert-butyl 4-(4-bromophenyl)-3,6-dihydro-2H-pyridine-1-carboxylate (750 mg, 2.22 mmol, 62.73% yield) as yellow solid. LCMS (ESI+): 339.2 $[M+H]^+$ Step 2: A solution of tert-butyl 4-(4-bromophenyl)-3,6-dihydro-2H-pyridine-1-carboxylate (700 mg, 2.22 mmol) in 1,4-dioxane (15 mL) and water (5 mL) was taken up in a microwave vial and added 3-[3-[[ethyl(methyl)sulfamoyl]amino]-2,6-difluoro-benzoyl]-5-(4,4,5,5-tetramethyl-1,3,2-dioxaborolan-2-yl)-1H-pyrrolo[2,3-b]pyridine (1.15 g, 2.22 mmol) and potassium phosphate tribasic anhydrous (1.41 g, 6.65 mmol) at room temperature under nitrogen. The reaction mixture was degassed with nitrogen for 10 minutes, then added XPhos Pd G2 (174.46 mg, 221.74 μmol) at same temperature. The reaction mixture was irradiated under microwave at 120° C. for 1.5 hours. After completion, reaction mixture was diluted with water (30 mL) and extracted with ethyl acetate (3×50 mL). The combined organic layers were dried over sodium sulphate, filtered and concentrated under reduced pressure to get crude product. The obtained crude product was further purified by silica gel column chromatography with 50% ethyl acetate in petroleum ether as a eluent to afford tert-butyl 4-[4-[3-[3-[[ethyl(methyl)sulfamoyl]amino]-2,6-difluoro-benzoyl]-1H-pyrrolo[2,3-b]pyridin-5-yl]phenyl]-3,6-dihydro-2H-pyridine-1-carboxylate (380 mg, 368.26 µmol, 16.61% yield) as yellow solid. LCMS (ESI+): 652.2 $[M+H]^+$.

Step 3: To a stirred solution of tert-butyl 4-[4-[3-[3-[[ethyl(methyl)sulfamoyl]amino]-2,6-difluoro-benzoyl]-1H-pyrrolo[2,3-b]pyridin-5-yl]phenyl]-3,6-dihydro-2H-pyridine-1-carboxylate (400 mg, 613.76 µmol) in Dichloromethane (10 mL) was added TFA (209.94 mg, 1.84 mmol, 141.85 µL) at 0° C. The reaction mixture was stirred for 2 hours at 25° C. After completion of reaction, reaction mixture was concentrated to remove solvent and washed with diethyl ether (20 mL) to afford 3-[3-[[ethyl(methyl)sulfamoyl]amino]-2,6-difluoro-benzoyl]-5-[4-(1,2,3,6-tetrahydropyridin-4-yl)phenyl]-1H-pyrrolo[2,3-b]pyridine (300 mg, 355.15 µmol, 57.87% yield) as yellow solid, which was used without further purification. LCMS (ESI+): 552.2 $[M+H]^+$.

Step 4: Target compound was prepared via PyBOP mediated acid-amine coupling reaction (procedure D). Amide coupling was carried out using 2-[4-[4-[(2,6-dioxo-3-piperidyl)amino]phenyl]-1-piperidyl]acetic acid (103.78 mg, 271.78 µmop, 3-[3-[[ethyl(methyl)sulfamoyl]amino]-2,6-difluoro-benzoyl]-5-[4-(1,2,3,6-tetrahydropyridin-4-yl)phenyl]-1H-pyrrolo[2,3-b]pyridine (200 mg, 362.57 µmol), PyBOP (187.63 mg, 360.56 µmol), and N,N-diisopropylethylamine (194.16 mg, 1.50 mmol, 261.67 µL) to afford 5-[4-[1-[2-[4-[4-[(2,6-dioxo-3-piperidyl)amino]phenyl]-1-piperidyl]acetyl]-3,6-dihydro-2H-pyridin-4-yl]phenyl]-3-[3-[[ethyl(methyl)sulfamoyl]amino]-2,6-difluoro-benzoyl]-1H-pyrrolo[2,3-b]pyridine (75 mg, 76.46 µmol, 25.45% yield) as light yellow solid. LCMS (ESI+): 880.3 $[M+H]^+$. $^1H$ NMR (400 MHz, DMSO-$d_6$): δ 13.01 (s, 1H), 10.77 (s, 1H), 9.71 (s, 1H), 8.74 (s, 1H), 8.64 (s, 1H), 8.15 (s, 1H), 7.77 (d, J=8.40 Hz, 2H), 7.63-7.56 (m, 3H), 7.29 (t, J=8.00 Hz, 1H), 6.99-6.96 (m, 2H), 6.63 (d, J=8.40 Hz, 2H), 6.32 (s, 1H), 5.67 (d, J=7.20 Hz, 1H), 4.32-4.25 (m, 2H), 4.17 (s, 1H), 3.79-3.75 (m, 2H), 3.33-3.09 (m, 6H), 2.73 (s, 3H), 2.71-2.67 (m, 2H), 2.61-2.43 (m, 4H), 2.11-2.08 (m, 1H), 1.88-1.69 (m, 6H), 1.02 (t, J=7.20 Hz, 3H).

Example 93

5-[4-[4-[2-[4-[4-[(2,6-dioxo-3-piperidyl)amino]phenyl]-1-piperidyl]acetyl]piperazin-1-yl]-3,5-difluoro-phenyl]-3-[3-[[ethyl(methyl)sulfamoyl]amino]-2,6-difluoro-benzoyl]-1H-pyrrolo[2,3-b]pyridine

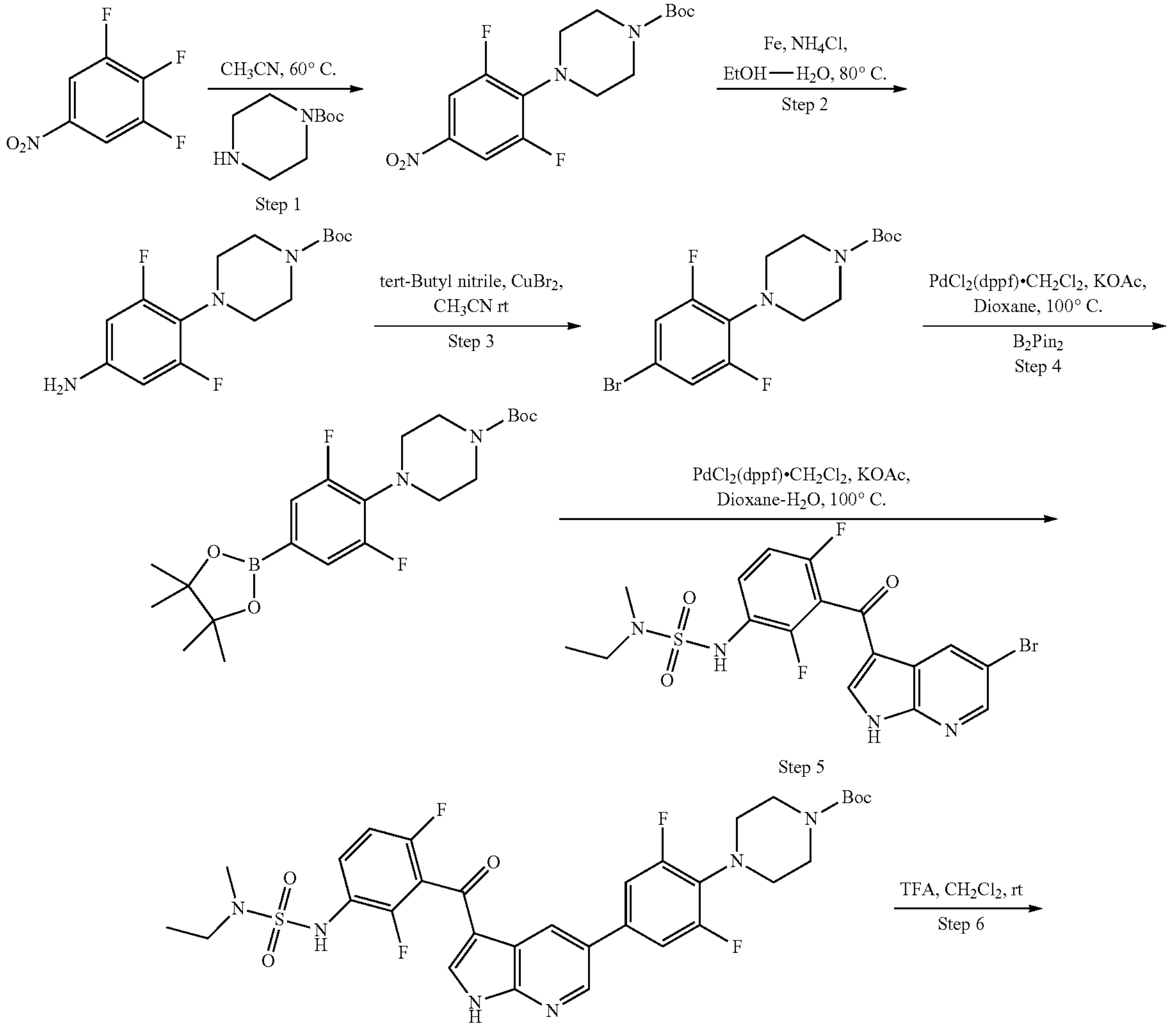

-continued

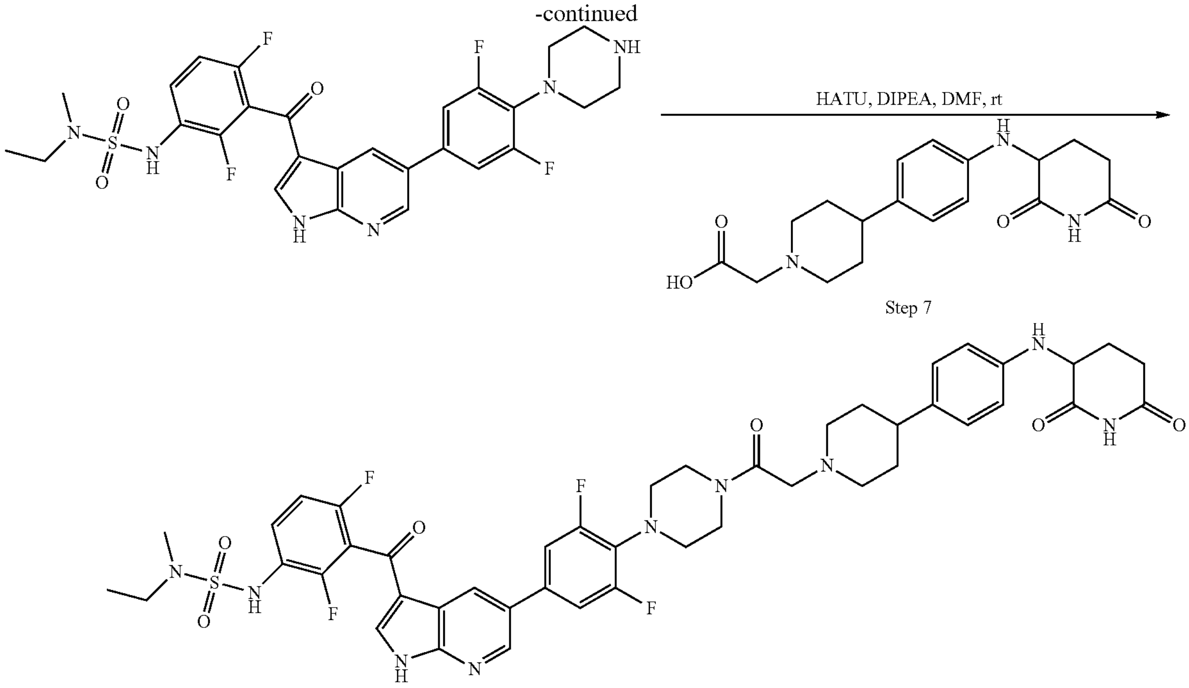

Step 1: To a solution of 1,2,3-trifluoro-5-nitro-benzene (2.0 g, 11.29 mmol) in acetonitrile (20 mL) was added tert-butyl piperazine-1-carboxylate (4.21 g, 22.59 mmol) at room temperature. The resulting solution was heated to 60° C. for 12 hours. After completion, the resulting solution was cooled to room temperature, concentrated under reduced pressure. The crude compound was purified by silica gel column chromatography with 30% ethyl acetate in petroleum ether as a eluent to afford tert-butyl 4-(2,6-difluoro-4-nitro-phenyl)piperazine-1-carboxylate (3.5 g, 10.18 mmol, 90.15% yield) as a yellow solid. LCMS (ESI+): 244.1 $[M+H-100]^+$ Step 2: To a solution of tert-butyl 4-(2,6-difluoro-4-nitrophenyl)piperazine-1-carboxylate (1.5 g, 4.37 mmol) in ethanol (15 mL) and water (1.5 mL) was added iron powder (731.97 mg, 13.11 mmol) and ammonium chloride (584.27 mg, 10.92 mmol) at room temperature under nitrogen. The resulting solution was heated to 80° C. for 4 hours. After completion, the resulting solution was cooled to room temperature, filtered through a celite bed and washed with ethyl acetate (50 ml). The collected filtrates were concentrated under reduced pressure. The crude compound was purified by silica gel column chromatography with 40% ethyl acetate in petroleum ether as a eluent to afford tert-butyl 4-(4-amino-2,6-difluoro-phenyl)piperazine-1-carboxylate (1.0 g, 3.03 mmol, 69.42% yield) as a greenish solid. LCMS (ESI+): 314.0 $[M+H]^+$.

Step 3: To a solution of copper(II) bromide (962.30 mg, 4.31 mmol) in acetonitrile (9 mL) was added tert-butyl nitrite (592.37 mg, 5.74 mmol, 683.25 and tert-butyl 4-(4-amino-2,6-difluoro-phenyl)piperazine-1-carboxylate (0.9 g, 2.87 mmol) at 0° C. under nitrogen. The resulting solution was stirred at rt for 5 hours. After completion, the resulting solution was quenched with 10% aqueous $NaHCO_3$ solution (10 mL), and extracted with Ethyl acetate (2×20 ml). The separated organic layer was concentrated under reduced pressure. The crude compound was purified by silica gel column chromatography with 40% ethyl acetate in petroleum ether as a eluent to afford tert-butyl 4-(4-bromo-2,6-difluoro-phenyl)piperazine-1-carboxylate (0.55 g, 976.44 μmol, 34.00% yield) as a red solid. LCMS (ESI+): 276.8 $[M+H-100]^+$.

Step 4: To a solution of tert-butyl 4-(4-bromo-2,6-difluoro-phenyl)piperazine-1-carboxylate (0.55 g, 1.46 mmol) in 1,4-dioxane (10 mL) and water (0.1 mL) was added potassium acetate (429.28 mg, 4.37 mmol), bis(pinacolato) diboron (555.37 mg, 2.19 mmol) at room temperature under nitrogen. The reaction mixture was degassed with nitrogen for 10 minutes, then added [1,1'-Bis(diphenylphosphino) ferrocene]dichloropalladium(II), complex with dichloromethane (119.07 mg, 145.80 μmol) at same temperature. The resulting solution was heated to 95° C. for 4 hours. After completion, the resulting solution was cooled to room temperature, filtered through a celite bed and washed with ethyl acetate (60 ml). The collected filtrates were concentrated under reduced pressure. The crude compound was purified by silica gel column chromatography with 40% ethyl acetate in petroleum ether as a eluent to afford tert-butyl 4-[2,6-difluoro-4-(4,4,5,5-tetramethyl-1,3,2-dioxaborolan-2-yl) phenyl]piperazine-1-carboxylate (0.32 g, 587.52 μmol, 40.30% yield) as a red solid. LCMS (ESI+): 425.0 $[M+H]^+$.

Step 5: To a solution of 5-bromo-3-[3-[[ethyl(methyl) sulfamoyl]amino]-2,6-difluoro-benzoyl]-1H-pyrrolo[2,3-b] pyridine (0.3 g, 633.86 μmol) in 1,4-dioxane (3 mL) and water (0.3 mL) was added sodium carbonate (201.55 mg, 1.90 mmol) and tert-butyl 4-[2,6-difluoro-4-(4,4,5,5-tetramethyl-1,3,2-dioxaborolan-2-yl)phenyl]piperazine-1-carboxylate (322.73 mg, 760.63 μmol) at room temperature under nitrogen. The reaction mixture was degassed with nitrogen for 10 minutes, then added [1,1'-Bis(diphenylphosphino)ferrocene]dichloropalladium(II), complex with dichloromethane (51.76 mg, 63.39 μmol) at same temperature. The resulting solution was heated to 100° C. for 12 hours. After completion, the resulting solution was cooled to room temperature, filtered through a celite bed and washed with ethyl acetate (50 ml). The collected filtrates were concentrated under reduced pressure. The crude compound was purified by silica gel column chromatography with 40% ethyl acetate in petroleum ether as a eluent to afford tert-butyl 4-[4-[3-[3-[[ethyl(methyl)sulfamoyl]amino]-2,6-difluoro-benzoyl]-1H-pyrrolo[2,3-b]pyridin-5-yl]-2,6-difluoro-phenyl]piperazine-1-carboxylate (0.24 g, 320.09 µmol, 50.50% yield) as a pale red solid. LCMS (ESI+): 691.3 $[M+H]^+$.

Step 6: To a solution of tert-butyl 4-[4-[3-[3-[[ethyl (methyl)sulfamoyl]amino]-2,6-difluoro-benzoyl]-1H-pyrrolo[2,3-b]pyridin-5-yl]-2,6-difluoro-phenyl]piperazine-1-carboxylate (0.24 g, 347.47 µmol) in Dichloromethane (3 mL) was added trifluoroacetic acid (396.20 mg, 3.47 mmol, 267.70 µL) at room temperature under nitrogen. The resulting solution was stirred at room temperature for 2 hours. After completion, resulting solution was concentrated under reduced pressure. The resulting crude product 5-(3,5-difluoro-4-piperazin-1-yl-phenyl)-3-[3-[[ethyl(methyl)sulfamoyl]amino]-2,6-difluoro-benzoyl]-1H-pyrrolo[2,3-b]pyridine (0.22 g, 276.70 µmol, 79.63% yield) was as such taken for next step without purification. LCMS (ESI+): 591.1 $[M]^+$.

Step 7: To a solution of 5-(3,5-difluoro-4-piperazin-1-yl-phenyl)-3-[3-[[ethyl(methyl)sulfamoyl]amino]-2,6-difluoro-benzoyl]-1H-pyrrolo[2,3-b]pyridine (0.2 g, 283.84 µmol) in N,N-Dimethylformamide (2 mL) was added 2-[4-[4-[(2,6-dioxo-3-piperidyl)amino]phenyl]-1-piperidyl]acetic acid (98.04 mg, 213.40 µmol) and N,N-Diisopropylethylamine (183.42 mg, 1.42 mmol, 247.20 µL) at room temperature under nitrogen, followed by addition of HATU (161.89 mg, 425.76 µmol) at same temperature. The resulting solution was stirred at room temperature for 5 hours. After completion, resulting solution was concentrated under reduced pressure. The crude product was purified by mass-directed preparative HPLC [Mobile-phase A: 0.1% TFA in water, Mobile-phase B: Acetonitrile] to get the 5-[4-[4-[2-[4-[4-[(2,6-dioxo-3-piperidyl)amino]phenyl]-1-piperidyl] acetyl]piperazin-1-yl]-3,5-difluoro-phenyl]-3-[3-[[ethyl (methyl)sulfamoyl]amino]-2,6-difluoro-benzoyl]-1H-pyrrolo[2,3-b]pyridine (90 mg, 85.19 µmol, 30.01% yield, trifluoroacetic acid salt) as an off-white solid. LCMS (ESI+): 918.2 $[M+H]^+$. $^1H$ NMR (400 MHz, DMSO-$d_6$): δ 10.80 (s, 1H), 9.71 (s, 1H), 9.51 (bs, 1H), 8.75 (d, J=2.4 Hz, 1H), 8.64 (s, 1H), 8.17 (s, 1H), 7.59-7.55 (m, 3H), 7.28-7.25 (m, 1H), 6.99-6.97 (m, 2H), 6.67-6.65 (m, 2H), 4.60-4.56 (m, 1H), 4.55-4.32 (m, 2H), 3.78-3.72 (m, 2H), 3.68-3.52 (m, 4H), 3.42-3.25 (m, 2H), 3.22-3.12 (m, 6H), 2.75 (s, 3H), 2.68-2.55 (m, 3H), 2.22-1.78 (m, 6H), 1.02 (t, J=7.2 Hz, 3H).

Example 94

5-[4-[[4-[2-[4-[4-[(2,6-dioxo-3-piperidyl)amino] phenyl]-1-piperidyl]-2-oxo-ethyl]piperazin-1-yl] methyl]phenyl]-3-[3-[[ethyl(methyl)sulfamoyl] amino]-2,6-difluoro-benzoyl]-1H-pyrrolo[2,3-b] pyridine

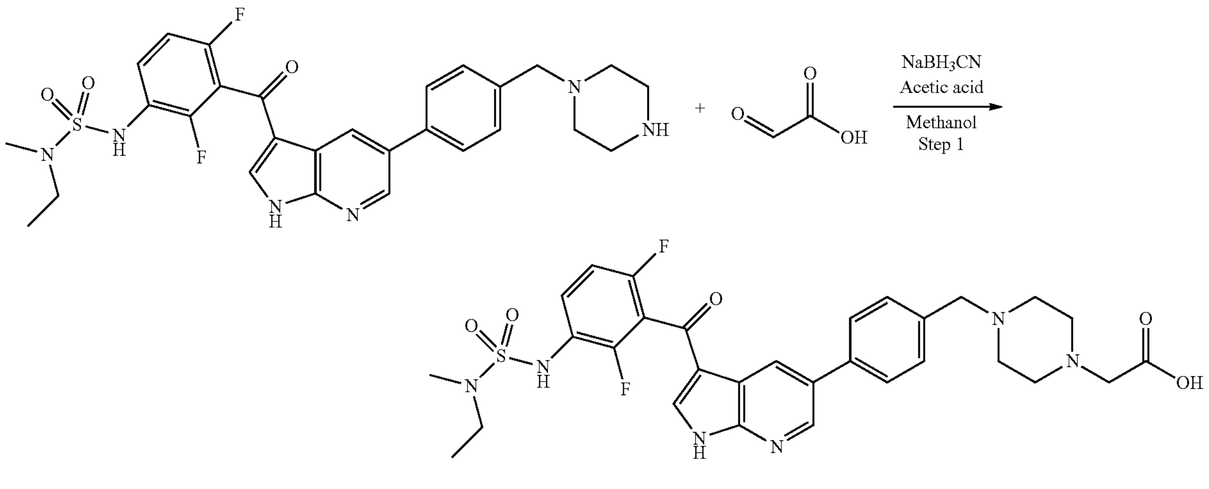

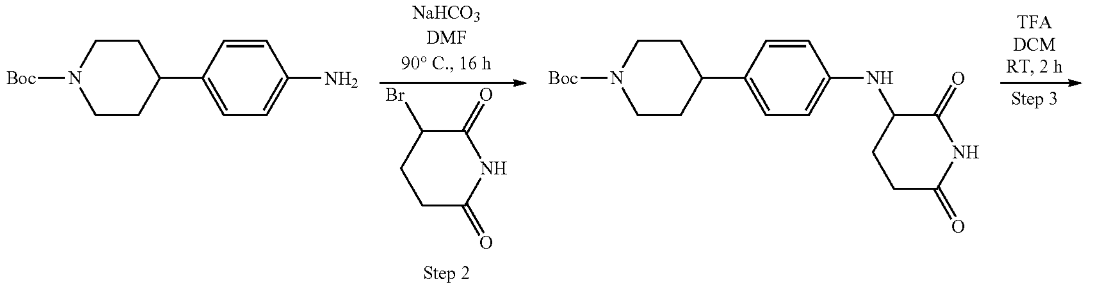

-continued

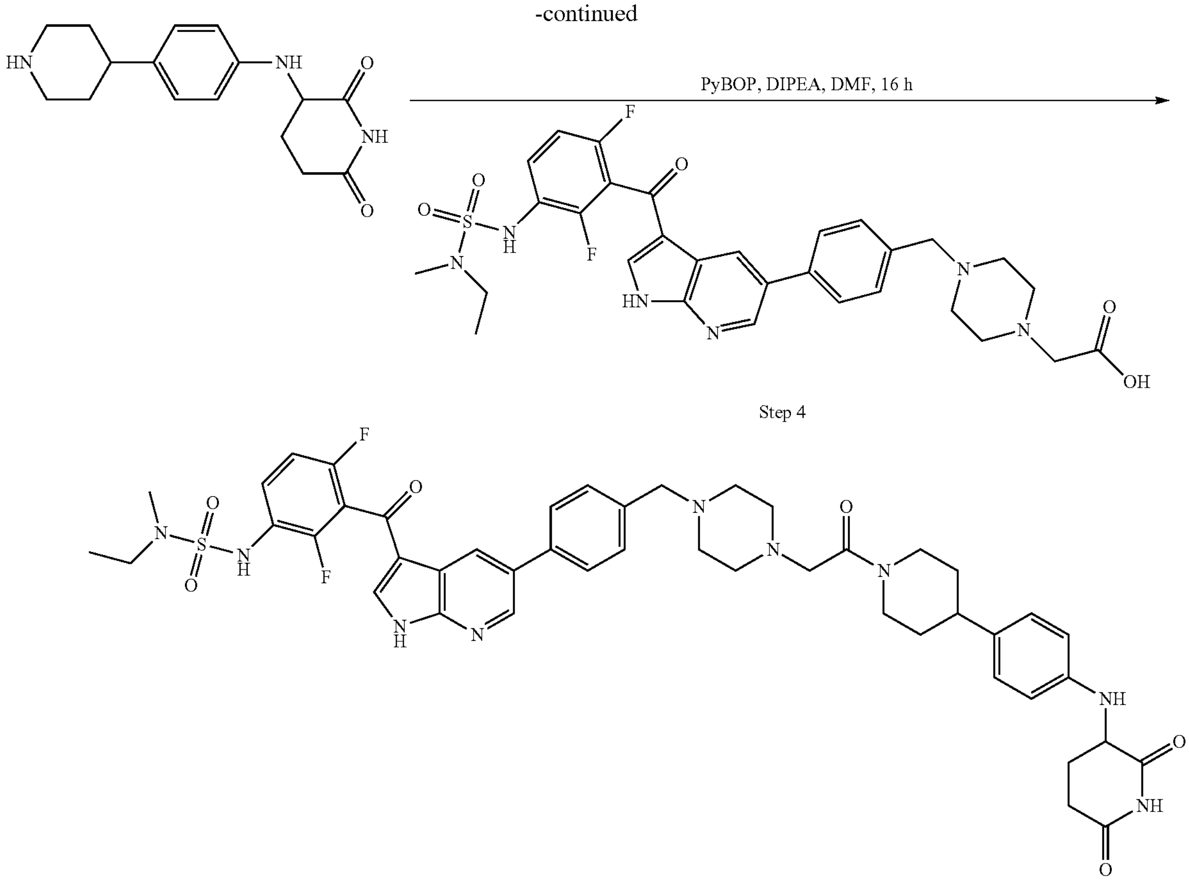

Step 1: To a stirred solution of 3-[3-[[ethyl(methyl)sulfamoyl]amino]-2,6-difluoro-benzoyl]-5-[4-(piperazin-1-ylmethyl)phenyl]-1H-pyrrolo[2,3-b]pyridine (200 mg, 351.72 μmol) and glyoxalic acid monohydrate (64.75 mg, 703.44 μmol) in methanol (4 mL) was added sodium cyanoborohydride (53.05 mg, 844.12 μmol) and a catalytic amount of acetic acid. The reaction mixture was stirred at room temperature for 12 h. After completion, the reaction mixture was concentrated under reduced pressure to give crude compound 2-[4-[[4-[3-[3-[[ethyl(methyl)sulfamoyl]amino]-2,6-difluoro-benzoyl]-1H-pyrrolo[2,3-b]pyridin-5-yl]phenyl]methyl]piperazin-1-yl]acetic acid (200 mg, 244.50 μmol, 69.52% yield) as off-white solid. LCMS (ESI+): 627.0 $[M+H]^+$.

Step 2: To a stirred solution of tert-butyl 4-(4-aminophenyl)piperidine-1-carboxylate (1.5 g, 5.43 mmol) in N,N-Dimethylformamide (15 mL) was added 3-bromopiperidine-2,6-dione (2.08 g, 10.85 mmol) and sodium bicarbonate (1.37 g, 16.28 mmol, 633.25 μL) at room temperature. The reaction mixture was stirred at 90° C. for 16 h. After completion, the reaction mixture was diluted with water and extracted with ethyl acetate (3×200 mL), washed the organic layer with brine solution. The combined organic layers were dried over sodium sulphate and concentrated under reduced pressure. Crude product obtained was purified by silica gel column chromatography using 30% ethyl acetate in petroleum ether as eluent to afford 3-[4-(4-piperidyl)anilino]piperidine-2,6-dione (540 mg, 1.68 mmol, 30.95% yield) as off-white solid. LCMS (ESI+): 332.4 $[M+H-56]^+$.

Step 3: To a stirred solution of tert-butyl 4-[4-[(2,6-dioxo-3-piperidyl)amino]phenyl]piperidine-1-carboxylate (540 mg, 1.39 mmol) in dichloromethane (10 mL) was added trifluoroacetic acid (2.22 g, 19.47 mmol, 1.5 mL) at 0° C. and the resulting reaction mixture was stirred for 2 h at room temperature. Reaction mixture was concentrated under reduced pressure. The residue obtained was co-distilled with toluene (2×50 mL), dried under reduced pressure to afford 3-[4-(4-piperidyl)anilino]piperidine-2,6-dione (700 mg, 2.19 mmol) as pale green sticky compound. LCMS (ESI+): 288.2 $[M+H]^+$.

Step 4: To a stirred solution of 2-[4-[[4-[3-[3-[[ethyl(methyl)sulfamoyl]amino]-2,6-difluoro-benzoyl]-1H-pyrrolo[2,3-b]pyridin-5-yl]phenyl]methyl]piperazin-1-yl]acetic acid (20 mg, 31.91 μmol) in N,N-Dimethylformamide (0.5 mL) was added 3-[4-(4-piperidyl)anilino]piperidine-2,6-dione (9.17 mg, 31.91 μmol) and N,N-Diisopropylethylamine (20.62 mg, 159.57 μmol, 27.79 μL) at room temperature under nitrogen, followed by the addition of PyBOP (19.93 mg, 38.30 μmol). The reaction mixture was stirred at room temperature for 16 h. After completion, the reaction mixture was diluted with water (1.0 mL), extracted with ethyl acetate (3×1.5 mL). The combined organics were removed under Genevac at 50° C. (1 bar pressure) for 3 h. The obtained crude product was purified by mass-directed preparative HPLC [Mobile-phase A: 0.1% TFA in water, Mobile-phase B: Acetonitrile, Wave length: 215 nm, Column: Sunfire C18 OBD (19 mm×100 mm; 5 micron)] to give 5-[4-[[4-[2-[4-[4-[(2,6-dioxo-3-piperidyl)amino]phenyl]-1-piperidyl]-2-oxo-ethyl]piperazin-1-yl]methyl]phenyl]-3-[3-[[ethyl(methyl)sulfamoyl]amino]-2,6-difluoro-benzoyl]-1H-pyrrolo[2,3-b]pyridine (3.78 mg, 3.72 μmol, 11.65% yield) as off-white solid. LCMS (ESI+): 896.8 $[M+H]^+$. $^1H$ NMR (400 MHz, DMSO-$d_6$): δ 13.04 (s, 1H), 10.78 (s, 1H), 9.71 (s, 1H), 8.74 (s, 1H), 8.64 (s, 1H), 8.17 (d, J=2.20 Hz, 1H), 7.84-7.83 (m, 2H), 7.59-7.58 (m, 3H), 7.28-7.27 (m, 1H), 6.96 (d, J=8.36 Hz, 2H), 6.63 (d, J=8.40 Hz, 2H), 4.47-4.55 (m, 1H), 4.29-4.25 (m, 2H), 3.82-3.75 (m, 3H), 3.15-3.11 (m, 6H), 3.09-3.02 (m, 4H), 2.74 (s, 3H), 2.71-2.68 (m, 3H), 2.08-2.06 (m, 1H), 1.86-1.72 (m, 6H), 1.64-1.52 (m, 1H), 1.45-1.35 (m, 1H), 1.03 (t, J=7.12 Hz, 3H).

Example 95

5-[4-[[4-[2-[4-[4-[(2,6-dioxo-3-piperidyl)amino]phenyl]piperazin-1-yl]acetyl]piperazin-1-yl]methyl]phenyl]-3-[3-[[ethyl(methyl)sulfamoyl]amino]-2,6-difluoro-benzoyl]-1H-pyrrolo[2,3-b]pyridine Step 1: To a stirred solution of tert-butyl 4-(4-aminophenyl)piperazine-1-carboxylate (0.7 g, 2.52 mmol) in N,N-dimethylformamide (10 mL) were added Sodium bicarbonate (530.03 mg, 6.31 mmol, 245.39 μL) followed by 3-bromopiperidine-2,6-dione (969.18 mg, 5.05 mmol) at room temperature under nitrogen atmosphere. The reaction mixture was heated at 80° C. for 12 h. Reaction mixture was cooled to room temperature, added to water (40 mL) and extracted with ethyl acetate (2×40 mL). The combined organic layers were washed with brine (40 mL), dried over sodium sulphate, filtered and concentrated under reduced pressure. The crude product was purified by silica gel column chromatography using 40% ethyl acetate in petroleum ether as an eluent to afford tert-butyl 4-[4-[(2,6-dioxo-

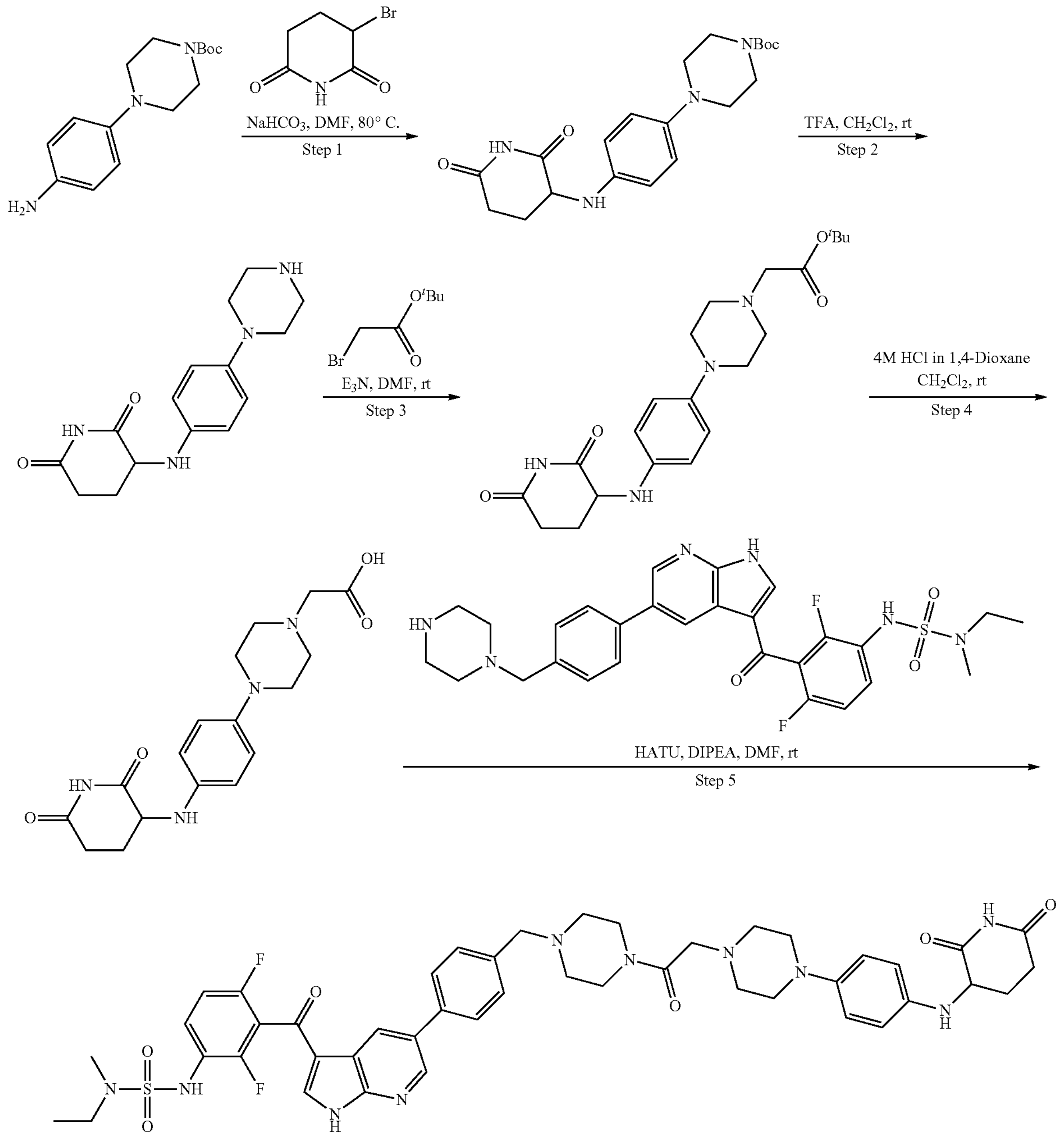

3-piperidyl)amino]phenyl]piperazine-1-carboxylate (0.48 g, 1.03 mmol, 40.86% yield) as a dark green solid. LCMS (ESI+): 389.5 $[M+H]^+$.

Step 2: To a stirred solution of tert-butyl 4-[4-[(2,6-dioxo-3-piperidyl)amino]phenyl]piperazine-1-carboxylate (480 mg, 1.24 mmol) in dichloromethane (10 mL) was added TFA (1.48 g, 12.98 mmol, 1 mL) at 0° C. The reaction mixture was warmed to room temperature and stirred for 1 h. The reaction mixture was concentrated under reduced pressure. The resulting crude product was triturated with pentane/diethyl ether (1:1) and dried to afford 3-(4-piperazin-1-ylanilino)piperidine-2,6-dione (600 mg, crude) as a brown solid. LCMS (ESI+): 289.3 $[M+H]^+$.

Step 3: To a stirred solution of 3-(4-piperazin-1-ylanilino) piperidine-2,6-dione (0.2 g, 693.62 μmol) in N,N-dimethylformamide (3.0 mL) were added Triethylamine (448.23 mg, 4.43 mmol, 617.39 μL) followed by tert-butyl 2-bromoacetate (162.35 mg, 832.34 μmol, 122.07 μL) at room temperature under nitrogen atmosphere. The reaction mixture was heated at 80° C. for 12 h. Reaction mixture was cooled to room temperature, added to water (30 mL) and extracted with ethyl acetate (2×30 mL). The combined organic layers were washed with ice water (2×30 mL), dried over sodium sulphate, filtered and concentrated under reduced pressure. The crude product was purified by silica gel column chromatography using 60% ethyl acetate in petroleum ether as an eluent to afford tert-butyl 2-[4-[4-[(2,6-dioxo-3-piperidyl) amino]phenyl]piperazin-1-yl]acetate (80 mg, 192.32 μmol, 27.73% yield) as a light brown solid. LCMS (ESI+): 403.2 $[M+H]^+$.

Step 4: To a stirred solution of tert-butyl 2-[4-[4-[(2,6-dioxo-3-piperidyl)amino]phenyl]piperazin-1-yl]acetate (80.0 mg, 198.76 μmol) in dichloromethane (6.0 mL) was added 4 M HCl in 1,4-dioxane (198.76 μmol, 3 mL) at 0° C. The reaction mixture was warmed to room temperature and stirred for 12 h. Reaction mixture was concentrated under reduced pressure, and the resulting crude product was triturated with pentane/diethyl ether(1:1) and dried to afford 2-[4-[4-[(2,6-dioxo-3-piperidyl)amino]phenyl]piperazin-1-yl]acetic acid (60.0 mg, crude) as a green solid. LCMS (ESI+): 347.1 $[M+H]^+$.

Step 5: Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-[4-(piperazin-1-ylmethyl)phenyl]-1H-pyrrolo[2,3-b]pyridine (20 mg, 35.17 μmol), 2-[4-[4-[(2,6-dioxo-3-piperidyl)amino]phenyl]piperazin-1-yl]acetic acid (12.18 mg, 35.17 μmol), N,N-diisopropylethylamine (22.73 mg, 175.86 μmol, 30.63 μL) and HATU (16.05 mg, 42.21 μmol) to afford 5-[4-[[4-[2-[4-[4-[(2,6-dioxo-3-piperidyl)amino]phenyl]piperazin-1-yl] acetyl]piperazin-1-yl]methyl]phenyl]-3-[3-[[ethyl(methyl) sulfamoyl]amino]-2,6-difluoro-benzoyl]-1H-pyrrolo[2,3-b] pyridine (13.65 mg, 15.01 μmol, 42.69% yield) as yellow solid. LCMS (ESI+): 897.8 $[M+H]^+$. $^1H$ NMR (400 MHz, DMSO-$d_6$): δ 13.08 (s, 1H), 10.79 (s, 1H), 10.00 (s, 1H), 9.73 (s, 1H), 8.77 (d, J=2.00 Hz, 1H), 8.70 (s, 1H), 8.19 (d, J=2.80 Hz, 2H), 7.91 (d, J=8.00 Hz, 1H), 7.63 (dd, J=6.00, 14.80 Hz, 2H), 7.58 (dd, J=6.00, 8.80 Hz, 1H), 7.29 (t, J=8.40 Hz, 1H), 6.83 (d, J=8.00 Hz, 2H), 6.66 (d, J=8.80 Hz, 2H), 4.40-4.22 (m, 6H), 3.17-3.11 (m, 9H), 3.12 (q, J=7.12 Hz, 2H), 2.74 (s, 3H), 2.72-2.57 (m, 8H), 2.12-2.08 (m, 1H), 1.88-1.84 (m, 1H), 1.03 (t, J=7.12 Hz, 3H).

Example 96-106

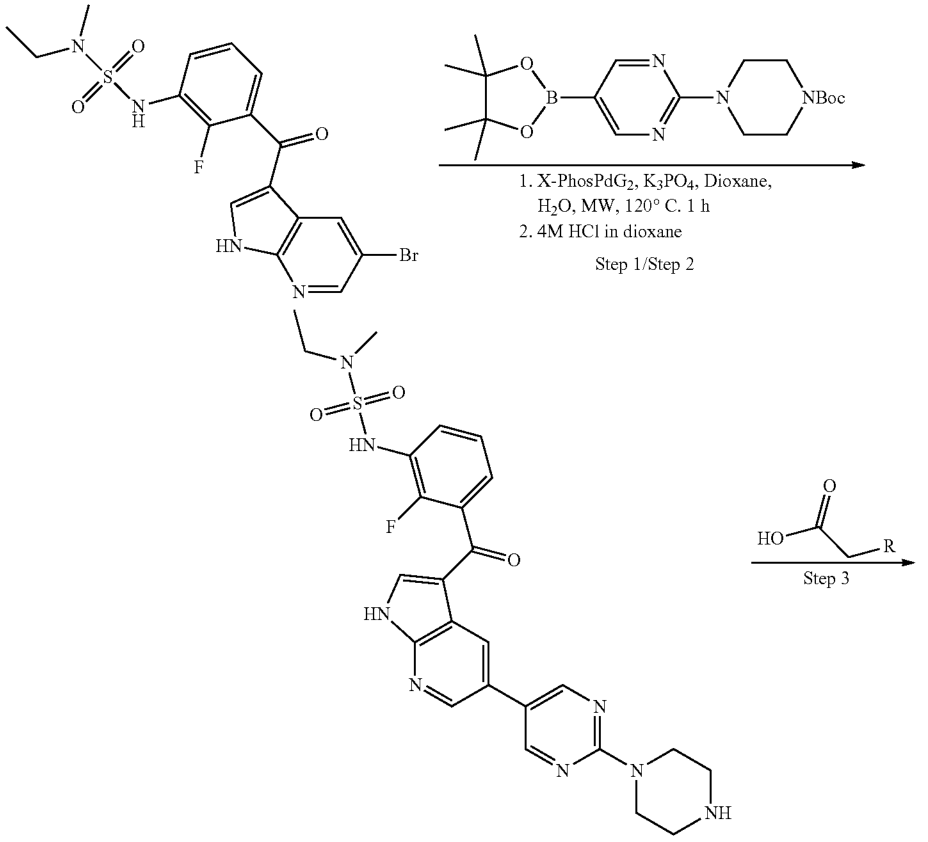

-continued

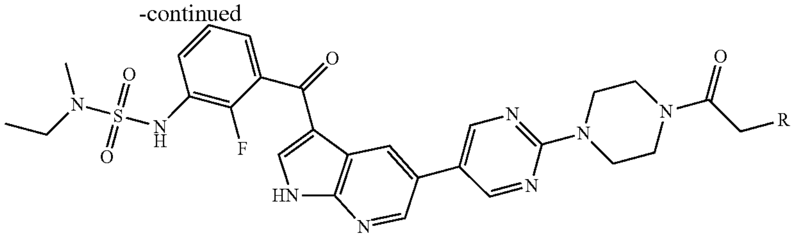

Synthesis of intermediate 3-[3-[[ethyl(methyl)sulfamoyl]amino]-2-fluoro-benzoyl]-5-(2-piperazin-1-ylpyrimidin-5-yl)-1H-pyrrolo[2,3-b]pyridine Step 1: To a solution of 5-bromo-3-[3-[[ethyl(methyl)sulfamoyl]amino]-2-fluoro-benzoyl]-1H-pyrrolo[2,3-b]pyridine (700 mg, 1.54 mmol) in 1,4-dioxane (10 mL) and water (2 mL) in a microwave vial was added tert-butyl 4-[5-(4,4,5,5-tetramethyl-1,3,2-dioxaborolan-2-yl)pyrimidin-2-yl]piperazine-1-carboxylate (600.04 mg, 1.54 mmol), Potassium phosphate tribasic (anhydrous) (979.06 mg, 4.61 mmol) at room temperature under nitrogen atmosphere. The reaction mixture was degassed with nitrogen for 10 minutes and added XPhos Pd G2 (120.74 mg, 153.74 μmol). The reaction mixture was irradiated under microwave at 100° C. for 1 h. After completion of the reaction, the reaction mixture was diluted with water (60 mL) and extracted with ethyl acetate (2×100 mL). The combined organic layers were dried over sodium sulphate, filtered and concentrated under reduced pressure. The crude compound was purified by silica gel column chromatography with 70% ethyl acetate in petroleum ether as eluent to afford tert-butyl-4-[5-[3-[3-[[ethyl(methyl)sulfamoyl]amino]-2-fluoro-benzoyl]-1H-pyrrolo[2,3-b]pyridin-5-yl]pyrimidin-2-yl]piperazine-1-carboxylate (610 mg, 725.84 μmol, 47.21% yield) as a yellow solid. LCMS (ESI+): 639.3 $[M+H]^+$. $^1H$ NMR (400 MHz, DMSO-$d_6$): δ 12.87 (bs, 1H), 9.75 (bs, 1H), 8.77 (s, 2H), 8.64 (d, J=2.80 Hz, 1H), 8.56 (d, J=2.80 Hz, 1H), 7.97 (s, 1H), 7.61-7.55 (m, 1H), 7.38-7.27 (m, 2H), 3.92-3.78 (m, 4H), 3.43-3.38 (m, 4H), 3.12 (qt, J=9.60 Hz, 2H), 2.73 (s, 3H), 1.43 (s, 9H), 1.03 (t, J=9.60 Hz, 3H).

Step 2: To a stirred solution of tert-butyl 4-[5-[3-[3-[[ethyl(methyl)sulfamoyl]amino]-2-fluoro-benzoyl]-1H-pyrrolo[2,3-b]pyridin-5-yl]pyrimidin-2-yl]piperazine-1-carboxylate (610 mg, 955.05 μmol) in 1,4-dioxane (3 mL) was added 4M HCl in 1,4-dioxane (955.05 μmol, 4 mL) and stirred the reaction mixture at room temperature for 4 h. The reaction mixture was concentrated under reduced pressure to afford 3-[3-[[ethyl(methyl)sulfamoyl]amino]-2-fluoro-benzoyl]-5-(2-piperazin-1-ylpyrimidin-5-yl)-1H-pyrrolo[2,3-b]pyridine (600 mg, 845.13 μmol, 88.49% yield) as light brown solid. LCMS (ESI+): 539.2 $[M+H]^+$.

Example 96

5-[2-[4-[2-[4-[4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine

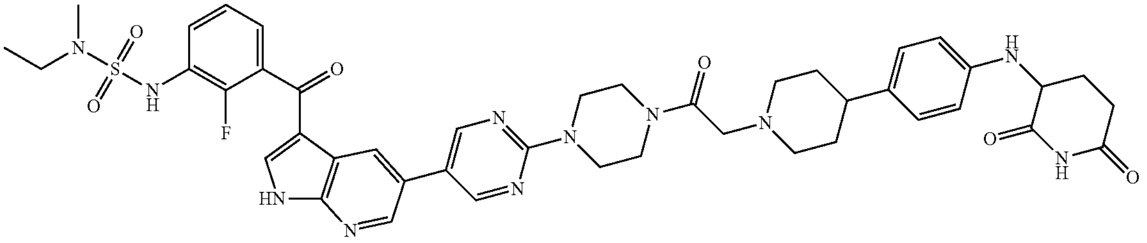 [SMILES: CCN(C)S(=O)(=O)Nc1cccc(C(=O)c2c[nH]c3ncc(-c4cnc(N5CCN(C(=O)CN6CCC(c7ccc(NC8CCC(=O)NC8=O)cc7)CC6)CC5)nc4)cc23)c1F]

Target compound was prepared via COMU mediated acid-amine coupling reaction (procedure B). Amide coupling was carried out using 3-[3-[[ethyl(methyl)sulfamoyl]amino]-2-fluoro-benzoyl]-5-(2-piperazin-1-ylpyrimidin-5-yl)-1H-pyrrolo[2,3-b]pyridine (70 mg, 129.97 μmol), 2-[4-[4-[(2,6-dioxo-3-piperidyl)amino]phenyl]-1-piperidyl]acetic acid (44.89 mg, 129.97 μmol), N,N-Diisopropylethylamine (50.39 mg, 389.90 μmol, 67.91 μL) and COMU (83.49 mg, 194.95 μmol) to afford 5-[2-[4-[2-[4-[4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine (11.4 mg, 12.56 μmol, 9.66% yield) as pale pink solid. LCMS (ESI+): 866.2 $[M+H]^+$. $^1H$ NMR (400 MHz, DMSO-$d_6$): δ 12.88 (bs, 1H), 10.77 (s, 1H), 9.78 (bs, 1H), 8.79 (s, 2H), 8.66 (d, J=2.40 Hz, 1H), 8.58 (d, J=2.40 Hz, 1H), 7.99 (s, 1H), 7.61 (t, J=6.0 Hz, 1H), 7.40-7.32 (m, 2H), 6.97 (d, J=8.8 Hz, 2H), 6.62 (d, J=8.8 Hz, 2H), 5.66 (d, J=7.6 Hz, 1H), 4.26-4.24 (m, 1H), 3.89-3.81 (m, 4H), 3.80-3.71 (m, 2H), 3.63-3.58 (m, 2H), 3.33-3.22 (m, 2H), 3.12 (qt, J=9.60 Hz, 2H), 2.97-2.95 (m, 2H), 2.73 (s, 3H), 2.70-2.67 (m, 1H), 2.60-2.59 (m, 1H), 2.20-2.05 (m, 3H), 1.90-1.82 (m, 1H), 1.78-1.72 (m, 2H), 1.68-1.52 (m, 2H), 1.02 (t, J=7.2 Hz, 3H).

Example 97

5-[2-[4-[2-[4-[4-[(2,6-dioxo-3-piperidyl)amino]-2-fluoro-phenyl]-1-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine

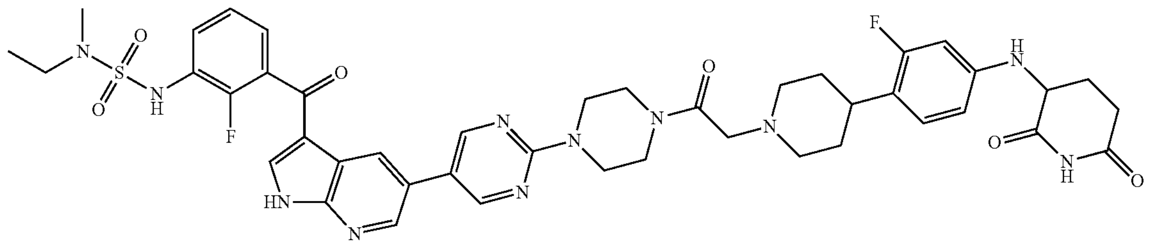 [SMILES: CCN(C)S(=O)(=O)Nc1cccc(C(=O)c2c[nH]c3ncc(-c4cnc(N5CCN(C(=O)CN6CCC(c7ccc(NC8CCC(=O)NC8=O)cc7F)CC6)CC5)nc4)cc23)c1F]

Target compound was prepared via HATU mediated acid-amine coupling reaction (procedure A). Amide coupling was carried out using 3-[3-[[ethyl(methyl)sulfamoyl]amino]-2-fluoro-benzoyl]-5-(2-piperazin-1-ylpyrimidin-5-yl)-1H-pyrrolo[2,3-b]pyridine (200 mg, 347.79 μmol), 2-[4-[4-[(2,6-dioxo-3-piperidyl)amino]-2-fluoro-phenyl]-1-piperidyl] acetic acid (126.38 mg, 316.08 μmol), DIPEA (179.79 mg, 1.39 mmol, 242.31 μL) and HATU (132.24 mg, 347.79 μmol) to afford 5-[2-[4-[2-[4-[4-[(2,6-dioxo-3-piperidyl)amino]-2-fluoro-phenyl]-1-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine (35 mg, 36.84 μmol, 10.59% yield) as off white solid. LCMS (ESI+): 884.2 $[M+H]^+$. $^1H$ NMR (400 MHz, DMSO-$d_6$): δ 10.78 (s, 1H), 8.80 (s, 2H), 8.67 (d, J=2.40 Hz, 1H), 8.59 (d, J=2.40 Hz, 1H), 8.16 (s, 1H), 7.99 (s, 1H), 7.62-7.60 (m, 1H), 7.41-7.39 (m, 1H), 7.39-7.37 (m, 1H), 7.00 (t, J=9.2 Hz, 1H), 6.48-6.42 (m, 2H), 6.00 (d, J=7.6 Hz, 1H), 4.40-4.30 (m, 1H), 3.89-3.82 (m, 4H), 3.71-3.69 (m, 2H), 3.61-3.59 (m, 2H), 3.33-3.22 (m, 2H), 3.15 (qt, J=7.2 Hz, 2H), 3.05-2.98 (m, 2H), 2.72 (s, 3H), 2.65-2.55 (m, 2H), 2.30-2.15 (m, 2H), 2.12-2.05 (m, 1H), 1.82-1.72 (m, 1H), 1.75-1.65 (m, 4H), 1.68-1.52 (m, 2H), 1.02 (t, J=7.2 Hz, 3H).

Example 98

5-[2-[4-[2-[1-[4-[(2,6-dioxo-3-piperidyl)amino]-2-fluoro-phenyl]-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine

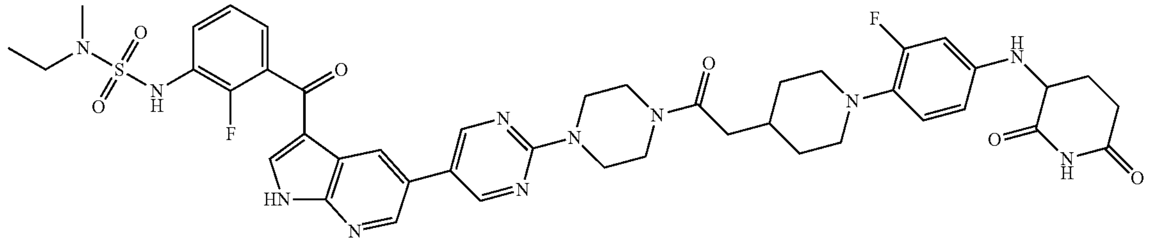 [SMILES: CCN(C)S(=O)(=O)Nc1cccc(C(=O)c2c[nH]c3ncc(-c4cnc(N5CCN(C(=O)CC6CCN(c7ccc(NC8CCC(=O)NC8=O)cc7F)CC6)CC5)nc4)cc23)c1F]

Target compound was prepared via HATU mediated acid-amine coupling reaction (procedure A). Amide coupling was carried out using 3-[3-[[ethyl(methyl)sulfamoyl]amino]-2-fluoro-benzoyl]-5-(2-piperazin-1-ylpyrimidin-5-yl)-1H-pyrrolo[2,3-b]pyridine (200 mg, 347.79 μmol), 2-[1-[4-[(2,6-dioxo-3-piperidyl)amino]-2-fluoro-phenyl]-4-piperidyl] acetic acid (126.38 mg, 316.08 μmol), N,N-Diisopropylethylamine (179.80 mg, 1.39 mmol, 242.32 μL) and HATU (132.24 mg, 347.79 μmol) to afford 5-[2-[4-[2-[1-[4-[(2,6-dioxo-3-piperidyl)amino]-2-fluoro-phenyl]-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine (40 mg, 40.96 μmol, 11.78% yield) as off white solid. LCMS (ESI+): 884.2 $[M+H]^+$. $^1H$ NMR (400 MHz, DMSO-$d_6$): δ 12.95 (s, 1H), 10.78 (s, 1H), 8.79 (s, 2H), 8.66 (d, J=2.40 Hz, 1H), 8.58 (d, J=2.40 Hz, 1H), 7.99 (s, 1H), 7.57-7.62 (m, 1H), 7.30-7.38 (m, 2H), 6.84 (t, J=9.60 Hz, 1H), 6.50 (dd, J=2.40, 15.20 Hz, 1H), 6.42 (dd, J=2.00, 8.80 Hz, 1H), 5.79 (d, J=8.00 Hz, 1H), 4.21-4.29 (m, 1H), 3.86 (s, 2H), 3.81 (s, 2H), 3.59-3.65 (m, 4H), 3.10-3.15 (m, 4H), 2.68-2.75 (m, 1H), 2.74 (s, 3H), 2.50-2.61 (m, 2H), 2.33-2.37 (m, 2H), 2.05-2.12 (m, 1H), 1.78-1.87 (m, 4H), 1.30-1.45 (m, 2H), 1.02 (t, J=7.20 Hz, 3H).

Example 99

5-[2-[4-[2-[1-[4-[(2,6-dioxo-3-piperidyl)amino]phenyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine

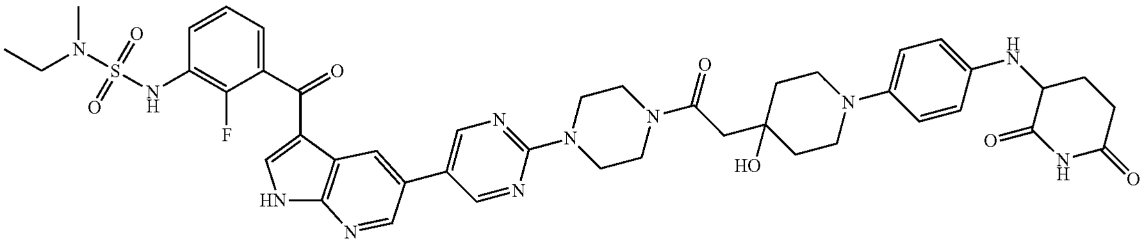 [SMILES: CCN(C)S(=O)(=O)Nc1cccc(C(=O)c2c[nH]c3ncc(-c4cnc(N5CCN(C(=O)CC6(O)CCN(c7ccc(NC8CCC(=O)NC8=O)cc7)CC6)CC5)nc4)cc23)c1F]

Target compound was prepared via HATU mediated acid-amine coupling reaction (procedure A). Amide coupling was carried out using 3-[3-[[ethyl(methyl)sulfamoyl]amino]-2-fluoro-benzoyl]-5-(2-piperazin-1-ylpyrimidin-5-yl)-1H-pyrrolo[2,3-b]pyridine (200 mg, 347.79 μmol), 2-[1-[4-[(2,6-dioxo-3-piperidyl)amino]phenyl]-4-hydroxy-4-piperidyl]acetic acid (125.69 mg, 315.92 μmol), N,N-Diisopropylethylamine (179.80 mg, 1.39 mmol, 242.32 μL) and HATU (132.24 mg, 347.79 μmol) to afford 5-[2-[4-[2-[1-[4-[(2,6-dioxo-3-piperidyl)amino]phenyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine (50 mg, 51.58 μmol, 14.83% yield) as off white solid. LCMS (ESI+): 882.3 $[M+H]^+$. $^1H$ NMR (400 MHz, DMSO-$d_6$): δ 12.89 (d, J=3.20 Hz, 1H), 10.83 (s, 2H), 9.77 (s, 1H), 8.81 (s, 2H), 8.67 (d, J=2.00 Hz, 1H), 8.59 (d, J=2.00 Hz, 1H), 8.00 (d, J=2.40 Hz, 1H), 7.58-7.62 (m, 1H), 7.31-7.50 (m, 3H), 6.77 (s, 2H), 6.34 (s, 1H), 5.40 (s, 1H), 4.36-4.45 (m, 1H), 3.84-3.90 (m, 5H), 3.61-3.70 (m, 6H), 3.33-3.48 (m, 2H), 3.14 (q, J=6.80 Hz, 2H), 2.61-2.77 (m, 2H), 2.75 (s, 3H), 2.46-2.54 (m, 2H), 2.08-2.20 (m, 3H), 1.82-1.97 (m, 3H), 1.03 (t, J=6.80 Hz, 3H).

Example 100

5-[2-[4-[2-[4-[4-[(2,6-dioxo-3-piperidyl)amino]phenyl]-3,3-difluoro-1-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine Target compound was prepared via HATU mediated acid-amine coupling reaction (procedure A). Amide coupling was carried out using 3-[3-[[ethyl(methyl)sulfamoyl]amino]-2-fluoro-benzoyl]-5-(2-piperazin-1-ylpyrimidin-5-yl)-1H-pyrrolo[2,3-b]pyridine (200 mg, 347.79 μmol), 2-[4-[4-[(2,6-dioxo-3-piperidyl)amino]phenyl]-3,3-difluoro-1-piperidyl]acetic acid (160 mg, 382.93 μmol), N,N-Diisopropylethylamine (1.48 g, 11.48 mmol, 2.0 mL) and HATU (160 mg, 420.80 μmol) to afford 5-[2-[4-[2-[4-[4-[(2,6-dioxo-3-piperidyl)amino]phenyl]-3,3-difluoro-1-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine (56 mg, 59.82 μmol, 17.20% yield) as off-white solid. LCMS (ESI+): 902.3 $[M+H]^+$. $^1H$ NMR (400 MHz, DMSO-$d_6$): δ 12.90 (s, 1H), 10.77 (s, 1H), 9.85 (s, 1H), 8.80 (s, 2H), 8.67 (dd, J=2.40, Hz, 2H), 8.59 (s, 1H), 8.00 (s, 1H), 7.60-7.60 (m, 1H), 7.39-7.32 (m, 2H), 7.02 (d, J=8.40 Hz, 2H), 6.64 (d, J=8.80 Hz, 2H), 5.82 (d, J=7.60 Hz, 1H), 4.37-4.20 (m, 1H), 3.89-3.58 (m, 8H), 3.43-3.34 (m, 3H), 3.15-3.11 (m, 3H), 2.74 (s, 3H), 2.51-2.50 (m, 4H), 2.09-1.92 (m, 4H), 1.03 (t, J=7.20 Hz, 3H).

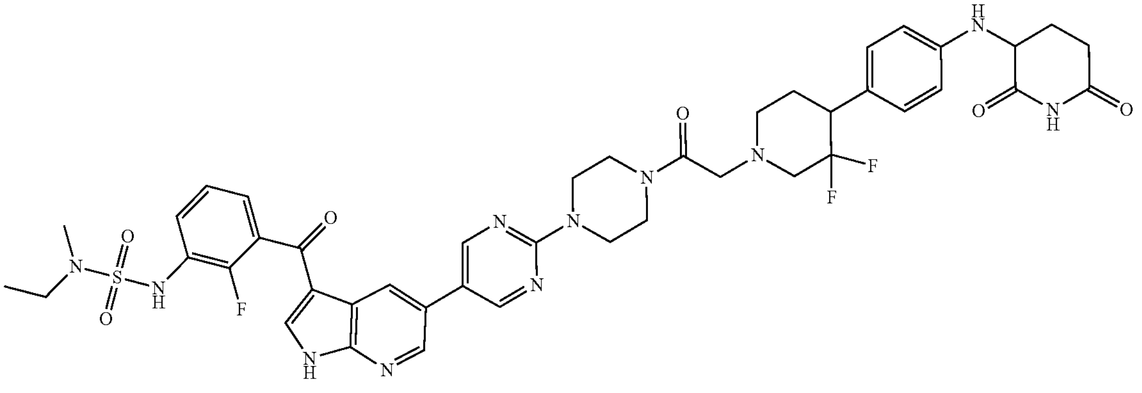 [SMILES: CCN(C)S(=O)(=O)Nc1cccc(C(=O)c2c[nH]c3ncc(-c4cnc(N5CCN(C(=O)CN6CCC(c7ccc(NC8CCC(=O)NC8=O)cc7)C(F)(F)C6)CC5)nc4)cc23)c1F]

Example 101

5-[2-[4-[2-[1-[4-[(2,6-dioxo-3-piperidyl)amino]-2-fluoro-phenyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine

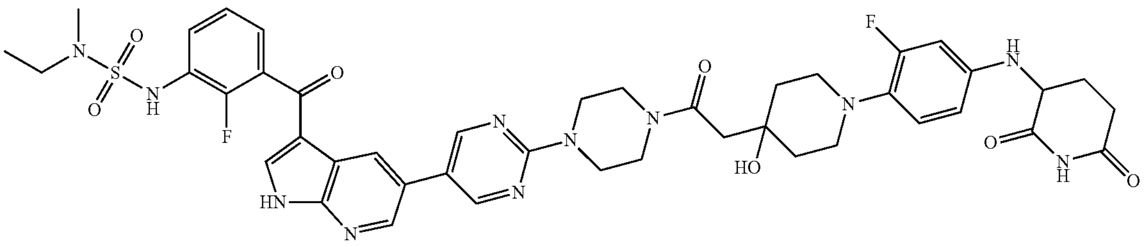 [SMILES: CCN(C)S(=O)(=O)Nc1cccc(C(=O)c2c[nH]c3ncc(-c4cnc(N5CCN(C(=O)CC6(O)CCN(c7ccc(NC8CCC(=O)NC8=O)cc7F)CC6)CC5)nc4)cc23)c1F]

Target compound was prepared via HATU mediated acid-amine coupling reaction (procedure A). Amide coupling was carried out using 1-[1-[4-[(2,6-dioxo-3-piperidyl)amino]-2-fluoro-phenyl]-4-hydroxy-4-piperidyl]acetic acid (477.27 mg, 1.15 mmol), DIPEA (674.24 mg, 5.22 mmol, 908.69 HATU (436.39 mg, 1.15 mmol) and 3-[3-[[ethyl(methyl)sulfamoyl]amino]-2-fluoro-benzoyl]-5-(2-piperazin-1-ylpyrimidin-5-yl)-1H-pyrrolo[2,3-b]pyridine (0.6 g, 1.04 mmol). The desired product was purified by reverse phase column chromatography (0.1% Formic acid in water:Acetonitrile) and fractions were lyophilized to afford 5-[2-[4-[2-[1-[4-[(2,6-dioxo-3-piperidyl)amino]-2-fluoro-phenyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine (152 mg, 158.06 μmol, 15.15% yield) as off white solid. LCMS (ESI+): 900.4 $[M+H]^+$. $^1H$ NMR (400 MHz, DMSO-$d_6$): δ 12.88 (s, 1H), 10.79 (s, 1H), 9.78 (s, 1H), 8.80 (s, 2H), 8.66 (d, J=2.40 Hz, 1H), 8.59 (d, J=2.00 Hz, 1H), 7.99 (s, 1H), 7.57-7.62 (m, 1H), 7.28-7.36 (m, 2H), 6.87 (t, J=9.60 Hz, 1H), 6.50 (dd, J=2.40, 15.00 Hz, 1H), 6.43 (d, J=2.00 Hz, 1H), 5.79 (d, J=7.60 Hz, 1H), 4.87 (s, 1H), 4.24-4.29 (m, 1H), 3.87-3.83 (m, 4H), 3.70-3.64 (m, 4H), 3.13 (q, J=7.20 Hz, 2H), 2.84-2.92 (m, 4H), 2.74 (s, 3H), 2.48-2.67 (m, 3H), 2.07-2.11 (m, 1H), 1.67-1.83 (m, 5H), 1.02 (t, J=6.80 Hz, 3H).

Example 102

5-[2-[4-[2-[1-[4-[(2,6-dioxo-3-piperidyl)amino]-2-fluoro-phenyl]-3-hydroxy-pyrrolidin-3-yl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine

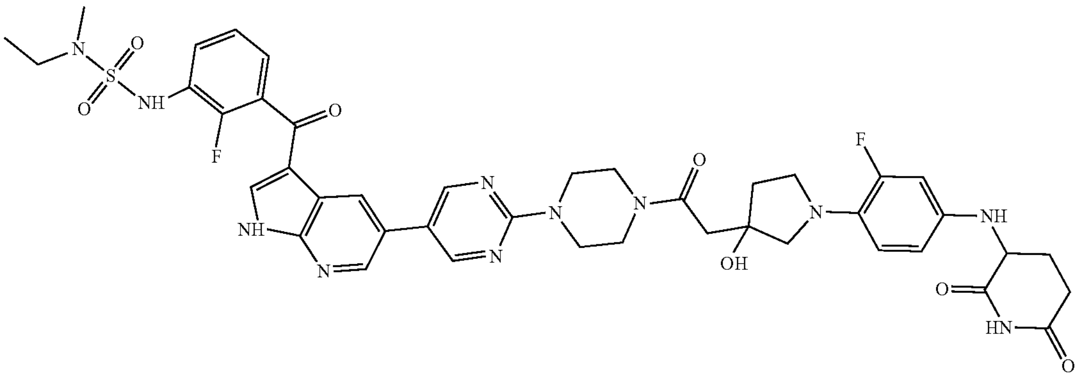 [SMILES: CCN(C)S(=O)(=O)Nc1cccc(C(=O)c2c[nH]c3ncc(-c4cnc(N5CCN(C(=O)CC6(O)CCN(c7ccc(NC8CCC(=O)NC8=O)cc7F)C6)CC5)nc4)cc23)c1F]

Target compound was prepared via HATU mediated acid-amine coupling reaction (procedure A). Amide coupling was carried out using 2-[1-[4-[(2,6-dioxo-3-piperidyl)amino]-2-fluoro-phenyl]-3-hydroxy-pyrrolidin-3-yl]acetic acid (461.17 mg, 1.15 mmol), N-ethyl-N-isopropyl-propan-2-amine (674.23 mg, 5.22 mmol, 908.66 HATU (438.71 mg, 1.15 mmol) and 3-[3-[[ethyl(methyl)sulfamoyl]amino]-2-fluoro-benzoyl]-5-(2-piperazin-1-ylpyrimidin-5-yl)-1H-pyrrolo[2,3-b]pyridine (0.6 g, 1.04 mmol) to afford 5-[2-[4-[2-[1-[4-[(2,6-dioxo-3-piperidyl)amino]-2-fluoro-phenyl]-3-hydroxy-pyrrolidin-3-yl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine (139 mg, 156.30 μmol, 14.98% yield) as dark blue solid. LCMS (ESI+): 887.3 [M+H]$^1$H NMR (400 MHz, DMSO-$d_6$): δ 12.88 (s, 1H), 10.78 (s, 1H), 9.79 (s, 1H), 8.80 (s, 2H), 8.66 (d, J=2.40 Hz, 1H), 8.58 (d, J=2.40 Hz, 1H), 7.99 (s, 1H), 7.57-7.62 (m, 1H), 7.31-7.36 (m, 2H), 6.54-6.61 (m, 2H), 6.40-6.42 (m, 1H), 5.53 (d, J=7.60 Hz, 1H), 4.99 (s, 1H), 4.18-4.21 (m, 1H), 3.87-3.82 (m, 4H), 3.64-3.67 (m, 4H), 3.43-3.46 (m, 1H), 3.10-3.16 (m, 4H), 2.79 (s, 2H), 2.67-2.77 (m, 2H), 2.72 (s, 3H), 2.47-2.59 (m, 1H), 2.08-2.11 (m, 1H), 1.81-1.99 (m, 3H), 1.02 (t, J=7.20 Hz, 3H).

Example 103

5-[2-[4-[2-[1-[2-chloro-4-[(2,6-dioxo-3-piperidyl)amino]phenyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine

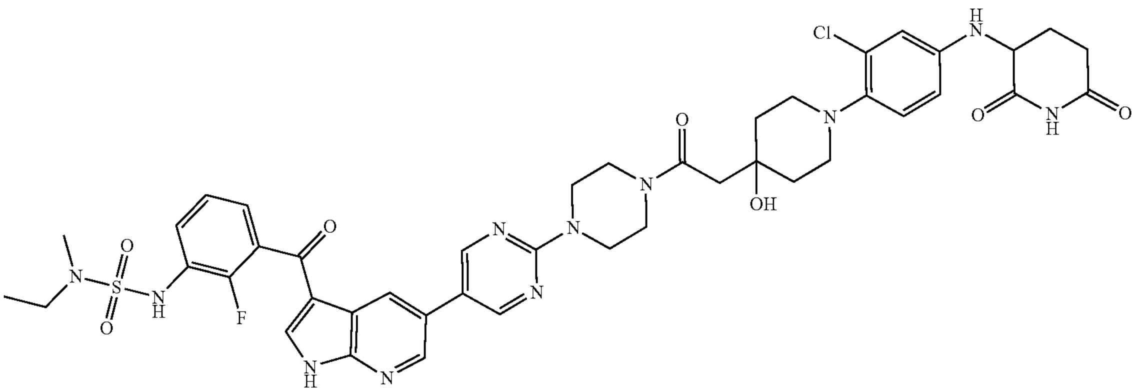 [SMILES: CCN(C)S(=O)(=O)Nc1cccc(C(=O)c2c[nH]c3ncc(-c4cnc(N5CCN(C(=O)CC6(O)CCN(c7ccc(NC8CCC(=O)NC8=O)cc7Cl)CC6)CC5)nc4)cc23)c1F]

To a solution of 2-[1-[2-chloro-4-[(2,6-dioxo-3-piperidyl)amino]phenyl]-4-hydroxy-4-piperidyl]acetic acid (400 mg, 925.29 μmol) and 3-[3-[[ethyl(methyl)sulfamoyl]amino]-2-fluoro-benzoyl]-5-(2-piperazin-1-ylpyrimidin-5-yl)-1H-pyrrolo[2,3-b]pyridine (548.19 mg, 953.28 μmol) in N,N-Dimethylformamide (3 mL) were added N,N-Diisopropylethylamine (597.94 mg, 4.63 mmol, 805.84 μL) and HATU (387.00 mg, 1.02 mmol) and stirred at room temperature for 16 h. After completion, excess N,N-Dimethylformamide and N,N-Diisopropylethylamine were distilled off under reduced pressure using Rotavapor at 45° C. to get the crude product which was purified by C-18 reverse phase column (100 g) chromatography by using 0.1% HCOOH in Acetonitrile and water as eluents to afford 5-[2-[4-[2-[1-[2-chloro-4-[(2,6-dioxo-3-piperidyl)amino]phenyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine (110 mg, 112.69 μmol, 12.18% yield) as off white solid. LCMS (ESI+): 916.3 [M+H]$^+$. $^1$H NMR (400 MHz, DMSO-$d_6$): δ 12.90 (br s, 1H), 10.78 (s, 1H), 8.79 (s, 2H), 8.65 (d, J=2.0 Hz, 1H), 8.58 (d, J=2.4 Hz, 1H), 8.38 (s, 1H), 7.96 (s, 1H), 7.54-7.59 (m, 1H), 7.18-7.22 (m, 2H), 6.98 (d, J=8.80 Hz, 1H), 6.76 (s, 1H), 6.61 (dd, J=2.80, 8.80 Hz, 1H), 5.85 (d, J=7.60 Hz, 1H), 4.91 (s, 1H), 4.27-4.33 (m, 1H), 3.90-3.85 (m, 5H), 3.65-3.70 (m, 5H), 3.08 (q, J=7.20 Hz, 3H), 2.88-2.90 (m, 2H), 2.81-2.84 (m, 2H), 2.68 (s, 4H), 2.06-2.10 (m, 1H), 1.69-1.77 (m, 5H), 1.02 (t, J=7.20 Hz, 3H).

Example 104

5-[2-[4-[2-[1-[5-[(2,6-dioxo-3-piperidyl)amino]-3-fluoro-2-pyridyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine

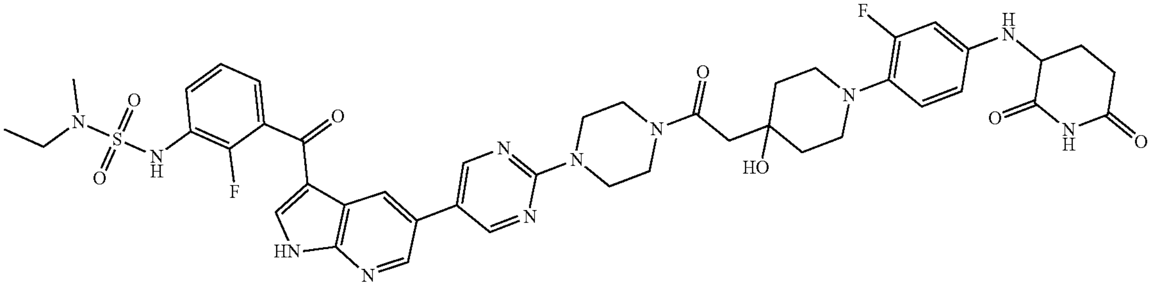 [SMILES: CCN(C)S(=O)(=O)Nc1cccc(C(=O)c2c[nH]c3ncc(-c4cnc(N5CCN(C(=O)CC6(O)CCN(c7ccc(NC8CCC(=O)NC8=O)cc7F)CC6)CC5)nc4)cc23)c1F]

Target compound was prepared via COMU mediated acid-amine coupling reaction (procedure B). Amide coupling was carried out using 2-[1-[5-[(2,6-dioxo-3-piperidyl)amino]-3-fluoro-2-pyridyl]-4-hydroxy-4-piperidyl]acetic acid (603.66 mg, 1.45 mmol), 3-[3-[[ethyl(methyl)sulfamoyl]amino]-2-fluoro-benzoyl]-5-(2-piperazin-1-ylpyrimidin-5-yl)-1H-pyrrolo[2,3-b]pyridine (600 mg, 1.11 mmol), COMU (620.22 mg, 1.45 mmol), N,N-diisopropylethylamine (863.85 mg, 6.68 mmol, 1.16 mL) to afford 5-[2-[4-[2-[1-[5-[(2,6-dioxo-3-piperidyl)amino]-3-fluoro-2-pyridyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine (143 mg, 153.28 μmol, 13.76% yield) as pale brown solid. LCMS (ESI+): 901.2 $[M+H]^+$. $^1H$ NMR (400 MHz, DMSO-$d_6$): δ 12.89 (s, 1H), 10.82 (s, 1H), 9.79 (s, 1H), 8.80 (s, 1H), 8.66-8.58 (m, 2H), 7.99 (s, 1H), 7.61-7.57 (m, 2H), 7.33-7.31 (m, 2H), 7.01 (d, J=2.00 Hz, 1H), 5.90 (d, J=7.60 Hz, 1H), 4.90 (s, 1H), 4.31-4.28 (m, 1H), 3.86-3.64 (m, 8H), 3.34-3.25 (m, 3H), 3.14-3.09 (m, 4H), 2.74 (s, 3H), 2.59-2.50 (m, 4H), 2.13-2.09 (m, 1H), 1.91-1.86 (m, 1H), 1.75-1.66 (m, 4H), 1.02 (t, J=7.20 Hz, 3H).

Example 105

5-[2-[4-[2-[1-[5-[(2,6-dioxo-3-piperidyl)amino]-2-pyridyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine To a solution of 2-[1-[5-[(2,6-dioxo-3-piperidyl)amino]-2-pyridyl]-4-hydroxy-4-piperidyl]acetic acid (207.95 mg, 521.40 μmol) and 3-[3-[[ethyl(methyl)sulfamoyl]amino]-2-fluoro-benzoyl]-5-(2-piperazin-1-ylpyrimidin-5-yl)-1H-pyrrolo[2,3-b]pyridine (300 mg, 521.69 μmol) in N,N-Dimethylformamide (5 mL) were added N-ethyl-N-isopropyl-propan-2-amine (337.12 mg, 2.61 mmol, 454.34 COMU (268.11 mg, 626.02 μmol) and stirred at room temperature for 3 h. After completion, excess N,N-Dimethylformamide and N,N-Diisopropylethylamine were distilled off under reduced pressure at 45° C. to get the crude product which was purified by reverse phase column chromatography by using 100 g C-18 column using 0.1% $NH_4OAc$ in acetonitrile and water as eluents to afford 5-[2-[4-[2-[1-[5-[(2,6-dioxo-3-piperidyl)amino]-2-pyridyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine (125 mg, 141.22 μmol, 27.07% yield) as purple solid. LCMS (ESI+): 883.4 $[M+H]^+$. $^1H$ NMR (400 MHz, DMSO-$d_6$): δ 12.74 (br s, 1H), 10.78 (s, 1H), 8.79 (s, 2H), 8.64 (d, J=2.40 Hz, 1H), 8.57 (d, J=2.00 Hz, 1H), 7.95 (s, 1H), 7.70 (s, 1H), 7.54 (t, J=7.20 Hz, 1H), 7.15-7.03 (m, 3H), 5.36 (d, J=7.20 Hz, 1H), 4.93 (s, 1H), 4.18-4.21 (m, 1H), 3.82-3.86 (m, 4H), 3.65-3.68 (m, 6H), 3.11-3.16 (m, 4H), 2.57-2.65 (m, 6H), 2.08-2.14 (m, 1H), 1.87 (s, 2H), 1.63 (s, 4H), 1.01 (t, J=7.20 Hz, 3H).

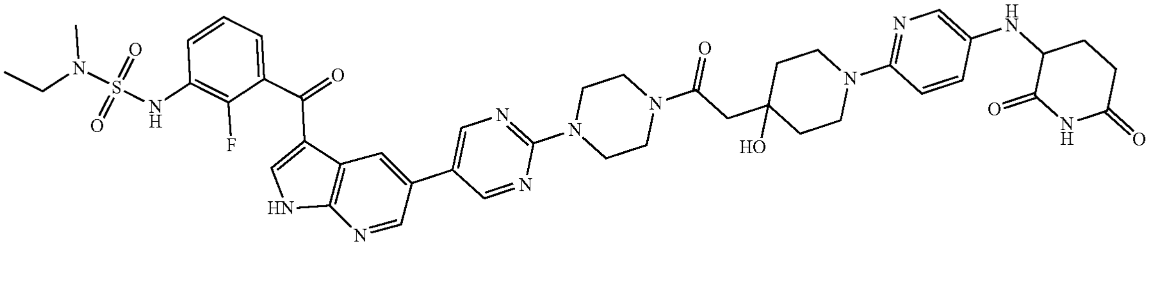 [SMILES: CCN(C)S(=O)(=O)Nc1cccc(C(=O)c2c[nH]c3ncc(-c4cnc(N5CCN(C(=O)CC6(O)CCN(c7ccc(NC8CCC(=O)NC8=O)cn7)CC6)CC5)nc4)cc23)c1F]

Example 106

5-[2-[4-[2-[1-[4-[(2,6-dioxo-3-piperidyl)amino]-2-(trifluoromethyl)phenyl]-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine Step 2: To a stirred solution of tert-butyl 2-[1-[4-nitro-2-(trifluoromethyl)phenyl]-4-piperidyl]acetate (550 mg, 1.42 mmol) in Ethanol (10 mL) and Water (2 mL) were added Ammonium chloride (151.50 mg, 2.83 mmol, 99.02 μL) and Iron powder (395.42 mg, 7.08 mmol, 50.31 μL) at room temperature. The reaction mixture was heated to 80° C. for 4 h. After completion, the reaction mixture was cooled to

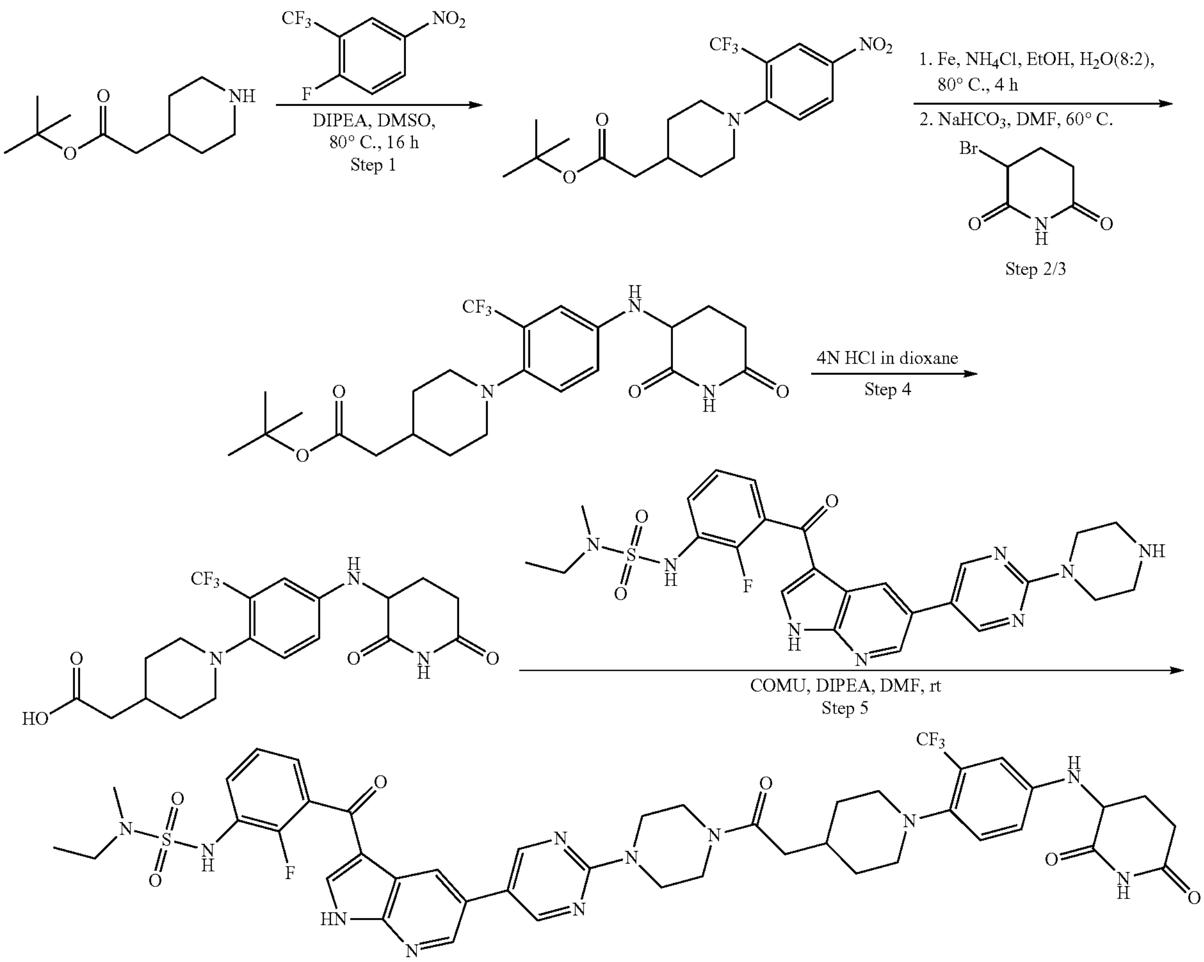

Step 1: To a stirred solution of tert-butyl 2-(4-piperidyl)acetate (350 mg, 1.76 mmol) in Acetonitrile (8 mL) in a sealed tube, triethyl amine (888.57 mg, 8.78 mmol, 1.22 mL) and 1-fluoro-4-nitro-2-(trifluoromethyl)benzene (367.23 mg, 1.76 mmol, 241.60 μL) were added at room temperature under nitrogen atmosphere. The reaction mixture was stirred at 80° C. for 16 h. After completion, the reaction mixture was cooled to room temperature, diluted with water (300 mL) and extracted with ethyl acetate (3×150 mL). The combined organic layers were washed with brine solution (200 mL), dried over Sodium sulphate, filtered and concentrated under reduced pressure. The crude compound was purified by silica gel column chromatography with 10-20% ethyl acetate in petroleum ether as a eluent to afford tert-butyl 2-[1-[4-nitro-2-(trifluoromethyl)phenyl]-4-piperidyl]acetate (550 mg, 1.27 mmol, 72.57% yield) as a yellow solid. $^1H$ NMR (400 MHz, DMSO-d6): δ 8.52 (d, J=2.80 Hz, 1H), 8.31 (dd, J=2.40, 9.00 Hz, 1H), 7.26 (t, J=8.80 Hz, 1H), 3.40 (d, J=12.40 Hz, 2H), 2.86-2.94 (m, 2H), 2.25 (d, J=6.80 Hz, 2H), 1.95-1.99 (m, 1H), 1.90 (d, J=27.20 Hz, 2H), 1.45-1.60 (m, 2H), 1.49 (s, 9H).

room temperature, then filtered through celite and filtrate was diluted with water (200 mL) and extracted with ethyl acetate (3×100 mL). The combined organic layers were washed with brine solution (150 mL) and dried over anhydrous Sodium sulphate, filtered and concentrated under reduced pressure to afford tert-butyl 2-[1-[4-amino-2-(trifluoromethyl)phenyl]-4-piperidyl]acetate (490 mg, 1.33 mmol, 93.65% yield) as a pale brown solid. Crude product was taken to next step without purification. LCMS (ESI+): 359.0 $[M+H]^+$.

Step 3: To a stirred solution of tert-butyl 2-[1-[4-amino-2-(trifluoromethyl)phenyl]-4-piperidyl]acetate (490 mg, 1.37 mmol) in N,N-Dimethylformamide (10 mL), was added Sodium bicarbonate (344.56 mg, 4.10 mmol, 159.52 μL) and 3-bromopiperidine-2,6-dione (1.31 g, 6.84 mmol) at room temperature. Then the reaction mixture was heated at 80° C. for 16 h. After completion, the reaction mixture was cooled to room temperature, diluted with water (150 mL) and extracted with ethyl acetate (3×150 mL). The combined organic layers were washed with brine solution (150 mL), dried over Sodium sulphate, filtered and concentrated under reduced pressure. The crude compound was purified by silica gel column chromatography with 20%-30% ethyl acetate in petroleum ether as eluent to afford tert-butyl 2-[1-[4-[(2,6-dioxo-3-piperidyl)amino]-2-(trifluoromethyl) phenyl]-4-piperidyl]acetate (700 mg, 1.01 mmol, 74.16% yield) as a pale brown solid. LCMS (ESI+): 470.2 $[M+H]^+$.

Step 4: To a stirred solution of tert-butyl 2-[1-[4-[(2,6-dioxo-3-piperidyl)amino]-2-(trifluoromethyl)phenyl]-4-piperidyl]acetate (700 mg, 1.49 mmol) in Dichloromethane (15 mL) was added Hydrogen chloride (4M in 1,4-dioxane, 543.62 mg, 14.91 mmol, 679.52 μL) at 0-5° C. under nitrogen. The reaction mixture was stirred at room temperature for 16 h. After completion, the reaction mixture was concentrated under reduced pressure to afford crude compound 2-[1-[4-[(2,6-dioxo-3-piperidyl)amino]-2-(trifluoromethyl)phenyl]-4-piperidyl]acetic acid (500 mg, 878.07 μmol, 58.89% yield) as a brown gummy compound. LCMS (ESI+): 414.2 $[M+H]^+$.

Step 5: Target compound was prepared via COMU mediated acid-amine coupling reaction (procedure B). Amide coupling was carried out using 3-[3-[[ethyl(methyl)sulfamoyl]amino]-2-fluoro-benzoyl]-5-(2-piperazin-1-ylpyrimidin-5-yl)-1H-pyrrolo[2,3-b]pyridine (200.37 mg, 348.43 μmol), 2-[1-[4-[(2,6-dioxo-3-piperidyl)amino]-2-(trifluoromethyl)phenyl]-4-piperidyl]acetic acid (144.04 mg, 320.19 μmol), N,N-Diisopropylethylamine (180.13 mg, 1.39 mmol, 242.76 μL) and COMU (164.14 mg, 383.27 μmol) to afford 5-[2-[4-[2-[1-[4-[(2,6-dioxo-3-piperidyl)amino]-2-(trifluoromethyl)phenyl]-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine (28 mg, 28.09 μmol, 8.06% yield) as off white solid. LCMS (ESI+): 934.2 $[M+H]^+$. $^1H$ NMR (400 MHz, DMSO-$d_6$): δ 12.95 (s, 1H), 10.79 (s, 1H), 9.85 (s, 1H), 8.80 (s, 2H), 8.66 (d, J=2.40 Hz, 1H), 8.58 (d, J=2.40 Hz, 1H), 7.99 (s, 1H), 7.57-7.61 (m, 1H), 7.30-7.34 (m, 3H), 6.88-6.92 (m, 2H), 6.17 (d, J=8.00 Hz, 1H), 4.30-4.39 (m, 1H), 3.86 (s, 2H), 3.81 (s, 2H), 3.62 (s, 4H), 3.13 (q, J=7.20 Hz, 2H), 2.63-2.81 (m, 3H), 2.75 (s, 3H), 2.45-2.57 (m, 2H), 2.38 (d, J=6.80 Hz, 2H), 2.07-2.11 (m, 2H), 1.76-1.91 (m, 2H), 1.71-1.76 (m, 2H), 1.24-1.36 (m, 2H), 1.03 (t, J=7.20 Hz, 3H).

Example 107-115

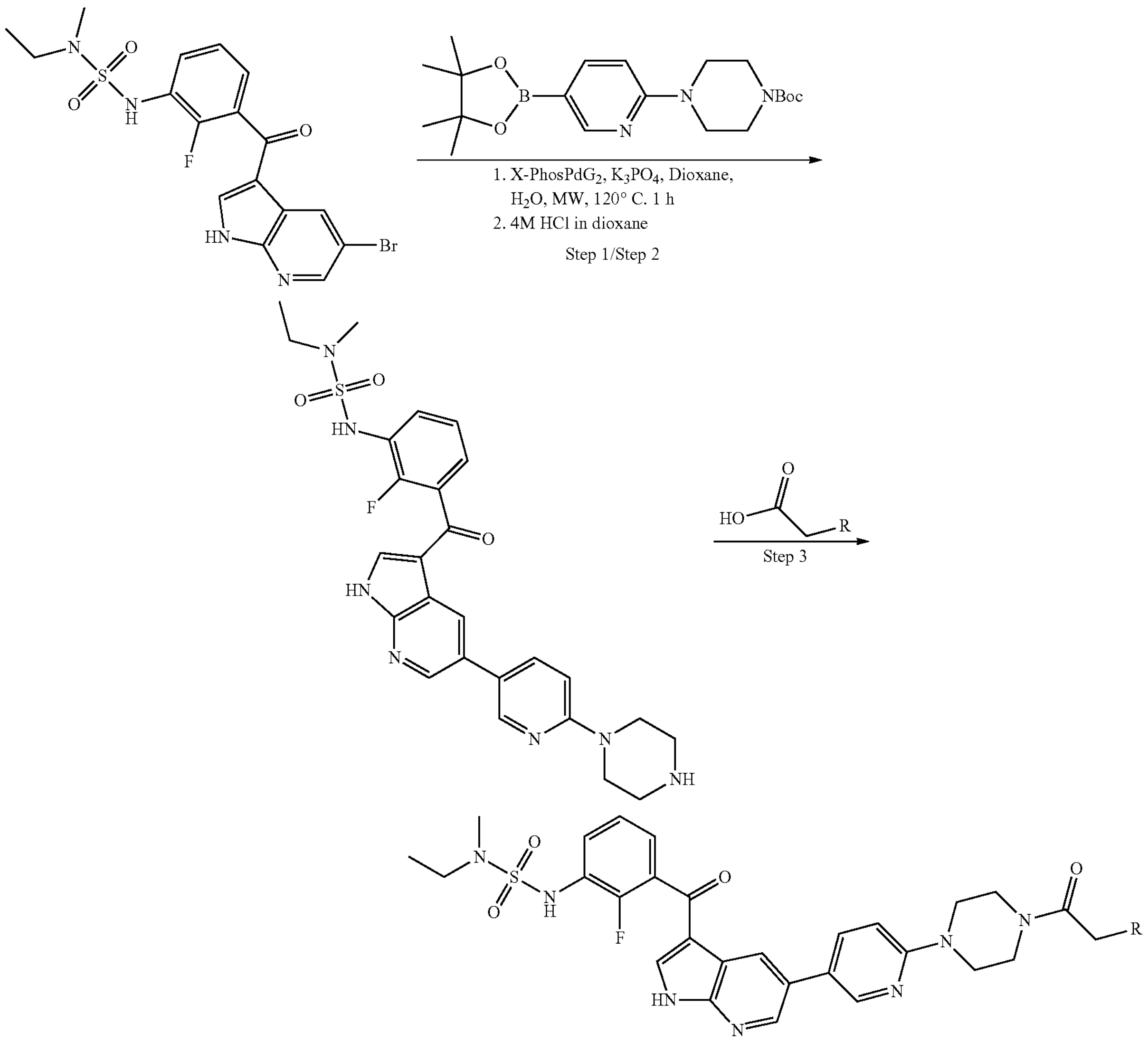

Synthesis of intermediate 3-[3-[[ethyl(methyl)sulfamoyl]amino]-2-fluoro-benzoyl]-5-(6-piperazin-1-yl-3-pyridyl)-1H-pyrrolo[2,3-b]pyridine Step 1: To a solution of 5-bromo-3-[3-[[ethyl(methyl) sulfamoyl]amino]-2-fluoro-benzoyl]-1H-pyrrolo[2,3-b] pyridine (800 mg, 1.76 mmol) in 1,4-dioxane (10 mL) and water (2 mL) in a microwave vial was added tert-butyl 4-[5-(4,4,5,5-tetramethyl-1,3,2-dioxaborolan-2-yl)-2-pyridyl]piperazine-1-carboxylate (684.02 mg, 1.76 mmol) and potassium phosphate tribasic (anhydrous) (1.12 g, 5.27 mmol) at room temperature under nitrogen atmosphere. The reaction mixture was degassed with nitrogen for 10 minutes and added XPhos Pd G2 (137.98 mg, 175.71 μmol). The reaction mixture was irradiated under microwave at 120° C. for 1 h. After completion of the reaction, the reaction mixture was diluted with water (60 mL) and extracted with ethyl acetate (2×100 mL). The combined organic layers were dried over sodium sulphate, filtered and concentrated under reduced pressure. The crude compound was purified by silica gel column chromatography with 70% ethyl acetate in petroleum ether as a eluent to afford tert-butyl 4-[5-[3-[3-[[ethyl(methyl)sulfamoyl]amino]-2-fluoro-benzoyl]-1H-pyrrolo[2,3-b]pyridin-5-yl]-2-pyridyl]piperazine-1-carboxylate (650 mg, 784.82 μmol, 44.67% yield) as a yellow solid. LCMS (ESI+): 638.2 $[M+H]^+$.

Step 2: To a stirred solution of tert-butyl 4-[5-[3-[3-[[ethyl (methyl)sulfamoyl]amino]-2-fluoro-benzoyl]-1H-pyrrolo[2,3-b]pyridin-5-yl]-2-pyridyl]piperazine-1-carboxylate (650 mg, 1.02 mmol) in 1,4-dioxane (4 mL) was added 4M HCl in 1,4-Dioxane (1.02 mmol, 6 mL) and stirred at room temperature for 4 h. The reaction mixture was concentrated under reduced pressure to get 3-[3-[[ethyl(methyl)sulfamoyl]amino]-2-fluoro-benzoyl]-5-(6-piperazin-1-yl-3-pyridyl)-1H-pyrrolo[2,3-b]pyridine (600 mg, 859.13 μmol, 84.29% yield) as light brown solid. LCMS (ESI+): 538.2 $[M+H]^+$.

Example 107

5-[6-[4-[2-[4-[4-[(2,6-dioxo-3-piperidyl)amino]phenyl]-1-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine

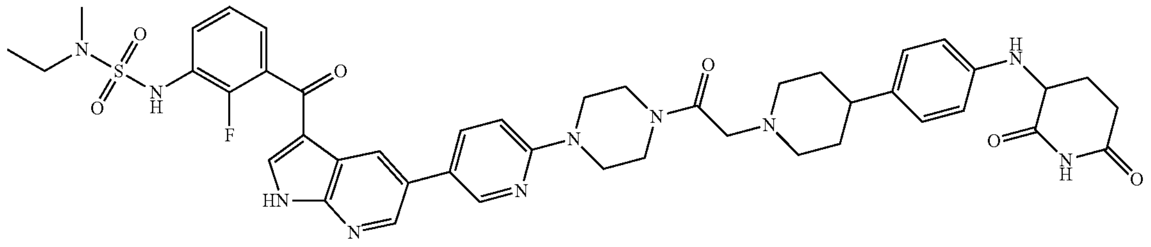 [SMILES: CCN(C)S(=O)(=O)Nc1cccc(C(=O)c2c[nH]c3ncc(-c4ccc(N5CCN(C(=O)CN6CCC(c7ccc(NC8CCC(=O)NC8=O)cc7)CC6)CC5)nc4)cc23)c1F]

Target compound was prepared via HATU mediated acid-amine coupling reaction (procedure A). Amide coupling was carried out using 3-[3-[[ethyl(methyl)sulfamoyl]amino]-2-fluoro-benzoyl]-5-(6-piperazin-1-yl-3-pyridyl)-1H-pyrrolo [2,3-b]pyridine (100 mg, 186.01 μmol), 2-[4-[4-[(2,6-dioxo-3-piperidyl)amino]phenyl]-1-piperidyl]acetic acid (64.25 mg, 186.01 μmol), DIPEA (96.16 mg, 744.04 μmol, 129.6 μL) and HATU (70.73 mg, 186.01 μmol) to yield 5-[6-[4-[2-[4-[4-[(2,6-dioxo-3-piperidyl)amino]phenyl]-1-piperidyl]acetyl]piperazin-1-yl]-3-pyridyl]-3-[3-[[ethyl(methyl) sulfamoyl]amino]-2-fluoro-benzoyl]-1H-pyrrolo[2,3-b] pyridine (29 mg, 31.95 μmol, 17.18% yield) as off white solid. LCMS (ESI+): 865.0 $[M+H]^+$. $^1H$ NMR (400 MHz, DMSO-$d_6$): δ 12.85 (bs, 1H), 10.77 (s, 1H), 9.83 (bs, 1H), 8.66 (s, 1H), 8.56 (d, J=2.00 Hz, 1H), 8.51 (d, J=2.00 Hz, 1H), 7.96-7.94 (m, 2H), 7.61-7.57 (m, 1H), 7.36-7.30 (m, 2H), 7.02 (d, J=9.2 Hz, 1H), 6.95 (d, J=8.4 Hz, 2H), 6.59 (d, J=8.4 Hz, 2H), 5.66 (d, J=7.2 Hz, 1H), 4.27-4.23 (m, 1H), 3.75-3.73 (m, 2H), 3.65-3.63 (m, 2H), 3.62-3.58 (m, 4H), 3.25-3.23 (m, 2H), 3.12 (qt, J=7.2 Hz, 2H), 2.95-2.93 (m, 2H), 2.73 (s, 3H), 2.75-2.70 (m, 2H), 2.58-2.55 (m, 1H), 2.35-2.30 (m, 2H), 2.13-2.07 (m, 3H), 1.83-1.71 (m, 1H), 1.72-1.57 (m, 4H), 1.03 (t, J=8.40 Hz, 3H).

Example 108

5-[6-[4-[2-[4-[4-[(2,6-dioxo-3-piperidyl)oxy]phenyl]-1-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine

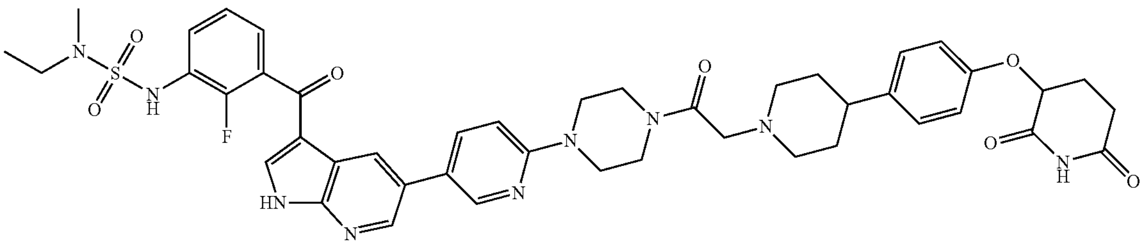 [SMILES: CCN(C)S(=O)(=O)Nc1cccc(C(=O)c2c[nH]c3ncc(-c4ccc(N5CCN(C(=O)CN6CCC(c7ccc(OC8CCC(=O)NC8=O)cc7)CC6)CC5)nc4)cc23)c1F]

Target compound was prepared via HATU mediated acid-amine coupling reaction (procedure A). Amide coupling was carried out using 3-[3-[[ethyl(methyl)sulfamoyl]amino]-2-fluoro-benzoyl]-5-(6-piperazin-1-yl-3-pyridyl)-1H-pyrrolo[2,3-b]pyridine (20 mg, 37.20 μmol), 2-[4-[4-[(2,6-dioxo-3-piperidyl)oxy]phenyl]-1-piperidyl]acetic acid (12.89 mg, 37.20 μmol), N,N-Diisopropylethylamine (19.24 mg, 148.8 μmol, 25.92 μL) and HATU (14.15 mg, 37.20 μmol) to yield 5-[6-[4-[2-[4-[4-[(2,6-dioxo-3-piperidyl)oxy]phenyl]-1-piperidyl]acetyl]piperazin-1-yl]-3-pyridyl]-3-[3[[ethyl(methyl)sulfamoyl]amino]-2-fluoro-benzoyl]-1H-pyrrolo[2,3-b]pyridine (5.5 mg, 6.07 μmol, 16.32% yield) as off white solid. LCMS (ESI+): 866.3 $[M+H]^+$. $^1H$ NMR (400 MHz, DMSO-$d_6$): δ 12.85 (bs, 1H), 10.90 (s, 1H), 9.83 (bs, 1H), 8.65 (d, J=2.40 Hz, 1H), 8.56 (d, J=2.00 Hz, 1H), 8.50 (d, J=2.80 Hz, 1H), 7.97-7.94 (m, 2H), 7.61-7.57 (m, 1H), 7.35-7.28 (m, 2H), 7.17-7.15 (d, J=8.8 Hz, 2H), 7.02 (d, J=8.8 Hz, 1H), 6.94 (d, J=9.6 Hz, 2H), 5.15-5.12 (m, 1H), 3.68-3.66 (m, 2H), 3.65-3.62 (m, 2H), 3.60-3.58 (m, 4H), 3.25-3.23 (m, 2H), 3.12 (qt, J=6.8 Hz, 2H), 2.95-2.93 (m, 2H), 2.73 (s, 3H), 2.75-2.70 (m, 2H), 2.57-2.53 (m, 1H), 2.13-2.07 (m, 4H), 1.75-1.71 (m, 2H), 1.70-1.55 (m, 2H), 1.02 (t, J=8.40 Hz, 3H).

Example 109

5-[6-[4-[2-[1-[4-[(2,6-dioxo-3-piperidyl)amino]phenyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine

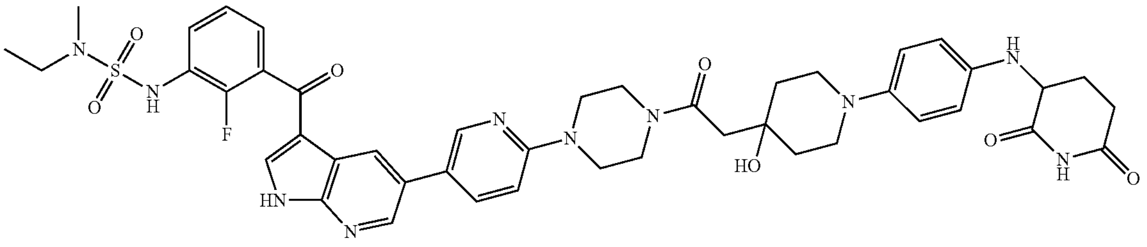

Target compound was prepared via HATU mediated acid-amine coupling reaction (procedure A). Amide coupling was carried out using 3-[3-[[ethyl(methyl)sulfamoyl]amino]-2-fluoro-benzoyl]-5-(6-piperazin-1-yl-3-pyridyl)-1H-pyrrolo[2,3-b]pyridine (200 mg, 348.39 μmol), 2-[1-[4-[(2,6-dioxo-3-piperidyl)amino]phenyl]-4-hydroxy-4-piperidyl]acetic acid (125.91 mg, 316.46 μmol), N,N-Diisopropylethylamine (180.11 mg, 1.39 mmol, 242.73 μL) and HATU (132.47 mg, 348.39 μmol) to afford 5-[6-[4-[2-[1-[4-[(2,6-dioxo-3-piperidyl)amino]phenyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine (50 mg, 51.56 μmol, 14.80% yield) as off-white solid. LCMS (ESI+): 881.3 $[M+H]^+$. $^1H$ NMR (400 MHz, DMSO-$d_6$): δ 12.85 (d, J=2.40 Hz, 1H), 10.79 (s, 1H), 9.79 (s, 1H), 8.66 (d, J=2.40 Hz, 1H), 8.56 (d, J=2.00 Hz, 1H), 8.51 (d, J=2.40 Hz, 1H), 7.95-7.97 (m, 2H), 7.58-7.62 (m, 1H), 7.31-7.41 (m, 2H), 7.18 (bs, 1H), 7.02 (d, J=8.80 Hz, 2H), 6.90 (bs, 1H), 6.61 (s, 2H), 5.00 (s, 1H), 4.25-4.32 (m, 1H), 3.55-3.75 (m, 8H), 3.35-3.45 (m, 3H), 3.14 (q, J=6.80 Hz, 2H), 2.55-2.75 (m, 3H), 2.74 (s, 3H), 2.42-2.51 (m, 2H), 2.08-2.18 (m, 2H), 1.60-2.00 (m, 4H), 1.02 (t, J=7.20 Hz, 3H).

Example 110

5-[6-[4-[2-[4-[4-[(2,6-dioxo-3-piperidyl)amino]phenyl]-3,3-difluoro-1-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine

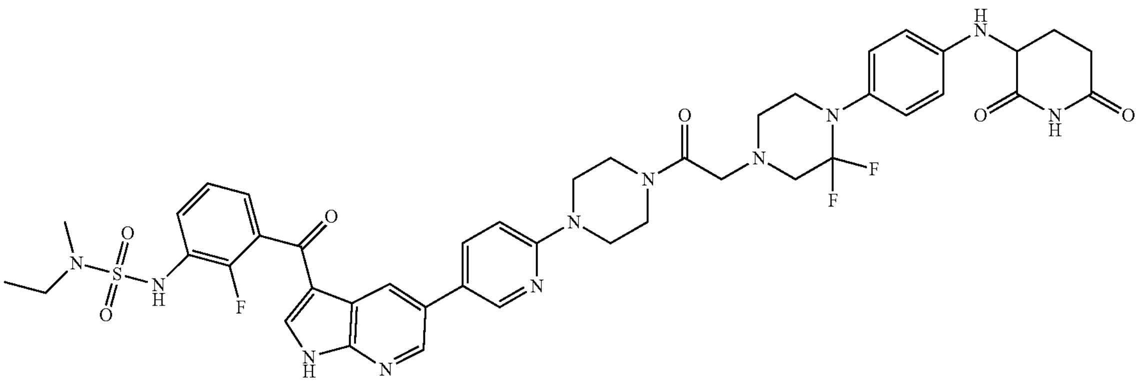 [SMILES: CCN(C)S(=O)(=O)Nc1cccc(C(=O)c2c[nH]c3ncc(-c4ccc(N5CCN(C(=O)CN6CCN(c7ccc(NC8CCC(=O)NC8=O)cc7)C(F)(F)C6)CC5)nc4)cc23)c1F]

Target compound was prepared via HATU mediated acid-amine coupling reaction (procedure A). Amide coupling was carried out using 3-[3-[[ethyl(methyl)sulfamoyl]amino]-2-fluoro-benzoyl]-5-(6-piperazin-1-yl-3-pyridyl)-1H-pyrrolo[2,3-b]pyridine (200 mg, 348.39 μmol), 2-[4-[4-[(2,6-dioxo-3-piperidyl)amino]phenyl]-3,3-difluoro-1-piperidyl]acetic acid (160 mg, 382.93 μmol), N,N-Diisopropylethylamine (1.48 g, 11.48 mmol, 2.0 mL) and HATU (150 mg, 394.50 μmol) to afford 5-[6-[4-[2-[4-[4-[(2,6-dioxo-3-piperidyl)amino]phenyl]-3,3-difluoro-1-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine (61 mg, 61.86 μmol, 17.76% yield) as a pale yellow solid. LCMS (ESI+): 901.4 $[M+H]^+$. $^1H$ NMR (400 MHz, DMSO-$d_6$): δ 12.84 (s, 1H), 10.79 (s, 1H), 9.78 (s, 1H), 8.66 (s, 1H), 8.54 (dd, J=2.40, 19.40 Hz, 2H), 7.99-7.96 (m, 2H), 7.61-7.60 (m, 1H), 7.40-7.33 (m, 2H), 7.06-7.01 (m, 3H), 6.64 (d, J=8.80 Hz, 2H), 3.37-3.20 (m, 1H), 3.68-3.62 (m, 8H), 3.34-3.11 (m, 6H), 2.75 (s, 3H), 2.61-2.50 (m, 4H), 2.34-2.09 (m, 4H), 1.03 (t, J=7.20 Hz, 3H).

Example 111

5-[6-[4-[2-[1-[4-[(2,6-dioxo-3-piperidyl)amino]-2-fluoro-phenyl]-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine

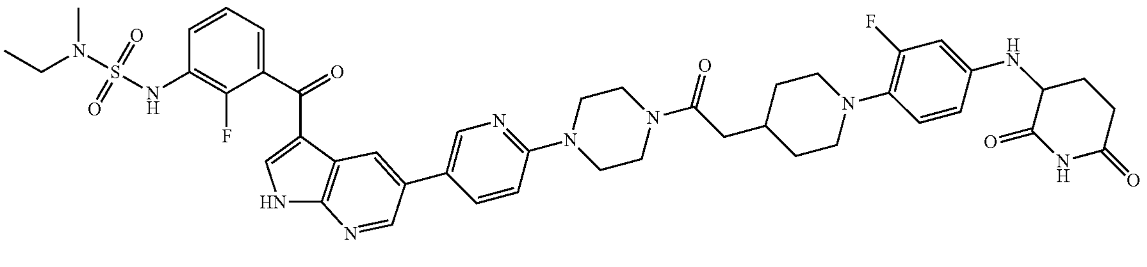 [SMILES: CCN(C)S(=O)(=O)Nc1cccc(C(=O)c2c[nH]c3ncc(-c4ccc(N5CCN(C(=O)CC6CCN(c7ccc(NC8CCC(=O)NC8=O)cc7F)CC6)CC5)nc4)cc23)c1F]

Target compound was prepared via HATU mediated acid-amine coupling reaction (procedure A). Amide coupling was carried out using 3-[3-[[ethyl(methyl)sulfamoyl]amino]-2-fluoro-benzoyl]-5-(6-piperazin-1-yl-3-pyridyl)-1H-pyrrolo[2,3-b]pyridine (250 mg, 435.49 μmol), 2-[1-[4-[(2,6-dioxo-3-piperidyl)amino]-2-fluoro-phenyl]-4-piperidyl]acetic acid (158.25 mg, 395.78 μmol), N,N-Diisopropylethylamine (225.13 mg, 1.74 mmol, 303.41 μL) and HATU (165.59 mg, 435.49 μmol) to afford 5-[6-[4-[2-[1-[4-[(2,6-dioxo-3-piperidyl)amino]-2-fluoro-phenyl]-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine (69 mg, 73.98 μmol, 16.99% yield) as off white solid. LCMS (ESI+): 883.4 $[M+H]^+$. $^1H$ NMR (400 MHz, DMSO-$d_6$): δ 12.84 (s, 1H), 10.78 (s, 1H), 9.82 (s, 1H), 8.66 (d, J=2.40 Hz, 1H), 8.56 (d, J=2.00 Hz, 1H), 8.51 (d, J=2.80 Hz, 1H), 7.97 (s, 1H), 7.95 (d, J=2.40 Hz, 1H), 7.58-7.62 (m, 1H), 7.30-7.37 (m, 2H), 7.02 (d, J=8.80 Hz, 1H), 6.84 (t, J=9.60 Hz, 1H), 6.52 (d, J=2.80 Hz, 1H), 6.50 (d, J=14.80 Hz, 1H), 5.79 (d, J=7.60 Hz, 1H), 4.21-4.31 (m, 1H), 3.57-3.65 (m, 9H), 3.10-3.16 (m, 5H), 2.65-2.80 (m, 2H), 2.74 (s, 3H), 2.53-2.60 (m, 4H), 2.31-2.41 (m, 2H), 2.02-2.11 (m, 1H), 1.70-1.85 (m, 2H), 1.02 (t, J=7.20 Hz, 3H).

Example 112

5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine

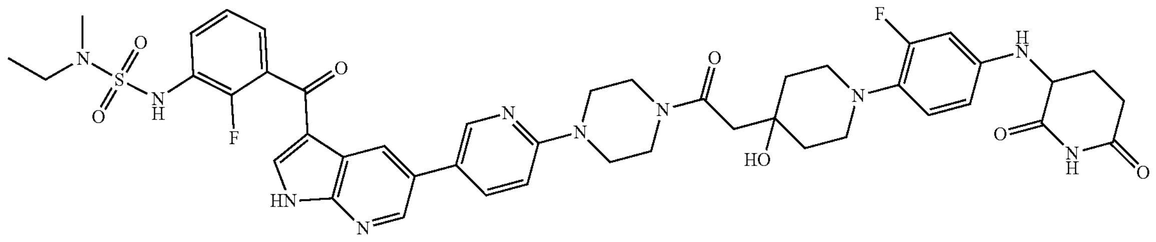 [SMILES: CCN(C)S(=O)(=O)Nc1cccc(C(=O)c2c[nH]c3ncc(-c4ccc(N5CCN(C(=O)CC6(O)CCN(c7ccc(NC8CCC(=O)NC8=O)cc7F)CC6)CC5)nc4)cc23)c1F]

Target compound was prepared via HATU mediated acid-amine coupling reaction (procedure A). Amide coupling was carried out using 2-[1-[4-[(2,6-dioxo-3-piperidyl)amino]-2-fluoro-phenyl]-4-hydroxy-4-piperidyl]acetic acid (478.09 mg, 1.15 mmol), N-ethyl-N-isopropyl-propan-2-amine (675.39 mg, 5.23 mmol, 910.23 μL) and HATU (437.14 mg, 1.15 mmol) and 3-[3-[[ethyl(methyl)sulfamoyl]amino]-2-fluoro-benzoyl]-5-(6-piperazin-1-yl-3-pyridyl)-1H-pyrrolo[2,3-b]pyridine (0.6 g, 1.05 mmol). The desired product was purified from crude by reverse phase column chromatography (0.1% Formic acid in water:Acetonitrile) and fractions were lyophilized to afford 5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine (113.97 mg, 117.95 μmol, 11.29% yield) as off white solid. LCMS (ESI+): 899.4 $[M+H]^+$. $^1H$ NMR (400 MHz, DMSO-$d_6$): δ 12.85 (s, 1H), 10.79 (s, 1H), 9.79 (s, 1H), 8.66 (d, J=2.00 Hz, 1H), 8.56 (d, J=2.00 Hz, 1H), 8.51 (d, J=2.80 Hz, 1H), 7.95-7.98 (m, 2H), 7.58-7.62 (m, 1H), 7.38-7.42 (m, 1H), 7.31-7.34 (m, 1H), 7.02 (d, J=8.80 Hz, 1H), 6.84-6.89 (m, 1H), 6.52 (d, J=2.40 Hz, 1H), 6.49 (d, J=2.40 Hz, 1H), 5.81 (s, 1H), 4.88 (s, 1H), 4.31-4.21 (m, 1H), 3.71-3.59 (m, 8H), 3.14 (q, J=6.80 Hz, 2H), 2.95-2.81 (m, 4H), 2.55-2.78 (m, 4H), 2.72 (s, 3H), 2.14-2.05 (m, 1H), 1.61-1.95 (m, 5H), 1.02 (t, J=7.20 Hz, 3H).

Example 113

5-[6-[4-[2-[1-[5-[(2,6-dioxo-3-piperidyl)amino]-2-pyridyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine

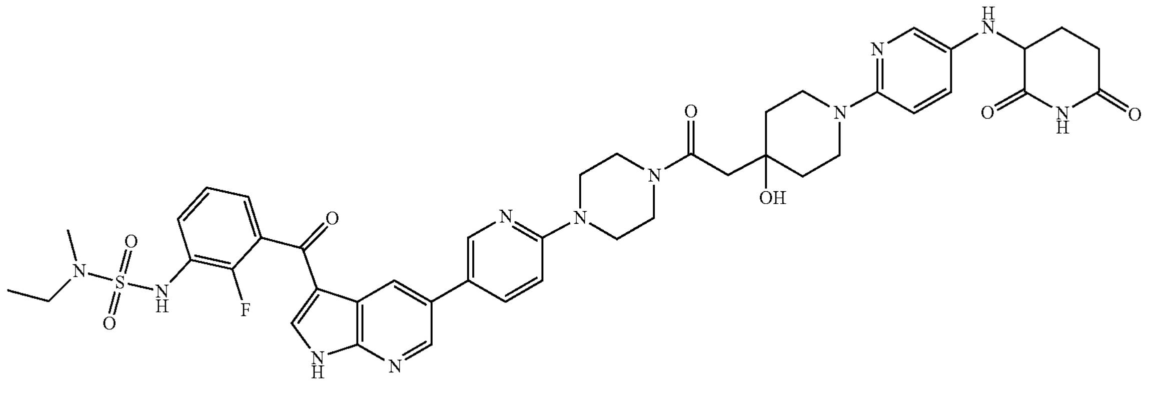 [SMILES: CCN(C)S(=O)(=O)Nc1cccc(C(=O)c2c[nH]c3ncc(-c4ccc(N5CCN(C(=O)CC6(O)CCN(c7ccc(NC8CCC(=O)NC8=O)cn7)CC6)CC5)nc4)cc23)c1F]

Target compound was prepared via HATU mediated acid-amine coupling reaction (procedure A). Amide coupling was carried out using 3-[3-[[ethyl(methyl)sulfamoyl]amino]-2-fluoro-benzoyl]-5-(6-piperazin-1-yl-3-pyridyl)-1H-pyrrolo[2,3-b]pyridine (500 mg, 870.98 μmol, hydrochloric acid salt), 2-[1-[5-[(2,6-dioxo-3-piperidyl)amino]-2-pyridyl]-4-hydroxy-4-piperidyl]acetic acid (416.86 mg, 1.05 mmol, hydrochloric acid salt), HATU (496.76 mg, 1.31 mmol) and N,N-Diisopropylethylamine (562.82 mg, 4.35 mmol, 758.52 μL) to afford 5-[6-[4-[2-[1-[5-[(2,6-dioxo-3-piperidyl)amino]-2-pyridyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine (148 mg, 152.39 μmol, 17.50% yield, Formate salt) as an off-white solid. LCMS (ESI+): 882.4 $[M+H]^+$. $^1H$ NMR (400 MHz, DMSO-$d_6$): δ 12.86 (brs, 1H), 10.89 (brs, 1H), 9.79 (s, 1H), 8.67 (d, J=2.40 Hz, 1H), 8.58 (d, J=2.40 Hz, 1H), 8.51 (d, J=2.80 Hz, 1H), 7.99 (m, 2H), 7.62-7.58 (m, 2H), 7.41-7.31 (m, 4H), 7.06 (d, J=8.40 Hz, 1H), 5.20 (brs, 1H), 4.36 (m, 1H), 3.61-3.78 (m, 13H), 3.14 (q, J=7.20 Hz, 2H), 2.75 (s, 3H), 2.62-3.15 (m, 7H), 2.11 (m, 1H), 1.96 (m, 1H), 1.75 (m, 1H), 1.02 (t, J=7.20 Hz, 3H).

Example 114

5-[6-[4-[2-[1-[4-[(2,6-dioxo-3-piperidyl)amino]-2-fluoro-phenyl]-3-hydroxy-pyrrolidin-3-yl]acetyl]piperazin-1-yl]-3-pyridyl]-3-[3-[[ethyl(methyl)sulfamoyl]amino]-2-fluoro-benzoyl]-1H-pyrrolo[2,3-b]pyridine

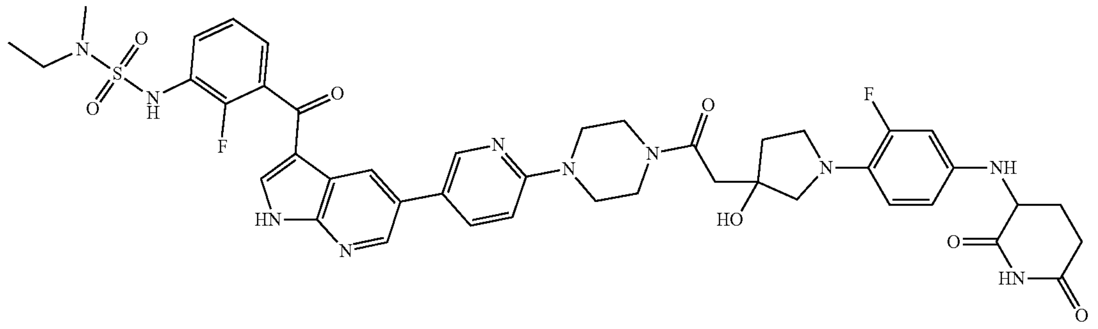 [SMILES: CCN(C)S(=O)(=O)Nc1cccc(C(=O)c2c[nH]c3ncc(-c4ccc(N5CCN(C(=O)CC6(O)CCN(c7ccc(NC8CCC(=O)NC8=O)cc7F)C6)CC5)nc4)cc23)c1F]

Target compound was prepared via HATU mediated acid-amine coupling reaction (procedure A). Amide coupling was carried out using 3-[3-[[ethyl(methyl)sulfamoyl]amino]-2-fluoro-benzoyl]-5-(6-piperazin-1-yl-3-pyridyl)-1H-pyrrolo[2,3-b]pyridine (600 mg, 1.05 mmol), 2-[1-[4-[(2,6-dioxo-3-piperidyl)amino]-2-fluoro-phenyl]-3-hydroxy-pyrrolidin-3-yl]acetic acid (550 mg, 1.37 mmol), N,N-Diisopropylethylamine (1.48 g, 11.48 mmol, 2.0 mL) and HATU (450 mg, 1.18 mmol) to afford 5-[6-[4-[2[1-[4-[(2,6-dioxo-3-piperidyl)amino]-2-fluoro-phenyl]-3-hydroxy-pyrrolidin-3-yl]acetyl]piperazin-1-yl]-3-pyridyl]-3-[3-[[ethyl(methyl)sulfamoyl]amino]-2-fluoro-benzoyl]-1H-pyrrolo[2,3-b]pyridine (121 mg, 131.36 μmol, 12.57% yield) as a grey solid. LCMS (ESI+): 885.3 $[M+H]^+$. $^1H$ NMR (400 MHz, DMSO-$d_6$): δ 12.90 (s, 1H), 10.71 (s, 1H), 8.66 (s, 1H), 8.56 (s, 1H), 8.52-8.51 (m, 2H), 7.98-7.95 (m, 2H), 7.60-7.60 (m, 1H), 7.34-7.32 (m, 2H), 7.02 (d, J=9.20 Hz, 1H), 6.58-6.43 (m, 3H), 5.53 (d, J=7.60 Hz, 1H), 4.99 (s, 1H), 4.22-4.15 (m, 1H), 3.67-3.59 (m, 9H), 3.16-3.11 (m, 4H), 2.79-2.73 (m, 2H), 2.52-2.50 (m, 6H), 2.08-1.80 (m, 4H), 1.02 (t, J=7.20 Hz, 3H).

Example 115

5-[6-[4-[2-[1-[5-[(2,6-dioxo-3-piperidyl)amino]-3-fluoro-2-pyridyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine

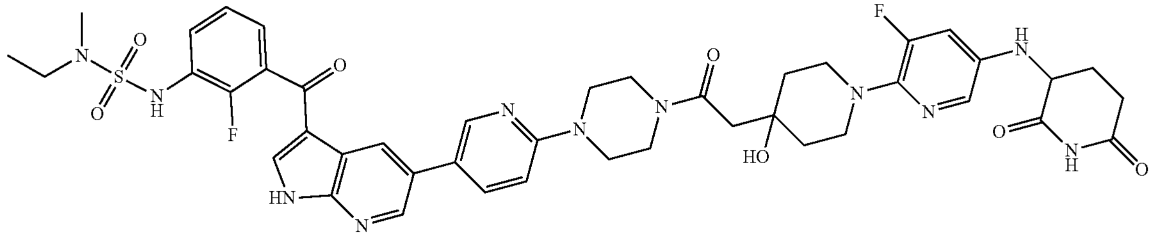

Target compound was prepared via COMU mediated acid-amine coupling reaction (procedure B). Amide coupling was carried out using 2-[1-[5-[(2,6-dioxo-3-piperidyl)amino]-3-fluoro-2-pyridyl]-4-hydroxy-4-piperidyl]acetic acid (566.36 mg, 1.36 mmol), 3-[3-[[ethyl(methyl)sulfamoyl]amino]-2-fluoro-benzoyl]-5-(6-piperazin-1-yl-3-pyridyl)-1H-pyrrolo[2,3-b]pyridine (600 mg, 1.05 mmol), COMU (581.90 mg, 1.36 mmol) and N,N-diisopropylethylamine (810.49 mg, 6.27 mmol, 1.09 mL) to afford 5-[6-[4-[2-[1-[5-[(2,6-dioxo-3-piperidyl)amino]-3-fluoro-2-pyridyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine (117 mg, 124.64 μmol, 11.92% yield) as pale brown solid. LCMS (ESI+): 900.3 $[M+H]^+$. $^1H$ NMR (400 MHz, DMSO-d6): δ 12.85 (s, 1H), 10.81 (s, 1H), 9.78 (s, 1H), 8.66 (d, J=2.00 Hz, 1H), 8.56-8.51 (m, 2H), 7.98-7.95 (m, 2H), 7.62-7.57 (m, 2H), 7.41-7.38 (m, 1H), 7.32 (t, J=8.00 Hz, 1H), 7.02 (t, J=8.40 Hz, 2H), 4.91 (s, 1H), 4.38-4.20 (m, 1H), 3.65-3.59 (m, 8H), 3.34-3.33 (m, 4H), 3.31-3.25 (m, 4H), 2.75 (s, 3H), 2.53-2.50 (m, 3H), 2.34-2.33 (m, 1H), 1.92-1.68 (m, 5H), 1.03 (t, J=7.20 Hz, 3H).

Examples 116-120

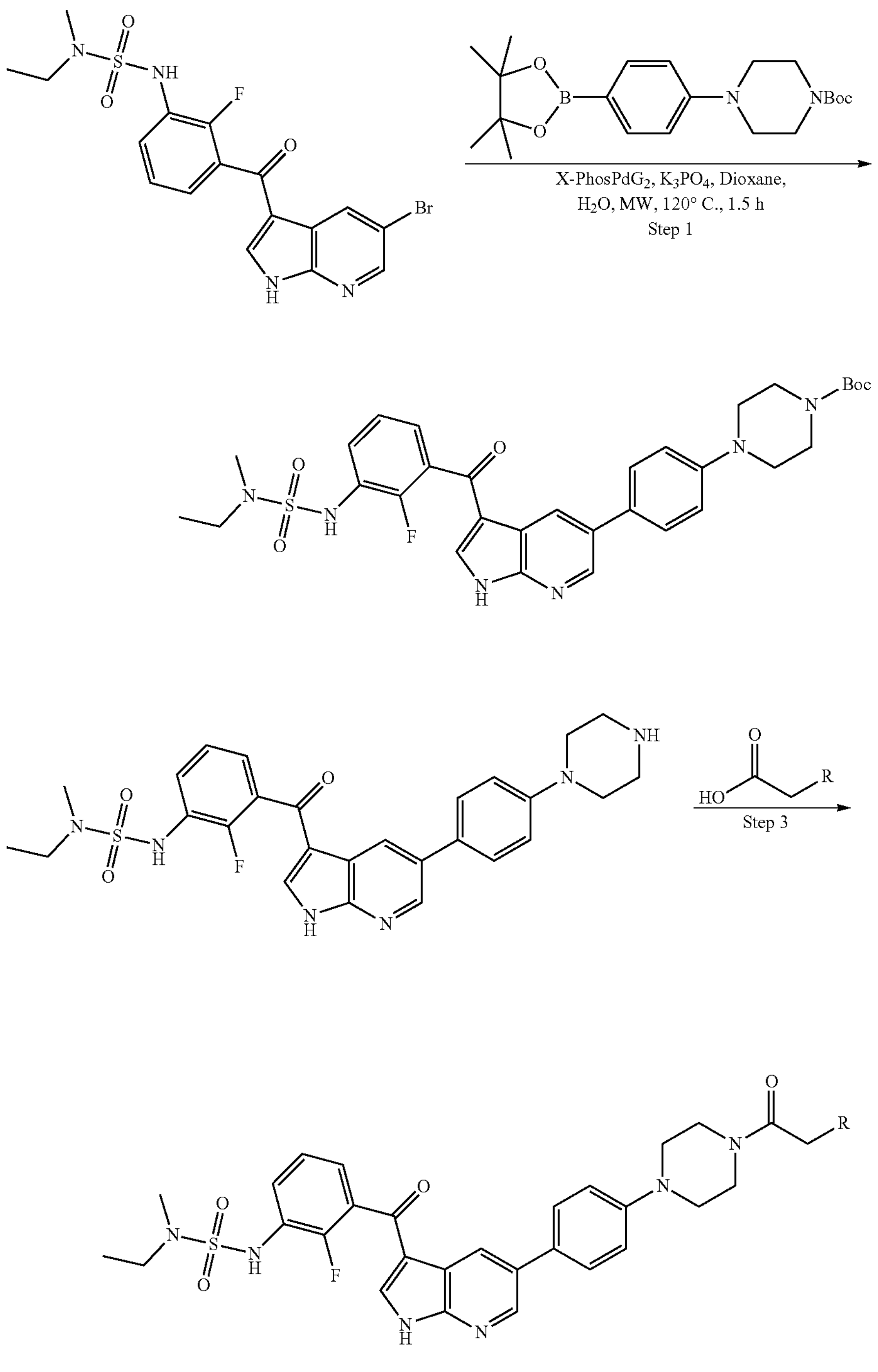

Synthesis of intermediate 3-[3-[[ethyl(methyl)sulfamoyl]amino]-2-fluoro-benzoyl]-5-(4-piperazin-1-ylphenyl)-1H-pyrrolo[2,3-b]pyridine Step 1: A solution of 5-bromo-3-[3-[[ethyl(methyl)sulfamoyl]amino]-2-fluoro-benzoyl]-1H-pyrrolo[2,3-b]pyridine (3.2 g, 7.04 mmol) in 1,4 dioxane (40.0 mL) and Water (8.0 mL) was taken in a microwave vial and added tert-butyl 4-[4-(4,4,5,5-tetramethyl-1,3,2-dioxaborolan-2-yl)phenyl] piperazine-1-carboxylate (3.27 g, 8.44 mmol), Potassium phosphate tribasic (anhydrous) (4.48 g, 21.08 mmol) at room temperature under nitrogen. The reaction mixture was degassed with nitrogen for 10 minutes, XPhos Pd G2 (553 mg, 702.84 μmol) was added to the reaction mixture and heated to 120° C. for 2 h under microwave irradiation. After completion of the reaction, the reaction mixture was diluted with water (10 mL) and extracted with ethyl acetate (2×10 mL). The combined organic layers were dried over Sodium sulphate, filtered and concentrated under reduced pressure. The crude compound was purified by 100-200 silica gel column chromatography with 80% ethyl acetate in petroleum ether as a eluent to afford tert-butyl 4-[4-[3-[3-[[ethyl(methyl)sulfamoyl]amino]-2-fluoro-benzoyl]-1H-pyrrolo[2,3-b]pyridin-5-yl]phenyl]piperazine-1-carboxylate (2.6 g, 2.74 mmol, 38.98% yield) as a yellow solid. LCMS (ESI+): 637.3 [M+H]+.

Step 2: To a stirred solution of tert-butyl 4-[4-[3-[3-[[ethyl(methyl)sulfamoyl]amino]-2-fluoro-benzoyl]-1H-pyrrolo[2,3-b]pyridin-5-yl]phenyl]piperazine-1-carboxylate (2.6 g, 4.08 mmol) in 1,4-Dioxane (20.0 mL) was added 4M HCl in 1,4 Dioxane (4M, 20.0 mL) at 0° C. and the resulting reaction mixture was stirred for 1 h at room temperature. Reaction mixture was concentrated under reduced pressure. The residue obtained was triturated with diethyl ether (2×15 mL), dried under reduced pressure to afford 3-[3-[[ethyl(methyl)sulfamoyl]amino]-2-fluoro-benzoyl]-5-(4-piperazin-1-ylphenyl)-1H-pyrrolo[2,3-b]pyridine (2.0 g, 2.90 mmol, 70.94% yield) as yellow solid. LCMS (ESI+): 537.1 [M+H]+.

Example 116

5-[4-[4-[2-[1-[4-[(2,6-dioxo-3-piperidyl)amino]phenyl]-4-hydroxy-4-piperidyl]acetyl]piperazin-1-yl]phenyl]-3-[3-[[ethyl(methyl)sulfamoyl]amino]-2-fluoro-benzoyl]-1H-pyrrolo[2,3-b]pyridine

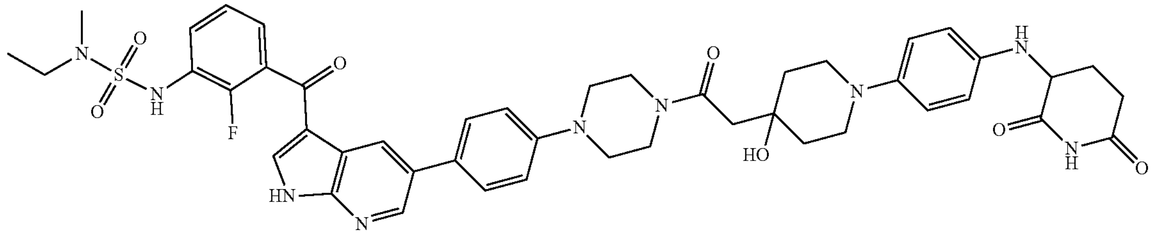 [SMILES: CCN(C)S(=O)(=O)Nc1cccc(C(=O)c2c[nH]c3ncc(-c4ccc(N5CCN(C(=O)CC6(O)CCN(c7ccc(NC8CCC(=O)NC8=O)cc7)CC6)CC5)cc4)cc23)c1F]

Target compound was prepared via HATU mediated acid-amine coupling reaction (procedure A). Amide coupling was carried out using 3-[3-[[ethyl(methyl)sulfamoyl]amino]-2-fluoro-benzoyl]-5-(4-piperazin-1-ylphenyl)-1H-pyrrolo[2,3-b]pyridine (520 mg, 907.38 μmol), 2-[1-[4-[(2,6-dioxo-3-piperidyl)amino]phenyl]-4-hydroxy-4-piperidyl]acetic acid (327.92 mg, 824.22 μmol), N,N-Diisopropylethylamine (469.09 mg, 3.63 mmol, 632.19 μL) and HATU (345.01 mg, 907.38 μmol) to afford 5-[4-[4-[2-[1-[4-[(2,6-dioxo-3-piperidyl)amino]phenyl]-4-hydroxy-4-piperidyl]acetyl]piperazin-1-yl]phenyl]-3-[3-[[ethyl(methyl)sulfamoyl]amino]-2-fluoro-benzoyl]-1H-pyrrolo[2,3-b]pyridine (185 mg, 199.30 μmol, 21.96% yield) as off-white solid. LCMS (ESI+): 880.4 [M+H]+. $^1$H NMR (400 MHz, DMSO-d6): δ 12.81 (d, J=3.20 Hz, 1H), 10.84 (s, 1H), 10.72 (s, 1H), 9.78 (s, 1H), 8.66 (d, J=2.40 Hz, 1H), 8.58 (d, J=2.00 Hz, 1H), 7.96 (d, J=2.40 Hz, 1H), 7.58-7.64 (m, 3H), 7.31-7.41 (m, 4H), 7.13 (d, J=8.80 Hz, 2H), 6.77 (d, J=8.00 Hz, 2H), 6.35-6.47 (m, 1H), 5.34 (s, 1H), 4.37-4.45 (m, 1H), 3.65-3.80 (m, 5H), 3.24-3.45 (m, 6H), 3.14 (q, J=6.80 Hz, 2H), 2.65-2.85 (m, 2H), 2.75 (s, 3H), 2.50-2.58 (m, 2H), 2.07-2.15 (m, 3H), 1.87-1.96 (m, 3H), 1.03 (t, J=7.20 Hz, 3H).

Example 117

5-[4-[4-[2-[1-[5-[(2,6-dioxo-3-piperidyl)amino]-2-pyridyl]-4-hydroxy-4-piperidyl]acetyl]piperazin-1-yl]phenyl]-3-[3-[[ethyl(methyl)sulfamoyl]amino]-2-fluoro-benzoyl]-1H-pyrrolo[2,3-b]pyridine

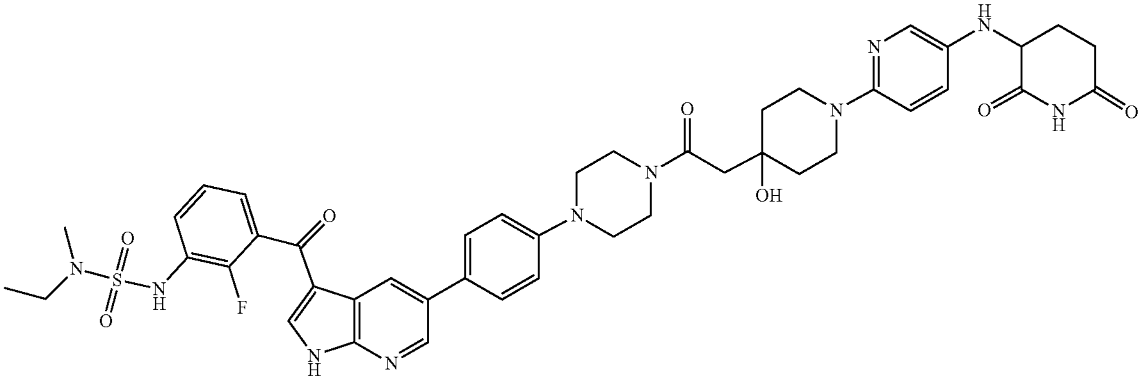 [SMILES: CCN(C)S(=O)(=O)Nc1cccc(C(=O)c2c[nH]c3ncc(-c4ccc(N5CCN(C(=O)CC6(O)CCN(c7ccc(NC8CCC(=O)NC8=O)cn7)CC6)CC5)cc4)cc23)c1F]

To a solution of 3-[3-[[ethyl(methyl)sulfamoyl]amino]-2-fluoro-benzoyl]-5-(4-piperazin-1-ylphenyl)-1H-pyrrolo[2,3-b]pyridine (500.0 mg, 931.76 μmol), 2-[1-[5-[(2,6-dioxo-3-piperidyl)amino]-2-pyridyl]-4-hydroxy-4-piperidyl]acetic acid (337.65 mg, 931.76 μmol) in N,N-Dimethylformamide (3.0 mL) were added COMU (598.56 mg, 1.40 mmol), N,N-Diisopropylethylamine (602.12 mg, 4.66 mmol, 811.48 μL) and stirred at room temperature for 14 h. The reaction mixture was concentrated under Genvac and was purified by reverse phase C18 column chromatography (100 g RediSep column) using 0.1% HCOOH in acetonitrile and water as eluents to afford 5-[4-[4-[2-[1-[5-[(2,6-dioxo-3-piperidyl)amino]-2-pyridyl]-4-hydroxy-4-piperidyl]acetyl]piperazin-1-yl]phenyl]-3-[3-[[ethyl(methyl)sulfamoyl]amino]-2-fluoro-benzoyl]-1H-pyrrolo[2,3-b]pyridine (150 mg, 160.35 μmol, 17.21% yield) as off white solid. LCMS (ESI+): 881.0 $[M+H]^+$. $^1H$ NMR (400 MHz, DMSO-$d_6$): δ 12.81 (s, 1H), 10.85 (s, 1H), 9.78 (s, 1H), 8.65 (d, J=2.40 Hz, 1H), 8.58 (d, J=2.00 Hz, 1H), 7.96 (d, J=2.40 Hz, 1H), 7.64-7.58 (m, 4H), 7.38-7.31 (m, 3H), 7.12 (d, J=8.80 Hz, 2H), 5.10-5.05 (m, 1H), 4.86-4.78 (m, 1H), 4.33-4.28 (m, 1H), 3.73-3.69 (m, 6H), 3.34-3.22 (m, 6H), 3.14 (q, J=7.20 Hz, 2H), 2.74 (s, 3H), 2.67-2.55 (m, 3H), 2.13-2.08 (m, 1H), 1.93-1.89 (m, 1H), 1.76-1.70 (m, 4H), 1.02 (t, J=7.20 Hz, 3H).

Example 118

5-[4-[4-[2-[1-[4-[(2,6-dioxo-3-piperidyl)amino]-2-fluoro-phenyl]-3-hydroxy-pyrrolidin-3-yl]acetyl]piperazin-1-yl]phenyl]-3-[3-[[ethyl(methyl)sulfamoyl]amino]-2-fluoro-benzoyl]-1H-pyrrolo[2,3-b]pyridine Target compound was prepared via HATU mediated acid-amine coupling reaction (procedure A). Amide coupling was carried out using 3-[3-[[ethyl(methyl)sulfamoyl]amino]-2-fluoro-benzoyl]-5-(4-piperazin-1-ylphenyl)-1H-pyrrolo[2,3-b]pyridine (540 mg, 942.28 μmol), 2-[1-[4-[(2,6-dioxo-3-piperidyl)amino]-2-fluoro-phenyl]-3-hydroxy-pyrrolidin-3-yl]acetic acid (344.27 mg, 856.77 μmol), N,N-Diisopropylethylamine (487.13 mg, 3.77 mmol, 656.51 μL) and HATU (358.28 mg, 942.28 μmol) to afford 5-[4-[4-[2-[1-[4-[(2,6-dioxo-3-piperidyl)amino]-2-fluoro-phenyl]-3-hydroxy-pyrrolidin-3-yl]acetyl]piperazin-1-yl]phenyl]-3-[3-[[ethyl(methyl)sulfamoyl]amino]-2-fluoro-benzoyl]-1H-pyrrolo[2,3-b]pyridine (152 mg, 163.49 μmol, 17.35% yield) as off white solid. LCMS (ESI+): 884.4 $[M+H]^+$. $^1H$ NMR (400 MHz, DMSO-$d_6$): δ 12.80 (s, 1H), 10.77 (s, 1H), 9.85 (s, 1H), 8.65 (d, J=2.40 Hz, 1H), 8.57 (d, J=2.40 Hz, 1H), 7.94 (s, 1H), 7.56-7.63 (m, 3H), 7.20-7.30 (m, 2H), 7.12 (d, J=8.80 Hz, 2H), 6.51-6.60 (m, 2H), 6.42 (d, J=2.40 Hz, 1H), 5.52 (d, J=7.60 Hz, 1H), 4.99 (s, 1H), 4.18-4.23 (m, 1H), 3.65-3.75 (m, 4H), 3.43-3.45 (m, 1H), 3.08-3.27 (m, 8H), 2.58-2.78 (m, 3H), 2.73 (s, 3H), 2.05-2.15 (m, 2H), 1.78-2.00 (m, 4H), 1.02 (t, J=7.20 Hz, 3H).

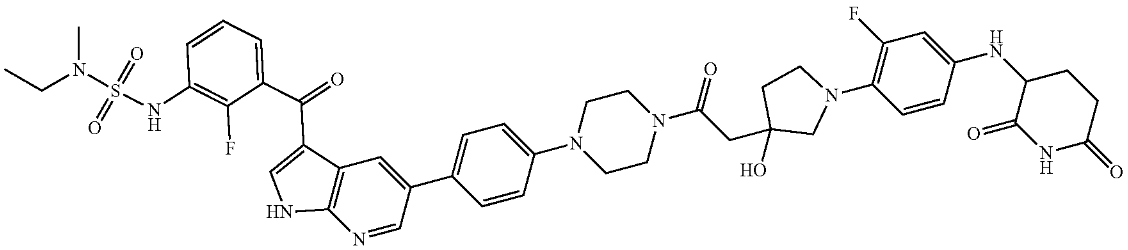 [SMILES: CCN(C)S(=O)(=O)Nc1cccc(C(=O)c2c[nH]c3ncc(-c4ccc(N5CCN(C(=O)CC6(O)CCN(c7ccc(NC8CCC(=O)NC8=O)cc7F)C6)CC5)cc4)cc23)c1F]

Example 119

5-[4-[4-[2-[1-[4-[(2,6-dioxo-3-piperidyl)amino]-2-fluoro-phenyl]-4-hydroxy-4-piperidyl]acetyl]piperazin-1-yl]phenyl]-3-[3-[[ethyl(methyl)sulfamoyl]amino]-2-fluoro-benzoyl]-1H-pyrrolo[2,3-b]pyridine

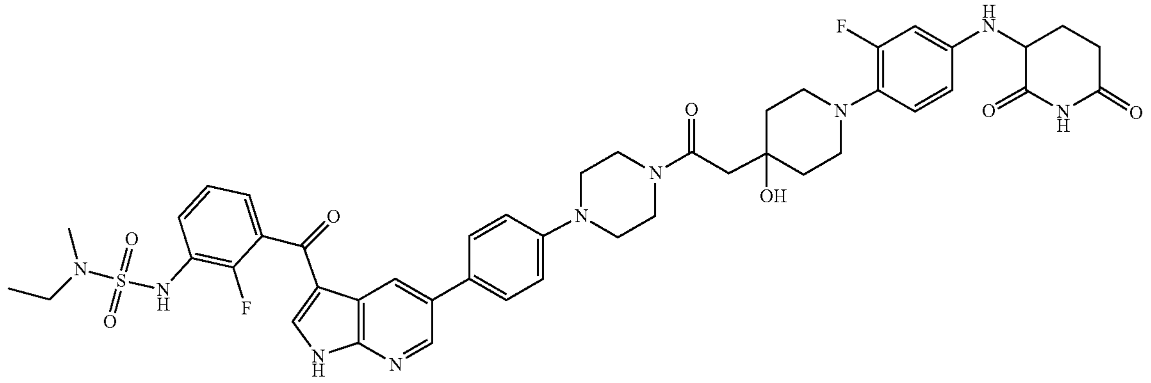 [SMILES: CCN(C)S(=O)(=O)Nc1cccc(C(=O)c2c[nH]c3ncc(-c4ccc(N5CCN(C(=O)CC6(O)CCN(c7ccc(NC8CCC(=O)NC8=O)cc7F)CC6)CC5)cc4)cc23)c1F]

To a solution of 2-[1-[4-[(2,6-dioxo-3-piperidyl)amino]-2-fluoro-phenyl]-4-hydroxy-4-piperidyl]acetic acid (350 mg, 841.66 μmol), 3-[3-[[ethyl(methyl)sulfamoyl]amino]-2-fluoro-benzoyl]-5-(4-piperazin-1-ylphenyl)-1H-pyrrolo[2,3-b]pyridine (506.46 mg, 883.75 μmol) in N,N-Dimethylformamide (4 mL) were added HATU (352.03 mg, 925.83 μmol), N,N-Diisopropylethylamine (435.12 mg, 3.37 mmol, 586.41 μL) and stirred at room temperature for 14 h. After completion, excess N,N-Dimethylformamide and N,N-Diisopropylethylamine were distilled under reduced pressure using rotavapor at 45° C. to get the crude product which was purified by reverse phase column chromatography by using C-18 column (100 g) eluting with 0.1% HCOOH in acetonitrile and water to afford 5-[4-[4-[2-[1-[4-[(2,6-dioxo-3-piperidyl)amino]-2-fluoro-phenyl]-4-hydroxy-4-piperidyl]acetyl]piperazin-1-yl]phenyl]-3-[3-[[ethyl(methyl)sulfamoyl]amino]-2-fluoro-benzoyl]-1H-pyrrolo[2,3-b]pyridine (120 mg, 123.14 μmol, 14.63% yield) as off white solid. LCMS (ESI+): 898.0 [M+H]+. $^1$H NMR (400 MHz, DMSO-$d_6$): δ 12.80 (bs, 1H), 10.80 (s, 1H), 8.65 (d, J=2.00 Hz, 1H), 8.57 (d, J=2.40 Hz, 1H), 7.95 (s, 1H), 7.57-7.64 (m, 3H), 7.28-7.36 (m, 2H), 7.12 (d, J=8.80 Hz, 2H), 6.86 (t, J=9.20 Hz, 1H), 6.41-6.53 (m, 2H), 5.78 (d, J=7.60 Hz, 1H), 4.87 (s, 1H), 4.23-4.29 (m, 1H), 3.75-3.65 (m, 4H), 3.29-3.22 (m, 4H), 3.12 (t, J=6.80 Hz, 2H), 2.88-2.92 (m, 4H), 2.68-2.73 (m, 4H), 2.59 (s, 3H), 2.07-2.11 (m, 1H), 1.66-1.89 (m, 4H), 1.02 (t, J=6.80 Hz, 3H).

Example 120

5-[4-[4-[2-[1-[5-[(2,6-dioxo-3-piperidyl)amino]-3-fluoro-2-pyridyl]-4-hydroxy-4-piperidyl]acetyl]piperazin-1-yl]phenyl]-3-[3-[[ethyl(methyl)sulfamoyl]amino]-2-fluoro-benzoyl]-1H-pyrrolo[2,3-b]pyridine

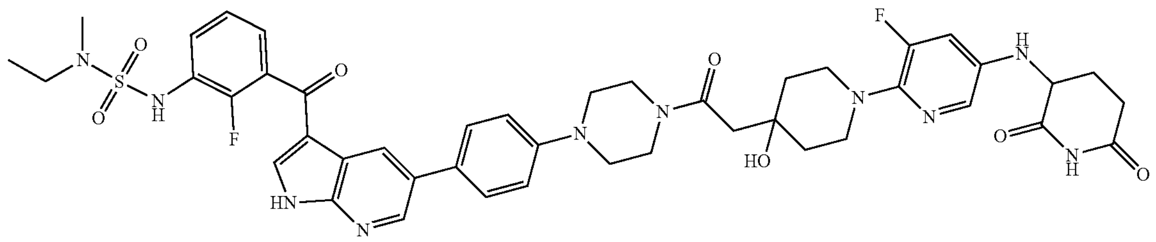 [SMILES: CCN(C)S(=O)(=O)Nc1cccc(C(=O)c2c[nH]c3ncc(-c4ccc(N5CCN(C(=O)CC6(O)CCN(c7ncc(NC8CCC(=O)NC8=O)cc7F)CC6)CC5)cc4)cc23)c1F]

Target compound was prepared via COMU mediated acid-amine coupling reaction (procedure B). Amide coupling was carried out using 2-[1-[5-[(2,6-dioxo-3-piperidyl) amino]-3-fluoro-2-pyridyl]-4-hydroxy-4-piperidyl]acetic acid (567.33 mg, 1.36 mmol), 3-[3-[[ethyl(methyl)sulfamoyl]amino]-2-fluoro-benzoyl]-5-(4-piperazin-1-ylphenyl)-1H-pyrrolo[2,3-b]pyridine (600 mg, 1.05 mmol), COMU (582.90 mg, 1.36 mmol), and N,N-diisopropylethylamine (811.86 mg, 6.28 mmol, 1.09 mL) to afford 5-[4-[4-[2-[1-[5-[(2,6-dioxo-3-piperidyl)amino]-3-fluoro-2-pyridyl]-4-hydroxy-4-piperidyl]acetyl]piperazin-1-yl]phenyl]-3-[3-[[ethyl(methyl)sulfamoyl]amino]-2-fluoro-benzoyl]-1H-pyrrolo[2,3-b]pyridine (127 mg, 140.98 μmol, 13.47% yield) as pale brown solid. LCMS (ESI+): 899.2 $[M+H]^+$. $^1H$ NMR (400 MHz, DMSO-d6): δ 12.87 (s, 1H), 10.81 (s, 1H), 9.77 (s, 1H), 8.65 (d, J=2.40 Hz, 1H), 8.57 (d, J=2.00 Hz, 2H), 7.95 (s, 1H), 7.63-7.57 (m, 4H), 7.42-7.30 (m, 2H), 7.12 (d, J=8.80 Hz, 2H), 7.09-6.90 (m, 1H), 5.87 (d, J=7.60 Hz, 1H), 4.90 (s, 1H), 4.38-4.29 (m, 1H), 3.74-3.69 (m, 4H), 3.31-3.22 (m, 6H), 3.16-3.07 (m, 6H), 2.74 (s, 3H), 2.60-2.51 (m, 3H), 2.34-2.33 (m, 1H), 1.92-1.65 (m, 4H), 1.02 (t, J=7.20 Hz, 3H).

Example 121

3-[2-chloro-3-[[ethyl(methyl)sulfamoyl]amino]-6-fluoro-benzoyl]-5-[2-[4-[2-[4-[4-[(2,6-dioxo-3-piperidyl)amino]phenyl]-1-piperidyl]acetyl]piperazin-1-yl]pyrimidin-5-yl]-1H-pyrrolo[2,3-b]pyridine

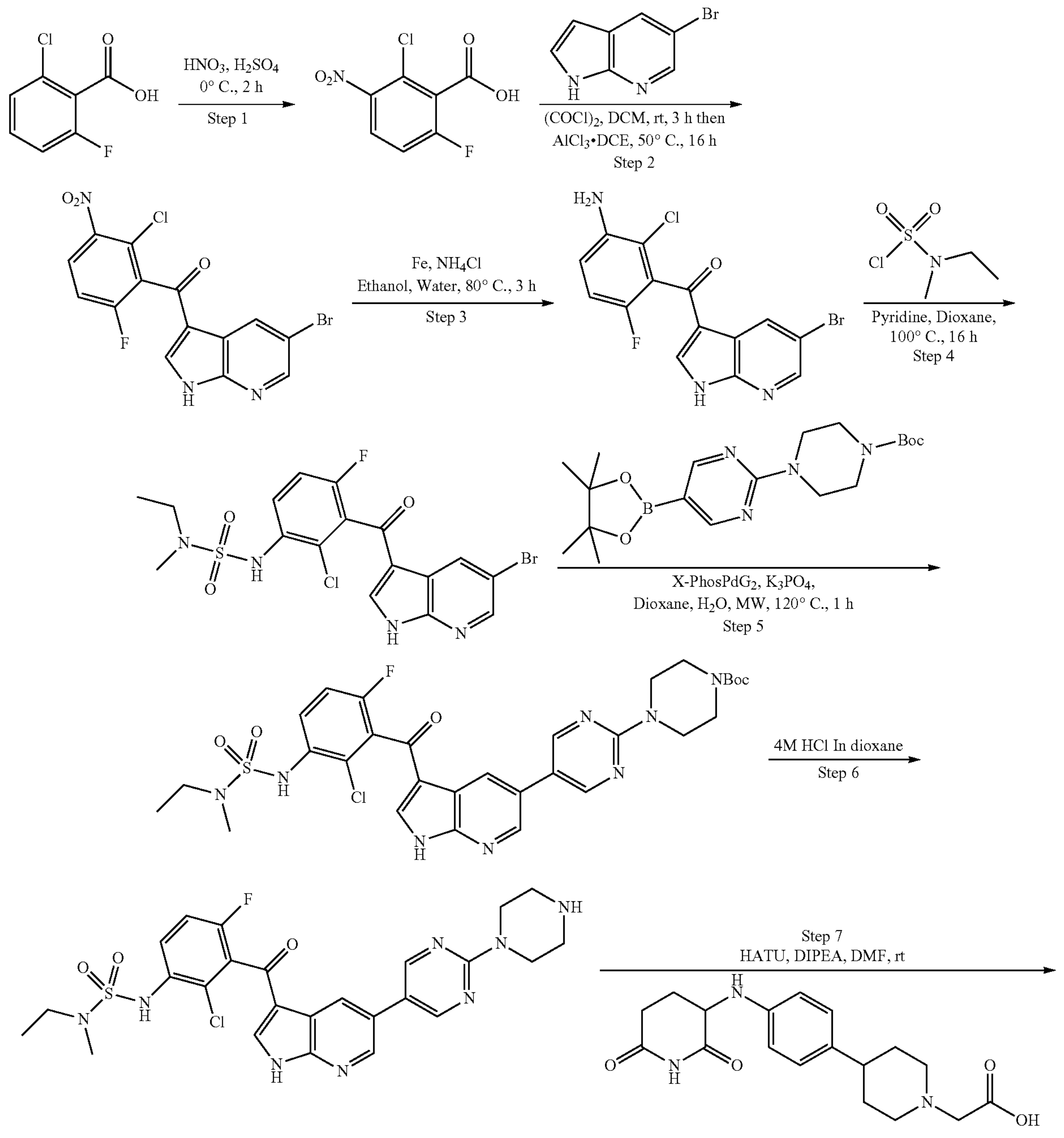

4p

-continued

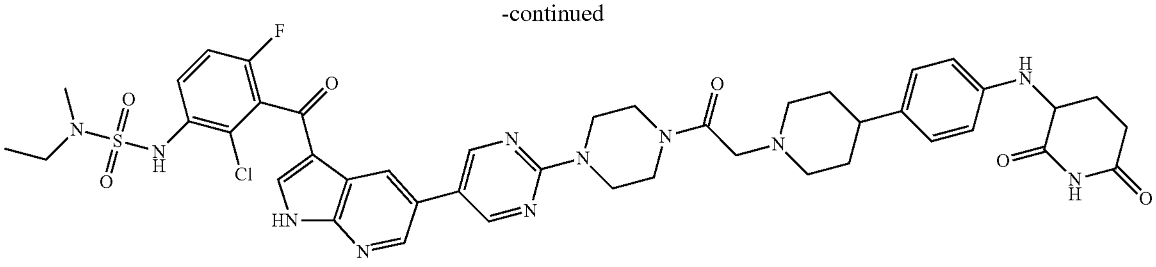

Step 1: To a stirred solution of 2-chloro-6-fluoro-benzoic acid (5.0 g, 28.64 mmol) in concentrated sulfuric acid (15 mL) was added Nitric Acid (2.17 g, 34.37 mmol) at 0° C. and the resulting reaction mixture was stirred at room temperature for 2 h. After completion, the reaction mixture was poured into ice-water (700 mL) and extracted with ethyl acetate (3×400 mL). The combined organic layers were washed with brine solution and dried over anhydrous sodium sulphate, filtered and concentrated under reduced pressure to afford the desired product 2-chloro-6-fluoro-3-nitro-benzoic acid (6.1 g, 27.23 mmol, 95.06% yield, 98% purity) as a white solid. Desired product was confirmed by $^{1}$H NMR. $^{1}$H NMR (400 MHz, DMSO-d6): δ 8.27 (dd, J=5.60, 9.20 Hz, 1H), 7.66 (t, J=9.20 Hz, 1H).

Step 2: To a stirred solution of 2-chloro-6-fluoro-3-nitro-benzoic acid (6.8 g, 30.97 mmol) in Dichloromethane (60 mL) was added Oxalyl chloride (9.83 g, 77.43 mmol, 6.73 mL) followed by the addition of N,N-Dimethylformamide (226.37 mg, 3.10 mmol, 239.80 μL) at 0-5° C. under nitrogen. The reaction mixture was stirred at room temperature for 3 h. After completion, the reaction mixture was concentrated under reduced pressure to get the acid chloride (crude). To a stirred solution of 5-bromo-1H-pyrrolo[2,3-b]pyridine (6.10 g, 30.97 mmol) in Dichloroethane (80 mL) was added anhydrous Aluminum chloride (16.52 g, 123.89 mmol, 6.77 mL) at 0-5° C. under nitrogen, followed by the addition of the acid chloride (dissolved in DCE, 80 mL) at the same temperature. The reaction mixture was stirred at room temperature for 30 minutes and then heated to 50° C. for 18 h. After completion, the reaction mixture was cooled to 0-5° C. and cold water (800 mL) added. The reaction mixture was extracted with ethyl acetate (3×400 mL). The combined organic layers were dried over Sodium sulphate, filtered and concentrated under reduced pressure. The crude compound was washed with ethyl acetate (350 mL) to afford (5-bromo-1H-pyrrolo[2,3-b]pyridin-3-yl)-(2-chloro-6-fluoro-3-nitro-phenyl)methanone (7.2 g, 17.88 mmol, 57.74% yield) as a brown solid. LCMS (ESI+): 397.9 [M+H]$^{+}$.

Step 3: To a stirred solution of (5-bromo-1H-pyrrolo[2,3-b]pyridin-3-yl)-(2-chloro-6-fluoro-3-nitro-phenyl)methanone (7.2 g, 18.06 mmol) in Ethanol (70 mL) and Water (10 mL) added Iron powder (5.04 g, 90.32 mmol, 641.80 μL) at room temperature. The reaction mixture was heated to 80° C. for 3 h. After completion, the reaction mixture was cooled to room temperature, then filtered through celite pad and filtrate was diluted with water (700 mL) and extracted with ethyl acetate (3×400 mL). The combined organic layers were washed with brine solution (400 mL) and dried over anhydrous Sodium sulphate, filtered and concentrated under reduced pressure. The crude compound was purified by silica gel column chromatography eluting with 40-45% ethyl acetate in petroleum ether to afford (3-amino-2-chloro-6-fluoro-phenyl)-(5-bromo-1H-pyrrolo[2,3-b]pyridin-3-yl)methanone (5.7 g, 14.69 mmol, 81.33% yield) as a pale brown solid. LCMS (ESI+): 370.0 [M+H]$^{+}$.

Step 4: To a solution of (3-amino-2-chloro-6-fluoro-phenyl)-(5-bromo-1H-pyrrolo[2,3-b]pyridin-3-yl)methanone (2.5 g, 6.78 mmol) in 1,4-Dioxane (10 mL) was added Pyridine (7.78 g, 98.35 mmol, 7.95 mL) followed by the addition of N-ethyl-N-methyl-sulfamoyl chloride (6.74 g, 42.73 mmol, 5.26 mL) at room temperature under nitrogen. The reaction mixture was heated to 100° C. for 16 h. After completion, water (300 mL) was added to the reaction mixture and extracted with ethyl acetate (3×200 mL). The combined organic layers were washed with brine solution (200 mL), dried over sodium sulphate, filtered and concentrated under reduced pressure. The crude compound was purified by silica gel column chromatography with 52-60% ethyl acetate in petroleum ether as a eluent to afford 5-bromo-3-[2-chloro-3-[[ethyl(methyl)sulfamoyl]amino]-6-fluoro-benzoyl]-1H-pyrrolo[2,3-b]pyridine (2.3 g, 4.52 mmol, 66.60% yield) as a pale yellow solid. LCMS (ESI+): 488.9 [M+H]$^{+}$.

Step 5: A solution of 5-bromo-3-[2-chloro-3-[[ethyl(methyl)sulfamoyl[amino]-6-fluoro-benzoyl]-1H-pyrrolo[2,3-b]pyridine (700 mg, 1.43 mmol) in 1,4-Dioxane (10 mL) and Water (2.5 mL) taken in a microwave vial, and added $K_3PO_4$ (910.20 mg, 4.29 mmol) followed by the addition of tert-butyl 4-[5-(4,4,5,5-tetramethyl-1,3,2-dioxaborolan-2-yl)pyrimidin-2-yl]piperazine-1-carboxylate (836.76 mg, 2.14 mmol) at room temperature under nitrogen. The reaction mixture was irradiated under microwave at 120° C. for 2 h. After completion, water (300 mL) was added to the reaction mixture and extracted with ethyl acetate (3×200 mL). The combined organic layers were washed with brine solution (200 mL), dried over sodium sulphate, filtered and concentrated under reduced pressure. The crude compound was purified by silica gel column chromatography with 80-90% ethyl acetate in pet-ether as a eluent to afford tert-butyl 4-[5-[3-[2-chloro-3-3-[[ethyl(methyl)sulfamoyl]amino]-6-fluoro-benzoyl]-1H-pyrrolo[2,3-b]pyridin-5-yl]pyrimidin-2-yl]piperazine-1-carboxylate (500 mg, 690.78 μmol, 48.33% yield) as a pale yellow solid. LCMS (ESI+): 672.9 [M+H]$^{+}$.

Step 6: A solution of tert-butyl 4-[5-[3-[2-chloro-3-[[ethyl(methyl)sulfamoyl]amino]-6-fluoro-benzoyl]-1H-pyrrolo[2,3-b]pyridin-5-yl]pyrimidin-2-yl]piperazine-1-carboxylate (500 mg, 742.77 μmol) in Dichloromethane (10 mL) added to a hydrogen chloride solution (4M in 1,4-dioxane, 270.82 mg, 7.43 mmol, 338.53 μL) at 0° C. under nitrogen. Then stirred the reaction at room temperature for 4 h. After completion, the reaction mixture was concentrated under reduced pressure to get the crude compound. This crude compound was triturated with ethyl acetate to afford 3-[2-chloro-3-[[ethyl(methyl)sulfamoyl]amino]-6-fluoro-benzoyl]-5-(2-piperazin-1-ylpyrimidin-5-yl)-1H-pyrrolo[2,3-b]

pyridine (500 mg, 705.49 μmol, 94.98% yield) as a pale-yellow solid. LCMS (ESI+): 573.1 $[M+H]^+$.

Step 7: Target compound was prepared via HATU mediated acid-amine coupling reaction (procedure A). Amide coupling was carried out using 3-[2-chloro-3-[[ethyl(methyl)sulfamoyl]amino]-6-fluoro-benzoyl]-5-(2-piperazin-1-ylpyrimidin-5-yl)-1H-pyrrolo[2,3-b]pyridine (250 mg, 410.17 μmol), N-ethyl-N-isopropyl-propan-2-amine (265.06 mg, 2.05 mmol, 357.22 μL) and 2-[4-[4-[(2,6-dioxo-3-piperidyl)amino]phenyl]-1-piperidyl]acetic acid (172.29 mg, 451.19 μmol) and HATU (187.15 mg, 492.21 μmol). The crude compound was purified by preparative-HPLC (Mobile phase: 10 mM $NH_4OAc$ in in water:Acetonitrile) and fractions were lyophilized to afford 3-[2-chloro-3-[[ethyl(methyl)sulfamoyl]amino]-6-fluoro-benzoyl]-5-[2-[4-[2-[4-[4-[(2,6-dioxo-3-piperidyl)amino]phenyl]-1-piperidyl]acetyl]piperazin-1-yl]pyrimidin-5-yl]-1H-pyrrolo[2,3-b]pyridine (62.2 mg, 66.87 μmol, 16.30% yield) as a pale green solid. LCMS (ESI+): 900.3 $[M+H]^+$. $^1H$ NMR (400 MHz, DMSO-$d_6$): δ 12.95 (s, 1H), 10.77 (s, 1H), 9.51 (s, 1H), 8.80 (s, 2H), 8.68 (d, J=2.00 Hz, 1H), 8.50 (bs, 1H), 8.07 (s, 1H), 7.66 (dd, J=5.60, 9.00 Hz, 1H), 7.43 (t, J=8.80 Hz, 1H), 6.97 (d, J=8.40 Hz, 2H), 6.62 (d, J=8.40 Hz, 2H), 5.67 (d, J=7.20 Hz, 1H), 4.21-4.31 (m, 1H), 3.90 (s, 2H), 3.83 (s, 2H), 3.70 (s, 2H), 3.61 (s, 2H), 3.14 (q, J=7.20 Hz, 2H), 2.95-3.15 (m, 2H), 2.65-2.80 (m, 2H), 2.74 (s, 3H), 2.45-2.62 (m, 3H), 2.44-2.35 (m, 1H), 2.05-2.15 (m, 2H), 1.82-1.91 (m, 1H), 1.55-1.80 (m, 4H), 1.04 (t, J=6.80 Hz, 3H).

Example 123

5-[2-[4-[2-[4-[4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-6-fluoro-2-methyl-benzoyl]-1H-pyrrolo[2,3-b]pyridine

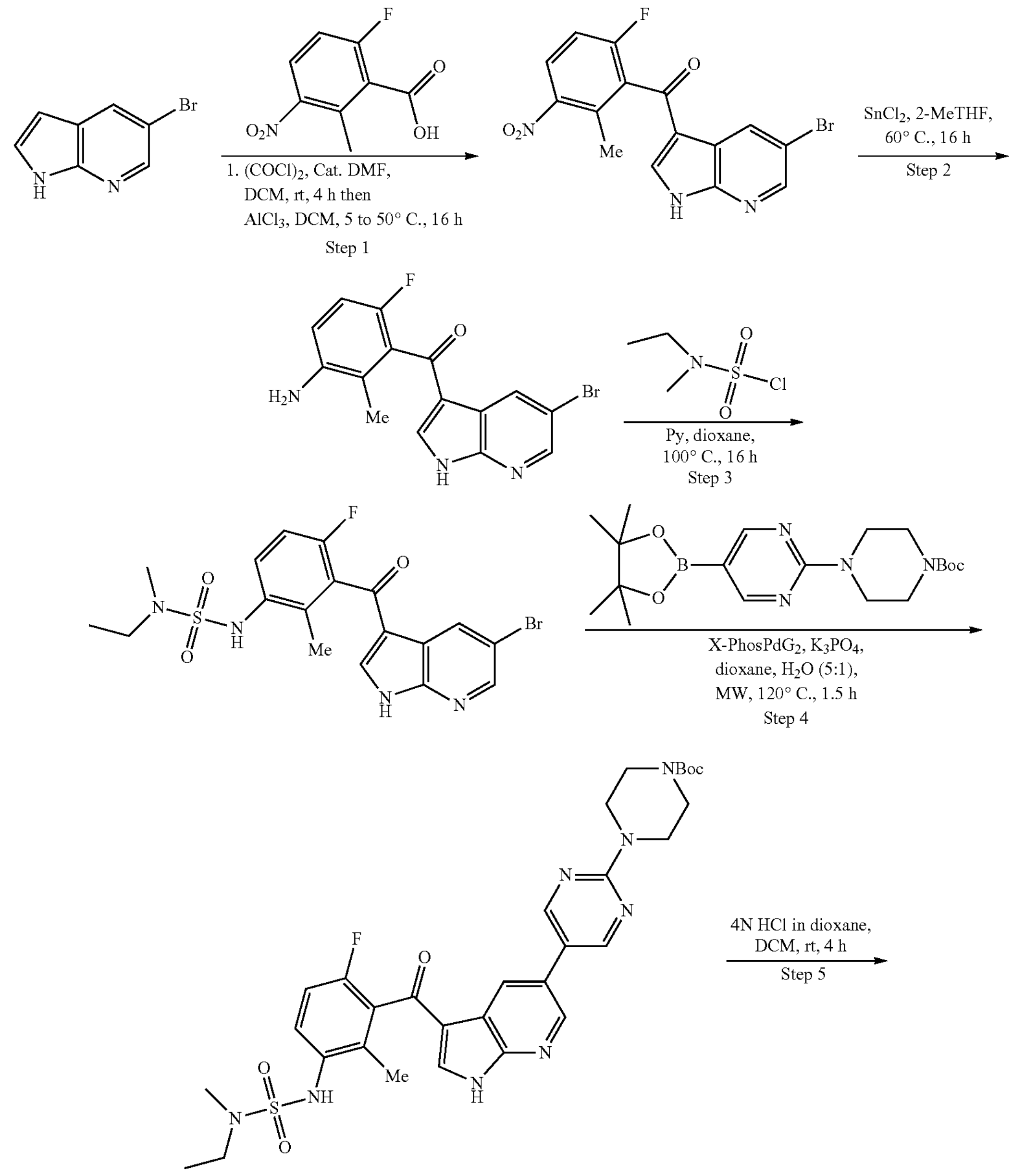

-continued

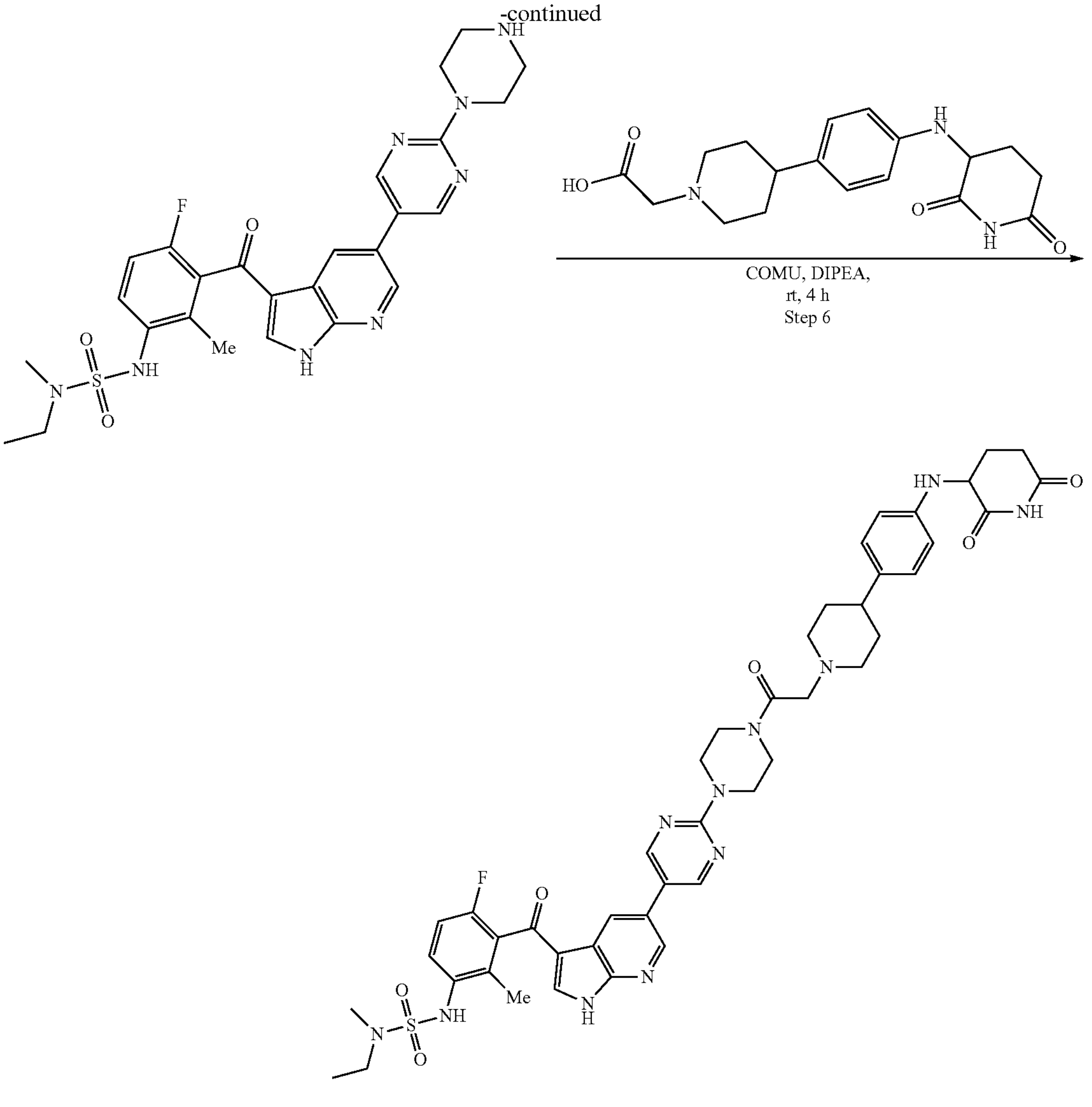

Step 1: To a stirred solution of 6-fluoro-2-methyl-3-nitro-benzoic acid (0.67 g, 3.36 mmol) in Dichloromethane (20 mL), was added Oxalyl chloride (854.12 mg, 6.73 mmol, 585.02 µL) dropwise at 5° C., followed by N,N-Dimethyl-formamide (0.05 mL). The reaction mixture was stirred at room temperature for 4 h under nitrogen atmosphere. After completion, the reaction mixture was concentrated under reduced pressure to afford crude acid chloride. In another round bottom flask, 5-bromo-1H-pyrrolo[2,3-b]pyridine (530.34 mg, 2.69 mmol) was taken in 1,2-DCE (30 mL) and added $AlCl_3$ (1.79 g, 13.46 mmol, 735.46 µL) at 5° C. The reaction mixture was stirred at 5° C. for 30 minutes. The crude acid chloride solution in 1,2-DCE (10 mL) was added by dropwise to the reaction mixture at 5° C. The reaction mixture was stirred at room temperature for 0.5 h then heated to 50° C. for 16 h. After completion, the reaction mixture was diluted with water (50 mL) and extracted with ethyl acetate (3x70 mL). Combined organic layers dried over sodium sulphate, filtered and concentrated under reduced pressure to afford crude. Desired product was purified from crude by column chromatography (60-120 silica gel), by using 30-40% ethyl acetate in petroleum ether as eluent to afford 5-bromo-1H-pyrrolo[2,3-b]pyridin-3-yl)-(6-fluoro-2-methyl-3-nitro-phenyl)methanone (1 g, 2.63 mmol, 78.31% yield) as light yellow solid. LCMS (ESI+): 378.0 $[M+H]^+$ Step 2: To a stirred solution of (5-bromo-1H-pyrrolo[2,3-b]pyridin-3-yl)-(6-fluoro-2-methyl-3-nitro-phenyl)methanone (1 g, 2.64 mmol) in 2-Methyl THF (30 mL), was added Tin chloride (2.76 g, 10.58 mmol) at room temperature. The reaction mixture was stirred at 60° C. for 16 h. After completion, the reaction mixture was diluted with 10% sodium bicarbonate solution (50 mL) and extracted with ethyl acetate (3x70 mL). Combined organic layers dried over sodium sulphate, filtered and concentrated under reduced pressure to afford crude. Desired product was purified by column chromatography (60-120 silica gel), by using 50-60% ethyl acetate in petroleum ether as eluent to afford (3-amino-6-fluoro-2-methyl-phenyl)-(5-bromo-1H-pyrrolo[2,3-b]pyridin-3-yl)methanone (0.47 g, 942.24 µmol, 35.63% yield) as light yellow solid. LCMS (ESI+): 348.0 $[M+H]^+$ Step 3: (3-amino-6-fluoro-2-methyl-phenyl)-(5-bromo-1H-pyrrolo[2,3-b]pyridin-3-yl)methanone (0.43 g, 1.24 mmol) in 1,4-dioxane (12 mL) was taken in a sealed tube and added Pyridine (976.91 mg, 12.35 mmol, 998.89 µL)

and N-ethyl-N-methyl-sulfamoyl chloride (1.17 g, 7.41 mmol, 912.49 The reaction mixture was stirred at 100° C. for 16 h. After completion, the reaction mixture was diluted with water (30 mL) and extracted with Dichloromethane (3×50 mL). Combined organic layers washed with 1.5N HCl solution (2×30 mL), dried over sodium sulphate, filtered and concentrated under reduced pressure to afford crude. Desired product was purified from crude by column chromatography (60-120 silica gel), by using 40-50% ethyl acetate in petroleum ether as eluent to afford 5-bromo-3-[3-[[ethyl(methyl)sulfamoyl]amino]-6-fluoro-2-methyl-benzoyl]-1H-pyrrolo[2,3-b]pyridine (0.22 g, 371.63 μmol, 30.09% yield) as light yellow solid. LCMS (ESI+): 469.0 $[M+H]^+$.

Step 4: 5-bromo-3-[3-[[ethyl(methyl)sulfamoyl]amino]-6-fluoro-2-methyl-benzoyl]-1H-pyrrolo[2,3-b]pyridine (0.2 g, 426.14 μmop in 1,4-Dioxane (10 mL) and Water (2 mL) was taken in a sealed tube and added $K_3PO_4$ (271.37 mg, 1.28 mmol) and tert-butyl 4-[5-(4,4,5,5-tetramethyl-1,3,2-dioxaborolan-2-yl)pyrimidin-2-yl]piperazine-1-carboxylate (249.47 mg, 639.21 μmol). The reaction mixture was purged with nitrogen gas for 10 minutes and added XPhos Pd G2 (33.53 mg, 42.61 μmol), again purged with nitrogen gas for 5 minutes. The reaction mixture was irradiated under microwave at 120° C. for 1.5 h. After completion, the reaction mixture was diluted with water (70 mL), extracted with ethyl acetate (3×100 mL). Combined organic layers dried over sodium sulphate, filtered and concentrated under reduced pressure to afford crude. The crude was purified by column chromatography (60-120 silica gel), using 70-80% ethyl acetate in petroleum ether as eluent to afford tert-butyl 4-[5-[3-[3-[[ethyl(methyl)sulfamoyl]amino]-6-fluoro-2-methyl-benzoyl]-1H-pyrrolo[2,3-b]pyridin-5-yl]pyrimidin-2-yl]piperazine-1-carboxylate (0.17 g, 234.21 μmol, 54.96% yield) as off white solid. LCMS (ESI+): 653.2 $[M+H]^+$ Step 5: To a stirred solution of tert-butyl 4-[5-[3-[3-[[ethyl(methyl)sulfamoyl]amino]-6-fluoro-2-methyl-benzoyl]-1H-pyrrolo[2,3-b]pyridin-5-yl]pyrimidin-2-yl]piperazine-1-carboxylate (0.17 g, 260.44 μmol) in DCM (15 mL), was added Hydrogen chloride solution (4M in 1,4-dioxane, 1.60 g, 43.88 mmol, 2 mL) at 5° C. The reaction mixture was stirred at room temperature for 4 h. After completion, the reaction mixture was concentrated under reduced pressure to afford crude 3-[3-[[ethyl(methyl)sulfamoyl]amino]-6-fluoro-2-methyl-benzoyl]-5-(2-piperazin-1-ylpyrimidin-5-yl)-1H-pyrrolo[2,3-b]pyridine (0.17 g, 235.54 μmol, 90.44% yield) as light yellow solid. LCMS (ESI+): 553.1 $[M+H]^+$.

Step 6: Target compound was prepared via COMU mediated acid-amine coupling reaction (procedure B). Amide coupling was carried out using 2-[4-[4-[(2,6-dioxo-3-piperidyl)amino]phenyl]-1-piperidyl]acetic acid (93.81 mg, 245.67 μmol), N-ethyl-N-isopropyl-propan-2-amine (35.10 mg, 271.61 μmol, 47.31 COMU (116.32 mg, 271.61 μmol) and 3-[3-[[ethyl(methyl)sulfamoyl]amino]-6-fluoro-2-methyl-benzoyl]-5-(2-piperazin-1-ylpyrimidin-5-yl)-1H-pyrrolo[2,3-b]pyridine (0.16 g, 271.61 μmol) to afford 5-[2-[4-[2-[4-[4-[(2,6-dioxo-3-piperidyl)amino]phenyl]-1-piperidyl]acetyl]piperazin-1-yl]pyrimidin-5-yl]-3-[3-[[ethyl(methyl)sulfamoyl]amino]-6-fluoro-2-methyl-benzoyl]-1H-pyrrolo[2,3-b]pyridine (99.22 mg, 108.42 μmol, 39.92% yield) as light greenish solid. LCMS (ESI+): 880.3 $[M+H]^+$. $^1H$ NMR (400 MHz, DMSO-$d_6$): δ 12.90 (s, 1H), 10.77 (s, 1H), 9.13 (s, 1H), 8.77 (s, 2H), 8.66 (d, J=2.00 Hz, 1H), 7.91 (s, 1H), 7.43-7.46 (m, 1H), 7.22 (t, J=8.80 Hz, 1H), 6.97 (d, J=8.40 Hz, 2H), 6.61 (d, J=8.40 Hz, 2H), 5.66 (d, J=7.60 Hz, 1H), 4.21-4.31 (m, 1H), 3.89 (s, 2H), 3.81 (s, 2H), 3.72 (s, 2H), 3.59 (s, 2H), 3.23 (s, 2H), 3.14 (q, J=6.80 Hz, 2H), 2.96 (d, J=10.80 Hz, 2H), 2.65-2.78 (m, 2H), 2.76 (s, 3H), 2.55-2.60 (m, 1H), 2.19 (s, 3H), 2.08-2.17 (m, 3H), 1.81-1.91 (m, 1H), 1.05 (t, J=7.20 Hz, 3H).

Example 124

5-[2-[1-[2-[4-[4-[(2,6-dioxo-3-piperidyl)amino]-2-fluoro-phenyl]-1-piperidyl]acetyl]-4-piperidyl]ethynyl]-3-[3-[[ethyl(methyl)sulfamoyl]amino]-2,6-difluoro-benzoyl]-1H-pyrrolo[2,3-b]pyridine

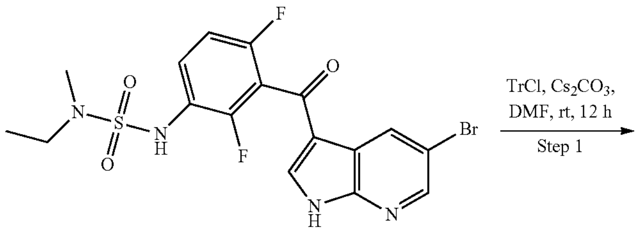

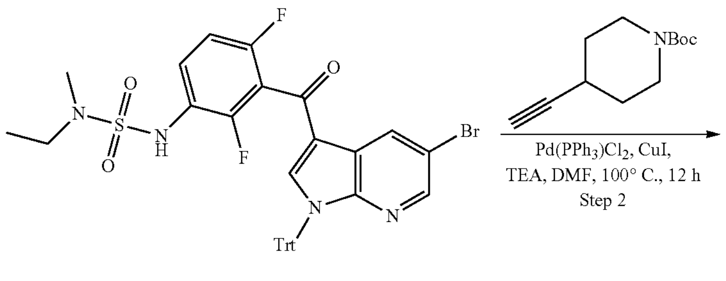

-continued

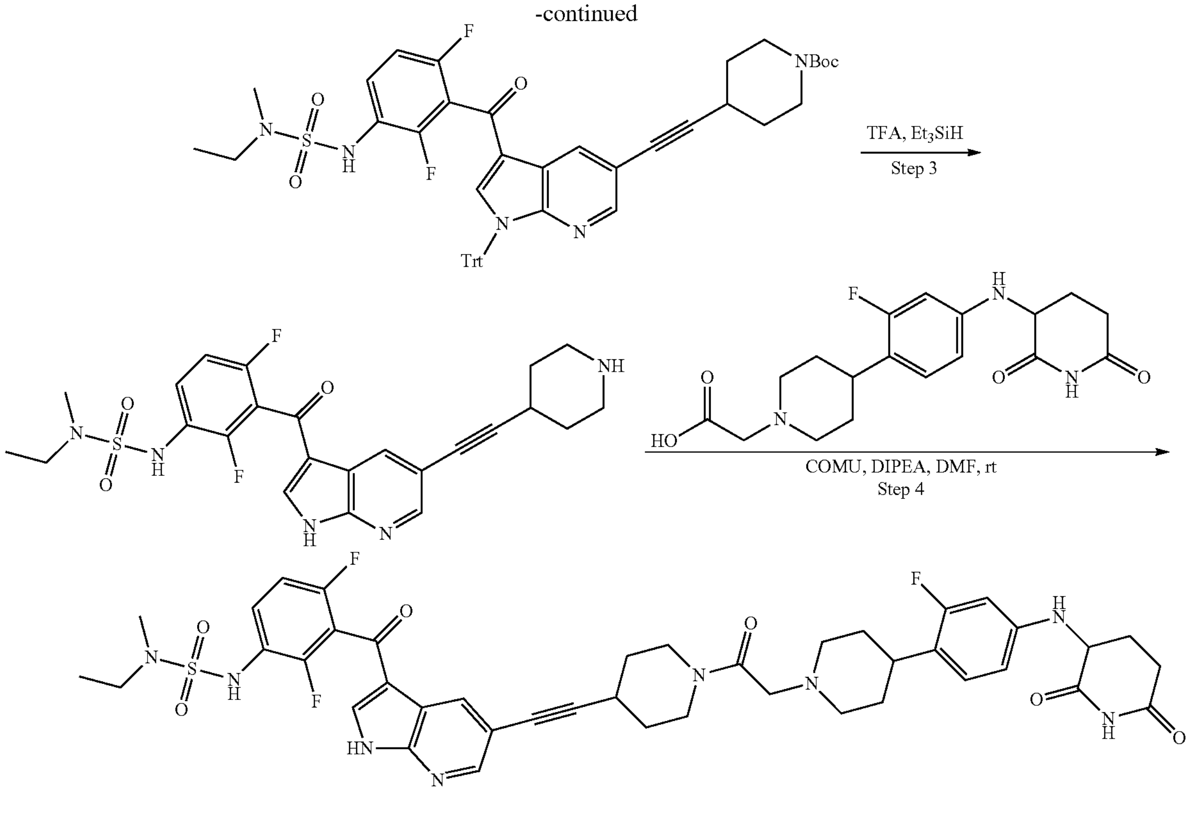

Step 1: To a stirred solution of 5-bromo-3-[3-[[ethyl (methyl)sulfamoyl]amino]-2,6-difluoro-benzoyl]-1H-pyrrolo[2,3-b]pyridine (1 g, 2.11 mmol) in N,N-Dimethyl formamide (10 mL) were added Cesium carbonate (2.75 g, 8.45 mmol) and [chloro(diphenyl)methyl]benzene (1.47 g, 5.28 mmol) at room temperature. The reaction mixture was stirred at room temperature for 12 h. After completion, the reaction mixture was diluted with water (20 mL) and extracted with ethyl acetate (2×50 mL). The combined organic layers were dried over sodium sulphate, concentrated. The crude compound was purified by silica gel column chromatography using 40-50% ethyl acetate in petroleum ether to afford 5-bromo-3-[3-[[ethyl(methyl)sulfamoyl]amino]-2,6-difluoro-benzoyl]-1-trityl-pyrrolo[2,3-b]pyridine (1 g, 1.36 mmol, 64.15% yield) as pale yellow solid. LCMS (ESI+): 713.0 $[M-H]^+$.

Step 2: To a stirred solution of 5-bromo-3-[3-[[ethyl (methyl)sulfamoyl]amino]-2,6-difluoro-benzoyl]-1-trityl-pyrrolo[2,3-b]pyridine (300 mg, 419.23 μmol), ethynyl(trimethyl)silane (123.53 mg, 1.26 mmol, 177.74 μL) in Acetonitrile (6 mL) was added Copper (I) iodide (79.84 mg, 419.23 μmol, 14.21 μL) and Triethylamine (42.42 mg, 419.23 μmol, 58.43 μL). The reaction mixture was degassed for 20 minutes and $Pd(PPh_3)_2Cl_2$ (294.25 mg, 419.23 μmol) was added. The reaction mixture was heated to 80° C. for 12 h. After completion, the reaction mixture was diluted with water (10 mL) and extracted with ethyl acetate (2×25 mL). The combined organic layers were dried over sodium sulphate, filtered and concentrated. The crude compound was purified by silica gel column chromatography compound using 40-50% ethyl acetate in petroleum ether to afford 3-[3-[[ethyl(methyl)sulfamoyl]amino]-2,6-difluoro-benzoyl]-5-(2-trimethylsilylethynyl)-1-trityl-pyrrolo[2,3-b] pyridine (120 mg, 163.73 μmol, 39.06% yield) as pale yellow solid. LCMS (ESI+): 744.9 $[M+H]^+$.

Step 3: To a stirred solution of tert-butyl 4-[2-[3-[3-[[ethyl (methyl)sulfamoyl]amino]-2,6-difluoro-benzoyl]-1-trityl-pyrrolo[2,3-b]pyridin-5-yl]ethynyl]piperidine-1-carboxylate (250 mg, 296.22 μmol) in Dichloromethane (3 mL) at 0° C. were added Trifluoroacetic acid (33.78 mg, 296.22 μmol, 22.82 μL) and Triisopropylsilane (46.91 mg, 296.22 μmol, 60.68 μL) dropwise. The reaction mixture was stirred at room temperature for 1 h. After completion, the reaction mixture was concentrated under vacuum. The crude compound was washed with petroleum ether and dried to get 3-[3-[[ethyl(methyl)sulfamoyl]amino]-2,6-difluoro-benzoyl]-5-[2-(4-piperidyl)ethynyl]-1H-pyrrolo[2,3-b]pyridine (200 mg, 259.92 μmol, 87.75% yield) as brown gummy compound. LCMS (ESI+): 501.8 $[M+H]^+$.

Step 4: Target compound was prepared via COMU mediated acid-amine coupling reaction (procedure B). Amide coupling was carried out using 3-[3-[[ethyl(methyl)sulfamoyl]amino]-2,6-difluoro-benzoyl]-5-[2-(4-piperidyl)ethynyl]-1H-pyrrolo[2,3-b]pyridine (90 mg, 179.44 μmol), 2-[4-[4-[(2,6-dioxo-3-piperidyl)amino]-2-fluoro-phenyl]-1-piperidyl]acetic acid (65.21 mg, 179.44 μmol), DIPEA (69.58 mg, 538.33 μmol, 93.77 μL) and COMU (115.28 mg, 269.17 μmol) to afford 5-[2-[1-[2-[4-[4-[(2,6-dioxo-3-piperidyl)amino]-2-fluoro-phenyl]-1-piperidyl]acetyl]-4-piperidyl]ethynyl]-3-[3-[[ethyl(methyl)sulfamoyl]amino]-2,6-difluoro-benzoyl]-1H-pyrrolo[2,3-b]pyridine (13.01 mg, 14.89 μmol, 8.30% yield) as solid. LCMS (ESI+): 847.3 $[M+H]^+$. $^1H$ NMR (400 MHz, DMSO-$d_6$): δ 13.05 (s, 1H), 10.78 (s, 1H), 9.72 (s, 1H), 8.43-8.45 (m, 2H), 8.16 (s, 1H), 7.55-7.61 (m, 1H), 7.27 (t, J=8.40 Hz, 1H), 6.98-7.02 (m, 1H), 6.28-6.46 (m, 2H), 6.00 (d, J=8.00 Hz, 1H), 4.24-4.35 (m, 1H), 3.88-3.91 (m, 2H), 3.24-3.43 (m, 4H), 3.11 (q, J=6.80 Hz, 2H), 2.93-3.03 (m, 4H), 2.65-2.82 (m, 2H), 2.73 (s, 3H), 2.59-2.69 (m, 2H), 1.86-2.09 (m, 5H), 1.57-1.85 (m, 5H), 1.03 (t, J=7.20 Hz, 3H).

Example 125
5-[4-[1-[2-[1-[4-[(2,6-dioxo-3-piperidyl)amino]-2-fluoro-phenyl]-4-hydroxy-4-piperidyl]acetyl]-4-piperidyl]-3-fluoro-phenyl]-3-[3-[[ethyl(methyl)sulfamoyl]amino]-2,6-difluoro-benzoyl]-1H-pyrrolo[2,3-b]pyridine
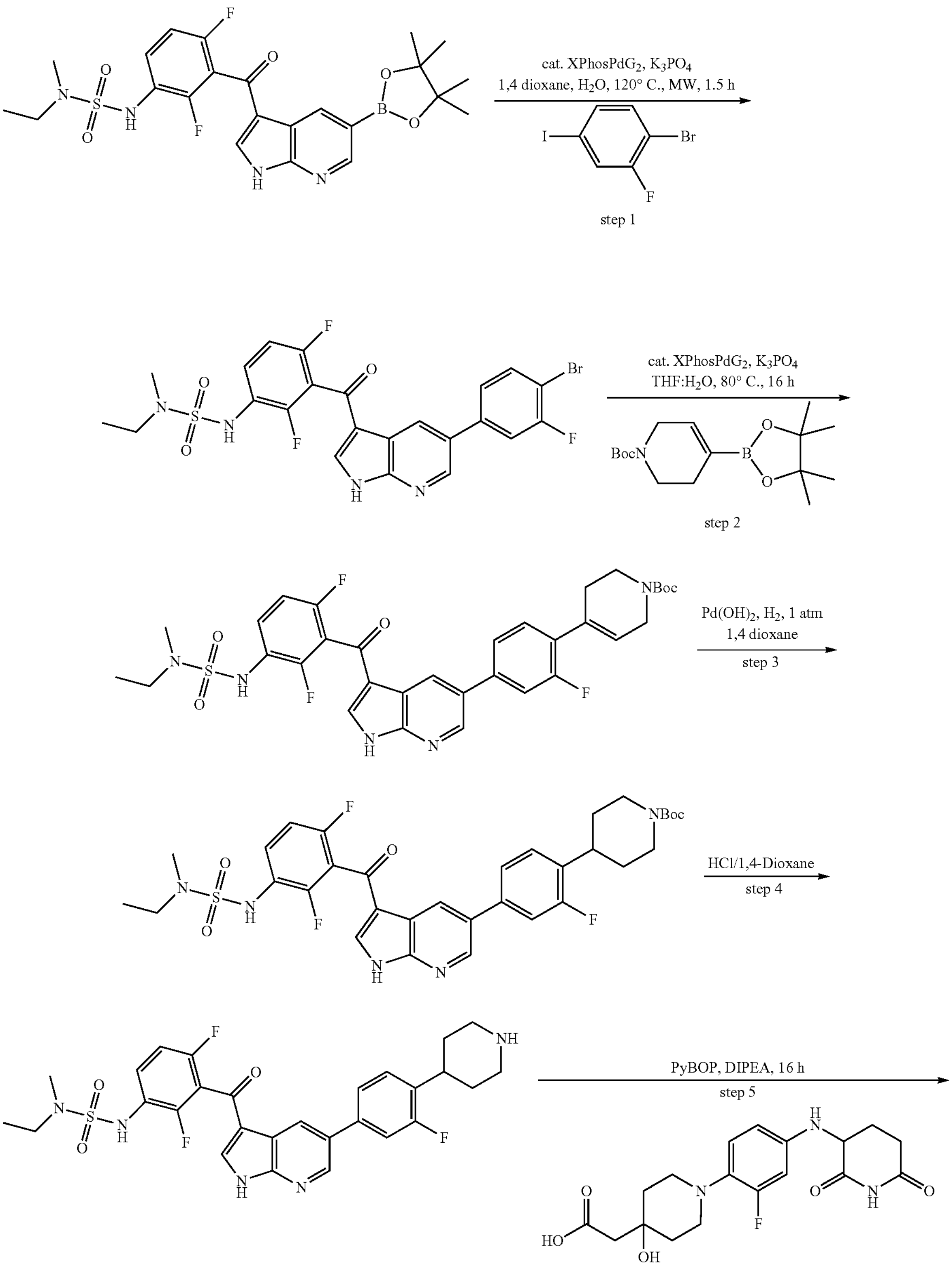

-continued

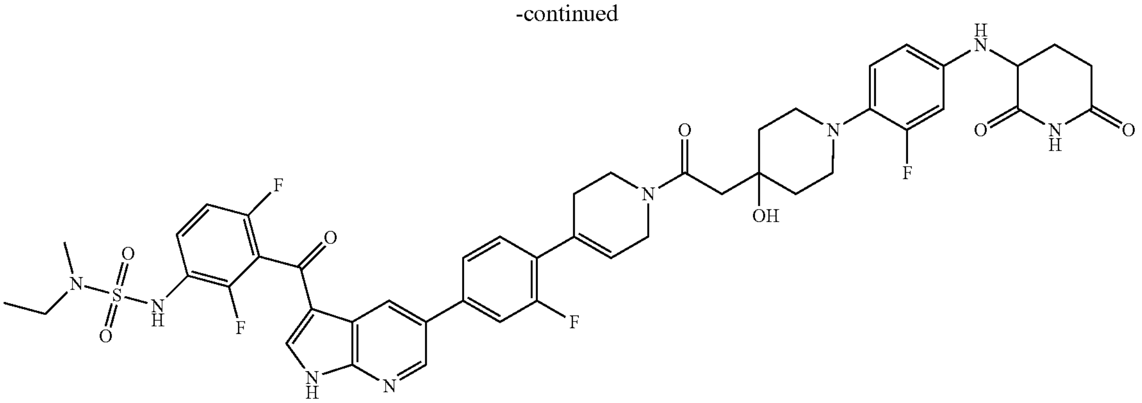

Step 1: 1-bromo-2-fluoro-4-iodo-benzene (1 g, 3.32 mmol) and 3-[3-[[ethyl(methyl)sulfamoyl]amino]-2,6-difluoro-benzoyl]-5-(4,4,5,5-tetramethyl-1,3,2-dioxaborolan-2-yl)-1H-pyrrolo[2,3-b]pyridine (1.73 g, 3.32 mmol) were combined in 1,4-dioxane (10 mL) and Water (4 mL). The reaction mixture was degassed with nitrogen for 10 minutes, then potassium phosphate tribasic anhydrous (2.12 g, 9.97 mmol) was added. The mixture was degassed for 5 minutes, followed by addition of XPhos Pd G2 (261.49 mg, 332.34 μmol). The reaction mixture was stirred for 1.5 h at 120° C. in a microwave. The reaction mixture was diluted with water (50 mL) and compound extracted in ethyl acetate (2×50 mL). The combined organic layers were dried over anhydrous sodium sulphate and concentrated under reduced pressure. The crude was purified by silica gel column chromatography on 0-70% ethyl acetate/petroleum ether as eluent system to give 5-(4-bromo-3-fluoro-phenyl)-3-[3-[[ethyl(methyl)sulfamoyl]amino]-2,6-difluoro-benzoyl]-1H-pyrrolo[2,3-b]pyridine (800 mg, 817.80 μmol, 24.61% yield) as yellow solid. LCMS (ESI+): 569.0 $[M+H]^+$ Step 2: 5-(4-bromo-3-fluoro-phenyl)-3-[3-[[ethyl(methyl)sulfamoyl]amino]-2,6-difluoro-benzoyl]-1H-pyrrolo[2,3-b]pyridine (400 mg, 705.00 μmol) and tert-butyl 4-(4,4,5,5-tetramethyl-1,3,2-dioxaborolan-2-yl)-3,6-dihydro-2H-pyridine-1-carboxylate (217.99 mg, 705.00 μmol) were taken up in THF (10 mL). The reaction mixture was degassed with nitrogen for 10 minutes, then potassium phosphate tribasic anhydrous (448.94 mg, 2.11 mmol) was added. The reaction mixture was degassed for 5 min, followed by addition of XPhos Pd G2 (55.47 mg, 70.50 mol). The reaction mixture was stirred for 16 h at 80° C. After completion, the reaction was diluted with water (50 mL) and compound extracted in ethyl acetate (2×30 mL). The combined organic layers were dried over anhydrous sodium sulphate and concentrated under reduced pressure. The crude was purified by silica gel column chromatography on 0-60% ethyl acetate/petroleum ether as eluent system to afford tert-butyl 4-[4-[3-[3-[[ethyl(methyl)sulfamoyl]amino]-2,6-difluoro-benzoyl]-1H-pyrrolo[2,3-b]pyridin-5-yl]-2-fluoro-phenyl]-3,6-dihydro-2H-pyridine-1-carboxylate (250 mg, 235.18 mol, 33.36% yield) as yellow solid. LCMS (ESI+): 670.0 $[M+H]^+$.

Step 3: To a stirred solution of tert-butyl 4-[4-[3-[3-[[ethyl(methyl)sulfamoyl]amino]-2,6-difluoro-benzoyl]-1H-pyrrolo[2,3-b]pyridin-5-yl]-2-fluoro-phenyl]-3,6-dihydro-2H-pyridine-1-carboxylate (350 mg, 522.61 mol) in 1,4-dioxane (5 mL) was added Palladium hydroxide on carbon, 20 wt. % (146.79 mg, 1.05 mmol). The reaction mixture was stirred for 16 h at 25° C. under $H_2$ atmosphere (balloon pressure). After completion, the reaction mixture filtered through celite by washing with 10% Dichloromethane/Methanol (100 mL). The filtrate was concentrated under reduced pressure. The crude product was further purified by silica gel column chromatography on 0-50% ethyl acetate/petroleum ether as eluent system to afford tert-butyl 4-[4-[3-[3-[[ethyl(methyl)sulfamoyl]amino]-2,6-difluoro-benzoyl]-1H-pyrrolo[2,3-b]pyridin-5-yl]-2-fluoro-phenyl]piperidine-1-carboxylate (230 mg, 263.65 mol, 50.45% yield) as orange solid. LCMS (ESI+): 672.3 $[M+H]^+$.

Step 4: To a stirred solution of tert-butyl 4-[4-[3-[3-[[ethyl(methyl)sulfamoyl]amino]-2,6-difluoro-benzoyl]-1H-pyrrolo[2,3-b]pyridin-5-yl]-2-fluoro-phenyl]piperidine-1-carboxylate (230 mg, 342.40 mol) in Dichloromethane (5 mL) was added Hydrogen chloride solution (4.0M in dioxane) (62.42 mg, 1.71 mmol, 78.03 μL) at 0° C. The reaction mixture was stirred for 1 h at 25° C. After completion, the reaction mixture was concentrated to remove solvent and washed with diethyl ether (20 mL) and to get 3-[3-[[ethyl(methyl)sulfamoyl]amino]-2,6-difluoro-benzoyl]-5-[3-fluoro-4-(4-piperidyl) phenyl]-1H-pyrrolo[2,3-b]pyridine (200 mg, 246.68 μmol, 72.04% yield) as light yellow solid. LCMS (ESI+): 571.8 $[M+H]^+$.

Step 5: Target compound was prepared via PyBOP mediated acid-amine coupling reaction (procedure D). Amide coupling was carried out using 2-[1-[4-[(2,6-dioxo-3-piperidyl)amino]-2-fluoro-phenyl]-4-hydroxy-4-piperidyl]acetic acid (122.47 mg, 322.82 μmol), 3-[3-(dimethyl sulfamoylamino)-2,6-difluoro-benzoyl]-5-[3-fluoro-4-(4-piperidyl)phenyl]-1H-pyrrolo[2,3-b]pyridine (180 mg, 322.82 μmol), PyBOP (167.99 mg, 322.82 μmol) and N,N-diisopropylethylamine (41.72 mg, 322.82 μmol, 56.23 μL) to afford 5-[4-[1-[2-[1-[4-[(2,6-dioxo-3-piperidyl)amino]-2-fluoro-phenyl]-4-hydroxy-4-piperidyl]acetyl]-4-piperidyl]-3-fluoro-phenyl]-3-[3-[[ethyl(methyl)sulfamoyl]amino]-2,6-difluoro-benzoyl]-1H-pyrrolo[2,3-b]pyridine (41 mg, 38.49 μmol, 11.92% yield) as grey solid. LCMS (ESI+): 933.0 $[M+H]^+$. $^1H$ NMR (400 MHz, DMSO-$d_6$): δ 13.01 (s, 1H), 10.78 (s, 1H), 9.72 (s, 1H), 8.78-8.73 (m, 1H), 8.66-8.62 (m, 1H), 8.17-8.14 (m, 1H), 7.68-7.50 (m, 1H), 7.48 (t, J=8.00 Hz, 1H), 7.29 (t, J=8.40 Hz, 1H), 6.51 (d, J=14.80 Hz, 2H), 6.43 (d, J=8.80 Hz, 2H), 5.78 (s, 1H), 5.04-4.91 (m, 1H), 4.70-4.60 (m, 1H), 4.38-4.20 (m, 2H), 3.85-3.70 (m, 1H), 3.33-3.02 (m, 6H), 2.93-2.89 (m, 4H), 2.73 (s, 3H), 2.68-2.53 (m, 4H), 2.18-2.05 (m, 1H), 1.87-1.70 (m, 8H), 1.02 (t, J=7.20 Hz, 3H).

Example 127
5-[2-[4-[4-[4-[(2,6-dioxo-3-piperidyl)amino]phenyl]piperidine-1-carbonyl]-1-piperidyl]pyrimidin-5-yl]-3-[3-[[ethyl(methyl)sulfamoyl]amino]-2,6-difluoro-benzoyl]-1H-pyrrolo[2,3-b]pyridine
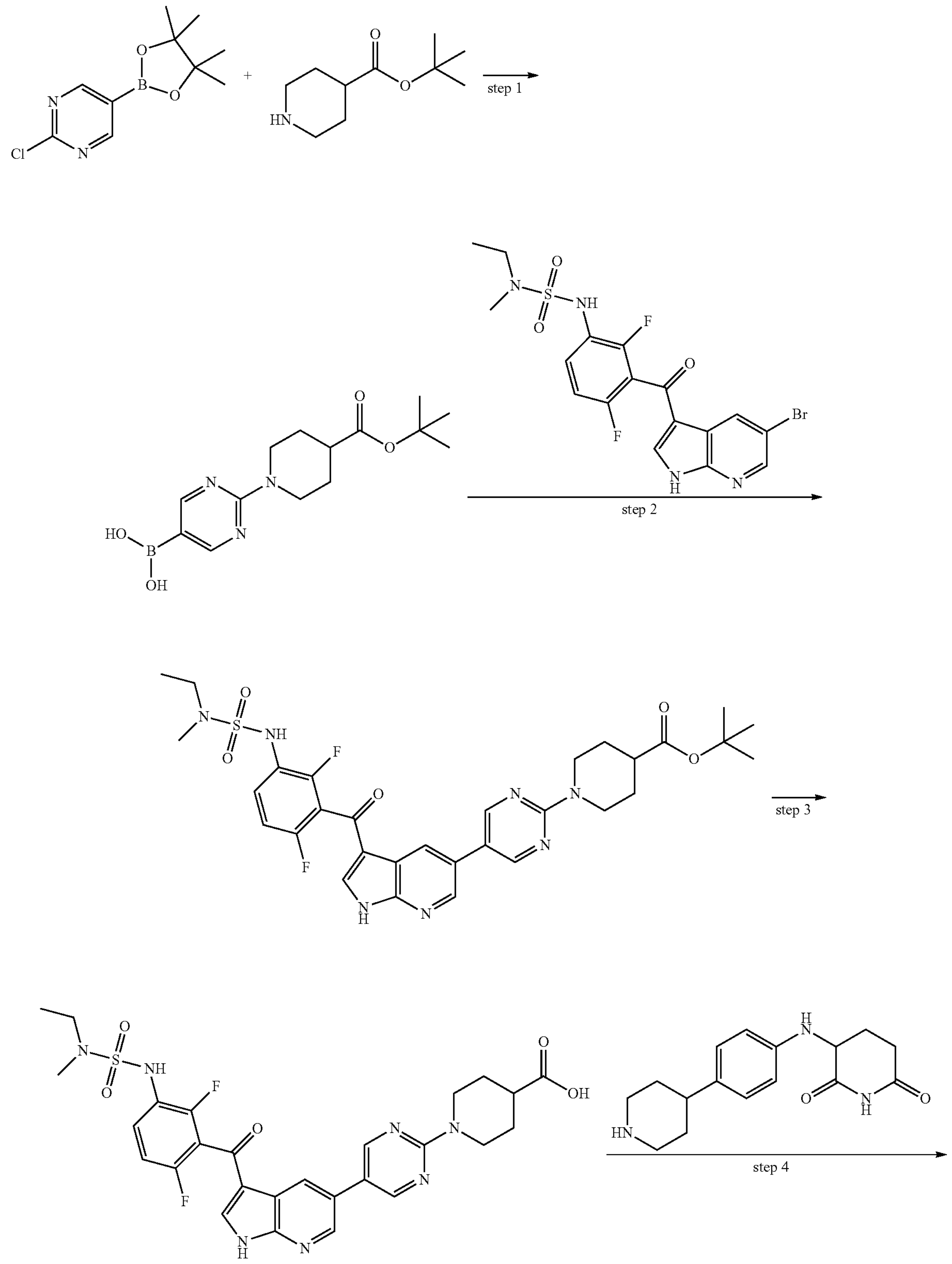

-continued

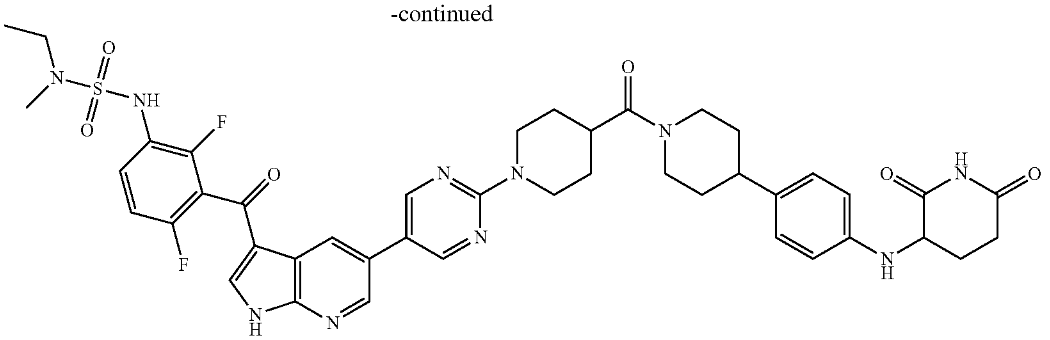

Step 1: To a mixture of 2-chloro-5-(4,4,5,5-tetramethyl-1,3,2-dioxaborolan-2-yl)pyrimidine (389.44 mg, 1.62 mmol) and tert-butyl piperidine-4-carboxylate (300 mg, 1.62 mmol) in 1,4-dioxane (3.5 mL) was added Triethylamine (245.79 mg, 2.43 mmol, 338.55. The resulting solution was heated at 100° C. for 4 h. Reaction mixture was then cooled to room temperature and concentrated under reduced pressure. The crude product [2-(4-tert-butoxycarbonyl-1-piperidyl)pyrimidin-5-yl]boronic acid (450 mg, 1.39 mmol, 85.95% yield) was carried forward without further purification. LCMS (ES+): 308.3 $[M+H]^+$ Step 2: [2-(4-tert-butoxycarbonyl-1-piperidyl)pyrimidin-5-yl]boronic acid (363.42 mg, 1.18 mmol) and 5-bromo-3-[3-[[ethyl(methyl)sulfamoyl]amino]-2,6-difluoro-benzoyl]-1H-pyrrolo[2,3-b]pyridine (140 mg, 295.80 μmol) were dissolved in water (0.3 mL) and 1,4-dioxane (1.15 mL) with XPhos Pd G3 (25.04 mg, 29.58 μmol) and Potassium phosphate tribasic anhydrous (188.37 mg, 887.40 μmol). The contents were purged with argon before being sealed in a microwave vessel. The mixture was stirred at room temperature for 5 min to ensure dissolution of solids. The reaction was then heated in a microwave at 120° C. for 3 h. After cooling, the reaction was diluted with water and extracted with EtOAc. The combined organic layers were dried with sodium sulphate, filtered and concentrated. The crude material was then purified by column chromatography (40-85% EtOAc in hexanes) to afford the product tert-butyl 1-[5-[3-[3-[[ethyl(methyl)sulfamoyl]amino]-2,6-difluoro-benzoyl]-1H-pyrrolo[2,3-b]pyridin-5-yl]pyrimidin-2-yl]piperidine-4-carboxylate (144 mg, 208.63 μmol, 70.53% yield). LCMS (ES+): 656.2 $[M+H]^+$ Step 3: tert-butyl 1-[5-[3-[3-[[ethyl(methyl)sulfamoyl]amino]-2,6-difluoro-benzoyl]-1H-pyrrolo[2,3-b]pyridin-5-yl]pyrimidin-2-yl]piperidine-4-carboxylate (144 mg, 219.61 μmol) was dissolved in DCM (3.6 mL) and TFA (2.4 mL). The mixture was stirred for 2 h at room temperature, at which time the reaction had reached completion. Solvent was removed, and excess TFA was removed by azeotrope to give the product 1-[5-[3-[3-[[ethyl(methyl)sulfamoyl]amino]-2,6-difluoro-benzoyl]-1H-pyrrolo[2,3-b]pyridin-5-yl]pyrimidin-2-yl]piperidine-4-carboxylic acid (150 mg, 199.68 μmol, 90.93% yield, trifluoroacetic acid salt), which was carried forward without further purification. LCMS (ES+): 600.5 $[M+H]^+$ Step 4: To a mixture of 3-[4-(4-piperidyl)anilino]piperidine-2,6-dione (24.16 mg, 84.08 μmol) and 1-[5-[3-[3-[[ethyl(methyl)sulfamoyl]amino]-2,6-difluoro-benzoyl]-1H-pyrrolo[2,3-b]pyridin-5-yl]pyrimidin-2-yl]piperidine-4-carboxylic acid (60 mg, 84.08 μmol, trifluoroacetic acid salt) in DMF (1.5 mL) was added N,N-Diisopropylethylamine (43.47 mg, 336.31 μmol, 58.58 uL) followed by Bis(2-oxo-3-oxazolidinyl)phosphinic chloride, 97% (29.96 mg, 117.71 μmol). The resulting solution was stirred at room temperature overnight. The reaction mixture was then diluted with water and extracted with ethyl acetate. The combined organic layers were dried with anhydrous sodium sulphate, filtered and concentrated under reduced pressure. The crude was purified by column chromatography (silica, gradient: 10-65% acetonitrile in water with 0.1% trifluoroacetic acid) to afford purified material. The combined pure fractions were slightly concentrated under vacuum and neutralized with saturated sodium bicarbonate. The aqueous material was extracted with ethyl acetate, and the combined organic layers were dried with anhydrous sodium sulfate to afford 5-[2-[4-[4-[4-[(2,6-dioxo-3-piperidyl)amino]phenyl]piperidine-1-carbonyl]-1-piperidyl]pyrimidin-5-yl]-3-[3-[[ethyl (methyl)sulfamoyl]amino]-2,6-difluoro-benzoyl]-1H-pyrrolo[2,3-b]pyridine (16.8 mg, 18.37 μmol, 21.85% yield). LCMS (ES+): 869.8 $[M+H]^+$. $^1$H NMR (400 MHz, DMSO-$d_6$): δ 12.99 (d, J=3.3 Hz, 1H), 10.77 (s, 1H), 9.70 (s, 1H), 8.76 (s, 2H), 8.67 (d, J=2.1 Hz, 1H), 8.54 (s, 1H), 8.13 (d, J=3.2 Hz, 1H), 7.59 (td, J=8.9, 5.7 Hz, 1H), 7.27 (q, J=8.1, 7.4 Hz, 1H), 6.98 (d, J=8.0 Hz, 2H), 6.63 (d, J=8.2 Hz, 3H), 4.75 (d, J=12.9 Hz, 2H), 4.55 (d, J=13.2 Hz, 1H), 4.28 (dd, J=11.3, 4.8 Hz, 1H), 4.17 (d, J=13.6 Hz, 2H), 3.12 (d, J=7.2 Hz, 9H), 1.99-1.66 (m, 6H), 1.63-1.41 (m, 3H), 1.26 (q, J=6.4 Hz, 4H), 1.03 (t, J=7.1 Hz, 3H).

Example 128

N-[1-[4-[(2,6-dioxo-3-piperidyl)amino]-2-fluoro-phenyl]-4-piperidyl]-1-[5-[3-[3-[[ethyl(methyl)sulfamoyl]amino]-2,6-difluoro-benzoyl]-1H-pyrrolo[2,3-b]pyridin-5-yl]pyrimidin-2-yl]piperidine-4-carboxamide

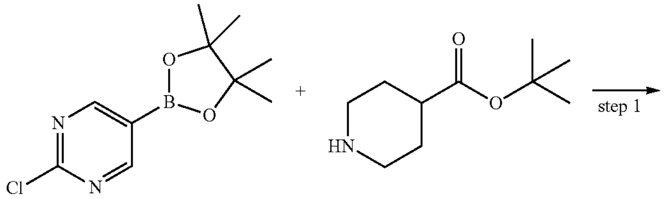

-continued

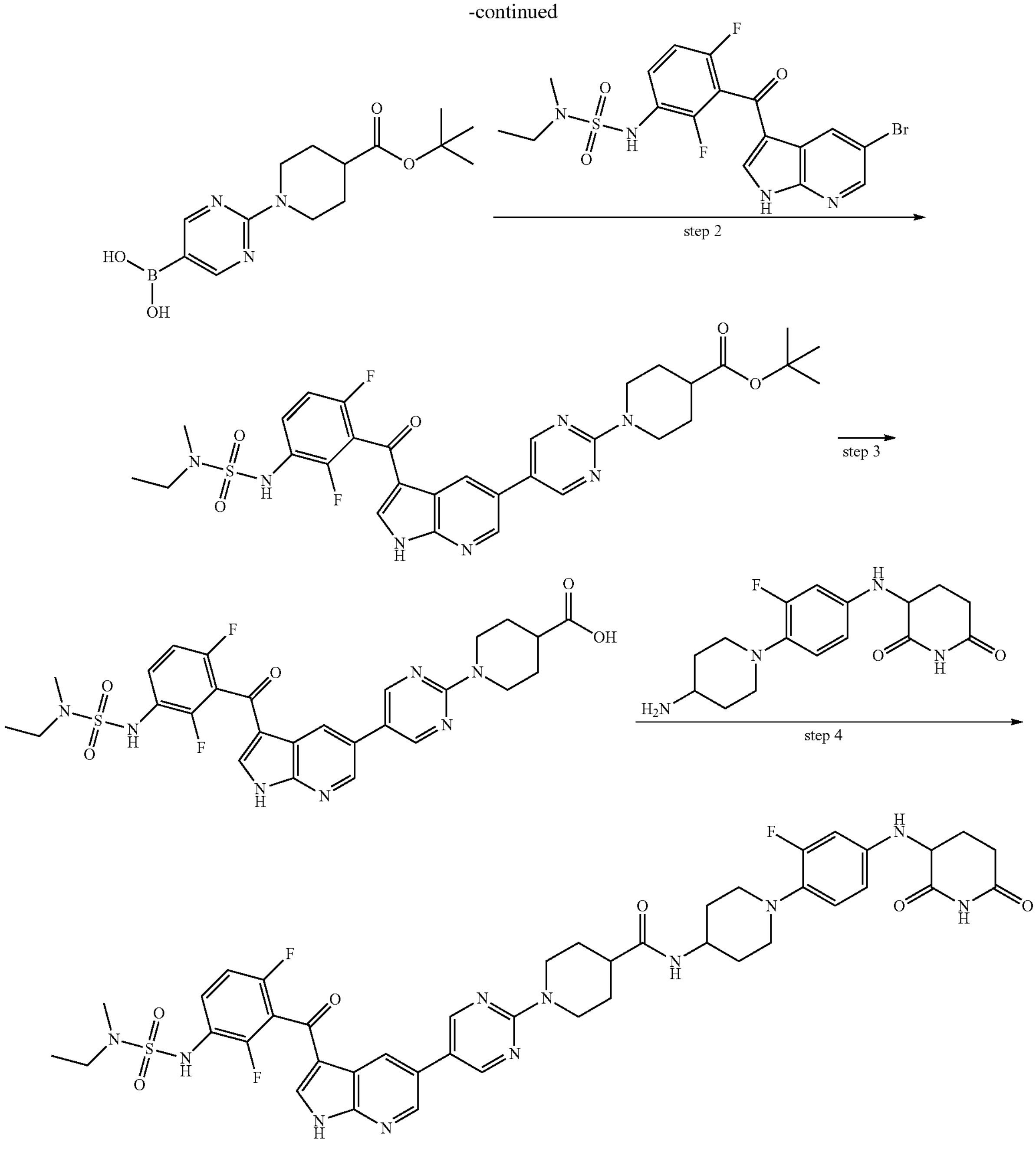

Step 1: To a mixture of 2-chloro-5-(4,4,5,5-tetramethyl-1,3,2-dioxaborolan-2-yl)pyrimidine (389.44 mg, 1.62 mmol) and tert-butyl piperidine-4-carboxylate (300 mg, 1.62 mmol) in dioxanes (3.5 mL) was added triethylamine (245.79 mg, 2.43 mmol, 338.55 uL). The resulting mixture was heated at 100° C. for 4 hr. The reaction mixture was then cooled to room temperature, and concentrated under reduced pressure. The crude product [2-(4-tert-butoxycarbonyl-1-piperidyl)pyrimidin-5-yl]boronic acid (450 mg, 1.39 mmol, 85.95% yield) was carried forward without further purification. LCMS (ES+): 308.3 $[M+H]^+$ Step 2: To a mixture of [2-(4-tert-butoxycarbonyl-1-piperidyl)pyrimidin-5-yl]boronic acid (363.42 mg, 1.18 mmol) and 5-bromo-3-[3-[[ethyl(methyl)sulfamoyl]amino]-2,6-difluoro-benzoyl]-1H-pyrrolo[2,3-b]pyridine (140 mg, 295.80 μmol) in water (0.3 mL) and dioxanes (1.15 mL) was added Xphos G3 Pd (25.04 mg, 29.58 μmol) and potassium phosphate tribasic anhydrous (188.37 mg, 887.40 μmol). The contents were purged with argon before being sealed in a microwave vessel. The mixture was stirred at room temperature for 5 min to ensure dissolution of solids. The reaction was then heated in a microwave at 120° C. for 3 hr. After cooling, the reaction was diluted with water and extracted with ethyl acetate. The combined organic layers were dried with anhydrous sodium sulphate and concentrated. The crude material was then purified by column chromatography (silica, gradient: 40-85% ethyl acetate in hexanes) to afford the product tert-butyl 1-[5-[3-[3-[[ethyl (methyl)sulfamoyl]amino]-2,6-difluoro-benzoyl]-1H-pyrrolo[2,3-b]pyridin-5-yl]pyrimidin-2-yl]piperidine-4-carboxylate (144 mg, 208.63 μmol, 70.53% yield). LCMS (ES+): 656.2 $[M+H]^+$ Step 3: To a solution of tert-butyl 1-[5-[3-[3-[[ethyl(methyl)sulfamoyl]amino]-2,6-difluoro-benzoyl]-1H-pyrrolo[2,3-b]pyridin-5-yl]pyrimidin-2-yl]piperidine-4-carboxylate (144 mg, 219.61 μmol) in DCM (3.6 mL) was added TFA (2.4 mL). The resulting mixture was stirred for 2 hr at room temperature. The reaction mixture was concentrated in vacuo, and excess TFA was removed by azeotrope to give the product 1-[5-[3-[3-[[ethyl(methyl)sulfamoyl]amino]-2,6-difluoro-benzoyl]-1H-pyrrolo[2,3-b]pyridin-5-yl]pyrimidin-2-yl]piperidine-4-carboxylic acid (150 mg, 199.68 μmol, 90.93% yield), which was carried forward without further purification. LCMS (ES+): 600.5 $[M+H]^+$ Step 4: To a mixture of 3-[4-(4-amino-1-piperidyl)-3-fluoro-anilino]piperidine-2,6-dione (14.37 mg, 44.84 μmol) and 1-[5-[3-[3-[[ethyl(methyl)sulfamoyl]amino]-2,6-difluoro-benzoyl]-1H-pyrrolo[2,3-b]pyridin-5-yl]pyrimidin-2-yl]piperidine-4-carboxylic acid (32 mg, 44.84 μmol) in DMF (0.8 mL) was added N,N-diisopropylethylamine (23.18 mg, 179.36 μmol, 31.24 uL) and Bis(2-oxo-3-oxazolidinyl)phosphinic chloride, 97% (15.98 mg, 62.78 μmol). The resulting mixture was stirred at room temperature for 3 hr. The crude mixture was then purified by column chromatography (silica, gradient: 0-50% acetonitrile in water with 0.1% trifluoroacetic acid) to afford the product N-[1-[4-[(2,6-dioxo-3-piperidyl)amino]-2-fluoro-phenyl]-4-piperidyl]-1-[5-[3-[3-[[ethyl(methyl)sulfamoyl]amino]-2,6-difluoro-benzoyl]-1H-pyrrolo[2,3-b]pyridin-5-yl]pyrimidin-2-yl]piperidine-4-carboxamide (5 mg, 4.68 μmol, 10.43% yield). LCMS (ES+): 902.8 $[M+H]^+$. $^1H$ NMR (400 MHz, DMSO-$d_6$): δ 12.99 (d, J=3.3 Hz, 1H), 10.79 (s, 1H), 9.70 (s, 1H), 8.76 (s, 2H), 8.67 (d, J=2.1 Hz, 1H), 8.55 (s, 1H), 8.14 (d, J=3.1 Hz, 1H), 7.87 (d, J=7.5 Hz, 1H), 7.59 (td, J=9.0, 5.8 Hz, 1H), 7.28 (t, J=8.8 Hz, 1H), 6.56 (d, J=14.9 Hz, 1H), 6.47 (d, J=8.8 Hz, 1H), 4.82-4.69 (m, 2H), 4.30 (dd, J=11.9, 4.8 Hz, 1H), 3.14 (dq, J=14.3, 7.6, 7.1 Hz, 4H), 3.00 (t, J=11.8 Hz, 3H), 2.74 (s, 3H), 2.58 (d, J=14.9 Hz, 3H), 2.09 (dq, J=13.6, 4.7 Hz, 1H), 1.95-1.73 (m, 5H), 1.73-1.46 (m, 4H), 1.26 (q, J=6.5 Hz, 4H), 1.03 (t, J=7.1 Hz, 3H).

Example 129

5-[2-[(3R)-3-[4-[4-[(2,6-dioxo-3-piperidyl)amino]phenyl]piperidine-1-carbonyl]pyrrolidin-1-yl]pyrimidin-5-yl]-3-[3-[[ethyl(methyl)sulfamoyl]amino]-2,6-difluoro-benzoyl]-1H-pyrrolo[2,3-b]pyridine

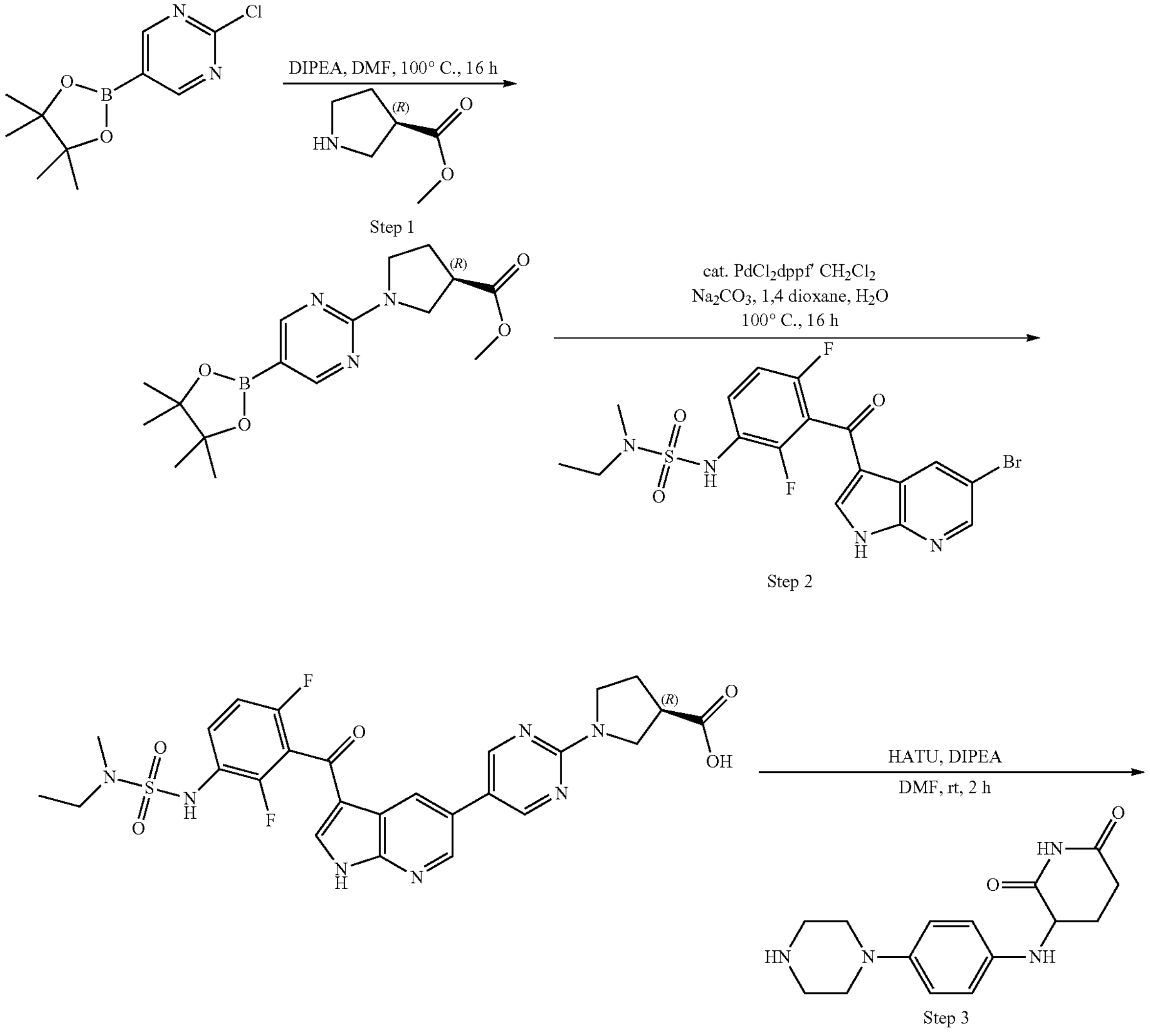

-continued

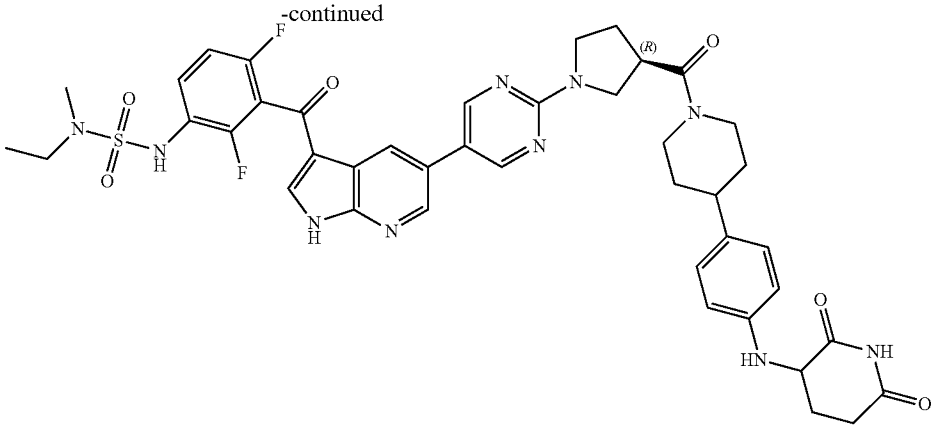

Step 1: To a stirred solution of 2-chloro-5-(4,4,5,5-tetramethyl-1,3,2-dioxaborolan-2-yl)pyrimidine (580.84 mg, 2.42 mmol) in N,N-dimethylformamide (5 mL) was taken in a seal tube and added N,N-diisopropylethylamine (1.25 g, 9.66 mmol, 1.68 mL) at room temperature followed by methyl (3R)-pyrrolidine-3-carboxylate (400 mg, 2.42 mmol). The resulted mixture was stirred at 100° C. in closed seal tube, for 16 h. After completion, water (50 mL) was added to the reaction mixture and pH adjected to 6-7 by 1.5 N HCl solution and extracted with 5% methanol in Dichloromethane (3×100 mL). Combined organic layers were dried over sodium sulphate and after filtration concentrated under reduced pressure to afford methyl (3R)-1-[5-(4,4,5,5-tetramethyl-1,3,2-dioxaborolan-2-yl)pyrimidin-2-yl]pyrrolidine-3-carboxylate (650 mg, 1.89 mmol, 78.35% yield) as pale brown solid. LCMS (ESI+): 334.2 $[M+H]^+$.

Step 2: To a stirred solution of 5-bromo-3-[3-[[ethyl(methyl)sulfamoyl]amino]-2,6-difluoro-benzoyl]-1H-pyrrolo[2,3-b]pyridine (500 mg, 1.06 mmol) was taken in mixture of 1,4-dioxane (8 mL) and water (2 mL) in a seal tube and added methyl (3R)-1-[5-(4,4,5,5-tetramethyl-1,3,2-dioxaborolan-2-yl)pyrimidin-2-yl]pyrrolidine-3-carboxylate (387.19 mg, 1.16 mmol) and $Na_2CO_3$ (335.91 mg, 3.17 mmol, 132.77 μL) at room temperature under nitrogen. The reaction mixture was degassed with nitrogen for 10 minutes, then added $Pd(dppf)Cl_2 \cdot CH_2Cl_2$ (86.27 mg, 105.64 μmol) at same temperature. The reaction mixture was heated to 100° C. for 16 h in closed seal tube. After completion, water (100 mL) was added to the reaction mixture and extracted with ethyl acetate (3×50 mL), after separation organic layer kept aside, collected aqueous layer pH adjected to 6-7 by 1.5N HCl solution and product extracted by 5% methanol in dichloromethane (2×100 mL). Combined organic layers were dried over dried over anhydrous sodium sulphate, filtered and filtrate was evaporated under reduced pressure to afford (3R)-1-[5-[3-[3-[[ethyl(methyl)sulfamoyl]amino]-2,6-difluoro-benzoyl]-1H-pyrrolo[2,3-b]pyridin-5-yl]pyrimidin-2-yl]pyrrolidine-3-carboxylic acid (230 mg, 274.51 μmol, 25.98% yield) as pale brown solid. Note: In this reaction we observed that hydrolysis did not proceed to completion, methyl ester of desired compound 120 mg was recovered from first organic (Ethyl acetate) layer. LCMS (ESI+): 586.2 $[M+H]^+$.

Step 3: Target compound was prepared via T3P mediated acid-amine coupling reaction (procedure C). Amide coupling was carried out using (3R)-1-[5-[3-[3-[[ethyl(methyl)sulfamoyl]amino]-2,6-difluoro-benzoyl]-1H-pyrrolo[2,3-b]pyridin-5-yl]pyrimidin-2-yl]pyrrolidine-3-carboxylic acid (170.00 mg, 290.31 μmol), 3-[4-(4-piperidyl)anilino]piperidine-2,6-dione (103.41 mg, 319.34 μmol), T3P (110.84 mg, 348.37 μmol) and N,N-diisopropylethylamine (225.12 mg, 1.74 mmol, 303.39 μL) to afford 5-[2-[(3R)-3-[4-[4-[(2,6-dioxo-3-piperidyl)amino]phenyl]piperidine-1-carbonyl]pyrrolidin-1-yl]pyrimidin-5-yl]-3-[3-[[ethyl(methyl)sulfamoyl]amino]-2,6-difluoro-benzoyl]-1H-pyrrolo[2,3-b]pyridine (34.2 mg, 37.90 μmol, 13.05% yield) as pale green solid. LCMS (ESI+): 855.2 $[M+H]^+$. $^1H$ NMR (400 MHz, DMSO-$d_6$): δ 12.99 (s, 1H), 10.78 (s, 1H), 9.72 (s, 1H), 8.75 (s, 1H), 8.66 (s, 1H), 8.54 (s, 1H), 8.14 (s, 1H), 7.62-7.56 (m, 1H), 7.30-7.26 (m, 1H), 6.99 (d, J=8.40 Hz, 2H), 6.63 (d, J=8.40 Hz, 2H), 5.70 (d, J=7.20 Hz, 1H), 4.57 (d, J=11.60 Hz, 1H), 4.30-4.15 (m, 2H), 3.85-3.56 (m, 5H), 3.20-3.10 (m, 3H), 2.73 (s, 3H), 2.52-2.50 (m, 5H), 2.24-2.11 (m, 3H), 1.89-1.74 (m, 3H), 1.60-1.35 (m, 2H), 1.02 (t, J=7.20 Hz, 3H).

Example 130

5-[2-[(3S)-3-[4-[4-[(2,6-dioxo-3-piperidyl)amino]phenyl]piperidine-1-carbonyl]pyrrolidin-1-yl]pyrimidin-5-yl]-3-[3-[[ethyl(methyl)sulfamoyl]amino]-2,6-difluoro-benzoyl]-1H-pyrrolo[2,3-b]pyridine

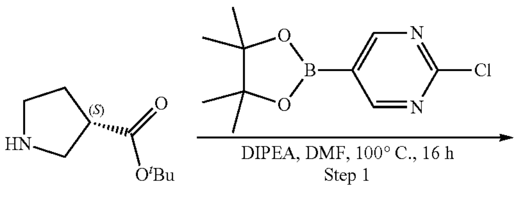

-continued

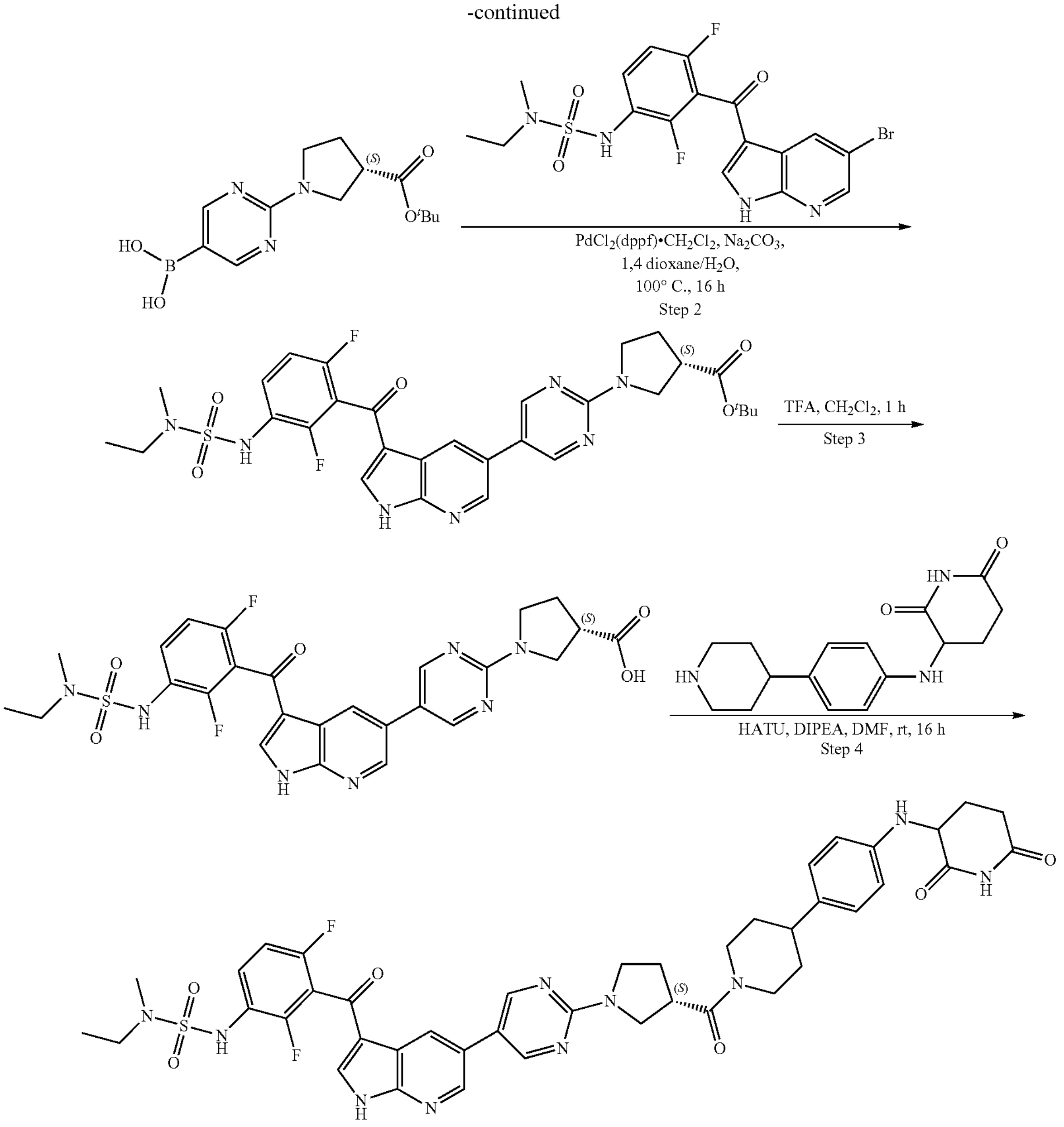

Step 1: To a mixture of tert-butyl (3S)-pyrrolidine-3-carboxylate (800 mg, 4.67 mmol) and 2-chloro-5-(4,4,5,5-tetramethyl-1,3,2-dioxaborolan-2-yl)pyrimidine (1.50 g, 6.24 mmol) in N,N-dimethylformamide (5.0 mL) was added N,N-diisopropylethylamine (2.02 g, 15.59 mmol, 2.72 mL) at room temperature under nitrogen atmosphere. The reaction mixture was heated at 100° C. for 16 h. The reaction mixture was cooled to room temperature, added to water (100 mL) and extracted with 10% methanol in dichloromethane (2×100 mL). The combined organic layers were washed with brine (100 mL), dried over sodium sulphate, filtered and concentrated under reduced pressure to afford [2-[(3S)-3-tert-butoxycarbonylpyrrolidin-1-yl]pyrimidin-5-yl]boronic acid (1.3 g, 1.67 mmol, 32.07% yield) as a brown solid. LCMS (ESI+): 294.1 $[M+H]^-$.

Step 2: A mixture of 5-bromo-3-[3-[[ethyl(methyl)sulfamoyl]amino]-2,6-difluoro-benzoyl]-1H-pyrrolo[2,3-b]pyridine (500 mg, 1.06 mmol), tert-butyl (3S)-1-[5-(4,4,5,5-tetramethyl-1,3,2-dioxaborolan-2-yl)pyrimidin-2-yl]pyrrolidine-3-carboxylate (396.45 mg, 1.06 mmol) and Sodium carbonate (335.91 mg, 3.17 mmol, 132.77 μL) in 1,4-Dioxane (5.6 mL)/Water (1.4 mL) was purged with nitrogen for 10 minutes followed by the addition of [1,1'-bis(diphenylphosphino)ferrocene]dichloropalladium(II), complex with dichloromethane (86.27 mg, 105.64 μmol) at room temperature. The reaction mixture was heated at 100° C. for 16 h. Reaction mixture was cooled to room temperature, diluted with dichloromethane (20 mL) and filtered through celite. The resulting filtrate was washed with brine (20 mL), dried over sodium sulphate, filtered and concentrated under reduced pressure. The crude product was purified by silica gel column chromatography using 5% methanol in dichloromethane as an eluent to afford tert-butyl (3S)-1-[5-[3-[3-[[ethyl(methyl)sulfamoyl]amino]-2,6-difluoro-benzoyl]-1H-pyrrolo[2,3-b]pyridin-5-yl]pyrimidin-2-yl]pyrrolidine-3-carboxylate (410 mg, 556.33 μmol, 52.66% yield) as a brown solid. LCMS (ESI+): 642.2 $[M+H]^+$.

Step: 3: To a solution of tert-butyl (3S)-1-[5-[3-[3-[[ethyl(methyl)sulfamoyl]amino]-2,6-difluoro-benzoyl]-1H-pyrrolo[2,3-b]pyridin-5-yl]pyrimidin-2-yl]pyrrolidine-3-carboxylate (410 mg, 638.94 μmol) in dichloromethane (5.0 mL) was added trifluoroacetic acid (5.92 g, 51.92 mmol, 4 mL) at 0° C. under nitrogen atmosphere. The reaction mixture was warmed to room temperature and stirred for 3 h. Reaction mixture was concentrated under reduced pressure and dried to afford (3S)-1-[5-[3-[3-[[ethyl(methyl)sulfamoyl]amino]-2,6-difluoro-benzoyl]-1H-pyrrolo[2,3-b]pyridin-5-yl]pyrimidin-2-yl]pyrrolidine-3-carboxylic acid (375 mg, 455.90 μmol, 71.35% yield) as a brown oil. LCMS (ESI+): 586.2 $[M+H]^+$.

Step 4: Target compound was prepared via HATU mediated acid-amine coupling reaction (procedure A). Amide coupling was carried out using (3S)-1-[5-[3-[3-[[ethyl(methyl)sulfamoyl]amino]-2,6-difluoro-benzoyl]-1H-pyrrolo[2,3-b]pyridin-5-yl]pyrimidin-2-yl]pyrrolidine-3-carboxylic acid (375 mg, 640.39 μmol), 3-[4-(4-piperidyl)anilino]piperidine-2,6-dione (184.02 mg, 568.28 μmol, hydrochloric acid salt), DIPEA (827.66 mg, 6.40 mmol, 1.12 mL) and HATU (365.24 mg, 960.58 μmol) to afford 5-[2-[(3S)-3-[4-[4-[(2,6-dioxo-3-piperidyl)amino]phenyl]piperidine-1-carbonyl]pyrrolidin-1-yl]pyrimidin-5-yl]-3-[3-[[ethyl(methyl)sulfamoyl]amino]-2,6-difluoro-benzoyl]-1H-pyrrolo[2,3-b]pyridine (55.52 mg, 60.55 μmol, 9.45% yield, formic acid salt) as a brown solid. LCMS (ESI): 853.2 $[M-H]^+$. $^1H$ NMR (400 MHz, DMSO-$d_6$): δ 12.95 (s, 1H), 10.78 (s, 1H), 8.75 (s, 2H), 8.66 (d, J=2.40 Hz, 1H), 8.53 (s, 1H), 8.12 (s, 1H), 7.61-7.55 (m, 1H), 7.25 (t, J=8.40 Hz, 1H), 6.99 (d, J=8.40 Hz, 2H), 6.63 (d, J=8.40 Hz, 2H), 5.69 (d, J=7.60 Hz, 2H), 4.50-4.65 (m, 1H), 4.22-4.32 (m, 1H), 4.06-4.21 (m, 1H), 3.83-3.81 (m, 1H), 3.66-3.80 (m, 2H), 3.67-3.58 (m, 2H), 3.11 (q, J=7.20 Hz, 2H), 2.75-2.72 (m, 4H), 2.74 (s, 3H), 2.68-2.56 (m, 3H), 2.13-2.09 (m, 3H), 1.86-1.82 (m, 3H), 1.02 (t, J=7.20 Hz, 3H).

Example 131

5-[2-[(3S)-3-[2-[4-[4-[(2,6-dioxo-3-piperidyl)amino]phenyl]-1-piperidyl]-2-oxo-ethyl]pyrrolidin-1-yl]pyrimidin-5-yl]-3-[3-[[ethyl(methyl)sulfamoyl]amino]-2,6-difluoro-benzoyl]-1H-pyrrolo[2,3-b]pyridine

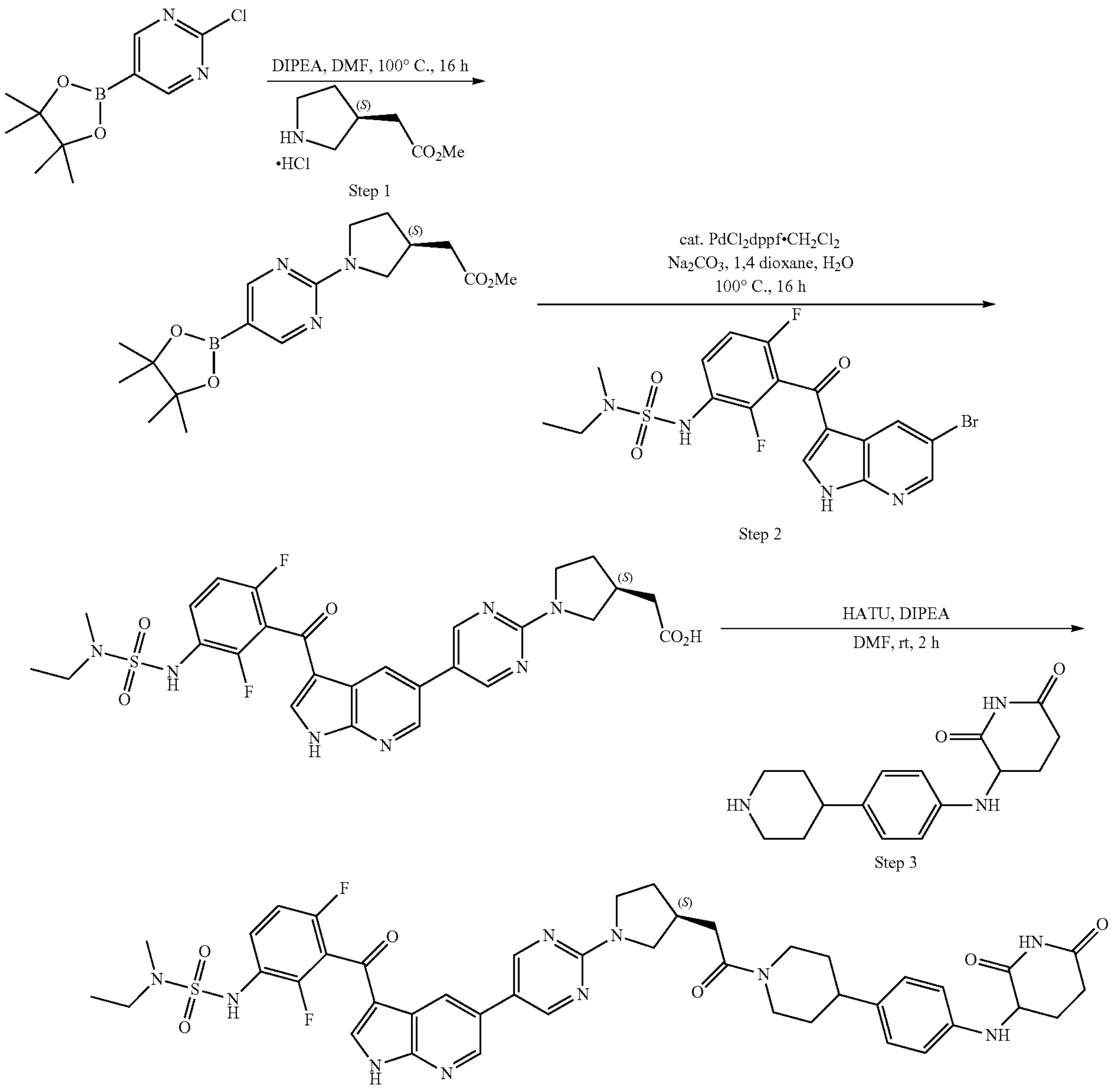

Step 1: To stirred solution of 2-chloro-5-(4,4,5,5-tetramethyl-1,3,2-dioxaborolan-2-yl)pyrimidine (923.79 mg, 3.84 mmol) in DMF (5 mL) in a seal tube was added N-ethyl-N-isopropyl-propan-2-amine (1.81 g, 13.97 mmol, 2.43 mL) at room temperature followed by methyl 2-[(3S)-pyrrolidin-3-yl]acetate (500 mg, 3.49 mmol, hydrochloric acid salt). The resulted mixture was stirred at 100° C. in closed seal tube, for 16 hours. Reaction mixture diluted with water (100 mL) and product extracted by ethyl acetate (2×100 mL). Combined organic layers were dried over sodium sulphate, concentrated under reduced pressure afford crude methyl 2-[(3 S)-1-[5-(4,4,5,5-tetramethyl-1,3,2-dioxaborolan-2-yl) pyrimidin-2-yl]pyrrolidin-3-yl]acetate (640 mg, 1.64 mmol, 46.98% yield) as pale brown semi solid. LCMS (ESI+): 266.1 $[M+H-82]^+$ (boronic acid mass).

Step 2: Compound 5-bromo-3-[3-[[ethyl(methyl)sulfamoyl]amino]-2,6-difluoro-benzoyl]-1H-pyrrolo[2,3-b]pyridine (500 mg, 1.06 mmol) was taken in mixture of water (3 mL) and 1,4-dioxane (12 mL) in a seal tube and added methyl 2-[(3S)-1-[5-(4,4,5,5-tetramethyl-1,3,2-dioxaborolan-2-yl)pyrimidin-2-yl]pyrrolidin-3-yl]acetate (440.17 mg, 1.27 mmol) and disodium carbonate (335.91 mg, 3.17 mmol) at room temperature under nitrogen. The reaction mixture was degassed with nitrogen for 10 min, added Pd(dppf)$Cl_2$:dichloromethane complex (86.27 mg, 105.64 μmol) at same temperature. The reaction mixture was heated at 100° C. for 16 h in closed seal tube. Reaction mixture diluted with water (100 mL) and ethyl acetate (100 mL). The layers were separated and the pH of the aqueous layer was adjusted to 5-6 by 1.5N HCl. The aqueous layer was extracted further by ethyl acetate (2×100 mL). The combined organic layers were dried over sodium sulphate, concentrated under reduced pressure afford crude 2-[(3S)-1-[5-[3-[3-[[ethyl(methyl)sulfamoyl]amino]-2,6-difluoro-benzoyl]-1H-pyrrolo[2,3-b]pyridin-5-yl]pyrimidin-2-yl] pyrrolidin-3-yl]acetic acid (240 mg, 313.81 μmol, 29.70% yield) as pale brown solid. LCMS (ESI+): 600.2 $[M+H]^+$.

Step 3: Target compound was prepared via HATU mediated acid-amine coupling reaction (procedure A). Amide coupling was carried out using 2-[(3S)-1-[5-[3-[3-[[ethyl (methyl)sulfamoyl]amino]-2,6-difluoro-benzoyl]-1H-pyrrolo[2,3-b]pyridin-5-yl]pyrimidin-2-yl]pyrrolidin-3-yl]acetic acid (230 mg, 383.58 μmol) in DMF (2 mL), N-ethyl-N-isopropyl-propan-2-amine (297.45 mg, 2.30 mmol, 400.88 HATU (175.02 mg, 460.30 μmol) and 3-[4-(4-piperidyl)anilino]piperidine-2,6-dione (136.63 mg, 421.94 μmol, hydrochloric acid salt) to afford 5-[2-[(3S)-3-[2-[4-[4-[(2,6-dioxo-3-piperidyl)amino]phenyl]-1-piperidyl]-2-oxo-ethyl]pyrrolidin-1-yl]pyrimidin-5-yl]-3-[3-[[ethyl (methyl)sulfamoyl]amino]-2,6-difluoro-benzoyl]-1H-pyrrolo[2,3-b]pyridine (145 mg, 149.44 μmol, 38.96% yield, formate salt) as off white solid. LCMS (ESI+): 869.3 $[M+H]^+$. $^1H$ NMR (400 MHz, DMSO-$d_6$): δ 12.99 (s, 1H), 10.77 (s, 1H), 9.71 (s, 1H), 8.74 (s, 2H), 8.66 (d, J=2.40 Hz, 1H), 8.56 (bs, 1H), 8.13 (d, J=2.80 Hz, 1H), 7.60-7.58 (m, 1H), 7.28-7.27 (m, 1H), 6.97 (d, J=8.80 Hz, 2H), 6.62 (d, J=8.80 Hz, 2H), 5.66-5.55 (m, 1H), 4.56-4.50 (m, 1H), 4.28-4.27 (m, 1H), 4.05-3.95 (m, 1H), 3.86-3.84 (m, 1H), 3.71-3.70 (m, 1H), 3.53-3.51 (m, 1H), 3.21-3.19 (m, 1H), 3.14-3.06 (m, 3H), 2.74 (s, 3H), 2.71-2.68 (m, 1H), 2.68-2.53 (m, 6H), 2.25-2.08 (m, 2H), 1.95-1.73 (m, 4H), 1.55-1.33 (m, 2H), 1.03 (t, J=7.20 Hz, 3H).

Example 132

5-[2-[6-[4-[4-[(2,6-dioxo-3-piperidyl)amino]phenyl] piperidine-1-carbonyl]-2-azaspiro[3.3]heptan-2-yl] pyrimidin-5-yl]-3-[3-[[ethyl(methyl)sulfamoyl] amino]-2,6-difluoro-benzoyl]-1H-pyrrolo[2,3-b] pyridine

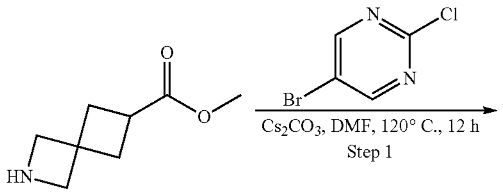

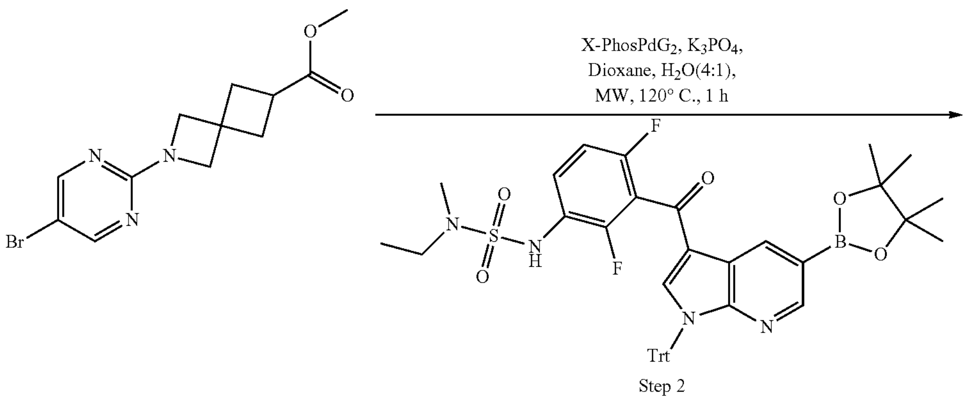

-continued

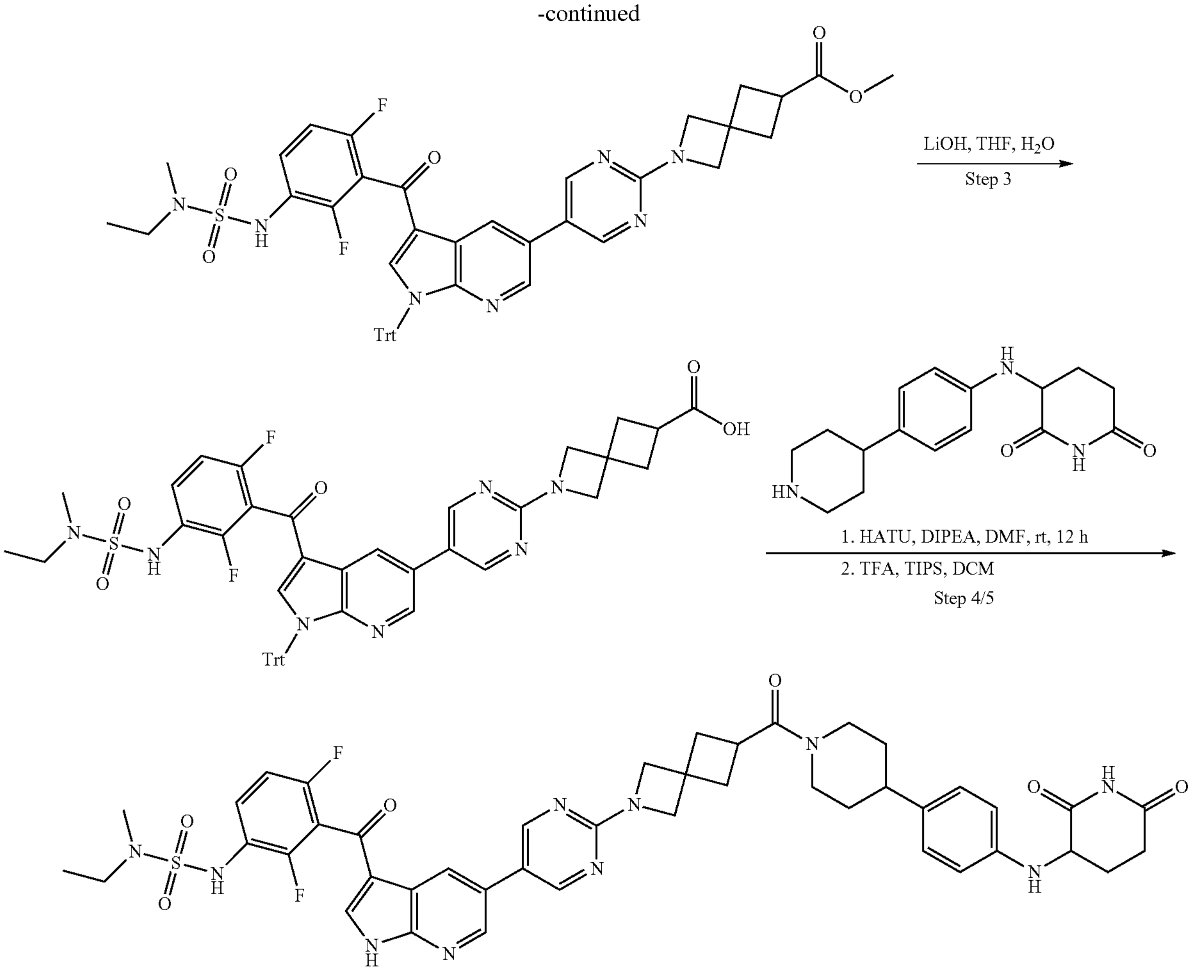

Step 1: To a stirred solution of methyl 2-azaspiro[3.3]heptane-6-carboxylate (780 mg, 4.07 mmol) in N,N-dimethylformamide (10 mL) was added 5-bromo-2-chloro-pyrimidine (865.94 mg, 4.48 mmol) followed by cesium carbonate (1.69 g, 5.18 mmol, 736.89 μL) was added at room temperature and the resulting reaction mixture was heated at 100° C. for 12 h. After completion, ice water was added to the reaction mixture and solid precipitated out were filtered through Buchner funnel and dried under vacuum pressure to afford methyl 2-(5-bromopyrimidin-2-yl)-2-azaspiro[3.3]heptane-6-carboxylate (1 g, 3.17 mmol, 77.82% yield) as brown solid. LCMS (ESI+): 314.0 $[M+H]^+$ Step 2: A solution of methyl 2-(5-bromopyrimidin-2-yl)-2-azaspiro[3.3]heptane-6-carboxylate (245.58 mg, 786.71 μmol) in 1,4-dioxane (3 mL), water (0.5 mL) was taken in a microwave vial and added 3-[3-[[ethyl(methyl)sulfamoyl]amino]-2,6-difluoro-benzoyl]-5-(4,4,5,5-tetramethyl-1,3,2-dioxaborolan-2-yl)-1-trityl-pyrrolo[2,3-b]pyridine (500 mg, 655.59 μmol), potassium phosphate (417.48 mg, 1.97 mmol). The reaction mixture was degassed for 30 minutes and added XPhos Pd G2 (25.79 mg, 32.78 μmol). The reaction mixture was irradiated under microwave at 120° C. for 1 h. After completion, the reaction mixture was concentrated, diluted with water extracted with Ethyl acetate, organic layer was dried over sodium sulphate and concentrated under reduced pressure, purified by column chromatography to afford methyl 2-[5-[3-[3-[[ethyl(methyl)sulfamoyl]amino]-2,6-difluoro-benzoyl]-1-trityl-pyrrolo[2,3-b]pyridin-5-yl]pyrimidin-2-yl]-2-azaspiro[3.3]heptane-6-carboxylate (320 mg, 349.03 μmol, 53.24% yield). LCMS (ESI+): 868.3 $[M+H]^+$.

Step 3: To a stirred solution of methyl 2-[5-[3-[3-[[ethyl(methyl)sulfamoyl]amino]-2,6-difluoro-benzoyl]-1-trityl-pyrrolo[2,3-b]pyridin-5-yl]pyrimidin-2-yl]-2-azaspiro[3.3]heptane-6-carboxylate (20 mg, 23.04 μmol) in water (1 mL), THF (4 mL) was added lithium hydroxide monohydrate (966.95 ug, 23.04 μmol, 0.64 μL) and stirred at room temperature for 12 h. After completion, reaction mixture was concentrated, diluted with water extracted with ethyl acetate. Combined organic layers were dried over sodium sulphate and concentrated under reduced pressure to afford 2-[5-[3-[3-[[ethyl(methyl)sulfamoyl]amino]-2,6-difluoro-benzoyl]-1-trityl-pyrrolo[2,3-b]pyridin-5-yl]pyrimidin-2-yl]-2-azaspiro[3.3]heptane-6-carboxylic acid (15 mg, 15.40 μmol, 66.82% yield). LCMS (ESI+): 854.3 $[M+H]^+$.

Step 4: To a stirred solution of 2-[5-[3-[3-[[ethyl(methyl)sulfamoyl]amino]-2,6-difluoro-benzoyl]-1-trityl-pyrrolo[2,3-b]pyridin-5-yl]pyrimidin-2-yl]-2-azaspiro[3.3]heptane-6-carboxylic acid (300 mg, 351.32 μmol), 3-[4-(4-piperidyl)anilino]piperidine-2,6-dione (111.05 mg, 386.45 μmol) in N,N-dimethyl formamide (3 mL) was added HATU (200.37 mg, 526.97 μmol), N, N-diisopropylethylamine (371.00 mg, 2.87 mmol, 0.5 mL). The resulting reaction mixture was stirred at room temperature for 16 h. After completion, the reaction mixture was diluted with water and extracted with Ethyl Acetate. Combined organic layers were dried over sodium sulphate, filtered and concentrated under reduced pressure to afford crude 5-[2-[6-[4-[4-[(2,6-dioxo-3-piperidyl)amino]phenyl]piperidine-1-carbonyl]-2-azaspiro[3.3]heptan-2-yl]pyrimidin-5-yl]-3-[3-[[ethyl(methyl)sulfamoyl]amino]-2,6-difluoro-benzoyl]-1-trityl-pyrrolo[2,3-b]pyridine (400 mg, 105.05 μmol, 29.90% yield). LCMS (ESI): 1121.3 $[M-H]^+$.

Step 5: To the stirred solution of 5-[2-[6-[4-[4-[(2,6-dioxo-3-piperidyl)amino]phenyl]piperidine-1-carbonyl]-2-azaspiro[3.3]heptan-2-yl]pyrimidin-5-yl]-3-[3-[[ethyl(methyl)sulfamoyl]amino]-2,6-difluoro-benzoyl]-1-trityl-pyrrolo[2,3-b]pyridine (150 mg, 133.54 μmol) in dichloromethane (3 mL) was added trifluoroacetic acid (152.26 mg, 1.34 mmol, 102.88 μL) followed by tri-isopropyl silane (39.26 mg, 200.31 μmol) at room temperature under inert atmosphere. The reaction mixture was stirred at room temperature for 4 h. After completion, the reaction mixture was evaporated under reduced pressure to get crude. The crude compound was purified by reverse phase chromatography by using 0.1% formic acid in water and acetonitrile to get the 5-[2-[6-[4-[4-[(2,6-dioxo-3-piperidyl)amino]phenyl]piperidine-1-carbonyl]-2-azaspiro[3.3]heptan-2-yl]pyrimidin-5-yl]-3-[3-[[ethyl(methyl)sulfamoyl]amino]-2,6-difluoro-benzoyl]-1H-pyrrolo[2,3-b]pyridine (13.45 mg, 12.90 μmol, 9.66% yield) as off white solid. LCMS (ESI): 880.9 $[M-H]^+$. $^1H$ NMR (400 MHz, DMSO-$d_6$): δ 10.78 (s, 1H), 8.73 (s, 2H), 8.64 (d, J=2.40 Hz, 1H), 8.55 (s, 1H), 8.11 (s, 1H), 7.53-7.57 (m, 1H), 7.22 (t, J=8.80 Hz, 1H), 6.96 (d, J=8.40 Hz, 2H), 6.61 (d, J=8.40 Hz, 2H), 5.68 (d, J=7.60 Hz, 1H), 4.51 (d, J=13.20 Hz, 1H), 4.24-4.30 (m, 1H), 4.18 (s, 2H), 3.98-4.00 (m, 2H), 3.83 (d, J=12.80 Hz, 1H), 3.37-3.31 (m, 1H), 3.09 (q, J=7.20 Hz, 2H), 3.01-3.11 (m, 1H), 2.70 (s, 3H), 2.49-2.62 (m, 8H), 2.08-2.10 (m, 1H), 1.79-1.90 (m, 1H), 1.70-1.76 (m, 2H), 1.36-1.42 (m, 2H), 1.02 (t, J=7.20 Hz, 3H).

Example 133

5-[2-[6-[2-[4-[4-[(2,6-dioxo-3-piperidyl)amino]phenyl]-1-piperidyl]-2-oxo-ethyl]-2-azaspiro[3.3]heptan-2-yl]pyrimidin-5-yl]-3-[3-[[ethyl(methyl)sulfamoyl]amino]-2,6-difluoro-benzoyl]-1H-pyrrolo[2,3-b]pyridine

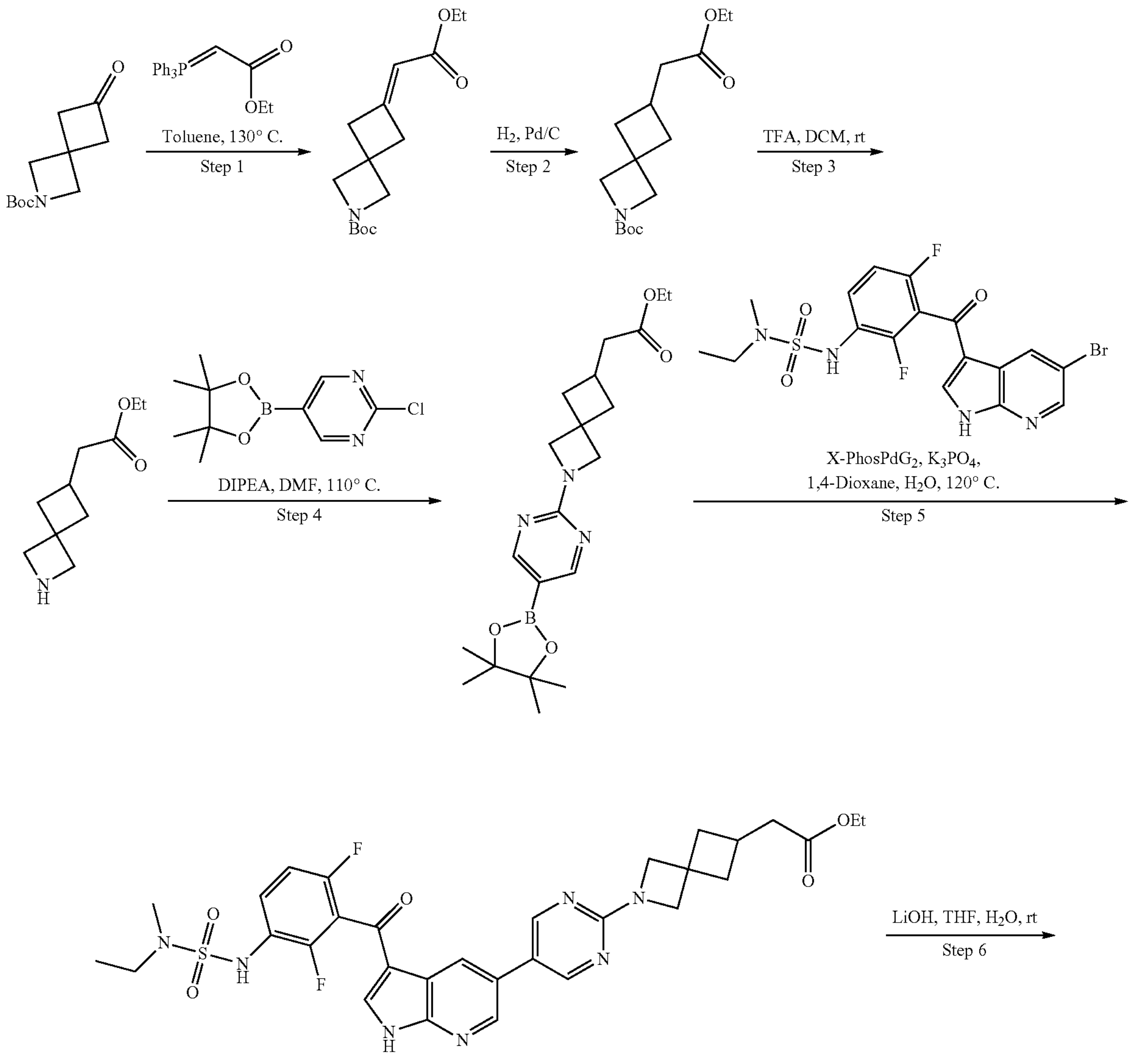

-continued

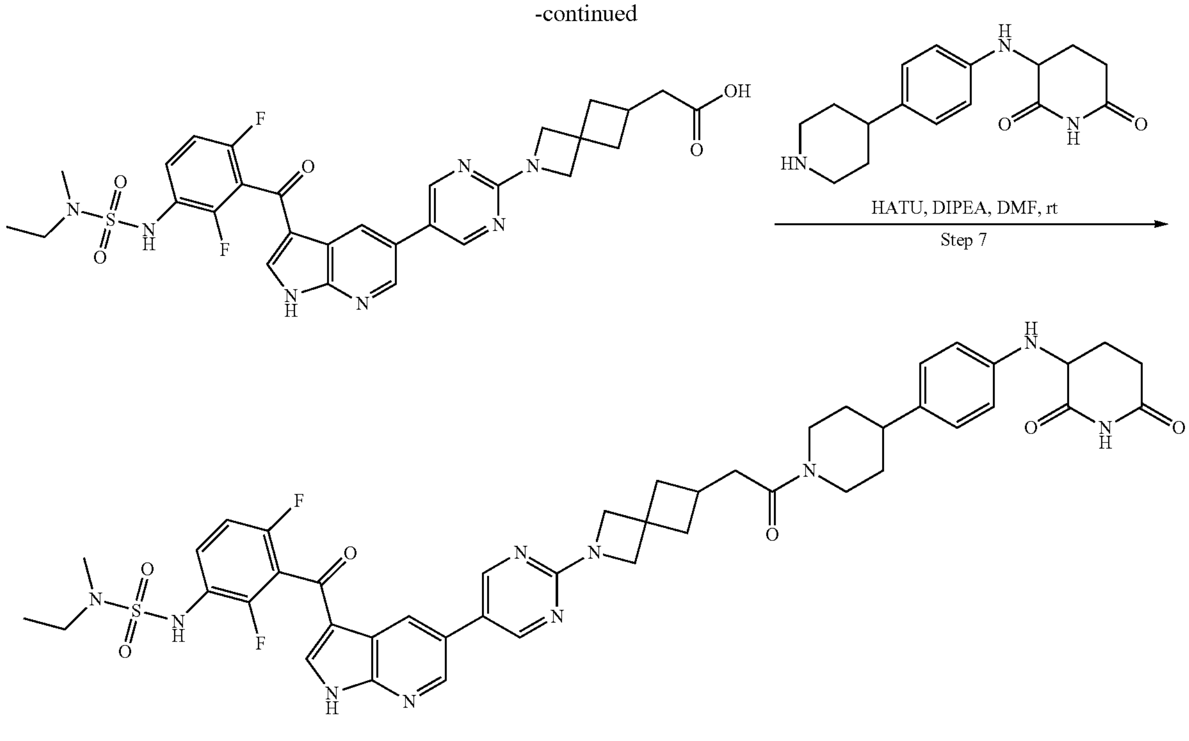

Step 1: To a stirred solution of tert-butyl 6-oxo-2-azaspiro[3.3]heptane-2-carboxylate (1.5 g, 7.10 mmol) in toluene (40 mL) was added to ethyl 2-(triphenyl-1-phosphaneylidene)acetate (2.48 g, 7.10 mmol) at room temperature under a nitrogen atmosphere. The reaction mixture was heated at 130° C. for 12 h. The reaction mixture was diluted with ice water (20 mL) and extracted with ethyl acetate (2×50 mL). The combined organic layers were dried over sodium sulphate, filtered and concentrated under reduced pressure. The crude product was by silica gel column chromatography using 10% ethyl acetate in petroleum ether as an eluent to afford tert-butyl 6-(2-ethoxy-2-oxo-ethylidene)-2-azaspiro[3.3]heptane-2-carboxylate (1.7 g, 5.74 mmol, 80.84% yield) as an oily liquid. LCMS (ESI+): 182.1 [M−100+H]+.

Step 2: To a solution of tert-butyl 6-(2-ethoxy-2-oxo-ethylidene)-2-azaspiro[3.3]heptane-2-carboxylate (100 mg, 355.43 mmol) in ethanol (10 mL) was added palladium, 10% on carbon (100 mg, 355.43 μmol) at room temperature. The reaction mixture stirred under pressure of Hydrogen (1 atm) at room temperature for 12 h. The reaction mixture was filtered through celite, and the resulting filtrate was concentrated under reduced pressure to afford tert-butyl 6-(2-ethoxy-2-oxo-ethyl)-2-azaspiro[3.3]heptane-2-carboxylate (80 mg, 276.68 μmol, 77.84% yield) as an off-white solid. LCMS (ESI+): 184.2 [M−100+H]+.

Step 3: To a stirred solution of tert-butyl 6-(2-ethoxy-2-oxo-ethyl)-2-azaspiro[3.3]heptane-2-carboxylate (1.7 g, 6.00 mmol) in dichloromethane (20 mL) was added trifluoroacetic acid (4.44 g, 38.94 mmol, 3 mL) at 0° C. The reaction mixture was warmed to room temperature and stirred for 5 h. The reaction mixture was concentrated under reduced pressure, triturated with diethyl ether and dried to afford ethyl 2-(2-azaspiro[3.3]heptan-6-yl)acetate (2.2 g, 4.51 mmol, 75.25% yield, trifluoroacetic acid salt) as a light brown solid. LCMS (ESI+): 183.9 [M+H]+.

Step 4: To a mixture of ethyl 2-(2-azaspiro[3.3]heptan-6-yl)acetate (200 mg, 672.79 μmol, trifluoroacetic acid salt) and 2-chloro-5-(4,4,5,5-tetramethyl-1,3,2-dioxaborolan-2-yl)pyrimidine (162 mg, 673.61 μmol) in N,N-dimethylformamide (1 mL) was added N,N-diisopropylethylamine (435 mg, 3.37 mmol, 586.25 μL) at room temperature under nitrogen atmosphere. The reaction mixture was heated at 100° C. for 12 h. Reaction mixture was cooled to room temperature, added to ice water, resulting solid was filtered, washed with cold water and dried to afford [2-[6-(2-ethoxy-2-oxo-ethyl)-2-azaspiro[3.3]heptan-2-yl]pyrimidin-5-yl]boronic acid (250 mg, 573.51 μmol, 85.24% yield) as an off-white solid. LCMS (ESI+): 388.2 [M+H]+.

Step 5: A mixture of [2-[6-(2-ethoxy-2-oxo-ethyl)-2-azaspiro[3.3]heptan-2-yl]pyrimidin-5-yl]boronic acid (500 mg, 1.64 mmol), 5-bromo-3-[3-[[ethyl(methyl)sulfamoyl]amino]-2,6-difluoro-benzoyl]-1H-pyrrolo[2,3-b]pyridine (650 mg, 1.37 mmol) and potassium phosphate tribasic anhydrous (900 mg, 4.24 mmol) in 1,4-Dioxane (5.0 mL)/Water (1.0 mL) was purged with nitrogen gas for 20 min followed by the addition of Xphos Pd G2 (60 mg, 76.26 μmol). The reaction mixture was irradiated under microwave at 120° C. for 1 h. The reaction mixture was filtered through celite bed, resulting filtrate was concentrated under reduced pressure. The crude product was purified by silica gel column chromatography using 5% methanol in dichloromethane as an eluent to afford ethyl 2-[2-[5-[3-[3-[[ethyl(methyl)sulfamoyl]amino]-2,6-difluoro-benzoyl]-1H-pyrrolo[2,3-b]pyridin-5-yl]pyrimidin-2-yl]-2-azaspiro[3.3]heptan-6-yl]acetate (750 mg, 894.91 μmol, 65.16% yield) as a brown solid. LCMS (ESI+): 654.3 [M+H]+.

Step 6: To a stirred solution of ethyl 2-[2-[5-[3-[3-[[ethyl(methyl)sulfamoyl]amino]-2,6-difluoro-benzoyl]-1H-pyrrolo[2,3-b]pyridin-5-yl]pyrimidin-2-yl]-2-azaspiro[3.3]heptan-6-yl]acetate (700 mg, 1.07 mmol) in tetrahydrofuran (4.0 mL)/water (4.0 mL) was added lithium hydroxide, monohydrate (140.00 mg, 3.34 mmol, 92.72 μL) at room temperature. The reaction mixture was stirred at room temperature for 3 h. The reaction mixture was diluted with ice water (20 mL), acidified to pH~3 using 1.5 N aqueous HCl solution and extracted with ethyl acetate (2×50 mL). The combined organic layers were dried over sodium sulphate, filtered and concentrated under reduced pressure to afford 2-[2-[5-[3-[3-[[ethyl(methyl)sulfamoyl]amino]-2,6-difluoro-benzoyl]-1H-pyrrolo[2,3-b]pyridin-5-yl]pyrimidin-2-yl]-2-azaspiro[3.3]heptan-6-yl]acetic acid (350 mg, 396.46 μmol, 37.02% yield, hydrochloric acid salt) as an off-white solid. LCMS (ESI+): 626.2 $[M+H]^+$.

Step 7: Target compound was prepared via HATU mediated acid-amine coupling reaction (procedure A). Amide coupling was carried out using 2-[2-[5-[3-[3-[[ethyl(methyl)sulfamoyl]amino]-2,6-difluoro-benzoyl]-1H-pyrrolo[2,3-b]pyridin-5-yl]pyrimidin-2-yl]-2-azaspiro[3.3]heptan-6-yl]acetic acid (200 mg, 319.67 μmol), 3-[4-(4-piperidyl)anilino]piperidine-2,6-dione (93 mg, 323.64 μmol), HATU (182 mg, 478.66 μmol) and DIPEA (210 mg, 1.62 mmol, 283.02 μL) to afford 5-[2-[6-[2-[4-[4-[(2,6-dioxo-3-piperidyl)amino]phenyl]-1-piperidyl]-2-oxo-ethyl]-2-azaspiro[3.3]heptan-2-yl]pyrimidin-5-yl]-3-[3-[[ethyl(methyl)sulfamoyl]amino]-2,6-difluoro-benzoyl]-1H-pyrrolo[2,3-b]pyridine (33.53 mg, 34.87 μmol, 10.91% yield) as an off-white solid. LCMS (ESI+): 895.3 $[M+H]^+$. $^1$H NMR (400 MHz, DMSO-$d_6$): δ 12.94 (s, 1H), 10.77 (s, 1H), 8.73 (d, J=8.00 Hz, 2H), 8.64 (d, J=2.00 Hz, 1H), 8.53 (s, 1H), 8.13 (s, 1H), 7.58 (dd, J=9.20, 15.00 Hz, 1H), 7.27 (t, J=8.80 Hz, 1H), 6.96 (d, J=8.40 Hz, 2H), 6.62 (d, J=8.00 Hz, 2H), 5.67 (d, J=7.20 Hz, 1H), 4.53-4.28 (m, 1H), 4.27-3.97 (m, 1H), 3.94-3.20 (m, 5H), 3.14-2.79 (m, 3H), 2.78 (s, 3H), 2.73-2.57 (m, 6H), 2.38-2.13 (m, 4H), 2.12-2.08 (m, 2H), 1.92-1.84 (m, 3H), 1.77-1.36 (m, 3H), 1.02 (t, J=6.80 Hz, 3H).

Example 134

N-[1-[4-[(2,6-dioxo-3-piperidyl)amino]-2-fluoro-phenyl]-4-piperidyl]-2-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]acetamide

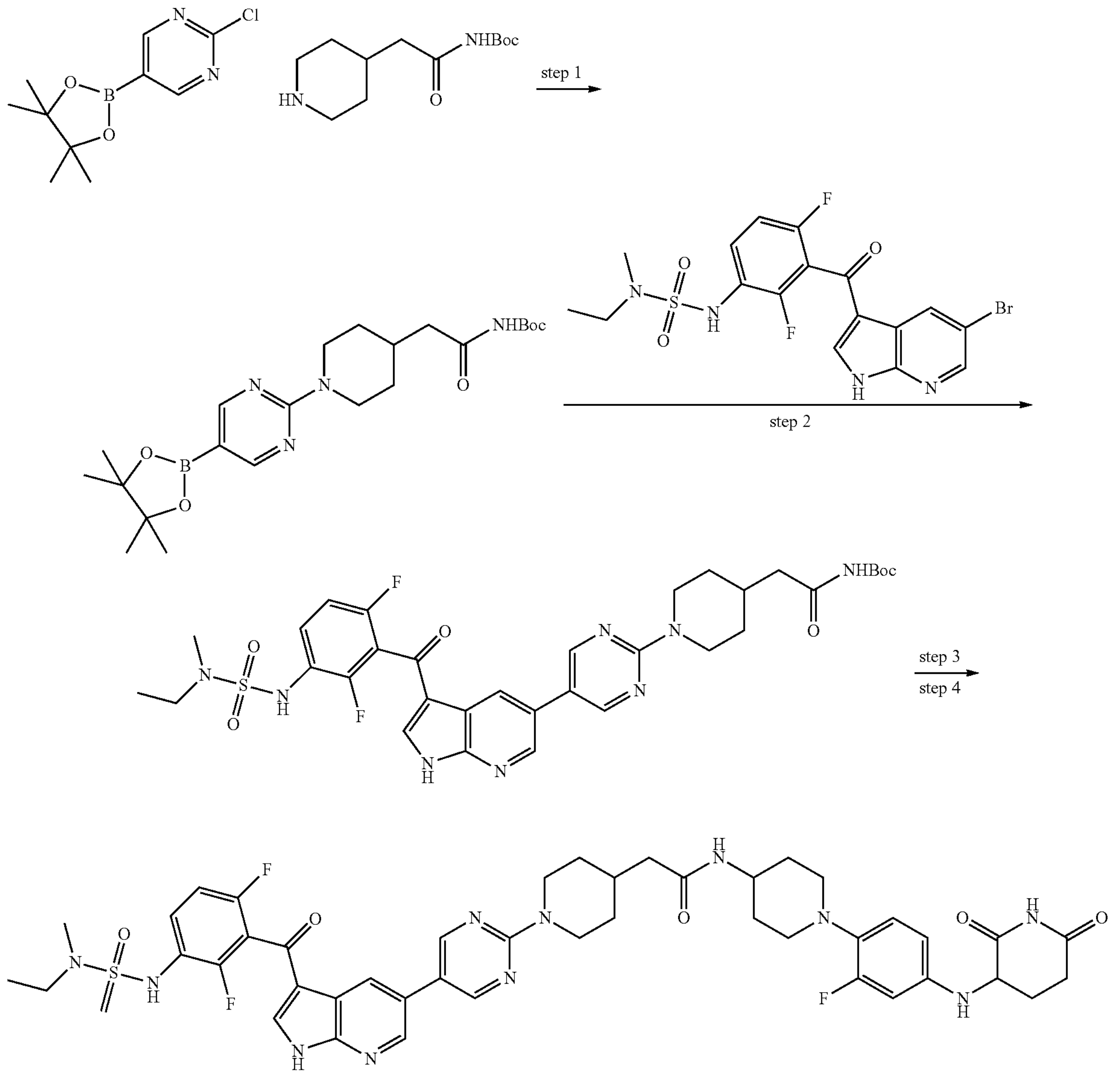

Step 1: 2-chloro-5-(4,4,5,5-tetramethyl-1,3,2-dioxaborolan-2-yl)pyrimidine (200 mg, 831.62 μmol) and tert-butyl 2-(4-piperidyl)acetate (182.31 mg, 914.78 μmol, 15.80 uL) were dissolved in dioxanes (1 mL) with triethylamine (126.23 mg, 1.25 mmol, 173.87 uL). The mixture was heated to 90° C. for 3 hr. At this time, the crude reaction was concentrated to give the product tert-butyl 2-[1-[5-(4,4,5,5-tetramethyl-1,3,2-dioxaborolan-2-yl)pyrimidin-2-yl]-4-piperidyl]acetate (335 mg, 830.60 μmol, 99.88% yield) which was carried forward without further purification. LCMS (ES+): 322.1 $[M+H]^+$ (Mass reflects loss of pinacol ester group)

Step 2: The tert-butyl 2-[1-[5-(4,4,5,5-tetramethyl-1,3,2-dioxaborolan-2-yl)pyrimidin-2-yl]-4-piperidyl]acetate (319.56 mg, 792.32 μmol), 5-bromo-3-[3-[[ethyl(methyl)sulfamoyl]amino]-2,6-difluoro-benzoyl]-1H-pyrrolo[2,3-b]pyridine (250 mg, 528.22 μmol), potassium phosphate tribasic anhydrous (336.37 mg, 1.58 mmol) were diluted in water (1 mL) and dioxanes (5 mL). The microwave tube was purged with argon gas for 10 min. The Xphos G3 Pd (44.71 mg, 52.82 μmol) was added. The tube was sealed and heated 100° C. in the microwave for 3 hours. The crude mixture was diluted in water (5 ml) and then extracted with 20 mL of ethyl acetate (3×). The organic layers were combined and dried over $MgSO_4$. The crude material was purified by column chromatography column 0-20% MeOH in DCM to afford tert-butyl 2-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]acetate (129 mg, 192.61 μmol, 36.46% yield) as a yellow powder. LCMS (ESI+): 670.3 $[M+H]^+$.

Step 3: The tert-butyl 2-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]acetate (129.81 mg, 193.82 μmol) were diluted in DCM (2 mL) and TFA (552.50 mg, 4.85 mmol, 373.31 uL) was added. The material was concentrated and residual water was removed by concentration several times with toluene as solvent. The 2-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]acetic acid (120 mg, 195.56 μmol, 100.90% yield) was taken forward crude. LCMS (ESI+): 614.1 $[M+H]^+$.

Step 4: Target compound was prepared via procedure B, by modifying the amide 3-[4-(4-amino-1-piperidyl)-3-fluoro-anilino]piperidine-2,6-dione (40.72 mg, 127.11 μmol), 2-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]acetic acid (65 mg, 105.93 μmol), 1.5 of DIPEA and 1.5 eq of COMU. The crude material was purified by reverse phase column chromatography (MeCN & Water (0.01% TFA)) to afford N-[1-[4-[(2,6-dioxo-3-piperidyl)amino]-2-fluoro-phenyl]-4-piperidyl]-2-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]acetamide (4.9 mg, 4.56 μmol, 4% yield) as off-white solid. LCMS (ESI+): 916.3 $[M+H]^+$.

Example 135

1-[4-[(2,6-dioxo-3-piperidyl)amino]-2-fluoro-phenyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]-N-methyl-piperidine-4-carboxamide

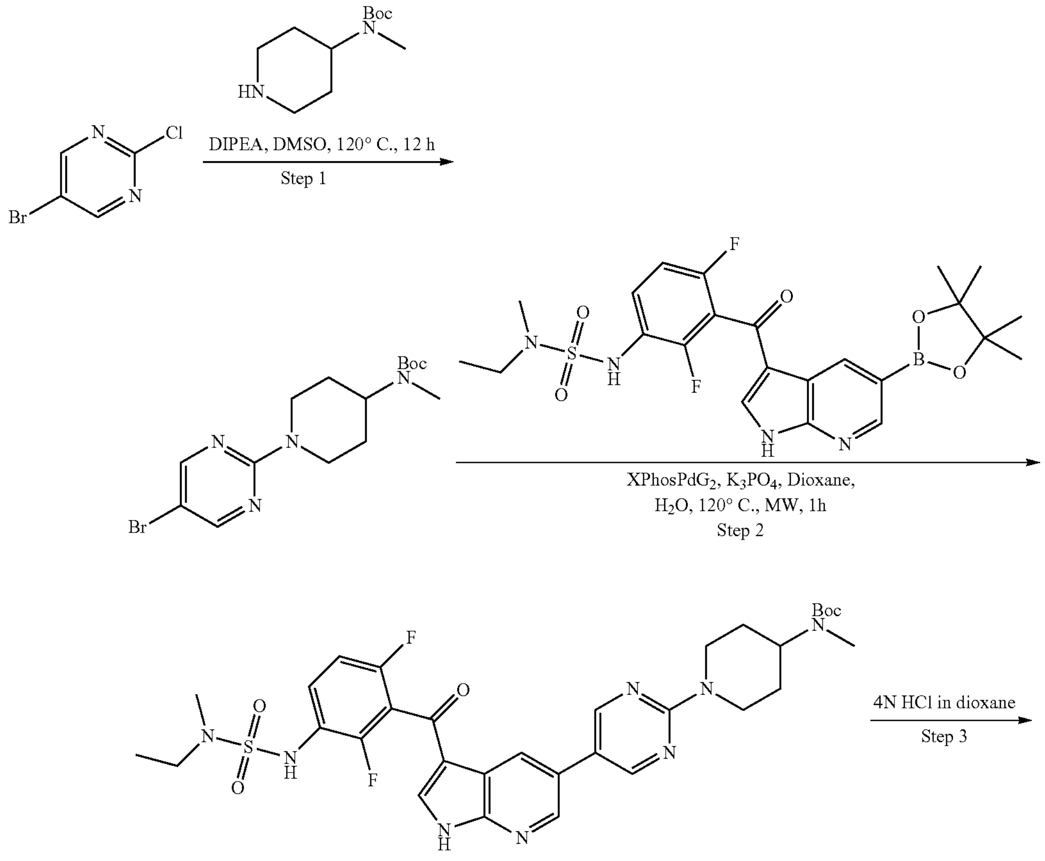

-continued

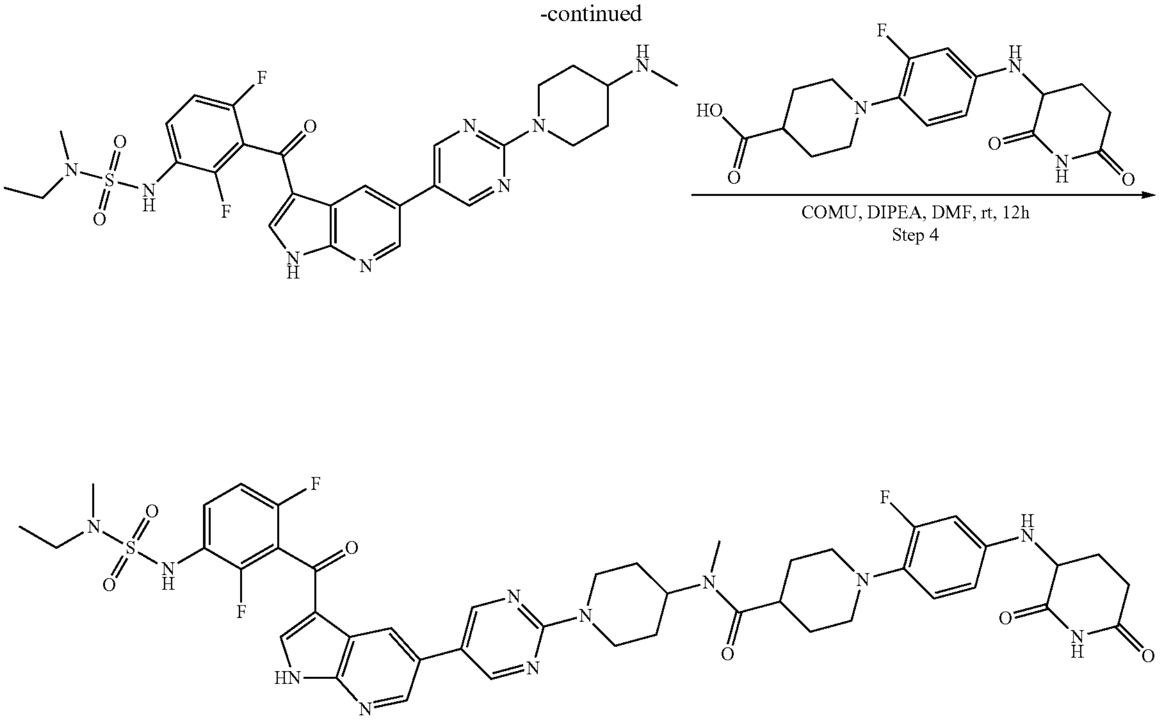

Step 1: To a stirred solution of 5-bromo-2-chloro-pyrimidine (1 g, 5.17 mmol), tert-butyl N-methyl-N-(4-piperidyl) carbamate (1.33 g, 6.20 mmol) in dimethyl sulfoxide (10 mL) was added N,N-diisopropylethylamine (2.00 g, 15.51 mmol, 2.70 mL). The reaction mixture was heated to 120° C. for 12 h. After completion, the reaction mixture was diluted with water (20 mL) and extracted with ethyl acetate (2×50 mL). The combined organic layers were dried over sodium sulphate, filtered and concentrated under vacuum to afford a crude residue. The crude material was purified by silica gel column chromatography using 20-30% ethyl acetate in pet-ether to afford tert-butyl N-[1-(5-bromopyrimidin-2-yl)-4-piperidyl]-N-methyl-carbamate (1.2 g, 3.04 mmol, 58.77% yield) as off-white solid. LCMS (ESI+): 371.1 $[M+H]^+$ Step 2: To a stirred solution of 3-[3-[[ethyl(methyl)sulfamoyl]amino]-2,6-difluoro-benzoyl]-5-[4,4,5,5-tetramethyl-1,3,2-dioxaborolan-2-yl)-1H-pyrrolo[2,3-b]pyridine (300 mg, 576.53 tert-butyl N-1-(5-bromopyrimidin-2-yl)-4-piperidyl]-N-methyl-carbamate (235.45 mg, 634.18 μmol) in dioxane (4 mL), water (1 mL) in a microwave vial, was added $K_3PO_4$ (367.13 mg, 1.73 mmol). The reaction mixture was degassed for 20 minutes and Xphos Pd G2 (136.08 mg, 172.96 μmol) was added. The reaction mixture was irradiated under microwave at 120° C. for 1 h. After completion, the reaction mixture was diluted with water (20 mL) and extracted with ethyl acetate (2×30 mL). The combined organic layers were dried over sodium sulphate, filtered and concentrated under vacuum to afford crude. The crude compound was purified by silica gel column chromatography compound using 70-100% ethyl acetate in pet-ether to afford tert-butyl N-[1-[5-[3-[3-[[ethyl(methyl)sulfamoyl] amino]-2,6-difluoro-benzoyl]-1H-pyrrolo[2,3-b]pyridin-5-yl]pyrimidin-2-yl]-4-piperidyl]-N-methyl-carbamate (200 mg, 189.85 μmol, 32.93% yield) as brown solid. LCMS (ESI+): 685.3 $[M+H]^+$.

Step 3: To a stirred solution of tert-butyl N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]-N-methyl-carbamate (200 mg, 292.08 μmol) in Dichloromethane (5 mL) at 0° C. was added HCl solution (4M in dioxane, 10.65 mg, 292.08 μmol, 13.31 The reaction mixture was stirred at room temperature for 2 h. The reaction mixture was concentrated under vacuum to afford crude 3-[3-[[ethyl(methyl)sulfamoyl]amino]-2,6-difluoro-benzoyl]-5-[2-[4-(methylamino)-1-piperidyl]pyrimidin-5-yl]-1H-pyrrolo[2,3-b]pyridine (200 mg, 225.41 μmol, 77.17% yield) as brown solid. LCMS (ESI+): 585.1 $[M+H]^+$ Step 4: Target compound was prepared via COMU mediated acid-amine coupling reaction (procedure B). Amide coupling was carried out using 5-[2-(4-amino-1-piperidyl) pyrimidin-5-yl]-3-[3-[[ethyl(methyl)sulfamoyl]amino]-2,6-difluoro-benzoyl]-1H-pyrrolo[2,3-b]pyridine (220 mg, 385.55 μmol), 1-[4-[(2,6-dioxo-3-piperidyl)amino]-2-fluoro-phenyl]piperidine-4-carboxylic acid (134.69 mg, 385.55 DIPEA (149.49 mg, 1.16 mmol, 201.47 μL) and COMU (181.63 mg, 424.11 μmol) to yield 1-[4-[(2,6-dioxo-3-piperidyl)amino]-2-fluoro-phenyl]-N-[1-[5-[3-[3-[[ethyl (methyl)sulfamoyl]amino]-2,6-difluoro-benzoyl]-1H-pyrrolo[2,3-b]pyridin-5-yl]pyrimidin-2-yl]-4-piperidyl] piperidine-4-carboxamide (26.20 mg, 27.77 μmol, 7.20% yield) as off white solid. LCMS (ESI+): 916.2 $[M+H]^+$. $^1H$ NMR (400 MHz, DMSO-$d_6$): δ 13.05 (s, 1H), 10.78 (s, 1H), 9.71 (s, 1H), 8.77 (s, 2H), 8.68 (d, J=2.00 Hz, 1H), 8.56 (s, 1H), 8.14 (s, 1H), 7.56-7.62 (m, 1H), 7.26-7.31 (m, 1H), 6.84-6.89 (m, 1H), 6.49-6.55 (m, 1H), 6.38-6.45 (m, 1H), 5.81 (d, J=7.20 Hz, 1H), 4.88 (d, J=12.80 Hz, 2H), 4.55-4.65 (m, 1H), 4.24-4.29 (m, 1H), 4.12-4.18 (m, 1H), 3.11-3.17 (m, 5H), 2.88-2.99 (m, 1H), 2.87 (s, 2H), 2.56-2.76 (m, 5H), 2.74 (s, 3H), 2.05-2.15 (m, 1H), 1.61-1.91 (m, 9H), 1.03 (t, J=7.20 Hz, 3H).

Example 136

1-[4-[(2,6-dioxo-3-piperidyl)amino]-2-fluoro-phenyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]piperidine-4-carboxamide

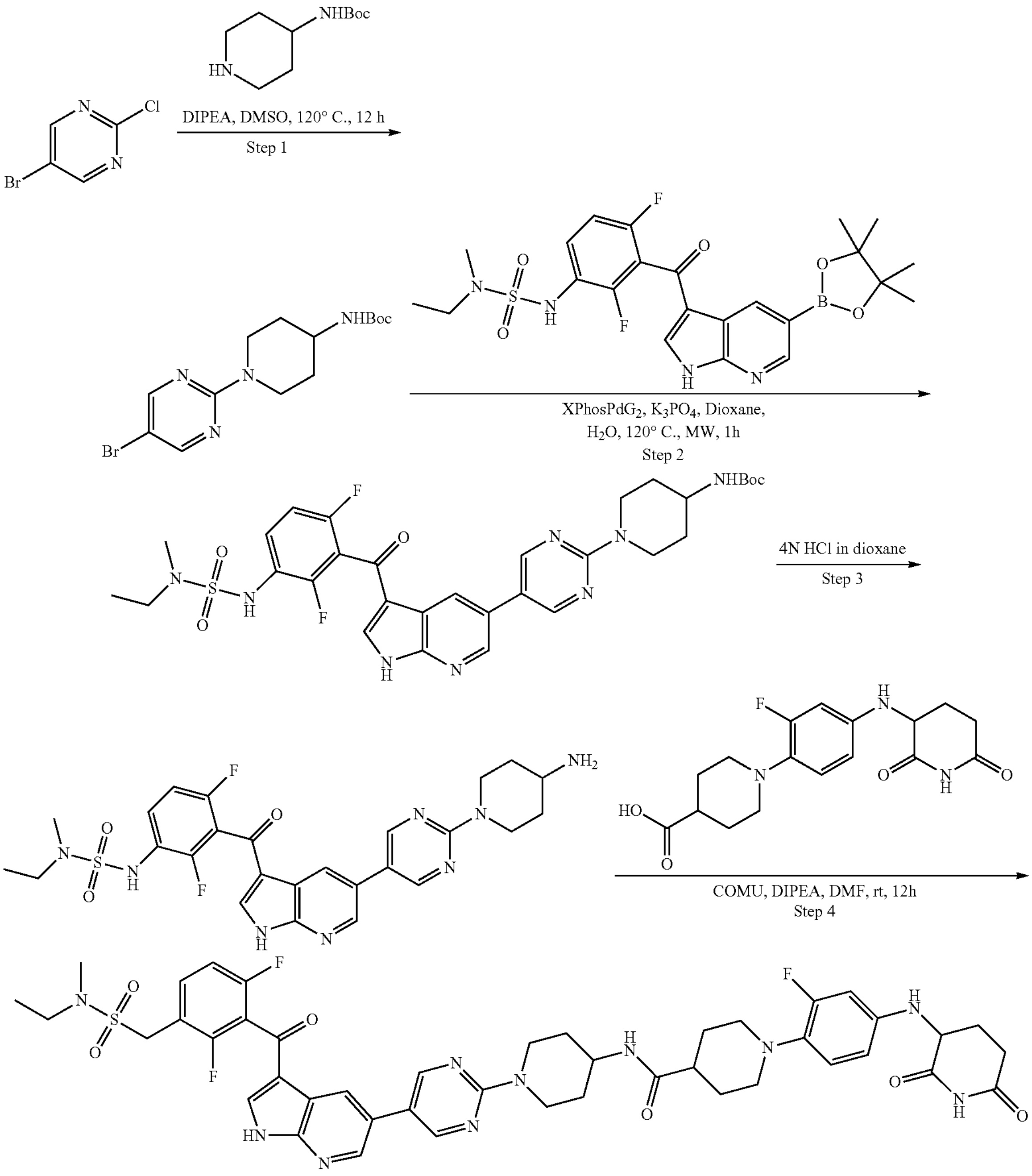

Step 1: To a stirred solution of 5-bromo-2-chloro-pyrimidine (1 g, 5.17 mmol), tert-butyl N-(4-piperidyl)carbamate (1.24 g, 6.20 mmol) in dimethyl sulfoxide (10 mL) was added N,N-diisopropylethylamine (2.00 g, 15.51 mmol, 2.70 mL). The reaction mixture was heated to 120° C. for 12 h. After completion, the reaction mixture was diluted with water (20 mL) and extracted with ethyl acetate (2×30 mL). The combined organic layers were dried over sodium sulphate, filtered and concentrated under vacuum to afford crude. The crude compound was washed with petroleum ether to afford tert-butyl N-[1-(5-bromopyrimidin-2-yl)-4-piperidyl]carbamate (2 g, 5.09 mmol, 98.54% yield) as brown solid. LCMS (ESI+): 357.1 $[M+H]^+$ Step 2: To a stirred solution of 3-[3-[[ethyl(methyl)sulfamoyl]amino]-2,6-difluoro-benzoyl]-5-(4,4,5,5-tetramethyl-1,3,2-dioxaborolan-2-yl)-1H-pyrrolo[2,3-b]pyridine (300 mg, 576.53 tert-butyl N-[1-(5-bromopyrimidin-2-yl)-4-piperidyl]carbamate (226.56 mg, 634.18 μmol) in 1,4-dioxane (4 mL), water (1 mL) was added $K_3PO_4$ (367.13 mg, 1.73 mmol). The reaction mixture was degassed for 20 minutes and Xphos Pd G2 (136.08 mg, 172.96 μmol) was added. The reaction mixture was subjected to microwave irradiation at 120° C. for 1 h. After completion, the reaction mixture was diluted with water (20 mL) and extracted with ethyl acetate (2×30 mL). The combined organic layers were dried over sodium sulphate, filtered and concentrated under vacuum to afford crude. The crude compound was purified by silica gel column chromatography compound eluted with 70-100% ethyl acetate in petroleum ether to afford tert-butyl N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]carbamate (220 mg, 232.88 μmol, 40.39% yield) as a brown solid. LCMS (ESI+): 671.2 $[M+H]^+$.

Step 3: To a stirred solution of tert-butyl N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl] carb amate (220 mg, 328.00 μmol) in dichloromethane (5 mL) at 0° C. was added HCl solution (4M in 1,4-dioxane, 11.96 mg, 328.00 μmol, 14.95 The reaction mixture was stirred at room temperature for 2 h. The reaction mixture was concentrated under vacuum to get crude 5-[2-(4-amino-1-piperidyl)pyrimidin-5-yl]-3-[3-[[ethyl(methyl)sulfamoyl]amino]-2,6-difluoro-benzoyl]-1H-pyrrolo[2,3-b]pyridine (220 mg, 239.18 μmol, 72.92% yield) as brown solid. LCMS (ESI+): 571.1 $[M+H]^+$ Step 4: Target compound was prepared via COMU mediated acid-amine coupling reaction (procedure B). Amide coupling was carried out using 5-[2-(4-amino-1-piperidyl)pyrimidin-5-yl]-3-[3-[[ethyl(methyl)sulfamoyl]amino]-2,6-difluoro-benzoyl]-1H-pyrrolo[2,3-b]pyridine (220 mg, 385.55 μmol), 1-[4-[(2,6-dioxo-3-piperidyl)amino]-2-fluoro-phenyl]piperidine-4-carboxylic acid (134.69 mg, 385.55 μmol), DIPEA (149.49 mg, 1.16 mmol, 201.47 μL) and COMU ((181.63 mg, 424.11 μmol) to yield 1-[4-[(2,6-dioxo-3-piperidyl)amino]-2-fluoro-phenyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]-N-methyl-piperidine-4-carboxamide (39.81 mg, 41.93 μmol, 10.21% yield) as off white solid. LCMS (ESI+): 902.4 $[M+H]^+$. $^1H$ NMR (400 MHz, DMSO-$d_6$): δ 13.05 (s, 1H), 10.78 (s, 1H), 8.76 (s, 2H), 8.66 (d, J=2.40 Hz, 1H), 8.54 (s, 1H), 8.11 (s, 1H), 7.78 (d, J=7.60 Hz, 1H), 7.53-7.59 (m, 1H), 7.19-7.24 (m, 1H), 6.84 (t, J=9.20 Hz, 1H), 6.51 (dd, J=2.40, 14.80 Hz, 1H), 6.42 (dd, J=2.00, 8.40 Hz, 1H), 5.80 (d, J=8.00 Hz, 1H), 4.60 (d, J=13.60 Hz, 2H), 4.22-4.32 (m, 1H), 3.85-3.96 (m, 1H), 3.06-3.33 (m, 6H), 2.55-2.80 (m, 5H), 2.74 (s, 3H), 2.07-2.20 (m, 2H), 1.73-1.91 (m, 6H), 1.24-1.39 (m, 2H), 1.02 (t, J=7.20 Hz, 3H).

Example 137

4-[4-[(2,6-dioxo-3-piperidyl)amino]phenyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]piperidine-1-carboxamide

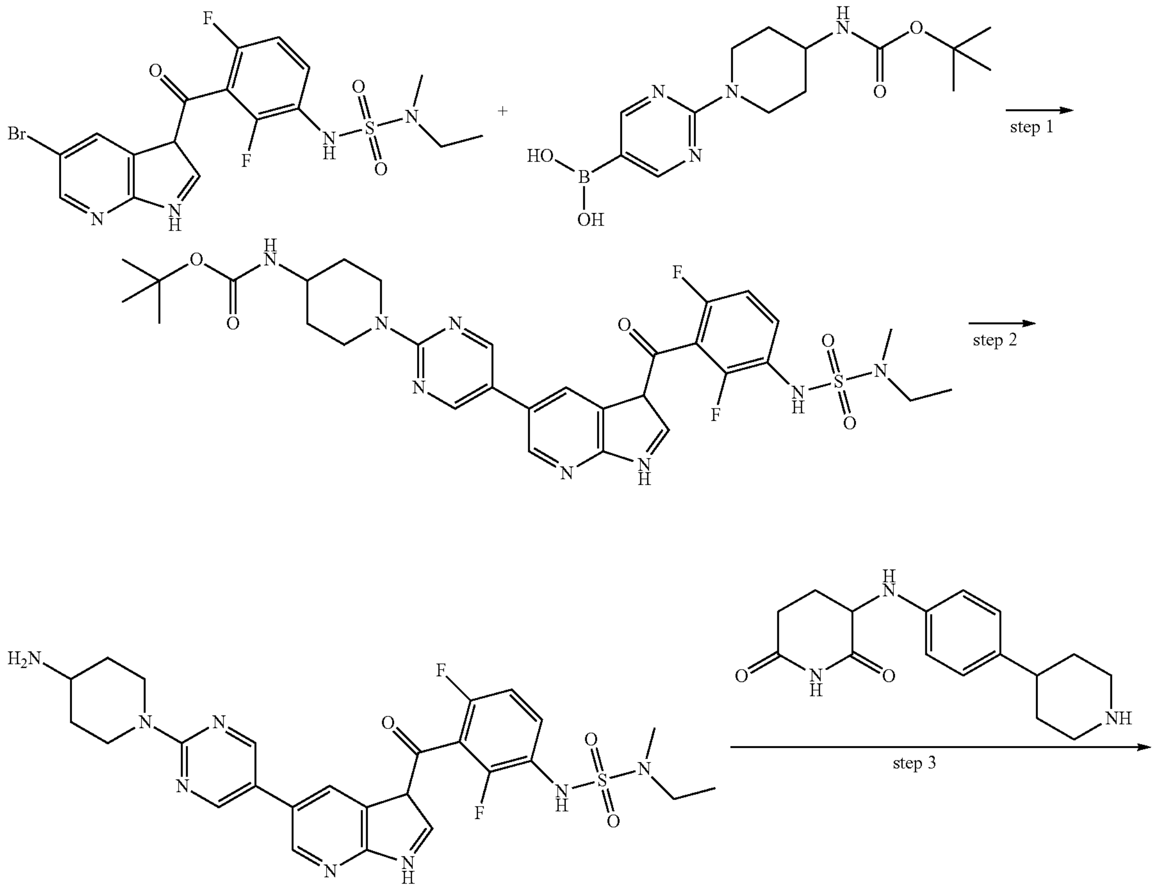

-continued

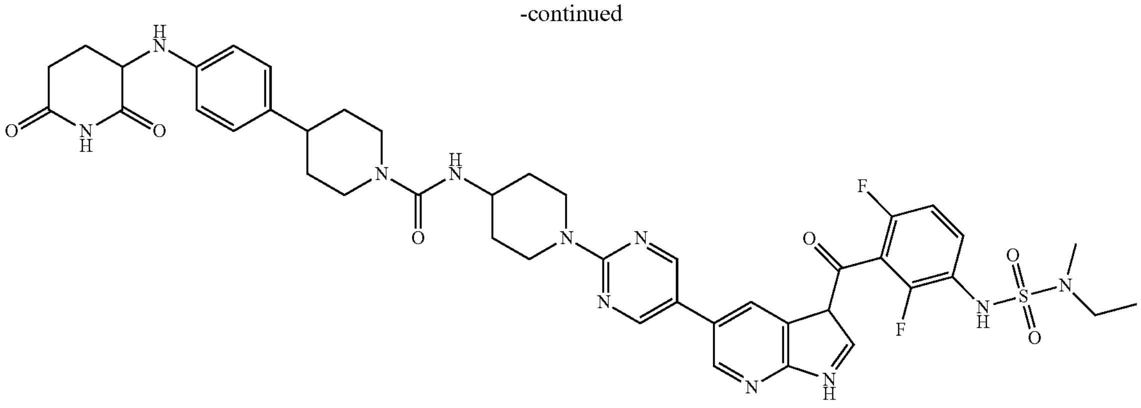

Step 1: A solution of 5-bromo-3-[3-[[ethyl(methyl)sulfamoyl]amino]-2,6-difluoro-benzoyl]-1H-pyrrolo[2,3-b]pyridine (600 mg, 1.27 mmol) in 1,4-dioxane (8.79 mL) and water (2.20 mL) mixture was taken in a microwave vial and added [2-[4-(tert-butoxycarbonylamino)-1-piperidyl]pyrimidin-5-yl]boronic acid (530.94 mg, 1.65 mmol), Potassium phosphate tribasic anhydrous (840.02 mg, 3.96 mmol) at room temperature under nitrogen. The reaction mixture was degassed with nitrogen for 10 min, then added XPhos Pd G2 (49.87 mg, 63.39 μmol) at same temperature. The reaction mixture was heated to 120° C. for 1 h in microwave. After completion, water was added to the reaction mixture and extracted with ethyl acetate (2×200 mL). The combined organic layers were dried over sodium sulphate, filtered and concentrated under reduced pressure. The crude compound was purified by silica gel column chromatography with 80% ethyl acetate in hexanes as a eluent to afford tert-butyl N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]carbamate (380 mg, 538.22 μmol, 42.46% yield) as a yellow solid. LCMS (ES+): 671.8 $[M+H]^+$ Step 2: Brought tert-butyl N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]carbamate (380 mg, 566.55 μmol) up in 1,4-dioxane (25 mL) and added Hydrogen chloride solution 4.0M in 1,4-dioxane (20.66 mg, 566.55 μmol, 25.82 uL). Stirred at room temperature for 4 hours and concentrated to afford 5-[2-(4-amino-1-piperidyl)pyrimidin-5-yl]-3-[3-[[ethyl(methyl)sulfamoyl]amino]-2,6-difluoro-benzoyl]-1H-pyrrolo[2,3-b]pyridine (335 mg, 524.24 μmol, 92.53% yield, hydrochloric acid salt) as an off-white solid, which was carried forward without further purification. LCMS (ES+): 571.5 $[M+H]^+$ Step 3: At 0° C. brought 3-[4-(4-piperidyl)anilino]piperidine-2,6-dione (43.05 mg, 132.94 HCl salt) up in THF (1 mL)/DCM (1 mL) and added DIPEA (93.71 mg, 725.11 μmol, 126.30 uL) followed by triphosgene (14.34 mg, 48.34 μmol). Let the reaction warm room temperature and stirred for 2 hours. 5-[2-(4-amino-1-piperidyl)pyrimidin-5-yl]-3-[3-[[ethyl(methyl)sulfamoyl]amino]-2,6-difluoro-benzoyl]-1H-pyrrolo[2,3-b]pyridine (82.74 mg, 120.85 trifluoroacetic acid salt) was partially dissolved in THF (1 mL)/DCM (1 mL) and 2 eq DIPEA was then added. The material did not fully dissolve. Added 2 mL more THF and sonicated. Added solution to rxn. Rinsed and sonicated second vessel with 2 mL THF, all solid seemed in solution. The reaction mixture was heated to 70° C. overnight. After cooling, the reaction was partitioned between DCM and Water. The organic layer was dried over sodium sulphate and concentrated. The crude material was purified via RP isco (0-100% ACN/Water w TFA) to give 4-[4-[(2,6-dioxo-3-piperidyl)amino]phenyl]-N-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]piperidine-1-carboxamide (24 mg, 23.09 μmol, 19.10% yield, trifluoroacetic acid salt) as an off-white solid after lyophilization. LCMS (ES+): 443.2 $[M/2+H]^+$, 884.9 $[M+H]^+$. $^1H$ NMR (400 MHz, DMSO-$d_6$): δ 12.99 (d, J=3.3 Hz, 1H), 10.78 (s, 1H), 9.70 (s, 1H), 8.77 (s, 2H), 8.72-8.64 (m, 1H), 8.55 (s, 1H), 8.13 (d, J=3.0 Hz, 1H), 7.59 (td, J=9.0, 5.9 Hz, 1H), 7.28 (t, J=8.8 Hz, 1H), 6.96 (d, J=8.2 Hz, 2H), 6.63 (d, J=8.2 Hz, 2H), 6.30-6.16 (m, 1H), 4.73-4.61 (m, 2H), 4.33-4.22 (m, 2H), 4.14-4.00 (m, 5H), 3.19-2.98 (m, 4H), 2.84-2.63 (m, 5H), 2.63-2.55 (m, 2H), 2.10 (dq, J=13.5, 5.0 Hz, 1H), 1.94-1.79 (m, 3H), 1.67 (dd, J=13.2, 3.5 Hz, 2H), 1.50-1.33 (m, 4H), 1.03 (t, J=7.1 Hz, 3H).

Example 138

N-[1-[4-[(2,6-dioxo-3-piperidyl)amino]-2-fluoro-phenyl]-4-piperidyl]-4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazine-1-carboxamide

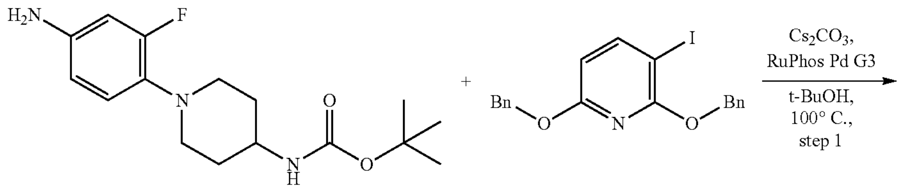

-continued

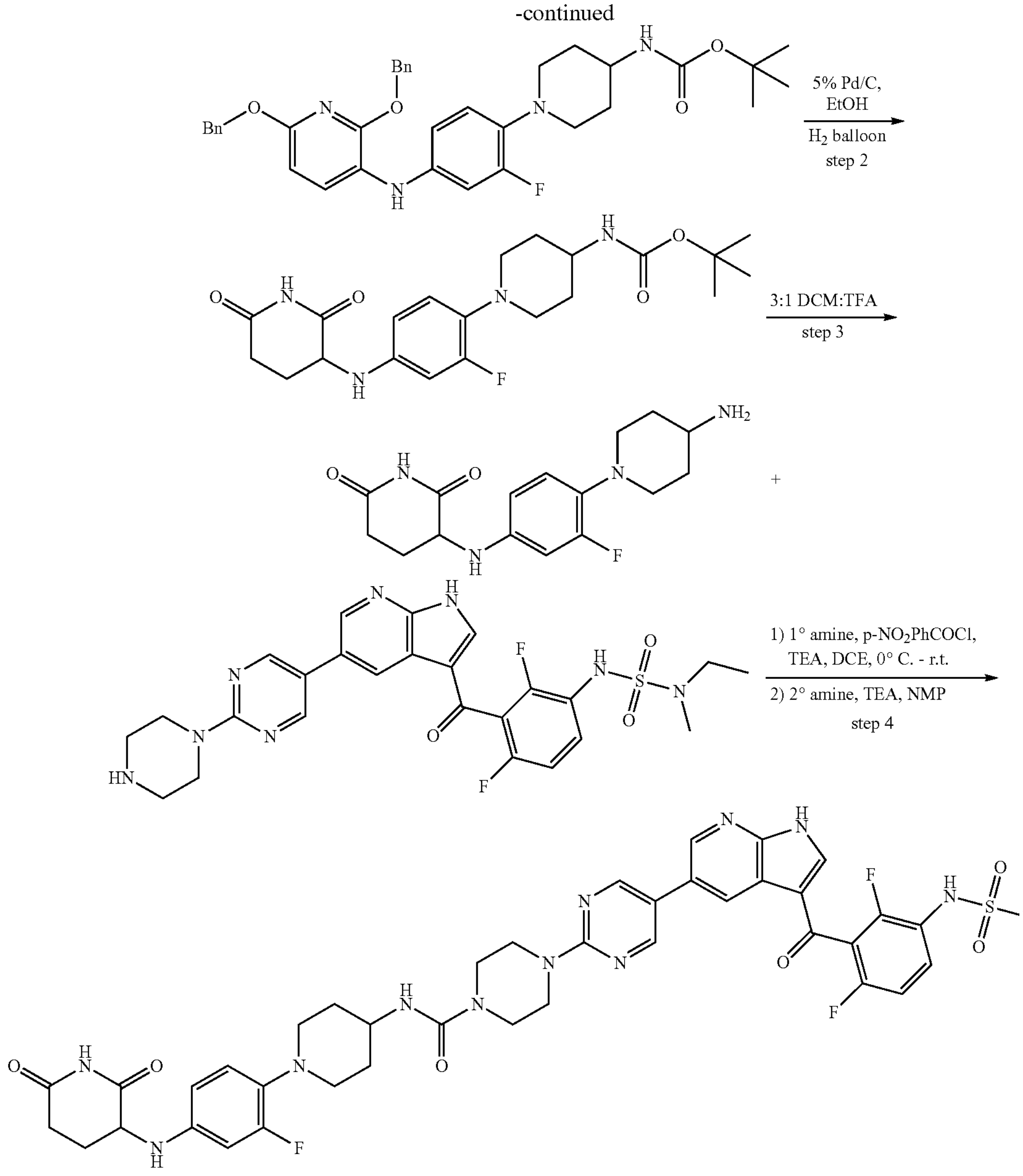

Step 1: To a stirred solution of tert-butyl N-[1-(4-amino-2-fluoro-phenyl)-4-piperidyl]carbamate (150 mg, 484.84 μmol) and 2,6-dibenzyloxy-3-iodo-pyridine (222.53 mg, 533.33 μmol) in t-BuOH (4.85 mL) was added Cesium carbonate (473.92 mg, 1.45 mmol) and solution was degassed well by purging with argon. RuPhos Pd G3 (44.80 mg, 48.48 μmol) was then added and the reaction was degassed again. The reaction mixture was heated at 100° C. for 18 h. The reaction mixture was then diluted with ethyl acetate, filtered over a small pad of celite and washed well with ethyl acetate. The combined organics were washed with water and brine, filtered, dried over anhydrous sodium sulphate and concentrated under reduced pressure to get crude material as an oil which was purified by column chromatography using silica eluted at 40% EA hexane to get pure tert-butyl N-[1-[4-[(2,6-dibenzyloxy-3-pyridyl)amino]-2-fluoro-phenyl]-4-piperidyl]carbamate (100 mg, 158.68 μmol, 32.73% yield) as pale yellow solid. LCMS (ESI+): 600 $[M+H]^+$ Step 2: Brought tert-butyl N-[1-[4-[(2,6-dibenzyloxy-3-pyridyl)amino]-2-fluoro-phenyl]-4-piperidyl]carbamate (75 mg, 125.27 μmol) up in EtOH (5 mL) and added Palladium, 5% on activated carbon paste, 5R437 (4.00 mg, 37.58 μmol) before purging flask and solvent with an $H_2$ balloon. Stirred reaction at room temperature under a hydrogen atmosphere (balloon pressure) for 16 hours. Filtered reaction over celite, washing with EtOH (3×) and EtOAc (3×) before concentrating to afford tert-butyl N-[1-[4-[(2,6-dioxo-3-piperidyl)amino]-2-fluoro-phenyl]-4-piperidyl]carbamate (50 mg, 112.97 μmol, 90.18% yield) as a dry oil, which was carried forward without further purification. LCMS (ESI+): 421 $[M+H]^+$ Step 3: Brought tert-butyl N-[1-[4-[(2,6-dioxo-3-piperidyl)amino]-2-fluoro-phenyl]-4-piperidyl]carbamate (50 mg, 118.91 μmol) up in DCM (2 mL) and added TFA (740.00 mg, 6.49 mmol, 500 uL). Stirred for 3 hours and concentrated from toluene (3×) to afford 3-[4-(4-amino-1- piperidyl)-3-fluoro-anilino]piperidine-2,6-dione (45 mg, 98.42 μmol, 82.76% yield, trifluoroacetic acid salt) as an oil which was used in the next step without further. LCMS (ESI+): 321 [M+H]$^+$ Step 4: Brought 3-[4-(4-amino-1-piperidyl)-3-fluoro-anilino]piperidine-2,6-dione (21.38 mg, 49.21 μmol, trifluoroacetic acid salt) up in DCE (431.77 uL) and cooled to 0° C. Added TEA (22.63 mg, 223.68 μmol, 31.18 uL) followed by (4-nitrophenyl) carbonochloridate (9.92 mg, 49.21 μmol) and let gradually warm to room temperature. After 2 hours, the reaction was cooled to 0° C. and added a solution of 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (30 mg, 44.74 μmol, trifluoroacetic acid salt) and TEA (22.63 mg, 223.68 μmol, 31.18 uL) in NMP (431.77 uL). Let the reaction stir while gradually warming to room temperature overnight. The reaction was concentrated and loaded directly onto a reverse phase isco column for purification (0-100% ACN/water w/ TFA) to give N-[1-[4-[(2,6-dioxo-3-piperidyl)amino]-2-fluoro-phenyl]-4-piperidyl]-4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazine-1-carboxamide (8 mg, 7.47 nmol, 16.71% yield, trifluoroacetic acid salt) as solid after lyophilization. LCMS (ESI+): 904 [M+H]$^+$. $^1$H NMR (400 MHz, DMSO-$d_6$): δ 12.93 (d, J=3.3 Hz, 1H), 10.75 (s, 1H), 9.62 (s, 1H), 8.72 (s, 2H), 8.60 (d, J=2.2 Hz, 1H), 8.49 (s, 1H), 8.07 (d, J=3.0 Hz, 1H), 7.51 (td, J=9.0, 5.9 Hz, 1H), 7.25-7.16 (m, 1H), 6.55 (d, J=14.8 Hz, 1H), 6.46 (d, J=8.5 Hz, 2H), 6.20-5.40 (m, 4H) 4.33-4.24 (m, 1H), 3.78-3.71 (m, 4H), 3.69-3.62 (m, 1H), 3.39 (dd, J=6.7, 3.9 Hz, 4H), 3.32 (s, 1H), 3.05 (q, J=7.1 Hz, 3H), 2.66 (s, 4H), 2.52 (dt, J=16.7, 3.9 Hz, 1H), 2.07-1.96 (m, 2H), 1.88 (s, 1H), 1.86-1.76 (m, 2H), 1.75 (s, 1H), 0.95 (t, J=7.1 Hz, 3H).

Example 139

N-[1-[4-[(2,6-dioxo-3-piperidyl)amino]phenyl]-4-piperidyl]-4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazine-1-carboxamide

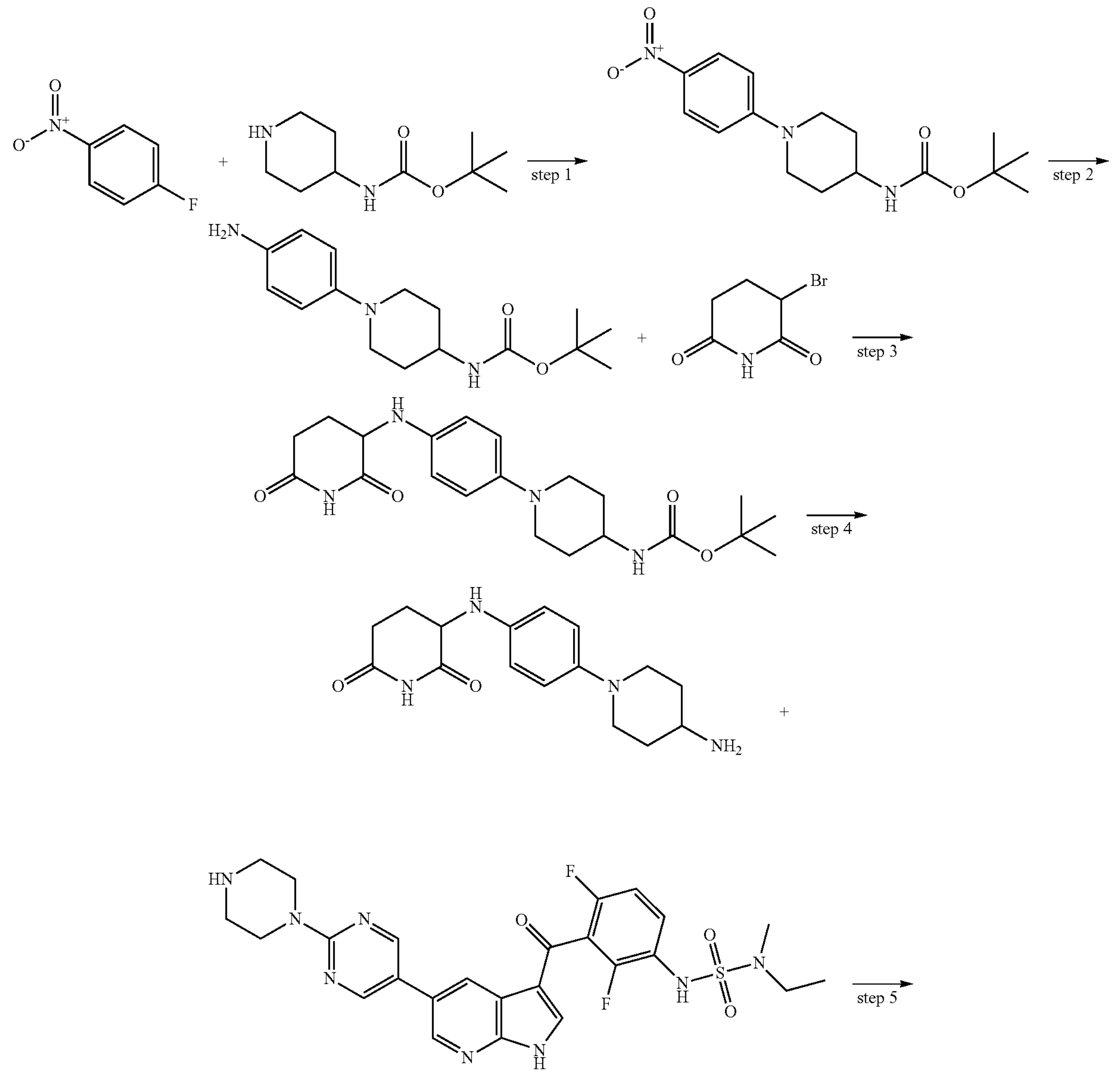

-continued

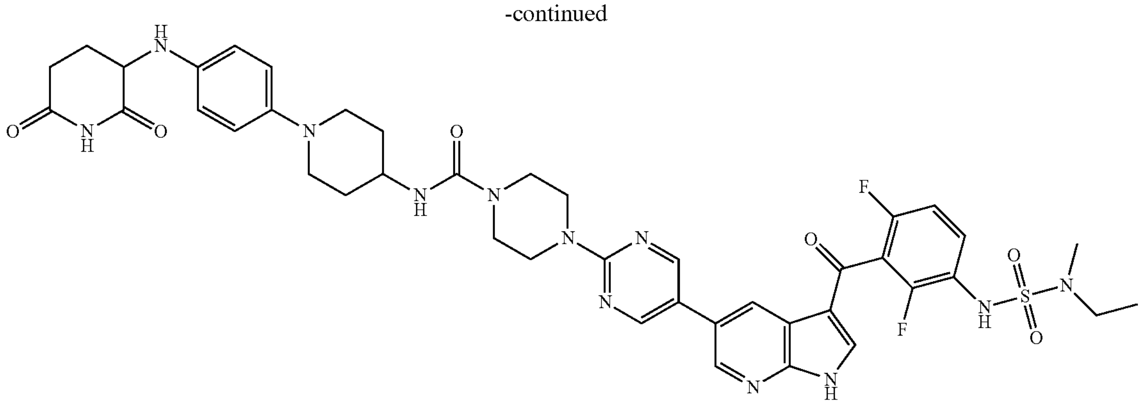

Step 1: Brought 1-fluoro-4-nitro-benzene (2 g, 14.17 mmol, 1.50 mL) and tert-butyl N-(4-piperidyl)carbamate (2.84 g, 14.17 mmol) up in acetonitrile (7.73 mL) and added diisopropylethylamine (3.66 g, 28.35 mmol, 4.94 mL) before heating to 110° C. overnight. Cooled to room temperature and concentrated residue before purifying by flash chromatography (0-60% EtOAc/hx) to give tert-butyl N-[1-(4-nitrophenyl)-4-piperidyl]carbamate (4.2 g, 13.07 mmol, 92.20% yield) as a yellow solid. LCMS (ES+): 322.3 $[M+H]^+$ Step 2: Brought tert-butyl N-[1-(4-nitrophenyl)-4-piperidyl]carbamate (4.2 g, 13.07 mmol) up in ethanol (103.08 mL)/water (25.77 mL) and added iron powder (3.65 g, 65.35 mmol, 464.27 uL) and ammonium chloride (2.10 g, 39.21 mmol, 1.37 mL) before heating to 80° C. After 12 hours, cooled to room temperature and diluted with EtOH before filtering through celite. Concentrated filtrate and partitioned between EtOAc and sat. bicarb solution. dried organic layer over sodium sulphate and concentrated before purifying residue by flash chromatography (0-10% MeOH/DCM) to give tert-butyl N-[1-(4-aminophenyl)-4-piperidyl]carbamate (1.9 g, 6.19 mmol, 47.40% yield) as a yellow solid. LCMS (ES+): 292.3 $[M+H]^+$ Step 3: Brought 3-bromopiperidine-2,6-dione (2.50 g, 13.04 mmol) and tert-butyl N-[1-(4-aminophenyl)-4-piperidyl]carbamate (1.9 g, 6.52 mmol) up in DMF (6.27 mL) and added sodium bicarbonate (547.77 mg, 6.52 mmol, 253.60 uL). Heated to 80° C. overnight before cooling to room temperature and partitioning between EtOAc and water. Washed organic layer w 5% LiCl in water 3× before drying over sodium sulphate and concentrating. Purified by flash chromotography (0-15% MeOH/DCM) to give tert-butyl N-[1-[4-[(2,6-dioxo-3-piperidyl)amino]phenyl]-4-piperidyl]carbamate (2.0 g, 4.72 mmol, 72.40% yield) an amorphous solid. LCMS (ES+): 403.4 $[M+H]^+$ Step 4: Brought tert-butyl N-[1-[4-[(2,6-dioxo-3-piperidyl)amino]phenyl]-4-piperidyl]carbamate (1 g, 2.48 mmol) up in DCM (6 mL) and added TFA (2.96 g, 25.96 mmol, 2 mL. Stirred for 8 hours and concentrated from toluene (3×) to give 3-[4-(4-amino-1-piperidyl)anilino]piperidine-2,6-dione (900 mg, 2.05 mmol, 82.64% yield, trifluoroacetic acid salt) as an off-white solid, which was carried forward without further purification. LCMS (ES+): 303.3 $[M+H]^+$ Step 5: Brought 3-[4-(4-amino-1-piperidyl)anilino]piperidine-2,6-dione (67.13 mg, 161.22 trifluoroacetic acid salt) up in DCM (592.83 uL) and cooled to 0° C. Added TEA (74.15 mg, 732.83 μmol, 102.14 uL) followed by (4-nitrophenyl) carbonochloridate (32.50 mg, 161.22 μmol) and let gradually warm to room temperature. After 2 hours, the reaction was cooled to 0° C. and added a solution of 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (115 mg, 146.57 trifluoroacetic acid salt) and TEA (74.15 mg, 732.83 μmol, 102.14 uL) in NMP (592.83 uL). Let the reaction stir while gradually warming to room temperature overnight. Diluted reaction with DCM and partitioned with water. Kept organic layer and dried over sodium sulfate and concentrated before purifying by isco 0-20% MeOH/DCM. Concentrated pure fracs and lyophilized free base from 1:1 ACN:water to give N-[1-[4-[(2,6-dioxo-3-piperidyl)amino]phenyl]-4-piperidyl]-4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazine-1-carb oxamide (20 mg, 21.13 μmol, 14.42% yield) as an off-white solid. LCMS (ES+): 443.7 $[M/2+H]^+$, 885.8 $[M+H]^+$. $^1H$ NMR (400 MHz, DMSO-$d_6$): δ 12.99 (s, 1H), 10.75 (s, 1H), 9.70 (s, 1H), 8.79 (s, 2H), 8.67 (d, J=2.2 Hz, 1H), 8.56 (s, 1H), 8.14 (s, 1H), 7.59 (td, J=9.0, 5.9 Hz, 1H), 7.28 (td, J=8.8, 1.6 Hz, 1H), 6.77 (dd, J=8.5, 5.8 Hz, 2H), 6.66-6.57 (m, 2H), 6.39 (d, J=7.5 Hz, 1H), 5.36 (d, J=7.2 Hz, 1H), 4.20 (ddd, J=11.6, 7.2, 4.8 Hz, 1H), 3.85-3.75 (m, 3H), 3.66-3.52 (m, 1H), 3.49-3.37 (m, 5H), 3.12 (q, J=7.1 Hz, 2H), 2.74 (s, 4H), 2.64-2.55 (m, 3H), 2.20-2.06 (m, 1H), 1.92-1.75 (m, 3H), 1.66-1.51 (m, 2H), 1.48-1.34 (m, 1H), 1.03 (t, J=7.1 Hz, 3H).

Example 140

N-[1-[4-[(2,6-dioxo-3-piperidyl)amino]-2-fluoro-phenyl]-4-piperidyl]-4-[5-[3-[3-[[ethyl(methyl)sulfamoyl]amino]-2,6-difluoro-benzoyl]-1H-pyrrolo[2,3-b]pyridin-5-yl]-2-pyridyl]piperazine-1-carboxamide

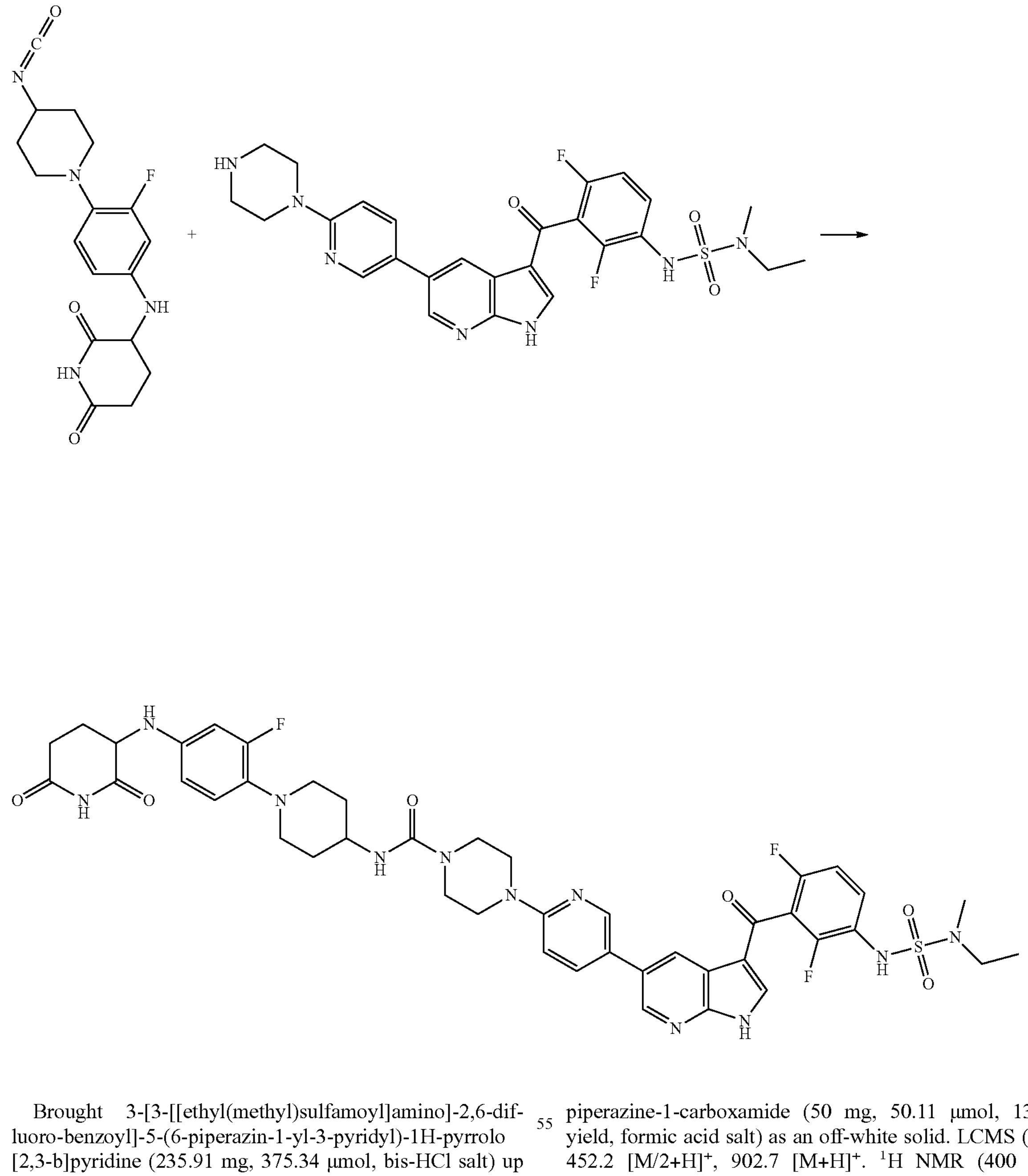

Brought 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (235.91 mg, 375.34 μmol, bis-HCl salt) up in DMF (2 mL) and added DIPEA (145.53 mg, 1.13 mmol, 196.13 uL) at 0° C. Added a solution of 3-[3-fluoro-4-(4-isocyanato-1-piperidyl)anilino]piperidine-2,6-dione (130 mg, 375.34 μmol) in DCM (1 mL) and let the reaction warm to r.t. After stirring overnight, concentrated off DCM and loaded directly onto reverse phase isco (0-100% ACN/water w formic acid). After lyophilization, isolated N-[1-[4-[(2,6-dioxo-3-piperidyl)amino]-2-fluoro-phenyl]-4-piperidyl]-4-[5-[3-[3-[[ethyl(methyl)sulfamoyl]amino]-2,6-difluoro-benzoyl]-1H-pyrrolo[2,3-b]pyridin-5-yl]-2-pyridyl]piperazine-1-carboxamide (50 mg, 50.11 μmol, 13.35% yield, formic acid salt) as an off-white solid. LCMS (ES+): 452.2 $[M/2+H]^+$, 902.7 $[M+H]^+$. $^1H$ NMR (400 MHz, DMSO-d6): δ 12.93 (s, 1H), 10.75 (s, 1H), 9.68 (s, 1H), 8.65 (d, J=2.2 Hz, 1H), 8.53-8.46 (m, 2H), 8.10 (s, 1H), 7.94 (dd, J=8.9, 2.6 Hz, 1H), 7.56 (td, J=9.0, 5.9 Hz, 1H), 7.26 (td, J=9.3, 8.9, 1.5 Hz, 1H), 6.99 (d, J=8.9 Hz, 1H), 6.84 (t, J=9.4 Hz, 1H), 6.53-6.44 (m, 1H), 6.44-6.34 (m, 2H), 5.77 (d, J=7.6 Hz, 1H), 4.24 (ddd, J=12.0, 7.6, 4.9 Hz, 1H), 3.55 (dd, J=7.0, 3.5 Hz, 5H), 3.44 (t, J=5.2 Hz, 4H), 3.09 (q, J=6.9 Hz, 4H), 2.71 (s, 3H), 2.78-2.51 (m, 4H), 2.12-2.05 (m, 1H), 2.06 (s, 1H), 1.83 (dd, J=16.5, 8.2 Hz, 3H), 1.62 (d, J=11.0 Hz, 1H), 1.60-1.53 (m, 1H), 1.00 (t, J=7.1 Hz, 3H).

Example 141
N-[1-[4-[(2,6-dioxo-3-piperidyl)amino]-2-fluoro-phenyl]-4-piperidyl]-4-[5-[3-[3-[[ethyl(methyl)sulfamoyl]amino]-2-fluoro-benzoyl]-1H-pyrrolo[2,3-b]pyridin-5-yl]pyrimidin-2-yl]piperazine-1-carboxamide
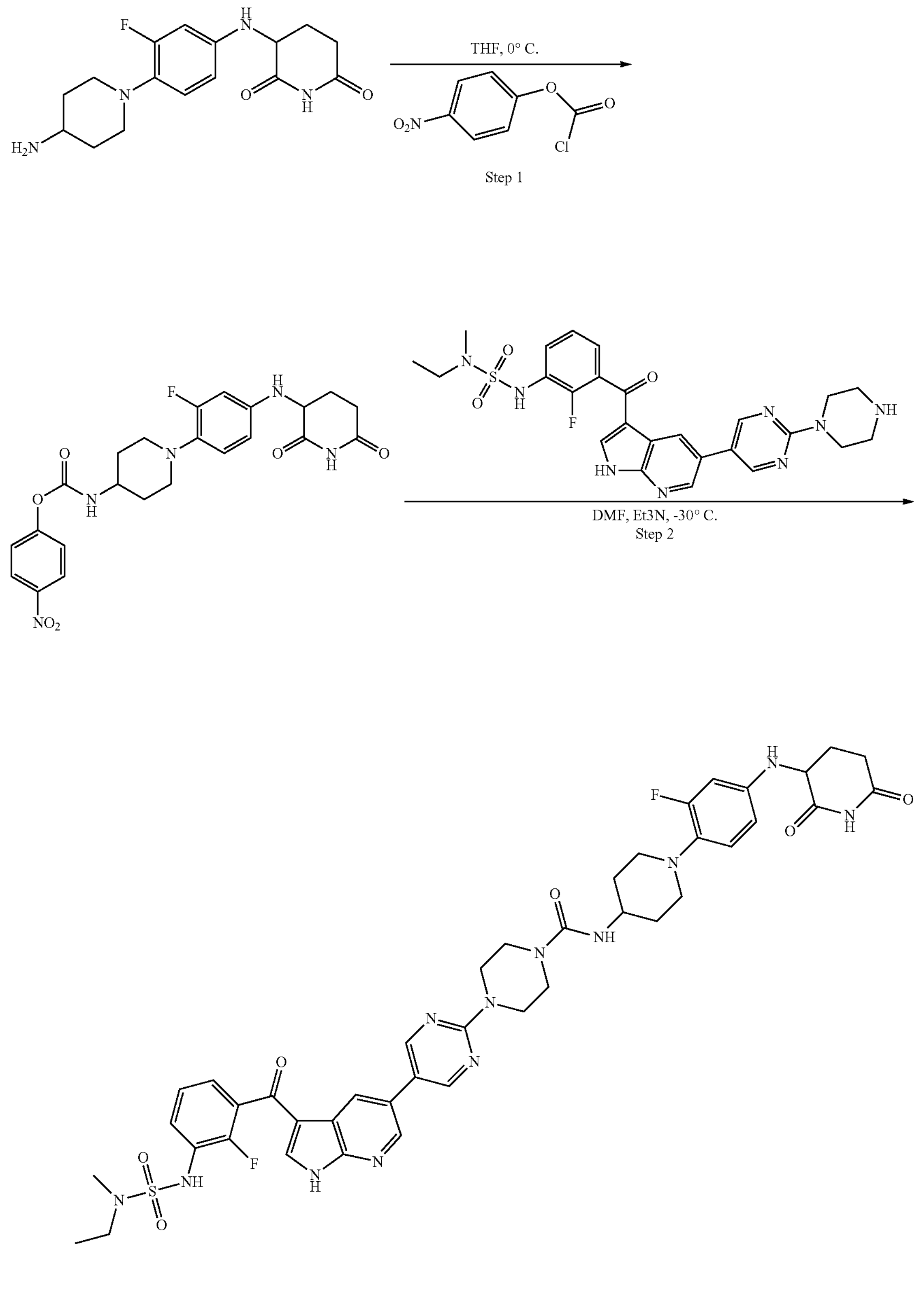

Step 1: To a solution of 3-[4-(4-amino-1-piperidyl)-3-fluoro-anilino]piperidine-2,6-dione (0.7 g, 1.96 mmol, hydrochloric acid salt) in THF (7 mL) was added triethylamine (992.55 mg, 9.81 mmol, 1.37 mL) and (4-nitrophenyl)carbonochloridate (474.50 mg, 2.35 mmol) at 0° C. under nitrogen. The resulting solution was warmed to room temperature and stirred for 3 hours. After completion, resulting solution was concentrated under reduced pressure to get crude (4-nitrophenyl) N-[1-[4-[(2,6-dioxo-3-piperidyl)amino]-2-fluoro-phenyl]-4-piperidyl]carbamate (1.27 g, 1.95 mmol, 99.36% yield) as a brown solid. LCMS (ESI+): 486.2 $[M+H]^+$.

Step 2: To a solution of (4-nitrophenyl) N-[1-[4-[(2,6-dioxo-3-piperidyl)amino]-2-fluoro-phenyl]-4-piperidyl]carbamate (250.00 mg, 514.97 μmol) in DMF (3 mL) was added solution of 3-[3-[[ethyl(methyl)sulfamoyl]amino]-2-fluoro-benzoyl]-5-(2-piperazin-1-ylpyrimidin-5-yl)-1H-pyrrolo[2,3-b]pyridine (124.81 mg, 217.04 μmol, hydrochloric acid salt) in DMF (1 mL) and triethylamine (260.55 mg, 2.57 mmol, 358.88 μL) at −30° C. under nitrogen. The resulting solution was gradually warmed to room temperature for 6 hours. After completion, the reaction mixture was concentrated under reduced pressure. The crude compound was purified by reverse phase column chromatography [Column: 100 g Redisep Rf C18, Mobile-phase A: 0.1% ammonium acetate, Mobile-phase B: ACN] to get the N-[1-[4-[(2,6-dioxo-3-piperidyl)amino]-2-fluoro-phenyl]-4-piperidyl]-4-[5-[3-[3-[[ethyl(methyl)sulfamoyl]amino]-2-fluoro-benzoyl]-1H-pyrrolo[2,3-b]pyridin-5-yl]pyrimidin-2-yl]piperazine-1-carboxamide (94 mg, 105.26 μmol, 20.44% yield) as an off-white solid. LCMS (ESI): 885.3 $[M+H]^+$. $^1H$ NMR (400 MHz, DMSO-$d_6$): δ 10.79 (s, 1H), 8.78 (s, 2H), 8.66 (s, 1H), 8.58 (s, 1H), 7.98 (s, 1H), 7.59-7.59 (m, 1H), 7.30-7.28 (m, 2H), 6.86-6.86 (m, 1H), 6.51 (d, J=12.40 Hz, 1H), 6.42 (d, J=6.80 Hz, 2H), 5.82-5.80 (m, 1H), 4.30-4.25 (m, 1H), 3.81-3.79 (m, 4H), 3.60-3.50 (m, 1H), 3.46-3.43 (m, 4H), 3.15-3.09 (m, 4H), 2.74-2.71 (m, 2H), 2.72 (s, 3H), 2.62-2.53 (m, 2H), 2.15-2.05 (m, 1H), 1.84-1.81 (m, 3H), 1.60-1.62 (m, 2H), 1.02 (t, J=7.20 Hz, 3H).

Example 142

5-[2-[4-[2-[4-[4-[(2,6-dioxo-3-piperidyl)amino]phenyl]-1-hydroxy-cyclohexyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

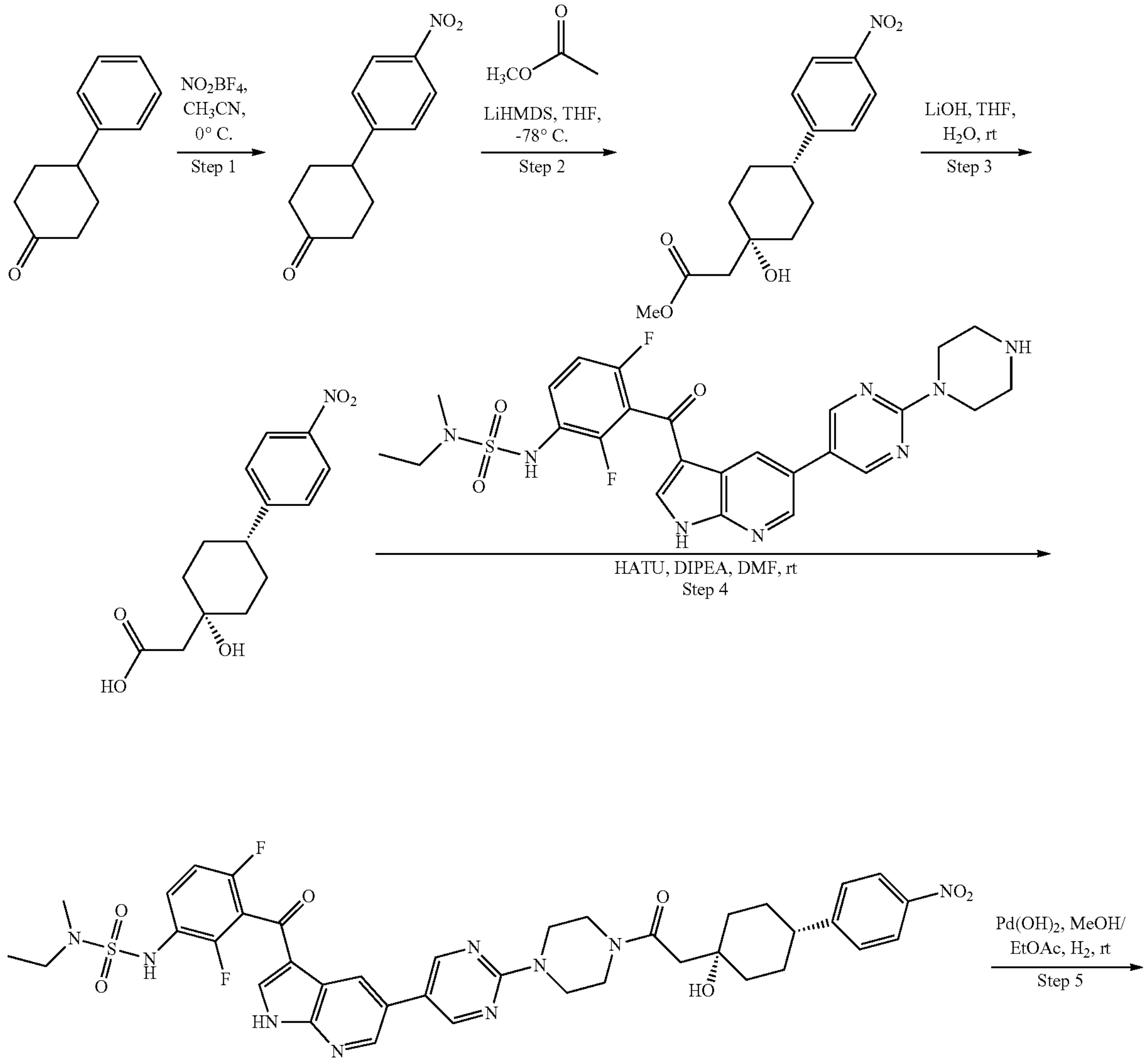

-continued

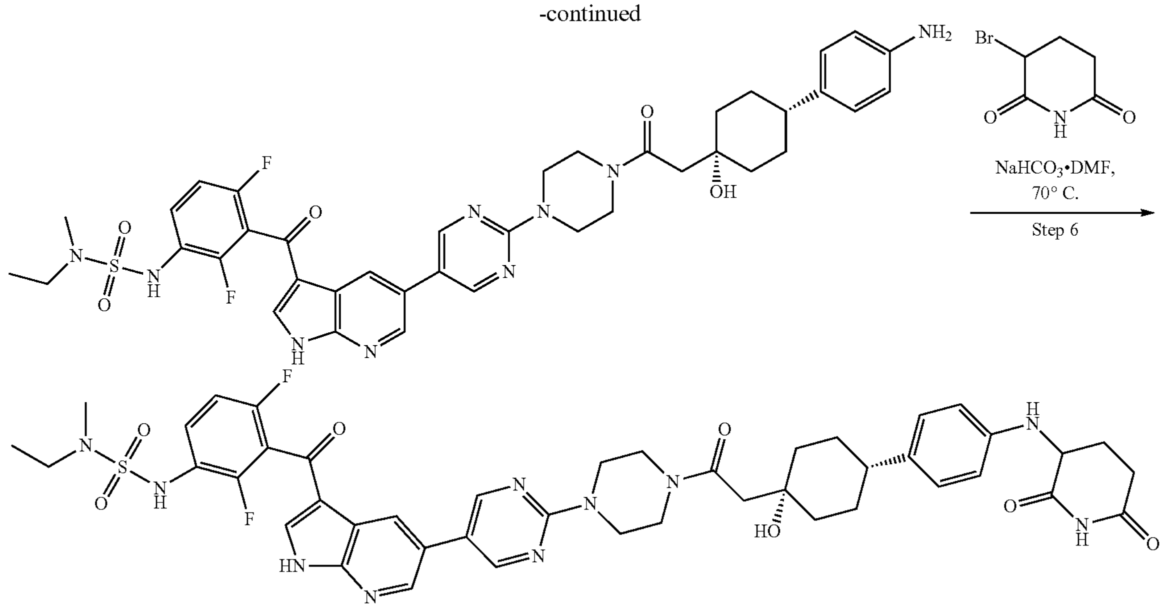

Step 1: To a stirred solution of 4-phenylcyclohexanone (10 g, 2.87 mmol) in acetonitrile (100 mL) was added portion wise nitronium tetrafluoroborate (10.67 g, 80.35 mmol) at −5° C. The reaction mixture was stirred at 0° C. for 3 h. Reaction mixture was added to cold water (100 mL) at 0° C. and extracted with ethyl acetate (3×150 mL). The combined organic layers were dried over sodium sulphate, filtered and concentrated. The crude product was purified by silica gel column chromatography with 30% ethyl acetate in petroleum ether as an eluent to afford 4-(4-nitrophenyl) cyclohexanone (3.8 g, 17.33 mmol, 30.20% yield) as green solid. $^1$H NMR (400 MHz, DMSO-d$_6$): δ 8.22 (d, J=8.80 Hz, 2H), 7.44 (d, J=8.80 Hz, 2H), 3.14-3.21 (m, 1H), 2.56-2.59 (m, 4H), 2.25-2.30 (m, 2H), 1.94-2.05 (m, 2H).

Step 2: To a stirred solution of methyl acetate (1.22 g, 16.42 mmol, 1.30 mL) in tetrahydrofuran (30 mL) was added 1.0 M LiHMDS in tetrahydrofuran (3.43 g, 20.53 mmol, 20.52 mL) at −78° C. dropwise under nitrogen atmosphere. The reaction mixture was stirred at −78° C. for 15 minutes followed by the addition of 4-(4-nitrophenyl) cyclohexanone (1.8 g, 8.21 mmol) in tetrahydrofuran (10 mL). Reaction mixture was stirred at −78° C. for 3 h. Reaction mixture was quenched with saturated aqueous $NH_4Cl$ solution (50 mL) at 0° C. and extracted with ethyl acetate (3×20 mL). Combined organic layers were dried over sodium sulphate, filtered and concentrated. The crude product was purified by silica gel column chromatography with 40% ethyl acetate in petroleum ether as an eluent to afford methyl 2-[1-hydroxy-4-(4-nitrophenyl)cyclohexyl] acetate (1.2 g, 4.09 mmol, 49.83% yield) as a green liquid. $^1$H NMR (400 MHz, DMSO-d$_6$): δ 8.15 (d, J=8.80 Hz, 2H), 7.60 (d, J=8.80 Hz, 2H), 4.67 (d, J=6.00 Hz, 1H), 3.59 (s, 3H), 2.72-2.63 (m, 3H), 1.97 (m, 2H), 1.76 (m, 2H), 1.59-1.66 (m, 2H), 1.49-1.53 (m, 2H).

Step 3: To a stirred solution of methyl 2-[1-hydroxy-4-(4-nitrophenyl)cyclohexyl]acetate (498.63 mg, 1.70 mmol) in tetrahydrofuran (12 mL)/water (12 mL)/methanol (12 mL) was added LiOH (285.35 mg, 6.80 mmol, 188.98 μL) at room temperature. The reaction mixture was stirred at room temperature for 16 h. Reaction mixture was acidified to pH ~1 using aqueous 1.5 N HCl solution, resulting solids were filtered, washed with water (20 mL) and dried to afford 2-[1-hydroxy-4-(4-nitrophenyl)cyclohexyl]acetic acid (0.37 g, 1.14 mmol, 67.02% yield) as a green solid. LCMS (ESI): 278.1 [M−H]$^+$.

Step 4: To a mixture of 3-[3-[[ethyl(methyl)sulfamoyl] amino]-2,6-difluoro-benzoyl]-5-(2-piperazin-1-ylpyrimidin-5-yl)-1H-pyrrolo[2,3-b]pyridine (0.2 g, 359.33 μmol) and 2-[1-hydroxy-4-(4-nitrophenyl)cyclohexyl]acetic acid (100.36 mg, 359.33 μmol) in N,N-dimethylformamide (10 mL) were added and N,N-diisopropylethylamine (185.76 mg, 1.44 mmol, 250.36 μL) followed by HATU (136.63 mg, 359.33 μmol) at room temperature under nitrogen atmosphere. The reaction mixture was stirred at room temperature for 16 h. Reaction mixture was added to water (20 mL) and extracted with ethyl acetate (3×30 mL). Combined organic layers were washed with brine (3×20 mL), dried over sodium sulphate, filtered and concentrated under reduced pressure. The crude product was purified by silica gel column chromatography with 80% ethyl acetate in petroleum ether as an eluent to afford 3-[3-[[ethyl(methyl) sulfamoyl]amino]-2,6-difluoro-benzoyl]-5-[2-[4-[2-[1-hydroxy-4-(4-nitrophenyl)cyclohexyl]acetyl]piperazin-1-yl] pyrimidin-5-yl]-1H-pyrrolo[2,3-b]pyridine (0.22 g, 233.03 μmol, 64.85% yield) as a light yellow solid. LCMS (ESI+): 818.8 [M+H]$^+$.

Step 5: A mixture of 3-[3-[[ethyl(methyl)sulfamoyl] amino]-2,6-difluoro-benzoyl]-5-[2-[4-[2-[1-hydroxy-4-(4-nitrophenyl)cyclohexyl]acetyl]piperazin-1-yl]pyrimidin-5-yl]-1H-pyrrolo[2,3-b]pyridine (0.22 g, 268.99 μmol) and 20% dihydroxypalladium (130 g, 925.70 mmol) in methanol (10 mL)/ethyl acetate (10 mL) was stirred under the pressure of $H_2$ gas (1 atm) at room temperature for 16 h. Reaction mixture was filtered through celite bed and washed with methanol. The resulting filtrate was concentrated under reduced pressure and dried to afford 5-[2-[4-[2-[4-[4-(4-aminophenyl)-1-hydroxy-cyclohexyl]acetyl]piperazin-1-yl] pyrimidin-5-yl]-3-[[ethyl(methyl)sulfamoyl]amino]-2,6-difluoro-benzoyl]-1H-pyrrolo[2,3-b]pyridine (0.135 g, 105.46 μmol, 39.21% yield) as a light yellow solid. LCMS (ESI+): 788.2 [M+H]$^+$.

Step 6: To a stirred solution of 5-[2-[4-[2-[4-(4-amino-phenyl)-1-hydroxy-cyclohexyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (130 mg, 165.00 μmol) in N, N-dimethylformamide (3 mL) was added $NaHCO_3$ (41.58 mg, 495.00 μmol, 19.25 μL) followed by 3-bromopiperidine-2,6-dione (79.20 mg, 412.50 μmol) at room temperature under nitrogen atmosphere. The reaction mixture was heated at 70° C. for 16 h. Reaction mixture was diluted with water (10 mL) and extracted with 10% isopropanol in dichloromethane (3×30 mL). Combined organic layers were washed with cold water (3×20 mL), dried over sodium sulphate, filtered and concentrated under reduced pressure. The crude product was purified by preparative-HPLC [Mobile-phase A: 0.1% formic acid in water, Mobile-phase B: ACN, Wavelength: 215 nm] to afford 5-[2-[4-[2-[4-[4-[(2,6-dioxo-3-piperidyl)amino]phenyl]-1-hydroxy-cyclohexyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (15.57 mg, 16.08 μmol, 9.75% yield) as a light green solid. LCMS (ESI+): 899.8 $[M+H]^+$. $^1H$ NMR (400 MHz, DMSO-$d_6$): δ 12.80 (bs, 1H), 10.77 (s, 1H), 8.80 (s, 2H), 8.66 (d, J=2.00 Hz, 2H), 8.55 (bs, 1H), 8.34 (bs, 1H), 8.09 (s, 1H), 7.51-7.56 (m, 1H), 7.13-7.18 (m, 1H), 7.01 (d, J=8.40 Hz, 2H), 6.62 (d, J=8.40 Hz, 2H), 5.63 (d, J=7.20 Hz, 1H), 5.02 (s, 1H), 4.28 (m, 1H), 3.34-3.88 (m, 9H), 3.07 (q, J=7.20 Hz, 2H), 2.67-2.79 (m, 7H), 2.10 (m, 2H), 1.86-1.91 (m, 3H), 1.52-1.69 (m, 4H), 1.02 (t, J=7.20 Hz, 3H).

Example 143

5-[6-[4-[2-[4-[4-[(2,6-dioxo-3-piperidyl)amino]phenyl]-1-piperidyl]ethyl]piperazin-1-yl]-3-pyridyl]-3-[3-[[ethyl(methyl)sulfamoyl]amino]-2,6-difluoro-benzoyl]-1H-pyrrolo[2,3-b]pyridine

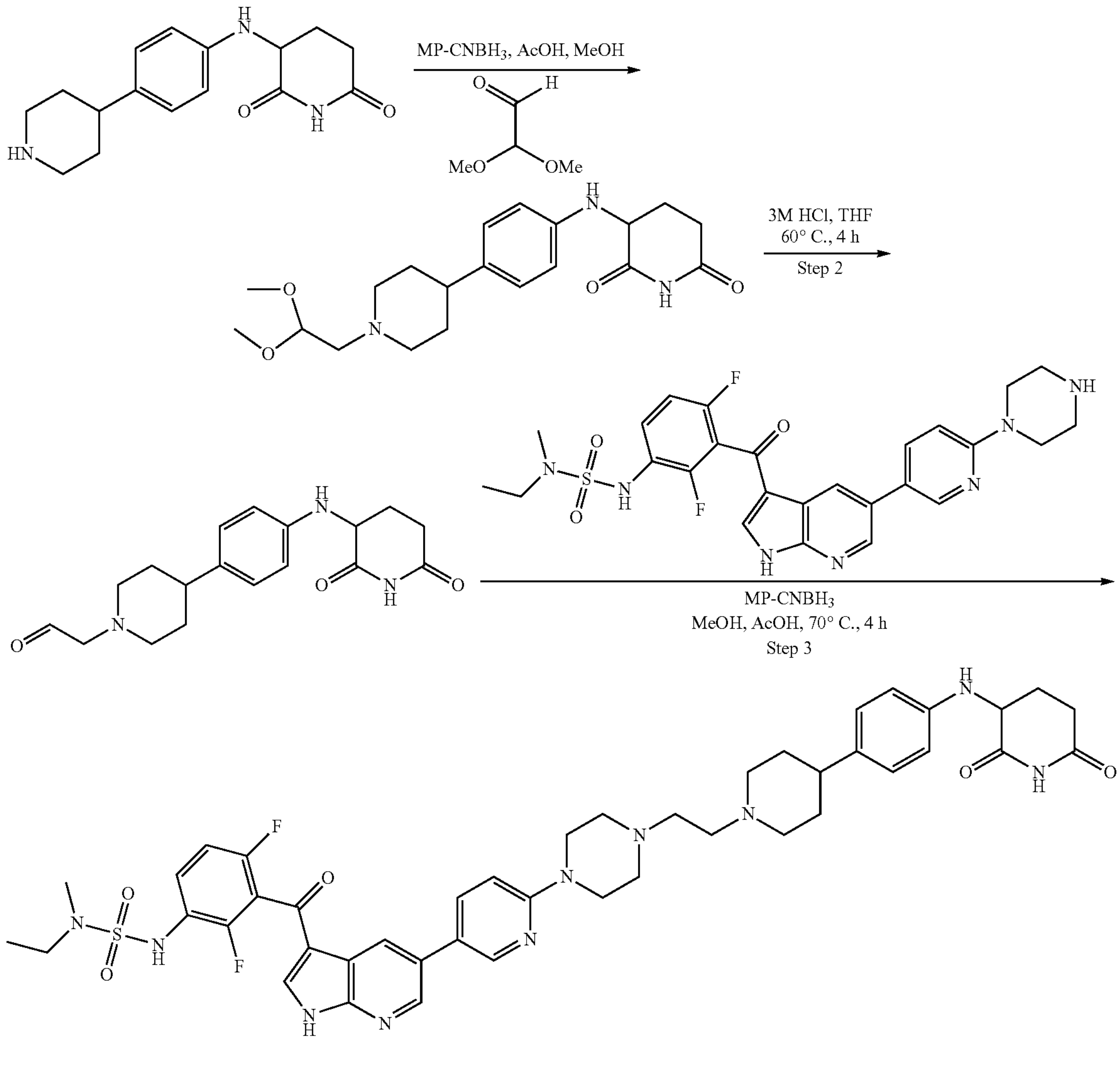

Step 1: To a stirred solution of 3-[4-(4-piperidyl)anilino]piperidine-2,6-dione (405 mg, 1.25 mmol) in methanol (5.0 mL) was added 2,2-dimethoxyacetaldehyde (260.41 mg, 1.50 mmol, 226.44 μL) at room temperature, followed by the addition of acetic acid (7.51 mg, 125.07 μmol, 7.15 μL) and MP-Cyanoborohydride (1.0 g, 1.25 mmol) at same temperature. The reaction mixture was stirred at room temperature for 6 h. After completion, the reaction mixture was filtered and filtrate was concentrated under reduced pressure. The crude compound was purified by silica gel column chromatography with 10% methanol in DCM as a eluent to afford 3-[4-[1-(2,2-dimethoxyethyl)-4-piperidyl]anilino]piperidine-2,6-dione (190 mg, 384.59 μmol, 30.75% yield) as a grey solid. LCMS (ESI+): 376.3 $[M+H]^+$ Step 2: To a stirred solution of 3-[4-[1-(2,2-dimethoxyethyl)-4-piperidyl]anilino]piperidine-2,6-dione (190 mg, 506.04 μmol) in THF (2.0 mL) was added 3 M HCl (3.20 g, 87.77 mmol, 4.0 mL) at room temperature. The reaction mixture was heated to 60° C. for 8 h. After completion, the reaction mixture was concentrated under reduced pressure. Water (20 mL) was added to the crude compound and lyophilized to afford 2-[4-[4-[(2,6-dioxo-3-piperidyl)amino]phenyl]-1-piperidyl]acetaldehyde (179 mg, 326.83 μmol, 64.59% yield) as a brown solid. This crude compound was taken forward without any further purification. LCMS (ESI): 330.3 $[M+H]^+$ Step 3: To a stirred solution of 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (25 mg, 42.23 μmol, hydrochloric acid salt) in methanol (2.0 mL) was added 2-[4-[4-[(2,6-dioxo-3-piperidyl)amino]phenyl]-1-piperidyl]acetaldehyde (37.50 mg, 102.50 μmol) at room temperature, followed by the addition of acetic acid (253.56 ug, 4.22 μmol, 241 μL) (2 drops) and MP-Cyanoborohydride (50 mg, 42.23 μmol) at same temperature. The reaction mixture was heated to 70° C. for 4 h. After completion, the reaction mixture was filtered, and filtrate was concentrated under reduced pressure. The crude compound was purified by preparative-HPLC (10 mM Ammonium acetate: ACN) and fractions were lyophilized to afford 5-[6-[4-[2-[4-[4-[(2,6-dioxo-3-piperidyl)amino]phenyl]-1-piperidyl]ethyl]piperazin-1-yl]-3-pyridyl]-3-[3-[[ethyl(methyl)sulfamoyl]amino]-2,6-difluoro-benzoyl]-1H-pyrrolo[2,3-b]pyridine (2.90 mg, 2.99 μmol, 7.08% yield) as off-white solid. LCMS (ESI+): 869.3 $[M+H]^+$. $^1$H NMR (400 MHz, DMSO-$d_6$): δ 12.90 (s, 1H), 10.78 (s, 1H), 8.66 (s, 1H), 8.52-8.49 (m, 2H), 8.12 (s, 1H), 7.93 (d, J=7.60 Hz, 1H), 7.58-7.55 (m, 1H), 7.27 (t, J=8.40 Hz, 1H), 6.99-6.95 (m, 3H), 6.61 (d, J=8.00 Hz, 2H), 5.66 (d, J=7.20 Hz, 1H), 4.36-4.20 (m, 1H), 3.56-3.35 (m, 5H), 3.13-3.06 (m, 4H), 2.72-2.50 (m, 12H), 2.35-2.33 (m, 2H), 2.12-2.09 (m, 3H), 1.88-1.61 (m, 5H), 1.03-1.00 (m, 3H).

Example 144

5-[6-[4-[2-[4-[4-[(2,6-dioxo-3-piperidyl)oxy]phenyl]-1-piperidyl]ethyl]piperazin-1-yl]-3-pyridyl]-3-[3-[[ethyl(methyl)sulfamoyl]amino]-2,6-difluoro-benzoyl]-1H-pyrrolo[2,3-b]pyridine

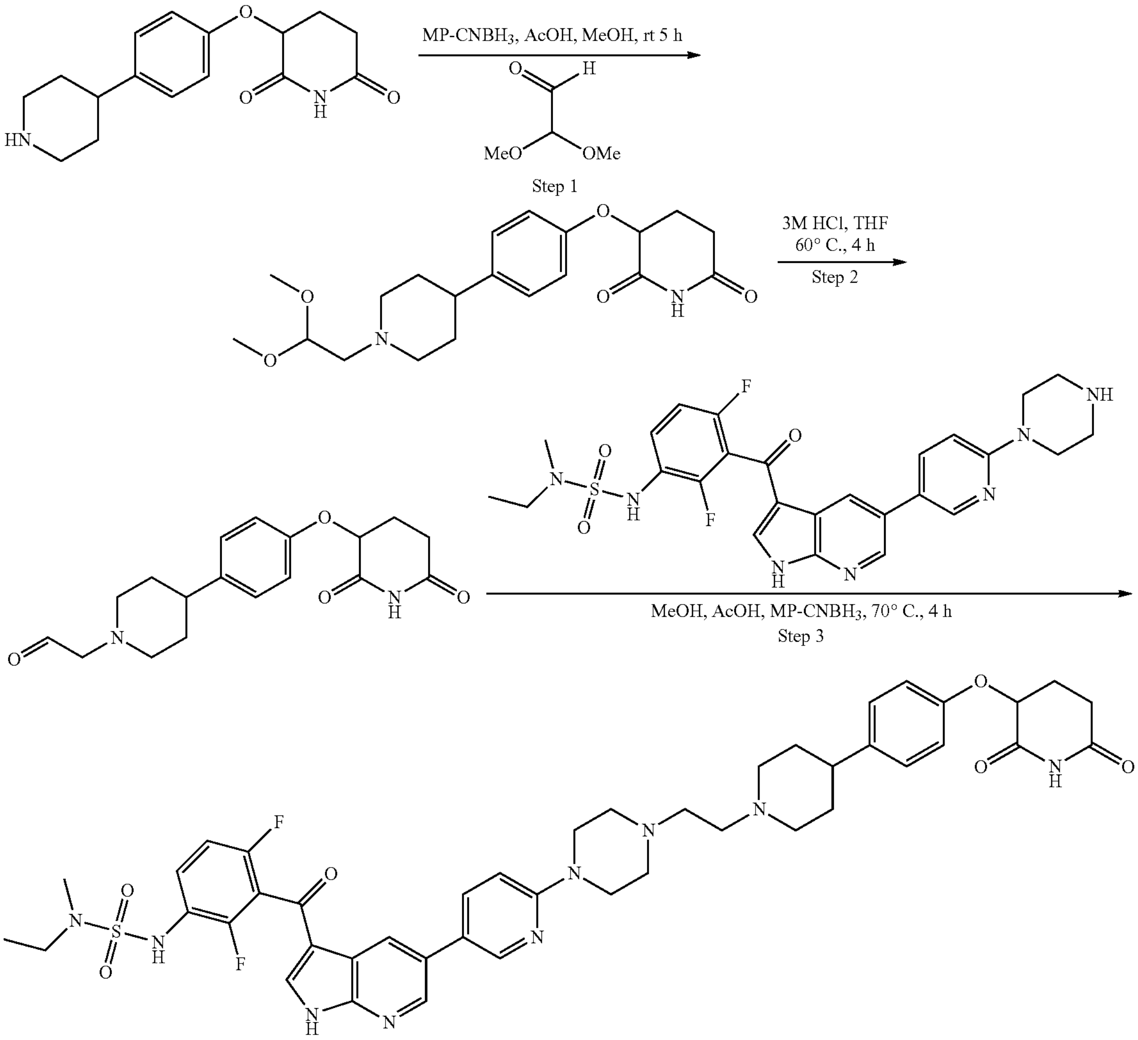

Step 1: To a stirred solution of 3-[4-(4-piperidyl)phenoxy]piperidine-2,6-dione (220 mg, 677.34 μmol) in methanol (5.0 mL) was added 2,2-dimethoxyacetaldehyde (130 mg, 749.25 μmol, 113.04 μL) at room temperature, followed by the addition of acetic acid (4.07 mg, 67.73 μmol, 3.87 μL) and MP-Cyanoborohydride (500 mg, 677.34 μmol) at same temperature. The reaction mixture was stirred at room temperature for 5 h. After completion, the reaction mixture was filtered, and filtrate was concentrated under reduced pressure. The crude compound was purified by silica gel column chromatography with 10% methanol in DCM as a eluent to afford 3-[4-[1-(2,2-dimethoxyethyl)-4-piperidyl]phenoxy]piperidine-2,6-dione (164 mg, 435.00 μmol, 64.22% yield) as off-white solid. LCMS (ESI+): 377.3 $[M+H]^+$ Step 2: A solution of 3-[4-[1-(2,2-dimethoxyethyl)-4-piperidyl]phenoxy]piperidine-2,6-dione (140 mg, 371.90 μmol) in trifluoroacetic acid (4.44 g, 38.94 mmol, 3.0 mL) was stirred at room temperature for 24 h. After completion, the reaction mixture was concentrated under reduced pressure to afford 2-[4-[4-[(2,6-dioxo-3-piperidyl)oxy]phenyl]-1-piperidyl]acetaldehyde (156 mg, 213.32 μmol, 57.36% yield) as a light brown gummy liquid, which was carried forward to next step without any purification. LCMS (ESI+): 331.1 $[M+H]^+$ Step 3: To a stirred solution of 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (20 mg, 33.78 μmol, hydrochloric acid salt) in methanol (2.0 mL) was added 2-[4-[4-[(2,6-dioxo-3-piperidyl)oxy]phenyl]-1-piperidyl]acetaldehyde (30.02 mg, 67.56 μmol) at room temperature, followed by the addition of acetic acid (202.85 μg, 3.38 μmol, 193 μL) (2 drops) and MP-Cyanoborohydride (50 mg, 33.78 μmol) at same temperature. The reaction mixture was heated to 70° C. for 5 h. After completion, the reaction mixture was filtered, and filtrate was concentrated under reduced pressure. The crude compound was purified by preparative-HPLC and fractions were lyophilized to afford 5-[6-[4-[2-[4-[4-[(2,6-dioxo-3-piperidyl)oxy]phenyl]-1-piperidyl]ethyl]piperazin-1-yl]-3-pyridyl]-3-[3-[[ethyl(methyl)sulfamoyl]amino]-2,6-difluoro-benzoyl]-1H-pyrrolo[2,3-b]pyridine (5.65 mg, 5.70 μmol, 16.88% yield) as a pale yellow gummy liquid (hygroscopic). LCMS (ESI+): 870.2 $[M+H]^+$. $^1$H NMR (400 MHz, DMSO-$d_6$): δ 12.99 (s, 1H), 10.94 (s, 1H), 9.71 (s, 1H), 8.69 (s, 1H), 8.57-8.54 (m, 2H), 8.14 (s, 1H), 8.04 (d, J=7.24 Hz, 1H), 7.61-7.54 (m, 1H), 7.30-7.10 (m, 4H), 7.01-6.97 (m, 2H), 6.89-6.87 (m, 1H), 5.20-5.16 (m, 1H), 3.62-3.60 (m, 10H), 3.14-3.09 (m, 5H), 2.73-2.50 (m, 6H), 2.03-1.87 (m, 8H), 1.02 (t, J=7.12 Hz, 3H).

Example 145

5-[2-[4-[2-[4-[4-[(2,6-dioxo-3-piperidyl)amino]phenyl]-1-hydroxy-cyclohexyl]ethyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

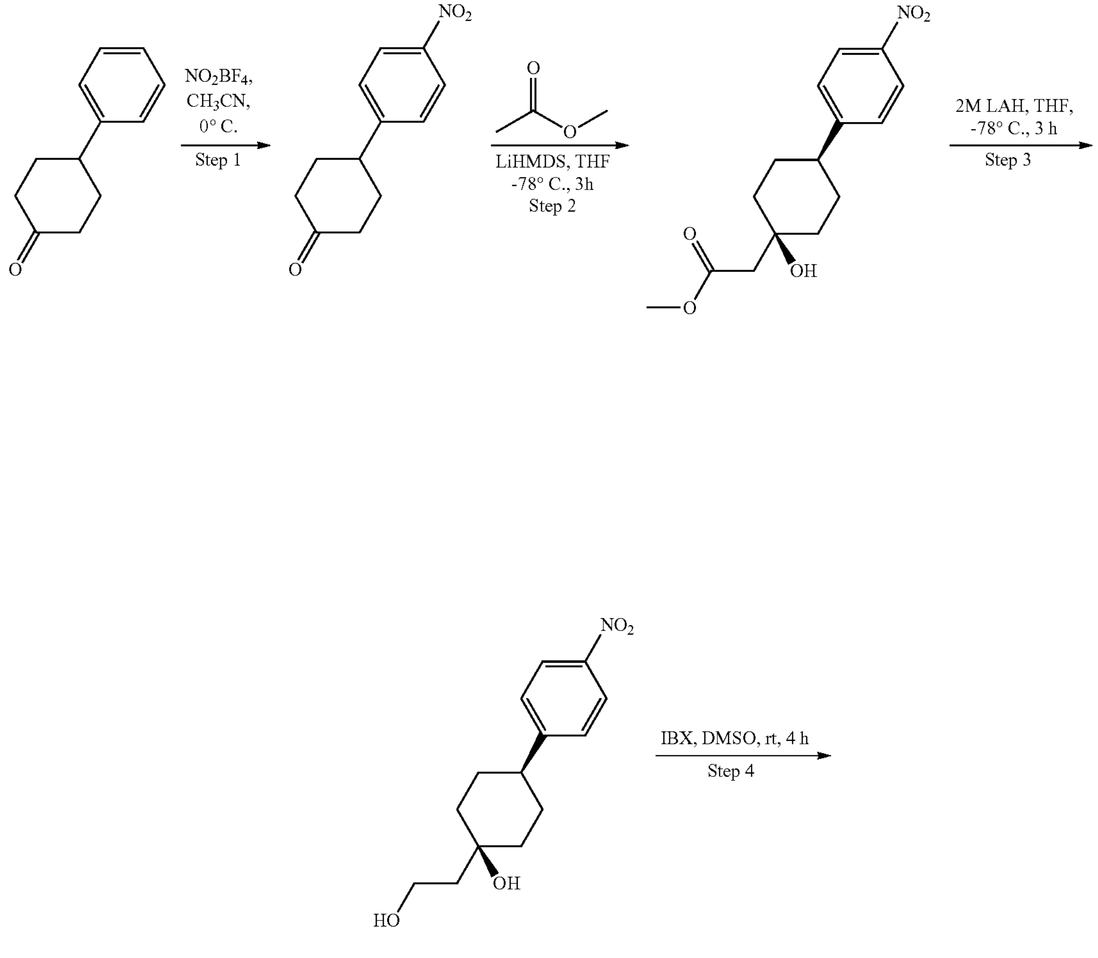

-continued

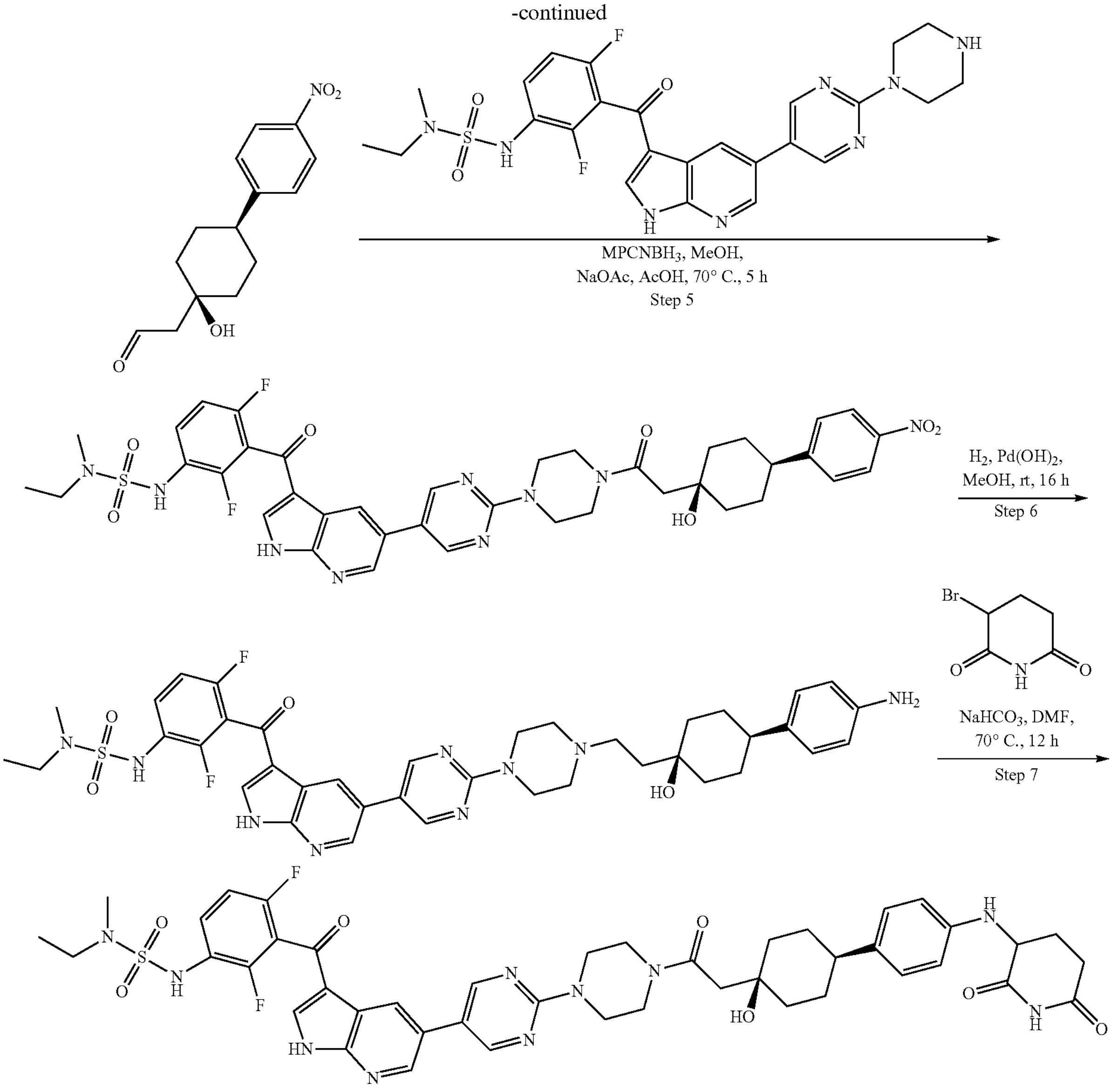

Step 1: To a stirred solution of 4-phenylcyclohexanone (10 g, 2.87 mmol) in Acetonitrile (100 mL), was added nitronium tetrafluoroborate (10.67 g, 80.35 mmol) portion wise at −5° C. The reaction mixture was stirred at 0° C. for 3 h. After completion, the reaction mixture was diluted with cold water (100 mL) and extracted with ethyl acetate (3×150 mL). Combined organic layers were dried over sodium sulphate, filtered and concentrated. Crude compound was purified by column chromatography (60-120 silica gel) using 25-30% ethyl acetate in petroleum ether as eluent to afford 4-(4-nitrophenyl)cyclohexanone (3.8 g, 17.33 mmol, 30.20% yield) as green solid. $^1$H NMR (400 MHz, DMSO-$d_6$): δ 8.22 (d, J=8.80 Hz, 2H), 7.44 (d, J=8.80 Hz, 2H), 3.14-3.21 (m, 1H), 2.57-2.59 (m, 4H), 2.25-2.31 (m, 2H), 1.94-2.05 (m, 2H).

Step 2: To a stirred solution of methyl acetate (675.79 mg, 9.12 mmol, 723.54 μL) in dry THF (15 mL), was added LiHMDS (1.0M in THF, 11.40 mmol, 11.40 mL) by dropwise under nitrogen atmosphere at −78° C. Reaction mixture was stirred at −78° C. for 15 minutes and then 4-(4-nitrophenyl)cyclohexanone (1 g, 4.56 mmol) in THF (15 mL) solution was added by dropwise at −78° C. and continued the reaction mixture at the same temperature for 3 h. After completion, the reaction mixture was quenched with saturated ammonium chloride solution (40 mL) at 0° C. and extracted with ethyl acetate (3×50 mL). Combined organic layers dried over sodium sulphate, filtered and concentrated. Crude compound was purified by column chromatography (60-120 silica gel) using 35-45% ethyl acetate in pet-ether as eluent to afford methyl 2-[1-hydroxy-4-(4-nitrophenyl)cyclohexyl]acetate (0.5 g, 1.70 mmol, 37.37% yield) as green liquid. $^1$H NMR (400 MHz, DMSO-$d_6$): δ 8.15 (d, J=8.80 Hz, 2H), 7.59 (d, J=8.40 Hz, 2H), 4.67 (d, J=6.00 Hz, 1H), 3.59 (s, 3H), 2.65-2.63 (m, 3H), 1.90-1.99 (m, 2H), 1.64-1.75 (m, 2H), 1.47-1.61 (m, 4H).

Step 3: To a stirred solution of methyl 2-[1-hydroxy-4-(4-nitrophenyl)cyclohexyl]acetate (0.9 g, 3.07 mmol) in THF (20 mL), was added lithium aluminium hydride (9.21 mmol, 4.60 mL) dropwise at −78° C. under nitrogen atmosphere and continued the reaction mixture for 3 h at the same temperature. After completion, the reaction mixture was quenched with saturated ammonium chloride solution (40 mL) at 0° C. dropwise and extracted with ethyl acetate (3×50 mL). Combined organic layers dried over sodium sulphate, filtered and concentrated. Desired crude was purified by column chromatography (60-120 silica gel) by using 60-70% ethyl acetate in petroleum ether as eluent to afford 1-(2-hydroxyethyl)-4-(4-nitrophenyl)cyclohexanol (0.35 g, 1.32 mmol, 42.99% yield) as yellow liquid. $^1$H NMR (400 MHz, DMSO-$d_6$): δ 8.13-8.17 (m, 2H), 7.51-7.57 (m, 2H), 4.35-4.40 (m, 2H), 3.58-3.63 (m, 2H), 2.66-2.72 (m, 1H), 1.70-1.77 (m, 6H), 1.42-1.65 (m, 4H).

Step 4: To a stirred solution of 1-(2-hydroxyethyl)-4-(4-nitrophenyl)cyclohexanol (350.00 mg, 1.32 mmol) in DMSO (15 mL), was added 2-Iodoxybenzoic acid (1.11 g, 3.96 mmol) at 5° C. Reaction mixture was stirred at room temperature for 4 h. After completion, the reaction mixture was quenched with 10% sodium bicarbonate solution (100 mL) at 0° C. and extracted with ethyl acetate (3×50 mL). Combined organic layers washed with water (30 mL), dried over sodium sulphate, filtered and concentrated to afford crude 2-[1-hydroxy-4-(4-nitrophenyl)cyclohexyl]acetaldehyde (0.31 g, 1.18 mmol, 89.25% yield) as light yellow liquid.

$^1$H NMR (400 MHz, DMSO-$d_6$): δ 9.82 (s, 1H), 8.15 (d, J=8.40 Hz, 2H), 7.60 (d, J=8.40 Hz, 2H), 4.96 (s, 1H), 2.65-2.71 (m, 3H), 1.90-1.87 (m, 2H), 1.77-1.74 (m, 2H), 1.58-1.63 (m, 4H).

Step 5: To a stirred solution of 2-[1-hydroxy-4-(4-nitrophenyl)cyclohexyl]acetaldehyde (0.28 g, 1.06 mmol) in methanol (15 mL), were added MP-aCyanoborohydride (700 mg), cetic acid (49.27 mg, 820.50 μmol, 46.92 μL), sodium acetate (165.99 mg, 2.02 mmol, 108.49 μL) and 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (0.3 g, 505.86 μmol) at room temperature. Reaction mixture was stirred at 70° C. for 5 h. After completion, reaction mixture was filtered and concentrated, diluted with water (40 mL) and extracted with ethyl acetate (3×70 mL). Combined organic layers dried over sodium sulphate, filtered and concentrated to afford crude. Crude compound was purified by column chromatography (60-120 silica gel), by using 5-10% methanol in DCM as eluent to afford 3-[3-[[ethyl(methyl)sulfamoyl]amino]-2,6-difluoro-benzoyl]-5-[2-[4-[2-[1-hydroxy-4-(4-nitrophenyl)cyclohexyl]ethyl]piperazin-1-yl]pyrimidin-5-yl]-1H-pyrrolo[2,3-b]pyridine (0.18 g, 160.66 μmol, 31.76% yield) as light brown solid. LCMS (ESI+): 803.7 [M+H]$^+$ Step 6: To a stirred solution of 3-[3-[[ethyl(methyl)sulfamoyl]amino]-2,6-difluoro-benzoyl]-5-[2-[4-[2-[1-hydroxy-4-(4-nitrophenyl)cyclohexyl]ethyl]piperazin-1-yl]pyrimidin-5-yl]-1H-pyrrolo[2,3-b]pyridine (180 mg, 223.92 μmol) in Methanol (10 mL) and ethyl acetate (10 mL), was added $Pd(OH)_2$ (120 mg, 854.49 μmol). The reaction mixture was stirred at room temperature for 16 h. After completion, the reaction mixture was purged with nitrogen, catalyst was removed by filtration through celite pad. The filtrate was concentrated under reduced pressure to afford crude 5-[2-[4-[2-[4-(4-aminophenyl)-1-hydroxy-cyclohexyl]ethyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (0.14 g, 151.25 μmol, 67.55% yield) as off white solid. LCMS (ESI+): 774.3 [M+H]$^+$ Step 7: In sealed tube, to a stirred solution of 5-[2-[4-[2[4-(4-aminophenyl)-1-hydroxy-cyclohexyl]ethyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (125.15 mg, 161.72 μmol) in DMF (3 mL), was added $NaHCO_3$ (40.76 mg, 485.15 μmol, 18.87 μL) and 3-bromopiperidine-2,6-dione (77.63 mg, 404.29 μmol). The reaction mixture was stirred at 70° C. for 16 h. After completion of the reaction, reaction mixture was diluted with water (10 mL) and extracted with 10% IPA in DCM (3×30 mL). Combined organic layers washed with cold water (3×20 mL), dried over sodium sulphate, filtered and concentrated to afford crude. The crude compound was purified by preparative-HPLC (0.1% formic acid in water:acetonitrile) and fractions were lyophilized to afford desired product 5-[2-[4-[2-[4-[4-[(2,6-dioxo-3-piperidyl)amino]phenyl]-1-hydroxy-cyclohexyl]ethyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (23.24 mg, 23.44 μmol, 14.49% yield) as light green solid. LCMS (ESI+): 885.3 [M+H]$^+$. $^1$H NMR (400 MHz, DMSO-d6): δ 13.00 (s, 1H), 10.77 (s, 1H), 9.70 (s, 1H), 8.78 (s, 2H), 8.68 (d, J=2.40 Hz, 1H), 8.56 (s, 1H), 8.14 (s, 1H), 7.56-7.62 (m, 1H), 7.26-7.31 (m, 1H), 6.98 (d, J=8.80 Hz, 2H), 6.61 (d, J=8.80 Hz, 2H), 5.63 (d, J=7.20 Hz, 1H), 4.31-4.21 (m, 1H), 3.12 (q, J=7.20 Hz, 2H), 2.51-2.79 (m, 7H), 2.71 (s, 3H), 2.42-2.33 (m, 2H), 2.15-2.05 (m, 1H), 1.92-1.59 (m, 8H), 1.59-1.41 (m, 4H), 1.03 (t, J=7.20 Hz, 3H).

Example 146

5-[2-[4-[2-[4-[4-[(2,6-dioxo-3-piperidyl)amino]phenyl]-2-oxo-1-piperidyl]ethyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

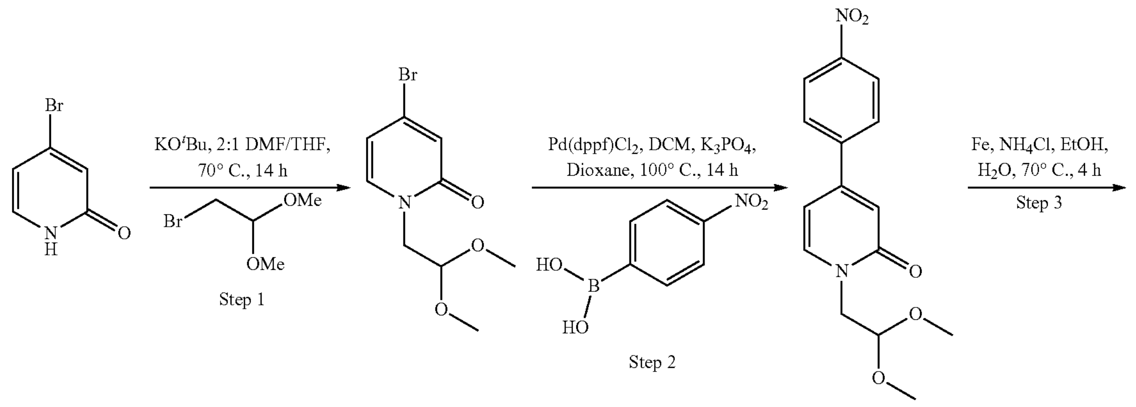

-continued

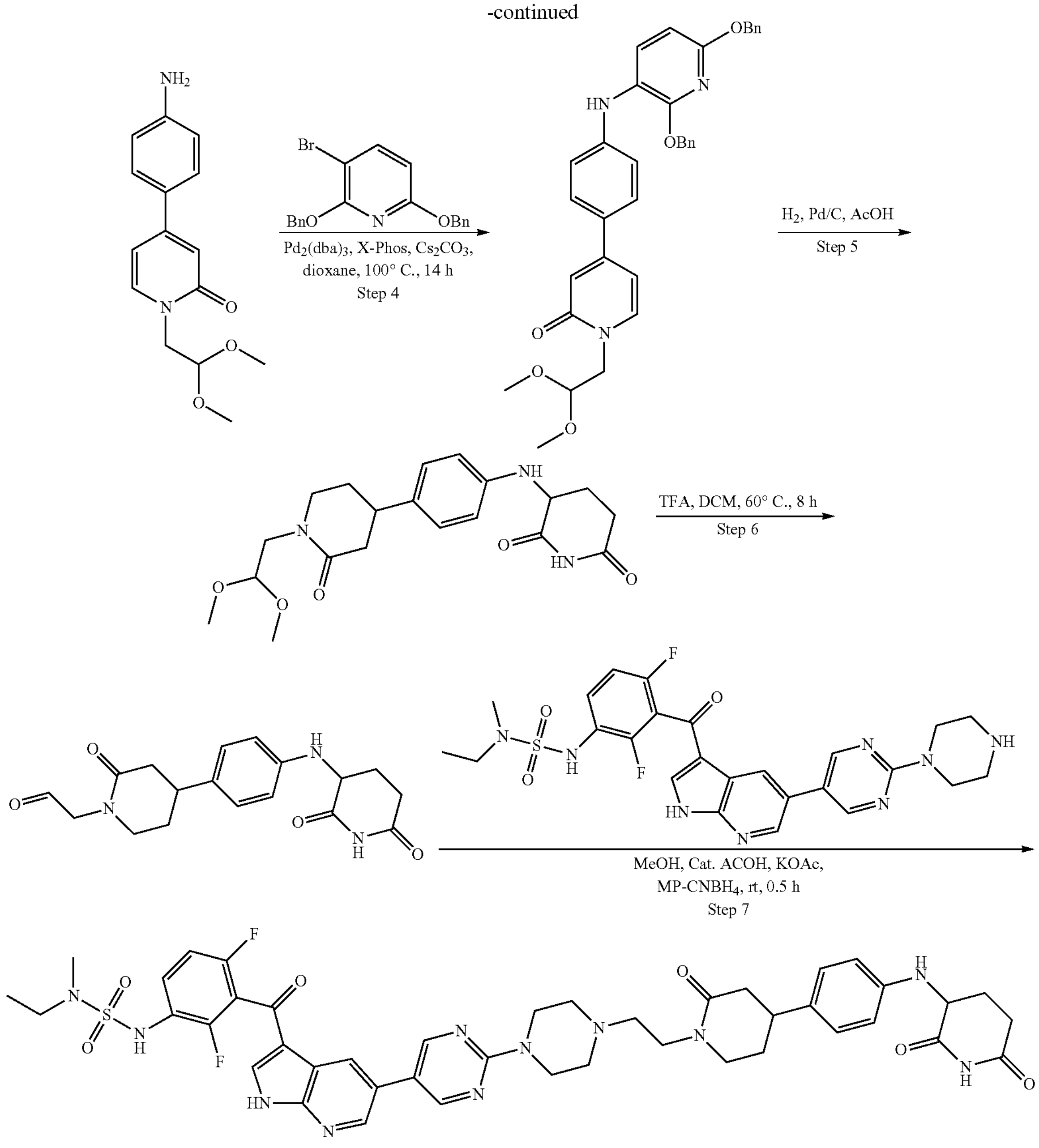

Step 1: To a stirred solution of 4-bromo-1H-pyridin-2-one (5 g, 28.74 mmol) in N,N-dimethylformamide (40 mL) and THF (10 mL) were added potassium 2-methylpropan-2-olate (6.45 g, 57.47 mmol), tetrabutylammonium bromide (926.37 mg, 2.87 mmol) and 2-bromo-1,1-dimethoxy-ethane (9.71 g, 57.47 mmol, 6.79 mL) at room temperature. The reaction mixture was stirred at 70° C. for 14 h. After completion of reaction, ice cold water was added and extracted with ethyl acetate (2×100 mL). The combined organic layers were washed with brine (20 mL), dried over anhydrous sodium sulphate, filtered and filtrate was evaporated under reduced pressure to get the desired crude compound. Crude compound was purified by column chromatography (60-120 silica gel), by using 40-55% ethyl acetate in petroleum ether as eluent to afford 4-bromo-1-(2,2-dimethoxyethyl)pyridin-2-one (4.51 g, 14.11 mmol, 49.10% yield). LCMS (ESI+): 263.9 $[M+H]^+$.

Step 2: 4-bromo-1-(2,2-dimethoxyethyl)pyridin-2-one (4.5 g, 17.17 mmol) in 1,4 Dioxane (80 mL) was taken in sealed tube, and added $K_3PO_4$ (10.93 g, 51.51 mmol) and (4-nitrophenyl)boronic acid (3.44 g, 20.60 mmol). The reaction mixture was purged with nitrogen gas for 10 minutes and added $Pd(dppf)Cl_2$·dichloromethane (1.40 g, 1.72 mmol) again purged with nitrogen gas for 5 minutes. The reaction mixture was stirred at 90° C. for 14 h. After completion, the reaction mixture was diluted with water (100 mL), extracted with ethyl acetate (3×100 mL). Combined organic layers dried over sodium sulphate, filtered and concentrated under reduced pressure to afford crude. Desired product was purified from crude by column chromatography (60-120 silica gel), by using 40-55% ethyl acetate in petroleum ether as eluent to afford 1-(2,2-dimethoxyethyl)-4-(4-nitrophenyl)pyridin-2-one (3.5 g, 11.18 mmol, 65.14% yield). LCMS (ESI+): 305.1 $[M+H]^+$.

Step 3: A solution of 1-(2,2-dimethoxyethyl)-4-(4-nitrophenyl)pyridin-2-one (5.0 g, 16.43 mmol) in water (8 mL), ethanol (32 mL) was added iron powder (4.59 g, 82.16 mmol, 583.72 μL), ammonium chloride (2.64 g, 49.29 mmol, 1.72 mL) and heated at 70° C. for 4 h. The reaction mixture was filtered and extracted with ethyl acetate (100 mL). The organic layer was washed with $NaHCO_3$ solution (40 mL), water (30 mL), brine (30 mL), dried over sodium sulphate and concentrated under reduced pressure to get 4-(4-aminophenyl)-1-(2,2-dimethoxyethyl)pyridin-2-one (3.4 g, 11.48 mmol, 69.85% yield) as off white solid. LCMS (ESI+): 274.9 $[M+H]^+$.

Step 4: A solution of 4-(4-aminophenyl)-1-(2,2-dimethoxyethyl)pyridin-2-one (800 mg, 2.92 mmol), 2,6-dibenzyloxy-3-bromo-pyridine (1.08 g, 2.92 mmol), Cesium carbonate (2.38 g, 7.29 mmol) in 1,4-dioxane (20 mL) was degassed with nitrogen for 10 minutes. To this bis dibenzylideneacetone palladium (267.06 mg, 291.64 μmol), X-Phos (139.03 mg, 291.64 μmol) was added to the reaction mixture and heated to 100° C. for 14 h. After completion of the reaction, the reaction mixture was diluted with water (60 mL) and extracted with ethyl acetate (2×100 mL). The combined organic layers were dried over sodium sulphate, filtered and concentrated under reduced pressure. The crude compound was purified by silica gel column chromatography with 70% ethyl acetate in petroleum ether as eluent to afford 4-[4-[(2,6-dibenzyloxy-3-pyridyl)amino]phenyl]-1-(2,2-dimethoxyethyl)pyridin-2-one (1.1 g, 1.81 mmol, 62.03% yield) as a yellow solid. LCMS (ESI+): 564.3 $[M+H]^+$.

Step 5: A solution of 4-[4-[(2,6-dibenzyloxy-3-pyridyl)amino]phenyl]-1-(2,2-dimethoxyethyl)pyridin-2-one (1.2 g, 2.13 mmol) in Ethyl acetate (8 mL), 1,4-dioxane (8 mL) was degassed for 10 minutes, palladium hydroxide on carbon (20 wt. % 50% water, 600 mg, 4.27 mmol) was added to the reaction mixture and stirred under $H_2$ balloon pressure (1 atm) for 14 h. The reaction mixture was filtered through celite and concentrated under reduced pressure to get crude, which was triturated with diethyl ether to afford 3-[4-[1-(2,2-dimethoxyethyl)-2-oxo-4-piperidyl]anilino]piperidine-2,6-dione (650 mg, 1.57 mmol, 73.61% yield) as a light green solid. LCMS (ESI+): 388.1 $[M-H]^+$.

Step 6: To a solution of 3-[4-[1-(2,2-dimethoxyethyl)-2-oxo-4-piperidyl]anilino]piperidine-2,6-dione (600 mg, 1.54 mmol) in Dichloromethane (3 mL) was added Trifluoroacetic acid (7.40 g, 64.90 mmol, 5 mL) and heated at 60° C. for 5 h. The reaction mixture was concentrated under reduced pressure to get crude, which was triturated with diethyl ether to afford 2-[4-[4-[(2,6-dioxo-3-piperidyl)amino]phenyl]-2-oxo-1-piperidyl]acetaldehyde (500 mg, 972.89 μmol, 63.15% yield) as light green solid. LCMS (ESI+): 344.1 $[M+H]^+$.

Step 7: To a stirred solution of 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (250 mg, 449.17 μmol) in methanol (20 mL) was added 2-[4-[4-[(2,6-dioxo-3-piperidyl)amino]phenyl]-2-oxo-1-piperidyl]acetaldehyde (354.74 mg, 1.03 mmol) at room temperature, followed by the addition of Potassium Acetate (44.08 mg, 449.17 μmol, 28.08 acetic acid (5.39 mg, 89.83 μmol, 5.14 μL) and MP-Cyanoborohydride (800 mg, 449.17 μmol) and stirred at room temperature for 30 minutes. The reaction mixture was filtered and concentrated the filtrate reduced pressure to get crude which was purified by reverse phase column chromatography by using 48% Acetonitrile in 0.1% $NH_4OAc$ in water to afford 5-[2-[4-[2-[4-[4-[(2,6-dioxo-3-piperidyl)amino]phenyl]-2-oxo-1-piperidyl]ethyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (60 mg, 67.33 μmol, 14.99% yield) as off white solid. LCMS (ESI+): 884.3 $[M+H]^+$. $^1H$ NMR (400 MHz, DMSO-$d_6$): δ 12.99 (s, 1H), 10.78 (s, 1H), 9.71 (s, 1H), 8.77 (s, 2H), 8.67 (d, J=2.00 Hz, 1H), 8.55 (s, 1H), 8.14 (s, 1H), 7.56-7.62 (m, 1H), 7.28 (t, J=8.00 Hz, 1H), 7.00 (d, J=8.40 Hz, 2H), 6.64 (d, J=8.80 Hz, 2H), 5.73 (d, J=7.20 Hz, 1H), 4.22-4.32 (m, 1H), 3.85-3.78 (m, 4H), 3.45-3.52 (m, 4H), 3.11 (q, J=6.80 Hz, 2H), 2.86-2.95 (m, 1H), 2.71-2.78 (m, 2H), 2.75 (s, 3H), 2.59-2.63 (m, 1H), 2.51-2.57 (m, 2H), 2.41-2.45 (m, 2H), 2.31-2.36 (m, 1H), 2.06-2.15 (m, 1H), 1.76-1.95 (m, 4H), 1.02 (t, J=7.20 Hz, 3H).

Example 147

5-[6-[4-[2-[4-[4-[(2,6-dioxo-3-piperidyl)oxy]phenyl]-1-piperidyl]ethyl]-3-oxo-piperazin-1-yl]-3-pyridyl]-3-[3-[[ethyl(methyl)sulfamoyl]amino]-2,6-difluoro-benzoyl]-1H-pyrrolo[2,3-b]pyridine

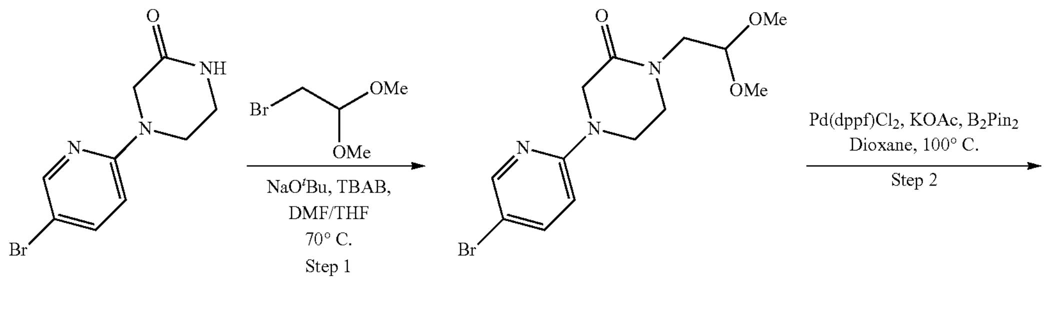

-continued

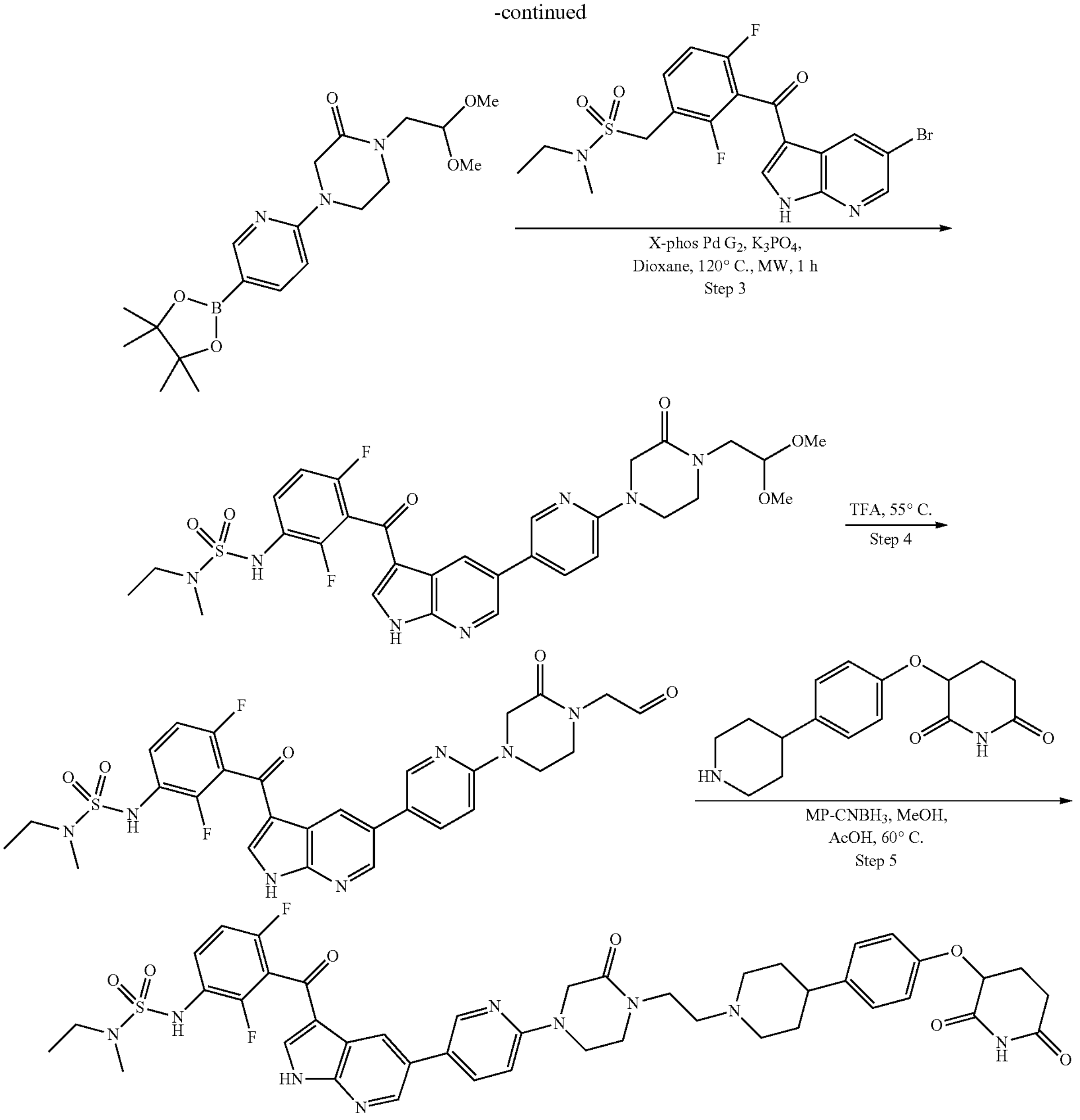

Step 1: To a solution of 4-(5-bromo-2-pyridyl)piperazin-2-one (200 mg, 780.95 μmol) in tetrahydrofuran (1.0 mL) and N,N'-dimethylformamide (4.0 mL) were added potassium tert-butoxide (131.45 mg, 1.17 mmol), tetrabutylammonium bromide (50.35 mg, 156.19 μmol) followed by 2-bromo-1,1-dimethoxy-ethane (263.99 mg, 1.56 mmol, 184.61 μL) at room temperature under nitrogen atmosphere. The reaction mixture was heated at 70° C. for 16 h. The reaction was cooled to room temperature, added to water (15 mL) and extracted with ethyl acetate (2×30 mL). The combined organic layers were dried over sodium sulphate, filtered and concentrated under reduced pressure. The crude product was purified by silica gel column chromatography with 80% ethyl acetate in petroleum ether as an eluent to afford 4-(5-bromo-2-pyridyl)-1-(2,2-dimethoxyethyl)piperazin-2-one (70 mg, 161.94 μmol, 20.74% yield) as an off-white oil. LCMS (ESI+): 344.2 $[M+H]^+$.

Step 2: A mixture of 4-(5-bromo-2-pyridyl)-1-(2,2-dimethoxyethyl)piperazin-2-one (2.0 g, 5.81 mmol), bis(pinacolato)diboron (2.21 g, 8.72 mmol) and Potassium acetate (1.71 g, 17.43 mmol) in 1,4-dioxane (25 mL) was purged with nitrogen gas for 10 min. [1,1'-Bis(diphenylphosphino) ferrocene]dichloropalladium(II), complex with dichloromethane (474.51 mg, 581.05 μmol) was added at room temperature. The reaction mixture was heated at 95° C. for 3 h. Reaction mixture was cooled to room temperature, filtered through celite bed and washed with dichloromethane. The resulting filtrate was concentrated under reduced pressure to get the crude product. The crude product was purified by silica gel column chromatography with 80% ethyl acetate in petroleum ether as an eluent to afford 1-(2,2-dimethoxyethyl)-4-[5-(4,4,5,5-tetramethyl-1,3,2-dioxaborolan-2-yl)-2-pyridyl]piperazin-2-one (1.1 g, 2.08 mmol, 35.80% yield) as a brown solid. LCMS (ESI+): 392.2 $[M+H]^+$.

Step 3: A mixture of 5-bromo-3-[3-[[ethyl(methyl)sulfamoyl]amino]-2,6-difluoro-benzoyl]-1H-pyrrolo[2,3-b]pyridine (1.45 g, 3.06 mmol), 1-(2,2-dimethoxyethyl)-4-[5-(4,4,5,5-tetramethyl-1,3,2-dioxaborolan-2-yl)-2-pyridyl]piperazin-2-one (1.20 g, 3.06 mmol) and sodium carbonate (974.15 mg, 9.19 mmol) in 1,4-dioxane (18 mL)/water (3 mL) was purged with nitrogen gas for 15 minutes followed by the addition of [1,1'-Bis(diphenylphosphino)ferrocene]dichloropalladium(II), complex with dichloromethane (250.19 mg, 306.37 μmol) at room temperature. The reaction mixture was heated at 100° C. for 16 h. Reaction mixture was cooled to room temperature, filtered through celite bed and washed with dichloromethane (50 mL). The resulting filtrate was washed with brine (30 mL), dried over sodium sulphate, filtered and concentrated under reduced pressure. The crude compound was purified by silica gel column chromatography with 80% ethyl acetate in petroleum ether as an eluent to afford 5-[6-[4-(2,2-dimethoxyethyl)-3-oxo-piperazin-1-yl]-3-pyridyl]-3-[3-[[ethyl(methyl)sulfamoyl]amino]-2,6-difluoro-benzoyl]-1H-pyrrolo[2,3-b]pyridine (510 mg, 699.61 μmol, 22.84% yield) as a brown solid. LCMS (ESI+): 658.9 $[M+H]^+$.

Step 4: A mixture of 5-[6-[4-(2,2-dimethoxyethyl)-3-oxo-piperazin-1-yl]-3-pyridyl]-3-[3-[[ethyl(methyl)sulfamoyl]amino]-2,6-difluoro-benzoyl]-1H-pyrrolo[2,3-b]pyridine (120 mg, 182.46 μmol) in trifluoroacetic acid (5.92 g, 51.92 mmol, 4 mL) was heated at 55° C. for 6 h. The reaction mixture was cooled to room temperature, concentrated under reduced pressure, co-distilled with dichloromethane (2×20 mL) and dried to afford crude product 3-[3-[[ethyl(methyl)sulfamoyl]amino]-2,6-difluoro-benzoyl]-5-[6-[3-oxo-4(2-oxoethyl)piperazin-1-yl]-3-pyridyl]-1H-pyrrolo[2,3-b]pyridine (90 mg, 111.58 μmol, 61.16% yield) as a brown oil. LCMS (ESI+): 612.1 $[M+H]^+$.

Step 5: To a mixture of 3-[3-[[ethyl(methyl)sulfamoyl]amino]-2,6-difluoro-benzoyl]-5-[6-[3-oxo-4-(2-oxoethyl)piperazin-1-yl]-3-pyridyl]-1H-pyrrolo[2,3-b]pyridine (180 mg, 248.06 μmol) and 3-[4-(4-piperidyl)phenoxy]piperidine-2,6-dione (101.14 mg, 311.40 μmol) in methanol (8.0 mL) were added glacial acetic acid (14.90 mg, 248.06 μmol, 0.4 mL) followed MP-Cyanoborohydride (180 mg, 248.06 μmol) at room temperature. The reaction mixture was heated at 55° C. for 16 h. Reaction mixture was cooled to room temperature, filtered and washed with methanol (5 mL). The resulting filtrate was concentrated under reduced pressure to get the crude product. The crude compound was purified by reverse phase C18 column chromatography [Mobile-phase A: 0.1% TFA in water, Mobile-phase B: ACN, Wave length: 215 nm, column: 50 g Redisep C18] to afford 5-[6-[4-[2-[4-[4-[(2,6-dioxo-3-piperidyl)oxy]phenyl]-1-piperidyl]ethyl]-3-oxo-piperazin-1-yl]-3-pyridyl]-3-[3-[[ethyl(methyl)sulfamoyl]amino]-2,6-difluoro-benzoyl]-1H-pyrrolo[2,3-b]pyridine (25.38 mg, 26.67 μmol, 10.75% yield) as an off-white solid. LCMS (ESI+): 884.7 $[M+H]^+$. $^1H$ NMR (400 MHz, DMSO-$d_6$): δ 12.96 (bs, 1H), 10.91 (s, 1H), 9.85 (bs, 1H), 8.67 (d, J=2.40 Hz, 1H), 8.54 (d, J=2.40 Hz, 2H), 8.13 (d, J=7.20 Hz, 2H), 8.00 (dd, J=2.40, 8.80 Hz, 1H), 7.58 (m, 1H), 7.28 (t, J=8.40 Hz, 1H), 7.14 (d, J=8.80 Hz, 2H), 7.02 (d, J=8.80 Hz, 1H), 6.92 (d, J=8.80 Hz, 2H), 5.13 (dd, J=4.80, 10.60 Hz, 1H), 4.04 (s, 2H), 3.90 (m, 2H), 3.56 (m, 4H), 3.12 (q, J=7.20 Hz, 3H), 2.73 (s, 3H), 2.57 (m, 3H), 2.18 (m, 6H), 1.75 (m, 2H), 1.65 (m, 2H), 1.02 (t, J=7.20 Hz, 3H).

Example 148

5-[6-[4-[2-[1-[4-[(2,6-dioxo-3-piperidyl)amino]phenyl]-4-piperidyl]ethyl]-3-oxo-piperazin-1-yl]-3-pyridyl]-3-[3-[[ethyl(methyl)sulfamoyl]amino]-2,6-difluoro-benzoyl]-1H-pyrrolo[2,3-b]pyridine

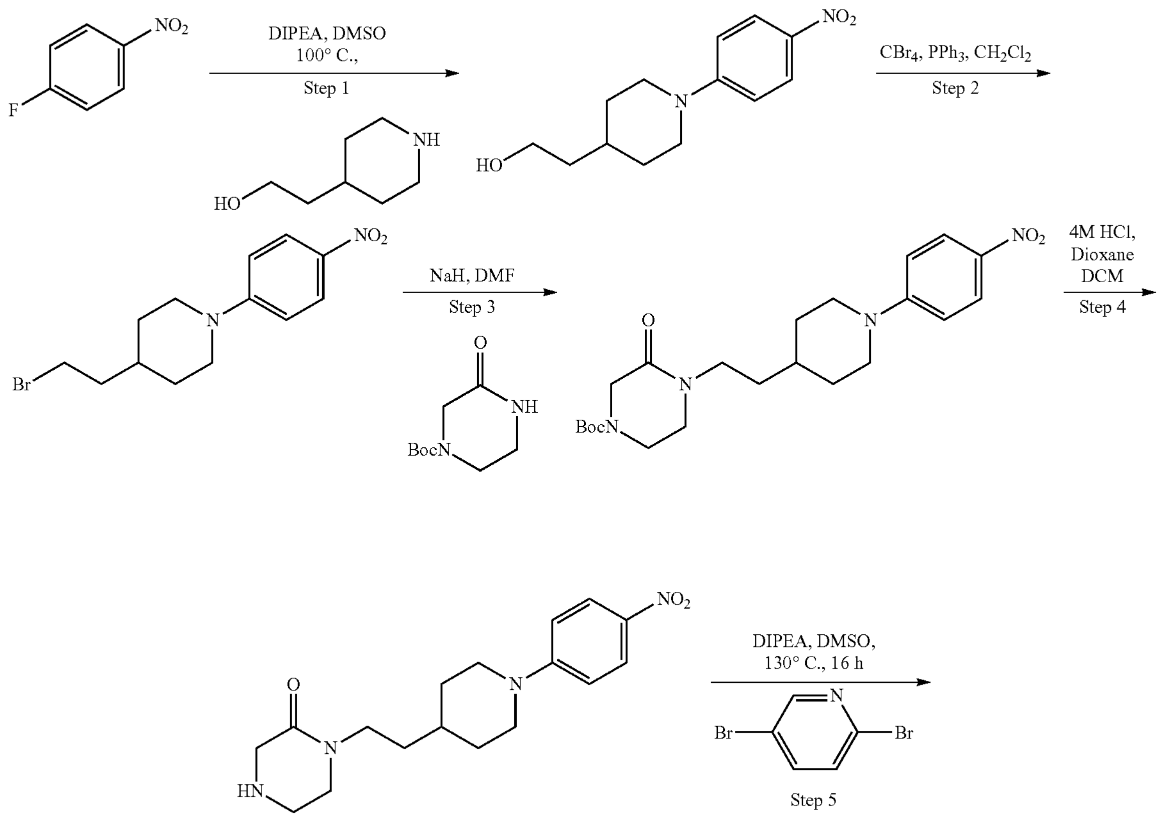

-continued
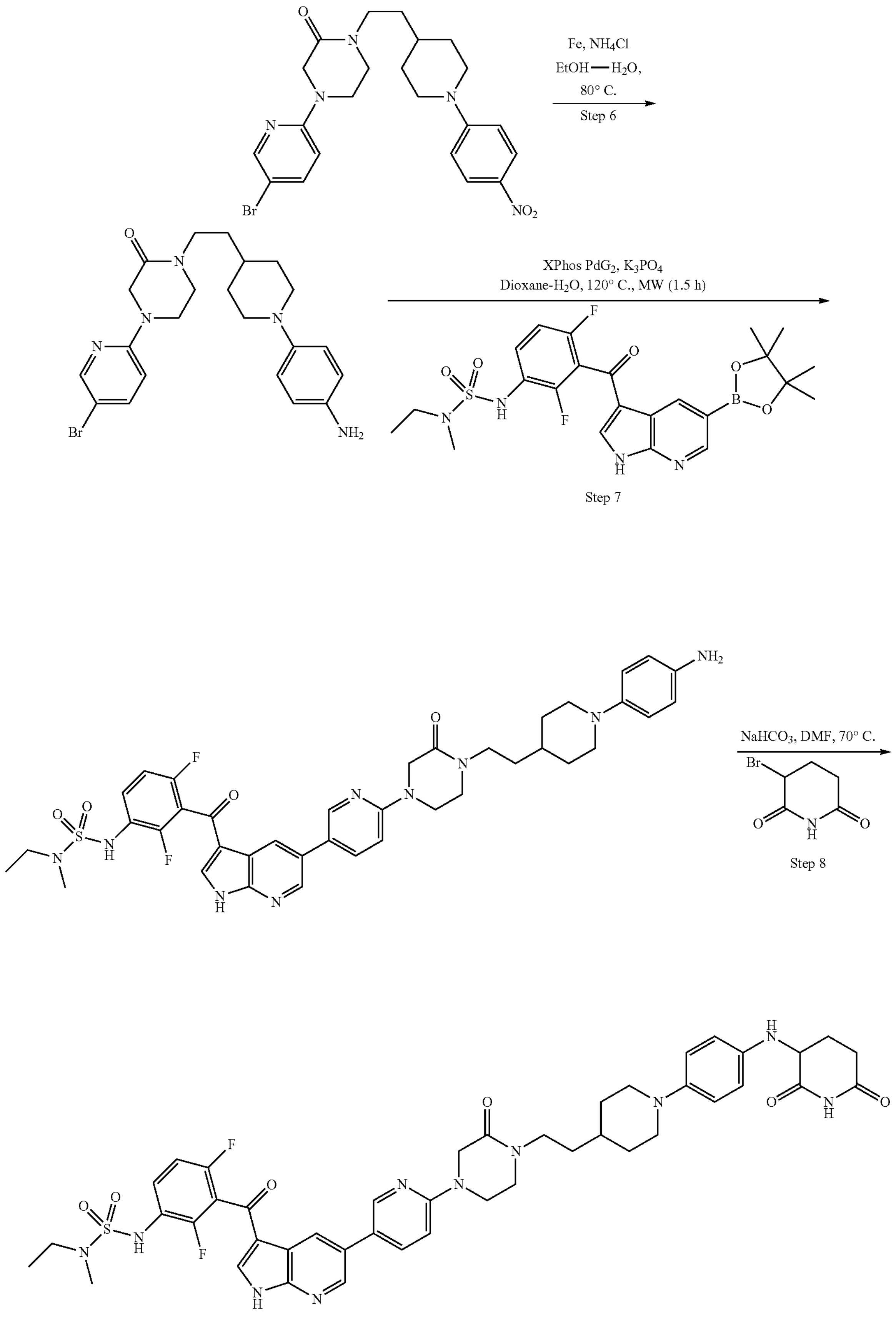

Step 1: To an oven-dried sealed tube (250 mL) was added 2-(4-piperidyl)ethanol (4 g, 30.96 mmol), 1-fluoro-4-nitrobenzene (4.81 g, 34.06 mmol, 3.61 mL) and DMSO (30 mL). N,N-diisopropylethylamine (12.00 g, 92.88 mmol, 16.18 mL) was added at 25° C., and the reaction mixture was allowed to stir overnight at 100° C. The resulting mixture was quenched with ice water, and the precipitate was collected by filtration over a Buchner funnel, washing with water. The yellow solid obtained was taken forward to the next step without further purification to provide 2-[1-(4-nitrophenyl)-4-piperidyl]ethanol (4.5 g, 17.08 mmol, 55.17% yield). LCMS (ESI+): 251.2 $[M+H]^+$.

Step 2: An oven-dried round bottom flask was charged with a solution of 2-[1-(4-nitrophenyl)-4-piperidyl]ethanol (1.5 g, 5.99 mmol) in dichloromethane (15 mL), Triphenylphosphine (1.57 g, 5.99 mmol) and carbon tetrabromide (1.99 g, 5.99 mmol, 581.12 μL) were added at 0° C. The reaction mixture was stirred at room temperature for 16 h. The reaction mixture was quenched with water (50 mL), and the product was extracted with dichloromethane (2×150 mL). The combined organic layer was dried over anhydrous sodium sulphate and concentrated under reduced pressure to afford 4-(2-bromoethyl)-1-(4-nitrophenyl)piperidine (1.7 g, 5.32 mmol, 88.76% yield) as a yellow solid. LCMS (ESI+): 313.0 $[M+H]^+$.

Step 3: An oven-dried round bottom flask was charged with tert-butyl 3-oxopiperazine-1-carboxylate (1.28 g, 6.39 mmol) and N,N-dimethylformamide (30 mL). Sodium hydride (in oil dispersion) 60% dispersion in mineral oil (367.03 mg, 15.96 mmol) was added at 0° C., and the reaction mixture was allowed to stir for 30 minutes. A solution of 4-(2-bromoethyl)-1-(4-nitrophenyl)piperidine (2 g, 6.39 mmol) in N,N-Dimethylformamide (15 mL) was then added to the mixture at 0° C., and stirring was continued for 3 h at 25° C. The resulting mixture was quenched with aqueous ammonium chloride and extracted with ethyl acetate (3×100 mL). The combined organic extracts were washed with water and brine solution, dried over anhydrous sodium sulphate, filtered and concentrated under reduced pressure. The resulting crude mixture was washed with diethyl ether 50 mL in petroleum ether to afford tert-butyl 4-[2-[1-(4-nitrophenyl)-4-piperidyl]ethyl]-3-oxo-piperazine-1-carboxylate (2.5 g, 5.36 mmol, 83.91% yield) as a yellow solid. LCMS (ESI+): 433.2 $[M+H]^+$.

Step 4: To a stirred solution of tert-butyl 4-[2-[1-(4-nitrophenyl)-4-piperidyl]ethyl]-3-oxo-piperazine-1-carboxylate (3 g, 6.94 mmol) in dichloromethane (10 mL), 4 M hydrochloric acid solution in dioxane (6.94 mmol, 20 mL) was added slowly at 0° C. The reaction mixture was stirred at room temperature for 4 h. The reaction mixture was concentrated under reduced pressure to afford 1-[2-[1-(4-nitrophenyl)-4-piperidyl]ethyl]piperazin-2-one (2.5 g, 6.78 mmol, 97.71% yield) off white solid. LCMS (ESI+): 333.1 $[M+H]^+$.

Step 5: An oven-dried sealed tube (100 mL) was charged with 1-[2-[1-(4-nitrophenyl)-4-piperidyl]ethyl]piperazin-2-one (2.5 g, 7.52 mmol) and 2,5-dibromopyridine (1.78 g, 7.52 mmol) in DMSO (25 mL). N,N-diisopropylethylamine (4.86 g, 37.61 mmol, 6.55 mL) was added at room temperature, and stirring was continued overnight at 130° C. The resulting mixture was quenched with water and extracted with ethyl acetate (3×100 ml). The combined organic extracts were washed with water and brine, dried over anhydrous sodium sulphate, filtered, and concentrated under reduced pressure to afford crude product which was purified by silica gel flush chromatography to obtain 4-(5-bromo-2-pyridyl)-1-[2-[1-(4-nitrophenyl)-4-piperidyl]ethyl]piperazin-2-one (1.5 g, 2.40 mmol, 31.85% yield) as yellow solid. LCMS (ESI+): 488.0 $[M+H]^+$.

Step 6: To a stirred solution of 4-(5-bromo-2-pyridyl)-1-[2-[1-(4-nitrophenyl)-4-piperidyl]ethyl]piperazin-2-one (700 mg, 1.43 mmol) in water (4 mL) and ethanol (12 mL) was added iron powder (400.22 mg, 7.17 mmol, 50.92 μL) and ammonium chloride (230.01 mg, 4.30 mmol, 150.33 μL) at room temperature. The reaction mixture was heated to 80° C. for 3 h. The reaction mixture was filtered, and the filtrate was concentrated under reduced pressure. The crude material thus obtained was diluted with 10% methanol in dichloromethane (15 mL) and washed with water and brine. The organic layer was dried over sodium sulphate and concentrated under reduced pressure to provide 1-[2-[1-(4-aminophenyl)-4-piperidyl]ethyl]-4-(5-bromo-2-pyridyl)piperazin-2-one (550 mg, 1.10 mmol, 77.01% yield) as brown solid. LCMS (ESI+): 460.0 $[M+H]^+$.

Step 7: To a stirred solution of 1-[2-[1-(4-aminophenyl)-4-piperidyl]ethyl]-4-(5-bromo-2-pyridyl)piperazin-2-one (200 mg, 436.31 μmol) in 1,4-dioxane (3 mL) and water (7 mL) in a microwave vial, was added 3-[3-[[ethyl(methyl)sulfamoyl]amino]-2,6-difluoro-benzoyl]-5-(4,4,5,5-tetramethyl-1,3,2-dioxaborolan-2-yl)-1H-pyrrolo[2,3]pyridine (272.44 mg, 523.57 μmol) and tripotassium phosphate (277.84 mg, 1.31 mmol) at room temperature under nitrogen. The reaction mixture was degassed with nitrogen for 10 min, then XPhos Pd G2 (68.59 mg, 87.17 μmol) was added. The reaction mixture was irradiated in a microwave at 120° C. for 1 h. Water and 5% methanol in dichloromethane (2×35 ml) were added to the reaction mixture. The combined organic layers were washed with water and brine, dried over sodium sulphate and concentrated under reduced pressure. The crude product was purified by silica gel column chromatography using methanol/$CH_2Cl_2$ used as an eluent (0-10%) to afford 5-[6-[4-[2-[1-(4-aminophenyl)-4-piperidyl]ethyl]-3-oxo-piperazin-1-yl]-3-pyridyl]-3-[3-[[ethyl(methyl)sulfamoyl]amino]-2,6-difluoro-benzoyl]-1H-pyrrolo[2,3-b]pyridine (120 mg, 132.15 μmol, 30.29% yield) as pale brown solid. LCMS (ESI+): 772.1 $[M+H]^+$.

Step 8: To a stirred solution of 3-bromopiperidine-2,6-dione (136.82 mg, 712.55 μmol) in N,N-dimethylformamide (5 mL) was added sodium hydrogen carbonate (59.86 mg, 712.55 μmol, 27.71 μL) and 5-[6-[4-[2-[1-(4-aminophenyl)-4-piperidyl]ethyl]-3-oxo-piperazin-1-yl]-3-pyridyl]-3-[3-[[ethyl(methyl)sulfamoyl]amino]-2,6-difluoro-benzoyl]-1H-pyrrolo[2,3-b]pyridine (220 mg, 285.02 μmol) at room temperature. The resulting solution was heated to 75° C. for 16 h. The solution was diluted with water (10 ml) and extracted with 10% dichloromethane/methanol (2×10 mL). The combined organic layers were washed with water, brine, dried over sodium sulphate and concentrated under reduced pressure. The crude product was purified by mass-directed preparative HPLC [Mobile-phase A: 0.1% TFA in water, Mobile-phase B: acetonitrile] to afford 5-[6-[4-[2-[1-[4-[(2,6-dioxo-3-piperidyl)amino]phenyl]-4-piperidyl]ethyl]-3-oxo-piperazin-1-yl]-3-pyridyl]-3-[3-[[ethyl(methyl)sulfamoyl]amino]-2,6-difluoro-benzoyl]-1H-pyrrolo[2,3-b]pyridine (30 mg, 29.87 μmol, 10.48% yield) as an off-white solid. LCMS (ESI+): 883.2 $[M+H]^+$. $^1H$ NMR (400 MHz, DMSO-$d_6$): δ 12.97 (s, 1H), 10.83 (s, 1H), 10.62 (s, 1H), 9.71 (s, 1H), 8.69 (s, 1H), 8.55 (s, 2H), 8.13 (s, 1H), 8.03-8.00 (m, 1H), 7.62-7.56 (m, 1H), 7.39 (d, J=7.60 Hz, 2H), 7.28 (t, J=8.00 Hz, 1H), 7.06 (d, J=24.00 Hz, 1H), 6.77 (d, J=8.80 Hz, 1H), 6.36 (s, 1H), 4.41-4.39 (m, 1H), 4.17 (s, 2H), 3.91-3.89 (m, 3H), 3.57-3.30 (m, 6H), 3.12 (q, J=7.20 Hz, 2H), 2.76-2.72 (m, 4H), 2.58-2.50 (m, 3H), 2.08-1.94 (m, 3H), 1.93-1.89 (m, 1H), 1.57 (s, 4H), 1.03 (t, J=7.20 Hz, 3H).

Example 149
5-[2-[4-[2-[4-[4-[(2,6-dioxo-3-piperidyl)amino]phenyl]-1-piperidyl]ethyl]-4-hydroxy-1-piperidyl]pyrimidin-5-yl]-3-[3-[[ethyl(methyl)sulfamoyl]amino]-2,6-difluoro-benzoyl]-1H-pyrrolo[2,3-b]pyridine
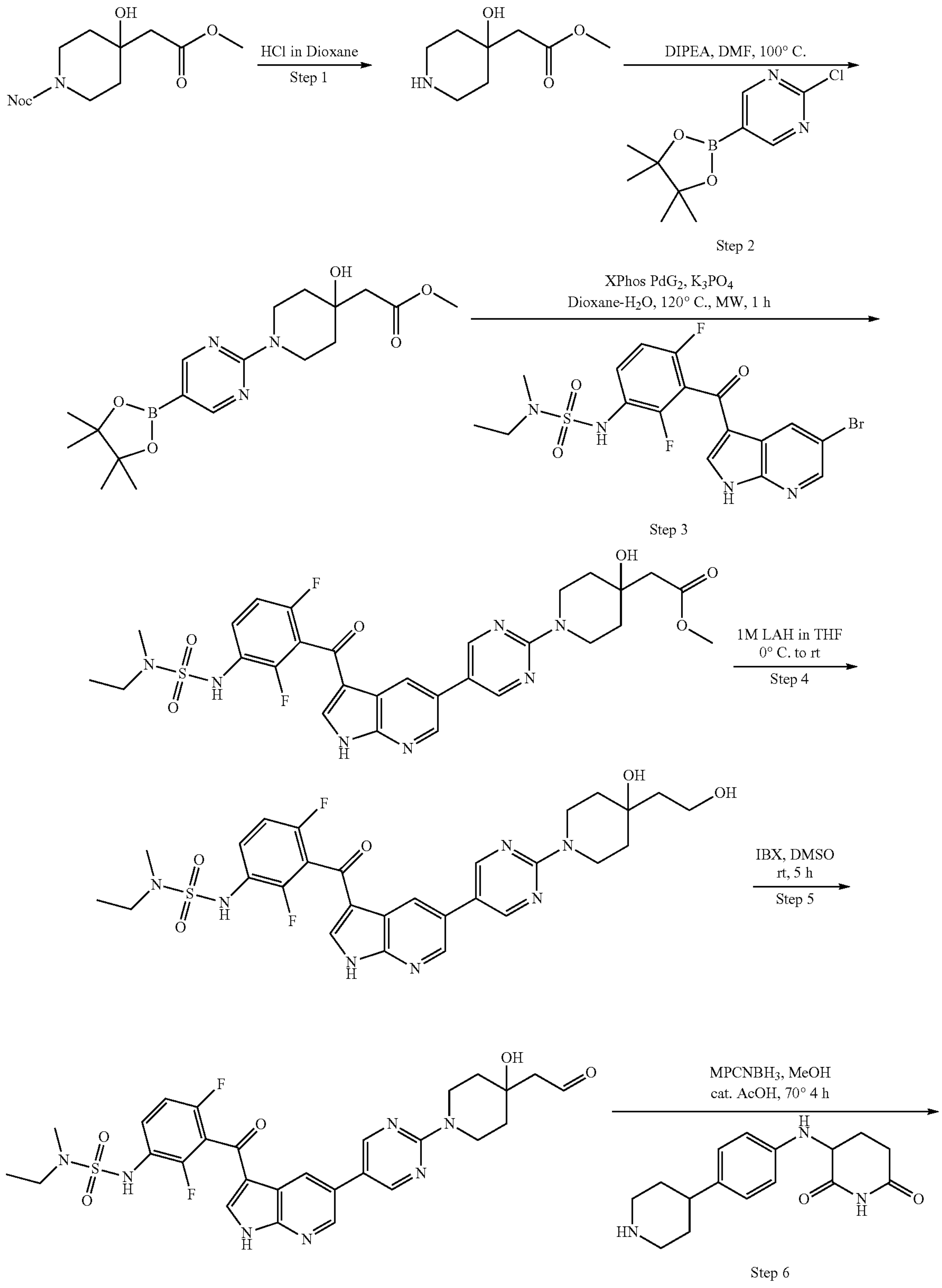

-continued

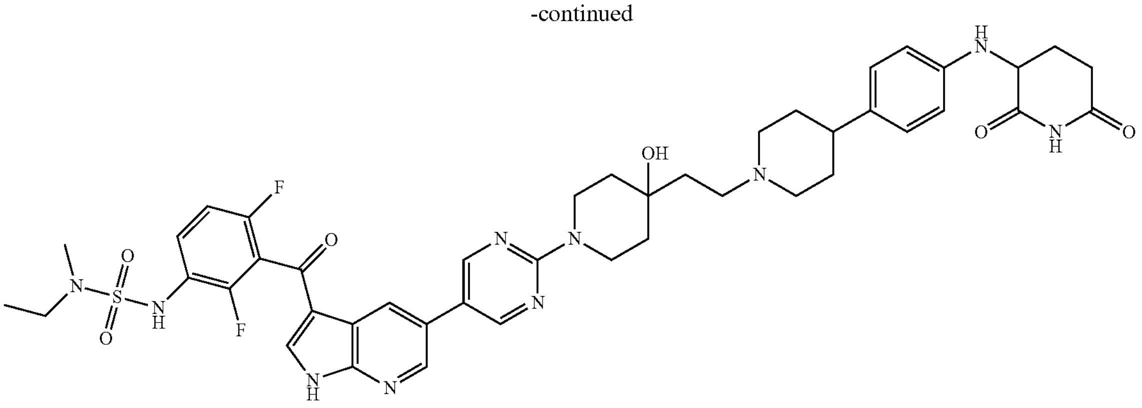

Step 1: To a stirred solution of tert-butyl 4-hydroxy-4-(2-methoxy-2-oxo-ethyl)piperidine-1-carboxylate (2.7 g, 9.88 mmol) in dichloromethane (5 mL) at 0° C. was added 4 M hydrochloric acid in 1,4-dioxane (9.88 mmol, 10 mL). The reaction mixture was warmed to room temperature, and stirring was continued for 2 h. The reaction mixture was concentrated under reduced pressure, and the crude residue was triturated with toluene to afford methyl 2-(4-hydroxy-4-piperidyl)acetate (2 g, 9.44 mmol, 95.60% yield) as white solid. LCMS (ESI+): 174.0 $[M+H]^+$.

Step 2: An oven-dried sealed tube was charged with methyl 2-(4-hydroxy-4-piperidyl)acetate (2 g, 11.55 mmol) and N,N-dimethylformamide (60 mL). To the mixture was added 2-chloro-5-(4,4,5,5-tetramethyl-1,3,2-dioxaborolan-2-yl)pyrimidine (3.05 g, 12.70 mmol) and N,N-diisopropylethylamine (4.86 g, 37.61 mmol, 6.55 mL) at room temperature, and the reaction mixture was stirred for 16 h at 120° C. The resulting mixture was quenched with ice water and extracted with ethyl acetate. The combined organic extracts were washed with water and brine, dried over anhydrous sodium sulphate, filtered, and concentrated under reduced pressure to afford methyl 2-[4-hydroxy-1-[5-(4,4,5,5-tetramethyl-1,3,2-dioxaborolan-2-yl)pyrimidin-2-yl]-4-piperidyl]acetate (4 g, 9.86 mmol, 85.40% yield) as brownish yellow solid. LCMS (ESI+): 378.2 $[M+H]^+$.

Step 3: To a stirred solution of methyl 2-[4-hydroxy-1-[5-(4,4,5,5-tetramethyl-1,3,2-dioxaborolan-2-yl)pyrimidin-2-yl]-4-piperidyl]acetate (1.20 g, 3.17 mmol) in 1,4 dioxane (8 mL) and water (2 mL) were added methyl 2-[4-hydroxy-1-[5-(4,4,5,5-tetramethyl-1,3,2-dioxaborolan-2-yl)pyrimidin-2-yl]-4-piperidyl]acetate (1.20 g, 3.17 mmol) and tripotassium phosphate (1.35 g, 6.34 mmol) at room temperature under nitrogen. The reaction mixture was degassed with nitrogen for 10 min, then XPhos Pd G2 (166.07 mg, 211.29 μmol) was added. The reaction mixture was heated at 100° C. for 16 h in a sealed tube. To quench the reaction, water was added, followed by ethyl acetate. The organic layer was collected, evaporated under reduced pressure, and the crude residue purified by column chromatography to obtain methyl 2-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-hydroxy-4-piperidyl]acetate (750 mg, 466.08 μmol, 22.06% yield) as off white solid. LCMS (ESI+): 644.2 $[M+H]^+$.

Step 4: To a stirred solution of methyl 2-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-hydroxy-4-piperidyl]acetate (700 mg, 1.09 mmol) in THF (10 mL) at −78° C. was added very slowly lithium aluminum hydride (36.89 mg, 1.09 mmol, 1.5 mL). The reaction mixture was allowed to warm to room temperature and stir for 2 h. The reaction was quenched by addition of ammonium chloride solution. The organic phase was collected, concentrated under reduced pressure and the crude residue purified by silica gel column chromatography to afford 3-[3-[[ethyl(methyl)sulfamoyl]amino]-2,6-difluoro-benzoyl]-5-[2-[4-hydroxy-4-(2-hydroxyethyl)-1-piperidyl]pyrimidin-5-yl]-1H-pyrrolo[2,3-b]pyridine (270 mg, 372.78 μmol, 34.28% yield) as off white solid. LCMS (ESI+): 616.2 $[M+H]^+$.

Step 5: To a stirred solution of 3-[3-[[ethyl(methyl)sulfamoyl]amino]-2,6-difluoro-benzoyl]-5-[2-[4-hydroxy-4-(2-hydroxyethyl)-1-piperidyl]pyrimidin-5-yl]-1H-pyrrolo[2,3-b]pyridine (230 mg, 373.59 μmol) in DMSO (0.5 mL) was added IBX (125.53 mg, 448.31 μmol) at room temperature. The resultant mixture was stirred for 4 h at room temperature. Water and ethyl acetate were added to the reaction mixture. The layers were separated, and the aqueous was further extracted with ethyl acetate (2×100 mL). The combined organic layers were dried over sodium sulphate and concentrated under reduced pressure to afford 3-[3-[[ethyl(methyl)sulfamoyl]amino]-2,6-difluoro-benzoyl]-5-[2-[4-hydroxy-4-(2-oxoethyl)-1-piperidyl]pyrimidin-5-yl]-1H-pyrrolo[2,3-b]pyridine (230 mg, 293.48 μmol, 78.56% yield) as pale brown solid. LCMS (ESI+): 614.2 $[M+H]^+$.

Step 6: To a stirred solution of 3-[3-[[ethyl(methyl)sulfamoyl]amino]-2,6-difluoro-benzoyl]-5-[2-[4-hydroxy-4-(2-oxoethyl)-1-piperidyl]pyrimidin-5-yl]-1H-pyrrolo[2,3-b]pyridine (230 mg, 374.82 μmol) in methanol (2 mL) was added 3-[4-(4-piperidyl)anilino]piperidine-2,6-dione (145.65 mg, 449.78 μmol), acetic acid (2.25 mg, 37.48 μmol, 2.14 μL) and MP-$CNBH_3$ (460 mg) at room temperature. The resultant mixture was stirred for 4 h at 70° C. The reaction mixture was cooled to room temperature, filtered through filter paper, and the residue washed with methanol (50 mL) and evaporated under reduced pressure to obtain crude product as pale green oil (300 mg). The crude material was further purified by reverse phase purification to afford 5-[2-[4-[2-[4-[4-[(2,6-dioxo-3-piperidyl)amino]phenyl]-1-piperidyl]ethyl]-4-hydroxy-1-piperidyl]pyrimidin-5-yl]-3-[3-[[ethyl(methyl)sulfamoyl]amino]-2,6-difluoro-benzoyl]-1H-pyrrolo[2,3-b]pyridine (32 mg, 33.57 μmol, 8.96% yield) as pale green solid. LCMS (ESI+): 885.3 $[M+H]^+$. $^1H$ NMR (400 MHz, DMSO-$d_6$): δ 13.00 (s, 1H), 10.77 (s, 1H), 8.73 (s, 2H), 8.66 (s, 1H), 8.53 (s, 1H), 8.12 (s, 1H), 7.60-7.54 (m, 1H), 7.24 (t, J=9.20 Hz, 1H), 6.96 (d, J=8.40 Hz, 2H), 6.61 (d, J=8.80 Hz, 2H), 5.66 (d, J=7.60 Hz, 1H), 4.40-4.27 (m, 3H), 3.44-3.04 (m, 4H), 2.68-2.67 (m, 2H), 2.34-2.01 (m, 3H), 1.87-1.84 (m, 2H), 1.74-1.70 (m, 2H), 1.62-1.48 (m, 11H), 1.02 (t, J=7.20 Hz, 3H).

Example 150
5-[[4-[4-[(2,6-dioxo-3-piperidyl)amino]phenyl]-1-piperidyl]methyl]-2-[5-[3-[3-[[ethyl(methyl)sulfamoyl]amino]-2,6-difluoro-benzoyl]-1H-pyrrolo[2,3-b]pyridin-5-yl]pyrimidin-2-yl]-3,4-dihydro-1H-isoquinoline
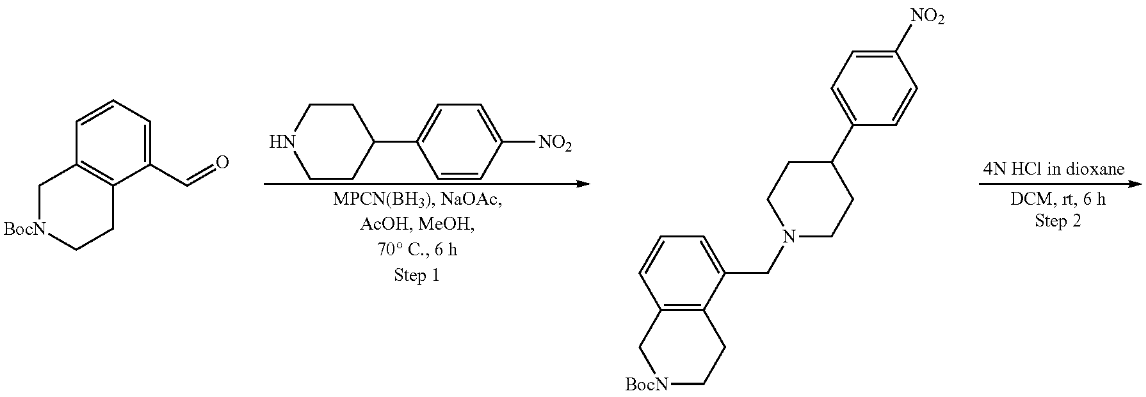
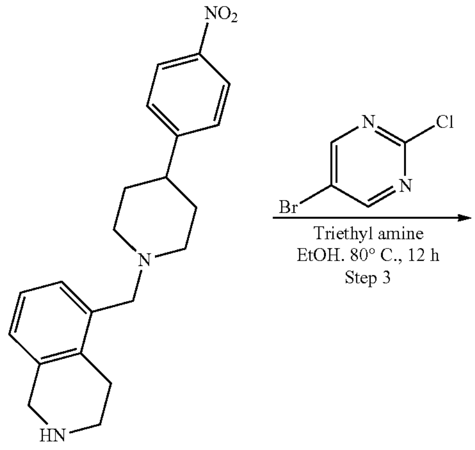
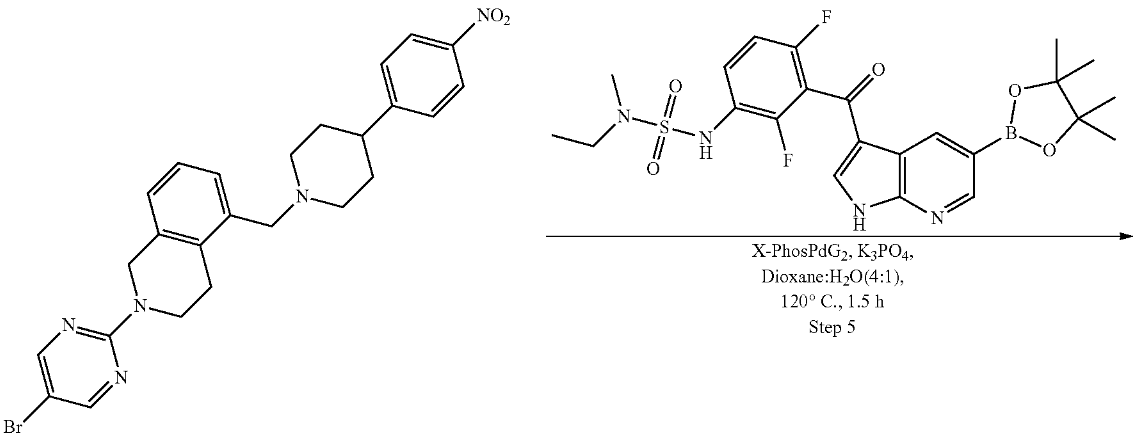

-continued
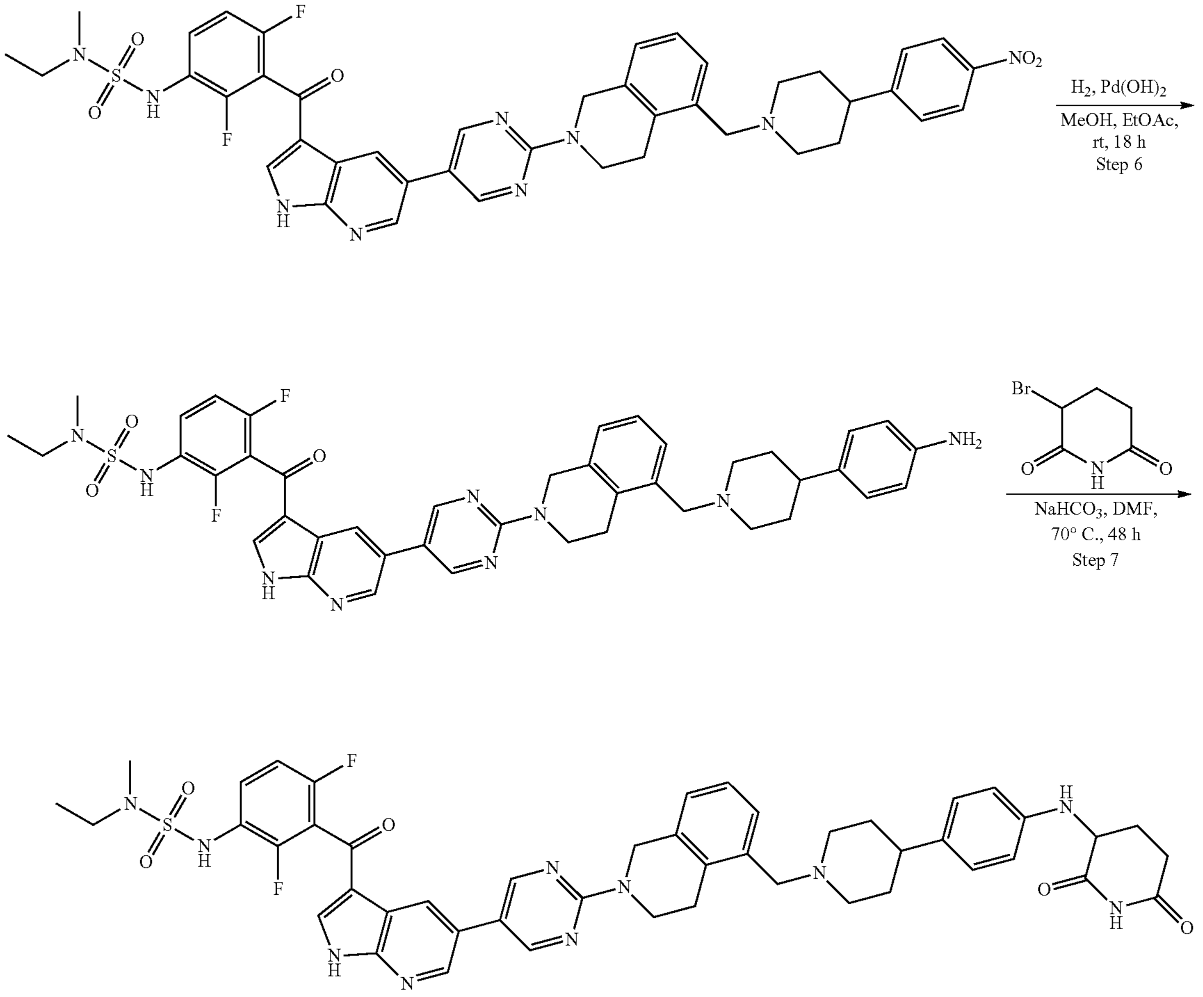
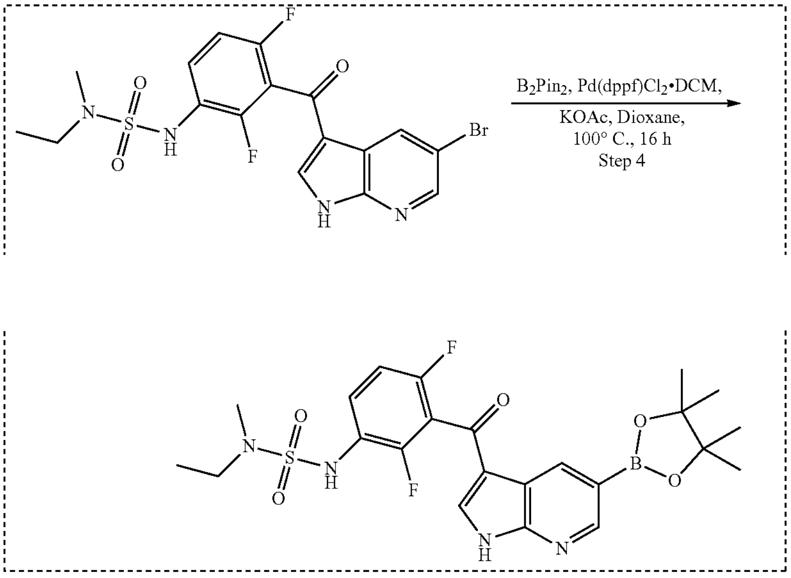

Step 1: To a stirred solution of tert-butyl 5-formyl-3,4-dihydro-1H-isoquinoline-2-carboxylate (950.28 mg, 3.64 mmol) in methanol (20 mL), was added MP-Cyanoborohydride (3.64 mmol), acetic acid (327.57 mg, 5.45 mmol, 311.97 anhydrous sodium acetate (1.19 g, 14.55 mmol, 779.92 μL) and 4-(4-nitrophenyl)piperidine (0.75 g, 3.64 mmol) at room temperature. The reaction mixture was stirred at 70° C. for 6 h. The reaction mixture was filtered and concentrated, diluted with water (30 mL), and extracted with ethyl acetate (3×50 mL). The combined organic layers were dried over sodium sulphate, filtered, and concentrated under reduced pressure. The crude material was purified by silica gel column chromatography using 40-50% ethyl acetate in petroleum ether as eluent to afford tert-butyl 5-[[4-(4-nitrophenyl)-1-piperidyl]methyl]-3,4-dihydro-1H-isoquinoline-2-carboxylate (1.25 g, 2.13 mmol, 58.67% yield) as light brown gummy liquid. LCMS (ESI+): 452.0 $[M+H]^+$.

Step 2: To a stirred solution of tert-butyl 5-[[4-(4-nitrophenyl)-1-piperidyl]methyl]-3,4-dihydro-1H-isoquinoline-2-carboxylate (1.25 g, 2.77 mmol) in dichloromethane (20 mL) was added hydrogen chloride solution (4M in 1,4-dioxane, 9.60 g, 263.30 mmol, 12 mL) at 5° C. The reaction mixture was stirred at room temperature for 6 h. After completion, the reaction mixture was concentrated under reduced pressure to afford crude 5-[[4-(4-nitrophenyl)-1-piperidyl]methyl]-1,2,3,4-tetrahydroisoquinoline (1.1 g, 1.97 mmol, 71.03% yield) as off white solid. LCMS (ESI+): 352.0 $[M+H]^+$.

Step 3: To a stirred solution of 5-[[4-(4-nitrophenyl)-1-piperidyl]methyl]-1,2,3,4-tetrahydroisoquinoline (0.6 g, 1.55 mmol) in ethanol (20 mL) were added triethylamine (782.59 mg, 7.73 mmol, 1.08 mL) and 5-bromo-2-chloro-pyrimidine (598.39 mg, 3.09 mmol) at room temperature. The reaction mixture was stirred at 80° C. for 12 h, then diluted with water (30 mL) and extracted with ethyl acetate (3×50 mL). The combined organic layers were dried over sodium sulphate, filtered, and concentrated under reduced pressure. The crude residue was purified by column chromatography using 15-20% ethyl acetate in petroleum ether as eluent to afford 2-(5-bromopyrimidin-2-yl)-5-[[4-(4-nitrophenyl)-1-piperidyl]methyl]-3,4-dihydro-1H-isoquinoline (0.49 g, 950.10 μmol, 61.42% yield) as light yellow solid. LCMS (ESI+): 509.8 $[M+H]^+$.

Step 4: 5-bromo-3-[3-[[ethyl(methyl)sulfamoyl]amino]-2,6-difluoro-benzoyl]-1H-pyrrolo[2,3-b]pyridine (1.5 g, 3.17 mmol) was dissolved in 1,4-dioxane (15 mL) in a sealed tube. To the reaction mixture were added 4,4,5,5-tetramethyl-2-(4,4,5,5-tetramethyl-1,3,2-dioxaborolan-2-yl)-1,3,2-dioxaborolane (1.61 g, 6.34 mmol) and potassium acetate (933.13 mg, 9.51 mmol, 594.35 μL). The reaction mixture was purged with nitrogen gas for 10 minutes. $Pd(dppf)Cl_2$·dichloromethane (258.82 mg, 316.93 μmol) was added, and the reaction mixture was purged again with nitrogen for 5 minutes and stirred at 100° C. for 16 h. The reaction mixture was diluted with water (50 mL), extracted with ethyl acetate (3×70 mL). The combined organic layers were dried over sodium sulfate, filtered and concentrated under reduced pressure. The crude residue was purified by column chromatography using 80-90% ethyl acetate in petroleum ether as eluent to afford 3-[3-[[ethyl(methyl)sulfamoyl]amino]-2,6-difluoro-benzoyl]-5-(4,4,5,5-tetramethyl-1,3,2-dioxaborolan-2-yl)-1H-pyrrolo[2,3-b]pyridine (1.35 g, 2.17 mmol, 68.32% yield) as light red solid. LCMS (ESI+): 521.2 $[M+H]^+$.

Step 5: A mixture of 2-(5-bromopyrimidin-2-yl)-5-[[4-(4-nitrophenyl)-1-piperidyl]methyl]-3,4-dihydro-1H-isoquinoline (0.46 g, 904.78 μmol), 1,4-dioxane (15 mL), and water (3.5 mL) was combined in a microwave vial. Tripotassium phosphate (576.16 mg, 2.71 mmol) and 3-[3-[[ethyl(methyl)sulfamoyl]amino]-2,6-difluoro-benzoyl]-5-(4,4,5,5-tetramethyl-1,3,2-dioxaborolan-2-yl)-1H-pyrrolo[2,3-b]pyridine (564.97 mg, 1.09 mmol) were added. The reaction mixture was purged with nitrogen gas for 10 minutes. XPhos Pd G2 (71.19 mg, 90.59 μmol) was added, and the reaction mixture was purged again with nitrogen for 5 minutes. The reaction mixture was irradiated in a microwave at 120° C. for 1.5 h. The reaction mixture was diluted with water (50 mL) and extracted with ethyl acetate (3×70 mL). The combined organic layers were dried over sodium sulphate, filtered, and concentrated under reduced pressure. The crude residue was purified by column chromatography (60-120 silica gel) using 100% ethyl acetate in petroleum ether as eluent to afford 2-[5-[3-[3-[[ethyl(methyl)sulfamoyl]amino]-2,6-difluoro-benzoyl]-1H-pyrrolo[2,3-b]pyridin-5-yl]pyrimidin-2-yl]-5-[[4-(4-nitrophenyl)-1-piperidyl]methyl]-3,4-dihydro-1H-isoquinoline (0.32 g, 30.54% yield) as light brown solid. LCMS (ESI+): 822.3 $[M+H]^+$.

Step 6: To a stirred solution of 2-[5-[3-[3-[[ethyl(methyl)sulfamoyl]amino]-2,6-difluoro-benzoyl]-1H-pyrrolo[2,3-b]pyridin-5-yl]pyrimidin-2-yl]-5-[[4-(4-nitrophenyl)-1-piperidyl]methyl]-3,4-dihydro-1H-isoquinoline (320.39 mg, 389.81 μmol) in methanol (7 mL) and ethyl acetate (7 mL), was added $Pd(OH)_2$ (273.72 mg, 1.95 mmol). The resultant reaction mixture was subjected for hydrogenation (1 atm) at room temperature for 16 h. The reaction mixture was purged with nitrogen, and catalyst was removed by filtration through celite pad. The filtrate was concentrated under reduced pressure to afford crude 5-[[4-(4-aminophenyl)-1-piperidyl]methyl]-2-[5-[3-[3-[[ethyl(methyl)sulfamoyl]amino]-2,6-difluoro-benzoyl]-1H-pyrrolo[2,3-b]pyridin-5-yl]pyrimidin-2-yl]-3,4-dihydro-1H-isoquinoline (0.2 g, 105.67 μmol, 27.11% yield) as light yellow solid. LCMS (ESI+): 792.3 $[M+H]^+$.

Step 7: To a solution of 5-[[4-(4-aminophenyl)-1-piperidyl]methyl]-2-[5-[3-[3-[[ethyl(methyl)sulfamoyl]amino]-2,6-difluoro-benzoyl]-1H-pyrrolo[2,3-b]pyridin-5-yl]pyrimidin-2-yl]-3,4-dihydro-1H-isoquinoline (0.2 g, 252.55 μmol) in N, N-dimethylformamide (10 mL) in a sealed tube was added sodium bicarbonate (84.86 mg, 1.01 mmol, 39.29 μL) and 3-bromopiperidine-2,6-dione (169.73 mg, 883.94 μmol) at room temperature. The reaction mixture was stirred at 70° C. for 48 h. The reaction mixture was diluted with water (20 mL) and extracted with 10% isopropyl alcohol in dichloromethane (3×30 mL). The combined organic layers were washed with cold water (3×20 mL), dried over sodium sulphate, filtered, and concentrated under reduced pressure. The crude material was purified by preparative-HPLC (10 mM ammonium acetate in water/acetonitrile) to afford 5-[[4-[4-[(2,6-dioxo-3-piperidyl)amino]phenyl]-1-piperidyl]methyl]-2-[5-[3-[3-[[ethyl(methyl)sulfamoyl]amino]-2,6-difluoro-benzoyl]-1H-pyrrolo[2,3-b]pyridin-5-yl]pyrimidin-2-yl]-3,4-dihydro-1H-isoquinoline (17.19 mg, 17.17 μmol, 6.80% yield) as green solid. LCMS (ESI+): 903.0 $[M+H]^+$. $^1H$ NMR (400 MHz, DMSO-$d_6$): δ 13.02 (s, 1H), 10.78 (s, 1H), 9.71 (s, 1H), 8.84 (s, 2H), 8.69 (d, J=2.00 Hz, 1H), 8.59 (s, 1H), 8.15 (d, J=3.20 Hz, 1H), 7.56-7.62 (m, 1H), 7.47-7.45 (m, 2H), 7.26-7.39 (m, 2H), 6.94 (d, J=8.40 Hz, 2H), 6.63 (d, J=8.40 Hz, 2H), 5.75 (s, 1H), 5.03 (s, 2H), 4.41 (d, J=4.40 Hz, 2H), 4.21-4.30 (m, 1H), 4.10-4.13 (m, 2H), 3.48-3.52 (m, 2H), 3.15-3.23 (m, 2H), 3.09-3.15 (m, 5H), 2.74 (s, 3H), 2.63-2.71 (m, 2H), 2.01-2.15 (m, 1H), 1.80-1.95 (m, 5H), 1.02 (t, J=7.20 Hz, 3H).

Example 151
5-[2-[6-[4-[4-[(2,6-dioxo-3-piperidyl)amino]phenyl]-1-piperidyl]-2-azaspiro[3.3]heptan-2-yl]pyrimidin-5-yl]-3-[3-[[ethyl(methyl)sulfamoyl]amino]-2,6-difluoro-benzoyl]-1H-pyrrolo[2,3-b]pyridine
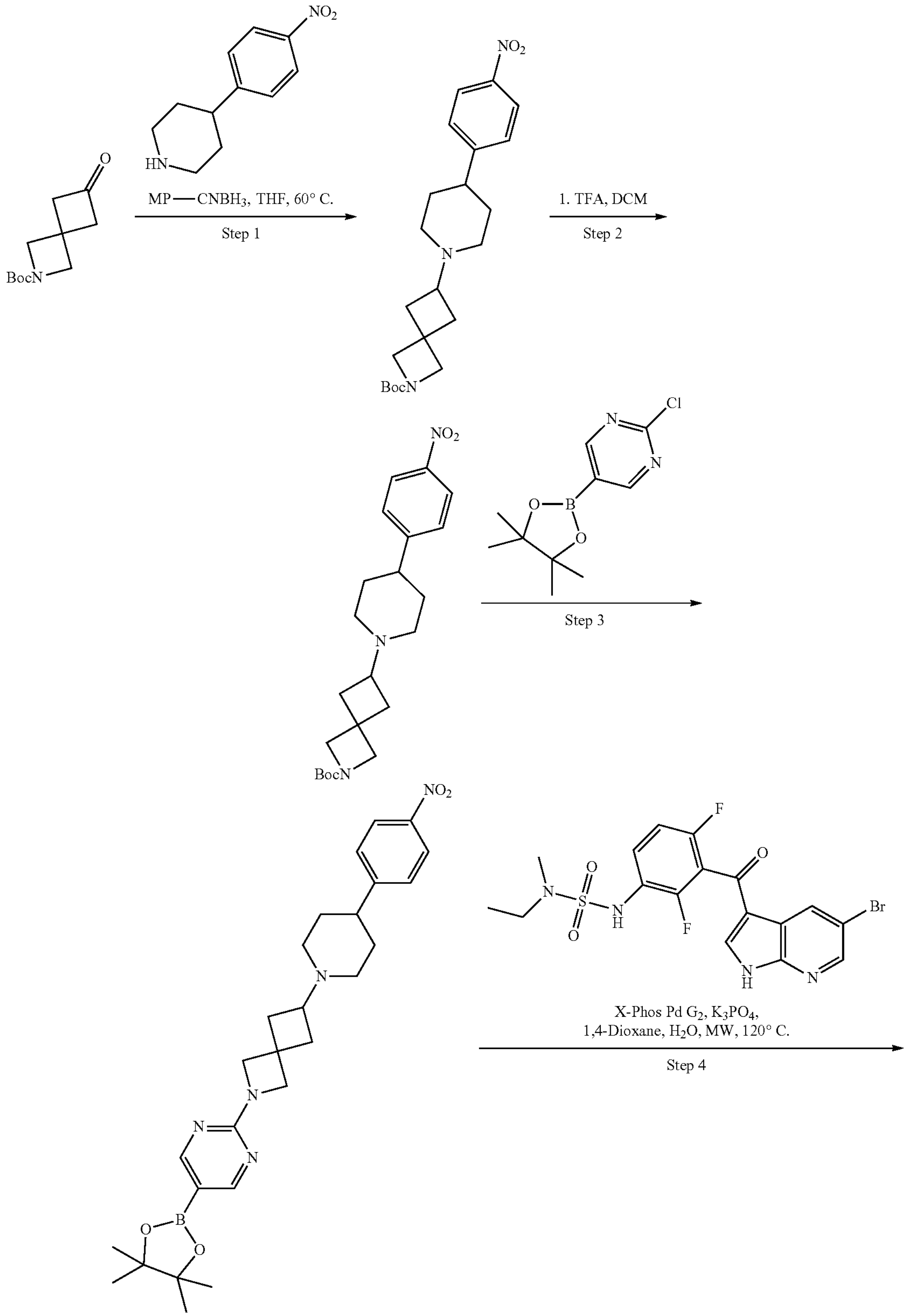

-continued

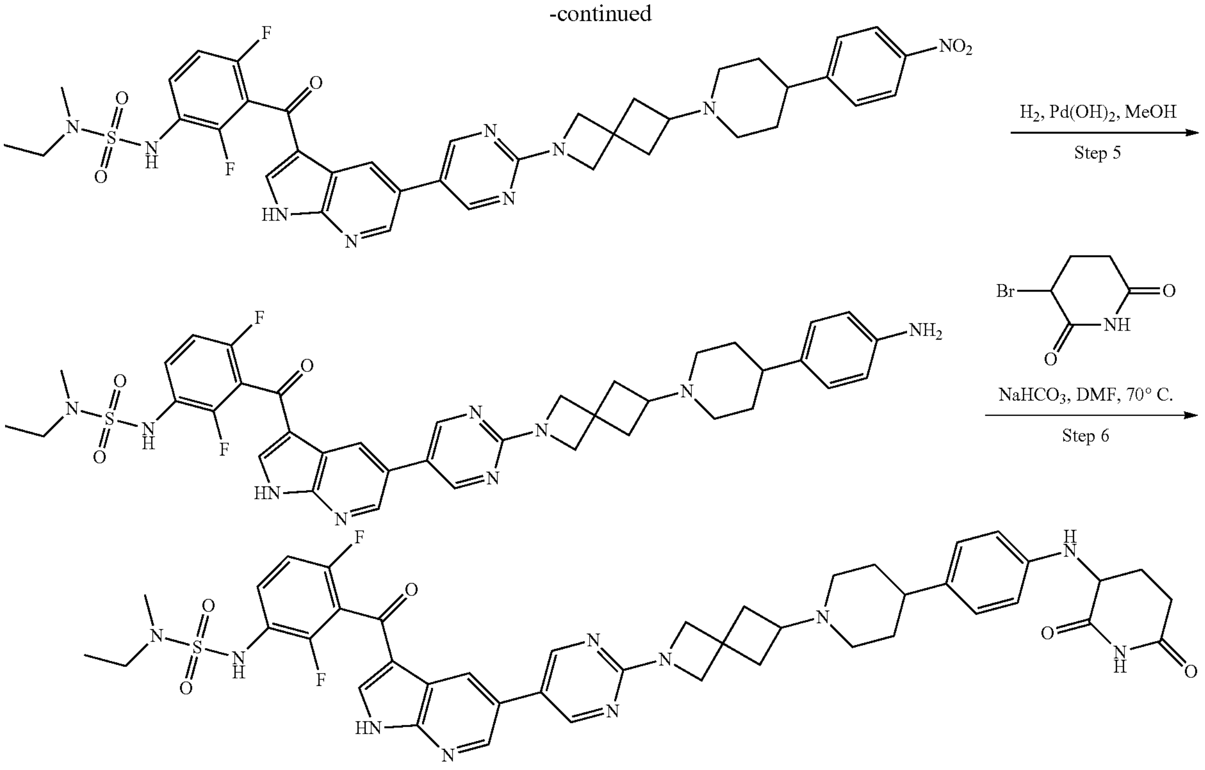

Step 1: To a mixture of 4-(4-nitrophenyl)piperidine (1.0 g, 4.85 mmol) and tert-butyl 6-oxo-2-azaspiro[3.3]heptane-2-carboxylate (1.02 g, 4.85 mmol) in methanol (20 mL) were added acetic acid (105.00 mg, 1.75 mmol, 0.1 mL) followed by MPCNBH$_3$ (1.0 g, 4.85 mmol) at room temperature. The reaction mixture was heated at 70° C. for 16 h. The reaction mixture was filtered, and the resulting filtrate was concentrated under reduced pressure. The filtrate was added to water (20 mL) and extracted with ethyl acetate (2×50 mL). The combined organic layers were dried over sodium sulphate, filtered, and concentrated under reduced pressure. The crude product was purified by silica gel column chromatography using 50% ethyl acetate in petroleum ether to afford tert-butyl 6-[4-(4-nitrophenyl)-1-piperidyl]-2-azaspiro[3.3]heptane-2-carboxylate (1.5 g, 2.88 mmol, 59.33% yield) as an oily liquid. LCMS (ESI+): 402.2 [M+H]$^+$.

Step 2: To a stirred solution of tert-butyl 6-[4-(4-nitrophenyl)-1-piperidyl]-2-azaspiro[3.3]heptane-2-carboxylate (1.5 g, 3.74 mmol) in dichloromethane (10 mL) was added trifluoroacetic acid (2.96 g, 25.96 mmol, 2 mL) at 0° C. The reaction mixture was warmed to room temperature and stirred for 2 h. The reaction mixture was concentrated under reduced pressure, and the resulting crude product was triturated with diethyl ether and dried to afford 6-[4-(4-nitrophenyl)-1-piperidyl]-2-azaspiro[3.3]heptane (1.3 g, 2.19 mmol, 58.64% yield, trifluoroacetic acid salt) as a brown solid. LCMS (ESI+): 302.1 [M+H]$^+$.

Step 3: To a mixture of 6-[4-(4-nitrophenyl)-1-piperidyl]-2-azaspiro[3.3]heptane (1.3 g, 4.31 mmol) and 2-chloro-5-(4,4,5,5-tetramethyl-1,3,2-dioxaborolan-2-yl)pyrimidine (1.04 g, 4.31 mmol) in N,N-dimethylformamide (15 mL) was added N,N-diisopropylethylamine (557.48 mg, 4.31 mmol, 751.32 μL) at room temperature under nitrogen atmosphere. The reaction mixture was heated at 100° C. for 12 h. The reaction mixture was cooled room temperature and poured into ice water (30 mL). The resulting solid was filtered, washed with cold water, and dried under vacuum to afford [2-[6-[4-(4-nitrophenyl)-1-piperidyl]-2-azaspiro[3.3]heptan-2-yl]pyrimidin-5-yl]boronic acid (1.4 g, 2.32 mmol, 53.68% yield) as an off-white solid. LCMS (ESI+): 506.3 [M+H]$^+$.

Step 4: A mixture of [2-[6-[4-(4-nitrophenyl)-1-piperidyl]-2-azaspiro[3.3]heptan-2-yl]pyrimidin-5-yl]boronic acid (600 mg, 1.42 mmol), 5-bromo-3-[3-[[ethyl(methyl)sulfamoyl]amino]-2,6-difluoro-benzoyl]-1H-pyrrolo[2,3-b]pyridine (500 mg, 1.06 mmol), and anhydrous tripotassium phosphate (673 mg, 3.17 mmol) in 1,4-dioxane (5 mL) and water (1 mL) was purged with nitrogen gas for 20 min. Xphos Pd G2 (42 mg, 53.38 μmol) was added at room temperature. The reaction mixture was irradiated under microwave 120° C. for 1 h. The reaction mixture was filtered through a bed of Celite, and the resulting filtrate was concentrated under reduced pressure. The crude product was purified by silica gel column chromatography using 5% methanol in dichloromethane to afford 3-[3-[[ethyl(methyl)sulfamoyl]amino]-2,6-difluoro-benzoyl]-5-[2-[6-[4-(4-nitrophenyl)-1-piperidyl]-2-azaspiro[3.3]heptan-2-yl]pyrimidin-5-yl]-1H-pyrrolo[2,3-b]pyridine (800 mg, 393.87 μmol, 37.28% yield) as a brown solid. LCMS (ESI+): 771.0 [M−H]$^+$.

Step 5: To a solution of 3-[3-[[ethyl(methyl)sulfamoyl]amino]-2,6-difluoro-benzoyl]-5-[2-[6-[4-(4-nitrophenyl)-1-piperidyl]-2-azaspiro[3.3]heptan-2-yl]pyrimidin-5-yl]-1H-pyrrolo[2,3-b]pyridine (500 mg, 647.81 μmol) in 1,4-dioxane (25 mL) was added dihydroxypalladium (200 mg, 1.42 mmol) at room temperature. The reaction mixture was stirred under hydrogen gas (1 atm) at room temperature for 12 h. The reaction mixture was filtered through a bed of Celite, and the resulting filtrate was concentrated under reduced pressure to afford 5-[2-[6-[4-(4-aminophenyl)-1-piperidyl]-2-azaspiro[3.3]heptan-2-yl]pyrimidin-5-yl]-3-[3-[[ethyl(methyl)sulfamoyl]amino]-2,6-difluoro-benzoyl]-1H-pyrrolo[2,3-b]pyridine (480 mg, 478.80 μmol, 73.91% yield) as an off-white solid. LCMS (ESI+): 742.3 $[M+H]^+$.

Step 6: To a stirred solution of 5-[2-[6-[4-(4-aminophenyl)-1-piperidyl]-2-azaspiro[3.3]heptan-2-yl]pyrimidin-5-yl]-3-[3-[[ethyl(methyl)sulfamoyl]amino]-2,6-difluoro-benzoyl]-1H-pyrrolo[2,3-b]pyridine (450 mg, 606.59 μmol) in N,N-dimethylformamide (2.0 mL) were added sodium bicarbonate (153.00 mg, 1.82 mmol, 70.83 μL) followed by 3-bromopiperidine-2,6-dione (290 mg, 1.51 mmol). The reaction mixture was heated at 70° C. for 16 h. The reaction mixture was added to ice water (20 mL) and extracted with ethyl acetate (2×50 mL). The combined organic layers were dried over sodium sulphate, filtered and concentrated under reduced pressure. The crude residue was purified by silica gel column chromatography using 50% ethyl acetate in petroleum ether as eluent to afford 5-[2-[6-[4-[4-[(2,6-dioxo-3-piperidyl)amino]phenyl]-1-piperidyl]-2-azaspiro[3.3]heptan-2-yl]pyrimidin-5-yl]-3-[3-[[ethyl(methyl)sulfamoyl]amino]-2,6-difluoro-benzoyl]-1H-pyrrolo[2,3-b]pyridine (8.29 mg, 9.51 μmol, 1.57% yield) as a brown solid. LCMS (ESI+): 853.3 $[M+H]^+$. $^1$H NMR (400 MHz, DMSO-$d_6$): δ 10.78 (s, 1H), 8.73 (d, J=5.20 Hz, 2H), 8.66 (dd, J=2.00, 9.00 Hz, 1H), 8.53 (s, 1H), 8.27 (s, 1H), 8.12 (s, 1H), 7.61-7.55 (m, 1H), 7.27-7.20 (m, 1H), 6.96 (d, J=8.40 Hz, 1H), 6.61 (d, J=8.40 Hz, 1H), 5.65 (d, J=7.60 Hz, 1H), 4.27 (m, 1H), 4.15 (s, 2H), 4.02 (s, 2H), 3.10 (q, J=7.20 Hz, 2H), 2.89 (d, J=10.40 Hz, 2H), 2.74 (s, 3H), 2.74 (m, 4H), 2.39-2.33 (m, 2H), 2.10-2.06 (m, 5H), 2.03-1.79 (m, 3H), 1.77-1.68 (m, 2H), 1.56-1.04 (m, 3H), 1.02 (t, J=7.20 Hz, 3H).

Example 152

5-[4-[(2,6-dioxo-3-piperidyl)amino]phenyl]-2-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]-6,7-dihydro-4H-pyrazolo[4,3-c]pyridine

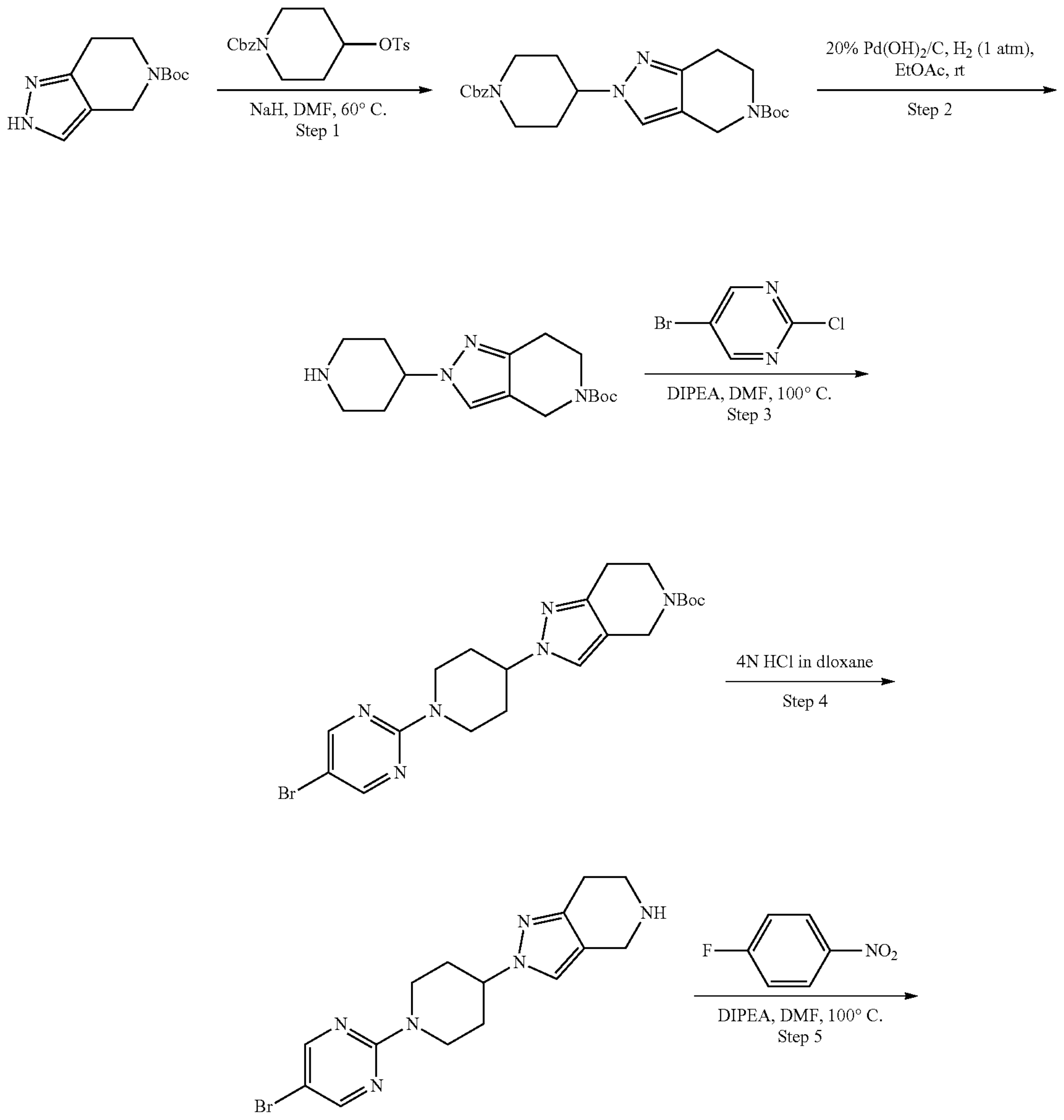

-continued
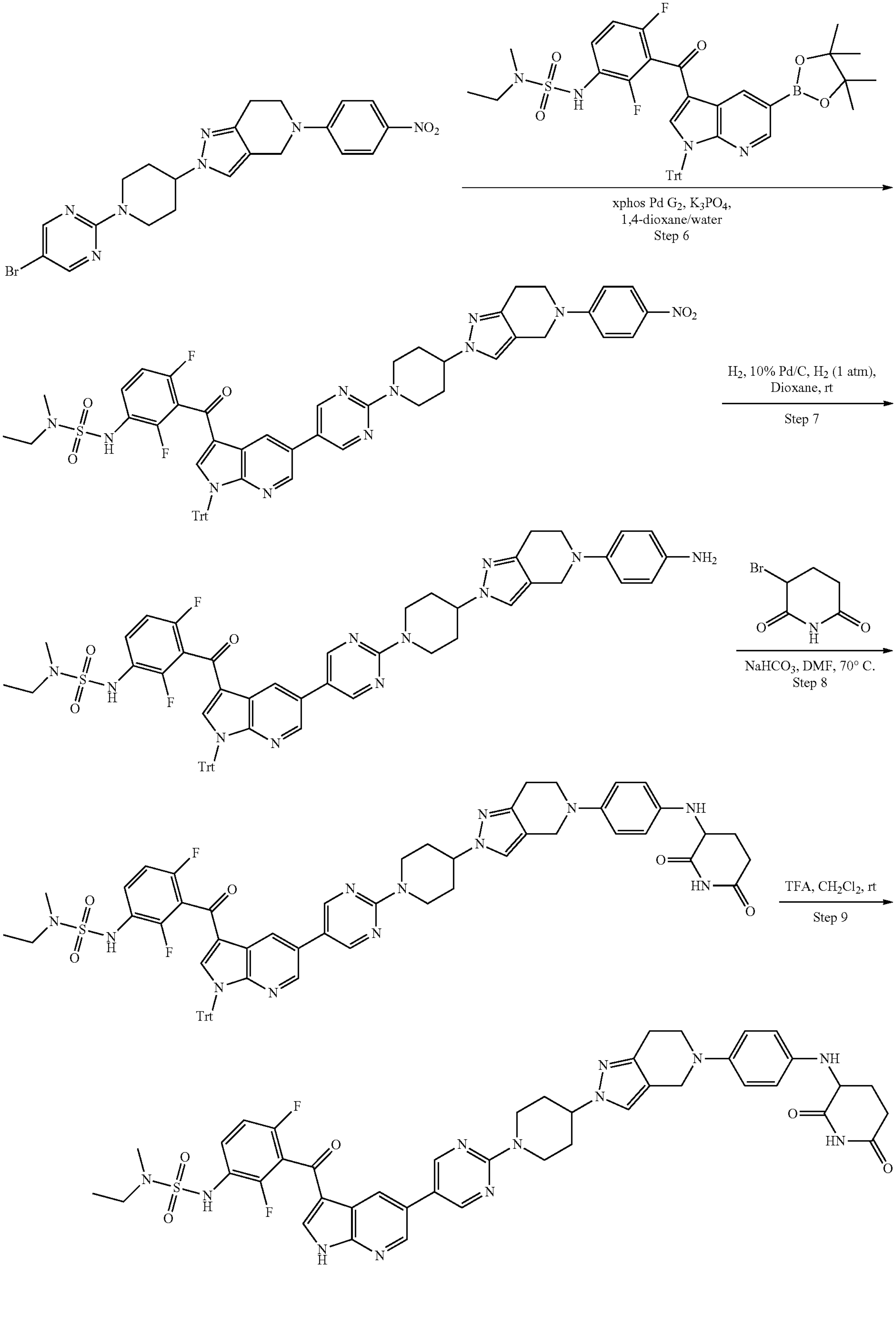

Step 1: To a solution of tert-butyl 2,4,6,7-tetrahydropyrazolo[4,3-c]pyridine-5-carboxylate (300 mg, 1.34 mmol) in N,N-dimethylformamide (4.0 mL) was added sodium hydride (60% dispersion in mineral oil, 37.07 mg, 1.61 mmol) at 0° C. under nitrogen atmosphere. The reaction mixture was warmed to room temperature and stirred for 1 hour. The reaction mixture was again cooled to 0° C., and benzyl 4-(p-tolylsulfonyloxy)piperidine-1-carboxylate (575.64 mg, 1.48 mmol) in N,N-dimethylformamide (3.0 mL) was added. The reaction mixture was heated at 60° C. for 5 h, then cooled to 0° C. and quenched with aqueous ammonium chloride solution (10 mL). The layers were separated, and the aqueous further extracted with ethyl acetate (2×20 mL). The combined organic layers were washed with brine (20 mL), dried over sodium sulphate, filtered, and concentrated under reduced pressure. The crude product was purified by silica gel column chromatography using 60% ethyl acetate in petroleum ether as an eluent to afford tert-butyl 2-(1-benzyloxycarbonyl-4-piperidyl)-6,7-dihydro-4H-pyrazolo[4,3-c]pyridine-5-carboxylate (240 mg, 538.08 μmol, 40.05% yield) as a colorless liquid. LCMS (ESI+): 441.0 $[M+H]^+$.

Step 2: To a solution of tert-butyl 2-(1-benzyloxycarbonyl-4-piperidyl)-6,7-dihydro-4H-pyrazolo[4,3-c]pyridine-5-carboxylate (1.60 g, 3.63 mmol) in ethyl acetate (20 mL) was added 10% $Pd(OH)_2$ on carbon (1.0 g, 7.12 mmol) at room temperature under nitrogen atmosphere. The reaction mixture was stirred under hydrogen gas (1 atm) at room temperature for 16 h. The reaction mixture was filtered through a bed of Celite, washed with ethyl acetate (10 mL), and concentrated under reduced pressure to afford tert-butyl 2-(4-piperidyl)-6,7-dihydro-4H-pyrazolo[4,3-c]pyridine-5-carboxylate (1.0 g, 3.13 mmol, 86.27% yield) as a colorless gum. LCMS (ESI+): 307.2 $[M+H]^+$.

Step 3: To a mixture of tert-butyl 2-(4-piperidyl)-6,7-dihydro-4H-pyrazolo[4,3-c]pyridine-5-carboxylate (900 mg, 2.94 mmol) and 5-bromo-2-chloro-pyrimidine (681.79 mg, 3.52 mmol) in N,N-dimethylformamide (6.0 mL) was added N,N-diisopropylethylamine (1.52 g, 11.75 mmol, 2.05 mL) at room temperature under nitrogen atmosphere. The reaction mixture was heated at 100° C. for 16 h. The reaction mixture was poured into water (100 mL) and extracted with ethyl acetate (2×100 mL). The combined organic layers were washed with brine (100 mL), dried over sodium sulphate, filtered, and concentrated under reduced pressure. The crude product was purified by silica gel column chromatography using 40% ethyl acetate in petroleum ether as eluent to afford tert-butyl 2-[1-(5-bromopyrimidin-2-yl)-4-piperidyl]-6,7-dihydro-4H-pyrazolo[4,3-c]pyridine-5-carboxylate (1.0 g, 2.07 mmol, 70.53% yield). LCMS (ESI+): 465.1 $[M+2+H]^+$.

Step 4: To a solution of tert-butyl 2-[1-(5-bromopyrimidin-2-yl)-4-piperidyl]-6,7-dihydro-4H-pyrazolo[4,3-c]pyridine-5-carboxylate (1.0 g, 2.16 mmol) in 1,4-dioxane (10 mL) was added 4M hydrochloric acid solution in 1,4-dioxane (16.0 g, 438.83 mmol, 20 mL) at 0° C. The reaction mixture was warmed to room temperature and stirred for 16 h. The reaction mixture was concentrated under reduced pressure and dried to afford 2-[1-(5-bromopyrimidin-2-yl)-4-piperidyl]-4,5,6,7-tetrahydropyrazolo[4,3-c]pyridine (750 mg, 1.84 mmol, 85.20% yield, hydrochloric acid salt). LCMS (ESI+): 364.1 $[M+H]^+$.

Step 5: To a mixture of 2-[1-(5-bromopyrimidin-2-yl)-4-piperidyl]-4,5,6,7-tetrahydropyrazolo[4,3-c]pyridine (1.0 g, 2.50 mmol, hydrochloric acid salt) and 1-fluoro-4-nitrobenzene (353 mg, 2.50 mmol, 265.41 μL) in N,N-dimethylformamide (7.0 mL) was added N-ethyl-N-isopropyl-propan-2-amine (1.29 g, 10.01 mmol, 1.74 mL) at room temperature under nitrogen atmosphere. The reaction mixture was heated at 100° C. for 16 h. The reaction mixture was cooled to room temperature, poured into water (100 ml), and extracted with ethyl acetate (2×100 mL). The combined organic layers were washed with brine (200 mL), dried over sodium sulphate, filtered, and concentrated under reduced pressure. The crude product was purified by silica gel column chromatography using 40% ethyl acetate in petroleum ether as eluent to afford 2-[1-(5-bromopyrimidin-2-yl)-4-piperidyl]-5-(4-nitrophenyl)-6,7-dihydro-4H-pyrazolo[4,3-c]pyridine (1.0 g, 2.02 mmol, 80.88% yield) as a yellow solid. LCMS (ESI+): 485.1 $[M+H]^+$.

Step 6: A mixture of 2-[1-(5-bromopyrimidin-2-yl)-4-piperidyl]-5-(4-nitrophenyl)-6,7-dihydro-4H-pyrazolo[4,3-c]pyridine (660 mg, 1.36 mmol), 3-[3-[[ethyl(methyl)sulfamoyl]amino]-2,6-difluoro-benzoyl]-5-(4,4,5,5-tetramethyl-1,3,2-dioxaborolan-2-yl)-1-trityl-pyrrolo[2,3-b]pyridine (1.14 g, 1.50 mmol) and tripotassium phosphate (867.74 mg, 4.09 mmol) in 1,4-dioxane (7.0 mL) and water (3.0 mL) was purged with nitrogen gas for 10 minutes. Xphos Pd G2 (107.21 mg, 136.27 μmol) was added at room temperature. The reaction mixture and was irradiated in a microwave at 120° C. for 2 h. The reaction mixture was cooled to room temperature, filtered through a bed of Celite, and washed with ethyl acetate (20 mL). The resulting filtrate was concentrated under reduced pressure. The crude product was purified by silica gel column chromatography using 70% ethyl acetate in petroleum ether as eluent to afford 2-[1-[5-[3-[3-[[ethyl(methyl)sulfamoyl]amino]-2,6-difluoro-benzoyl]-1-trityl-indol-5-yl]pyrimidin-2-yl]-4-piperidyl]-5-(4-nitrophenyl)-6,7-dihydro-4H-pyrazolo[4,3-c]pyridine (300 mg, 288.70 μmol, 21.19% yield) as a brown solid. LCMS (ESI+): 1041.4 $[M+H]^+$.

Step 7: To a solution of 2-[1-[5-[3-[3-[[ethyl(methyl)sulfamoyl]amino]-2,6-difluoro-benzoyl]-1-trityl-indol-5-yl]pyrimidin-2-yl]-4-piperidyl]-5-(4-nitrophenyl)-6,7-dihydro-4H-pyrazolo[4,3-c]pyridine (30.0 mg, 28.87 μmol) in 1,4-dioxane (3.0 mL) was added 10% palladium on carbon (30.0 mg, 281.90 μmol) at room temperature under nitrogen atmosphere. The reaction mixture was stirred under hydrogen gas (1 atm) at room temperature for 16 h. The reaction mixture was filtered through a bed of Celite and washed with ethyl acetate (10 mL). The resulting filtrate was concentrated under reduced pressure to afford 5-(4-aminophenyl)-2-[1-[5-[3-[3-[[ethyl(methyl)sulfamoyl]amino]-2,6-difluoro-benzoyl]-1-trityl-indol-5-yl]pyrimidin-2-yl]-4-piperidyl]-6,7-dihydro-4H-pyrazolo[4,3-c]pyridine (25.0 mg, 20.31 μmol, 70.36% yield) as a light brown solid. LCMS (ESI+): 1010.3 $[M+H]^+$.

Step 8: To a solution of 5-(4-aminophenyl)-2-[1-[5-[3-[3-[[ethyl(methyl)sulfamoyl]amino]-2,6-difluoro-benzoyl]-1-trityl-pyrrolo[2,3-b]pyridin-5-yl]pyrimidin-2-yl]-4-piperidyl]-6,7-dihydro-4H-pyrazolo[4,3-c]pyridine (280 mg, 277.18 μmol) in N,N-dimethylformamide (3.0 mL) were added sodium bicarbonate (69.86 mg, 831.55 μmol) followed by 3-bromopiperidine-2,6-dione (106.44 mg, 554.37 μmol) at room temperature under nitrogen atmosphere. The reaction mixture was stirred at 70° C. for 16 h. The reaction mixture was cooled to room temperature and poured into to water (3 mL). The resulting precipitate was filtered, washed with water (2 mL) and dried to afford 5-[4-[(2,6-dioxo-3-piperidyl)amino]phenyl]-2-[1-[5-[3-[3-[[ethyl(methyl)sulfamoyl]amino]-2,6-difluoro-benzoyl]-1-trityl-pyrrolo[2,3-b]pyridin-5-yl]pyrimidin-2-yl]-4-piperidyl]-6,7-dihydro-4H-pyrazolo[4,3-c]pyridine (200 mg, 81.02 μmol, 29.23% yield) as a light blue solid. LCMS (ESI+): 879.0 [M+H−242]$^+$ (trityl deprotected mass was observed).

Step 9: To a suspension of 5-[4-[(2,6-dioxo-3-piperidyl)amino]phenyl]-2-[1-[5-[3-[3-[[ethyl(methyl)sulfamoyl]amino]-2,6-difluoro-benzoyl]-1-trityl-pyrrolo[2,3-b]pyridin-5-yl]pyrimidin-2-yl]-4-piperidyl]-6,7-dihydro-4H-pyrazolo[4,3-c]pyridine (200 mg, 178.37 μmol) in dichloromethane (3.0 mL) were added trifluoroacetic acid (2.96 g, 25.96 mmol, 2 mL) followed by triisopropylsilane (773.0 mg, 4.88 mmol, 1 mL) at room temperature under nitrogen atmosphere. The reaction mixture was warmed to room temperature and stirred for 3 h. The reaction mixture was concentrated under reduced pressure, and the resulting crude product was purified by reverse phase column chromatography [mobile-phase A: 0.1% formic acid in water, mobile-phase B: ACN; column: 100 g Redisep $R_f$ C18] to afford 5-[4-[(2,6-dioxo-3-piperidyl)amino]phenyl]-2-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]-6,7-dihydro-4H-pyrazolo[4,3-c]pyridine (31.5 mg, 33.80 μmol, 18.95% yield, formic acid salt) as an off-white solid. LCMS (ESI+): 879.0 [M+H]$^+$. $^1$H NMR (400 MHz, DMSO-$d_6$): δ 10.78 (s, 1H), 8.79 (s, 2H), 8.68 (d, J=2.40 Hz, 1H), 8.56 (s, 1H), 8.35 (s, 1H), 8.11 (s, 1H), 7.59-7.52 (m, 1H), 7.26 (s, 1H), 7.20 (t, J=8.80 Hz, 1H), 6.86 (d, J=8.80 Hz, 2H), 6.63 (d, J=9.20 Hz, 2H), 5.42 (d, J=7.20 Hz, 1H), 4.85 (d, J=13.20 Hz, 1H), 4.35-4.50 (m, 1H), 4.15-4.35 (m, 1H), 3.96 (s, 2H), 3.20-3.13 (m, 3H), 3.08 (q, J=6.80 Hz, 2H), 2.75-2.85 (m, 2H), 2.66-2.75 (m, 2H), 2.69 (s, 3H), 2.50-2.63 (m, 2H), 2.14-2.10 (m, 1H), 1.95-1.91 (m, 3H), 1.87-1.84 (m, 1H), 1.01 (t, J=7.20 Hz, 3H).

Example 153

5-[2-[4-[4-[4-[4-[(2,6-dioxo-3-piperidyl)amino]phenyl]-1-piperidyl]pyrazol-1-yl]-1-piperidyl]pyrimidin-5-yl]-3-[3-[[ethyl(methyl)sulfamoyl]amino]-2,6-difluoro-benzoyl]-1H-pyrrolo[2,3-b]pyridine

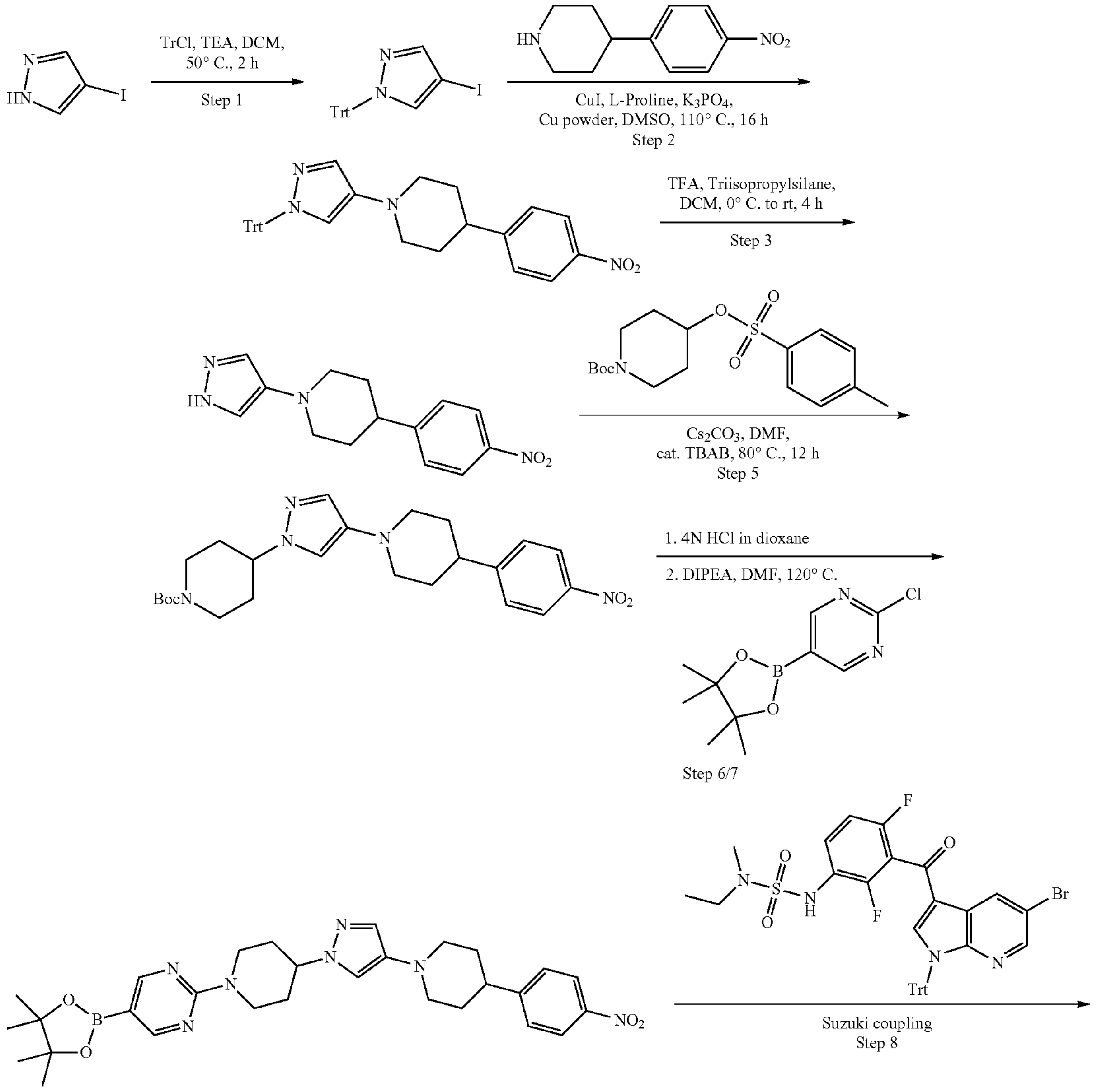

-continued

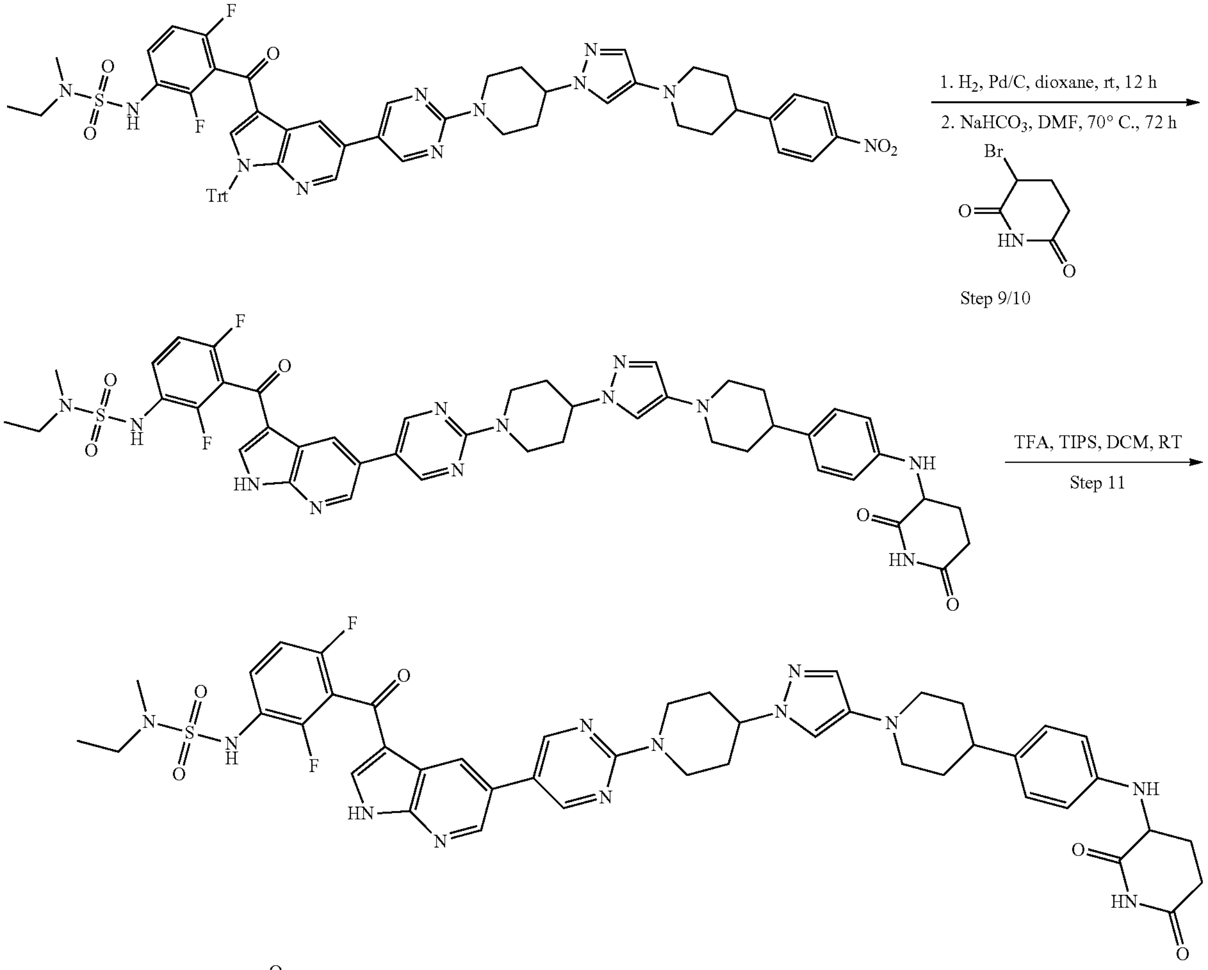

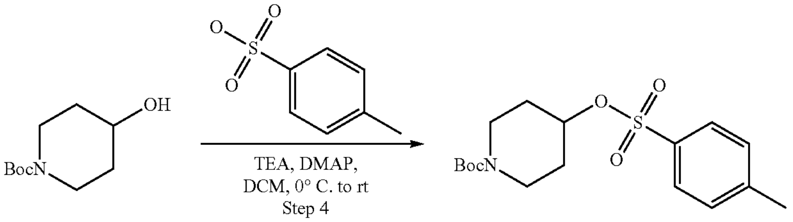

Step 1: To a stirred solution of 4-iodo-1H-pyrazole (7.0 g, 36.09 mmol) in dichloromethane (100 mL) was added triethylamine (9.44 g, 93.27 mmol, 13.0 mL) followed by [chloro(diphenyl)methyl]benzene (11.10 g, 39.82 mmol) at 0-5° C. under nitrogen atmosphere. The reaction mixture was heated to 50° C. for 2 h. Water (200 mL) was added to the reaction mixture, and the aqueous phase was extracted with dichloromethane (3×200 mL). The combined organic layers were dried over sodium sulphate, filtered, and concentrated under reduced pressure. The crude material was purified by neutral alumina column chromatography with 30% ethyl acetate in petroleum ether as eluent to afford 4-iodo-1-trityl-pyrazole (7.20 g, 14.85 mmol, 41.16% yield) as a white solid. $^1H$ NMR (400 MHz, DMSO-$d_6$): δ 7.75 (d, J=0.40 Hz, 1H), 7.45 (d, J=0.40 Hz, 1H), 7.36-7.39 (m, 9H), 7.03-7.05 (m, 6H).

Step 2: To a solution of 4-iodo-1-trityl-pyrazole (4.0 g, 9.17 mmol) in DMSO (50 mL) in a sealed tube was added 4-(4-nitrophenyl)piperidine (3.0 g, 14.55 mmol), anhydrous tripotassium phosphate (7.0 g, 32.98 mmol), and L-proline (220 mg, 1.91 mmol, 161.76 μL) at room temperature. The reaction mixture was degassed with nitrogen for 15 minutes, and copper (I) iodide (350 mg, 1.84 mmol) and copper (120 mg, 1.89 mmol) were added. The reaction mixture was heated to 110° C. for 16 h. Cold water (100 mL) was added, and the reaction mixture and stirred at room temperature for 30 min. The solid was collected by filtration and dried under vacuum. The crude material was purified by silica gel column chromatography using 70% ethyl acetate in dichloromethane as eluent to afford 4-(4-nitrophenyl)-1-(1-tritylpyrazol-4-yl)piperidine (1.50 g, 2.65 mmol, 28.85% yield) as a yellow solid. LCMS (ESI+): 515.2 $[M+H]^+$.

Step 3: To a stirred solution of 4-(4-nitrophenyl)-1-(1-tritylpyrazol-4-yl)piperidine (1.0 g, 1.94 mmol) in dichloromethane (10 mL) was added trifluoroacetic acid (7.40 g, 64.90 mmol, 5.0 mL) and triisopropyl silane (386.50 mg, 2.44 mmol, 0.500 mL) at 0-5° C. under nitrogen atmosphere. The reaction mixture was stirred at room temperature for 12 h. The reaction mixture was concentrated under reduced pressure and washed with n-pentane (2×50 mL) to afford 4-(4-nitrophenyl)-1-(1H-pyrazol-4-yl)piperidine (700 mg, 1.57 mmol, 80.92% yield) as a brown solid. This crude compound was used in the next step without further purification. LCMS (ESI+): 273.1 $[M+H]^+$.

Step 4: To a stirred solution of tert-butyl 4-hydroxypiperidine-1-carboxylate (2.0 g, 9.94 mmol) in dichloromethane (20 mL) was added triethylamine (2.10 g, 20.75 mmol, 3.0 mL) and 4-(dimethylamino)pyridine (130 mg, 1.06 mmol) at 0-5° C. under nitrogen. 4-methylbenzenesulfonyl chloride (2.30 g, 12.06 mmol) was added, and the reaction mixture was stirred at room temperature for 24 h. Water (100 mL) was added to the reaction mixture, and the aqueous phase extracted with dichloromethane (2×100 mL). The combined organic layers were dried over sodium sulphate, filtered, and concentrated under reduced pressure. The crude material was purified by silica gel column chromatography using 30% ethyl acetate in petroleum ether as eluent to afford tert-butyl 4-(p-tolylsulfonyloxy)piperidine-1-carboxylate (2.60 g, 7.13 mmol, 71.78% yield) as an off-white solid. LCMS (ESI+): 300.1 $[M-56]^+$.

Step 5: To a solution of 4-(4-nitrophenyl)-1-(1H-pyrazol-4-yl)piperidine (700 mg, 1.81 mmol) in N,N-dimethylformamide (10 mL) in a sealed tube was added cesium carbonate (3.0 g, 9.21 mmol) and tetrabutylammonium bromide (60 mg, 186.12 μmol) at room temperature. The reaction mixture was stirred at room temperature for 15 minutes, then tert-butyl 4-(p-tolylsulfonyloxy)piperidine-1-carboxylate (1.1 g, 3.09 mmol) was added. The reaction mixture was heated to 100° C. for 12 h. Water (100 mL) was added to the reaction mixture, and the aqueous phase was extracted with ethyl acetate (2×200 mL). The combined organic layers were dried over sodium sulphate, filtered, and concentrated under reduced pressure. The crude compound was purified by silica gel column chromatography with 90% ethyl acetate in petroleum ether as eluent to afford tert-butyl 4-[4-[4-(4-nitrophenyl)-1-piperidyl]pyrazol-1-yl]piperidine-1-carboxylate (690 mg, 1.38 mmol, 76.07% yield) as yellow solid. LCMS (ESI+): 456.2 $[M+H]^+$.

Step 6: To a stirred solution of tert-butyl 4-[4-[4-(4-nitrophenyl)-1-piperidyl]pyrazol-1-yl]piperidine-1-carboxylate (690 mg, 1.51 mmol) in 1,4-dioxane (5.0 mL) was added 4M hydrogen chloride solution in 1,4-dioxane (8.00 g, 219.41 mmol, 10 mL) at 0-5° C. under nitrogen atmosphere. The reaction mixture was stirred at room temperature for 5 h. The reaction mixture was concentrated under reduced pressure and washed with diethyl ether (2×50 mL) to afford 4-(4-nitrophenyl)-1-[1-(4-piperidyl)pyrazol-4-yl] piperidine (620 mg, 1.50 mmol, 99.23% yield) as a yellow solid. This crude compound was used in the next step without any purification. LCMS (ESI+): 356.2 $[M+H]^+$.

Step 7: To a solution of 4-(4-nitrophenyl)-1-[1-(4-piperidyl)pyrazol-4-yl]piperidine (620 mg, 1.58 mmol) in N,N-dimethylformamide (10 mL) in a sealed tube was added N,N-diisopropylethylamine (2.23 g, 17.22 mmol, 3.0 mL) and 2-chloro-5-(4,4,5,5-tetramethyl-1,3,2-dioxaborolan-2-yl)pyrimidine (460 mg, 1.91 mmol) at room temperature. The reaction mixture was heated to 100° C. for 12 h. Water (50 mL) was added, and the aqueous phase was extracted with ethyl acetate (2×100 mL). The combined organic layers were dried over sodium sulphate, filtered, and concentrated under reduced pressure to afford 2-[4-[4-[4-(4-nitrophenyl)-1-piperidyl]pyrazol-1-yl]-1-piperidyl]-5-tetramethyl-1,3,2-dioxaborolan-2-yl)pyrimidine (550 mg, 835.62 μmol, 52.82% yield) as a light brown solid. This crude compound was taken forward to the next step without further purification. LCMS (ESI+): 560.3 $[M+H]^+$.

Step 8: 5-bromo-3-[3-[[ethyl(methyl)sulfamoyl]amino]-2,6-difluoro-benzoyl]-1-trityl-pyrrolo[2,3-b]pyridine (600 mg, 838.45 μmol), 1,4-dioxane (8.0 mL) and water (2.0 mL) were combined in a microwave vial. 2-[4-[4-[4-(4-nitrophenyl)-1-piperidyl]pyrazol-1-yl]-1-piperidyl]-5-(4,4,5,5-tetramethyl-1,3,2-dioxaborolan-2-yl)pyrimidine (500 mg, 893.71 μmol), and anhydrous tripotassium phosphate (550 mg, 2.59 mmol) were added at room temperature under nitrogen. The reaction mixture was degassed with nitrogen for 10 minutes, then XPhos Pd G2 (70 mg, 88.97 μmol) was added. The reaction mixture was irradiated in a microwave at 120° C. for 1 h. Water (50 mL) was added to the reaction mixture, and the aqueous phase was extracted with ethyl acetate (2×200 mL). The combined organic layers were dried over sodium sulphate, filtered, and concentrated under reduced pressure. The crude compound was purified by silica gel column chromatography using 90% ethyl acetate in petroleum ether as eluent to afford 3-[3-[[ethyl(methyl) sulfamoyl]amino]-2,6-difluoro-benzoyl]-5-[2-[4-[4-[4-(4-nitrophenyl)-1-piperidyl]pyrazol-1-yl]-1-piperidyl]pyrimidin-5-yl]-1-trityl-pyrrolo[2,3-b]pyridine (490 mg, 422.02 μmol, 50.33% yield) as a yellow solid. LCMS (ESI+): 1068.3 $[M+H]^+$.

Step 9: To a stirred solution of 3-[3-[[ethyl(methyl)sulfamoyl]amino]-2,6-difluoro-benzoyl]-5-[2-[4-[4-[4-(4-nitrophenyl)-1-piperidyl]pyrazol-1-yl]-1-piperidyl]pyrimidin-5-yl]-1-trityl-pyrrolo[2,3-b]pyridine (450 mg, 421.27 μmol) in 1,4-dioxane (10 mL) was added 10% palladium on carbon (230 mg, 2.16 mmol). The resultant mixture was stirred under hydrogen gas atmosphere (1 atm) at room temperature for 16 h. The reaction mixture was purged with nitrogen gas, and the catalyst was removed by filtration through a pad of Celite. The filtrate was concentrated under reduced pressure. The crude compound was purified by silica gel column chromatography using 80-90% ethyl acetate in petroleum ether as a eluent to afford 5-[2-[4-[4-[4-(4-aminophenyl)-1-piperidyl]pyrazol-1-yl]-1-piperidyl]pyrimidin-5-yl]-3-[3-[[ethyl(methyl)sulfamoyl]amino]-2,6-difluoro-benzoyl]-1-trityl-pyrrolo[2,3-b]pyridine (400 mg, 288.96 μmol, 68.59% yield) as a yellow solid. LCMS (ESI+): 1038.4 $[M+H]^+$.

Step 10: To a solution of 5-[2-[4-[4-[4-(4-aminophenyl)-1-piperidyl]pyrazol-1-yl]-1-piperidyl]pyrimidin-5-yl]-3-[3-[[ethyl(methyl)sulfamoyl]amino]-2,6-difluoro-benzoyl]-1-trityl-pyrrolo[2,3-b]pyridine (400 mg, 385.28 μmol) in N,N-dimethylformamide (10 mL) in a sealed tube was added sodium bicarbonate (120 mg, 1.43 mmol, 55.56 μL) and 3-bromopiperidine-2,6-dione (190 mg, 989.53 μmol) at room temperature. The reaction mixture was heated to 70° C. for 72 h. Water (50 mL) was added to the reaction mixture, and the aqueous phase was extracted with ethyl acetate (2×100 mL). The combined organic layers were dried over sodium sulphate, filtered and concentrated under reduced pressure to afford 5-[2-[4-[4-[4-[4-[(2,6-dioxo-3-piperidyl)amino]phenyl]-1-piperidyl]pyrazol-1-yl]-1-piperidyl]pyrimidin-5-yl]-3-[3-[[ethyl(methyl)sulfamoyl] amino]-2,6-difluoro-benzoyl]-1-trityl-pyrrolo[2,3-b] pyridine (510 mg, 146.44 μmol, 38.01% yield) as a brown gummy liquid. The crude product was taken forward to the next step without further purification. LCMS (ESI+): 1149.4 $[M+H]^+$.

Step 11: To a stirred solution of 5-[2-[4-[4-[4-[4-[(2,6-dioxo-3-piperidyl)amino]phenyl]-1-piperidyl]pyrazol-1-yl]-1-piperidyl]pyrimidin-5-yl]-3-[3-[[ethyl(methyl)sulfamoyl] amino]-2,6-difluoro-benzoyl]-1-trityl-pyrrolo[2,3-b] pyridine (510 mg, 443.74 μmol) in dichloromethane (5.0 mL) was added trifluoroacetic acid (7.40 g, 64.90 mmol, 5.0 mL) and triisopropyl silane (98% pure, 386.50 mg, 2.44 mmol, 0.50 mL) at 0-5° C. under nitrogen atmosphere. The reaction mixture was stirred at room temperature for 4 h. The reaction mixture was concentrated under reduced pressure, and the crude residue was washed with diethyl ether (2×50 mL). The crude material was purified by preparative-HPLC (0.1% TFA in water and acetonitrile) to afford 5-[2-[4-[4-[4-[4-[(2,6-dioxo-3-piperidyl)amino]phenyl]-1-piperidyl]pyrazol-1-yl]-1-piperidyl]pyrimidin-5-yl]-3-[3-[[ethyl(methyl)sulfamoyl]amino]-2,6-difluoro-benzoyl]-1H-pyrrolo[2,3-b]pyridine (19 mg, 17.32 μmol, 3.90% yield) as a yellow solid. LCMS (ESI+): 907.2 $[M+H]^+$. $^1H$ NMR (400 MHz, DMSO-$d_6$): δ 13.02 (d, J=3.20 Hz, 1H), 10.80 (s, 1H), 9.73 (s, 1H), 8.81 (s, 2H), 8.69 (d, J=2.00 Hz, 1H), 8.58 (s, 1H), 8.15 (d, J=2.80 Hz, 1H), 8.00 (s, 1H), 7.56-7.60 (m, 2H), 7.25-7.31 (m, 1H), 6.99 (d, J=−8.00 Hz, 2H), 6.65 (d, J=8.40 Hz, 2H), 4.85 (d, J=13.20 Hz, 1H), 4.47-4.51 (m, 1H), 4.29 (dd, J=4.80, 11.40 Hz, 1H), 3.65-3.45 (m, 2H), 3.08-3.20 (m, 6H), 2.65-2.80 (m, 2H), 2.74 (s, 3H), 2.55-2.65 (m, 2H), 2.09-2.11 (m, 3H), 1.79-1.95 (m, 7H), 1.02 (t, J=7.20 Hz, 3H).

Example 154

N-[1-[4-[(2,6-dioxo-3-piperidyl)amino]-2-fluoro-phenyl]-4-piperidyl]-4-[5-[3-[3-[[ethyl(methyl)sulfamoyl]amino]-2-fluoro-benzoyl]-1H-pyrrolo[2,3-b]pyridin-5-yl]-2-pyridyl]piperazine-1-carboxamide

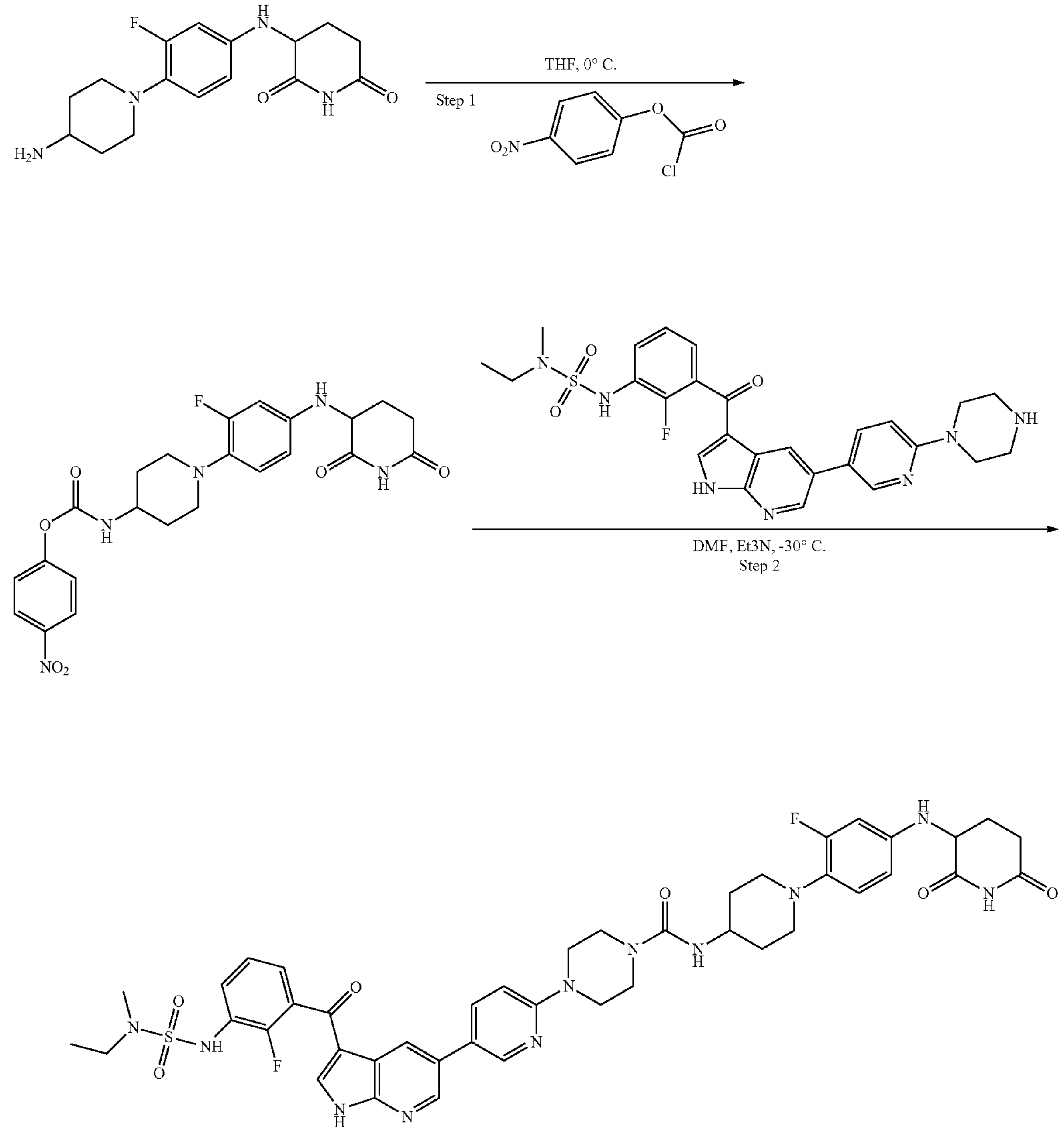

Step 1: To a solution of 3-[4-(4-amino-1-piperidyl)-3-fluoro-anilino]piperidine-2,6-dione (0.7 g, 1.96 mmol, hydrochloric acid salt) in tetrahydrofuran (7 mL) was added triethylamine (992.55 mg, 9.81 mmol, 1.37 mL) and (4-nitrophenyl) carbonochloridate (474.50 mg, 2.35 mmol) at 0° C. under nitrogen atmosphere. The resulting solution was warmed to room temperature and stirred for 3 hours. The reaction was concentrated under reduced pressure to obtain crude (4-nitrophenyl) N-[1-[4-[(2,6-dioxo-3-piperidyl)amino]-2-fluoro-phenyl]-4-piperidyl]carbamate (1.27 g, 1.95 mmol, 99.36% yield) as a brown solid. The material was taken forward to the following step without further manipulation. LCMS (ESI+): 486.2 $[M+H]^+$.

Step 2: To a solution of (4-nitrophenyl) N-[1-[4-[(2,6-dioxo-3-piperidyl)amino]-2-fluoro-phenyl]-4-piperidyl]carbamate (350.00 mg, 720.96 μmol) in N,N-dimethylformamide (4 mL) was added a solution of 3-[3-[[ethyl(methyl)sulfamoyl]amino]-2-fluoro-benzoyl]-5-(6-piperazin-1-yl-3-pyridyl)-1H-pyrrolo[2,3-b]pyridine (174.42 mg, 324.43 μmol) in N,N-dimethylformamide (1 ml) and triethylamine (364.77 mg, 3.60 mmol, 502.44 μL) at −30° C. The resulting solution was slowly warmed to room temperature and stirred for 6 hours. The reaction was concentrated under reduced pressure, and the crude compound was purified by reverse phase column chromatography [Column: 100 g Redisep Rf C18, mobile-phase A: 0.1% ammonium acetate, mobile-phase B: ACN] to furnish N-[1-[4-[(2,6-dioxo-3-piperidyl)amino]-2-fluoro-phenyl]-4-piperidyl]-4-[5-[3-[3-[[ethyl(methyl)sulfamoyl]amino]-2-fluoro-benzoyl]-1H-pyrrolo[2,3-b]pyridin-5-yl]-2-pyridyl]piperazine-1-carboxamide (92 mg, 102.56 μmol, 14.23% yield) as an off-white solid. LCMS (ESI+): 884.3 $[M+H]^+$. $^1$H NMR (400 MHz, DMSO-$d_6$): δ 12.85 (d, J=2.80 Hz, 1H), 10.79 (s, 1H), 9.79 (s, 1H), 8.66 (d, J=2.40 Hz, 1H), 8.56 (d, J=2.00 Hz, 1H), 8.50 (d, J=2.40 Hz, 1H), 7.98-7.94 (m, 2H), 7.62-7.58 (m, 1H), 7.41-7.31 (m, 2H), 7.03-7.01 (m, 1H), 6.88-6.83 (m, 1H), 6.56-6.38 (m, 3H), 5.80-5.80 (m, 1H), 4.27-4.24 (m, 1H), 3.57-3.55 (m, 4H), 3.46-3.44 (m, 4H), 3.16-3.11 (m, 4H), 2.74 (s, 3H), 2.68-2.65 (m, 4H), 2.10-2.07 (m, 1H), 1.86-1.81 (m, 3H), 1.65-1.60 (m, 2H), 1.02 (t, J=7.20 Hz, 3H).

Example 155

3-[2-chloro-3-[[ethyl(methyl)sulfamoyl]amino]-6-fluoro-benzoyl]-5-[4-[4-[2-[1-[4-[(2,6-dioxo-3-piperidyl)amino]-2-fluoro-phenyl]-4-hydroxy-4-piperidyl]acetyl]piperazin-1-yl]phenyl]-1H-pyrrolo[2,3-b]pyridine

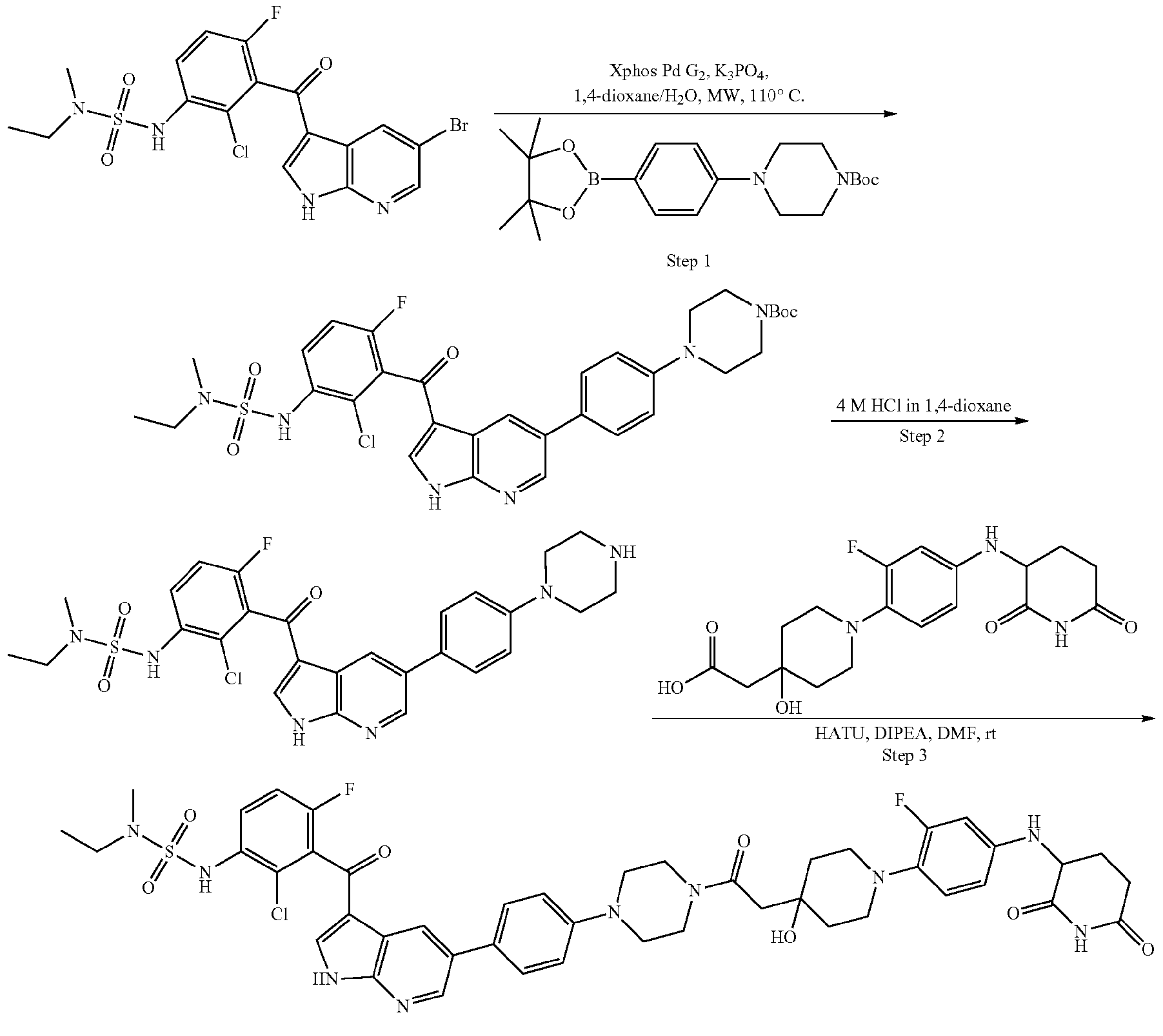

Step 1: 5-bromo-3-[2-chloro-3-[[ethyl(methyl)sulfamoyl]amino]-6-fluoro-benzoyl]-1H-pyrrolo[2,3-b]pyridine (500 mg, 1.02 mmol) in 1,4-dioxane (12 mL) and water (2 mL) were combined in a microwave vial. tert-Butyl 4-[4-(4,4,5,5-tetramethyl-1,3,2-dioxaborolan-2-yl)phenyl]piperazine-1-carboxylate (475.73 mg, 1.23 mmol) and anhydrous tripotassium phosphate (650.14 mg, 3.06 mmol) were added at room temperature under nitrogen atmosphere. The reaction mixture was degassed with nitrogen for 10 minutes, and XPhos Pd G2 (80.17 mg, 102.09 mol) was added. The reaction mixture was irradiated under microwave at 110° C. for 1 h. The reaction mixture was diluted with water (60 mL) and extracted with ethyl acetate (2×100 mL). The combined organic layers were dried over sodium sulphate, filtered, and concentrated under reduced pressure. The crude compound was purified by silica gel column chromatography using 70% ethyl acetate in petroleum ether as eluent to afford tert-butyl butyl 4-[4-[3-[2-chloro-3-[[ethyl(methyl)sulfamoyl]amino]-6-fluoro-benzoyl]-1H-pyrrolo[2,3-b]pyridin-5-yl]phenyl]piperazine-1-carboxylate (250 mg, 249.56 mol, 24.44% yield) as light brown solid. LCMS (ESI+): 670.9 $[M+H]^+$.

Step 2: To a 0° C. solution of tert-butyl 4-[4-[3-[2-chloro-3-[[ethyl(methyl)sulfamoyl]amino]-6-fluoro-benzoyl]-1H-pyrrolo[2,3-b]pyridin-5-yl]phenyl]piperazine-1-carboxylate (196 mg, 292.02 mol) in 1,4-dioxane (4 mL) was added 4M hydrochloric acid solution in 1,4-dioxane (292.02 mol, 4 mL). The reaction mixture was stirred for 2 h at room temperature. The reaction mixture was concentrated under reduced pressure and triturated with petroleum ether wash to provide 3-[2-chloro-3-[[ethyl(methyl)sulfamoyl]amino]-6-fluoro-benzoyl]-5-(4-piperazin-1-ylphenyl)-1H-pyrrolo[2,3-b]pyridine (180 mg, 277.59 mol, 95.06% yield) as off yellow solid. LCMS (ESI+): 571.0 $[M+H]^+$.

Step 3: Target compound was prepared via HATU mediated acid-amine coupling reaction (procedure A). Amide coupling was carried out using 3-[2-chloro-3-[[ethyl(methyl)sulfamoyl]amino]-6-fluoro-benzoyl]-5-(4-piperazin-1-ylphenyl)-1H-pyrrolo[2,3-b]pyridine (210 mg, 345.66 mol), 2-[1-[4-[(2,6-dioxo-3-piperidyl)amino]-2-fluoro-phenyl]-4-hydroxy-4-piperidyl]acetic acid (143.74 mg, 345.66 mol), N-ethyl-N-isopropyl-propan-2-amine (178.70 mg, 1.38 mmol, 240.83 μL) and HATU (144.58 mg, 380.23 μmol). Crude compound was purified by reverse phase column chromatography by using 150 g snap cartridge eluted with 40% acetonitrile in 0.1% formic acid in water to afford 3-[2-chloro-3-[[ethyl(methyl)sulfamoyl]amino]-6-fluoro-benzoyl]-5-[4-[4-[2-[1-[4-[(2,6-dioxo-3-piperidyl)amino]-2-fluoro-phenyl]-4-hydroxy-4-piperidyl]acetyl]piperazin-1-yl]phenyl]-1H-pyrrolo[2,3-b]pyridine (58 mg, 58.74 μmol, 16.99% yield, formic acid salt) as an off-white solid. LCMS (ESI−): 930.2 $[M-H]^-$. $^1H$ NMR (400 MHz, DMSO-$d_6$): δ 12.85 (s, 1H), 10.78 (s, 1H), 8.65 (s, 1H), 8.27 (s, 1H), 7.97 (s, 1H), 7.56-7.63 (m, 3H), 7.21-7.30 (m, 1H), 7.11 (d, J=8.80 Hz, 2H), 6.86 (t, J=9.60 Hz, 1H), 6.50 (dd, J=2.00, 15.00 Hz, 1H), 6.42 (d, J=8.80 Hz, 1H), 5.78 (d, J=7.60 Hz, 1H), 4.87 (s, 1H), 4.21-4.31 (m, 1H), 3.70-4.25 (m, 4H), 3.21-3.30 (m, 4H), 3.06 (q, J=7.20 Hz, 2H), 2.85-2.94 (m, 4H), 2.64-2.77 (m, 2H), 2.68 (s, 3H), 2.07-2.10 (m, 1H), 2.64-2.55 (m, 2H), 1.66-1.87 (m, 5H), 1.01 (t, J=7.20 Hz, 3H).

Example 156

5-[6-[4-[2-[1-[2-chloro-4-[(2,6-dioxo-3-piperidyl)amino]phenyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine

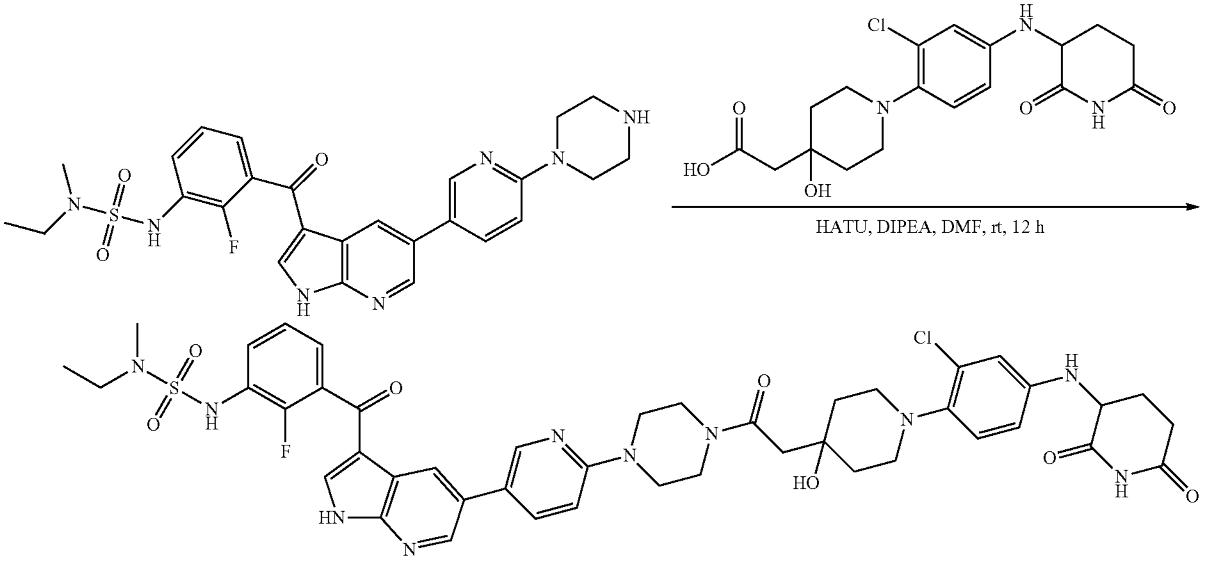

Target compound was prepared via HATU mediated acid-amine coupling reaction (procedure A). Amide coupling was carried out using 3-[3-[[ethyl(methyl)sulfamoyl]amino]-2-fluoro-benzoyl]-5-(6-piperazin-1-yl-3-pyridyl)-1H-pyrrolo[2,3-b]pyridine (290 mg, 505.17 μmol), 2-[1-[2-chloro-4-[(2,6-dioxo-3-piperidyl)amino]phenyl]-4-hydroxy-4-piperidyl]acetic acid (200 mg, 505.26 μmol), N,N-diisopropylethylamine (1.48 g, 11.48 mmol, 2.0 mL) and HATU (220 mg, 578.60 μmol). The crude compound was purified by reverse phase column chromatography using 150 g snap cartridge eluted with 50% acetonitrile in 0.1% formic acid in water to afford 5-[6-[4-[2-[1-[2-chloro-4-[(2,6-dioxo-3-piperidyl)amino]phenyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine (118 mg, 121.69 μmol, 24.09% yield) as off-white solid.

LCMS (ESI+): 915.3 [M+H]$^+$. $^1$H NMR (400 MHz, DMSO-$d_6$): δ 12.85 (s, 1H), 10.79 (s, 1H), 9.79 (s, 1H), 8.66 (d, J=2.40 Hz, 1H), 8.56 (d, J=2.00 Hz, 1H), 8.51 (d, J=2.80 Hz, 1H), 7.95-7.98 (m, 2H), 7.58-7.62 (m, 1H), 7.40 (dd, J=1.20, 7.60 Hz, 1H), 7.30-7.38 (m, 1H), 7.00 (dd, J=8.80, 17.20 Hz, 2H), 6.98 (d, J=8.80 Hz, 1H), 6.76 (d, J=2.40 Hz, 1H), 5.84 (s, 1H), 4.91 (s, 1H), 4.35-4.23 (m, 1H), 3.59-3.72 (m, 8H), 3.13 (q, J=7.20 Hz, 2H), 2.63-2.93 (m, 5H), 2.74 (s, 3H), 2.60 (s, 2H), 2.55-2.51 (m, 1H), 2.06-2.08 (m, 1H), 1.68-1.88 (m, 5H), 1.02 (t, J=7.20 Hz, 3H).

Example 157

5-[2-[4-[2-[1-[2-chloro-4-[(2,6-dioxo-3-piperidyl)amino]phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

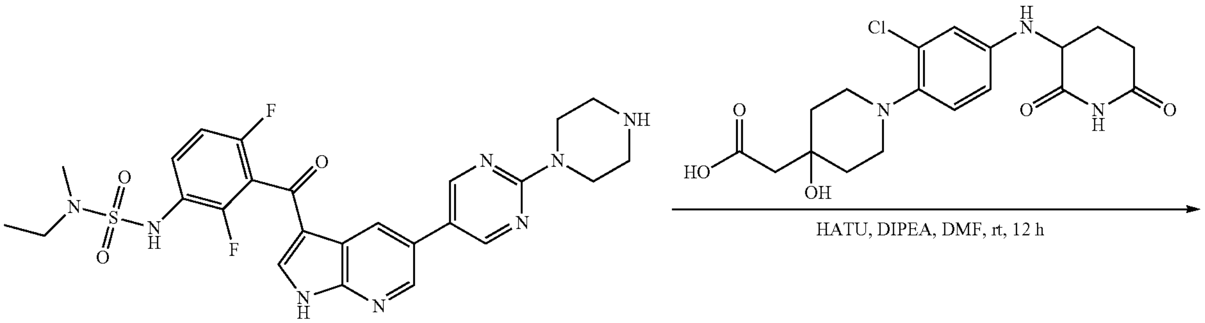

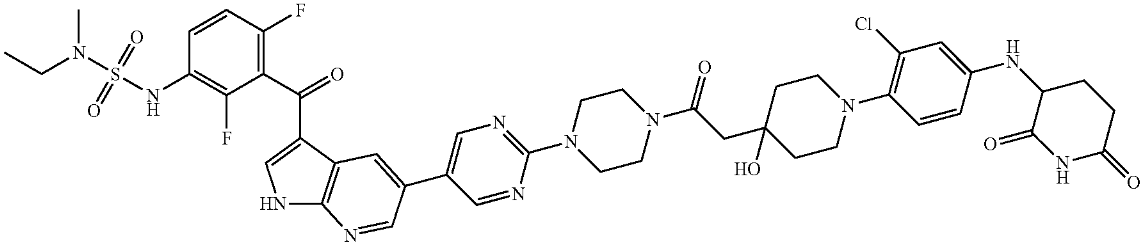

Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (300 mg, 505.86 μmol), 2-[1-[2-chloro-4-[(2,6-dioxo-3-piperidyl)amino]phenyl]-4-hydroxy-4-piperidyl]acetic acid (201 mg, 507.79 μmol), N,N-diisopropylethylamine (1.48 g, 11.48 mmol, 2.0 mL) and HATU (220 mg, 578.60 μmol). The crude compound was purified by reverse phase column chromatography using 150 g snap cartridge eluting with 50% acetonitrile in 0.1% formic acid in water to afford 5-[2-[4-[2-[1-[2-chloro-4-[(2,6-dioxo-3-piperidyl)amino]phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (183 mg, 185.61 μmol, 36.69% yield) as off-white solid. LCMS (ESI+): 932.3 [M+H]$^+$. $^1$H NMR (400 MHz, DMSO-$d_6$): δ 13.00 (s, 1H), 10.78 (s, 1H), 8.81 (s, 2H), 8.67 (d, J=2.40 Hz, 1H), 8.56 (s, 1H), 8.33 (s, 1H), 8.11 (s, 1H), 7.53-7.59 (m, 1H), 7.20 (t, J=8.80 Hz, 1H), 6.98 (d, J=8.80 Hz, 1H), 6.76 (d, J=2.40 Hz, 1H), 6.61 (dd, J=2.40, 8.80 Hz, 1H), 5.84 (d, J=8.00 Hz, 1H), 4.91 (s, 1H), 4.26-4.34 (m, 1H), 3.86-3.88 (m, 4H), 3.82-3.83 (m, 4H), 3.08 (q, J=6.80, Hz, 2H), 2.67-2.93 (m, 4H), 2.71 (s, 3H), 2.61 (s, 2H), 2.06-2.09 (m, 1H), 1.69-1.87 (m, 5H), 1.02 (t, J=6.80 Hz, 3H).

Example 158

5-[2-[4-[2-[1-[4-(2,6-dioxo-3-piperidyl)-2-fluoro-phenyl]-4-hydroxy-4-piperidyl]acetyl]piperazin-1-yl]pyrimidin-5-yl]-3-[3-[[ethyl(methyl)sulfamoyl] amino]-2,6-difluoro-benzoyl]-1H-pyrrolo[2,3-b] pyridine (Compound 158)

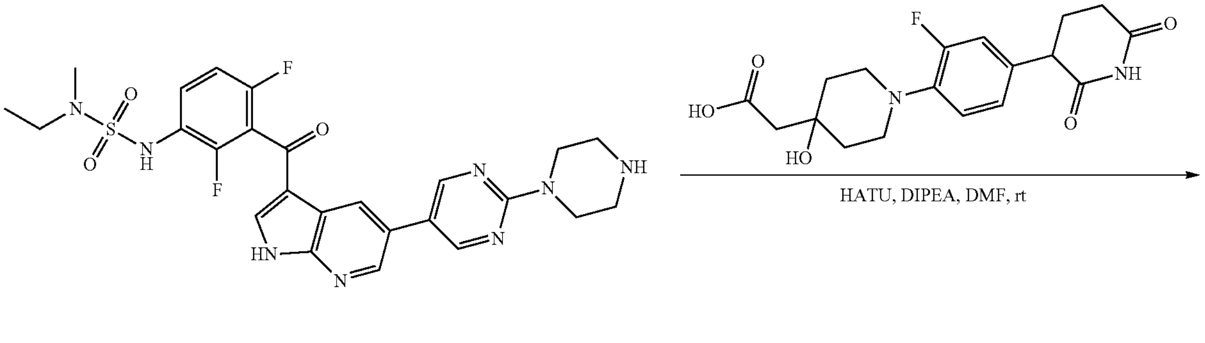

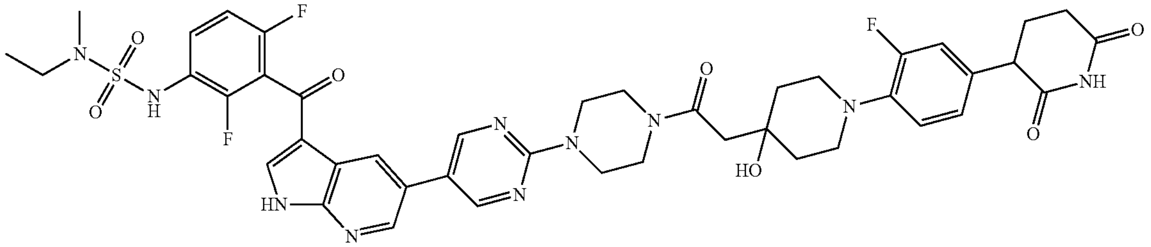

Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (370 mg, 623.90 µmol) in N, N-dimethylformamide (5.0 mL), 2-[1-[4-(2,6-dioxo-3-piperidyl)-2-fluoro-phenyl]-4-hydroxy-4-piperidyl]acetic acid (251 mg, 626.20 µmol), N,N-diisopropylethylamine (1.48 g, 11.48 mmol, 2.0 mL) and HATU (270 mg, 710.10 µmol) at room temperature. The crude compound was purified by reverse phase column chromatography using 150 g snap cartridge eluted with 50% acetonitrile in 0.1% Formic acid in water to afford 5-[2-[4-[2-[1-[4-(2,6-dioxo-3-piperidyl)-2-fluoro-phenyl]-4-hydroxy-4-piperidyl]acetyl]piperazin-1-yl]pyrimidin-5-yl]-3-[3-[[ethyl(methyl)sulfamoyl] amino]-2,6-difluoro-benzoyl]-1H-pyrrolo[2,3-b]pyridine (178 mg, 185.68 µmol, 29.76% yield) as off-white solid. LCMS (ESI+): 903.3 $[M+H]^+$. $^1$H NMR (400 MHz, DMSO-$d_6$): δ 13.00 (s, 1H), 10.81 (s, 1H), 9.88 (s, 1H), 8.81 (s, 2H), 8.68 (d, J=2.40 Hz, 1H), 8.57 (s, 1H), 8.14 (s, 1H), 7.55-7.61 (m, 1H), 7.24-7.28 (m, 1H), 6.99-7.04 (m, 2H), 6.96 (d, J=1.60 Hz, 1H), 4.93 (s, 1H), 3.81-3.88 (m, 5H), 3.64-3.79 (m, 4H), 3.02-3.33 (m, 6H), 2.73 (s, 3H), 2.62-2.72 (m, 3H), 2.55-2.50 (m, 1H), 2.14-2.24 (m, 1H), 2.00-2.05 (m, 1H), 1.70-1.81 (m, 4H), 1.02 (t, J=7.20 Hz, 3H).

Examples 158a AND 158b

5-[2-[4-[2-[1-[4-[(3S)-2,6-dioxo-3-piperidyl]-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (Example 158a) and 5-[2-[4-[2-[1-[4-((3R)2,6-dioxo-3-piperidyl)-2-fluoro-phenyl]-4-hydroxy-4-piperidyl]acetyl]piperazin-1-yl] pyrimidin-5-yl]-3-[3-[[ethyl(methyl)sulfamoyl] amino]-2,6-difluoro-benzoyl]-1H-pyrrolo[2,3-b] pyridine (Example 158b)

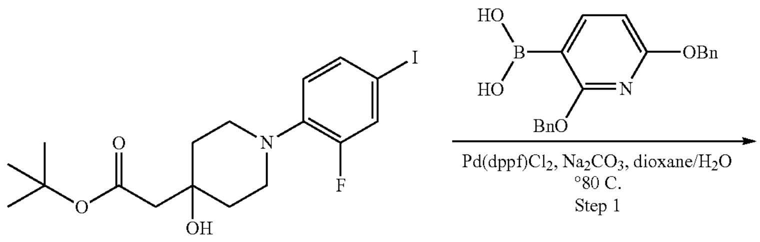

-continued
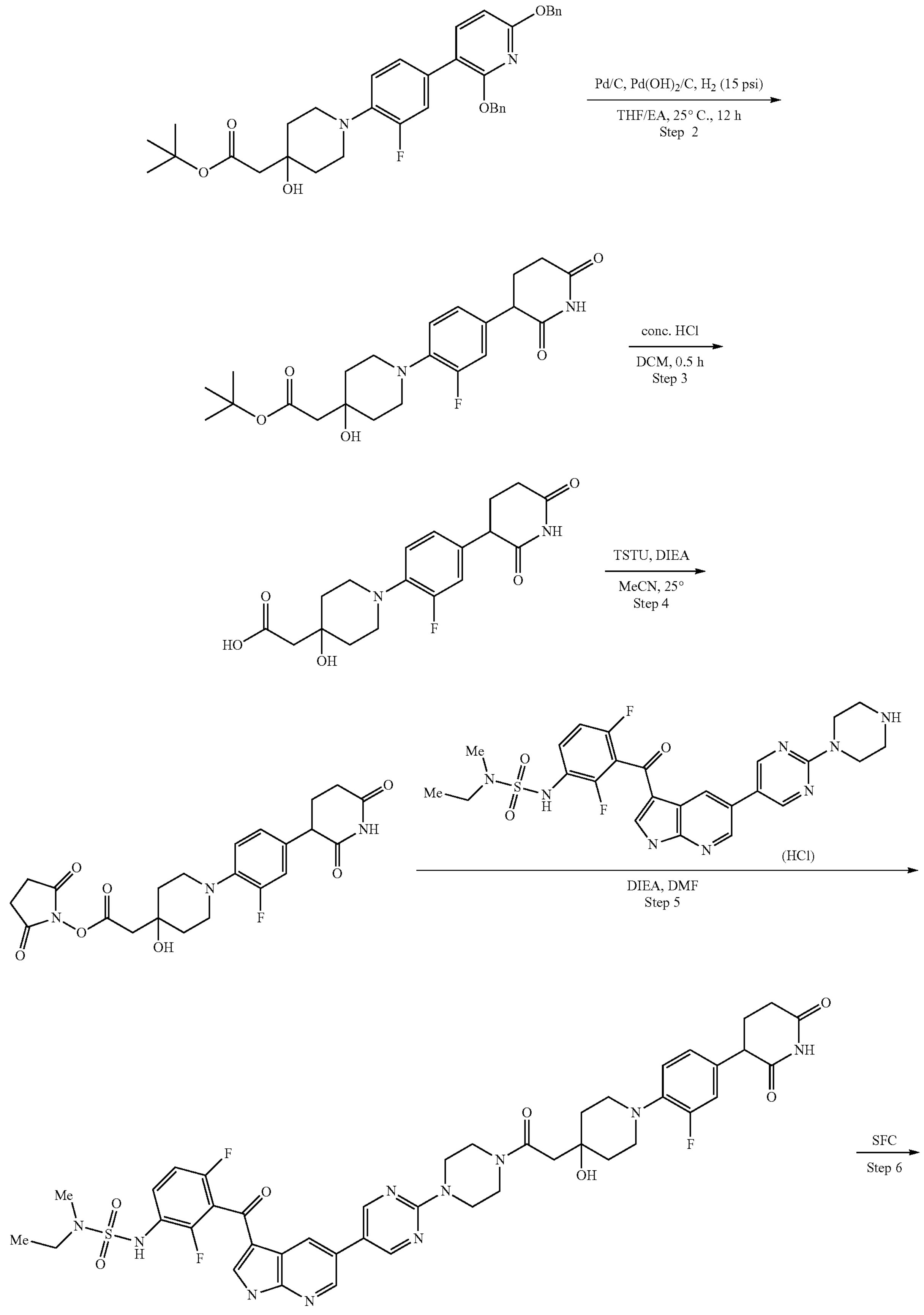

-continued

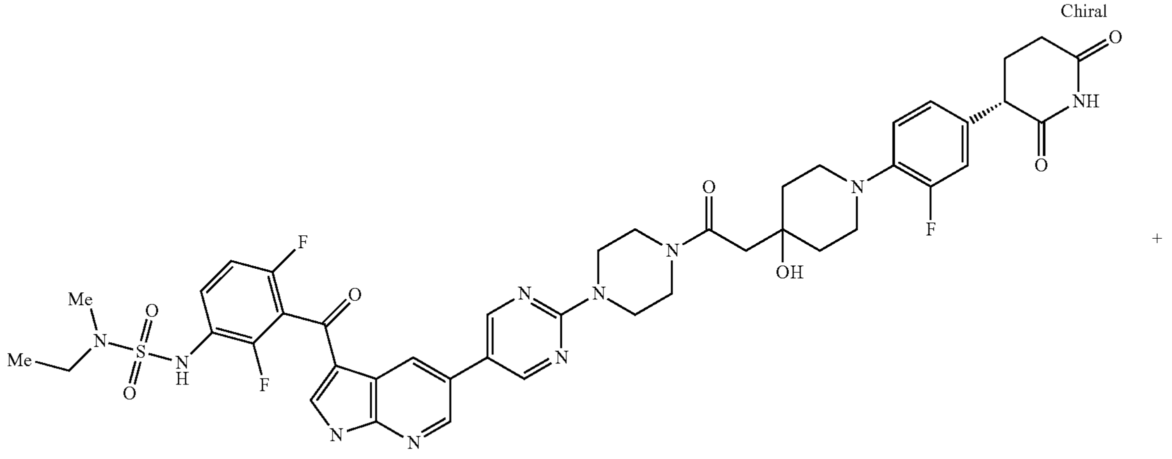

Early-eluting peak
Arbitrarily assigned as S enantiomer

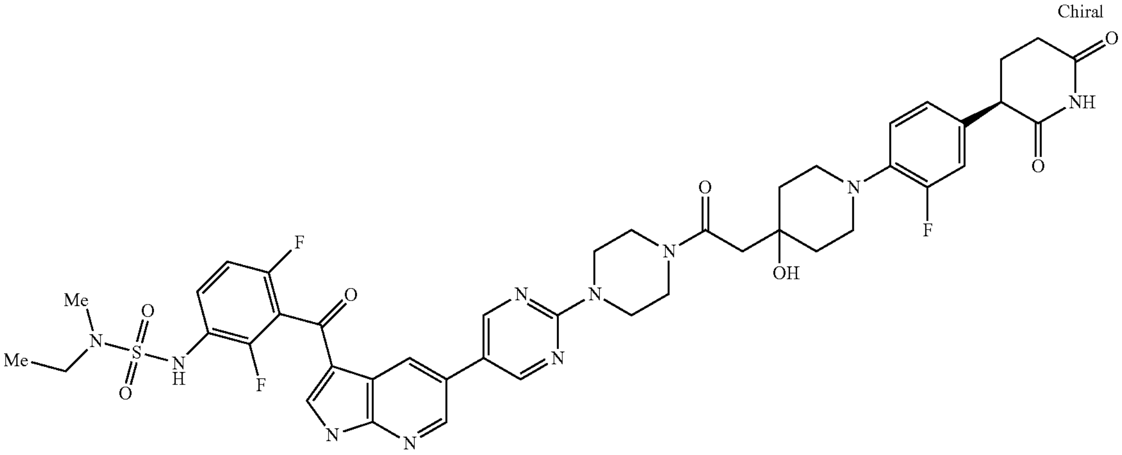

Later-eluting peak
Arbitrarily assigned as R enantiomer

Step 1: To a solution of tert-butyl 2-[1-(2-fluoro-4-iodo-phenyl)-4-hydroxy-4-piperidyl]acetate (100 g, 209.07 mmol, 1.0 eq), 2,6-dibenzyloxy-3-pyridyl)boronic acid (79.05 g, 229.97 mmol, 1.1 eq), $Na_2CO_3$ (44.32 g, 418.13 mmol, 2 eq) in dioxane (1125 mL) and water (375 mL) was added Pd(dppf)$Cl_2$ (7.65 g, 10.45 mmol, 0.05 eq) at 25° C. under $N_2$. The mixture was stirred for 12 h at 80° C. After completion of the reaction, water (400 mL) was added, the mixture was filtered through Celite, and washed with ethyl acetate (500 mL). The aqueous phase was extracted with ethyl acetate (2×300 mL). The combined organic layers were washed with brine (2×200 mL), dried and concentrated to give a residue. The residue was purified by flash silica gel chromatography (ISCO®; 1200 g SepaFlash® Silica Flash Column, Eluent of 0-10% Ethyl acetate/Petroleum ether) to give tert-butyl 2-[1-[4-(2,6-dibenzyloxy-3-pyridyl)-2-fluoro-phenyl]-4-hydroxy-4-piperidyl]acetate (112 g, 183.33 mmol, 87.69% yield) as a yellow solid.

LCMS m/z (ESI): 599.3 $[M+H]^+$.

Step 2: To a mixture of 10% Pd/C (4.5 g) and $Pd(OH)_2/C$ (4.50 g) in tetrahydrofuran (900 mL) and ethyl acetate (900 mL) was added tert-butyl 2-[1-[4-(2,6-dibenzyloxy-3-pyridyl)-2-fluoro-phenyl]-4-hydroxy-4-piperidyl]acetate (90 g, 150.33 mmol, 1.0 eq) at 25° C. under $N_2$. The mixture was stirred at 25° C. for 16 h under $H_2$ (15 psi) atmosphere. After completion of the reaction, the mixture was filtered through a pad of Celite. The filtrate was concentrated under reduced pressure to give a residue. The crude product was stirred in petroleum ether/ethyl acetate (5/1, 10V) at 25° C. for 12 h, and filtered to give tert-butyl 2-[1-[4-(2,6-dioxo-3-piperidyl)-2-fluoro-phenyl]-4-hydroxy-4-piperidyl]acetate (59 g, 136.11 mmol, 90.54% yield) as a white solid.

LCMS m/z (ESI): 421.3 $[M+H]^+$.

Step 3: To a solution of tert-butyl 2-[1-[4-(2,6-dioxo-3-piperidyl)-2-fluoro-phenyl]-4-hydroxy-4-piperidyl]acetate (52 g, 120.58 mmol, 1.0 eq) in dichloromethane (520 mL) was added aqueous HCl solution (12 M, 40.19 mL, 4.0 eq). The mixture was stirred at 25° C. for 0.5 h. After completion of the reaction, the mixture was concentrated under vacuum to give a residue. Saturated aq. $NaHCO_3$ solution (~220 mL) was added to the residue and the precipitate was collected by filtration, washed with water (5 V), dried under vacuum to give the desired product 2-[1-[4-(2,6-dioxo-3-piperidyl)-2-fluoro-phenyl]-4-hydroxy-4-piperidyl]acetic acid (41 g, 100.34 mmol, 83.22% yield, HCl salt) as a white solid.

LCMS m/z (ESI): 365.3 $[M+H]^+$.

Step 4: To a mixture of 2-[1-[4-(2,6-dioxo-3-piperidyl)-2-fluoro-phenyl]-4-hydroxy-4-piperidyl]acetic acid (10 g, 24.95 mmol, 1 eq, HCl salt) in acetonitrile (100 mL) was added N-ethyl-N-isopropylpropan-2-amine (6.45 g, 49.90 mmol, 8.69 mL, 2 eq), N,N,N',N'-Tetramethyl-O—(N-succinimidyl)uronium tetrafluoroborate (11.27 g, 37.42 mmol, 1.5 eq). The mixture was stirred at 25° C. for 3 h. After completion of the reaction, the mixture was filtered. The filtered cake was washed with water (3×5V) and dried under vacuum to give (2,5-dioxopyrrolidin-1-yl) 2-[1-[4-(2,6-dioxo-3-piperidyl)-2-fluoro-phenyl]-4-hydroxy-4-piperidyl] acetate (9.4 g, 20.15 mmol, 80.75% yield) as a light pink solid. LCMS m/z (ESI): 462.2 [M+H]$^+$.

Step 5: A solution of (2,5-dioxopyrrolidin-1-yl) 2-[1-[4-(2,6-dioxo-3-piperidyl)-2-fluoro-phenyl]-4-hydroxy-4-piperidyl]acetate (8.8 g, 18.69 mmol, 1.0 eq), 3-[3-[[ethyl (methyl)sulfamoyl]amino]-2,6-difluoro-benzoyl]-5-(2-piperazin-1-ylpyrimidin-5-yl)-1H-pyrrolo[2,3-b]pyridine (11.13 g, 18.69 mmol, 1.0 eq, HCl salt), and N-ethyl-N-isopropylpropan-2-amine (4.83 g, 37.38 mmol, 6.51 mL, 2 eq) in N,N-dimethylformamide (88 mL) was stirred for 3 h at 25° C. After completion of the reaction, the mixture was added to water (30 V) dropwise, and the resulting mixture was stirred for 30 min at 25° C. The precipitate was filtered. The filtered cake was washed with water (3×3 V) and dried under vacuum to give the crude product. The crude product was stirred in acetonitrile (10 V) at 25° C. for 12 h, filtered, and washed with water (3×5 V). The filtered cake was collected and dried in vacuum oven for 60 h at 40° C. to afford 5-[2-[4-[2-[1-[4-(2,6-dioxo-3-piperidyl)-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (14 g, 15.21 mmol, 81.39% yield) as light brown solid.

LCMS m/z (ESI): 903.4 [M+H]$^+$.

$^1$H NMR (400 MHz, DMSO-d6): δ=10.81 (s, 1H), 8.80 (s, 2H), 8.68 (d, J=1.7 Hz, 1H), 8.57 (br s, 1H), 8.14 (s, 1H), 7.65-7.51 (m, 1H), 7.28 (br t, J=8.7 Hz, 1H), 7.10-6.88 (m, 3H), 4.94 (s, 1H), 3.94-3.60 (m, 10H), 3.18-2.97 (m, 6H), 2.73 (s, 3H), 2.71-2.58 (m, 3H), 2.19 (dq, J=3.3, 12.0 Hz, 1H), 2.06-1.95 (m, 1H), 1.88-1.65 (m, 4H), 1.02 (t, J=7.1 Hz, 3H) ppm.

Step 6: Racemate 5-[2-[4-[2-[1-[4-(2,6-dioxo-3-piperidyl)-2-fluoro-phenyl]-4-hydroxy-4-piperidyl]acetyl]piperazin-1-yl]pyrimidin-5-yl]-3-[3-[[ethyl(methyl)sulfamoyl] amino]-2,6-difluoro-benzoyl]-1H-pyrrolo[2,3-b]pyridine (400 mg, 0.443 mmol) was dissolved in dimethyl sulfoxide (15 mL) and acetonitrile (25 mL). The solution was subjected to SFC separation. Instrument: Waters 80Q. Column: REGIS (s,s) WHELK-01 (250 mm×50 mm, 10 um); Mobile Phase: 80% IPA+ACN (Neu) in Supercritical $CO_2$, Flow Rate: 80 g/min, Cycle Time: 5.7 min, total time: 200 min. Single injection volume: 1.0 ml, Back Pressure: 100 bar to keep the $CO_2$ in Supercritical flow. The fractions were obtained and concentrated under reduced pressure at 35° C. to give compound 5-[2-[4-[2-[1-[4-((3R)2,6-dioxo-3-piperidyl)-2-fluoro-phenyl]-4-hydroxy-4-piperidyl]acetyl]piperazin-1-yl]pyrimidin-5-yl]-3-[3-[[ethyl(methyl)sulfamoyl] amino]-2,6-difluoro-benzoyl]-1H-pyrrolo[2,3-b]pyridine (170 mg, 188.27 umol, 42.50% yield, 98.5% e.e.) as a white solid, and compound 5-[2-[4-[2-[1-[4-[(3 S)-2,6-dioxo-3-piperidyl]-2-fluoro-phenyl]-4-hydroxy-4-piperidyl]acetyl] piperazin-1-yl]pyrimidin-5-yl]-3-[3-[[ethyl(methyl)sulfamoyl]amino]-2,6-difluoro-benzoyl]-1H-pyrrolo[2,3-b] pyridine (140 mg, 155.05 umol, 35.00% yield, 98.5% e.e) as a white solid. The stereochemistry was assigned arbitrarily.

LCMS m/z (ESI): 903.5 [M+H]$^+$.

$^1$H NMR (Early-eluting peak) (400 MHz, DMSO-d6) δ=13.00 (d, J=2.8 Hz, 1H), 10.81 (s, 1H), 9.70 (s, 1H), 8.80 (s, 2H), 8.67 (d, J=2.2 Hz, 1H), 8.57 (s, 1H), 8.14 (d, J=2.7 Hz, 1H), 7.58 (t, J=6.1, 9.0 Hz, 1H), 7.27 (t, J=8.1 Hz, 1H), 7.09-6.86 (m, 3H), 4.92 (s, 1H), 3.94-3.56 (m, 10H), 3.16-2.97 (m, 6H), 2.73 (s, 3H), 2.67-2.59 (m, 3H), 2.25-2.13 (m, 1H), 2.05-1.96 (m, 1H), 1.86-1.67 (m, 4H), 1.04-0.98 (m, 3H) ppm.

$^1$H NMR (Later-eluting peak) (400 MHz, DMSO-d6) δ=13.00 (s, 1H), 11.10-10.46 (m, 1H), 9.71 (s, 1H), 8.81 (s, 2H), 8.68 (d, J=2.0 Hz, 1H), 8.57 (s, 1H), 8.14 (s, 1H), 7.67-7.52 (m, 1H), 7.33-7.22 (m, 1H), 7.08-6.91 (m, 3H), 4.93 (s, 1H), 3.96-3.56 (m, 9H), 3.16-2.98 (m, 6H), 2.74 (s, 3H), 2.67-2.59 (m, 3H), 2.20 (q, J=3.9, 12.2 Hz, 1H), 2.01 (d, J=4.6, 8.8 Hz, 1H), 1.88-1.67 (m, 4H), 1.02 (t, J=7.2 Hz, 3H) ppm Examples 158c and 158d 5-[2-[4-[2-[1-[4-[(3S)-3-deuterio-2,6-dioxo-3-piperidyl]-2-fluoro-phenyl]-4-hydroxy-4-piperidyl] acetyl]piperazin-1-yl]pyrimidin-5-yl]-3-[3-[[ethyl (methyl)sulfamoyl]amino]-2,6-difluoro-benzoyl]-1H-pyrrolo[2,3-b]pyridine (Example 158c) and 5-[2-[4-[2-[1-[4-[(3R)-3-deuterio-2,6-dioxo-3-piperidyl]-2-fluoro-phenyl]-4-hydroxy-4-piperidyl] acetyl]piperazin-1-yl]pyrimidin-5-yl]-3-[3-[[ethyl (methyl)sulfamoyl]amino]-2,6-difluoro-benzoyl]-1H-pyrrolo[2,3-b]pyridine (Example 158d)

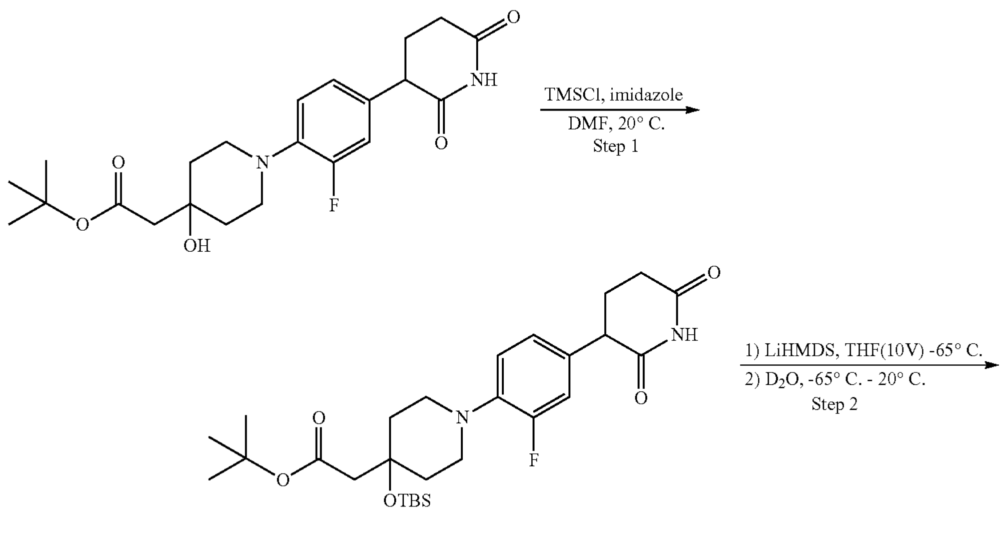

-continued
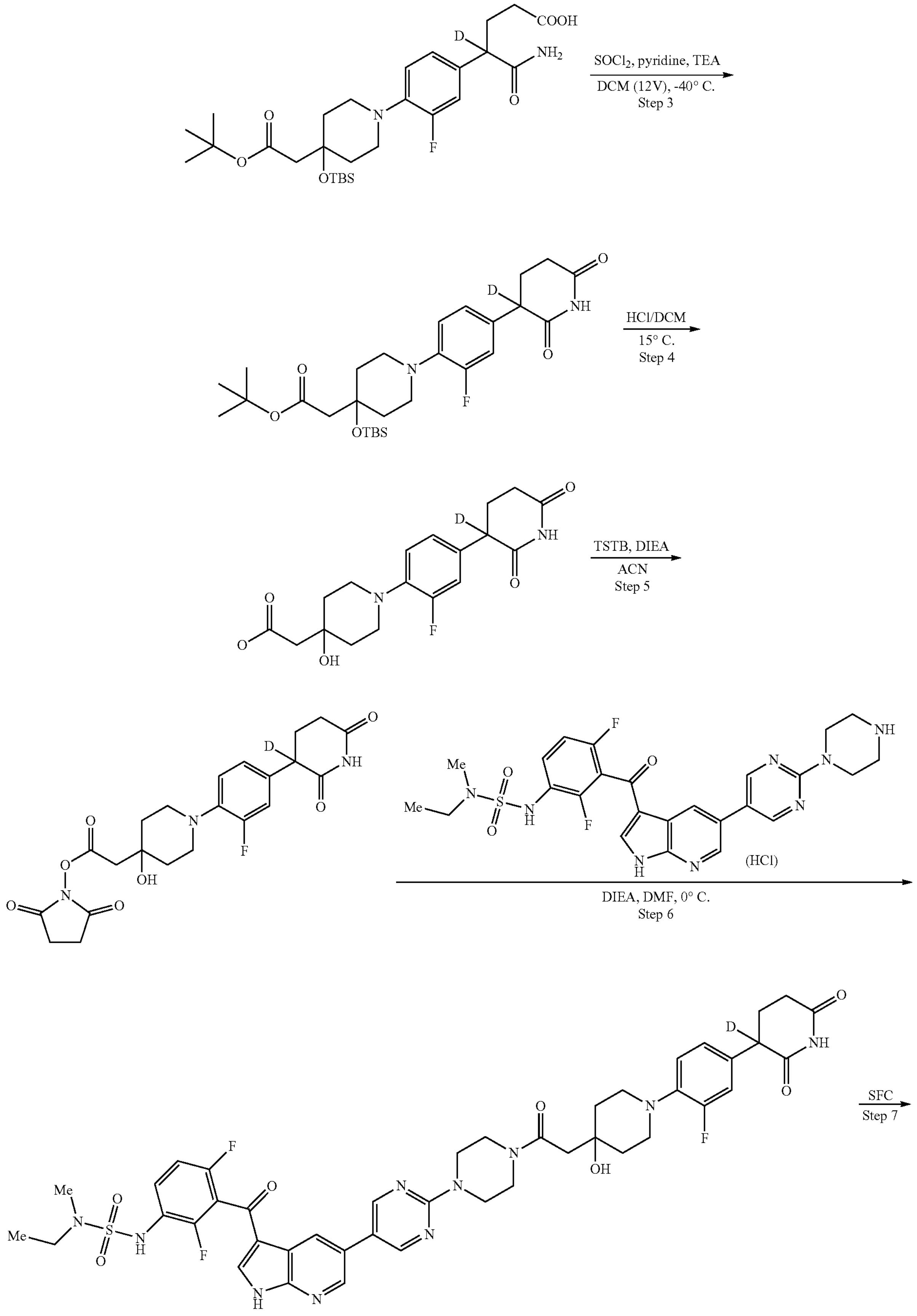

-continued

Chiral

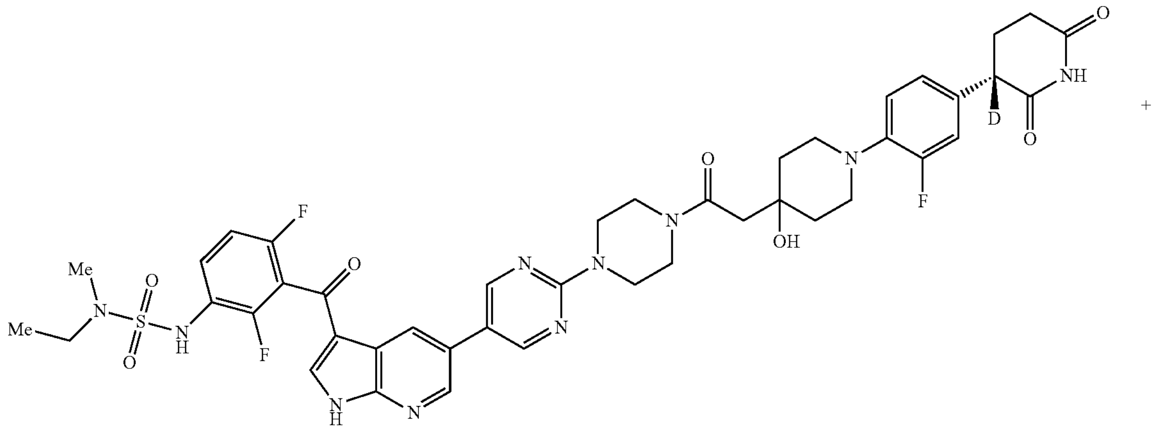

Early-eluting peak
Arbitrarily assigned as S

Chiral

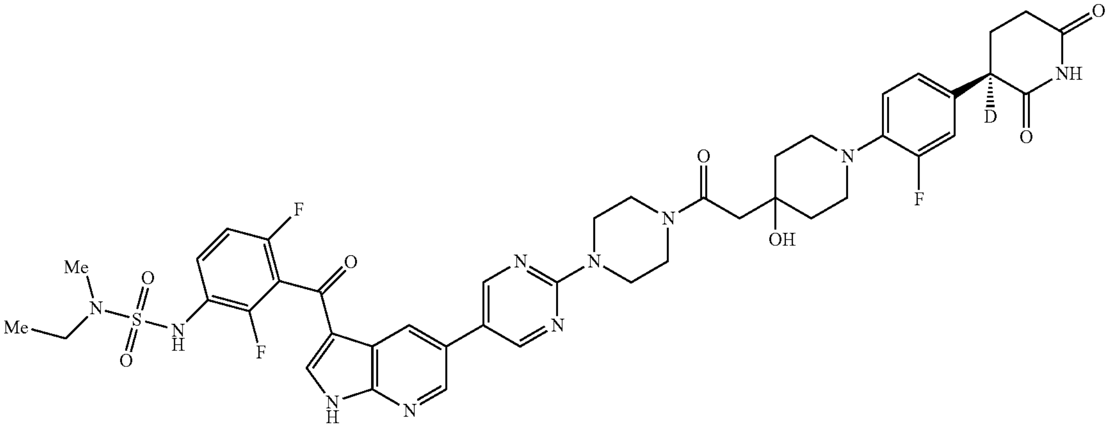

Early-eluting peak
Arbitrarily assigned as R

Step 1: To a solution of tert-butyl 2-[1-[4-(2,6-dioxo-3-piperidyl)-2-fluoro-phenyl]-4-hydroxy-4-piperidyl]acetate (5 g, 11.89 mmol, 1 eq) and trimethyl chlorosilane (2.71 g, 24.97 mmol, 3.17 mL, 2.1 eq) in N,N-dimethylformamide (40 mL) was added imidazole (2.43 g, 35.67 mmol, 3 eq). The mixture was stirred for 1 h at 20° C. After completion of the reaction, the reaction mixture was quenched by addition of water (100 mL) and extracted with ethyl acetate (3×30 mL). The combined organic layers were washed with brine (4×30 mL), dried over sodium sulfate, filtered, and concentrated under reduced pressure to give tert-butyl 2-[1-[4-(2,6-dioxo-3-piperidyl)-2-fluoro-phenyl]-4-trimethylsilyloxy-4-piperidyl]acetate (5.8 g, crude) as a white solid.

Step 2: To a solution of tert-butyl 2-[1-[4-(2,6-dioxo-3-piperidyl)-2-fluoro-phenyl]-4-trimethylsilyloxy-4-piperidyl]acetate (2.5 g, 5.07 mmol, 1 eq) in tetrahydrofuran (25 mL) was added lithium bis(trimethylsilyl)amide (1 M, 12.69 mL, 2.5 eq) at −70° C. under nitrogen. The mixture was stirred for 1 h at −70° C., and deuteroxide (1.25 g, 62.50 mmol, 12.32 eq) was added.

The reaction mixture was warmed to 15° C. slowly, and stirred for 12 h at 15° C. After completion of the reaction, the reaction mixture was subjected to reversed-phase HPLC purification (0.1% ammonium hydroxide) directly to give 5-amino-4[4-[4-(2-tert-butoxy-2-oxo-ethyl)-4-trimethylsilyloxy-1-piperidyl]-3-fluoro-phenyl]-4-deuterio-5-oxo-pentanoic acid (2.3 g, 4.05 mmol, 79.7% yield) as a white solid.

LCMS m/z (ESI): 513.2 $[M+H]^+$.

Step 3: To a solution of 5-amino-4-[4-[4-(2-tert-butoxy-2-oxo-ethyl)-4-trimethylsilyloxy-1-piperidyl]-3-fluoro-phenyl]-4-deuterio-5-oxo-pentanoic acid (2.2 g, 4.30 mmol, 1 eq) in dichloromethane (40 mL) was added thionyl chloride (2.56 g, 21.50 mmol, 1.56 mL, 5 eq) at −40° C. After completion of the addition, N,N-dimethylformamide (157.13 mg, 2.15 mmol, 165.40 uL, 0.5 eq) was added and the resulting mixture was stirred for 2 h, maintaining at −40° C. Then pyridine (1.70 g, 21.50 mmol, 1.74 mL, 5 eq) was added. After stirring for another 40 minutes, triethylamine (2.18 g, 21.50 mmol, 2.99 mL, 5 eq) was added and the mixture was stirred for 2 h at −40° C. Dichloromethane (20 mL) was added and the mixture was washed with saturated aqueous sodium bicarbonate solution (2×30 mL), water (2×20 mL), and with brine (2×20 mL). The washed organic layer was dried and concentrated under vacuum to give a residue. The residue was purified by column chromatography ($SiO_2$, petroleum ether/ethyl acetate=10/1 to 1/2) to give tert-butyl 2-[1-[4-(3-deuterio-2,6-dioxo-3-piperidyl)-2-fluoro-phenyl]-4-trimethylsilyloxy-4-piperidyl]acetate (1.1 g, 2.12 mmol, 49.4% yield) as a light brown solid.

LCMS m/z (ESI): 494.2 $[M+H]^+$.

Step 4: To a solution of tert-butyl 2-[1-[4-(3-deuterio-2,6-dioxo-3-piperidyl)-2-fluoro-phenyl]-4-trimethylsilyloxy-4-piperidyl]acetate (1.0 g, 2.03 mmol, 1 eq) in dichloromethane (10 mL) was added hydrochloric acid (12 M, 675.23 uL, 4 eq) at 15° C., and the mixture was stirred for 1 h at 15° C. After completion of the reaction, the mixture was concentrated under vacuum to give a residue. Saturated aq. sodium bicarbonate solution was added and the mixture was adjusted to pH~5. The precipitate was filtered to give 2-[1-[4-(3-deuterio-2,6-dioxo-3-piperidyl)-2-fluoro-phenyl]-4-hydroxy-4-piperidyl]acetic acid (680 mg, 1.81 mmol, 89.1% yield, HCl salt) as a blue solid.

LCMS m/z (ESI): 366.1 $[M+H]^+$.

Step 5: To a solution of 2-[1-[4-(3-deuterio-2,6-dioxo-3-piperidyl)-2-fluoro-phenyl]-4-hydroxy-4-piperidyl]acetic acid (680.00 mg, 1.69 mmol, 1 eq, HCl salt) in acetonitrile (6.8 mL) was added N,N-diisopropylethylamine (437.41 mg, 3.38 mmol, 589.50 uL, 2 eq) and O—(N-Succinimidyl)-1,1,3,3-tetramethyluronium tetrafluoroborate (764.16 mg, 2.54 mmol, 1.5 eq) at 15° C. The mixture was stirred for 1 h at 25° C. After completion of the reaction, the mixture was filtered to give the crude product. The crude product was washed with water (3×4 mL) to give (2,5-dioxopyrrolidin-1-yl) 2-[1-[4-(3-deuterio-2,6-dioxo-3-piperidyl)-2-fluoro-phenyl]-4-hydroxy-4-piperidyl]acetate (606 mg, 1.28 mmol, 75.5% yield) as an off-white solid.

LCMS m/z (ESI): 463.1 $[M+H]^+$.

Step 6: A solution of (2,5-dioxopyrrolidin-1-yl) 2-[1-[4-(3-deuterio-2,6-dioxo-3-piperidyl)-2-fluoro-phenyl]-4-hydroxy-4-piperidyl]acetate (600 mg, 1.26 mmol, 1.0 eq), 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (753.91 mg, 1.26 mmol, 1.0 eq, HCl salt), and N,N-diisopropylethylamine (325.30 mg, 2.52 mmol, 438.42 uL, 2.0 eq) in N,N-dimethylformamide (6 mL) was stirred for 7 h at 0° C. The mixture was added to water (30 mL) in dropwise, stirred for 30 min at 25° C., and was filtered. The filtered cake was washed with water (3×3 mL) and dried under vacuum to give the crude product. The crude product was triturated with acetonitrile (10 V) at 25° C. for 12 h and filtered. The filtered cake was washed with water (3×5V) and dried under vacuum to give 5-[2-[4-[2-[1-[4-(3-deuterio-2,6-dioxo-3-piperidyl)-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (940 mg, 1.01 mmol, 79.9% yield) as an off-white solid.

LCMS m/z (ESI): 904.3 $[M+H]^+$.

Step 7 (SFC Separation)

The racemate 5-[2-[4-[2-[1-[4-(3-deuterio-2,6-dioxo-3-piperidyl)-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (940 mg, 1.01 mmol, 95.7% purity) was separated by SFC (column: REGIS (s,s) WHELK-O1 (250 mm*50 mm, 10 um); mobile phase: [IPA-ACN]; B %: 80%-80%, 4.6 min; 250 min) and further purified by prep-HPLC (column: Phenomenex Synergi C18 150*25 mm*10 um; mobile phase: [water(0.225% FA)-ACN]; B %: 30%-60%, 10 min; column: Phenomenex Synergi C18 150*25 mm*10 um; mobile phase: [water(0.225% FA)-ACN]; B %: 30%-60%, 10 min) to give 5-[2-[4-[2-[1-[4-[(3 S)-3-deuterio-2,6-dioxo-3-piperidyl]-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (310 mg, 340.20 umol, 34.2% yield, >99% e.e.) as a white solid and 5-[2-[4-[2-[1-[4-[(3R)-3-deuterio-2,6-dioxo-3-piperidyl]-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (214 mg, 234.14 umol, 23.5% yield, 93.4% e.e.) was obtained as a white solid. The degree of deuteration was estimated between 80 to 85% based on 41 NMR analyses. The stereochemistry was assigned arbitrarily.

LCMS m/z (ESI): 904.3 $[M+H]^+$ and 904.3 $[M+H]^+$.

$^1$HNMR (Early-eluting peak) (400 MHz, DMSO-d6+$CD_3OD$): δ=8.65 (s, 2H), 8.57 (br s, 1H), 8.53 (d, J=2.2 Hz, 1H), 7.87 (s, 1H), 7.56 (dt, J=5.7, 8.9 Hz, 1H), 7.14-7.04 (m, 1H), 7.01-6.92 (m, 1H), 6.88 (br d, J=11.6 Hz, 2H), 3.92-3.77 (m, 4H), 3.64 (br d, J=5.0 Hz, 4H), 3.15-2.93 (m, 6H), 2.71 (s, 3H), 2.65-2.55 (m, 3H), 2.20-1.97 (m, 2H), 1.85-1.68 (m, 4H), 0.99 (t, J=7.2 Hz, 3H) ppm.

$^1$H NMR (Later-eluting peak) (400 MHz, DMSO-d6+$CD_3OD$): δ=8.68-8.62 (m, 2H), 8.61-8.55 (m, 1H), 8.52 (d, J=2.2 Hz, 1H), 8.42-8.38 (m, 1H), 7.86 (s, 1H), 7.62-7.51 (m, 1H), 7.12-7.03 (m, 1H), 7.00-6.92 (m, 1H), 6.89 (s, 1H), 6.88-6.84 (m, 1H), 3.96-3.76 (m, 4H), 3.75-3.57 (m, 4H), 3.14-2.93 (m, 6H), 2.71 (s, 3H), 2.64-2.55 (m, 3H), 2.19-1.99 (m, 2H), 1.86-1.69 (m, 4H), 0.99 (t, J=7.2 Hz, 3H) ppm.

Example 158e

[1-[4-(2,6-dioxo-3-piperidyl)-2-fluoro-phenyl]-4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl]dihydrogen phosphate

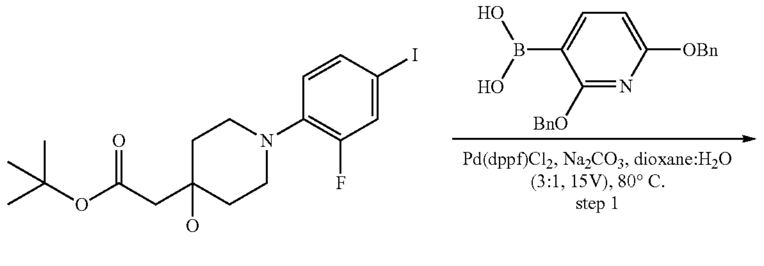

-continued
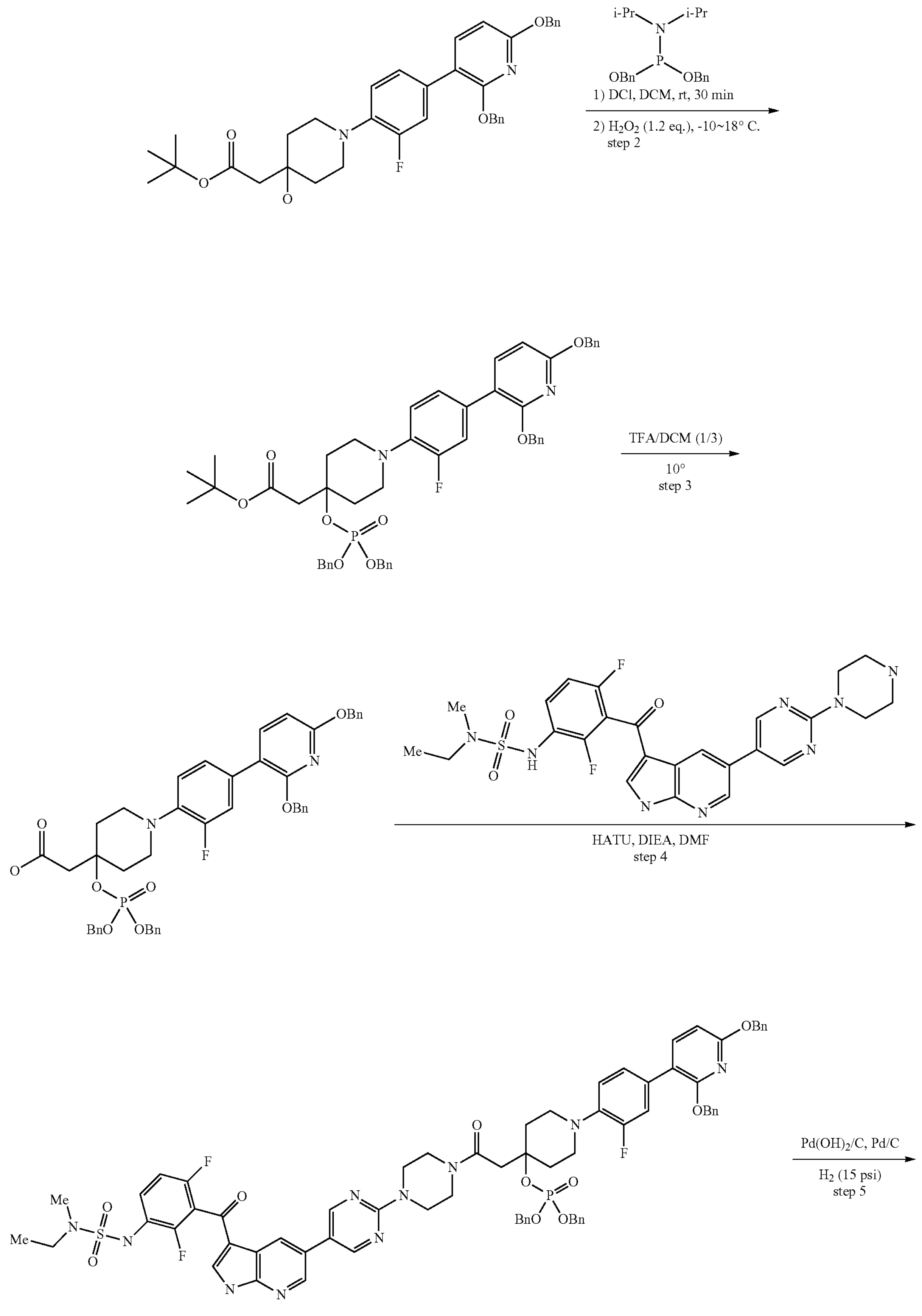

-continued

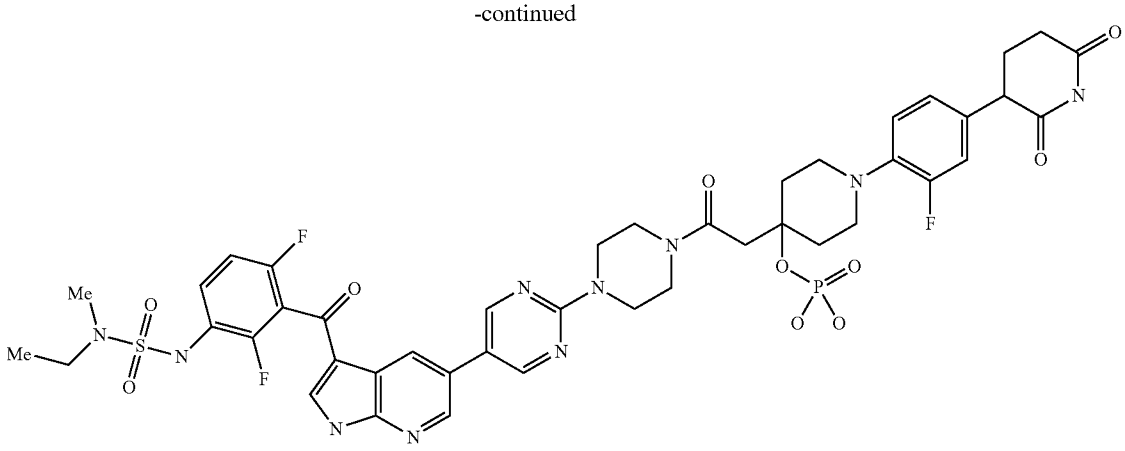

Step 1: To a solution of tert-butyl 2-[1-(2-fluoro-4-iodo-phenyl)-4-hydroxy-4-piperidyl]acetate (7.7 g, 16.10 mmol, 1.0 eq), 2,6-dibenzyloxy-3-pyridyl)boronic acid (5.99 g, 17.71 mmol, 1.1 eq), sodium carbonate (3.41 g, 32.20 mmol, 2.0 eq) in dioxane (81 mL) and water (27 mL) was added Pd(dppf)$Cl_2$ (588.95 mg, 804.90 umol, 0.05 eq) at 25° C. under nitrogen. The mixture was stirred for 12 h at 80° C. under nitrogen. Water (20 mL) was added. The mixture was filtered through a pad of Celite, and washed with ethyl acetate (3×40 mL). The aqueous phase was extracted with ethyl acetate (2×20 mL). The combined organic layers were washed with brine (2×20 mL), dried over sodium sulfate, filtered, and concentrated under vacuum to give a residue. The residue was purified by flash silica gel chromatography (ISCO®; 80 g SepaFlash® Silica Flash Column, eluent of 0-5% ethyl acetate/petroleum ether gradient 60 mL/min) to give tert-butyl 2-[1-[4-(2,6-dibenzyloxy-3-pyridyl)-2-fluoro-phenyl]-4-hydroxy-4-piperidyl]acetate (7.2 g, 11.79 mmol, 73.2% yield) as a light brown solid. LCMS m/z (ESI): 599.4 $[M+H]^+$.

Step 2: To a solution of tert-butyl 2-[1-[4-(2,6-dibenzyloxy-3-pyridyl)-2-fluoro-phenyl]-4-hydroxy-4-piperidyl]acetate (1.0 g, 1.67 mmol, 1 eq) and N-dibenzyloxyphosphanyl-N-isopropyl-propan-2-amine (1.15 g, 3.34 mmol, 1.12 mL, 2 eq) in dichloromethane (10 mL) was added 1H-imidazole-4,5-dicarbonitrile (591.76 mg, 5.01 mmol, 3 eq) at 18° C. The mixture was stirred for 20 min at 18° C. under nitrogen. Hydrogen peroxide (227.22 mg, 2.00 mmol, 192.56 uL, 30% w/w, 1.2 eq) was added at −10° C. and the mixture was stirred for 2 h at 18° C. under nitrogen. Dichloromethane (10 mL) and water (5 mL) were added to the reaction mixture. The separated organic layer was washed with water (3×10 mL), saturated sodium sulfite (3×10 mL), and brine (3×10 mL). The washed organic layer was dried over sodium sulfate, filtered, and concentrated under vacuum to give a residue. The residue was purified by column chromatography ($SiO_2$, 300~400 mesh, petroleum ether/ethyl acetate=10/1 to 4/1) to give tert-butyl 2-[4-dibenzyloxyphosphoryloxy-1-[4-(2,6-dibenzyloxy-3-pyridyl)-2-fluoro-phenyl]-4-piperidyl]acetate (1.26 g, 1.32 mmol, 79.1% yield) as a yellow oil.

LCMS m/z (ESI): 859.3 $[M+H]^+$.

Step 3: To a solution of tert-butyl 2-[4-dibenzyl oxyphosphoryloxy-1-[4-(2,6-dibenzyloxy-3-pyridyl)-2-fluoro-phenyl]-4-piperidyl]acetate (1.1 g, 1.28 mmol, 1 eq) in dichloromethane (6 mL) was added trifluoroacetic acid (3.08 g, 27.01 mmol, 2 mL, 21.09 eq) dropwise under nitrogen. The resulting mixture was stirred for 20 min at 15° C. and then was concentrated under vacuum to give the crude 2-[4-dibenzyloxyphosphoryloxy-1-[4-(2,6-dibenzyloxy-3-pyridyl)-2-fluoro-phenyl]-4-piperidyl]acetic acid (1.2 g, TFA salt) as a light brown oil, which was used directly in the next step. LCMS m/z (ESI): 803.3 $[M+H]^+$.

Step 4: To a solution of 2-[4-dibenzyloxyphosphoryloxy-1-[4-(2,6-dibenzyloxy-3-pyridyl)-2-fluoro-phenyl]-4-piperidyl]acetic acid (1.0 g, 872.56 umol, 1.1 eq, TFA salt) in N,N-dimethylformamide (10 mL) was added 2-(7-azabenzotriazol-1-yl)-N,N,N,N-tetramethyluronium hexafluorophosphate (301.61 mg, 793.24 umol, 1.0 eq) and N,N-diisopropylethylamine (102.52 mg, 793.24 umol, 138.16 uL, 1 eq), and the mixture was stirred for 1 h at 20° C. 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (528.27 mg, 793.24 umol, 1 eq, 3HCl salt) and N,N-diisopropylethylamine (410.07 mg, 3.17 mmol, 552.66 uL, 4 eq) were added. The resulting mixture was stirred for 12 h at 15° C. The reaction mixture was filtered and the filtrate was subjected to reversed-phase HPLC purification (0.1% ammonium hydroxide) to give dibenzyl [1-[4-(2,6-dibenzyloxy-3-pyridyl)-2-fluoro-phenyl]-4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl]phosphate (500 mg, 346.65 umol, 43.7% yield) as a light yellow solid.

LCMS m/z (ESI): 1341.4 $[M+H]^+$.

Step 5: To a solution of dibenzyl [1-[4-(2,6-dibenzyloxy-3-pyridyl)-2-fluoro-phenyl]-4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl] phosphate (100 mg, 74.55 umol, 1 eq) in DMF (2.5 mL) was added 10% Pd/C (65 mg) and $Pd(OH)_2/C$ (65 mg) under $N_2$. The suspension was degassed and purged with $H_2$ several times. The resulting mixture was stirred at 30° C. for 2.5 hours under $H_2$ (15 psi). The mixture was filtered and the filtrate was subjected to prep-HPLC purification (column: Phenomenex luna C18 150*25 mm*10 um; mobile phase: [water (0.225% FA)-ACN]; B %: 36%-66%, 10 min) to give [1-[4-(2,6-dioxo-3-piperidyl)-2-fluoro-phenyl]-4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-piperidyl] dihydrogen phosphate (8 mg, 8.15 umol, 10.9% yield) as a white solid.

LCMS m/z (ESI): 982.9 $[M+H]^+$.

$^1$HNMR (400 MHz, DMSO-d6): δ=10.79 (s, 1H), 8.76 (s, 2H), 8.65 (br s, 1H), 8.54 (d, J=2.2 Hz, 1H), 8.08 (s, 1H), 7.56 (dt, J=5.7, 8.9 Hz, 1H), 7.22-7.14 (m, 1H), 7.01-6.92 (m, 1H), 6.88 (br d, J=11.6 Hz, 2H), 3.92-3.77 (m, 4H), 3.64 (br d, J=5.0 Hz, 4H), 3.15-2.93 (m, 6H), 2.71 (s, 3H), 2.65-2.55 (m, 3H), 2.20-1.97 (m, 2H), 1.85-1.68 (m, 4H), 0.99 (t, J=7.2 Hz, 3H) ppm.

Example 159

5-[6-[4-[2-[1-[4-(2,6-dioxo-3-piperidyl)-2-fluoro-phenyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine

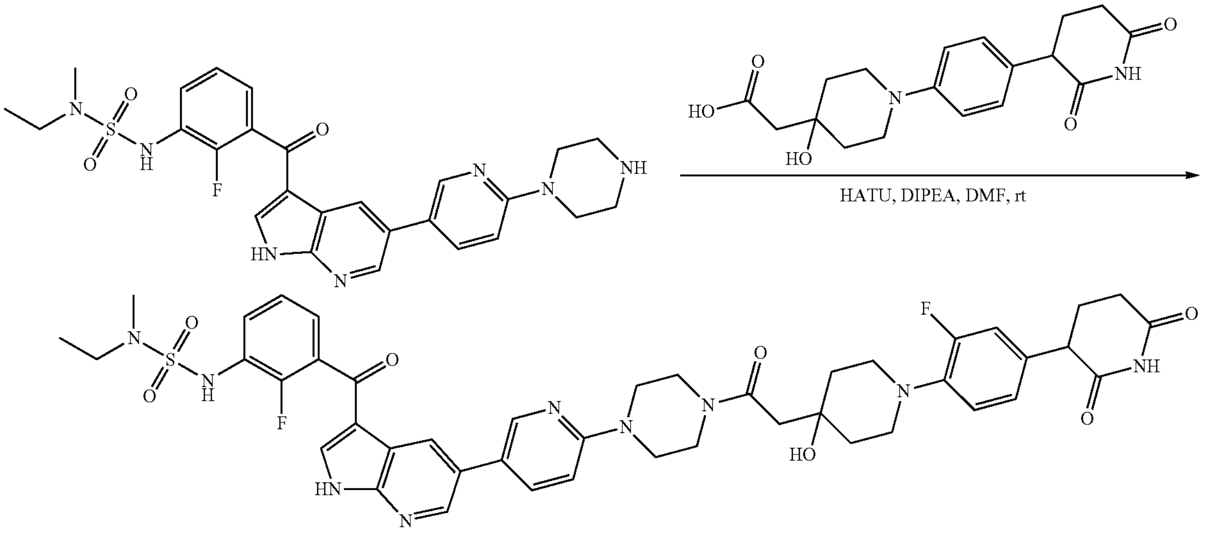

Target compound was prepared via HATU mediated acid-amine coupling reaction (procedure A). Amide coupling was carried out using 3-[3-[[ethyl(methyl)sulfamoyl]amino]-2-fluoro-benzoyl]-5-(6-piperazin-1-yl-3-pyridyl)-1H-pyrrolo[2,3-b]pyridine (350 mg, 609.68 μmol), 2-[1-[4-(2,6-dioxo-3-piperidyl)-2-fluoro-phenyl]-4-hydroxy-4-piperidyl]acetic acid (250 mg, 623.71 μmol), N,N-diisopropylethylamine (1.48 g, 11.48 mmol, 2.0 mL) and HATU (260 mg, 683.80 μmol). The crude compound was purified by reverse phase column chromatography by using 150 g snap cartridge eluted with 50% acetonitrile in 0.1% ammonium acetate in water to afford 5-[6-[4-[2-[1-[4-(2,6-dioxo-3-piperidyl)-2-fluoro-phenyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine (150 mg, 166.21 μmol, 27.26% yield) as off-white solid. LCMS (ESI−): 882.3 $[M-H]^+$. $^1H$ NMR (400 MHz, DMSO-$d_6$): δ 12.84 (s, 1H), 10.82 (s, 1H), 9.78 (s, 1H), 8.66 (d, J=2.00 Hz, 1H), 8.56 (d, J=2.00 Hz, 1H), 8.51 (d, J=2.40 Hz, 1H), 7.96 (t, J=2.80 Hz, 2H), 7.58-7.62 (m, 1H), 7.40 (dd, J=6.00, 9.80 Hz, 1H), 7.36 (t, J=8.00 Hz, 1H), 6.96-7.03 (m, 4H), 4.94 (s, 1H), 3.78-3.82 (m, 1H), 3.57-3.72 (m, 8H), 3.01-3.17 (m, 6H), 2.75 (s, 3H), 2.62-2.69 (m, 3H), 2.57-2.50 (m, 1H), 2.10-2.21 (m, 1H), 1.95-2.02 (m, 1H), 1.70-1.81 (m, 4H), 1.02 (t, J=6.80 Hz, 3H).

Example 160

5-[6-[4-[2-[1-[4-(2,6-dioxo-3-piperidyl)-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine

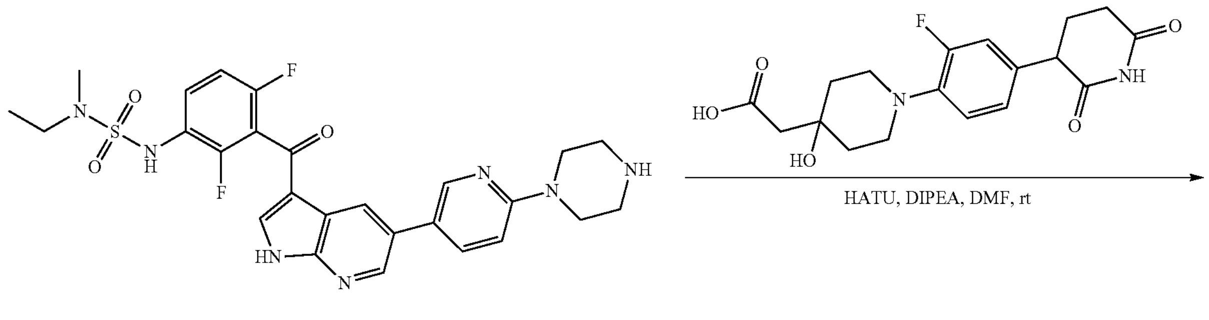

-continued

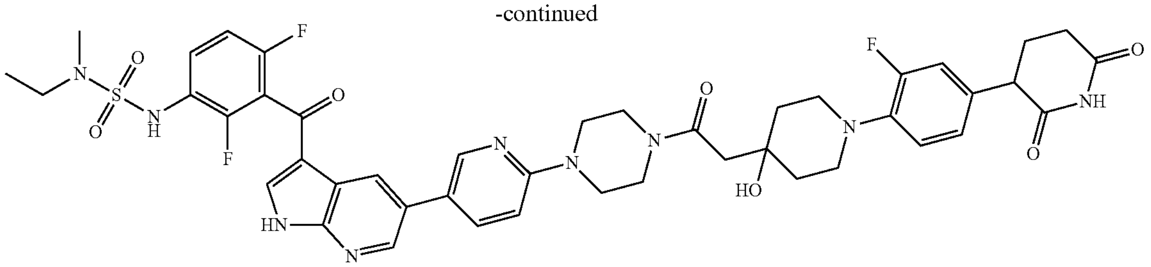

Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (220 mg, 371.58 μmol), 2-[1-[4-(2,6-dioxo-3-piperidyl)-2-fluoro-phenyl]-4-hydroxy-4-piperidyl] acetic acid (150 mg, 374.23 μmol), N,N-diisopropylethylamine (1.48 g, 11.48 mmol, 2.0 mL) and HATU (160 mg, 420.80 μmol). The crude compound was purified by reverse phase column chromatography by using 150 g snap cartridge eluted with 50% acetonitrile in 0.1% formic acid in water to afford 5-[6-[4-[2-[1-[4-(2,6-dioxo-3-piperidyl)-2-fluoro-phenyl]-4-hydroxy-4-piperidyl] acetyl]piperazin-1-yl]-3-pyridyl]-3-[3-[[ethyl(methyl)sulfamoyl]amino]-2,6-difluoro-benzoyl]-1H-pyrrolo[2,3-b] pyridine (102 mg, 107.20 μmol, 28.85% yield) as off-white solid. LCMS (ESI+): 902.3 $[M+H]^+$. $^1H$ NMR (400 MHz, DMSO-$d_6$): δ 12.96 (s, 1H), 10.82 (s, 1H), 9.83 (s, 1H), 8.68 (d, J=2.40 Hz, 1H), 8.52 (d, J=2.40 Hz, 2H), 8.12 (s, 1H), 7.98 (dd, J=2.40, 8.80 Hz, 1H), 7.55-7.61 (m, 1H), 7.27 (t, J=8.00 Hz, 1H), 6.96-7.03 (m, 4H), 4.94 (s, 1H), 3.80 (dd, J=4.80, 12.00 Hz, 1H), 3.60-3.72 (m, 8H), 3.08-3.33 (m, 6H), 2.73 (s, 3H), 2.62-2.72 (m, 4H), 2.10-2.22 (m, 1H), 2.02-2.08 (m, 1H), 1.70-1.81 (m, 4H), 1.02 (t, J=7.20 Hz, 3H).

Example 161

6-[4-[(2,6-dioxo-3-piperidyl)amino]phenyl]-2-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]-5,7-dihydro-4H-pyrazolo[3,4-c] pyridine

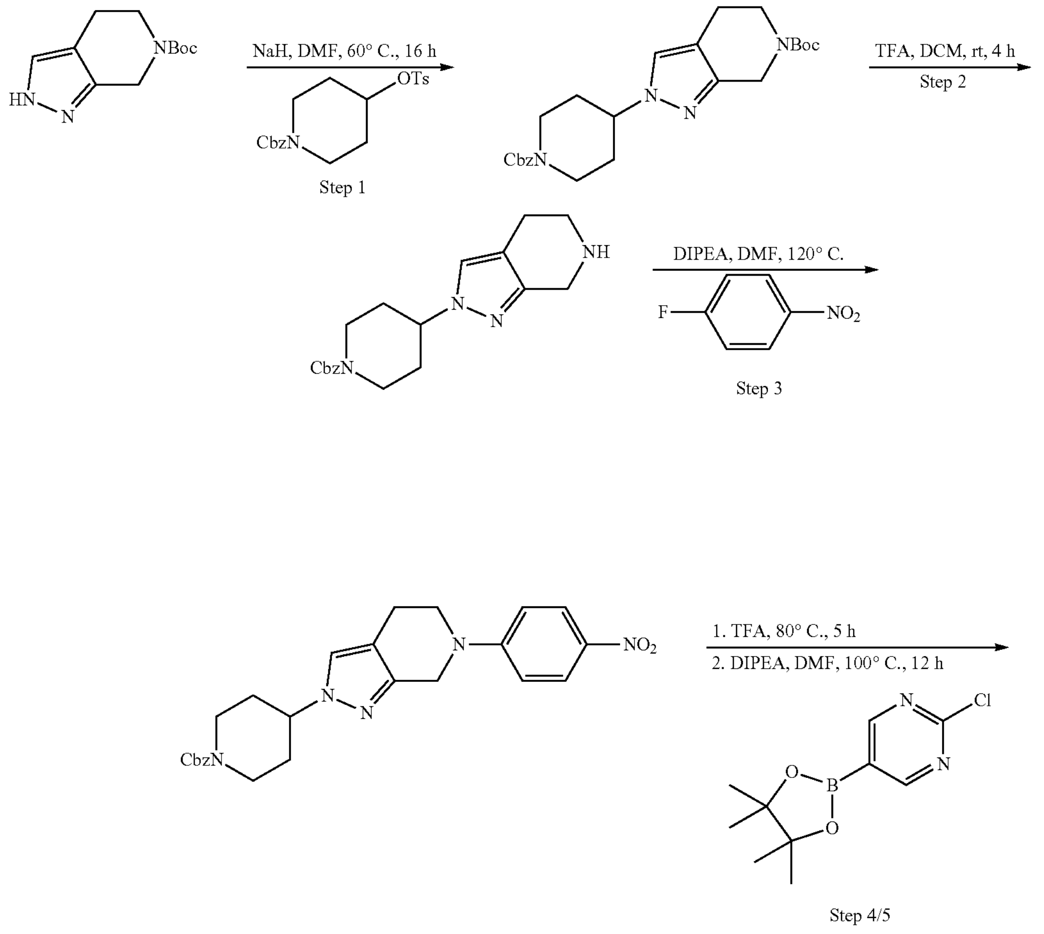

-continued

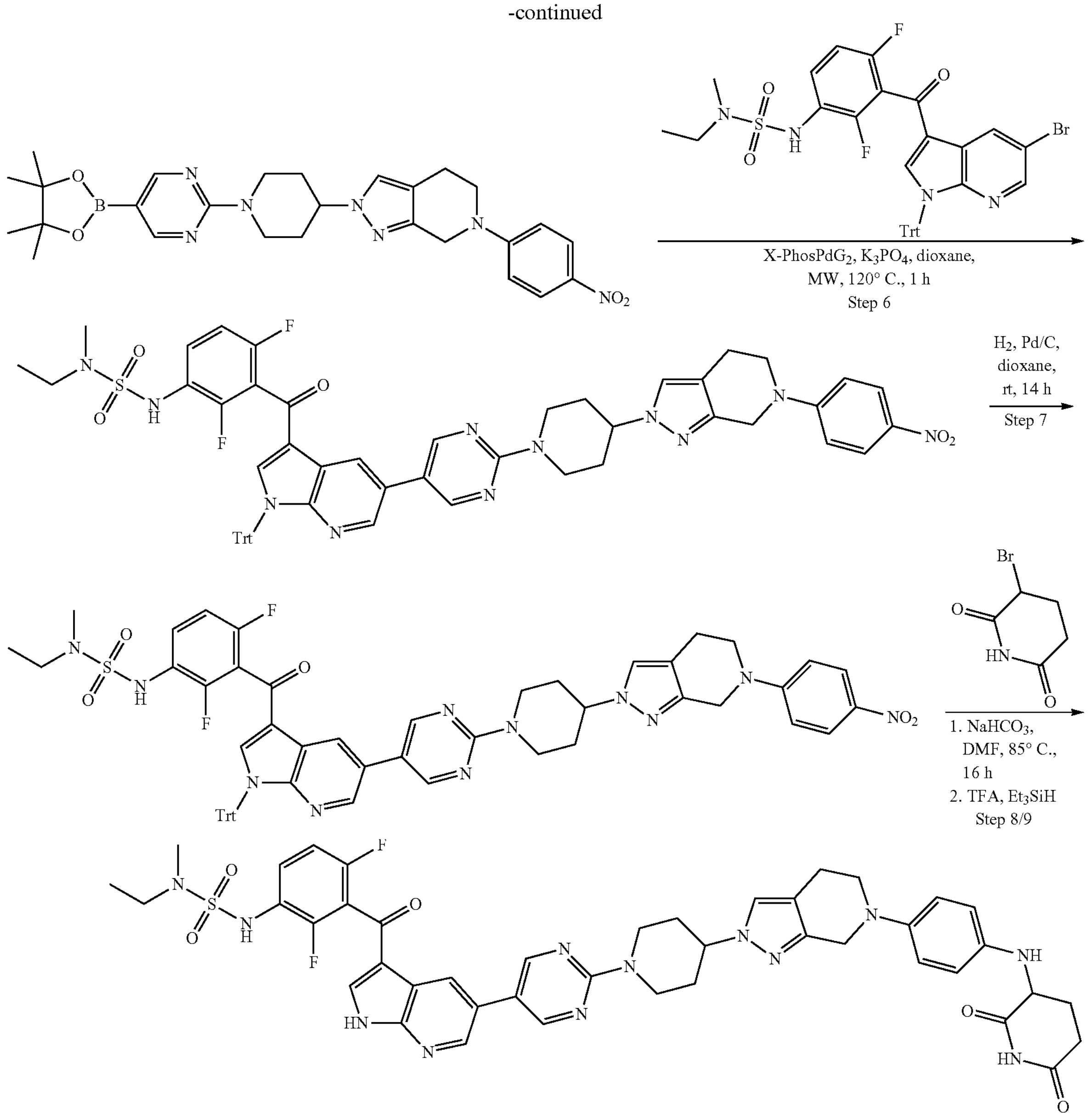

Step 1: To a stirred suspension of sodium hydride (60% dispersion in mineral oil, 310 mg, 13.48 mmol) in N,N-dimethylformamide (40 mL) was added tert-butyl 2,4,5,7-tetrahydropyrazolo[3,4-c]pyridine-6-carboxylate (2.0 g, 8.96 mmol, as a solution in N,N-dimethylformamide) at 0-5° C. under nitrogen. The reaction mixture was stirred at room temperature for 1 h. The reaction mixture was cooled to 0-5° C., and benzyl 4-(p-tolylsulfonyloxy)piperidine-1-carboxylate (5.24 g, 13.45 mmol) was added as a solution in N,N-dimethylformamide (40 mL). The reaction mixture was heated to 60° C. for 16 h. The reaction mixture was cooled to 0-5° C., and saturated ammonium chloride solution (100 mL) was added. The aqueous phase was extracted with ethyl acetate (2×200 mL). The combined organic layers were dried over sodium sulphate, filtered, and concentrated under reduced pressure. This crude material was purified by silica gel column chromatography using 40% ethyl acetate in dichloromethane as eluent to afford tert-butyl 2-(1-benzyloxycarbonyl-4-piperidyl)-5,7-dihydro-4H-pyrazolo[3,4-c]pyridine-6-carboxylate (1.40 g, 3.05 mmol, 34.03% yield) as an off-white gummy liquid. LCMS (ESI+): 441.3 $[M+H]^+$. Note: Desired regio-isomer was confirmed by NOESY and NOE studies.

Step 2: To a stirred solution of tert-butyl 2-(1-benzyloxycarbonyl-4-piperidyl)-5,7-dihydro-4H-pyrazolo[3,4-c]pyridine-6-carboxylate (950 mg, 2.16 mmol) in dichloromethane (10 mL) was added trifluoroacetic acid (2.96 g, 25.96 mmol, 2.0 mL) at 0-5° C. under nitrogen. The reaction mixture was stirred at room temperature for 4 h. The reaction mixture was concentrated under reduced pressure and triturated with diethyl ether (2×50 mL) to afford benzyl 4-(4,5,6,7-tetrahydropyrazolo[3,4-c]pyridin-2-yl)piperidine-1-carboxylate (905 mg, 1.93 mmol, 89.58% yield) as a yellowish gummy liquid, which was carried forward without further purification. $^1H$ NMR (400 MHz, DMSO-$d_6$): δ 9.09 (s, 2H), 7.70 (s, 1H), 7.33-7.40 (m, 5H), 5.10 (s, 2H), 4.30-4.40 (m, 1H), 4.09-4.22 (m, 4H), 3.33 (d, J=6.00 Hz, 2H), 2.79-2.90 (m, 2H), 2.75 (dd, J=0.40, 10.40 Hz, 2H), 1.96-1.99 (m, 2H), 1.77-1.83 (m, 2H).

Step 3: To a solution of benzyl 4-(4,5,6,7-tetrahydropyrazolo[3,4-c]pyridin-2-yl)piperidine-1-carboxylate (850 mg, 1.87 mmol) in N,N-dimethylformamide (10 mL) in a sealed tube was added N,N-diisopropylethylamine (3.71 g, 28.71 mmol, 5.0 mL) and 1-fluoro-4-nitro-benzene (320 mg, 2.27 mmol, 240.60 μL) at room temperature. The reaction mixture was heated to 100° C. for 12 h. Water (100 mL) was added to the reaction mixture, and the aqueous phase was extracted with ethyl acetate (2×100 mL). The combined organic layers were dried over sodium sulphate, filtered and concentrated under reduced pressure. The crude compound was purified by silica gel column chromatography with 70% ethyl acetate in petroleum ether as eluent to afford benzyl 4-[6-(4-nitrophenyl)-5,7-dihydro-4H-pyrazolo[3,4-c]pyridin-2-yl]piperidine-1-carboxylate (820 mg, 1.52 mmol, 81.27% yield) as a yellow solid. LCMS (ESI+): 462.1 $[M+H]^+$.

Step 4: A solution of benzyl 4-[6-(4-nitrophenyl)-5,7-dihydro-4H-pyrazolo[3,4-c]pyridin-2-yl]piperidine-1-carboxylate (750 mg, 1.63 mmol) in trifluoroacetic acid (10.36 g, 90.86 mmol, 7.0 mL) was heated to 80° C. in a sealed tube for 5 h. The reaction mixture was concentrated under reduced pressure and co-distilled with toluene (2×50 mL) to afford 6-(4-nitrophenyl)-2-(4-piperidyl)-5,7-dihydro-4H-pyrazolo[3,4-c]pyridine (1.3 g, 1.56 mmol, 96.05% yield) as a brown gummy liquid. LCMS (ESI+): 328.1 $[M+H]^+$.

Step 5: To a solution of 6-(4-nitrophenyl)-2-(4-piperidyl)-5,7-dihydro-4H-pyrazolo[3,4-c]pyridine (500 mg, 1.53 mmol) in N,N-dimethylformamide (3 mL) in a sealed tube was added N,N-diisopropylethylamine (1.48 g, 11.48 mmol, 2 mL) and 2-chloro-5-(4,4,5,5-tetramethyl-1,3,2-dioxaborolan-2-yl)pyrimidine (367.30 mg, 1.53 mmol) at room temperature. The reaction mixture was heated to 100° C. for 12 h. Water (50 mL) was added to the reaction mixture, and the aqueous phase was extracted with ethyl acetate (2×100 mL). The combined organic layers were dried over sodium sulphate, filtered, and concentrated under reduced pressure to afford crude 6-(4-nitrophenyl)-2-[1-[5-(4,4,5,5-tetramethyl-1,3,2-dioxaborolan-2-yl)pyrimidin-2-yl]-4-piperidyl]-5,7-dihydro-4H-pyrazolo[3,4-c]pyridine (700 mg, 368.83 μmol, 24.15% yield) as a yellow solid. This crude compound was take forward to the next step without further purification. LCMS (ESI+): 532.3 $[M+H]^+$.

Step 6: To a room temperature solution of 5-bromo-3-[3-[[ethyl(methyl)sulfamoyl]amino]-2,6-difluoro-benzoyl]-1-trityl-pyrrolo[2,3-b]pyridine (0.500 g, 698.71 μmol) in 1,4-dioxane (8 mL) and water (2 mL) in a microwave vial was added 6-(4-nitrophenyl)-2-[1-[5-(4,4,5,5-tetramethyl-1,3,2-dioxaborolan-2-yl)pyrimidin-2-yl]-4-piperidyl]-5,7-dihydro-4H-pyrazolo[3,4-c]pyridine (700 mg, 1.32 mmol) and anhydrous tripotassium phosphate (444.95 mg, 2.10 mmol) under nitrogen. The reaction mixture was degassed with nitrogen for 10 minutes, then heated to 120° C. for 1 h in a microwave. Water (10 mL) was added to the reaction mixture, and the aqueous phase was extracted with ethyl acetate (2×20 mL). The combined organic layers were dried over sodium sulphate, filtered and concentrated under reduced pressure to afford 2-[1-[5-[3-[3-[[ethyl(methyl)sulfamoyl]amino]-2,6-difluoro-benzoyl]-1-trityl-pyrrolo[2,3-b]pyridin-5-yl]pyrimidin-2-yl]-4-piperidyl]-6-(4-nitrophenyl)-5,7-dihydro-4H-pyrazolo[3,4-c]pyridine (550 mg, 454.74 μmol, 65.08% yield) as a yellow gummy liquid, which was used in the next step without further purification. LCMS (ESI+): 1040.4 $[M+H]^+$.

Step 7: A stirred room temperature solution of 2-[1-[5-[3-[3-[[ethyl(methyl)sulfamoyl]amino]-2,6-difluoro-benzoyl]-1-trityl-pyrrolo[2,3-b]pyridin-5-yl]pyrimidin-2-yl]-4-piperidyl]-6-(4-nitrophenyl)-5,7-dihydro-4H-pyrazolo[3,4-c]pyridine (550.00 mg, 528.77 μmol) in 1,4-dioxane (15 mL) was degassed for 10 minutes. Palladium on carbon (0.350 g, 2.88 mmol) was added to the reaction mixture, and stirring at room temperature under hydrogen gas (1 atm) was continued for 14 h. After completion, the reaction mixture was purged with nitrogen, catalyst was removed by filtration through celite pad. The filtrate was concentrated under reduced pressure. The crude material was purified by silica gel column chromatography using 80-90% ethyl acetate in petroleum ether as eluent to afford 6-(4-aminophenyl)-2-[1-[5-[3-[3-[[ethyl(methyl)sulfamoyl]amino]-2,6-difluoro-benzoyl]-1-trityl-pyrrolo[2,3-b]pyridin-5-yl]pyrimidin-2-yl]-4-piperidyl]-5,7-dihydro-4H-pyrazolo[3,4-c]pyridine (600 mg, 463.29 μmol, 87.62% yield) as a yellow solid. LCMS (ESI+): 1010.3 $[M+H]^+$.

Step 8: To a solution of 6-(4-aminophenyl)-2-[1-[5-[3-[3-[[ethyl(methyl)sulfamoyl]amino]-2,6-difluoro-benzoyl]-1-trityl-pyrrolo[2,3-b]pyridin-5-yl]pyrimidin-2-yl]-4-piperidyl]-5,7-dihydro-4H-pyrazolo[3,4-c]pyridine (600.00 mg, 593.96 μmol) in N,N-dimethylformamide (3 mL) in a sealed tube was added 3-bromopiperidine-2,6-dione (285.12 mg, 1.48 mmol) and sodium bicarbonate (174.64 mg, 2.08 mmol) at room temperature. The reaction mixture was heated to 85° C. for 16 h. Water (10 mL) was added to the reaction mixture, and the aqueous phase was extracted with ethyl acetate (2×20 mL). The combined organic layers were dried over sodium sulphate, filtered, and concentrated under reduced pressure. The crude residue was purified by column chromatography (70-80% ethyl acetate in petroleum ether) to afford 6-[4-[(2,6-dioxo-3-piperidyl)amino]phenyl]-2-[1-[5-[3-[3-[[ethyl(methyl)sulfamoyl]amino]-2,6-difluoro-benzoyl]-1-trityl-pyrrolo[2,3-b]pyridin-5-yl]pyrimidin-2-yl]-4-piperidyl]-5,7-dihydro-4H-pyrazolo[3,4-c]pyridine (250 mg, 168.67 μmol, 28.40% yield) as a brown gummy liquid along with 170 mg mixture with 39% purity. LCMS (ESI+): 1121.3 $[M+H]^+$.

Step 9: To a stirred solution of 6-[4-[(2,6-dioxo-3-piperidyl)amino]phenyl]-2-[1-[5-[3-[3-[[ethyl(methyl)sulfamoyl]amino]-2,6-difluoro-benzoyl]-1-trityl-pyrrolo[2,3-b]pyridin-5-yl]pyrimidin-2-yl]-4-piperidyl]-5,7-dihydro-4H-pyrazolo[3,4-c]pyridine (250.00 mg, 168.67 μmol) in dichloromethane (2.50 mL) was added triisopropyl silane (3.32 g, 16.95 mmol, 0.5 mL) and trifluoroacetic acid (1.93 g, 16.95 mmol, 1.31 mL) at 0-5° C. under nitrogen. The reaction mixture was stirred at room temperature for 4 h. The reaction mixture was diluted with 10% isopropyl alcohol in dichloromethane (30 mL) and washed with brine (10 ml). The organic layer was concentrated under reduced pressure to provide crude material which was further purified by reverse phase column chromatography by using 150 g snap cartridge eluted with 40% acetonitrile in 0.1% formic acid in water to afford 6-[4-[(2,6-dioxo-3-piperidyl)amino]phenyl]-2-[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]-5,7-dihydro-4H-pyrazolo[3,4-c]pyridine (69 mg, 74.23 μmol, 44.0% yield) as black solid. LCMS (ESI+): 879.4 $[M+H]^+$. $^1$H NMR (400 MHz, DMSO-$d_6$): δ 13.00 (s, 1H), 10.77 (s, 1H), 9.80 (s, 1H), 8.79 (s, 2H), 8.69 (s, 1H), 8.68 (s, 1H), 8.14 (s, 1H), 7.56 (d, J=4.80 Hz, 2H), 7.21-7.31 (m, 1H), 6.84 (d, J=8.80 Hz, 2H), 6.63 (d, J=8.80 Hz, 2H), 5.40 (d, J=7.20 Hz, 1H), 4.84 (d, J=13.60 Hz, 1H), 4.16-4.25 (m, 1H), 4.40-4.48 (m, 1H), 4.03 (s, 2H), 3.27 (t, J=5.60 Hz, 2H), 3.08-3.17 (m, 4H), 2.73 (s, 3H), 2.54-2.72 (m, 5H), 2.73 (s, 3H), 2.08-2.12 (m, 3H), 1.83-1.89 (m, 3H), 1.02 (t, J=7.20 Hz, 3H).

Example 162

5-[2-[4-[2-[1-[4-(2,6-dioxo-3-piperidyl)-2-fluoro-phenyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine

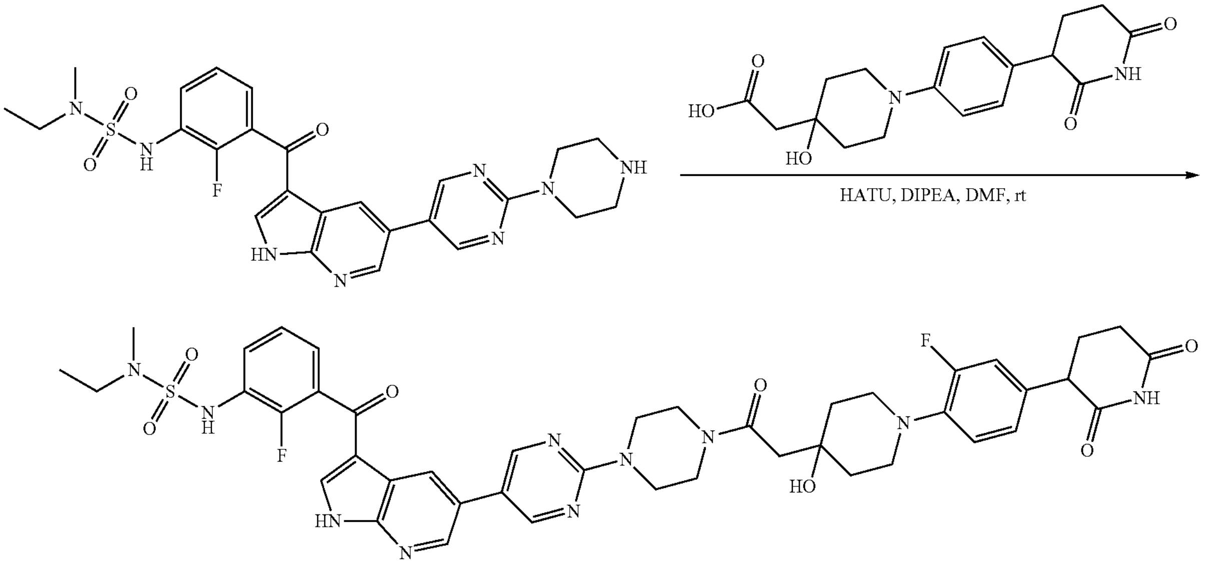

Target compound was prepared via HATU mediated acid-amine coupling reaction (procedure A). Amide coupling was carried out using 3-[3-[[ethyl(methyl)sulfamoyl]amino]-2-fluoro-benzoyl]-5-(2-piperazin-1-ylpyrimidin-5-yl)-1H-pyrrolo[2,3-b]pyridine (220 mg, 382.57 μmol), 2-[1-[4-(2,6-dioxo-3-piperidyl)-2-fluoro-phenyl]-4-hydroxy-4-piperidyl]acetic acid (160 mg, 399.17 μmol), N,N-diisopropylethylamine (1.48 g, 11.48 mmol, 2.0 mL) and HATU (170 mg, 447.10 μmol) at room temperature. The crude compound was purified by reverse phase column chromatography by using 150 g snap cartridge eluted with 50% acetonitrile in 0.1% ammonium acetate in water to afford 5-[2-[4-[2-[1-[4-(2,6-dioxo-3-piperidyl)-2-fluoro-phenyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine (72 mg, 80.72 μmol, 21.10% yield) as off-white solid. LCMS (ESI+): 885.3 $[M+H]^+$. $^1H$ NMR (400 MHz, DMSO-$d_6$): δ 12.89 (d, J=2.80 Hz, 1H), 10.82 (s, 1H), 9.78 (s, 1H), 8.80 (s, 2H), 8.66 (d, J=2.00 Hz, 1H), 8.59 (d, J=2.00 Hz, 1H), 7.99 (d, J=0.80 Hz, 1H), 7.58-7.62 (m, 1H), 7.38-7.41 (m, 1H), 7.33-7.35 (m, 1H), 6.96-7.03 (m, 3H), 4.93 (s, 1H), 3.78-3.88 (m, 5H), 3.65-3.70 (m, 4H), 3.02-3.17 (m, 6H), 2.75 (s, 3H), 2.62-2.69 (m, 3H), 2.55-2.51 (m, 1H), 2.15-2.25 (m, 1H), 1.95-2.05 (m, 1H), 1.71-1.81 (m, 4H), 1.03 (t, J=7.20 Hz, 3H).

Example 163

3-(2,4-dioxohexahydropyrimidin-1-yl)-6-[4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-hydroxy-1-piperidyl]-1-methyl-indazole

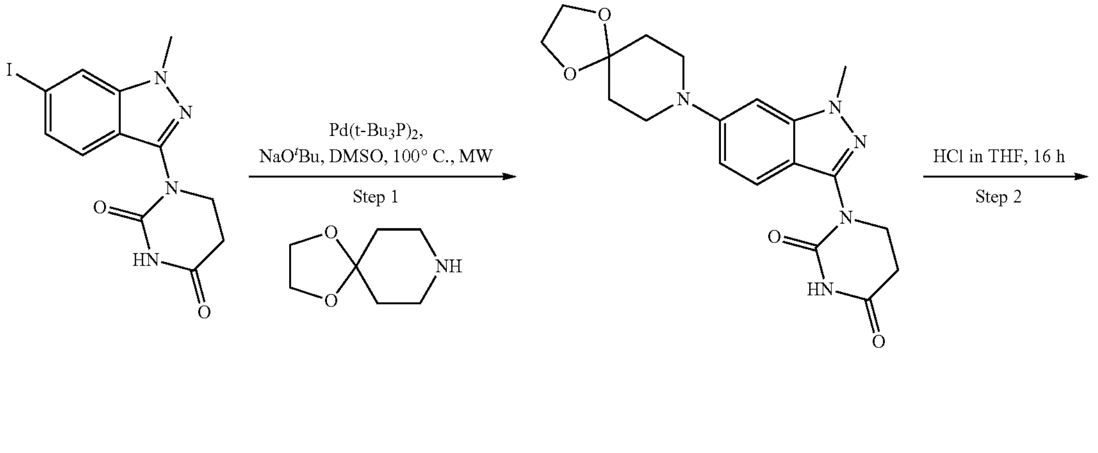

-continued

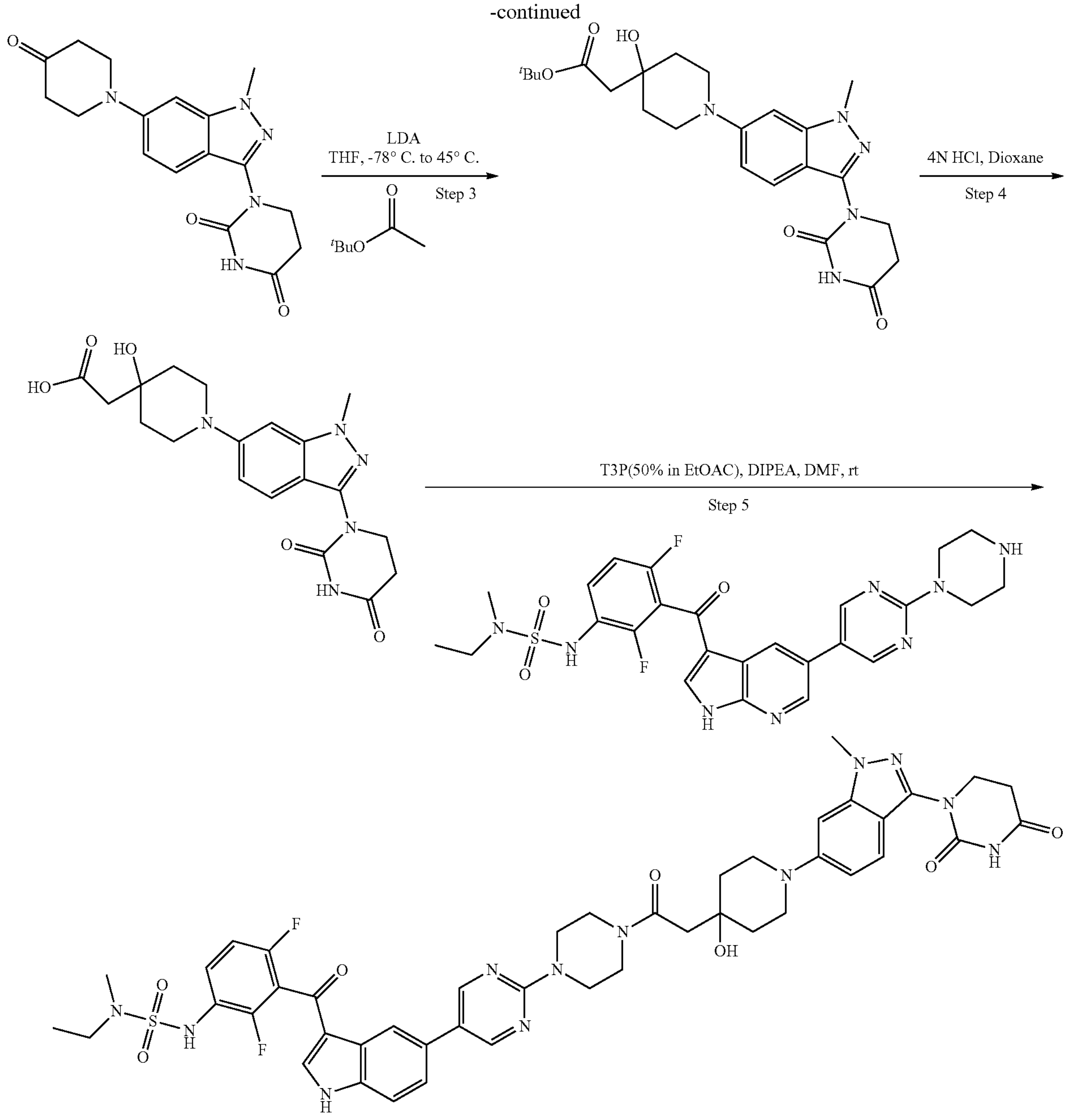

Step 1: To a solution of 1-(6-iodo-1-methyl-indazol-3-yl)hexahydropyrimidine-2,4-dione (1.5 g, 4.05 mmol) in DMSO (15 mL) was added sodium tert-butoxide (467.33 mg, 4.86 mmol) and 1,4-dioxa-8-azaspiro[4.5]decane (638.27 mg, 4.46 mmol, 569.88 μL) at room temperature under nitrogen. The reaction mixture was degassed with nitrogen for 5 min. Bis(tri-tert-butylphosphine)palladium(0) (414.20 mg, 810.49 μmol) was added, then the reaction mixture was stirred at 100° C. for 1 hour under microwave irradiation. The reaction mixture was diluted with water (50 mL), and the aqueous phase was extracted with ethyl acetate (2×50 mL). The combined organic layers were washed with brine solution (50 mL), and the organic layer was dried over sodium sulphate, filtered, and concentrated under reduced pressure. The crude residue thus obtained was purified by column chromatography on 60-120 silica gel using 3-4% of methanol in dichloromethane as eluent to afford 1-[6-(1,4-dioxa-8-azaspiro[4.5]decan-8-yl)-1-methyl-indazol-3-yl]hexahydropyrimidine-2,4-dione (850 mg, 1.85 mmol, 45.55% yield) as pale brown semi-solid. LCMS (ESI+): 386.1 $[M+H]^+$.

Step 2: To a solution of 1-[6-(1,4-dioxa-8-azaspiro[4.5]decan-8-yl)-1-methyl-indazol-3-yl]hexahydropyrimidine-2,4-dione (850 mg, 2.21 mmol) in tetrahydrofuran (4 mL) was added hydrochloric acid (36% w/w aqueous solution, 6.40 g, 175.53 mmol, 8 mL) at room temperature under nitrogen. The reaction mixture was stirred at room temperature for 16 hours. Saturated aqueous sodium bicarbonate solution (50 mL) was added slowly to adjust the pH to 8.0, and the product was extracted using ethyl acetate (3×75 mL). The combined organic layers were dried over anhydrous sodium sulphate and concentrated under reduced pressure to yield crude product which was triturated with diethyl ether (15 mL) to afford 1-[1-methyl-6-(4-oxo-1-piperidyl)indazol-3- yl]hexahydropyrimidine-2,4-dione (400 mg, 1.00 mmol, 45.43% yield) as brown solid. LCMS (ESI+): 342.1 $[M+H]^+$.

Step 3: To stirred solution of tert-butyl acetate (503.61 mg, 4.34 mmol, 583.56 μL) in tetrahydrofuran (25 mL) was added (diisopropylamino)lithium (2 M solution, 2.17 mL) at −78° C. and stirred for 1 hour at the same temperature. The resultant solution was then added quickly using syringe to a solution of 1-[1-methyl-6-(4-oxo-1-piperidyl)indazol-3-yl]hexahydropyrimidine-2,4-dione (370 mg, 1.08 mmol) in tetrahydrofuran (25 mL) at −78° C. The reaction mixture was slowly warmed to room temperature and stirred for 16 h at room temperature. The reaction was quenched using saturated aqueous ammonium chloride solution (50 mL), and the product was extracted using ethyl acetate (4×50 mL). The combined organic layers were dried over sodium sulphate and concentrated under reduced pressure get crude product which was purified by column chromatography on 60-120 silica gel using acetone and petroleum ether as eluents to afford tert-butyl 2-[1-[3-(2,4-dioxohexahydropyrimidin-1-yl)-1-methyl-indazol-6-yl]-4-hydroxy-4-piperidyl]acetate (180 mg, 374.54 μmol, 34.56% yield) as pale brown solid. LCMS (ESI+): 458.0 $[M+H]^+$.

Step 4: To a stirred solution of tert-butyl 2[1-[3-(2,4-dioxohexahydropyrimidin-1-yl)-1-methyl-indazol-6-yl]-4-hydroxy-4-piperidyl]acetate (180 mg, 393.42 μmol) in 1,4-dioxane (0.2 mL) was added hydrogen chloride solution (4.0M in 1,4-dioxane, 4.00 g, 109.71 mmol, 5 mL) at 0-5° C. The reaction mixture was stirred at room temperature for 16 hours. The solvent was removed by concentrating the reaction mixture under reduced pressure to afford 2[1-[3-(2,4-dioxohexahydropyrimidin-1-yl)-1-methyl-indazol-6-yl]-4-hydroxy-4-piperidyl]acetic acid (145 mg, 307.63 μmol, 78.19% yield, hydrochloric acid salt) as pale yellow solid which was used in the next step without further purification. LCMS (ESI+): 402.2 $[M+H]^+$.

Step 5: Target compound was prepared via T3P mediated acid-amine coupling reaction (procedure C) using 2-[1-[3-(2,4-dioxohexahydropyrimidin-1-yl)-1-methyl-indazol-6-yl]-4-hydroxy-4-piperidyl]acetic acid (147.67 mg, 337.24 μmol, hydrochloric acid salt) in N,N-dimethylformamide (2 mL), N-ethyl-N-isopropyl-propan-2-amine (261.51 mg, 2.02 mmol, 352.44 μL), T3P (128.76 mg, 404.69 μmop and 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (200 mg, 337.24 μmol, hydrochloric acid salt). The product was purified by reverse phase C18 150 g column using 0.1% formic acid solution in water/acetonitrile as eluents to afford 3-(2,4-dioxohexahydropyrimidin-1-yl)-6-[4-[2-[4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazin-1-yl]-2-oxo-ethyl]-4-hydroxy-1-piperidyl]-1-methyl-indazole (99 mg, 99.87 μmol, 29.61% yield, formate salt) as pale yellow solid. LCMS (ESI+): 939.9 $[M+H]^+$. $^1H$ NMR (400 MHz, DMSO-d6): δ 13.00 (m, 1H), 10.52 (s, 1H), 9.84-9.74 (m, 1H), 8.81 (s, 2H), 8.68 (d, J=2.40 Hz, 1H), 8.57 (m, 1H), 8.14 (s, 1H), 7.61-7.55 (m, 1H), 7.44 (d, J=9.20 Hz, 1H), 7.26 (t, J=8.80 Hz, 1H), 6.93 (dd, J=2.00, 9.20 Hz, 1H), 6.85 (s, 1H), 4.97 (s, 1H), 3.90-3.83 (m, 9H), 3.69-3.65 (m, 4H), 3.55-3.50 (m, 2H), 3.19-3.10 (m, 4H), 2.72 (s, 3H), 2.76-2.72 (m, 2H), 2.62-2.60 (m, 2H), 1.79-1.70 (m, 4H), 1.02 (t, J=6.80 Hz, 3H).

Example 164

5-[6-[4-[2-[1-[4-(2,4-dioxohexahydropyrimidin-1-yl)-2-fluoro-phenyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine

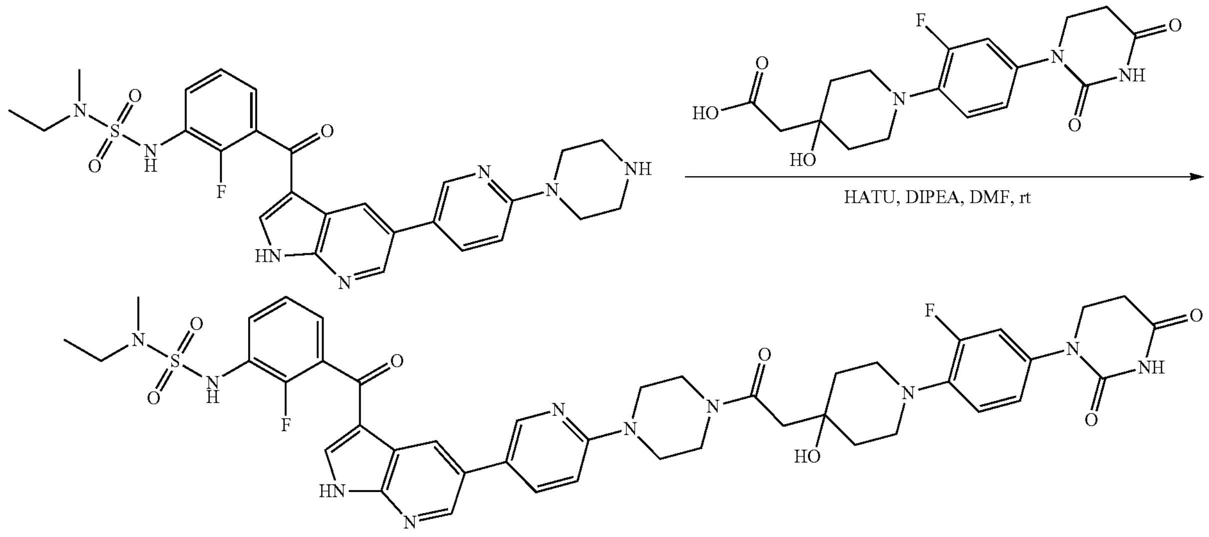

Target compound was prepared via HATU mediated acid-amine coupling reaction (procedure A). Amide coupling was carried out using 3-[3-[[ethyl(methyl)sulfamoyl]amino]-2-fluoro-benzoyl]-5-(6-piperazin-1-yl-3-pyridyl)-1H-pyrrolo[2,3-b]pyridine (300 mg, 558.03 μmol), 2-[1-[4-(2,4-dioxohexahydropyrimidin-1-yl)-2-fluoro-phenyl]-4-hydroxy-4-piperidyl]acetic acid (224.27 mg, 613.83 μmol), N,N-diisopropylethylamine (360.60 mg, 2.79 mmol, 485.98 μL) and HATU (233.40 mg, 613.83 μmol). The crude compound was purified by reverse phase column chromatography using a 100 g snap cartridge eluted with 37% acetonitrile in 0.1% ammonium acetate in water to afford 5-[6-[4-[2-[1-[4-(2,4-dioxohexahydropyrimidin-1-yl)-2-fluoro-phenyl]-4-hydroxy-4-piperidyl]acetyl]piperazin-1-yl]-3-pyridyl]-3-[3-[[ethyl(methyl)sulfamoyl]amino]-2-fluoro-benzoyl]-1H-pyrrolo[2,3-b]pyridine (58.97 mg, 65.94 μmol, 11.82% yield) as an off white solid. LCMS (ESI−): 883.0 $[M-H]^-$. $^1H$ NMR (400 MHz, DMSO-$d_6$): δ 12.90 (s, 1H), 10.37 (s, 1H), 9.77 (s, 1H), 8.66 (d, J=2.40 Hz, 1H), 8.56 (d, J=2.40 Hz, 1H), 8.51 (d, J=2.80 Hz, 1H), 7.95-7.98 (m, 2H), 7.58-7.61 (m, 1H), 7.31-7.37 (m, 2H), 7.17-7.15 (m, 1H), 7.05-7.07 (m, 3H), 4.95 (s, 1H), 3.60-3.76 (m, 10H), 3.02-3.15 (m, 3H), 2.74 (s, 3H), 2.67-2.70 (m, 3H), 2.62 (s, 2H), 2.51-2.55 (m, 2H), 1.79-1.82 (m, 2H), 1.71-1.74 (m, 2H), 1.02 (t, J=7.20 Hz, 3H).

Example 165

5-[2-[4-[2-[1-[4-(2,4-dioxohexahydropyrimidin-1-yl)-2-fluoro-phenyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine

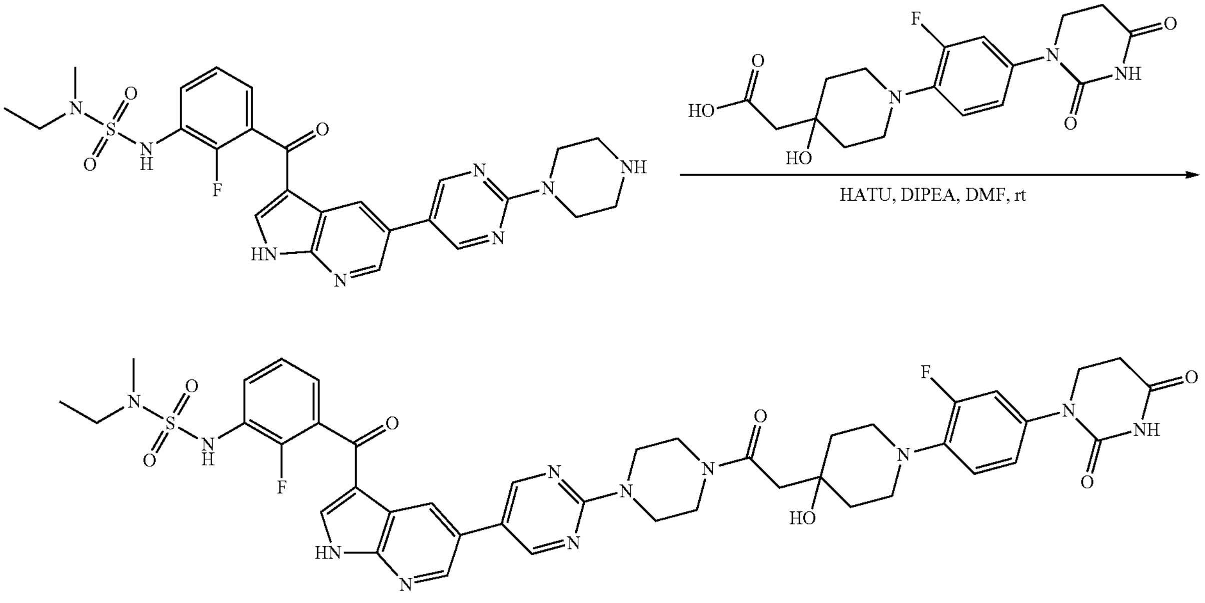

Target compound was prepared via HATU mediated acid-amine coupling reaction (procedure A). Amide coupling was carried out using 3-[3-[[ethyl(methyl)sulfamoyl]amino]-2-fluoro-benzoyl]-5-(2-piperazin-1-ylpyrimidin-5-yl)-1H-pyrrolo[2,3-b]pyridine (350 mg, 608.64 μmol), 2-[1-[4-(2,4-dioxohexahydropyrimidin-1-yl)-2-fluoro-phenyl]-4-hydroxy-4-piperidyl]acetic acid (300 mg, 625.81 μmol), N,N-diisopropylethylamine (1.48 g, 11.48 mmol, 2.0 mL) and HATU (260 mg, 683.80 μmol). The crude compound was purified by reverse phase column chromatography using a 150 g snap cartridge eluted with 50% acetonitrile in 0.1% ammonium acetate in water to afford 5-[2-[4-[2-[1-[4-(2,4-dioxohexahydropyrimidin-1-yl)-2-fluoro-phenyl]-4-hydroxy-4-piperidyl]acetyl]piperazin-1-yl]pyrimidin-5-yl]-3-[3-[[ethyl(methyl)sulfamoyl]amino]-2-fluoro-benzoyl]-1H-pyrrolo[2,3-b]pyridine (85 mg, 92.69 μmol, 15.23% yield) as off-white solid. LCMS (ESI−): 884.2 $[M-H]^+$. $^1H$ NMR (400 MHz, DMSO-$d_6$): δ 12.89 (d, J=2.80 Hz, 1H), 10.37 (s, 1H), 9.78 (s, 1H), 8.80 (s, 2H), 8.67 (d, J=2.40 Hz, 1H), 8.59 (d, J=2.40 Hz, 1H), 8.00 (d, J=2.00 Hz, 1H), 7.58-7.62 (m, 1H), 7.39 (dd, J=1.60, 6.00 Hz, 1H), 7.35-7.33 (m, 1H), 7.07 (d, J=2.40 Hz, 1H), 7.00-7.06 (m, 2H), 4.94 (s, 1H), 3.82-3.89 (m, 4H), 3.65-3.76 (m, 6H), 3.03-3.17 (m, 6H), 2.75 (s, 3H), 2.68-2.70 (m, 2H), 2.62 (s, 2H), 1.71-1.82 (m, 4H), 1.03 (t, J=7.20 Hz, 3H).

Example 166

5-[2-[4-[2-[1-[4-[[(3S)-2,6-dioxo-3-piperidyl]amino]-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

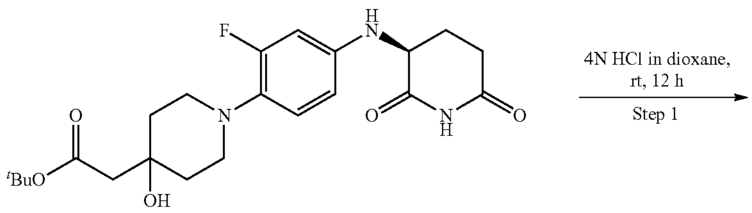

-continued

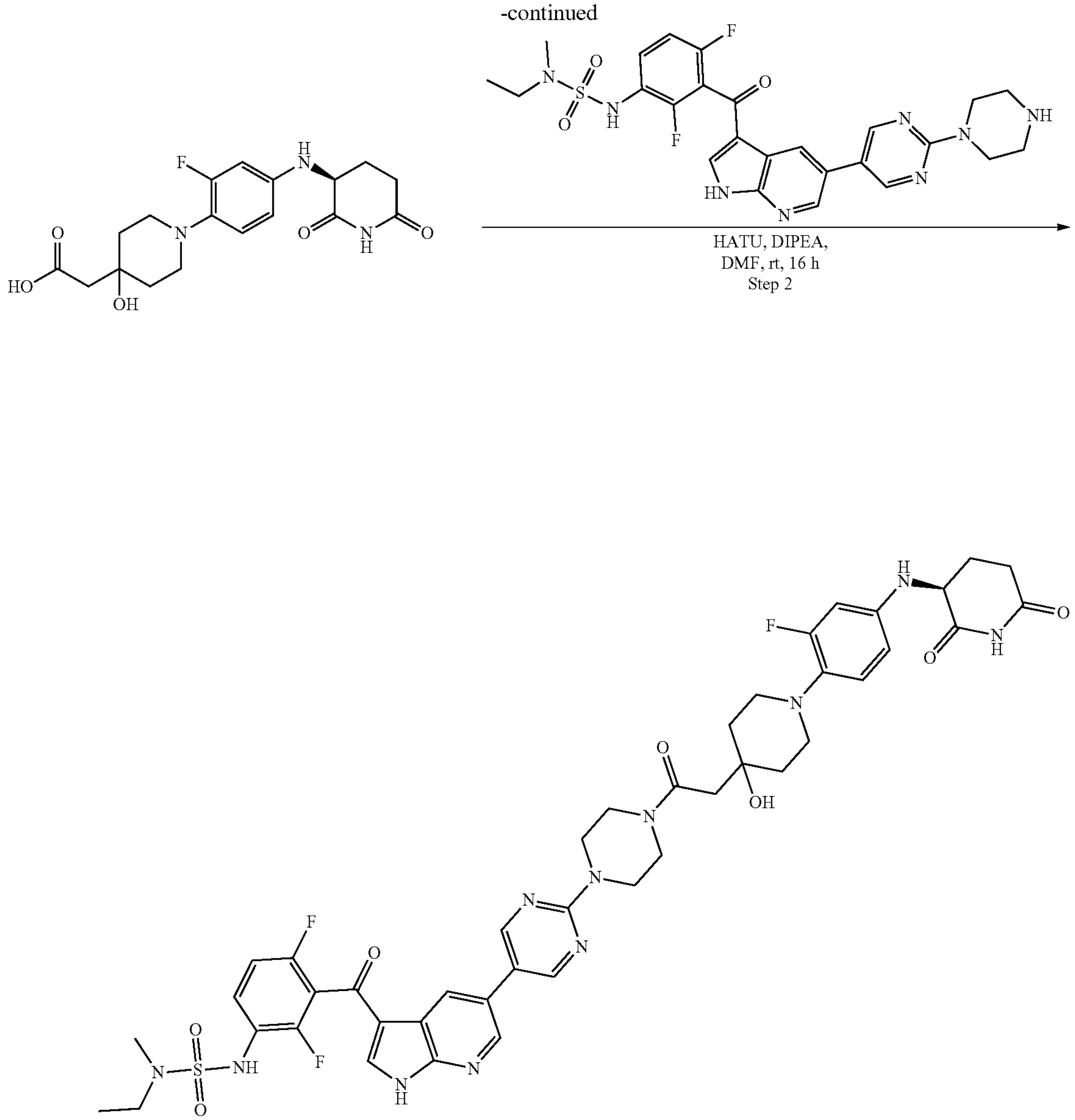

Step 1: To a solution of tert-butyl 2-[1-[4-[[(3S)-2,6-dioxo-3-piperidyl]amino]-2-fluoro-phenyl]-4-hydroxy-4-piperidyl]acetate (500 mg, 1.15 mmol) in dichloromethane (4 mL) was added hydrogen chloride (4M in 1,4-dioxane, 10 mL) at 0° C. The resultant reaction solution was stirred at room temperature for 6 h. The reaction mixture was concentrated under reduced pressure to provide a crude residue which was triturated with petroleum ether to afford 2-[1-[4-[[(3 S)-2,6-dioxo-3-piperidyl]amino]-2-fluoro-phenyl]-4-hydroxy-4-piperidyl]acetic acid (420 mg, 808.00 μmol, 70.37% yield) as off white solid. LCMS (ESI+): 380.3 $[M+H]^+$.

Step 2: Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (450 mg, 758.79 μmol), 2-[1-[4-[[(3S)-2,6-dioxo-3-piperidyl]amino]-2-fluoro-phenyl]-4-hydroxy-4-piperidyl]acetic acid (315.54 mg, 758.79 μmol), HATU (288.52 mg, 758.79 μmol) and N,N-diisopropylethylamine (392.27 mg, 3.04 mmol, 528.66 The crude compound was purified by reverse phase column chromatography eluted with 40% acetonitrile in 0.1% formic acid in water to afford 5-[2-[4-[2-[1-[4-[[(3S)-2,6-dioxo-3-piperidyl]amino]-2-fluoro-phenyl]-4-hydroxy-4-piperidyl]acetyl]piperazin-1-yl]pyrimidin-5-yl]-3-[3-[[ethyl (methyl)sulfamoyl]amino]-2,6-difluoro-benzoyl]-1H-pyrrolo[2,3-b]pyridine (205 mg, 209.05 μmol, 27.55% yield) as off white solid. LCMS (ESI+): 918.3 $[M+H]^+$. $^1H$ NMR (400 MHz, DMSO-$d_6$): δ 13.01 (d, J=3.20 Hz, 1H), 10.79 (s, 1H), 9.72 (s, 1H), 8.81 (s, 2H), 8.68 (d, J=2.40 Hz, 1H), 8.57 (s, 1H), 8.15 (d, J=3.20 Hz, 1H), 7.56-7.62 (m, 1H), 7.28 (t, J=7.60 Hz, 1H), 6.87 (s, 1H), 6.44-6.53 (m, 2H), 5.71 (s, 1H), 4.95 (s, 1H), 4.25-4.35 (m, 1H), 3.88-3.83 (m, 4H), 3.65-3.70 (m, 4H), 3.12 (q, J=7.20 Hz, 2H), 2.80-2.95 (m, 3H), 2.65-2.75 (m, 1H), 2.74 (s, 3H), 2.61 (s, 2H), 2.57-2.51 (m, 2H), 2.07-2.10 (m, 1H), 1.72-1.87 (m, 5H), 1.03 (t, J=7.20 Hz, 3H).

Note: Absolute stereochemistry for the target compound was arbitrarily assigned as S-isomer (first eluted isomer).

Example 167

5-[2-[4-[2-[1-[4-(2,4-dioxohexahydropyrimidin-1-yl)-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

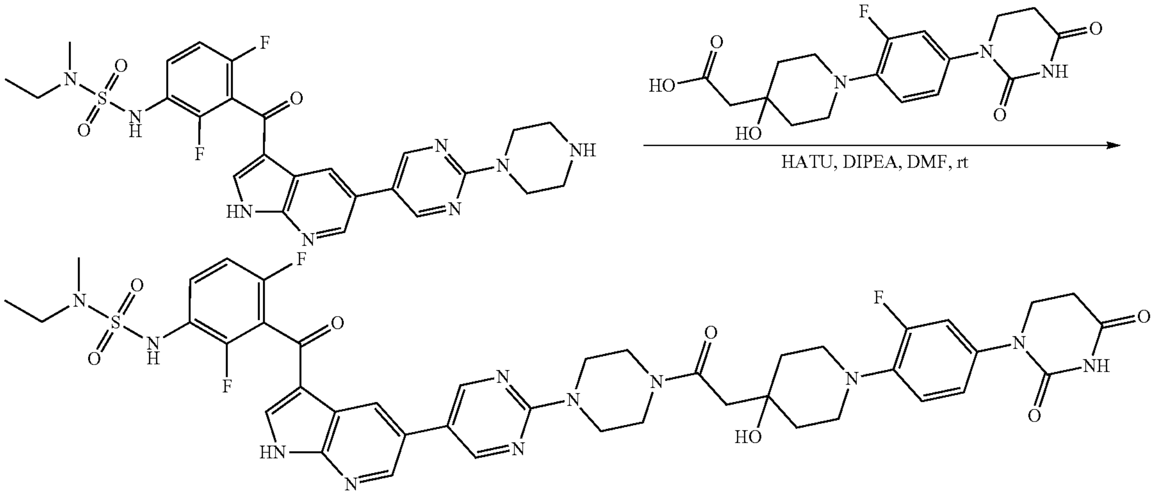

Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (300 mg, 505.86 μmol), 2-[1-[4-(2,4-dioxohexahydropyrimidin-1-yl)-2-fluoro-phenyl]-4-hydroxy-4-piperidyl]acetic acid (223.59 mg, 556.45 HATU (192.34 mg, 505.86 μmol) and N,N-diisopropylethylamine (261.52 mg, 2.02 mmol, 352.45 The crude compound was purified by reverse phase column chromatography by using 50 g snap eluted with 50% acetonitrile in 0.1% ammonium acetate in water to afford 5-[2-[4-[2-[1-[4-(2,4-dioxohexahydropyrimidin-1-yl)-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (120 mg, 130.36 μmol, 25.77% yield) as an off white solid. LCMS (ESI−): 901.8 $[M-H]^-$. $^1H$ NMR (400 MHz, DMSO-$d_6$): δ 13.01 (s, 1H), 10.38 (s, 1H), 9.85 (s, 1H), 8.81 (s, 2H), 8.68 (d, J=2.00 Hz, 1H), 8.55 (s, 1H), 8.14 (s, 1H), 7.57 (dd, J=3.20, 8.80 Hz, 1H), 7.21-7.27 (m, 1H), 7.15-7.19 (m, 1H), 7.06-7.08 (m, 2H), 4.94 (s, 1H), 3.83-3.88 (m, 4H), 3.64-3.76 (m, 6H), 3.00-3.13 (m, 6H), 2.67-2.75 (m, 1H), 2.74 (s, 3H), 2.57-2.50 (m, 1H), 2.62 (s, 2H), 1.71-1.82 (m, 4H), 1.02 (t, J=6.80 Hz, 3H).

Example 168

5-[6-[4-[2-[1-[4-(2,4-dioxohexahydropyrimidin-1-yl)-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine

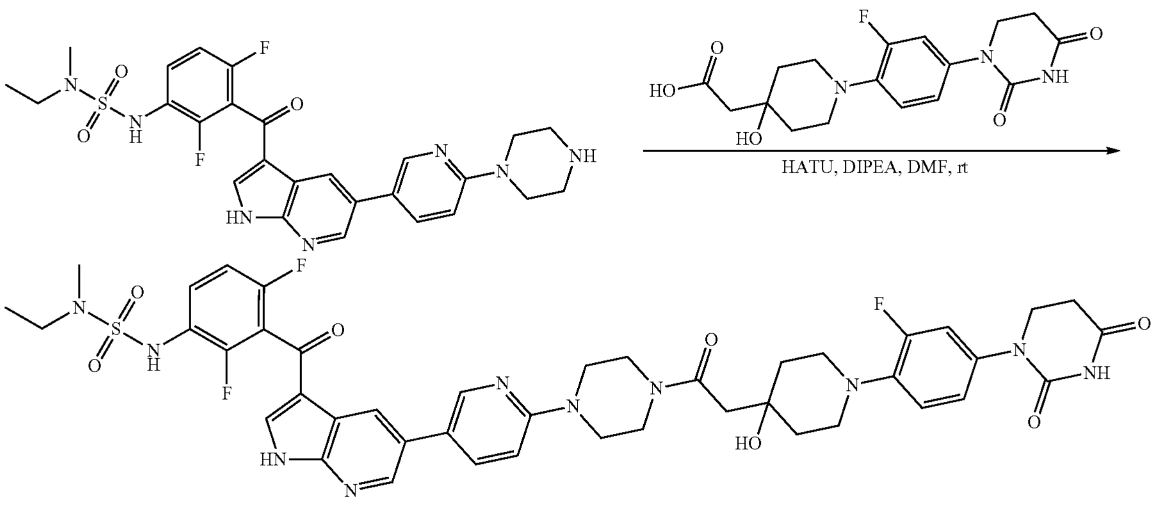

Target compound was prepared via HATU mediated acid-amine coupling reaction (procedure A). Amide coupling was carried out using 2-[1-[4-(2,4-dioxohexahydropyrimidin-1-yl)-2-fluoro-phenyl]-4-hydroxy-4-piperidyl]acetic acid (250 mg, 684.27 μmol) and 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (380.18 mg, 684.27 μmol), N,N-Diisopropylethylamine (244.07 mg, 1.89 mmol, 328.94 μL) and HATU (197.47 mg, 519.33 μmol) at room temperature. Crude compound was purified by reverse phase column chromatography by using 120 g snap eluted with 45% acetonitrile in 0.1% ammonium acetate in water to afford 5-[6-[4-[2-[1-[4-(2,4-dioxohexahydropyrimidin-1-yl)-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine (74 mg, 79.09 μmol, 11.56% yield) as an off white solid. LCMS (ESI+): 903.3 $[M+H]^+$. $^1H$ NMR (400 MHz, DMSO-$d_6$): δ 12.95 (s, 1H), 10.37 (s, 1H), 9.72 (s, 1H), 8.68 (d, J=2.40 Hz, 2H), 8.52 (d, J=2.40 Hz, 1H), 8.12 (s, 1H), 7.98 (dd, J=2.40, 8.80 Hz, 1H), 7.55-7.61 (m, 1H), 7.26 (t, J=9.20 Hz, 1H), 7.15-7.19 (m, 1H), 7.06-7.10 (m, 3H), 4.95 (s, 1H), 3.60-3.76 (m, 10H), 3.03-3.13 (m, 6H), 2.72 (s, 3H), 2.67-2.72 (m, 2H), 2.62 (s, 2H), 1.82-1.79 (m, 2H), 1.74-1.71 (m, 2H), 1.02 (t, J=7.20 Hz, 3H).

Example 169

5-[4-[4-[2-[1-[4-(2,4-dioxohexahydropyrimidin-1-yl)-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine

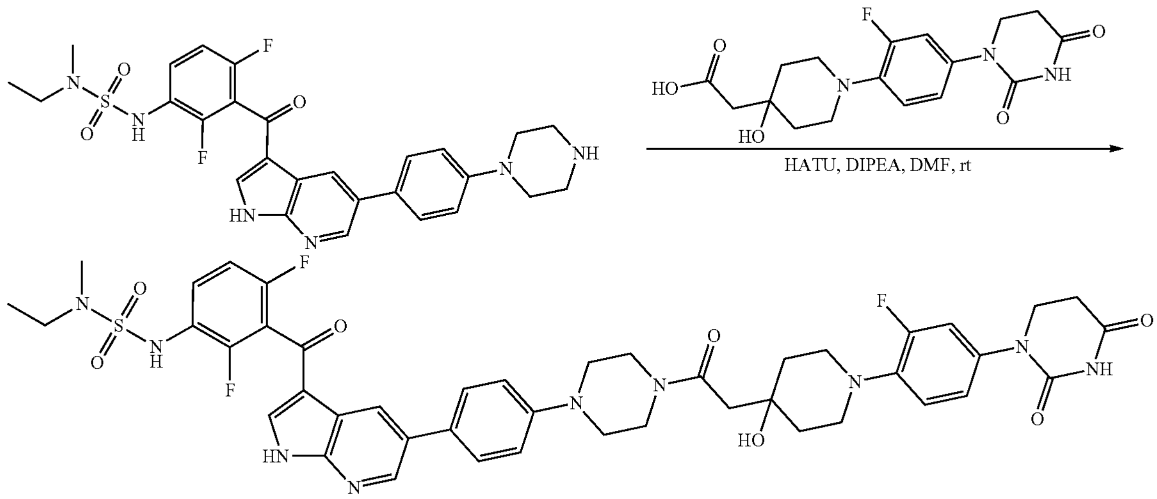

Target compound was prepared via HATU mediated acid-amine coupling reaction (procedure A). Amide coupling was carried out using 2-[1-[4-(2,4-dioxohexahydropyrimidin-1-yl)-2-fluoro-phenyl]-4-hydroxy-4-piperidyl]acetic acid (296.44 mg, 811.38 μmol) and 3-[3-[[ethyl(methyl)sulfamoyl]amino]-2,6-difluoro-benzoyl]-5-(4-piperazin-1-ylphenyl)-1H-pyrrolo[2,3-b]pyridine (450 mg, 811.38 μmol), N,N-Diisopropylethylamine (419.46 mg, 3.25 mmol, 565.31 μL) and HATU (339.36 mg, 892.52 μmol) at room temperature. Crude compound was purified by reverse phase column chromatography by using 120 g snap eluted with 45% acetonitrile in 0.1% ammonium acetate in water to afford 5-[4-[4-[2-[1-[4-(2,4-dioxohexahydropyrimidin-1-yl)-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine (179 mg, 196.67 μmol, 24.24% yield) as a yellow solid. LCMS (ESI+): 902.4 $[M+H]^+$. $^1H$ NMR (400 MHz, DMSO-$d_6$): δ 12.93 (s, 1H), 10.37 (s, 1H), 9.72 (s, 1H), 8.67 (d, J=2.00 Hz, 1H), 8.55 (s, 1H), 8.11 (s, 1H), 7.56-7.65 (m, 3H), 7.28 (t, J=8.80 Hz, 1H), 7.11-7.18 (m, 5H), 4.94 (s, 1H), 3.70-3.76 (m, 6H), 3.23-3.28 (m, 4H), 3.02-3.14 (m, 6H), 2.73 (s, 3H), 2.67-2.72 (m, 2H), 2.62 (s, 2H), 1.79-1.82 (m, 2H), 1.70-1.73 (m, 2H), 1.02 (t, J=6.80 Hz, 3H).

Example 170

3-[2-chloro-3-[[ethyl(methyl)sulfamoyl]amino]-6-fluoro-benzoyl]-5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-1H-pyrrolo[2,3-b]pyridine

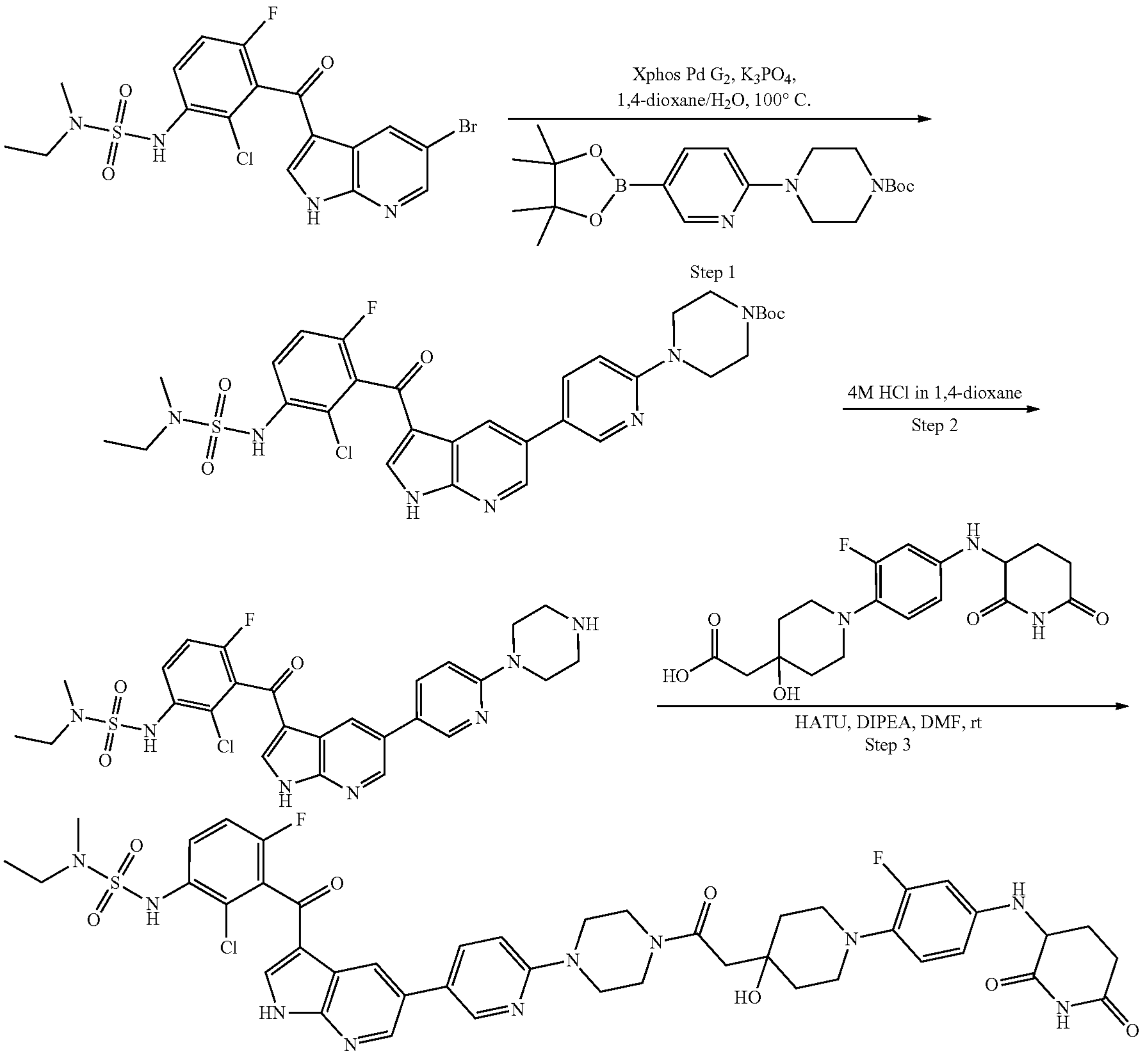

Step 1: A solution of 5-bromo-3-[2-chloro-3-[[ethyl(methyl)sulfamoyl]amino]-6-fluoro-benzoyl]-1H-pyrrolo[2,3-b]pyridine (500 mg, 1.02 mmol) in 1,4-dioxane (12 mL), water (2 mL) was taken in a microwave vial and added tert-butyl 4-[5-(4,4,5,5-tetramethyl-1,3,2-dioxaborolan-2-yl)-2-pyridyl]piperazine-1-carboxylate (476.94 mg, 1.23 mmol), potassium phosphate tribasic anhydrous (650.14 mg, 3.06 mmol) at room temperature under nitrogen atmosphere. The reaction mixture was degassed with nitrogen for 10 minutes, XPhos Pd G2 (80.17 mg, 102.09 μmol) was added to the reaction mixture. The reaction mixture was irradiated under microwave to 100° C. for 1 h. After completion, the reaction mixture was diluted with water (60 mL) and extracted with ethyl acetate (2×100 mL). The combined organic layers were dried over sodium sulphate, filtered and concentrated under reduced pressure. The crude compound was purified by silica gel column chromatography with 70% ethyl acetate in petroleum ether as a eluent to afford tert-butyl 4-[5-[3-[2-chloro-3-[[ethyl(methyl)sulfamoyl]amino]-6-fluoro-benzoyl]-1H-pyrrolo[2,3-b]pyridin-5-yl]-2-pyridyl]piperazine-1-carboxylate (320 mg, 390.38 μmol, 38.24% yield) as light brown solid. LCMS (ESI+): 671.9 $[M+H]^+$.

Step 2: To a stirred solution of tert-butyl 4-[5-[3-[2-chloro-3-[[ethyl(methyl)sulfamoyl]amino]-6-fluoro-benzoyl]-1H-pyrrolo[2,3-b]pyridin-5-yl]-2-pyridyl]piperazine-1-carboxylate (0.335 g, 498.39 mmol) in 1,4-dioxane (4 mL) was added 4M HCl in 1,4-dioxane (498.39 μmol, 4 mL) at 0° C. and stirred the reaction mixture at room temperature for 2 h. After completion, the reaction mixture was concentrated under reduced pressure followed by diethyl ether wash to get 3-[2-chloro-3-[[ethyl(methyl)sulfamoyl]amino]-6-fluoro-benzoyl]-5-(6-piperazin-1-yl-3-pyridyl)-1H-pyrrolo[2,3-b]pyridine (0.350 g, 452.89 μmol, 90.87% yield) as brown solid. LCMS (ESI+): 571.9 $[M+H]^+$.

Step 3: Target compound was prepared via HATU mediated acid-amine coupling reaction (procedure A). Amide coupling was carried out using 3-[2-chloro-3-[[ethyl (methyl)sulfamoyl]amino]-6-fluoro-benzoyl]-5-(6-piperazin-1-yl-3-pyridyl)-1H-pyrrolo[2,3-b]pyridine (0.350 g, 611.83 μmol), 2-[1-[4-[(2,6-dioxo-3-piperidyl)amino]-2-fluoro-phenyl]-4-hydroxy-4-piperidyl]acetic acid (255.33 mg, 673.01 μmol), N-ethyl-N-isopropyl-propan-2-amine (742.00 mg, 5.74 mmol, 1 mL) and HATU (255.90 mg, 673.01 μmol). The crude compound was purified by reverse phase column chromatography by using 150 g snap eluted with 40% acetonitrile in 0.1% HCOOH in water to afford 3-[2-chloro-3-[[ethyl(methyl)sulfamoyl]amino]-6-fluoro-benzoyl]-5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-1H-pyrrolo[2,3-b]pyridine (34.5 mg, 36.62 μmol, 5.99% yield) as an off white solid. LCMS (ESI+): 933.3 $[M+H]^+$. $^1H$ NMR (400 MHz, DMSO-$d_6$): δ 12.93 (s, 1H), 10.78 (s, 1H), 9.51 (s, 1H), 8.67 (d, J=2.00 Hz, 1H), 8.51 (s, 2H), 8.03 (s, 1H), 7.96 (d, J=8.40 Hz, 1H), 7.63-7.66 (m, 1H), 7.36-7.45 (m, 1H), 7.01 (d, J=8.80 Hz, 1H), 6.87 (dd, J=9.60, 11.80 Hz, 1H), 6.50 (dd, J=2.40, 14.80 Hz, 1H), 6.41-6.43 (m, 1H), 5.78 (d, J=7.60 Hz, 1H), 4.87 (s, 1H), 4.21-4.30 (m, 1H), 3.56-3.70 (m, 9H), 3.08-3.14 (m, 2H), 2.88-2.92 (m, 4H), 2.60-2.79 (m, 1H), 2.74 (s, 3H), 2.60 (s, 2H), 2.05-2.12 (m, 1H), 1.62-1.92 (m, 5H), 1.03 (t, J=7.20 Hz, 3H).

Example 171

5-[6-[4-[2-[4-[4-(2,6-dioxo-3-piperidyl)-3-oxo-piperazin-1-yl]-3,3-difluoro-1-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine

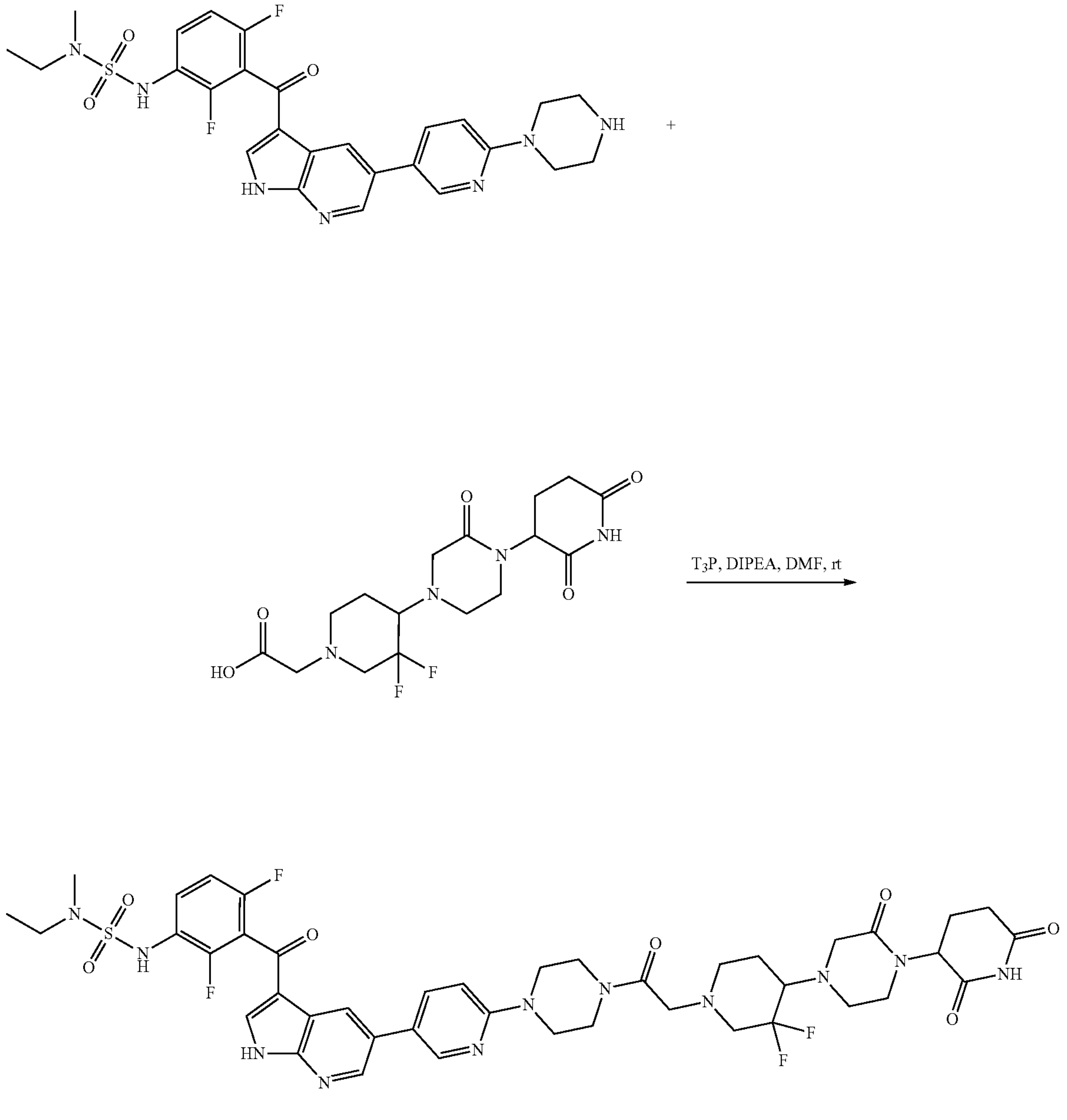

Target compound was prepared via T3P mediated acid-amine coupling reaction (procedure C). Amide coupling was carried out using 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (220 mg, 395.97 μmol), 2-[4-[4-(2,6-dioxo-3-piperidyl)-3-oxo-piperazin-1-yl]-3,3-difluoro-1-piperidyl]acetic acid (153.78 mg, 395.97 μmol), $T_3P$ (188.98 mg, 593.95 μmol) and N,N-Diisopropylethylamine (51.18 mg, 395.97 μmol, 68.97 μL) to afford 5-[6-[4-[2-[4-[4-(2,6-dioxo-3-piperidyl)-3-oxo-piperazin-1-yl]-3,3-difluoro-1-piperidyl]acetyl]piperazin-1-yl]-3-pyridyl]-3-[3-[[ethyl (methyl)sulfamoyl]amino]-2,6-difluoro-benzoyl]-1H-pyrrolo[2,3-b]pyridine (46.05 mg, 47.23 μmol, 11.93% yield) as brown solid. LCMS (ESI+): 926.3 $[M+H]^+$. $^1H$ NMR (400 MHz, DMSO-$d_6$): δ 12.76 (s, 1H), 10.86 (s, 1H), 8.67 (d, J=2.00 Hz, 1H), 8.52 (d, J=2.40 Hz, 2H), 8.34 (s, 1H), 8.09 (s, 1H), 7.97 (dd, J=2.40, 9.00 Hz, 1H), 7.52-7.58 (m, 1H), 7.19 (t, J=9.20 Hz, 1H), 7.03 (d, J=9.20 Hz, 1H), 4.92 (s, 1H), 3.56-3.67 (m, 8H), 3.35-3.45 (m, 6H), 3.20-3.25 (m, 1H), 3.08 (q, J=7.20 Hz, 2H), 2.92-3.02 (m, 4H), 2.65-2.81 (m, 1H), 2.68 (s, 3H), 2.55-2.60 (m, 1H), 2.29-2.34 (m, 2H), 1.72-1.90 (m, 3H), 1.01 (t, J=7.20 Hz, 3H).

Example 172

5-[4-[4-[2-[4-[4-(2,6-dioxo-3-piperidyl)-3-oxo-piperazin-1-yl]-3,3-difluoro-1-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine

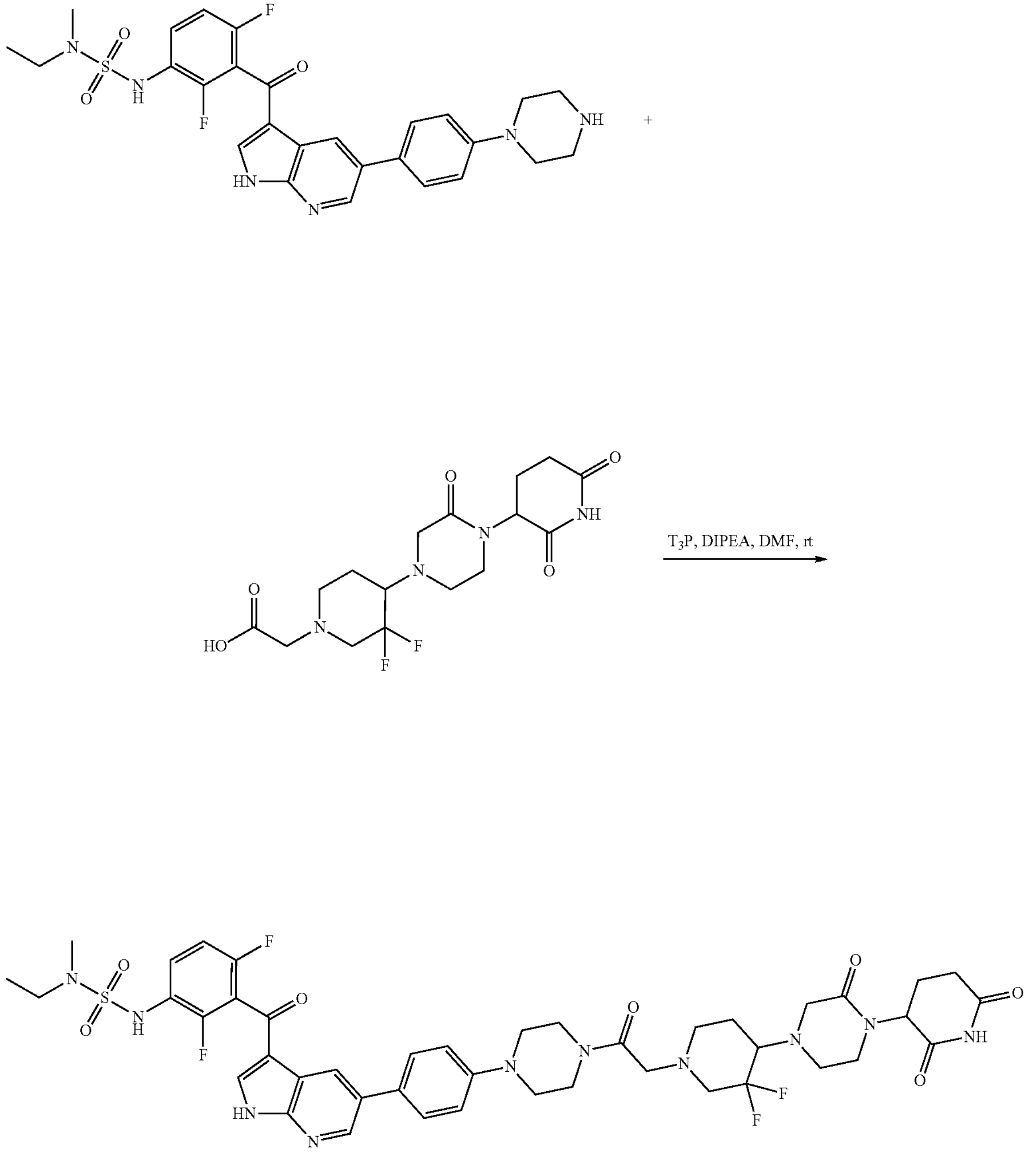

Target compound was prepared via T3P mediated acid-amine coupling reaction (procedure C). Amide coupling was carried out using 3-[3-[[ethyl(methyl)sulfamoyl]amino]-2,6-difluoro-benzoyl]-5-(4-piperazin-1-ylphenyl)-1H-pyrrolo[2,3-b]pyridine (250 mg, 450.77 μmol), 2-[4-[4-(2,6-dioxo-3-piperidyl)-3-oxo-piperazin-1-yl]-3,3-difluoro-1-piperidyl]acetic acid (175.06 mg, 450.77 μmol), $T_3P$ (215.14 mg, 676.15 μmol), N,N-Diisopropylethylamine (174.78 mg, 1.35 mmol, 235.55 μL) to afford 5-[4-[4-[2-[4-[4-(2,6-dioxo-3-piperidyl)-3-oxo-piperazin-1-yl]-3,3-difluoro-1-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine (63.77 mg, 62.56 μmol, 13.88% yield) as brown solid. LCMS (ESI−): 923.3 $[M-H]^-$. $^1H$ NMR (400 MHz, DMSO-$d_6$): δ 12.95 (s, 1H), 10.86 (s, 1H), 8.66 (d, J=2.00 Hz, 1H), 8.54 (s, 1H), 8.08 (s, 1H), 7.53-7.64 (m, 3H), 7.22 (t, J=8.40 Hz, 1H), 7.12 (d, J=8.80 Hz, 2H), 4.85-4.95 (m, 1H), 3.60-3.68 (m, 5H), 3.35-3.45 (m, 5H), 3.20-3.35 (m, 7H), 3.05-3.15 (m, 3H), 2.85-3.00 (m, 3H), 2.55-2.80 (m, 1H), 2.71 (s, 1H), 2.50-2.55 (m, 2H), 2.25-2.45 (m, 2H), 1.72-1.91 (m, 3H), 1.01 (t, J=7.20 Hz, 3H).

Example 173

5-[2-[4-[2-[4-[4-(2,6-dioxo-3-piperidyl)-3-oxo-piperazin-1-yl]-3,3-difluoro-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

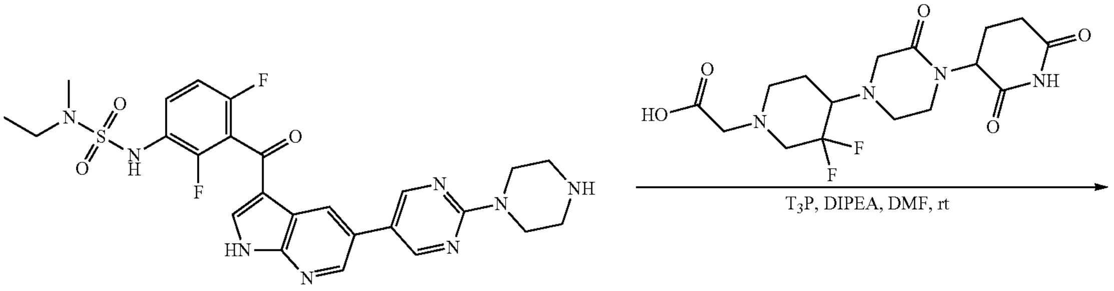

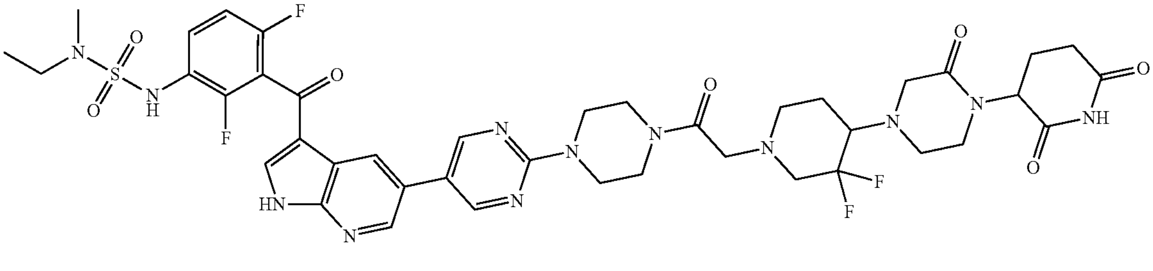

Target compound was prepared via $T_3P$ mediated acid-amine coupling reaction (procedure C). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (200 mg, 359.33 μmol), 1[4-[4-(2,6-dioxo-3-piperidyl)-3-oxo-piperazin-1-yl]-3,3-difluoro-1-piperidyl]acetic acid (139.55 mg, 359.33 μmol), $T_3P$ (188.65 mg, 592.90 μmol), N,N-Diisopropylethylamine (153.26 mg, 1.19 mmol, 206.54 μL) to afford 5-[2-[4-[2-[4-[4-(2,6-dioxo-3-piperidyl)-3-oxo-piperazin-1-yl]-3,3-difluoro-1-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (13.73 mg, 13.97 μmol, 3.53% yield) as brown solid. LCMS (ESI+): 927.3 $[M+H]^+$. $^1H$ NMR (400 MHz, DMSO-$d_6$): δ 13.00 (s, 1H), 10.86 (s, 1H), 9.80 (s, 1H), 8.81 (s, 2H), 8.68 (d, J=2.40 Hz, 1H), 8.57 (s, 1H), 8.14 (s, 1H), 7.55-7.61 (m, 1H), 7.26 (t, J=8.40 Hz, 1H), 4.90 (s, 1H), 3.81-3.85 (m, 4H), 3.57-3.63 (m, 4H), 3.31-3.41 (m, 3H), 3.05-3.35 (m, 6H), 2.80-3.01 (m, 4H), 2.55-2.80 (m, 1H), 2.72 (s, 3H), 2.55-2.50 (m, 1H), 2.25-2.49 (m, 3H), 1.70-1.90 (m, 3H), 1.02 (t, J=7.20 Hz, 3H).

Example 174

5-[2-[4-[2-[1-[4-[[(3R)-2,6-dioxo-3-piperidyl]amino]-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

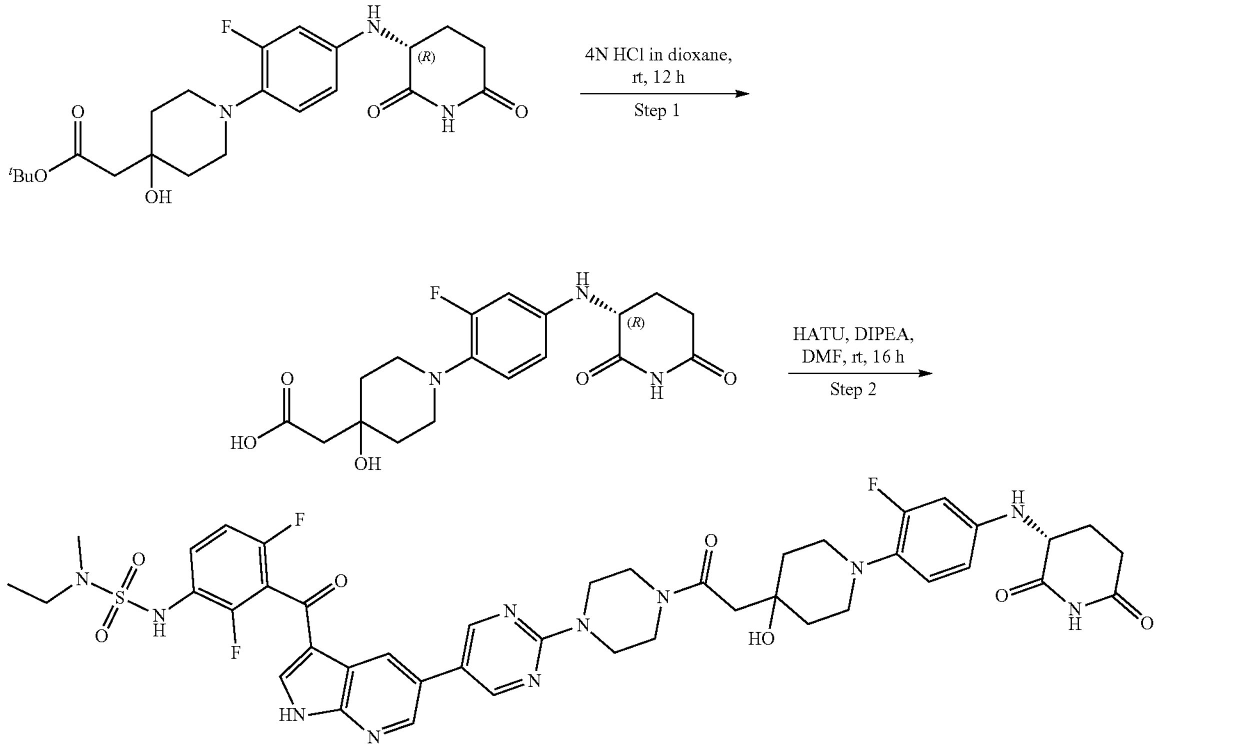

Step 1: To a stirred solution of tert-butyl 2-[1-[4-[[(3R)-2,6-dioxo-3-piperidyl]amino]-2-fluoro-phenyl]-4-hydroxy-4-piperidyl]acetate (500 mg, 1.15 mmol) in 1,4-dioxane (5 mL) was added hydrogen chloride solution in 1,4-dioxane (4M, 10 mL) at 0° C. under nitrogen atmosphere. The reaction mixture was stirred at room temperature for 16 h. After completion, the reaction mixture was concentrated under reduced pressure to get crude product. The crude mixture was triturated with diethyl ether to afford 2-[1-[4-[[(3R)-2,6-dioxo-3-piperidyl]amino]-2-fluoro-phenyl]-4-hydroxy-4-piperidyl]acetic acid (450 mg, 930.64 μmol, 81.06% yield). LCMS (ESI−): 378.2 $[M-H]^-$.

Step 2: Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (400 mg, 674.48 μmol), 2-[1-[4-[[(3R)-2,6-dioxo-3-piperidyl]amino]-2-fluoro-phenyl]-4-hydroxy-4-piperidyl]acetic acid (308.53 mg, 741.93 μmol), HATU (256.46 mg, 674.48 μmol), N,N-Diisopropylethylamine (348.68 mg, 2.70 mmol, 469.92 The crude compound was purified by reverse phase column chromatography by using 40% acetonitrile in 0.1% HCOOH in water to afford 5-[2-[4-[2-[1-[4-[[(3R)-2,6-dioxo-3-piperidyl]amino]-2-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (255 mg, 263.74 μmol, 39.10% yield) as off white solid. LCMS (ESI+): 918.3 $[M+H]^+$. $^1H$ NMR (400 MHz, DMSO-$d_6$): δ 12.96 (s, 1H), 10.79 (s, 1H), 8.81 (s, 2H), 8.68 (d, J=2.40 Hz, 1H), 8.57 (s, 1H), 8.13 (s, 1H), 7.54-7.60 (m, 1H), 7.24 (t, J=8.40 Hz, 1H), 6.87 (t, J=9.60 Hz, 1H), 6.51 (dd, J=2.40, 15.20 Hz, 1H), 6.42 (dd, J=2.40, 8.80 Hz, 1H), 5.79 (d, J=7.60 Hz, 1H), 4.87 (s, 1H), 4.24-4.27 (m, 1H), 3.82-3.88 (m, 4H), 3.64-3.70 (m, 4H), 3.10 (q, J=7.20 Hz, 2H), 2.74-2.92 (m, 4H), 2.65-2.80 (m, 1H), 2.74 (s, 1H), 2.55-2.60 (m, 3H), 2.55-2.50 (m, 3H), 2.07-2.10 (m, 1H), 1.67-1.87 (m, 5H), 1.02 (t, J=7.20 Hz, 3H).

Example 175

5-[4-[4-[2-[1-[4-(2,6-dioxo-3-piperidyl)-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine

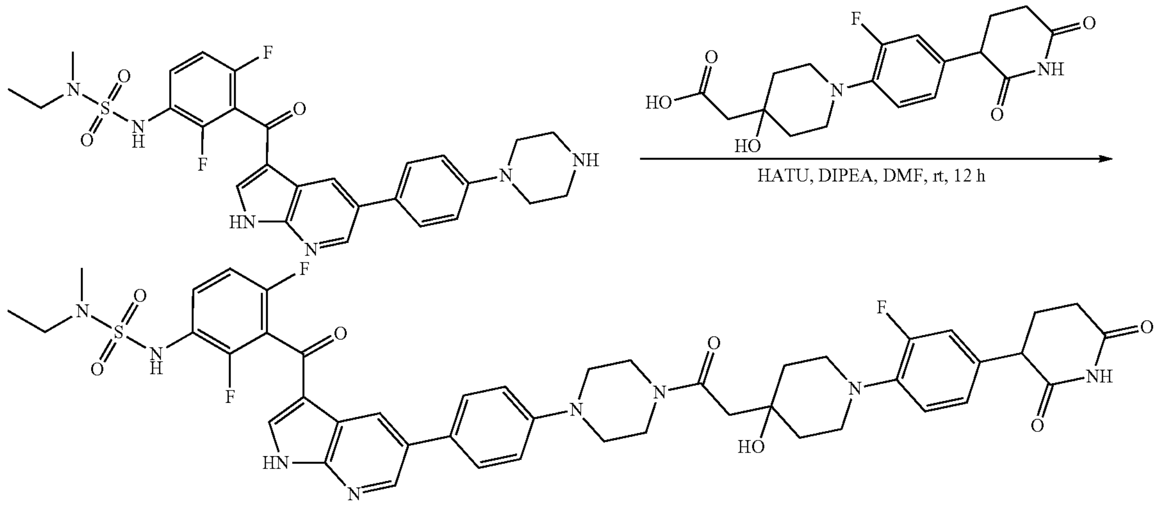

Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(4-piperazin-1-ylphenyl)-1H-pyrrolo[2,3-b]pyridine (250 mg, 422.96 μmol), 2-[1-[4-(2,6-dioxo-3-piperidyl)-2-fluoro-phenyl]-4-hydroxy-4-piperidyl]acetic acid (170 mg, 424.12 μmol) and N,N-Diisopropylethylamine (1.48 g, 11.48 mmol, 2.0 mL) and HATU (180 mg, 473.40 μmol). The crude compound was purified by reverse phase column chromatography by using 50% acetonitrile in 0.1% ammonium acetate in water to afford 5-[4-[4-[2-[1-[4-(2,6-dioxo-3-piperidyl)-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine (77 mg, 81.61 μmol, 19.29% yield) as a yellow solid. LCMS (ESI−): 899.3 $[M-H]^-$. $^1H$ NMR (400 MHz, DMSO-$d_6$): δ 12.95 (s, 1H), 10.82 (s, 1H), 9.72 (s, 1H), 8.67 (s, 1H), 8.55 (s, 1H), 8.11 (s, 1H), 7.56-7.65 (m, 3H), 7.26-7.30 (m, 1H), 7.12 (d, J=8.80 Hz, 2H), 6.96-7.04 (m, 3H), 4.94 (s, 1H), 3.65-3.80 (m, 5H), 3.21-3.35 (m, 4H), 3.01-3.12 (m, 6H), 2.73 (s, 1H), 2.63-2.72 (m, 3H), 2.45-2.55 (m, 3H), 2.10-2.27 (m, 1H), 1.94-2.05 (m, 1H), 1.64-1.85 (m, 4H), 1.02 (t, J=7.20 Hz, 3H).

Example 176

5-[6-[4-[2-[1-[4-[[(3S)-2,6-dioxo-3-piperidyl]amino]-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine

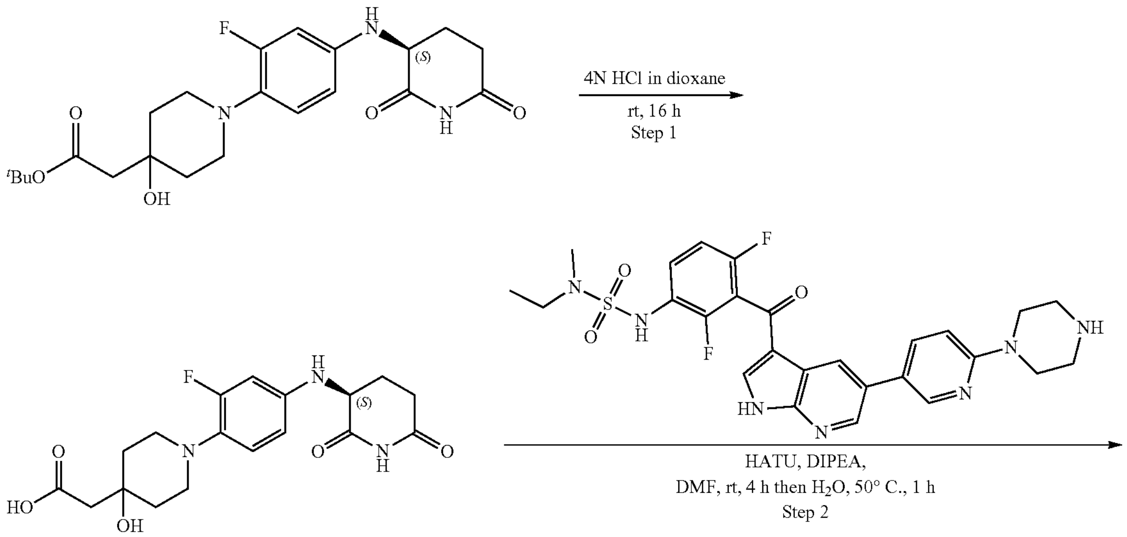

-continued

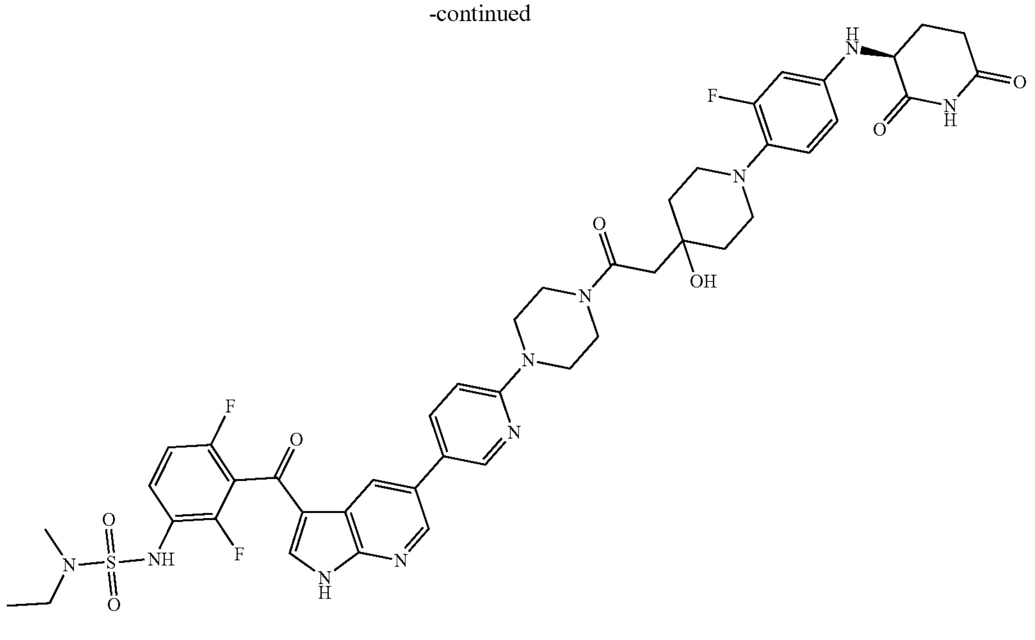

Step 1: To a stirred solution of tert-butyl (S)-2-[1-[4-[(2,6-dioxo-3-piperidyl)amino]-2-fluoro-phenyl]-4-hydroxy-4-piperidyl]acetate (500 mg, 1.15 mmol) in 1,4-dioxane (10 mL), was added hydrogen chloride solution in 1,4-dioxane (4M, 2.87 mL) at 0° C. The reaction mixture was stirred at room temperature for 16 h. After completion, the reaction mixture was concentrated under reduced pressure to afford (S)-2-[1-[4-[(2,6-dioxo-3-piperidyl)amino]-2-fluoro-phenyl]-4-hydroxy-4-piperidyl]acetic acid (470 mg, 1.10 mmol, 95.49% yield, hydrochloric acid salt) as a pale brown solid. LCMS (ESI+): 380.2 $[M+H]^+$.

Step 2: Target compound was prepared via HATU mediated acid-amine coupling reaction (procedure A). Amide coupling was carried out using (S)-2-[1-[4-[(2,6-dioxo-3-piperidyl)amino]-2-fluoro-phenyl]-4-hydroxy-4-piperidyl]acetic acid (231.78 mg, 557.38 μmol), N-ethyl-N-isopropyl-propan-2-amine (327.44 mg, 2.53 mmol, 441.30 μL) and HATU (211.93 mg, 557.38 μmol), 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (0.3 g, 506.71 μmol). The desired product was purified from crude by reverse phase column chromatography (10 mM ammonium acetate in water:Acetonitrile) and fractions were lyophilized to afford 5-[6-[4-[2-[1-[4-[[(3S)-2,6-dioxo-3-piperidyl]amino]-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine (0.185 g, 194.93 μmol, 38.47% yield) as an off white solid. LCMS (ESI−): 915.3 $[M-H]^-$. $^1H$ NMR (400 MHz, DMSO-$d_6$): δ 12.97 (s, 1H), 10.79 (s, 1H), 9.72 (s, 1H), 8.68 (d, J=2.00 Hz, 1H), 8.55 (s, 1H), 8.52 (d, J=2.00 Hz, 1H), 8.13 (d, J=2.00 Hz, 1H), 7.98 (dd, J=2.40, 8.80 Hz, 1H), 7.56-7.62 (m, 1H), 7.29 (dd, J=8.40, 12.80 Hz, 1H), 7.02 (d, J=9.20 Hz, 1H), 6.86 (t, J=9.60 Hz, 1H), 6.52 (d, J=2.80 Hz, 1H), 6.44 (t, J=8.80 Hz, 1H), 5.78 (d, J=7.60 Hz, 1H), 4.88 (s, 1H), 4.23-4.29 (m, 1H), 3.60-3.72 (m, 8H), 3.11 (q, J=7.20 Hz, 2H), 2.85-2.92 (m, 4H), 2.60-2.74 (m, 1H), 2.73 (s, 3H), 2.54-2.60 (m, 3H), 2.06-2.08 (m, 1H), 1.65-1.90 (m, 5H), 1.02 (t, J=7.20 Hz, 3H).

Example 177

5-[6-[4-[2-[1-[4-[[(3R)-2,6-dioxo-3-piperidyl]amino]-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine (Compound 177)

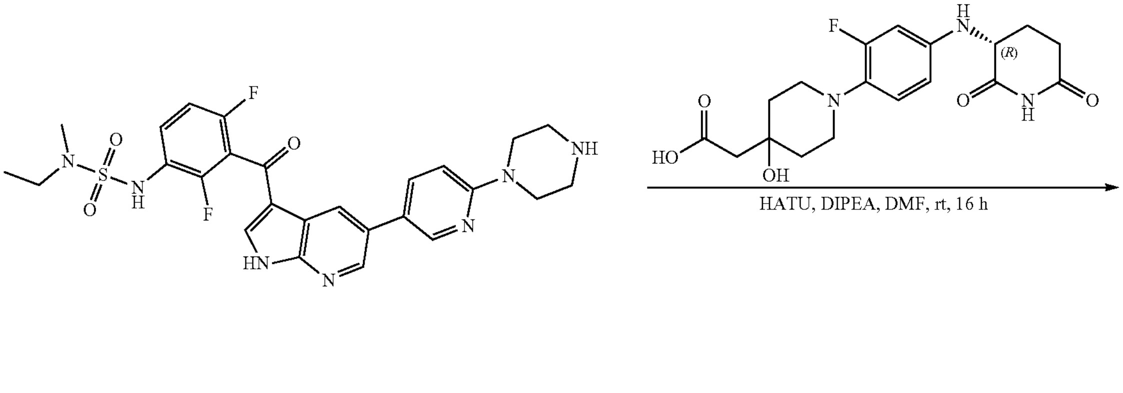

-continued

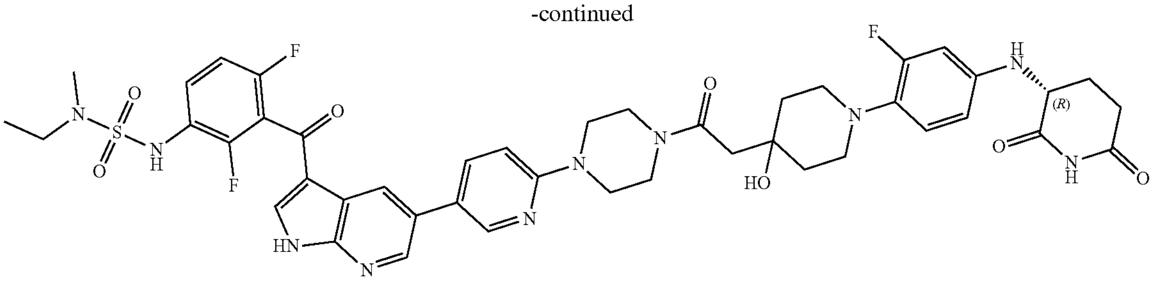

Target compound was prepared via HATU mediated acid-amine coupling reaction (procedure A). Amide coupling was carried out using 2-[1-[4-[[(3R)-2,6-dioxo-3-piperidyl]amino]-2-fluoro-phenyl]-4-hydroxy-4-piperidyl]acetic acid (341.42 mg, 899.93 μmol) and 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (500 mg, 899.93 μmol), N,N-Dimethylformamide (465.24 mg, 3.60 mmol, 627.01 μL) and HATU (376.40 mg, 989.92 μmol). The crude compound was purified by reverse phase column chromatography by using eluted with 45% acetonitrile in 0.1% ammonium acetate in water to afford 5-[6-[4-[2-[1-[4-[[(3R)-2,6-dioxo-3-piperidyl]amino]-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine (200 mg, 207.64 μmol, 23.07% yield) as a yellow solid. LCMS (ESI+): 917.3 $[M+H]^+$. $^1H$ NMR (400 MHz, DMSO-$d_6$): δ 12.95 (s, 1H), 10.79 (s, 1H), 8.67 (d, J=2.00 Hz, 1H), 8.52 (d, J=2.40 Hz, 2H), 8.10 (s, 1H), 7.98 (dd, J=2.80, 9.00 Hz, 1H), 7.53-7.59 (m, 1H), 7.20 (t, J=8.80 Hz, 1H), 7.02 (d, J=8.80 Hz, 1H), 6.86 (t, J=10.00 Hz, 1H), 6.50 (dd, J=2.40, 14.80 Hz, 1H), 6.42 (d, J=8.80 Hz, 1H), 5.79 (d, J=7.60 Hz, 1H), 4.88 (s, 1H), 4.21-4.31 (m, 1H), 3.60-3.70 (m, 8H), 3.08 (q, J=7.20 Hz, 1H), 2.85-2.92 (m, 4H), 2.69-2.74 (m, 1H), 2.74 (s, 3H), 2.51-2.59 (m, 3H), 2.51-2.49 (m, 1H), 2.01-2.09 (m, 1H), 1.67-1.90 (m, 5H), 1.01 (t, J=7.20 Hz, 3H).

Example 178

5-[4-[4-[2-[1-[4-[[(3R)-2,6-dioxo-3-piperidyl]amino]-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine

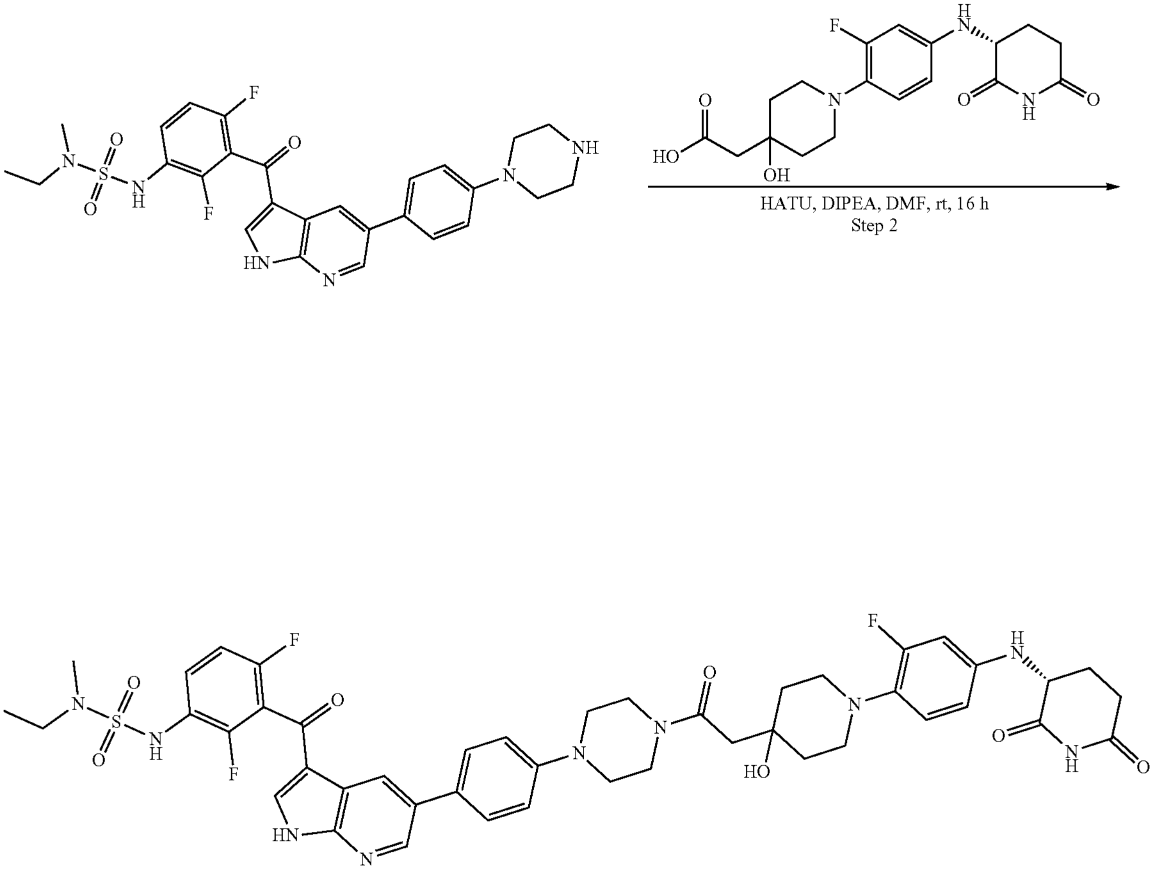

Target compound was prepared via HATU mediated acid-amine coupling reaction (procedure A). Amide coupling was carried out using 2-[1-[4-[[(3R)-2,6-dioxo-3-piperidyl]amino]-2-fluoro-phenyl]-4-hydroxy-4-piperidyl]acetic acid (239.42 mg, 631.07 μmol), 3-[3-[[ethyl(methyl)sulfamoyl]amino]-2,6-difluoro-benzoyl]-5-(4-piperazin-1-ylphenyl)-1H-pyrrolo[2,3-b]pyridine (350 mg, 631.07 μmol), N,N-Diisopropylethylamine (326.24 mg, 2.52 mmol, 439.68 μL) and HATU (263.95 mg, 694.18 μmol). The crude compound was purified by reverse phase column chromatography eluted with 45% acetonitrile in 0.1% ammonium acetate in water to afford 5-[4-[4-[2-[1-[4-[[(3R)-2,6-dioxo-3-piperidyl]amino]-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine (130 mg, 140.22 μmol, 22.22% yield) as off white solid. LCMS (ESI−): 914.2 $[M-H]^-$. $^1H$ NMR (400 MHz, DMSO-$d_6$): δ 12.94 (s, 1H), 10.79 (s, 1H), 8.66 (d, J=2.40 Hz, 1H), 8.54 (s, 1H), 8.07 (s, 1H), 7.63 (d, J=−8.00 Hz, 2H), 7.54 (dd, J=6.00, 9.20 Hz, 1H), 7.17-7.21 (m, 1H), 7.12 (d, J=8.80 Hz, 2H), 6.86 (t, J=9.60 Hz, 1H), 6.50 (dd, J=2.40, 15.20 Hz, 1H), 6.38-6.43 (m, 1H), 5.79 (d, J=8.00 Hz, 1H), 4.87 (s, 1H), 4.20-4.30 (m, 1H), 3.70-3.75 (m, 4H), 3.27-3.34 (m, 4H), 3.07 (q, J=7.20 Hz, 2H), 2.84-2.92 (m, 4H), 2.71-2.78 (m, 1H), 2.74 (s, 3H), 2.51-2.59 (m, 3H), 2.05-2.09 (m, 1H), 1.66-1.86 (m, 5H), 1.01 (t, J=6.80 Hz, 3H).

Example 179

5-[4-[4-[2-[1-[4-[[(3S)-2,6-dioxo-3-piperidyl]amino]-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(4-piperazin-1-ylphenyl)-1H-pyrrolo[2,3-b]pyridine (370 mg, 667.14 μmol), (S)-2-[1-[4-[(2,6-dioxo-3-piperidyl)amino]-2-fluoro-phenyl]-4-hydroxy-4-piperidyl]acetic acid (253.10 mg, 667.14 μmol), HATU (380.50 mg, 1.00 mmol), N,N-Diisopropylethylamine (258.67 mg, 2.00 mmol, 348.61 μL) to afford 5-[4-[4-[2-[1-[4-[[(3S)-2,6-dioxo-3-piperidyl]amino]-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine (103.42 mg, 112.16 μmol, 16.81% yield) as brown solid. LCMS (ESI+): 916.3 $[M+H]^+$. $^1H$ NMR (400 MHz, DMSO-$d_6$): δ 12.90 (s, 1H), 10.79 (s, 1H), 9.72 (s, 1H), 8.67 (d, J=2.40 Hz, 1H), 8.55 (s, 1H), 8.10 (s, 1H), 7.61-7.55 (m, 3H), 7.27 (t, J=8.40 Hz, 1H), 7.12 (d, J=8.80 Hz, 2H), 6.89-6.84 (m, 1H), 6.50 (dd, J=2.40, 15.00 Hz, 1H), 6.42 (dd, J=2.00, 8.80 Hz, 1H), 5.79 (d, J=8.00 Hz, 1H), 4.87 (s, 1H), 4.26-4.24 (m, 1H), 3.75-3.70 (m, 4H), 3.34-3.22 (m, 4H), 3.13-3.08 (m, 2H), 2.89-2.85 (m, 4H), 2.72 (s, 3H), 2.74-2.69 (m, 1H), 2.68-2.67 (m, 2H), 2.08-2.07 (m, 1H), 1.83-1.66 (m, 6H), 1.02 (t, J=7.20 Hz, 3H).

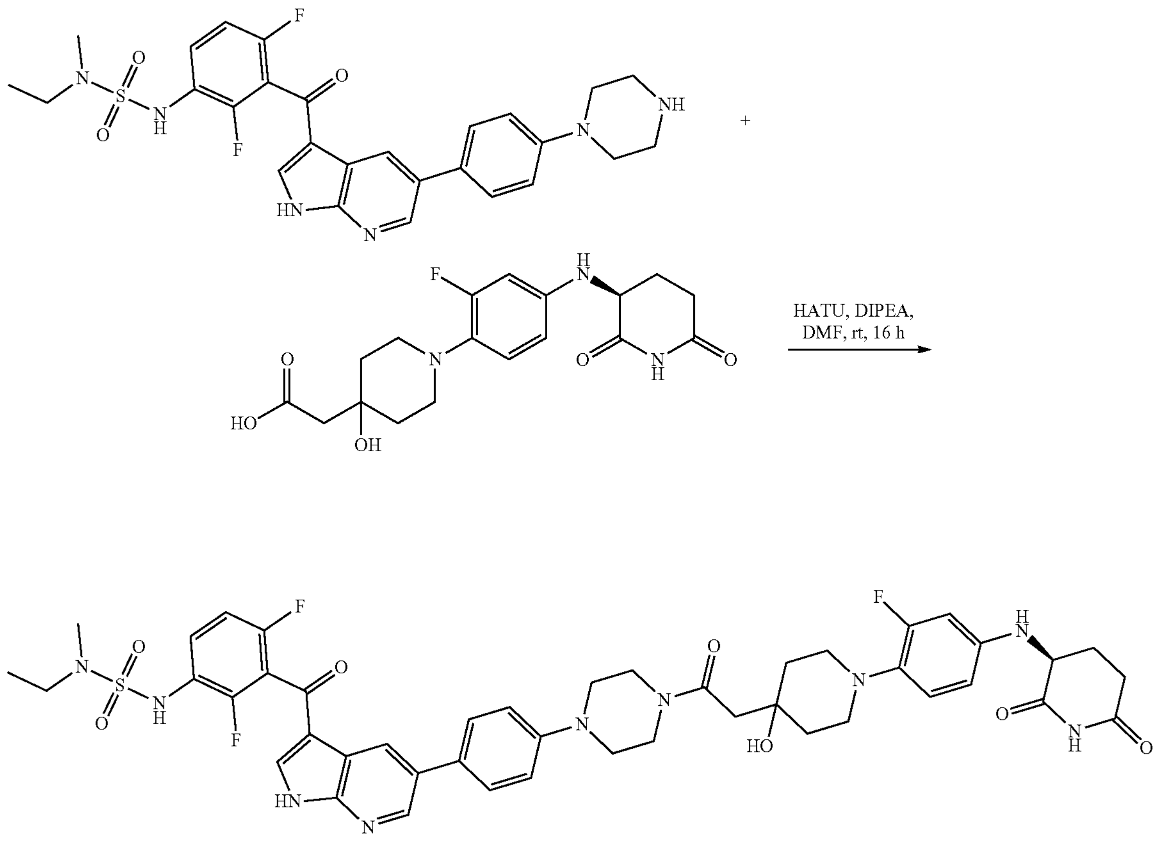

Example 180

5-[3-chloro-4-[4-[2-[1-[4-[(2,6-dioxo-3-piperidyl)amino]-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine

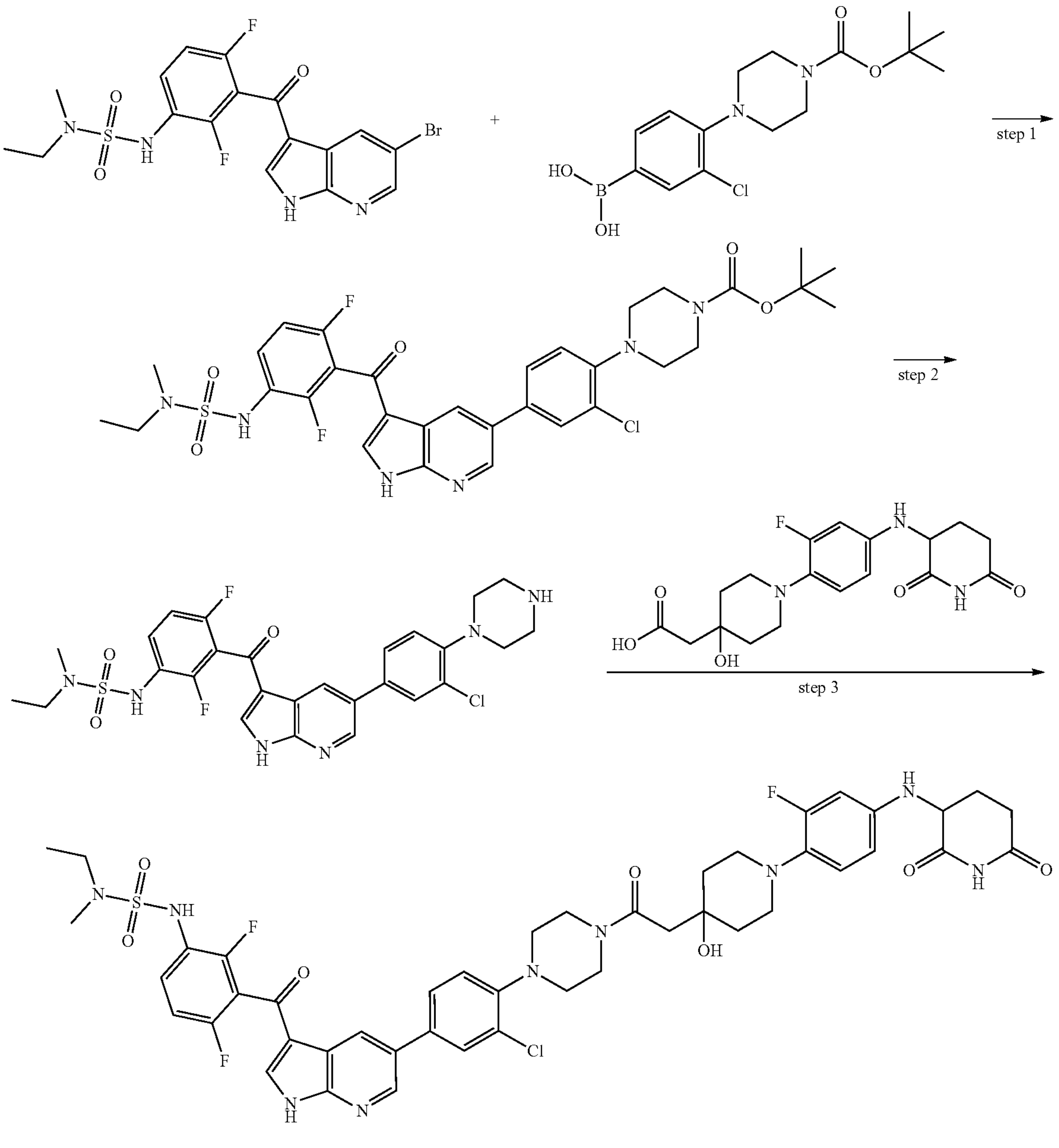

Step 1: 5-bromo-3-[3-[[ethyl(methyl)sulfamoyl]amino]-2,6-difluoro-benzoyl]-1H-pyrrolo[2,3-b]pyridine (0.2 g, 422.57 μmol) and [4-(4-tert-butoxycarbonylpiperazin-1-yl)-3-chloro-phenyl]boronic acid (143.93 mg, 422.57 μmol) were dissolved in 1,4-dioxane (1.2 mL) and Water (0.3 mL) with tri potassium phosphate (269.10 mg, 1.27 mmol) and XPhos Pd G3 (17.88 mg, 21.13 μmol). The reaction was purged with argon before being sealed in a microwave vessel. The contents were stirred at room temperature for 5 min to ensure dissolution of solids. At this time, the reaction was stirred in a microwave at 110° C. for 2 hr. After cooling, the reaction was diluted with water and extracted with ethyl acetate. The combined organic layers were dried with sodium sulphate and concentrated. The crude material was then purified by column chromatography (35-95% ethyl acetate in hexanes) to afford the product tert-butyl 4-[2-chloro-4-[3-[3-[[ethyl(methyl)sulfamoyl]amino]-2,6-difluoro-benzoyl]-1H-pyrrolo[2,3-b]pyridin-5-yl]phenyl]piperazine-1-carboxylate (272 mg, 374.94 μmol, 88.73% yield) as an off-white solid. LCMS (ESI+): 689.4 $[M+H]^+$ Step 2: To a solution of tert-butyl 4-[2-chloro-4-[3-[3-[[ethyl(methyl)sulfamoyl]amino]-2,6-difluoro-benzoyl]-

1H-pyrrolo[2,3-b]pyridin-5-yl]phenyl]piperazine-1-carboxylate (272 mg, 394.68 μmol) in 1,4-dioxanes (6.8 mL) was added hydrogen chloride solution in 1,4-dioxane (4 M, 3.45 mL). The resulting solution was stirred at room temperature for 16 hr. At this time, the resulting solid was isolated by vacuum filtration, washing with MTBE, to afford the product 5-(3-chloro-4-piperazin-1-yl-phenyl)-3-[3-[[ethyl(methyl)sulfamoyl]amino]-2,6-difluoro-benzoyl]-1H-pyrrolo[2,3-b]pyridine (225 mg, 305.75 μmol, 77.47% yield, hydrochloric acid salt), which was used without further purification. LCMS (ESI+): 589.7 $[M+H]^+$ Step 3: To a solution of 2-[1-[4-[(2,6-dioxo-3-piperidyl)amino]-2-fluoro-phenyl]-4-hydroxy-4-piperidyl]acetic acid (43.38 mg, 87.93 μmol, trifluoroacetic acid salt) in DMF (0.7 mL) at 0° C. was added N,N-Diisopropylethylamine (15.50 mg, 119.90 μmol, 20.88 uL) and HATU (75.98 mg, 199.83 μmol). The resulting mixture stirred at this temperature for 30 min. A solution of 5-(3-chloro-4-piperazin-1-yl-phenyl)-3-[3-[[ethyl(methyl)sulfamoyl]amino]-2,6-difluoro-benzoyl]-1H-pyrrolo[2,3-b]pyridine (50 mg, 79.93 μmol, hydrochloric acid salt) in DMF (0.7 mL) was added at 0° C., and the reaction warmed to room temperature before stirring for 2 hr. 6 drops of sat. aq. sodium bicarbonate was added and the reaction mixture stirred overnight. The crude reaction was purified by column chromatography (10-60% acetonitrile in water with 0.1% formic acid) to afford the product 5-[3-chloro-4-[4-[2-[1-[4-[(2,6-dioxo-3-piperidyl)amino]-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine (15.08 mg, 14.38 μmol, 17.99% yield, formic acid salt) as an off-white solid. LCMS (ESI+): 950.6 $[M+H]^+$. $^1H$ NMR (400 MHz, DMSO-$d_6$) δ 12.92 (d, J=3.3 Hz, 1H), 10.71 (s, 1H), 9.64 (s, 1H), 8.64 (d, J=2.2 Hz, 1H), 8.53 (s, 1H), 8.08 (d, J=3.6 Hz, 2H), 7.77 (d, J=2.2 Hz, 1H), 7.63 (dd, J=8.3, 2.3 Hz, 1H), 7.51 (td, J=9.0, 5.9 Hz, 1H), 7.26-7.18 (m, 2H), 6.80 (t, J=9.2 Hz, 1H), 6.44 (d, J=14.9 Hz, 1H), 6.35 (d, J=8.7 Hz, 1H), 5.70 (s, 1H), 4.88-4.68 (m, 1H), 4.19 (s, 1H), 3.67 (d, J=17.6 Hz, 4H), 3.10-2.92 (m, 7H), 2.83 (d, J=16.0 Hz, 4H), 2.52 (s, 3H), 2.09-1.95 (m, 2H), 1.86-1.52 (m, 6H), 0.95 (t, J=7.1 Hz, 3H).

Example 181

5-[1-[1-[2-[1-[4-[(2,6-dioxo-3-piperidyl)amino]-2-fluoro-phenyl]-4-hydroxy-4-piperidyl]acetyl]-4-piperidyl]-2-oxo-4-pyridyl]-3-[3-[[ethyl(methyl)sulfamoyl]amino]-2,6-difluoro-benzoyl]-1H-pyrrolo[2,3-b]pyridine

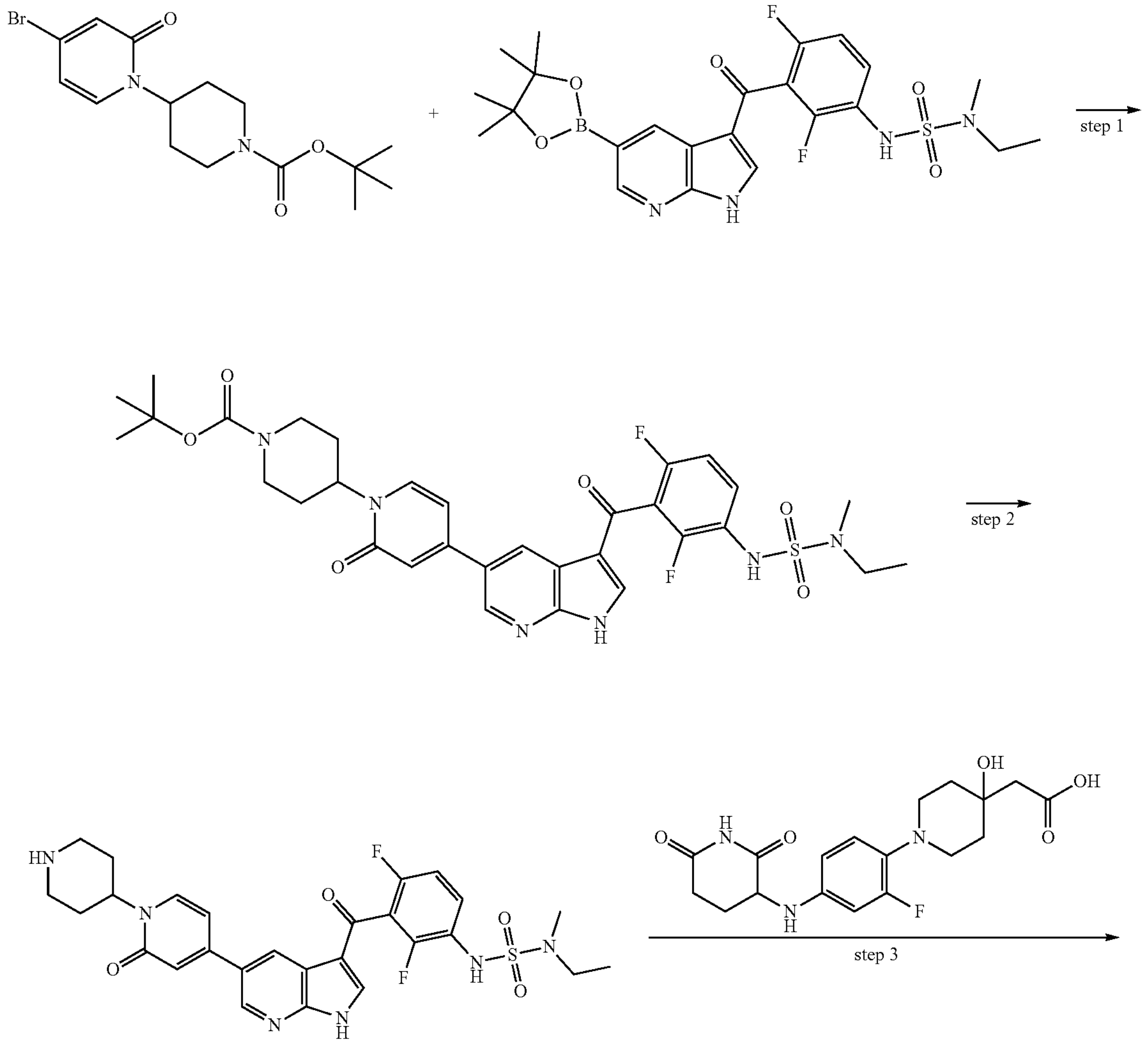

-continued

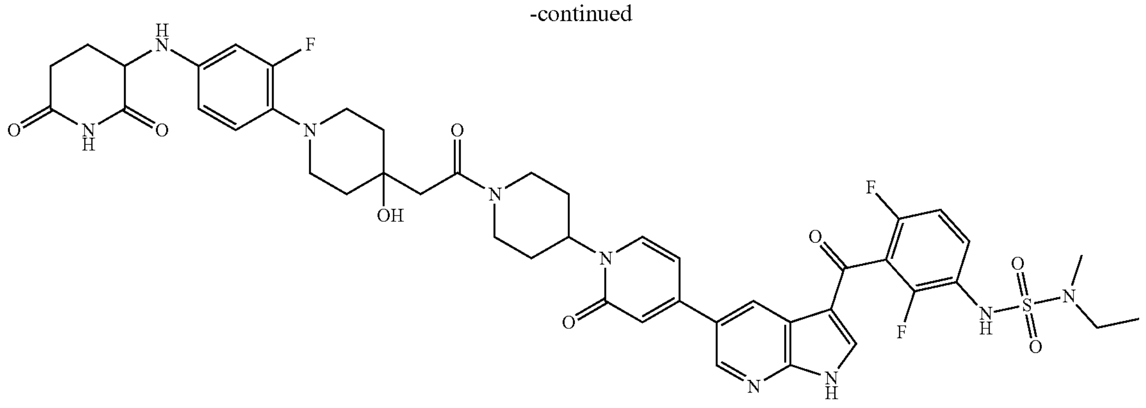

Step 1: To a stirred solution of tert-butyl 4-(4-bromo-2-oxo-1-pyridyl)piperidine-1-carboxylate (26.77 mg, 74.95 μmol) was dissolved in 1,4-dioxane (926.98 uL) were added 3-[3-[[ethyl(methyl)sulfamoyl]amino]-2,6-difluoro-benzoyl]-5-(4,4,5,5-tetramethyl-1,3,2-dioxaborolan-2-yl)-1H-pyrrolo[2,3-b]pyridine (30 mg, 57.65 μmol) and tripotassium phosphate (36.71 mg, 172.96 μmol) in water (92.70 uL). The reaction mixture was degassed with nitrogen for 10 minutes. Then Xphos Pd G2 (4.53 mg, 5.77 μmol) was added and degassed with nitrogen for 5 minutes. Then heated to 120° C. at microwave for 2 h. The reaction mixture was cooled to room temperature, filtered through celite bed, celite bed washed with ethyl acetate (10 mL) and organic layer was separated. The organic layer washed with brine (5 mL), dried over sodium sulphate and concentrated under reduced vacuum to yield crude residue. The crude was purified by silica gel column chromatography using 0-100% ethyl acetate in hexanes as a eluent yielded tert-butyl 4-[4-[3-[3-[[ethyl(methyl)sulfamoyl]amino]-2,6-difluoro-benzoyl]-1H-pyrrolo[2,3-b]pyridin-5-yl]-2-oxo-1-pyridyl]piperidine-1-carboxylate (25 mg, 37.27 μmol, 64.65% yield) as a yellow solid. LCMS (ESI+): 671.4 $[M+H]^+$ Step 2: Brought tert-butyl 4-[4-[3-[3-[[ethyl(methyl)sulfamoyl]amino]-2,6-difluoro-benzoyl]-1H-pyrrolo[2,3-b]pyridin-5-yl]-2-oxo-1-pyridyl]piperidine-1-carboxylate (25 mg, 37.27 μmol) up in dioxane (2 mL) and added hydrogen chloride solution in 1,4-dioxane (4 M, 2 mL) and stirred at room temperature overnight. Diluted with MBTE and filtered to give 3-[3-[[ethyl(methyl)sulfamoyl]amino]-2,6-difluoro-benzoyl]-5-[2-oxo-1-(4-piperidyl)-4-pyridyl]-1H-pyrrolo[2,3-b]pyridine (22 mg, 34.43 μmol, 92.37% yield, hydrochloric acid salt) as a crude white solid. LCMS (ES+): 571.3 $[M+H]^+$ Step 3: Brought up 2-[1-[4-[(2,6-dioxo-3-piperidyl)amino]-2-fluoro-phenyl]-4-hydroxy-4-piperidyl]acetic acid (19.67 mg, 39.86 μmol, trifluoroacetic acid salt) in DMF (1 mL) and added DIPEA (23.42 mg, 181.20 μmol, 31.56 uL) before cooling the reaction to 0° C. and adding HATU (15.16 mg, 39.86 μmol). After stirring for 30 minutes, added 3-[3-[[ethyl(methyl)sulfamoyl]amino]-2,6-difluoro-benzoyl]-5-[2-oxo-1-(4-piperidyl)-4-pyridyl]-1H-pyrrolo[2,3-b]pyridine (22 mg, 36.24 μmol, hydrochloric acid salt) and let gradually warm over 3 hours. Added 10 drops of saturated sodium bicarbonate solution and 10 drops of water and continued stirring overnight. Loaded reaction onto RP isco (0-100% ACN/water w TFA) to give 5-[1-[1-[2-[1-[4-[(2,6-dioxo-3-piperidyl)amino]-2-fluoro-phenyl]-4-hydroxy-4-piperidyl]acetyl]-4-piperidyl]-2-oxo-4-pyridyl]-3-[3-[[ethyl (methyl)sulfamoyl]amino]-2,6-difluoro-benzoyl]-1H-pyrrolo[2,3-b]pyridine (9 mg, 8.17 μmol, 22.56% yield, trifluoroacetic acid salt) as an off-white solid after lyophilization. LCMS (ESI+): 467.1 $[M/2+H]^+$, 932.5 $[M+H]^+$. $^1H$ NMR (400 MHz, DMSO-$d_6$) δ 13.01 (s, 1H), 10.70 (s, 1H), 9.64 (s, 2H), 8.75 (d, J=2.3 Hz, 1H), 8.65 (s, 1H), 8.20 (d, J=5.4 Hz, 1H), 8.12 (s, 1H), 7.51 (td, J=9.0, 6.0 Hz, 1H), 7.33 (dd, J=5.3, 1.6 Hz, 1H), 7.21 (td, J=9.3, 8.9, 1.5 Hz, 1H), 7.13 (d, J=1.9 Hz, 1H), 6.79 (dd, J=10.0, 8.7 Hz, 1H), 6.48-6.28 (m, 3H), 5.70 (d, J=7.6 Hz, 1H), 5.31-5.19 (m, 1H), 4.87 (s, 1H), 4.23-4.11 (m, 1H), 3.99-3.87 (m, 1H), 3.87-3.75 (m, 1H), 3.46-3.33 (m, 1H), 3.25-3.17 (m, 4H), 3.04 (q, J=7.1 Hz, 2H), 2.89-2.73 (m, 3H), 2.66 (s, 3H), 2.55-2.46 (m, 2H), 2.07-1.88 (m, 3H), 1.83-1.46 (m, 6H), 0.95 (t, J=7.1 Hz, 3H).

Example 182

5-[2-[4-[[1-[4-[(2,6-dioxo-3-piperidyl)amino]-2-fluoro-phenyl]-4-piperidyl]methoxy]-1-piperidyl]pyrimidin-5-yl]-3-[3-[[ethyl(methyl)sulfamoyl]amino]-2,6-difluoro-benzoyl]-1H-pyrrolo[2,3-b]pyridine

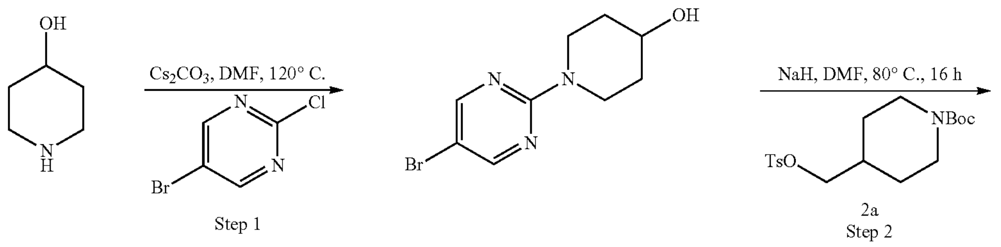

-continued
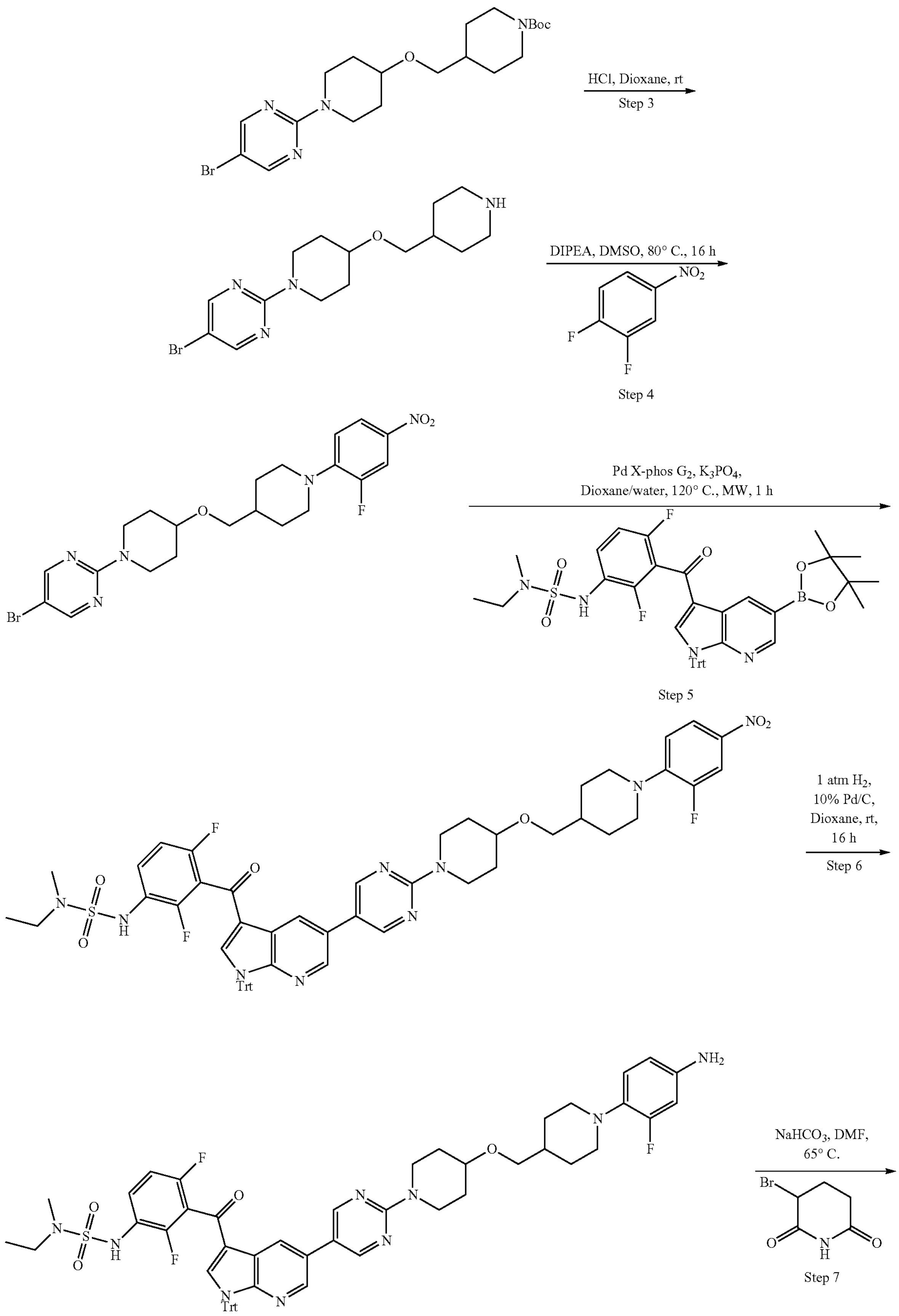

-continued

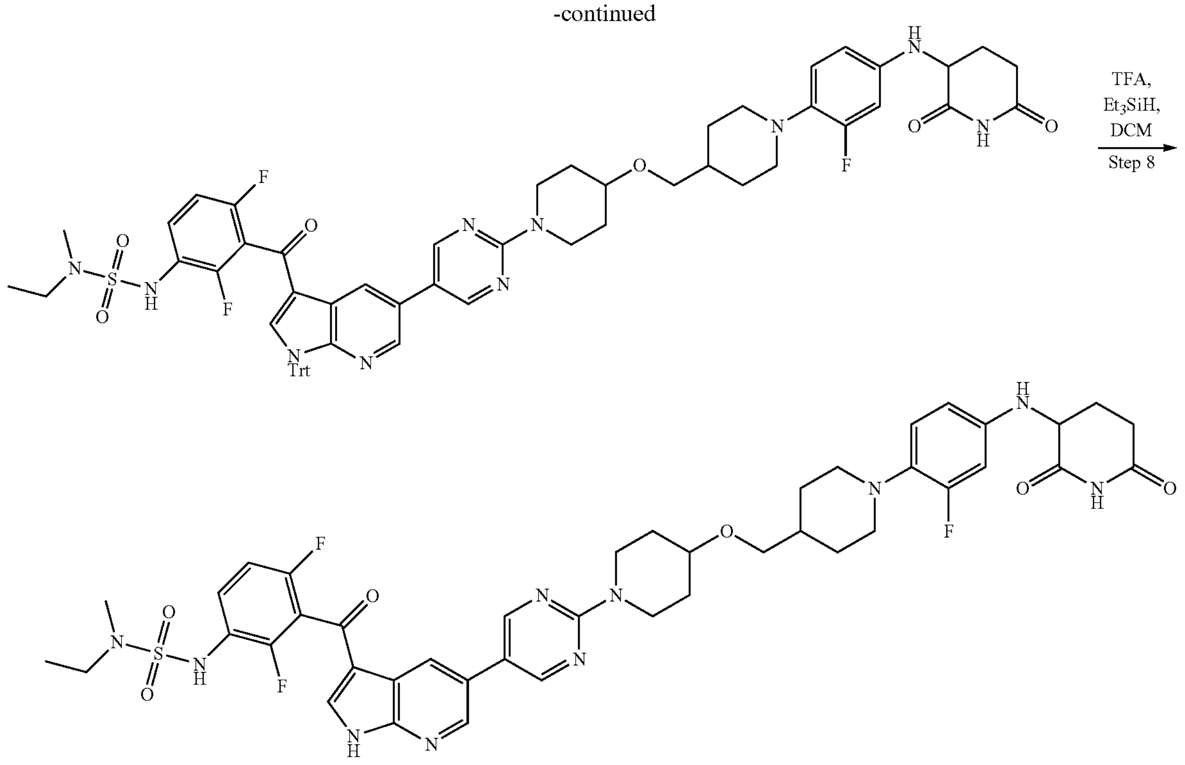

Step 1: To a stirred solution of piperidin-4-ol (2.88 g, 28.43 mmol) and 5-bromo-2-chloro-pyrimidine (5 g, 25.85 mmol) in DMF (70 mL) was added cesium carbonate (25.27 g, 77.55 mmol) at room temperature. The reaction mixture was stirred for 16 hours at 120° C. After completion, the reaction was diluted with cold water (150 mL) and extracted using ethyl acetate (2×150 mL). The combined organic layers were dried over anhydrous sodium sulphate, filtered and concentrated under reduced pressure to yield crude product which was purified by column chromatography on silica using 10-20% ethyl acetate in petroleum ether as eluent to yield 1-(5-bromopyrimidin-2-yl)piperidin-4-ol (6 g, 22.55 mmol, 87.23% yield) as a white solid. LCMS (ESI+): 258.0 $[M+H]^+$.

Step 2: To a stirred solution of sodium hydride (60% dispersion in mineral oil) (534.41 mg, 22.27 mmol) in DMF (20 mL) was added 1-(5-bromopyrimidin-2-yl)piperidin-4-ol (3 g, 11.62 mmol) in DMF (10 mL) at 0° C. The reaction was heated at 60° C. for 1 h. Then cooled the reaction to 0° C. and tert-butyl 4-(p-tolylsulfonyloxymethyl)piperidine-1-carboxylate (4.29 g, 11.62 mmol) in DMF (10 mL) was added. The reaction mixture was further stirred at 80° C. for 16 hours. The reaction was then quenched with cold water (150 mL) and compound extracted using ethyl acetate (2×100 mL). The combined organic layers were dried over anhydrous sodium sulphate and concentrated under reduced pressure to yield crude product which was purified by silica gel column chromatography using 20%-30% ethyl acetate in petroleum ether as an eluent to afford tert-butyl4-[[1-(5-bromopyrimidin-2-yl)-4-piperidyl]oxymethyl]piperidine-1-carboxylate (2.9 g, 4.27 mmol, 36.71% yield) as an off white solid. LCMS (ESI+): 355.1 $[M-100+H]^+$ Step 3: To a solution of tert-butyl 4-[[1-(5-bromopyrimidin-2-yl)-4-piperidyl]oxymethyl]piperidine-1-carboxylate (2 g, 4.39 mmol) in dichloromethane (20 mL) was added hydrogen chloride solution (4.0M in 1,4-dioxane, 21.96 mmol, 1.00 mL) at 0° C. The reaction mixture was stirred for 2 hours at 25° C. The reaction was concentrated under reduced pressure to yield crude which was washed with diethyl ether (50 mL) to afford 5-bromo-2-[4-(4-piperidylmethoxy)-1-piperidyl]pyrimidine (2 g, 4.00 mmol, 91.01% yield) as a yellow solid. LCMS (ESI+): 357.0 $[M+H]^+$ Step 4: To a stirred solution of 5-bromo-2-[4-(4-piperidylmethoxy)-1-piperidyl]pyrimidine (2.2 g, 6.19 mmol) and 1,2-difluoro-4-nitro-benzene (985.16 mg, 6.19 mmol, 684.14 μL) in DMF (30 mL) was added N,N-Diisopropylethylamine (800.31 mg, 6.19 mmol, 1.08 mL) and the reaction mixture was stirred at 90° C. for 16 hours. After completion, the reaction was diluted with water (150 mL) and compound was extracted using ethyl acetate (2×150 mL). The combined organic layers were dried over anhydrous sodium sulphate and concentrated under reduced pressure to yield crude which was purified by column chromatography on silica using 40-50% ethyl acetate in petroleum ether as eluent to afford 5-bromo-2-[4-[[1-(2-fluoro-4-nitro-phenyl)-4-piperidyl]methoxy]-1-piperidyl] pyrimidine (1.5 g, 2.73 mmol, 44.10% yield) as a yellow solid. LCMS (ESI+): 495.9 $[M+H]^+$.

Step 5: To a stirred solution of 5-bromo-2-[4-[[1-(2-fluoro-4-nitro-phenyl)-4-piperidyl]methoxy]-1-piperidyl] pyrimidine (500 mg, 1.01 mmol) in 1,4-Dioxane (8 mL)/water (2 mL) were added 3-[3-[[ethyl(methyl)sulfamoyl] amino]-2,6-difluoro-benzoyl]-5-(4,4,5,5-tetramethyl-1,3,2-dioxaborolan-2-yl)-1-trityl-pyrrolo[2,3-b]pyridine (1.16 g, 1.52 mmol) and potassium phosphate tribasic anhydrous (429.38 mg, 2.02 mmol). The reaction mixture was degassed with nitrogen for 15 min and Xphos Pd G2 (79.50 mg, 101.14 μmol) was added to the reaction mixture and further purged the reaction with nitrogen gas for 5 mins. The reaction was then heated at 120° C. for 1 hours under microwave irradiation. After completion, the reaction mixture was diluted with ethyl acetate (25 mL) and washed with water (2×10 mL). The organic layer washed with brine solution (25 mL), dried over sodium sulphate and concentrated under reduced pressure to get the crude product which was purified by silica gel column chromatography using 50%-60% ethyl acetate in petroleum ether as an eluent to afford 3-[3-[[ethyl(methyl)sulfamoyl]amino]-2,6-difluoro-benzoyl]-5-[2-[4-[[1-fluoro-4-nitro-phenyl)-4-piperidyl] methoxy]-1-piperidyl]pyrimidin-5-yl]-1-trityl-pyrrolo[2,3-b]pyridine (500 mg, 429.08 μmol, 42.42% yield) as a yellow solid. LCMS (ESI+): 1050.8 $[M+H]^+$ Step 6: To a stirred solution of 3-[3-[[ethyl(methyl)sulfamoyl]amino]-2,6-difluoro-benzoyl]-5-[2-[4-[[1-(2-fluoro-4-nitro-phenyl)-4-piperidyl]methoxy]-1-piperidyl]pyrimidin-5-yl]-1-trityl-pyrrolo[2,3-b]pyridine (1 g, 952.24 μmol) in 1,4-Dioxane (30 mL) was added Palladium 10% on carbon (1.01 g, 9.52 mmol) under $N_2$ atmosphere and reaction was stirred under $H_2$ atmosphere pressure at room temperature for 16 hours. After completion, the reaction mixture was purged with nitrogen, catalyst was removed by filtration through celite bed. Celite bed further washed with ethyl acetate (150 mL). The filtrate was concentrated under reduced pressure to afford crude product which was washed with dry hexane (2×50 mL) to get 5-[2-[4-[[1-(4-amino-2-fluoro-phenyl)-4-piperidyl]methoxy]-1-piperidyl]pyrimidin-5-yl]-3-[3-[[ethyl(methyl)sulfamoyl]amino]-2,6-difluoro-benzoyl]-1-trityl-pyrrolo[2,3-b]pyridine (840 mg, 680.04 μmol, 71.41% yield) as a light brown solid. LCMS (ESI+): 1020.9 $[M+H]^+$ Step 7: To a stirred solution of 5-[2-[4-[[1-(4-amino-2-fluoro-phenyl)-4-piperidyl]methoxy]-1-piperidyl]pyrimidin-5-yl]-3-[3-[[ethyl(methyl)sulfamoyl]amino]-2,6-difluoro-benzoyl]-1-trityl-pyrrolo[2,3-b]pyridine (840 mg, 823.39 μmol) in DMF (20 mL) were added sodium bicarbonate (207.52 mg, 2.47 mmol, 96.07 μL) and 3-bromopiperidine-2,6-dione (395.25 mg, 2.06 mmol) at room temperature in sealed tube. The reaction mixture was stirred at 65° C. for 16 hours. After completion of the reaction, the reaction mixture was diluted with ethyl acetate (100 mL), washed with cold water (3×50 mL). Combined organic layer was dried over sodium sulphate and concentrated under reduced pressure to afford crude which was purified by column chromatography (60-120 silica gel) using 80-100% ethyl acetate in petroleum ether as eluent to afford 5-[2-[4-[[1-[4-[(2,6-dioxo-3-piperidyl)amino]-2-fluoro-phenyl]-4-piperidyl]methoxy]-1-piperidyl]pyrimidin-5-yl]-3-[3-[[ethyl(methyl)sulfamoyl]amino]-2,6-difluoro-benzoyl]-1-trityl-pyrrolo[2,3-b]pyridine (450 mg, 262.54 μmol, 31.88% yield) as a light blue solid. LCMS (ESI+): 1131.9 $[M+H]^+$ Step 8: To a stirred solution of 5-[2-[4-[[1-[4-[(2,6-dioxo-3-piperidyl)amino]-2-fluoro-phenyl]-4-piperidyl]methoxy]-1-piperidyl]pyrimidin-5-yl]-3-[3-[[ethyl(methyl)sulfamoyl] amino]-2,6-difluoro-benzoyl]-1-trityl-pyrrolo[2,3-b] pyridine (400 mg, 353.59 μmol) in dichloromethane (10 mL) were added 2,2,2-trifluoroacetic acid (3.70 g, 32.45 mmol, 2.5 mL) and triisopropylsilane, 98% (618.40 mg, 3.91 mmol, 0.8 mL) at 0° C. under nitrogen atmosphere. The reaction mixture was stirred at room temperature for 2 hours. After completion, the reaction mixture was concentrated under vacuum to afford crude product which was purified by 100 g C18-reverse phase column chromatography (0.1% formic acid in water/acetonitrile as eluents) to afford 5-[2-[4-[[1-[4-[(2,6-dioxo-3-piperidyl)amino]-2-fluoro-phenyl]-4-piperidyl]methoxy]-1-piperidyl]pyrimidin-5-yl]-3-[3-[[ethyl(methyl)sulfamoyl]amino]-2,6-difluoro-benzoyl]-1H-pyrrolo[2,3-b]pyridine (132.5 mg, 140.72 μmol, 39.80% yield, formic acid salt) as pale blue solid. LCMS (ESI+): 888.8 $[M+H]^+$. $^1H$ NMR (400 MHz, DMSO-$d_6$): δ 13.00 (s, 1H), 10.79 (s, 1H), 9.72 (s, 1H), 8.76 (s, 2H), 8.67 (d, J=2.00 Hz, 1H), 8.55 (s, 1H), 8.14 (d, J=3.20 Hz, 1H), 7.62-7.56 (m, 1H), 7.28 (t, J=9.20 Hz, 1H), 6.85-6.82 (m, 1H), 6.51 (d, J=14.80 Hz, 1H), 6.42 (d, J=7.20 Hz, 1H), 5.80 (s, 1H), 4.25-4.21 (m, 3H), 3.60-3.48 (m, 3H), 3.38 (d, J=6.40 Hz, 2H), 3.14-3.09 (m, 4H), 2.73 (s, 3H), 2.72-2.71 (m, 1H), 2.59-2.55 (m, 3H), 2.15-2.04 (m, 1H), 1.90-1.89 (m, 3H), 1.79-1.75 (m, 2H), 1.68-1.55 (m, 1H), 1.52-1.40 (m, 2H), 1.37-1.34 (m, 2H), 1.02 (t, J=7.20 Hz, 3H).

Example 183

5-[6-[4-[2-[1-[4-[(2,6-dioxo-3-piperidyl)amino]-3-fluoro-phenyl]-4-hydroxy-4-piperidyl]acetyl]piperazin-1-yl]-3-pyridyl]-3-[3-[[ethyl(methyl)sulfamoyl] amino]-2,6-difluoro-benzoyl]-1H-pyrrolo[2,3-b] pyridine

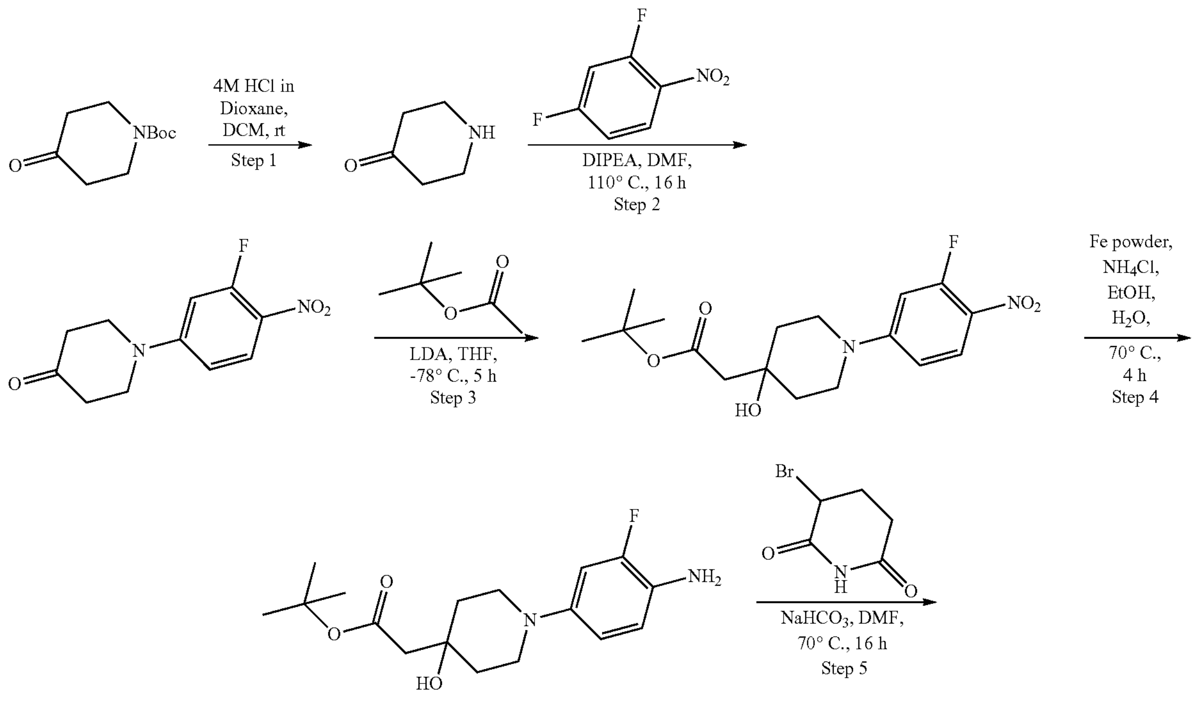

-continued

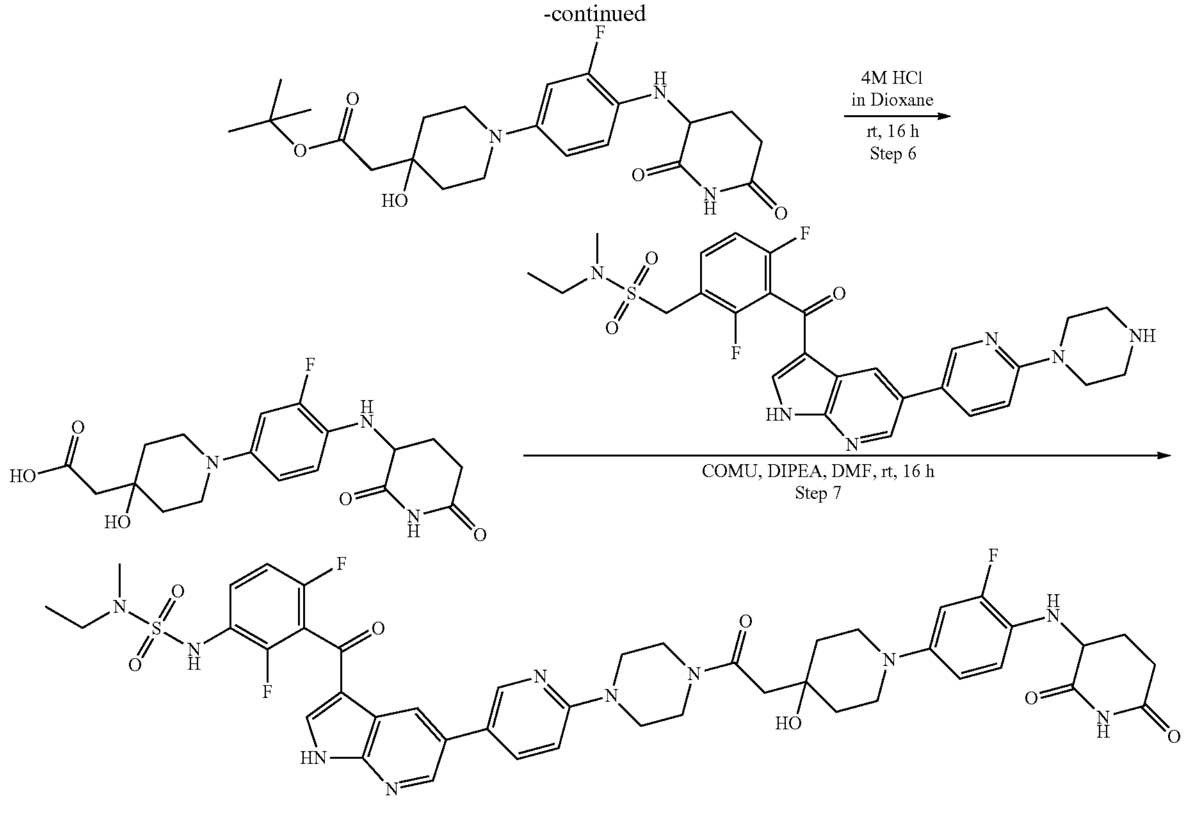

Step 1: To a solution of tert-butyl 4-oxopiperidine-1-carboxylate (19 g, 95.36 mmol) in anhydrous dichloromethane (50 mL), was added 4M hydrochloric acid in 1,4-dioxane (95.36 mmol, 80 mL) dropwise at 0° C. under nitrogen atmosphere. The reaction mixture was stirred at ambient temperature for 2 h. After completion, the reaction mixture was concentrated under reduced pressure to get crude. Crude compound was co-distilled with dichloromethane to afford piperidin-4-one (12.5 g, 91.27 mmol, 95.71% yield, hydrochloric acid salt) as off-white solid. $^1$H NMR (400 MHz, DMSO-$d_6$): δ 9.57 (s, 2H), 3.40-3.37 (m, 4H), 2.61-2.59 (m, 4H).

Step 2: To a stirred solution of piperidin-4-one (13 g, 131.14 mmol) in N,N-Dimethylformamide (80 mL) were added N,N-Diisopropylethylamine (67.80 g, 524.56 mmol, 91.37 mL) and 2,4-difluoro-1-nitro-benzene (20.86 g, 131.14 mmol, 14.39 mL) and the reaction mixture was stirred at 110° C. for 16 h. After completion, the reaction mixture was diluted with ethyl acetate (3×150 mL), washed with cold water (150 mL). The organic layer was washed with brine solution (150 mL), dried over sodium sulphate, filtered and concentrated under reduced pressure. Crude compound was purified by silica gel column chromatography eluted with 40% ethyl acetate in petroleum ether to afford 1-(3-fluoro-4-nitro-phenyl)piperidin-4-one (9 g, 36.65 mmol, 27.95% yield) as brown solid. LCMS (ESI+): 239.1 $[M+H]^+$.

Step 3: To a stirred solution of tert-butyl acetate (4.39 g, 37.8 mmol, 5.09 mL) in THF (150 mL), was added LDA (2M solution in THF) (75.6 mmol, 38 mL) during 20 minutes at −78° C. The reaction mixture was stirred at −78° C. for 1 h. 1-(3-fluoro-4-nitro-phenyl) piperidin-4-one (9.00 g, 37.8 mmol) in THF (50 mL) was added to the reaction mixture at −78° C. and stirred at the same temperature for 2 h. Then, the reaction mixture was slowly brought to −40° C. After completion, the reaction mixture was quenched with saturated $NH_4Cl$ solution (100 mL) and extracted with EtOAc (3×200 mL). The organic layer was washed with water (150 mL), brine (150 mL), dried over sodium sulphate, filtered and concentrated under reduced pressure. The crude compound which was purified by silica gel column chromatography eluted with 50% ethyl acetate in petroleum ether to afford tert-butyl 2-[1-(3-fluoro-4-nitro-phenyl)-4-hydroxy-4-piperidyl]acetate (10.5 g, 26.07 mmol, 69.01% yield) as brown solid. LCMS (ESI+): 355.1 $[M+H]^+$.

Step 4: To a stirred solution of tert-butyl 2-[1-(3-fluoro-4-nitro-phenyl)-4-hydroxy-4-piperidyl]acetate (11.91 g, 33.62 mmol) in water (40 mL) and ethanol (200 mL) was added Iron powder (9.39 g, 168.11 mmol, 1.19 mL) and Ammonium Chloride (5.40 g, 100.87 mmol, 3.53 mL). The reaction mixture was stirred at 70° C. for 4 h. After completion, the reaction mixture was filtered through celite and washed with ethyl acetate (200 mL). The filtrate was extracted with water (80 mL), $NaHCO_3$ solution (60 mL) and brine solution (60 mL). The organic layer was dried over sodium sulphate, filtered and concentrated under reduced pressure to get crude. Crude compound was purified by silica gel column chromatography eluted with 70% ethyl acetate in petroleum ether to afford tert-butyl 2-[1-(4-amino-3-fluoro-phenyl)-4-hydroxy-4-piperidyl]acetate (8.5 g, 24.63 mmol, 73.26% yield) as brown solid. LCMS (ESI+): 325.2 $[M+H]^+$.

Step 5: A solution of tert-butyl 2-[1-(4-amino-3-fluoro-phenyl)-4-hydroxy-4-piperidyl] acetate (4.00 g, 12.33 mmol) in N, N-Dimethylformamide (40 mL) was taken in a sealed tube and added sodium bicarbonate (3.63 g, 43.16 mmol, 1.68 mL) and 3-bromopiperdine-2,6-dione (5.92 g, 30.83 mmol). The reaction mixture was stirred at 70° C. for 16 h. After completion, the reaction mixture was diluted with water (70 mL) and extracted with ethyl acetate (3×100 mL). The combined organic layers were washed with brine solution (100 mL), dried over sodium sulphate, filtered and concentrated under reduced pressure to get crude. Crude compound was purified by silica gel column chromatography eluted with 70% ethyl acetate in petroleum ether to afford tert-butyl 2-[1-[4-[(2,6-dioxo-3-piperidyl)amino]-3-fluoro-phenyl]-4-hydroxy-4-piperidyl]acetate (4 g, 7.72 mmol, 62.57% yield) as a green solid. LCMS (ESI+): 436.1 $[M+H]^+$.

Step 6: To the stirred solution of tert-butyl 2-[1-[4-[(2,6-dioxo-3-piperidyl)amino]-3-fluoro-phenyl]-4-hydroxy-4-piperidyl]acetate (7.50 g, 17.22 mmol) in Dichloromethane (70 mL), was added 4M hydrochloric acid in 1,4-dioxane (17.22 mmol, 70 mL) at 5° C. under inert atmosphere and stirred at room temperature for 16 h. After completion, the reaction mixture was concentrated under reduced pressure and washed with diethyl ether (2×50 mL) and dried under high vacuum to get desired 2-[1-[4-[(2,6-dioxo-3-piperidyl)amino]-3-fluoro-phenyl]-4-hydroxy-4-piperidyl]acetic acid (8 g, 16.16 mmol, 93.83% yield) as off white solid. LCMS (ESI+): 380.0 $[M+H]^+$. $^1$H NMR (400 MHz, DMSO-$d_6$): δ 12.10 (bs, 1H), 10.85 (s, 1H), 7.64 (d, J=18.00 Hz, 1H), 7.42 (d, J=10.40 Hz, 1H), 6.94 (t, J=12.40 Hz, 1H), 6.10 (s, 1H), 4.45-4.55 (m, 1H), 3.41-3.50 (m, 4H), 2.70-2.89 (m, 2H), 2.30-2.49 (m, 4H), 2.10-2.17 (m, 2H), 1.90-1.95 (m, 2H).

Step 7: Target compound was prepared via COMU mediated acid-amine coupling reaction (procedure B). Amide coupling was carried out using 2-[1-[4-[(2,6-dioxo-3-piperidyl)amino]-3-fluoro-phenyl]-4-hydroxy-4-piperidyl]acetic acid (1.60 g, 4.22 mmol), N-ethyl-N-isopropyl-propan-2-amine (2.73 g, 21.11 mmol, 3.68 mL), COMU (1.99 g, 4.64 mmol) and 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (2.5 g, 4.22 mmol). The desired product was purified from crude by reverse phase column chromatography (10 mM ammonium acetate in water:Acetonitrile) and fractions were lyophilized to afford 5-[6-[4-[2-[1-[4-[(2,6-dioxo-3-piperidyl)amino]-3-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine (0.75 g, 756.24 μmol, 17.91% yield) as off white solid. LCMS (ESI−): 915.3 $[M-H]^-$. $^1$H NMR (400 MHz, DMSO-$d_6$): δ 12.97 (d, J=2.40 Hz, 1H), 10.82 (s, 1H), 9.73 (s, 1H), 8.68 (d, J=2.00 Hz, 1H), 8.53 (s, 2H), 8.13 (d, J=2.00 Hz, 1H), 7.98 (dd, J=2.40, 9.00 Hz, 1H), 7.55-7.62 (m, 1H), 7.28 (t, J=8.40 Hz, 1H), 7.02 (d, J=8.80 Hz, 1H), 6.62-6.78 (m, 2H), 6.59-6.62 (m, 1H), 5.04 (d, J=6.00 Hz, 1H), 4.89 (s, 1H), 4.20-4.30 (m, 1H), 3.60-3.69 (m, 8H), 3.19 (d, J=12.00 Hz, 2H), 3.11 (q, J=7.20 Hz, 2H), 2.93-2.98 (m, 2H), 2.70-2.78 (m, 1H), 2.73 (s, 3H), 2.58 (s, 2H), 2.56-2.51 (m, 1H), 2.08-2.12 (m, 1H), 1.94-2.00 (m, 1H), 1.66-1.76 (m, 4H), 1.02 (t, J=7.20 Hz, 3H).

Example 184

5-[4-[4-[2-[1-[4-[(2,6-dioxo-3-piperidyl)amino]-3-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine

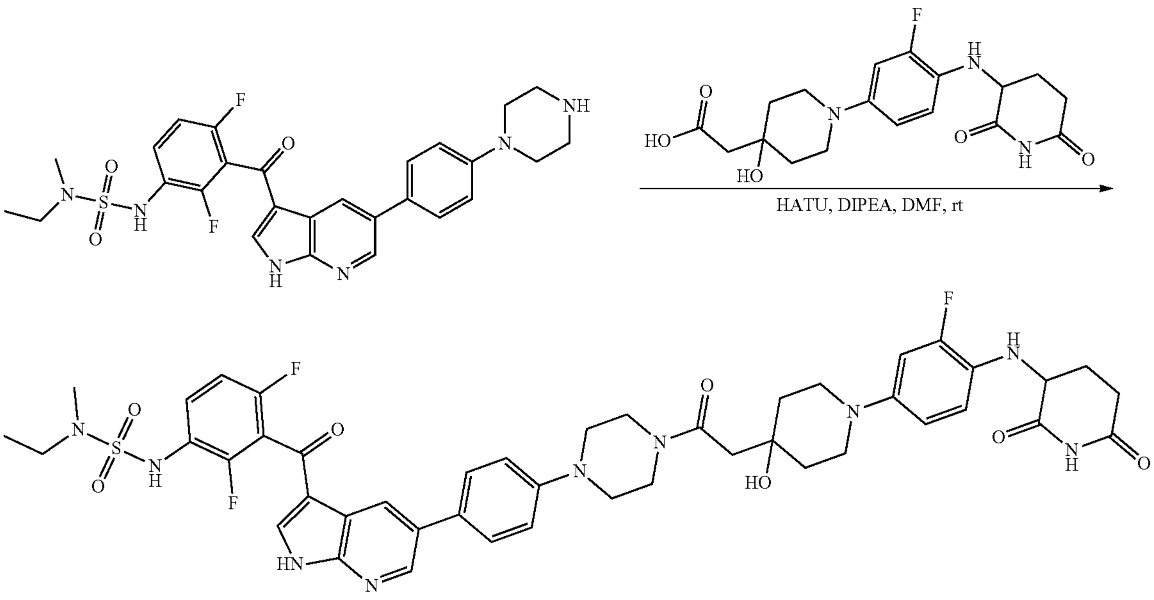

Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(4-piperazin-1-ylphenyl)-1H-pyrrolo[2,3-b]pyridine (600 mg, 1.02 mmol), 2-[1-[4-[(2,6-dioxo-3-piperidyl)amino]-3-fluoro-phenyl]-4-hydroxy-4-piperidyl]acetic acid (464.34 mg, 1.12 mmol), N,N-Diisopropylethylamine (524.77 mg, 4.06 mmol, 707.24 μL) and HATU (385.97 mg, 1.02 mmol) to afford 5-[4-[4-[2-[1-[4-[(2,6-dioxo-3-piperidyl)amino]-3-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine (160 mg, 159.83 μmol, 15.75% yield) as gray solid. LCMS (ESI+): 915.9 $[M+H]^+$. $^1$H NMR (400 MHz, DMSO-$d_6$): δ 12.94-12.93 (d, J=3.2 Hz, 1H), 10.81 (s, 1H), 9.72 (s, 1H), 8.67 (d, J=2.40 Hz, 1H), 8.55 (s, 1H), 8.11 (d, J=2.80 Hz, 1H), 7.56-7.65 (m, 3H), 7.29 (dd, J=8.00, 13.00 Hz, 1H), 7.12 (d, J=8.80 Hz, 2H), 6.74 (t, J=8.80 Hz, 2H), 6.61 (d, J=8.80 Hz, 1H), 5.04 (d, J=6.40 Hz, 1H), 4.88 (s, 1H), 4.21-4.31 (m, 1H), 3.69-3.73 (m, 4H), 3.18-3.27 (m, 5H), 3.11 (q, J=7.20 Hz, 2H), 2.93-2.98 (m, 2H), 2.63-2.76 (m, 1H), 2.74 (s, 3H), 2.58 (s, 2H), 2.51-2.56 (m, 2H), 2.06-2.12 (m, 1H), 1.91-2.01 (m, 1H), 1.65-1.74 (m, 4H), 1.02 (t, J=7.20 Hz, 3H).
Example 185
3-[6-chloro-3-[[ethyl(methyl)sulfamoyl]amino]-2-fluoro-benzoyl]-5-[2-[4-[2-[1-[4-[(2,6-dioxo-3-piperidyl)amino]-2-fluoro-phenyl]-4-hydroxy-4-piperidyl]acetyl]piperazin-1-yl]pyrimidin-5-yl]-1H-pyrrolo[2,3-b]pyridine
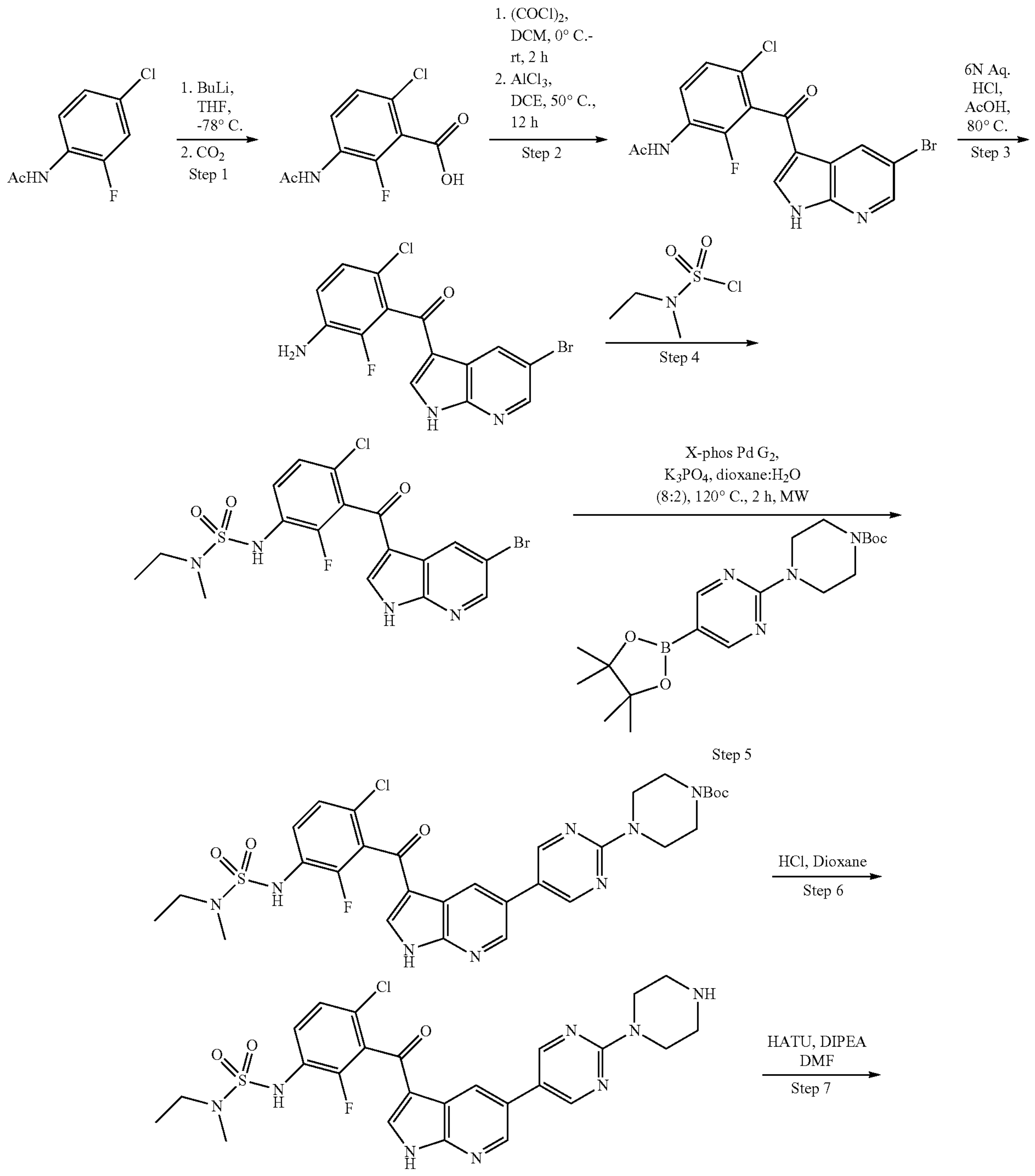

-continued

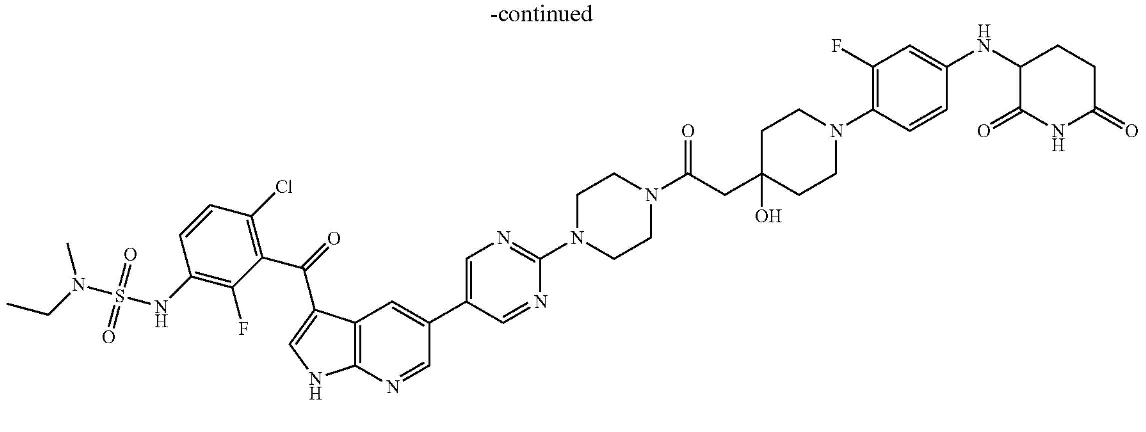

Step 1: To a well stirred solution of N-(4-chloro-2-fluoro-phenyl)acetamide (10.0 g, 53.31 mmol) in THF (300.0 mL) was added n-butyllithium 2.8M in hexane (106.62 mmol, 38.0 mL) dropwise at −78° C. The reaction mixture was maintained at same temperature for 3 hours and then was added crushed dry ice to the reaction mixture under nitrogen atmosphere. After stirring at −78° C. for 2 hours, 1.5N aq. HCl was slowly added to the reaction. The reaction mixture was warmed to room temperature and extracted with ethyl acetate (2×300 mL). The combined organic layers are washed with water and brine, dried over sodium sulphate. The solvent was evaporated under reduced pressure and the residue was stirred in 15% ethyl acetate/petroleum ether for 1 hour. The solid was filtered to yield 3-acetamido-6-chloro-2-fluoro-benzoic acid (8.0 g, 29.39 mmol, 55.14% yield) as pale brown solid. LCMS (ESI+): 232.0 $[M+H]^+$.

Step 2: To a stirred solution of 3-acetamido-6-chloro-2-fluoro-benzoic acid (3.0 g, 12.95 mmol) in dichloromethane (80.0 mL) was added oxalyl chloride (2.47 g, 19.43 mmol, 1.69 mL) dropwise at 0° C. followed by two drops of DMF. The reaction mixture was maintained at room temperature for 3 h. The volatiles were removed under reduced pressure. In another flask was taken 5-bromo-1H-pyrrolo[2,3-b]pyridine (2.04 g, 10.36 mmol) in 1,2-dichloroethane (30.0 mL) and was added aluminium chloride, anhydrous (6.91 g, 51.81 mmol, 2.83 mL) at 0° C. The resulting reaction mixture was warmed to room temperature and stirred for 1 hour. Then, the acid chloride prepared was dissolved in 1,2-dichloroethane (30.0 mL) and was added dropwise to this reaction mixture at 0° C. The resulting reaction mixture warmed to 50° C. and stirred for 16 hours. The reaction was quenched with saturated aqueous sodium sulphate solution and reaction was filtered through celite, washing with ethyl acetate. The filtrate was evaporated under reduced pressure to get crude product which was purified by silica gel column chromatography using 70-80% ethyl acetate/petroleum ether to afford N-[3-(5-bromo-1H-pyrrolo[2,3-b]pyridine-3-carbonyl)-4-chloro-2-fluoro-phenyl]acetamide (1.2 g, 2.53 mmol, 19.52% yield) as brown solid. LCMS (ESI+): 410.9 $[M+2H]^+$.

Step 3: To a well stirred solution of N-[3-(5-bromo-1H-pyrrolo[2,3-b]pyridine-3-carbonyl)-4-chloro-2-fluoro-phenyl]acetamide (1.2 g, 2.92 mmol) in acetic acid (12.0 mL) was added 6N aq. hydrochloric acid (2.92 mmol, 50.0 mL). The resulting reaction mixture was maintained at 120° C. for 16 hours. The volatiles were evaporated completely under reduced pressure. The crude was product obtained was dissolved in ethyl acetate and washed with saturated $NaHCO_3$ solution. The organic layer was evaporated under reduced pressure to get crude product which was purified by silica gel column chromatography using 70-80% ethyl acetate/petroleum ether to get pure (3-amino-6-chloro-2-fluoro-phenyl)-(5-bromo-1H-pyrrolo[2,3-b]pyridin-3-yl) methanone (0.8 g, 2.08 mmol, 71.26% yield) as a brown solid. LCMS (ESI+): 370.0 $[M+2H]^+$.

Step 4: To a well stirred solution of (3-amino-6-chloro-2-fluoro-phenyl)-(5-bromo-1H-pyrrolo[2,3-b]pyridin-3-yl) methanone (0.8 g, 2.17 mmol) in 1,4-dioxane (10.0 mL) were added pyridine (1.37 g, 17.36 mmol, 1.40 mL) and N-ethyl-N-methyl-sulfamoyl chloride (2.05 g, 13.02 mmol, 1.60 mL). The resulting reaction mixture was stirred at 100° C. for 16 hours. The reaction was cooled to room temperature and diluted with ethyl acetate (75 ml), washed with water (20 ml) and 1.5 N hydrochloric acid aq. (20 ml). The organic layer was dried over sodium sulphate, filtered and evaporated under reduced pressure to get crude product which was purified by silica gel column chromatography using 60-70% ethyl acetate/petroleum ether to yield 5-bromo-3-[6-chloro-3-[[ethyl(methyl)sulfamoyl]amino]-2-fluoro-benzoyl]-1H-pyrrolo[2,3-b]pyridine (0.6 g, 1.02 mmol, 47.19% yield) as off white solid. LCMS (ESI+): 491.0 $[M+H]^+$.

Step 5: A solution of 5-bromo-3-[6-chloro-3-[[ethyl(methyl)sulfamoyl]amino]-2-fluoro-benzoyl]-1H-pyrrolo[2,3-b]pyridine (0.6 g, 1.23 mmol) in 1,4-dioxane (8.0 mL) and water (1.5 mL) was degassed with $N_2$ for 15 minutes. Then tert-butyl 4-[5-(4,4,5,5-tetramethyl-1,3,2-dioxaborolan-2-yl)pyrimidin-2-yl]piperazine-1-carboxylate (573.78 mg, 1.47 mmol), potassium phosphate tribasic anhydrous (780.16 mg, 3.68 mmol) and XPhos Pd G2 (96.40 mg, 122.51 μmol) were added. The resulting reaction mixture was stirred at 120° C. for 2 hours under microwave irradiation. The reaction was then diluted with ethyl acetate, washed with water and brine solutions. The organic layer was dried over sodium sulphate, filtered and evaporated under reduced pressure. The crude product was purified by silica gel column chromatography using 80-90% ethyl acetate/petroleum ether to get yield tert-butyl 4-[5-[3-[6-chloro-3-[[ethyl(methyl)sulfamoyl]amino]-2-fluoro-benzoyl]-1H-pyrrolo[2,3-b]pyridin-5-yl]pyrimidin-2-yl]piperazine-1-carboxylate (0.4 g, 524.16 μmol, 42.61% yield) as off white solid. LCMS (ESI+): 672.9 $[M+H]^+$ Step 6: To a well stirred solution of tert-butyl 4-[5-[3-[6-chloro-3-[[ethyl(methyl)sulfamoyl]amino]-2-fluoro-benzoyl]-1H-pyrrolo[2,3-b]pyridin-5-yl]pyrimidin-2-yl]piperazine-1-carboxylate (0.4 g, 594.22 μmol) in dichloromethane (10 mL) was added hydrogen chloride solution 4.0M in 1,4-dioxane (216.66 mg, 5.94 mmol, 270.82 μL). The resulting reaction mixture was maintained at room temperature for 3 hours. The volatiles were removed under reduced pressure to yield 3-[6-chloro-3-[[ethyl(methyl)sulfamoyl]amino]-2-fluoro-benzoyl]-5-(2-piperazin-1-ylpyrimidin-5-yl)-1H-pyrrolo[2,3-b]pyridine as off white solid. LCMS (ESI+): 572.9 $[M+H]^+$ Step 7: Target compound was prepared via HATU mediated acid-amine coupling reaction (procedure A) using 2-[1-[4-[(2,6-dioxo-3-piperidyl)amino]-2-fluoro-phenyl]-4-hydroxy-4-piperidyl]acetic acid (252.44 mg, 607.05 μmol, hydrochloric acid salt), HATU (346.23 mg, 910.58 μmol), DIPEA (392.28 mg, 3.04 mmol, 528.68 μL) and 3-[6-chloro-3-[[ethyl(methyl)sulfamoyl]amino]-2-fluoro-benzoyl]-5-(2-piperazin-1-ylpyrimidin-5-yl)-1H-pyrrolo[2,3-b]pyridine (370 mg, 607.05 μmol, hydrochloric acid salt) in DMF (6.0 mL). The crude was purified by reverse phase column chromatography using [Mobile-phase A: 0.1% ammonium acetate in water, Mobile-phase B: ACN; column: 100 g Redisep Rf C18] to afford 3-[6-chloro-3-[[ethyl(methyl)sulfamoyl]amino]-2-fluoro-benzoyl]-5-[2-[4-[2-[1-[4-[(2,6-dioxo-3-piperidyl)amino]-2-fluoro-phenyl]-4-hydroxy-4-piperidyl]acetyl]piperazin-1-yl]pyrimidin-5-yl]-1H-pyrrolo[2,3-b]pyridine (78.21 mg, 82.99 μmol, 13.67% yield) as off white solid. LCMS (ESI+): 933.8 $[M+H]^+$. $^1H$ NMR (400 MHz, DMSO-$d_6$): δ 12.95 (s, 1H), 10.79 (s, 1H), 9.93 (s, 1H), 8.80 (s, 2H), 8.68 (d, J=2.00 Hz, 1H), 8.67-8.66 (bs, 1H), 8.10 (s, 1H), 7.56 (t, J=8.80 Hz, 1H), 7.45 (d, J=8.40 Hz, 1H), 6.87 (t, J=9.60 Hz, 1H), 6.51 (dd, J=2.40, 14.80 Hz, 1H), 6.42 (dd, J=2.40, 8.80 Hz, 1H), 5.78 (d, J=8.00 Hz, 1H), 4.87 (s, 1H), 4.26 (m, 1H), 3.87-3.85 (m, 4H), 3.68-3.66 (m, 4H), 3.14-3.11 (m, 2H), 2.92-2.85 (m, 4H), 2.73-2.71 (m, 4H), 2.60-2.58 (m, 3H), 2.08 (m, 1H), 1.92-1.70 (m, 5H), 1.03 (t, J=6.80 Hz, 3H).

Example 186

5-[5-cyano-6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine

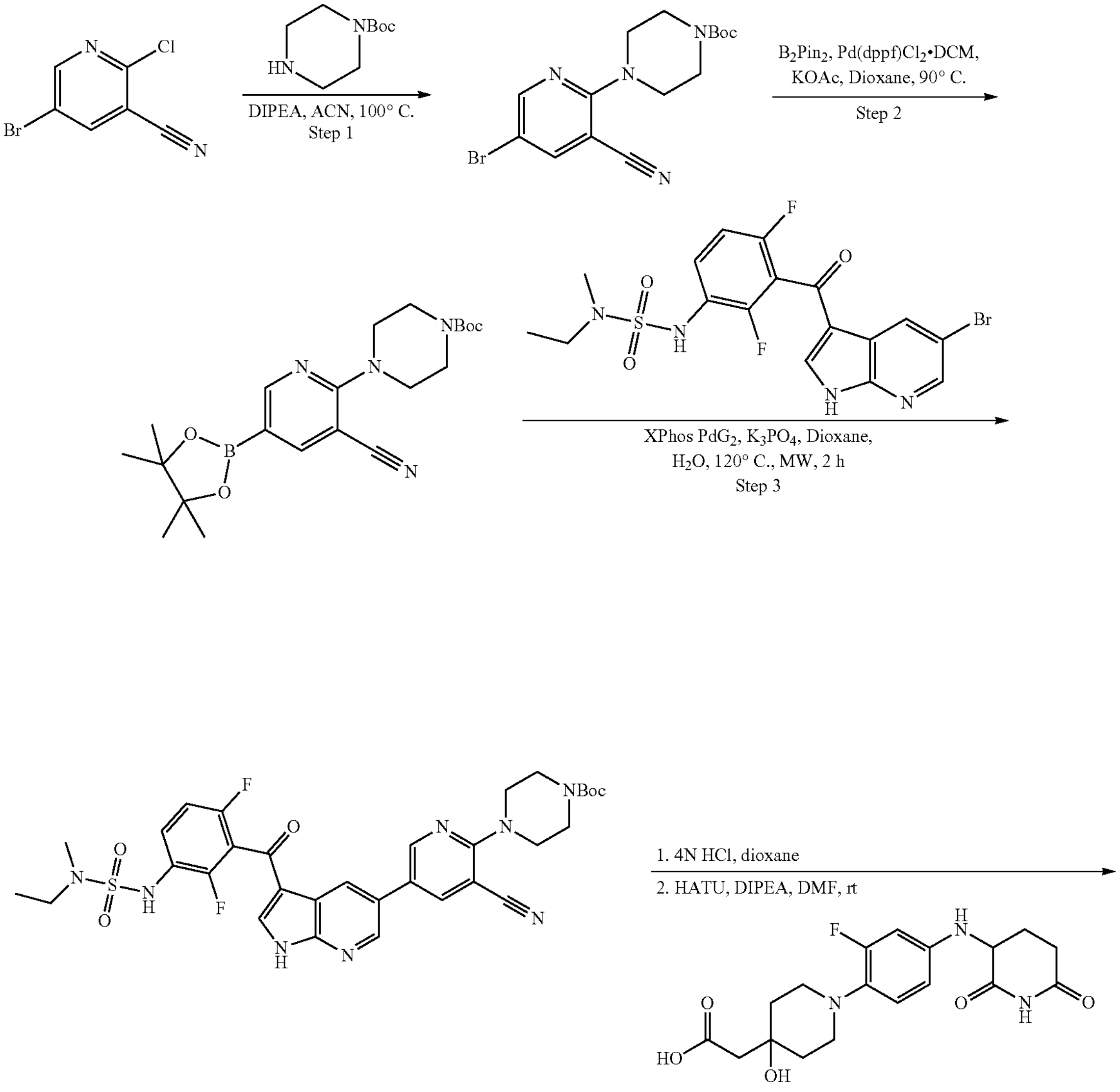

7

Step 4/5

-continued

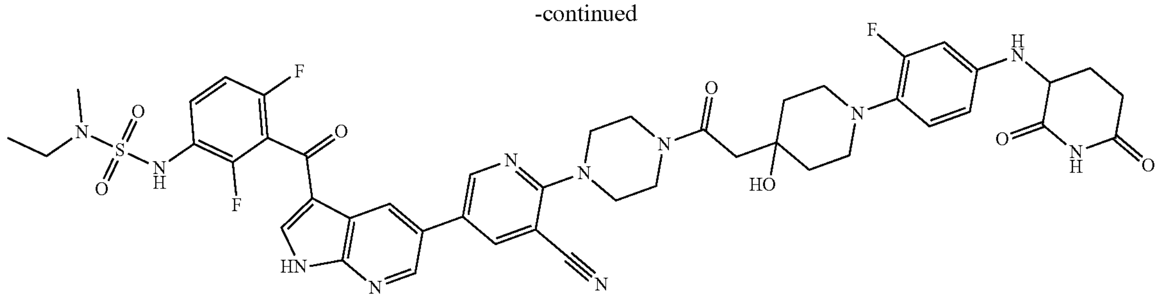

Step 1: To a stirred solution of 5-bromo-2-chloro-pyridine-3-carbonitrile (2 g, 9.20 mmol), tert-butyl piperazine-1-carboxylate (1.71 g, 9.20 mmol) in Acetonitrile (20 mL) was taken in a sealed tube and added N,N-Diisopropylethylamine (3.57 g, 27.59 mmol, 4.81 mL) at room temperature. The reaction mixture was heated to 100° C. for 12 h. After completion, the reaction mixture was diluted with water (10 mL) and extracted with ethyl acetate (2×30 mL). The combined organic layers were dried over sodium sulphate, filtered and concentrated under vacuum to get crude. The crude compound was purified by silica gel column chromatography, using 20-25% ethyl acetate in pet-ether to get tert-butyl 4-(5-bromo-3-cyano-2-pyridyl)piperazine-1-carboxylate (3 g, 8.09 mmol, 87.93% yield) as colorless solid. LCMS (ESI+): 267.1 $[M+H-100]^+$ Step 2: A solution of tert-butyl 4-(5-bromo-3-cyano-2-pyridyl)piperazine-1-carboxylate (2 g, 5.45 mmol), 4,4,5,5-tetramethyl-2-(4,4,5,5-tetramethyl-1,3,2-dioxaborolan-2-yl)-1,3,2-dioxaborolane (2.07 g, 8.17 mmol) in 1,4-dioxane (10 mL) was taken in a sealed tube and added Potassium Acetate (1.60 g, 16.34 mmol, 1.02 mL) at room temperature. The reaction mixture was degassed with nitrogen for 20 minutes and added Pd(dppf)$Cl_2$·Dichloromethane (444.74 mg, 544.60 μmol). The reaction mixture was heated to 100° C. for 12 h. The reaction mixture was diluted with water (30 mL) and extracted with ethyl acetate (2×50 mL). The combined organic layers were dried over sodium sulphate, filtered and concentrated under vacuum to get crude tert-butyl 4-[3-cy ano-5-(4,4,5,5-tetramethyl-1,3,2-dioxaborolan-2-yl)-2-pyridyl]piperazine-1-carboxylate (2.5 g, 5.25 mmol, 96.40% yield) as brown solid. LCMS (ESI+): 233.1 $[M+H-100]^+$ Step 3: A mixture of 5-bromo-3-[3-[[ethyl(methyl)sulfamoyl]amino]-2,6-difluoro-benzoyl]-1H-pyrrolo[2,3-b]pyridine (600 mg, 1.27 mmol) and tert-butyl 4-[3-cyano-5-(4,4,5,5-tetramethyl-1,3,2-dioxaborolan-2-yl)-2-pyridyl]piperazine-1-carboxylate (630.27 mg, 1.52 mmol) in 1,4-dioxane (8 mL), Water (2 mL) was taken in a microwave vial and added Potassium phosphate tribasic anhydrous (807.28 mg, 3.80 mmol) at room temperature. The reaction mixture was degassed for 20 minutes and added Xphos Pd G2 (99.74 mg, 126.77 μmol). The reaction mixture was irradiated under microwave to 120° C. for 2 h. The reaction mixture was diluted with water (10 mL) and extracted with ethyl acetate (2×30 mL). The combined organic layers were dried over sodium sulphate, filtered and concentrated under vacuum to get crude. The crude compound was purified by silica gel column chromatography using 70-100% ethyl acetate in pet-ether to get tert-butyl 4-[3-cyano-5-[3-[3-[[ethyl(methyl)sulfamoyl]amino]-2,6-difluoro-benzoyl]-1H-pyrrolo[2,3]pyridin-5-yl]-2-pyridyl]piperazine-1-carboxylate (400 mg, 517.10 μmol, 40.79% yield) as brown solid. LCMS (ESI+): 681.2 $[M+H]^+$.

Step 4: To a stirred solution of tert-butyl 4-[3-cyano-5-[3-[3-[[ethyl(methyl)sulfamoyl]amino]-2,6-difluoro-benzoyl]-1H-pyrrolo[2,3-b]pyridin-5-yl]-2-pyridyl]piperazine-1-carboxylate (380 mg, 558.23 μmol) in 1,4-dioxane (5 mL) was added Hydrogen chloride solution in 1,4-dioxane (4 M, 139.56 μL). The reaction mixture was stirred at room temperature for 2 h. After completion, the reaction mixture was concentrated under vacuum to get crude 5-(5-cyano-6-piperazin-1-yl-3-pyridyl)-3-[3-[[ethyl(methyl)sulfamoyl]amino]-2,6-difluoro-benzoyl]-1H-pyrrolo[2,3-b]pyridine (400 mg, 557.47 μmol, 99.86% yield) as brown solid. LCMS (ESI+): 580.9 $[M+H]^+$ Step 5: target compound was prepared via HATU mediated acid-amine coupling reaction (procedure A). Amide coupling was carried out using 5-(5-cyano-6-piperazin-1-yl-3-pyridyl)-3-[3-[[ethyl(methyl)sulfamoyl]amino]-2,6-difluoro-benzoyl]-1H-pyrrolo[2,3-b]pyridine (400 mg, 688.93 μmol), 2-[1-[4-[(2,6-dioxo-3-piperidyl)amino]-2-fluoro-phenyl]-4-hydroxy-4-piperidyl]acetic acid (261.37 mg, 688.93 μmol), N,N-Diisopropylethylamine (267.12 mg, 2.07 mmol, 360.00 μL), HATU (392.93 mg, 1.03 mmol) to yield 5-[5-cyano-6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine (93.41 mg, 95.36 μmol, 13.84% yield) as off white solid. LCMS (ESI+): 942.2 $[M+H]^+$. $^1H$ NMR (400 MHz, DMSO-$d_6$): δ 13.03 (s, 1H), 10.79 (s, 1H), 9.72 (s, 1H), 8.84 (d, J=2.40 Hz, 1H), 8.74 (d, J=2.40 Hz, 1H), 8.69 (s, 1H), 8.59 (d, J=2.40 Hz, 1H), 8.16 (s, 1H), 7.56-7.62 (m, 1H), 7.28 (t, J=8.00 Hz, 1H), 6.86 (t, J=9.60 Hz, 1H), 6.51 (dd, J=2.00, 15.00 Hz, 1H), 6.42 (dd, J=2.40, 8.60 Hz, 1H), 5.79 (d, J=7.60 Hz, 1H), 4.84 (s, 1H), 4.24-4.26 (m, 1H), 3.71-3.78 (m, 8H), 3.12 (q, J=7.20 Hz, 2H), 2.85-2.95 (m, 4H), 2.65-2.75 (m, 1H), 2.74 (s, 3H), 2.59 (s, 2H), 2.50-2.56 (m, 1H), 2.00-2.13 (m, 1H), 1.67-1.87 (m, 5H), 1.03 (t, J=7.20 Hz, 3H).

Example 187
5-[5-[4-[2-[1-[4-[(2,6-dioxo-3-piperidyl)amino]-2-fluoro-phenyl]-4-hydroxy-4-piperidyl]acetyl]piperazin-1-yl]pyrazin-2-yl]-3-[3-[[ethyl(methyl)sulfamoyl]amino]-2,6-difluoro-benzoyl]-1H-pyrrolo[2,3-b]pyridine
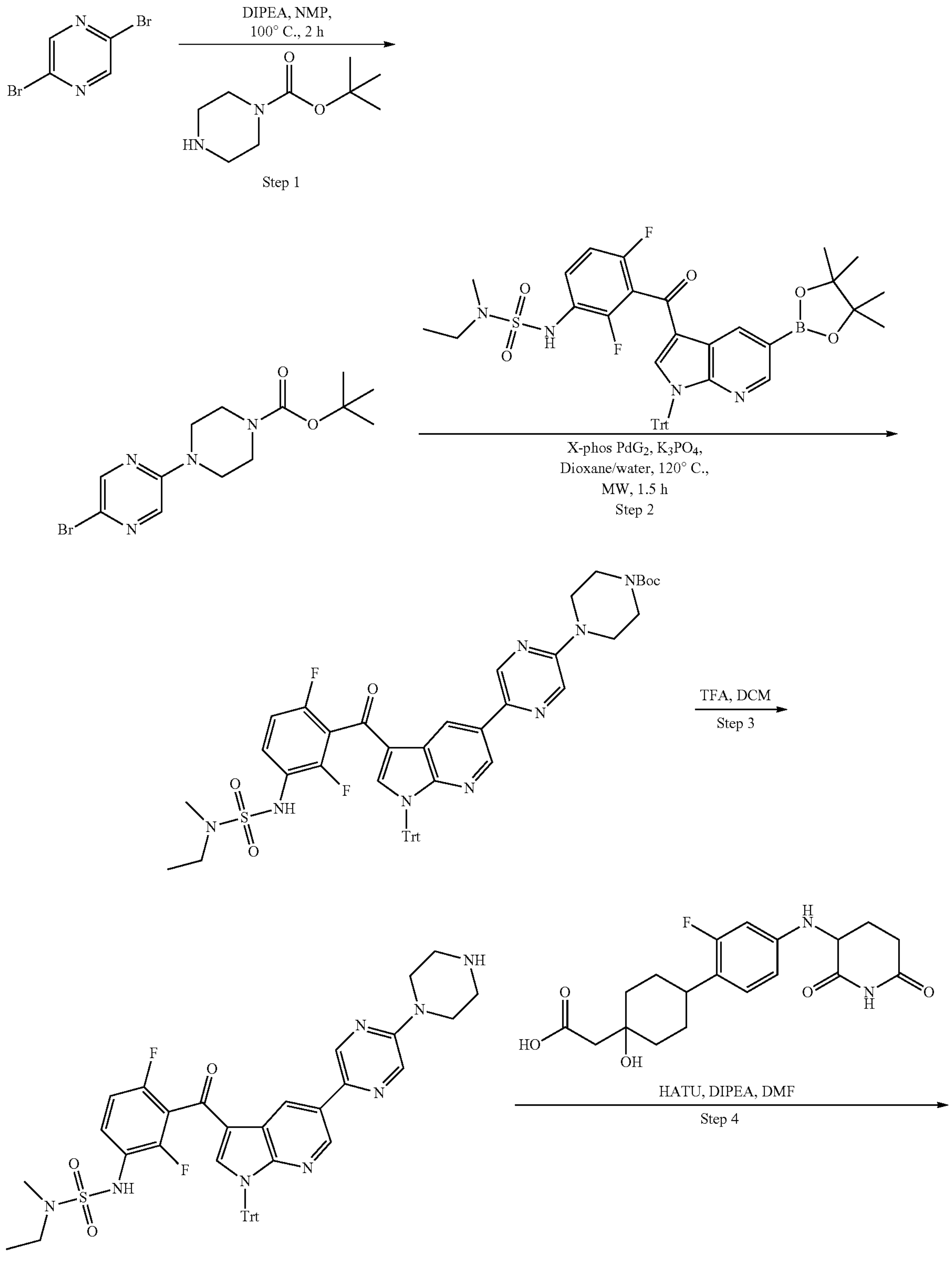

-continued

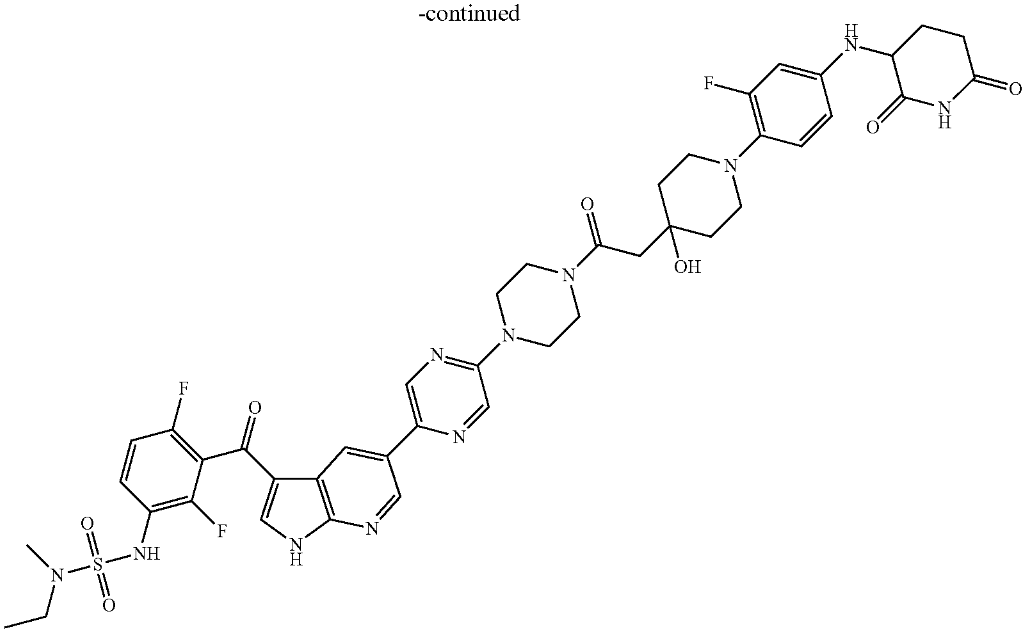

Step 1: To a stirred solution of 2,5-dibromopyrazine (10 g, 42.04 mmol) and tert-butylpiperazine-1-carboxylate (7.83 g, 42.04 mmol) in NMP (30 mL) was added DIPEA (5.43 g, 42.04 mmol, 7.32 mL). The reaction mixture was stirred for 2 hr at 120° C. After completion, reaction was cooled to room temperature and was diluted with water (400 mL). The compound extracted using ethyl acetate (2×300 mL). The combined organic layers were dried over anhydrous sodium sulphate, filtered and concentrated under reduced pressure to yield crude product which was purified by column chromatography on silica gel using 0-10% ethyl acetate/petroleum ether as eluent to afford tert-butyl 4-(5-bromopyrazin-2-yl) piperazine-1-carboxylate (11 g, 29.17 mmol, 69.38% yield) as yellow solid. LCMS (ESI+): 245 $[M-100+H]^+$ Step 2: A microwave vial was charged with tert-butyl 4-(5-bromopyrazin-2-yl)piperazine-1-carboxylate (905.20 mg, 2.64 mmol) and 3-[3-[[ethyl(methyl)sulfamoyl]amino]-2,6-difluoro-benzoyl]-5-(4,4,5,5-tetramethyl-1,3,2-dioxaborolan-2-yl)-1-trityl-pyrrolo[2,3-b]pyridine (2.01 g, 2.64 mmol) in water (4 mL) and 1,4-dioxane (10 mL). The solution was purged with $N_2$ gas for 5 min, followed by addition of potassium phosphate tribasic anhydrous (1.68 g, 7.91 mmol). After purging $N_2$ for another 5 min, XPhos Pd G2 (207.51 mg, 263.74 μmol) was added to the reaction mixture and the reaction mixture was heated at 120° C. in a MW apparatus for 90 min. The reaction was cooled to room temperature and diluted with water (100 mL) and compound was extracted using ethyl acetate (2×100 mL). The combined organic layers were dried over anhydrous sodium sulphate, filtered and concentrated under reduced pressure to yield crude product which was purified by column chromatography on silicagel using 0-40% ethyl acetate/petroleum ether as eluent system to yield tert-butyl 4-[5-[3-[3-[[ethyl (methyl)sulfamoyl]amino]-2,6-difluoro-benzoyl]-1-trityl-pyrrolo[2,3-b]pyridin-5-yl]pyrazin-2-yl]piperazine-1-carboxylate (1.3 g, 1.20 mmol, 45.51% yield) as yellow solid. LCMS (ESI+): 899.2 $[M+H]^+$ Step 3: To a stirred solution of tert-butyl 4-[5-[3-[3-[[ethyl (methyl)sulfamoyl]amino]-2,6-difluoro-benzoyl]-1-trityl-pyrrolo[2,3-b]pyridin-5-yl]pyrazin-2-yl]piperazine-1-carboxylate (650 mg, 723.01 μmol) in dichloromethane (6 mL) was added trifluoroacetic acid (2.17 mmol, 167.11 μL) at 0° C. The reaction was stirred at 25° C. for 2 hrs. After completion, the reaction was concentrated under reduced pressure to yield crude product. The solid obtained was washed with diethyl ether (40 mL) and to yield 3-[3-[[ethyl (methyl)sulfamoyl]amino]-2,6-difluoro-benzoyl]-5-(5-piperazin-1-ylpyrazin-2-yl)-1H-pyrrolo[2,3-b]pyridine (550 mg, 652.84 μmol, 90.29% yield, trifluoroacetic acid salt) as light yellow solid. LCMS (ESI+): 557.2 $[M+H]^+$.

Step 4: Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(5-piperazin-1-ylpyrazin-2-yl)-1H-pyrrolo[2,3-b]pyridine (300 mg, 539.00 μmol), 2-[1-[4-[(2,6-dioxo-3-piperidyl)amino]-2-fluoro-phenyl]-4-hydroxy-4-piperidyl]acetic acid (204.49 mg, 539.00 HATU (245.93 mg, 646.80 μmol), DIPEA (208.98 mg, 1.62 mmol, 281.65 μL) in DMF (4 mL). The crude product was purified by reverse phase chromatography using 0.1% HCOOH in water/acetonitrile as eluent to yield 4-[5-[3-[3-[1-[4-[(2,6-dioxo-3-piperidyl)amino]-2-fluoro-phenyl]-4-hydroxy-4-piperidyl]acetyl]piperazin-1-yl]pyrazin-2-yl]-3-[3-[[ethyl(methyl)sulfamoyl]amino]-2,6-difluoro-benzoyl]-1H-pyrrolo[2,3-b]pyridine (110 mg, 111.79 μmol, 20.74% yield, formic acid salt) as light brown solid. LCMS (ESI−): 916.2 $[M-H]^-$. $^1H$ NMR (400 MHz, DMSO-d6): δ 13.00 (s, 1H), 10.79 (s, 1H), 9.73 (s, 1H), 9.03 (d, J=2.00 Hz, 1H), 9.00 (s, 1H), 8.84 (s, 1H), 8.51 (s, 1H), 8.14 (m, 1H), 7.60 (t, J=2.80 Hz, 1H), 7.27 (t, J=6.00 Hz, 1H), 6.86 (m, 1H), 6.52-6.43 (m, 2H), 5.79-5.77 (d, J=8.40 Hz, 1H) 4.86 (s, 1H), 4.25-4.22 (m, 1H), 3.73-3.68 (m, 8H), 3.12 (q, J=7.20 Hz, 2H), 2.92-2.85 (m, 4H), 2.75 (m, 4H), 2.62-2.60 (m, 3H), 2.10 (m, 1H), 1.86-1.81 (m, 5H), 1.02 (t, J=7.20 Hz, 3H).

Example 188
5-[6-[4-[2-[1-[4-[(2,6-dioxo-3-piperidyl)amino]-2-fluoro-phenyl]-4-hydroxy-4-piperidyl]acetyl]piperazin-1-yl]-5-fluoro-3-pyridyl]-3-[3-[[ethyl(methyl)sulfamoyl]amino]-2,6-difluoro-benzoyl]-1H-pyrrolo[2,3-b]pyridine
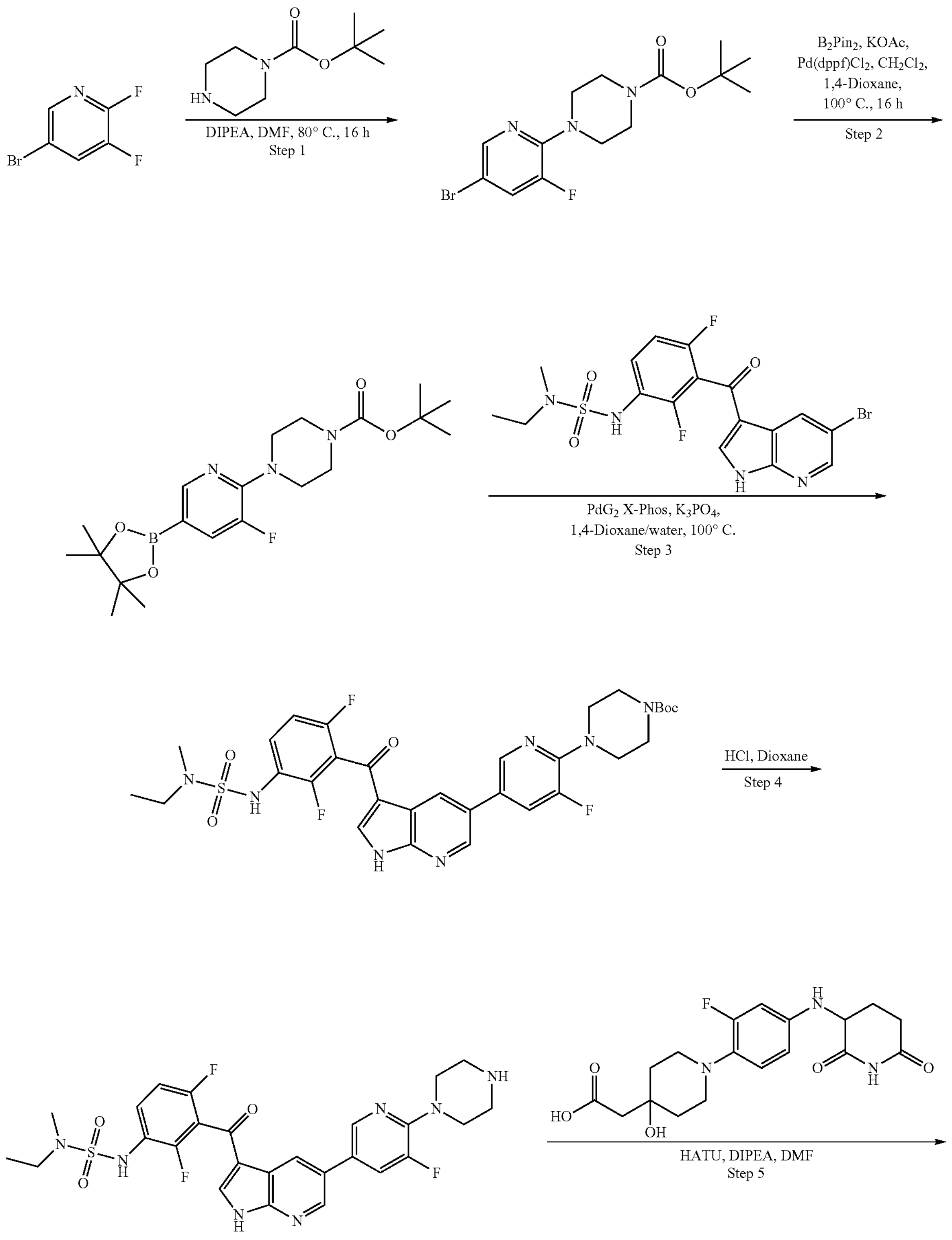

-continued

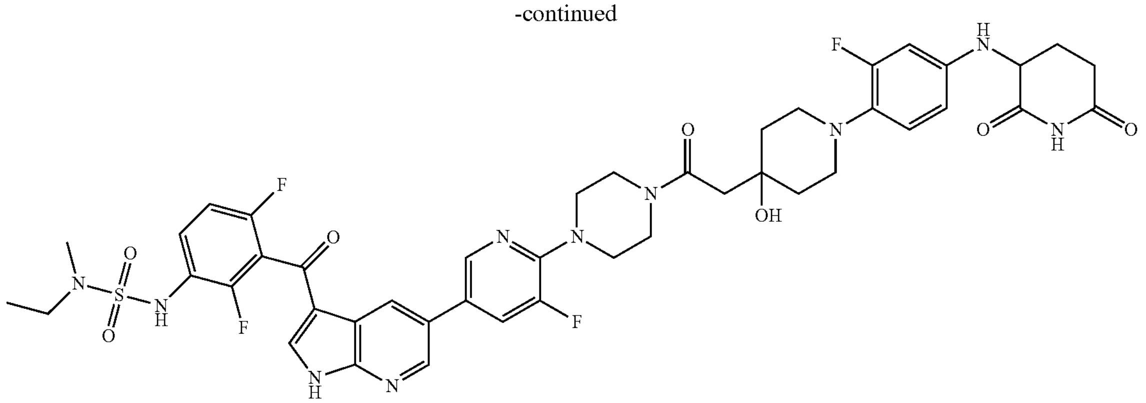

Step 1: To a solution of 5-bromo-2,3-difluoro-pyridine (7 g, 36.09 mmol) in DMF (50 mL) were added tert-butylpiperazine-1-carboxylate (6.72 g, 36.09 mmol) and DIPEA (13.99 g, 108.26 mmol, 18.86 mL) at room temperature under nitrogen atmosphere. The reaction mixture was heated at 80° C. for 16 hours. Reaction mixture was cooled to room temperature, added to water (50 mL) and extracted with ethyl acetate (2×50 mL). The combined organic layers were dried over sodium sulphate, filtered and concentrated under reduced pressure. The crude product was purified by silica gel column chromatography with 15% ethyl acetate in petroleum ether as an eluent to afford tert-butyl 4-(5-bromo-3-fluoro-2-pyridyl)piperazine-1-carboxylate (8.5 g, 23.12 mmol, 64.08% yield) as colorless liquid. LCMS (ESI+): 304.01 $[M-56+H]^+$ Step 2: A mixture of tert-butyl 4-(5-bromo-3-fluoro-2-pyridyl)piperazine-1-carboxylate (2.5 g, 6.94 mmol), Bis (pinacolato)diboron (1.76 g, 6.94 mmol) and potassium acetate (2.04 g, 20.82 mmol, 1.30 mL) in 1,4-dioxane (15 mL) was purged with nitrogen gas for 10 min. Then [1,1'-Bis(diphenylphosphino)ferrocene]dichloropalladium(II), complex with dichloromethane (566.32 mg, 694.02 µmol) was added and the reaction mixture was heated at 100° C. for 16 hours in a seal tube. Reaction mixture was cooled to room temperature, filtered through celite bed and washed with dichloromethane. The resulting filtrate was concentrated under reduced pressure to get the crude product which was purified by silica gel column chromatography using 80% ethyl acetate in petroleum ether as an eluent to afford tert-butyl 4-[3-fluoro-5-(4,4,5,5-tetramethyl-1,3,2-dioxaborolan-2-yl)-2-pyridyl]piperazine-1-carboxylate (2 g, 3.98 mmol, 57.31% yield) as a white solid. LCMS (ESI+): 408.2 $[M+H]^+$.

Step 3: A mixture of 5-bromo-3-[3-[[ethyl(methyl)sulfamoyl]amino]-2,6-difluoro-benzoyl]-1H-pyrrolo[2,3-b]pyridine (500 mg, 1.06 mmol), tert-butyl 4-[3-fluoro-5-(4,4,5,5-tetramethyl-1,3,2-dioxaborolan-2-yl)-2-pyridyl] piperazine-1-carboxylate (430.27 mg, 1.06 mmol) and potassium phosphate tribasic anhydrous (672.75 mg, 3.17 mmol) in a mixture of 1,4-dioxane (4 mL)/water (1 mL) was purged with nitrogen gas for 15 minutes followed by the addition of Xphos Pd G2 (83.04 mg, 105.64 µmol) at room temperature. The reaction mixture was heated at 100° C. for 1 hour under microwave irradiation. Reaction mixture was cooled to room temperature, filtered through celite bed and washed with dichloromethane (30 mL). The resulting filtrate was washed with brine (20 mL), dried over sodium sulphate, filtered and concentrated under reduced pressure. The crude compound was purified by silica gel column chromatography with 65% ethyl acetate in petroleum ether as an eluent to afford tert-butyl 4-[5-[3-[3-[[ethyl(methyl)sulfamoyl] amino]-2,6-difluoro-benzoyl]-1H-pyrrolo[2,3-b]pyridin-5-yl]-3-fluoro-2-pyridyl]piperazine-1-carboxylate (630 mg, 832.26 µmol, 78.78% yield) as off white solid. LCMS (ESI+): 674.2 $[M+H]^+$ Step 4: To a solution of tert-butyl 4-[5-[3-[3-[[ethyl (methyl)sulfamoyl]amino]-2,6-difluoro-benzoyl]-1H-pyrrolo[2,3-b]pyridin-5-yl]-3-fluoro-2-pyridyl]piperazine-1-carboxylate (630 mg, 935.13 µmol) in anhydrous dichloromethane (2 mL), 4M HCl in 1,4-dioxane (935.13 µmol, 5 mL) was added at room temperature and stirred for 2 hours. The reaction mixture was concentrated under reduced pressure, co-distilled with toluene (2×10 mL) and washed with diethyl ether (2×10 mL), dried to afford 3-[3-[[ethyl(methyl)sulfamoyl]amino]-2,6-difluoro-benzoyl]-5-(5-fluoro-6-piperazin-1-yl-3-pyridyl)-1H-pyrrolo[2,3-b] pyridine (600 mg, 924.51 µmol, 98.87% yield, hydrochloric acid salt) as white solid compound. LCMS (ESI+): 574.0 $[M+H]^+$.

Step 5: Target compound was prepared via HATU mediated acid-amine coupling reaction (procedure A) using 3-[3-[[ethyl(methyl)sulfamoyl]amino]-2,6-difluoro-benzoyl]-5-(5-fluoro-6-piperazin-1-yl-3-pyridyl)-1H-pyrrolo[2,3-b] pyridine (300 mg, 523.02 µmol), 2-[1-[4-[(2,6-dioxo-3-piperidyl)amino]-2-fluoro-phenyl]-4-hydroxy-4-piperidyl] acetic acid (198.43 mg, 523.02 µmop, DIPEA (405.57 mg, 3.14 mmol, 546.59 µL) and HATU (238.64 mg, 627.63 µmol) in DMF (3 mL). The product was purified by reverse phase C18 column chromatography [Mobile-phase A: 0.1% HCOOH in water, Mobile-phase B: ACN, Wave length: 215 nm, Column: 120 g Redisep C18] to afford 5-[6-[4-[2-[1-[4-[(2,6-dioxo-3-piperidyl)amino]-2-fluoro-phenyl]-4-hydroxy-4-piperidyl]acetyl]piperazin-1-yl]-5-fluoro-3-pyridyl]-3-[3-[[ethyl(methyl)sulfamoyl]amino]-2,6-difluoro-benzoyl]-1H-pyrrolo[2,3-b]pyridine (250 mg, 250.87 µmol, 47.97% yield, formic acid salt) as light green solid. LCMS (ESI−): 933.2 $[M-H]^-$. $^1H$ NMR (400 MHz, DMSO-$d_6$): δ 13.03 (s, 1H), 10.80 (s, 1H), 9.73 (s, 1H), 8.73 (d, J=2.40 Hz, 1H), 8.62 (s, 1H), 8.45 (s, 1H), 8.16-8.14 (m, 1H), 8.08-8.04 (m, 1H), 7.62-7.56 (m, 1H), 7.31-7.26 (t, J=9.2 Hz, 1H), 6.87 (s, 1H), 6.54-6.44 (m, 2H), 5.79 (s, 1H), 4.86 (s, 1H), 4.28 (s, 1H), 3.72 (m, 4H), 3.51 (m, 4H), 3.12 (q, J=6.80 Hz, 2H), 2.92-2.88 (m, 4H), 2.73-2.70 (m, 4H), 2.60-2.58 (m, 3H), 2.10-2.07 (m, 1H), 1.87-1.72 (m, 5H), 1.02 (t, J=7.20 Hz, 3H).

Example 189
5-[4-[4-[2-[1-[4-[(2,6-dioxo-3-piperidyl)amino]-2-fluoro-phenyl]-4-hydroxy-4-piperidyl]acetyl]piperazin-1-yl]-2-methyl-phenyl]-3-[3-[[ethyl(methyl)sulfamoyl]amino]-2,6-difluoro-benzoyl]-1H-pyrrolo[2,3-b]pyridine
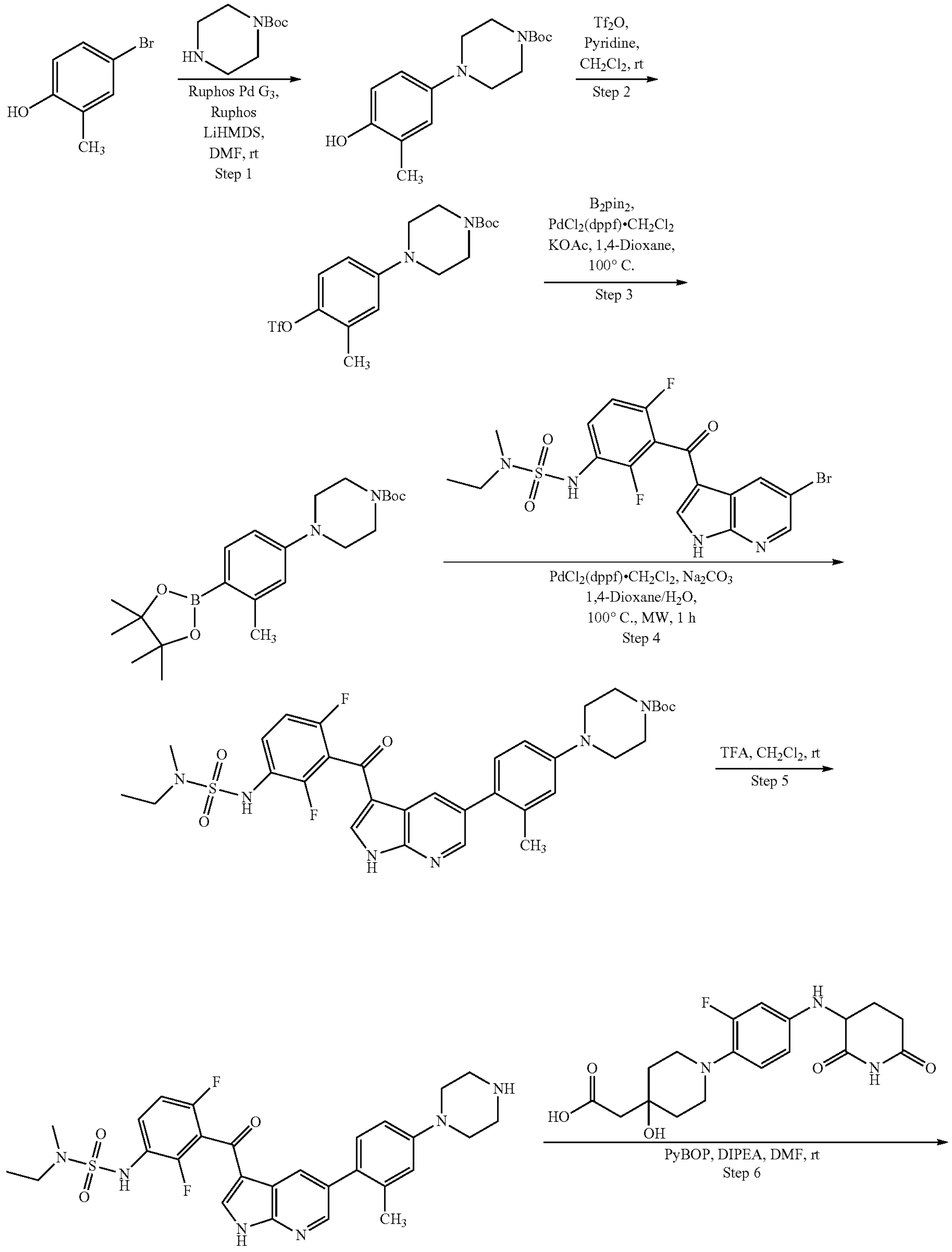

-continued

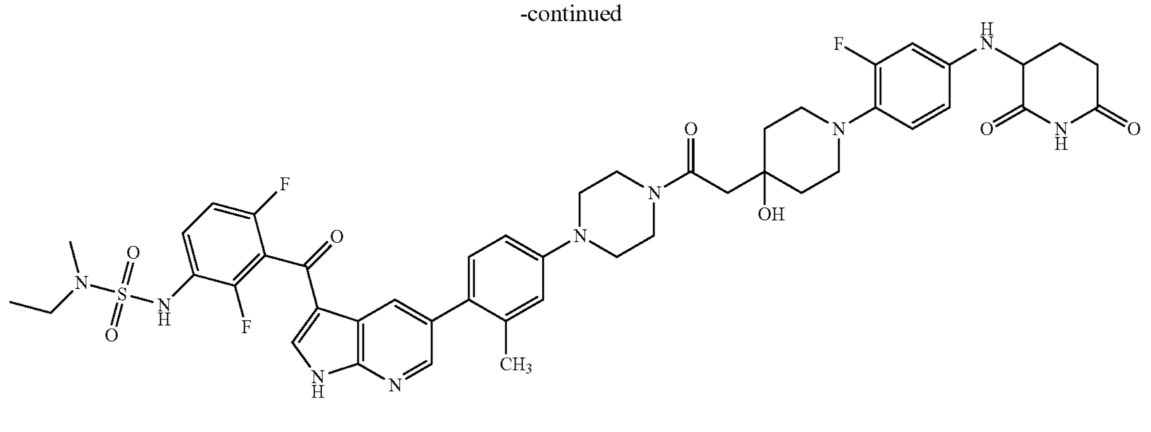

Step 1: A mixture of 4-bromo-2-methyl-phenol (1.0 g, 5.35 mmol) and tert-butyl piperazine-1-carboxylate (1.19 g, 6.42 mmol) in N,N-dimethylformamide (12.0 mL) was purged with nitrogen for 15 minutes followed by the addition of RuPhos Pd $G_3$ (223.59 mg, 267.33 μmol) and Ruphos (124.74 mg, 267.33 μmol) at room temperature. The reaction mixture was cooled to 0° C. and added LiHMDS (1.0 M, 16.04 mL) dropwise under nitrogen atmosphere. The reaction mixture was warmed to room temperature and stirred for 18 h. Reaction mixture was cooled to 0° C., quenched with aqueous $NH_4Cl$ solution (50 mL) and extracted with ethyl acetate (2×50 mL). Combined organic layers were washed with brine (100 mL), dried over sodium sulphate, filtered and concentrated under reduced pressure. The crude product was purified by silica gel column chromatography using 50% ethyl acetate in petroleum ether as an eluent to afford tert-butyl 4-(4-hydroxy-3-methyl-phenyl)piperazine-1-carboxylate (880 mg, 2.11 mmol, 39.40% yield) as an off-white solid. LCMS (ESI+): 293.1 $[M+H]^+$.

Step 2: To a solution of tert-butyl 4-(4-hydroxy-3-methyl-phenyl)piperazine-1-carboxylate (700 mg, 2.39 mmol) in dichloromethane (20.0 mL) were added pyridine (473.45 mg, 5.99 mmol, 484.10 μL) followed by triflic anhydride (810.60 mg, 2.87 mmol, 482.50 μL) at 0° C. under nitrogen atmosphere. The reaction mixture was warmed to room temperature and stirred for 1 h. Reaction mixture was diluted with dichloromethane (100 mL), washed with brine (2×100 mL), dried over sodium sulphate, filtered and concentrated under reduced pressure. The crude product was purified by silica gel column chromatography using 20% ethyl acetate in petroleum ether as an eluent to afford tert-butyl 4-[3-methyl-4-(trifluoromethylsulfonyloxy)phenyl]piperazine-1-carboxylate (685 mg, 1.58 mmol, 66.00% yield) as an off-white solid. LCMS (ESI+): 369.1 $[M-56+H]^+$.

Step 3: A mixture of tert-butyl 4-[3-methyl-4-(trifluoromethylsulfonyloxy)phenyl]piperazine-1-carboxylate (685 mg, 1.61 mmol), 4,4,5,5-tetramethyl-2-(4,4,5,5-tetramethyl-1,3,2-dioxaborolan-2-yl)-1,3,2-dioxaborolane (491.80 mg, 1.94 mmol) and potassium acetate (395.97 mg, 4.03 mmol, 252.21 μL) in 1,4-dioxane (9.0 mL) was purged with nitrogen for 15 minutes followed by the addition of cyclopentyl(diphenyl)phosphane;dichloromethane;dichloropalladium; iron (131.80 mg, 161.39 μmol) at room temperature. The reaction mixture was heated at 100° C. for 16 h. Reaction mixture was cooled to room temperature, diluted with ethyl acetate (50 mL) and filtered through celite bed. The filtrate was washed with brine (50 mL), dried over sodium sulphate, filtered and concentrated under reduced pressure. The crude product was purified by silica gel column chromatography using 50% ethyl acetate in petroleum ether as an eluent to afford tert-butyl 4-[3-methyl-4-(4,4,5,5-tetramethyl-1,3,2-dioxaborolan-2-yl)phenyl]piperazine-1-carboxylate (560 mg, 1.34 mmol, 82.79% yield) as an off-white solid. LCMS (ESI+): 403.1 $[M+H]^+$.

Step 4: A mixture of 5-bromo-3-[3-[[ethyl(methyl)sulfamoyl]amino]-2,6-difluoro-benzoyl]-1H-pyrrolo[2,3-b]pyridine (500 mg, 1.06 mmol), tert-butyl 4-[3-methyl-4-(4,4,5,5-tetramethyl-1,3,2-dioxaborolan-2-yl)phenyl]piperazine-1-carboxylate (850.08 mg, 2.11 mmol) and sodium carbonate (279.93 mg, 2.64 mmol, 110.64 μL) in 1,4-Dioxane (12.0 mL)/water (1.5 mL) was purged with nitrogen for 15 minutes followed by the addition of cyclopentyl(diphenyl)phosphane;dichloromethane;dichloropalladium;iron (86.27 mg, 105.64 μmol) at room temperature. The reaction mixture was irradiated under microwave at 100° C. for 1 h. Reaction mixture was cooled to room temperature, filtered through celite bed, resulting filtrate was diluted with ethyl acetate (50 mL) and washed with brine (2×50 mL). Organic layer was separated, dried over sodium sulphate, filtered and concentrated under reduced pressure. The crude product was purified twice by silica gel column chromatography using 50% ethyl acetate in petroleum ether as an eluent followed by reverse phase column chromatography [Mobile-phase A: 0.1% Formic acid water, Mobile-phase B: ACN; column: 100 g Redisep Rf C18] to afford tert-butyl 4-[4-[3-[3-[[ethyl(methyl)sulfamoyl]amino]-2,6-difluoro-benzoyl]-1H-pyrrolo[2,3-b]pyridin-5-yl]-3-methyl-phenyl]piperazine-1-carboxylate (225 mg, 327.64 μmol, 31.01% yield) as an off-white solid. LCMS (ESI+): 670.0 $[M+2H]^+$.

Step 5: To a solution tert-butyl 4-[4-[3-[3-[[ethyl(methyl)sulfamoyl]amino]-2,6-difluoro-benzoyl]-1H-pyrrolo[2,3-b]pyridin-5-yl]-3-methyl-phenyl]piperazine-1-carboxylate (225 mg, 336.45 μmol) in dichloromethane (4.0 mL) was added trifluoroacetic acid (767.23 mg, 6.73 mmol, 518.40 μL) at 0° C. The reaction mixture was warmed to room temperature and stirred for 1 h. Reaction mixture was concentrated under reduced pressure and triturated with diethyl ether (2×10 mL) and dried to afford 3-[3-[[ethyl(methyl)sulfamoyl]amino]-2,6-difluoro-benzoyl]-5-(2-methyl-4-piperazin-1-yl-phenyl)-1H-pyrrolo[2,3-b]pyridine (215 mg, 310.20 μmol, 92.20% yield, trifluoroacetic acid salt) as a light brown solid. LCMS (ESI+): 569.0 $[M+H]^+$.

Step 6: Target compound was prepared via PyBop mediated acid-amine coupling reaction (Method C). Amide coupling was carried out using 3-[3-[[ethyl(methyl)sulfamoyl]amino]-2,6-difluoro-benzoyl]-5-(2-methyl-4-piperazin-1-yl-phenyl)-1H-pyrrolo[2,3-b]pyridine (330 mg, 483.40 μmol, trifluoroacetic acid salt), 2-[1-[4-[(2,6-dioxo-3-piperidyl)amino]-2-fluoro-phenyl]-4-hydroxy-4-piperidyl]acetic acid (201.02 mg, 483.40 μmol, FA salt), benzotriazol-1-yloxy(tripyrrolidin-1-yl)phosphonium;hexafluorophosphate (377.34 mg, 725.10 μmol) and N,N-Diisopropylethylamine (312.38 mg, 2.42 mmol, 420.99 μL) to afford 5-[4-[4-[2-[1-[4-[(2,6-dioxo-3-piperidyl)amino]-2-fluoro-phenyl]-4-hydroxy-4-piperidyl]acetyl]piperazin-1-yl]-2-methyl-phenyl]-3-[3-[[ethyl(methyl)sulfamoyl]amino]-2,6-difluoro-benzoyl]-1H-pyrrolo[2,3-b]pyridine (245 mg, 247.36 μmol, 51.17% yield, FA salt) as an off-white solid. LCMS (ESI+): 930.3 $[M+H]^+$. $^1H$ NMR (400 MHz, DMSO-d6): δ 12.97 (s, 1H), 10.82 (s, 1H), 9.73 (s, 1H), 8.35 (d, J=2.00 Hz, 1H), 8.26 (s, 1H), 8.14 (s, 1H), 7.61-7.55 (m, 1H), 7.28 (t, J=8.00 Hz, 1H), 7.19 (d, J=8.40 Hz, 1H), 7.05-6.85 (m, 3H), 6.80-6.30 (m, 2H), 4.35 (m, 1H), 3.81-3.71 (m, 4H), 3.19-3.10 (m, 4H), 3.12-3.03 (m, 4H), 3.02-2.74 (m, 2H), 2.71 (s, 3H), 2.68-2.61 (m, 3H), 2.25 (s, 3H), 2.11-2.07 (m, 2H), 1.89-1.70 (m, 6H), 1.01 (t, J=6.80 Hz, 3H).

Example 190

(3R)—N-[3-[5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-1H-pyrrolo[2,3-b]pyridine-3-carbonyl]-2,4-difluoro-phenyl]-3-fluoro-pyrrolidine-1-sulfonamide

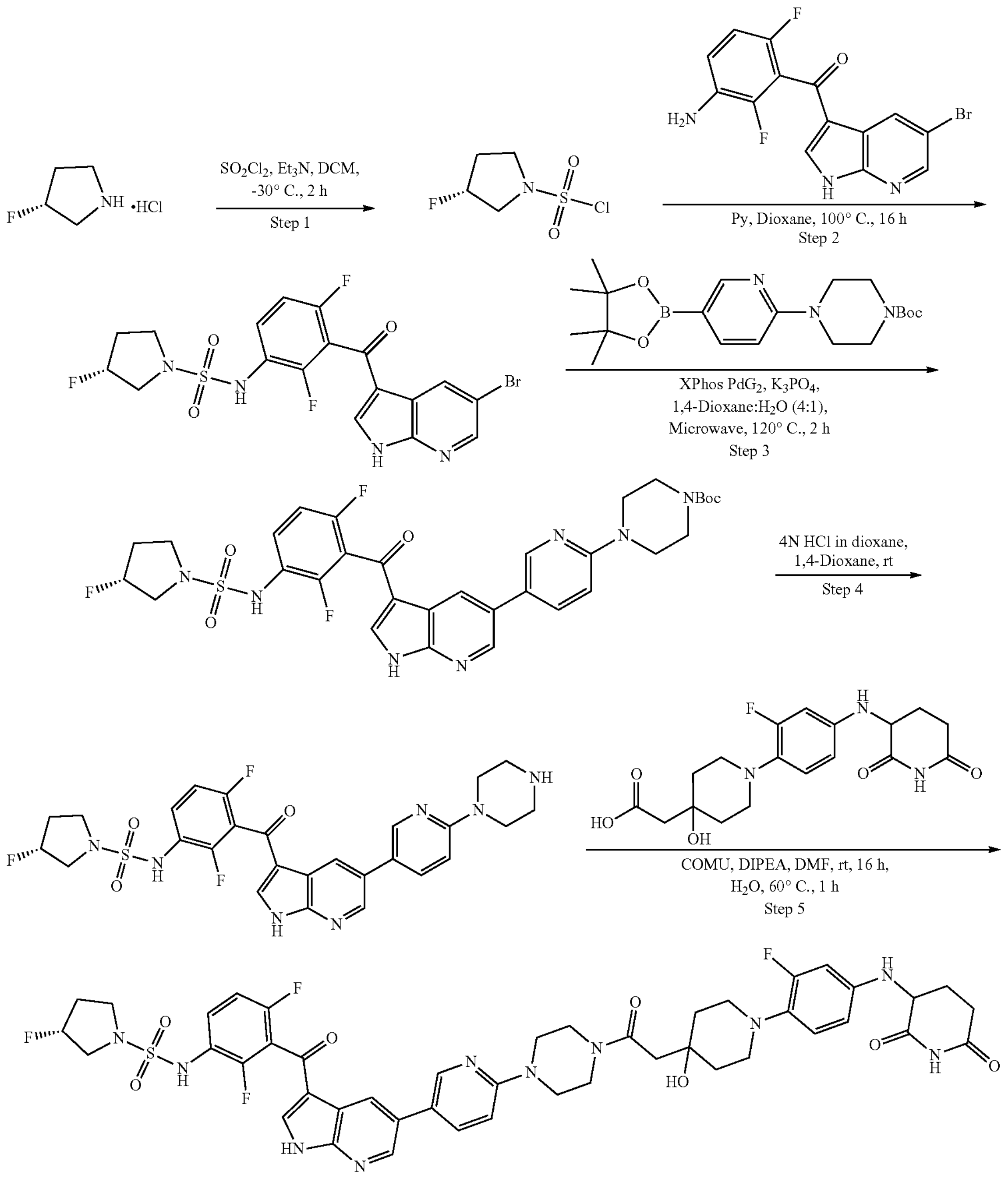

Step 1: To a stirred solution of (3R)-3-fluoropyrrolidine (4 g, 31.85 mmol) in Dichloromethane (30 mL), was added N,N-Diisopropylethylamine (6.59 g, 50.97 mmol, 8.88 mL) at room temperature and stirred for 10 minutes under nitrogen atmosphere. Reaction mixture was cooled to −30° C., sulfuryl chloride (10.75 g, 79.64 mmol) was added by dropwise. The reaction mixture was stirred at −30° C. for 2 h. After completion, reaction mixture was quenched with water (50 mL) by dropwise at 0° C., extracted with ethyl acetate (3×70 mL). Combined organic layers washed with 1.5N hydrochloric acid solution (2×50 mL), organic layers dried over sodium sulphate, filtered and concentrated under reduced pressure to afford crude (3R)-3-fluoropyrrolidine-1-sulfonyl chloride (4 g, 21.32 mmol, 66.93% yield) as off white solid. $^1$H NMR (400 MHz, DMSO-$d_6$): δ 5.35-5.55 (m, 1H), 3.40-3.78 (m, 4H), 2.27-2.44 (m, 2H).

Step 2: A solution of (3-amino-2,6-difluoro-phenyl)-(5-bromo-1H-pyrrolo[2,3-b]pyridin-3-yl)methanone (1.5 g, 4.26 mmol) in 1,4-Dioxane (30 mL) was taken in a sealed tube and added Pyridine (3.37 g, 42.60 mmol, 3.45 mL) and (3R)-3-fluoropyrrolidine-1-sulfonyl chloride (4.00 g, 21.30 mmol, 14.69 mL) at room temperature. The reaction mixture was stirred at 100° C. for 16 h. After completion, the reaction mixture was diluted with water (50 mL), extracted with ethyl acetate (3×70 mL). Combined organic layers washed with 1.5N hydrochloric acid solution (3×30 mL), dried over sodium sulphate, filtered and concentrated to get the crude compound. Desired product was purified from crude by column chromatography (60-120 silica gel) using 70-80% ethyl acetate in petroleum ether as eluent to afford (3R)—N-[3-(5-bromo-1H-pyrrolo[2,3-b]pyridine-3-carbonyl)-2,4-difluoro-phenyl]-3-fluoro-pyrrolidine-1-sulfonamide (0.75 g, 1.28 mmol, 30.14% yield) as light yellow solid. LCMS (ESI−): 500.8 [M−H]$^-$.

Step 3: A solution of tert-butyl 4-[5-(4,4,5,5-tetramethyl-1,3,2-dioxaborolan-2-yl)-2-pyridyl]piperazine-1-carboxylate (580.12 mg, 1.49 mmol) in 1,4-Dioxane (10 mL) and Water (2.5 mL) taken in sealed tube and added Potassium phosphate tribasic anhydrous (632.63 mg, 2.98 mmol) and tert-butyl 4-[5-(4,4,5,5-tetramethyl-1,3,2-dioxaborolan-2-yl)-2-pyridyl]piperazine-1-carboxylate (580.12 mg, 1.49 mmol). The reaction mixture was purged with nitrogen gas for 10 minutes and then added XPhos Pd G2 (78.17 mg, 99.35 μmol) and continued purging with nitrogen gas for 5 minutes. The reaction mixture was irradiated under microwave at 120° C. for 2 h. After completion, the reaction mixture was diluted with water (50 mL), extracted with ethyl acetate (3×70 mL). Combined organic layers dried over sodium sulphate, filtered and concentrated to get the crude. Desired product was purified from crude by column chromatography (60-120 silica gel) by using 80-90% ethyl acetate in petroleum ether as eluent to afford tert-butyl 4-[5-[3-[2,6-difluoro-3-[[(3R)-3-fluoropyrrolidin-1-yl]sulfonylamino]benzoyl]-1H-pyrrolo[2,3-b]pyridin-5-yl]-2-pyridyl]piperazine-1-carboxylate (0.5 g, 629.56 μmol, 63.37% yield) as light yellow solid. LCMS (ESI+): 686.2 [M+H]$^+$.

Step 4: To a stirred solution of tert-butyl 4-[5-[3-[2,6-difluoro-3-[[(3R)-3-fluoropyrrolidin-1-yl]sulfonylamino]benzoyl]-1H-pyrrolo[2,3-b]pyridin-5-yl]-2-pyridyl]piperazine-1-carboxylate (0.5 g, 729.17 μmol) in 1,4-Dioxane (10 mL), was added Hydrogen chloride solution in 1,4-dioxane (4M, 5 mL) at 5° C. under nitrogen atmosphere. The reaction mixture was stirred at room temperature for 12 h. After completion, the reaction mixture was concentrated under reduced pressure to afford crude (3R)—N-[2,4-difluoro-3-[5-(6-piperazin-1-yl-3-pyridyl)-1H-pyrrolo[2,3-b]pyridine-3-carbonyl]phenyl]-3-fluoro-pyrrolidine-1-sulfonamide (0.55 g, 815.28 μmol) as off white solid. LCMS (ESI+): 585.9 [M+H]$^+$.

Step 5: target compound was prepared via HATU mediated acid-amine coupling reaction (procedure A). Amide coupling was carried out using 2-[1-[4-[(2,6-dioxo-3-piperidyl)amino]-2-fluoro-phenyl]-4-hydroxy-4-piperidyl]acetic acid (292.74 mg, 703.97 μmol), N-ethyl-N-isopropyl-propan-2-amine (831.06 mg, 6.43 mmol, 1.12 mL), HATU (268.95 mg, 707.33 μmol) and (3R)—N-[2,4-difluoro-3-[5-(6-piperazin-1-yl-3-pyridyl)-1H-pyrrolo[2,3-b]pyridine-3-carbonyl]phenyl]-3-fluoro-pyrrolidine-1-sulfonamide (0.4 g, 643.02 μmol). The desired product was purified from crude by reverse phase column chromatography (0.1% Formic acid in water:Acetonitrile) and fractions were lyophilized to afford (3R)—N-[3-[5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-1H-pyrrolo[2,3-b]pyridine-3-carbonyl]-2,4-difluoro-phenyl]-3-fluoro-pyrrolidine-1-sulfonamide (189.45 mg, 187.75 μmol, 29.20% yield) as off white solid. LCMS (ESI+): 946.9 [M+H]$^+$. $^1$H NMR (400 MHz, DMSO-d6): δ 12.97 (d, J=2.80 Hz, 1H), 10.78 (s, 1H), 9.86 (s, 1H), 8.68 (d, J=2.40 Hz, 1H), 8.51-8.53 (m, 2H), 8.11 (d, J=3.20 Hz, 1H), 7.99 (dd, J=2.40, 8.80 Hz, 1H), 7.60-7.66 (m, 1H), 7.28 (t, J=9.20 Hz, 1H), 7.02 (d, J=8.80 Hz, 1H), 6.87 (s, 1H), 6.35-6.55 (m, 2H), 5.79 (s, 1H), 5.24-5.37 (m, 1H), 4.90 (s, 1H), 3.60-3.70 (m, 8H), 3.35-3.49 (m, 3H), 3.30-3.33 (m, 2H), 2.81-3.00 (m, 3H), 2.71-2.80 (m, 1H), 2.61 (s, 2H), 2.56-2.50 (m, 1H), 2.07-2.12 (m, 4H), 1.62-1.91 (m, 5H).

Example 191

(3R)—N-[3-[5-[4-[4-[2-[1-[4-[(2,6-dioxo-3-piperidyl)amino]-2-fluoro-phenyl]-4-hydroxy-4-piperidyl]acetyl]piperazin-1-yl]phenyl]-1H-pyrrolo[2,3-b]pyridine-3-carbonyl]-2,4-difluoro-phenyl]-3-fluoro-pyrrolidine-1-sulfonamide

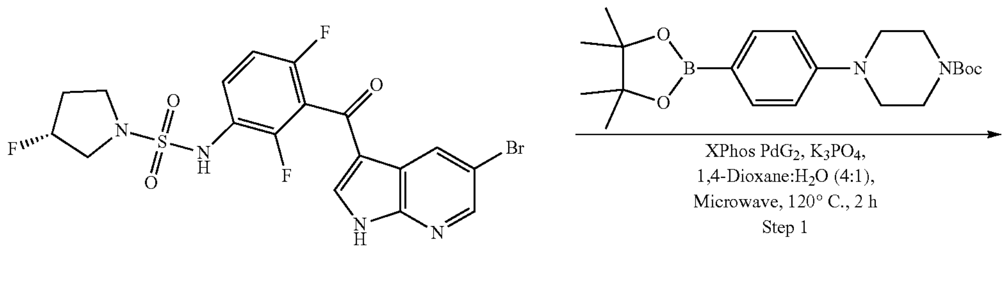

-continued

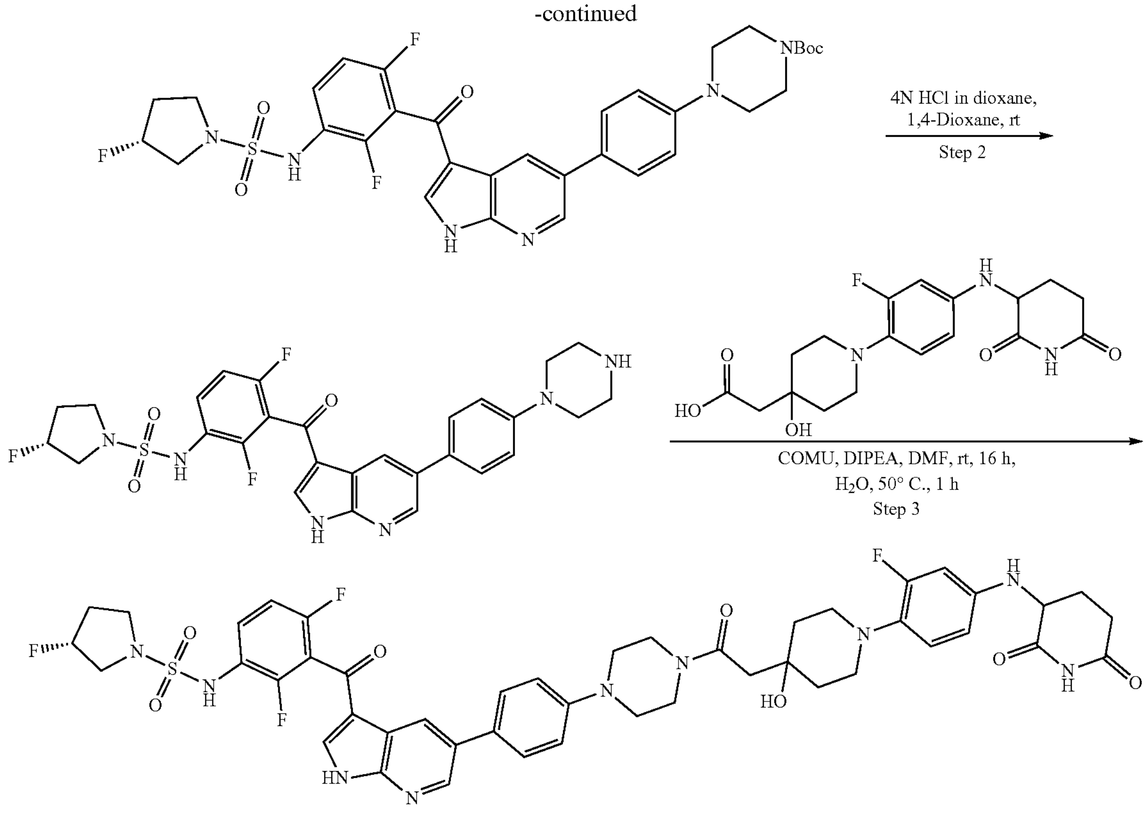

Step 1: A solution of (3R)—N-[3-(5-bromo-1H-pyrrolo[2,3-b]pyridine-3-carbonyl)-2,4-difluoro-phenyl]-3-fluoro-pyrrolidine-1-sulfonamide (0.7 g, 1.39 mmol) in 1,4-Dioxane (10 mL) and Water (2.5 mL) was taken in a sealed tube and added Potassium phosphate tribasic anhydrous (885.69 mg, 4.17 mmol) and tert-butyl 4-[4-(4,4,5,5-tetramethyl-1,3,2-dioxaborolan-2-yl)phenyl]piperazine-1-carboxylate (810.11 mg, 2.09 mmol). The reaction mixture was purged with nitrogen gas for 10 minutes and then added XPhos Pd G2 (109.43 mg, 139.08 μmol) and continued purging with nitrogen gas for 5 minutes. The reaction mixture was irradiated under microwave at 120° C. for 2 h. After completion, the reaction mixture was diluted with water (50 mL), extracted with ethyl acetate (3x70 mL). Combined organic layers were dried over sodium sulphate, filtered and concentrated. Desired product was purified from crude by column chromatography (60-120 silica gel) using 80-90% ethyl acetate in petroleum ether as eluent to afford tert-butyl 4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazine-1-carboxylate (0.4 g, 478.50 μmol, 34.40% yield) as light pink solid. LCMS (ESI+): 685.2 $[M+H]^+$.

Step 2: To a stirred solution of tert-butyl 4-[4-[3-[2,6-difluoro-3-[[(3R)-3-fluoropyrrolidin-1-yl]sulfonylamino]benzoyl]-1H-pyrrolo[2,3-b]pyridin-5-yl]phenyl]piperazine-1-carboxylate (0.4 g, 584.17 μmol) in 1,4-Dioxane (10 mL), was added 4M Hydrogen chloride solution in dioxane (4M, 5 mL) at 5° C. under nitrogen atmosphere. The reaction mixture was stirred at room temperature for 16 h. After completion, the reaction mixture was concentrated under reduced pressure to afford crude (3R)—N-[2,4-difluoro-3-[5-(4-piperazin-1-ylphenyl)-1H-pyrrolo[2,3-b]pyridine-3-carbonyl]phenyl]-3-fluoro-pyrrolidine-1-sulfonamide (0.43 g, 597.08 μmol) as light yellow solid. LCMS (ESI+): 585.2 $[M+H]^+$.

Step 3: target compound was prepared via HATU mediated acid-amine coupling reaction (procedure A). Amide coupling was carried out using 2-[1-[4-[(2,6-dioxo-3-piperidyl)amino]-2-fluoro-phenyl]-4-hydroxy-4-piperidyl]acetic acid (345.49 mg, 830.82 μmol), N-ethyl-N-isopropyl-propan-2-amine (894.81 mg, 6.92 mmol, 1.21 mL) and HATU (289.58 mg, 761.59 μmol) and (3R)—N-[2,4-difluoro-3-[5-(4-piperazin-1-ylphenyl)-1H-pyrrolo[2,3-b]pyridine-3-carbonyl]phenyl]-3-fluoro-pyrrolidine-1-sulfonamide (0.43 g, 692.35 μmol). The desired product was purified from crude by reverse phase column chromatography (0.1% Formic acid in water:Acetonitrile) and fractions were lyophilized to afford (3R)—N-[3-[5-[4-[4-[2-[1-[4-[(2,6-dioxo-3-piperidyl)amino]-2-fluoro-phenyl]-4-hydroxy-4-piperidyl]acetyl]piperazin-1-yl]phenyl]-1H-pyrrolo[2,3-b]pyridine-3-carbonyl]-2,4-difluoro-phenyl]-3-fluoro-pyrrolidine-1-sulfonamide (98.12 mg, 98.29 μmol, 14.20% yield) as light green solid. LCMS (ESI+): 945.9 $[M+H]^+$. $^1H$ NMR (400 MHz, DMSO-$d_6$): δ 12.93 (d, J=2.80 Hz, 1H), 10.79 (s, 1H), 9.87 (s, 1H), 8.67 (d, J=2.40 Hz, 1H), 8.55 (s, 1H), 8.09 (d, J=2.40 Hz, 1H), 7.60-7.66 (m, 3H), 7.28 (t, J=8.00 Hz, 1H), 7.12 (d, J=8.80 Hz, 2H), 6.81-6.91 (m, 1H), 6.51 (d, J=14.40 Hz, 1H), 6.42 (d, J=8.00 Hz, 1H), 5.78 (s, 1H), 5.37-5.24 (m, 1H), 4.87 (s, 1H), 4.21-4.31 (m, 1H), 3.75-3.70 (m, 4H), 3.49 (s, 1H), 3.20-3.40 (m, 8H), 2.80-2.95 (m, 4H), 2.65-2.70 (m, 1H), 2.60 (s, 2H), 2.05-2.17 (m, 3H), 1.62-1.9 (m, 5H).

Example 192
5-[4-[4-[2-[1-[4-[(2,6-dioxo-3-piperidyl)amino]-2-fluoro-phenyl]-4-hydroxy-4-piperidyl]acetyl]piperazin-1-yl]-3-methyl-phenyl]-3-[3-[[ethyl(methyl)sulfamoyl]amino]-2,6-difluoro-benzoyl]-1H-pyrrolo[2,3-b]pyridine
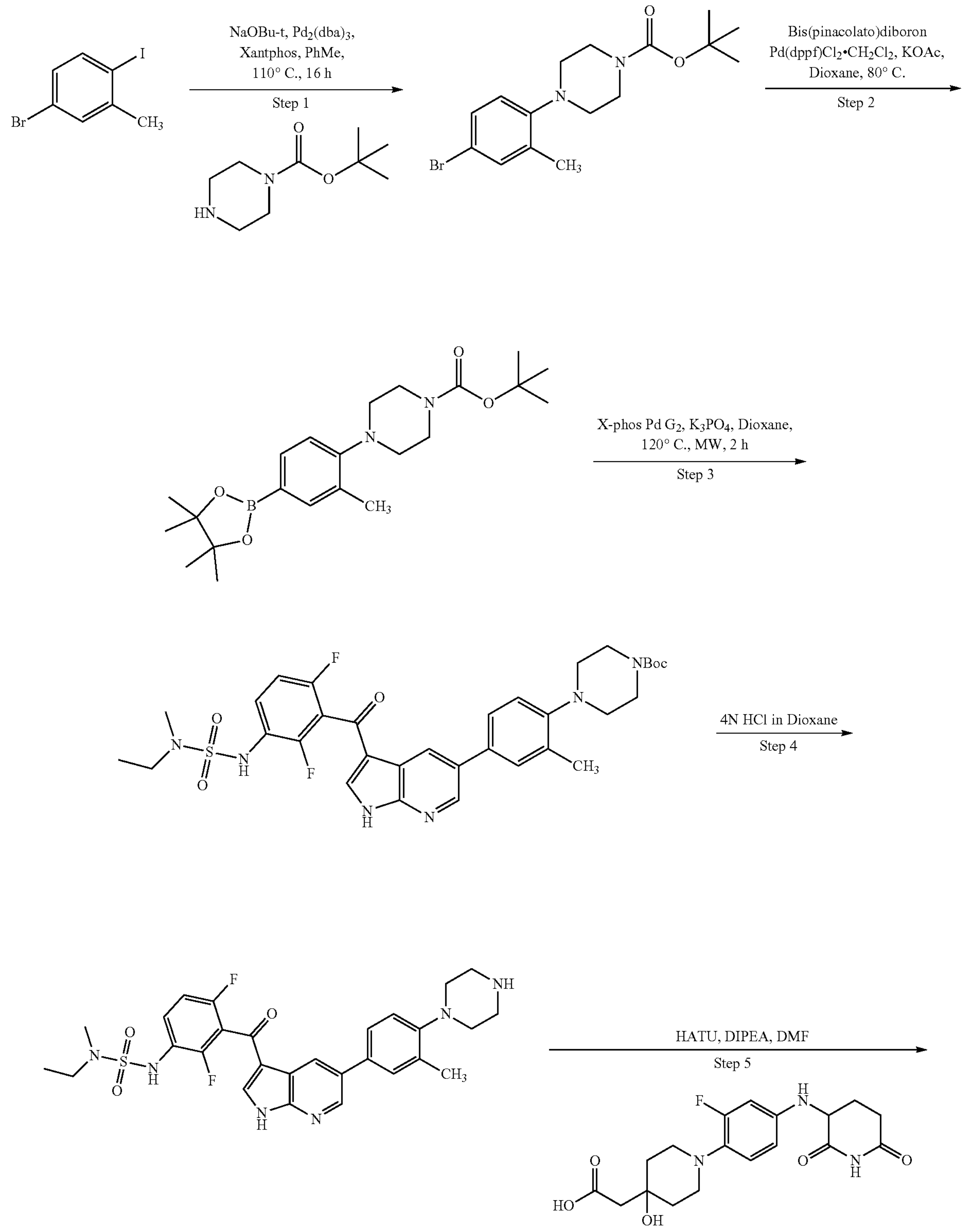

-continued

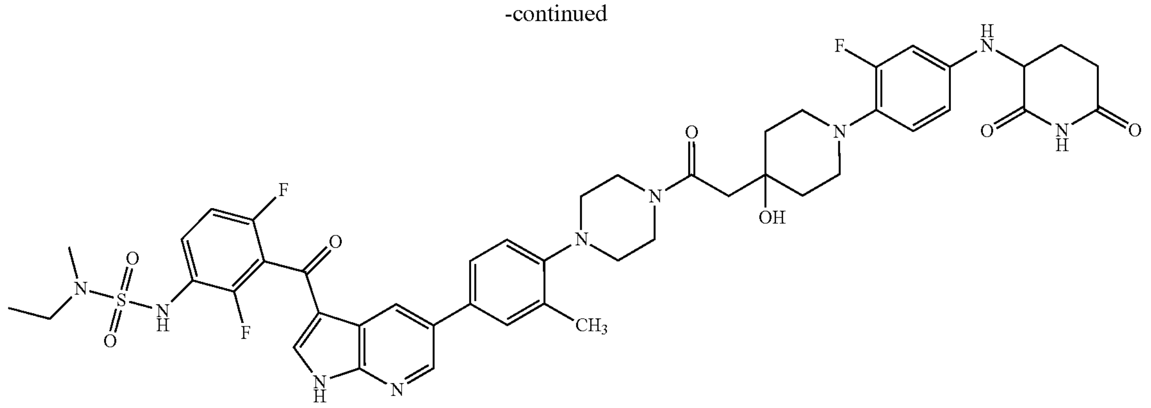

Step 1: To a stirred solution of 4-bromo-1-iodo-2-methylbenzene (10.0 g, 33.68 mmol, 4.67 mL) in toluene (100.0 mL) was added tert-butyl piperazine-1-carboxylate (6.27 g, 33.68 mmol) and sodium-2-methylpropan-2-olate (6.47 g, 67.36 mmol), degassed with nitrogen for 2 minutes and then added (5-diphenylphosphanyl-9,9-dimethyl-xanthen-4-yl)-diphenyl-phosphane (1.95 g, 3.37 mmol) and (1E,4E)-1,5-diphenylpenta-1,4-dien-3-one;palladium (3.08 g, 3.37 mmol). The reaction mixture was further degassed with nitrogen for 5 minutes then stirred at 110° C. for 16 h. The reaction mixture was suspended in ethyl acetate (50.0 mL) and filtered with celite pad. The celite pad was washed with ethyl acetate (50.0 mL). The filtrate was evaporated to afford the crude product which was purified by flash silica gel chromatography using 15% ethyl acetate in petroleum ether as eluents to afford tert-butyl 4-(4-bromo-2-methyl-phenyl) piperazine-1-carboxylate (1.3 g, 1.96 mmol, 5.83% yield) as colorless liquid. LCMS (ESI+): 357.0 $[M+2H]^+$ Step 2: To a stirred solution of tert-butyl 4-(4-bromo-2-methyl-phenyl)piperazine-1-carboxylate (1.2 g, 3.38 mmol) in 1,4-dioxane (10.0 mL) was added 4,4,5,5-tetramethyl-2-(4,4,5,5-tetramethyl-1,3,2-dioxaborolan-2-yl)-1,3,2-dioxaborolane (1.29 g, 5.07 mmol), degassed the mixture under nitrogen for 2 min and then added potassium acetate (828.74 mg, 8.44 mmol, 527.86 and cyclopentyl(diphenyl)phosphane;dichloromethane;dichloropalladium;iron (275.84 mg, 337.77 µmol) to the reaction. The reaction was further degassed and heated at 100° C. for 16 h. The reaction mixture was filtered through celite, washing with ethyl acetate (50.0 mL). The filtrate was evaporated to afford the crude product which was purified by flash silica chromatography using 30% Ethyl acetate in petroleum ether as eluents to afford tert-butyl 4-[2-methyl-4-(4,4,5,5-tetramethyl-1,3,2-dioxaborolan-2-yl)phenyl]piperazine-1-carboxylate (1.3 g, 2.81 mmol, 83.17% yield) as colorless liquid. LCMS (ESI+): 403.3 $[M+H]^+$.

Step 3: A solution of 5-bromo-3-[3-[[ethyl(methyl)sulfamoyl]amino]-2,6-difluoro-benzoyl]-1H-pyrrolo[2,3-b]pyridine (500.0 mg, 1.06 mmol) in 1,4-dioxane (5.0 mL) and water (2.0 mL) was taken in a microwave vial and added tert-butyl 4-[2-methyl-4-(4,4,5,5-tetramethyl-1,3,2-dioxaborolan-2-yl)phenyl]piperazine-1-carboxylate (552.55 mg, 1.37 mmol) and tripotassium;phosphate (672.73 mg, 3.17 mmol) at room temperature under nitrogen. The reaction mixture was degassed with nitrogen for 5 min and then XPhos Pd G2 (83.12 mg, 105.64 µmol) was added. Further degassed the reaction under nitrogen and then stirred at 120° C. for 2 h in under microwave irradiation. The reaction was diluted with water (10.0 mL) and extracted with ethyl acetate (2×10.0 mL). The combined organic layers were washed with saturated brine solution (10.0 mL), dried over sodium sulphate, filtered and concentrated under reduced pressure to get crude which was purified by silica gel column chromatography using 70% ethyl acetate in petroleum ether as a eluent followed by reverse phase column chromatography by using 100 g-C18 snap eluted with 95% acetonitrile in 0.1% formic acid in water to afford tert-butyl 4-[4-[3-[3-[[ethyl(methyl)sulfamoyl]amino]-2,6-difluoro-benzoyl]-1H-pyrrolo[2,3-b]pyridin-5-yl]-2-methyl-phenyl]piperazine-1-carboxylate (300.0 mg, 438.37 µmol, 41.50% yield) as off white solid. LCMS (ESI+): 669.3 $[M+H]^+$.

Step 4: To a stirred solution of tert-butyl 4-[4-[3-[3-[[ethyl(methyl)sulfamoyl]amino]-2,6-difluoro-benzoyl]-1H-pyrrolo[2,3-b]pyridin-5-yl]-2-methyl-phenyl]piperazine-1-carboxylate (300.0 mg, 448.60 µmol) in dichloromethane (2.0 mL) was added hydrogen chloride solution in 1,4-dioxane (4.0 M, 2.0 mL) at 0° C. and the resulting reaction mixture was stirred for 1 h at room temperature. After completion, the reaction mixture was concentrated under reduced pressure. The residue obtained was triturated with diethyl ether (2×10 mL), dried under reduced pressure to afford 3-[3-[[ethyl(methyl)sulfamoyl]amino]-2,6-difluoro-benzoyl]-5-(3-methyl-4-piperazin-1-yl-phenyl)-1H-pyrrolo[2,3-b]pyridine (270.0 mg, 436.26 µmol, 97.25% yield, hydrochloric acid salt) as yellow solid. LCMS (ESI+): 569.0 $[M+H]^+$.

Step 5: Target compound was prepared via HATU mediated acid-amine coupling reaction (procedure D) using 2-[1-[4-[(2,6-dioxo-3-piperidyl)amino]-2-fluoro-phenyl]-4-hydroxy-4-piperidyl]acetic acid (166.79 mg, 439.65 µmop, DIPEA (284.11 mg, 2.20 mmol, 382.89 PyBOP (343.18 mg, 659.47 µmol) and 3-[3-[[ethyl(methyl)sulfamoyl]amino]-2,6-difluoro-benzoyl]-5-(3-methyl-4-piperazin-1-yl-phenyl)-1H-pyrrolo[2,3-b]pyridine (250.0 mg, 439.65 µmol) in DMF (3.0 mL). The product was purified by reverse phase column chromatography by using 100 g snap eluted with 41% Acetonitrile in 0.1% Formic acid in water to afford 5-[4-[4-[2-[1-[4-[(2,6-dioxo-3-piperidyl)amino]-2-fluoro-phenyl]-4-hydroxy-4-piperidyl]acetyl]piperazin-1-yl]-3-methyl-phenyl]-3-[3-[[ethyl(methyl)sulfamoyl]amino]-2,6-difluoro-benzoyl]-1H-pyrrolo[2,3-b]pyridine (255.0 mg, 254.54 µmol, 57.90% yield, formic acid salt) as off white solid. LCMS (ESI−): 928.3 $[M-H]^+$. $^1H$ NMR (400 MHz, DMSO-d6): δ 12.96 (s, 1H), 10.79 (s, 1H), 9.73 (s, 1H), 8.68 (s, 1H), 8.57 (s, 1H), 8.13 (d, J=2.80 Hz, 1H), 7.62-7.53 (m, 3H), 7.29 (t, J=8.00 Hz, 1H), 7.17 (d, J=Hz, 1H), 6.89 (s, 1H), 6.68-6.32 (m, 2H), 5.89 (s, 1H), 4.92 (s, 1H), 4.25 (s, 1H), 3.72-3.70 (m, 4H), 3.06 (q, J=6.8 Hz, 2H), 2.96-2.95 (m, 8H), 2.80-2.70 (m, 4H), 2.53-2.50 (m, 2H), 2.48 (s, 3H), 2.10-2.05 (m, 1H), 1.90-1.70 (m, 6H), 1.02 (t, J=7.20 Hz, 3H).

Example 193

3-(2,4-dioxohexahydropyrimidin-1-yl)-6-[4-[2-[4-[5-[3-[3-[[ethyl(methyl)sulfamoyl]amino]-2,6-difluoro-benzoyl]-1H-pyrrolo[2,3-b]pyridin-5-yl]-2-pyridyl]piperazin-1-yl]-2-oxo-ethyl]-4-hydroxy-1-piperidyl]-1-methyl-indazole

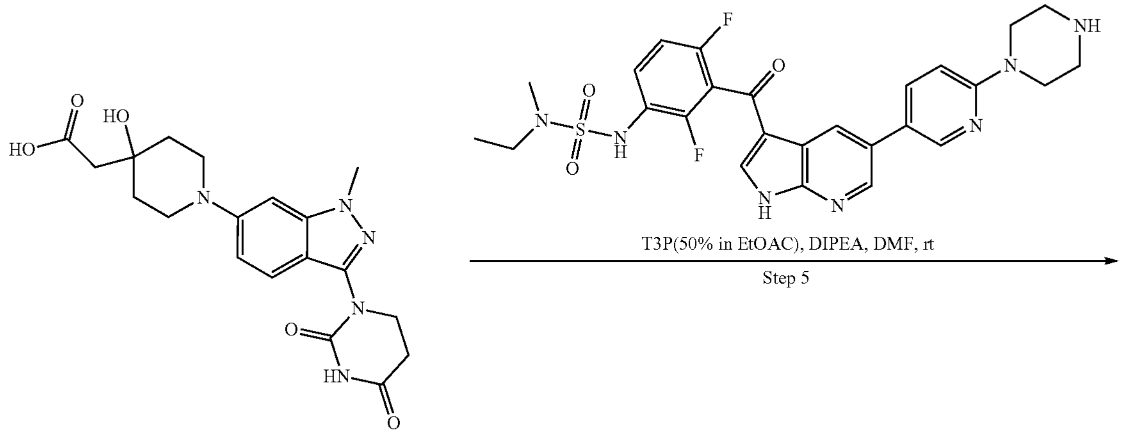

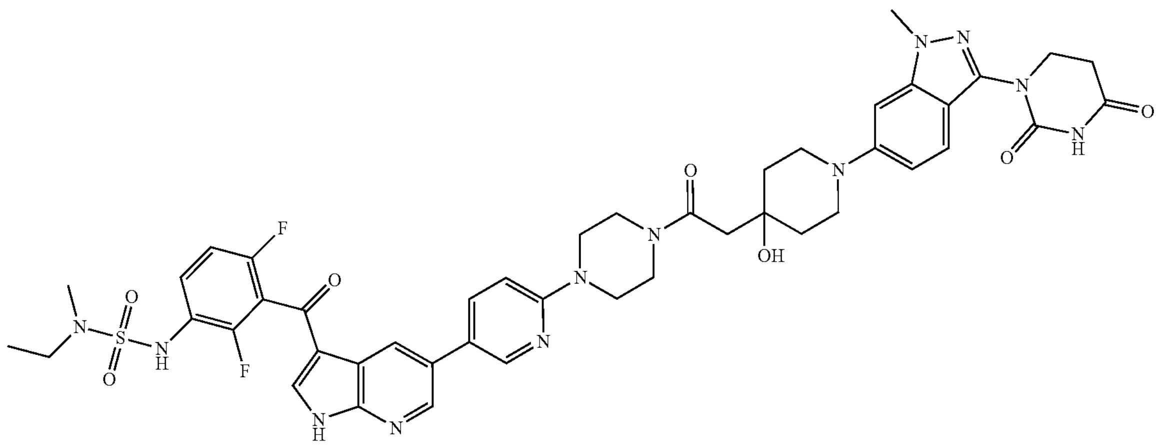

Target compound was prepared via T3P mediated acid-amine coupling reaction (procedure C) using 2[1-[3-(2,4-dioxohexahydropyrimidin-1-yl)-1-methyl-indazol-6-yl]-4-hydroxy-4-piperidyl]acetic acid (125.73 mg, 287.13 μmol, hydrochloric acid salt), N-ethyl-N-isopropyl-propan-2-amine (222.65 mg, 1.72 mmol, 300.07 μL), T3P (109.63 mg, 344.56 μmol), 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (170 mg, 287.13 μmol, hydrochloric acid salt) in DMF (2 mL). Then product was purified by reverse phase C18 column chromatography [Mobile-phase A: 0.1% HCOOH in water, Mobile-phase B: ACN, Wave length: 254 nm, Column: 100 g Redisep C18] to afford 3-(2,4-dioxohexahydropyrimidin-1-yl)-6-[4-[2-[4-[5-[3-[3-[[ethyl(methyl)sulfamoyl]amino]-2,6-difluoro-benzoyl]-1H-pyrrolo[2,3-1)]pyridin-5-yl]-2-pyridyl]piperazin-1-yl]-2-oxo-ethyl]-4-hydroxy-1-piperidyl]-1-methyl-indazole (93.3 mg, 33.0% yield, formic acid salt) as off white solid. LCMS (ESI+): 939.2 $[M+H]^+$. $^1H$ NMR (400 MHz, DMSO-$d_6$): δ 12.97 (s, 1H), 10.51 (s, 1H), 9.72 (s, 1H), 8.68 (d, J=2.40 Hz, 1H), 8.52-8.50 (m, 2H), 8.13 (s, 1H), 7.98 (dd, J=2.40, 8.80 Hz, 1H), 7.62-7.56 (m, 1H), 7.44 (d, J=9.20 Hz, 1H), 7.31-7.26 (m, 1H), 7.02 (d, J=8.80 Hz, 1H), 6.93 (d, J=9.20 Hz, 1H), 6.91 (s, 1H), 4.98 (s, 1H), 3.91-3.89 (m, 5H), 3.71-3.52 (m, 10H), 3.19-3.18 (m, 2H), 3.11 (q, J=7.20 Hz, 2H), 2.76-2.72 (m, 5H), 2.61 (s, 2H), 1.79-1.70 (m, 4H), 1.02 (t, J=7.20 Hz, 3H).

Example 194

5-[6-[4-[2-[1-[4-(2,4-dioxohexahydropyrimidin-1-yl)-2-fluoro-phenyl]-4-hydroxy-4-piperidyl]acetyl] piperazin-1-yl]-5-fluoro-3-pyridyl]-3-[3-[[ethyl (methyl)sulfamoyl]amino]-2,6-difluoro-benzoyl]-1H-pyrrolo[2,3-b]pyridine

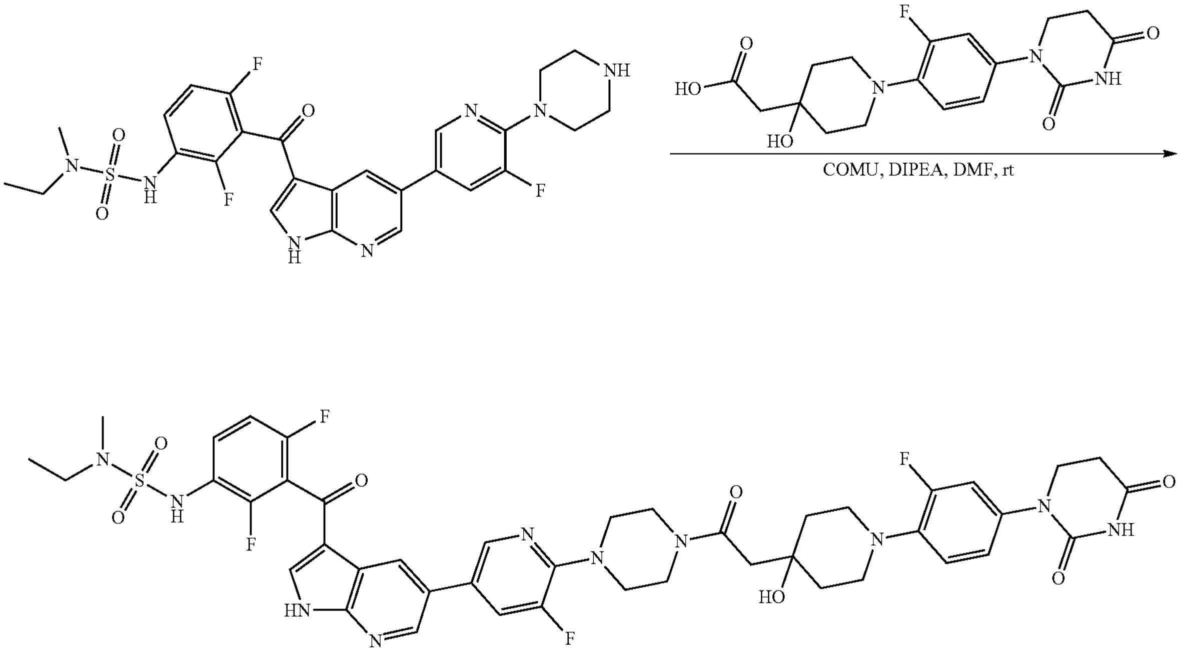

target compound was prepared via COMU mediated acid-amine coupling reaction (procedure B). Amide coupling was carried out using 3-[3-[[ethyl(methyl)sulfamoyl] amino]-2,6-difluoro-benzoyl]-5-(5-fluoro-6-piperazin-1-yl-3-pyridyl)-1H-pyrrolo[2,3-b]pyridine (260 mg, 453.29 μmol), 2-[1-[4-(2,4-dioxohexahydropyrimidin-1-yl)-2-fluoro-phenyl]-4-hydroxy-4-piperidyl]acetic acid (182.17 mg, 498.61 μmol), N, N-Diisopropylethylamine (234.34 mg, 1.81 mmol, 315.82 μL) and COMU (194.13 mg, 453.29 μmol) to afford 5-[6-[4-[2-[1-[4-(2,4-dioxohexahydropyrimidin-1-yl)-2-fluoro-phenyl]-4-hydroxy-4-piperidyl] acetyl]piperazin-1-yl]-5-fluoro-3-pyridyl]-3-[3-[[ethyl (methyl)sulfamoyl]amino]-2,6-difluoro-benzoyl]-1H-pyrrolo[2,3-b]pyridine (185 mg, 190.56 μmol, 42.04% yield) as off white solid. LCMS (ESI−): 919.2 $[M-H]^-$. $^1H$ NMR (400 MHz, DMSO-$d_6$): δ 12.95 (s, 1H), 10.37 (s, 1H), 8.72 (d, J=2.40 Hz, 1H), 8.62 (s, 1H), 8.26 (s, 1H), 8.14 (s, 1H), 8.05 (dd, J=1.60, 14.40 Hz, 1H), 7.54-7.60 (m, 1H), 7.24 (t, J=9.20 Hz, 1H), 7.15-7.19 (m, 1H), 7.05-7.07 (m, 2H), 4.93 (s, 1H), 3.68-3.76 (m, 6H), 3.48-3.53 (m, 4H), 3.02-3.13 (m, 6H), 2.71 (s, 3H), 2.69 (dd, J=2.00, 8.00 Hz, 2H), 2.61 (s, 1H), 2.51-2.56 (m, 1H), 1.70-1.81 (m, 4H), 1.02 (t, J=7.20 Hz, 3H).

Example 195

5-[4-[4-[2-[1-[4-[(2,6-dioxo-3-piperidyl) amino]-2-fluoro-phenyl]-4-hydroxy-4-piperidyl]acetyl]piperazin-1-yl]-3,5-difluoro-phenyl]-3-[3-[[ethyl(methyl) sulfamoyl]amino]-2,6-difluoro-benzoyl]-1H-pyrrolo [2,3-b]pyridine

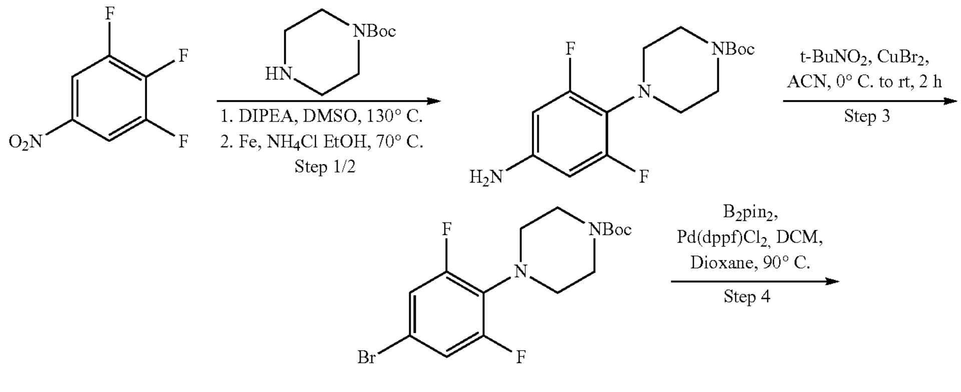

-continued

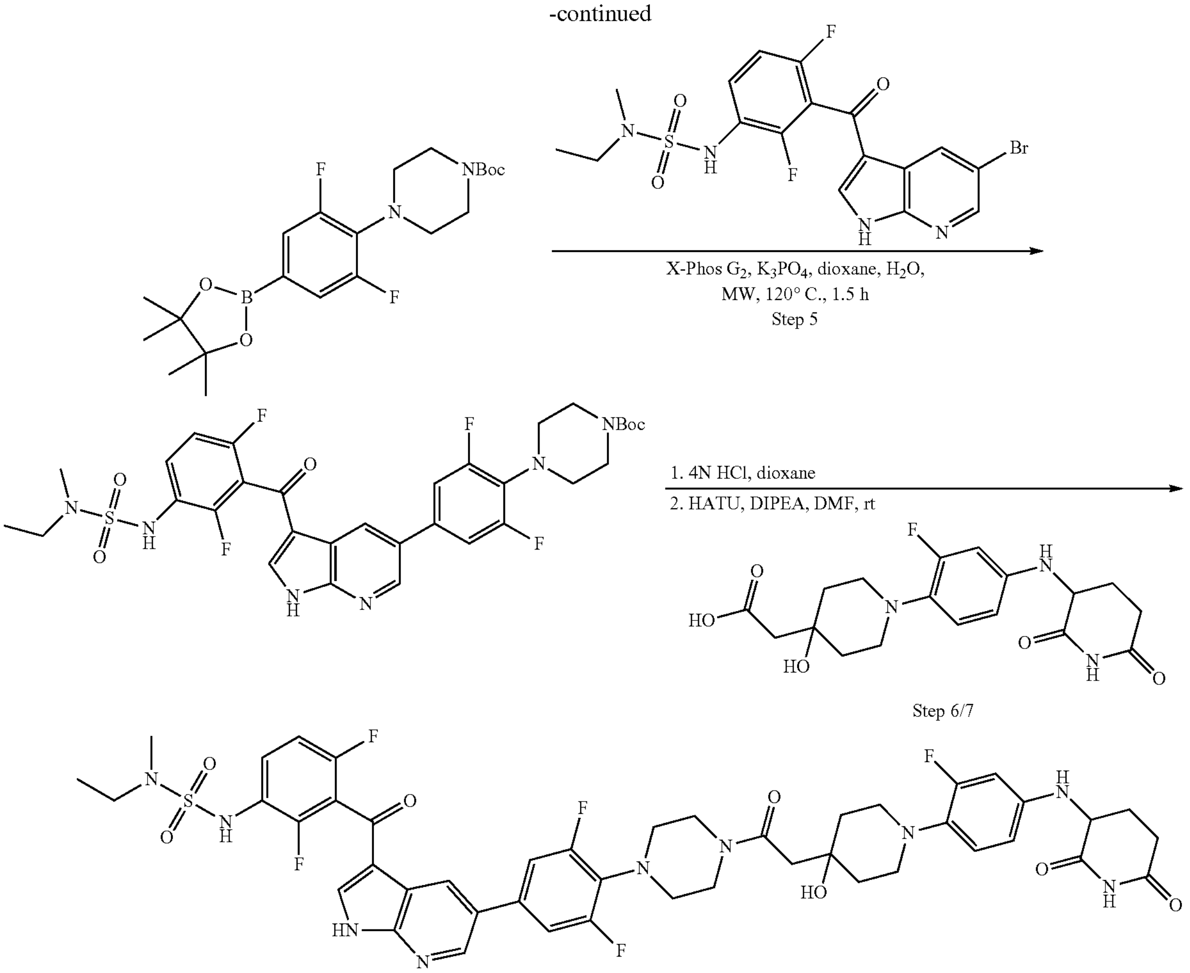

Step 1: To a stirred solution of 1,2,3-trifluoro-5-nitrobenzene (5 g, 28.24 mmol) and tert-butyl piperazine-1-carboxylate (5.26 g, 28.24 mmol) in N,N-Dimethylformamide (50 mL) was added N, N-Diisopropylethylamine (18.25 g, 141.18 mmol, 24.59 mL) at room temperature. The reaction mixture was heated to 110° C. for 12 h. After completion, the reaction mixture was diluted with water (10 mL) and extracted with ethyl acetate (2×30 mL). The combined organic layers were dried over sodium sulphate, filtered and concentrated under vacuum to get crude. The crude compound was purified by silica gel column chromatography using 20-25% ethyl acetate in petroleum ether to get tert-butyl 4-(2,6-difluoro-4-nitro-phenyl) piperazine-1-carboxylate (9.6 g, 27.96 mmol, 99.03% yield) as yellow solid. $^1$H NMR (400 MHz, DMSO-$d_6$): δ 8.02 (d, J=10.00 Hz, 2H), 3.45 (t, J=4.80 Hz, 4H), 3.23-3.30 (m, 4H), 1.43 (s, 9H).

Step 2: To a stirred solution of tert-butyl 4-(2,6-difluoro-4-nitro-phenyl) piperazine-1-carboxylate (9.6 g, 27.96 mmol) in Ethanol (80 mL) and Water (10 mL) were added Iron (7.81 g, 139.81 mmol, 993.43 μL) and Ammonium Chloride (4.49 g, 83.89 mmol, 2.93 mL) at room temperature. The reaction mixture was stirred at 70° C. for 4 h. After completion, the reaction mixture was filtered through celite and washed with ethyl acetate (300 mL). The filtrate was washed with water (100 mL), $NaHCO_3$ solution (60 mL) and brine (60 mL). The organic layer was dried over sodium sulphate and concentrated under reduced pressure to get crude, which was purified by silica gel column chromatography using 60% ethyl acetate in petroleum ether to afford tert-butyl 4-(4-amino-2,6-difluoro-phenyl) piperazine-1-carboxylate (7.1 g, 21.35 mmol, 76.36% yield) as light yellow solid. LCMS (ESI+): 214.1 $[M+H-100]^+$ Step 3: To a stirred solution of tert-butyl nitrite (987.29 mg, 9.57 mmol, 1.14 mL) and copper dibromide (2.85 g, 12.77 mmol, 605.36 μL) in Acetonitrile (20 mL) was added tert-butyl 4-(4-amino-2,6-difluoro-phenyl) piperazine-1-carboxylate (2 g, 6.38 mmol) at 0-5° C. under nitrogen. The reaction mixture was stirred at room temperature for 4 h. After completion, the reaction mixture was diluted with water (8 mL) and extracted with ethyl acetate (3×10 mL). The organic layer was washed with brine solution (10 mL), dried over sodium sulphate, concentrated under reduced pressure to get crude which was purified by column chromatography on silica gel eluted with 70% ethyl acetate in petroleum ether to afford tert-butyl 4-(4-bromo-2,6-difluoro-phenyl) piperazine-1-carboxylate (1.79 g, 3.16 mmol, 49.51% yield). LCMS (ESI+): 277.0 $[M+H-100]^+$ Step 4: A solution of tert-butyl 4-(4-bromo-2,6-difluorophenyl) piperazine-1-carboxylate (1 g, 2.65 mmol) in 1,4-Dioxane (15 mL) was taken in a sealed tube and added potassium acetate (780.51 mg, 7.95 mmol, 497.14 μL) and 4,4,5,5-tetramethyl-2-(4,4,5,5-tetramethyl-1,3,2-dioxaborolan-2-yl)-1,3,2-dioxaborolane (1.01 g, 3.98 mmol) at room temperature. The reaction mixture was purged with nitrogen gas for 10 minutes added Pd(dppf)$Cl_2$.Dichloromethane (216.49 mg, 265.09 μmol) and continued purging with nitrogen gas for 5 minutes. The reaction mixture was heated at 100° C. for 16 h. After completion, the reaction mixture was diluted with water (20 mL), extracted with ethyl acetate (3×20 mL). Combined organic layers dried over sodium sulphate, filtered and concentrated under reduced pressure to afford crude tert-butyl 4-[2,6-difluoro-4-(4,4,5,5-tetramethyl-1,3,2-dioxaborolan-2-yl) phenyl]piperazine-1-carboxylate (850 mg, 1.37 mmol, 51.54% yield). LCMS (ESI+): 325.2 $[M+H-100]^+$ Step 5: A solution of tert-butyl 4-[2,6-difluoro-4-(4,4,5,5-tetramethyl-1,3,2-dioxaborolan-2-yl) phenyl]piperazine-1-carboxylate (750 mg, 1.77 mmol) in 1,4-Dioxane (8 mL) and Water (1.5 mL) was taken in a microwave vial and added Potassium phosphate tribasic anhydrous (865.88 mg, 4.08 mmol) followed by 5-bromo-3-[3-[[ethyl(methyl)sulfamoyl]amino]-2,6-difluoro-benzoyl]-1H-pyrrolo[2,3-b] pyridine (643.55 mg, 1.36 mmol). The reaction mixture was purged with nitrogen gas for 10 minutes and added XPhos Pd G2 (106.98 mg, 135.97 μmol) and continued purging with nitrogen gas for 5 minutes. The reaction mixture was irradiated under microwave at 110° C. for 1.5 h. After completion, the reaction mixture was diluted with water (15 mL), extracted with ethyl acetate (3×20 mL). Combined organic layers dried over sodium sulphate, filtered and concentrated under reduced pressure to afford crude. Crude compound was purified by column chromatography (60-120 silica gel), by using 30-45% ethyl acetate in petroleum ether as eluent to afford tert-butyl 4-[4-[3-[3-[[ethyl(methyl)sulfamoyl]amino]-2,6-difluoro-benzoyl]-1H-pyrrolo[2,3-b] pyridin-5-yl]-3,5-difluoro-phenyl]piperazine-1-carboxylate (320 mg, 405.66 μmol, 29.83% yield). LCMS (ESI+): 691.0 $[M+H]^+$ Step 6: To a stirred solution of tert-butyl 4-[4-[3-[3-[[ethyl (methyl)sulfamoyl]amino]-2,6-difluoro-benzoyl]-1H-pyrrolo[2,3-b]pyridin-5-yl]-2,6-difluoro-phenyl]piperazine-1-carboxylate (320 mg, 463.29 μmol) in 1,4-Dioxane (2 mL) was added Hydrogen chloride solution in 1,4-dioxane (4 M, 3 mL) at 0° C. The reaction mixture was stirred at room temperature for 2 h. After completion of the reaction, the reaction mixture was concentrated under vacuum. The crude compound was washed with diethyl ether to get 5-(3,5-difluoro-4-piperazin-1-yl-phenyl)-3-[3-[[ethyl(methyl)sulfamoyl]amino]-2,6-difluoro-benzoyl]-1H-pyrrolo[2,3-b] pyridine (310 mg, 447.81 μmol, 96.66% yield). LCMS (ESI+): 591.0 $[M+H]^+$.

Target compound was prepared via COMU mediated acid-amine coupling reaction (procedure B). Amide coupling was carried out using 5-(3,5-difluoro-4-piperazin-1-yl-phenyl)-3-[3-[[ethyl(methyl)sulfamoyl]amino]-2,6-difluoro-benzoyl]-1H-pyrrolo[2,3-b]pyridine (300 mg, 507.97 μmol), 2-[1-[4-[(2,6-dioxo-3-piperidyl)amino]-2-fluoro-phenyl]-4-hydroxy-4-piperidyl]acetic acid (211.98 mg, 558.76 μmol), N,N-Diisopropylethylamine (328.25 mg, 2.54 mmol, 442.39 μL) and COMU (239.30 mg, 558.76 μmol). The crude compound was purified by reverse phase column chromatography, compound eluted with 40-45% formic acid buffer in Acetonitrile to get 5-[4-[4-[2-[1-[4-[(2,6-dioxo-3-piperidyl) amino]-2-fluoro-phenyl]-4-hydroxy-4-piperidyl] acetyl]piperazin-1-yl]-3,5-difluoro-phenyl]-3-[3-[[ethyl (methyl)sulfamoyl]amino]-2,6-difluoro-benzoyl]-1H-pyrrolo[2,3-b]pyridine (119.93 mg, 118.99 μmol, 23.42% yield) as off white solid LCMS (ESI−): 950.9 $[M-H]^-$. $^1H$ NMR (400 MHz, DMSO-$d_6$): δ 13.05 (s, 1H), 10.78 (s, 1H), 9.72 (s, 1H), 8.74 (d, J=2.80 Hz, 1H), 8.63 (s, 1H), 8.16 (s, 1H), 7.52-7.59 (m, 3H), 7.21-7.31 (m, 1H), 6.80-6.90 (m, 1H), 6.41-6.53 (m, 2H), 5.78 (d, J=10.40 Hz, 1H), 4.86 (s, 1H), 4.21-4.31 (m, 1H), 3.61-3.71 (m, 4H), 3.05-3.41 (m, 7H), 2.80-3.00 (m, 3H), 2.64-2.75 (m, 1H), 2.73 (s, 3H), 2.58 (s, 2H), 2.50-2.55 (m, 1H), 2.01-2.15 (m, 1H), 1.60-1.95 (m, 5H), 1.02 (t, J=9.20 Hz, 3H).

Example 196

5-[2-[6-[1-[4-[(2,6-dioxo-3-piperidyl)amino]-2-fluoro-phenyl]-4-piperidyl]-6-hydroxy-2-azaspiro [3.3]heptan-2-yl]pyrimidin-5-yl]-3-[3-[[ethyl (methyl)sulfamoyl]amino]-2,6-difluoro-benzoyl]-1H-pyrrolo[2,3-b]pyridine

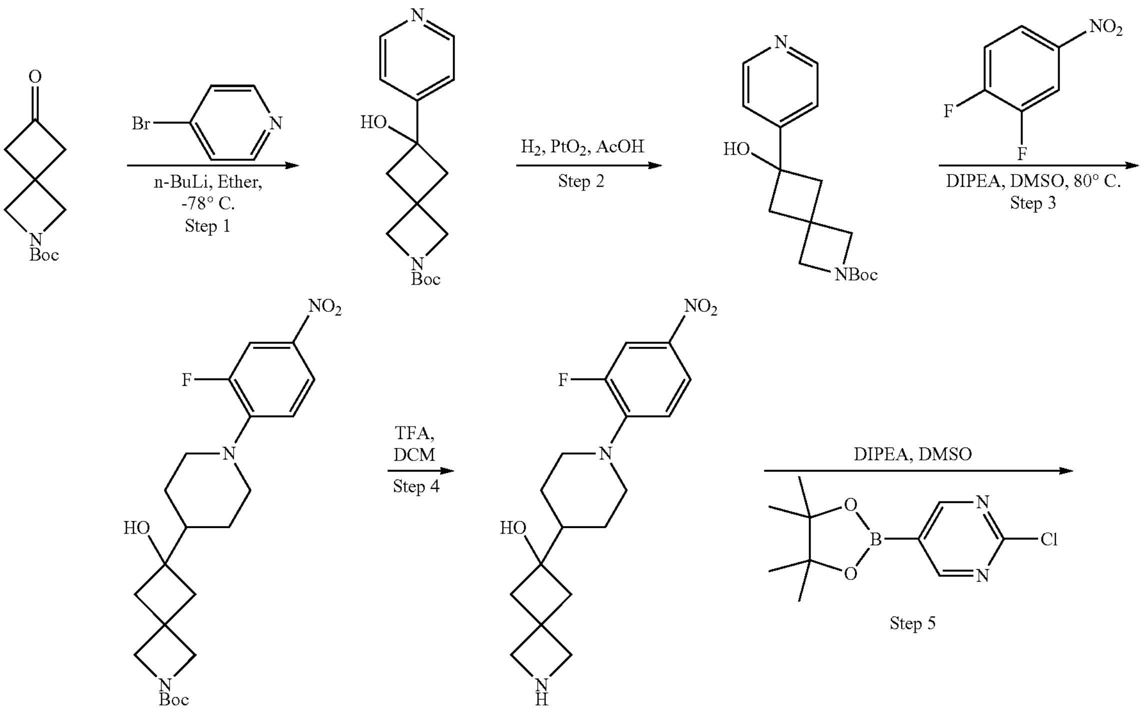

-continued

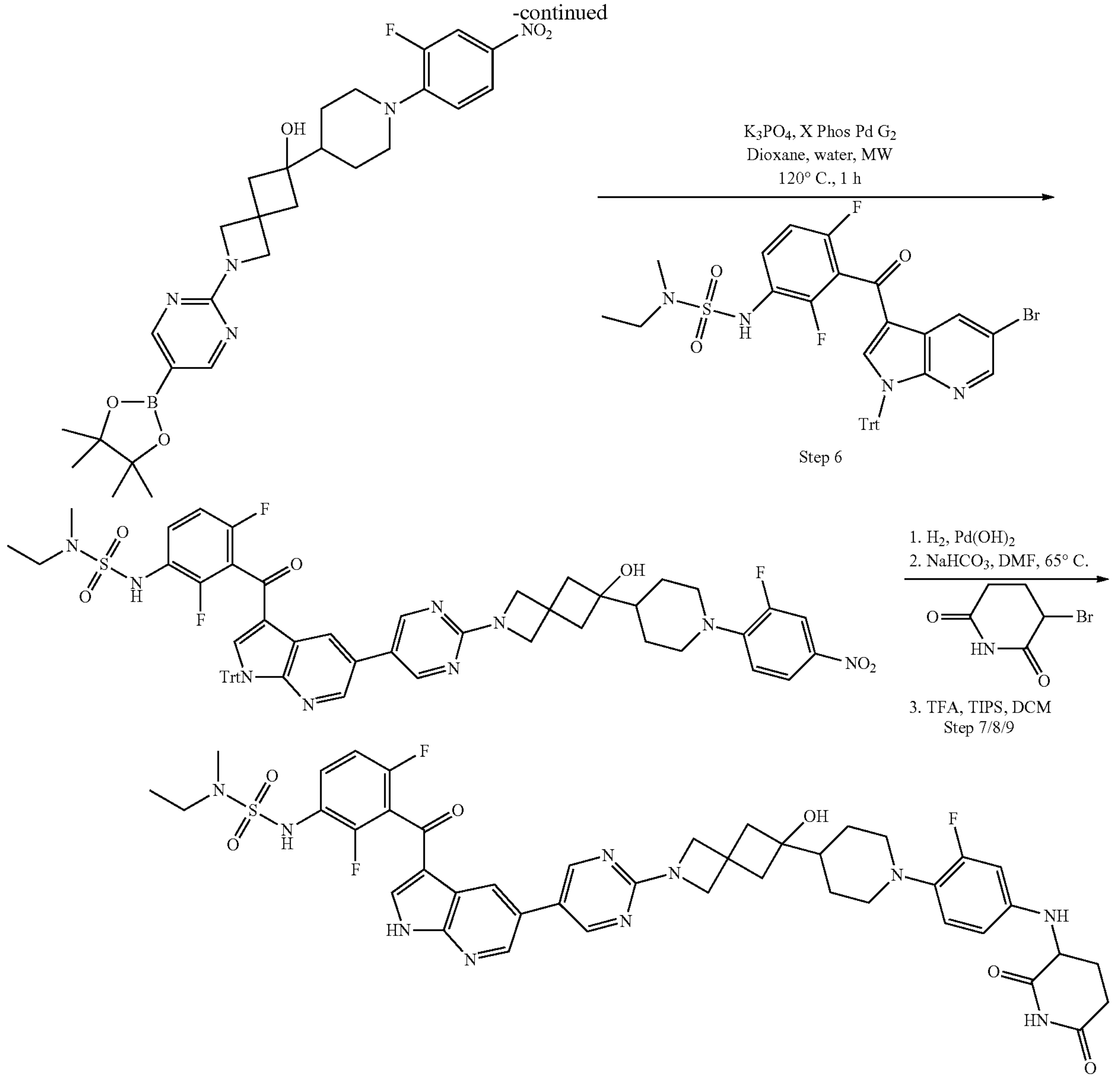

Step 1. 4-bromopyridine (1.0 g, 6.33 mmol) was taken in a dry multi neck round bottomed flak and dissolved in dry Diethyl ether (25 mL) and cooled to −78° C. To the reaction, n-butyl lithium (1.6 M, 5.93 mL) was added dropwise and continued reaction mixture for 1 h at the same temperature. Then, tert-butyl 6-oxo-2-azaspiro[3.3]heptane-2-carboxylate (1.47 g, 6.96 m mol) was added at −78° C. and continued the reaction at the same temperature for 4 h. After completion, reaction mixture was quenched with saturated $NH_4Cl$ solution and extracted with Ethyl acetate (3×50 mL) and water (50 mL). The combined organic layers were dried over anhydrous sodium sulphate and concentrated under vacuum to get the crude compound. The crude compound was purified by silica gel column chromatography using 10% methanol in Dichloromethane as a eluent to afford tert-butyl 6-hydroxy-6-(4-pyridyl)-2-azaspiro[3.3]heptane-2-carboxylate (850 mg, 2.90 mmol, 45.79% yield) as off white solid. LCMS (ESI+): 291.1 $[M+H]^+$ Step 2: A solution of tert-butyl 6-hydroxy-6-(4-pyridyl)-2-azaspiro[3.3]heptane-2-carboxylate (850 mg, 2.93 mmol) in Ethanol (12 mL) and acetic acid (87.90 mg, 1.46 mmol) was taken in a tiny clave and added Platinum (IV) oxide (664.75 mg, 2.93 mmol) at room temperature. The reaction mixture subjected to hydrogenation with 5 $Kg/Cm^3$ pressure at room temperature for 16 h. After completion, the reaction mixture was filtered through celite pad and the filtrate was concentrated under reduced pressure. The crude compound was triturated with diethyl ether to afford tert-butyl 6-hydroxy-6-(4-piperidyl)-2-azaspiro[3.3]heptane-2-carboxylate (700 mg, 2.34 mmol, 79.87% yield) as off white solid. LCMS (ESI+): 297.0 $[M+H]^+$.

Step 3: A solution of tert-butyl 6-hydroxy-6-(4-piperidyl)-2-azaspiro[3.3]heptane-2-carboxylate (500 mg, 1.69 mmol) in Dimethylsulfoxide (7 mL) taken in a sealed tube and added N, N-Diisopropylethylamine (654.05 mg, 5.06 mmol, 881.48 μL) and 1,2-difluoro-4-nitro-benzene (295.20 mg, 1.86 mmol, 205.00 μL) at room temperature under nitrogen atmosphere. The reaction mixture was heated to 80° C. for 16 h. After completion, reaction mixture was cooled to room temperature and extracted with ethyl acetate (3×70 mL) and water (70 mL). The combined organic layers were dried over anhydrous sodium sulphate and concentrated under vacuum to get the crude compound. The crude compound was purified by silica gel column chromatography using 30-40% ethyl acetate in petroleum ether as a eluent to afford tert-butyl 6-[1-(2-fluoro-4-nitro-phenyl)-4-piperidyl]-6-hydroxy-2-azaspiro[3.3]heptane-2-carboxylate (320 mg, 639.28 μmol, 37.90% yield) as a yellow solid. LCMS (ESI+): 436.2 $[M+H]^+$ Step 4: To a stirred solution of tert-butyl 6-[1-(2-fluoro-4-nitro-phenyl)-4-piperidyl]-6-hydroxy-2-azaspiro[3.3]heptane-2-carboxylate (320 mg, 734.81 μmol) in dichloromethane (5 mL) was added trifluoro acetic acid (418.93 mg, 3.67 mmol, 283.06 μL) at 0° C. The reaction mixture stirred at room temperature for 4 h. After completion, the reaction mixture was concentrated under reduced pressure to afford 6-[1-(2-fluoro-4-nitro-phenyl)-4-piperidyl]-2-azaspiro[3.3]heptan-6-ol (320 mg, 647.98 μmol, 88.18% yield) as a brown gummy compound, which was carried forward without further purification. LCMS (ESI+): 336.2 $[M+H]^+$.

Step 5: A solution of 6-[1-(2-fluoro-4-nitro-phenyl)-4-piperidyl]-2-azaspiro[3.3]heptan-6-ol (320 mg, 954.16 μmol) in N,N-Dimethylformamide (4 mL) was taken in a sealed tube and added N,N-Diisopropylethylamine (369.96 mg, 2.86 mmol, 498.59 μL) and 2-chloro-5-(4,4,5,5-tetramethyl-1,3,2-dioxaborolan-2-yl)pyrimidine (344.21 mg, 1.43 mmol) at room temperature under nitrogen atmosphere. The reaction mixture was heated to 100° C. for 16 h. After completion, the reaction mixture was cooled to room temperature and extracted with ethyl acetate (3×100 mL) and water (70 mL). The combined organic layers were dried over anhydrous sodium sulphate and concentrated under vacuum to get the crude compound. The crude compound was triturated using 30-40% ethyl acetate in petroleum ether to afford [2-[6-[1-(2-fluoro-4-nitro-phenyl)-4-piperidyl]-6-hydroxy-2-azaspiro[3.3]heptan-2-yl]pyrimidin-5-yl]boronic acid/ester (220 mg, 437.82 μmol, 45.89% yield) as a yellow solid. LCMS (ESI+): 458.1 $[M+H]^+$.

Step 6: A solution of 5-bromo-3-[3-[[ethyl(methyl)sulfamoyl]amino]-2,6-difluoro-benzoyl]-1-trityl-pyrrolo[2,3-b]pyridine (300.48 mg, 419.89 μmol) in 1,4-dioxane (4 mL) and Water (1 mL) mixture taken in microwave vial and added $K_3PO_4$ (267.39 mg, 1.26 mmol) and [2-[6-[1-(2-fluoro-4-nitro-phenyl)-4-piperidyl]-6-hydroxy-2-azaspiro[3.3]heptan-2-yl]pyrimidin-5-yl]boronic acid/ester (288 mg, 629.84 μmol) at room temperature under nitrogen atmosphere. The reaction mixture was degassed with nitrogen for 10 minutes and added XPhos Pd G2 (33.03 mg, 41.99 μmol) at same temperature. The reaction mixture was irradiated under microwave at 120° C. for 90 minutes. After completion, water (200 mL) was added to the reaction mixture and extracted with ethyl acetate (3×150 mL). The combined organic layers were washed with brine solution (200 mL), dried over sodium sulphate, filtered and concentrated under reduced pressure to get the crude. The crude compound was purified by silica gel column chromatography with 90-100% ethyl acetate in petroleum ether as a eluent to afford 3-[3-[[ethyl(methyl)sulfamoyl]amino]-2,6-difluoro-benzoyl]-5-[2-[6-[1-(2-fluoro-4-nitro-phenyl)-4-piperidyl]-6-hydroxy-2-azaspiro[3.3]heptan-2-yl]pyrimidin-5-yl]-1-trityl-pyrrolo[2,3-b]pyridine (400 mg, 353.77 μmol, 84.25% yield) as yellow solid. LCMS (ESI+): 1048.9 $[M+H]^+$.

Step 7: To a stirred solution of 3-[3-[[ethyl(methyl)sulfamoyl]amino]-2,6-difluoro-benzoyl]-5-[2-[6-[1-(2-fluoro-4-nitro-phenyl)-4-piperidyl]-6-hydroxy-2-azaspiro[3.3]heptan-2-yl]pyrimidin-5-yl]-1-trityl-pyrrolo[2,3-b]pyridine (400 mg, 381.63 μmol) in ethyl acetate (8 mL) was charged with 5% Palladium hydroxide on carbon (300 mg, 2.43 mmol) and the resulting reaction mixture was saturated with hydrogen by bubbling hydrogen gas through for 10 minutes and subjected to hydrogenation (1 atm) at room temperature for 16 h. After completion, the reaction mixture was filtered through celite pad using ethyl acetate and filtrate was concentrated under reduced pressure to get the crude. The crude compound was triturated with diethyl ether to afford 5-[2-[6-[1-(4-amino-2-fluoro-phenyl)-4-piperidyl]-6-hydroxy-2-azaspiro[3.3]heptan-2-yl]pyrimidin-5-yl]-3-[3-[[ethyl(methyl)sulfamoyl]amino]-2,6-difluoro-benzoyl]-1-trityl-pyrrolo[2,3-b]pyridine (340 mg, 290.53 μmol, 76.13% yield) as a pale yellow solid. LCMS (ESI+): 1018.3 $[M+H]^+$ Step 8: A solution of 5-[2-[6-[1-(4-amino-2-fluoro-phenyl)-4-piperidyl]-6-hydroxy-2-azaspiro[3.3]heptan-2-yl]pyrimidin-5-yl]-3-[3-[[ethyl(methyl)sulfamoyl]amino]-2,6-difluoro-benzoyl]-1-trityl-pyrrolo[2,3-b]pyridine (340 mg, 333.94 μmol) in N,N-Dimethylformamide (5 mL) taken in a sealed tube and added Sodium bicarbonate (84.16 mg, 1.00 mmol, 38.96 μL) followed by 3-bromopiperidine-2,6-dione (320.60 mg, 1.67 mmol) at room temperature under nitrogen atmosphere. The reaction mixture was heated to 70° C. for 48 h. After completion, reaction mixture was cooled to room temperature, diluted with water (100 mL) and extracted with ethyl acetate (3×150 mL). The combined organic layers were washed with ice cold water (3×200 mL), dried over sodium sulphate, filtered and concentrated under reduced pressure to get the crude. The crude compound was purified by silica gel column chromatography with 60-70% ethyl acetate in petroleum ether as a eluent to afford 5-[2-[6-[1-[4-[(2,6-dioxo-3-piperidyl)amino]-2-fluoro-phenyl]-4-piperidyl]-6-hydroxy-2-azaspiro[3.3]heptan-2-yl]pyrimidin-5-yl]-3-[3-[[ethyl(methyl)sulfamoyl]amino]-2,6-difluoro-benzoyl]-1-trityl-pyrrolo[2,3-b]pyridine (330 mg, 237.79 μmol, 71.21% yield) as a pale grey solid. LCMS (ESI+): 1129.9 $[M+H]^+$ Step 9: To a stirred solution of 5-[2-[6-[1-[4-[(2,6-dioxo-3-piperidyl)amino]-2-fluoro-phenyl]-4-piperidyl]-6-hydroxy-2-azaspiro[3.3]heptan-2-yl]pyrimidin-5-yl]-3-[3-[[ethyl(methyl)sulfamoyl]amino]-2,6-difluoro-benzoyl]-1-trityl-pyrrolo[2,3-b]pyridine (230 mg, 203.67 μmol) in Dichloromethane (5 mL) were added Tri-isopropyl silane, 98% (309.20 mg, 1.95 mmol, 0.4 mL) and trifluoroacetic acid (1.48 g, 12.98 mmol, 1 mL) at 0° C. under nitrogen atmosphere. The reaction mixture was stirred at room temperature for 4 h under nitrogen atmosphere. After completion, the reaction mixture was concentrated under vacuum to afford crude. The desired product was purified from crude by reverse phase column chromatography (0.1% Formic acid in water:Acetonitrile) and fractions were lyophilized to afford 5-[2-[6-[1-[4-[(2,6-dioxo-3-piperidyl)amino]-2-fluoro-phenyl]-4-piperidyl]-6-hydroxy-2-azaspiro[3.3]heptan-2-yl]pyrimidin-5-yl]-3-[3-[[ethyl(methyl)sulfamoyl]amino]-2,6-difluoro-benzoyl]-1H-pyrrolo[2,3-b]pyridine (44.67 mg, 45.87 μmol, 22.52% yield) as a pale green solid. LCMS (ESI+): 887.3 $[M+H]^+$. $^1H$ NMR (400 MHz, DMSO-$d_6$): δ 12.97 (s, 1H), 10.79 (s, 1H), 9.86 (s, 1H), 8.73 (s, 2H), 8.65 (d, J=2.00 Hz, 1H), 8.54 (s, 1H), 8.13 (s, 1H), 7.54-7.60 (m, 1H), 7.26 (t, J=8.40 Hz, 1H), 6.85 (t, J=9.60 Hz, 1H), 6.53 (d, J=2.40 Hz, 1H), 6.49 (d, J=2.40 Hz, 1H), 5.79 (d, J=7.60 Hz, 1H), 4.77 (s, 1H), 4.20-4.30 (m, 1H), 4.12-4.26 (m, 4H), 3.20 (d, J=10.80 Hz, 2H), 3.10 (q, J=7.20 Hz, 2H), 2.65-2.76 (m, 1H), 2.74 (s, 3H), 2.41-2.60 (m, 5H), 2.17 (d, J=12.80 Hz, 2H), 2.08-2.10 (m, 1H), 1.76-1.90 (m, 1H), 1.62-1.70 (m, 2H), 1.41-1.50 (m, 2H), 1.02 (t, J=7.20 Hz, 3H).

Example 197

5-[6-[4-[2-[1-[2-(difluoromethyl)-4-[(2,6-dioxo-3-piperidyl)amino]phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine

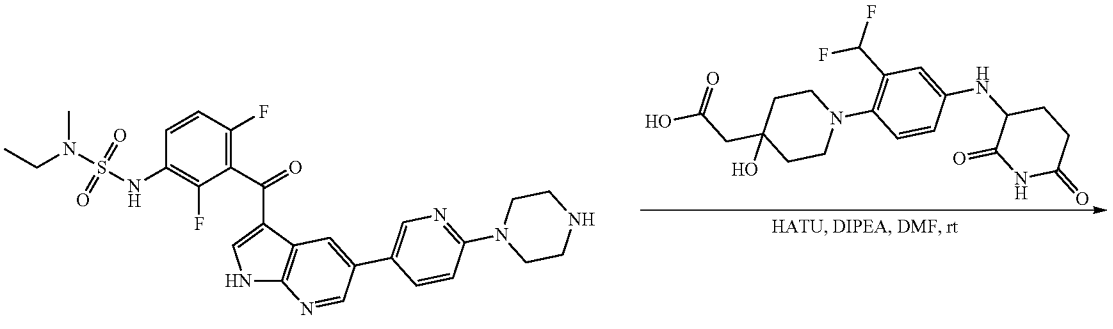

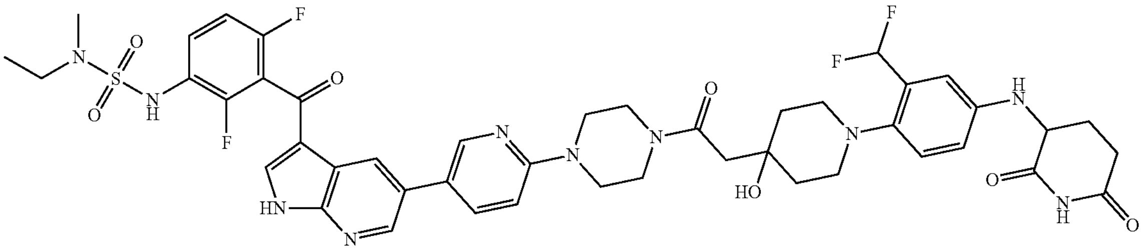

Target compound was prepared via HATU mediated acid-amine coupling reaction (procedure A). Amide coupling was carried out 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (370 mg, 665.95 μmol), 2-[1-[2-(difluoromethyl)-4-[(2,6-dioxo-3-piperidyl)amino]phenyl]-4-hydroxy-4-piperidyl]acetic acid (273.97 mg, 665.95 HATU (379.82 mg, 998.92 μmol) and N,N-Diisopropylethylamine (258.21 mg, 2.00 mmol, 347.99 μL) to yield 5-[6-[4-[2-[1-[2-(difluoromethyl)-4-[(2,6-dioxo-3-piperidyl)amino]phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine (134.55 mg, 133.41 μmol, 20.03% yield) as off white solid. LCMS (ESI+): 949.2 $[M+H]^+$. $^1H$ NMR (400 MHz, DMSO-$d_6$): δ 13.00 (s, 1H), 10.78 (s, 1H), 9.91 (s, 1H), 8.68 (d, J=2.00 Hz, 1H), 1.56 (s, 1H), 8.52 (d, J=2.40 Hz, 1H), 8.11 (s, 1H), 7.98 (dd, J=2.40, 8.80 Hz, 1H), 7.55-7.61 (m, 1H), 7.25 (t, J=8.00 Hz, 1H), 7.15 (d, J=8.40 Hz, 1H), 7.11 (s, 1H), 7.02 (d, J=-8.00 Hz, 1H), 6.76-6.85 (m, 2H), 5.98 (d, J=8.00 Hz, 1H), 4.91 (s, 1H), 4.31-4.41 (m, 1H), 3.65-3.73 (m, 8H), 3.10 (q, J=7.20 Hz, 2H), 2.95-3.01 (m, 2H), 2.71-2.80 (m, 1H), 2.73 (s, 3H), 2.55-2.70 (m, 3H), 2.61 (s, 2H), 2.05-2.12 (m, 1H), 1.65-1.95 (m, 5H), 1.02 (t, J=7.20 Hz, 3H).

Example 198

5-[4-[4-[2-[1-[4-[(2,6-dioxo-3-piperidyl)amino]-2-fluoro-phenyl]-4-hydroxy-4-piperidyl]acetyl]piperazin-1-yl]-3-fluoro-phenyl]-3-[3-[[ethyl(methyl)sulfamoyl]amino]-2,6-difluoro-benzoyl]-1H-pyrrolo[2,3-b]pyridine

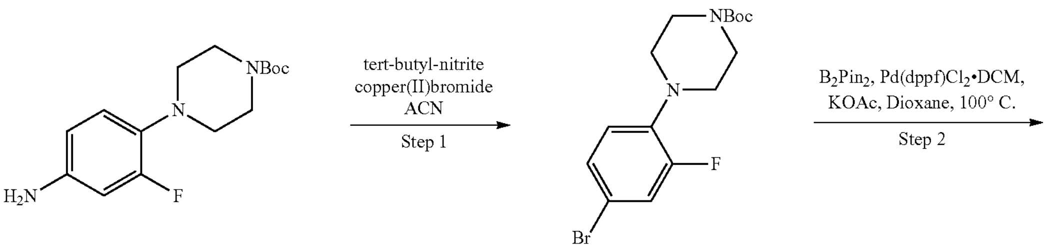

-continued

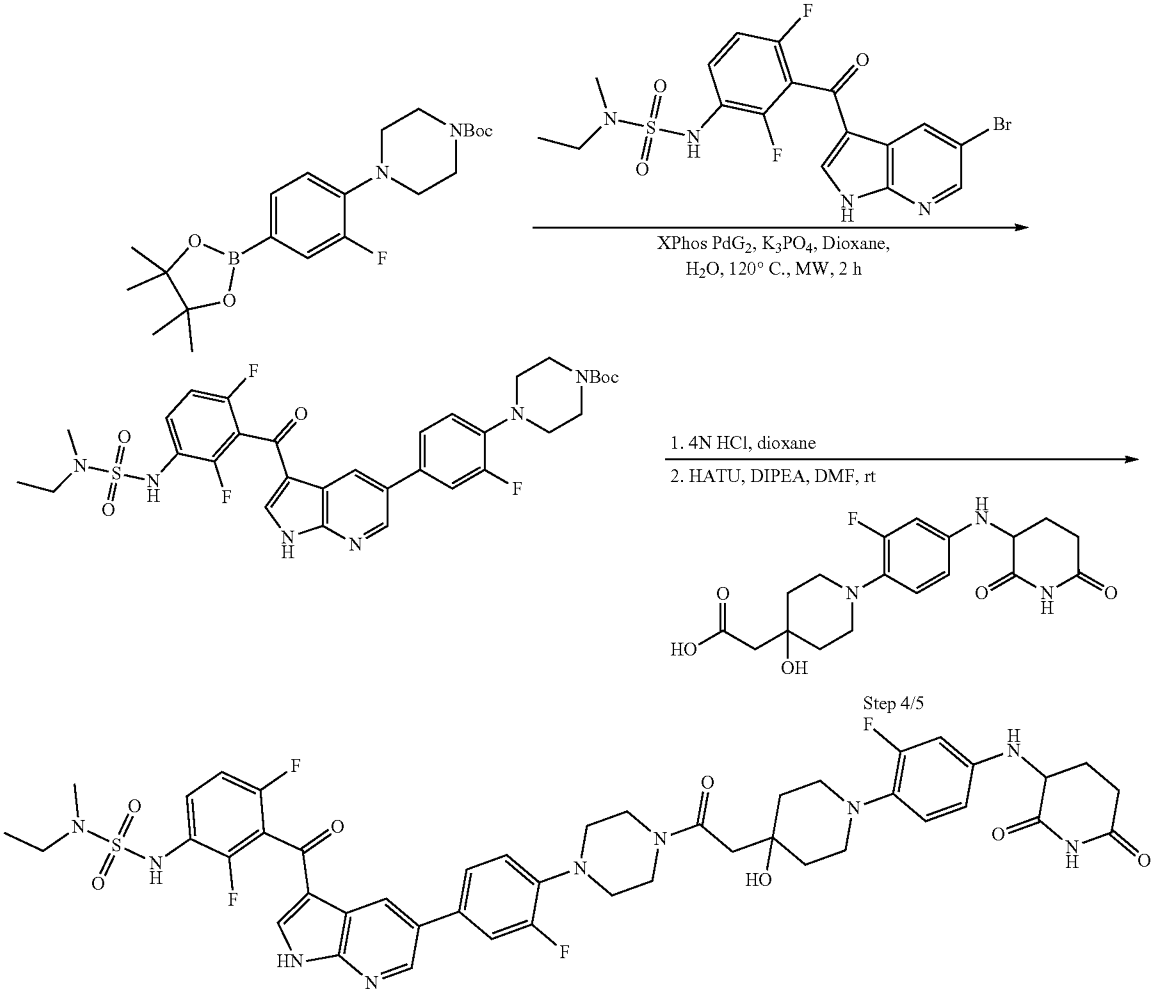

Step 1: A mixture of copper (II) bromide (1.18 g, 5.28 mmol, 250.47 μL), tert-Butyl nitrite, tech. 90% (628.46 mg, 6.09 mmol, 724.86 μL) was taken in Acetonitrile (20 mL) and added tert-butyl 4-(4-amino-2-fluoro-phenyl)piperazine-1-carboxylate (1.2 g, 4.06 mmol) 0° C. The reaction mixture was and stirred for 3 h at room temperature. The reaction mixture was diluted with ethyl acetate (100 mL), washed with water (40 mL), brine (40 mL). The combined organic layers were dried over sodium sulphate and concentrated under reduced pressure to get crude. The crude compound was purified by column chromatography on silica gel eluted with 5% ethyl acetate in petroleum ether to afford tert-butyl 4-(4-bromo-2-fluoro-phenyl)piperazine-1-carboxylate (600 mg, 1.40 mmol, 34.53% yield) as light brown sticky solid. LCMS (ESI+): 259.0 $[M-100+H]^+$.

Step 2: A solution of tert-butyl 4-(4-bromo-2-fluoro-phenyl)piperazine-1-carboxylate (600 mg, 1.67 mmol), $B_2Pin_2$ (897.13 mg, 2.51 mmol) in 1,4-dioxane (8 mL) was placed in seal tube and degassed with nitrogen for 15 minutes. $Pd(dppf)Cl_2$.Dichloromethane (136.40 mg, 167.02 μmol), Potassium Acetate (491.76 mg, 5.01 mmol, 313.22 μL) were added to the reaction mixture and heated at 100° C. for 14 h. The reaction mixture was diluted with ethyl acetate (100 mL), washed with water (30 mL) and brine (30 mL). The combined organic layers was dried over sodium sulphate and concentrated under reduced pressure to get crude which was purified by column chromatography on silica gel eluted with 10% ethyl acetate in petroleum ether to afford tert-butyl 4-[2-fluoro-4-(4,4,5,5-tetramethyl-1,3,2-dioxaborolan-2-yl)phenyl]piperazine-1-carboxylate (540 mg, 917.06 μmol, 54.91% yield) as brown solid. LCMS (ESI+): 407.2 $[M+H]^+$.

Step 3: A solution of 5-bromo-3-[3-[[ethyl(methyl)sulfamoyl]amino]-2,6-difluoro-benzoyl]-1H-pyrrolo[2,3-b]pyridine (500 mg, 1.06 mmol) in 1,4-dioxane (12 mL), Water (2 mL) was taken in a microwave vial and added tert-butyl 4-[2-fluoro-4-(4,4,5,5-tetramethyl-1,3,2-dioxaborolan-2-yl)phenyl]piperazine-1-carboxylate (429.23 mg, 1.06 mmol), anhydrous Potassium phosphate (672.75 mg, 3.17 mmol) at room temperature under nitrogen atmosphere. The reaction mixture was degassed with nitrogen for 10 minutes, XPhos Pd G2 (82.96 mg, 105.64 μmol) was added to the reaction mixture and irradiated in microwave at 100° C. for 1 h.

After completion, the reaction mixture was diluted with water (60 mL) and extracted with ethyl acetate (2×100 mL). The combined organic layers were dried over sodium sulphate, filtered and concentrated under reduced pressure. The crude compound was purified by silica gel column chromatography with 70% ethyl acetate in petroleum ether as a eluent to afford tert-butyl 4-[4-[3-[3-[[ethyl(methyl)sulfamoyl]amino]-2,6-difluoro-benzoyl]-1H-pyrrolo[2,3-b]pyridin-5-yl]-2-fluoro-phenyl]piperazine-1-carboxylate (250 mg, 273.52 μmol, 25.89% yield) as light brown solid. LCMS (ESI+): 673.3 $[M+H]^+$.

Step 4: To a stirred solution of tert-butyl 4-[4-[3-[3-[[ethyl(methyl)sulfamoyl]amino]-2,6-difluoro-benzoyl]-1H-pyrrolo[2,3-b]pyridin-5-yl]-2-fluoro-phenyl]piperazine-1-carboxylate (220 mg, 327.03 μmol) in 1,4-dioxane (2 mL) was added Hydrogen chloride in 1,4-dioxane, (4M, 5 mL) at 0° C. under nitrogen atmosphere. The reaction mixture was stirred at room temperature for 4 h. After completion, the reaction mixture was concentrated under reduced pressure to get crude product. The crude mixture was triturated with diethyl ether to afford 3-[3-[[ethyl(methyl)sulfamoyl]amino]-2,6-difluoro-benzoyl]-5-(3-fluoro-4-piperazin-1-yl-phenyl)-1H-pyrrolo[2,3-b]pyridine (215 mg, 322.64 μmol, 98.66% yield). LCMS (ESI+): 573.2 $[M+H]^+$ Step 5: Target compound was prepared via HATU mediated acid-amine coupling reaction (procedure A). Amide coupling was carried out using 2-[1-[4-[(2,6-dioxo-3-piperidyl)amino]-2-fluoro-phenyl]-4-hydroxy-4-piperidyl]acetic acid (149.08 mg, 392.94 μmol), 3-[3-[[ethyl(methyl)sulfamoyl]amino]-2,6-difluoro-benzoyl]-5-(3-fluoro-4-piperazin-1-yl-phenyl)-1H-pyrrolo[2,3-b]pyridine (225 mg, 392.94 μmol), N,N-Diisopropylethylamine (203.14 mg, 1.57 mmol, 273.77 μL) and HATU (164.35 mg, 432.24 μmol).

The crude compound was purified by reverse phase column chromatography by using 120 g snap eluted with 45% Acetonitrile in 0.1% formic acid in water to afford 5-[4-[4-[2-[1-[4-[(2,6-dioxo-3-piperidyl)amino]-2-fluoro-phenyl]-4-hydroxy-4-piperidyl]acetyl]piperazin-1-yl]-3-fluoro-phenyl]-3-[3-[[ethyl(methyl)sulfamoyl]amino]-2,6-difluoro-benzoyl]-1H-pyrrolo[2,3-b]pyridine (110 mg, 106.30 μmol, 27.05% yield) as off white solid. LCMS (ESI+): 934.3 $[M+H]^+$. $^1H$ NMR (400 MHz, DMSO-$d_6$): δ 12.95 (s, 1H), 10.79 (s, 1H), 8.70 (d, J=2.40 Hz, 1H), 8.58 (s, 1H), 8.36 (s, 1H), 8.10 (s, 1H), 7.52-7.64 (m, 3H), 7.19 (t, J=8.80 Hz, 2H), 6.86 (t, J=9.60 Hz, 1H), 6.51 (dd, J=2.40, 15.20 Hz, 1H), 6.42 (dd, J=2.40, 8.60 Hz, 1H), 5.79 (d, J=7.60 Hz, 1H), 4.87 (s, 1H), 4.21-4.30 (m, 1H), 3.71-3.76 (m, 4H), 3.05-3.15 (m, 6H), 2.89-2.94 (m, 4H), 2.66-2.75 (m, 1H), 2.72 (s, 3H), 2.59 (s, 2H), 2.51-2.56 (m, 1H), 2.05-2.09 (m, 1H), 1.67-1.87 (m, 5H), 1.01 (t, J=7.20 Hz, 3H).

Example 199

5-[2-[6-[1-[4-[(2,6-dioxo-3-piperidyl)amino]-2-fluoro-phenyl]-4-piperidyl]-2-azaspiro[3.3]heptan-2-yl]pyrimidin-5-yl]-3-[3-[[ethyl(methyl)sulfamoyl]amino]-2,6-difluoro-benzoyl]-1H-pyrrolo[2,3-b]pyridine

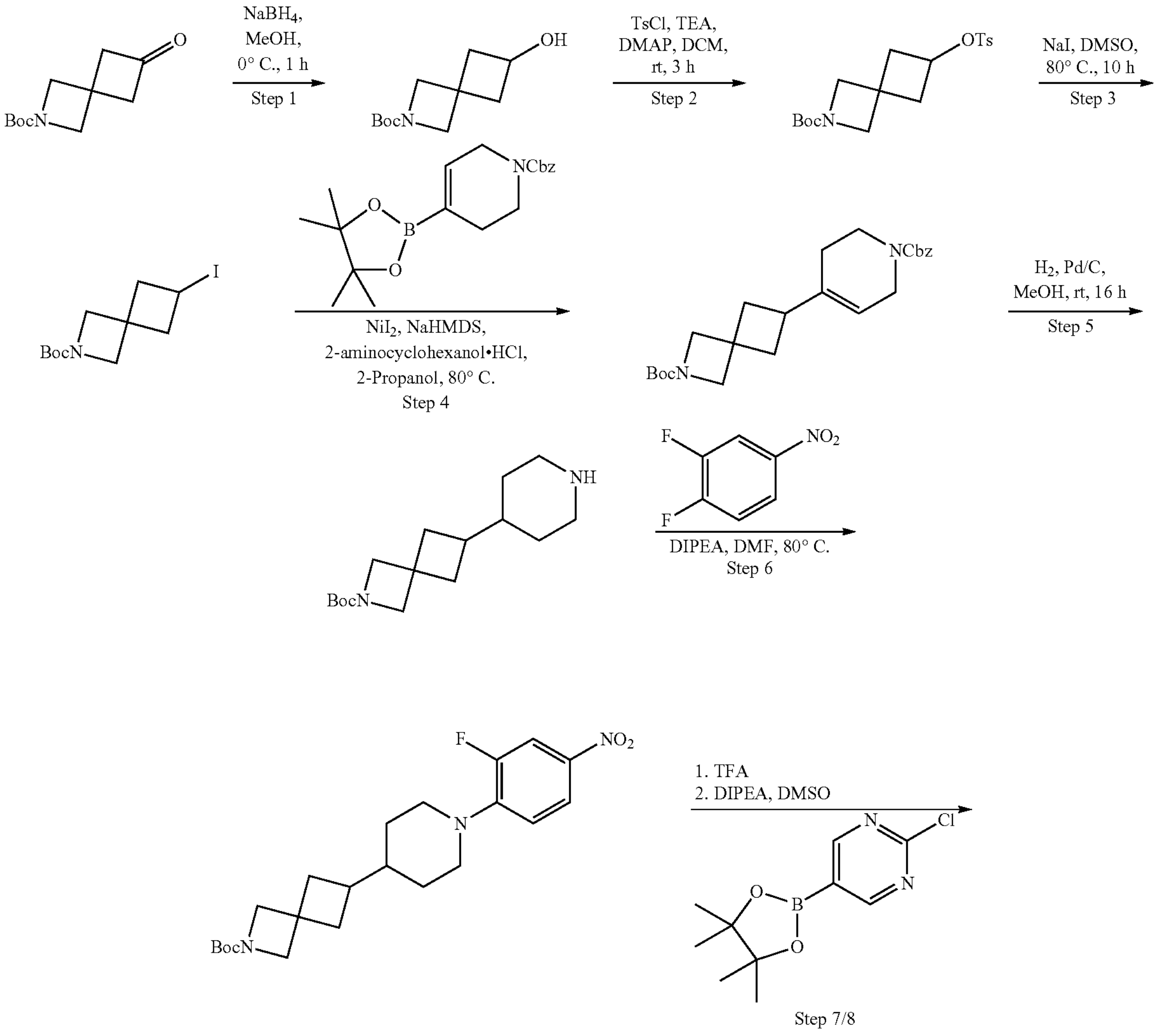

-continued

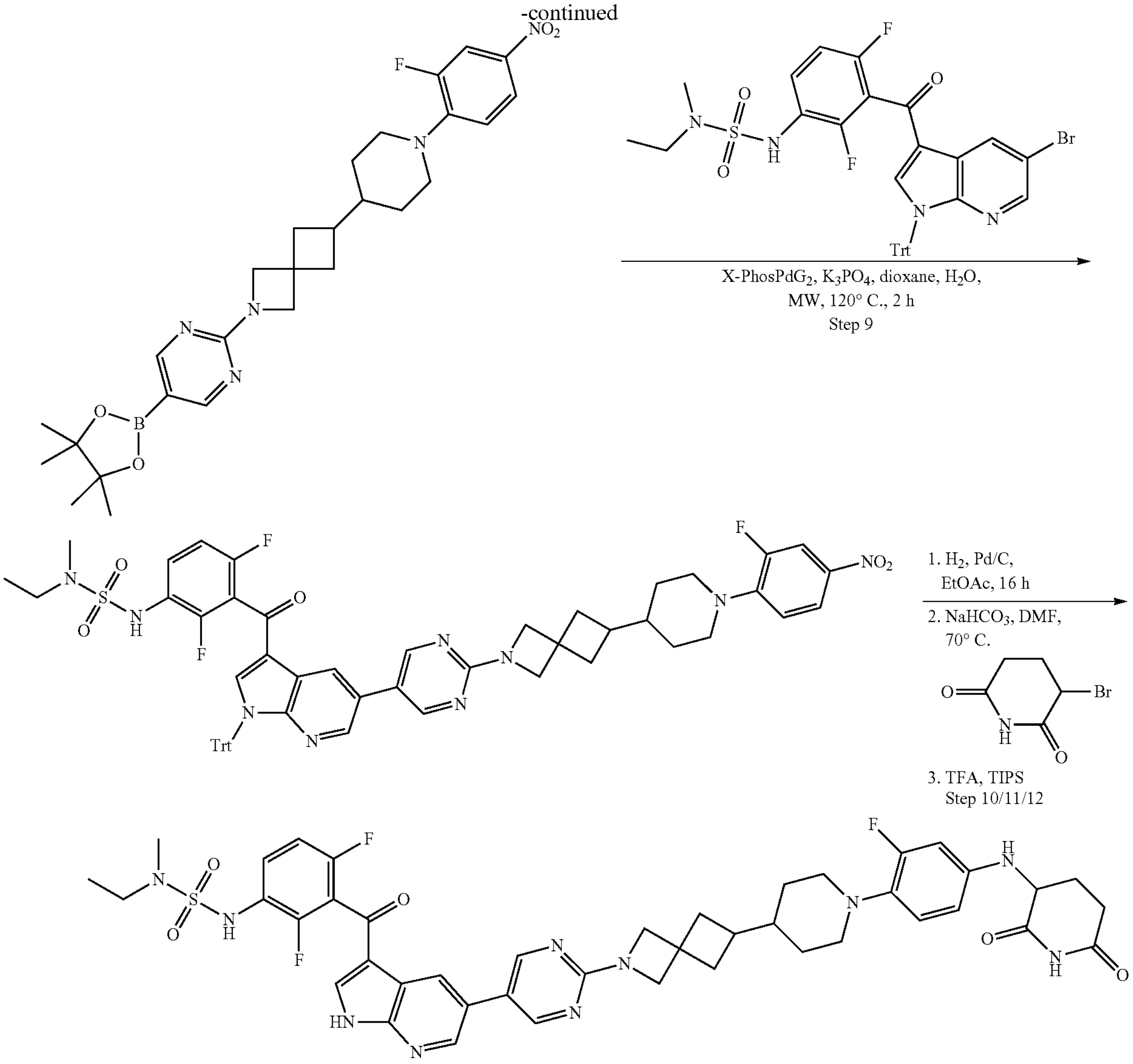

Step 1: To a stirred solution of tert-butyl 6-oxo-2-azaspiro[3.3]heptane-2-carboxylate (15 g, 71.00 mmol) in Methanol (150 mL) was added Sodium Borohydride (6.72 g, 177.51 mmol, 6.28 mL) at 0° C., then stirred the reaction at 0° C. for 1 h. After completion, reaction mixture was concentrated on rotavapor, then extracted with Dichloromethane (3×250 mL) and water (200 mL). The combined organic layers were dried over sodium sulphate, filtered and concentrated to get the crude compound. The crude compound was triturated with Petroleum ether washing to afford tert-butyl 6-hydroxy-2-azaspiro[3.3]heptane-2-carboxylate (14.2 g, 65.92 mmol, 92.83% yield) as white solid. LCMS (ESI+): 113.9 [M+H−100]$^+$ Step 2: To a stirred solution of tert-butyl 6-hydroxy-2-azaspiro[3.3]heptane-2-carboxylate (15 g, 70.33 mmol) in Dichloromethane (150 mL) was added to the Triethylamine (21.35 g, 211.00 mmol, 29.41 mL), 4-methylbenzenesulfonyl chloride (13.41 g, 70.33 mmol) and catalytic amount of N,N-dimethylpyridin-4-amine (859.24 mg, 7.03 mmol) at 0° C. The reaction mixture was stirred at room temperature for 3 h. After completion of the reaction, reaction mixture was extracted with Dichloromethane (3×200 mL) and water (300 mL). The combined organic layers were dried over anhydrous sodium sulphate and concentrated under vacuum to get the crude compound. The crude compound was purified by silica gel column chromatography with 40% ethyl acetate in petroleum ether as a eluent to afford tert-butyl 6-(p-tolylsulfonyloxy)-2-azaspiro[3.3]heptane-2-carboxylate (16.2 g, 43.20 mmol, 61.43% yield) as an off white solid. LCMS (ESI+): 268.1 [M+H−100]$^+$ Step 3: A solution of tert-butyl 6-(p-tolylsulfonyloxy)-2-azaspiro[3.3]heptane-2-carboxylate (16.2 g, 44.09 mmol) in DMSO (160 mL) was taken in a sealed tube and added sodium iodide (26.43 g, 176.35 mmol, 7.20 mL) at room temperature. The reaction mixture was heated at 80° C. for 16 h. After completion, the reaction mixture was diluted with cold water (100 mL) and extracted with Dichloromethane (3×100 mL). The combined organic layers were dried over anhydrous sodium sulphate, filtered and concentrated to get the crude compound. The crude compound was triturated using petroleum ether to afford tert-butyl 6-iodo-2-azaspiro[3.3]heptane-2-carboxylate (13 g, 39.82 mmol, 90.33% yield) as an off-white solid. LCMS (ESI+): 268.0 [M+H−56]$^+$ Step 4: To a stirred solution of tert-butyl 6-iodo-2-azaspiro[3.3]heptane-2-carboxylate (4 g, 12.38 mmol) in 2-propanol (60 mL) were added benzyl 4-(4,4,5,5-tetramethyl-1,3,2-dioxaborolan-2-yl)-3,6-dihydro-2H-pyridine-1-carboxylate (5.10 g, 14.85 mmol), (1R,2R)-2-aminocyclohexanol hydrochloride (187.68 mg, 1.24 mmol) and Nile (386.80 mg, 1.24 mmol) and the resulting reaction mixture was purged with nitrogen gas for 15 minutes followed by NaHMDS (1 M, 24.75 mL) was added. The resulting reaction mixture was heated at 80° C. for 3 h. After completion, water (50 mL) was added to the reaction mixture and extracted with ethyl acetate (2×50 mL). The combined organic layers were dried over anhydrous sodium sulphate, filtered and filtrate was evaporated under reduced pressure to get the desired crude. Further obtained crude was purified by silica gel chromatography using 25% Ethyl acetate in Petroleum ether as eluent to afford tert-butyl 6-(1-benzyloxycarbonyl-3,6-dihydro-2H-pyridin-4-yl)-2-azaspiro[3.3]heptane-2-carboxylate (3.1 g, 5.79 mmol, 46.75% yield) as a yellow liquid. LCMS (ESI−): 311.0 $[M-100-H]^-$ Step 5: To a stirred solution of tert-butyl 6-(1-benzyloxycarbonyl-3,6-dihydro-2H-pyridin-4-yl)-2-azaspiro[3.3]heptane-2-carboxylate (2.5 g, 6.06 mmol) in Methanol (30 mL) was added 10% Palladium on carbon (1 g, 9.40 mmol) and the resulting reaction mixture was subjected for hydrogenation (1 atm) for 16 h at room temperature. After completion, reaction mixture was filtered through celite and filtrate was concentrated under reduced pressure to get the desired crude tert-butyl 6-(4-piperidyl)-2-azaspiro[3.3]heptane-2-carboxylate (1.35 g, 3.71 mmol, 61.17% yield) as a gummy liquid, which was used without further purification. LCMS (ESI+): 281.0 $[M+H]^+$ Step 6: A solution of tert-butyl 6-(4-piperidyl)-2-azaspiro[3.3]heptane-2-carboxylate (74.41 mg, 265.36 μmol) in N,N-Dimethylformamide (2 mL) was taken in sealed tube and added N-ethyl-N-isopropyl-propan-2-amine (171.48 mg, 1.33 mmol, 231.10 μL) and 1,2-difluoro-4-nitro-benzene (42.22 mg, 265.36 μmol, 29.32 μL) at room temperature and the resulting reaction mixture was heated at 80° C. for 16 h. After completion, the reaction mixture was added water and extracted with ethyl acetate (2×30 mL). The combined organic layers were dried over anhydrous sodium sulphate, filtered and filtrate was evaporated under reduced pressure to get the desired crude. crude compound was purified by silica gel chromatography using 25% Ethyl acetate in Petroleum ether as eluent to afford tert-butyl 6-[1-(2-fluoro-4-nitro-phenyl)-4-piperidyl]-2-azaspiro[3.3]heptane-2-carboxylate (60 mg, 92.97 μmol, 35.04% yield) as a yellow liquid. LCMS (ESI+): 420.1 $[M+H]^+$ Step 7: To a stirred solution of tert-butyl 6-[1-(2-fluoro-4-nitro-phenyl)-4-piperidyl]-2-azaspiro[3.3]heptane-2-carboxylate (1.2 g, 2.86 mmol) in Dichloromethane (12 mL) was added 2,2,2-trifluoroacetic acid (1.63 g, 14.30 mmol, 1.10 mL) at 0° C., and the resulting reaction mixture was stirred at room temperature for 12 h. After completion, reaction mixture was concentrated under reduced pressure to get the desired product 6-[1-(2-fluoro-4-nitro-phenyl)-4-piperidyl]-2-azaspiro[3.3]heptane (950 mg, 1.21 mmol, 42.14% yield) as a brown solid, which was carried forward without further purification. LCMS (ESI+): 320.2 $[M+H]^+$ Step 8: To a stirred solution of 6-[1-(2-fluoro-4-nitro-phenyl)-4-piperidyl]-2-azaspiro[3.3]heptane (950 mg, 2.19 mmol) and 5-chloro-2-(4,4,5,5-tetramethyl-1,3,2-dioxaborolan-2-yl)pyrimidine (527.16 mg, 2.19 mmol) in N,N-Dimethylformamide (10 mL) was added N-ethyl-N-isopropyl-propan-2-amine (283.29 mg, 2.19 mmol, 381.80 μL) at room temperature and the resulting reaction mixture was heated at 80° C. for 24 h. After completion, the reaction mixture was added water and extracted with ethyl acetate (2×30 mL). The combined organic layers were dried over anhydrous sodium sulphate, filtered and filtrate was evaporated under reduced pressure to get the desired crude 6-[1-(2-fluoro-4-nitro-phenyl)-4-piperidyl]-2-[2-(4,4,5,5-tetramethyl-1,3,2-dioxaborolan-2-yl)pyrimidin-5-yl]-2-azaspiro[3.3]heptane (500 mg, 525.40 μmol, 23.97% yield) as a brown semi solid, which was carried forward without further purification. LCMS (ESI+): 524.3 $[M+H]^+$.

Step 9: A solution of 5-bromo-3-[3-[[ethyl(methyl)sulfamoyl]amino]-2,6-difluoro-benzoyl]-1-trityl-pyrrolo[2,3-b]pyridine (450 mg, 628.84 μmol) in 1,4 Dioxnae (10 mL) was taken in a microwave vial and added 6-[1-(2-fluoro-4-nitro-phenyl)-4-piperidyl]-2-[5-(4,4,5,5-tetramethyl-1,3,2-dioxaborolan-2-yl)pyrimidin-2-yl]-2-azaspiro[3.3]heptane (493.71 mg, 943.26 μmol) followed by $K_3PO_4$ (400.44 mg, 1.89 mmol) in Water (2 mL). The resulting reaction mixture was purged with nitrogen gas for 10 minutes. Then XPhos Pd G2 (49.48 mg, 62.88 μmol) was added under inert atmosphere and the reaction mixture was irradiated under microwave at 120° C. for 90 minutes. After completion, the reaction mixture was added water and extracted with ethyl acetate (2×40 mL). The combined organic layers were dried over anhydrous sodium sulphate, filtered and filtrate was evaporated under reduced pressure to get crude compound. Crude was purified by silica gel chromatography using 55% Ethyl acetate in Petroleum ether as eluent to afford 3-[3-[[ethyl(methyl)sulfamoyl]amino]-2,6-difluoro-benzoyl]-5-[2-[6-[1-(2-fluoro-4-nitro-phenyl)-4-piperidyl]-2-azaspiro[3.3]heptan-2-yl]pyrimidin-5-yl]-1-trityl-pyrrolo[2,3-b]pyridine (550 mg, 522.22 μmol, 83.04% yield) as a gummy liquid. LCMS (ESI+): 1032.9 $[M+H]^+$ Step 10: To a stirred solution of 3-[3-[[ethyl(methyl)sulfamoyl]amino]-2,6-difluoro-benzoyl]-5-[2-[6-[1-(2-fluoro-4-nitro-phenyl)-4-piperidyl]-2-azaspiro[3.3]heptan-2-yl]pyrimidin-5-yl]-1-trityl-pyrrolo[2,3-b]pyridine (500 mg, 484.43 μmol) in ethyl acetate (10 mL) was added 20% of Palladium hydroxide on carbon (68.03 mg, 484.43 μmol) and the resulting reaction mixture was subjected for hydrogenation at 1 atm pressure under hydrogenation at room temperature for 12 h. After completion, reaction mixture was filtered through celite and filtrate was concentrated under reduced pressure to get the desired compound 5-[2-[6-[1-(4-amino-2-fluoro-phenyl)-4-piperidyl]-2-azaspiro[3.3]heptan-2-yl]pyrimidin-5-yl]-3-[3-[[ethyl(methyl)sulfamoyl]amino]-2,6-difluoro-benzoyl]-1-trityl-pyrrolo[2,3-b]pyridine (300 mg, 293.37 μmol, 60.56% yield) as a pale yellow solid, which was carried forward without further purification. LCMS (ESI+): 1002.9 $[M+H]^+$ Step 11: To a stirred solution of 5-[2-[6-[1-(4-amino-2-fluoro-phenyl)-4-piperidyl]-2-azaspiro[3.3]heptan-2-yl]pyrimidin-5-yl]-3-[3-[[ethyl(methyl)sulfamoyl]amino]-2,6-difluoro-benzoyl]-1-trityl-pyrrolo[2,3-b]pyridine (500 mg, 498.92 μmol) in N,N-Dimethylformamide (6 mL) was added 3-bromopiperidine-2,6-dione (287.40 mg, 1.50 mmol) and Sodium bicarbonate (146.70 mg, 1.75 mmol, 67.91 μL) at room temperature and the resulting reaction mixture was heated at 80° C. for 48 h. After completion, water was added to the reaction mixture and extracted with ethyl acetate (2×30 mL). The combined organic layers were dried over anhydrous sodium sulphate, filtered and filtrate was evaporated under reduced pressure to get the desired crude. Crude compound was purified by silica gel chromatography using 55% Ethyl acetate in Petroleum ether as eluent to afford 5-[2-[6-[1-[4-[(2,6-dioxo-3-piperidyl)amino]-2-fluoro-phenyl]-4-piperidyl]-2-azaspiro[3.3]heptan-2-yl]pyrimidin-5- yl]-3-[3-[[ethyl(methyl)sulfamoyl]amino]-2,6-difluoro-benzoyl]-1-trityl-pyrrolo[2,3-b]pyridine (300 mg, 250.62 μmol, 50.23% yield) as a brown solid. LCMS (ESI+): 1114.3 $[M+H]^+$ Step 12: To a stirred solution of 5-[2-[6-[1-[4-[(2,6-dioxo-3-piperidyl)amino]-2-fluoro-phenyl]-4-piperidyl]-2-azaspiro[3.3]heptan-2-yl]pyrimidin-5-yl]-3-[3-[[ethyl(methyl)sulfamoyl]amino]-2,6-difluoro-benzoyl]-1-trityl-pyrrolo[2,3-b]pyridine (350 mg, 314.39 μmol) in Dichloromethane (5 mL) were added Trifluoroacetic acid (1.48 g, 12.98 mmol, 1 mL) and Tri-isopropyl silane(386.50 mg, 2.44 mmol, 0.5 mL) at 0° C. and the resulting reaction mixture was warmed to room temperature for 2 h. After completion, reaction mixture was concentrated under reduced pressure. The residue obtained was purified by Reverse phase purification [Mobile-phase A: 10 mM Formic acid in water, Mobile-phase B: ACN] to get the desired product 5-[2-[6-[1-[4-[(2,6-dioxo-3-piperidyl)amino]-2-fluoro-phenyl]-4-piperidyl]-2-azaspiro[3.3]heptan-2-yl]pyrimidin-5-yl]-3-[3-[[ethyl(methyl)sulfamoyl]amino]-2,6-difluoro-benzoyl]-1H-pyrrolo[2,3-b]pyridine (65 mg, 70.18 μmol, 22.32% yield) as an off white solid. LCMS (ESI+): 871.9 $[M+H]^+$. $^1H$ NMR (400 MHz, DMSO-$d_6$): δ 13.00 (s, 1H), 10.79 (s, 1H), 10.00 (s, 1H), 8.73 (s, 2H), 8.64 (d, J=2.00 Hz, 1H), 8.53 (s, 1H), 8.13 (s, 1H), 7.54-7.60 (m, 1H), 7.24 (t, J=8.40 Hz, 1H), 6.84 (t, J=9.60 Hz, 1H), 6.50 (dd, J=2.40, 15.20 Hz, 1H), 6.42 (dd, J=2.00, 8.60 Hz, 1H), 5.79 (d, J=7.60 Hz, 1H), 4.20-4.30 (m, 1H), 4.16 (s, 2H), 4.00 (s, 2H), 3.07-3.14 (m, 4H), 2.65-2.75 (m, 1H), 2.74 (s, 3H), 2.45-2.60 (m, 3H), 2.30-2.34 (m, 3H), 2.07-2.12 (m, 1H), 1.75-1.96 (m, 4H), 1.67-1.70 (m, 2H), 1.16-1.24 (m, 3H), 1.02 (t, J=7.20 Hz, 3H).

Example 200

5-[3-(difluoromethyl)-4-[4-[2-[1-[4-[(2,6-dioxo-3-piperidyl)amino]-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine

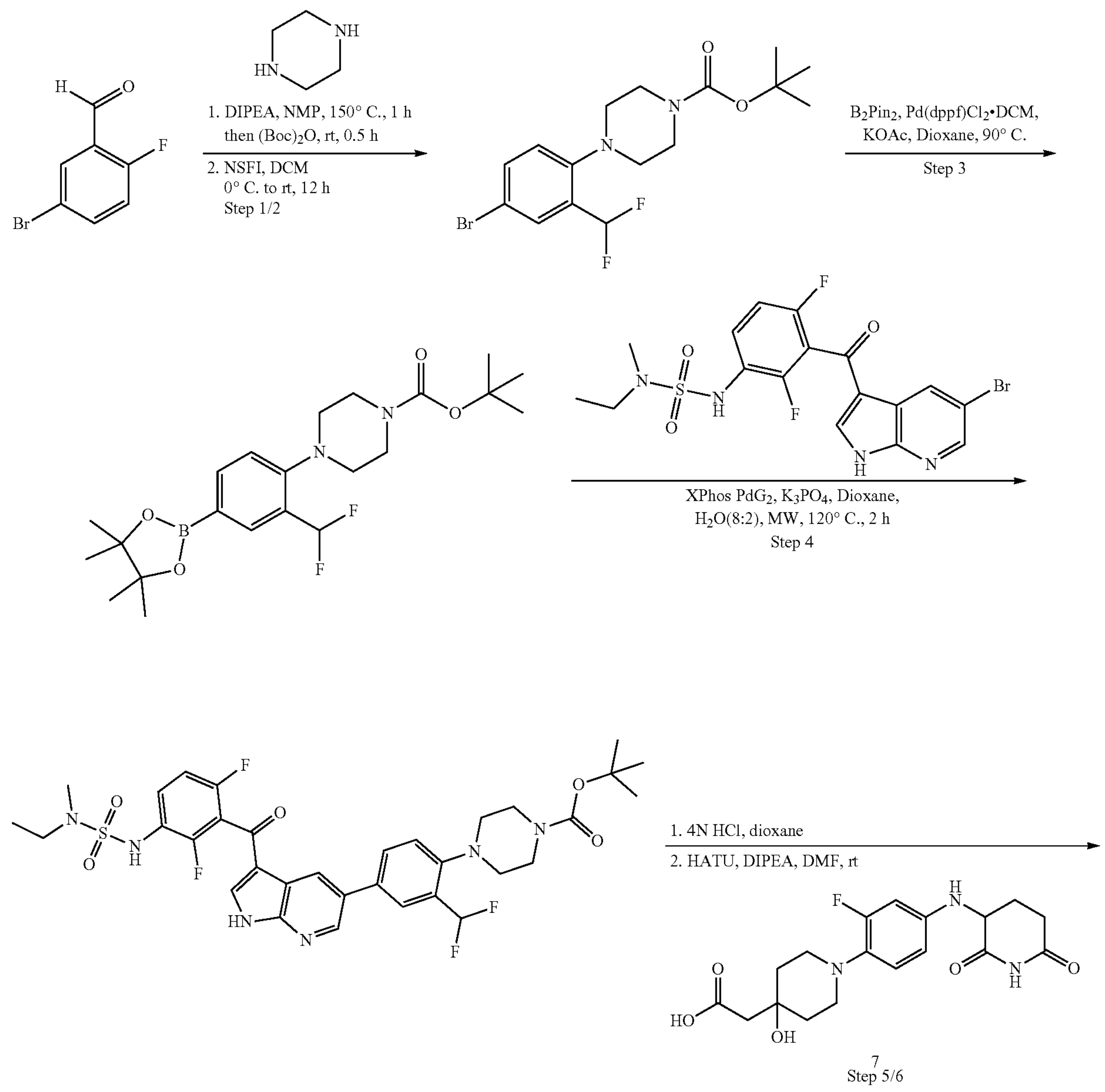

-continued

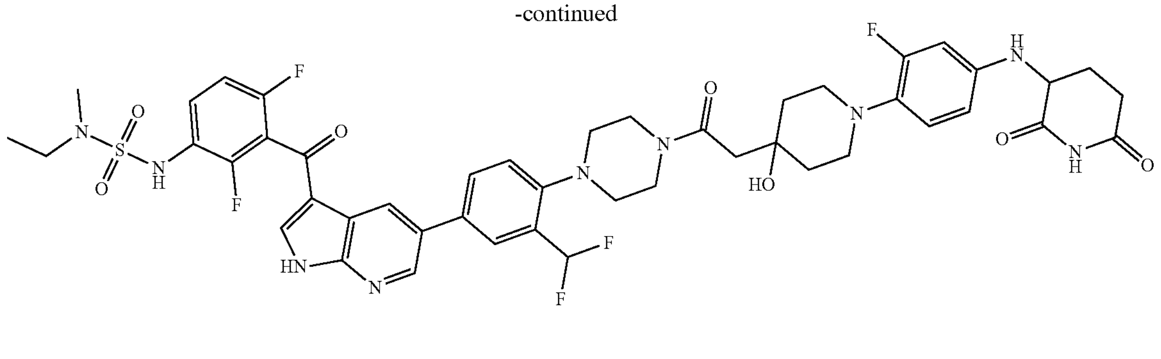

Step 1: To a stirred solution of 5-bromo-2-fluoro-benzaldehyde (5.0 g, 24.63 mmol) in N-Methyl-2-pyrrolidone (50 mL) was added piperazine (4.50 g, 52.24 mmol) and N,N-Diisopropylethylamine (9.65 g, 74.63 mmol, 13.0 mL) at room temperature under nitrogen atmosphere. The reaction mixture was degassed with nitrogen for 15 minutes and heated to 150° C. for 1 h. After the reaction mixture was cooled to room temperature and added Di-tert-butyl dicarbonate (11.41 g, 52.29 mmol, 12.0 mL) at same temperature. The reaction mixture was stirred at room temperature for 30 minutes. After completion, the reaction mixture was quenched with 2N HCl (100 mL) solution and extracted with ethyl acetate (2×200 mL). The combined organic layers were dried over sodium sulphate, filtered and concentrated under reduced pressure. The crude compound was purified by silica gel column chromatography with 10% ethyl acetate in petroleum ether as a eluent to afford tert-butyl 4-(4-bromo-2-formyl-phenyl)piperazine-1-carboxylate (3.5 g, 7.58 mmol, 30.79% yield) as a pale brown solid. LCMS (ESI+): 369.1 $[M+H]^+$ Step 2: To a stirred solution of tert-butyl 4-(4-bromo-2-formyl-phenyl)piperazine-1-carboxylate (3.0 g, 8.12 mmol) in Dichloromethane (50 mL) was added Di-ethylaminosulfur trifluoride (3.66 g, 22.71 mmol, 3.0 mL) at 0-5° C. under nitrogen. The reaction mixture was stirred at room temperature for 12 h. After completion, saturated aqueous sodium bicarbonate solution (100 mL) was added to the reaction mixture at 0-5° C. and extracted with ethyl acetate (2×200 mL). The combined organic layers were dried over sodium sulphate, filtered and concentrated under reduced pressure. The crude compound was purified by silica gel column chromatography with 8% ethyl acetate in petroleum ether as a eluent to afford tert-butyl 4-[4-bromo-2-(difluoromethyl) phenyl]piperazine-1-carboxylate (1.30 g, 3.26 mmol, 40.08% yield) as a pale yellow solid. LCMS (ESI+): 391.1 $[M+H]^+$ Step 3: A solution of tert-butyl 4-[4-bromo-2-(difluoromethyl)phenyl]piperazine-1-carboxylate (1.2 g, 3.07 mmol) in 1,4-Dioxane (20 mL) was taken in a sealed tube and added 4,4,5,5-tetramethyl-2-(4,4,5,5-tetramethyl-1,3,2-dioxaborolan-2-yl)-1,3,2-dioxaborolane (1.20 g, 4.73 mmol), Potassium Acetate (910 mg, 9.27 mmol, 579.62 μL) at room temperature under nitrogen. The reaction mixture was degassed with nitrogen for 15 minutes and added Pd(dppf) $Cl_2$.Dichloromethane (280 mg, 342.87 μmol) at same temperature. The reaction mixture was heated to 80° C. for 12 h. After completion, the reaction mixture was filtered through Celite and washed with ethyl acetate. Water (50 mL) was added to the filtrate and extracted with ethyl acetate (2×100 mL). The combined organic layers were dried over sodium sulphate, filtered and concentrated under reduced pressure. The crude compound was purified by silica gel column chromatography with 60% ethyl acetate in petroleum ether as a eluent to afford tert-butyl 4-[2-(difluoromethyl)-4-(4,4,5,5-tetramethyl-1,3,2-dioxaborolan-2-yl)phenyl]piperazine-1-carboxylate (1.0 g, 2.21 mmol, 72.15% yield) as off-white solid. LCMS (ESI+): 439.2 $[M+H]^+$ Step 4: A solution of 5-bromo-3-[3-[[ethyl(methyl)sulfamoyl]amino]-2,6-difluoro-benzoyl]-1H-pyrrolo[2,3-b]pyridine (1.0 g, 2.11 mmol) in 1,4-Dioxane (8.0 mL) and Water (2.0 mL) mixture was taken in a microwave vial and added tert-butyl 4-[2-(difluoromethyl)-4-(4,4,5,5-tetramethyl-1,3,2-dioxaborolan-2-yl)phenyl]piperazine-1-carboxylate (1.02 g, 2.32 mmol), Potassium phosphate tribasic anhydrous (1.40 g, 6.60 mmol) at room temperature under nitrogen. The reaction mixture was degassed with nitrogen for 10 minutes and added XPhos Pd G2 (170 mg, 216.06 μmol) at same temperature. The reaction mixture was irradiated under microwave at 120° C. for 2 h. After completion, the reaction mixture was filtered through celite and washed with ethyl acetate. Water (50 mL) was added to the filtrate and extracted with ethyl acetate (2×100 mL). The combined organic layers were dried over sodium sulphate, filtered and concentrated under reduced pressure. The crude compound was purified by silica gel column chromatography with 90% ethyl acetate in petroleum ether as a eluent to afford tert-butyl 4-[2-(difluoromethyl)-4-[3-[3-[[ethyl(methyl)sulfamoyl]amino]-2,6-difluoro-benzoyl]-1H-pyrrolo[2,3-b]pyridin-5-yl]phenyl]piperazine-1-carboxylate (410 mg, 564.33 μmol, 26.71% yield) as a pale yellow solid. LCMS (ESI+): 705.1 $[M+H]^+$ Step 5: To a stirred solution of tert-butyl 4-[2-(difluoromethyl)-4[2-[3-[[ethyl(methyl)sulfamoyl]amino]-2,6-difluoro-benzoyl]-1H-pyrrolo[2,3-b]pyridin-5-yl]phenyl]piperazine-1-carboxylate (410 mg, 581.78 μmol) in Dichloromethane (4.0 mL) was added Hydrogen chloride solution in 1,4-dioxane (4.0 M, 2.0 mL) at 0-5° C. under nitrogen. The reaction mixture was stirred at room temperature for 5 h. After completion, the reaction mixture was concentrated under reduced pressure and washed with diethyl ether (2×30 mL) to afford 5-[3-(difluoromethyl)-4-piperazin-1-yl-phenyl]-3-[3-[[ethyl(methyl)sulfamoyl] amino]-2,6-difluoro-benzoyl]-1H-pyrrolo[2,3-b]pyridine (380 mg, 580.90 μmol, 99.85% yield) as a yellow solid, which was carried forward without further purification. LCMS (ESI+): 605.1 $[M+H]^+$ Step 6: Target compound was prepared via HATU mediated acid-amine coupling reaction (procedure A). Amide coupling was carried out using 5-[3-(difluoromethyl)-4-piperazin-1-yl-phenyl]-3-[3-[[ethyl(methyl)sulfamoyl] amino]-2,6-difluoro-benzoyl]-1H-pyrrolo[2,3-b]pyridine (350 mg, 545.95 μmol), 2-[1-[4-[(2,6-dioxo-3-piperidyl) amino]-2-fluoro-phenyl]-4-hydroxy-4-piperidyl]acetic acid (7, 230 mg, 553.09 μmol), N,N-Diisopropylethylamine (1.48 g, 11.48 mmol, 2.0 mL) and HATU (250 mg, 657.50 μmol). The crude compound was purified by reverse phase column chromatography by using 150 g snap eluted with 50% Acetonitrile in 0.1% Ammonium acetate in water to afford 5-[3-(difluoromethyl)-4-[4-[2-[1-[4-[(2,6-dioxo-3-piperidyl)amino]-2-fluoro-phenyl]-4-hydroxy-4-piperidyl]acetyl]piperazin-1-yl]phenyl]-3-[3-[[ethyl(methyl)sulfamoyl]amino]-2,6-difluoro-benzoyl]-1H-pyrrolo[2,3-b]pyridine (240 mg, 246.26 μmol, 45.11% yield) as off-white solid. LCMS (ESI+): 966.3 $[M+H]^+$. $^1H$ NMR (400 MHz, DMSO-$d_6$): δ 13.02 (s, 1H), 10.78 (s, 1H), 9.71 (s, 1H), 8.73 (d, J=2.00 Hz, 1H), 8.62 (s, 1H), 8.16 (d, J=2.00 Hz, 1H), 7.90-7.94 (m, 2H), 7.57-7.62 (m, 1H), 7.49 (d, J=8.40 Hz, 1H), 7.20-7.34 (m, 2H), 6.87 (t, J=9.60 Hz, 1H), 6.51 (dd, J=2.00, 15.00 Hz, 1H), 6.43 (d, J=8.80 Hz, 1H), 5.78 (s, 1H), 4.87 (s, 1H), 4.23-4.29 (m, 1H), 3.74-3.78 (m, 4H), 3.11 (q, J=7.20 Hz, 2H), 2.78-2.98 (m, 8H), 2.65-2.77 (m, 1H), 2.73 (s, 3H), 2.60 (s, 2H), 2.50-2.56 (m, 1H), 2.08-2.12 (m, 1H), 1.68-1.88 (m, 5H), 1.02 (t, J=7.20 Hz, 3H).

Example 201

3-[6-chloro-3-[[ethyl(methyl)sulfamoyl]amino]-2-fluoro-benzoyl]-5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-1H-pyrrolo[2,3-b]pyridine

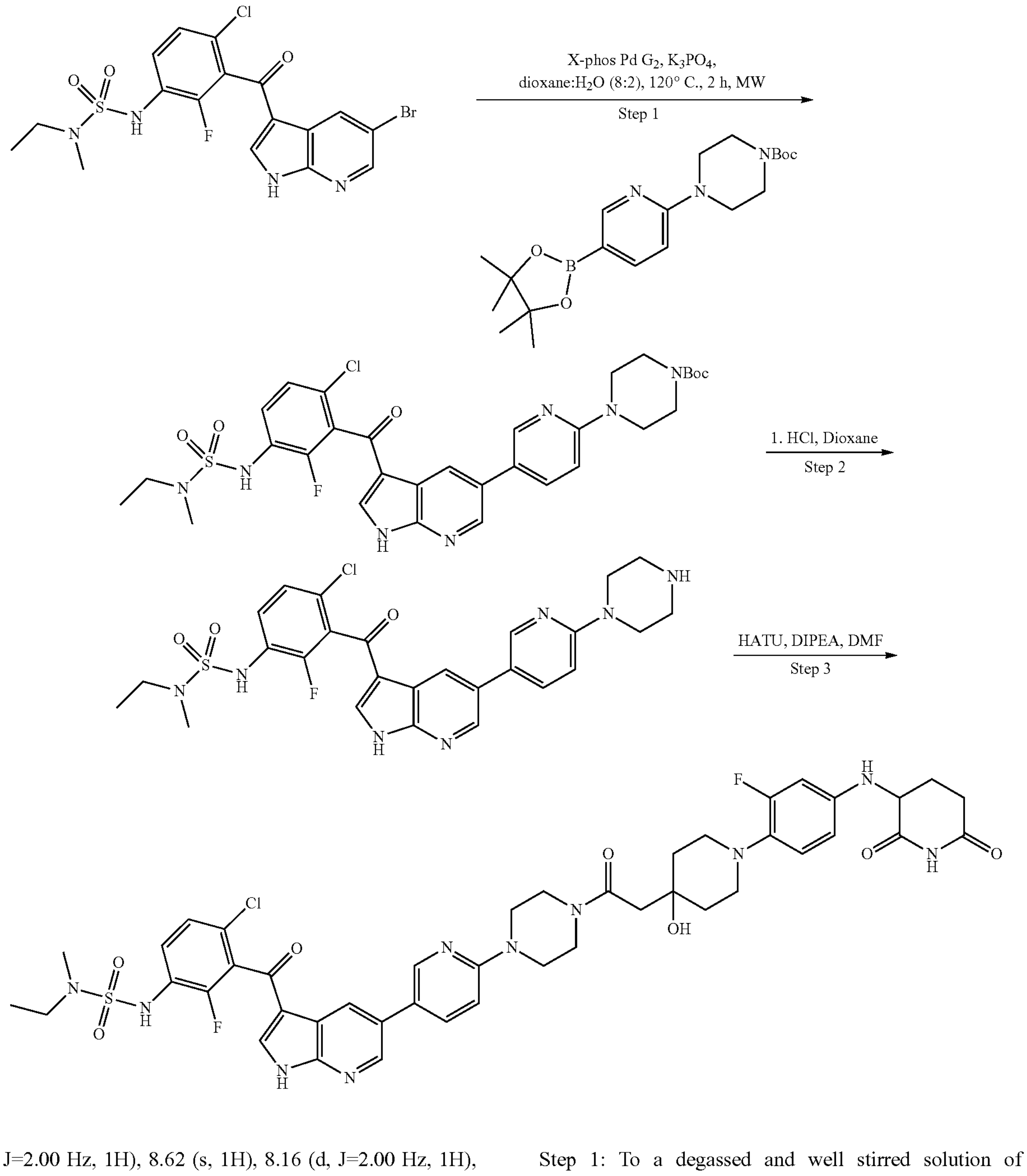

Step 1: To a degassed and well stirred solution of 5-bromo-3-[6-chloro-3-[[ethyl(methyl)sulfamoyl]amino]-2-fluoro-benzoyl]-1H-pyrrolo[2,3-b]pyridine (0.7 g, 1.43 mmol) in 1,4-dioxane (8.0 mL) and water (1.5 mL) was added tert-butyl 4-[5-(4,4,5-trimethyl-1,3,2-dioxaborolan-2- yl)-2-pyridyl]piperazine-1-carboxylate (643.65 mg, 1.72 mmol), XPhos Pd G2 (112.39 mg, 143.00 μmol), Potassium phosphate tribasic anhydrous (910.18 mg, 4.29 mmol). The resulting reaction mixture was irradiated at 120° C. in a microwave reactor for 2 hours. The reaction was then diluted with ethyl acetate and was washed with water and brine solution. The organic layer was dried over sodium sulphate, filtered and evaporated under reduced pressure to get crude which was purified by silica gel column chromatography using (80-90%) ethyl acetate/petroleum ether as eluents to afford tert-butyl 4-[5-[3-[6-chloro-3-[[ethyl(methyl)sulfamoyl]amino]-2-fluoro-benzoyl]-1H-pyrrolo[2,3-b]pyridin-5-yl]-2-pyridyl]piperazine-1-carboxylate (350 mg, 491.96 μmol, 34.40% yield) as off white solid. LCMS (ESI+): 671.9 $[M+H]^+$ Step 2: To a well stirred solution of tert-butyl 4-[5-[3-[6-chloro-3-[[ethyl(methyl)sulfamoyl]amino]-2-fluoro-benzoyl]-1H-pyrrolo[2,3-b]pyridin-5-yl]-2-pyridyl]piperazine-1-carboxylate (350 mg, 520.70 μmol) in Hydrogen chloride solution 4.0M in dioxane (284.78 mg, 7.81 mmol, 355.97 μL) at 0° C. The resulting reaction mixture was maintained at room temperature for 3 hours. After completion, the reaction mixture was concentrated under reduced pressure to get the crude product. The crude was co-distilled with dichloromethane twice. to afford 3-[6-chloro-3-[[ethyl(methyl)sulfamoyl]amino]-2-fluoro-benzoyl]-5-(6-piperazin-1-yl-3-pyridyl)-1H-pyrrolo[2,3-b]pyridine (300 mg, 233.19 μmol, 44.78% yield, hydrochloric acid salt) which was carried forward without further purification. LCMS (ESI+): 572.0 $[M+2H]^+$.

Step 3: Target compound was prepared via HATU mediated acid-amine coupling reaction (procedure A) using 2-[1-[4-[(2,6-dioxo-3-piperidyl)amino]-2-fluoro-phenyl]-4-hydroxy-4-piperidyl]acetic acid (188.61 mg, 453.56 μmol, hydrochloric acid salt), HATU (215.57 mg, 566.96 μmol), N,N-Diisopropylethylamine (244.25 mg, 1.89 mmol, 329.18 μL) and 3-[6-chloro-3-[[ethyl(methyl)sulfamoyl]amino]-2-fluoro-benzoyl]-5-(6-piperazin-1-yl-3-pyridyl)-1H-pyrrolo[2,3-b]pyridine (230 mg, 377.97 μmol, hydrochloric acid salt) in DMF (2.5 mL). The crude was purified by reverse phase column chromatography using [Mobile-phase A: 0.1% ammonium acetate in water, Mobile-phase B: ACN; column: 100 g Redisep Rf C18] to afford 3-[6-chloro-3-[[ethyl(methyl)sulfamoyl]amino]-2-fluoro-benzoyl]-5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-1H-pyrrolo[2,3-b]pyridine (58.23 mg, 47.58 μmol, 12.59% yield) as off white solid. LCMS (ESI+): 933.2 $[M+H]^+$. $^1H$ NMR (400 MHz, DMSO-$d_6$): δ 12.95 (s, 1H), 10.79 (s, 1H), 9.93 (s, 1H), 8.67 (d, J=2.00 Hz, 1H), 8.51 (s, 2H), 8.08 (s, 1H), 7.97 (d, J=7.60 Hz, 1H), 7.56 (t, J=8.40 Hz, 1H), 7.46 (d, J=8.80 Hz, 1H), 7.02 (d, J=9.20 Hz, 1H), 6.86 (t, J=9.60 Hz, 1H), 6.52 (d, J=2.40 Hz, 1H), 6.49 (d, J=2.40 Hz, 1H), 5.78 (d, J=7.60 Hz, 1H), 4.88 (s, 1H), 4.26 (m, 1H), 3.65-3.66 (m, 8H), 3.14 (q, J=7.2 Hz, 2H), 2.92-2.85 (m, 4H), 2.75-2.71 (m, 4H), 2.56-2.53 (m, 3H), 2.08-2.07 (m, 1H), 1.86-1.81 (m, 3H), 1.78-1.75 (m, 2H), 1.03 (t, J=7.20 Hz, 3H).

Example 202

3-(2,4-dioxohexahydropyrimidin-1-yl)-6-[4-[2-[4-[4-[3-[3-[[ethyl(methyl)sulfamoyl]amino]-2,6-difluoro-benzoyl]-1H-pyrrolo[2,3-b]pyridin-5-yl]phenyl]piperazin-1-yl]-2-oxo-ethyl]-4-hydroxy-1-piperidyl]-1-methyl-indazole

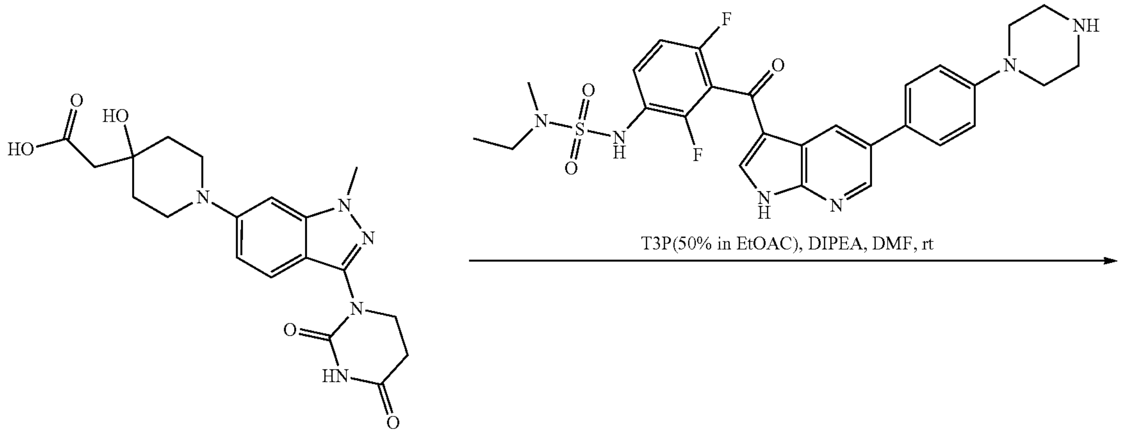

-continued

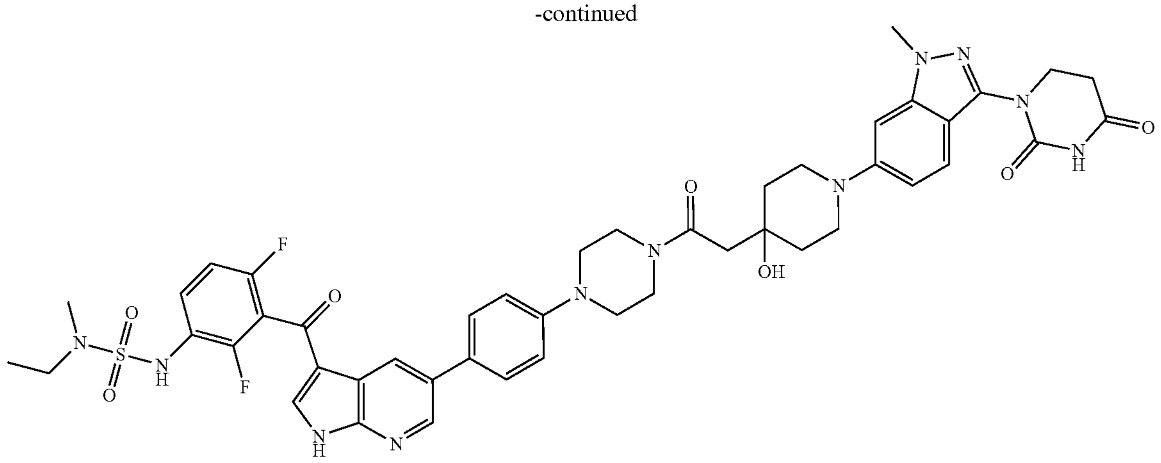

Target compound was prepared via T3P mediated acid-amine coupling reaction (procedure C) using 2[1-[3-(2,4-dioxohexahydropyrimidin-1-yl)-1-methyl-indazol-6-yl]-4-hydroxy-4-piperidyl]acetic acid (48.15 mg, 109.97 μmol, hydrochloric acid salt), N-ethyl-N-isopropyl-propan-2-amine (85.27 mg, 659.82 μmol, 114.93 μL), T3P (41.99 mg, 131.96 μmol) and 3-[3-[[ethyl(methyl)sulfamoyl]amino]-2,6-difluoro-benzoyl]-5-(4-piperazin-1-ylphenyl)-1H-pyrrolo[2,3-b]pyridine (65 mg, 109.97 μmol, hydrochloric acid salt) in DMF (2 mL). The product was purified by reverse phase C18 column chromatography [Mobile-phase A: 0.1% HCOOH in water, Mobile-phase B: ACN, Wave length: 254 nm, Column: 100 g Redisep C18] to afford 3-(2,4-dioxo-hexahydropyrimidin-1-yl)-6-[4-[2-[4-[4-[3-[3-[[ethyl(methyl)sulfamoyl]amino]-2,6-difluoro-benzoyl]-1H-pyrrolo[2,3-b]pyridin-5-yl]phenyl]piperazin-1-yl]-2-oxo-ethyl]-4-hydroxy-1-piperidyl]-1-methyl-indazole (35 mg, 35.11 μmol, 31.92% yield, formic acid salt) as pale yellow solid. LCMS (ESI+): 938.2 $[M+H]^+$. $^1H$ NMR (400 MHz, DMSO-$d_6$): δ 12.93 (d, J=2.80 Hz, 1H), 10.51 (s, 1H), 9.72 (s, 1H), 8.67 (d, J=2.40 Hz, 1H), 8.57-8.50 (m, 1H), 8.11 (d, J=2.00 Hz, 1H), 7.65-7.55 (m, 3H), 7.43 (d, J=9.20 Hz, 1H), 7.29-7.27 (m, 1H), 7.12-7.10 (m, 2H), 6.93-6.90 (m, 1H), 6.84 (d, J=1.20 Hz, 1H), 5.00 (s, 1H), 3.90-3.89 (m, 5H), 3.72-3.70 (m, 4H), 3.53-3.51 (m, 2H), 3.27-3.19 (m, 6H), 3.11 (q, J=7.20 Hz, 2H), 2.75-2.72 (m, 5H), 2.56-2.54 (m, 2H), 1.79-1.69 (m, 4H), 1.01 (t, J=7.20 Hz, 3H).

Example 203

5-[2-[2-[1-[4-[(2,6-dioxo-3-piperidyl)amino]-2-fluoro-phenyl]-4-piperidyl]-2,6-diazaspiro[3.3]heptan-6-yl]pyrimidin-5-yl]-3-[3-[[ethyl(methyl)sulfamoyl]amino]-2,6-difluoro-benzoyl]-1H-pyrrolo[2,3-b]pyridine

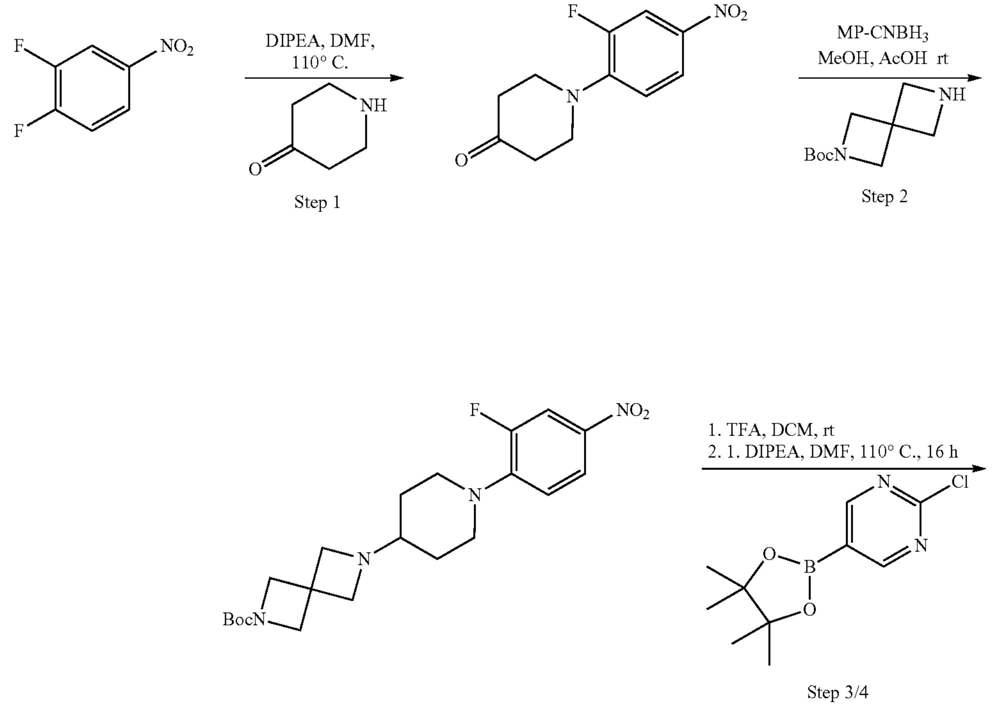

-continued
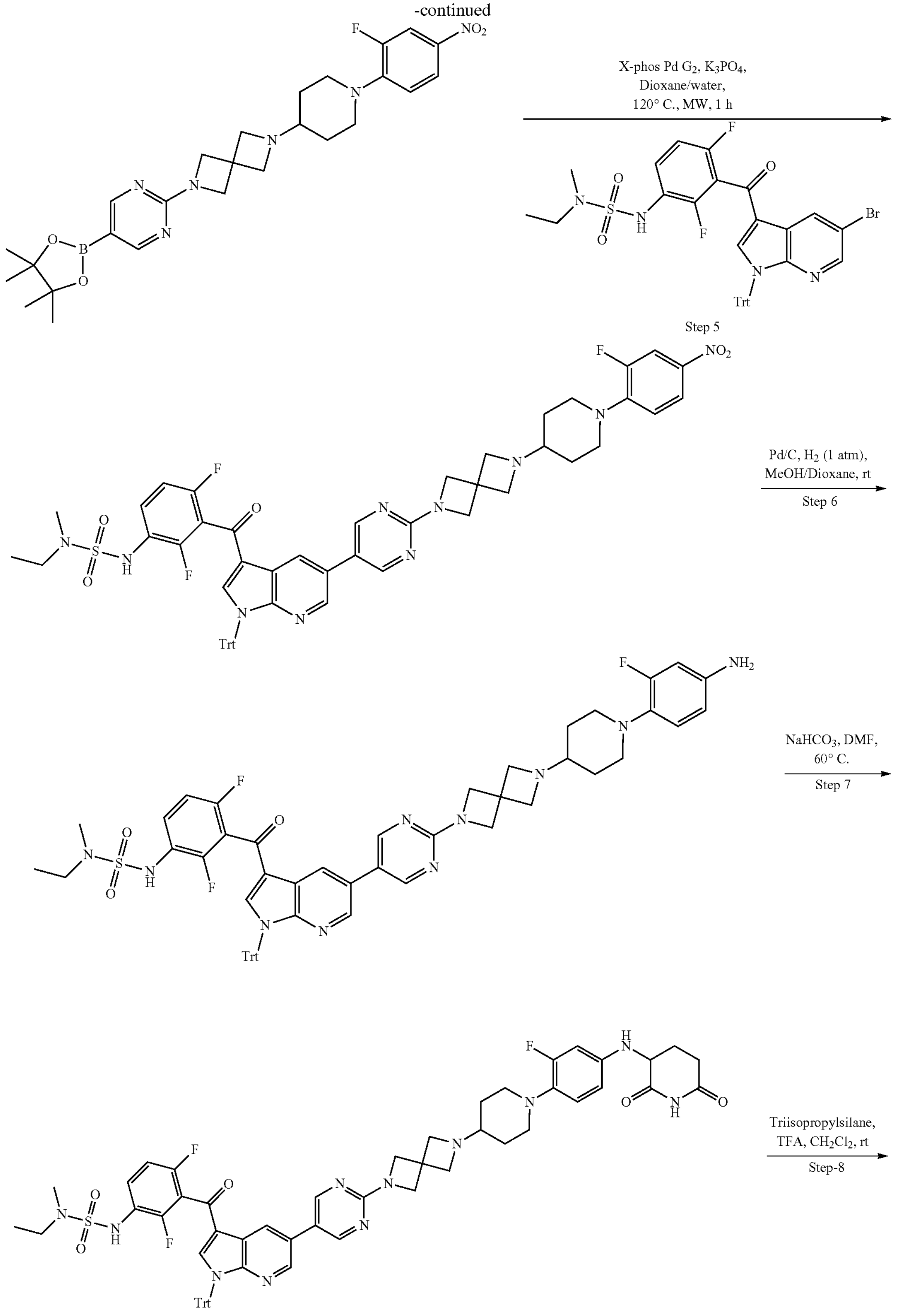

-continued

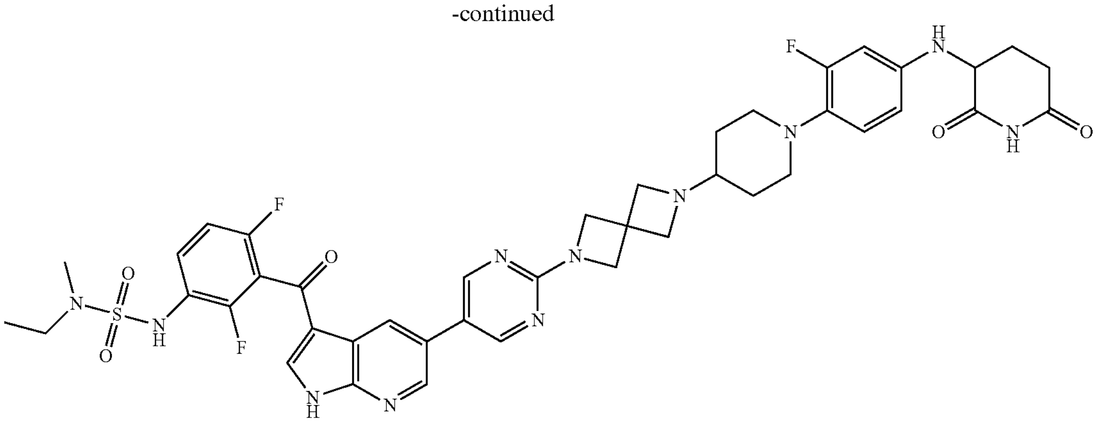

Step 1: To a solution of piperidin-4-one (1.62 g, 11.94 mmol, HCl salt) in DMF (20 mL) was added DIPEA (7.72 g, 59.71 mmol, 10.40 mL) followed by 1,2-difluoro-4-nitro-benzene (1.9 g, 11.94 mmol, 1.32 mL) at room temperature under nitrogen. The resulting solution was stirred at 110° C. for 12 h. After completion, resulting solution was diluted with water (20 ml), solid obtained was filtered and dried to get 1-(2-fluoro-4-nitro-phenyl)piperidin-4-one (2.2 g, 8.37 mmol, 70.06% yield) as a yellow solid, which was carried forward without further purification. LCMS (ESI+): 239.1 $[M+H]^+$.

Step 2: To a solution of tert-butyl 2,6-diazaspiro[3.3]heptane-2-carboxylate (998.74 mg, 5.04 mmol) in methanol (12 mL) was added 1-(2-fluoro-4-nitro-phenyl)piperidin-4-one (1.2 g, 5.04 mmol), MP-$CNBH_3$ (1.2 g, 5.04 mmol) and acetic acid (302.51 mg, 5.04 mmol, 288.11 μL) at room temperature under nitrogen atmosphere. The resulting solution was stirred at room temperature for 3 h. After completion, resulting solution was filtered and concentrated under reduced pressure. The residue obtained was dissolved in ethyl acetate (40 ml), washed with water (10 ml) and organic layer was dried over sodium sulphate, filtered and concentrated under reduced pressure. The resulting crude product was purified by silica gel (50 g) column chromatography using MeOH-dichloromethane (0-5%) as eluents to get tert-butyl 6-[1-(2-fluoro-4-nitro-phenyl)-4-piperidyl]-2,6-diazaspiro[3.3]heptane-2-carboxylate (1.0 g, 2.28 mmol, 45.34% yield) as a yellow solid. LCMS (ESI+): 421.1 $[M+H]^+$.

Step 3: To a solution of tert-butyl 6-[1-(2-fluoro-4-nitro-phenyl)-4-piperidyl]-2,6-diazaspiro[3.3]heptane-2-carboxylate (1 g, 2.38 mmol) in dichloromethane (10 mL) was added trifluoroacetic acid (2.71 g, 23.78 mmol, 1.83 mL) at 0° C. under nitrogen. The resulting solution was stirred at room temperature for 1 hr. After completion, resulting solution was concentrated under reduced pressure to get crude 2-[1-(2-fluoro-4-nitro-phenyl)-4-piperidyl]-2,6-diazaspiro[3.3]heptane (0.95 g, 1.90 mmol, 79.73% yield, trifluoroacetic acid salt) as a liquid. LCMS (ESI+): 321.2 $[M+H]^+$.

Step 4: To a solution of 2-[1-(2-fluoro-4-nitro-phenyl)-4-piperidyl]-2,6-diazaspiro[3.3]heptane (0.95 g, 2.19 mmol, trifluoroacetic acid salt) in DMF (10 mL) was added DIPEA (1.41 g, 10.94 mmol, 1.90 mL) followed by 2-chloro-5-(4,4,5,5-tetramethyl-1,3,2-dioxaborolan-2-yl)pyrimidine (525.96 mg, 2.19 mmol) at room temperature under nitrogen. The resulting solution was stirred at 100° C. for 12 h. After completion, resulting solution was diluted with water (20 ml), solid obtained was filtered and dried to get 2-[1-(2-fluoro-4-nitro-phenyl)-4-piperidyl]-6-[5-(4,4,5,5-tetramethyl-1,3,2-dioxaborolan-2-yl)pyrimidin-2-yl]-2,6-diazaspiro[3.3]heptane (0.75 g, 679.36 μmol, 31.06% yield) as a yellow solid, which was carried forward without further purification. LCMS (ESI+): 525.2 $[M+H]^+$.

Step 5: To a solution of 2-[1-(2-fluoro-4-nitro-phenyl)-4-piperidyl]-6-[5-(4,4,5,5-tetramethyl-1,3,2-dioxaborolan-2-yl)pyrimidin-2-yl]-2,6-diazaspiro[3.3]heptane (659.52 mg, 1.26 mmol) in water (2 mL) and 1,4-Dioxane (10 mL) was added 5-bromo-3-[3-[[ethyl(methyl)sulfamoyl]amino]-2,6-difluoro-benzoyl]-1-trityl-pyrrolo[2,3-b]pyridine (0.6 g, 838.45 μmol), Potassium phosphate tribasic anhydrous (533.93 mg, 2.52 mmol) at rt under nitrogen atmosphere. The resulting solution was degassed with nitrogen for 10 mins, then XPhos Pd G2 (65.97 mg, 83.85 μmol) was added and heated at 120° C. for 2 hr under microwave irradiation. The resulting solution was cooled to room temperature, filtered through a celite bed and washed with ethyl acetate (80 ml). The collected filtrate was washed with water (10 ml), the separated organic layer was dried over sodium sulphate, filtered and concentrated under reduced pressure. The resulting crude product was purified by silica gel (50 g) column chromatography using MeOH/dichloromethane (0-5%) as eluents to get 3-[3-[[ethyl(methyl)sulfamoyl]amino]-2,6-difluoro-benzoyl]-5-[2-[2-[1-(2-fluoro-4-nitro-phenyl)-4-piperidyl]-2,6-diazaspiro[3.3]heptan-6-yl]pyrimidin-5-yl]-1-trityl-pyrrolo[2,3-b]pyridine (0.65 g, 597.32 μmol, 71.24% yield) as a yellow solid. LCMS (ESI+): 1033.3 $[M+H]^+$.

Step 6: To a solution of 3-[3-[[ethyl(methyl)sulfamoyl]amino]-2,6-difluoro-benzoyl]-5-[2-[2-[1-(2-fluoro-4-nitro-phenyl)-4-piperidyl]-2,6-diazaspiro[3.3]heptan-6-yl]pyrimidin-5-yl]-1-trityl-pyrrolo[2,3-b]pyridine (0.65 g, 629.16 μmol) in methanol (4 mL) and 1,4-Dioxane (10 mL) was added dry Palladium on carbon 10% (66 mg) under Hz-pressure. The resulting solution was stirred at room temperature for 5 hr under hydrogen atmosphere. After completion, the reaction mixture was filtered through a celite bed and washed with 10% MeOH in dichloromethane (50 ml). The collected filtrates were concentrated under reduced pressure to get the crude 5-[2-[2-[1-(4-amino-2-fluoro-phenyl)-4-piperidyl]-2,6-diazaspiro[3.3]heptan-6-yl]pyrimidin-5-yl]-3-[3-[[ethyl(methyl)sulfamoyl]amino]-2,6-difluoro-benzoyl]-1-trityl-pyrrolo[2,3-b]pyridine (0.55 g, 509.13 μmol, 80.92% yield), which was carried forward without further purification. LCMS (ESI+): 1003.3 $[M+H]^+$.

Step 7: To a solution of 5-[2-[2-[1-(4-amino-2-fluoro-phenyl)-4-piperidyl]-2,6-diazaspiro[3.3]heptan-6-yl]pyrimidin-5-yl]-3-[3-[[ethyl(methyl)sulfamoyl]amino]-2,6-difluoro-benzoyl]-1-trityl-pyrrolo[2,3-b]pyridine (0.55 g, 548.28 μmol) in DMF (6 mL) was added $NaHCO_3$ (230.30 mg, 2.74 mmol) followed by 3-bromopiperidine-2,6-dione (315.82 mg, 1.64 mmol) at room temperature under nitrogen. The resulting solution was heated at 70° C. for 16 hr. The resulting solution was cooled to room temperature, diluted with water (5 ml), extracted with ethyl acetate (30 ml), the separated organic layer was dried over sodium sulphate and concentrated under reduced pressure. The crude compound was purified by reverse phase column chromatography[Column: 100 g Redisep Rf C18, Mobile-phase A: 0.1% Ammonium acetate, Mobile-phase B: ACN] to get 5-[2-[2-[1-[4-[(2,6-dioxo-3-piperidyl)amino]-2-fluoro-phenyl]-4-piperidyl]-2,6-diazaspiro[3.3]heptan-6-yl]pyrimidin-5-yl]-3-[3-[[ethyl(methyl)sulfamoyl]amino]-2,6-difluoro-benzoyl]-1-trityl-pyrrolo[2,3-b]pyridine (60 mg, 45.41 μmol, 8.28% yield) as a grey solid. LCMS (ESI+): 1114.3 [ M+H]$^+$ Step 8: To a stirred solution of 5-[2-[2-[1-[4-[(2,6-dioxo-3-piperidyl)amino]-2-fluoro-phenyl]-4-piperidyl]-2,6-diazaspiro[3.3]heptan-6-yl]pyrimidin-5-yl]-3-[3-[[ethyl(methyl)sulfamoyl]amino]-2,6-difluoro-benzoyl]-1-trityl-pyrrolo[2,3-b]pyridine (50 mg, 44.87 μmol) in dichloromethane (4 mL) was added triisopropylsilane (15.46 mg, 97.63 μmol, 0.02 mL) and 2,2,2-trifluoroacetic acid (148.00 mg, 1.30 mmol, 0.1 mL) at 0° C. The reaction mixture was stirred at room temperature for 2 h and the reaction mixture was concentrated at 35° C. under reduced pressure to get crude compound which was purified by reverse phase column chromatography [Mobile-phase A: 0.1% Ammonium acetate in water, Mobile-phase B: ACN; column: 100 g Redisep Rf C18] to afford 5-[2-[2-[1-[4-[(2,6-dioxo-3-piperidyl)amino]-2-fluoro-phenyl]-4-piperidyl]-2,6-diazaspiro[3.3]heptan-6-yl]pyrimidin-5-yl]-3-[3-[[ethyl(methyl)sulfamoyl]amino]-2,6-difluoro-benzoyl]-1H-pyrrolo[2,3-b]pyridine (20 mg, 21.12 μmol, 47.06% yield) as off-white solid. LCMS (ESI+): 872.1 [M+H]$^+$. $^1$H NMR (400 MHz, DMSO-$d_6$): δ 13.08 (s, 1H), 10.79 (s, 1H), 9.73 (s, 1H), 8.75 (s, 2H), 8.65 (d, J=2.40 Hz, 1H), 8.54 (s, 1H), 8.15 (s, 1H), 7.61-7.55 (m, 1H), 7.28 (t, J=8.80 Hz, 1H), 6.84 (t, J=9.20 Hz, 1H), 6.50 (d, J=2.40 Hz, 1H), 6.42 (d, J=8.80 Hz, 1H), 5.81 (d, J=7.20 Hz, 1H), 4.27 (t, J=4.40 Hz, 5H), 3.36-3.34 (m, 4H), 3.14-3.07 (m, 4H), 2.75-2.67 (m, 4H), 2.58-2.56 (m, 3H), 2.11-2.07 (m, 2H), 1.86-1.85 (m, 1H), 1.73-1.71 (m, 2H), 1.36-1.24 (m, 2H), 1.02 (t, J=7.20 Hz, 3H).

Example 204

5-[2-[4-[2-[1-[2-(difluoromethyl)-4-[(2,6-dioxo-3-piperidyl)amino]phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

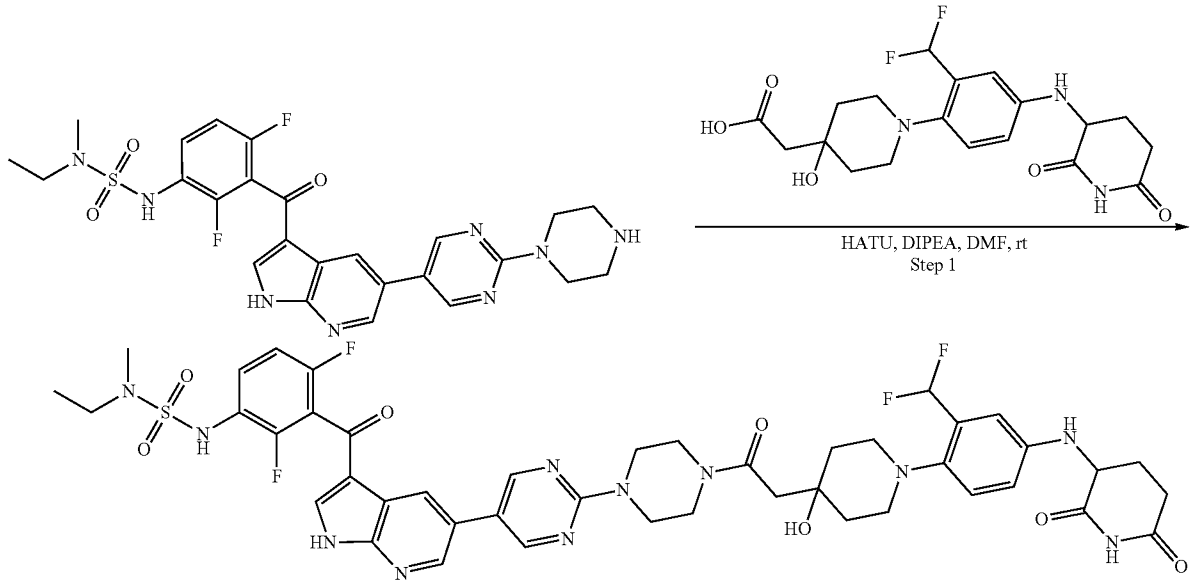

Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (350 mg, 628.83 μmol), 2-[1-[2-(difluoromethyl)-4-[(2,6-dioxo-3-piperidyl)amino]phenyl]-4-hydroxy-4-piperidyl]acetic acid (258.70 mg, 628.83 μmol), HATU (286.92 mg, 754.60 μmol) and N,N-Diisopropylethylamine (406.36 mg, 3.14 mmol, 547.66 μL) to yield 5-[2-[4-[2-[1-[2-(difluoromethyl)-4-[(2,6-dioxo-3-piperidyl)amino]phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (235.16 mg, 225.34 μmol, 35.83% yield) as an off white solid. LCMS (ESI+): 950.2 [M+H]$^+$. $^1$H NMR (400 MHz, DMSO-$d_6$): δ 13.00 (s, 1H), 10.80 (s, 1H), 8.81 (s, 2H), 8.68 (d, J=2.40 Hz, 1H), 8.57 (s, 1H), 8.14 (s, 1H), 7.55-7.61 (m, 1H), 7.25 (t, J=4.40 Hz, 1H), 7.16 (d, J=8.80 Hz, 1H), 7.11 (s, 1H), 6.80-6.85 (m, 2H), 5.98 (d, J=8.00 Hz, 1H), 4.91 (s, 1H), 4.31-4.41 (m, 1H), 3.88-3.90 (m, 4H), 3.82-3.83 (m, 4H), 3.11 (q, J=7.20 Hz, 2H), 2.95-3.00 (m, 2H), 2.55-2.80 (m, 5H), 2.72 (s, 3H), 2.50-2.54 (m, 1H), 2.06-2.12 (m, 1H), 1.65-1.95 (m, 5H), 1.02 (t, J=7.20 Hz, 3H).

Example 205

5-[6-[4-[2-[1-[4-(2,6-dioxo-3-piperidyl)-2-fluoro-phenyl]-4-hydroxy-4-piperidyl]acetyl]piperazin-1-yl]-5-fluoro-3-pyridyl]-3-[3-[[ethyl(methyl)sulfamoyl]amino]-2,6-difluoro-benzoyl]-1H-pyrrolo[2,3-b]pyridine

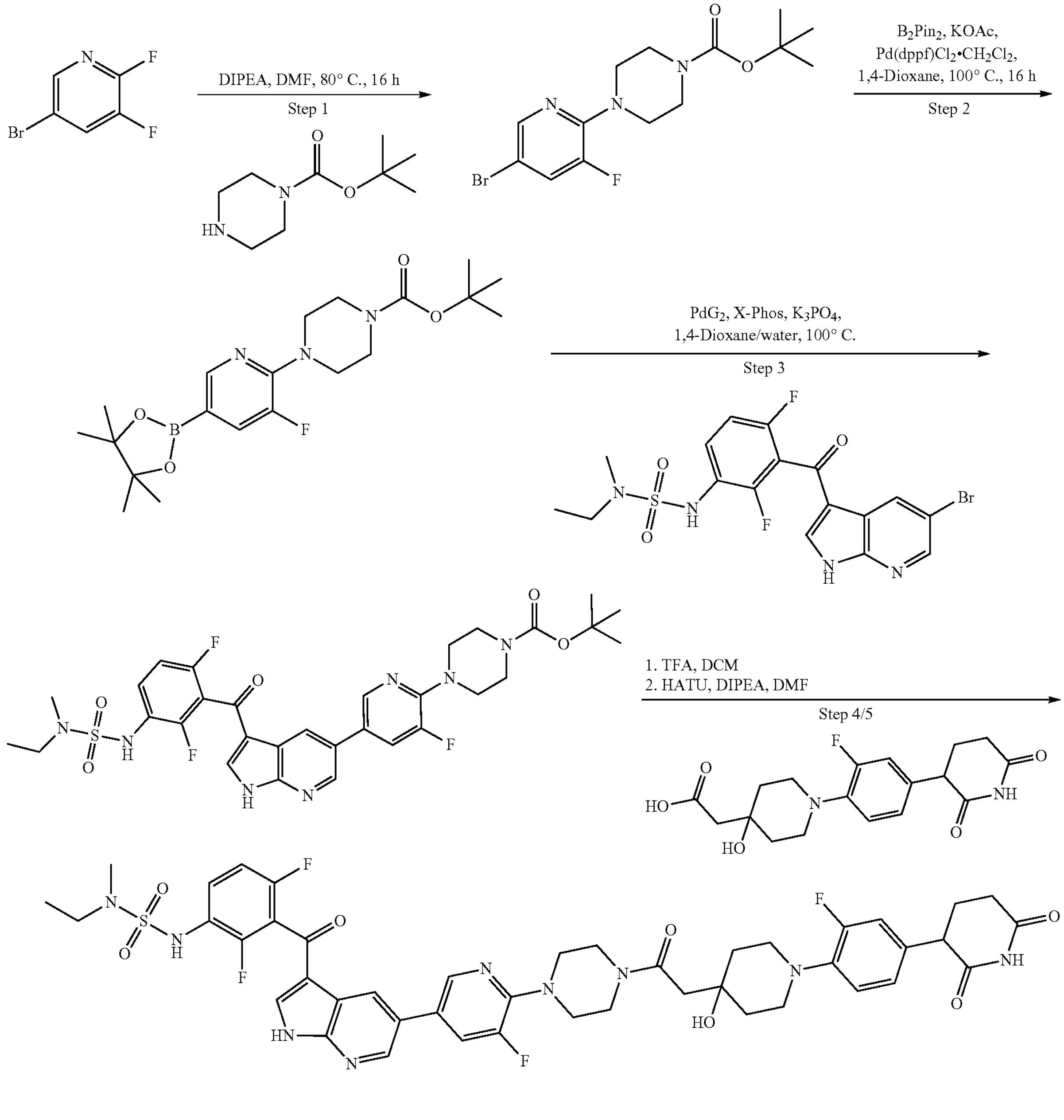

Step 1: To a solution of 5-bromo-2,3-difluoro-pyridine (7 g, 36.09 mmol) in Dimethylformamide was added tert-butyl piperazine-1-carboxylate (6.72 g, 36.09 mmol) followed by N,N-Diisopropylethylamine (13.99 g, 108.26 mmol, 18.86 mL) and the reaction mixture was heated at 80° C. for 16 h. After completion, the reaction mixture was diluted with ethyl acetate (50 mL), washed with cold water (50 mL). The organic layer was washed with brine solution (50 mL), dried over sodium sulphate and concentrated under reduced pressure to get crude. The crude compound was purified by silica gel column chromatography eluted with 15% ethyl acetate in petroleum ether to afford tert-butyl 4-(5-bromo-3-fluoro-2-pyridyl)piperazine-1-carboxylate (8.5 g, 23.12 mmol, 64.08% yield) as colorless liquid. LCMS (ESI+): 304.1 $[M-56+H]^+$ Step 2: A solution of tert-butyl 4-(5-bromo-3-fluoro-2-pyridyl)piperazine-1-carboxylate (3, 2.5 g, 6.94 mmol) in 1,4-dioxane (15 mL) was taken in a sealed tube and added 4,4,5,5-tetramethyl-2-(4,4,5,5-tetramethyl-1,3,2-dioxaborolan-2-yl)-1,3,2-dioxaborolane (1.76 g, 6.94 mmol) and Potassium Acetate (2.04 g, 20.82 mmol, 1.30 mL) degassed with nitrogen for 15 minutes. Then, Pd(dppf)$Cl_2$. Dichloromethane complex (566.32 mg, 694.02 μmol) was added to the reaction mixture and heated at 100° C. for 16 h. After completion, the reaction mixture was filtered through celite. The organic layer was dried over sodium sulphate and concentrated under reduced pressure to get tert-butyl 4-[3-fluoro-5-(4,4,5,5-tetramethyl-1,3,2-dioxaborolan-2-yl)-2-pyridyl]piperazine-1-carboxylate (2 g, 3.98 mmol, 57.31% yield) as off-white solid compound, which was carried forward without further purification. LCMS (ESI+): 408.2 $[M+H]^+$.

Step 3: A solution of 5-bromo-3-[3-[[ethyl(methyl)sulfamoyl]amino]-2,6-difluoro-benzoyl]-1H-pyrrolo[2,3-b]pyridine (500 mg, 1.06 mmol) in 1,4-Dioxane (8 mL) and Water (2 mL) was taken in a microwave vial and added tert-butyl 4-[3-fluoro-5-(4,4,5,5-tetramethyl-1,3,2-dioxaborolan-2-yl)-2-pyridyl]piperazine-1-carboxylate (473.30 mg, 1.16 mmol) and anhydrous Potassium phosphate tribasic (672.73 mg, 3.17 mmol). The reaction mixture was degassed with nitrogen gas for 20 minutes and added XPhos Pd G2 (83.04 mg, 105.64 μmol). The reaction mixture was irradiated under microwave at 100° C. for 1 h. After completion, water (20 mL) was added to the reaction and extracted with ethyl acetate (2×20 mL), organic layer was evaporated under reduced pressure to get crude which was purified through column chromatography using 65% ethyl acetate in petroleum ether as eluent to get tert-butyl 4-[5-[3-[3-[[ethyl(methyl)sulfamoyl]amino]-2,6-difluoro-benzoyl]-1H-pyrrolo[2,3-b]pyridin-5-yl]-3-fluoro-2-pyridyl]piperazine-1-carboxylate (650 mg, 906.93 μmol, 85.85% yield) as off white solid. LCMS (ESI+): 674.2 $[M+H]^+$.

Step 4: To a stirred solution of tert-butyl 4-[5-[3-[3-[[ethyl(methyl)sulfamoyl]amino]-2,6-difluoro-benzoyl]-1H-pyrrolo[2,3-b]pyridin-5-yl]-3-fluoro-2-pyridyl]piperazine-1-carboxylate (600 mg, 890.60 μmol) in anhydrous Dichloromethane (2 mL), TFA (1.02 g, 8.91 mmol, 686.14 μL) was added dropwise at 0° C. under nitrogen atmosphere. The resulting mixture was stirred at ambient temperature for 2 h. After completion, solvent was removed from the reaction mixture under reduced pressure to get a crude compound. Crude product was triturated with Diethyl ether (2×25 mL) to get 3-[3-[[ethyl(methyl)sulfamoyl]amino]-2,6-difluoro-benzoyl]-5-(5-fluoro-6-piperazin-1-yl-3-pyridyl)-1H-pyrrolo[2,3-b]pyridine (600 mg, 794.05 μmol, 89.16% yield) as off-white solid, which was carried forward without further purification. LCMS (ESI+): 574.1 $[M+H]^+$ Step 5: Target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(5-fluoro-6-piperazin-1-yl-3-pyridyl)-1H-pyrrolo[2,3-b]pyridine (350 mg, 509.01 μmol), 2-[1-[4-(2,6-dioxo-3-piperidyl)-2-fluoro-phenyl]-4-hydroxy-4-piperidyl]acetic acid (210 mg, 523.92 μmol), N,N-Diisopropylethylamine (1.48 g, 11.48 mmol, 2.0 mL) and HATU (240 mg, 631.20 μmol). The crude compound was purified by reverse phase column chromatography by using 150 g snap eluted with 50% acetonitrile in 0.1% ammonium acetate in water to afford 5-[6-[4-[2-[1-[4-(2,6-dioxo-3-piperidyl)-2-fluoro-phenyl]-4-hydroxy-4-piperidyl]acetyl]piperazin-1-yl]-5-fluoro-3-pyridyl]-3-[3-[[ethyl(methyl)sulfamoyl]amino]-2,6-difluoro-benzoyl]-1H-pyrrolo[2,3-b]pyridine (147 mg, 158.56 μmol, 31.15% yield) as off-white solid. LCMS (ESI+): 920.2 $[M+H]^+$. $^1H$ NMR (400 MHz, DMSO-$d_6$): δ 13.02 (s, 1H), 10.82 (s, 1H), 9.72 (s, 1H), 8.73 (d, J=2.00 Hz, 1H), 8.62 (s, 1H), 8.45 (s, 1H), 8.16 (s, 1H), 8.06 (dd, J=1.60, −14.40 Hz, 1H), 7.56-7.62 (m, 1H), 7.28 (t, J=8.00 Hz, 1H), 7.02-7.04 (m, 3H), 4.93 (s, 1H), 3.70-3.82 (m, 5H), 3.48-3.70 (m, 4H), 2.99-3.14 (m, 6H), 2.73 (s, 3H), 2.63-2.68 (m, 1H), 2.61 (s, 2H), 2.50-2.56 (m, 1H), 2.12-2.25 (m, 1H), 1.95-2.05 (m, 1H), 1.70-1.83 (m, 4H), 1.02 (t, J=7.20 Hz, 3H).

Example 206

5-[2-[4-[2-[1-[2-chloro-4-[[(3S)-2,6-dioxo-3-piperidyl]amino]phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

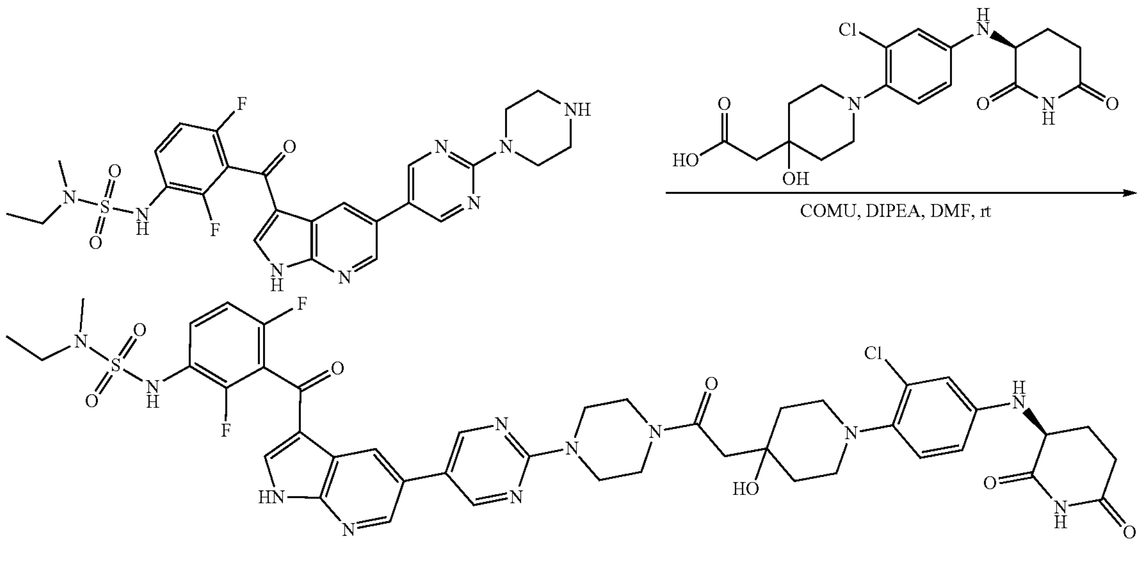

Target compound was prepared via COMU mediated acid-amine coupling reaction (procedure B). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (350 mg, 628.83 μmol), 2-[1-[2-chloro-4-[[(3S)-2,6-dioxo-3-piperidyl]amino]phenyl]-4-hydroxy-4-piperidyl]acetic acid (248.92 mg, 628.83 μmol), N,N-Diisopropylethylamine (243.82 mg, 1.89 mmol, 328.59 μL) and COMU (296.24 mg, 691.72 μmol) to afford 5-[2-[4-[2-[1-[2-chloro-4-[[(3 S)-2,6-dioxo-3-piperidyl]amino]phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (140.6 mg, 139.13 μmol, 22.13% yield) as brown solid. LCMS (ESI−): 932.2 $[M-H]^-$. $^1H$ NMR (400 MHz, DMSO-$d_6$): δ 12.96 (s, 1H), 10.78 (s, 1H), 9.90 (s, 1H), 8.81 (s, 2H), 8.68 (d, J=2.00 Hz, 1H), 8.57 (s, 1H), 8.14 (s, 1H), 7.55-7.61 (m, 1H), 7.27 (t, J=8.00 Hz, 1H), 6.98 (d, J=8.80 Hz, 1H), 6.76 (d, J=2.40 Hz, 1H), 6.61 (dd, J=2.40, 8.80 Hz, 1H), 5.84 (d, J=8.00 Hz, 1H), 4.91 (s, 1H), 4.27-4.33 (m, 1H), 3.83-3.88 (m, 4H), 3.65-3.70 (m, 4H), 3.11 (q, J=7.20 Hz, 2H), 2.84-2.93 (m, 4H), 2.65-2.75 (m, 1H), 2.73 (s, 3H), 2.61 (s, 2H), 2.55-2.60 (m, 1H), 2.05-2.10 (m, 1H), 1.65-1.91 (m, 5H), 1.02 (t, J=7.20 Hz, 3H).

Example 207

5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-3-[3-[[ethyl(methyl)sulfamoyl]amino]-2,5-difluoro-benzoyl]-1H-pyrrolo[2,3-b]pyridine

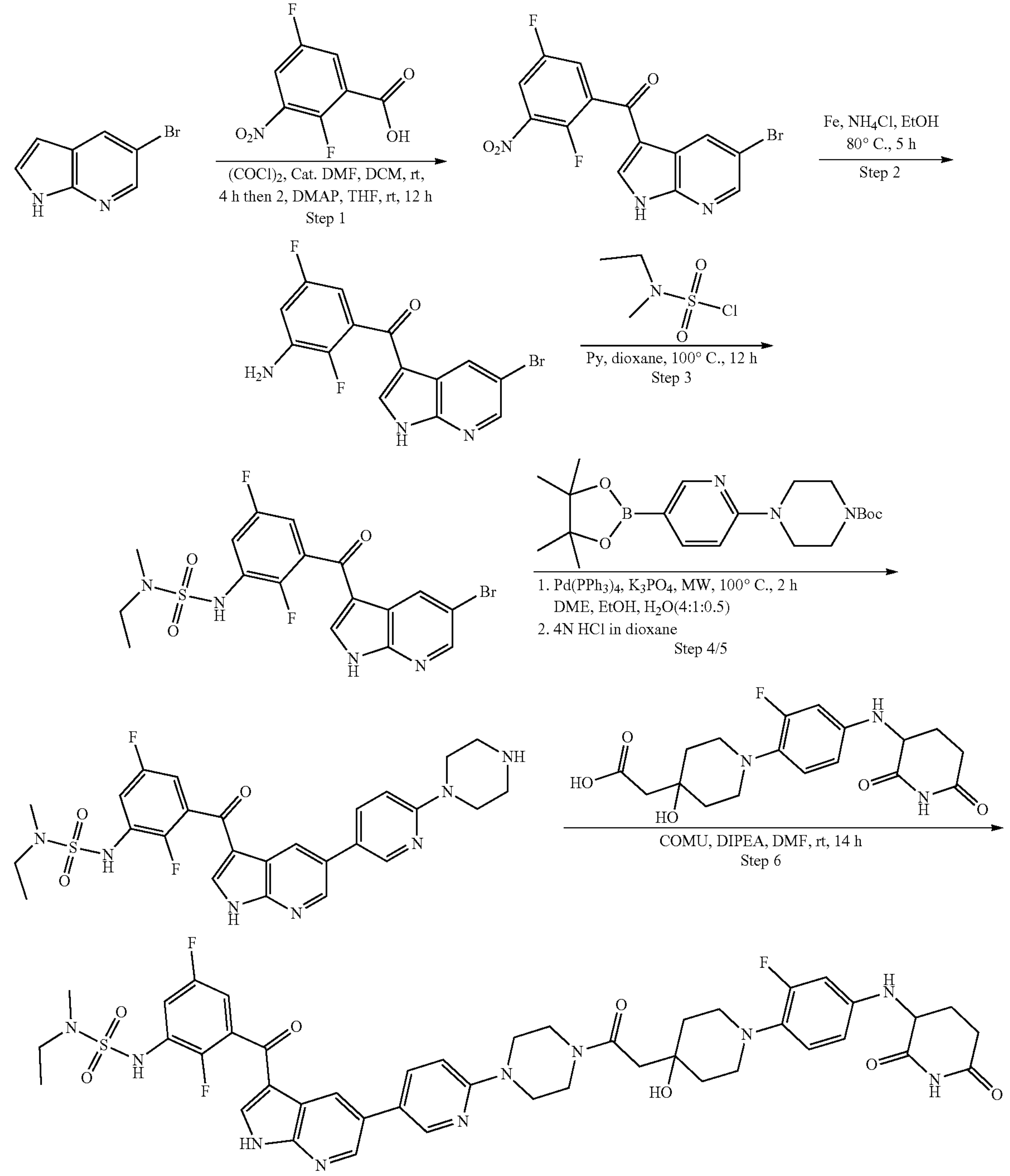

Step 1: To a stirred solution of 2,5-difluoro-3-nitrobenzoic acid (3.0 g, 14.77 mmol) in Dichloromethane (50 mL) was added N,N-Dimethylformamide (107.97 mg, 1.48 mmol, 114.37 μL) followed by the addition of oxalyl chloride (3.80 g, 29.91 mmol, 2.60 mL) at 0-5° C. under nitrogen. The reaction mixture was stirred at room temperature for 4 h. After completion, the reaction mixture was concentrated under reduced pressure to get acid chloride (crude). A solution of 5-bromo-1H-pyrrolo[2,3-b]pyridine (3.0 g, 15.23 mmol) in dichloroethane (30 mL) was taken in a separate round bottom flask and added anhydrous aluminum chloride (8.0 g, 60.00 mmol, 3.28 mL) at 0-5° C. under nitrogen atmosphere, followed by the addition of above acid chloride in DCE (30 mL) at same temperature. The reaction mixture was stirred at room temperature for 30 minutes and heated at 50° C. for 16 h. After completion, the reaction mixture was cooled to 0-5° C. and added cold water (100 mL) and extracted with ethyl acetate (3×300 mL). The combined organic layers were dried over sodium sulphate, filtered and concentrated under reduced pressure. The crude compound was triturated with ethyl acetate to afford (5-bromo-1H-pyrrolo[2,3-b]pyridin-3-yl)-(2,5-difluoro-3-nitro-phenyl)methanone (2.50 g, 5.82 mmol, 39.42% yield) as a brown solid, which was carried forward without further purification. LCMS (ESI+): 381.9 [M+H]$^+$.

Step 2: To a stirred solution of (5-bromo-1H-pyrrolo[2,3-b]pyridin-3-yl)-(2,5-difluoro-3-nitro-phenyl)methanone (2.50 g, 6.54 mmol) in Ethanol (40 mL) and Water (10 mL) was added iron powder (1.90 g, 34.02 mmol, 241.73 μL), ammonium chloride (700 mg, 13.09 mmol, 457.52 μL) at room temperature. The reaction mixture was heated to 80° C. for 5 h. After completion, the reaction mixture was filtered through celite and filtrate was extracted with ethyl acetate (3×300 mL). The combined organic layers were dried over sodium sulphate, filtered and concentrated under reduced pressure. The crude compound was purified by silica gel column chromatography with 90% ethyl acetate in petroleum ether as a eluent to afford (3-amino-2,5-difluoro-phenyl)-(5-bromo-1H-pyrrolo[2,3-b]pyridin-3-yl)methanone (1.20 g, 3.00 mmol, 45.84% yield) as a pale brown solid. LCMS (ESI+): 351.7 [M+H]$^+$.

Step 3: A solution of (3-amino-2,5-difluoro-phenyl)-(5-bromo-1H-pyrrolo[2,3-b]pyridin-3-yl)methanone (1.20 g, 3.41 mmol) in 1,4-Dioxane (20 mL) was taken in sealed tube and added Pyridine (3.91 g, 49.46 mmol, 4.0 mL), followed by the addition of N-ethyl-N-methyl-sulfamoyl chloride (3.33 g, 21.11 mmol, 2.60 mL) at room temperature under nitrogen atmosphere. The reaction mixture was heated to 100° C. for 12 h. After completion, water was added to the reaction mixture and extracted with ethyl acetate (3×200 mL). The combined organic layers were washed with brine solution, dried over sodium sulphate, filtered and concentrated under reduced pressure. The crude compound was purified by silica gel column chromatography with 70% ethyl acetate in petroleum ether as a eluent to afford 5-bromo-3-[3-[[ethyl(methyl)sulfamoyl]amino]-2,5-difluoro-benzoyl]-1H-pyrrolo[2,3-b]pyridine (300 mg, 443.70 μmol, 13.02% yield) as a yellow solid. LCMS (ESI+): 473 [M+H]$^+$.

Step 4: A solution of 5-bromo-3-[3-[[ethyl(methyl)sulfamoyl]amino]-2,5-difluoro-benzoyl]-1H-pyrrolo[2,3-b]pyridine (240 mg, 507.09 μmol) in water (1 mL) and 1,4-dioxane (3 mL) was taken in a micro vial and added tert-butyl 4-[5-(4,4,5,5-tetramethyl-1,3,2-dioxaborolan-2-yl)-2-pyridyl]piperazine-1-carboxylate (236.89 mg, 608.50 μmol) and Potassium phosphate tribasic anhydrous (322.92 mg, 1.52 mmol). The reaction mixture was degassed for 10 minutes, followed by the addition of XPhos Pd G2 (39.90 mg, 50.71 μmol) at room temperature. The reaction mixture was irradiated under microwave at 120° C. for 2 h. After completion, water (20 mL) was added and extracted with ethyl acetate (2×50 mL). The combined organic layers were dried over sodium sulphate, filtered and concentrated under reduced pressure to get crude mixture. The crude compound was purified by column chromatography using 80% ethyl acetate in petroleum ether as a eluent to afford tert-butyl 4-[5-[3-[3-[[ethyl(methyl)sulfamoyl]amino]-2,5-difluoro-benzoyl]-1H-pyrrolo[2,3-b]pyridin-5-yl]-2-pyridyl]piperazine-1-carboxylate (220 mg, 243.58 μmol, 48.04% yield) as off white solid. LCMS (ESI+): 656.2 [M+H]$^-$.

Step 5: To a stirred solution of tert-butyl 4-[5-[3-[3-[[ethyl(methyl)sulfamoyl]amino]-2,5-difluoro-benzoyl]-1H-pyrrolo[2,3-b]pyridin-5-yl]-2-pyridyl]piperazine-1-carboxylate (220 mg, 335.51 μmol) in 1,4-dioxane (5 mL) was added Hydrogen chloride solution in 1,4-dioxane (4M, 5 mL) at 0° C. under nitrogen atmosphere. The reaction mixture was stirred at room temperature for 4 h. After completion, the reaction mixture was concentrated under reduced pressure to get crude product. The crude compound was triturated with diethyl ether to afford 3-[3-[[ethyl(methyl)sulfamoyl]amino]-2,5-difluoro-benzoyl]-5-(6-piperazin-1-yl-3-pyridyl)-1H-pyrrolo[2,3-b]pyridine (225 mg, 319.98 μmol, 87.42% yield) as off-white solid. LCMS (ESI+): 556.1 [M+H]$^+$.

Step 6: Target compound was prepared via COMU mediated acid-amine coupling reaction (procedure B). Amide coupling was carried out using 3-[3-[[ethyl(methyl)sulfamoyl]amino]-2,5-difluoro-benzoyl]-5-(6-piperazin-1-yl-3-pyridyl)-1H-pyrrolo[2,3-b]pyridine (205 mg, 368.97 μmol) and 2-[1-[4-[(2,6-dioxo-3-piperidyl)amino]-2-fluoro-phenyl]-4-hydroxy-4-piperidyl]acetic acid (139.98 mg, 368.97 μmol), N,N-Diisopropylethylamine (190.75 mg, 1.48 mmol, 257.07 μL) and COMU (173.82 mg, 405.87 μmol). Crude compound was purified by reverse phase column chromatography by using 120 g snap eluted with 45% Acetonitrile in 0.1% formic acid in water to afford 5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-3-[3-[[ethyl(methyl)sulfamoyl]amino]-2,5-difluoro-benzoyl]-1H-pyrrolo[2,3-b]pyridine (106 mg, 106.88 μmol, 28.97% yield) as off white solid. LCMS (ESI+): 917.3 [M+H]$^+$. $^1$H NMR (400 MHz, DMSO-$d_6$): δ 12.85 (s, 1H), 10.78 (s, 1H), 8.65 (d, J=2.00 Hz, 1H), 8.58 (d, J=2.00 Hz, 1H), 8.52 (d, J=2.40 Hz, 1H), 8.23 (s, 1H), 8.05 (s, 1H), 7.97 (dd, J=2.40, 8.80 Hz, 1H), 7.27-7.32 (m, 1H), 7.02 (d, J=8.80 Hz, 1H), 6.84-6.95 (m, 2H), 6.50 (dd, J=2.00, 14.80 Hz, 1H), 6.42 (d, J=8.40 Hz, 1H), 5.78 (d, J=7.60 Hz, 1H), 4.88 (s, 1H), 4.20-4.30 (m, 1H), 3.59-3.71 (m, 8H), 3.10 (q, J=7.20 Hz, 2H), 2.81-2.95 (m, 4H), 2.61-2.79 (m, 1H), 2.74 (s, 3H), 2.59 (s, 2H), 2.51-2.56 (m, 1H), 2.07-2.11 (m, 1H), 1.67-1.87 (m, 5H), 1.04 (t, J=7.20 Hz, 3H).

Example 208

5-[6-[4-[2-[1-[2-chloro-4-[[(3S)-2,6-dioxo-3-piperidyl]amino]phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine

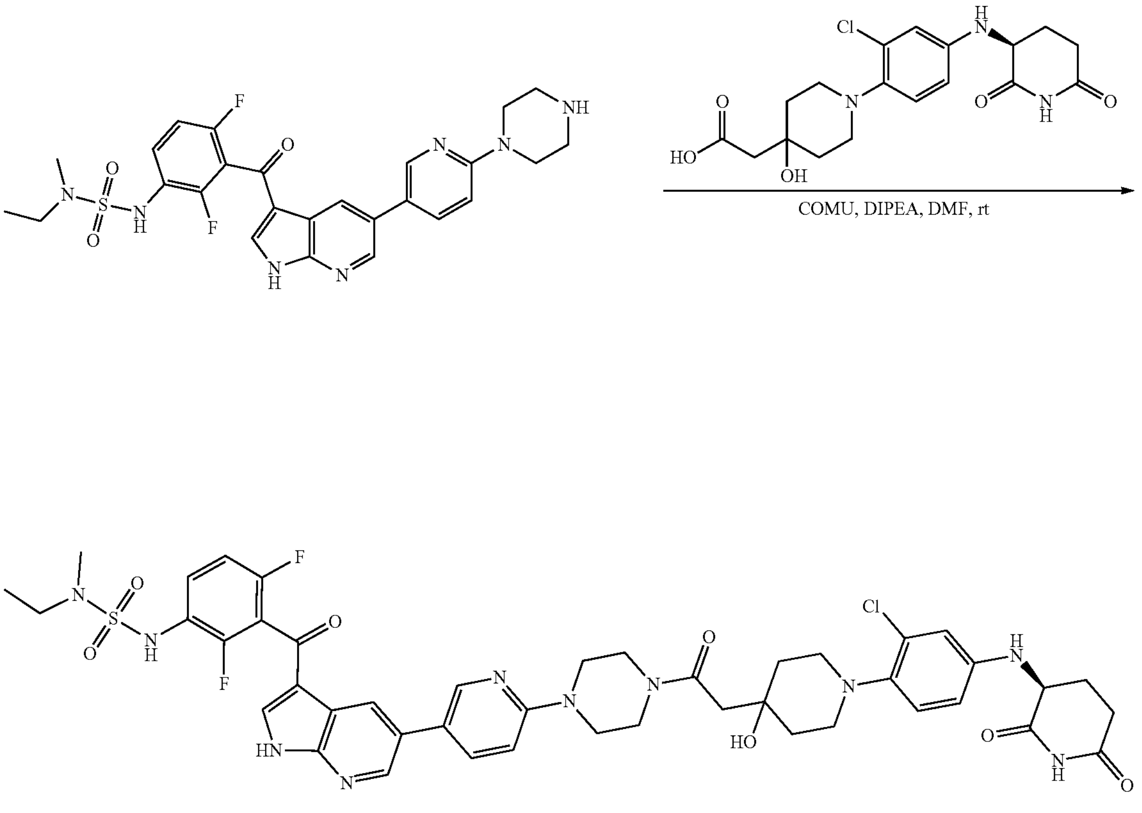

Target compound was prepared via COMU mediated acid-amine coupling reaction (procedure B). Amide coupling was carried out using 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (350 mg, 629.95 μmol), 2-[1-[2-chloro-4-[[(3S)-2,6-dioxo-3-piperidyl]amino]phenyl]-4-hydroxy-4-piperidyl]acetic acid (249.36 mg, 629.95 μmol), N,N-Diisopropylethylamine (244.25 mg, 1.89 mmol, 329.18 μL) and COMU (296.77 mg, 692.95 μmol) to afford 5-[6-[4-[2-[1-[2-chloro-4-[[(3 S)-2,6-dioxo-3-piperidyl]amino]phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine (48.64 mg, 49.01 μmol, 7.78% yield) as brown solid. LCMS (ESI+): 932.8 $[M+H]^+$. $^1H$ NMR (400 MHz, DMSO-$d_6$): δ 12.96 (s, 1H), 10.78 (s, 1H), 10.00 (s, 1H), 8.67 (d, J=2.40 Hz, 1H), 8.55 (s, 1H), 8.52 (d, J=2.40 Hz, 1H), 8.10 (s, 1H), 7.98 (dd, J=2.40, 8.60 Hz, 1H), 7.57 (dd, J=3.20, 9.20 Hz, 1H), 7.23 (t, J=8.40 Hz, 1H), 6.97-7.00 (m, 2H), 6.76 (d, J=2.40 Hz, 1H), 6.61 (dd, J=2.40, 8.80 Hz, 1H), 5.84 (d, J=7.60 Hz, 1H), 4.91 (s, 1H), 4.26-4.31 (m, 1H), 3.60-3.71 (m, 8H), 3.09 (q, J=6.80 Hz, 2H), 2.84-2.93 (m, 4H), 2.65-2.75 (m, 1H), 2.74 (s, 3H), 2.61 (s, 2H), 2.55-2.60 (m, 1H), 2.06-2.10 (m, 1H), 1.68-1.73 (m, 5H), 1.02 (t, J=7.20 Hz, 3H).

Example 209

5-[2-[4-[2-[1-[2-chloro-4-[[(3R)-2,6-dioxo-3-piperidyl]amino]phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

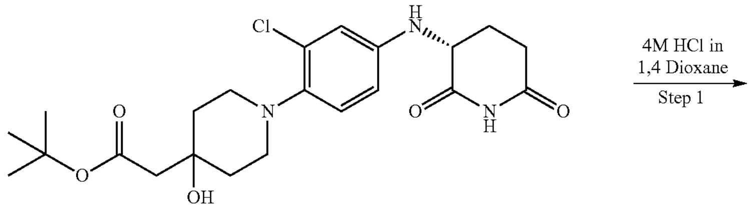

-continued

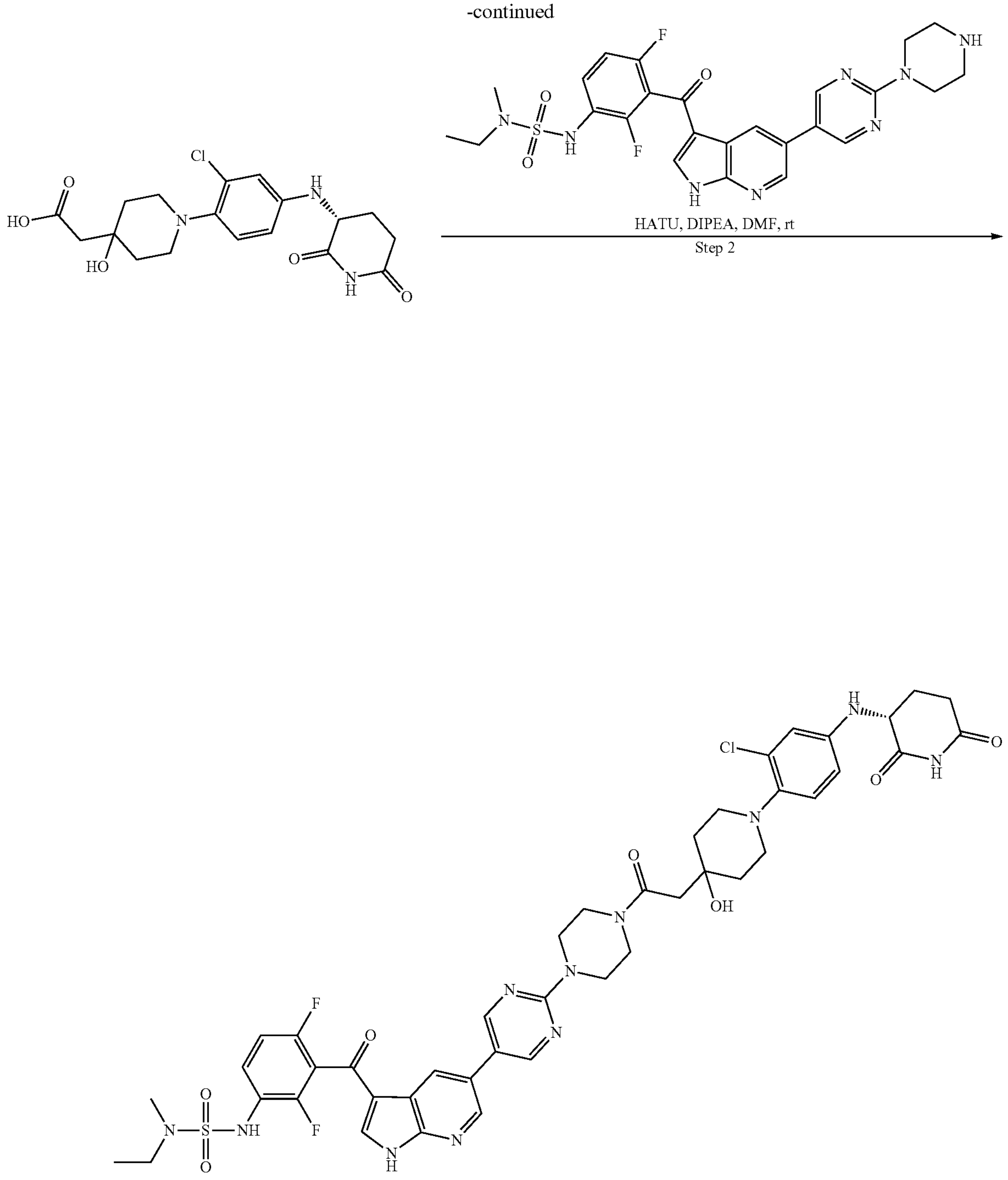

Step 1: To a solution of tert-butyl 2-[1-[2-chloro-4-[[(3R)-2,6-dioxo-3-piperidyl]amino]phenyl]-4-hydroxy-4-piperidyl]acetate (800 mg, 1.77 mmol) in Dichloromethane (10 mL) was added hydrogen chloride solution in 1,4-dioxane (4M, 10 mL) at 0° C. and stirred at room temperature for 6 h. After completion, the reaction mixture was concentrated under reduced pressure to get crude which was triturated with petroleum ether to afford 2-[1-[2-chloro-4-[[(3R)-2,6-dioxo-3-piperidyl]amino]phenyl]-4-hydroxy-4-piperidyl] acetic acid (750 mg, 1.64 mmol, 92.82% yield) as off white solid. LCMS (ESI+): 396.0 $[M+H]^+$.

Step 2: target compound was prepared via HATU mediated acid-amine coupling reaction (procedure A). Amide coupling was carried out using 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (300 mg, 505.86 μmol), 2-[1-[2-chloro-4-[[(3R)-2,6-dioxo-3-piperidyl] amino]phenyl]-4-hydroxy-4-piperidyl]acetic acid (200.24 mg, 463.20 μmol), N,N-Diisopropylethylamine (261.51 mg, 2.02 mmol, 352.44 μL) and HATU (192.34 mg, 505.86 μmol) to afford 5-[2-[4-[2-[1-[2-chloro-4-[[(3R)-2,6-dioxo-3-piperidyl]amino]phenyl]-4-hydroxy-4-piperidyl]acetyl] piperazin-1-yl]pyrimidin-5-yl]-3-[3-[[ethyl(methyl)sulfamoyl]amino]-2,6-difluoro-benzoyl]-1H-pyrrolo[2,3-b] pyridine (97 mg, 97.95 μmol, 19.36% yield) as off white solid. LCMS (ESI+): 934.2 $[M+H]^+$.

Example 210
5-[4-[4-[2-[1-[4-[(2,6-dioxo-3-piperidyl)amino]-2-fluoro-phenyl]-4-hydroxy-4-piperidyl]acetyl]piperazin-1-yl]-2-fluoro-phenyl]-3-[3-[[ethyl(methyl)sulfamoyl]amino]-2,6-difluoro-benzoyl]-1H-pyrrolo[2,3-b]pyridine
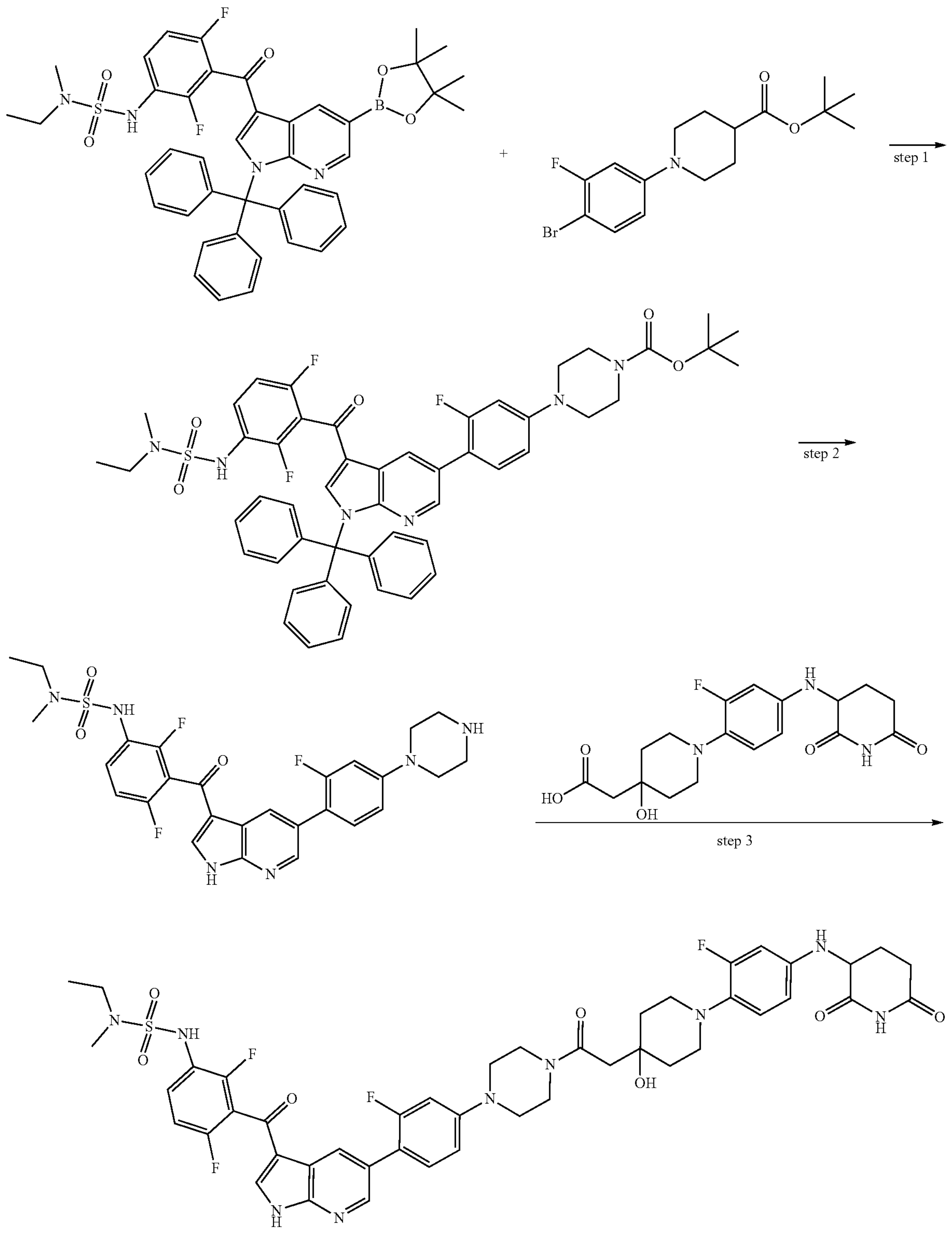

Step 1: 3-[3-[[ethyl(methyl)sulfamoyl]amino]-2,6-difluoro-benzoyl]-5-(4,4,5,5-tetramethyl-1,3,2-dioxaborolan-2-yl)-1-trityl-pyrrolo[2,3-b]pyridine (250 mg, 327.80 μmol) and tert-butyl 4-(4-bromo-3-fluoro-phenyl)piperazine-1-carboxylate (117.76 mg, 327.80 μmol) were dissolved in 1,4-dioxane (1.1 mL) and Water (280.00 uL) with Tri potassium phosphate (208.74 mg, 983.39 μmol) and X Phos Pd G3 (13.87 mg, 16.39 μmol). The reaction was purged with argon before being sealed in a microwave vessel. The contents were stirred at room temperature for 5 min to ensure dissolution of solids. The reaction was stirred in a microwave at 115° C. for 2 hr. After cooling, the reaction was diluted with water and extracted with ethyl acetate. The combined organic layers were dried over sodium sulphate and concentrated. The crude material was then purified by column chromatography (20-80% ethyl acetate in hexanes) to afford the product tert-butyl 4-[4-[3-[3-[[ethyl(methyl)sulfamoyl]amino]-2,6-difluoro-benzoyl]-1-trityl-pyrrolo[2,3-b]pyridin-5-yl]-3-fluoro-phenyl]piperazine-1-carboxylate (291 mg, 286.22 μmol, 87.32% yield). LCMS (ESI+): 915.6 $[M+H]^+$ Step 2: To a solution of tert-butyl 4-[4-[3-[3-[[ethyl(methyl)sulfamoyl]amino]-2,6-difluoro-benzoyl]-1-trityl-pyrrolo[2,3-b]pyridin-5-yl]-3-fluoro-phenyl]piperazine-1-carboxylate (295 mg, 322.39 μmol) in 1,4-dioxanes (5.5 mL) was added Hydrogen chloride solution in dioxane (4 M, 3.22 mL). The resulting solution was stirred at room temperature for 24 hr. At this time, the resulting solid was isolated by vacuum filtration, washing with MTBE, to afford the product 3-[3-[[ethyl(methyl)sulfamoyl]amino]-2,6-difluoro-benzoyl]-5-(2-fluoro-4-piperazin-1-yl-phenyl)-1H-pyrrolo[2,3-b]pyridine (125 mg, 194.97 μmol, 60.48% yield, hydrochloric acid salt), which was used without further purification. LCMS (ESI+): 573.3 $[M+H]^+$ Step 3: To a stirred solution of 2-[1-[4-[(2,6-dioxo-3-piperidyl)amino]-2-fluoro-phenyl]-4-hydroxy-4-piperidyl]acetic acid (54.47 mg, 130.98 μmol, hydrochloric acid salt) in DMF (0.75 mL) at 0° C. was added N,N-Diisopropylethylamine (56.43 mg, 436.60 μmol, 76.05 uL) and COMU (41.14 mg, 96.05 μmol). The resulting mixture stirred at this temperature for 30 min. At this time, a solution of 3-[3-[[ethyl(methyl)sulfamoyl]amino]-2,6-difluoro-benzoyl]-5-(2-fluoro-4-piperazin-1-yl-phenyl)-1H-pyrrolo[2,3-b]pyridine (50 mg, 87.32 μmol, hydrochloric acid salt) in DMF (0.75 mL) was added at 0° C. before warming to room temperature and stirring for 2 hr. 8 drops sat. aq. sodium bicarbonate solution was added, and the resulting mixture stirred for 3 hr. The crude reaction mixture was then purified by column chromatography (10-55% MeCN in $H_2O$ with 0.1% formic acid) to afford the product 5-[4-[4-[2-[1-[4-[(2,6-dioxo-3-pi peri dyl)amino]-2-fluoro-phenyl]-4-hydroxy-4-piperidyl]acetyl]piperazin-1-yl]-2-fluoro-phenyl]-3-[3-[[ethyl(methyl)sulfamoyl]amino]-2,6-difluoro-benzoyl]-1H-pyrrolo[2,3-b]pyridine (38.64 mg, 37.46 μmol, 42.90% yield, formic acid salt) as an off-white solid. LCMS (ESI+): 934.6 $[M+H]^+$. $^1H$ NMR (400 MHz, DMSO-d6) δ 12.89 (s, 1H), 10.70 (s, 1H), 8.53-8.39 (m, 2H), 8.04 (s, 1H), 7.49 (td, J=9.0, 6.0 Hz, 1H), 7.43 (t, J=9.2 Hz, 1H), 7.17 (t, J=8.8 Hz, 1H), 6.94-6.85 (m, 2H), 6.79 (dd, J=10.0, 8.7 Hz, 1H), 6.48-6.40 (m, 1H), 6.34 (dd, J=8.7, 2.5 Hz, 1H), 5.70 (d, J=7.6 Hz, 1H), 4.78 (s, 1H), 4.18 (ddd, J=12.0, 7.5, 4.7 Hz, 1H), 3.63 (d, J=21.3 Hz, 4H), 3.22 (d, J=7.6 Hz, 3H), 3.02 (q, J=7.2 Hz, 2H), 2.92-2.74 (m, 4H), 2.63 (s, 5H), 2.51 (s, 4H), 2.07-1.97 (m, 1H), 1.87-1.52 (m, 5H), 0.94 (t, J=7.1 Hz, 3H).

Example 211

5-[6-[4-[2-[1-[4-[(2,6-dioxo-3-piperidyl)amino]-2-fluoro-phenyl]-4-hydroxy-4-piperidyl]acetyl]piperazin-1-yl]-5-methylsulfonyl-3-pyridyl]-3-[3-[[ethyl(methyl)sulfamoyl]amino]-2,6-difluoro-benzoyl]-1H-pyrrolo[2,3-b]pyridine

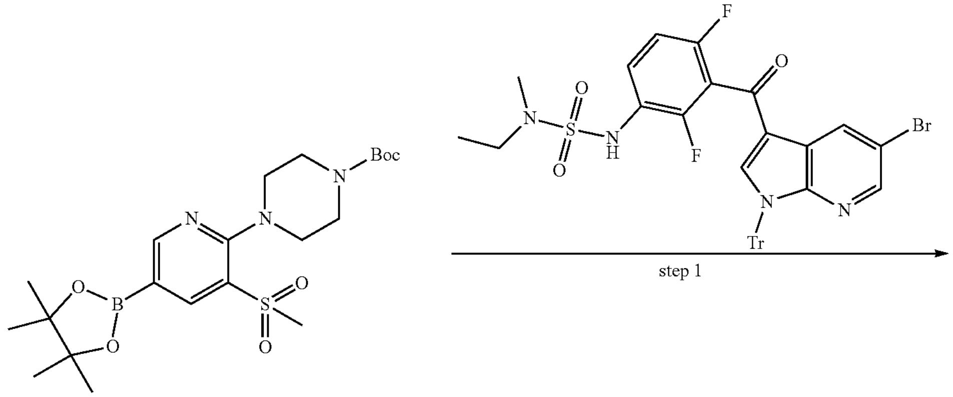

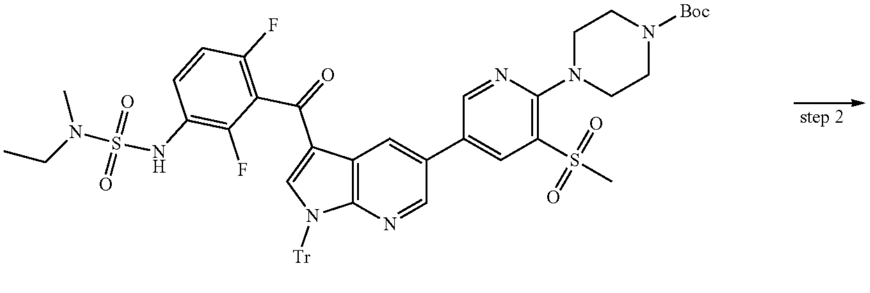

-continued

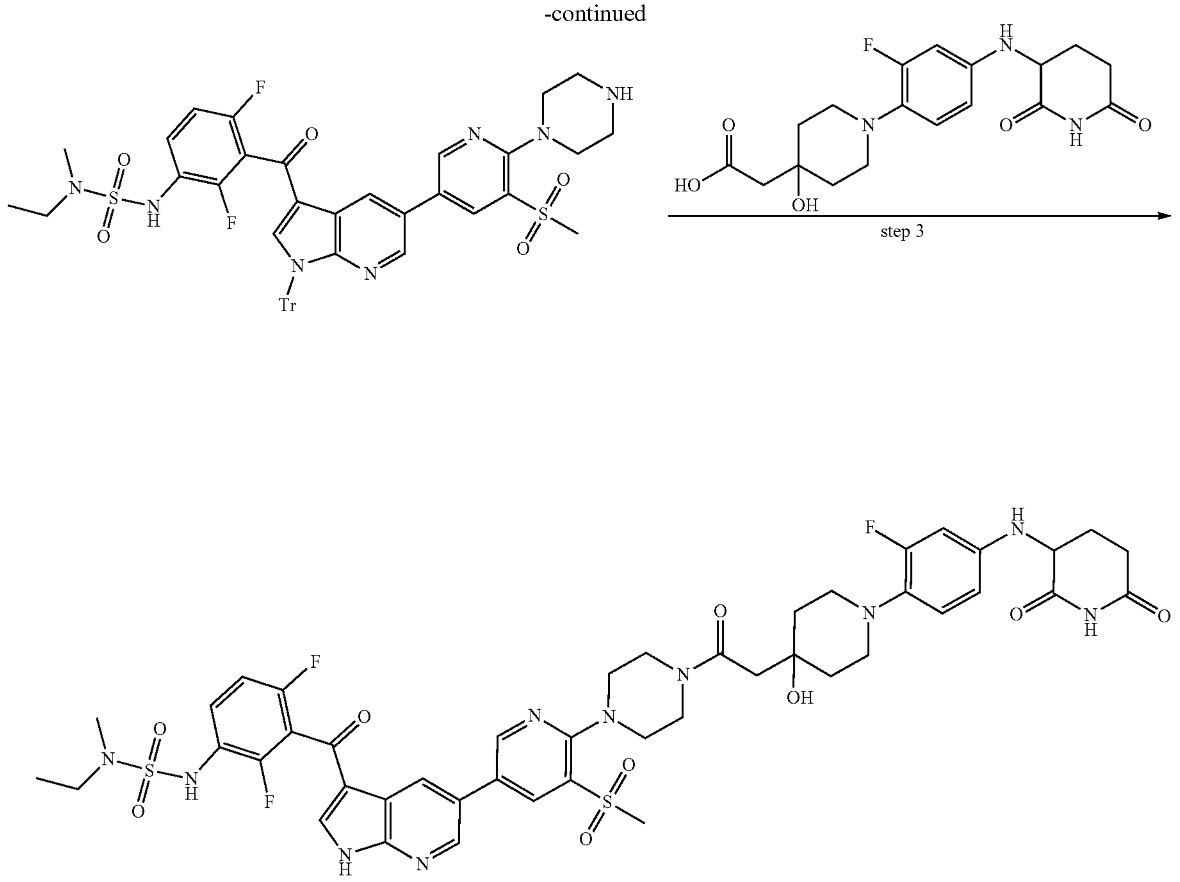

Step 1: The tert-butyl 4-(5-bromopyrazin-2-yl)piperazine-1-carboxylate (905.20 mg, 2.64 mmol) and 3-[3-[[ethyl (methyl)sulfamoyl]amino]-2,6-difluoro-benzoyl]-5-(4,4,5,5-tetramethyl-1,3,2-dioxaborolan-2-yl)-1-trityl-pyrrolo[2,3-b]pyridine (353.83 mg, 463.93 μmol), potassium phosphate tribasic anhydrous (227.26 mg, 1.07 mmol) were diluted in water (1.5 mL) and 1,4-dioxanes (8 mL). The 20 ml micro-wave tube was purged with argon gas for 10 min. The Xphos G3 Pd (104.65 mg, 123.63 μmol) was added. The tube was sealed and heated 120° C. in the microwave. The crude mixture was diluted in water (5 ml) and then extracted with ethyl acetate (3x20 mL). The organic layers were combined and dried over $MgSO_4$. The crude material was purified by column chromatography column 0-40% ethyl acetate in Petroleum ether to yield tert-butyl 4-[5-[3-[3-[[ethyl (methyl)sulfamoyl]amino]-2,6-difluoro-benzoyl]-1-trityl-pyrrolo[2,3-b]pyridin-5-yl]-3-methylsulfonyl-2-pyridyl] piperazine-1-carboxylate (260 mg, 266.36 μmol, 74.64% yield). LCMS (ESI+): 976.6 $[M+H]^+$.

Step 2: To a solution of tert-butyl 4-[5-[3-[3-[[ethyl (methyl)sulfamoyl]amino]-2,6-difluoro-benzoyl]-1-trityl-pyrrolo[2,3-b]pyridin-5-yl]-3-methylsulfonyl-2-pyridyl] piperazine-1-carboxylate (200 mg, 204.89 μmol) in 1,4 dioxane (3 mL) was added hydrochloric acid in 1,4-dioxane (533.33 mg, 14.63 mmol, 666.67 uL) at 0° C. The resulted mixture was stirred at room temperature overnight. After stirring overnight, the reaction is filtered and the solid was dried to afford 3-[3-[[ethyl(methyl)sulfamoyl]amino]-2,6-difluoro-benzoyl]-5-(5-methylsulfonyl-6-piperazin-1-yl-3-pyridyl)-1H-pyrrolo[2,3-b]pyridine (125 mg, 197.26 μmol, 96.27% yield) as a white solid. LCMS (ESI+): 634.1 $[M+H]^+$.

Step 3: Target compound was prepared via procedure C, by modifying the amide coupling with 2-[1-[4-[(2,6-dioxo-3-piperidyl)amino]-2-fluoro-phenyl]-4-hydroxy-4-piperidyl]acetic acid (107.06 g, 282.20 mmol) and 3-[3-[[ethyl (methyl)sulfamoyl]amino]-2,6-difluoro-benzoyl]-5-(5-methyl sulfonyl-6-piperazin-1-yl-3-pyridyl)-1H-pyrrolo[2,3-b]pyridine (125 g, 197.26 mmol) and 6 eq of DIPEA. The crude material was purified by reverse phase column chromatography (MeCN & Water (0.01% TFA). The product elutes around 40%. The product was free based in saturated bicarbonateonate solution in ethyl acetate. The material was then purified by column chromatography (0-30% methanol in dichloromethane) to afford 5-[6-[4-[2-[1-[4-[(2,6-dioxo-3-piperidyl)amino]-2-fluoro-phenyl]-4-hydroxy-4-piperidyl]acetyl]piperazin-1-yl]-5-methyl sulfonyl-3-pyridyl]-3-[3-[[ethyl(methyl)sulfamoyl]amino]-2,6-difluoro-benzoyl]-1H-pyrrolo[2,3-b]pyridine (123.8 mg, 121.9 μmol, 62% yield) as off-white solid. LCMS (ESI+): 995.1 $[M+H]^+$. $^1H$ NMR (400 MHz, DMSO-$d_6$): δ 13.00 (s, 1H), 10.70 (s, 1H), 9.64 (s, 1H), 8.98 (d, J=2.4 Hz, 1H), 8.73 (d, J=2.3 Hz, 1H), 8.64 (s, 1H), 8.47 (d, J=2.4 Hz, 1H), 8.11 (s, 1H), 7.56-7.46 (m, 1H), 7.19 (t, J=8.7 Hz, 1H), 6.79 (t, J=9.3 Hz, 1H), 6.43 (dd, J=15.0, 2.5 Hz, 1H), 6.35 (dd, J=8.7, 2.5 Hz, 1H), 5.70 (d, J=7.6 Hz, 1H), 4.78 (s, 1H), 4.24-4.13 (m, 1H), 3.77-3.63 (m, 4H), 3.42 (s, 3H), 3.25-3.21 (m, 9H), 3.20-3.15 (m, 2H), 3.04 (q, J=7.1 Hz, 2H), 2.90-2.76 (m, 5H), 2.73-2.60 (m, 4H), 2.52 (s, 3H), 2.50-2.46 (m, OH), 2.02 (dt, J=9.1, 4.0 Hz, 1H), 1.85-1.66 (m, 3H), 1.65-1.57 (m, 2H), 0.95 (t, J=7.1 Hz, 3H).

Example 212
5-[4-[4-[2-[1-[4-[(2,6-dioxo-3-piperidyl)amino]-2-fluoro-phenyl]-4-hydroxy-4-piperidyl]acetyl]piperazin-1-yl]-3-(trifluoromethyl)phenyl]-3-[3-[[ethyl(methyl)sulfamoyl]amino]-2,6-difluoro-benzoyl]-1H-pyrrolo[2,3-b]pyridine
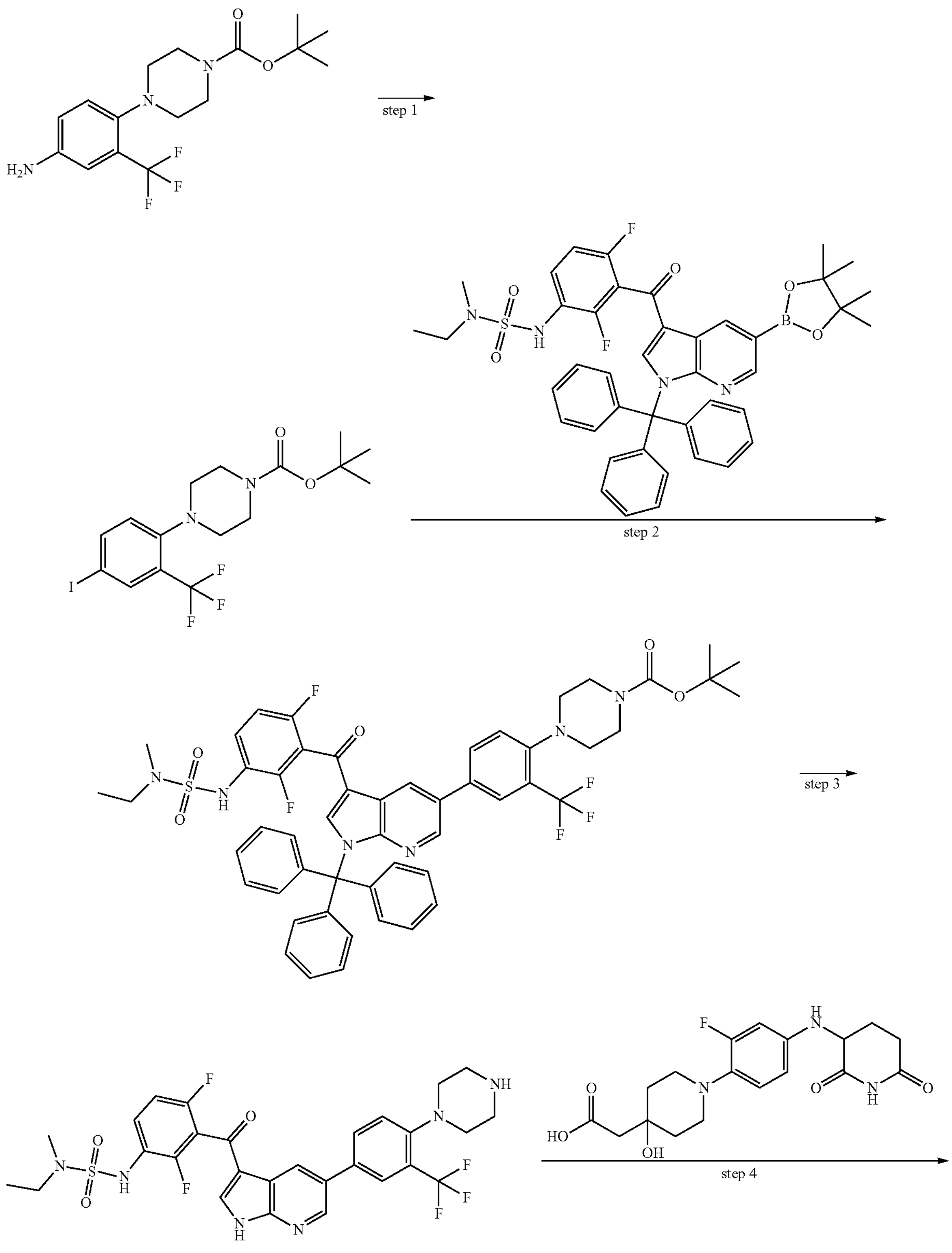

-continued

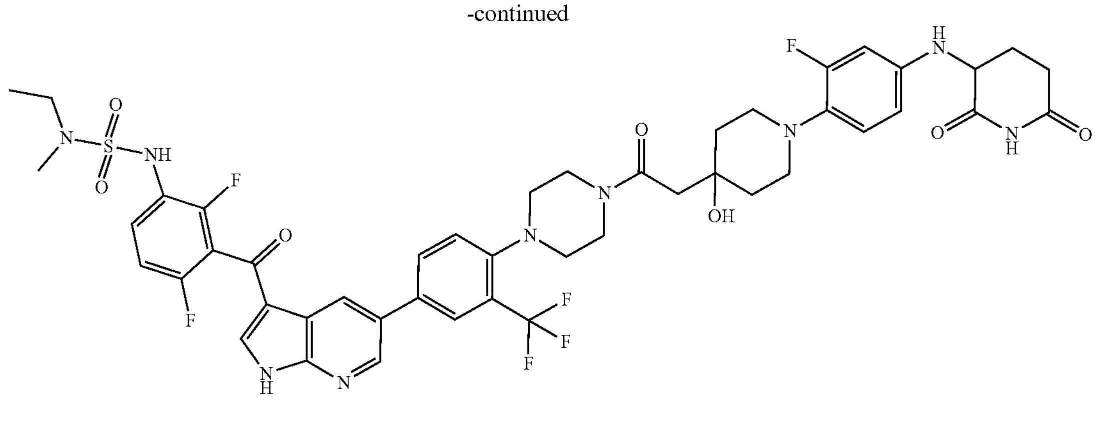

Step 1: To a solution of tert-butyl 4-[4-amino-2-(trifluoromethyl)phenyl]piperazine-1-carboxylate (200 mg, 579.11 µmol) in acetonitrile (5 mL) and water (5 mL) was added p-Toluenesulfonic acid monohydrate (343.69 mg, 1.81 mmol, 277.17 uL) at 0° C. At the same temperature was added a solution of Sodium Nitrite (81.91 mg, 1.19 mmol, 37.75 uL) in water (5 mL). The reaction stirred at the same temperature for 1 hr before a solution of Potassium iodide (212.45 mg, 1.28 mmol, 68.09 uL) in acetonitrile (5 mL) was added. The resulting mixture was then stirred at room temperature overnight. The reaction was diluted with water and extracted with ethyl acetate before being dried with sodium sulphate. The combined organic layers were concentrated, and the crude residue was purified by column chromatography (0-100% ethyl acetate in hexanes) to afford the product tert-butyl 4-[4-iodo-2-(trifluoromethyl)phenyl] piperazine-1-carboxylate (217 mg, 451.84 µmol, 78.02% yield). LCMS (ESI+): 401.1 $[M-tBu]^+$ Step 2: A mixture of 3-[3-[[ethyl(methyl)sulfamoyl] amino]-2,6-difluoro-benzoyl]-5-(4,4,5,5-tetramethyl-1,3,2-dioxaborolan-2-yl)-1-trityl-pyrrolo[2,3-b]pyridine (367.76 mg, 482.20 µmol), tert-butyl 4-[4-iodo-2-(trifluoromethyl) phenyl]piperazine-1-carboxylate (220 mg, 482.20 µmol), Tri potassium phosphate (307.07 mg, 1.45 mmol), and XPhos Pd G3 (20.41 mg, 24.11 µmol) were dissolved in 1,4-dioxane (1.6 mL) and Water (0.4 mL). The reaction mixture was with argon, and was stirred at room temperature for 5 min for dissolution of solids. The reaction was then heated in a microwave for 115° C. for 2 hr. After cooling, the reaction was diluted with water and extracted with ethyl acetate. The combined organic layers were dried with sodium sulphate and concentrated. The crude material was then purified by column chromatography (35-80% ethyl acetate in hexanes) to afford the product tert-butyl 4-[4-[3-[3-[[ethyl(methyl)sulfamoyl]amino]-2,6-difluoro-benzoyl]-1-trityl-pyrrolo[2,3-b]pyridin-5-yl]-2-(trifluoromethyl)phenyl]piperazine-1-carboxylate (386 mg, 379.99 µmol, 78.80% yield). LCMS (ESI+): 965.9 $[M+H]^+$ Step 3: To a solution of tert-butyl 4-[4-[3-[3-[[ethyl (methyl)sulfamoyl]amino]-2,6-difluoro-benzoyl]-1-trityl-pyrrolo[2,3-b]pyridin-5-yl]-2-(trifluoromethyl)phenyl]piperazine-1-carboxylate (386 mg, 399.98 µmol) in 1,4-dioxanes (6.8 mL) was added Hydrogen chloride solution in 1,4-dioxane (4 M, 9.00 mL). The reaction stirred at room temperature overnight. The reaction was concentrated and the crude material was purified by column chromatography (20-80% acetonitrile in water with 0.1% formic acid) to afford the product 3-[3-[[ethyl(methyl)sulfamoyl]amino]-2,6-difluoro-benzoyl]-5-[4-piperazin-1-yl-3-(trifluoromethyl) phenyl]-1H-pyrrolo[2,3-b]pyridine (112 mg, 159.13 µmol, 39.78% yield, formic acid salt). LCMS (ESI+): 623.9 $[M+H]^+$ Step 4: To a solution of 2-[1-[4-[(2,6-dioxo-3-piperidyl) amino]-2-fluoro-phenyl]-4-hydroxy-4-piperidyl]acetic acid (48.51 mg, 116.66 µmol, hydrochloric acid salt) in DMF (0.75 mL) was added N,N-Diisopropylethylamine (57.99 mg, 448.68 µmol, 78.15 uL) and COMU (42.27 mg, 98.71 µmol) at 0° C. The mixture stirred for 30 min before a solution of 3-[3-[[ethyl(methyl)sulfamoyl]amino]-2,6-difluoro-benzoyl]-5-[4-piperazin-1-yl-3-(trifluoromethyl)phenyl]-1H-pyrrolo[2,3-b]pyridine (60 mg, 89.74 mol, formic acid salt) in DMF (0.75 mL) was added at 0° C. The reaction warmed to room temperature and stirred for 2 hr. The crude reaction was then purified by column chromatography (15-60% acetonitrile in water with 0.1% formic acid) to afford the product 5-[4-[4-[2-[1-[4-[(2,6-dioxo-3-piperidyl) amino]-2-fluoro-phenyl]-4-hydroxy-4-piperidyl]acetyl]piperazin-1-yl]-3-(trifluoromethyl)phenyl]-3-[3-[[ethyl (methyl)sulfamoyl]amino]-2,6-difluoro-benzoyl]-1H-pyrrolo[2,3-b]pyridine (52 mg, 47.96 mol, 53.45% yield, formic acid salt) as an off-white solid.

LCMS (ESI+): 984.6 $[M+H]^+$. $^1H$ NMR (400 MHz, DMSO-d6) δ 13.04 (s, 1H), 10.78 (s, 1H), 8.76 (d, J=2.2 Hz, 1H), 8.64 (s, 1H), 8.18 (s, 1H), 8.06 (dd, J=8.3, 2.2 Hz, 1H), 7.99 (d, J=2.2 Hz, 1H), 7.72 (d, J=8.4 Hz, 1H), 7.59 (td, J=9.0, 5.9 Hz, 1H), 7.28 (td, J=8.8, 1.6 Hz, 1H), 6.87 (t, J=9.4 Hz, 1H), 6.56-6.46 (m, 1H), 6.43 (dd, J=8.7, 2.6 Hz, 1H), 5.78 (d, J=7.6 Hz, 1H), 4.86 (s, 1H), 4.26 (ddd, J=11.9, 7.6, 4.8 Hz, 1H), 3.70 (d, J=16.3 Hz, 4H), 3.11 (q, J=7.1 Hz, 2H), 2.92 (dq, J=18.9, 11.4, 8.0 Hz, 8H), 2.73 (s, 5H), 2.59 (s, 3H), 2.15-2.02 (m, 1H), 1.93-1.64 (m, 5H), 1.02 (t, J=7.1 Hz, 3H).

Example 213
5-[2-[4-[2-[1-[2-chloro-4-(2,4-dioxohexahydropyrimidin-1-yl)phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine
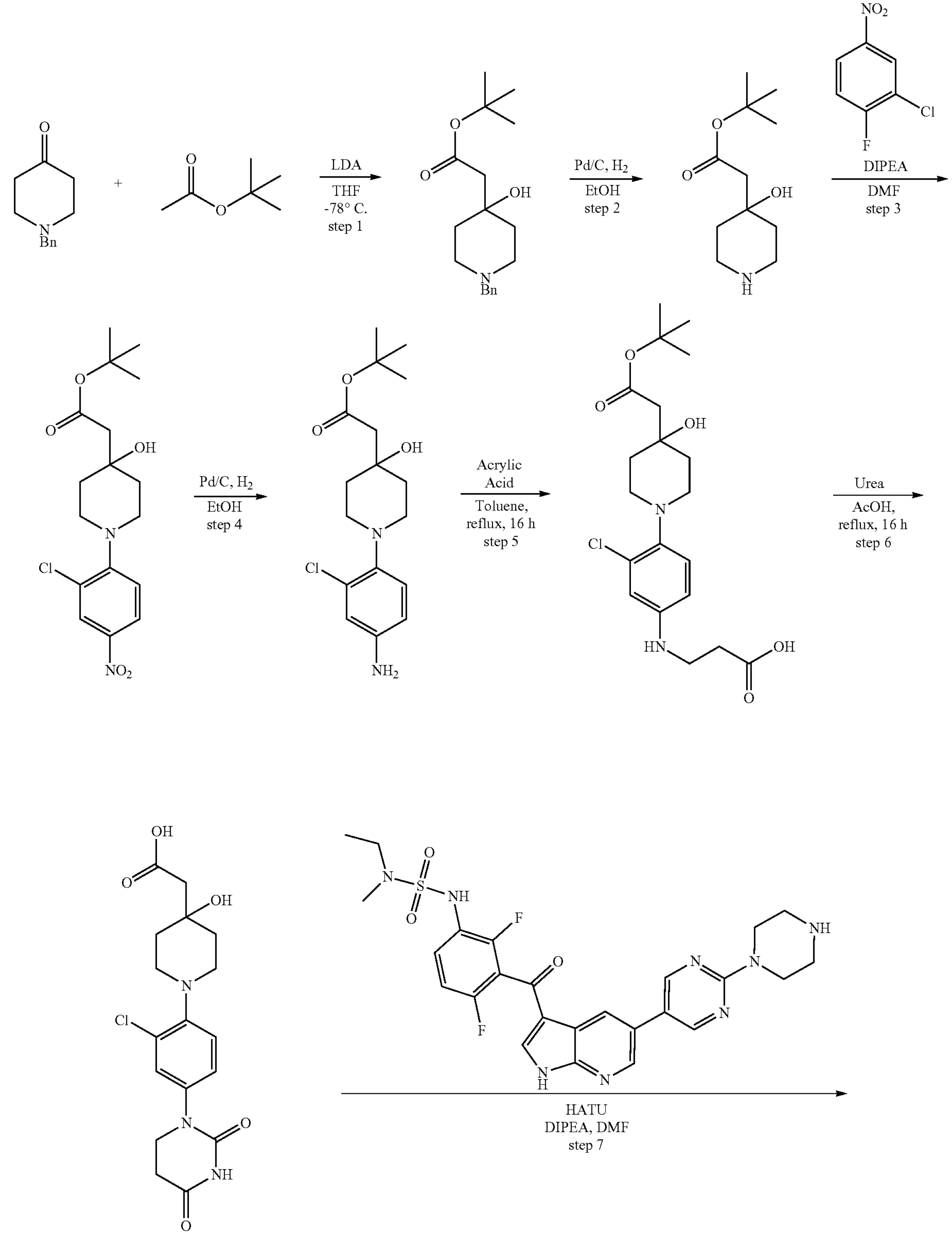

-continued

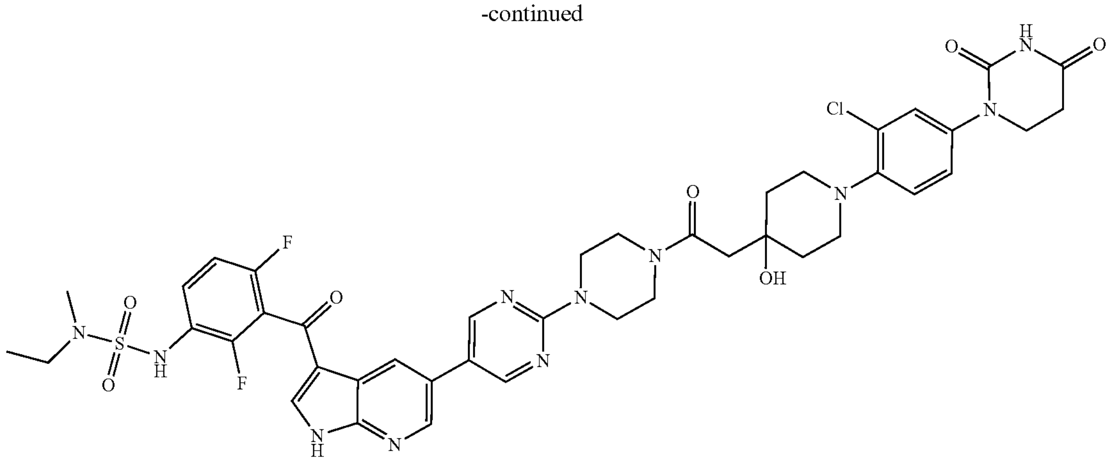

Step 1: A round bottomed flask was charged with THF (60 mL) before was added (diisopropylamino)lithium (2 M, 29.06 mL) (THF/heptane/ethylbenzene) under nitrogen flow at ~10 to 15° C. The solution was cooled to −66° C. (dry ice/ethanol bath). tert-butyl acetate (6.44 g, 55.48 mmol, 7.47 mL) was added dropwise via an addition funnel. The internal temperature was kept between −60° C. to −66° C. during the addition. After addition, the reaction solution was stirred for another 15 minutes. A solution of 1-benzylpiperidin-4-one (10 g, 52.84 mmol, 9.79 mL) in THF (20 mL) was added dropwise/slowly via addition funnel. The internal temperature was below −59° C. during the addition. After 20 minutes, the cooling bath was removed, and the reaction solution was stirred at 5 to 20° C. for 1.5 hours. The mixture was cooled back down to 0-5° C. Reaction was quenched with saturated aqueous NH4Cl solution (100 mL). The internal temperature was kept below 10° C. during quenching. The reaction mixture was then extracted with ethyl acetate (2×100 mL). Combined organic was washed with brine solution (100 mL) and was dried over sodium sulphate. The combined layers were filtered and concentrated under vacuo to give tert-butyl 2-(1-benzyl-4-hydroxy-4-piperidyl) acetate (16.14 g, 52.85 mmol, 100% yield). $^{1}$H NMR (400 MHz, Chloroform-d) δ 7.43-6.88 (m, 5H), 3.57 (s, 1H), 3.46 (s, 2H), 2.52 (dt, J=8.5, 3.9 Hz, 2H), 2.43-2.22 (m, 5H), 1.70-1.49 (m, 5H), 1.40 (s, 9H).

Step 2: tert-butyl 2-(1-benzyl-4-hydroxy-4-piperidyl)acetate (7.8 g, 25.54 mmol) was dissolved in Ethanol (100 mL). The solution was sparged with nitrogen for 5 to 10 minutes. The solution was evacuated and backfilled with nitrogen couple times. Palladium, 10% on carbon, type E101 NE/W (1.36 g, 12.77 mmol) was then added. After evacuated and backfilled with nitrogen couple more times, the reaction mixture was subjected to hydrogenation ($H_2$ balloon) at ambient temperature. After 16 h, the mixture was filtered through a celite pad before being washed with ethyl acetate (3×40 mL) and concentrated to a solid residue which was used without further purification. tert-butyl 2-(4-hydroxy-4-piperidyl)acetate (3.47 g, 16.12 mmol, 63% yield). $^{1}$H NMR (400 MHz, Chloroform-d): δ 3.23-3.00 (m, 2H), 3.00-2.90 (m, 2H), 2.78 (dt, J=12.5, 4.2 Hz, 2H), 2.34 (s, 2H), 1.71-1.57 (m, 2H), 1.55-1.44 (m, 2H), 1.42 (s, 9H).

Step 3: To a stirred solution of 2-chloro-1-fluoro-4-nitrobenzene (1.96 g, 11.15 mmol) in DMF (50 mL) was added DIPEA (2.40 g, 18.58 mmol, 3.24 mL). The reaction mixture was heated to 110° C. for 1 h. Upon reaction completion, the reaction mixture was diluted with water (20 mL) and extracted with ethyl acetate (2×100 mL). The combined organic layers were washed with brine (1×100 mL) then dried over sodium sulphate, filtered and concentrated under vacuum to furnish a crude solid. The crude compound was purified by flash column chromatography eluting with Hexanes/ethyl acetate (up to 30% ethyl acetate) to afford tert-butyl 2-[1-(2-chloro-4-nitro-phenyl)-4-hydroxy-4-piperidyl]acetate (2.61 g, 7.04 mmol, 75% yield) as yellow solid. LCMS (ESI+): 371.2 $[M+H]^+$.

Step 4: Initially a flask was charged with tert-butyl 2-[1-(2-chloro-4-nitro-phenyl)-4-hydroxy-4-piperidyl]acetate (1.23 g, 3.30 mmol) under a nitrogen atmosphere before having Palladium, 10% on carbon (0.250 g, 6.61 mmol) added and being suspended in Ethanol (40 mL). The mixture was then sparged with $H_2$ for 20 mins before stirring was continued at room temperature for 6 hours. Upon reaction completion the mixture was filtered through a celite pad and washed with ethyl acetate. The filtrate was concentrated to a crude residue which was purified via flash column chromatography (Hexanes:ethyl acetate, up to 30%) to afford a solid material tert-butyl 2-[1-(4-amino-2-chloro-phenyl)-4-hydroxy-4-piperidyl]acetate (785 mg, 2.30 mmol, 70% yield). LCMS (ESI+): 341.1 $[M+H]^+$.

Step 5: Initially tert-butyl 2-[1-(4-amino-2-chloro-phenyl)-4-hydroxy-4-piperidyl]acetate (625 mg, 1.83 mmol) was dissolved in Toluene (4.51 mL) before Acrylic acid, 99%, stab. with ca 200 ppm 4-methoxyphenol (792.84 mg, 11.00 mmol, 755.08 uL) was added and the mixture was stirred at 100° C. for 16 h. The mixture was then concentrated down to a residue and submitted to the following step without further purification 3-[4-[4-(2-tert-butoxy-2-oxo-ethyl)-4-hydroxy-1-piperidyl]-3-chloro-anilino]propanoic acid (757 mg, 1.83 mmol, quant.) LCMS (ESI+): 413.2 $[M+H]^+$.

Step 6: Initially urea (440.41 mg, 7.33 mmol, 328.66 uL) was dissolved in AcOH (8.84 mL) before 3-[4-[4-(2-tert-butoxy-2-oxo-ethyl)-4-hydroxy-1-piperidyl]-3-chloro-anilino]propanoic acid (757 mg, 1.83 mmol) was added and the mixture was stirred at 100° C. for 16 h. After 16 h the mixture was concentrated to a residue and resuspended in 4 N hydrochloric acid in 1,4-dioxane (8 mL) and heated to 50° C. for 2 h. The crude material was then subjected to flash column chromatography (up to 20% methanol in dichloromethane) to furnish 2-[1-[2-chloro-4-(2,4-dioxohexahydropyrimidin-1-yl)phenyl]-4-hydroxy-4-piperidyl]acetic acid (173 mg, 453.10 µmol, 25% yield). LCMS (ESI+): 382.2 $[M+H]^+$.

Step 7: 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (128.26 mg, 191.26 μmol, trifluoroacetic acid salt), 2-[1-[2-chloro-4-(2,4-dioxohexahydropyrimidin-1-yl)phenyl]-4-hydroxy-4-piperidyl]acetic acid (80 mg, 191.26 μmol, hydrochloric acid salt) and DIPEA (98.88 mg, 765.05 μmol, 133.26 uL) were suspended in DMF (3 mL) before HATU (72.72 mg, 191.26 μmol) was added in one portion. The mixture was stirred for 1 h before immediately being purified via reverse phase flash column chromatography (acetonitrile/water, 0.1% Formic Acid, 0:1 to 1:1) and lyophilized to a solid 5-[2-[4-[2-[1-[2-chloro-4-(2,4-dioxohexahydropyrimidin-1-yl)phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (73 mg, 71.76 μmol, 37% yield, formate salt). LCMS (ESI+): 920.5 $[M+H]^+$. $^1H$ NMR (400 MHz, DMSO-$d_6$) δ 13.00 (d, J=3.4 Hz, 1H), 10.38 (s, 1H), 9.70 (s, 1H), 8.80 (s, 2H), 8.68 (d, J=2.3 Hz, 1H), 8.57 (s, 1H), 8.14 (d, J=3.2 Hz, 1H), 7.57 (dd, J=9.1, 5.8 Hz, 1H), 7.41 (d, J=2.4 Hz, 1H), 7.23 (dt, J=22.6, 8.9 Hz, 3H), 4.03-3.49 (m, 10H), 3.11 (q, J=7.1 Hz, 2H), 3.07-2.88 (m, 4H), 2.82-2.59 (m, 8H), 1.79 (dt, J=30.2, 10.1 Hz, 4H), 1.02 (t, J=7.1 Hz, 3H).

Example 214

5-[6-[4-[2-[1-[2-chloro-4-(2,4-dioxohexahydropyrimidin-1-yl)phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine

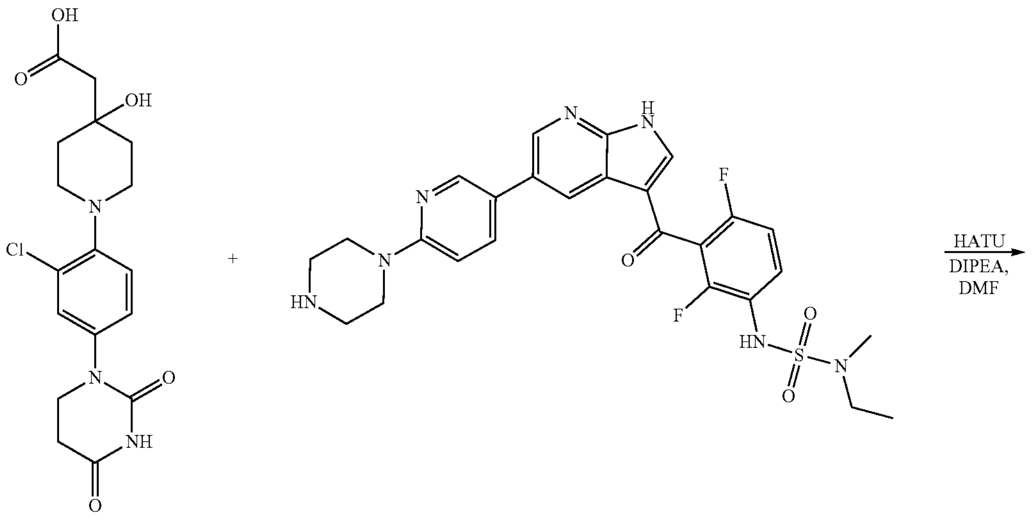

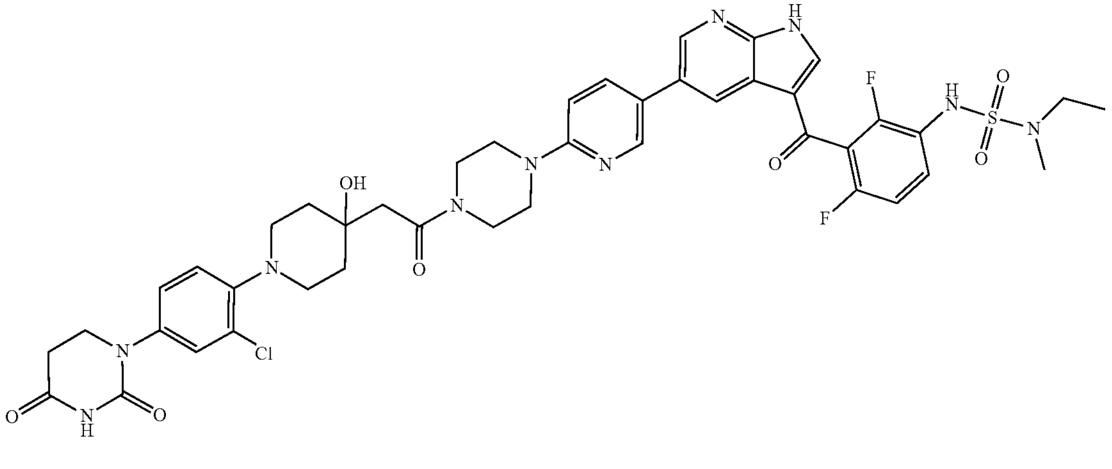

Initially 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (80.05 mg, 119.54 μmol, trifluoroacetic acid salt), 2-[1-[2-chloro-4-(2,4-dioxohexahydropyrimidin-1-yl)phenyl]-4-hydroxy-4-piperidyl]acetic acid (50 mg, 119.54 μmol, hydrochloric acid salt) and DIPEA (61.80 mg, 478.16 μmol, 83.28 uL) were suspended in DMF (3 mL) before HATU (45.45 mg, 119.54 μmol) was added in one portion and the mixture was stirred at room temperature for 1 h. Upon reaction completion, the mixture was subjected to reverse phase flash column chromatography (acetonitrile: water, 0.1% formic acid, 0:1 to 1:1) to give a solid 5-[6-[4-[2-[1-[2-chloro-4-(2,4-dioxohexahydropyrimidin-1-yl)phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine (40.1 mg, 39.46 μmol, 33% yield, formate salt). LCMS (ESI+): 919.5 $[M+H]^+$. $^1H$ NMR (400 MHz, DMSO-$d_6$): δ 10.37 (s, 1H), 8.67 (d, J=2.2 Hz, 1H), 8.52 (d, J=2.7 Hz, 1H), 8.13 (d, J=7.1 Hz, 1H), 7.97 (dd, J=8.9, 2.6 Hz, 1H), 7.58 (td, J=9.0, 5.9 Hz, 1H), 7.41 (d, J=2.4 Hz, 1H), 7.33-7.13 (m, 3H), 7.01 (d, J=9.0 Hz, 1H), 4.96 (s, 1H), 3.82-3.54 (m, 10H), 3.32 (s, 3H), 3.11 (q, J=7.1 Hz, 2H), 3.06-2.91 (m, 4H), 2.71 (d, J=14.9 Hz, 5H), 2.63 (s, 2H), 1.91-1.60 (m, 4H), 1.01 (t, J=7.1 Hz, 3H).

Example 215

5-[6-[4-[2-[1-[2-chloro-4-(2,4-dioxohexahydropyrimidin-1-yl)-5-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine

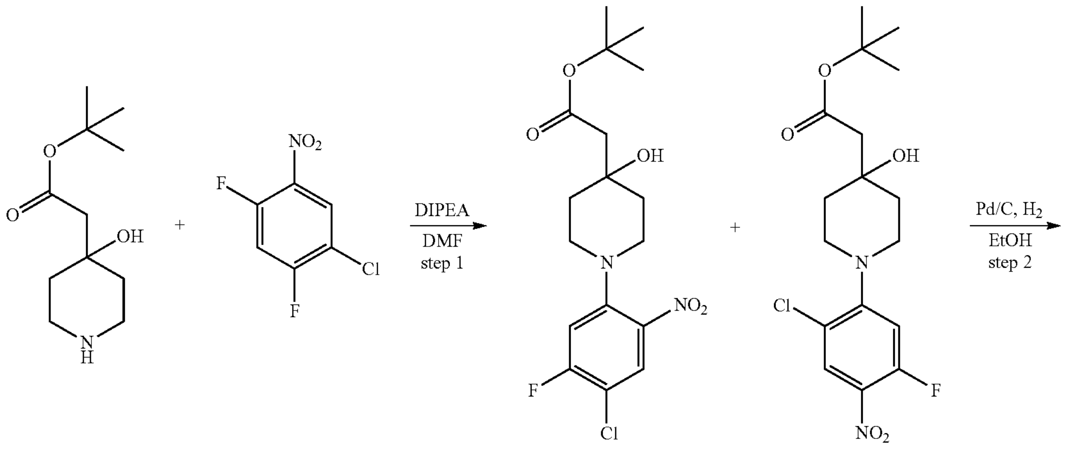

Regioisomer A

Regioisomer B

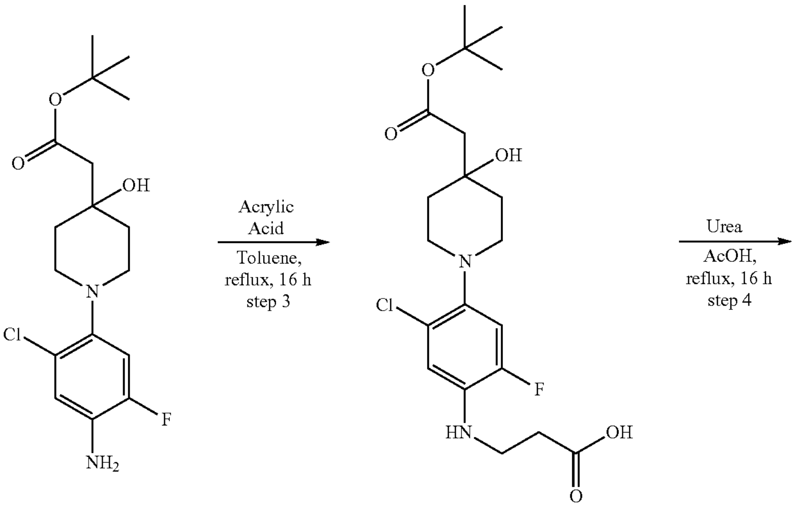

-continued

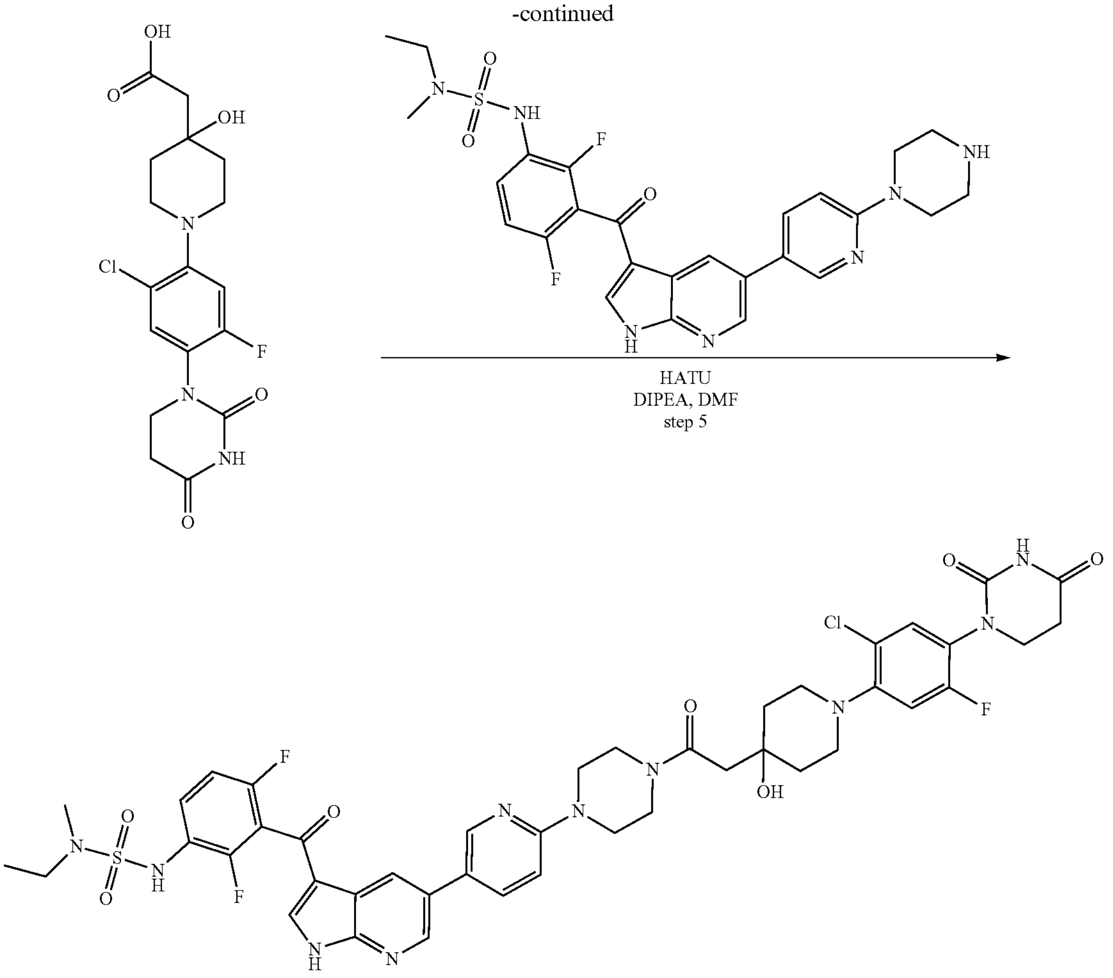

Step 1: Initially tert-butyl 2-(4-hydroxy-4-piperidyl)acetate (1.62 g, 7.51 mmol) was dissolved in DMF (9.16 mL) and cooled to 0° C. before DIPEA (2.91 g, 22.53 mmol, 3.92 mL) was added followed by 1-chloro-2,4-difluoro-5-nitrobenzene (1.45 g, 7.51 mmol, 914.22 uL) dropwise. The mixture was stirred at 100° C. for 1 h. The mixture was diluted with water (20 mL) and extracted with ethyl acetate (2×100 mL). The combined organic layers were washed with LiCl (5% aq. soln, 1×100 mL), brine (100 mL) before being dried over sodium sulphate, filtered and concentrated to a crude solid. The crude material was purified via flash column chromatography eluting with Hexanes:ethyl acetate (up to 30%) to afford two regioisomers;

Regioisomer A tert-butyl 2-[1-(4-chloro-5-fluoro-2-nitrophenyl)-4-hydroxy-4-piperidyl]acetate (1.37 g, 3.53 mmol, 47% yield). $^1$H NMR (400 MHz, Chloroform-d): δ 7.95 (d, J=7.7 Hz, 1H), 6.88 (d, J=11.0 Hz, 1H), 3.86 (s, 1H), 3.25 (dt, J=12.1, 7.4 Hz, 2H), 3.07-2.92 (m, 2H), 2.43 (s, 2H), 1.77 (dd, J=7.5, 3.7 Hz, 4H), 1.47 (s, 9H).

Regioisomer B tert-butyl 2-[1-(2-chloro-5-fluoro-4-nitrophenyl)-4-hydroxy-4-piperidyl]acetate (0.802 g, 2.06 mmol, 27% yield). $^1$H NMR (400 MHz, Chloroform-d): δ 8.10 (d, J=7.8 Hz, 1H), 6.79 (d, J=13.0 Hz, 1H), 3.87 (s, 1H), 3.37 (dq, J=11.7, 2.7, 2.2 Hz, 2H), 3.21 (td, J=11.8, 3.1 Hz, 2H), 2.44 (s, 2H), 1.90-1.70 (m, 4H), 1.47 (s, 9H).

Note: Regioisomer B was taken forward to step 2.

Step 2: Initially tert-butyl 2-[1-(2-chloro-5-fluoro-4-nitrophenyl)-4-hydroxy-4-piperidyl]acetate (707 mg, 1.82 mmol) and Palladium, 10% on carbon (0.250 g, 3.64 mmol) were suspended in Ethanol (12.82 mL) under a nitrogen atmosphere. The mixture was stirred at room temperature with sparging of the suspension using a $H_2$ balloon (20 mins). Stirring was continued for 6 h before the mixture was filtered through a celite pad which was subsequently washed with ethyl acetate. The combined filtrate layers were concentrated to a residue which was then purified via flash column chromatography (Hexanes:ethyl acetate, up to 100% ethyl acetate) to furnish a solid material 2-[1-(4-amino-2-chloro-5-fluoro-phenyl)-4-hydroxy-4-piperidyl]acetate (644 mg, 1.79 mmol, 98% yield). LCMS (ESI+): 360.1 [M+H]$^+$.

Step 3: 2-[1-(4-amino-2-chloro-5-fluoro-phenyl)-4-hydroxy-4-piperidyl]acetate (644 mg, 1.79 mmol) was dissolved in Toluene (4.51 mL) before Acrylic acid, 99%, stab. with ca 200 ppm 4-methoxyphenol (775.98 mg, 10.77 mmol, 739.03 uL) was added and the mixture was stirred at 100° C. for 16 h. After 16 h of stirring, an additional crop of Acrylic Acid (6 eq) was then added and heating was continued for 16 h. After cooling, the mixture was concentrated down to a residue and to afford 3-[4-[4-(2-tert-butoxy-2-oxo-ethyl)-4-hydroxy-1-piperidyl]-5-chloro-2-fluoro-anilino]propanoic acid (773 mg, 1.70 mmol, 95% yield), which was carried forward without further purification. LCMS (ESI+): 432.2 [M+H]$^+$.

Step 4: urea (430.94 mg, 7.18 mmol, 321.60 uL) was dissolved in AcOH (8.84 mL) before 3-[4-[4-(2-tert-butoxy- 2-oxo-ethyl)-4-hydroxy-1-piperidyl]-5-chloro-2-fluoro-anilino]propanoic acid (773 mg, 1.79 mmol) was added and the mixture was stirred at 100° C. for 16 h. The mixture was then concentrated down to a residue, which was resuspended in 4 N hydrochloric acid in 1,4-dioxane (8 mL) before being heated for 3 h at 50° C. Upon reaction completion, the mixture was concentrated down to a residue which was purified via flash column chromatography (up to 20% methanol in dichloromethane) to afford 2-[1-[2-chloro-4-(2,4-dioxohexahydropyrimidin-1-yl)-5-fluoro-phenyl]-4-hydroxy-4-piperidyl]acetic acid (387 mg, 967.98 μmol, 54% yield). LCMS (ESI+): 400.2 [M+H]+.

Step 5: 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (159.11 mg, 237.62 μmol, trifluoroacetic acid salt), 2-[1-[2-chloro-4-(2,4-dioxohexahydropyrimidin-1-yl)-5-fluoro-phenyl]-4-hydroxy-4-piperidyl]acetic acid (95 mg, 237.62 μmol, hydrochloric acid salt) and DIPEA (122.84 mg, 950.47 μmol, 165.55 uL) were suspended in DMF (3 mL) before HATU (90.35 mg, 237.62 μmol) was added in one portion and the mixture was stirred for 1 h. Upon reaction completion, the mixture was immediately purified via reverse phase flash column chromatography (acetonitrile:water, 0.1% formic acid, 0:1 to 1:1) to give a solid 5-[6-[4-[2-[1-[2-chloro-4-(2,4-dioxohexahydropyrimidin-1-yl)-5-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine (8.8 mg, 8.50 μmol, 4% yield, formate salt). LCMS (ESI+): 937.5 [M+H]+. $^1$H NMR (400 MHz, DMSO-$d_6$) δ 12.96 (d, J=3.3 Hz, 1H), 10.48 (s, 1H), 9.70 (s, 1H), 8.68 (d, J=2.3 Hz, 1H), 8.64-8.39 (m, 2H), 8.23-8.05 (m, 1H), 8.01 (dd, J=8.9, 2.6 Hz, 1H), 7.64-7.47 (m, 2H), 7.28 (td, J=8.8, 1.6 Hz, 1H), 7.08 (dd, J=26.5, 10.5 Hz, 2H), 3.88-3.52 (m, 11H), 3.19-2.94 (m, 6H), 2.71 (d, J=10.4 Hz, 5H), 2.63 (s, 2H), 1.89-1.66 (m, 4H), 1.02 (t, J=7.1 Hz, 3H).

Example 216

5-[2-[4-[2-[1-[2-chloro-4-(2,4-dioxohexahydropyrimidin-1-yl)-5-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine

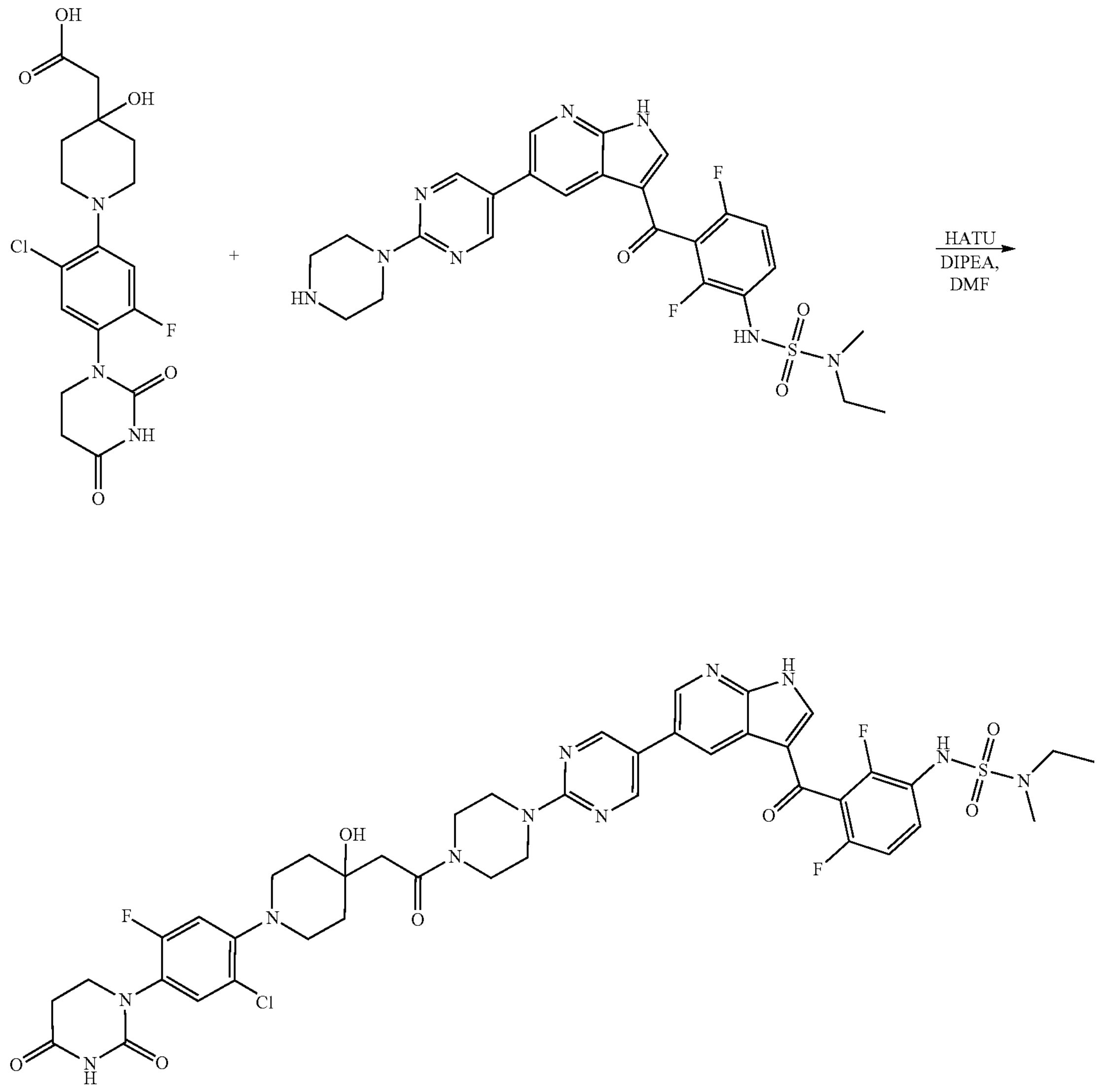

3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (149.28 mg, 222.61 μmol, trifluoroacetic acid salt), 2-[1-[2-chloro-4-(2,4-dioxohexahydropyrimidin-1-yl)-5-fluoro-phenyl]-4-hydroxy-4-piperidyl]acetic acid (89 mg, 222.61 μmol, hydrochloric acid salt) and DIPEA (115.08 mg, 890.44 μmol, 155.10 uL) were suspended in DMF (3 mL) before HATU (84.64 mg, 222.61 μmol) was added in one portion. The mixture was stirred for 1 h before immediately being purified via reverse phase flash column chromatography (acetonitrile/water, 0.1% Formic Acid, 0:1 to 1:1) and lyophilized to a solid 5-[2-[4-[2-[1-[2-chloro-4-(2,4-dioxohexahydropyrimidin-1-yl)-5-fluoro-phenyl]-4-hydroxy-4-piperidyl]acetyl]piperazin-1-yl]pyrimidin-5-yl]-3-[3-[[ethyl(methyl)sulfamoyl]amino]-2,6-difluoro-benzoyl]-1H-pyrrolo[2,3-b]pyridine (23 mg, 24.51 μmol, 11% yield, formate salt). LCMS (ESI+): 938.5 $[M+H]^+$. $^1H$ NMR (400 MHz, DMSO-$d_6$): δ 10.49 (s, 1H), 8.80 (s, 2H), 8.67 (d, J=2.2 Hz, 1H), 8.56 (s, 1H), 8.13 (s, 1H), 7.67-7.49 (m, 2H), 7.25 (td, J=8.8, 1.6 Hz, 1H), 7.12 (d, J=12.0 Hz, 1H), 4.98 (s, 1H), 3.99-3.74 (m, 5H), 3.67 (dq, J=13.6, 5.1 Hz, 7H), 3.07 (ddd, J=26.1, 13.3, 8.5 Hz, 6H), 2.71 (d, J=6.6 Hz, 5H), 2.63 (s, 2H), 1.97-1.66 (m, 4H), 1.02 (t, J=7.1 Hz, 3H).

Example 217

3-[3-[[cyclopropyl(methyl)sulfamoyl]amino]-2,6-difluoro-benzoyl]-5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-1H-pyrrolo[2,3-b]pyridine

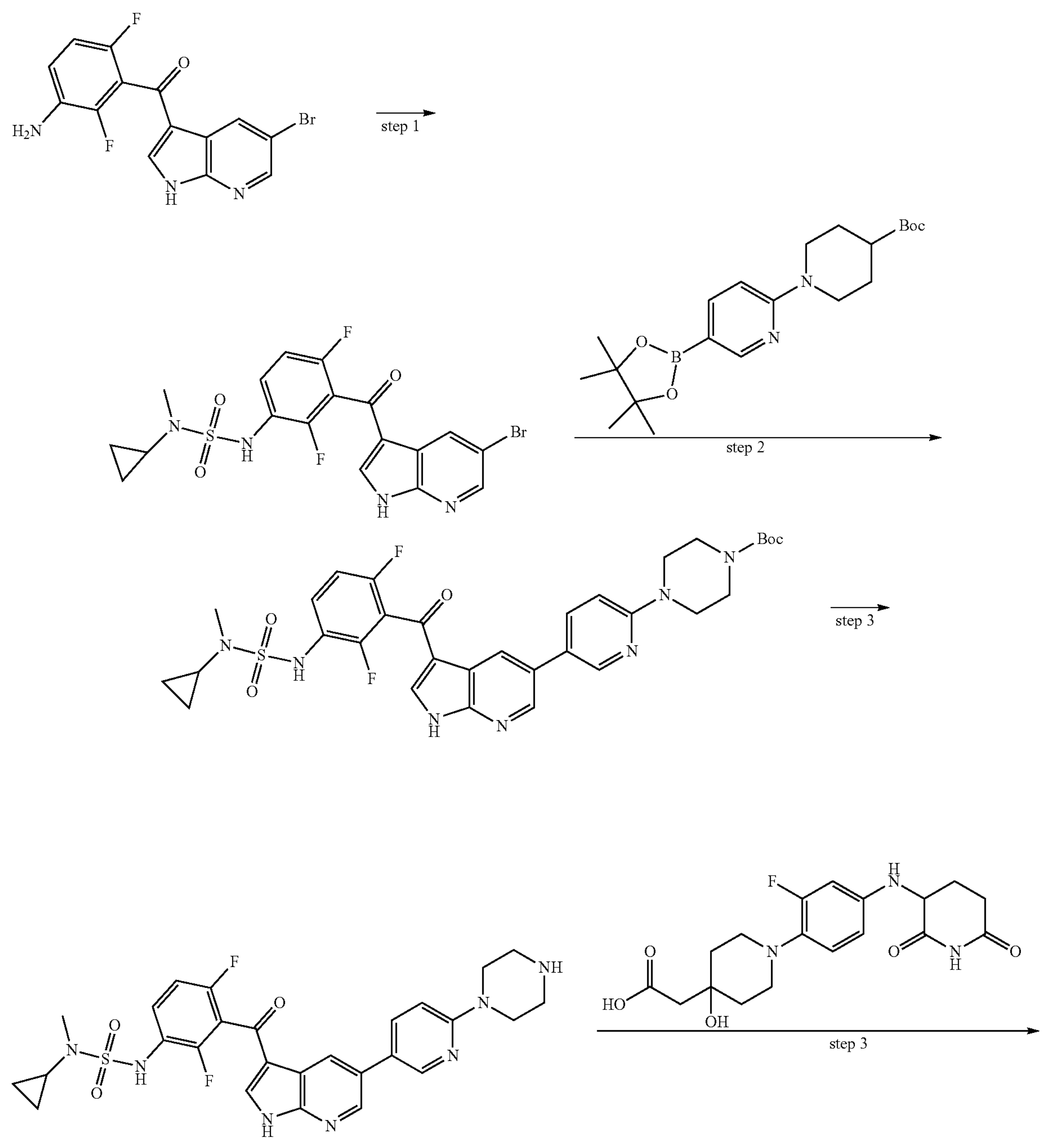

-continued

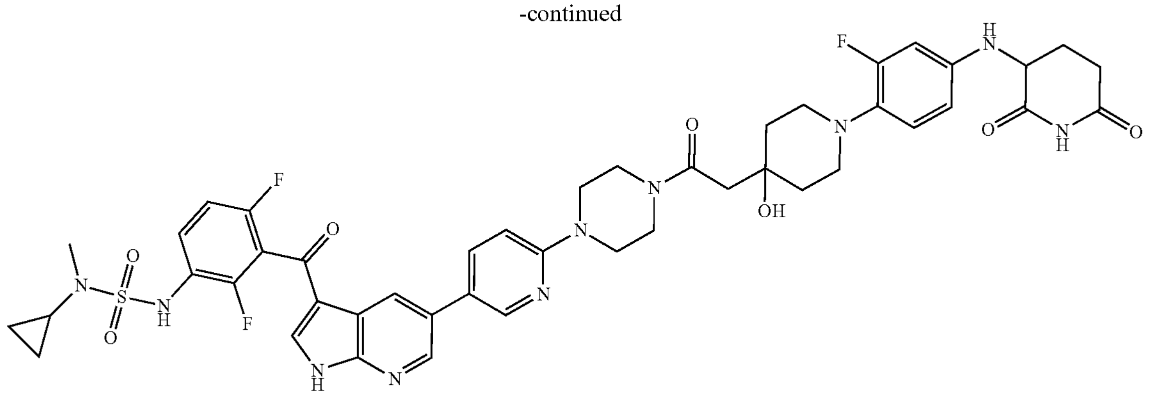

Step 1: (3-amino-2,6-difluoro-phenyl)-(5-bromo-1H-pyrrolo[2,3-b]pyridin-3-yl)methanone (500 mg, 1.42 mmol) was dissolved/suspended in pyridine (1.01 g, 12.78 mmol, 1.03 mL). 4-dimethylaminopyridine (17.35 mg, 141.99 μmop was added at ambient temperature. N-cyclopropyl-N-methyl-sulfamoyl chloride (481.72 mg, 2.84 mmol) was added slowly via syringe. The reaction was heated to 50° C. until complete. The crude mixture was partitioned between ethyl acetate 2× and 1M HCl solution. Combined organic was washed with 1M HCl and aqueous 18% NaCl solution. Washed organic was dried over sodium sulphate, filtered, and concentrated in vacuo. The crude mixture was purified by column chromatography column 0-100% ethyl acetate in hexanes to afford 5-bromo-3-[3-[[cyclopropyl(methyl)sulfamoyl]amino]-2,6-difluoro-benzoyl]-1H-pyrrolo[2,3-b]pyridine (600 mg, 1.24 mmol, 87.07% yield). LCMS (ESI+): 485.0 $[M+H]^+$ Step 2: The tert-butyl 4-[5-(4,4,5,5-tetramethyl-1,3,2-dioxaborolan-2-yl)-2-pyridyl]piperazine-1-carboxylate (625.69 mg, 1.61 mmol), 5-bromo-3-[3-[[cyclopropyl (methyl)sulfamoyl]amino]-2,6-difluoro-benzoyl]-1H-pyrrolo[2,3-b]pyridine (600 mg, 1.24 mmol), potassium phosphate tribasic anhydrous (787.32 mg, 3.71 mmol) were diluted in water (1.5 mL) and 1,4-dioxanes (8 mL). The 20 ml microwave tube was purged with argon gas for 10 min. The Xphos G3 Pd (104.65 mg, 123.63 μmol) was added. The tube was sealed and heated 120° C. in the microwave until complete. The crude mixture was diluted in water (5 ml) and then extracted with 20 mL of ethyl acetate (3×). The organic layers were combined and dried over MgSO4. The crude material was purified by column chromatography column 0-20% methanol in dichloromethane to afford tert-butyl 4-[6-[3-[3-[[cyclopropyl(methyl)sulfamoyl]amino]-2,6-difluoro-benzoyl]-1H-pyrrolo[2,3-b]pyridin-5-yl]-3-pyridyl] piperazine-1-carboxylate (175 mg, 209.67 μmol, 16.96% yield) as a yellow powder. LCMS (ESI+): 668.2 $[M+H]^+$.

Step 3: To a solution of tert-butyl 4-[5-[3-[3-[[cyclopropyl (methyl)sulfamoyl]amino]-2,6-difluoro-benzoyl]-1H-pyrrolo[2,3-b]pyridin-5-yl]-2-pyridyl]piperazine-1-carboxylate (175 mg, 262.08 μmol) in 1,4-dioxane (3 mL) was added HCl in 1,4-dioxane (682.20 mg, 18.71 mmol, 852.75 uL) at 0° C. The resulted mixture was stirred at room temperature overnight. After overnight the reaction is filtered to afford 3-[3-[[cyclopropyl(methyl)sulfamoyl]amino]-2,6-difluoro-benzoyl]-5-(6-piperazin-1-yl-3-pyridyl)-1H-pyrrolo[2,3-b] pyridine (150 mg, 264.27 μmol, 94.75% yield) as a white solid. LCMS (ESI+): 568.1 $[M+H]^+$.

Step 4: Target compound was prepared via procedure C, by modifying the 2-[1-[4-[(2,6-dioxo-3-piperidyl)amino]-2-fluoro-phenyl]-4-hydroxy-4-piperidyl]acetic acid (143.43 mg, 378.06 μmol) and 3-[3-[[cyclopropyl(methyl)sulfamoyl]amino]-2,6-difluoro-benzoyl]-5-(6-piperazin-1-yl-3-pyridyl)-1H-pyrrolo[2,3-b]pyridine (150 mg, 264.27 μmol), and 6 eq of DIPEA. The crude material was purified by reverse phase column chromatography (acetonitrile & Water (0.01% TFA)). The product was free based in saturated bicarbonate solution in ethyl acetate. The material was then purified column chromatography (0-30% methanol in dichloromethane) to afford 3-[3-[[cyclopropyl(methyl)sulfamoyl]amino]-2,6-difluoro-benzoyl]-5-[6-[4-[2-[1-[4-[(2,6-dioxo-3-piperidyl)amino]-2-fluoro-phenyl]-4-hydroxy-4-piperidyl]acetyl]piperazin-1-yl]-3-pyridyl]-1H-pyrrolo[2,3-b] pyridine (9.2 mg, 9.21 μmol, 3.49% yield). LCMS (ESI+): 929 $[M+H]^+$. $^1$H NMR (400 MHz, DMSO-$d_6$) δ 10.70 (s, 1H), 9.48 (s, 1H), 8.65 (d, J=2.2 Hz, 1H), 8.54 (s, 1H), 8.47 (d, J=2.6 Hz, 1H), 8.20 (s, 1H), 7.92 (dd, J=8.9, 2.6 Hz, 1H), 7.58-7.48 (m, 1H), 7.27-7.16 (m, 2H), 6.95 (d, J=9.0 Hz, 1H), 6.83-6.74 (m, 1H), 6.43 (dd, J=14.9, 2.6 Hz, 1H), 6.35 (dd, J=8.7, 2.6 Hz, 1H), 6.03 (ddt, J=17.0, 10.5, 5.4 Hz, 1H), 5.70 (d, J=7.6 Hz, 1H), 5.11 (dq, J=10.3, 1.4 Hz, 1H), 5.00-4.90 (m, 2H), 4.79 (s, 1H), 4.18 (ddd, J=12.0, 7.6, 4.8 Hz, 1H), 3.65-3.50 (m, 8H), 2.89-2.75 (m, 4H), 2.73-2.60 (m, 1H), 2.54-2.45 (m, 6H), 2.06-1.98 (m, 1H), 1.86-1.66 (m, 3H), 1.65-1.57 (m, 2H).

Example 218
5-[6-[4-[2-[1-[2,5-dichloro-4-(2,4-dioxohexahydro-pyrimidin-1-yl)phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine
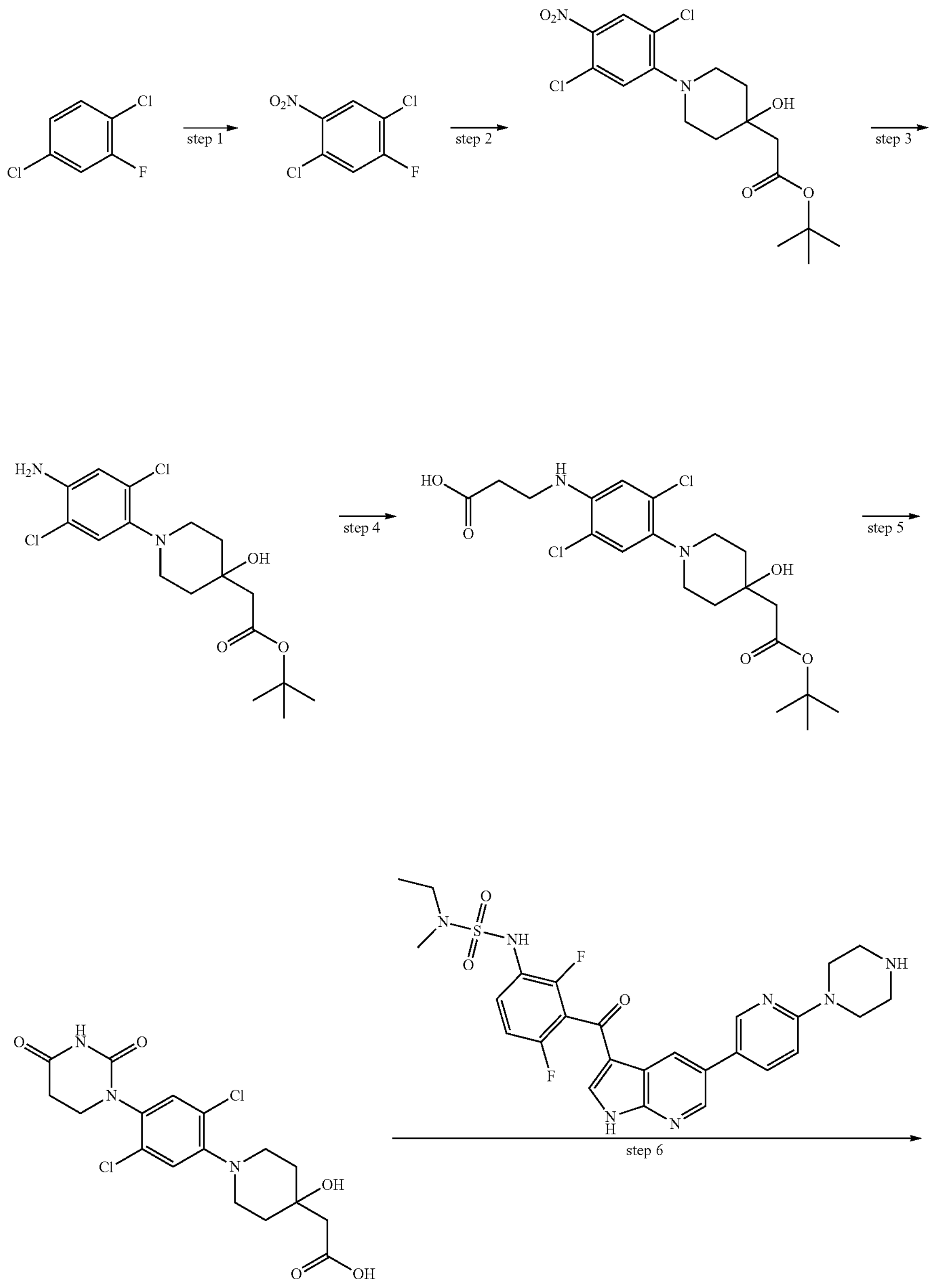

-continued

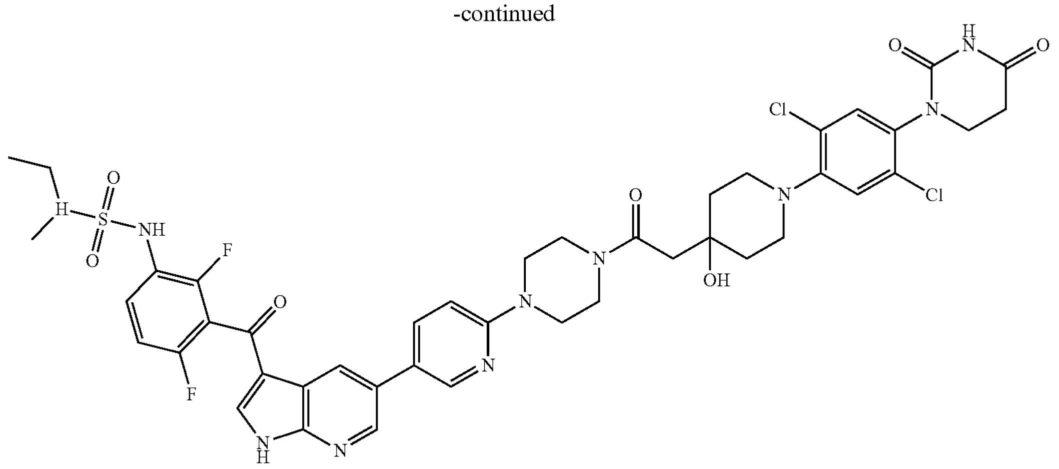

Step 1: 1,4-dichloro-2-fluoro-benzene (5 g, 30.30 mmol, 3.57 mL) was added to a stirring solution of sulfuric acid (14.86 g, 151.52 mmol, 8.12 mL) and allowed to stir on ice at 0° C., in accordance with the reported reference (WO2019/067702A1). To this stirring solution on ice was added nitric acid 90% dropwise over 10 minutes. After addition was complete, the reaction was allowed to run at room temperature for 3 hrs. The reaction was poured onto ice water and extracted with ethyl acetate and saturated sodium bicarbonate solution. Organic layers were then dried with brine and sodium sulphate and dried to give the pure product as a dark orange crystal (6.1 g, 93% yield), which was carried forward without further purification. $^1$H NMR (400 MHz, Chloroform-d): δ 8.08 (d, J=6.9 Hz, 1H), 7.40 (d, J=8.0 Hz, 1H).

Step 2: tert-butyl 2-(4-hydroxy-4-piperidyl)acetate (500 mg, 2.32 mmol) and 1,4-dichloro-2-fluoro-5-nitro-benzene (487.69 mg, 2.32 mmol, 133.53 uL) were combined in DMF (2.89 mL) and treated with DIPEA (1.20 g, 9.29 mmol, 1.62 mL). The solution was stirred at room temperature for 4 h. The reaction was partitioned between water and ethyl acetate. The organic layers were dried with brine and sodium sulphate and concentrated down to a bright yellow solid (625 mg, 63% yield) which was used in the next step without any further purification. LCMS (ESI+): 405, 349

Step 3: tert-butyl 2-[1-(2,5-dichloro-4-nitro-phenyl)-4-hydroxy-4-piperidyl]acetate (625 mg, 1.54 mmol) was charged into a sealed vial and solvated with a 5:1:1 mixture of ethanol, THF, and water, respectively, to 0.2 M. To this stirring solution platinum 3% on carbon sulfided (150.42 mg, 771.09 μmol) was added followed by ammonium formate (388.97 mg, 6.17 mmol). The mixture was heated at 70° C. overnight. The crude material was directly filtered through Celite using ethyl acetate. The filtrate was directly partitioned between saturated sodium bicarbonate and ethyl acetate. The organic layers were dried with sodium sulphate and directly concentrated down in vacuo to a brown oil (520 mg, 83% yield). The crude product was directly used in the next step without further purification. LCMS (ESI+): found m/z 375, 377

Step 4: tert-butyl 2-[1-(4-amino-2,5-dichloro-phenyl)-4-hydroxy-4-piperidyl]acetate (493 mg, 1.31 mmol) was charged into a sealed vial and solvated to 0.3 M with Toluene (3.5 mL). To this stirring solution was added Acrylic acid, 99%, stab. with ca 200 ppm 4-methoxyphenol (284.00 mg, 3.94 mmol, 270.47 uL) and the reaction allowed to stir at reflux for 4 hr. The solvent was removed in vacuo to give the crude product as a brown oil (587 mg, 85% yield). The oil was progressed with no further purification. LCMS (ESI+): found m/z 447

Step 5: 3-[4-[4-(2-tert-butoxy-2-oxo-ethyl)-4-hydroxy-1-piperidyl]-2,5-dichloro-anilino]propanoic acid (501.03 mg, 1.12 mmol) was charged into a sealed vial along with urea (235.42 mg, 3.92 mmol, 175.68 uL) and solvated to 0.3 M with acetic acid, glacial (3.56 mL). The reaction was refluxed for 16 h. The solvent was removed in vacuo and trace amounts of acetic acid removed by azeotroping with toluene and methanol. The crude product was directly purified using reverse phase chromatography (10-90% acetonitrile in water w/ 0.1% formic acid additive over 15 minutes) to give the pure cyclized acid as a light brown solid (242 mg, 46% yield). LCMS (ESI+): found m/z 416

Step 6: To a solution of 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (229.24 mg, 342.34 μmol), 2-[1-[2,5-dichloro-4-(2,4-dioxohexahydropyrimidin-1-yl)phenyl]-4-hydroxy-4-piperidyl]acetic acid (150 mg, 360.36 μmol) in DMF (3.23 mL) were added HATU (137.02 mg, 360.36 μmol), DIPEA (279.43 mg, 2.16 mmol, 376.60 uL) and stirred at room temperature for 16 h. Product was directly purified using a mass-directed reverse-phase prep HPLC (25-35% acetonitrile in water w/ 0.1% TFA additive over 9 min) to afford an off-white solid (12 mg, 3% yield). LCMS (ESI+): 477 $[M/2+H]^+$. $^1$H NMR (400 MHz, DMSO-$d_6$): δ 13.01 (d, J=3.3 Hz, 1H), 10.48 (s, 1H), 9.71 (s, 1H), 8.70 (d, J=2.2 Hz, 1H), 8.63-8.57 (m, 1H), 8.50 (d, J=2.7 Hz, 1H), 8.15 (q, J=4.3, 3.6 Hz, 2H), 7.66-7.53 (m, 2H), 7.31-7.23 (m, 2H), 7.19 (d, J=8.8 Hz, 1H), 5.21 (s, 31H), 3.81-3.50 (m, 10H), 3.46 (t, J=6.6 Hz, 1H), 3.09 (dd, J=18.8, 11.7 Hz, 6H), 2.74 (s, 5H), 2.64 (s, 1H), 2.08 (s, 1H), 1.89-1.68 (m, 4H), 1.26 (dd, J=11.0, 4.9 Hz, 1H), 1.03 (t, J=7.1 Hz, 3H).

Example 219
5-[6-[4-[2-[1-[5-chloro-4-(2,4-dioxohexahydropyrimidin-1-yl)-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine
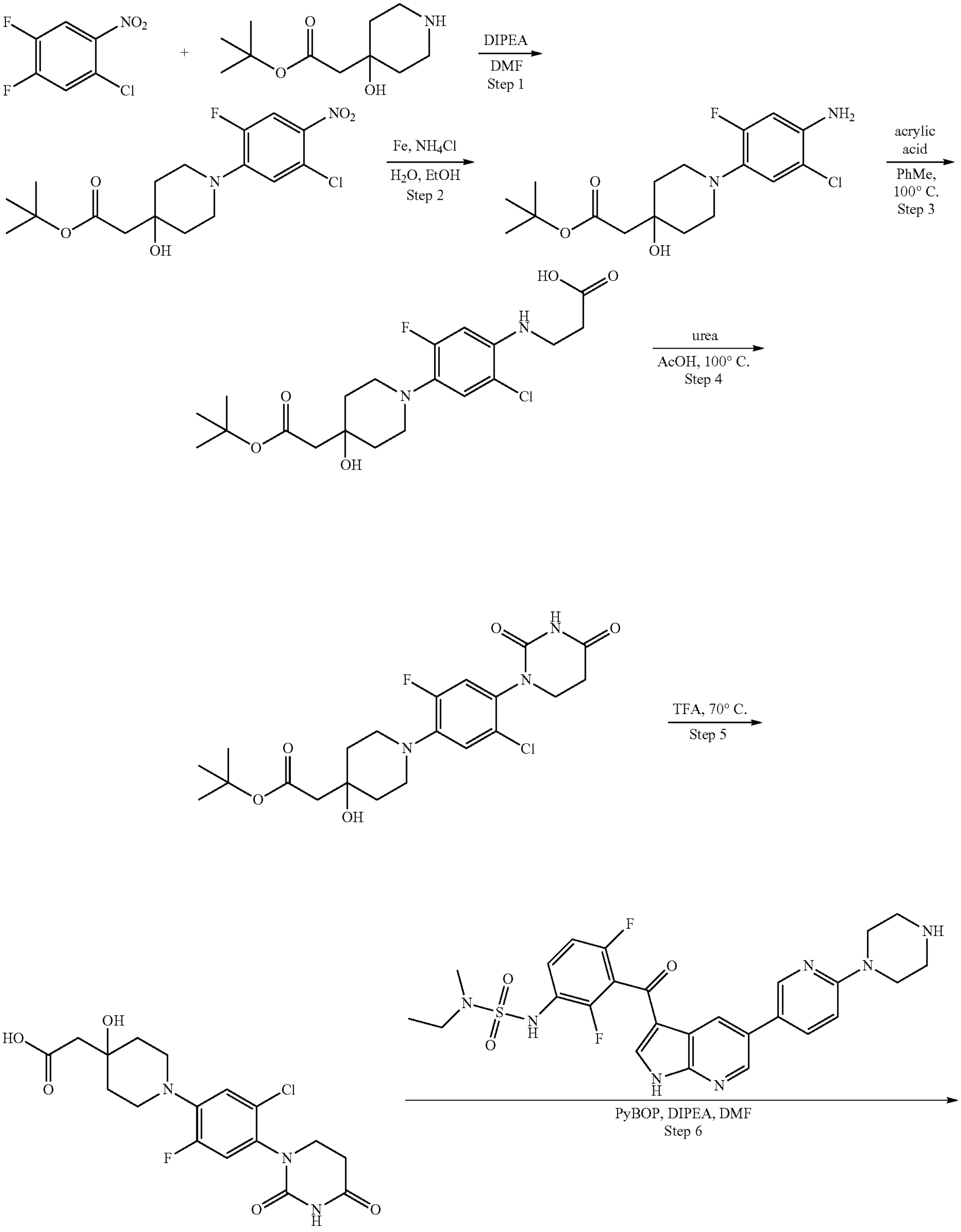

-continued

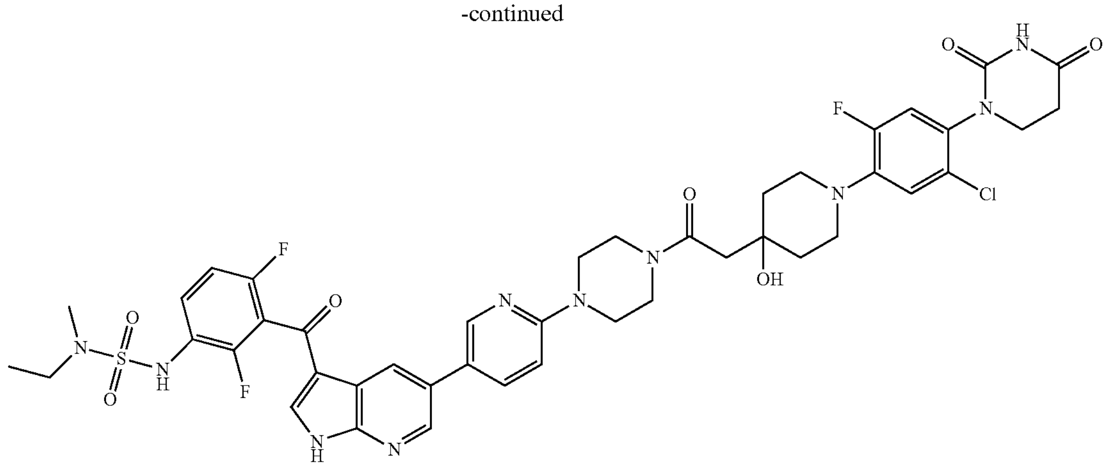

Step 1: tert-butyl 2-(4-hydroxy-4-piperidyl)acetate (1.04 g, 4.83 mmol) and 1-chloro-4,5-difluoro-2-nitro-benzene (934.92 mg, 4.83 mmol) in DMF (7.92 mL) at 0° C. were treated with DIPEA (1.25 g, 9.66 mmol, 1.68 mL). The solution was stirred at room temperature. Upon completion, the solution was diluted with water and ethyl acetate. The layers were separated, and the organic layer washed with water (2×20 mL) and brine (20 mL). The organic layer was dried over sodium sulphate, filtered and solvent removed. The residue was purified by flash column chromatography, eluting with 0-50% ethyl acetate in Hexanes to give tert-butyl 2-[1-(2-chloro-5-fluoro-4-nitro-phenyl)-4-hydroxy-4-piperidyl]acetate (1.71 g, 4.40 mmol, 91% yield) LCMS (ESI+): 389.155 $[M+H]^+$. $^1H$ NMR (400 MHz, Chloroform-d): δ 7.80 (d, J=12.9 Hz, 1H), 6.99 (d, J=7.9 Hz, 1H), 3.51-3.42 (m, 2H), 3.40-3.30 (m, 2H), 2.43 (s, 2H), 1.86-1.79 (m, 2H), 1.78-1.68 (m, 2H), 1.48 (s, 9H).

Step 2: tert-butyl 2-[1-(5-chloro-2-fluoro-4-nitro-phenyl)-4-hydroxy-4-piperidyl]acetate (286.1 mg, 735.82 μmol) in Ethanol (357.88 μL) was treated with Iron powder (205.48 mg, 3.68 mmol, 26.14 ammonium chloride (118.08 mg, 2.21 mmol, 77.17 μL) and water (68.17 The mixture was stirred vigorously at room temperature overnight, and subsequently heated at 70° C. Upon completion, the mixture was diluted with ethyl acetate and filtered through Celite, washing with ethyl acetate. The solvent was removed under reduced pressure and the residue purified by flash column chromatography, eluting with 0-100% ethyl acetate in Hexanes to give tert-butyl 2-[1-(4-amino-5-chloro-2-fluoro-phenyl)-4-hydroxy-4-piperidyl]acetate (234 mg, 652.11 μmol, 89% yield). LCMS (ESI+): 359.150 $[M+H]^+$. $^1H$ NMR (400 MHz, DMSO-$d_6$): δ 6.86 (d, J=8.7 Hz, 1H), 6.58 (d, J=13.9 Hz, 1H), 5.15 (s, 2H), 4.46 (s, 1H), 2.89-2.80 (m, 4H), 2.34 (s, 2H), 1.80-1.69 (m, 2H), 1.67-1.60 (m, 2H), 1.41 (s, 9H).

Step 3: tert-butyl 2-[1-(4-amino-5-chloro-2-fluoro-phenyl)-4-hydroxy-4-piperidyl]acetate (206.6 mg, 575.75 μmol) in Toluene (3.94 mL) was treated with acrylic acid (207.45 mg, 2.88 mmol, 197.57 μL) and heated at 100° C. Upon completion of the reaction, the solvent was removed under reduced pressure to give crude 3-[4-[4-(2-tert-butoxy-2-oxo-ethyl)-4-hydroxy-1-piperidyl]-2-chloro-5-fluoro-anilino]propanoic acid, which was used in the next step without purification.

LCMS (ESI+): 431.264 $[M+H]^+$

Step 4: Crude 3-[4-[4-(2-tert-butoxy-2-oxo-ethyl)-4-hydroxy-1-piperidyl]-2-chloro-5-fluoro-anilino]propanoic acid in acetic acid (1.94 mL) was treated with urea (103.74 mg, 1.73 mmol) and heated at 100° C. overnight. Upon completion, the solvent was removed under reduced pressure and the residue azeotroped with toluene (5 mL). The residue contained a mixture of tert-butyl 2-[1-[5-chloro-4-(2,4-dioxohexahydropyrimidin-1-yl)-2-fluoro-phenyl]-4-hydroxy-4-piperidyl]acetate and 2-[1-[5-chloro-4-(2,4-dioxohexahydropyrimidin-1-yl)-2-fluoro-phenyl]-4-hydroxy-4-piperidyl]acetic acid and was used in the next step without purification. LCMS (ESI+): 456.171 $[M+H]^+$ Step 5: The crude mixture of tert-butyl 2-[1-[5-chloro-4-(2,4-dioxohexahydropyrimidin-1-yl)-2-fluoro-phenyl]-4-hydroxy-4-piperidyl]acetate and 2-[1-[5-chloro-4-(2,4-dioxohexahydropyrimidin-1-yl)-2-fluoro-phenyl]-4-hydroxy-4-piperidyl]acetic acid was taken up in TFA (1 mL) and heated at 70° C. The solvent was removed under reduced pressure and the residue purified via reverse phase column chromatography, eluting with 5-100% acetonitrile in water (with 0.1% TFA modifier) to give 2-[1-[5-chloro-4-(2,4-dioxohexahydropyrimidin-1-yl)-2-fluoro-phenyl]-4-hydroxy-4-piperidyl]acetic acid (112.5 mg, 218.95 μmol, 44% yield over three steps, trifluoroacetic acid salt). LCMS (ESI+): 400.107 $[M+H]^+$ Step 6: 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (153.25 mg, 228.86 μmol, trifluoroacetic acid salt) and 2-[1-[5-chloro-4-(2,4-dioxohexahydropyrimidin-1-yl)-2-fluoro-phenyl]-4-hydroxy-4-piperidyl]acetic acid (91.5 mg, 228.86 μmop in DMF (3.03 mL) at 0° C. were treated with DIPEA (177.47 mg, 1.37 mmol, 239.18 μL) and PyBOP (131.01 mg, 251.75 μmol) and allowed to come to room temperature. Upon completion, the mixture was purified directly by reverse phase column chromatography, eluting with 5-100% acetonitrile in water (with 0.1% TFA modifier). The product containing fractions were combined and free-based with sodium bicarbonate and purified by normal phase column chromatography, eluting with 0-15% methanol in dichloromethane to give 5-[6-[4-[2-[1-[5-chloro-4-(2,4-dioxohexahydropyrimidin-1-yl)-2-fluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine (18.2 mg, 18.44 μmol, 8% yield) as a white solid. LCMS (ESI+): 937.179 $[M+H]^+$. $^1H$ NMR (400 MHz, DMSO-$d_6$) δ 12.95 (d, J=3.3 Hz, 1H), 10.45 (s, 1H), 9.70 (s, 1H), 8.67 (d, J=2.2 Hz, 1H), 8.56-8.49 (m, 1H), 8.12 (d, J=3.0 Hz, 2H), 7.97 (dd, J=8.8, 2.6 Hz, 1H), 7.62-7.53 (m, 1H), 7.37 (d, J=13.1 Hz, 1H), 7.31-7.24 (m, 1H), 7.15 (d, J=8.7 Hz, 1H), 7.01 (d, J=8.9 Hz, 1H), 4.97 (s, 1H), 3.74-3.54 (m, 10H), 3.23-3.01 (m, 6H), 2.72 (s, 3H), 2.72-2.68 (m, 1H), 2.04-1.95 (m, 1H), 1.85-1.75 (m, 2H), 1.74-1.68 (m, 2H), 1.27-1.22 (m, 3H), 1.01 (t, J=7.1 Hz, 3H).

Example 220
5-[6-[4-[2-[1-[4-(2,4-dioxohexahydropyrimidin-1-yl)-2,5-difluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine
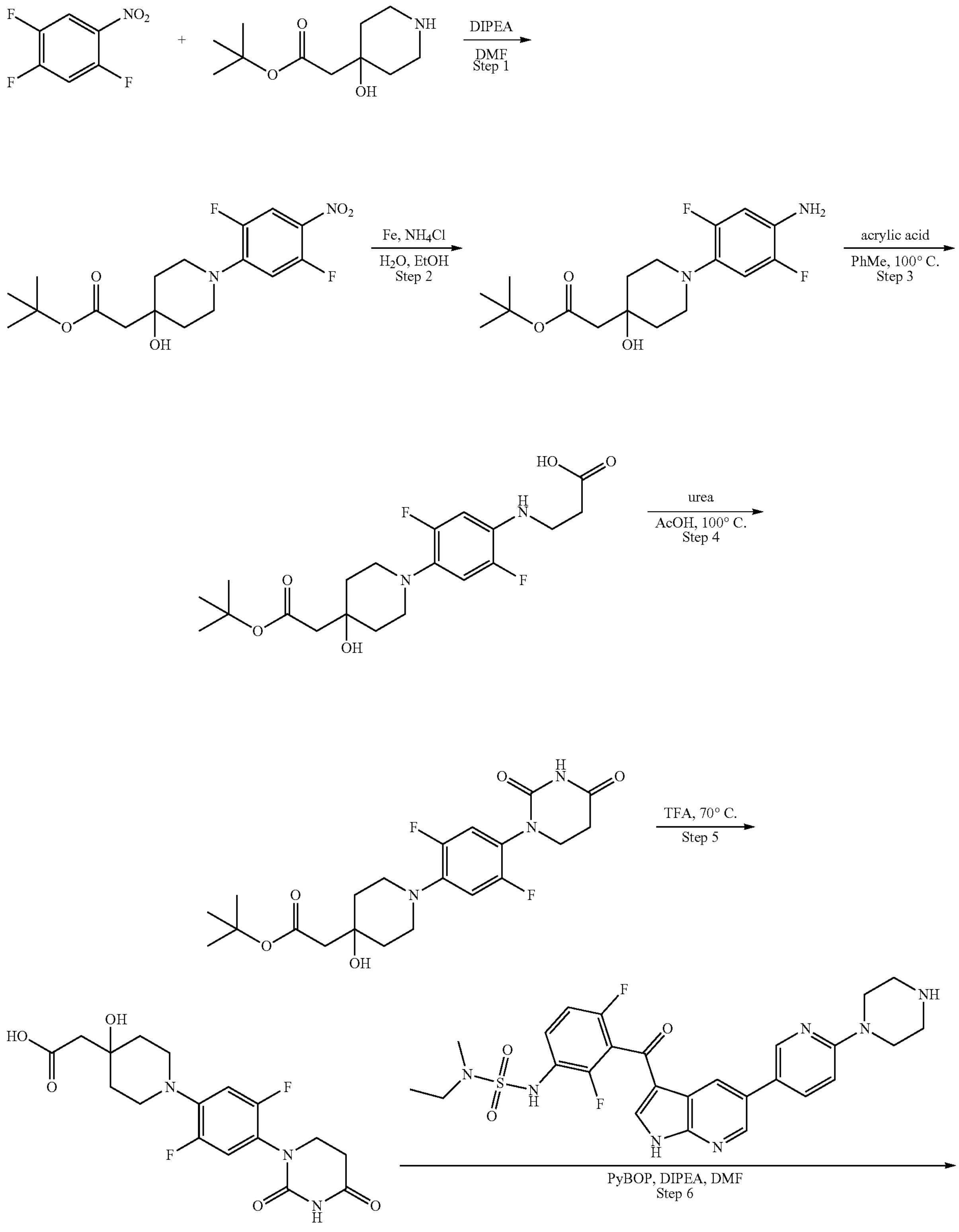

-continued

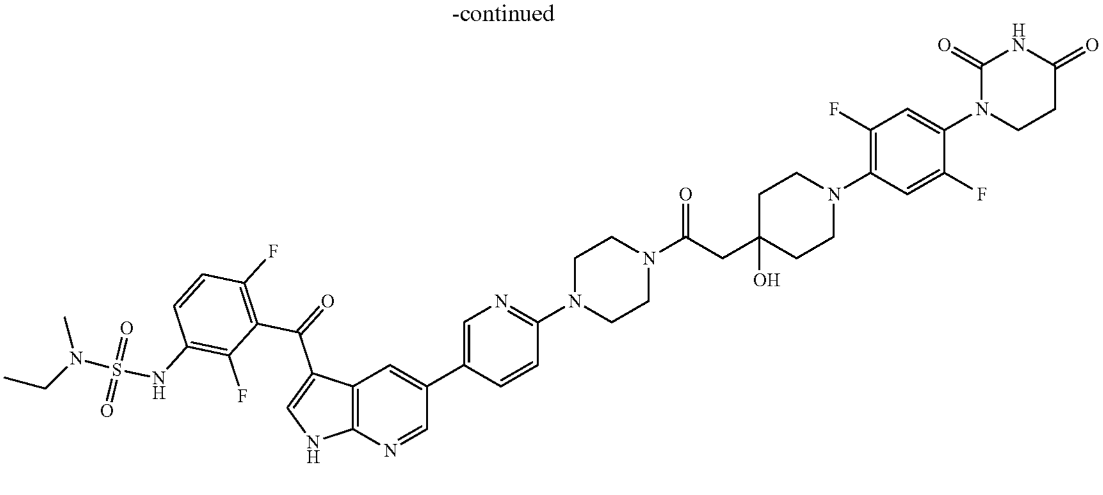

Step 1: tert-butyl 2-(4-hydroxy-4-piperidyl)acetate (250 mg, 1.16 mmol) and 1,2,4-trifluoro-5-nitro-benzene (205.63 mg, 1.16 mmol, 133.53 μL) were combined in DMF (2.08 mL) and treated with DIPEA (600.32 mg, 4.64 mmol, 809.06 μL). The solution was stirred at room temperature for 4 h. The solution was diluted with water and ethyl acetate, the layers separated and organic the layer washed with water (2×10 mL) and brine (10 mL). The organic layer was dried over sodium sulphate, filtered and solvent removed. The residue was purified by flash column chromatography, eluting with 0-50% ethyl acetate in Hexanes to give tert-butyl 2-[1-(2,5-difluoro-4-nitro-phenyl)-4-hydroxy-4-piperidyl] acetate (297.3 mg, 798.41 μmol, 69% yield) and tert-butyl 2-[1-(4,5-difluoro-2-nitro-phenyl)-4-hydroxy-4-piperidyl] acetate (40.8 mg, 109.57 μmol, 9% yield; not shown).

tert-butyl 2-[1-(2,5-difluoro-4-nitro-phenyl)-4-hydroxy-4-piperidyl]acetate: LCMS (ESI+): 373.202 $[M+H]^+$; $^1H$ NMR (400 MHz, Chloroform-d): δ 7.79 (dd, J=13.1, 7.1 Hz, 1H), 6.66 (dd, J=13.4, 7.3 Hz, 1H), 3.91 (s, 1H), 3.56-3.46 (m, 2H), 3.42-3.31 (m, 2H), 2.42 (s, 2H), 1.87-1.77 (m, 2H), 1.76-1.67 (m, 2H), 1.48 (s, 9H).

tert-butyl 2-[1-(4,5-difluoro-2-nitro-phenyl)-4-hydroxy-4-piperidyl]acetate (not shown): $^1H$ NMR (400 MHz, Chloroform-d): δ 7.79 (dd, J=10.0, 8.2 Hz, 1H), 6.98 (dd, J=12.0, 7.0 Hz, 1H), 3.27-3.16 (m, 2H), 3.03-2.95 (m, 2H), 2.43 (s, 2H), 1.83-1.75 (m, 4H), 1.48 (s, 9H).

Step 2: tert-butyl 2-[1-(2,5-difluoro-4-nitro-phenyl)-4-hydroxy-4-piperidyl]acetate (297.3 mg, 798.41 μmol) in Ethanol (1 mL) was treated with Iron powder (222.94 mg, 3.99 mmol), ammonium chloride (128.13 mg, 2.40 mmol, 83.74 μL) and water (100 μL). The mixture was stirred vigorously at room temperature overnight, and subsequently heated at 70° C. Upon completion, the mixture was diluted with ethyl acetate and filtered through Celite, washing with ethyl acetate. The solvent was removed under reduced pressure and the residue purified by flash column chromatography, eluting with 0-100% ethyl acetate in Hexanes to give tert-butyl 2-[1-(4-amino-2,5-difluoro-phenyl)-4-hydroxy-4-piperidyl]acetate (293 mg, 855.77 μmol, quantitative yield). LCMS (ESI+): 343.148 $[M+H]^+$. $^1H$ NMR (400 MHz, DMSO-d6): δ 6.74 (dd, J=12.8, 8.0 Hz, 1H), 6.52 (dd, J=13.5, 8.4 Hz, 1H), 4.92 (s, 2H), 4.45 (s, 1H), 2.88-2.80 (m, 4H), 2.34 (s, 2H), 1.81-1.69 (m, 2H), 1.67-1.59 (m, 2H), 1.41 (s, 9H).

Step 3: tert-butyl 2-[1-(4-amino-2,5-difluoro-phenyl)-4-hydroxy-4-piperidyl]acetate (50 mg, 146.04 μmol) in Toluene (1 mL) was treated with acrylic acid (9.47 mg, 131.43 μmol, 9.02 μL) and heated at 100° C. After 5 h, additional acrylic acid (21.05 mg, 292.07 μmol, 20.05 μL) was added and the reaction continued overnight. Upon completion, the mixture was concentrated under reduced pressure to give crude 3-[4-[4-(2-tert-butoxy-2-oxo-ethyl)-4-hydroxy-1-piperidyl]-2,5-difluoro-anilino]propanoic acid, which was used in the next step without purification. LCMS (ESI+): 415.260 $[M+H]^+$ Step 4: Crude 3-[4-[4-(2-tert-butoxy-2-oxo-ethyl)-4-hydroxy-1-piperidyl]-2,5-difluoro-anilino]propanoic acid in acetic acid (500 μL) was treated with urea (26.30 mg, 438.00 μmol) and heated at 100° C. overnight. Upon complete consumption of starting material, the solvent was removed under reduced pressure and the residue azeotroped with toluene (3 mL). The residue contained a mixture of tert-butyl 2-[1-[4-(2,4-dioxohexahydropyrimidin-1-yl)-2,5-difluoro-phenyl]-4-hydroxy-4-piperidyl]acetate and 2-[1-[4-(2,4-dioxohexahydropyrimidin-1-yl)-2,5-difluoro-phenyl]-4-hydroxy-4-piperidyl]acetic acid and was used in the next step without purification. LCMS (ESI+) (6): 440.267 $[M+H]^+$ Step 5: The crude mixture of tert-butyl 2-[1-[4-(2,4-dioxohexahydropyrimidin-1-yl)-2,5-difluoro-phenyl]-4-hydroxy-4-piperidyl]acetate and 2-[1-[4-(2,4-dioxohexahydropyrimidin-1-yl)-2,5-difluoro-phenyl]-4-hydroxy-4-piperidyl]acetic acid was taken up in TFA (300 μL) and heated at 70° C. The solvent was removed under reduced pressure and the residue purified via reverse phase column chromatography, eluting with 5-100% MeCN in water (with 0.1% TFA modifier) to give 2-[1-[4-(2,4-dioxohexahydropyrimidin-1-yl)-2,5-difluoro-phenyl]-4-hydroxy-4-piperidyl]acetic acid (28.4 mg, 57.10 μmol, 39% yield over three steps, trifluoroacetic acid salt). LCMS (ESI+): 384.204 $[M+H]^+$ Step 6: 3-[3-[[ethyl(methyl)sulfamoyl]amino]-2,6-difluoro-benzoyl]-5-(6-piperazin-1-yl-3-pyridyl)-1H-pyrrolo[2,3-b]pyridine (49.61 mg, 74.08 μmol, trifluoroacetic acid salt) and 2-[1-[4-(2,4-dioxohexahydropyrimidin-1-yl)-2,5-difluoro-phenyl]-4-hydroxy-4-piperidyl]acetic acid (28.4 mg, 57.10 μmol, trifluoroacetic acid salt) in DMF (1.12 mL) at 0° C. were treated with DIPEA (57.45 mg, 444.51 μmol, 77.43 μL) and PyBOP (42.41 mg, 81.49 μmol) and allowed to come to room temperature. Upon completion, the mixture was purified directly by reverse phase column chromatography, eluting with 5-100% acetonitrile in water (with 0.1% TFA modifier). The product-containing fractions were combined and free-based with sodium bicarbonate and purified by normal phase column chromatography, eluting with 0-15% methanol in dichloromethane to give 5-[6-[4-[2-[1-[4-(2,4-dioxohexahydropyrimidin-1-yl)-2,5-difluoro-phenyl]-4-hydroxy-4-piperidyl]acetyl]piperazin-1-yl]-3-pyridyl]-3-[3-[[ethyl(methyl)sulfamoyl]amino]-2,6-difluoro-benzoyl]-1H-pyrrolo[2,3-b]pyridine (9.3 mg, 9.19 μmol, 12% yield) as a white solid. LCMS (ESI+): 921.273 $[M+H]^+$. $^1H$ NMR (400 MHz, DMSO-$d_6$): δ 12.95 (d, J=3.3 Hz, 1H), 10.46 (s, 1H), 9.70 (s, 1H), 8.67 (d, J=2.2 Hz, 1H), 8.52 (d, J=2.6 Hz, 2H), 8.12 (d, J=3.2 Hz, 1H), 7.97 (dd, J=8.9, 2.6 Hz, 1H), 7.62-7.54 (m, 1H), 7.32-7.24 (m, 2H), 7.04-6.94 (m, 2H), 4.97 (s, 1H), 3.73-3.56 (m, 9H), 3.19-2.99 (m, 6H), 2.73 (s, 3H), 2.69 (t, J=6.8 Hz, 2H), 2.61 (s, 2H), 2.09-1.95 (m, 1H), 1.85-1.75 (m, 1H), 1.74-1.66 (m, 2H), 1.24 (s, 2H), 1.01 (t, J=7.1 Hz, 3H).

Example 221

5-[4-[4-[2-[1-[4-[(2,6-dioxo-3-piperidyl)amino]-2-fluoro-phenyl]-4-hydroxy-4-piperidyl]acetyl]piperazin-1-yl]-2,5-difluoro-phenyl]-3-[3-[[ethyl(methyl)sulfamoyl]amino]-2,6-difluoro-benzoyl]-1H-pyrrolo[2,3-b]pyridine

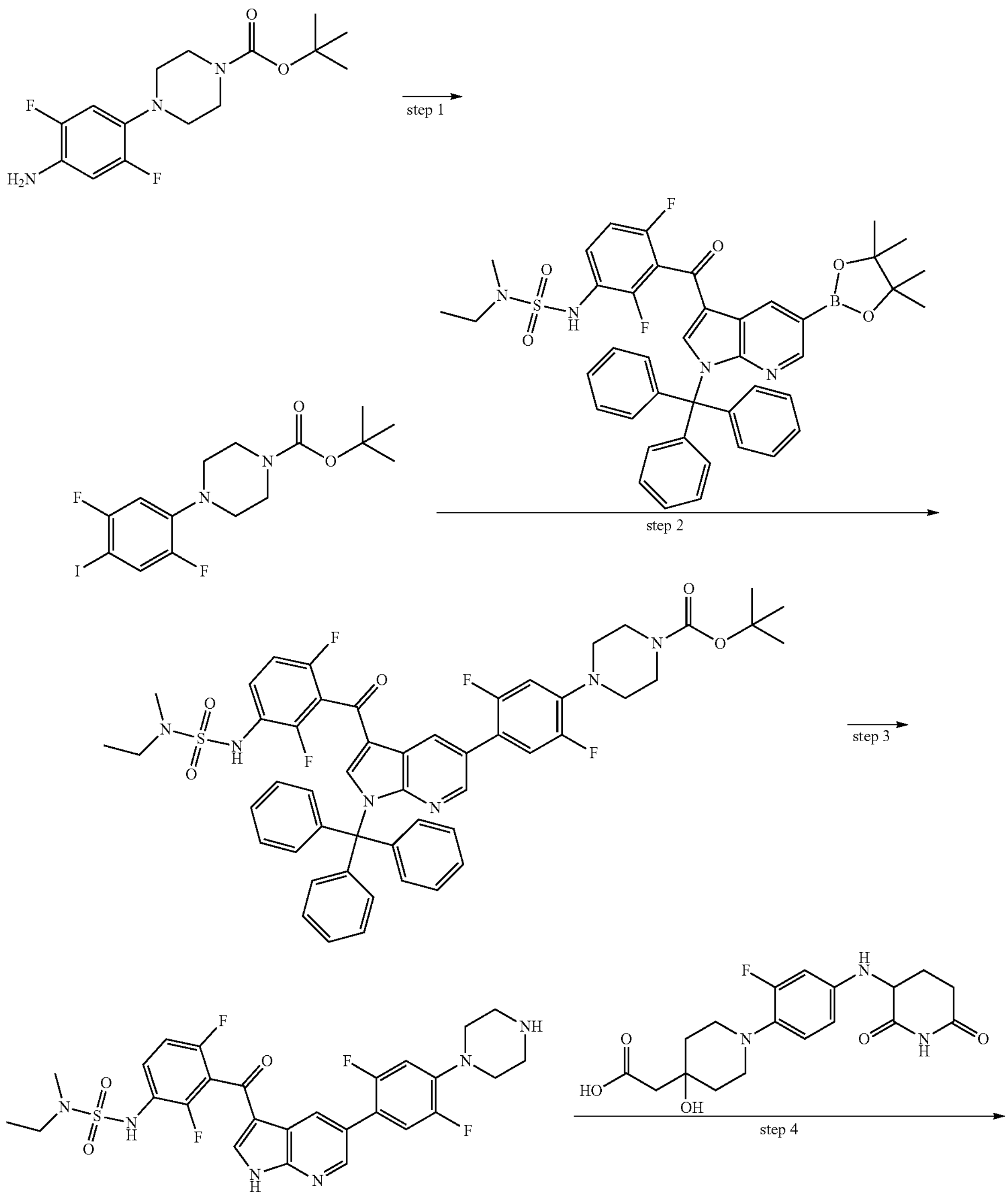

-continued

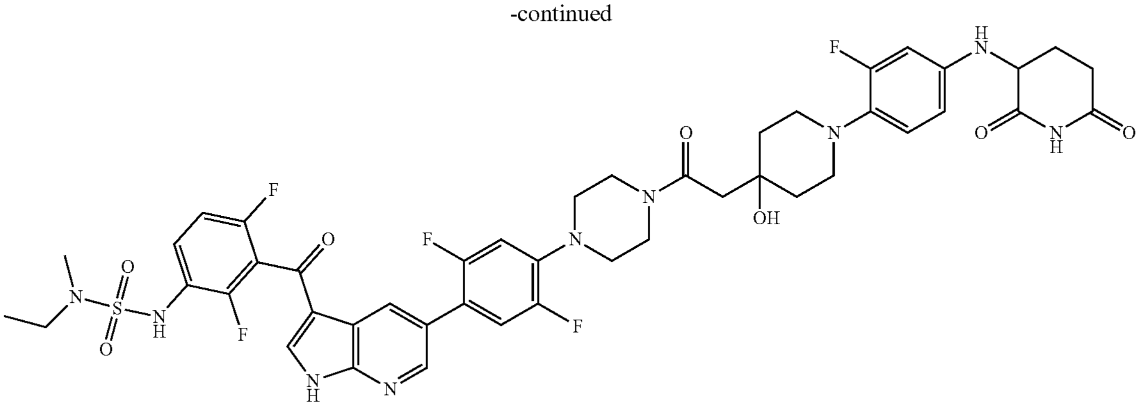

Step 1: To a solution of tert-butyl 4-(4-amino-2,5-difluoro-phenyl)piperazine-1-carboxylate (116 mg, 370.20 μmol) in acetonitrile (3.2 mL) and water (3.2 mL) was added p-Toluenesulfonic acid monohydrate, 97% (219.71 mg, 1.16 mmol, 177.18 uL) at 0° C., followed by the addition of sodium nitrite (52.36 mg, 758.91 μmol, 24.13 uL) in water (3.2 mL) at the same temperature. The reaction mixture was stirred at 0° C. for 1 h, then added KI (135.81 mg, 818.15 μmol, 43.53 uL) in water (3.2 mL) was added at the same temperature. The reaction mixture was stirred at room temperature for 16 h. After completion, water was added to the reaction mixture and extracted with ethyl acetate. The combined organic layers were dried over sodium sulphate, filtered and concentrated to afford tert-butyl 4-(2,5-difluoro-4-iodo-phenyl)piperazine-1-carboxylate (175 mg, 358.89 μmol, 96.94% yield), which was used without further purification. LCMS (ESI+): 369.1 [M-tBu]$^+$ Step 2: To a mixture of 3-[3-[[ethyl(methyl)sulfamoyl]amino]-2,6-difluoro-benzoyl]-5-(4,4,5,5-tetramethyl-1,3,2-dioxaborolan-2-yl)-1-trityl-pyrrolo[2,3-b]pyridine (265.89 mg, 348.64 μmol) and tert-butyl 4-(2,5-difluoro-4-iodo-phenyl)piperazine-1-carboxylate (170 mg, 348.64 μmol) in dioxanes (1.2 mL) and water (0.3 mL) was added Potassium phosphate tribasic anhydrous (222.01 mg, 1.05 mmol) and Xphos Pd G3 (14.76 mg, 17.43 μmol). The resulting mixture was purged with argon before being sealed in a microwave vessel and stirring for 5 min at room temperature. Then the reaction mixture was stirred at 115° C. for 2 hr in a microwave. After cooling, the reaction was diluted with water and extracted with ethyl acetate. The combined organic layers were dried with sodium sulphate and concentrated. The crude material was then purified by column chromatography (20-80% ethyl acetate in hexanes) to afford the product tert-butyl 4-[4-[3-[3-[[ethyl(methyl)sulfamoyl]amino]-2,6-difluoro-benzoyl]-1-trityl-pyrrolo[2,3-b]pyridin-5-yl]-2,5-difluoro-phenyl]piperazine-1-carboxylate (103 mg, 104.87 μmol, 30.08% yield). LCMS (ESI+): 955.5 [M+Na]$^+$ Step 3: A solution of tert-butyl 4-[4-[3-[3-[[ethyl(methyl)sulfamoyl]amino]-2,6-difluoro-benzoyl]-1-trityl-pyrrolo[2,3-b]pyridin-5-yl]-2,5-difluoro-phenyl]piperazine-1-carboxylate (103 mg, 110.39 μmol) was dissolved in 1,4-dioxanes (1.5 mL) and Hydrogen chloride solution in 1,4-dioxane (4 M, 1.93 mL) was added. The reaction was stirred at room temperature overnight. The reaction mixture was then concentrated to afford 5-(2,5-difluoro-4-piperazin-1-yl-phenyl)-3-[3-[[ethyl(methyl)sulfamoyl]amino]-2,6-difluoro-benzoyl]-1H-pyrrolo[2,3-b]pyridine (69 mg, 104.54 μmol, 94.69% yield, hydrochloric acid salt), which was used without further purification. LCMS (ESI+): 591.5 [M+H]$^+$ Step 4: To a solution of 2-[1-[4-[(2,6-dioxo-3-piperidyl)amino]-2-fluoro-phenyl]-4-hydroxy-4-piperidyl]acetic acid (57.62 mg, 151.88 μmop in DMF (1 mL) at 0° C. was added N,N-Diisopropylethylamine (75.50 mg, 584.16 μmol, 101.75 uL) and COMU (55.04 mg, 128.52 μmol). The reaction stirred at this temperature for 30 min before a solution of 5-(2,5-difluoro-4-piperazin-1-yl-phenyl)-3-[3-[[ethyl(methyl)sulfamoyl]amino]-2,6-difluoro-benzoyl]-1H-pyrrolo[2,3-b]pyridine (69 mg, 116.83 μmol) in DMF (1 mL) was added. The reaction stirred for 2 hr at room temperature. 6 drops of sat. aq. sodium bicarbonate solution was added and the reaction stirred an additional 2 hr. The crude reaction was then purified by column chromatography (0-60% acetonitrile in $H_2O$ with 0.1% formic acid) to afford the product 5-[4-[4-[2-[1-[4-[(2,6-dioxo-3-piperidyl)amino]-2-fluoro-phenyl]-4-hydroxy-4-piperidyl]acetyl]piperazin-1-yl]-2,5-difluoro-phenyl]-3-[3-[[ethyl(methyl)sulfamoyl]amino]-2,6-difluoro-benzoyl]-1H-pyrrolo[2,3-b]pyridine (21.6 mg, 20.56 μmol, 17.60% yield, formic acid salt) as an off-white solid. LCMS (ESI+): 952.5 [M+H]$^+$. $^1$H NMR (400 MHz, DMSO-$d_6$): δ 13.03 (d, J=3.3 Hz, 1H), 10.78 (s, 1H), 9.71 (s, 1H), 8.57 (d, J=1.7 Hz, 2H), 8.17 (d, J=3.2 Hz, 1H), 7.68-7.48 (m, 2H), 7.34-7.23 (m, 1H), 7.08 (dd, J=12.5, 7.4 Hz, 1H), 6.87 (t, J=9.3 Hz, 1H), 6.51 (dd, J=14.9, 2.6 Hz, 1H), 6.42 (d, J=8.8 Hz, 1H), 5.78 (d, J=7.7 Hz, 1H), 4.84 (s, 1H), 4.26 (dt, J=12.0, 6.6 Hz, 1H), 3.73 (d, J=19.5 Hz, 5H), 3.18-3.07 (m, 6H), 2.99-2.83 (m, 4H), 2.73 (m, 6H), 2.59 (s, 3H), 2.16-2.06 (m, 1H), 1.68 (d, J=12.5 Hz, 2H), 1.02 (t, J=7.1 Hz, 3H).

N-BOC-Glutarimide Intermediates

General Procedure I: Condensations of Anilines with Bromo Glutarimide

A mixture of 3-bromopiperidine-2,6-dione (1 eq), an aniline compound of intermediate formula V (1-1.5 eq) and sodium hydrogencarbonate (4 eq) in acetonitrile (0.1-0.3 M) is heated at reflux for 12-36 h. Alternatively, 3-bromopiperidine-2,6-dione (1 eq), an aniline compound of intermediate formula V (1-1.5 eq) and DIPEA (3 eq) in N,N-dimethylformamide (0.2 M) is heated at 60° C. for 12-36 h. After cooling to room temperature the reaction mixture is partitioned between an organic solvent such as ethyl acetate or dichloromethane and 1M aqueous sodium bicarbonate solution. The layers are separated. The aqueous layer is extracted with one or two portions of organic solvent. The combined organic layers are washed with one portion of brine, dried over anhydrous sodium sulfate and concentrated to dryness. Purification by flash-chromatography or crystallization from a suitable solvent gives a compound of intermediate formula II-a.

General Procedure II: Condensations of Phenols with Bromo Glutarimide

A mixture of 3-bromopiperidine-2,6-dione (1.3 eq), a phenol compound of intermediate formula VII (1 eq) and sodium hydride (2.5 eq) in N,N-dimethylformamide (0.1-0.3 M) is heated at 90° C. for 12 h. After cooling to room temperature the reaction mixture is partitioned between an organic solvent such as ethyl acetate or dichloromethane and 1M aqueous sodium bicarbonate solution. The layers are separated. The aqueous layer is extracted with one or two portions of organic solvent. The combined organic layers are washed with one portion of brine, dried over anhydrous sodium sulfate and concentrated to dryness. Purification by flash-chromatography, prep-HPLC or crystallization from a suitable solvent gives a compound of intermediate formula II-b.

N-BOC-Glutarimide 1 tert-Butyl 4-(4-((2,6-dioxopiperidin-3-yl)amino) phenyl)piperidine-1-carboxylate

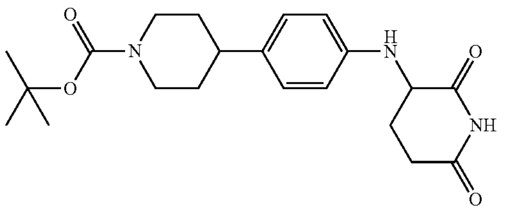

The title compound was obtained as blue solid in 86% yield according to the general procedure I from 3-bromopiperidine-2,6-dione and tert-butyl 4-(4-aminophenyl)piperidine-1-carboxylate. MS m/e: 332 ([M+H−$C_4H_8$]$^+$).

N-BOC-Glutarimide 2 tert-Butyl 4-(4-((2,6-dioxopiperidin-3-yl)amino) phenyl)piperazine-1-carboxylate

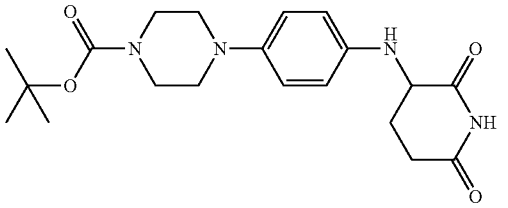 [SMILES: CC(C)(C)OC(=O)N1CCN(c2ccc(NC3CCC(=O)NC3=O)cc2)CC1]

The title compound was obtained as dark brown solid in 50% yield according to the general procedure I from 3-bromopiperidine-2,6-dione and tert-butyl 4-(4-aminophenyl) piperazine-1-carboxylate.

N-BOC-Glutarimide 3 tert-Butyl 5-[(2,6-dioxo-3-piperidyl)amino]isoindoline-2-carboxylate

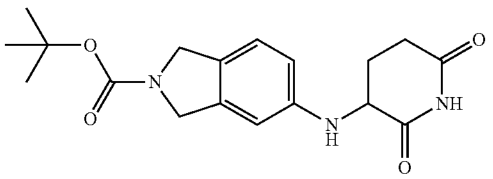 [SMILES: CC(C)(C)OC(=O)N1Cc2ccc(NC3CCC(=O)NC3=O)cc2C1]

The title compound was obtained as light blue solid in 69% yield according to the general procedure I from 3-bromopiperidine-2,6-dione and tert-butyl 5-aminoisoindoline-2-carboxylate. MS m/e: 346 ([M+H+]$^+$).

N-BOC-Glutarimide 4 tert-Butyl 4-[5-[(2,6-dioxo-3-piperidyl)amino]-2-pyridyl]piperidine-1-carboxylate

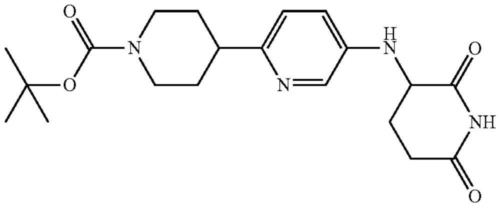

The title compound was obtained as green solid in 22% yield according to the general procedure I from 3-bromopiperidine-2,6-dione and tert-butyl 4-(5-amino-2-pyridyl)piperidine-1-carboxylate. MS m/e: 389.1 ([M+H+]$^+$).

N-BOC-Glutarimide 5 tert-Butyl 4-[4-[(2,4-dioxo-3-azabicyclo[3.1.1]heptan-1-yl)amino]phenyl]piperidine-1-carboxylate

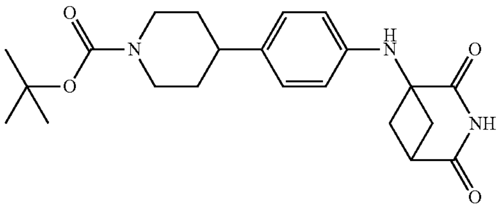 [SMILES: CC(C)(C)OC(=O)N1CCC(c2ccc(NC34CC(C3)C(=O)NC4=O)cc2)CC1]

a) Methyl 3-cyano-3-(4-iodoanilino)cyclobutanecarboxylate

To a stirred solution of methyl 3-oxocyclobutanecarboxylate (1.0 g, 7.80 mmol) in ethanol (10 mL) was added 4-iodoaniline (1.88 g, 8.59 mmol), and to it was added trimethylsilyl cyanide (774.29 mg, 7.80 mmol). The reaction mixture was stirred for 16 hours at room temperature. The solvent was evaporated. Purification by flash-chromatography with n-hexane/ethyl acetate as eluent gave the title compound (2.5 g, 89.94%) as off-white solid. MS m/e: 357.1 ([M+H+]$^+$).

b) methyl 3-carbamoyl-3-(4-iodoanilino)cyclobutanecarboxylate

A mixture of methyl 3-cyano-3-(4-iodoanilino)cyclobutanecarboxylate (4 g, 11.23 mmol), (1Z)-acetaldehyde oxime (1.99 g, 33.69 mmol) and indium(III) chloride (24.84 mg, 112.31 umol) in toluene (20 mL) was refluxed for 1 hr. After complete consumption of SM as monitored by TLC, resulting precipitate was collected by filtration to obtain methyl 3-carbamoyl-3-(4-iodoanilino)cyclobutanecarboxylate (3 g, 8.02 mmol, 71.39% yield). MS m/e: 375.2 ([M+H+]$^+$).

c) 1-(4-iodoanilino)-3-azabicyclo[3.1.1]heptane-2,4-dione

A mixture of methyl 3-carbamoyl-3-(4-iodoanilino)cyclobutanecarboxylate (3.0 g, 8.02 mmol) in acetonitrile (30 mL) and Triton B 40% as a solution in methanol (8.02 mmol) was stirred for 10 minutes. After complete consumption of the starting material the solvent was evaporated and the crude residue was purified by column chromatography to afford 1-(4-iodoanilino)-3-azabicyclo[3.1.1]heptane-2,4-dione (3.2 g, 9.35 mmol, 116.66% yield) as off-white solid. MS m/e: 343.2 ([M+H+]$^+$).

d) tert-butyl 4-[4-[(2,4-dioxo-3-azabicyclo[3.1.1]heptan-1-yl)amino]phenyl]-3,6-dihydro-2H-pyridine-1-carboxylate To the stirred solution of 1-(4-iodoanilino)-3-azabicyclo[3.1.1]heptane-2,4-dione (1.6 g, 4.68 mmol) and tert-butyl 4-(4,4,5,5-tetramethyl-1,3,2-dioxaborolan-2-yl)-3,6-dihydro-2Hpyridine-1-carboxylate (2.89 g, 9.35 mmol, 2 eq) in DMF (4 mL)/water (0.5 mL), sodium carbonate (495.66 mg, 4.68 mmol, 195.91 uL) was added and resulting solution was degassed with nitrogen for 15 minutes followed by the addition of cyclopentyl(diphenyl)phosphane dichloromethane dichloropalladium iron (381.91 mg, 467.66 umol). The reaction mixture was heated at 100° C. for 5 h in sealed tube. After complete consumption of SM the reaction mixture was filtered through celite bed and ice cooled water was added to the filtrate. The filtrate was extracted with ethyl acetate. The combined organic layer was washed with water/brine and separated, dried over anhydrous sodium sulfate, filtrated and concentrated in vacuum. Purification by column chromatography afforded the title compound (1.3 g, 3.27 mmol, 69.94% yield). MS m/e: 398 ([M+H+]$^+$).

e) tert-Butyl 4-[4-[(2,4-dioxo-3-azabicyclo[3.1.1]heptan-1-yl)amino]phenyl]piperidine-1-carboxylate A solution of tert-butyl 4-[4-[(2,4-dioxo-3-azabicyclo[3.1.1]heptan-1-yl)amino]phenyl]-3,6-dihydro-2H-pyridine-1-carboxylate (1.4 g, 3.52 mmol) in ethanol (20 mL) was hydrogenated under balloon pressure in presence of palladium on charcoal (374.84 mg, 3.52 mmol) at room temperature for 3 hr. The catalyst was removed by filtration through a celite bed. The filtrate was evaporated. Purification by column chromatography afforded the title compound (900 mg, 64%) as white solid. MS m/e: 344 ([M+H−C4H8]$^+$).

N-BOC-Glutarimide 6 tert-Butyl 4-[4-[(2,6-dioxo-3-piperidyl)oxy]phenyl]piperidine-1-carboxylate

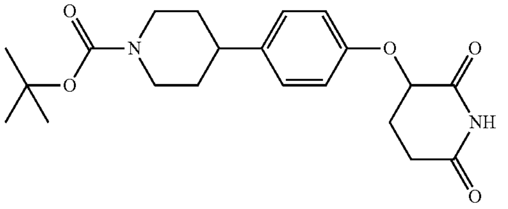

The title compound was obtained as light yellow solid in 61% yield according to the general procedure II from 3-bromopiperidine-2,6-dione and tert-butyl 4-(4-hydroxyphenyl)piperidine-1-carboxylate.

N-BOC-Glutarimide 7 tert-Butyl 4-[4-[(2,6-dioxo-3-piperidyl)oxy]phenyl]piperazine-1-carboxylate

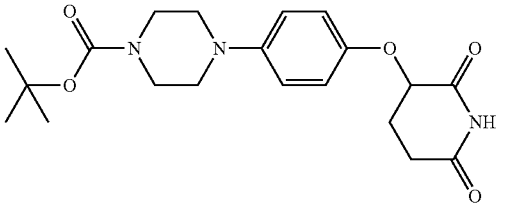

The title compound was obtained as green solid in 71% yield according to the general procedure II from 3-bromopiperidine-2,6-dione and tert-butyl 4-(4-hydroxyphenyl)piperazine-1-carboxylate. MS m/e: 390.1 ([M+H+]$^+$).

N-BOC-Glutarimide 8 tert-Butyl 4-[5-[(2,6-dioxo-3-piperidyl)oxy]-2-pyridyl]piperidine-1-carboxylate

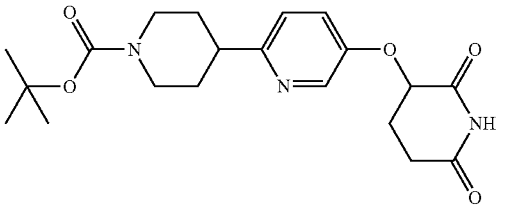 [SMILES: CC(C)(C)OC(=O)N1CCC(c2ccc(OC3CCC(=O)NC3=O)cn2)CC1]

The title compound was obtained as white solid in 36% yield according to the general procedure II from 3-bromopiperidine-2,6-dione and tert-butyl 4-(5-hydroxy-2-pyridyl)piperidine-1-carboxylate.

N-BOC-Glutarimide 9 tert-Butyl 4-[4-[(2,6-dioxo-3-piperidyl)amino]pyrazol-1-yl]piperidine-1-carboxylate

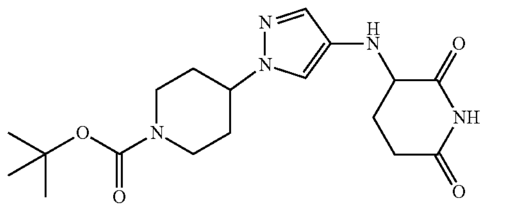 [SMILES: CC(C)(C)OC(=O)N1CCC(n2cc(NC3CCC(=O)NC3=O)cn2)CC1]

The title compound was obtained as blue solid in 75% yield according to the general procedure II from 3-bromopiperidine-2,6-dione and tert-butyl 4-(4-amino-1H-pyrazol-1-yl)piperidine-1-carboxylate. MS m/e: 378.2 ([M+H+]$^+$).

N-BOC-Glutarimide 10 tert-Butyl 4-[4-[[(3S)-2,6-dioxo-3-piperidyl]oxy]phenyl]piperidine-1-carboxylate

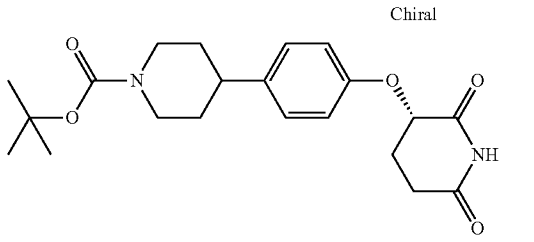 [SMILES: CC(C)(C)OC(=O)N1CCC(c2ccc(O[C@H]3CCC(=O)NC3=O)cc2)CC1]

and

N-BOC-Glutarimide 11 tert-Butyl 4-[4-[[(3R)-2,6-dioxo-3-piperidyl]oxy]phenyl]piperidine-1-carboxylate

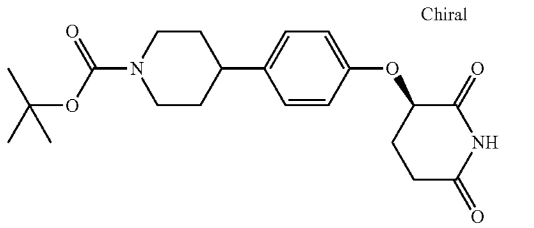 [SMILES: CC(C)(C)OC(=O)N1CCC(c2ccc(O[C@@H]3CCC(=O)NC3=O)cc2)CC1]

The racemic intermediate tert-butyl 4-[4-[(2,6-dioxo-3-piperidyl)oxy]phenyl]piperidine-1-carboxylate (2.5 g, 6.44 mmol) was chirally resoluted using chiral SFC method: Chiralpak IA (250×20 mm; 5 micron) eluting with 45% $CO_2$/55% Isopropylalcohol (FlowRate: 25 g/min), ABPR: 100 bar, Temperature: 35° C.

tert-Butyl 4-[4-[[(3S)-2,6-dioxo-3-piperidyl]oxy]phenyl]piperidine-1-carboxylate was obtained in 34% yield with a purity of 99%. The stereo center configuration of CRBN is arbitrarily assigned as the (S)—first eluting isomer. 1H NMR (400 MHz, DMSO-D6) ppm 10.91 (s, 1H), 7.14 (d, J=8.4 Hz, 2H), 6.93 (d, J=8.4 Hz, 2H), 5.16-5.12 (m, 1H), 4.06-4.04 (m, 2H), 2.78-2.57 (m, 5H), 2.17-2.09 (m, 2H), 1.73-1.70 (m, 2H), 1.48-1.41 (m, 11H). The stereo center configuration of CRBN is arbitrarily assigned to S as first eluting isomer.

tert-Butyl 4-[4-[[(3R)-2,6-dioxo-3-piperidyl]oxy]phenyl]piperidine-1-carboxylate was obtained in 34% yield with a purity of 99%. The stereo center configuration of CRBN is arbitrarily assigned as the (R)—second eluting isomer. 1H NMR (400 MHz, DMSO-D6) □ ppm 10.91 (s, 1H), 7.14 (d, J=8.4 Hz, 2H), 6.92 (d, J=8.4 Hz, 2H), 5.16-5.12 (m, 1H), 4.07-4.04 (m, 2H), 2.78-2.57 (m, 5H), 2.17-2.08 (m, 2H), 1.72-1.70 (m, 2H), 1.48-1.40 (m, 11H). The stereo center configuration of CRBN is arbitrarily assigned to R as second eluting isomer.

Intermediates of formula II

General Procedure III: Cleavage of the N-BOC Group

A mixture of an intermediate of intermediate formula VI or VIII (1 eq) in a solvent such as ethyl acetate or tetrahydrofuran (0.2 M) and 4M hydrogen chloride solution in 1,4-dioxane (10-20 eq) is stirred at room temperature for 12-48 h. Alternatively, a mixture of an intermediate of intermediate formula VI or VIII (1 eq) in dichlormethane (0.2 M) and trifluoroacetic acid (20 eq) is stirred for 2-16 h. The precipitate is collected by filtration and washed with a solvent such as ethyl acetate or tetrahydrofuran and dried in vacuo to give a compound of intermediate formula II-a or II-b respectively. Alternatively the solvent is evaporated and the residue is partitioned between an organic solvent such as ethyl acetate or dichloromethane and 1M aqueous sodium bicarbonate solution. The layers are separated. The aqueous layer is extracted with one or two portions of organic solvent. The combined organic layers are washed with one portion of brine, dried over anhydrous sodium sulfate and concentrated to dryness to give the free base of a compound of intermediate formula II-a or II-b respectively.

Glutarimide 1

3-[4-(4-Piperidyl)anilino]piperidine-2,6-dione hydrochloride

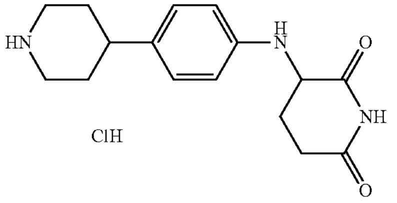 [SMILES: O=C1CCC(Nc2ccc(C3CCNCC3)cc2)C(=O)N1 ; Cl]

The title compound was obtained as dark blue solid in quantitative yield according to the general procedure III from tert-Butyl 4-(4-((2,6-dioxopiperidin-3-yl)amino)phenyl)piperidine-1-carboxylate. MS m/e: 287 ([M+H+]$^+$).

Glutarimide 2

3-[4-(4-(4-Piperidyl)anilino]piperazine-2,6-dione hydrochloride

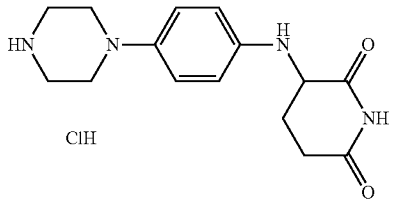 [SMILES: O=C1CCC(Nc2ccc(N3CCNCC3)cc2)C(=O)N1 ; Cl]

The title compound was obtained as dark blue solid in quantitative yield according to the general procedure III from tert-Butyl 4-(4-((2,6-dioxopiperidin-3-yl)amino)phenyl)piperazine-1-carboxylate. MS m/e: 289.1 ([M+H+]$^+$).

Glutarimide 3

3-(Isoindolin-5-ylamino)piperidine-2,6-dione hydrochloride

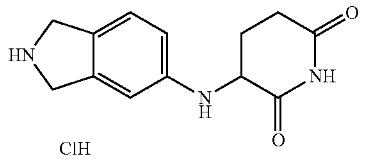 [SMILES: O=C1CCC(Nc2ccc3c(c2)CNC3)C(=O)N1 ; Cl]

The title compound was obtained as dark blue solid in quantitative yield according to the general procedure III from tert-butyl 5-((2,6-dioxopiperidin-3-yl)amino)isoindoline-2-carboxylate. MS m/e: 246 ([M+H+]$^+$).

Glutarimide 4

3-[[6-(4-Piperidyl)-3-pyridyl]amino]piperidine-2,6-dione hydrochloride

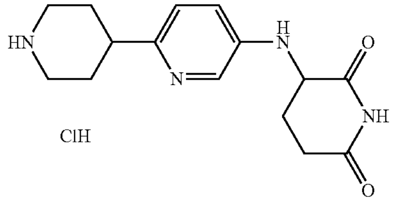 [SMILES: O=C1CCC(Nc2ccc(C3CCNCC3)nc2)C(=O)N1 ; Cl]

The title compound was obtained as yellow solid in quantitative yield according to the general procedure III from tert-butyl 4-[5-[(2,6-dioxo-3-piperidyl)amino]-2-pyridyl]piperidine-1-carboxylate. MS m/e: 289.1 ([M+H+]$^+$).

Glutarimide 5

1-[4-(4-Piperidyl)anilino]-3-azabicyclo[3.1.1]heptane-2,4-dione hydrochloride

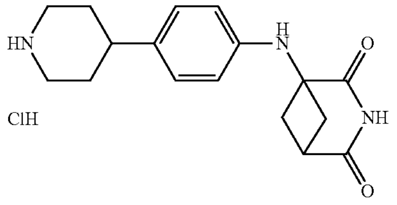 [SMILES: Cl ; O=C1NC(=O)C2(Nc3ccc(C4CCNCC4)cc3)CC1C2]

The title compound was obtained in quantitative yield according to the general procedure III from tert-butyl 4-[4-[(2,4-dioxo-3-azabicyclo[3.1.]heptan-1-yl)amino]phenyl] piperidine-1-carboxylate.

Glutarimide 6

3-[4-(4-Piperidyl)phenoxy]piperidine-2,6-dione hydrochloride

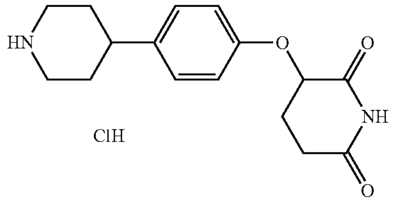 [SMILES: O=C1CCC(Oc2ccc(C3CCNCC3)cc2)C(=O)N1 ; Cl]

The title compound was obtained as white solid in 72% yield according to the general procedure III from tert-butyl 4-[4-[(2,6-dioxo-3-piperidyl)oxy]phenyl]piperidine-1-carboxylate. MS m/e: 289.1 ([M+H+]$^+$).

Glutarimide 7

3-(4-Piperazin-1-ylphenoxy)piperidine-2,6-dione hydrochloride

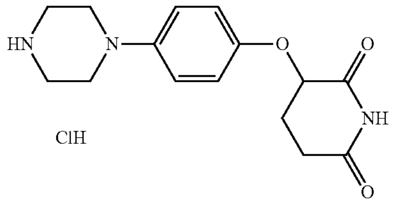 [SMILES: O=C1CCC(Oc2ccc(N3CCNCC3)cc2)C(=O)N1 ; Cl]

The title compound was obtained as grey solid in 88% yield according to the general procedure III from tert-butyl 4-[4-[(2,6-dioxo-3-piperidyl)oxy]phenyl]piperazine-1-carboxylate. MS m/e: 290 ([M+H+]$^+$).

Glutarimide 8

3-[[6-(4-Piperidyl)-3-pyridyl]oxy]piperidine-2,6-dione hydrochloride

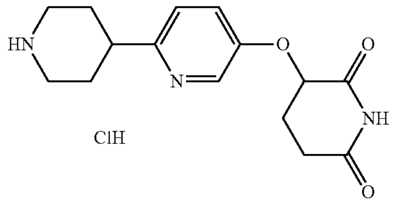 [SMILES: O=C1CCC(Oc2ccc(C3CCNCC3)nc2)C(=O)N1 ; Cl]

The title compound was obtained as white solid in 96% yield according to the general procedure III from tert-butyl 4-[5-[(2,6-dioxo-3-piperidyl)oxy]-2-pyridyl]piperidine-1-carboxylate.

Glutarimide 9

3-[[1-(4-Piperidyl)pyrazol-4-yl]amino]piperidine-2,6-dione hydrochloride

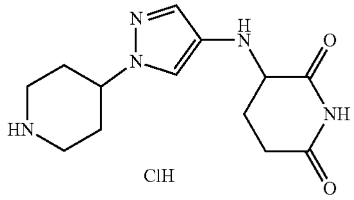 [SMILES: O=C1CCC(Nc2cnn(C3CCNCC3)c2)C(=O)N1 ; Cl]

The title compound was obtained as light blue solid in quantitative yield according to the general procedure III from tert-Butyl 4-[4-[(2,6-dioxo-3-piperidyl)amino]pyrazol-1-yl]piperidine-1-carboxylate. MS m/e: 278 ([M+H+]$^+$).

Glutarimide 10

3-[4-(4-piperidyl)phenyl]piperidine-2,6-dione hydrochloride

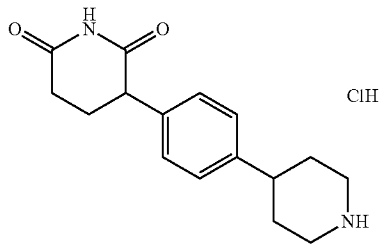 [SMILES: O=C1CCC(c2ccc(C3CCNCC3)cc2)C(=O)N1 ; Cl]

a) tert-Butyl 4-[4-(2,6-dibenzyloxy-3-pyridyl)phenyl]-3,6-dihydro-2H-pyridine-1-carboxylate The stirred solution of tert-butyl 4-[4-(4,4,5,5-tetramethyl-1,3,2-dioxaborolan-2-yl)phenyl]-3,6-dihydro-2H-pyridine-1-carboxylate (31 g, 80.46 mmol), sodium carbonate (21.32 g, 201.14 mmol, 8.43 mL) and 2,6-dibenzyloxy-3-bromo-pyridine (20.85 g, 56.32 mmol) in DMF (300 mL) and water (50 mL) was purged with argon for 20 minutes followed by the addition of and [1,1-Bis(diphenylphosphino)ferrocene]dichloropalladium(II), complex with dichloromethane (6.57 g, 8.05 mmol) and the reaction mixture was allowed to stirr for 14 hours at 90° C. The reaction mixture was cooled, concentrated under reduced pressure to afford the crude product, the crude product thus obtained was purified by flash chromatography to afford tert-butyl-4-[4-(2,6-dibenzyloxy-3-pyridyl)phenyl]-3,6-dihydro-2H-pyridine-1-carboxylate (23 g, 41.92 mmol, 52.10% yield) as light yellow solid.

b) tert-butyl 4-[4-(2,6-dioxo-3-piperidyl)phenyl]piperidine-1-carboxylate

A suspension of tert-butyl-4-[4-(2,6-dibenzyloxy-3-pyridyl)phenyl]-3,6-dihydro-2H-pyridine-1-carboxylate (23 g, 41.92 mmol) in Ethanol (80 mL) was degassed with nitrogen, Palladium, 10% on carbon, Type 487, dry (4.46 g, 4.19 mmol, 10% purity) and platinum(II)oxide (475.95 mg, 2.10 mmol) was added. The flask was filled with hydrogen and the reaction mixture was stirred for 2 hr. The reaction mixture was filtered over celite. The filtrate was concentrated to afford tert-butyl 4-[4-(2,6-dioxo-3-piperidyl)phenyl]piperidine-1-carboxylate (13 g, 34.90 mmol, 83.26% yield) as white solid.

c) 3-[4-(4-piperidyl)phenyl]piperidine-2,6-dione hydrochloride

To a stirred solution of tert-butyl 4-[4-(2,6-dioxo-3-piperidyl)phenyl]piperidine-1-carboxylate (12 g, 32.22 mmol) in 1,4-dioxane (100 mL) was added 4M hydrogen chloride solution in 1,4-dioxane (15 mL) at RT. Stirring was continued for 2 hr. The volatiles were evaporated in vacuo. The residue was triturated with diethyl ether. The precipitate was collected by filtration and dried under vacuum to afford the title compound (10.80 g, 39.66 mmol, quant.) as off-white solid. MS m/e: 273 ([M+H+]$^+$).

Glutarimide 11

3-[4-[1-(4-Piperidyl)-4-piperidyl]anilino]piperidine-2,6-dione dihydrochloride

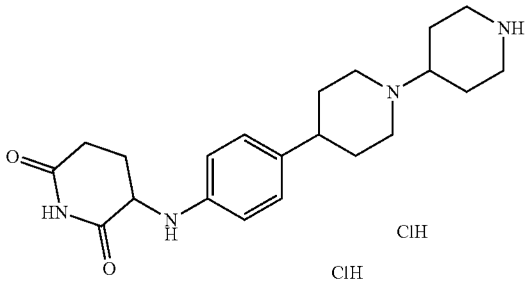 [SMILES: O=C1CCC(Nc2ccc(C3CCN(C4CCNCC4)CC3)cc2)C(=O)N1 ; Cl ; Cl]

a) tert-butyl 4-[4-[4-[(2,6-dioxo-3-piperidyl)amino]phenyl]-1-piperidyl]piperidine-1-carboxylate A mixture of 3-[4-(4-piperidyl)anilino]piperidine-2,6-dione hydrochloride (50 mg, 0.154 mmol, Eq: 1), tert-butyl 4-oxopiperidine-1-carboxylate (46.1 mg, 0.232 mmol, Eq:

1.5) and sodium acetate (25.3 mg, 0.309 mmol, Eq: 2) in dichloromethane (1.54 ml) was stirred for 75 min at RT. Addition of sodiumtriacetoxyborohydride (49.1 mg, 0.232 mmol, Eq: 1.5) Stirring was continued over night. Addition of a further portion of tert-butyl 4-oxopiperidine-1-carboxylate (22.6 mg, 0.154 mmol, Eq: 1) and sodium triacetoxyborohydride (32.7 mg, 0.154 mmol, Eq: 1) added. The reaction mixture was stirred for 24 hours. The RM was partitioned between 30 mL dichlormethane/methanol 9/1 (30 ml) and 1M aqueous sodium hydrogencarbonate solution. The layers were separated. The aqueous phase was extracted two 30 ml-portions of dichlormethane/methanol 9/1. The combined organic layers were washed with one 30-ml portion of brine, filtrated and concentrated in vacuo to give the crude title compound (93.3 mg, quant.) as green solid, which was used in the next step without further purification.

b) 3-[4-[1-(4-Piperidyl)-4-piperidyl]anilino]piperidine-2,6-dione dihydrochloride To a solution of tert-butyl 4-(4-((2,6-dioxopiperidin-3-yl) amino)phenyl)-[1,4'-bipiperidine]-1'-carboxylate (72.4 mg, 0.154 mmol) in THF (1.54 ml) was added 4 M hydrogenchloride solution in 1,4-dioxane (0.386 ml, 1.54 mmol) at RT. The RM was stirred over night. The precipitate was filtered and dried in vacuo to give the crude title compound (73 mg, quant.) as green solid. MS m/e: 371 ([M+H+]$^+$).

Glutarimide 12

3-[4-[1-(2-Aminoethyl)-4-piperidyl]anilino]piperidine-2,6-dione dihydrochloride

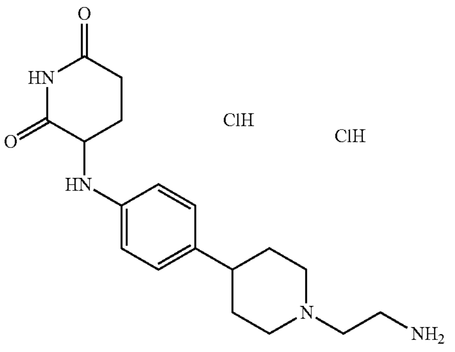 [SMILES: NCCN1CCC(c2ccc(NC3CCC(=O)NC3=O)cc2)CC1 ; Cl ; Cl]

a) tert-Butyl-N-[2-[4-[4-[(2,6-dioxo-3-piperidyl) amino]phenyl]-1-piperidyl]ethyl]carbamate A mixture of 3-[4-(4-piperidyl)anilino]piperidine-2,6-dione hydrochloride (50 mg, 0.154 mmol, Eq: 1), tert-butyl (2-oxoethyl)carbamate (36.9 mg, 0.232 mmol, Eq: 1.5) and sodium acetate (50.7 mg, 0.618 mmol, Eq: 4) dichloromethane (1.54 ml) was stirred for 75 min. Addition of sodiumtriacetoxyborohydride (49.1 mg, 0.232 mmol, Eq: 1.5). Stirring was continued for 72 h. The RM was partitioned between 30 mL dichlormethane/methanol 9/1 (30 ml) and 1M aqueous sodium hydrogencarbonate solution. The layers were separated. The aqueous phase was extracted two 30 ml-portions of dichlormethane/methanol 9/1. The combined organic layers were washed with one 30-ml portion of brine, filtrated and concentrated in vacuo. Purification by flash chromatography with dichlormethane/methanol as eluent gave the title compound (17 mg, 25%) as green solid. MS m/e: 431.3 ([M+H+]$^+$).

b) 3-[4-[1-(2-Aminoethyl)-4-piperidyl]anilino]piperidine-2,6-dione dihydrochloride To a solution of tert-butyl N-[2-[4-[4-[(2,6-dioxo-3-piperidyl)amino]phenyl]-1-piperidyl]ethyl]carbamate (86 mg, 0.200 mmol) in THF (2 ml) was added 4 M hydrogenchloride solution in 1,4-dioxane (0.499 ml, 2.00 mmol) at RT. The RM was stirred over night. The precipitate was filtered and dried in vacuo to give the crude title compound (71 mg, 88%) as green solid. MS m/e: 331 ([M+H+]$^+$).

Glutarimide 13

3-[4-(4-Amino-1-piperidyl)-3-fluoro-anilino]piperidine-2,6-dione trifluoroacetic acid

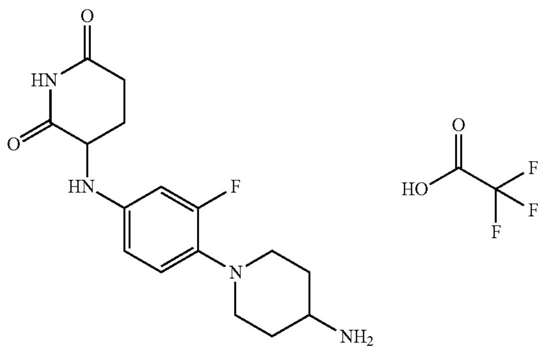 [SMILES: NC1CCN(c2ccc(NC3CCC(=O)NC3=O)cc2F)CC1 ; O=C(O)C(F)(F)F]

a) tert-Butyl-N-[1-[4-[(2,6-dibenzyloxy-3-pyridyl) amino]-2-fluoro-phenyl]-4-piperidyl]carbamate To a stirred solution of tert-butyl N-[1-(4-amino-2-fluoro-phenyl)-4-piperidyl]carbamate (150 mg, 484.84 umol) and 2,6-dibenzyloxy-3-iodo-pyridine (222.53 mg, 533.33 umol) in t-BuOH (4.85 mL) was added cesium carbonate (473.92 mg, 1.45 mmol) and solution was degassed well by purging with Ar. RuPhos Pd G3 (44.80 mg, 48.48 umol) was then added and the reaction was degassed again. The reaction mixture was heated at 100° C. for 18 h. The reaction mixture was then diluted with ethyl acetate, filtered over a small pad of celite and washed well with ethyl acetate. The combined organics were washed with water and brine, filtered, dried over anhydrous sodium sulphate and concentrated under reduced pressure to get crude material as an oil which was purified by column chromatography using silica eluted at 40% EA hexane to get pure title compound (100 mg, 33% yield, 95% purity) as pale yellow solid. LCMS: 600 ([M+H+]$^+$).

b) tert-Butyl-N-[1-[4-[(2,6-dioxo-3-piperidyl) amino]-2-fluoro-phenyl]-4-piperidyl]carbamate Brought tert-butyl-N-[1-[4-[(2,6-dibenzyloxy-3-pyridyl) amino]-2-fluoro-phenyl]-4-piperidyl]carbamate (75 mg, 125.27 umol) up in EtOH (5 mL) and added Palladium, 5% on activated carbon paste, 5R437 (4.00 mg, 37.58 umol) before purging flask with an hydrogen balloon (purged through solvent as well). Stirred reaction at r.t. under a hydrogen atmosphere (balloon pressure) for 16 hours. Filtered reaction over celite and washed celite pad 3×EtOH and 3×EtOAc before concentrating to a crude dry oil to give the crude title compound (50 mg, 90% yield, 95% purity) which was used in the next step without further purification. LCMS: 421 ([M+1-1]$^+$)

c) 3-[4-(4-Amino-1-piperidyl)-3-fluoro-anilino]piperidine-2,6-dione trifluoroacetic acid Brought tert-butyl-N-[1-[4-[(2,6-dioxo-3-piperidyl)amino]-2-fluoro-phenyl]-4-piperidyl]carbamate (50 mg, 118.91 umol) up in DCM (2 mL) and added TFA (740.00 mg, 6.49 mmol, 500 uL). Stirred for 3 hours and concentrated from toluene 3× to an oil (45 mg, 83% yield, 95% purity). The crude oil was used in the next step without further purification.

Dihydrouracil 1

1-[4-(4-Piperidyl)phenyl]hexahydropyrimidine-2,4-dione hydrochloride

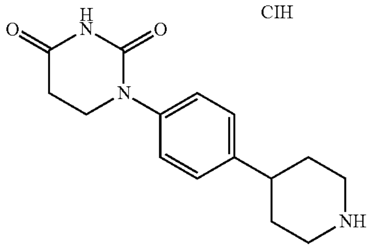 [SMILES: "CIH" ; O=C1CCN(c2ccc(C3CCNCC3)cc2)C(=O)N1]

a) tert-Butyl 4-[4-[(3-ethoxy-3-oxo-propyl)amino]phenyl]piperidine-1-carboxylate A mixture of tert-butyl 4-(4-aminophenyl)piperidine-1-carboxylate (16 g, 57.89 mmol), DBU Lactic acid ionic liquid (10.28 g, 34.74 mmol) and ethyl acrylate (7.53 g, 75.26 mmol, 8.02 mL) was stirred at 90° C. for 3 hours. The reaction mixture was cooled to room temperature, diluted with ethyl acetate and water. The layers were separated, organic layer was dried over anhydrous sodium sulfate, filtrated and concentrated in vacuo. Purification by flash chromatography using 5-10% ethyl acetate-hexane gave the title compound (12.5 g, 33.20 mmol, 57.35% yield) as gummy yellow liquid. MS m/e: 377.2 ([M+H+]$^+$).

b) tert-Butyl 4-[4-[cyano-(3-ethoxy-3-oxo-propyl)amino]phenyl]piperidine-1-carboxylate A mixture of tert-butyl 4-[4-[(3-ethoxy-3-oxo-propyl)amino]phenyl]piperidine-1-carboxylate (15 g, 39.84 mmol) in benzene (100 mL), carbononitridic bromide (6.75 g, 63.75 mmol, 3.34 mL) and sodium bicarbonate (5.36 g, 63.75 mmol, 2.48 mL) was stirred for 24 hours at room temperature. The reaction mixture was diluted with ethyl acetate (500 mL). Organic phase was washed with water, dried over sodium sulfate, filtrated and concentrated under vacuum. Purification by column chromatography using ethyl acetate-hexane gave the title compound (12.5 g, 31.13 mmol, 78.14% yield) as semi solid. MS m/e: 402.2 ([M+H+]$^+$).

c) tert-Butyl 4-[4-[carbamoyl-(3-ethoxy-3-oxo-propyl)amino]phenyl]piperidine-1-carboxylate A mixture of tert-Butyl 4-[4-[cyano-(3-ethoxy-3-oxo-propyl)amino]phenyl]piperidine-1-carboxylate (12.5 g, 31.1 mmol), trichloroindigane (2.07 g, 9.34 mmol) and (1Z)—acetaldehyde oxime (5.52 g, 93.40 mmol) in toluene (100 mL) was refluxed for 1 hour. The reaction mixture was concentrated under vacuum to obtain the crude title compound (12 g, 28.60 mmol, 91.88% yield) as gummy liquid, which was used in next step without further purification. MS m/e: 420.6 ([M+H+]$^+$).

d) tert-Butyl 4-[4-(2,4-dioxohexahydropyrimidin-1-yl)phenyl]piperidine-1-carboxylate A stirred solution of tert-butyl 4-[4-[carbamoyl-(3-ethoxy-3-oxo-propyl)amino]phenyl]piperidine-1-carboxylate (12 g, 28.60 mmol) in acetonitrile (120 mL) was heated at 60° C. followed by the addition of Titron B 40% in methanol (17.94 g, 42.91 mmol, 19.50 mL, 40% purity). Stirring was continued for 15 minutes. The reaction mixture was evaporated and the crude residue was purified by column chromatography to afford the title compound (8 g, 21.42 mmol, 74.89% yield) as white solid. MS m/e: 374.5 ([M+H+]$^+$).

e) 1-[4-(4-Piperidyl)phenyl]hexahydropyrimidine-2,4-dione hydrochloride

To a stirred suspension of tert-butyl 4-[4-(2,4-dioxohexahydropyrimidin-1-yl)phenyl]piperidine-1-carboxylate (13.50 g, 36.15 mmol) in 1,4-dioxane (40 mL) was added 4M hydrogen chloride in 1,4-dioxane (50 mL) at 0° C. The cooling bath was removed and stirring was continued for 3 hours at room temperature. Volatiles are removed under vacuum to afford the title compound (11.1 g, 35.53 mmol, 98.28% yield, 99.16% purity) as white solid. MS m/e: 374.5 ([M+H+]$^+$).

Dihydrouracil 2

1-[3-(4-Piperidyl)phenyl]hexahydropyrimidine-2,4-dione hydrochloride

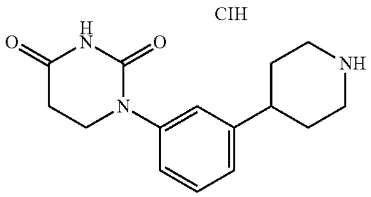

a) 4-(3-Nitro-phenyl)-3,6-dihydro-2H-pyridine-1-carboxylic acid tert-butyl ester The stirred solution of 1-bromo-3-nitro-benzene 1 (20 g, 99.01 mmol, 87.18 uL), sodium carbonate (31.48 g, 297.02 mmol, 12.44 mL) and tert-butyl 4-(4,4,5,5-tetramethyl-1,3,2-dioxaborolan-2-yl)-3,6-dihydro-2H-pyridine-1-carboxylate 2 (27.55 g, 89.11 mmol) in 1,4-dioxane (200 mL) and water (50 mL) was purged with argon for 20 minutes followed by the addition of tri-tert-butylphosphonium tetrafluoroborate (5.74 g, 19.80 mmol) and $Pd_2(dba)_3$ (9.07 g, 9.90 mmol) and the reaction mixture was allowed to stir for 14 hours at 90° C. Reaction mixture was cooled, concentrated under reduced pressure to afford the crude product. Crude product thus obtained was purified by flash chromatography using 0%-10% ethyl acetate-hexane to afford the title compound (29 g, 95.29 mmol, 96.24% yield) as light yellow solid.

b) 4-(3-Amino-phenyl)-piperidine-1-carboxylic acid tert-butyl ester

A stirred suspension of 4-(3-Nitro-phenyl)-3,6-dihydro-2H-pyridine-1-carboxylic acid tert-butyl ester (15 g, 49.29 mmol) in ethanol (400 mL) was degassed with nitrogen, palladium, 10% on carbon, Type 487, dry (5.25 g, 4.93 mmol, 10% purity) was added and the reaction mixture was stirred at room temperature under hydrogen atmosphere (40 psi) for 16 hours. Reaction mixture was filtered through celite bed, filtrate was concentrated to afford the title compound (12 g, 43.42 mmol, 88.10% yield) as white solid. MS m/e: 277.4 ($[M+H]^+$).

c) tert-Butyl 4-[3-[(3-ethoxy-3-oxo-propyl)amino]phenyl]piperidine-1-carboxylate A mixture of 4-(3-amino-phenyl)-piperidine-1-carboxylic acid tert-butyl ester (12 g, 43.42 mmol) and ethyl prop-2-enoate (6.52 g, 65.13 mmol, 7.06 mL) were warmed in presence of DBU-Lactic acid ionic liquid (5.26 g, 21.71 mmol) for 2 hours at 80° C. Reaction mixture was diluted with ethyl acetate. Organic phase was washed with water, brine, dried over sodium sulfate and concentrated under vacuum. The crude residue was purified by column chromatography to afford the title compound (12 g, 31.87 mmol, 73.41% yield) as gum. MS m/e: 377.4 ($[M+H]^+$).

d) tert-Butyl 4-[3-[cyano-(3-ethoxy-3-oxo-propyl)amino]phenyl]piperidine-1-carboxylate To the stirred solution of tert-butyl 4-[3-[(3-ethoxy-3-oxo-propyl)amino]phenyl]piperidine-1-carboxylate (16 g, 42.50 mmol) in benzene (40 mL), carbononitridic bromide (5.40 g, 51.00 mmol, 2.67 mL) and sodium bicarbonate (5.36 g, 63.75 mmol, 2.48 mL) was added simultaneously and stirred for 3 hours at room temperature. Reaction mixture was diluted with ethyl acetate (50 mL). Organic phase was washed with two 15-ml portions of water, separated, dried over sodium sulfate and concentrated under vacuum. The crude residue was purified by column chromatography to afford the title compound (16 g, 39.85 mmol, 93.77% yield). MS m/e: 402.3 ($[M+H]^+$).

e) tert-Butyl 4-[3-[carbamoyl-(3-ethoxy-3-oxo-propyl)amino]phenyl]piperidine-1-carboxylate A mixture of tert-butyl 4-[3-[cyano-(3-ethoxy-3-oxo-propyl)amino]phenyl]piperidine-1-carboxylate (16 g, 39.85 mmol), trichloroindigane (2.64 g, 11.96 mmol) and (1Z)-acetaldehyde oxime (7.06 g, 119.55 mmol) in toluene (25 mL) was refluxed for 1 hour. Resulting precipitate was filtered off and washed with toluene/ether several time to obtain crude title compound (15 g, 35.76 mmol, 89.72% yield) which was used in the next step without further purification. MS m/e: 402.3 ($[M+H]^+$).

f) tert-Butyl 4-[3-(2,4-dioxohexahydropyrimidin-1-yl)phenyl]piperidine-1-carboxylate A solution of tert-butyl 4-[3-[carbamoyl-(3-ethoxy-3-oxo-propyl)amino]phenyl]piperidine-1-carboxylate (16 g, 38.14 mmol) in acetonitrile (40 mL) was heated at 60° C. followed by the addition of Titron B solution [40% in MeOH, 57.21 mmol] in acetonitrile (10 mL). Stirring was continued for 10 minutes. Reaction mixture was evaporated and the crude residue was purified by column chromatography to afford the title compound (12 g, 32.13 mmol, 84.25% yield). MS m/e: 374.2 ($[M+H]^+$).

g) 1-[3-(4-Piperidyl)phenyl]hexahydropyrimidine-2,4-dione hydrochloride

To the solid tert-butyl 4-[3-(2,4-dioxohexahydropyrimidin-1-yl)phenyl]piperidine-1-carboxylate (12 g, 32.13 mmol), 4M HCl in 1,4-dioxane (25 mL) was added at 0° C. and stirred for 4 hours at room temperature. Volatiles are removed under vacuum, crude material was washed with two 25-ml portions of diethyl ether and lyophilized to afford the title compound (9.7 g, 35.49 mmol, quant.). MS m/e: 274.2 ($[M+H]^+$).

General Procedure IV: Alkylation and Deprotection

A mixture of an intermediate of intermediate formula II-a or II-b (1 eq), an alkyl halogenide (1 eq), potassium iodide (1 eq) and Huenig's Base (3-4 eq) in a solvent such as N,N-dimethylformamide or N-methylpyrrolidone (0.2 M) is stirred at 60° C. for 1-6 h. The reaction mixture is partitioned between an organic solvent such as ethyl acetate or dichloromethane and 1M aqueous sodium bicarbonate solution. The layers are separated. The aqueous layer is extracted with one or two portions of organic solvent. The combined organic layers are washed with one portion of brine, dried over anhydrous sodium sulfate and concentrated. Purification by flash-chromatography gives an intermediate of intermediate formula II-c. A mixture of an intermediate of intermediate formula II-c (1 eq) in a solvent such as ethyl acetate or tetrahydrofuran (0.2 M) and 4M hydrogen chloride solution in 1,4-dioxane (10-20 eq) is stirred at room temperature for 12-48 h. The precipitate is collected by filtration and washed with a solvent such as ethyl acetate or tetrahydrofuran and dried in vacuo to give a compound of intermediate formula II-d.

Acid 1

2-[4-[4-[(2,6-Dioxo-3-piperidyl)amino]phenyl]-1-piperidyl]acetic acid hydrochloride

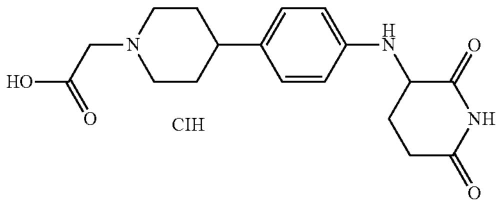

The title compound was obtained as dark blue solid in 64% yield according to the general procedure IV from 3-[4-(4-piperidyl)anilino]piperidine-2,6-dione hydrochloride and tert-butyl bromo acetate. MS m/e: 346 ($[M+H]^+$).

Acid 2

2-[4-[4-[(2,6-Dioxo-3-piperidyl)amino]phenyl]piperazin-1-yl]acetic acid hydrochloride

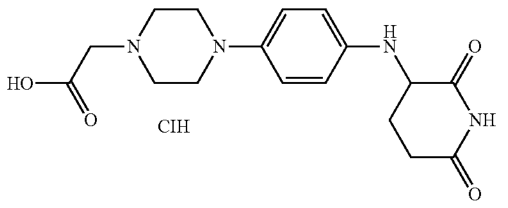

The title compound was obtained as black solid in 93% according to the general procedure IV from 3-[4-(4-piperidyl)anilino]piperazine-2,6-dione hydrochloride and tert-butyl bromo acetate. MS m/e: 347.1 ([M+H+]$^+$).

Acid 3

2-[4-[4-[(2,6-Dioxo-3-piperidyl)amino]phenyl]-1-piperidyl]acetic acid; hydrochloride

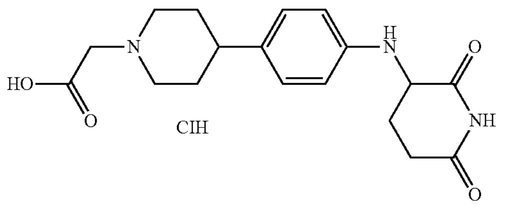

The title compound was obtained as dark blue solid in 64% yield according to the general procedure IV from 3-[4-(4-piperidyl)anilino]piperidine-2,6-dione hydrochloride and tert-butyl bromo acetate. MS m/e: 346 ([M+H+]$^+$).

Acid 4

4-[4-[4-[(2,6-dioxo-3-piperidyl)amino]phenyl]piperidyl]butanoic acid hydrochloride

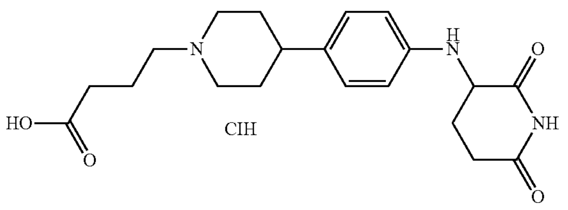

The title compound was obtained as brown solid in 68% according to the general procedure IV from 3-[4-(4-piperidyl)anilino]piperazine-2,6-dione hydrochloride and tert-butyl bromo acetate. MS m/e: 374.2 ([M+H+]$^+$).

Acid 5

2-[5-[(2,6-Dioxo-3-piperidyl)amino]isoindolin-2-yl] acetic acid hydrochloride

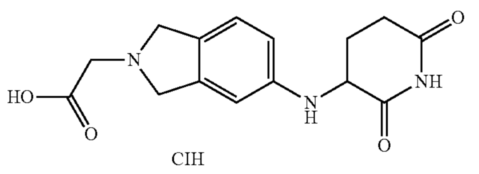 [SMILES: O=C(O)CN1Cc2ccc(NC3CCC(=O)NC3=O)cc2C1 ; "CIH"]

The title compound was obtained as green solid in 73% according to the general procedure IV from 3-(isoindolin-5-ylamino)piperidine-2,6-dione hydrochloride and tert-butyl bromo acetate. MS m/e: 304 ([M+H+]$^+$).

Acid 6

2-[4-[5-[(2,6-Dioxo-3-piperidyl)amino]-2-pyridyl]-1-piperidyl]acetic acid hydrochloride

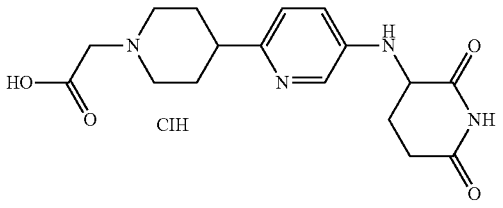

The title compound was obtained as dark blue solid in 94% according to the general procedure IV from 3-[[6-(4-piperidyl)-3-pyridyl]amino]piperidine-2,6-dione hydrochloride and tert-butyl bromo acetate. MS m/e: 347.2 ([M+H+]$^+$).

Acid 7

2-[4-[4-[(2,4-Dioxo-3-azabicyclo[3.1.1]heptan-1-yl)amino]phenyl]-1-piperidyl]acetic acid hydrochloride

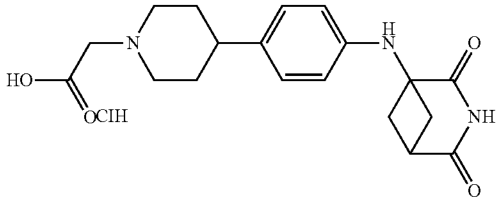

The title compound was obtained as light yellow solid in 54% according to the general procedure IV from 1-[4-(4-piperidyl)anilino]-3-azabicyclo[3.1.1]heptane-2,4-dione hydrochloride and tert-butyl bromo acetate. MS m/e: 358 ([M+H+]$^+$).

Acid 8

2-[[2-[4-[(2,6-Dioxo-3-piperidyl)amino]phenyl]acetyl]-methyl-amino]acetic acid hydrochloride

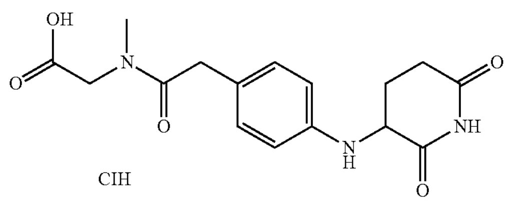 [SMILES: CN(CC(=O)O)C(=O)Cc1ccc(NC2CCC(=O)NC2=O)cc1 ; "CIH"]

a) tert-butyl 2-[4-[(2,6-dioxo-3-piperidyl)amino]phenyl]acetate

The title compound was obtained as yellow oil in 28% yield according to the general procedure I from 3-bromopiperidine-2,6-dione and tert-butyl 2-(4-aminophenyl)acetate.

b) 2-[4-[(2,6-dioxo-3-piperidyl)amino]phenyl]acetic acid

A solution of tert-butyl 2-[4-[(2,6-dioxo-3-piperidyl)amino]phenyl]acetate (0.85 g, 2.67 mmol, 1 eq) in 4 M HCl in 1,4-dioxane (20.0 ml, 80 mmol, 30 eq) was stirred at RT for 16 h. The precipitate was collected by filtration to give the title compound (0.675 g, 88%) as brown solid. MS m/e: 263 ($[M+H+]^+$).

c) tert-butyl 2-[[2-[4-[(2,6-dioxo-3-piperidyl)amino]phenyl]acetyl]-methyl-amino]acetate To a solution of 2-[4-[(2,6-dioxo-3-piperidyl)amino]phenyl]acetic acid (54.2 mg, 207 μmol, Eq: 1) in N,N-dimethylformamide (2.07 ml) was added HATU (78.6 mg, 207 μmol, Eq: 1). Stirring for 30 min was followed by addition of tert-butyl methylglycinate (30 mg, 207 μmol, Eq: 1) and DIPEA (107 mg, 144 μl, 826 μmol, Eq: 4) at RT and stirring was continued for 20 h. The reaction mixture was partitioned between ethyl acetate (40 ml) and 1 M sodium bicarbonate solution (40 ml). The layers were separated. The aqueous layer was extracted with two 30-ml portions of ethyl acetate. The combined organic layers were washed with one 40-ml portion of brine, dried over anhydrous sodium sulfate, filtered and concentrated in vacuo to give the crude title product (0.085 g, quant.) as amorphous red solid. MS m/e: 390 ($[M+H+]^+$).

d) 2-[[2-[4-[(2,6-dioxo-3-piperidyl)amino]phenyl]acetyl]-methyl-amino]acetic acid To a solution of tert-butyl 2-[[2-[4-[(2,6-dioxo-3-piperidyl)amino]phenyl]acetyl]-methyl-amino]acetate (80.5 mg, 207 μmol, Eq: 1) in ethyl acetate (1.03 ml) was added 4 M hydrogen chloride solution in 1,4-dioxane (1.03 ml, 4.13 mmol, Eq: 20) at RT and stirring was continued for 78 h. The product was collected by filtration, washed with cold ethyl acetate and dried in vacuo to give the title compound (0.033 g, 43%) as orange solid. MS m/e: 334 ($[M+H+]^+$).

Acid 9

2-[4-[4-[(2,6-Dioxo-3-piperidyl)amino]-2-fluoro-phenyl]-1-piperidyl]acetic acid hydrochloride

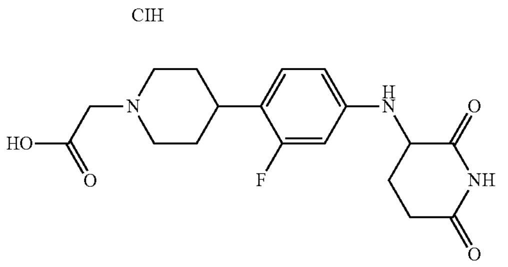 [SMILES: "CIH" ; O=C(O)CN1CCC(c2ccc(NC3CCC(=O)NC3=O)cc2F)CC1]

a) tert-Butyl 2-(4-(4-amino-2-fluorophenyl)piperidin-1-yl)acetate

In a 10 mL sealed tube, 3-fluoro-4-(piperidin-4-yl)aniline (500 mg, 2.57 mmol, Eq: 1) was combined with N,N-dimethylformamide (5.15 ml) to give a white solution. Tert-butyl 2-bromoacetate (502 mg, 2.57 mmol, Eq: 1) and Huenig's Base (665 mg, 899 μl, 5.15 mmol, Eq: 2) were added. The reaction mixture was heated at 60° C. for 4 h. The reaction mixture was partioned between water and ethyl acetate. The layers were separated. The aqueous layer was extracted with two 50-ml portions of ethyl acetate. The organic layers were combined, washed with one 50-ml portion of brine, dried over anhydrous sodium sulfate, filtered and concentrated in vacuo. Purification by flash chromatography gave the title compound (396 mg, 38%) as brown viscous oil. MS m/e: 309.2 ($[M+H+]^+$).

b) tert-Butyl 2-(4-(4-((2,6-dioxopiperidin-3-yl)amino)-2-fluorophenyl)piperidin-1-yl)acetate The title compund was obtained as green solid in 12% yield according the general procedure I from 3-bromopiperidine-2,6-dione and tert-butyl 2-(4-(4-amino-2-fluorophenyl)piperidin-1-yl)acetate. MS m/e: 420.4 ($[M+H+]^+$).

c) 2-[4-[4-[(2,6-Dioxo-3-piperidyl)amino]-2-fluoro-phenyl]-piperidyl]acetic acid hydrochloride The title compound was obtained as dark green solid in quantitative yield according the general procedure III from tert-butyl 2-(4-(4-((2,6-dioxopiperidin-3-yl)amino)-2-fluorophenyl)piperidin-1-yl)acetate. MS m/e: 364.3 ($[M+H+]^+$).

Acid 10

2-[4-[4-[(2,6-Dioxo-3-piperidyl)oxy]phenyl]-1-piperidyl]acetic acid hydrochloride

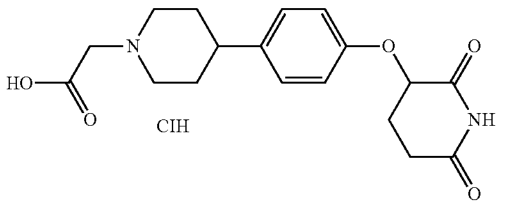

The title compound was obtained as white solid in 98% according to the general procedure IV from 3-[4-(4-piperidyl)phenoxy]piperidine-2,6-dione hydrochloride and tert-butyl bromo acetate. MS m/e: 347.1 ([M+H+]$^+$).

Acid 11

4-[4-[4-[(2,6-Dioxo-3-piperidyl)oxy]phenyl]-1-piperidyl]butanoic acid

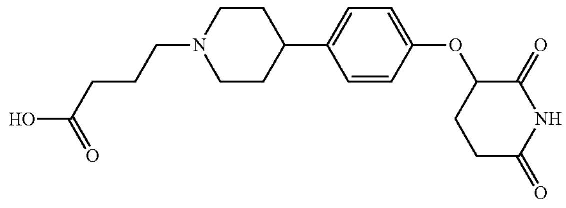 [SMILES: O=C(O)CCCN1CCC(c2ccc(OC3CCC(=O)NC3=O)cc2)CC1]

a) benzyl 4-[4-[4-[(2,6-dioxo-3-piperidyl)oxy]phenyl]-1-piperidyl]butanoate

A mixture of 3-[4-(4-piperidyl)phenoxy]piperidine-2,6-dione hydrochloride (1700.0 mg, 5.23 mmol, 1 eq), benzyl 4-bromobutanoate (2907.0 mg, 11.31 mmol, 2.16 eq) and N,N-diisopropylethylamine (4.5 mL, 25.84 mmol, 4.94 eq) in DMF (30 mL) was stirred at 25° C. for 48 h. The reaction mixture was heated at 60° C. for 4 h. The reaction mixture was partionated between water and ethyl acetate. The layers were separated. The aqueous layer was extracted with two 50-ml portions of ethyl acetate. The organic layers were combined, washed with one 50-ml portion of brine, dried over anhydrous sodium sulfate, filtered and concentrated in vacuo. Purification by flah-chromatography gave the title compound (1.26 g, 2.71 mmol, 57.58% yield) as a grey solid. MS m/e: 465.2 ([M+H+]$^+$).

b) 4-[4-[4-[(2,6-Dioxo-3-piperidyl)oxy]phenyl]-1-piperidyl]butanoic acid

A mixture of benzyl 4-[4-[4-[(2,6-dioxo-3-piperidyl)oxy]phenyl]-1-piperidyl]butanoate (1.26 g, 2.71 mmol, 1 eq) and palladium on carbon (500.0 mg, 0.470 mmol, 0.170 eq) in 2-propanol (30 mL) was stirred at 60° C. for 12 h with hydrogen atmosphere (15.0 psi). The catalyst was removed by filtration. The filtrate was concentrated in vacuo to give the title compound (535.1 mg, 1.3 mmol, 37.95% yield) as a light yellow solid. MS m/e: 376.2 ([M+H+]$^+$).

Acid 12

3-[4-[4-[(2,6-Dioxo-3-piperidyl)oxy]phenyl]-1-piperidyl]propanoic acid

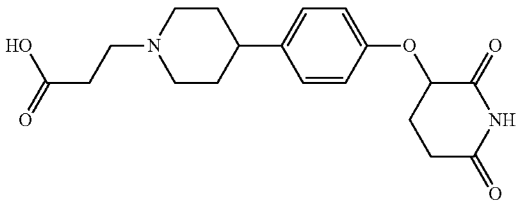 [SMILES: O=C(O)CCN1CCC(c2ccc(OC3CCC(=O)NC3=O)cc2)CC1]

The title compound was obtained as off-white solid in 96% according to the general procedure IV from 3-[4-(4-piperidyl)phenoxy]piperidine-2,6-dione hydrochloride and tert-butyl bromo propanoate. MS m/e: 361.3 ([M+H+]$^+$).

Acid 13

2-[4-[5-[(2,6-Dioxo-3-piperidyl)oxy]-2-pyridyl]-1-piperidyl]acetic acid hydrochloride

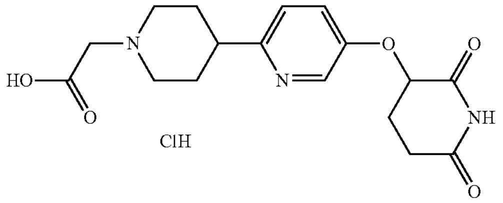 [SMILES: O=C(O)CN1CCC(c2ccc(OC3CCC(=O)NC3=O)cn2)CC1 ; Cl]

The title compound was obtained as light yellow solid in 68% according to the general procedure IV from 3-[[6-(4-piperidyl)-3-pyridyl]oxy]piperidine-2,6-dione hydrochloride and tert-butyl bromo acetate. MS m/e: 348 ([M+H+]$^+$).

Acid 14

2-[4-[4-[(2,6-Dioxo-3-piperidyl)amino]pyrazol-1-yl]-1-piperidyl]acetic acid;hydrochloride

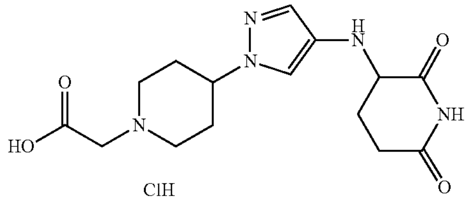 [SMILES: O=C(O)CN1CCC(n2cc(NC3CCC(=O)NC3=O)cn2)CC1 ; Cl]

The title compound was obtained as dark blue solid in 51% with a purity of 76% by ELSD according to the general procedure IV from 3-[[1-(4-piperidyl)pyrazol-4-yl]amino]piperidine-2,6-dione hydrochloride and tert-butyl bromo propanoate. MS m/e: 336 ([M+H+]$^+$).

Acid 15 cis-3-[4-[4-[(2,6-Dioxo-3-piperidyl)amino]phenyl]-1-piperidyl]cyclobutanecarboxylic acid

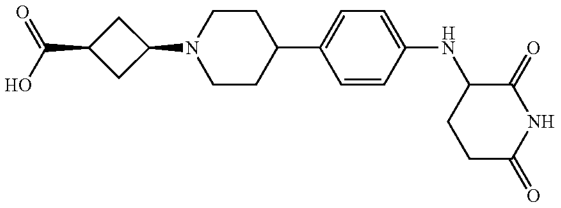 [SMILES: O=C1CCC(Nc2ccc(C3CCN([C@H]4C[C@@H](C(=O)O)C4)CC3)cc2)C(=O)N1]

a) cis-Benzyl 3-[4-(4-narophenyl)-1-piperidyl]cyclobutanecarboxylate

To a solution of 4-(4-nitrophenyl)piperidine (1 g, 4.85 mmol, Eq: 1) and benzyl 3-oxocyclobutane-1-carboxylate (990 mg, 4.85 mmol, Eq: 1) in dichloromethane (9.7 ml) was added sodium acetate (398 mg, 4.85 mmol, Eq: 1) and acetic acid (291 mg, 278 μl, 4.85 mmol, Eq: 1) at room temperature. After 1 h, sodium triacetoxyborohydride (2.06 g, 9.7 mmol, Eq: 2) was added. Stirring was continued for 20 h. The reaction mixture was partitioned between ethyl acetate (50 ml) and 1M aqueous sodium carbonate solution (50 ml). The layers were separated. The aqueous layer was extracted with one 50-ml portion of ethyl acetate. The combined organic layers were washed with one 20-ml portion of brine, dried over anhydrous sodium sulfate, filtered and concentrated in vacuo. Purification by flash-chromatography with dichloromethane/methanol as solvent and gave cis-benzyl 3-[4-(4-nitrophenyl)-1-piperidyl]cyclobutanecarboxylate (1.49 g, 78%) as light yellow solid and trans-benzyl 3-[4-(4-nitrophenyl)-1-piperidyl]cyclobutanecarboxylate (0.228 g, 12%) as yellow solid. MS m/e: 395.3 ([M+H+]$^+$).

b) cis-Benzyl 3-[4-(4-aminophenyl)-1-piperidyl]cyclobutanecarboxylate

To a solution of cis-benzyl 3-[4-(4-nitrophenyl)-1-piperidyl]cyclobutanecarboxylate (750 mg, 1.9 mmol, Eq: 1) in 2-methyltetrahydrofuran (9.51 ml) was added tin (II) chloride (1.08 g, 5.7 mmol, Eq: 3) at room temperature. The reaction mixture was heated at 60° C. for 20 h. The reaction mixture was partitioned between ethyl acetate (150 ml) and 1 M aqueous sodium carbonate solution (90 ml). The layers were separated. The aqueous layer was extracted with two 75-ml portions of ethyl acetate. The combined organic layers were washed with one 50-ml portion of brine, dried over anhydrous sodium sulfate, filtered and concentrated in vacuo. The crude material was purified by flash chromatography to give the title compound (399.2 mg, 61%) as orange waxy solid. MS m/e: 365.3 ([M+H+]$^+$).

c) cis-Benzyl 3-[4-[4-[(2,6-dioxo-3-piperidyl)amino]phenyl]-1-piperidyl]-cyclobutanecarboxylate To a solution of cis-benzyl 3-[4-(4-aminophenyl)-1-piperidyl]cyclobutanecarboxylate (399.2 mg, 1.1 mmol, Eq: 1) and 3-bromopiperidine-2,6-dione (210 mg, 1.1 mmol, Eq: 1) in acetonitrile (2.19 ml) was added sodium bicarbonate (368 mg, 4.38 mmol, Eq: 4). The reaction mixture was heated at 90° C. and stirring was continued for 2 d. The reaction mixture was partionated between water (100 ml) and ethyl acetate (100 ml). The layers were separated. The aqueous layer was extracted with two 75-ml portions of ethyl acetate. The combined organic layers were washed with one 50-ml portion of brine, dried over anhydrous sodium sulfate, filtered and concentrated in vacuo. The crude material was purified by flash chromatography with n-heptane/ethyl acetate as eluent to give the title compound (138 mg, 25%) as green solid. MS m/e: 476.4 ([M+H+]$^+$).

d) cis-3-[4-[4-[(2,6-Dioxo-3-piperidyl)amino]phenyl]-1-piperidyl]cyclobutanecarboxylic acid A 25-ml three necked round bottom flask was charged with cis-benzyl 3-[4-[4-[(2,6-dioxo-3-piperidyl)amino]phenyl]-1-piperidyl]-cyclobutanecarboxylate (137.5 mg, 275 Eq: 1) and methanol (1.37 ml). The flask was evacuated to approximately 120 mbar until the solvent began to bubble gently and back-filled with Argon after 5 s. This procedure was repeated twice. After addition of the catalyst Pd/C (1.46 mg, 13.7 μmol, Eq: 0.05), the flask was evacuated to 120 mbar, back-filled with hydrogen and stirred overnight. The catalyst was removed by filtration over Decalite and washed with methanol. The filtrate was concentrated in vacuo to give the title compound (25.8 mg, 21.9%) as light brown solid. MS m/e: 347.3 ([M+H+]$^+$).

Acid 16

2-[4-[4-(2,6-Dioxo-3-piperidyl)phenyl]-1-piperidyl]acetic acid hydrochloride

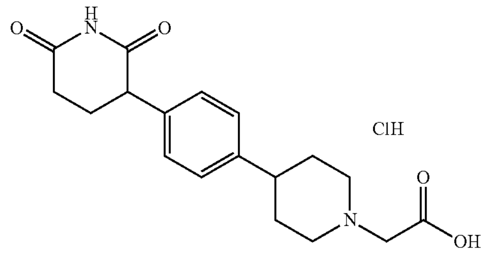 [SMILES: O=C(O)CN1CCC(c2ccc(C3CCC(=O)NC3=O)cc2)CC1 ; Cl]

The title compound was obtained as dark blue solid in 76% according to the general procedure IV from 3-[4-(4-piperidyl)phenyl]piperidine-2,6-dione hydrochloride and tert-butyl bromo acetate. MS m/e: 331.2 ([M+H+]$^+$).

Acid 17

4-[4-[4-(2,6-Dioxo-3-piperidyl)phenyl]-1-piperidyl]butanoic acid hydrochloride

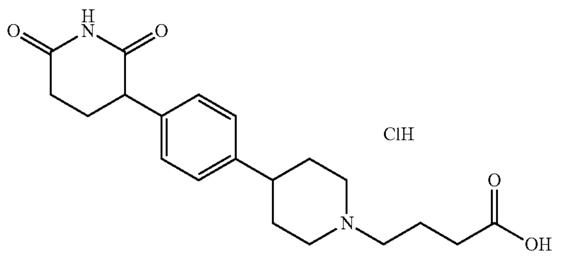 [SMILES: O=C(O)CCCN1CCC(c2ccc(C3CCC(=O)NC3=O)cc2)CC1 ; Cl]

The title compound was obtained as dark blue solid in 49% according to the general procedure IV from 3-[4-(4-piperidyl)phenyl]piperidine-2,6-dione hydrochloride and tert-butyl bromo butanoate. MS m/e: 359.3 ([M+H+]$^+$).

Acid 18

2-[4-[4-(2,4-Dioxohexahydropyrimidin-1-yl)phenyl]-1-piperidyl]acetic acid hydrochloride

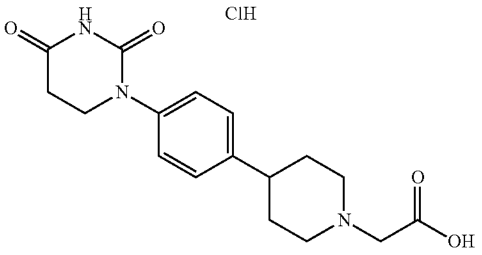 [SMILES: Cl ; O=C(O)CN1CCC(c2ccc(N3CCC(=O)NC3=O)cc2)CC1]

The title compound was obtained as light green solid in 86% according to the general procedure IV from 1-[4-(4-piperidyl)phenyl]hexahydropyrimidine-2,4-dione hydrochloride and tert-butyl bromo acetate. MS m/e: 332.2 ([M+H+]$^+$).

Acid 19

2-[4-[3-(2,4-dioxohexahydropyrimidin-1-yl)phenyl]-1-piperidyl]acetic acid hydrochloride

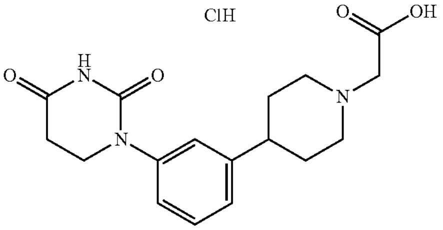 [SMILES: O=C(O)CN1CCC(c2cccc(N3CCC(=O)NC3=O)c2)CC1 ; Cl]

The title compound was obtained as white solid in 35% according to the general procedure IV from 1-[4-(4-piperidyl)phenyl]hexahydropyrimidine-2,4-dione hydrochloride and tert-butyl bromo acetate. MS m/e: 332.2 ([M+H+]$^+$).

Acid 20

2-[4-[4-[[(3R)-2,6-Dioxo-3-piperidyl]amino]phenyl]-1-piperidyl]acetic acid;2,2,2-trifluoroacetic acid

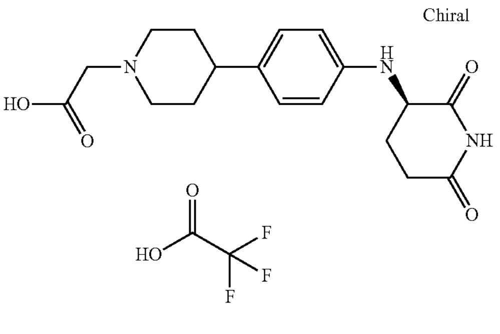 [SMILES: O=C(O)CN1CCC(c2ccc(N[C@@H]3CCC(=O)NC3=O)cc2)CC1 ; O=C(O)C(F)(F)F]

and

Acid 21

2-[4-[4-[[(3S)-2,6-Dioxo-3-piperidyl]amino]phenyl]-1-piperidyl]acetic acid;2,2,2-trifluoroacetic acid

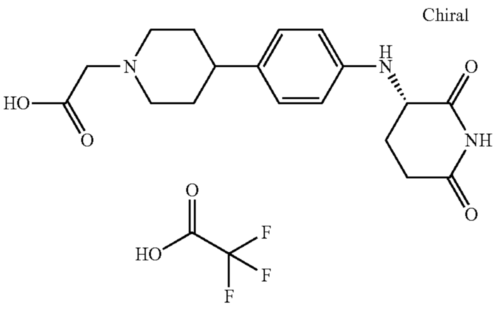 [SMILES: O=C(O)CN1CCC(c2ccc(N[C@H]3CCC(=O)NC3=O)cc2)CC1 ; O=C(O)C(F)(F)F]

a) tert-Butyl 2-[4-[4-[(2,6-dioxo-3-piperidyl)amino]phenyl]-1-piperidyl]acetate

To a stirred solution of 3-[4-(4-piperidyl)anilino]piperidine-2,6-dione (1, 4 g, 13.92 mmol) in N,N-Dimethylformamide (40 mL) was added triethylamine (7.04 g, 69.60 mmol, 9.70 mL) followed by tert-butyl 2-bromoacetate (2, 2.99 g, 15.31 mmol, 2.25 mL) and stirred the reaction mixture at 80° C. for 12 h. After completion of the reaction, water (150 mL) was added and extract with ethyl acetate (3×250 mL). The combined organic layers were dried over sodium sulphate, filtered and concentrated under reduced pressure. Purification by flash-chromatography gave the title compound (3.1 g, 55.45% yield) as green solid. MS m/e: 402.4 ([M+H+]$^+$). The racemic intermediate tert-butyl 2-[4-[4-[(2,6-dioxo-3-piperidyl)amino]phenyl]-1-piperidyl]acetate was chirally resoluted using chiral SFC method using Chiralcel OD-H column (250 mm×30 mm; 5 micron) eluting with 40% isopropyl alcohol/$CO_2$ (FlowRate: 3 ml/min; Outlet Pressure: 100 bar).

b) 2-[4-[4-[[(3R)-2,6-Dioxo-3-piperidyl]amino]phenyl]-1-piperidyl]acetic acid;2,2,2-trifluoroacetic acid The first eluting enatiomer (190 mg, 0.473 mmol) was dissolved in DCM (5.0 mL) and added TFA (1.48 g, 12.98 mmol, 1.0 mL) dropwise at 0° C. and stirred the reaction mixture for 3 h. After completion of the reaction, reaction mixture was concentrated under reduced pressure to give the title compound (140 mg, crude, 93.7% pure) as light green solid. MS m/e: 346.3 ([M+H+]$^+$). The stereo center configuration of CRBN is arbitrarily assigned as the (R)—first eluting isomer. [α]D=−25.999 (c=1.000, MeOH, 20° C.).

c) 2-[4-[4-[[(3S)-2,6-Dioxo-3-piperidyl]amino]phenyl]-1-piperidyl]acetic acid;2,2,2-trifluoroacetic acid The second eluting enantiomer (120 mg, 0.298 mmol) was dissolved in DCM (5.0 mL) and added TFA (1.48 g, 12.98 mmol, 1.0 mL) dropwise at 0° C. and stirred the reaction mixture for 3 h. After completion of the reaction, reaction mixture was concentrated under reduced pressure to give the title compound (118 mg, crude, 96.8% pure) as light green solid. MS m/e: 346.3 ([M+H+]$^+$). The stereo center configuration of CRBN is arbitrarily assigned as the (S)—second eluting isomer. [α]D=+25.111 (c=1.000, MeOH, 20° C.)

Acid 22

2-[4-[4-[[(3S)-2,6-Dioxo-3-piperidyl]oxy]phenyl]-1-piperidyl]acetic acid 2,2,2-trifluoroacetic acid

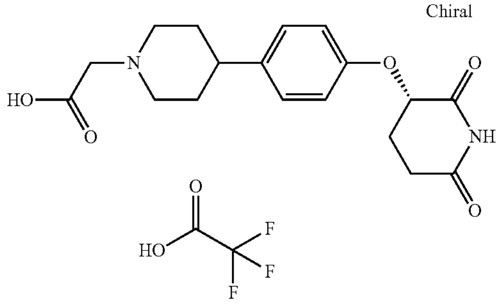 [SMILES: O=C(O)CN1CCC(c2ccc(O[C@H]3CCC(=O)NC3=O)cc2)CC1 ; O=C(O)C(F)(F)F]

The title compound was obtained as pale yellow solid in 82% according to the general procedure IV from (3S)-3-[4-(4-piperidyl)phenoxy]piperidine-2,6-dione and tert-butyl bromo acetate. MS m/e: 347.2 ([M+H+]$^+$).

Acid 23

2-[4-[4-[[(3R)-2,6-Dioxo-3-piperidyl]oxy]phenyl]-1-piperidyl]acetic acid 2,2,2-trifluoroacetic acid

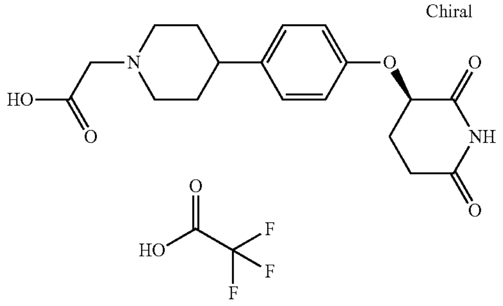 [SMILES: O=C(O)CN1CCC(c2ccc(O[C@@H]3CCC(=O)NC3=O)cc2)CC1 ; O=C(O)C(F)(F)F]

The title compound was obtained as pale yellow solid in 81% according to the general procedure IV from (3R)-3-[4-(4-piperidyl)phenoxy]piperidine-2,6-dione and tert-butyl bromo acetate. MS m/e: 347.3 ([M+H+]$^+$).

Intermediate of Formula (XIII)

(3-(3-Amino-2,6-difluorobenzoyl)-5-bromo-1H-pyrrolo[2,3-b]pyridin-1-yl)(2,6-dichlorophenyl) methanone

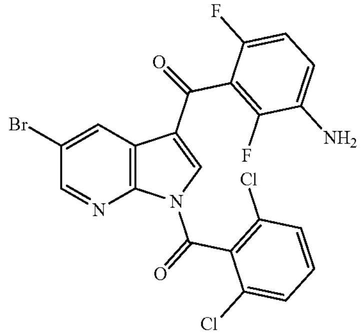 [SMILES: Nc1ccc(F)c(C(=O)c2cn(C(=O)c3c(Cl)cccc3Cl)c3ncc(Br)cc23)c1F]

To a solution of (3-amino-2,6-difluorophenyl)(5-bromo-1H-pyrrolo[2,3-b]pyridin-3-yl)methanone (2 g, 5.68 mmol, Eq: 1), triethylamine (690 mg, 950 μl, 6.82 mmol, Eq: 1.2) and DMAP (69.4 mg, 568 μmol, Eq: 0.1) in tetrahydrofuran (28.4 ml) was slowly added 2,6-dichlorobenzoyl chloride (1.19 g, 820 μl, 5.68 mmol, Eq: 1) at 0-5° C. The ice bath was removed and stirring was continued for 15 h. The solvent was evaporated. The residue was triturated in warm water/EtOH (60 ml, 5:1). The precipitate was collected by filtration, washed with water and dried in vacuo to give the title compound as off-white solid. MS m/e: 525 ([M+H+]$^+$).

Intermediates of Formula (XVI-a)

General Procedure V: Treatment of Anilines with Sulfamoyl Chlorides

A mixture of an intermediate of intermediate formula XIV (1 eq) and a sulfamoyl chloride of intermediate formula XV-a (3-4 eq) in pyridine (0.3 M) is stirred at 85° C. for 15-24 h. After cooling to room temperature the reaction mixture is partitioned between an organic solvent such as ethyl acetate or dichloromethane and 0.5M aqueous hydrogen chloride solution. The layers are separated. The aqueous layer is extracted with one or two portions of organic solvent. The combined organic layers are washed with one portion of 0.5 M aqueous hydrogen chloride solution, two 50-ml portions of 1 M sodium carbonate solution and one 50-ml portion of brine, dried over anhydrous sodium sulfate, filtered and concentrated in vacuo. Purification by flash-chromatography gives a compound of intermediate formula XVI-a.

Sulfamoyl Intermediate 1

5-Bromo-1-(2,6-dichlorobenzoyl)-3-[3-[[ethyl(methyl)sulfamoyl]amino]-2,6-difluoro-benzoyl]pyrrolo[2,3-b]pyridine

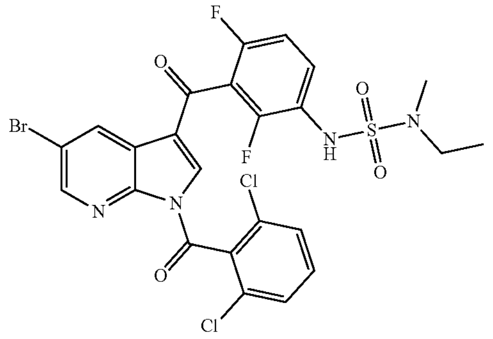 [SMILES: CCN(C)S(=O)(=O)Nc1ccc(F)c(C(=O)c2cn(C(=O)c3c(Cl)cccc3Cl)c3ncc(Br)cc23)c1F]

The title compound was obtained as off-white solid in 52% with a purity of 85% by UV according to the general procedure V from (3-(3-amino-2,6-difluorobenzoyl)-5-bromo-1H-pyrrolo[2,3-b]pyridin-1-yl)(2,6-dichlorophenyl)methanone and ethyl(methyl)sulfamoyl chloride. MS m/e: 646.9 ($[M+H+]^+$).

Sulfamoyl Intermediate 2

N-[3-[5-Bromo-1-(2,6-dichlorobenzoyl)pyrrolo[2,3-b]pyridine-3-carbonyl]-2,4-difluoro-phenyl]pyrrolidine-1-sulfonamide

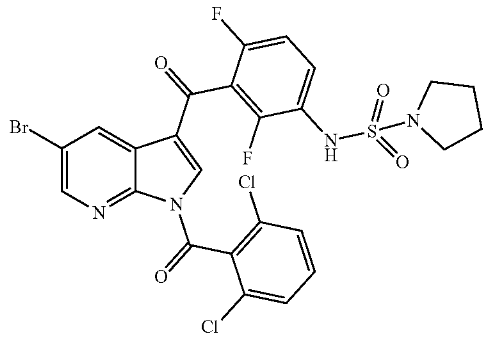

The title compound was obtained as off-white solid in 92% with a purity of 80% by UV, according to the general procedure V from (3-(3-amino-2,6-difluorobenzoyl)-5-bromo-1H-pyrrolo[2,3-b]pyridin-1-yl)(2,6-dichlorophenyl)methanone and cyclopentysulfamoyl chloride. MS m/e: 659.1 ($[M+H+]^+$).

Sulfamoyl Intermediate 3

(3R)—N-[3-[5-Bromo-1-(2,6-dichlorobenzoyl)pyrrolo[2,3-b]pyridine-3-carbonyl]-2,4-difluoro-phenyl]-3-fluoro-pyrrolidine-1-sulfonamide

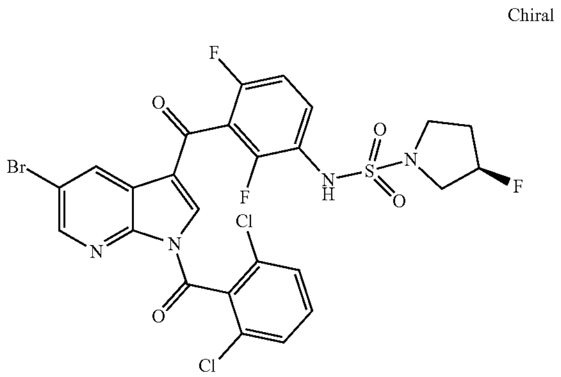 [SMILES: O=C(c1c(F)ccc(NS(=O)(=O)N2CC[C@@H](F)C2)c1F)c1cn(C(=O)c2c(Cl)cccc2Cl)c2ncc(Br)cc12]

The title compound was obtained as brown solid in 47% with a purity of 77% by UV, according to the general procedure V from (3-(3-amino-2,6-difluorobenzoyl)-5-bromo-1H-pyrrolo[2,3-b]pyridin-1-yl)(2,6-dichlorophenyl)methanone and (R)-3-fluoropyrrolidine-1-sulfonyl chloride. MS m/e: 675, 677 ($[M+H+]^+$).

Intermediates of Formula (XVI-b)

General Procedure VI: Treatment of Anilines with Sulfonyl Chlorides

A mixture of (3-(3-amino-2,6-difluorobenzoyl)-5-bromo-1H-pyrrolo[2,3-b]pyridin-1-yl)(2,6-dichlorophenyl)methanone (1 eq), a sulfonyl chloride of intermediate formula XV-b (3-4 eq) and pyridine (6 eq) in a solvent such as 1,4-dioxane, tetrahydrofuran or methyl tetrahydrofuran is stirred at 70-90° C. for 24-72 h. After cooling to room temperature the reaction mixture is partitioned between an organic solvent such as ethyl acetate or dichloromethane and 0.5M aqueous hydrogen chloride solution. The layers are separated. The aqueous layer is extracted with one or two portions of organic solvent. The combined organic layers are washed with one portion of 0.5 M aqueous hydrogen chloride solution, two 50-ml portions of 1 M sodium carbonate solution and one 50-ml portion of brine, dried over anhydrous sodium sulfate, filtered and concentrated in vacuo. Purification by flash-chromatography gives a compound of intermediate formula XVI-b.

Sulfonamide intermediate 1

RS—N-[3-[5-Bromo-1-(2,6-dichlorobenzoyl)pyrrolo[2,3-b]pyridine-3-carbonyl]-2,4-difluoro-phenyl]butane-2-sulfonamide

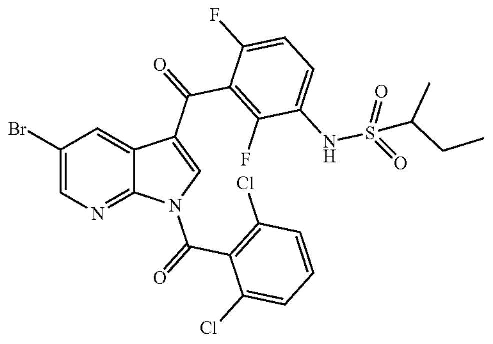 [SMILES: CCC(C)S(=O)(=O)Nc1ccc(F)c(C(=O)c2cn(C(=O)c3c(Cl)cccc3Cl)c3ncc(Br)cc23)c1F]

The title compound was obtained as off-white solid in 35% according to the general procedure VI from (3-(3-amino-2,6-difluorobenzoyl)-5-bromo-1H-pyrrolo[2,3-b]pyridin-1-yl)(2,6-dichlorophenyl)methanone and butane-2-sulfonyl chloride. MS m/e: 646.1 ([M+H+]$^+$).

Sulfonamide Intermediate 2

RS— N-[3-[5-Bromo-1-(2,6-dichlorobenzoyl)pyrrolo[2,3-b]pyridine-3-carbonyl]-2,4-difluoro-phenyl]cyclohexanesulfonamide

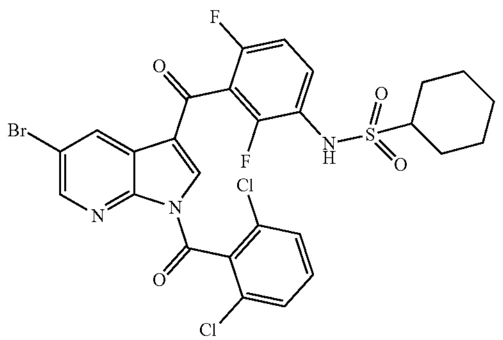 [SMILES: O=C(c1c(F)ccc(NS(=O)(=O)C2CCCCC2)c1F)c1cn(C(=O)c2c(Cl)cccc2Cl)c2ncc(Br)cc12]

The title compound was obtained as off-white solid in 34% according to the general procedure VI from (3-(3-amino-2,6-difluorobenzoyl)-5-bromo-1H-pyrrolo[2,3-b]pyridin-1-yl)(2,6-dichlorophenyl)methanone and cyclohexylsulfonyl chloride. MS m/e: 672.1 ([M+H+]$^+$).

Sulfonamide Intermediate 3

N-[3-[5-Bromo-1-(2,6-dichlorobenzoyl)pyrrolo[2,3-b]pyridine-3-carbonyl]-2,4-difluoro-phenyl]cyclopentanesulfonamide

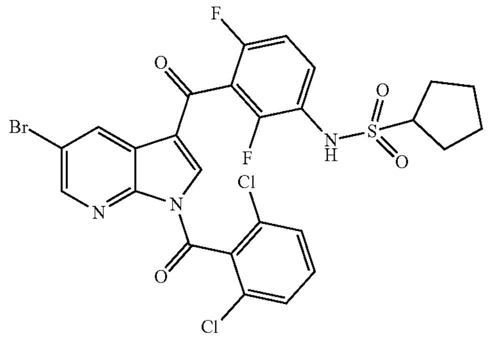 [SMILES: O=C(c1c(F)ccc(NS(=O)(=O)C2CCCC2)c1F)c1cn(C(=O)c2c(Cl)cccc2Cl)c2ncc(Br)cc12]

The title compound was obtained as light brown solid in 14% according to the general procedure VI from (3-(3-amino-2,6-difluorobenzoyl)-5-bromo-1H-pyrrolo[2,3-b]pyridin-1-yl)(2,6-dichlorophenyl)methanone and cyclopentylsulfonyl chloride. MS m/e: 658.1 ([M+H+]$^+$).

Sulfonamide Intermediate 4

N-[3-[5-Bromo-1-(2,6-dichlorobenzoyl)pyrrolo[2,3-b]pyridine-3-carbonyl]-2,4-difluoro-phenyl]propane-2-sulfonamide

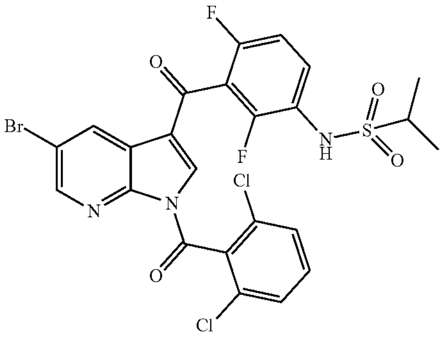 [SMILES: CC(C)S(=O)(=O)Nc1ccc(F)c(C(=O)c2cn(C(=O)c3c(Cl)cccc3Cl)c3ncc(Br)cc23)c1F]

The title compound was obtained as light brown solid in 9% according to the general procedure VI from (3-(3-amino-2,6-difluorobenzoyl)-5-bromo-1H-pyrrolo[2,3-b]pyridin-1-yl)(2,6-dichlorophenyl)methanone and isopropysulfonyl chloride. MS m/e: 632 ([M+H+]$^+$).

Intermediates of Formula (III)

General Procedure VII: c) Suzuki Cross Coupling, b) 2,6-Dichlorobenzoyl Deprotection, c) N-BOC Deprotection a) To a mixture of a sulfamoyl intermediate of intermediate formula XVI-a (1 eq) or a sulfonamide intermediate of intermediate formula XVI-b (1 eq), a boronic acid intermediate of intermediate formula XVII which is either commercially available or prepared by methods known in the art (1.5 eq) and potassium carbonate (3 eq) in 1,2-dimethoxyethane/water (4:1, 0.1-0.2 M), which has been purged with argon, are consecutively added triphenylphosphine (0.1 eq) and palladium(II) acetate (0.05 eq). The mixture is stirred at reflux for 3-20 h. After cooling to room temperature the reaction mixture is partitioned between an organic solvent such as ethyl acetate or dichloromethane and 1M sodium bicarbonate solution. The layers are separated. The aqueous layer is extracted with one or two portions of organic solvent. The combined organic layers are washed with one portion of brine, dried over anhydrous sodium sulfate, filtered and concentrated in vacuo. Purification by flash-chromatography gives an intermediate of intermediate formula XVIII.

b) To a solution of an intermediate of intermediate formula XVIII in methanol (0.1-0.3 M) is added potassium carbonate (3-5 eq). The mixture is stirred at reflux for 30-60 minutes. After cooling to room temperature the reaction mixture is filtrated over Decalite. The filtrate is concentrated in vacuo. Purification by flash-chromatography gives an intermediate of intermediate formula XIX.

c) A solution of an intermediate of general intermediate formula XIX (1 eq) in dichloromethane (0.1 M) and trifluoroacetic acid (20 eq) is stirred at room temperature for 6-20 h. Alternatively an intermediate of intermediate formula XIX is stirred at room temperature in a solvent such as ethyl acetate or tetrahydrofuran (0.1-0.2M) and 4M hydrogen chloride solution in 1,4-dioxane (10 eq) for 20-72 h. The precipitate is filtrated and washed with ethyl acetate to give the an intermediate of intermediate formula III-b as hydrochloride salt. Optionally the free base can be obtained by partitioning the hydrochloride or trifluoroacetic acid salt between 1 M aqueous sodium carbonate solution and an organic solvent, e.g. ethyl acetate or dichloromethane. The layers are separated and the aqueous layer is extracted with two portions of the organic solvent. The combined organic layers are dried over anhydrous sodium sulfate, filtered and concentrated in vacuo to give the free base of an intermediate of intermediate formula III-b.

Intermediate 1

3-[3-[[Ethyl(methyl)sulfamoyl]amino]-2,6-difluoro-benzoyl]-5-(6-piperazin-1-yl-3-pyridyl)-1H-pyrrolo[2,3-b]pyridine

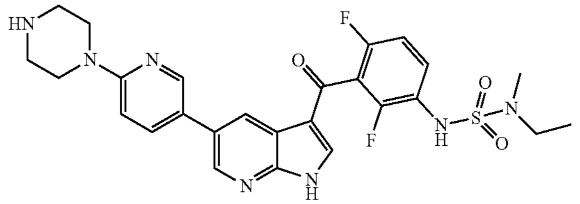 [SMILES: CCN(C)S(=O)(=O)Nc1ccc(F)c(C(=O)c2c[nH]c3ncc(-c4ccc(N5CCNCC5)nc4)cc23)c1F]

The title compound was obtained as light yellow solid according to the general procedure VII after two deprotection steps, from 5-bromo-1-(2,6-dichlorobenzoyl)-3-[3-[[ethyl(methyl)sulfamoyl]amino]-2,6-difluoro-benzoyl]pyrrolo[2,3-b]pyridine and (6-(4-(tert-butoxycarbonyl)piperazin-1-yl)pyridin-3-yl)boronic acid. MS m/e: 556 ([M+H+]$^{+}$).

Intermediate 2

3-[3-[[Ethyl(methyl)sulfamoyl]amino]-2,6-difluoro-benzoyl]-5-[4-(piperazin-1-ylmethyl)phenyl]-1H-pyrrolo[2,3-b]pyridine

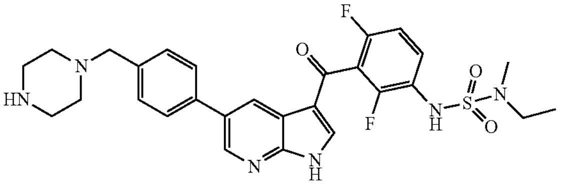 [SMILES: CCN(C)S(=O)(=O)Nc1ccc(F)c(C(=O)c2c[nH]c3ncc(-c4ccc(CN5CCNCC5)cc4)cc23)c1F]

The title compound was obtained as light brown solid according to the general procedure VII after two deprotection steps, from 5-bromo-1-(2,6-dichlorobenzoyl)-3-[3-[[ethyl(methyl)sulfamoyl]amino]-2,6-difluoro-benzoyl]pyrrolo[2,3-b]pyridine and tert-butyl 4-[[4-(4,4,5,5-tetramethyl-1,3,2-dioxaborolan-2-yl)phenyl]methyl]piperazine-1-carboxylate. MS m/e: 569 ([M+H+]$^{+}$).

Intermediate 3

3-[3-[[Ethyl(methyl)sulfamoyl]amino]-2,6-difluoro-benzoyl]-5-(2-piperazin-1-ylpyrimidin-5-yl)-1H-pyrrolo[2,3-b]pyridine

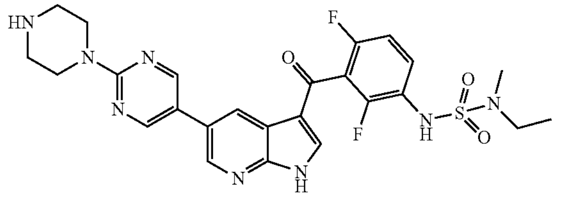

The title compound was obtained as off-white solid according to the general procedure VII after two deprotection steps, from 5-bromo-1-(2,6-dichlorobenzoyl)-3-[3-[[ethyl(methyl)sulfamoyl]amino]-2,6-difluoro-benzoyl]pyrrolo[2,3-b]pyridine and (2-(4-(tert-butoxycarbonyl)piperazin-1-yl)pyrimidin-5-yl)boronic acid. MS m/e: 557 ([M+H]$^{+}$).

Intermediate 4

3-[3-[[Ethyl(methyl)sulfamoyl]amino]-2,6-difluoro-benzoyl]-5-[6-(piperazin-1-ylmethyl)-3-pyridyl]-1H-pyrrolo[2,3-b]pyridine

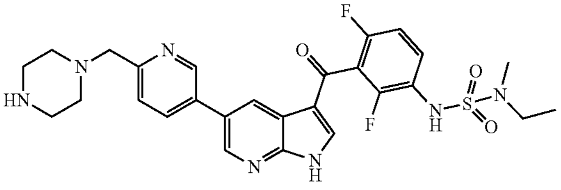 [SMILES: CCN(C)S(=O)(=O)Nc1ccc(F)c(C(=O)c2c[nH]c3ncc(-c4ccc(CN5CCNCC5)nc4)cc23)c1F]

The title compound was obtained as off-white solid according to the general procedure VII after two deprotection steps, from 5-bromo-1-(2,6-dichlorobenzoyl)-3-[3-[[ethyl(methyl)sulfamoyl]amino]-2,6-difluoro-benzoyl]pyrrolo[2,3-b]pyridine and (6-((4-(tert-butoxycarbonyl) piperazin-1-yl)methyl)pyridin-3-yl)boronic acid. MS m/e: 570 ([M+H+]$^+$).

Intermediate 5

3-[3-[[Ethyl(methyl)sulfamoyl]amino]-2,6-difluoro-benzoyl]-5-(4-piperazin-1-ylphenyl)-1H-pyrrolo[2,3-b]pyridine

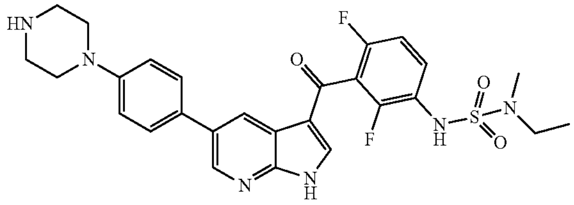 [SMILES: CCN(C)S(=O)(=O)Nc1ccc(F)c(C(=O)c2c[nH]c3ncc(-c4ccc(N5CCNCC5)cc4)cc23)c1F]

The title compound was obtained as light solid according to the general procedure VII after two deprotection steps, from 5-bromo-1-(2,6-dichlorobenzoyl)-3-[3-[[ethyl(methyl) sulfamoyl]amino]-2,6-difluoro-benzoyl]pyrrolo[2,3-b]pyridine and (4-(4-(tert-butoxycarbonyl)piperazin-1-yl)phenyl) boronic acid. MS m/e: 555 ([M+H+]$^+$).

Intermediate 6

N-[2,4-Difluoro-3-[5-(4-piperazin-1-ylphenyl)-1H-pyrrolo[2,3-b]pyridine-3-carbonyl]phenyl]pyrrolidine-1-sulfonamide

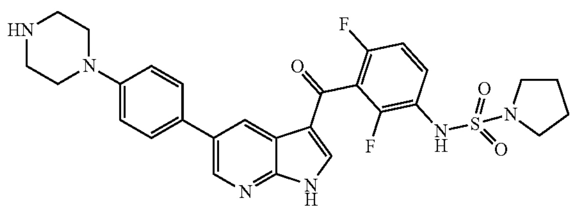 [SMILES: O=C(c1c(F)ccc(NS(=O)(=O)N2CCCC2)c1F)c1c[nH]c2ncc(-c3ccc(N4CCNCC4)cc3)cc12]

The title compound was obtained as white solid according to the general procedure VII after two deprotection steps, from N-[3-[5-bromo-1-(2,6-dichlorobenzoyl)pyrrolo[2,3-b] pyridine-3-carbonyl]-2,4-difluoro-phenyl]pyrrolidine-1-sulfonamide and (4-(4-(tert-butoxycarbonyl)piperazin-1-yl) phenyl)boronic acid. MS m/e: 567 ([M+H+]$^+$).

Intermediate 7

(3R)—N-[2,4-Difluoro-3-[5-(4-piperazin-1-ylphenyl)-1H-pyrrolo[2,3-b]pyridine-3-carbonyl]phenyl]-3-fluoro-pyrrolidine-1-sulfonamide trifluoro acetic acid Chiral

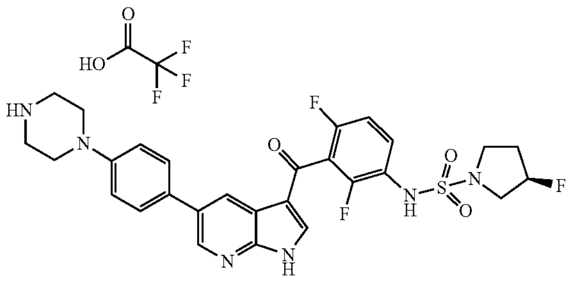

The title compound was obtained as white freeze dried solid according to the general procedure VII after two deprotection steps, from (3R)—N-[3-[5-bromo-1-(2,6-dichlorobenzoyl)pyrrolo[2,3-b]pyridine-3-carbonyl]-2,4-difluoro-phenyl]-3-fluoro-pyrrolidine-1-sulfonamide and (4-(4-(tert-butoxycarbonyl)piperazin-1-yl)phenyl)boronic acid. MS m/e: 585 ([M+H+]$^+$).

Intermediate 8

N-[2,4-difluoro-3-[5-(4-piperazin-1-ylphenyl)-1H-pyrrolo[2,3-b]pyridine-3-carbonyl]phenyl]cyclopentanesulfonamide trifluoroacetic acid

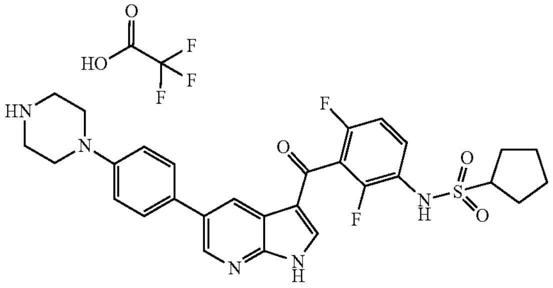 [SMILES: O=C(c1c(F)ccc(NS(=O)(=O)C2CCCC2)c1F)c1c[nH]c2ncc(-c3ccc(N4CCNCC4)cc3)cc12 ; O=C(O)C(F)(F)F]

The title compound was obtained as white solid according to the general procedure VII after two deprotection steps, from N-[3-[5-bromo-1-(2,6-dichlorobenzoyl)pyrrolo[2,3-b] pyridine-3-carbonyl]-2,4-difluoro-phenyl]cyclopentanesulfonamide and (4-(4-(tert-butoxycarbonyl)piperazin-1-yl)phenyl)boronic acid. MS m/e: 566 ([M+H+]$^+$).

Intermediate 9

1-[[4-[3-[3-[[Ethyl(methyl)sulfamoyl]amino]-2,6-difluoro-benzoyl]-1H-pyrrolo[2,3-b]pyridin-5-yl]phenyl]methyl]pyrrolidine-3-carboxylic acid

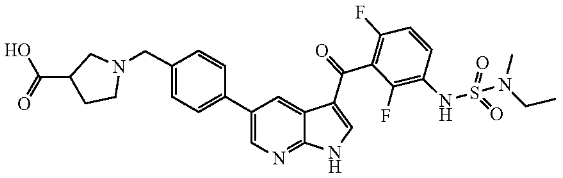 [SMILES: CCN(C)S(=O)(=O)Nc1ccc(F)c(C(=O)c2c[nH]c3ncc(-c4ccc(CN5CCC(C(=O)O)C5)cc4)cc23)c1F]

a) 3-[3-[[Ethyl(methyl)sulfamoyl]amino]-2,6-difluoro-benzoyl]-5-(4-formylphenyl)-1H-pyrrolo[2,3-b]pyridine A mixture of 5-bromo-3-[3-[[ethyl(methyl)sulfamoyl]amino]-2,6-difluoro-benzoyl]-1H-pyrrolo[2,3-b]pyridine (700 mg, 1.48 mmol, Eq: 1), (4-formylphenyl)boronic acid (444 mg, 2.96 mmol, Eq: 2), potassium carbonate (613 mg, 4.44 mmol, Eq: 3) and chloro(2-dicyclohexylphosphino-2,4,6-triisopropyl-1,1-biphenyl)[2-(2-amino-1,1-biphenyl)]palladium(II) (58.2 mg, 73.9 μmol, Eq: 0.05) in 1,4-dioxane (3.94 ml) and water (0.986 ml) was heated at 130° C. for 18 h. The reaction mixture was partitioned between ethyl acetate (50 ml) and 0.1 M aqueous hydrogen chloride solution (75 ml). The layers were separated. The aqueous layer was extracted with four 50-ml portions of ethyl acetate. The combined organic layers were washed with one 50-ml portion of brine, dried over anhydrous sodium sulfate, filtered and concentrated in vacuo. The residue was triturated in isopropanol (15-ml). The precipitate was collected by filtration, washed with isopropanol and dried in vacuo to give the title compound (0.468 g) as white solid. MS m/e: 499 ([M+H+]$^+$).

b) tert-Butyl 1-[[4-[3-[3-[[ethyl(methyl)sulfamoyl]amino]-2,6-difluoro-benzoyl]-1H-pyrrolo[2,3-b]pyridin-5-yl]phenyl]methyl]pyrrolidine-3-carboxylate In a 50 mL round-bottomed flask, a) 3-[3-[[Ethyl(methyl)sulfamoyl]amino]-2,6-difluoro-benzoyl]-5-(4-formylphenyl)-1H-pyrrolo[2,3-b]pyridine (200 mg, 401 μmol, Eq: 1) and (rac)-tert-butyl pyrrolidine-3-carboxylate (68.7 mg, 401 μmol, Eq: 1) were combined with dichloromethane (4.01 ml) to give a light brown suspension. Potassium acetate (98.4 mg, 1 mmol, Eq: 2.5) and acetic acid (60.2 mg, 57.4 μl, 1 mmol, Eq: 2.5) were added. The reaction mixture was stirred for 30 minutes. Sodium triacetoxyborohydride (425 mg, 2.01 mmol, Eq: 5) was added and stirring was continued for 5 h. The RM was diluted with ethyl acetate, 10% aqeous sodium bicarbonate solution and 1 ml MeOH to get a clear solution, then applicated over a cartouche and eluted with 100 ml ethyl acetate. The filtrate was evaporated. Purification by flash-chromatography with n-heptae/ethyl acetate as eluent gave the title compound (44 mg, 16%) as light yellow oil. MS m/e: 654.5 ([M+H+]$^+$).

c) 1-[[4-[3-[3-[[Ethyl(methyl)sulfamoyl]amino]-2,6-difluoro-benzoyl]-1H-pyrrolo[2,3-b]pyridin-5-yl]phenyl]methyl]pyrrolidine-3-carboxylic acid To a solution of tert-butyl 1-[[4-[3-[3-[[ethyl(methyl)sulfamoyl]amino]-2,6-difluoro-benzoyl]-1H-pyrrolo[2,3-b]pyridin-5-yl]phenyl]methyl]pyrrolidine-3-carboxylate (44 mg, 65.3 μmol, Eq: 1) in dichloromethane (653 μl) was added trifluoroacetic acid (149 mg, 101 μl, 1.31 mmol, Eq: 20). Stirring was continued for 3 d. The solvent and excess trifluoroacetic acid were evaporated. Purification by HPLC with water/acetonitrile as eluent gave the title compound (26 mg, 59%) with a purity of 88% according to HPLC. MS m/e: 598.4 ([M+H+]$^+$).

Intermediate 10

N-[3-[5-[4-[(4-Amino-1-piperidyl)methyl]phenyl]-1H-pyrrolo[2,3-b]pyridine-3-carbonyl]-2,4-difluoro-phenyl]pyrrolidine-1-sulfonamide

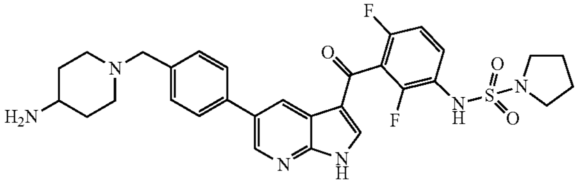 [SMILES: NC1CCN(Cc2ccc(-c3cnc4[nH]cc(C(=O)c5c(F)ccc(NS(=O)(=O)N6CCCC6)c5F)c4c3)cc2)CC1]

a) tert-Butyl N-[1-[[4-[3-(3-amino-2,6-difluoro-benzoyl)-1-(2,6-dichlorobenzoyl)pyrrolo[2,3-b]pyridin-5-yl]phenyl]methyl]-4-piperidyl]carbamate A mixture of tert-butyl N-[1-[[4-(4,4,5,5-tetramethyl-1,3,2-dioxaborolan-2-yl)phenyl]methyl]-4-piperidyl]carbamate (2000.0 mg, 4.8 mmol, 1 eq), (3-amino-2,6-difluoro-phenyl)-[5-bromo-1-(2,6-dichlorobenzoyl)pyrrolo[2,3-b]pyridin-3-yl]methanone hydrochloride (2697.62 mg, 4.8 mmol, 1 eq), 1,1'-bis(diphenylphosphino)ferrocene-palladium(II) dichloride dichloromethane complex (391.99 mg, 0.480 mmol, 0.100 eq) and potassium carbonate (2655.51 mg, 19.21 mmol, 4 eq) in 1,4-dioxane (50 mL) was stirred at 100° C. for 5 h under $N_2$. The mixture was filtered through celite, the filtrate was concentrated in vacuo to give a residue, which was purified by column chromatography to give the title compound (2200 mg, 2.99 mmol, 62.34% yield) as yellow foam.

b) tert-Butyl N-[1-[[4-[1-(2,6-dichlorobenzoyl)-3-[2,6-difluoro-3-(pyrrolidin-1-ylsulfonylamino)benzoyl]pyrrolo[2,3-b]pyridin-5-yl]phenyl]methyl]-4-piperidyl]carbamate A mixture of tert-butyl N-[1-[[4-[3-(3-amino-2,6-difluoro-benzoyl)-1-(2,6-dichlorobenzoyl)pyrrolo[2,3-b]pyridin-5-yl]phenyl]methyl]-4-piperidyl]carbamate (1000.0 mg, 1.36 mmol, 1 eq) and pyrrolidine-1-sulfonyl chloride (577.42 mg, 3.4 mmol, 2.5 eq) in pyridine (9.81 mL) was stirred at 80° C. for 16 h. The reaction mixture was concentrated in vacuo to give a residue, which was purified by column chromatography to give the title compound (1100 mg, 1.27 mmol, 93.12% yield) as light brown solid.

c) tert-Butyl N-[1-[[4-[3-[2,6-difluoro-3-(pyrrolidin-1-yl sulfonylamino)benzoyl]-1H-pyrrolo[2,3-b]pyridin-5-yl]phenyl]methyl]-4-piperidyl]carbamate To a solution of tert-butyl N-[1-[[4-[1-(2,6-dichlorobenzoyl)-3-[2,6-difluoro-3-(pyrrolidin-1-ylsulfonylamino)benzoyl]pyrrolo[2,3-b]pyridin-5-yl]phenyl]methyl]-4-piperidyl]carbamate (1.1 g, 1.27 mmol, 1 eq) in THF (30 mL) was added ammonium hydroxide (20.0 mL) at 25° C. The reaction was stirred at 25° C. for 12 h. The mixture was extracted with three 50-ml portions of ethyl acetate. The combined organic layers were dried over sodium sulphate and concentrated. Purification by flash-chromatography gave the title compound (800 mg, 1.15 mmol, 90.84% yield) as yellow foam.

d) N-[3-[5-[4-[(4-Amino-1-piperidyl)methyl]phenyl]-1H-pyrrolo[2,3-b]pyridine-3-carbonyl]-2,4-difluoro-phenyl]pyrrolidine-1-sulfonamide hydrochloride To a solution of tert-butyl N-[1-[[4-[3-[2,6-difluoro-3-(pyrrolidin-1-ylsulfonylamino)benzoyl]-1H-pyrrolo[2,3-b]pyridin-5-yl]phenyl]methyl]-4-piperidyl]carbamate (0.8 g, 1.15 mmol, 1 eq) in DCM (10 mL) was added 2,2,2-trifluoroacetic acid (3.0 mL, 1.15 mmol, 1 eq) at 25° C. The reaction was stirred at 25° C. for 12 h. The reaction mixture was concentrated and purified by prep-HPLC to give the title compound (700 mg, 1.11 mmol, 96.32% yield) as yellow solid.

Intermediate 11

5-[2-(4-Amino-1-piperidyl)pyrimidin-5-yl]-3-[3-[[ethyl(methyl)sulfamoyl]amino]-2,6-difluoro-benzoyl]-1H-pyrrolo[2,3-b]pyridine

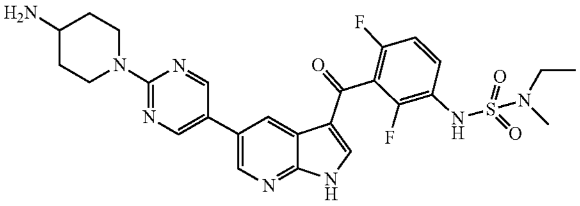 [SMILES: CCN(C)S(=O)(=O)Nc1ccc(F)c(C(=O)c2c[nH]c3ncc(-c4cnc(N5CCC(N)CC5)nc4)cc23)c1F]

The title compound was obtained as white solid according to the general procedure VII after two deprotection steps, from N-[3-[5-bromo-1-(2,6-dichlorobenzoyl)pyrrolo[2,3-b]pyridine-3-carbonyl]-2,4-difluoro-phenyl]cyclopentanesulfonamide and tert-butyl N-[1-[5-(4,4,5,5-tetramethyl-1,3,2-dioxaborolan-2-yl)pyrimidin-2-yl]-4-piperidyl]carbamate.

Intermediate 12

5-[6-(4-Amino-1-piperidyl)-3-pyridyl]-3-[3-[[ethyl(methyl)sulfamoyl]amino]-2,6-difluoro-benzoyl]-1H-pyrrolo[2,3-b]pyridine

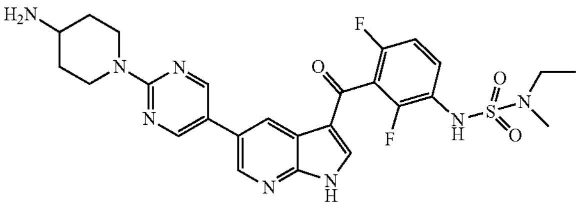 [SMILES: CCN(C)S(=O)(=O)Nc1ccc(F)c(C(=O)c2c[nH]c3ncc(-c4cnc(N5CCC(N)CC5)nc4)cc23)c1F]

The title compound was obtained as white solid according to the general procedure VII after two deprotection steps, from N-[3-[5-bromo-1-(2,6-dichlorobenzoyl)pyrrolo[2,3-b]pyridine-3-carbonyl]-2,4-difluoro-phenyl]cyclopentanesulfonamide and tert-butyl N-[1-[5-(4,4,5,5-tetramethyl-1,3,2-dioxaborolan-2-yl)-2-pyridyl]-4-piperidyl]carbamate. MS m/e: 570.3 ([M+H+]$^+$).

Intermediate 13

3-[3-[[Ethyl(methyl)sulfamoyl]amino]-2,6-difluoro-benzoyl]-5-(4-piperidyloxy)-1H-pyrrolo[2,3-b]pyridine

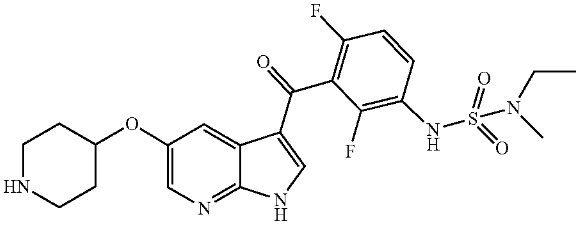 [SMILES: CCN(C)S(=O)(=O)Nc1ccc(F)c(C(=O)c2c[nH]c3ncc(OC4CCNCC4)cc23)c1F]

The title compound was obtained as light yellow solid according to the general procedure VII after two deprotection steps, from 5-bromo-1-(2,6-dichlorobenzoyl)-3-[3-[[ethyl(methyl)sulfamoyl]amino]-2,6-difluoro-benzoyl]pyrrolo[2,3-b]pyridine and tert-butyl 4-(4-(4,4,5,5-tetramethyl-1,3,2-dioxaborolan-2-yl)phenoxy)piperidine-1-carboxylate. MS m/e: 570.5 ([M+H+]$^+$).

Intermediate 14

3-[3-[[Ethyl(methyl)sulfamoyl]amino]-2,6-difluoro-benzoyl]-5-[2-(4-piperidyl)ethynyl]-1H-pyrrolo[2,3-b]pyridine

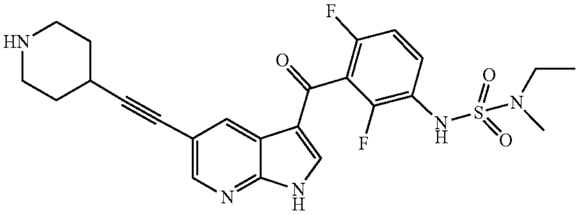 [SMILES: CCN(C)S(=O)(=O)Nc1ccc(F)c(C(=O)c2c[nH]c3ncc(C#CC4CCNCC4)cc23)c1F]

a) tert-Butyl 4-((1-(2,6-dichlorobenzoyl)-3-(3-((N-ethyl-N-methylsulfamoyl)amino)-2,6-difluorobenzoyl)-1H-pyrrolo[2,3-b]pyridin-5-yl)ethynyl)piperidine-1-carboxylate A solution of 5-bromo-1-(2,6-dichlorobenzoyl)-3-[3-[[ethyl(methyl)sulfamoyl]amino]-2,6-difluoro-benzoyl]pyrrolo[2,3-b]pyridine (1 g, 1.55 mmol, Eq: 1), tert-butyl 4-ethynylpiperidine-1-carboxylate (356 mg, 1.7 mmol, Eq: 1.1), copper (I) iodide (58.9 mg, 309 μmol, Eq: 0.2) in N,N-dimethylformamide (7.74 ml) was degassed with argon three times then bis(triphenylphosphine)palladium (II) chloride (109 mg, 155 μmol, Eq: 0.1) and triethyl amine (2.35 g, 3.24 ml, 23.2 mmol, Eq: 15) was added at room temperature. The reaction mixture was heated at 70° C. overnight. The reaction mixture was poured into 40 ml water and extracted with ethyl acetate (3×30 ml). The organic layers were combined, washed with brine (2×25 mL), dried over anhydrous sodium sulfate, filtered and concentrated in vacuo. The residue was triturated in TBME (30 ml). The solids were removed by filtration. The filtrate was concentrated in vacuo to give the crude title compound (1.46, quant.) as red solid with a purity of 88% according to HPLC. MS m/e: 775.5 ([M+H+]$^+$).

b) tert-Butyl 4-((3-(3-((N-ethyl-N-methylsulfamoyl) amino)-2,6-difluorobenzoyl)-1H-pyrrolo[2,3-b]pyridin-5-yl)ethynyl)piperidine-1-carboxylate A mixture of tert-butyl 4-((1-(2,6-dichlorobenzoyl)-3-(3-((N-ethyl-N-methyl sulfamoyl)amino)-2,6-difluorobenzoyl)-1H-pyrrolo[2,3-b]pyridin-5-yl)ethynyl)piperidine-1-carboxylate (1.2 g, 1.55 mmol, Eq: 1) and potassium carbonate (1.07 g, 7.75 mmol, Eq: 5) in methanol (15.5 ml) was heated at 60° C. for 45 min. The mixture was partionated between ethyl acetate (50 ml) and sat ammonium chloride solution (50 ml). The layers were separated. The aqueous layer was extracted with one 50-ml portion of ethyl acetate. The combined organic layers were washed with one 30-ml portion of brine, dried over anhydrous sodium sulfate, filtered and concentrated in vacuo. Purification by flash chromatography gave the title compound (882 mg, 87.1%) as dark red waxy solid. MS m/e: 602.5 ([M+H+]$^+$).

d) 3-[3-[[Ethyl(methyl)sulfamoyl]amino]-2,6-difluoro-benzoyl]-5-[2-(4-piperidyl)ethynyl]-1H-pyrrolo[2,3-b]pyridine A solution of tert-butyl 4-((3-(3-((N-ethyl-N-methylsulfamoyl)amino)-2,6-difluorobenzoyl)-1H-pyrrolo[2,3-b]pyridin-5-yl)ethynyl)piperidine-1-carboxylate (875 mg, 1.45 mmol, Eq: 1) and 2,2,2-trifluoroacetic acid (3.32 g, 2.24 ml, 29.1 mmol, Eq: 20) in dichloromethane (7.27 ml) was stirred for 1 h at room temperature. The solvents were evaporated. The residue was suspended in 1 M sodium carbonate (50 ml) and stirred over night. The precipitate was collected by filtration to give the title compound (130 mg, 17.8%) as yellow solid. MS m/e: 502.4 ([M+H+]$^+$).

Intermediate 15

3-[3-[[Ethyl(methyl)sulfamoyl]amino]-2,6-difluoro-benzoyl]-5-[2-(4-piperidyl)pyrimidin-5-yl]-1H-pyrrolo[2,3-b]pyridine 2,2,2-trifluoroacetic acid

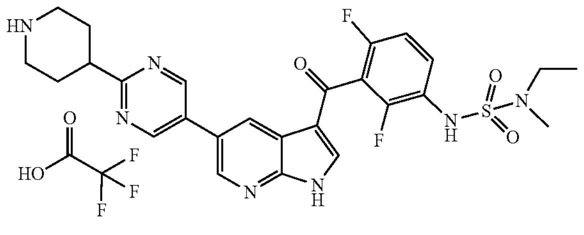

The title compound was obtained as light yellow solid according to the general procedure VII after two deprotection steps, from 5-bromo-1-(2,6-dichlorobenzoyl)-3-[3-[[ethyl(methyl)sulfamoyl]amino]-2,6-difluoro-benzoyl]pyrrolo[2,3-b]pyridine and [2-(1-tert-butoxycarbonyl-4-piperidyl)pyrimidin-5-yl]boronic acid. MS m/e: 556.3 ([M+H+]$^+$).

Intermediate 16

3-[3-[[Ethyl(methyl)sulfamoyl]amino]-2,6-difluoro-benzoyl]-5-[6-(4-piperidyl)-3-pyridyl]-1H-pyrrolo[2,3-b]pyridine 2,2,2-trifluoroacetic acid

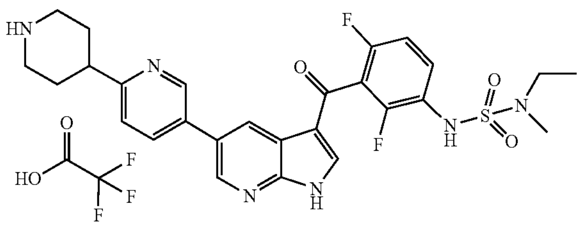

The title compound was obtained as light yellow solid according to the general procedure VII after two deprotection steps, from 5-bromo-1-(2,6-dichlorobenzoyl)-3-[3-[[ethyl(methyl)sulfamoyl]amino]-2,6-difluoro-benzoyl]pyrrolo[2,3-b]pyridine and [6-(1-tert-butoxycarbonyl-4-piperidyl)-3-pyridyl]boronic acid. MS m/e: 555 ([M+H+]$^+$).

Intermediate 17

3-[3-[[Ethyl(methyl)sulfamoyl]amino]-2,6-difluoro-benzoyl]-5-[4-(4-piperidyl)phenyl]-1H-pyrrolo[2,3-b]pyridine

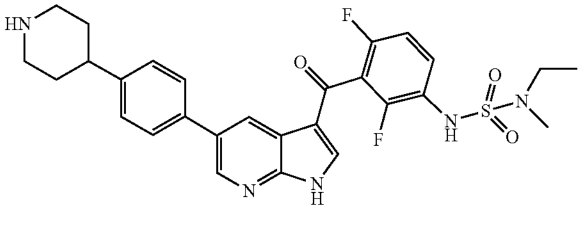 [SMILES: CCN(C)S(=O)(=O)Nc1ccc(F)c(C(=O)c2c[nH]c3ncc(-c4ccc(C5CCNCC5)cc4)cc23)c1F]

The title compound was obtained as off-white solid according to the general procedure VII after two deprotection steps, from 5-bromo-1-(2,6-dichlorobenzoyl)-3-[3-[[ethyl(methyl)sulfamoyl]amino]-2,6-difluoro-benzoyl]pyrrolo[2,3-b]pyridine and tert-butyl 4-(4-(4,4,5,5-tetramethyl-1,3,2-dioxaborolan-2-yl)phenyl)piperidine-1-carboxylate. MS m/e: 554 ([M+H+]$^+$).

Intermediate 18

5-[6-(3,8-Diazabicyclo[3.2.1]octan-3-yl)-3-pyridyl]-3-[3-[[ethyl(methyl)sulfamoyl]amino]-2,6-difluoro-benzoyl]-1H-pyrrolo[2,3-b]pyridine 2,2,2-trifluoro-acetic acid

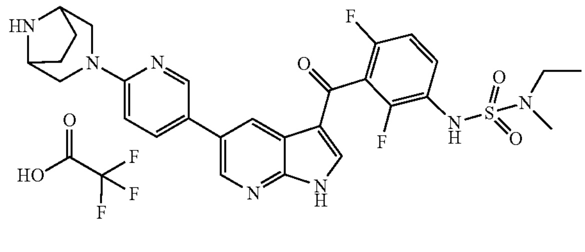

The title compound was obtained as light yellow solid according to the general procedure VII after two deprotection steps, from 5-bromo-1-(2,6-dichlorobenzoyl)-3-[3-[[ethyl(methyl)sulfamoyl]amino]-2,6-difluoro-benzoyl]pyrrolo[2,3-b]pyridine and tert-butyl 3-(5-(4,4,5,5-tetramethyl-1,3,2-dioxaborolan-2-yl)pyridin-2-yl)-3,8-diazabicyclo [3.2.1]octane-8-carboxylate. MS m/e: 582.5 ([M+H+]$^+$).

Intermediate 19

5-[6-(2,6-Diazaspiro[3.3]heptan-2-yl)-3-pyridyl]-3-[3-[[ethyl(methyl)sulfamoyl]amino]-2,6-difluoro-benzoyl]-1H-pyrrolo[2,3-b]pyridine

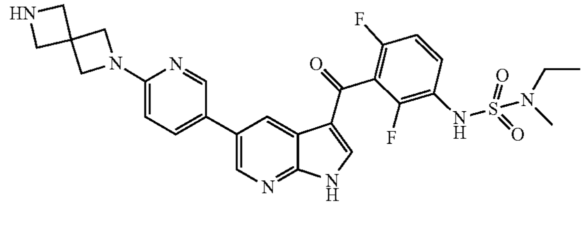 [SMILES: CCN(C)S(=O)(=O)Nc1ccc(F)c(C(=O)c2c[nH]c3ncc(-c4ccc(N5CC6(CNC6)C5)nc4)cc23)c1F]

a) tert-Butyl 6-(5-(3-(3-((N-ethyl-N-methylsulfamoyl)amino)-2,6-difluorobenzoyl)-1H-pyrrolo[2,3-b]pyridin-5-yl)pyridin-2-yl)-2,6-diazaspiro[3.3]heptane-2-carboxylate The title compound was obtained as light yellow solid according to the general procedure VII after one deprotection step, from 5-bromo-1-(2,6-dichlorobenzoyl)-3-[3-[[ethyl(methyl)sulfamoyl]amino]-2,6-difluoro-benzoyl]pyrrolo[2,3-b]pyridine and tert-butyl 6-(5-(4,4,5,5-tetramethyl-1,3,2-dioxaborolan-2-yl)pyridin-2-yl)-2,6-diazaspiro[3.3] heptane-2-carboxylate. MS m/e: 668.5 ([M+H+]$^+$).

b) 5-[6-(2,6-Diazaspiro[3.3]heptan-2-yl)-3-pyridyl]-3-[3-[[ethyl(methyl)sulfamoyl]amino]-2,6-difluoro-benzoyl]-1H-pyrrolo[2,3-b]pyridine A solution of tert-butyl 6-(5-(3-(3-((N-ethyl-N-methylsulfamoyl)amino)-2,6-difluorobenzoyl)-1H-pyrrolo[2,3-b] pyridin-5-yl)pyridin-2-yl)-2,6-diazaspiro[3.3]heptane-2-carboxylate (120 mg, 180 μmol, Eq: 1) and 1,1,1,3,3,3-hexafluoro-2-propanol (1.6 g, 1 ml, 9.5 mmol, Eq: 52.9) was heated to 120° C. and stirred for 20 h in a sealed tube. The solvent was evaporated. Purification by preparative HPLC with water/acetonitrile gave the title compound (60 mg, 56%) as white solid. MS m/e: 568.4 ([M+H+]$^+$).

Intermediate 20

4-[2-[3-[3-[[Ethyl(methyl)sulfamoyl]amino]-2,6-difluoro-benzoyl]-1H-pyrrolo[2,3-b]pyridin-5-yl] ethynyl]benzoic acid

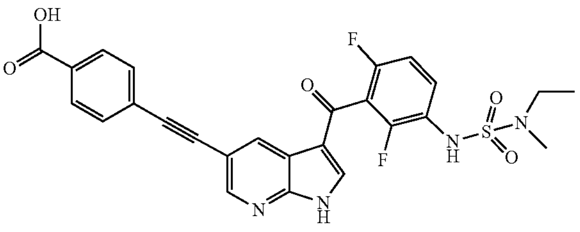 [SMILES: CCN(C)S(=O)(=O)Nc1ccc(F)c(C(=O)c2c[nH]c3ncc(C#Cc4ccc(C(=O)O)cc4)cc23)c1F]

a) tert-Butyl 4-((1-(2,6-dichlorobenzoyl)-3-(3-((N-ethyl-N-methylsulfamoyl)amino)-2,6-difluorobenzoyl)-1H-pyrrolo[2,3-b]pyridin-5-yl)ethynyl)benzoate A solution of 5-bromo-1-(2,6-dichlorobenzoyl)-3-[3-[[ethyl(methyl)sulfamoyl]amino]-2,6-difluoro-benzoyl]pyrrolo[2,3-b]pyridine (0.5 g, 0.77 mmol, Eq: 1), tert-butyl 4-ethynylbenzoate (235 mg, 1.16 mmol, Eq: 1.5) and copper (I) iodide (29.5 mg, 155 μmol, Eq: 0.2) in N,N-dimethylformamide (3.87 ml) was degassed. Bis(triphenylphosphine) palladium (II) chloride (54.3 mg, 77.4 μmol, Eq: 0.1) and TEA (1.17 g, 1.62 ml, 11.6 mmol, Eq: 15) was added and stirring was continued for 1 h at 70° C. The reaction mixture was poured into water (40 ml) and extracted with three 30-ml portions of ethyl acetate. The combined organic layers were washed with brine dried over anhydrous sodium sulfate, filtered and concentrated in vacuo. The residue was triturated with tert-butyl methyl ether (30 ml). The solids were removed by filtration and washed with tert-butyl methyl ether. The filtrate was concentrated in vacuo to give the crude title compound as dark brown solid. MS m/e: 767.4 ([M+H+]$^+$).

b) tert-Butyl 4-((3-(3-((N-ethyl-N-methylsulfamoyl) amino)-2,6-difluorobenzoyl)-1H-pyrrolo[2,3-b]pyridin-5-yl)ethynyl)benzoate To a solution of tert-butyl 4-((1-(2,6-dichlorobenzoyl)-3-(3-((N-ethyl-N-methyl sulfamoyl)amino)-2,6-difluorobenzoyl)-1H-pyrrolo[2,3-b]pyridin-5-yl)ethynyl)benzoate (0.898 g, 714 μmol, Eq: 1) in methanol (7.14 ml) was added potassium carbonate (493 mg, 3.57 mmol, Eq: 5) at room temperature. The reaction mixture was heated at 60° C. for 60 min. The mixture was partitioned between ethyl acetate (50 ml) and aqueous saturated ammonium chloride solution (50 ml). The layers were separated. The aqueous layer was extracted with one 50-ml portion of ethyl acetate. The combined organic layers were washed with one 30-ml portion of brine, dried over anhydrous sodium sulfate, filtered and concentrated in vacuo. The residue was triturated in toluene (5-ml). The precipitate was collected by filtration, washed with toluene and dried in vacuo to give the title compound (0.20 g, 47% yield) as pink solid. MS m/e: 595.3 ([M+H+]$^+$).

c) 4-[2-[3-[3-[[Ethyl(methyl)sulfamoyl]amino]-2,6-difluoro-benzoyl]-1H-pyrrolo[2,3-b]pyridin-5-yl]ethynyl]benzoic acid To a solution of tert-butyl 4-((3-(3-((N-ethyl-N-methylsulfamoyl)amino)-2,6-difluorobenzoyl)-1H-pyrrolo[2,3-b]pyridin-5-yl)ethynyl)benzoate (0.31 g, 519 μmol, 1 Eq) in dichloromethane (3 ml) was added trifluoroacetic acid (0.803 ml, 10.4 mmol, 20 Eq) and stirring was continued for 1 h. The solvent was evaporated in vacuo. The residue was triturated in ethyl acetate (5-ml). The precipitate was collected by filtration, washed with ethyl acetate and dried in vacuo to give the title compound as pink solid (0.215 g, 66%). MS m/e: 539 ([M+H+]$^+$).

Intermediate 21

N-[2,4-Difluoro-3-[5-(6-piperazin-1-yl-3-pyridyl)-1H-pyrrolo[2,3-b]pyridine-3-carbonyl]phenyl]pyrrolidine-1-sulfonamide 2,2,2-trifluoroacetic acid

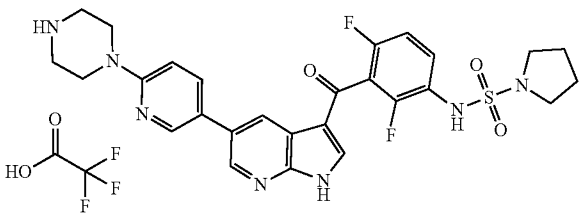

The title compound was obtained as light brown solid according to the general procedure VII after two deprotection steps, from N-[3-[5-bromo-1-(2,6-dichlorobenzoyl)pyrrolo[2,3-b]pyridine-3-carbonyl]-2,4-difluoro-phenyl]pyrrolidine-1-sulfonamide and (6-(4-(tert-butoxycarbonyl)piperazin-1-yl)pyridin-3-yl)boronic acid. MS m/e: 566.5 ([M+H+]$^+$).

Intermediate 22

N-[2,4-Difluoro-3-[5-[6-[rac-(1S,5R)-3,9-diazabicyclo[3.3.1]nonan-3-yl]-3-pyridyl]-1H-pyrrolo[2,3-b]pyridine-3-carbonyl]phenyl]pyrrolidine-1-sulfonamide;2,2,2-trifluoroacetic acid

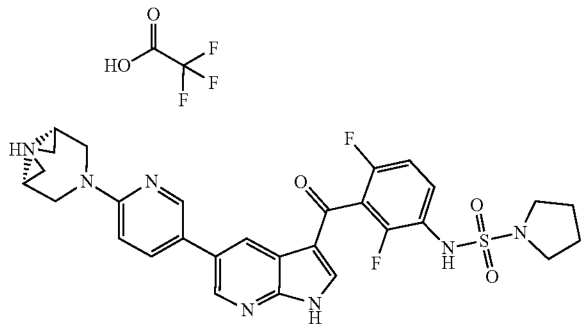

The title compound was obtained according to the general procedure VII after two deprotection steps, from N-[3-[5-bromo-1-(2,6-dichlorobenzoyl)pyrrolo[2,3-b]pyridine-3-carbonyl]-2,4-difluoro-phenyl]pyrrolidine-1-sulfonamide and tert-butyl 3-(5-(4,4,5,5-tetramethyl-1,3,2-dioxaborolan-2-yl)pyridin-2-yl)-3,9-diazabicyclo[3.3.1]nonane-9-carboxylate. MS m/e: 608.4 ([M+H+]$^+$).

Intermediate 23

N-[3-[5-[4-(Azetidin-3-yl)phenyl]-1H-pyrrolo[2,3-b]pyridine-3-carbonyl]-2,4-difluoro-phenyl]pyrrolidine-1-sulfonamide 2,2,2-trifluoroacetic acid

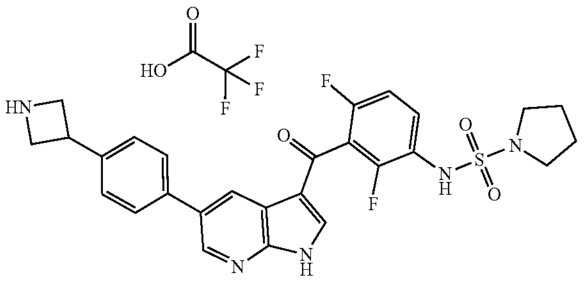

The title compound was obtained according to the general procedure VII after two deprotection steps, from N-[3-[5-bromo-1-(2,6-dichlorobenzoyl)pyrrolo[2,3-1)]pyridine-3-carbonyl]-2,4-difluoro-phenyl]pyrrolidine-1-sulfonamide and tert-butyl 3-(4-(4,4,5,5-tetramethyl-1,3,2-dioxaborolan-2-yl)phenyl)azetidine-1-carboxylate. MS m/e: 538.5 ([M+H+]$^+$).

Intermediate 24

3-[2-Bromo-3-[[ethyl(methyl)sulfamoyl]amino]benzoyl]-5-(6-piperazin-1-yl-3-pyridyl)-1H-pyrrolo[2,3-b]pyridine

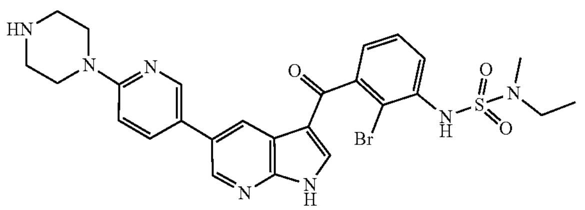 [SMILES: CCN(C)S(=O)(=O)Nc1cccc(C(=O)c2c[nH]c3ncc(-c4ccc(N5CCNCC5)nc4)cc23)c1Br]

a) (5-Bromo-1H-pyrrolo[2,3-b]pyridin-3-yl)(2-bromo-3-nitrophenyl)methanone

To a solution of 5-bromo-1H-pyrrolo[2,3-b]pyridine (2.66 g, 13.5 mmol, Eq: 1.1) in dichloromethane (123 ml) was added anhydrous aluminum chloride (6.53 g, 49 mmol, Eq: 4) at 0-5° C. Addition of 2-bromo-3-nitrobenzoyl chloride (3.24 g, 12.3 mmol, Eq: 1) as solution in dichloromethane (40 ml) at 0-5° C. The ice bath was removed and stirring was continued for 20 h. The reaction was poured on crushed ice/water (150 ml). The precipitate was collected by filtration after 72 h, washed with water and dried in vacuo to give the title compound (5.61 g, quant.) as off-white solid. MS m/e: 425.9, 427.8 ([M+H+]$^+$).

b) (3-Amino-2-bromophenyl)(5-bromo-1H-pyrrolo[2,3-b]pyridin-3-yl)methanone

To a solution of (5-bromo-1H-pyrrolo[2,3-b]pyridin-3-yl)(2-bromo-3-nitrophenyl)methanone (5.61 g, 13.2 mmol, Eq: 1) in 2-methyltetrahydrofuran (63 ml) was added tin (II) chloride (7.51 g, 39.6 mmol, Eq: 3) at RT. The reaction mixture was heated at 60° C. for 20 h. After quenching with sodium hydroxide (39.6 ml, 2 M) the precipitate was collected by filtration, washed with 2-methyltetrahydrofuran and dried in vacuo to give the title compound (5.17 g, 99%) as orange solid. MS m/e: 396.0, 397.9 ([M+H+]$^+$).

c) (3-Amino-2-bromo-phenyl)-[5-bromo-1-(2,6-dichlorobenzoyl)pyrrolo[2,3-b]pyridin-3-yl]methanone To a solution of (3-amino-2-bromophenyl)(5-bromo-1H-pyrrolo[2,3-b]pyridin-3-yl)methanone (5.17 g, 13.1 mmol, Eq: 1), triethylamine (1.59 g, 2.19 ml, 15.7 mmol, Eq: 1.2) and DMAP (160 mg, 1.31 mmol, Eq: 0.1) in tetrahydrofuran (65.4 ml) was slowly added 2,6-dichlorobenzoyl chloride (2.47 g, 1.69 ml, 11.8 mmol, Eq: 0.9) (1.69 ml) at 0-5° C. After completion of the reaction, water was added and stirring was continued for 10 minutes. The tetrahydrofuran was evaporated in vacuo. The reaction mixture was partitioned between ethyl acetate (100 ml) and water (100 ml). The layers were separated. The aqueous layer was extracted with three 100-ml portions of ethyl acetate. The combined organic layers were washed with one 100-ml portion of brine, dried over anhydrous sodium sulfate, filtered and concentrated in vacuo. The crude material was purified by flash chromatography with n-heptane/ethyl acetate as eluent to give the title compound (4.19 g, 56%) as orange solid. MS m/e: 567.9 ([M+H+]$^+$).

d) tert-Butyl 4-(5-(3-(3-amino-2-bromobenzoyl)-1-(2,6-dichlorobenzoyl)-1H-pyrrolo[2,3-b]pyridin-5-yl)pyridin-2-yl)piperazine-1-carboxylate To a mixture of (3-(3-amino-2-bromobenzoyl)-5-bromo-1H-pyrrolo[2,3-b]pyridin-1-yl)(2,6-dichlorophenyl)methanone (1 g, 1.76 mmol, Eq: 1), (6-(4-(tert-butoxycarbonyl)piperazin-1-yl)pyridin-3-yl)boronic acid (595 mg, 1.94 mmol, Eq: 1.1) and potassium carbonate (730 mg, 5.28 mmol, Eq: 3) in 1,2-dimethoxyethane (14.1 ml) and water (3.52 ml) were added triphenylphosphine (92.3 mg, 352 μmol, Eq: 0.2) and palladium (II) acetate (39.5 mg, 176 Eq: 0.1). The RM was purged with Argon by two vacuo/Argon cycles, then heated to 90° C. and stirred for 15 h. The reaction mixture was partitioned between ethyl acetate (50 ml) and water (30 ml). The layers were separated. The aqueous layer was extracted with two 50-ml portions of ethyl acetate. The combined organic layers were washed with one 40-ml portion of brine, dried over anhydrous sodium sulfate, filtered and concentrated in vacuo. The crude material was purified by flash chromatography with n-heptane/ethyl acetate as eluent. The solid obtained from the flash chromatography was triturated in methanol (10 ml). The precipitate was collected by filtration to give the title compound (1.06 g, 81%) as orange solid.

MS m/e: 751.1 ([M+H+]$^+$).

d) tert-Butyl 4-(5-(3-(2-bromo-3-((N-ethyl-N-methylsulfamoyl)amino)benzoyl)-1-(2,6-dichlorobenzoyl)-1H-pyrrolo[2,3-b]pyridin-5-yl)pyridin-2-yl)piperazine-1-carboxylate To a mixture of tert-butyl 4-(5-(3-(3-amino-2-bromobenzoyl)-1-(2,6-dichlorobenzoyl)-1H-pyrrolo[2,3-b]pyridin-5-yl)pyridin-2-yl)piperazine-1-carboxylate (0.55 g, 733 μmol, Eq: 1) and pyridine (580 mg, 593 μl, 7.33 mmol, Eq: 10) in 1,4-dioxane (3.66 ml) was added ethyl(methyl)sulfamoyl chloride (404 mg, 2.57 mmol, Eq: 3.5). The reaction mixture was heated at reflux for 20 h. The reaction mixture was partitioned between ethyl acetate (50 ml) and water (30 ml). The layers were separated. The aqueous layer was extracted with two 50-ml portions of ethyl acetate. The combined organic layers were washed with one 30-ml portion of brine, dried over anhydrous sodium sulfate, filtered and concentrated in vacuo. The residue was triturated in ethyl acetate (10-ml). The solids were removed by filtration and washed with ethyl acetate. The filtrate was concentrated in vacuo. The crude material was purified by flash chromatography with n-heptane/ethyl acetate as eluent to give the title compound (0.26 g, 29%) as light brown solid with a purity of 70%. MS m/e: 872.3 ([M+H+]$^+$).

e) tert-Butyl 4-(5-(3-(2-bromo-3-((N-ethyl-N-methylsulfamoyl)amino)benzoyl)-1H-pyrrolo[2,3-b]pyridin-5-yl)pyridin-2-yl)piperazine-1-carboxylate To a solution of tert-butyl 4-(5-(3-(2-bromo-3-((N-ethyl-N-methylsulfamoyl)amino)benzoyl)-1-(2,6-dichlorobenzoyl)-1H-pyrrolo[2,3-b]pyridin-5-yl)pyridin-2-yl)piperazine-1-carboxylate (0.26 g, 298 μmol, Eq: 1) in methanol (2.98 ml) was added potassium carbonate (206 mg, 1.49 mmol, Eq: 5) at RT. The reaction mixture was heated at 60° C. for 60 min. The mixture was partitioned between ethyl acetate (50 ml) and sat ammonium chloride solution (30 ml). The layers were separated. The aqueous layer was extracted with one 50-ml portion of ethyl acetate. The combined organic layers were washed with one 30-ml portion of brine, dried over $Na_2SO_4$, filtered and concentrated in vacuo. The crude material was purified by flash chromatography with n-heptane/ethyl acetate as eluent to give the title compound (0.122 g, 49%) as off-white solid with a purity of 83%. MS m/e: 698, 700 ([M+H+]$^+$).

f) 3-[2-Bromo-3-[[ethyl(methyl)sulfamoyl]amino]benzoyl]-5-(6-piperazin-1-ylpyridin-3-yl)-1H-pyrrolo[2,3-b]pyridine A suspension of tert-butyl 4-(5-(3-(2-bromo-3-((N-ethyl-N-methyl sulfamoyl)amino)benzoyl)-1H-pyrrolo[2,3-b]pyridin-5-yl)pyridin-2-yl)piperazine-1-carboxylate (0.122 g, 145 μmol, Eq: 1) and 4 M hydrogen chloride solution in 1,4-dioxane (362 μl, 1.45 mmol, Eq: 10) in tetrahydrofuran (1.45 ml) was stirred for 72 h at RT. The solvent was evaporated. Purification by preparative RP-HPLC gave the title compound (0.061 g, 70%) as white solid. MS m/e: 698, 700 ([M+H+]$^+$).

Intermediate 25

3-[2-Cyano-3-[[ethyl)methyl)sulfamoyl]amino]benzoyl]-5-(6-piperazin-1-ylpyridin-3-yl)-1H-pyrrolo[2,3-b]pyridine hydrochloride

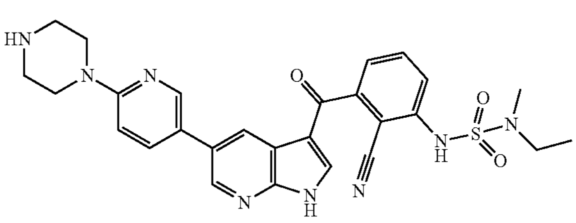 [SMILES: CCN(C)S(=O)(=O)Nc1cccc(C(=O)c2c[nH]c3ncc(-c4ccc(N5CCNCC5)nc4)cc23)c1C#N]

a) tert-butyl 4-(5-(3-(3-amino-2-cyanobenzoyl)-1-(2,6-dichlorobenzoyl)-1H-pyrrolo[2,3-b]pyridin-5-yl)pyridin-2-yl)piperazine-1-carboxylate A solution of tert-butyl 4-(5-(3-(3-amino-2-bromobenzoyl)-1-(2,6-dichlorobenzoyl)-1H-pyrrolo[2,3-b]pyridin-5-yl)pyridin-2-yl)piperazine-1-carboxylate (1 g, 1.33 mmol, Eq: 1) and and copper(I) cyanide (239 mg, 2.66 mmol, Eq: 2) in NMP (13.3 ml) was stirred at 120° C. for 2 h. The mixture was partitioned between ethyl acetate (50 ml) and 1 M sodium carbonate (50 ml). The layers were separated. The aqueous layer was extracted with two 50-ml portions of ethyl acetate. The combined organic layers were washed with one 50-ml portion of brine, dried over anhydrous sodium sulfate, filtered and concentrated in vacuo. The crude material was purified by flash chromatography with n-heptane/ethyl acetate as eluent to give the title compound (438 mg, 46.2%) as yellow solid. MS m/e: 697 ([M+H+]$^+$).

b) tert-butyl 4-[5-[3-[2-cyano-3-[[ethyl(methyl)sulfamoyl]amino]benzoyl]-1-(2,6-dichlorobenzoyl)pyrrolo[2,3-b]pyridin-5-yl]-2-pyridyl]piperazine-1-carboxylate To a solution of tert-butyl 4-(5-(3-(3-amino-2-cyanobenzoyl)-1-(2,6-dichlorobenzoyl)-1H-pyrrolo[2,3-b]pyridin-5-yl)pyridin-2-yl)piperazine-1-carboxylate (438 mg, 629 µmol, Eq: 1) in 1,4-dioxane (3.34 ml) were added pyridine (497 mg, 509 µl, 6.29 mmol, Eq: 10) and ethyl(methyl)sulfamoyl chloride (347 mg, 2.2 mmol, Eq: 3.5) at RT. The reaction mixture was heated at 115° C. overnight. Further ethyl(methyl)sulfamoyl chloride (347 mg, 2.2 mmol, Eq: 3.5) was added and stirring was continued for 3 days at 115° C. The solvent was evaporated. The residue was partitioned between ethyl acetate (30 ml) and water (30 ml). The layers were separated. The aqueous layer was extracted with two 25-ml portion of ethyl acetate. The combined organic layers were washed with one 30-ml portion of saturated ammonium chloride solution, one 25-ml portion of brine solution, dried over anhydrous sodium sulfate, filtered and concentrated in vacuo to give the crude title compound (0.4 g, 50.6%), which was used in the next step without further purification. MS m/e: 818.3 ([M+H+]$^+$).

c) tert-butyl 4-(5-(3-(2-cyano-3-((N-ethyl-N-methylsulfamoyl)amino)benzoyl)-1H-pyrrolo[2,3-b]pyridin-5-yl)pyridin-2-yl)piperazine-1-carboxylate To a solution of tert-butyl 4-(5-(3-(2-cyano-3-((N-ethyl-N-methyl sulfamoyl)amino)benzoyl)-1-(2,6-dichlorobenzoyl)-1H-pyrrolo[2,3-b]pyridin-5-yl)pyridin-2-yl)piperazine-1-carboxylate (0.4 g, 318 µmol, Eq: 1) in methanol (3.18 ml) was added potassium carbonate (220 mg, 1.59 mmol, Eq: 5) at RT. The mixture was stirred at 60° C. for 1 h. The reaction mixture was partitioned between ethyl acetate (30 ml) and saturated ammonium chloride solution (30 ml). The layers were separated. The aqueous layer was extracted with two 30-ml portions of ethyl acetate. The combined organic layers were washed with one 25-ml portion of brine, dried over anhydrous sodium sulfate, filtered and concentrated in vacuo. The crude product was purified by flash chromatography with dichloromethane/methanol as eluent to give the title compound (47 mg, 21%) as light yellow solid. MS m/e: 645.4 ([M+H+]$^+$).

d) 3-[2-Cyano-3-[[ethyl(methyl)sulfamoyl]amino]benzoyl]-5-(6-piperazin-1-ylpyridin-3-yl)-1H-pyrrolo[2,3-b]pyridine hydrochloride To a solution of tert-butyl 4-(5-(3-(2-cyano-3-((N-ethyl-N-methyl sulfamoyl)amino)benzoyl)-1H-pyrrolo[2,3-b]pyridin-5-yl)pyridin-2-yl)piperazine-1-carboxylate (47.2 mg, 65.9 µmol, Eq: 1) in tetrahydrofuran (329 µl) was added 4 M hydrogen chloride solution in 1,4-dioxane (165 µl, 659 µmol, Eq: 10) at RT. Stirring was continued for 5 h. The precipitate was collected by filtration, washed with tetrahydrofuran and dried in vacuo to give the title compound (30.2 mg, 70.2%) as yellow solid. MS m/e: 545.3 ([M+H+]$^+$).

Intermediate 26

RS—N-[2,4-Difluoro-3-[5-(6-piperazin-1-yl-3-pyridyl)-1H-pyrrolo[2,3-b]pyridine-3-carbonyl]phenyl]butane-2-sulfonamide

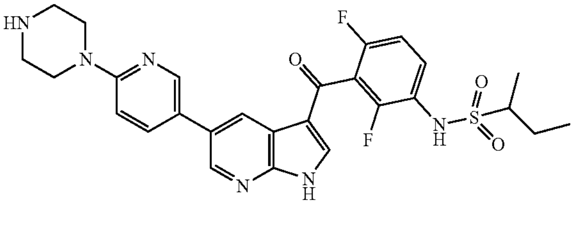 [SMILES: CCC(C)S(=O)(=O)Nc1ccc(F)c(C(=O)c2c[nH]c3ncc(-c4ccc(N5CCNCC5)nc4)cc23)c1F]

The title compound was obtained as off-white solid according to the general procedure VII after two deprotection steps, from RS—N-[3-[5-Bromo-1-(2,6-dichlorobenzoyl)pyrrolo[2,3-b]pyridine-3-carbonyl]-2,4-difluoro-phenyl]butane-2-sulfonamide and (6-(4-(tert-butoxycarbonyl)piperazin-1-yl)pyridin-3-yl)boronic acid. MS m/e: 555 ([M+H+]$^+$).

Intermediate 27

RS—N-[2,4-Difluoro-3-[5-(6-piperazin-1-yl-3-pyridyl)-1H-pyrrolo[2,3-b]pyridine-3-carbonyl]phenyl]cyclohexanesulfonamide

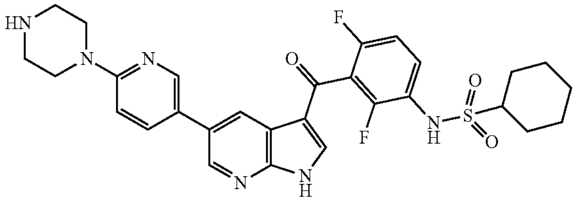 [SMILES: O=C(c1c(F)ccc(NS(=O)(=O)C2CCCCC2)c1F)c1c[nH]c2ncc(-c3ccc(N4CCNCC4)nc3)cc12]

The title compound was obtained as off-white solid according to the general procedure VII after two deprotection steps, from RS—N-[3-[5-Bromo-1-(2,6-dichlorobenzoyl)pyrrolo[2,3-b]pyridine-3-carbonyl]-2,4-difluoro-phenyl]cyclohexanesulfonamide and (6-(4-(tert-butoxycarbonyl)piperazin-1-yl)pyridin-3-yl)boronic acid. MS m/e: 581 ([M+H+]$^+$).

Intermediate 28

RS—N-[2,4-difluoro-3-[5-(6-piperazin-1-yl-3-pyridyl)-1H-pyrrolo[2,3-b]pyridine-3-carbonyl]phenyl]propane-2-sulfonamide

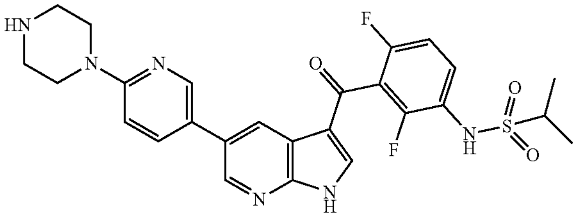 [SMILES: CC(C)S(=O)(=O)Nc1ccc(F)c(C(=O)c2c[nH]c3ncc(-c4ccc(N5CCNCC5)nc4)cc23)c1F]

The title compound was obtained as off-white solid according to the general procedure VII after two deprotection steps, from RS—N-[3-[5-Bromo-1-(2,6-dichlorobenzoyl)pyrrolo[2,3-b]pyridine-3-carbonyl]-2,4-difluoro-phenyl]propane-2-sulfonamide and (6-(4-(tert-butoxycarbonyl)piperazin-1-yl)pyridin-3-yl)boronic acid. MS m/e: 541 ([M+H+]+).

Intermediate 29

RS—N-[2,4-difluoro-3-[5-(4-piperazin-1-ylphenyl)-1H-pyrrolo[2,3-b]pyridine-3-carbonyl]phenyl]cyclopentanesulfonamide;2,2,2-trifluoroacetic acid

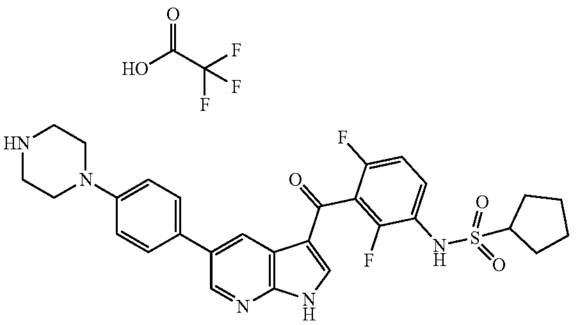 [SMILES: O=C(O)C(F)(F)F ; O=C(c1c(F)ccc(NS(=O)(=O)C2CCCC2)c1F)c1c[nH]c2ncc(-c3ccc(N4CCNCC4)cc3)cc12]

The title compound was obtained as yellow oil according to the general procedure VII after two deprotection steps, from RS—N-(3-(5-bromo-1-(2,6-dichlorobenzoyl)-1H-pyrrolo[2,3-b]pyridine-3-carbonyl)-2,4-difluorophenyl)cyclopentanesulfonamide and (4-(4-(tert-butoxycarbonyl)piperazin-1-yl)phenyl)boronic acid. MS m/e: 566.4 ([M+H+]$^+$).

Intermediate 30

2-[[1-[5-[3-[3-[[Ethyl(methyl)sulfamoyl]amino]-2,6-difluoro-benzoyl]-1H-pyrrolo[2,3-b]pyridin-5-yl]pyrimidin-2-yl]-4-piperidyl]-methyl-amino]acetic acid

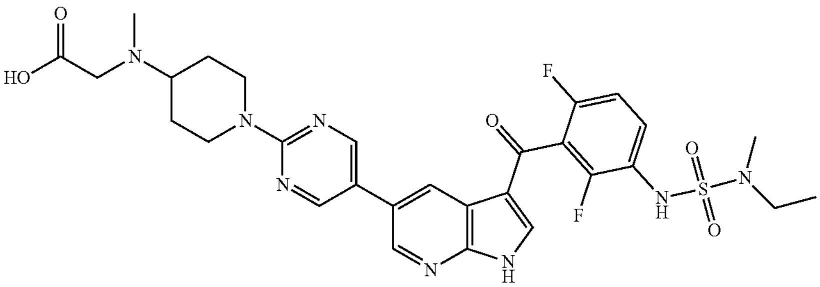 [SMILES: CCN(C)S(=O)(=O)Nc1ccc(F)c(C(=O)c2c[nH]c3ncc(-c4cnc(N5CCC(N(C)CC(=O)O)CC5)nc4)cc23)c1F]

a) 1-[5-(4,4,5,5-Tetramethyl-1,3,2-dioxaborolan-2-yl)pyrimidin-2-yl]piperidin-4-one To a solution of piperidin-4-one;hydrochloride (2.79 g, 20.58 mmol, 1.1 eq) in DMF (50 mL) was added 2-chloro-5-(4,4,5,5-tetramethyl-1,3,2-dioxaborolan-2-yl)pyrimidine (4.5 g, 18.71 mmol, 1 eq) and potassium carbonate (5.43 g, 39.29 mmol, 2.1 eq). Then the reaction was stirred at 100° C. for 12 h. Aqueous sodium chloride solution (300.0 ml) was added to quench the reaction, the reaction mixture was extracted with three 50-ml portions of ethyl acetate. The combined extracts were concentrated under reduced pressure to give a residue. The residue was purified by flash chromatography to give 1-[5-(4,4,5,5-tetramethyl-1,3,2-dioxaborolan-2-yl)pyrimidin-2-yl]piperidin-4-one (3 g, 9.9 mmol, 50.24% yield) as a white solid. MS m/e: 222.2 ([M+H+]+).

b) 1-(2,6-Dichlorobenzoyl)-3-[3-[[ethyl(methyl)sulfamoyl]amino]-2,6-difluoro-benzoyl]-5-[2-(4-oxo-1-piperidyl)pyrimidin-5-yl]pyrrolo[2,3-b]pyridine To a solution of 1-[5-(4,4,5,5-tetramethyl-1,3,2-dioxaborolan-2-yl)pyrimidin-2-yl]piperidin-4-one (1.13 g, 3.71 mmol, 1.2 eq) in 1,4-dioxane (40 mL) and water (4 mL) was added 5-bromo-1-(2,6-dichlorobenzoyl)-3-[3-[[ethyl(methyl)sulfamoyl]amino]-2,6-difluoro-benzoyl]pyrrolo[2,3-b]pyridine (2.0 g, 3.09 mmol, 1 eq), potassium carbonate (0.86 g, 6.19 mmol, 2 eq) and [1,1'-bis(diphenylphosphino)ferrocene]palladium(II) chloride (0.25 g, 0.310 mmol, 0.100 eq) at 25° C. Then the reaction was stirred at 100° C. under $N_2$ atmosphere for 2 h. The reaction mixture was concentrated under reduced pressure to give a residue. The residue was purified by flash chromatography to give 1-(2,6-dichlorobenzoyl)-3-[3-[[ethyl(methyl)sulfamoyl]amino]-2,6-difluoro-benzoyl]-5-[2-(4-oxo-1-piperidyl)pyrimidin-5-yl]pyrrolo[2,3-b]pyridine (1.5 g, 2.02 mmol, 60.05% yield) as a brown oil. MS m/e: 742 ([M+H+]$^+$).

c) tert-Butyl 2-[[1-[5-[1-(2,6-dichlorobenzoyl)-3-[3-[[ethyl(methyl)sulfamoyl]amino]-2,6-difluoro-benzoyl]pyrrolo[2,3-b]pyridin-5-yl]pyrimidin-2-yl]-4-piperidyl]amino]acetate To a solution of 1-(2,6-dichlorobenzoyl)-3-[3-[[ethyl(methyl)sulfamoyl]amino]-2,6-difluoro-benzoyl]-5-[2-(4-oxo-1-piperidyl)pyrimidin-5-yl]pyrrolo[2,3-b]pyridine (120.0 mg, 0.160 mmol, 1 eq) in 1,2-dichloroethane (12 mL) was added DIPEA (20.89 mg, 0.160 mmol, 1 eq) and and tert-butyl glycine hydrochloride (40.63 mg, 0.240 mmol, 1.5 eq). After 1 h, sodium cyanoborohydride (20.31 mg, 0.320 mmol, 2 eq) and acetic acid (9.7 mg, 0.160 mmol, 1 eq) were added to the reaction. Then the reaction was stirred at 30° C. for 12 h. The reaction mixture was concentrated under reduced pressure to give crude title compound (150 mg, 0.170 mmol, 108.22% yield), which was used for next step without further purification. MS m/e: 856.9 ([M+H+]$^+$).

d) tert-Butyl 2-[[1-[5-[1-(2,6-dichlorobenzoyl)-3-[3-[[ethyl(methyl)sulfamoyl]amino]-2,6-difluoro-benzoyl]pyrrolo[2,3-b]pyridin-5-yl]pyrimidin-2-yl]-4-piperidyl]methyl-amino]acetate To a solution of tert-butyl 2-[[1-[5-[1-(2,6-dichlorobenzoyl)-3-[3-[[ethyl(methyl)sulfamoyl]amino]-2,6-difluoro-benzoyl]pyrrolo[2,3-b]pyridin-5-yl]pyrimidin-2-yl]-4-piperidyl]amino]acetate (150.0 mg, 0.170 mmol, 1 eq) in 1,2-dichloroethane (12 mL) was added formaldehyde (28.38 mg, 0.350 mmol, 2 eq) and acetic acid (10.5 mg, 0.170 mmol, 1 eq) at 30° C. After 1 h, sodium cyanoborohydride (16.48 mg, 0.260 mmol, 1.5 eq) was added the reaction, then the reaction was stirred at 30° C. for 1 h. Aqueous sodium chloride solution (10.0 mL) was added to quench the reaction, the reaction mixture was extracted with three 10-ml portions of ethyl acetate. The combined extracts were concentrated under reduced pressure to give crude title compound (160 mg, 0.180 mmol, 104.95% yield), which was used for next step without further purification. MS m/e: 871.0 ([M+H+]$^+$).

e) tert-Butyl 2-[[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]methyl-amino]acetate To a solution of d) tert-butyl 2-[[1-[5-[1-(2,6-dichlorobenzoyl)-3-[3-[[ethyl(methyl)sulfamoyl]amino]-2,6-difluoro-benzoyl]pyrrolo[2,3-b]pyridin-5-yl]pyrimidin-2-yl]-4-piperidyl]-methyl-amino]acetate (160.0 mg, 0.180 mmol, 1 eq) in THF (5 mL) was added ammonium hydroxide (5.0 mL, 0.180 mmol, 1 eq) at 30° C. Then the reaction was stirred at 30° C. for 12 h. Aqueous sodium chloride solution (10.0 ml) was added to quench the reaction, the reaction mixture was extracted with three 10-ml portions of ethyl acetate. The combined extracts were concentrated under reduced pressure to give crude title compound (120 mg, 0.170 mmol, 93.57% yield), which was used for next step without further purification. MS m/e: 699.1 ([M+H+]$^+$).

f) 2-[[1-[5-[3-[3-[[Ethyl(methyl)sulfamoyl]amino]-2,6-difluoro-benzoyl]-1H-pyrrolo[2,3-b]pyridin-5-yl]pyrimidin-2-yl]-4-piperidyl]methyl-amino]acetic acid To a solution of tert-butyl 2-[[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]-methyl-amino]acetate (145.0 mg, 0.210 mmol, 1 eq) in DCM (2 mL) was added TFA (2.0 mL, 0.210 mmol, 1 eq) at 30° C. Then the reaction was stirred for 2 h. The reaction mixture was concentrated under reduced pressure to give a residue. The residue was purified by prep-HPLC and lyophilized to give the title compound (19 mg, 0.030 mmol, 14.25% yield) as a white solid. MS m/e: 643.1 ([M+H±]$^+$).

Intermediate 31

3-[3-[[Ethyl(methyl)sulfamoyl]amino]-2,6-difluoro-benzoyl]-5-[2-[4-(methylamino)-1-piperidyl]pyrimidin-5-yl]-1H-pyrrolo[2,3-b]pyridine

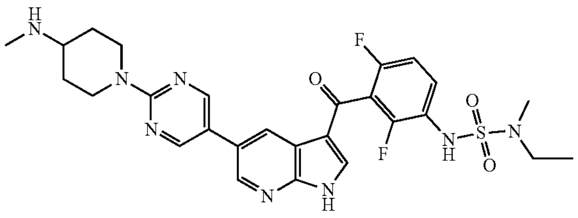 [SMILES: CCN(C)S(=O)(=O)Nc1ccc(F)c(C(=O)c2c[nH]c3ncc(-c4cnc(N5CCC(NC)CC5)nc4)cc23)c1F]

a) 3-[3-[[Ethyl(methyl)sulfamoyl]amino]-2,6-difluoro-benzoyl]-5-[2-(4-oxo-1-piperidyl)pyrimidin-5-yl]-1H-pyrrolo[2,3-b]pyridine To a solution of 1-(2,6-dichlorobenzoyl)-3-[3-[[ethyl (methyl)sulfamoyl]amino]-2,6-difluoro-benzoyl]-5-[2-(4-oxo-1-piperidyl)pyrimidin-5-yl]pyrrolo[2,3-b]pyridine (25.0 mg, 0.030 mmol, 1 eq) in THF (1 mL) was added and NH3/water (1.0 mL, 0.040 mmol, 1.1 eq). Then the reaction was stirred at 25° C. for 16 h. The reaction was poured into water (10 mL) and extracted with three 10-ml portions of ethyl acetate. The organic layer was concentrated under reduced pressure to give crude title compound (25 mg, 0.040 mmol, 130.37% yield) as yellow solid, which was used for next step without further purification.

b) 3-[3-[[Ethyl(methyl)sulfamoyl]amino]-2,6-difluoro-benzoyl]-5-[2-[4-(methylamino)-1-piperidyl] pyrimidin-5-yl]-1H-pyrrolo[2,3-b]pyridine To a solution of 3-[3-[[ethyl(methyl)sulfamoyl]amino]-2,6-difluoro-benzoyl]-5-[2-(4-oxo-1-piperidyl)pyrimidin-5-yl]-1H-pyrrolo[2,3-b]pyridine (25.0 mg, 0.040 mmol, 1 eq) in methanol (3.26 mL) was added DIPEA (6.24 mg, 0.050 mmol, 1.1 eq) and methylamine hydrochloride (3.26 mg, 0.050 mmol, 1.1 eq). The reaction mixture was turned to yellow. After 1 h, sodium cyanoborohydride (5.52 mg, 0.090 mmol, 2 eq) and acetic acid (2.64 mg, 0.040 mmol, 1 eq) were added to the reaction. Then the reaction was stirred at 25° C. for 3 h. The reaction was purified by prep-HPLC to give the title compound (10 mg, 0.020 mmol, 38.97% yield) as yellow gum. MS m/e: 585.0 ([M+H+]$^+$).

Intermediate 32

2-[[1-[5-[3-[3-[[Ethyl(methyl)sulfamoyl]amino]-2,6-difluoro-benzoyl]-1H-pyrrolo[2,3-b]pyridin-5-yl] pyrimidin-2-yl]-4-piperidyl]amino]acetic acid

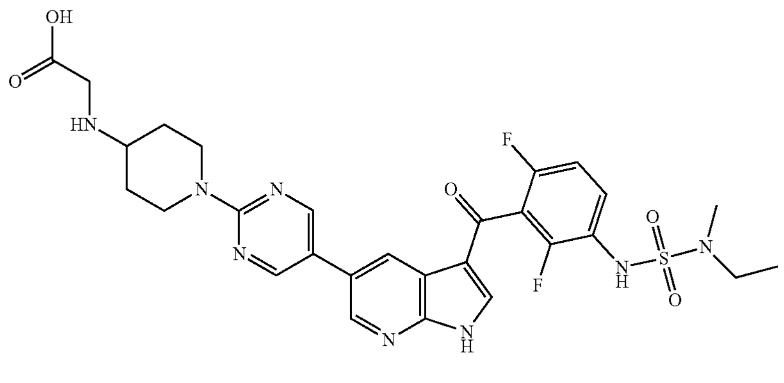 [SMILES: CCN(C)S(=O)(=O)Nc1ccc(F)c(C(=O)c2c[nH]c3ncc(-c4cnc(N5CCC(NCC(=O)O)CC5)nc4)cc23)c1F]

a) Methyl 2-[tert-butoxycarbonyl-[1-[5-(4,4,5,5-tetramethyl-1,3,2-dioxaborolan-2-yl)pyrimidin-2-yl]-4-piperidyl]amino]acetate To a solution of 1-[5-(4,4,5,5-tetramethyl-1,3,2-dioxaborolan-2-yl)pyrimidin-2-yl]piperidin-4-one (500.0 mg, 1.65 mmol, 1 eq), triethylamine (0.46 mL, 3.3 mmol, 2 eq) and glycine methyl ester hydrochloride (248.48 mg, 1.98 mmol, 1.2 eq) in methanol (21.87 mL) was stirred at 25° C. for 1 h. Sodium cyanoborohydride (310.92 mg, 4.95 mmol, 3 eq) was added, then the reaction was stirred at 25° C. for another 15 h. Then Di-tert-butyl dicarbonate (1078.64 mg, 4.95 mmol, 3 eq) and potassium carbonate (683.83 mg, 4.95 mmol, 3 eq) with water (21.87 mL) was added and the mixture was stirred at 25° C. for another 15 h. The mixture was extracted with three 50-ml portions of ethyl acetate. The combined organic layers were concentrated. The residue was purified by flash chromatography to give the title compound (300 mg, 0.760 mmol, 46.14% yield) as colorless gum. MS m/e: 395.1 ([M+H+]$^+$).

b) Methyl 2-[tert-butoxycarbonyl-[1-[5-[1-(2,6-dichlorobenzoyl)-3-[3-[[ethyl(methyl)sulfamoyl] amino]-2,6-difluoro-benzoyl]pyrrolo[2,3-b]pyridin-5-yl]pyrimidin-2-yl]-4-piperidyl]amino]acetate The reaction mixture of methyl 2-[tert-butoxy carbonyl-[1-[5-(4,4,5,5-tetramethyl-1,3,2-dioxaborolan-2-yl)pyrimidin-2-yl]-4-piperidyl]amino]acetate (200.0 mg, 0.420 mmol, 1.36 eq), 5-bromo-1-(2,6-dichlorobenzoyl)-3-[3-[[ethyl(methyl)sulfamoyl]amino]-2,6-difluoro-benzoyl]pyrrolo[2,3-b]pyridine (200.0 mg, 0.310 mmol, 1 eq), potassium carbonate (128.31 mg, 0.930 mmol, 3 eq) and 1,1'-bis (diphenylphosphino)ferrocene-palladium(II)dichloride dichloromethane complex (25.25 mg, 0.030 mmol, 0.100 eq) in water (0.500 mL) and 1,4-dioxane (5 mL) was stirred at 100° C. for 2 h. The reaction mixture was purified by prep-TLC to give the title compound (150 mg, 0.160 mmol, 52.93% yield) as yellow solid. MS m/e: 915.0 ([M+H+]$^+$).

c) 2-[tert-Butoxycarbonyl-[1-[5-[3-[3-[[ethyl (methyl)sulfamoyl]amino]-2,6-difluoro-benzoyl]-1H-pyrrolo[2,3-b]pyridin-5-yl]pyrimidin-2-yl]-4-piperidyl]amino]acetic acid To a solution of methyl 2-[tert-butoxycarbonyl-[1-[5-[1-(2,6-dichlorobenzoyl)-3-[3-[[ethyl(methyl)sulfamoyl] amino]-2,6-difluoro-benzoyl]pyrrolo[2,3-b]pyridin-5-yl]pyrimidin-2-yl]-4-piperidyl]amino]acetate (150.0 mg, 0.160 mmol, 1 eq) in methanol (3 mL) and water (0.500 mL) was added benzyltrimethylammoniumhydroxide (219.0 mg, 1.31 mmol, 8 eq). The reaction mixture was stirred at 75° C. for 16 h. The reaction mixture was purified by prep-HPLC to give the title compound (100 mg, 0.140 mmol, 83.77% yield) as white solid. MS m/e: 729 ([M+H+]$^+$).

d) 2-[[1-[5-[3-[3-[[Ethyl(methyl)sulfamoyl]amino]-2,6-difluoro-benzoyl]-1H-pyrrolo[2,3-b]pyridin-5-yl]pyrimidin-2-yl]-4-piperidyl]amino]acetic acid; 2,2,2-trifluoroacetic acid To 2-[tert-butoxycarbonyl-[1-[5-[3-[3-[[ethyl(methyl)sulfamoyl]amino]-2,6-difluoro-benzoyl]-1H-pyrrolo[2,3-b]

pyridin-5-yl]pyrimidin-2-yl]-4-piperidyl]amino]acetic acid (30.0 mg, 0.040 mmol, 1 eq) was added TFA (5.0 mL, 18 mmol, 437.26 eq). The reaction mixture was stirred at 25° C. for 4 h. The reaction mixture was concentrated to give the title compound (30 mg, 0.040 mmol, 109.57% yield) as yellow gum. MS m/e: 629.2 ([M+H+]$^+$).

Intermediate 33

3-[3-[[Ethyl(methyl)sulfamoyl]amino]-2,6-difluoro-benzoyl]-5-[6-[4-(methylamino)-1-piperidyl]-3-pyridyl]-1H-pyrrolo[2,3-b]pyridine

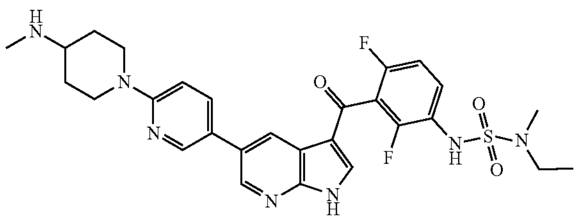 [SMILES: CCN(C)S(=O)(=O)Nc1ccc(F)c(C(=O)c2c[nH]c3ncc(-c4ccc(N5CCC(NC)CC5)nc4)cc23)c1F]

a) 1-(2,6-Dichlorobenzoyl)-3-[3-[[ethyl(methyl) sulfamoyl]amino]-2,6-difluoro-benzoyl]-5-[6-[4-(methylamino)-1-piperidyl]-3-pyridyl]pyrrolo[2,3-b] pyridine To a solution of 1-(2,6-dichlorobenzoyl)-3-[3-[[ethyl (methyl)sulfamoyl]amino]-2,6-difluoro-benzoyl]-5-[6-(4-oxo-1-piperidyl)-3-pyridyl]pyrrolo[2,3-b]pyridine (100.0 mg, 0.130 mmol, 1 eq) in 1,2-dichloroethane (5 mL) was added DIPEA (19.17 mg, 0.150 mmol, 1.1 eq) and methylamine hydrochloride (27.31 mg, 0.400 mmol, 3 eq). After 1 h, sodium cyanoborohydride (33.89 mg, 0.540 mmol, 4 eq) and acetic acid (8.1 mg, 0.130 mmol, 1 eq) was added to give a turbid solution. Then the reaction was stirred at 25° C. for 12 h. The reaction was concentrated under reduced pressure to give crude title compound (100 mg, 0.130 mmol, 98.01% yield) as a yellow solid, which was used for next step without further purification. MS m/e: 756.4 ([M+H+]$^+$).

b) 3-[3-[[Ethyl(methyl)sulfamoyl]amino]-2,6-difluoro-benzoyl]-5-[6-[4-(methylamino)-1-piperidyl]-3-pyridyl]-1H-pyrrolo[2,3-b]pyridine To a solution of 1-(2,6-dichlorobenzoyl)-3-[3-[[ethyl (methyl)sulfamoyl]amino]-2,6-difluoro-benzoyl]-5-[6-[4-(methylamino)-1-piperidyl]-3-pyridyl]pyrrolo[2,3-b]pyridine (95.0 mg, 0.130 mmol, 1 eq) in THF (2.38 mL) was added ammonium hydroxide solution (0.5 mL) at 25° C. to give a yellow mixture. Then the reaction was stirred at 25° C. for 12 h. Aqueous sodium chloride solution (10.0 mL) was added to quench the reaction. The reaction mixture was extracted with three 10-ml portions of ethyl acetate. The combined extracts were concentrated under reduced pressure, purified by prep-HPLC and lyophilized to give the title compound (30 mg, 0.050 mmol, 40.94% yield) as a yellow solid. MS m/e: 584.4 ([M+H+]$^+$).

Intermediate 34

2-[[1-[4-[3-[3-[[Ethyl(methyl)sulfamoyl]amino]-2,6-difluoro-benzoyl]-1H-pyrrolo[2,3-b]pyridin-5-yl] phenyl]-4-piperidyl]amino]acetic acid

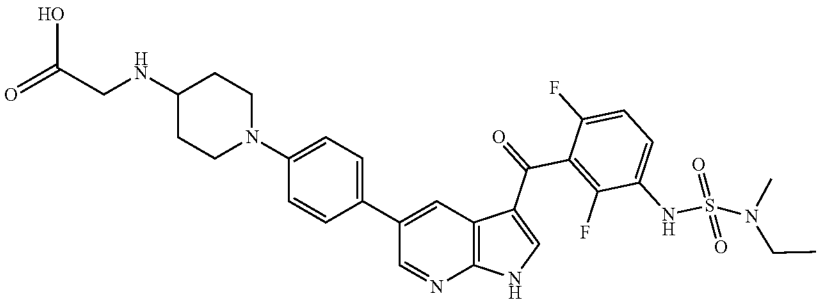 [SMILES: CCN(C)S(=O)(=O)Nc1ccc(F)c(C(=O)c2c[nH]c3ncc(-c4ccc(N5CCC(NCC(=O)O)CC5)cc4)cc23)c1F]

a) 8-[4-[1-(2,6-Dichlorobenzoyl)-3-[3-[[ethyl (methyl)sulfamoyl]amino]-2,6-difluoro-benzoyl] pyrrolo[2,3-b]pyridin-5-yl]phenyl]-1,4-dioxa-8-azaspiro[4.5]decane A mixture of 5-bromo-1-(2,6-dichlorobenzoyl)-3-[3-[[ethyl(methyl)sulfamoyl]amino]-2,6-difluoro-benzoyl]pyrrolo[2,3-b]pyridine (2000.0 mg, 3.09 mmol, 1 eq), 8-[4-(4,4,5,5-tetramethyl-1,3,2-dioxaborolan-2-yl)phenyl]-1,4-dioxa-8-azaspiro[4.5]decane (1175.21 mg, 3.4 mmol, 1.1 eq), potassium carbonate (1283.07 mg, 9.28 mmol, 3 eq), 1,1'-bis(diphenylphosphino)ferrocene-palladium(II)dichloride dichloromethane complex (126.26 mg, 0.150 mmol, 0.050 eq) in water (4 mL) and 1,4-dioxane (400 mL) was stirred at 100° C. for 2 h. The mixture was diluted with EtOAc (200 mL) and filtered. The filtrate was concentrated to to give the crude title compound (3.5 g, quantitative). MS m/e: 783.9 ([M+H+]$^+$).

b) 1-(2,6-Dichlorobenzoyl)-3-[3-[[ethyl(methyl) sulfamoyl]amino]-2,6-difluoro-benzoyl]-5-[4-(4-oxo-1-piperidyl)phenyl]pyrrolo[2,3-b]pyridine The crude 8-[4-[1-(2,6-dichlorobenzoyl)-3-[3-[[ethyl (methyl)sulfamoyl]amino]-2,6-difluoro-benzoyl]pyrrolo[2,3-b]pyridin-5-yl]phenyl]-1,4-dioxa-8-azaspiro[4.5]decane was dissolved in THF (60.7 mL) and sulfuric acid (aq) (50.0 mL, 3.09 mmol, 1 eq), then the mixture was stirred at 50° C. for 16 h. The reaction mixture was diluted with water (200 mL) and extracted with three 200-ml portions of ethyl acetate. The combined organic layer was concentrated and the residue was purified by flash-chromatography to give the title compound (1300 mg, 1.76 mmol, 56.73% yield) as yellow solid.

c) 2-[[1-[4-[3-[3-[[Ethyl(methyl)sulfamoyl]amino]-2,6-difluoro-benzoyl]-1H-pyrrolo[2,3-b]pyridin-5-yl]phenyl]-4-piperidyl]amino]acetic acid To a mixture of 1-(2,6-dichlorobenzoyl)-3-[3-[[ethyl(methyl)sulfamoyl]amino]-2,6-difluoro-benzoyl]-5-[4-(4-oxo-1-piperidyl)phenyl]pyrrolo[2,3-b]pyridine (500.0 mg, 0.680 mmol, 1 eq), glycine methyl ester hydrochloride (169.52 mg, 1.35 mmol, 2 eq) in methanol (10 mL) and DCE (20 mL) was added trimethylamine (119.72 mg, 2.03 mmol, 3 eq) and the mixture was stirred at 30° C. for 1 h. Then sodium cyanoborohydride (127.28 mg, 2.03 mmol, 3 eq) was added and the mixture was stirred for another 13 h. To the mixture was added sodium methoxide in MeOH (4.0 mL, 20 mmol, 29.62 eq) and the mixture was stirred at 30° C. for another 16 h. The mixture was concentrated and the adjusted to pH 4 with concentrated hydrochloric acid. The residue was purified by prep-HPLC to give the title compound (100 mg, 0.160 mmol, 23.64% yield) as light yellow solid.

Intermediate 35

2-[[1-[5-[3-[3-[[Ethyl(methyl)sulfamoyl]amino]-2,6-difluoro-benzoyl]-1H-pyrrolo[2,3-b]pyridin-5-yl]-2-pyridyl]-4-piperidyl]-methyl-amino]acetic acid

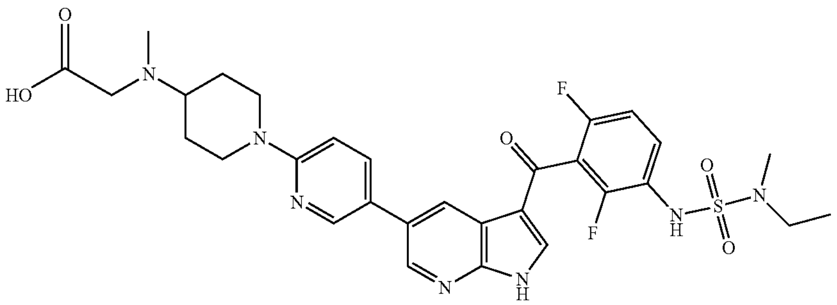 [SMILES: CCN(C)S(=O)(=O)Nc1ccc(F)c(C(=O)c2c[nH]c3ncc(-c4ccc(N5CCC(N(C)CC(=O)O)CC5)nc4)cc23)c1F]

The title compound was prepared in analogy to 2-[[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]-methyl-amino]acetic acid (intermediate 30). MS m/e: 642.2 ([M+H+]$^+$).

Intermediate 36

N-[3-[5-[6-[4-(3-Aminocyclobutoxy)-1-piperidyl]-3-pyridyl]-1H-pyrrolo[2,3-b]pyridine-3-carbonyl]-2,4-difluoro-phenyl]pyrrolidine-1-sulfonamide;2,2,2-trifluoroacetic acid

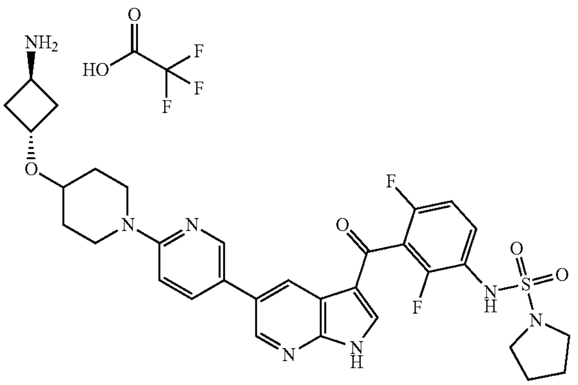 [SMILES: N[C@H]1C[C@H](OC2CCN(c3ccc(-c4cnc5[nH]cc(C(=O)c6c(F)ccc(NS(=O)(=O)N7CCCC7)c6F)c5c4)cn3)CC2)C1 ; O=C(O)C(F)(F)F]

The title compound was obtained as light yellow solid according to the general procedure VII after two deprotection steps, from N-(3-(5-bromo-1-(2,6-dichlorobenzoyl)-1H-pyrrolo[2,3-b]pyridine-3-carbonyl)-2,4-difluorophenyl)pyrrolidine-1-sulfonamide and tert-butyl ((1r,3r)-3-((1-(5-(4,4,5,5-tetramethyl-1,3,2-dioxaborolan-2-yl)-4,5-dihydropyridin-2-yl)piperidin-4-yl)oxy)cyclobutyl) carbamate. MS m/e: 652.2 ([M+H+]$^+$).

Intermediate 37

2-[[1-[5-[3-[3-[[Ethyl(methyl)sulfamoyl]amino]-2,6-difluoro-benzoyl]-1H-pyrrolo[2,3-b]pyridin-5-yl]-2-pyridyl]-4-piperidyl]amino]acetic acid

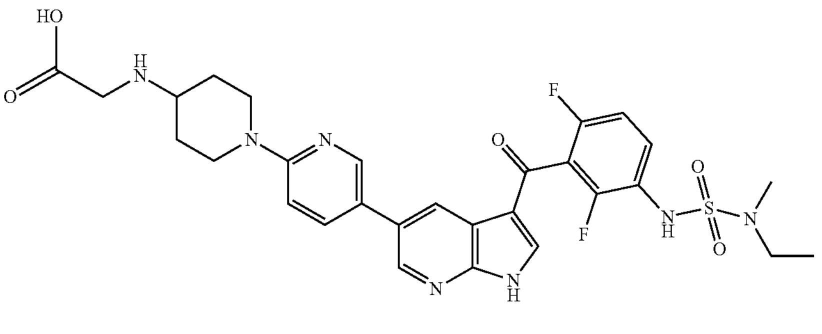 [SMILES: CCN(C)S(=O)(=O)Nc1ccc(F)c(C(=O)c2c[nH]c3ncc(-c4ccc(N5CCC(NCC(=O)O)CC5)nc4)cc23)c1F]

The title compound was prepared in analogy to 2-[[1-[4-[3-[3-[[ethyl(methyl)sulfamoyl]amino]-2,6-difluoro-benzoyl]-1H-pyrrolo[2,3-b]pyridin-5-yl]phenyl]-4-piperidyl]amino]acetic acid (intermediate 34). MS m/e: 628.3 ([M+H+]$^+$).

Intermediate 38

1-[5-[3-[3-[[Ethyl(methyl)sulfamoyl]amino]-2,6-difluoro-benzoyl]-1H-pyrrolo[2,3-b]pyridin-5-yl]pyrimidin-2-yl]piperidine-4-carboxylic acid

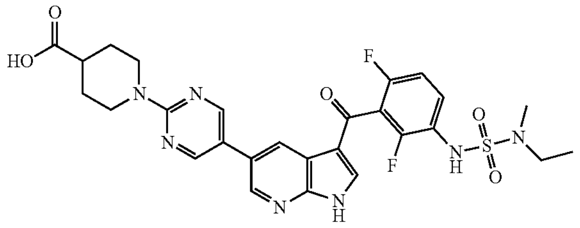 [SMILES: CCN(C)S(=O)(=O)Nc1ccc(F)c(C(=O)c2c[nH]c3ncc(-c4cnc(N5CCC(C(=O)O)CC5)nc4)cc23)c1F]

a) Methyl 1-(5-bromopyrimidin-2-yl)piperidine-4-carboxylate

To a solution of methyl 4-piperidinecarboxylate (1.0 g, 6.98 mmol, 1 eq) in ethanol (10 mL) was added DIPEA (4.5 g, 34.92 mmol, 5 eq) the mixture was stirred at room temperature for 15 min, then 5-bromo-2-chloropyrimidine (1.35 g, 6.98 mmol, 1 eq) was added and the mixture was stirred at 70° C. for 1 hour. The mixture was concentrated to get methyl 1-(5-bromopyrimidin-2-yl)piperidine-4-carboxylate (2 g, 6.66 mmol, 95.41% yield) as a yellow solid used directly in the next step. MS m/e: 302 ([M+H+]$^+$).

b) Methyl 1-[5-(4,4,5,5-tetramethyl-1,3,2-dioxaborolan-2-yl)pyrimidin-2-yl]piperidine-4-carboxylate A mixture of methyl 1-(5-bromopyrimidin-2-yl)piperidine-4-carboxylate (1.0 g, 3.33 mmol, 1 eq), bis(pinacolato)diboron (1.69 g, 6.66 mmol, 2 eq), potassium acetate (0.98 g, 10 mmol, 3 eq) and Pd(dppf)Cl2 (0.24 g, 0.330 mmol, 0.100 eq) in 1,4-dioxane (20 mL) was purged with $N_2$ for 3 times, and the mixture was stirred at 90° C. for 12 hours under $N_2$ atmosphere. The reaction mixture was filtered and the filtrate was concentrated in vacuo. Purification by prep-HPLC gave the title compound (900 mg, 2.59 mmol, 77.8% yield) as a yellow solid.

c) Methyl 1-[5-[1-(2,6-dichlorobenzoyl)-3-[3-[[ethyl(methyl)sulfamoyl]amino]-2,6-difluoro-benzoyl]pyrrolo[2,3-b]pyridin-5-yl]pyrimidin-2-yl]piperidine-4-carboxylate To a solution of 5-bromo-1-(2,6-dichlorobenzoyl)-3-[3-[[ethyl(methyl)sulfamoyl]amino]-2,6-difluoro-benzoyl]pyrrolo[2,3-b]pyridine (0.5 g, 0.770 mmol, 1 eq), cesium carbonate (1.55 mL, 2.32 mmol, 3 eq) and [2-(4-methoxycarbonyl-1-piperidyl)pyrimidin-5-yl]boronic acid (0.25 g, 0.930 mmol, 1.2 eq) in toluene (7.5 mL) was added Xphos-Pd-G3 (0.07 g, 0.080 mmol, 0.100 eq) and the reaction mixture was stirred at 90° C. for 12 h. The reaction mixture was concentrated to get the crude title compound (150 mg, 0.190 mmol, 24.65% yield) as a white solid. MS m/e: 786.3 ([M+H+]$^+$).

d) 1-[5-[3-[3-[[Ethyl(methyl)sulfamoyl]amino]-2,6-difluoro-benzoyl]-1H-pyrrolo[2,3-b]pyridin-5-yl]pyrimidin-2-yl]piperidine-4-carboxylic acid To a solution of methyl 1-[5-[1-(2,6-dichlorobenzoyl)-3-[3-[[ethyl(methyl)sulfamoyl]amino]-2,6-difluoro-benzoyl]pyrrolo[2,3-b]pyridin-5-yl]pyrimidin-2-yl]piperidine-4-carboxylate (110.0 mg, 0.140 mmol, 1 eq) in methanol (10 mL) was added potassium carbonate (57.89 mg, 0.420 mmol, 3 eq). The mixture was stirred at 60° C. for 2 hours. Then LiOH (7.83 mg, 0.280 mmol, 2 eq) and water (2 mL) was added the mixture was stirred at 60° C. for 2 hours. The reaction mixture was concentrated. The residue was partitioned between water (10 ml) and ethyl acetate (20 ml). The pH was adjusted to 1 by addition of hydrogen chloride in ethyl acetate. The layers were separated. The aqueous layer was extracted with two 20-ml portions of ethyl acetate. The combined organic layers were washed with one 50-ml portion of brine, dried over sodium sulphate, filtrated and concentrated in vacuo. Purification by prep-HPLC gave the title compound (51.6 mg, 0.090 mmol, 61.54% yield) as a white solid. MS m/e: 600.3 ([M+H+]$^+$).

Intermediate 39

2-[1-[5-[3-[3-[[Ethyl(methyl)sulfamoyl]amino]-2,6-difluoro-benzoyl]-1H-pyrrolo[2,3-b]pyridin-5-yl]pyrimidin-2-yl]-4-piperidyl]acetic acid

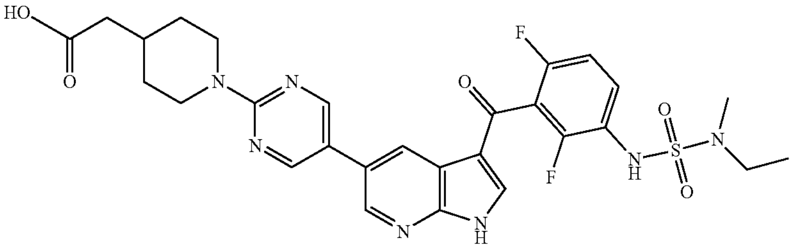 [SMILES: CCN(C)S(=O)(=O)Nc1ccc(F)c(C(=O)c2c[nH]c3ncc(-c4cnc(N5CCC(CC(=O)O)CC5)nc4)cc23)c1F]

The title compound was prepared in analogy to 1-[5-[3-[3-[[ethyl(methyl)sulfamoyl]amino]-2,6-difluoro-benzoyl]-1H-pyrrolo[2,3-b]pyridin-5-yl]pyrimidin-2-yl]piperidine-4-carboxylic acid (intermediate 38). MS m/e: 614.4 ([M+H+]$^+$).

Intermediate 40

(3R)—N-[3-[5-[6-(2,6-Diazaspiro[3.3]heptan-2-yl)-3-pyridyl]-1H-pyrrolo[2,3-b]pyridine-3-carbonyl]-2,4-difluoro-phenyl]-3-fluoro-pyrrolidine-1-sulfonamide;2,2,2-trifluoroacetic acid

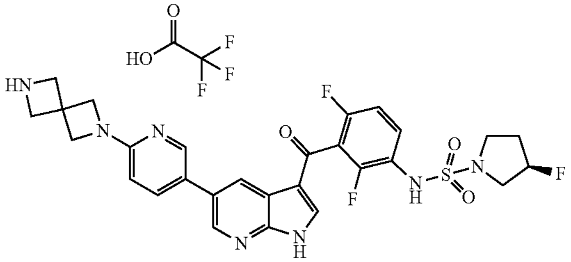 [SMILES: O=C(c1c(F)ccc(NS(=O)(=O)N2CC[C@@H](F)C2)c1F)c1c[nH]c2ncc(-c3ccc(N4CC5(CNC5)C4)nc3)cc12 ; O=C(O)C(F)(F)F]

The title compound was obtained as light yellow solid according to the general procedure VII after one deprotection step, from (R)—N-(3-(5-bromo-1-(2,6-dichlorobenzoyl)-1H-pyrrolo[2,3-b]pyridine-3-carbonyl)-2,4-difluoro-phenyl)-3-fluoropyrrolidine-1-sulfonamide and (6-(6-(tert-butoxycarbonyl)-2,6-diazaspiro[3.3]heptan-2-yl)pyridin-3-yl)boronic acid. MS m/e: 598.3 ([M+H+]$^+$).

Intermediate 41

N-[3-[5-[4-(2,6-Diazaspiro[3.3]heptan-2-yl)phenyl]-1H-pyrrolo[2,3-b]pyridine-3-carbonyl]-2,4-difluoro-phenyl]pyrrolidine-1-sulfonamide; 2,2,2-trifluoro-acetic acid

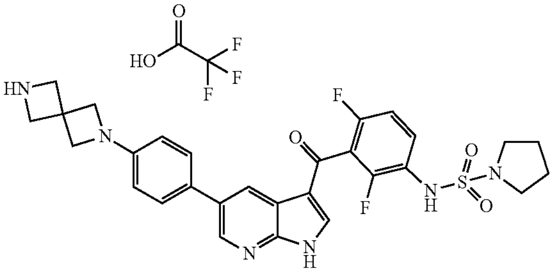

The title compound was obtained as yellow solid according to the general procedure VII after one deprotection step, from N-(3-(5-bromo-1-(2,6-dichlorobenzoyl)-1H-pyrrolo[2,3-b]pyridine-3-carbonyl)-2,4-difluorophenyl)pyrrolidine-1-sulfonamide and tert-butyl 6-(4-(4,4,5,5-tetramethyl-1,3,2-dioxaborolan-2-yl)phenyl)-2,6-di azaspiro[3.3]heptane-2-carboxylate. MS m/e: 579.2 ([M+H+]$^+$).

Intermediate 42

N-[3-[5-[2-(2,6-Diazaspiro[3.3]heptan-2-yl)pyrimidin-5-yl]-1H-pyrrolo[2,3-b]pyridine-3-carbonyl]-2,4-difluoro-phenyl]pyrrolidine-1-sulfonamide;2,2,2-trifluoroacetic acid

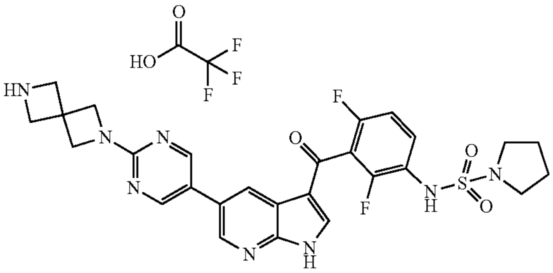 [SMILES: O=C(c1c(F)ccc(NS(=O)(=O)N2CCCC2)c1F)c1c[nH]c2ncc(-c3cnc(N4CC5(CNC5)C4)nc3)cc12 ; O=C(O)C(F)(F)F]

The title compound was obtained as white solid according to the general procedure VII after one deprotection step, from N-(3-(5-bromo-1-(2,6-dichlorobenzoyl)-1H-pyrrolo[2,3-b]pyridine-3-carbonyl)-2,4-difluorophenyl)pyrrolidine-1-sulfonamide and tert-butyl 6-(5-(4,4,5,5-tetramethyl-1,3,2-dioxaborolan-2-yl)pyrimidin-2-yl)-2,6-diazaspiro[3.3]heptane-2-carboxylate. MS m/e: 581.3 ([M+H+]$^+$).

Example of Formula I

General Procedure VIII: Amide Coupling

To a mixture of an acid of general intermediate formula II-d (1 eq) in a solvent such as N,N-dimethylformamide or N-methylpyrrolidone (0.1-0.3 M) is added a coupling reagent such as HATU (1-[bis(dimethyl amino)methylene]-1H-1,2,3-triazol[4,5-b]pyridinium 3-oxide hexafluorophosphate; 1 eq). The reaction mixture is stirred at room temperature for 30 minutes. An amine intermediate of general intermediate formula III-b is added and stirring is continued for 1-24 h. The reaction mixture is partitioned between an organic solvent such as ethyl acetate or dichloromethane/methanol (19:1) and 1M sodium bicarbonate solution. The layers are separated. The aqueous layer is extracted with one or two portions of organic solvent. The combined organic layers are washed with one portion of brine, dried over anhydrous sodium sulfate, filtered and concentrated in vacuo. Purification by flash-chromatography with dichloromethane/methanol gives a compound of intermediate formula I-b.

Example A 1

5-[6-[4-[2-[4-[4-(2,6-Dioxopiperidin-3-yl)oxyphenyl]piperidin-1-yl]acetyl]piperazin-1-yl]pyridin-3-yl]-3-[3-[[ethyl(methyl)sulfamoyl]amino]-2,6-difluorobenzoyl]-1H-pyrrolo[2,3-b]pyridine

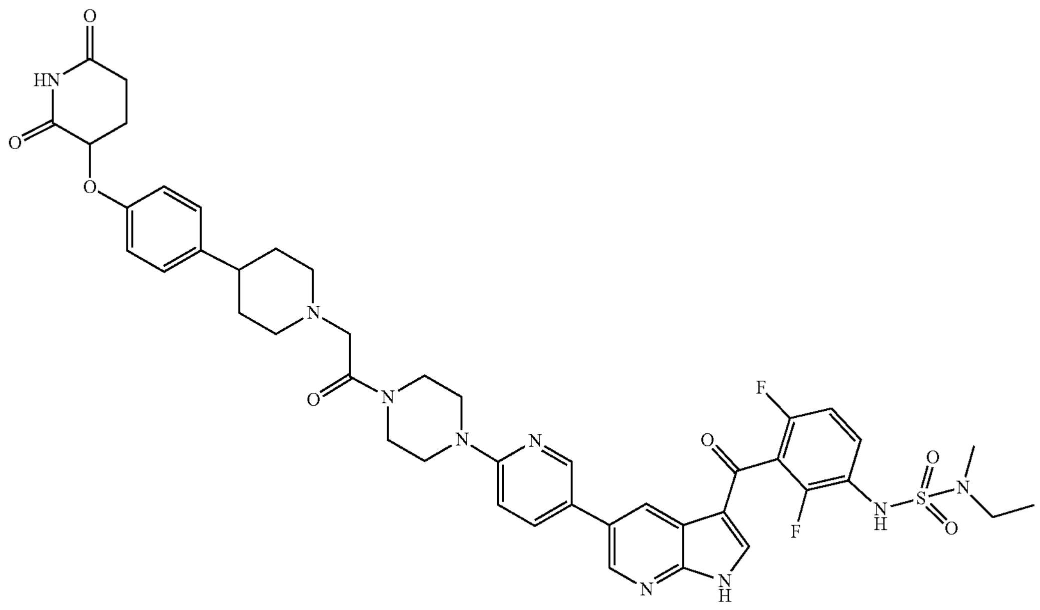 [SMILES: CCN(C)S(=O)(=O)Nc1ccc(F)c(C(=O)c2c[nH]c3ncc(-c4ccc(N5CCN(C(=O)CN6CCC(c7ccc(OC8CCC(=O)NC8=O)cc7)CC6)CC5)nc4)cc23)c1F]

The title compound was obtained as white solid in 69% yield according to general procedure VIII.

Amine: 3-[3-[[Ethyl(methyl)sulfamoyl]amino]-2,6-difluoro-benzoyl]-5-(6-piperazin-1-yl-3-pyridyl)-1H-pyrrolo[2,3-b]pyridine Acid: 2-[4-[4-[(2,6-Dioxo-3-piperidyl)oxy]phenyl]-1-piperidyl]acetic acid hydrochloride MS m/e: 884.7 ([M+H+]$^+$).

Example A 2

5-[6-[4-[4-[4-[4-(2,6-Dioxopiperidin-3-yl)oxyphenyl]piperidin-1-yl]butanoyl]piperazin-1-yl]pyridin-3-yl]-3-[3-[[ethyl(methyl)sulfamoyl]amino]-2,6-difluorobenzoyl]-1H-pyrrolo[2,3-b]pyridine

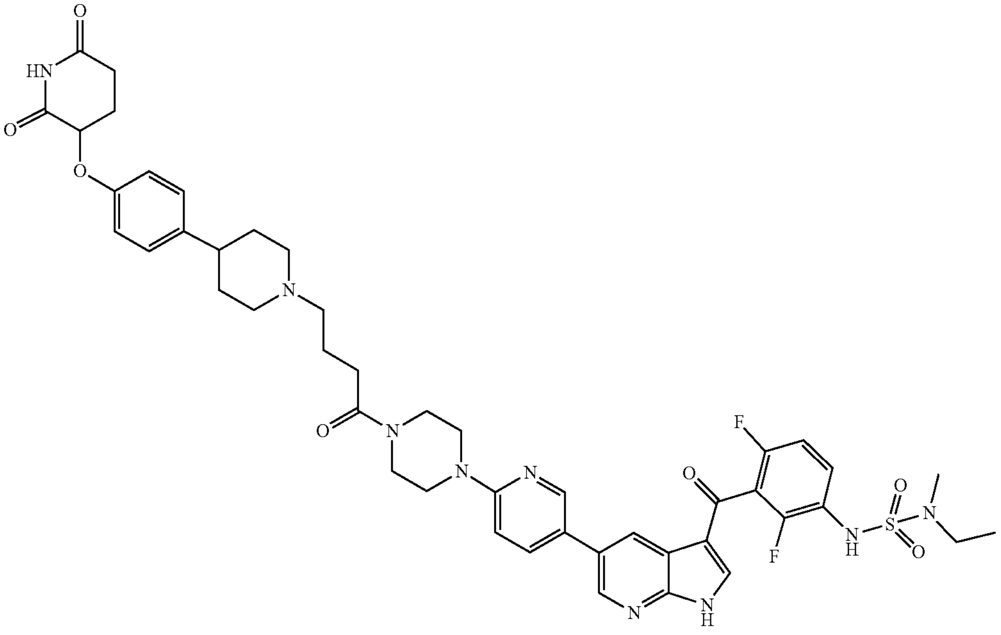 [SMILES: CCN(C)S(=O)(=O)Nc1ccc(F)c(C(=O)c2c[nH]c3ncc(-c4ccc(N5CCN(C(=O)CCCN6CCC(c7ccc(OC8CCC(=O)NC8=O)cc7)CC6)CC5)nc4)cc23)c1F]

The title compound was obtained as white solid in 69% yield according to general procedure VIII.

Amine: 3-[3-[[Ethyl(methyl)sulfamoyl]amino]-2,6-difluoro-benzoyl]-5-(6-piperazin-1-yl-3-pyridyl)-1H-pyrrolo [2,3-b]pyridine Acid: 4-[4-[4-[(2,6-Dioxo-3-piperidyl)oxy]phenyl]-1-piperidyl]butanoic acid MS m/e: 912.6 ([M+H+]$^+$)

Example A 3

5-[6-[4-[2-[4-[4-(2,6-Dioxopiperidin-3-yl)oxyphenyl]piperidin-1-yl]-2-oxoethyl]piperazin-1-yl]pyridin-3-yl]-3-[3-[[ethyl(methyl)sulfamoyl]amino]-2,6-difluorobenzoyl]-1H-pyrrolo[2,3-b]pyridine

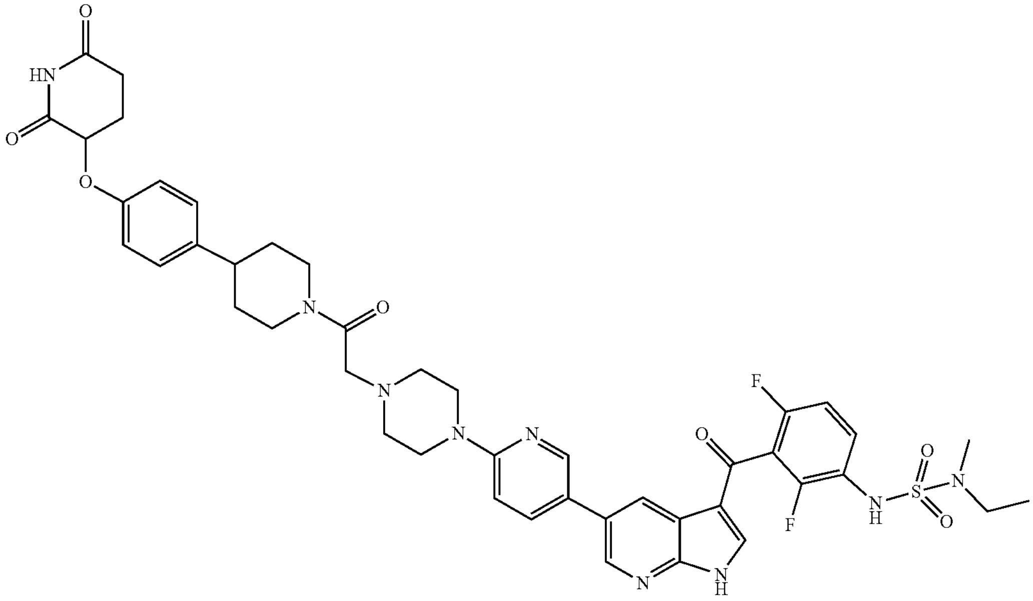 [SMILES: CCN(C)S(=O)(=O)Nc1ccc(F)c(C(=O)c2c[nH]c3ncc(-c4ccc(N5CCN(CC(=O)N6CCC(c7ccc(OC8CCC(=O)NC8=O)cc7)CC6)CC5)nc4)cc23)c1F]

To a solution of 3-(4-(piperidin-4-yl)phenoxy)piperidine-2,6-dione (12.5 mg, 43.4 μmol, Eq: 1) in N,N-dimethylformamide (560 μl) was added DIPEA (5.6 mg, 7.57 μl, 43.4 μmol, Eq: 1) and anhydrous sodium sulfate at 0-5° C. The cooling bath was removed after 10 minutes and the reaction mixture was allowed to return to RT. 3-[3-[[Ethyl(methyl) sulfamoyl]amino]-2,6-difluoro-benzoyl]-5-(6-piperazin-1-yl-3-pyridyl)-1H-pyrrolo[2,3-b]pyridine (24.1 mg, 43.4 μmol, Eq: 1) (31.1 mg, 56 μmol, Eq: 1) and DIPEA (5.6 mg, 7.57 μl, 43.4 μmol, Eq: 1) were added. Stirring was continued until completion of reaction. The reaction mixture was partitioned between ethyl acetate (20 ml) and 1 M sodium bicarbonate solution (15 ml). The layers were separated. The aqueous layer was extracted with one 15-ml portions of ethyl acetate. The combined organic layers were washed with three 20-ml portion of water and brine, dried over anhydrous sodium sulfate, filtered and concentrated in vacuo. The crude material was purified by flash chromatography with dichloromethane/methanol as eluent to give the title compound (14 mg, 34%) as light yellow solid. MS m/e: 884.6 ([M+H+]$^+$)

Example A 4

5-[4-[[4-[4-[4-(2,6-Dioxopiperidin-3-yl)oxyphenyl] piperazine-1-carbonyl]piperazin-1-yl]methyl]phenyl]-3-[3-[[ethyl(methyl)sulfamoyl]amino]-2,6-difluorobenzoyl]-1H-pyrrolo[2,3-b]pyridine

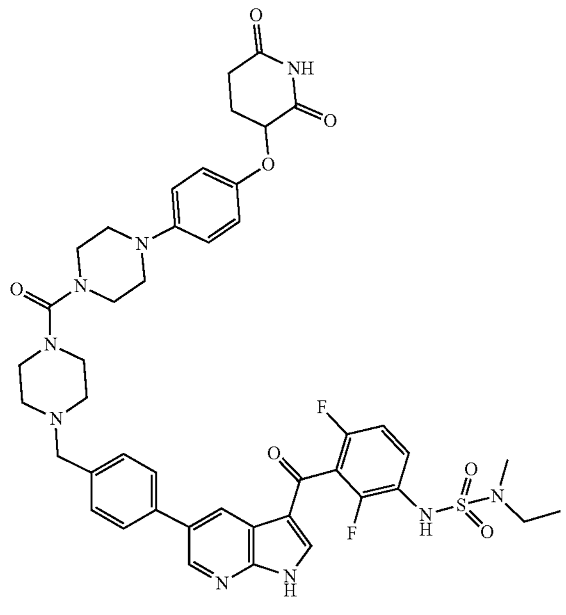 [SMILES: CCN(C)S(=O)(=O)Nc1ccc(F)c(C(=O)c2c[nH]c3ncc(-c4ccc(CN5CCN(C(=O)N6CCN(c7ccc(OC8CCC(=O)NC8=O)cc7)CC6)CC5)cc4)cc23)c1F]

a) 4-(4-((2,6-dioxopiperidin-3-yl)oxy)phenyl)piperazine-1-carbonyl chloride

To a solution of triphosgene (24.6 mg, 82.8 μmol, Eq: 1) in dichloromethane (828 μl) was added DIPEA (32.1 mg, 43.4 μl, 248 μmol, Eq: 3) at 0° C. Left to stir for 5 mins, until dark red colour change observed. 3-(4-(Piperazin-1-yl)phenoxy)piperidine-2,6-dione dihydrochloride (0.03 g, 82.8 μmol, Eq: 1) dissolved in DMF and DIPEA (21.4 mg, 28.9 μl, 166 μmol, Eq: 2) added to triphosgene solution and let stir until completion. The reaction mixture was partitioned between dichloromethane (15 ml) and 1 M aqueous hydrogen chloride solution (10 ml). The layers were separated. The aqueous layer was extracted with two 10-ml portions of dichloromethane. The combined organic layers were washed with one 10-ml portion of brine, dried over anhydrous sodium sulfate, filtered and concentrated in vacuo to give the crude title compound (18 mg, 51%) as off-white solid with a purity of 80%.

b) 5-[4-[[4-[4-[4-(2,6-Dioxopiperidin-3-yl)oxyphenyl]piperazine-1-carbonyl]piperazin-1-yl]methyl] phenyl]-3-[3-[[ethyl(methyl)sulfamoyl]amino]-2,6-difluorobenzoyl]-1H-pyrrolo[2,3-b]pyridine To a solution of 3-[3-[[ethyl(methyl)sulfamoyl]amino]-2,6-difluoro-benzoyl]-5-[4-(piperazin-1-ylmethyl)phenyl]-1H-pyrrolo[2,3-b]pyridine (29.1 mg, 51.2 μmol, Eq: 1) and 4-(4-((2,6-dioxopiperidin-3-yl)oxy)phenyl)piperazine-1-carbonyl chloride (18 mg, 51.2 μmol, Eq: 1) N,N-dimethylformamide was added DIPEA (6.61 mg, 8.94 μl, 51.2 μmol, Eq: 1) at RT. The reaction mixture was partitioned between ethyl acetate (10 ml) and 1 M aqueous hydrogen chloride solution (10 ml). The layers were separated. The combined organic layers were washed with 3 10-ml portion of water and brine, dried over anhydrous sodium sulfate, filtered and concentrated in vacuo. Purification by flash chromatography with dichloromethane/methanol as eluent gave the title compound (4 mg, 8%). MS m/e: 884.7 ([M+H+]$^+$)

Example A 5

5-[6-[4-[4-[4-[4-(2,6-Dioxopiperidin-3-yl)oxyphenyl]piperidin-1-yl]-4-oxobutyl]piperazin-1-yl]pyridin-3-yl]-3-[3-[[ethyl(methyl)sulfamoyl]amino]-2,6-difluorobenzoyl]-1H-pyrrolo[2,3-b]pyridine

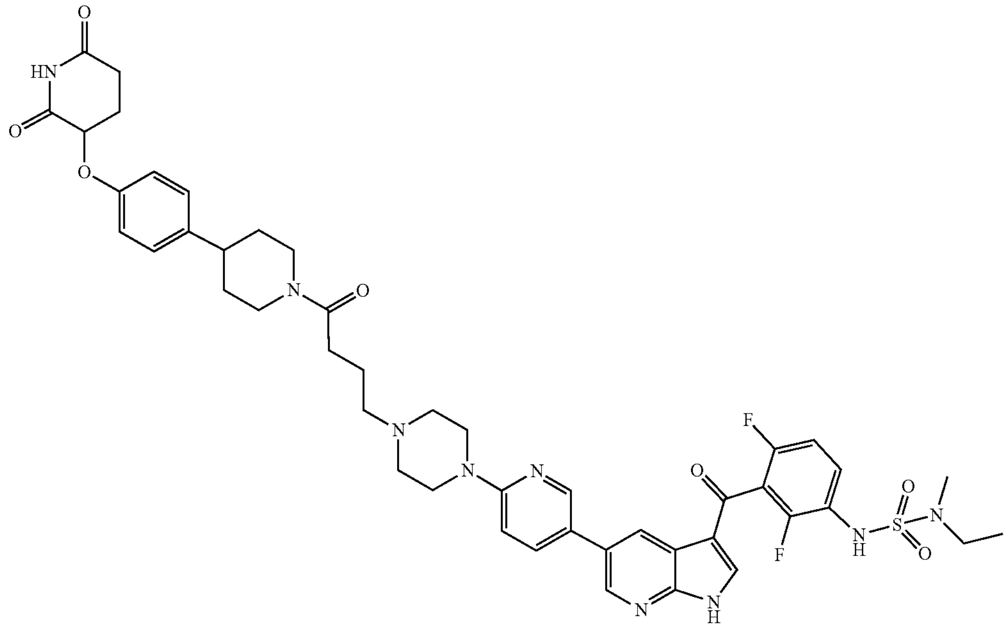 [SMILES: CCN(C)S(=O)(=O)Nc1ccc(F)c(C(=O)c2c[nH]c3ncc(-c4ccc(N5CCN(CCCC(=O)N6CCC(c7ccc(OC8CCC(=O)NC8=O)cc7)CC6)CC5)nc4)cc23)c1F]

a) tert-Butyl 4-(4-(5-(3-(3-((N-ethyl-N-methylsulfamoyl)amino)-2,6-difluorobenzoyl)-1H-pyrrolo[2,3-b]pyridin-5-yl)pyridin-2-yl)piperazin-1-yl)butanoate To a solution of tert-butyl 4-bromobutanoate (12.6 mg, 56.7 μmol, Eq: 0.9) and 3-[3-[[Ethyl(methyl)sulfamoyl]amino]-2,6-difluoro-benzoyl]-5-(6-piperazin-1-yl-3-pyridyl)-1H-pyrrolo[2,3-b]pyridine (0.035 g, 63 μmol, Eq: 1) in N,N-dimethylformamide (630 μl) was added DIPEA (24.4 mg, 33 μl, 189 μmol, Eq: 3) at RT. Stirring was continued for 16 h. The reaction mixture was partitioned between ethyl acetate (10 ml) and 1 M sodium bicarbonate solution (10 ml). The layers were separated. The combined organic layers were washed with three 10-ml portions of water and brine, dried over anhydrous sodium sulfate, filtered and concentrated in vacuo to give the crude title compound (40 mg, 89%) as off-white solid. MS m/e: 698.5 ([M+H+]$^+$).

b) 2,2,2-Trifluoroacetic acid compound with 4-(4-(5-(3-(3-((N-ethyl-N-methylsulfamoyl)amino)-2,6-difluorobenzoyl)-1H-pyrrolo[2,3-b]pyridin-5-yl)pyridin-2-yl)piperazin-1-yl)butanoic acid To a solution of tert-butyl 4-(4-(5-(3-(3-((N-ethyl-N-methylsulfamoyl)amino)-2,6-difluorobenzoyl)-1H-pyrrolo[2,3-1)]pyridin-5-yl)pyridin-2-yl)piperazin-1-yl)butanoate (40 mg, 57.3 μmol, Eq: 1) in dichloromethane (573 μl) was added trifluoroacetic acid (131 mg, 88.3 μl, 1.15 mmol, Eq: 20). Stirring was continued until completion of reaction. The solvent was evaporated in vacuo to give the crude title compound (50 mg, quantitative). MS m/e: 642.4 ([M+H+]$^+$).

c) N'-{3-[5-(6-{4-[4-(4-{4-[(2,6-Dioxopiperidin-3-yl)oxy]phenyl}piperidin-1-yl)-4-oxobutyl]piperazin-1-yl}pyridin-3-yl)-1H-pyrrolo[2,3-b]pyridine-3-carbonyl]-2,4-difluorophenyl}-N-ethyl-N-methylsulfuric diamide The title compound was obtained as light yellow solid in 16% yield according to general procedure VIII.

Amine: 3-(4-(Piperidin-4-yl)phenoxy)piperidine-2,6-dione hydrochloride

Acid: 2,2,2-Trifluoroacetic acid compound with 4-(4-(5-(3-(3-((N-ethyl-N-methylsulfamoyl)amino)-2,6-difluorobenzoyl)-1H-pyrrolo[2,3-b]pyridin-5-yl)pyridin-2-yl)piperazin-1-yl)butanoic acid MS m/e: 912.6 ([M+H+]$^+$)

Example A 6

5-[2-[4-[2-[4-[4-(2,6-Dioxopiperidin-3-yl)oxyphenyl]piperidin-1-yl]acetyl]piperazin-1-yl]pyrimidin-5-yl]-3-[3-[[ethyl(methyl)sulfamoyl]amino]-2,6-difluorobenzoyl]-1H-pyrrolo[2,3-b]pyridine

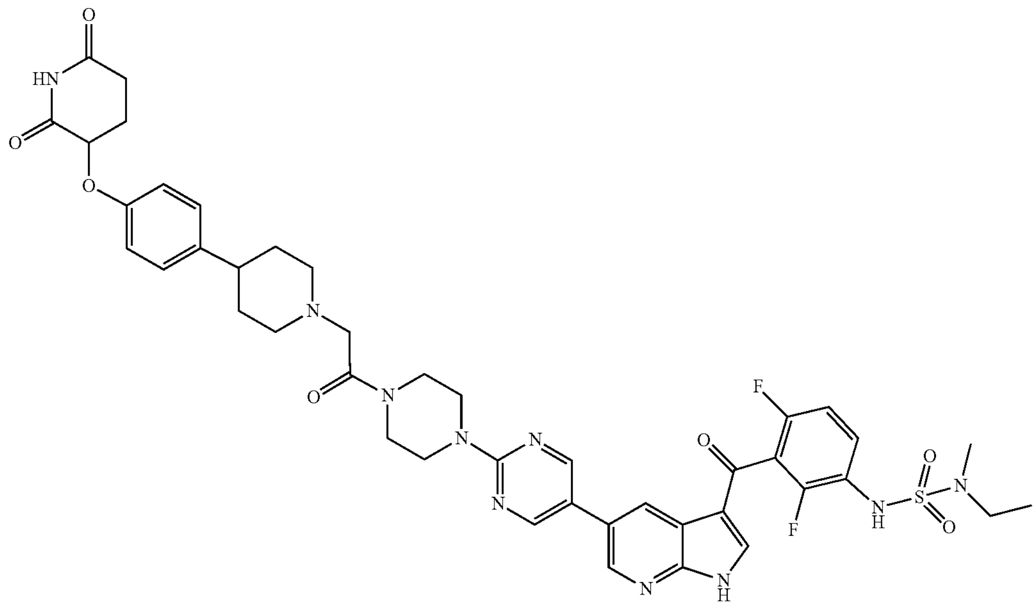 [SMILES: CCN(C)S(=O)(=O)Nc1ccc(F)c(C(=O)c2c[nH]c3ncc(-c4cnc(N5CCN(C(=O)CN6CCC(c7ccc(OC8CCC(=O)NC8=O)cc7)CC6)CC5)nc4)cc23)c1F]

The title compound was obtained as off-white solid in 53% yield according to general procedure VIII.

Amine: 3-[3-[[Ethyl(methyl)sulfamoyl]amino]-2,6-difluoro-benzoyl]-5-(2-piperazin-1-ylpyrimidin-5-yl)-1H-pyrrolo[2,3-b]pyridine Acid: 2-[4-[4-[(2,6-Dioxo-3-piperidyl)oxy]phenyl]-1-piperidyl]acetic acid hydrochloride MS m/e: 912.6 ([M+H+]$^{+}$).

2Example A 7

5-[6-[[4-[2-[4-[4-[(2,6-Dioxopiperidin-3-yl)amino]phenyl]piperidin-1-yl]-2-oxoethyl]piperazin-1-yl]methyl]pyridin-3-yl]-3-[3-[[ethyl(methyl)sulfamoyl]amino]-2,6-difluorobenzoyl]-1H-pyrrolo[2,3-b]pyridine;2,2,2-trifluoroacetic acid

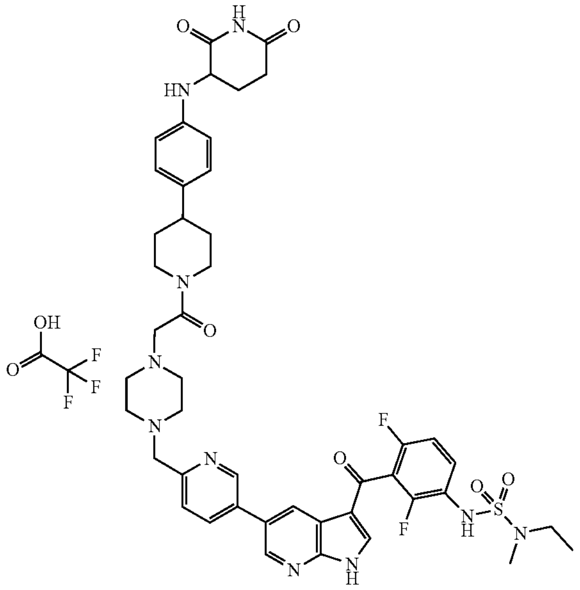

a) 2-[4-[[5-[3-[3-[[Ethyl(methyl)sulfamoyl]amino]-2,6-difluoro-benzoyl]-1H-pyrrolo[2,3-b]pyridin-5-yl]-2-pyridyl]methyl]piperazin-1-yl]acetic acid To a stirred solution of 3-[3-[[ethyl(methyl)sulfamoyl]amino]-2,6-difluoro-benzoyl]-5-[6-(piperazin-1-ylmethyl)-3-pyridyl]-1H-pyrrolo[2,3-b]pyridine (0.070 g, 123 μmol) and glyoxalic acid monohydrate (22.62 mg, 246 μmol) in methanol (2 mL) was added sodium cyanoborohydride (18.53 mg, 295 μmol) and catalytic amount of acetic acid. The reaction mixture was stirred at room temperature for 12 h. After completion of the reaction as judged by TLC, the reaction mixture was added water and extracted with ethyl acetate (3×50 mL) and washed the organic layer with brine solution. The combined organic layers were dried over sodium sulphate and concentrated under reduced pressure to give the crude title compound (50 mg, 86.6% pure) as off-white solid. MS m/e: 628.2 ([M+H+]$^+$).

c) 5-[6-[[4-[2-[4-[4-[(2,6-dioxopiperidin-3-yl)amino]phenyl]piperidin-1-yl]-2-oxoethyl]piperazin-1-yl]methyl]pyridin-3-yl]-3-[3-[[ethyl(methyl)sulfamoyl]amino]-2,6-difluorobenzoyl]-1H-pyrrolo[2,3-b]pyridine;2,2,2-trifluoroacetic acid A 8 mL screw cap vial was charged with 2-[4-[[5-[3-[3-[[ethyl(methyl)sulfamoyl]amino]-2,6-difluoro-benzoyl]-1H-pyrrolo[2,3-b]pyridin-5-yl]-2-pyridyl]methyl]piperazin-1-yl]acetic acid (20 mg, 31.86 μmol), 3-[4-(4-piperidyl)anilino]piperidine-2,6-dione (9.16 mg, 31.86 μmol) and DMF (0.5 mL). Addition of DIPEA (27 μL, 159.57 μmol)) and PyBOP (19.93 mg, 38.30 μmol) at room temperature and the resulting mixture was kept on an orbital shaker at room temperature for 16 h. After completion of the reaction as judged by TLC/LCMS, the reaction mixture was diluted with water (1.0 mL), extracted with ethyl acetate (3×1.5 mL). The combined organics were removed under Genevac at 50° C. (1 bar pressure) for 3 h. The obtained crude products were purified by mass-directed preparative HPLC either [Mobile-phase A: 0.1% TFA in $H_2O$, Mobile-phase B: ACN, Wave length: 215 nm, Column: Sunfire C18 OBD (19 mm×100 mm; 5 micron)] to get the title compound (10.6 mg, 34% yield, 89.5% pure) as yellow solid. MS m/e: 898.0 ([M+H+]$^+$)

Example A 8

5-[6-[4-[2-[4-[4-[(2,6-Dioxopiperidin-3-yl)amino]phenyl]piperidin-1-yl]acetyl]piperazin-1-yl]pyridin-3-yl]-3-[3-[[ethyl(methyl)sulfamoyl]amino]-2,6-difluorobenzoyl]-1H-pyrrolo[2,3-b]pyridine

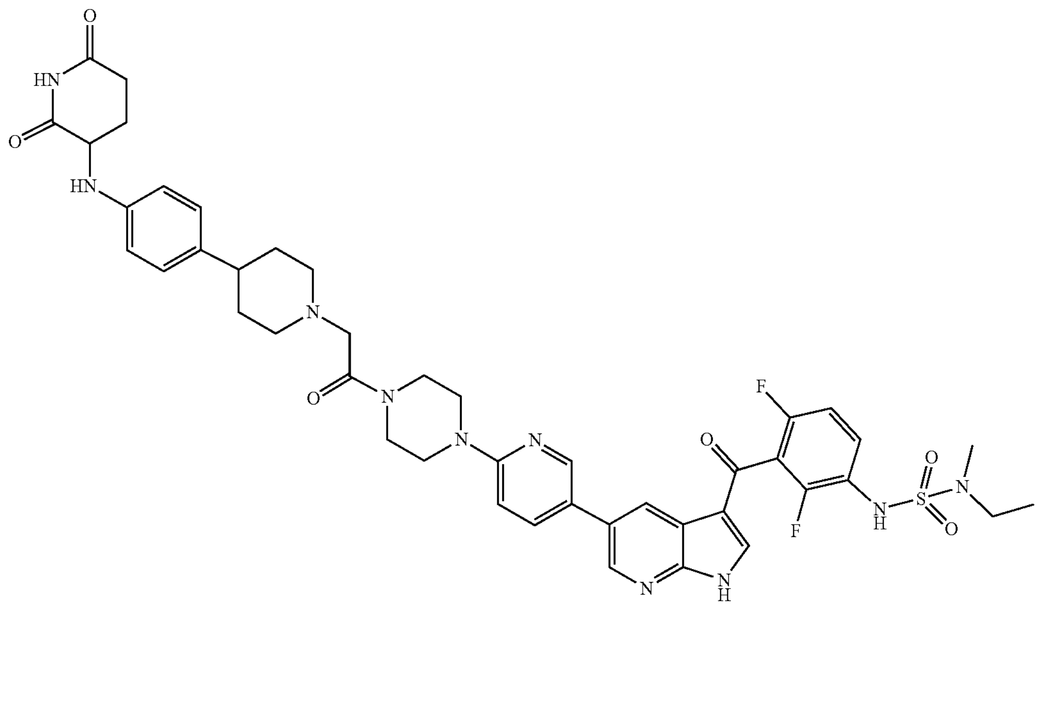 [SMILES: CCN(C)S(=O)(=O)Nc1ccc(F)c(C(=O)c2c[nH]c3ncc(-c4ccc(N5CCN(C(=O)CN6CCC(c7ccc(NC8CCC(=O)NC8=O)cc7)CC6)CC5)nc4)cc23)c1F]

The title compound was obtained as green solid in 40% yield according to general procedure VIII.

Amine: 3-[3-[[Ethyl(methyl)sulfamoyl]amino]-2,6-difluoro-benzoyl]-5-(6-piperazin-1-yl-3-pyridyl)-1H-pyrrolo[2,3-b]pyridine Acid: 2-[4-[4-[(2,6-Dioxo-3-piperidyl)amino]phenyl]-1-piperidyl]acetic acid hydrochloride MS m/e: 883.8 ([M+H+]$^+$)

Example A 9

5-[6-[[4-[2-[4-[4-[(2,6-Dioxopiperidin-3-yl)amino]phenyl]piperidin-1-yl]acetyl]piperazin-1-yl]methyl]pyridin-3-yl]-3-[3-[[ethyl(methyl)sulfamoyl]amino]-2,6-difluorobenzoyl]-1H-pyrrolo[2,3-b]pyridine

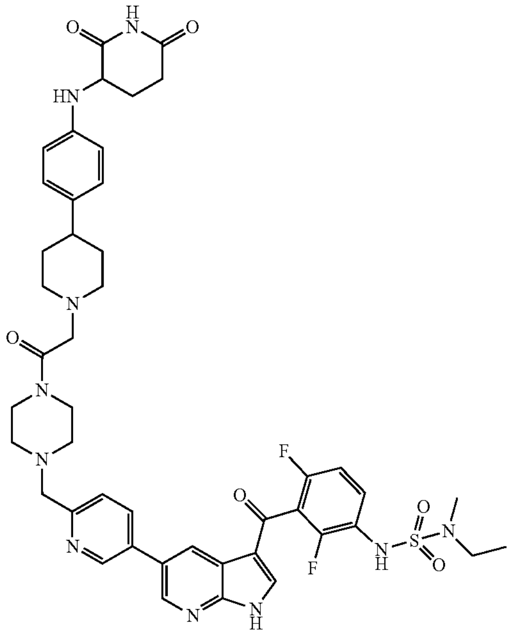 [SMILES: CCN(C)S(=O)(=O)Nc1ccc(F)c(C(=O)c2c[nH]c3ncc(-c4ccc(CN5CCN(C(=O)CN6CCC(c7ccc(NC8CCC(=O)NC8=O)cc7)CC6)CC5)nc4)cc23)c1F]

The title compound was obtained as white solid in 30% yield according to general procedure VIII

.

Amine: 3-[3-[[Ethyl(methyl)sulfamoyl]amino]-2,6-difluoro-benzoyl]-5-[6-(piperazin-1-ylmethyl)-3-pyridyl]-1H-pyrrolo[2,3-b]pyridine Acid: 2-[4-[4-[(2,6-Dioxo-3-piperidyl)amino]phenyl]-1-piperidyl]acetic acid hydrochloride MS m/e: 897.7 ([M+H+]$^+$)

Example A 10

5-[2-[4-[2-[4-[4-[(2,6-Dioxopiperidin-3-yl)amino]phenyl]piperidin-1-yl]acetyl]piperazin-1-yl]pyrimidin-5-yl]-3-[3-[[ethyl(methyl)sulfamoyl]amino]-2,6-difluorobenzoyl]-1H-pyrrolo[2,3-b]pyridine

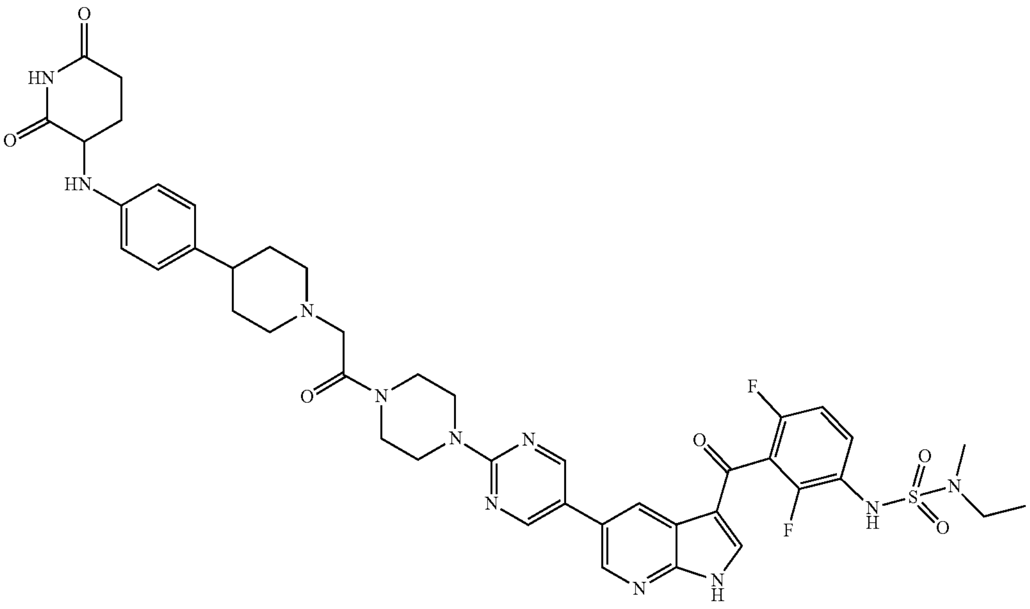 [SMILES: CCN(C)S(=O)(=O)Nc1ccc(F)c(C(=O)c2c[nH]c3ncc(-c4cnc(N5CCN(C(=O)CN6CCC(c7ccc(NC8CCC(=O)NC8=O)cc7)CC6)CC5)nc4)cc23)c1F]

The title compound was obtained as off-white solid in 41% yield according to general procedure VIII.

Amine: 3-[3-[[Ethyl(methyl)sulfamoyl]amino]-2,6-difluoro-benzoyl]-5-(2-piperazin-1-ylpyrimidin-5-yl)-1H-pyrrolo[2,3-b]pyridine Acid: 2-[4-[4-[(2,6-Dioxo-3-piperidyl)amino]phenyl]-1-piperidyl]acetic acid hydrochloride MS m/e: 884.6 ([M+H+]$^+$)

Example A 11

5-[6-[4-[2-[4-[4-[(2,6-Dioxopiperidin-3-yl)amino]phenyl]piperazin-1-yl]acetyl]piperazin-1-yl]pyridin-3-yl]-3-[3-[[ethyl(methyl)sulfamoyl]amino]-2,6-difluorobenzoyl]-1H-pyrrolo[2,3-b]pyridine

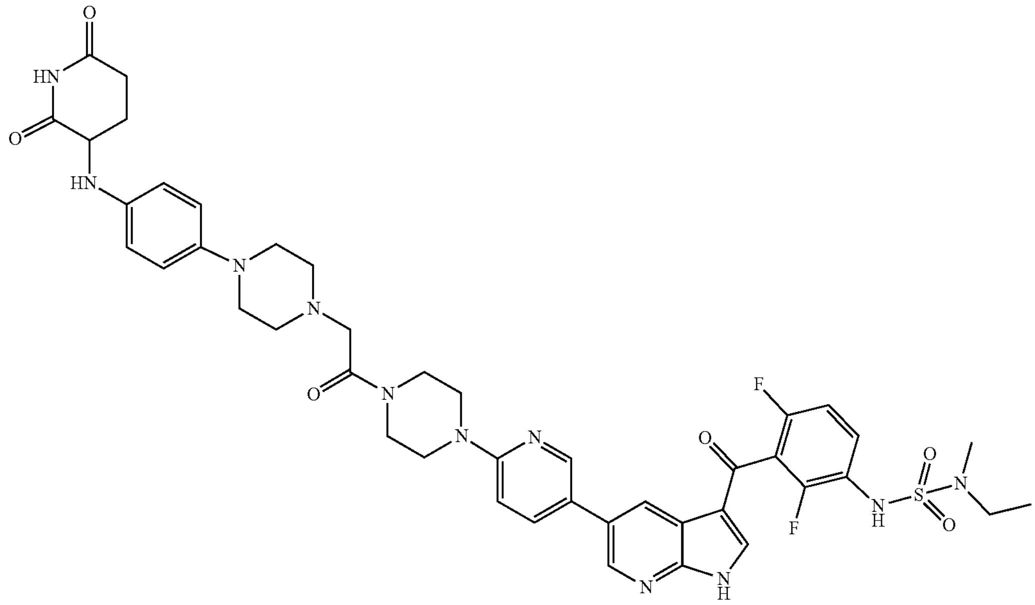 [SMILES: CCN(C)S(=O)(=O)Nc1ccc(F)c(C(=O)c2c[nH]c3ncc(-c4ccc(N5CCN(C(=O)CN6CCN(c7ccc(NC8CCC(=O)NC8=O)cc7)CC6)CC5)nc4)cc23)c1F]

The title compound was obtained as light yellow solid in 45% yield according to general procedure VIII.

Amine: 3-[3-[[Ethyl(methyl)sulfamoyl]amino]-2,6-difluoro-benzoyl]-5-(6-piperazin-1-yl-3-pyridyl)-1H-pyrrolo[2,3-b]pyridine Acid: 2-[4-[4-[(2,6-Dioxo-3-piperidyl)amino]phenyl]piperazin-1-yl]acetic acid hydrochloride MS m/e: 884.6 ([M+H+]$^+$)

Example A 12

5-[6-[[4-[2-[4-[4-[(2,6-Dioxopiperidin-3-yl)amino]phenyl]piperazin-1-yl]acetyl]piperazin-1-yl]methyl]pyridin-3-yl]-3-[3-[[ethyl(methyl)sulfamoyl]amino]-2,6-difluorobenzoyl]-1H-pyrrolo[2,3-b]pyridine

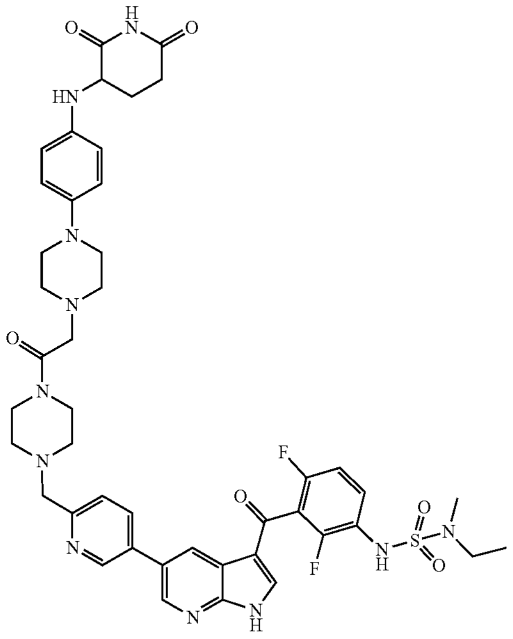 [SMILES: CCN(C)S(=O)(=O)Nc1ccc(F)c(C(=O)c2c[nH]c3ncc(-c4ccc(CN5CCN(C(=O)CN6CCN(c7ccc(NC8CCC(=O)NC8=O)cc7)CC6)CC5)nc4)cc23)c1F]

The title compound was obtained as light brown solid in 17% yield according to general procedure VIII.

Amine: 3-[3-[[Ethyl(methyl)sulfamoyl]amino]-2,6-difluoro-benzoyl]-5-[6-(piperazin-1-ylmethyl)-3-pyridyl]-1H-pyrrolo[2,3-b]pyridine Acid: 2-[4-[4-[(2,6-Dioxo-3-piperidyl)amino]phenyl]piperazin-1-yl]acetic acid hydrochloride MS m/e: 898.6 ([M+H+]$^+$).

Example A 13

5-[4-[[4-[1-[2-[4-[4-[(2,6-Dioxopiperidin-3-yl)amino]phenyl]piperidin-1-yl]acetyl]piperidin-4-yl]piperazin-1-yl]methyl]phenyl]-3-[3-[[ethyl(methyl)sulfamoyl]amino]-2,6-difluorobenzoyl]-1H-pyrrolo[2,3-b]pyridine

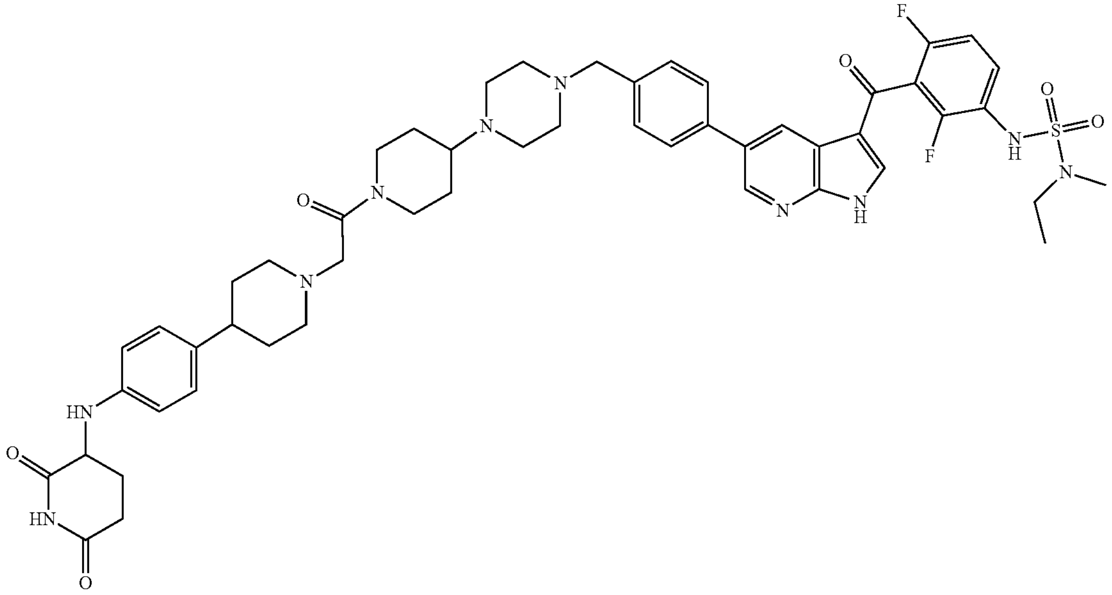 [SMILES: CCN(C)S(=O)(=O)Nc1ccc(F)c(C(=O)c2c[nH]c3ncc(-c4ccc(CN5CCN(C6CCN(C(=O)CN7CCC(c8ccc(NC9CCC(=O)NC9=O)cc8)CC7)CC6)CC5)cc4)cc23)c1F]

The title compound was obtained in 29% yield according to general procedure VIII.

Amine: 3-[3-[[Ethyl(methyl)sulfamoyl]amino]-2,6-difluoro-benzoyl]-5-[4-[[4-(4-piperidyl)piperazin-1-yl]methyl]phenyl]-1H-pyrrolo[2,3-b]pyridine trifluoroacetic acid Acid: 2-[4-[4-[(2,6-Dioxo-3-piperidyl)amino]phenyl]piperazin-1-yl]acetic acid hydrochloride MS m/e: 979.9 ([M+H+]$^+$)

Example A 14

5-[4-[4-[2-[4-[4-(2,6-Dioxopiperidin-3-yl)oxyphenyl]piperidin-1-yl]acetyl]piperazin-1-yl]phenyl]-3-[3-[[ethyl(methyl)sulfamoyl]amino]-2,6-difluorobenzoyl]-1H-pyrrolo[2,3-b]pyridine

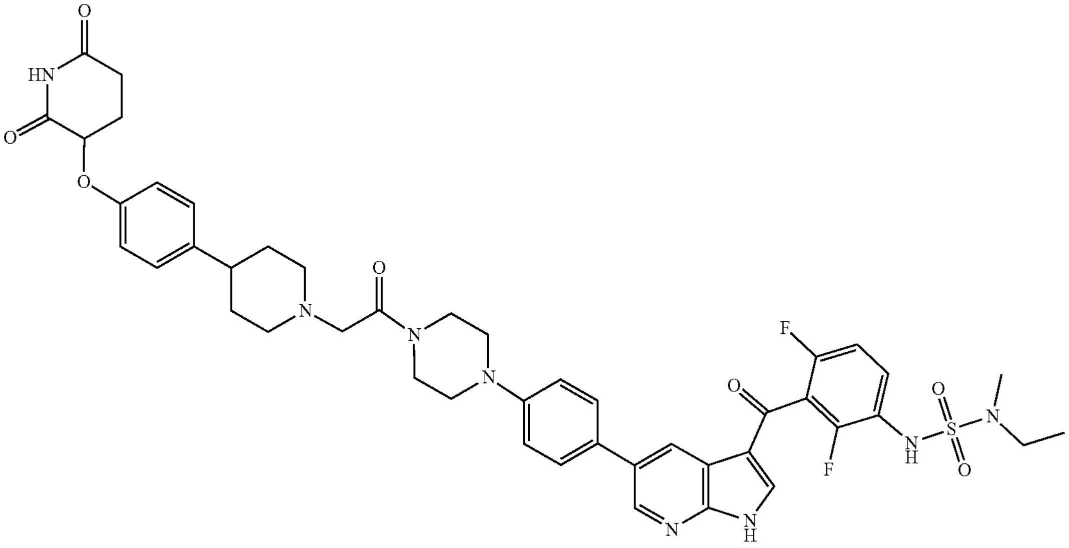 [SMILES: CCN(C)S(=O)(=O)Nc1ccc(F)c(C(=O)c2c[nH]c3ncc(-c4ccc(N5CCN(C(=O)CN6CCC(c7ccc(OC8CCC(=O)NC8=O)cc7)CC6)CC5)cc4)cc23)c1F]

The title compound was obtained as light green solid in 46% yield according to general procedure VIII.

Amine: 3-[3-[[Ethyl(methyl)sulfamoyl]amino]-2,6-difluoro-benzoyl]-5-(4-piperazin-1-ylphenyl)-1H-pyrrolo[2,3-b]pyridine trifluoroacetic acid Acid: 2-[4-[4-[(2,6-Dioxo-3-piperidyl)oxy]phenyl]-1-piperidyl]acetic acid hydrochloride MS m/e: 883.6 ([M+H+]$^+$)

Example A 15

5-[4-[4-[4-[4-[4-(2,6-Dioxopiperidin-3-yl)oxyphenyl]piperidin-1-yl]butanoyl]piperazin-1-yl]phenyl]-3-[3-[[ethyl(methyl)sulfamoyl]amino]-2,6-difluorobenzoyl]-1H-pyrrolo[2,3-b]pyridine

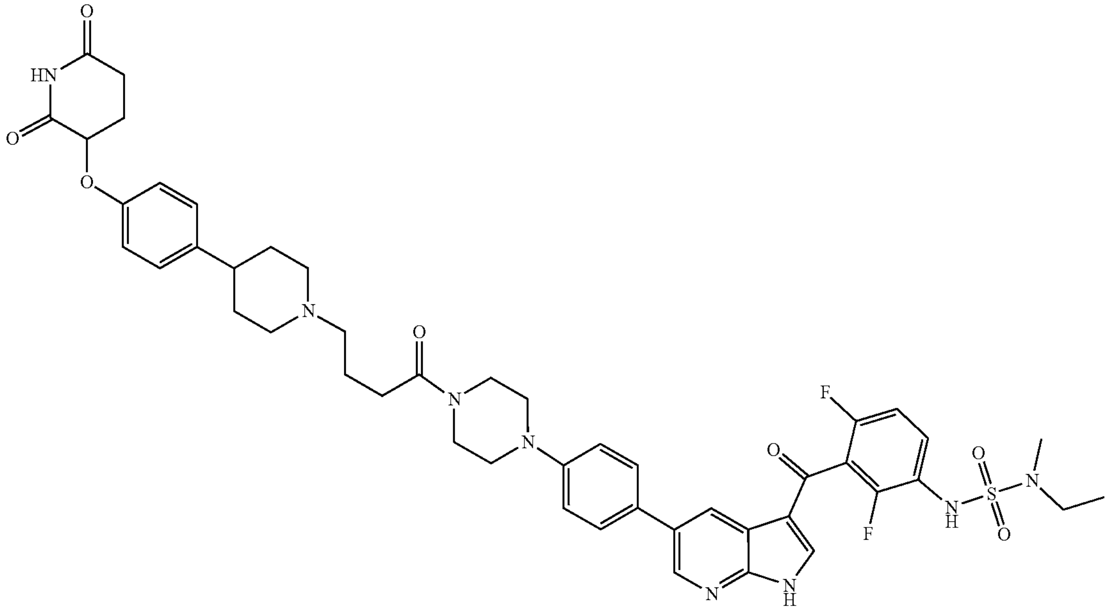 [SMILES: CCN(C)S(=O)(=O)Nc1ccc(F)c(C(=O)c2c[nH]c3ncc(-c4ccc(N5CCN(C(=O)CCCN6CCC(c7ccc(OC8CCC(=O)NC8=O)cc7)CC6)CC5)cc4)cc23)c1F]

The title compound was obtained in 18% yield according to general procedure VIII.

Amine: 3-[3-[[Ethyl(methyl)sulfamoyl]amino]-2,6-difluoro-benzoyl]-5-(4-piperazin-1-ylphenyl)-1H-pyrrolo[2,3-b]pyridine trifluoroacetic acid Acid: 4-[4-[4-[(2,6-Dioxo-3-piperidyl)oxy]phenyl]-1-piperidyl]butanoic acid MS m/e: 911.9 ([M+H+]$^+$)

Example A 16

5-[2-[4-[2-[4-[4-[(2,6-Dioxopiperidin-3-yl)amino]phenyl]piperazin-1-yl]acetyl]piperazin-1-yl]pyrimidin-5-yl]-3-[3-[[ethyl(methyl)sulfamoyl]amino]-2,6-difluorobenzoyl]-1H-pyrrolo[2,3-b]pyridine

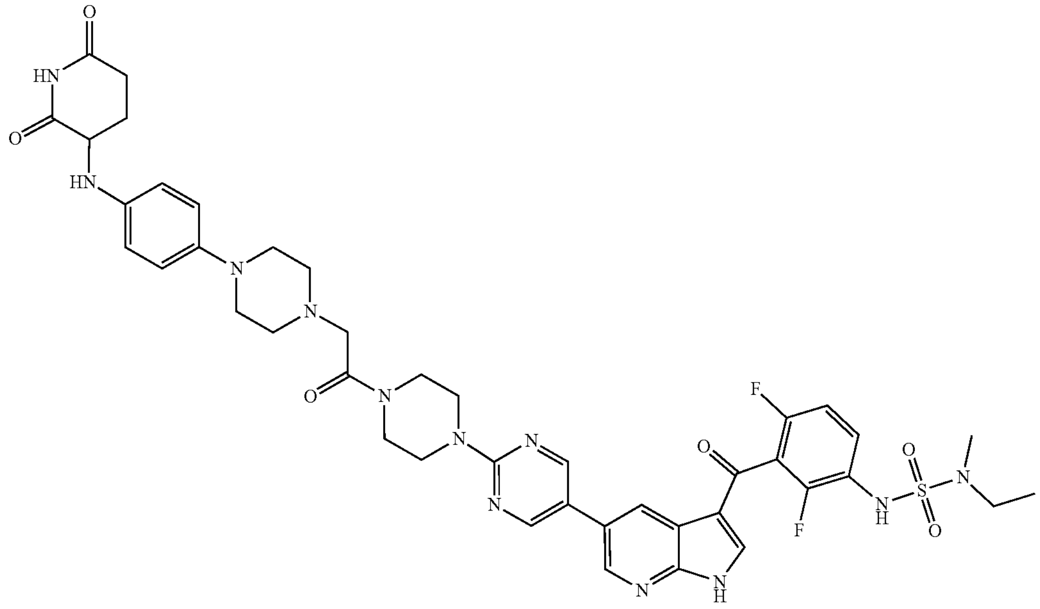 [SMILES: CCN(C)S(=O)(=O)Nc1ccc(F)c(C(=O)c2c[nH]c3ncc(-c4cnc(N5CCN(C(=O)CN6CCN(c7ccc(NC8CCC(=O)NC8=O)cc7)CC6)CC5)nc4)cc23)c1F]

The title compound was obtained as light brown solid in 37% yield according to general procedure VIII.

Amine: 3-[3-[[Ethyl(methyl)sulfamoyl]amino]-2,6-difluoro-benzoyl]-5-(2-piperazin-1-ylpyrimidin-5-yl)-1H-pyrrolo[2,3-b]pyridine Acid: 2-[4-[4-[(2,6-Dioxo-3-piperidyl)amino]phenyl]piperazin-1-yl]acetic acid hydrochloride MS m/e: 885.7 ([M+H+]$^+$)

Example A 17

5-[6-[4-[4-[4-[4-[(2,6-Dioxopiperidin-3-yl)amino]phenyl]piperidin-1-yl]butanoyl]piperazin-1-yl]pyridin-3-yl]-3-[3-[[ethyl(methyl)sulfamoyl]amino]-2,6-difluorobenzoyl]-1H-pyrrolo[2,3-b]pyridine

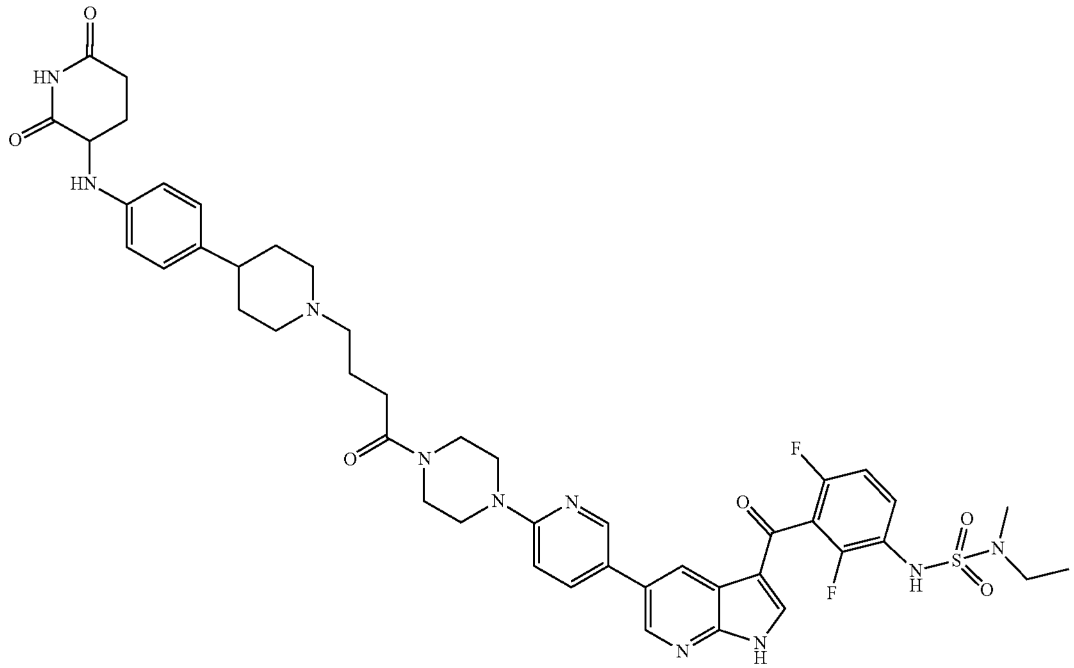 [SMILES: CCN(C)S(=O)(=O)Nc1ccc(F)c(C(=O)c2c[nH]c3ncc(-c4ccc(N5CCN(C(=O)CCCN6CCC(c7ccc(NC8CCC(=O)NC8=O)cc7)CC6)CC5)nc4)cc23)c1F]

The title compound was obtained as dark green solid in 17% yield according to general procedure VIII.

Amine: 3-[3-[[Ethyl(methyl)sulfamoyl]amino]-2,6-difluoro-benzoyl]-5-(6-piperazin-1-yl-3-pyridyl)-1H-pyrrolo[2,3-b]pyridine Acid: 2-[4-[4-[(2,6-Dioxo-3-piperidyl)amino]phenyl]piperazin-1-yl]acetic acid hydrochloride MS m/e: 911.6 ([M+H+]$^+$)

Example A 18

5-[2-[4-[4-[4-[4-[(2,6-Dioxopiperidin-3-yl)amino]phenyl]piperidin-1-yl]butanoyl]piperazin-1-yl]pyrimidin-5-yl]-3-[3-[[ethyl(methyl)sulfamoyl]amino]-2,6-difluorobenzoyl]-1H-pyrrolo[2,3-b]pyridine

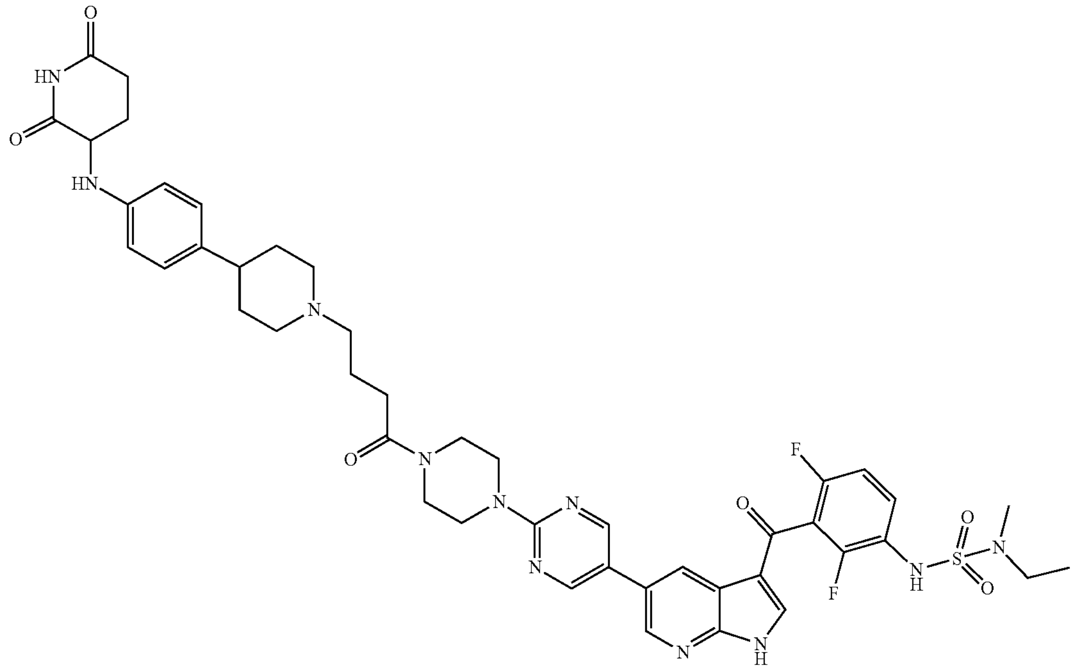 [SMILES: CCN(C)S(=O)(=O)Nc1ccc(F)c(C(=O)c2c[nH]c3ncc(-c4cnc(N5CCN(C(=O)CCCN6CCC(c7ccc(NC8CCC(=O)NC8=O)cc7)CC6)CC5)nc4)cc23)c1F]

The title compound was obtained as dark green solid in 10% yield according to general procedure VIII.

Amine: 3-[3-[[Ethyl(methyl)sulfamoyl]amino]-2,6-difluoro-benzoyl]-5-(2-piperazin-1-ylpyrimidin-5-yl)-1H-pyrrolo[2,3-b]pyridine Acid: 2-[4-[4-[(2,6-Dioxo-3-piperidyl)amino]phenyl]piperazin-1-yl]acetic acid hydrochloride MS m/e: 912.6 ([M+H+]$^+$)

Example A 19

5-[4-[[3-[4-[4-(2,6-Dioxopiperidin-3-yl)oxyphenyl]piperazine-1-carbonyl]pyrrolidin-1-yl]methyl]phenyl]-3-[3-[[ethyl(methyl)sulfamoyl]amino]-2,6-difluorobenzoyl]-1H-pyrrolo[2,3-b]pyridine

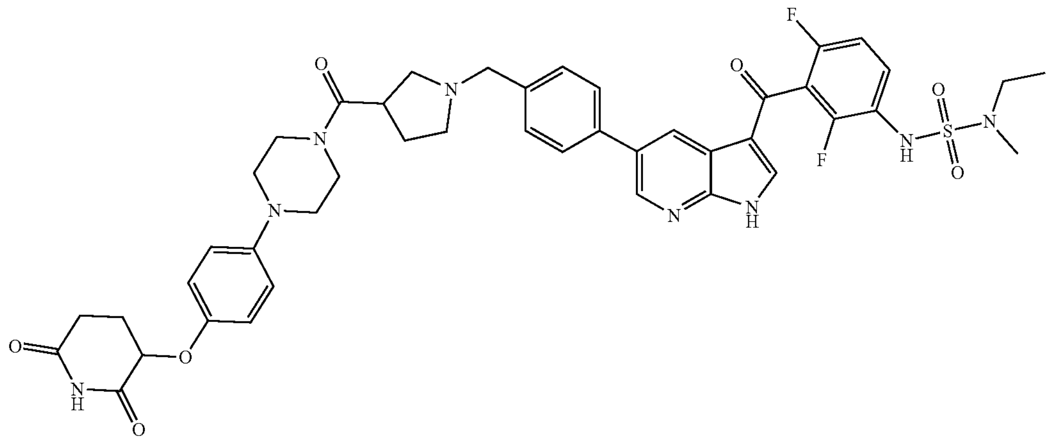 [SMILES: CCN(C)S(=O)(=O)Nc1ccc(F)c(C(=O)c2c[nH]c3ncc(-c4ccc(CN5CCC(C(=O)N6CCN(c7ccc(OC8CCC(=O)NC8=O)cc7)CC6)C5)cc4)cc23)c1F]

The title compound was obtained as white powder according to general procedure VIII.

Amine: 3-(4-piperazin-1-ylphenoxy)piperidine-2,6-dione hydrochloride

Acid: rac-1-[[4-[3-[3-[[ethyl(methyl)sulfamoyl]amino]-2,6-difluoro-benzoyl]-1H-pyrrolo[2,3-b]pyridin-5-yl]phenyl]methyl]pyrrolidine-3-carboxylic acid MS m/e: 869.7 ([M+H+]$^+$)

Example A 20

5-[4-[[3-[4-[4-(2,6-Dioxopiperidin-3-yl)oxyphenyl]piperidine-1-carbonyl]pyrrolidin-1-yl]methyl]phenyl]-3-[3-[[ethyl(methyl)sulfamoyl]amino]-2,6-difluorobenzoyl]-1H-pyrrolo[2,3-b]pyridine

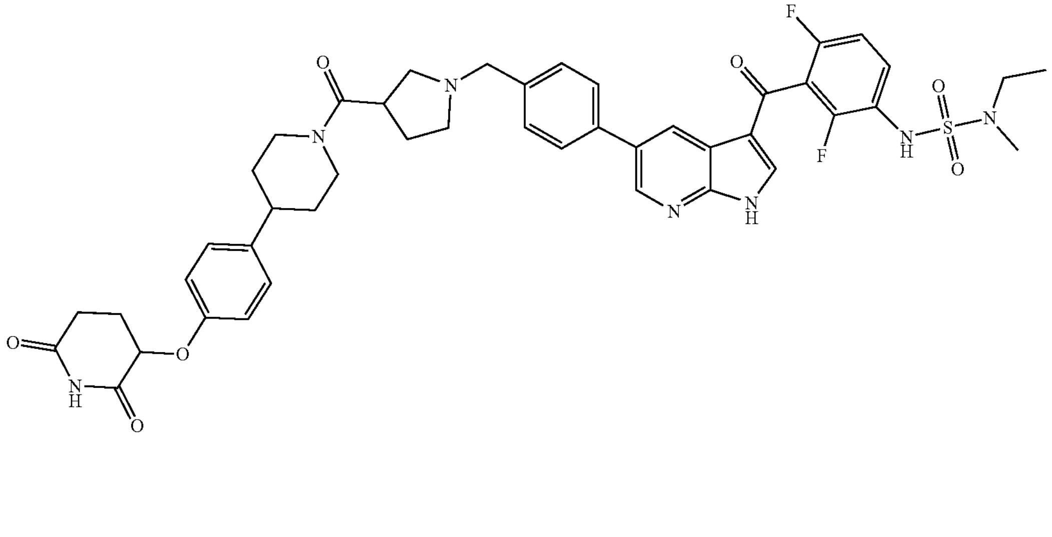 [SMILES: CCN(C)S(=O)(=O)Nc1ccc(F)c(C(=O)c2c[nH]c3ncc(-c4ccc(CN5CCC(C(=O)N6CCC(c7ccc(OC8CCC(=O)NC8=O)cc7)CC6)C5)cc4)cc23)c1F]

The title compound was obtained as white powder according to general procedure VIII.

Amine: 3-[4-(4-piperidyl)phenoxy]piperidine-2,6-dione hydrochloride

Acid: rac-1-[[4-[3-[3-[[ethyl(methyl)sulfamoyl]amino]-2,6-difluoro-benzoyl]-1H-pyrrolo[2,3-b]pyridin-5-yl]phenyl]methyl]pyrrolidine-3-carboxylic acid MS m/e: 868.8 ([M+H+]$^+$)

Example A 21

5-[4-[[4-[2-[4-[4-[(2,6-Dioxopiperidin-3-yl)amino]phenyl]piperidin-1-yl]-2-oxoethyl]piperazin-1-yl]methyl]phenyl]-3-[3-[[ethyl(methyl)sulfamoyl]amino]-2,6-difluorobenzoyl]-1H-pyrrolo[2,3-b]pyridine;2,2,2-trifluoroacetic acid

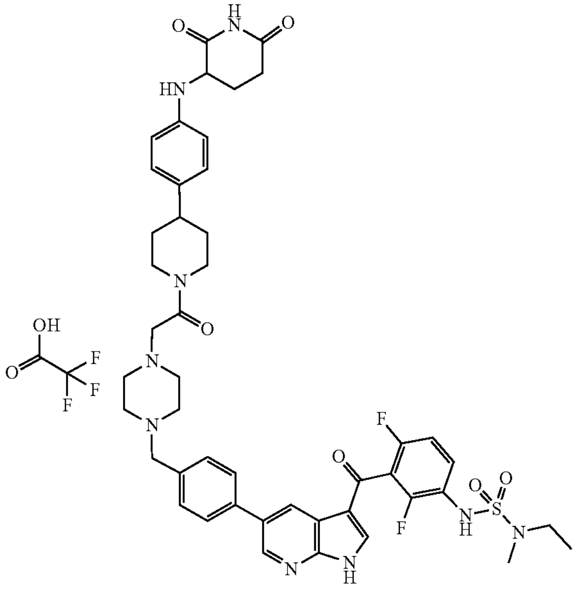

a) 2-[4-[[4-[3-[3-[[ethyl(methyl)sulfamoyl]amino]-2,6-difluoro-benzoyl]-1H-pyrrolo[2,3-b]pyridin-5-yl]phenyl]methyl]piperazin-1-yl]acetic acid To a stirred solution of 3-[3-[[ethyl(methyl)sulfamoyl]amino]-2,6-difluoro-benzoyl]-5-[4-(piperazin-1-ylmethyl)phenyl]-1H-pyrrolo[2,3-b]pyridine (200 mg, 351.72 μmol) and glyoxalic acid mono hydrate (64.75 mg, 703.44 μmol) in methanol (4 mL) was added sodium cyanoborohydride (53.05 mg, 844.12 μmol). The reaction mixture was stirred at room temperature for 12 h. After completion of the reaction as judged by TLC, the reaction mixture was added water and extracted with ethyl acetate (3×100 mL) and washed the organic layer with brine solution. The combined organic layers were dried over sodium sulphate, filtrated and concentrated under reduced pressure to give the crude title compound (200 mg, 244.50 μmol, 69.52% yield, 76.61% purity) as off-white solid. MS m/e: 627.0 ([M+H+]$^+$)

d) 5-[4-[[4-[2-[4-[4-[(2,6-dioxopiperidin-3-yl)amino]phenyl]piperidin-1-yl]-2-oxoethyl]piperazin-1-yl]methyl]phenyl]-3-[3-[[ethyl(methyl)sulfamoyl]amino]-2,6-difluorobenzoyl]-1H-pyrrolo[2,3-b]pyridine;2,2,2-trifluoroacetic acid A 8 mL screw cap vial was charged with 2-[4-[[4-[3-[3-[[ethyl(methyl)sulfamoyl]amino]-2,6-difluoro-benzoyl]-1H-pyrrolo[2,3-b]pyridin-5-yl]phenyl]methyl]piperazin-1-yl]acetic acid (20 mg, 31.91 μmol), 3-[4-(4-piperidyl)anilino]piperidine-2,6-dione (9.17 mg, 31.91 μmol) and DMF (0.5 mL). Addition of DIPEA (27 μL, 159.57 μmol)) and PyBOP (19.93 mg, 38.30 μmol) at room temperature. Stirring was continued for 16 h. After completion of the reaction as judged by TLC/LCMS, the reaction mixture was diluted with water (1.0 mL), extracted with ethyl acetate (3×1.5 mL). The combined organics were removed under Genevac at 50° C. (1 bar pressure) for 3 h. The obtained crude products were purified by mass-directed preparative HPLC [Mobile-phase A: 0.1% TFA in $H_2O$, Mobile-phase B: ACN, Wave length: 215 nm, Column: Sunfire C18 OBD (19 mm×100 mm; 5 micron)] to get the title compound (9.5 mg, 29% yield, 88.1% pure) as yellow solid. MS m/e: 897.0 ([M+H+]$^+$)

Example A 22

5-[4-[[4-[2-[4-[4-(2,6-Dioxopiperidin-3-yl)oxyphenyl]piperidin-1-yl]acetyl]piperazin-1-yl]methyl]phenyl]-3-[3-[[ethyl(methyl)sulfamoyl]amino]-2,6-difluorobenzoyl]-1H-pyrrolo[2,3-b]pyridine

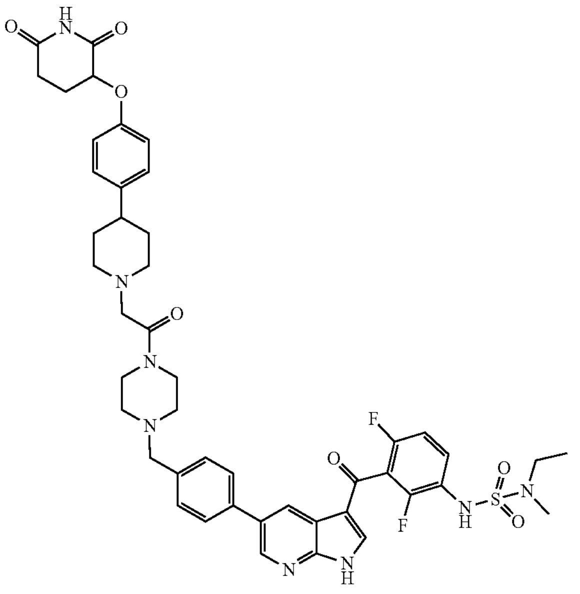 [SMILES: CCN(C)S(=O)(=O)Nc1ccc(F)c(C(=O)c2c[nH]c3ncc(-c4ccc(CN5CCN(C(=O)CN6CCC(c7ccc(OC8CCC(=O)NC8=O)cc7)CC6)CC5)cc4)cc23)c1F]

The title compound was obtained as light yellow solid in 42% yield according to general procedure VIII.

Amine: 3-[3-[[Ethyl(methyl)sulfamoyl]amino]-2,6-difluoro-benzoyl]-5-[4-(piperazin-1-ylmethyl)phenyl]-1H-pyrrolo[2,3-b]pyridine Acid: 2-[4-[4-[(2,6-dioxo-3-piperidyl)amino]phenyl]-1-piperidyl]acetic acid hydrochloride MS m/e: 897.7 ([M+H+]$^+$)

Example A 23

5-[4-[[4-[2-[4-[4-[(2,6-Dioxopiperidin-3-yl)amino]phenyl]piperidin-1-yl]acetyl]piperazin-1-yl]methyl]phenyl]-3-[3-[[ethyl(methyl)sulfamoyl]amino]-2,6-difluorobenzoyl]-1H-pyrrolo[2,3-b]pyridine

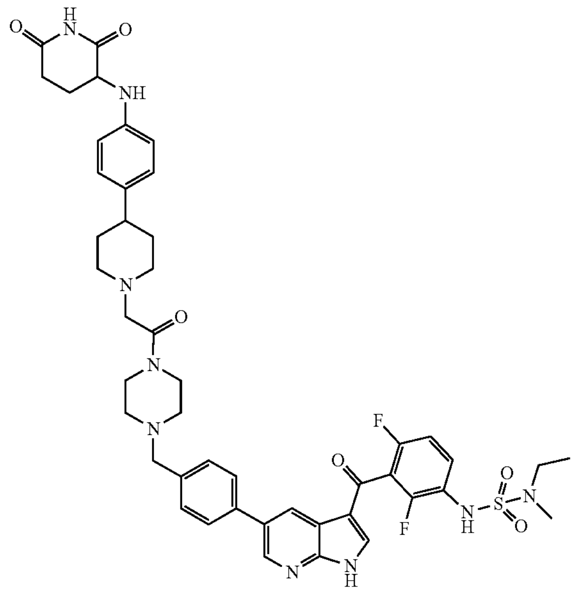 [SMILES: CCN(C)S(=O)(=O)Nc1ccc(F)c(C(=O)c2c[nH]c3ncc(-c4ccc(CN5CCN(C(=O)CN6CCC(c7ccc(NC8CCC(=O)NC8=O)cc7)CC6)CC5)cc4)cc23)c1F]

The title compound was obtained as light yellow solid in 42% yield according to general procedure VIII.

Amine: 3-[3-[[Ethyl(methyl)sulfamoyl]amino]-2,6-difluoro-benzoyl]-5-[4-(piperazin-1-ylmethyl)phenyl]-1H-pyrrolo[2,3-b]pyridine Acid: 2-[4-[4-[(2,6-dioxo-3-piperidyl)amino]phenyl]-1-piperidyl]acetic acid hydrochloride MS m/e: 897 ([M+H+]$^+$)

Example A 24

5-[4-[[4-[2-[4-[4-[(2,6-Dioxopiperidin-3-yl)amino]phenyl]piperazin-1-yl]acetyl]piperazin-1-yl]methyl]phenyl]-3-[3-[[ethyl(methyl)sulfamoyl]amino]-2,6-difluorobenzoyl]-1H-pyrrolo[2,3-b]pyridine; 2,2,2-trifluoroacetic acid

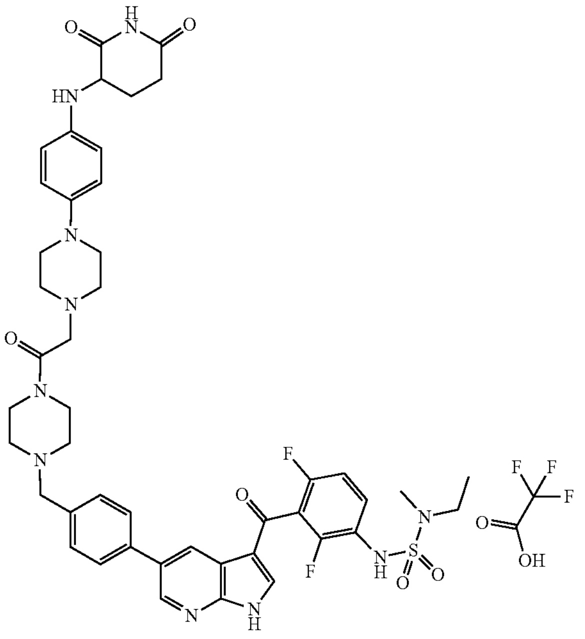

The title compound was obtained as light yellow solid in 43% yield according to general procedure VIII.

Amine: 3-[3-[[ethyl(methyl)sulfamoyl]amino]-2,6-difluoro-benzoyl]-5-[4-(piperazin-1-ylmethyl)phenyl]-1H-pyrrolo[2,3-b]pyridine Acid: 2-[4-[4-[(2,6-dioxo-3-piperidyl)amino]phenyl]piperazin-1-yl]acetic acid MS m/e: 897.8 ([M+H+]$^+$)

Example A 25

5-[4-[[4-[2-[4-[3-[(2,6-Dioxopiperidin-3-yl)amino]phenyl]piperazin-1-yl]acetyl]piperazin-1-yl]methyl]phenyl]-3-[3-[[ethyl(methyl)sulfamoyl]amino]-2,6-difluorobenzoyl]-1H-pyrrolo[2,3-b]pyridine; 2,2,2-trifluoroacetic acid

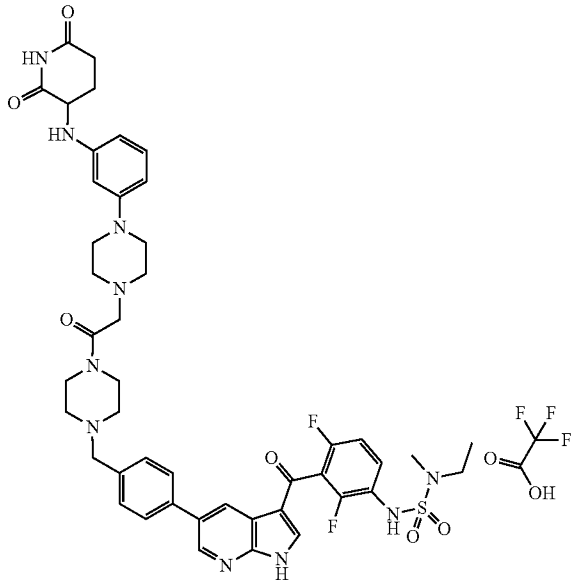

The title compound was obtained as light yellow solid in 75% yield according to general procedure VIII.

Amine: 3-[3-[[ethyl(methyl)sulfamoyl]amino]-2,6-difluoro-benzoyl]-5-[4-(piperazin-1-ylmethyl)phenyl]-1H-pyrrolo[2,3-b]pyridine Acid: 2-[4-[3-[(2,6-dioxo-3-piperidyl)amino]phenyl]piperazin-1-yl]acetic acid MS m/e: 897.8 ([M+H+]$^+$)

Example A 26

5-[4-[[4-[4-[4-[4-[(2,6-Dioxopiperidin-3-yl)amino]phenyl]piperidin-1-yl]butanoyl]piperazin-1-yl]methyl]phenyl]-3-[3-[[ethyl(methyl)sulfamoyl]amino]-2,6-difluorobenzoyl]-1H-pyrrolo[2,3-b]pyridine; 2,2,2-trifluoroacetic acid

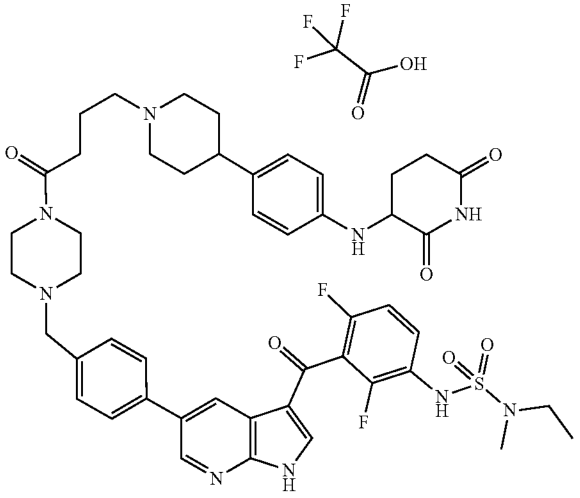 [SMILES: CCN(C)S(=O)(=O)Nc1ccc(F)c(C(=O)c2c[nH]c3ncc(-c4ccc(CN5CCN(C(=O)CCCN6CCC(c7ccc(NC8CCC(=O)NC8=O)cc7)CC6)CC5)cc4)cc23)c1F ; O=C(O)C(F)(F)F]

The title compound was obtained in 36% yield according to general procedure VIII.

Amine: 3-[3-[[ethyl(methyl)sulfamoyl]amino]-2,6-difluoro-benzoyl]-5-[4-(piperazin-1-ylmethyl)phenyl]-1H-pyrrolo[2,3-b]pyridine Acid: 4-[4-[4-[(2,6-dioxo-3-piperidyl)amino]phenyl]-1-piperidyl]butanoic acid MS m/e: 924.9 ([M+H+]$^+$)

Example A 27

N-[1-[[4-[3-[2,6-Difluoro-3-(pyrrolidin-1-ylsulfonylamino)benzoyl]-1H-pyrrolo[2,3-b]pyridin-5-yl]phenyl]methyl]piperidin-4-yl]-4-[4-(2,6-dioxopiperidin-3-yl)oxyphenyl]piperidine-1-carboxamide; formic acid

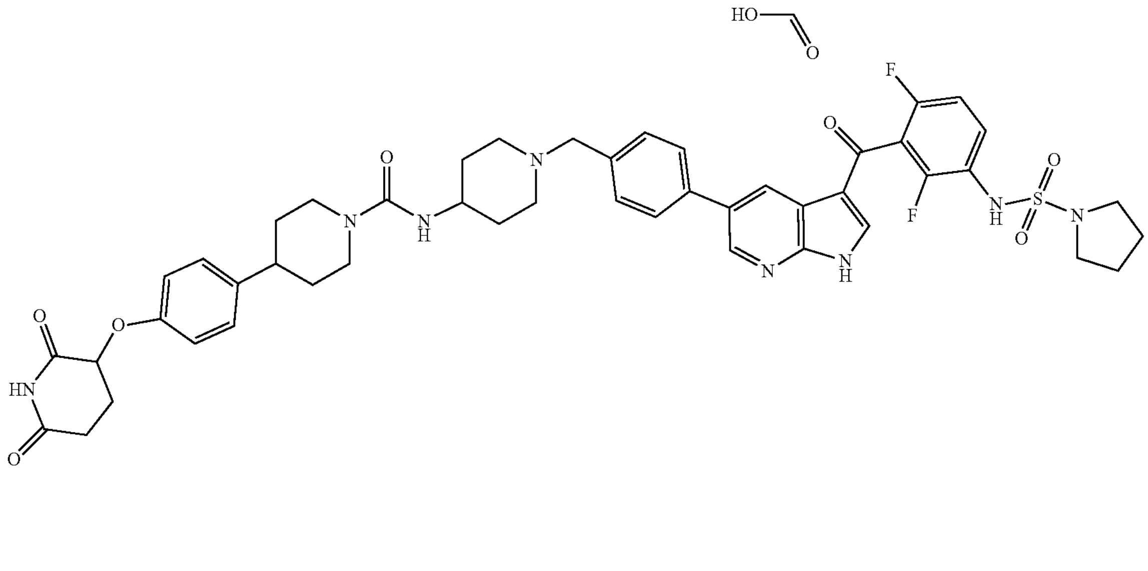 [SMILES: O=CO ; O=C1CCC(Oc2ccc(C3CCN(C(=O)NC4CCN(Cc5ccc(-c6cnc7[nH]cc(C(=O)c8c(F)ccc(NS(=O)(=O)N9CCCC9)c8F)c7c6)cc5)CC4)CC3)cc2)C(=O)N1]

To a solution of 3-[4-(4-piperidyl)phenoxy]piperidine-2,6-dione hydrochloride (28.0 mg, 0.090 mmol, 1 eq) in THF (10 mL) and DCM (10 mL) was added DIPEA (0.08 mL, 0.430 mmol, 5 eq) and bis(trichloromethyl) carbonate hydrochloride (9.48 mg, 0.030 mmol, 0.330 eq) at 25° C. After 1 h, N-[3-[5-[4-[(4-amino-1-piperidyl)methyl]phenyl]-1H-pyrrolo[2,3-b]pyridine-3-carbonyl]-2,4-difluorophenyl]pyrrolidine-1-sulfonamide (48.7 mg, 0.080 mmol, 0.950 eq) was added to the reaction. Then reaction mixture was stirred at 70° C. for 12 h. LCMS (WUX002055-256-P1A1) showed the starting material was consumed completely and major peak with desired MS. The reaction mixture was concentrated under reduced pressure to give a residue. The residue was purified by prep-HPLC and lyophilized to give the title compound (24 mg, 0.030 mmol, 29.71% yield) as a white solid. MS m/e: 909.1 ([M+H+]$^+$)

Example A 28

N-[3-[5-[6-[4-[2-[4-[4-(2,6-Dioxopiperidin-3-yl)oxyphenyl]piperidin-1-yl]acetyl]piperazin-1-yl]pyridin-3-yl]-1H-pyrrolo[2,3-b]pyridine-3-carbonyl]-2,4-difluorophenyl]butane-2-sulfonamide

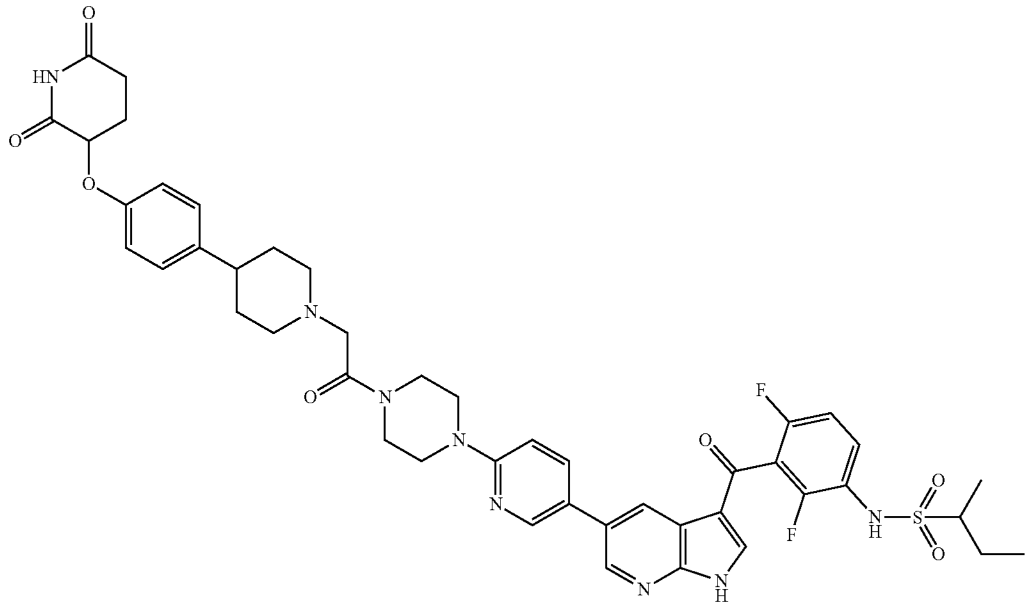 [SMILES: CCC(C)S(=O)(=O)Nc1ccc(F)c(C(=O)c2c[nH]c3ncc(-c4ccc(N5CCN(C(=O)CN6CCC(c7ccc(OC8CCC(=O)NC8=O)cc7)CC6)CC5)nc4)cc23)c1F]

The title compound was obtained as light yellow solid in 36% yield according to general procedure VIII.

Amine: rac-N-[2,4-Difluoro-3-[5-(6-piperazin-1-yl-3-pyridyl)-1H-pyrrolo[2,3-b]pyridine-3-carbonyl]phenyl]butane-2-sulfonamide Acid: 2-[4-[4-[(2,6-dioxo-3-piperidyl)oxy]phenyl]-1-piperidyl]acetic acid hydrochloride MS m/e: 883.6 ([M+H+]$^+$)

Example A 29

N-[3-[5-[6-[4-[2-[4-[4-[(2,6-Dioxopiperidin-3-yl)amino]phenyl]piperidin-1-yl]acetyl]piperazin-1-yl]pyridin-3-yl]-1H-pyrrolo[2,3-b]pyridine-3-carbonyl]-2,4-difluorophenyl]butane-2-sulfonamide

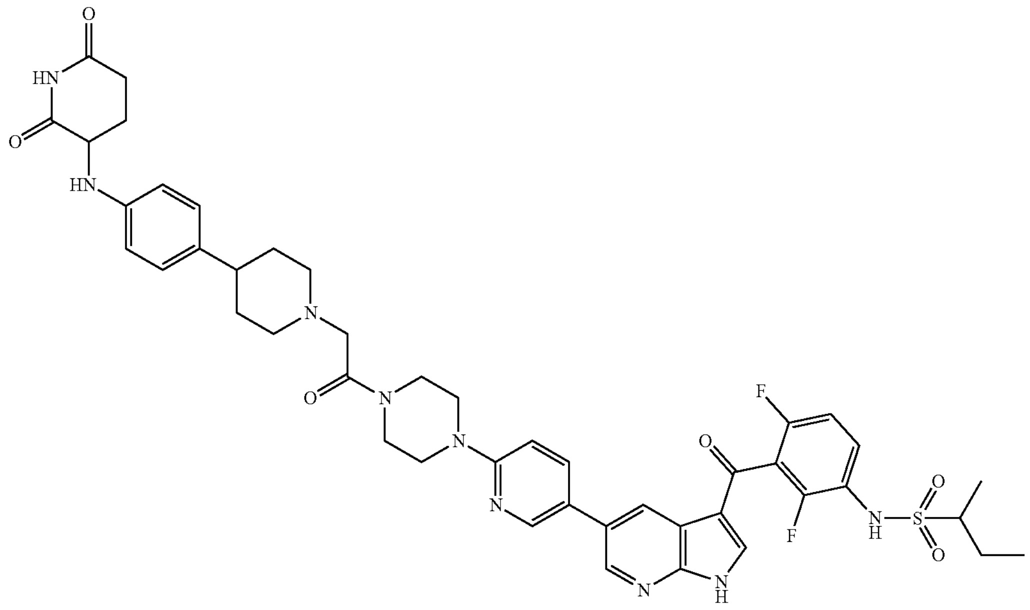 [SMILES: CCC(C)S(=O)(=O)Nc1ccc(F)c(C(=O)c2c[nH]c3ncc(-c4ccc(N5CCN(C(=O)CN6CCC(c7ccc(NC8CCC(=O)NC8=O)cc7)CC6)CC5)nc4)cc23)c1F]

The title compound was obtained as light yellow solid in 34% yield according to general procedure VIII.

Amine: rac-N-[2,4-Difluoro-3-[5-(6-piperazin-1-yl-3-pyridyl)-1H-pyrrolo[2,3-b]pyridine-3-carbonyl]phenyl]butane-2-sulfonamide Acid: 2-[4-[4-[(2,6-dioxo-3-piperidyl)amino]phenyl]-1-piperidyl]acetic acid hydrochloride MS m/e: 882.6 ([M+H+]$^+$)

Example A 30

5-[4-[1-[2-[4-[4-(2,6-Dioxopiperidin-3-yl)oxyphenyl]piperidin-1-yl]acetyl]piperidin-4-yl]oxyphenyl]-3-[3-[[ethyl(methyl)sulfamoyl]amino]-2,6-difluorobenzoyl]-1H-pyrrolo[2,3-b]pyridine

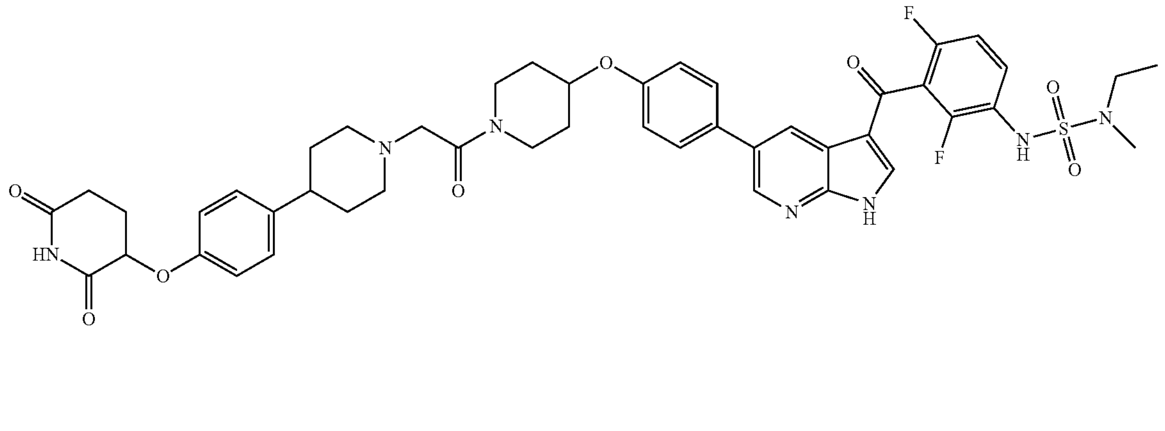 [SMILES: CCN(C)S(=O)(=O)Nc1ccc(F)c(C(=O)c2c[nH]c3ncc(-c4ccc(OC5CCN(C(=O)CN6CCC(c7ccc(OC8CCC(=O)NC8=O)cc7)CC6)CC5)cc4)cc23)c1F]

The title compound was obtained as off-white solid in 58% yield according to general procedure VIII.

Amine: 3-[3-[[Ethyl(methyl)sulfamoyl]amino]-2,6-difluoro-benzoyl]-5-[4-(4-piperidyloxy)phenyl]-1H-pyrrolo[2,3-b]pyridine Acid: 2-[4-[4-[(2,6-dioxo-3-piperidyl)oxy]phenyl]-1-piperidyl]acetic acid hydrochloride MS m/e: 898.4 ([M+H+]$^+$)

Example A 31

5-[4-[1-[2-[4-[4-[(2,6-dioxopiperidin-3-yl)amino]phenyl]piperidin-1-yl]acetyl]piperidin-4-yl]oxyphenyl]-3-[3-[[ethyl(methyl)sulfamoyl]amino]-2,6-difluorobenzoyl]-1H-pyrrolo[2,3-b]pyridine

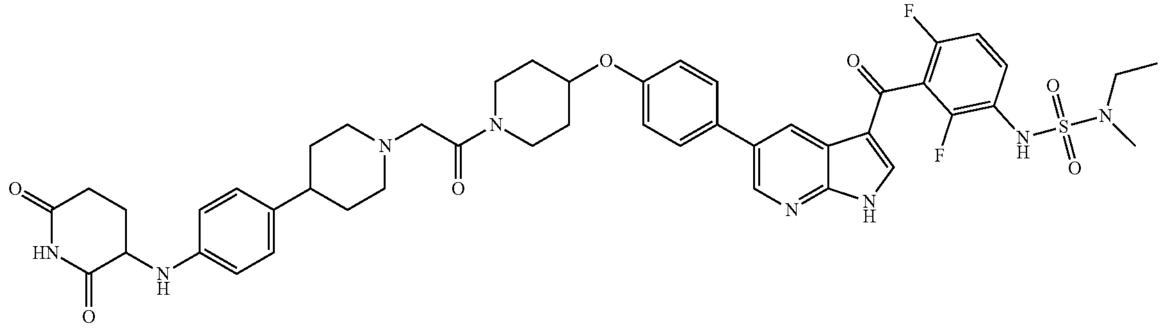

The title compound was obtained as yellow solid in 37% yield according to general procedure VIII.

Amine: 3-[3-[[Ethyl(methyl)sulfamoyl]amino]-2,6-difluoro-benzoyl]-5-[4-(4-piperidyloxy)phenyl]-1H-pyrrolo[2,3-b]pyridine Acid: 2-[4-[4-[(2,6-dioxo-3-piperidyl)amino]phenyl]-1-piperidyl]acetic acid hydrochloride MS m/e: 897.7 ([M+H+]$^+$)

Example A 32

N-[3-[5-[6-[4-[2-[4-[4-(2,6-Dioxopiperidin-3-yl)oxyphenyl]piperidin-1-yl]acetyl]piperazin-1-yl]pyridin-3-yl]-1H-pyrrolo[2,3-b]pyridine-3-carbonyl]-2,4-difluorophenyl]cyclohexanesulfonamide

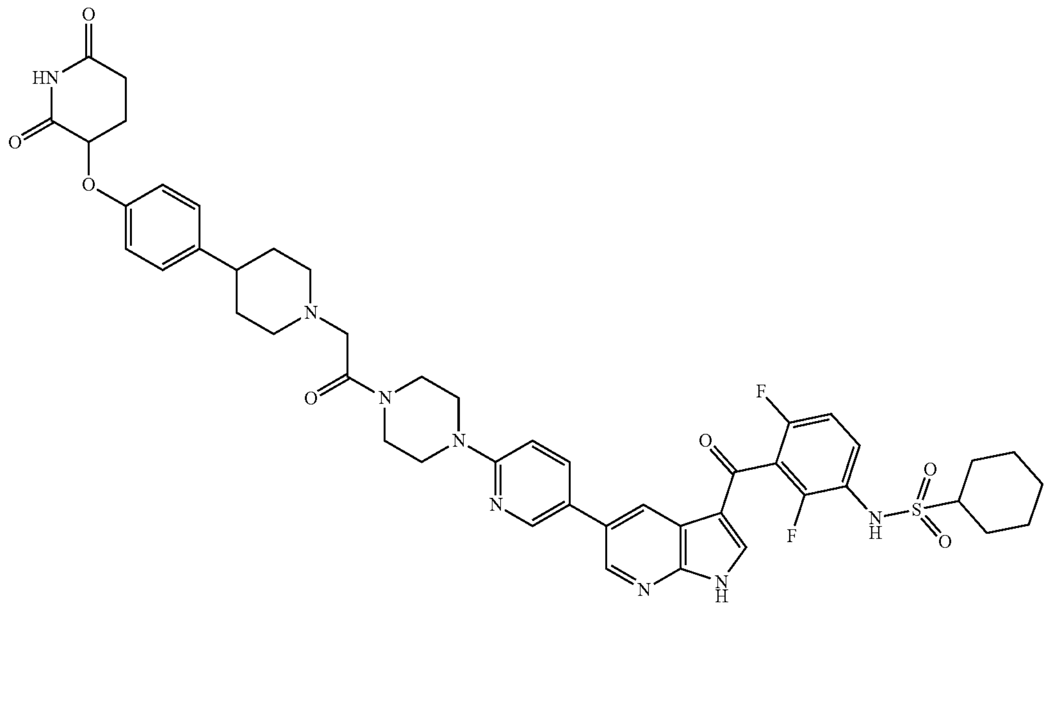 [SMILES: O=C1CCC(Oc2ccc(C3CCN(CC(=O)N4CCN(c5ccc(-c6cnc7[nH]cc(C(=O)c8c(F)ccc(NS(=O)(=O)C9CCCCC9)c8F)c7c6)cn5)CC4)CC3)cc2)C(=O)N1]

The title compound was obtained as light yellow solid in 37% yield according to general procedure VIII.

Amine: N-[2,4-difluoro-3-[5-(6-piperazin-1-yl-3-pyridyl)-1H-pyrrolo[2,3-b]pyridine-3-carbonyl]phenyl]cyclohexanesulfonamide Acid: 2-[4-[4-[(2,6-dioxo-3-piperidyl)oxy]phenyl]-1-piperidyl]acetic acid hydrochloride MS m/e: 455.6 ([M+2H+]$^{2+}$)

Example A 33

N-[3-[5-[6-[4-[2-[4-[4-[(2,6-Dioxopiperidin-3-yl)amino]phenyl]piperidin-1-yl]acetyl]piperazin-1-yl]pyridin-3-yl]-1H-pyrrolo[2,3-b]pyridine-3-carbonyl]-2,4-difluorophenyl]cyclohexanesulfonamide

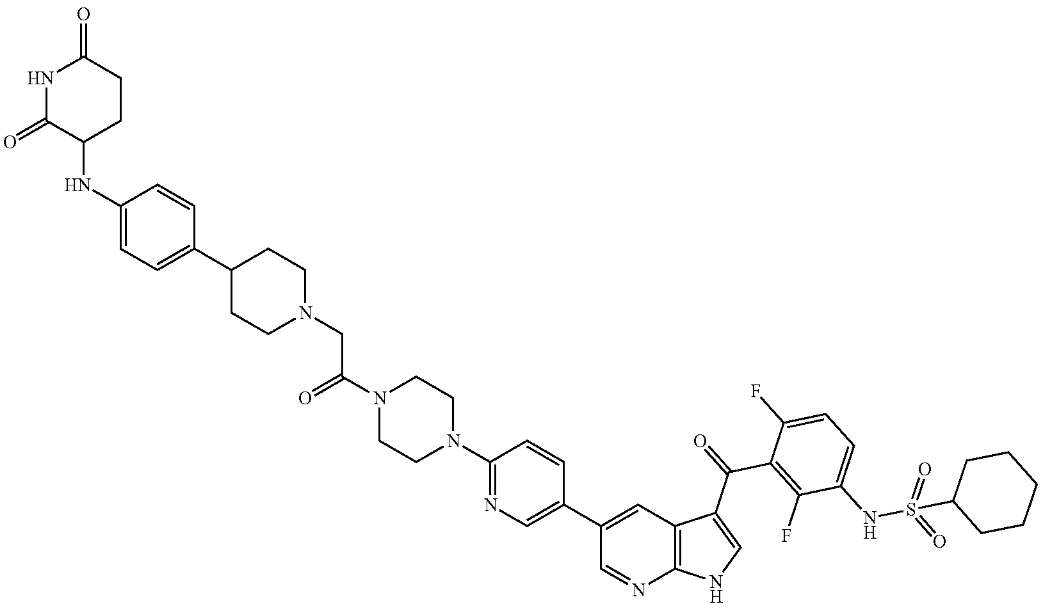 [SMILES: O=C1CCC(Nc2ccc(C3CCN(CC(=O)N4CCN(c5ccc(-c6cnc7[nH]cc(C(=O)c8c(F)ccc(NS(=O)(=O)C9CCCCC9)c8F)c7c6)cn5)CC4)CC3)cc2)C(=O)N1]

The title compound was obtained as light yellow solid in 34% yield according to general procedure VIII.

Amine: N-[2,4-difluoro-3-[5-(6-piperazin-1-yl-3-pyridyl)-1H-pyrrolo[2,3-b]pyridine-3-carbonyl]phenyl]cyclohexanesulfonamide Acid: 2-[4-[4-[(2,6-dioxo-3-piperidyl)amino]phenyl]-1-piperidyl]acetic acid hydrochloride MS m/e: 455.1 ([M+2H+]$^{2+}$)

Example A 34

4-[4-[(2,6-Dioxopiperidin-3-yl)amino]phenyl]-N-[1-[5-[3-[3-[[ethyl(methyl)sulfamoyl]amino]-2,6-difluorobenzoyl]-1H-pyrrolo[2,3-b]pyridin-5-yl]pyrimidin-2-yl]piperidin-4-yl]piperidine-1-carboxamide;formic acid

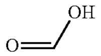

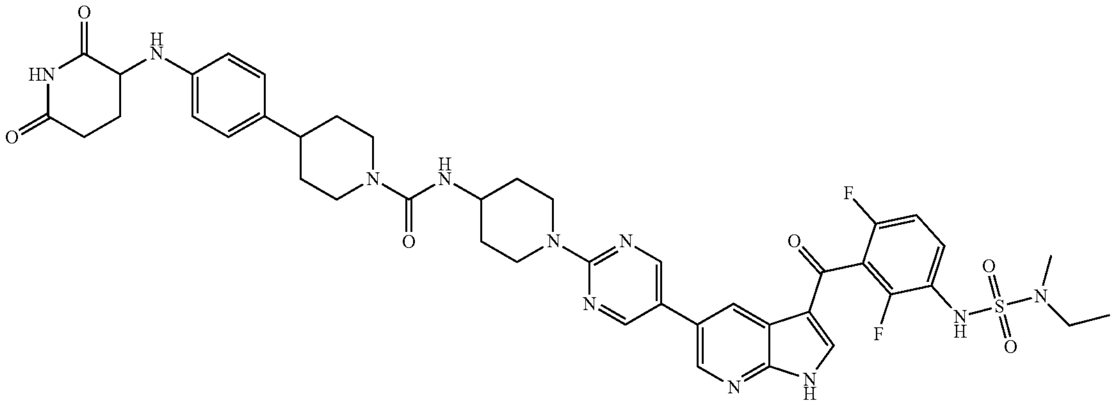

To a solution of compound 5-[2-(4-amino-1-piperidyl)pyrimidin-5-yl]-3-[3-[[ethyl(methyl)sulfamoyl]amino]-2,6-difluoro-benzoyl]-1H-pyrrolo[2,3-b]pyridine (50.0 mg, 0.08 mmol, 1 eq) in THF (25 mL) and DCM (5 mL) was added DIEA (53.22 mg, 0.41 mmol, 5 eq) and bis(trichloromethyl) carbonate (9.78 mg, 0.030 mmol, 0.4 eq) at 25° C. After 1 h, 3-[4-(4-piperidyl)anilino]piperidine-2,6-dione (26.75 mg, 0.08 mmol, 1 eq) was added to the reaction, then the reaction was stirred at 60° C. for 4 h. LCMS showed about 77% desired product MS: [M+H]+=885.0 was detected. The reaction mixture was concentrated under reduced pressure to give a residue. The residue was purified by prep-HPLC and lyophilized to give the title compound (6.7 mg, 0.010 mmol, 8.74% yield) as a white solid. MS obsd. (ESI+) [(M+H)+]: 885.0.

Example A 35

5-[6-[4-[3-[4-[4-(2,6-Dioxopiperidin-3-yl)oxyphenyl]piperidin-1-yl]propanoyl]piperazin-1-yl]pyridin-3-yl]-3-[3-[[ethyl(methyl)sulfamoyl]amino]-2,6-difluorobenzoyl]-1H-pyrrolo[2,3-b]pyridine

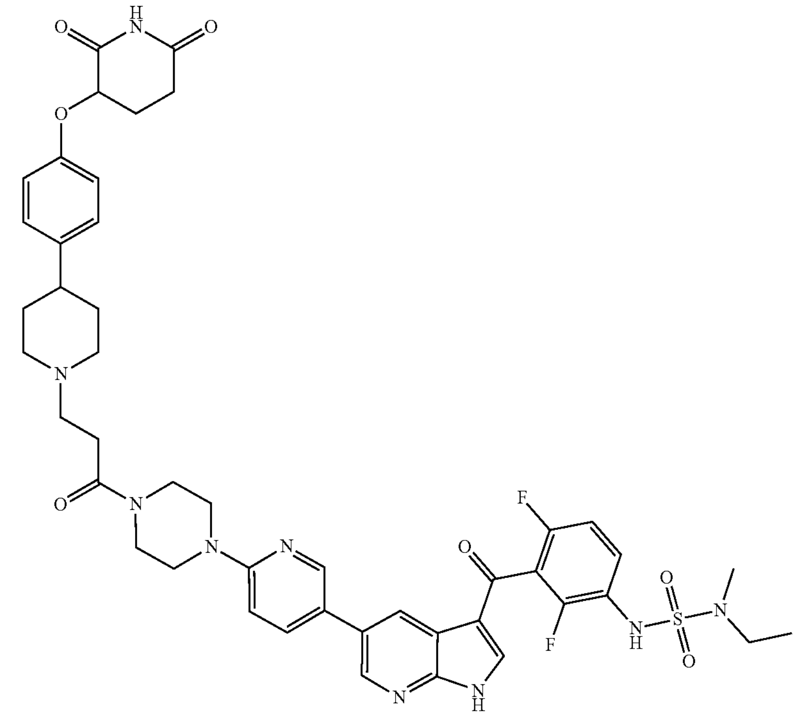 [SMILES: CCN(C)S(=O)(=O)Nc1ccc(F)c(C(=O)c2c[nH]c3ncc(-c4ccc(N5CCN(C(=O)CCN6CCC(c7ccc(OC8CCC(=O)NC8=O)cc7)CC6)CC5)nc4)cc23)c1F]

The title compound was obtained as off-white solid in 47% yield according to general procedure VIII.

Amine: 3-[3-[[ethyl(methyl)sulfamoyl]amino]-2,6-difluoro-benzoyl]-5-(6-piperazin-1-yl-3-pyridyl)-1H-pyrrolo[2,3-b]pyridine Acid: 3-[4-[4-[(2,6-dioxo-3-piperidyl)oxy]phenyl]-1-piperidyl]propanoic acid MS m/e: 889.5 ([M+H+]$^+$)

Example A 36

5-[4-[4-[2-[4-[4-[(2,6-Dioxopiperidin-3-yl)amino]phenyl]piperidin-1-yl]acetyl]piperazin-1-yl]phenyl]-3-[3-[[ethyl(methyl)sulfamoyl]amino]-2,6-difluorobenzoyl]-1H-pyrrolo[2,3-b]pyridine

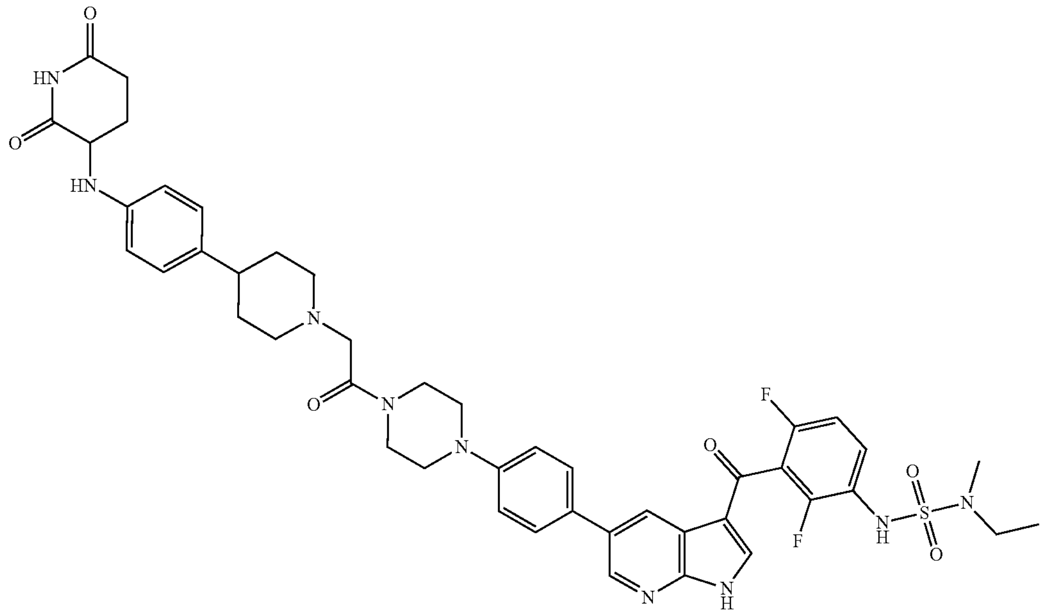 [SMILES: CCN(C)S(=O)(=O)Nc1ccc(F)c(C(=O)c2c[nH]c3ncc(-c4ccc(N5CCN(C(=O)CN6CCC(c7ccc(NC8CCC(=O)NC8=O)cc7)CC6)CC5)cc4)cc23)c1F]

The title compound was obtained as light green solid in 38% yield according to general procedure VIII.

Amine: 3-[3-[[ethyl(methyl)sulfamoyl]amino]-2,6-difluoro-benzoyl]-5-(4-piperazin-1-ylphenyl)-1H-pyrrolo[2,3-b]pyridine Acid: 2-[4-[4-[(2,6-dioxo-3-piperidyl)amino]phenyl]-1-piperidyl]acetic acid hydrochloride MS m/e: 882.6 ([M+H+]$^+$)

Example A 37

5-[6-[4-[2-[5-[(2,6-Dioxopiperidin-3-yl)amino]-1,3-dihydroisoindol-2-yl]acetyl]piperazin-1-yl]pyridin-3-yl]-3-[3-[[ethyl(methyl)sulfamoyl]amino]-2,6-difluorobenzoyl]-1H-pyrrolo[2,3-b]pyridine

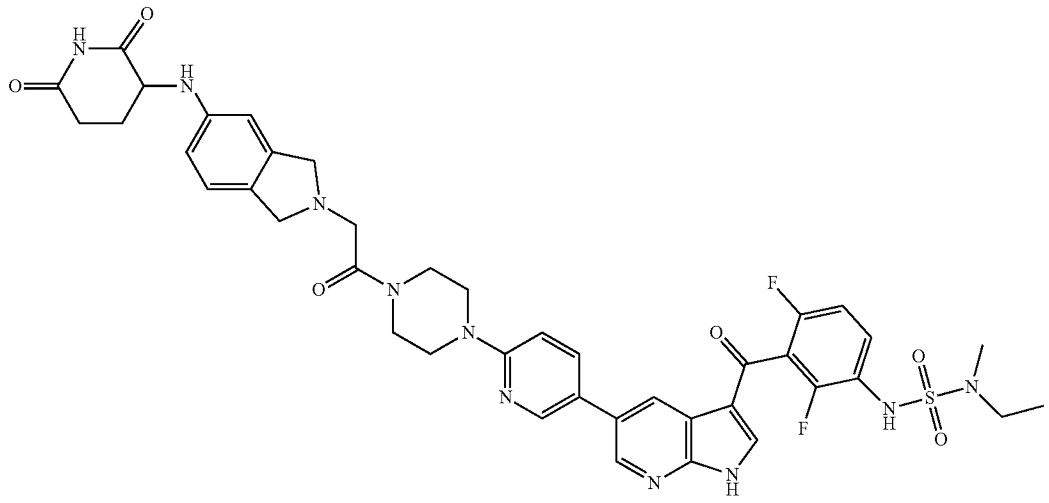 [SMILES: CCN(C)S(=O)(=O)Nc1ccc(F)c(C(=O)c2c[nH]c3ncc(-c4ccc(N5CCN(C(=O)CN6Cc7ccc(NC8CCC(=O)NC8=O)cc7C6)CC5)nc4)cc23)c1F]

The title compound was obtained as green solid in 51% yield according to general procedure VIII.

Amine: 3-[3-[[ethyl(methyl)sulfamoyl]amino]-2,6-difluoro-benzoyl]-5-(6-piperazin-1-yl-3-pyridyl)-1H-pyrrolo[2,3-b]pyridine Acid: 2-[5-[(2,6-dioxo-3-piperidyl)amino]isoindolin-2-yl]acetic acidhydrochloride MS m/e: 841.5 ([M+H+]$^+$)

Example A 38

5-[6-[[4-[2-[5-[(2,6-Dioxopiperidin-3-yl)amino]-1,3-dihydroisoindol-2-yl]acetyl]piperazin-1-yl]methyl]pyridin-3-yl]-3-[3-[[ethyl(methyl)sulfamoyl]amino]-2,6-difluorobenzoyl]-1H-pyrrolo[2,3-b]pyridine

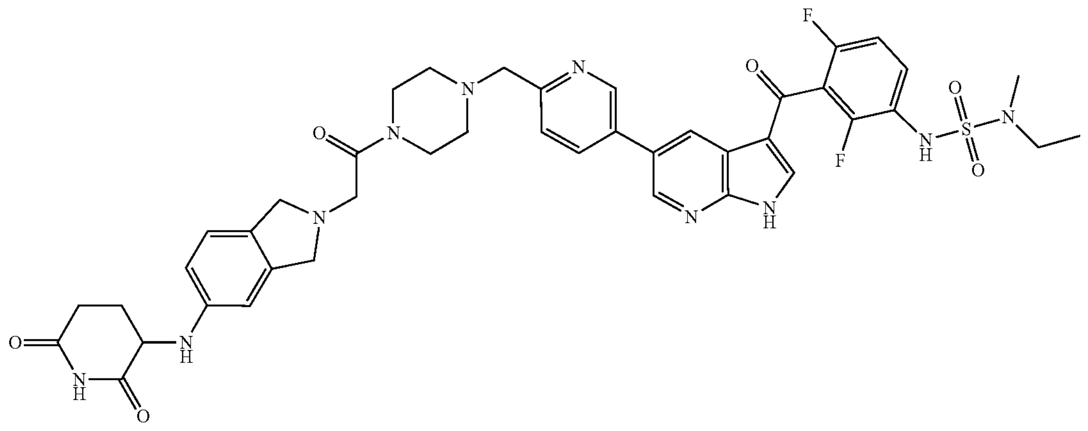 [SMILES: CCN(C)S(=O)(=O)Nc1ccc(F)c(C(=O)c2c[nH]c3ncc(-c4ccc(CN5CCN(C(=O)CN6Cc7ccc(NC8CCC(=O)NC8=O)cc7C6)CC5)nc4)cc23)c1F]

The title compound was obtained as grey solid in 48% yield according to general procedure VIII.

Amine: 3-[3-[[ethyl(methyl)sulfamoyl]amino]-2,6-difluoro-benzoyl]-5-[6-(piperazin-1-ylmethyl)-3-pyridyl]-1H-pyrrolo[2,3-b]pyridine Acid: 2-[5-[(2,6-dioxo-3-piperidyl)amino]isoindolin-2-yl]acetic acidhydrochloride MS m/e: 855.5 ([M+H+]$^+$)

Example A 39

2-[4-[(2,6-dioxopiperidin-3-yl)amino]phenyl]-N-[2-[4-[5-[3-[3-[[ethyl(methyl)sulfamoyl]amino]-2,6-difluorobenzoyl]-1H-pyrrolo[2,3-b]pyridin-5-yl]pyridin-2-yl]piperazin-1-yl]-2-oxoethyl]-N-methylacetamide

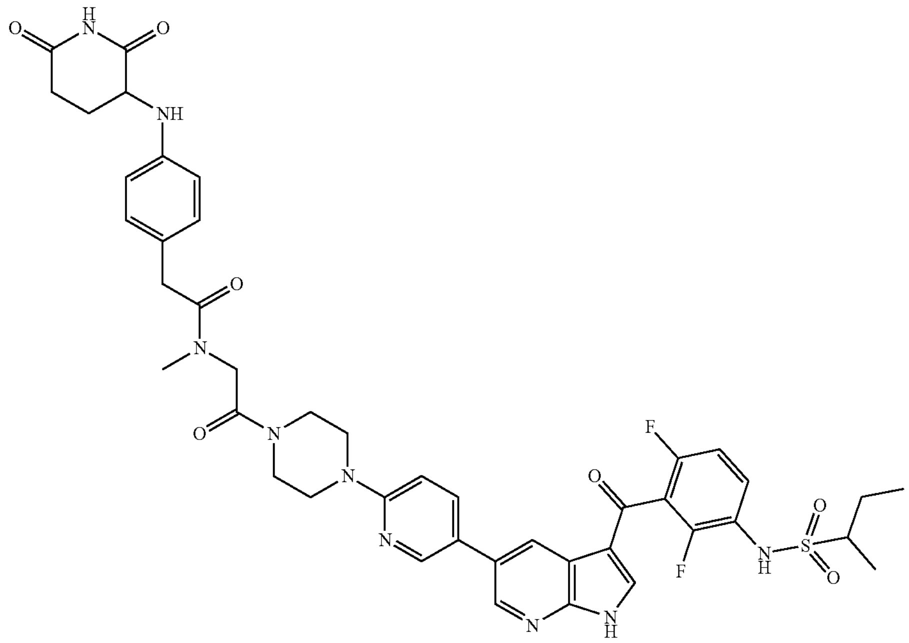 [SMILES: CCC(C)S(=O)(=O)Nc1ccc(F)c(C(=O)c2c[nH]c3ncc(-c4ccc(N5CCN(C(=O)CN(C)C(=O)Cc6ccc(NC7CCC(=O)NC7=O)cc6)CC5)nc4)cc23)c1F]

The title compound was obtained as light yellow solid in 41% yield according to general procedure VIII.

Amine: 3-[3-[[ethyl(methyl)sulfamoyl]amino]-2,6-difluoro-benzoyl]-5-(6-piperazin-1-yl-3-pyridyl)-1H-pyrrolo[2,3-b]pyridine Acid: 2-[[2-[4-[(2,6-Dioxo-3-piperidyl)amino]phenyl]acetyl]-methyl-amino]acetic acid hydrochloride MS m/e: 871.7 ([M+H+]$^+$)

Example A 40

4-[5-[(2,6-Dioxopiperidin-3-yl)amino]pyridin-2-yl]-N-[1-[5-[3-[3-[[ethyl(methyl)sulfamoyl]amino]-2,6-difluorobenzoyl]-1H-pyrrolo[2,3-b]pyridin-5-yl]pyrimidin-2-yl]piperidin-4-yl]piperidine-1-carboxamide;formic acid

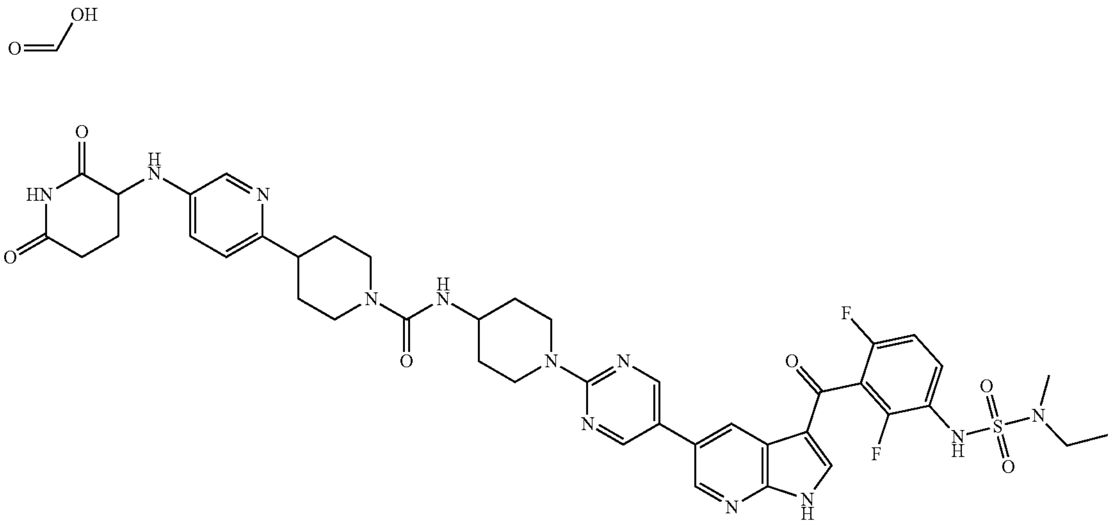 [SMILES: O=CO ; CCN(C)S(=O)(=O)Nc1ccc(F)c(C(=O)c2c[nH]c3ncc(-c4cnc(N5CCC(NC(=O)N6CCC(c7ccc(NC8CCC(=O)NC8=O)cn7)CC6)CC5)nc4)cc23)c1F]

To a solution of 5-[2-(4-amino-1-piperidyl)pyrimidin-5-yl]-3-[3-[[ethyl(methyl)sulfamoyl]amino]-2,6-difluoro-benzoyl]-1H-pyrrolo[2,3-b]pyridine (50.0 mg, 0.08 mmol, 1 eq) in THF (25 mL) and DCM (5 mL) was added DIPEA (53.22 mg, 0.41 mmol, 5 eq) and bis(trichloromethyl) carbonate (9.78 mg, 0.030 mmol, 0.4 eq) at 25° C. After 1 h, 3-[[6-(4-piperidyl)-3-pyridyl]amino]piperidine-2,6-dione (26.75 mg, 0.08 mmol, 1 eq) was added to the reaction, then the reaction was stirred at 60° C. for 4 h. The reaction mixture was concentrated under reduced pressure to give a residue. The residue was purified by prep-HPLC and lyophilized to give the title compound (6.7 mg, 0.010 mmol, 8.74% yield) as a white solid. MS m/e: 885 ([M+H+]$^+$)

Example A 41

4-[4-[(2,6-Dioxopiperidin-3-yl)amino]phenyl]-N-[1-[5-[3-[3-[[ethyl(methyl)sulfamoyl]amino]-2,6-difluorobenzoyl]-1H-pyrrolo[2,3-b]pyridin-5-yl]pyridin-2-yl]piperidin-4-yl]piperidine-1-carboxamide; formic acid

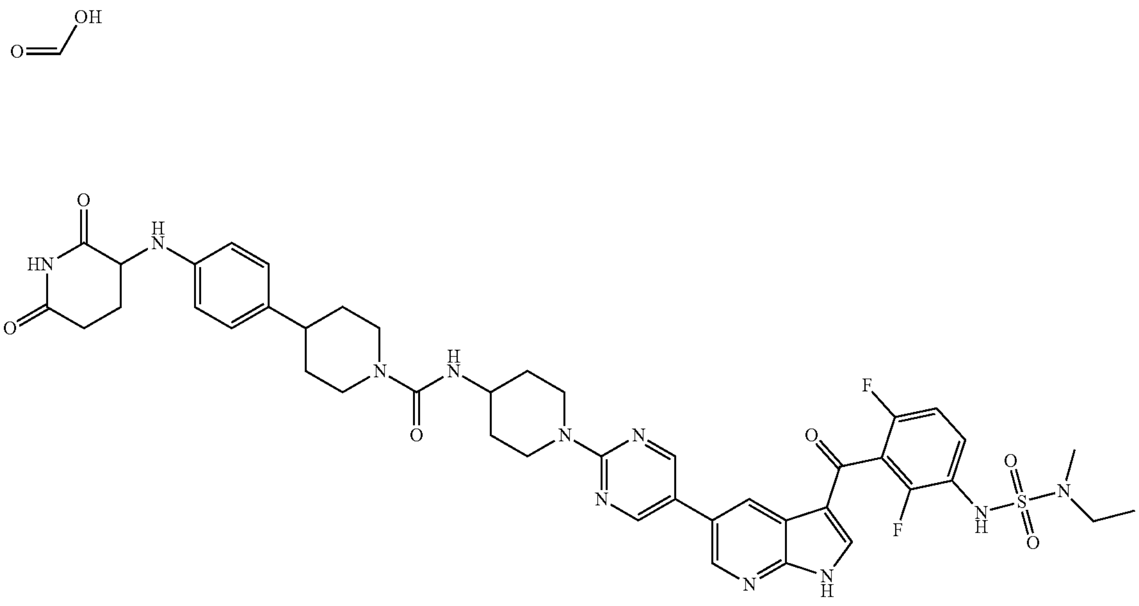 [SMILES: O=CO ; CCN(C)S(=O)(=O)Nc1ccc(F)c(C(=O)c2c[nH]c3ncc(-c4cnc(N5CCC(NC(=O)N6CCC(c7ccc(NC8CCC(=O)NC8=O)cc7)CC6)CC5)nc4)cc23)c1F]

To a solution of 5-[6-(4-amino-1-piperidyl)-3-pyridyl]-3-[3-[[ethyl(methyl)sulfamoyl]amino]-2,6-difluoro-benzoyl]-1H-pyrrolo[2,3-b]pyridine (50.0 mg, 0.08 mmol, 1 eq) in THF (25 mL) and DCM (5 mL) was added DIPEA (53.31 mg, 0.41 mmol, 5 eq) and bis(trichloromethyl) carbonate (9.79 mg, 0.030 mmol, 0.4 eq) at 25° C. After 1 h, 3-[4-(4-piperidyl)anilino]piperidine-2,6-dione (26.71 mg, 0.08 mmol, 1 eq) was added to the reaction, then the reaction was stirred at 60° C. for 4 h. LCMS showed about 79% desired product MS: $[M+H]^+$=883.0 was detected. The reaction mixture was concentrated under reduced pressure to give a residue. The residue was purified by prep-HPLC and lyophilized to give the title compound (12 mg, 0.010 mmol, 15.31% yield) as an off-white solid. MS m/e: 883 ($[M+H+]^+$)

Example A 42

4-[4-(2,6-Dioxopiperidin-3-yl)oxyphenyl]-N-[1-[5-[3-[3-[[ethyl(methyl)sulfamoyl]amino]-2,6-difluorobenzoyl]-1H-pyrrolo[2,3-b]pyridin-5-yl]pyridin-2-yl]piperidin-4-yl]piperidine-1-carboxamide;formic acid

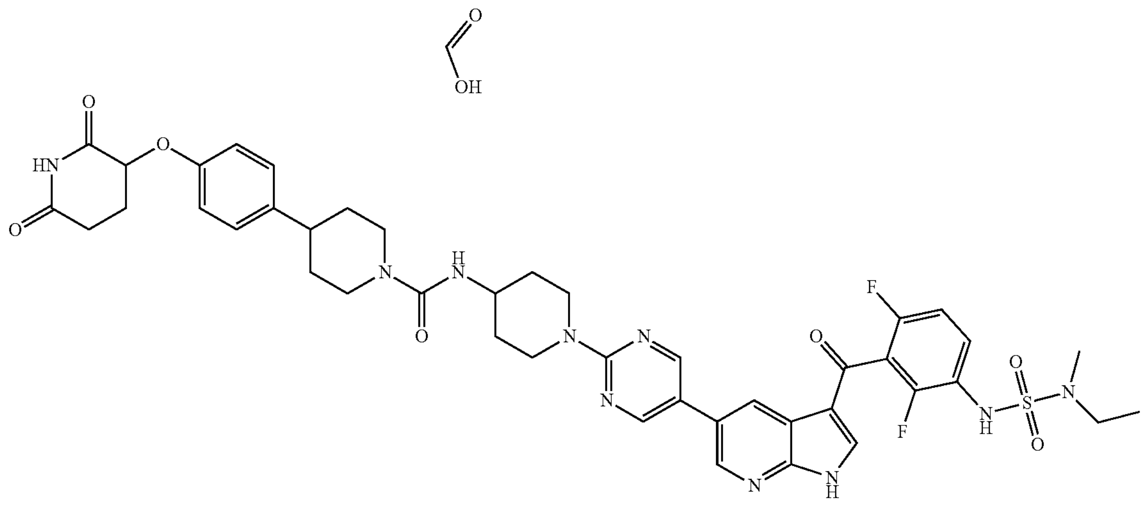 [SMILES: O=CO ; CCN(C)S(=O)(=O)Nc1ccc(F)c(C(=O)c2c[nH]c3ncc(-c4cnc(N5CCC(NC(=O)N6CCC(c7ccc(OC8CCC(=O)NC8=O)cc7)CC6)CC5)nc4)cc23)c1F]

To a solution of 5-[6-(4-amino-1-piperidyl)-3-pyridyl]-3-[3-[[ethyl(methyl)sulfamoyl]amino]-2,6-difluoro-benzoyl]-1H-pyrrolo[2,3-b]pyridine hydrochloride (20.0 mg, 0.030 mmol, 1 eq) in THF (10 mL) was added DIPEA (21.32 mg, 0.160 mmol, 5 eq) and bis(trichloromethyl)carbonate (3.92 mg, 0.010 mmol, 0.400 eq) at 25° C. After 1 h, 3-[4-(4-piperidyl)phenoxy]piperidine-2,6-dione hydrochloride (10.72 mg, 0.030 mmol, 1 eq) was added to the reaction, then the reaction was stirred at 60° C. for 12 h. The reaction mixture was concentrated under reduced pressure to give a residue. The residue was purified by prep-HPLC and lyophilized to give the title compound (12 mg, 0.010 mmol, 37.11% yield) as yellow solid. MS m/e: 884 ($[M+H+]^+$)

Example A 43

5-[2-[1-[2-[4-[4-[(2,6-Dioxopiperidin-3-yl)amino]phenyl]piperidin-1-yl]acetyl]piperidin-4-yl]ethynyl]-3-[3-[[ethyl(methyl)sulfamoyl]amino]-2,6-difluorobenzoyl]-1H-pyrrolo[2,3-b]pyridine

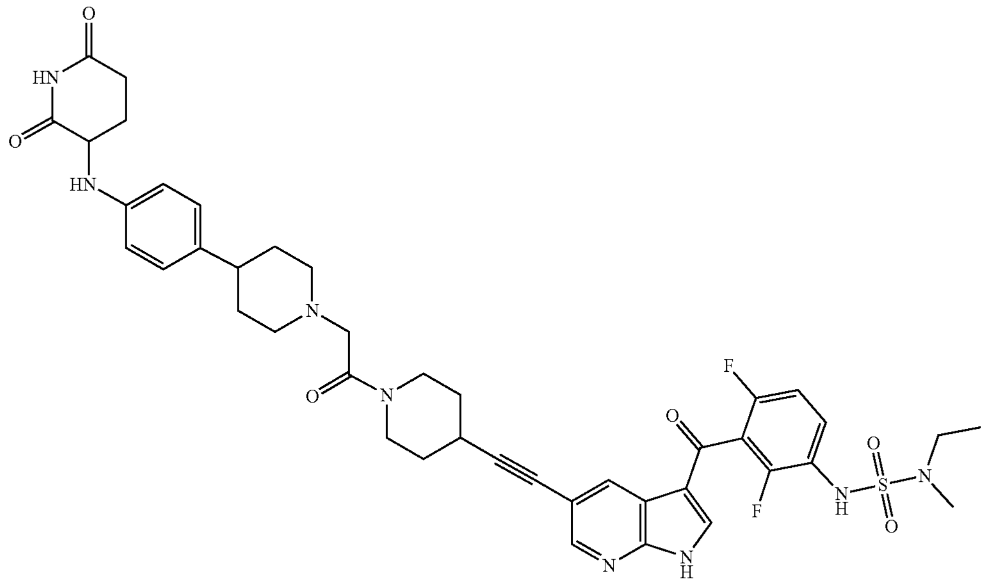 [SMILES: CCN(C)S(=O)(=O)Nc1ccc(F)c(C(=O)c2c[nH]c3ncc(C#CC4CCN(C(=O)CN5CCC(c6ccc(NC7CCC(=O)NC7=O)cc6)CC5)CC4)cc23)c1F]

The title compound was obtained as light yellow solid in 25% yield according to general procedure VIII.

Amine: 3-[3-[[ethyl(methyl)sulfamoyl]amino]-2,6-difluoro-benzoyl]-5-[2-(4-piperidypethynyl]-1H-pyrrolo[2,3-b]pyridine Acid: 2-[4-[4-[(2,6-dioxo-3-piperidyl)amino]phenyl]-1-piperidyl]acetic acid hydrochloride MS m/e: 829.6 ([M+H+]$^+$)

Example A 44

5-[4-[1-[2-[4-[4-[(2,6-Dioxopiperidin-3-yl)amino]phenyl]piperidin-1-yl]acetyl]piperidin-4-yl]phenyl]-3-[3-[[ethyl(methyl)sulfamoyl]amino]-2,6-difluorobenzoyl]-1H-pyrrolo[2,3-b]pyridine

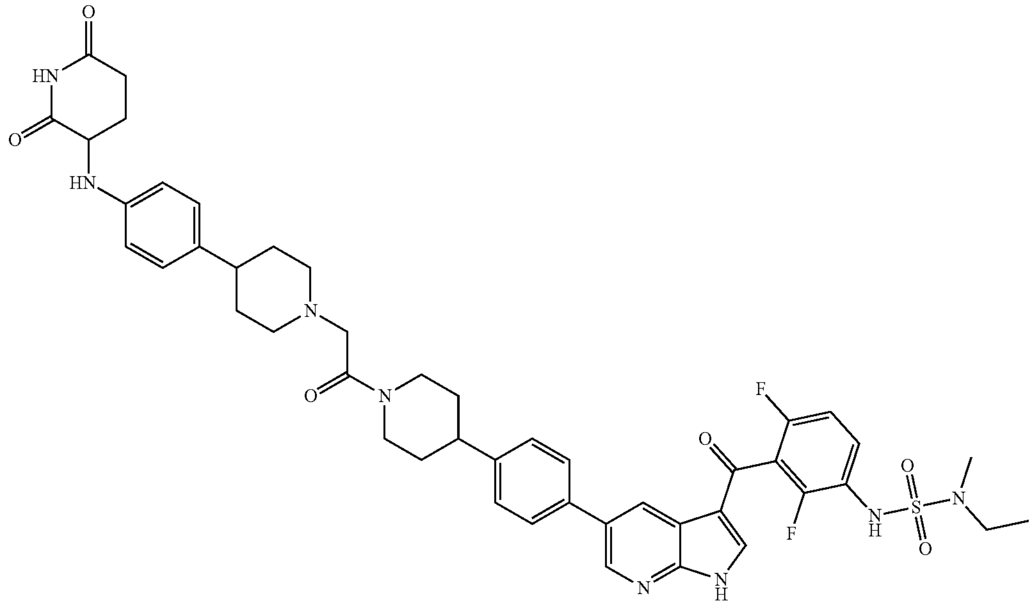 [SMILES: CCN(C)S(=O)(=O)Nc1ccc(F)c(C(=O)c2c[nH]c3ncc(-c4ccc(C5CCN(C(=O)CN6CCC(c7ccc(NC8CCC(=O)NC8=O)cc7)CC6)CC5)cc4)cc23)c1F]

The title compound was obtained as light green solid in 64% yield according to general procedure VIII.

Amine: 3-[3-[[ethyl(methyl)sulfamoyl]amino]-2,6-difluoro-benzoyl]-5-[4-(4-piperidyl)phenyl]-1H-pyrrolo[2,3-b]pyridine Acid: 2-[4-[4-[(2,6-dioxo-3-piperidyl)amino]phenyl]-1-piperidyl]acetic acid hydrochloride MS m/e: 882.7 ([M+H+]$^+$)

Example A 45

5-[6-[4-[2-[4-[5-(2,6-Dioxopiperidin-3-yl)oxypyridin-2-yl]piperidin-1-yl]acetyl]piperazin-1-yl]pyridin-3-yl]-3-[3-[[ethyl(methyl)sulfamoyl]amino]-2,6-difluorobenzoyl]-1H-pyrrolo[2,3-b]pyridine

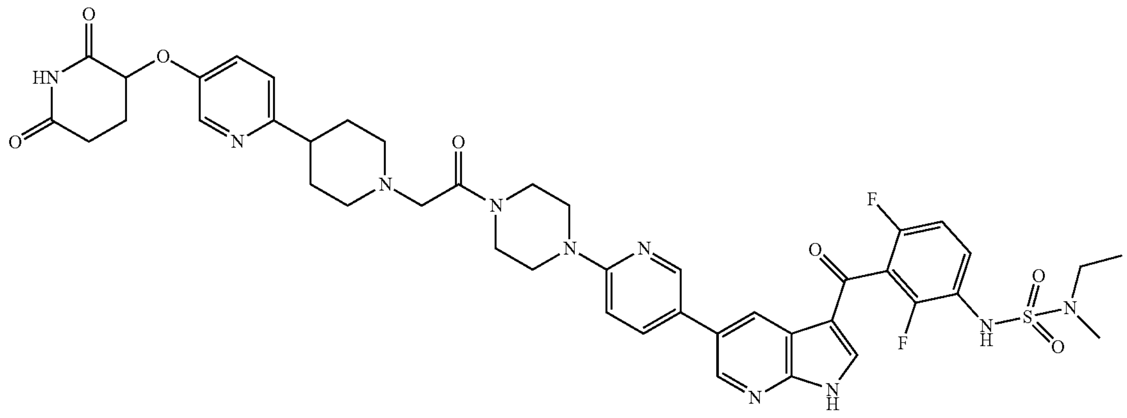 [SMILES: CCN(C)S(=O)(=O)Nc1ccc(F)c(C(=O)c2c[nH]c3ncc(-c4ccc(N5CCN(C(=O)CN6CCC(c7ccc(OC8CCC(=O)NC8=O)cn7)CC6)CC5)nc4)cc23)c1F]

The title compound was obtained as light yellow solid in 52% yield according to general procedure VIII.

Amine: 3-[3-[[ethyl(methyl)sulfamoyl]amino]-2,6-difluoro-benzoyl]-5-(6-piperazin-1-yl-3-pyridyl)-1H-pyrrolo[2,3-b]pyridine Acid: 2-[4-[5-[(2,6-dioxo-3-piperidyl)oxy]-2-pyridyl]-1-piperidyl]acetic acid hydrochloride MS m/e: 885.6 ([M+H+]$^+$)

Example A 46

5-[2-[1-[2-[4-[4-[(2,6-Dioxopiperidin-3-yl)amino]phenyl]piperidin-1-yl]acetyl]piperidin-4-yl]pyrimidin-5-yl]-3-[3-[[ethyl(methyl)sulfamoyl]amino]-2,6-difluorobenzoyl]-1H-pyrrolo[2,3-b]pyridine

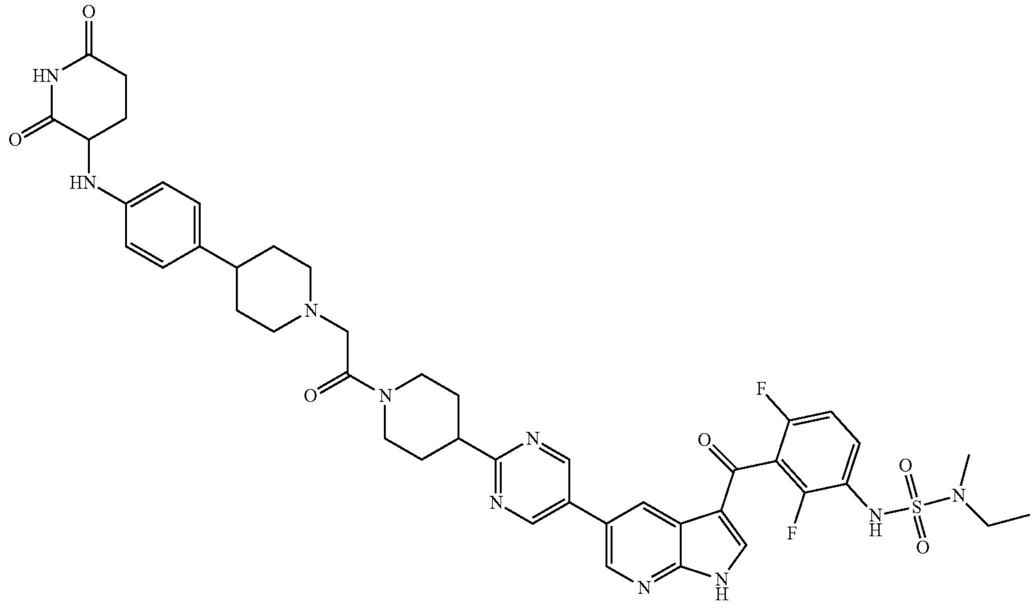

The title compound was obtained as light yellow solid in 73% yield according to general procedure VIII.

Amine: 3-[3-[[ethyl(methyl)sulfamoyl]amino]-2,6-difluoro-benzoyl]-5-[2-(4-piperidyl)pyrimidin-5-yl]-1H-pyrrolo[2,3-b]pyridine Acid: 2-[4-[4-[(2,6-dioxo-3-piperidyl)amino]phenyl]-1-piperidyl]acetic acid hydrochloride MS m/e: 883.5 ([M+H+]$^+$)

Example A 47

5-[6-[4-[2-[4-[4-[(2,4-Dioxo-3-azabicyclo[3.1.1]heptan-1-yl)amino]phenyl]piperidin-1-yl]acetyl]piperazin-1-yl]pyridin-3-yl]-3-[3-[[ethyl(methyl)sulfamoyl]amino]-2,6-difluorobenzoyl]-1H-pyrrolo[2,3-b]pyridine

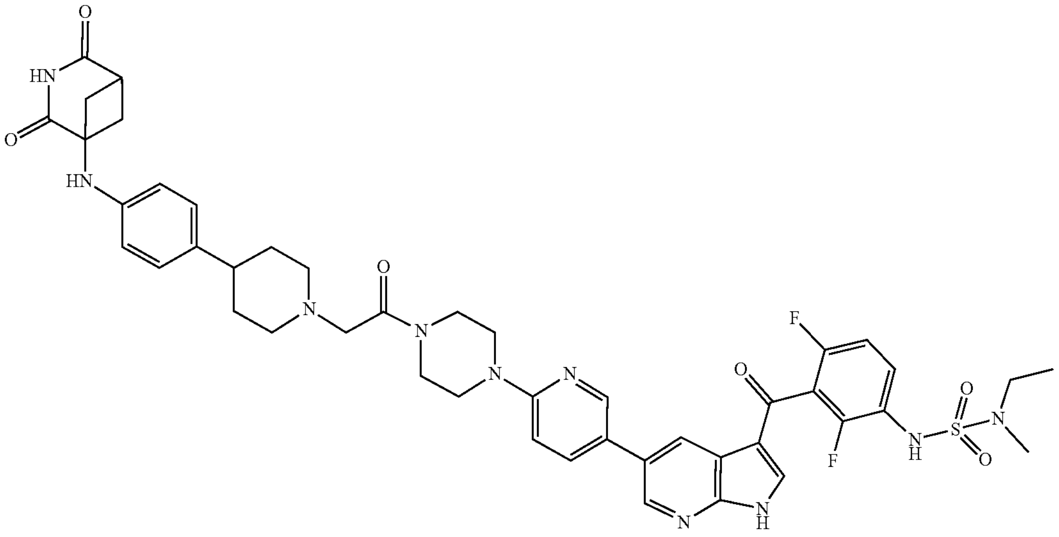 [SMILES: CCN(C)S(=O)(=O)Nc1ccc(F)c(C(=O)c2c[nH]c3ncc(-c4ccc(N5CCN(C(=O)CN6CCC(c7ccc(NC89CC(C8)C(=O)NC9=O)cc7)CC6)CC5)nc4)cc23)c1F]

The title compound was obtained as light yellow solid in 52% yield according to general procedure VIII.

Amine: 3-[3-[[ethyl(methyl)sulfamoyl]amino]-2,6-difluoro-benzoyl]-5-(6-piperazin-1-yl-3-pyridyl)-1H-pyrrolo[2,3-b]pyridine Acid: 2-[4-[4-[(2,4-dioxo-3-azabicyclo[3.1.1]heptan-1-yl)amino]phenyl]-1-piperidyl]acetic acid hydrochloride MS m/e: 895.7 ([M+H+]$^+$)

Example A 48

N-[3-[5-[4-[4-[2-[4-[4-[(2,6-Dioxopiperidin-3-yl)amino]phenyl]piperidin-1-yl]acetyl]piperazin-1-yl]phenyl]-1H-pyrrolo[2,3-b]pyridine-3-carbonyl]-2,4-difluorophenyl]pyrrolidine-1-sulfonamide

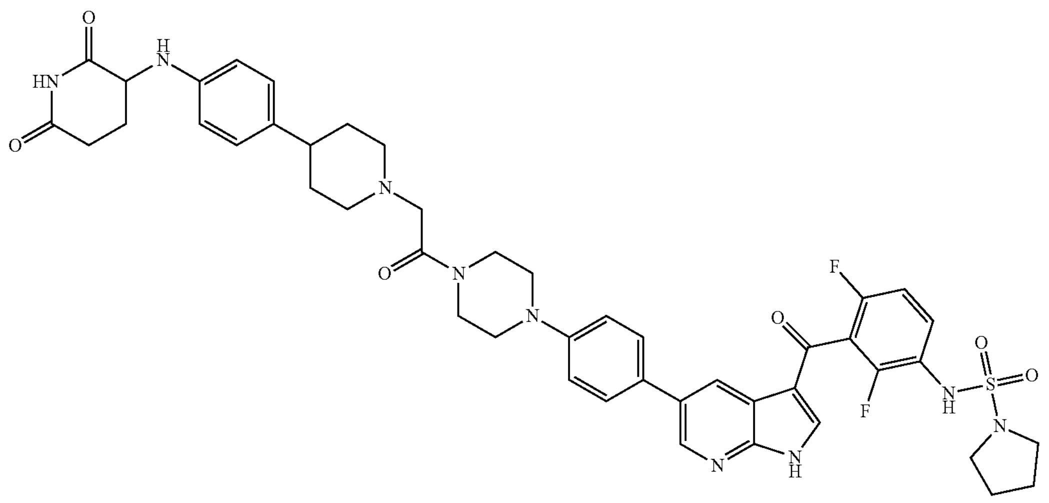 [SMILES: O=C1CCC(Nc2ccc(C3CCN(CC(=O)N4CCN(c5ccc(-c6cnc7[nH]cc(C(=O)c8c(F)ccc(NS(=O)(=O)N9CCCC9)c8F)c7c6)cc5)CC4)CC3)cc2)C(=O)N1]

The title compound was obtained in 13% yield according to general procedure VIII.

Amine: N-[2,4-difluoro-3-[5-(4-piperazin-1-ylphenyl)-1H-pyrrolo[2,3-b]pyridine-3-carbonyl]phenyl]pyrrolidine-1-sulfonamide Acid: 2-[4-[4-[(2,6-dioxo-3-piperidyl)amino]phenyl]-1-piperidyl]acetic acid hydrochloride MS m/e: 894.8 ([M+H+]$^+$)

Example A 49

5-[6-[1-[2-[4-[4-[(2,6-Dioxopiperidin-3-yl)amino]phenyl]piperidin-1-yl]acetyl]piperidin-4-yl]pyridin-3-yl]-3-[3-[[ethyl(methyl)sulfamoyl]amino]-2,6-difluorobenzoyl]-1H-pyrrolo[2,3-b]pyridine

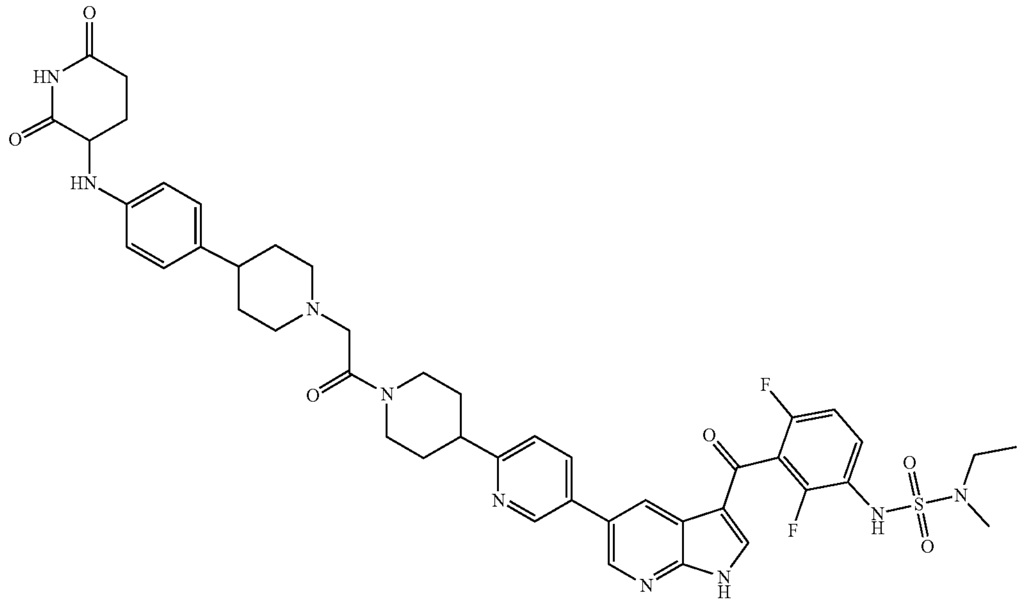 [SMILES: CCN(C)S(=O)(=O)Nc1ccc(F)c(C(=O)c2c[nH]c3ncc(-c4ccc(C5CCN(C(=O)CN6CCC(c7ccc(NC8CCC(=O)NC8=O)cc7)CC6)CC5)nc4)cc23)c1F]

The title compound was obtained as light yellow solid in 17% yield according to general procedure VIII.

Amine: 3-[3-[[Ethyl(methyl)sulfamoyl]amino]-2,6-difluoro-benzoyl]-5-[6-(4-piperidyl)-3-pyridyl]-1H-pyrrolo[2,3-b]pyridine 2,2,2-trifluoroacetic acid Acid: 2-[4-[4-[(2,6-dioxo-3-piperidyl)amino]phenyl]-1-piperidyl]acetic acid hydrochloride MS m/e: 883.6 ([M+H+]$^+$)

Example A 50

N-[3-[5-[4-[4-[2-[4-[4-(2,6-Dioxopiperidin-3-yl)oxyphenyl]piperidin-1-yl]acetyl]piperazin-1-yl]phenyl]-1H-pyrrolo[2,3-b]pyridine-3-carbonyl]-2,4-difluorophenyl]pyrrolidine-1-sulfonamide

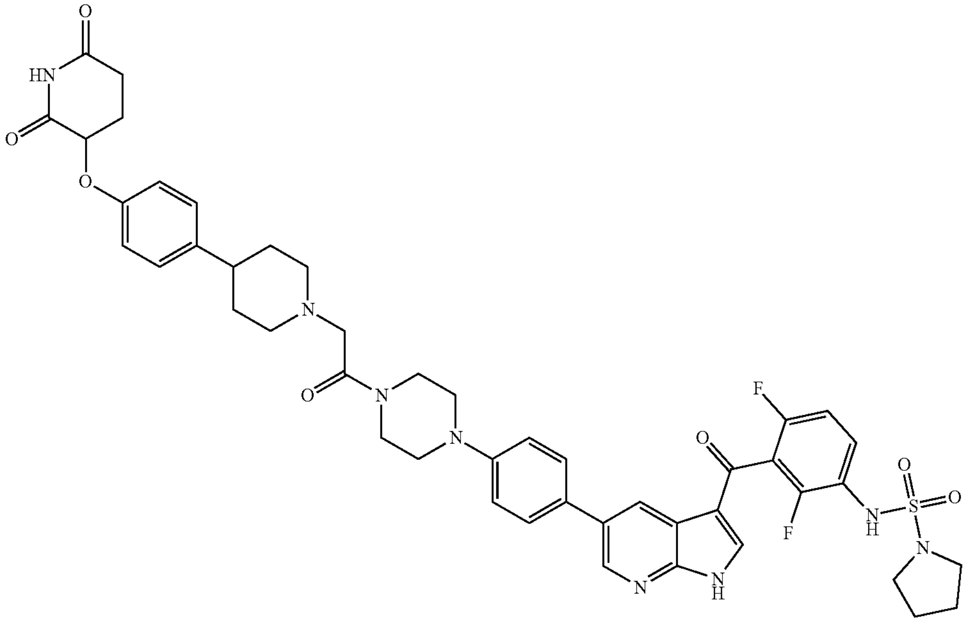 [SMILES: O=C1CCC(Oc2ccc(C3CCN(CC(=O)N4CCN(c5ccc(-c6cnc7[nH]cc(C(=O)c8c(F)ccc(NS(=O)(=O)N9CCCC9)c8F)c7c6)cc5)CC4)CC3)cc2)C(=O)N1]

The title compound was obtained as white solid in 16% yield according to general procedure VIII.

Amine: 3-[3-[[Ethyl(methyl)sulfamoyl]amino]-2,6-difluoro-benzoyl]-5-[6-(4-piperidyl)-3-pyridyl]-1H-pyrrolo[2,3-b]pyridine 2,2,2-trifluoroacetic acid Acid: 2-[4-[4-[(2,6-dioxo-3-piperidyl)oxy]phenyl]-1-piperidyl]acetic acid hydrochloride MS m/e: 893.3 ([M−H+]$^-$)

Example A 51

N-[3-[5-[4-[4-[2-[4-[4-[(2,6-Dioxopiperidin-3-yl) amino]phenyl]piperazin-1-yl]acetyl]piperazin-1-yl] phenyl]-1H-pyrrolo[2,3-b]pyridine-3-carbonyl]-2,4-difluorophenyl]pyrrolidine-1-sulfonamide

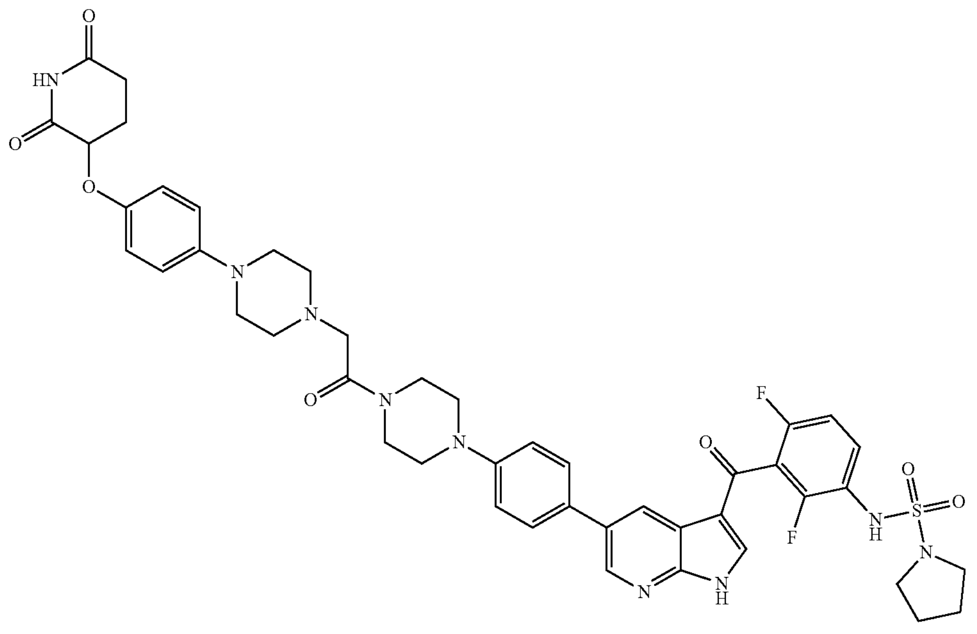

The title compound was obtained as white solid in 16% yield according to general procedure VIII.

Amine: 3-[3-[[Ethyl(methyl)sulfamoyl]amino]-2,6-difluoro-benzoyl]-5-[6-(4-piperidyl)-3-pyridyl]-1H-pyrrolo[2,3-b]pyridine 2,2,2-trifluoroacetic acid Acid: 2-[4-[4-[(2,6-dioxo-3-piperidyl)amino]phenyl]piperazin-1-yl]acetic acid hydrochloride MS m/e: 893.3 ([M−H+]$^-$)

Example A 52

N-[3-[5-[4-[4-[2-[4-[4-[(2,6-Dioxopiperidin-3-yl)amino]phenyl]piperidin-1-yl]acetyl]piperazin-1-yl]phenyl]-1H-pyrrolo[2,3-b]pyridine-3-carbonyl]-2,4-difluorophenyl]cyclopentanesulfonamide

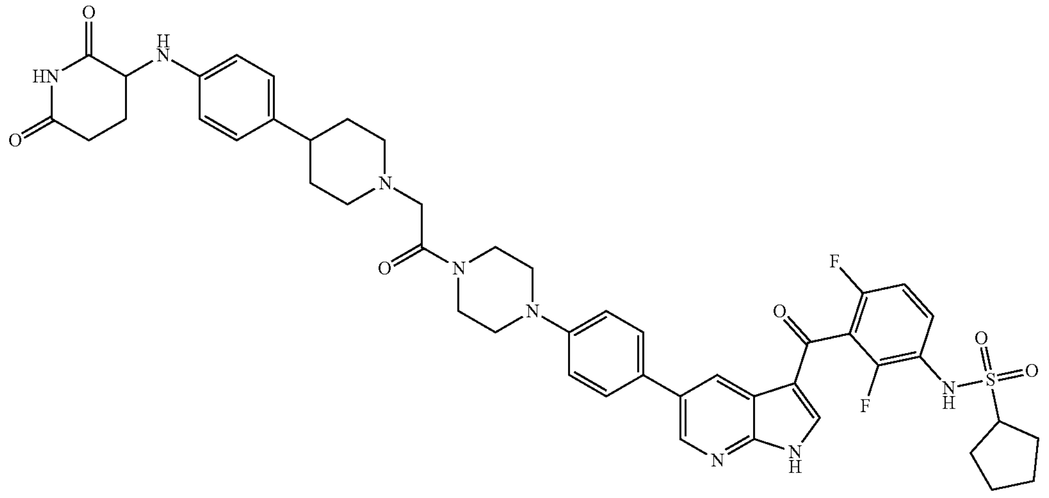 [SMILES: O=C1CCC(Nc2ccc(C3CCN(CC(=O)N4CCN(c5ccc(-c6cnc7[nH]cc(C(=O)c8c(F)ccc(NS(=O)(=O)C9CCCC9)c8F)c7c6)cc5)CC4)CC3)cc2)C(=O)N1]

The title compound was obtained as white solid in 8% yield with a purity of 77% according to general procedure VIII.

Amine: N-[2,4-difluoro-3-[5-(4-piperazin-1-ylphenyl)-1H-pyrrolo[2,3-b]pyridine-3-carbonyl]phenyl]cyclopentanesulfonamide trifluoroacetic acid Acid: 2-[4-[4-[(2,6-dioxo-3-piperidyl)amino]phenyl]-1-piperidyl]acetic acid hydrochloride MS m/e: 893.3 ([M+H+]$^+$)

Example A 53

N-[1-[[4-[3-[2,6-Difluoro-3-(pyrrolidin-1-ylsulfonylamino)benzoyl]-1H-pyrrolo[2,3-b]pyridin-5-yl]phenyl]methyl]piperidin-4-yl]-4-[4-[(2,6-dioxopiperidin-3-yl)amino]phenyl]piperidine-1-carboxamide; formic acid

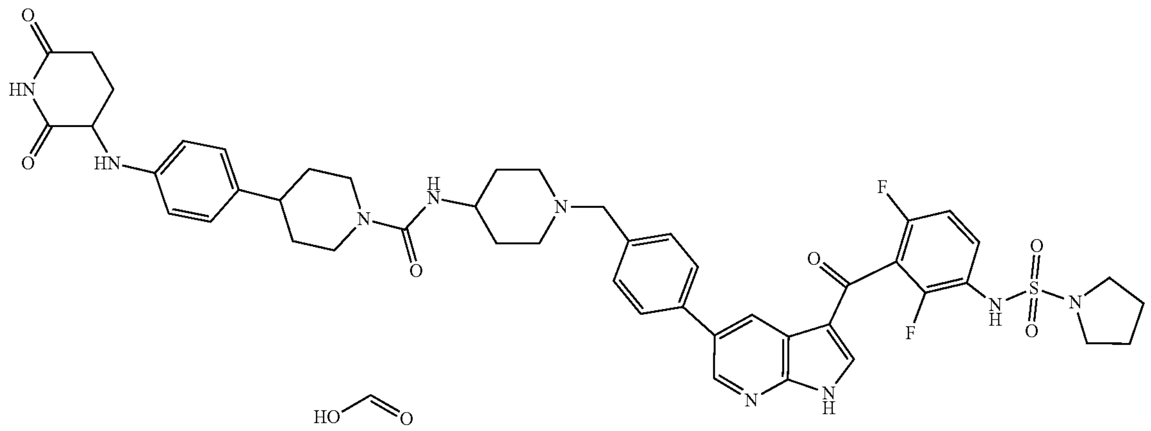 [SMILES: O=C1CCC(Nc2ccc(C3CCN(C(=O)NC4CCN(Cc5ccc(-c6cnc7[nH]cc(C(=O)c8c(F)ccc(NS(=O)(=O)N9CCCC9)c8F)c7c6)cc5)CC4)CC3)cc2)C(=O)N1 ; O=CO]

To a solution of 3-[4-(4-piperidyl)anilino]piperidine-2,6-dione hydrochloride (16.93 mg, 0.050 mmol, 1.1 eq) and N-ethyl-N-isopropylpropan-2-amine (36.86 mg, 0.290 mmol, 6 eq) in THF (10 mL) and DCM (10 mL), then bis(trichloromethyl)carbonate (5.64 mg, 0.020 mmol, 0.400 eq) was added at 25° C., the mixture was stirred at 25° C. for 1 hour. Then N-[3-[5-[4-[(4-amino-1-piperidyl)methyl]phenyl]-1H-pyrrolo[2,3-b]pyridine-3-carbonyl]-2,4-difluoro-phenyl]pyrrolidine-1-sulfonamide hydrochloride (30.0 mg, 0.050 mmol, 1 eq) was added to the mixture, the reaction mixture was stirred at 70° C. for 15 hours. The reaction mixture was concentrated under reduced pressure to give a residue. The residue was purified by prep-HPLC and lyophilized to give the title compound (6 mg, 0.010 mmol, 15.85% yield) as off-white solid. MS m/e: 908 ([M+H+]$^+$)

Example A 54

5-[2-[4-[2-[4-[4-[(2,6-Dioxopiperidin-3-yl)amino]-2-fluorophenyl]piperidin-1-yl]acetyl]piperazin-1-yl]pyrimidin-5-yl]-3-[3-[[ethyl(methyl)sulfamoyl]amino]-2,6-difluorobenzoyl]-1H-pyrrolo[2,3-b]pyridine

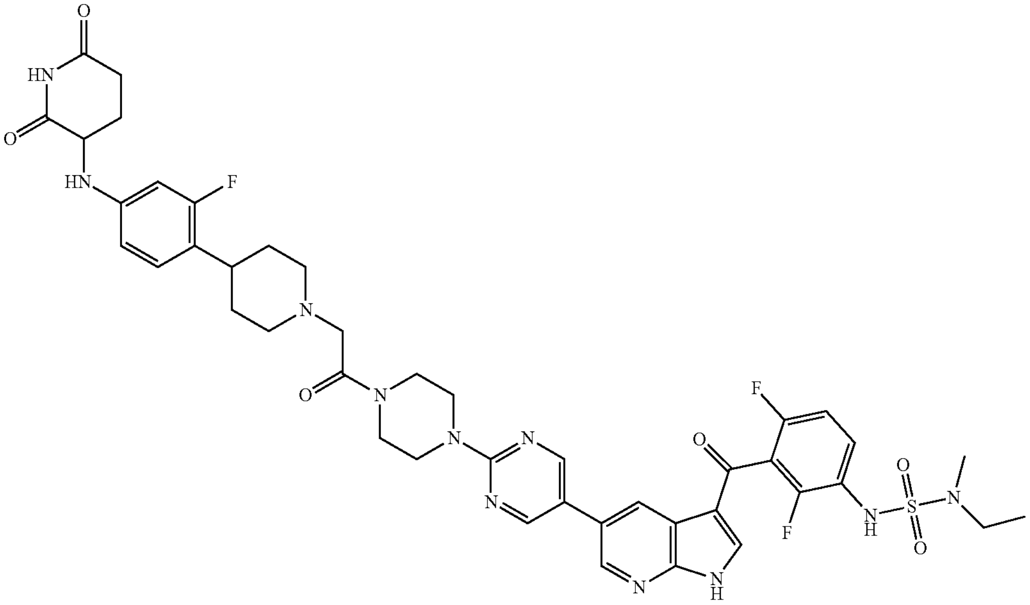 [SMILES: CCN(C)S(=O)(=O)Nc1ccc(F)c(C(=O)c2c[nH]c3ncc(-c4cnc(N5CCN(C(=O)CN6CCC(c7ccc(NC8CCC(=O)NC8=O)cc7F)CC6)CC5)nc4)cc23)c1F]

The title compound was obtained as light green solid in 50% yield according to general procedure VIII.

Amine: 3-[3-[[Ethyl(methyl)sulfamoyl]amino]-2,6-difluoro-benzoyl]-5-(2-piperazin-1-ylpyrimidin-5-yl)-1H-pyrrolo[2,3-b]pyridine Acid: 2-[4-[4-[(2,6-dioxo-3-piperidyl)amino]-2-fluoro-phenyl]-1-piperidyl]acetic acid hydrochloride MS m/e: 902 ([M+H+]$^+$)

Example A 55

5-[2-[4-[2-[4-[4-[(2,6-Dioxopiperidin-3-yl)amino]phenyl]piperidin-1-yl]-2-methylpropanoyl]piperazin-1-yl]pyrimidin-5-yl]-3-[3-[[ethyl(methyl)sulfamoyl]amino]-2,6-difluorobenzoyl]-1H-pyrrolo[2,3-b]pyridine

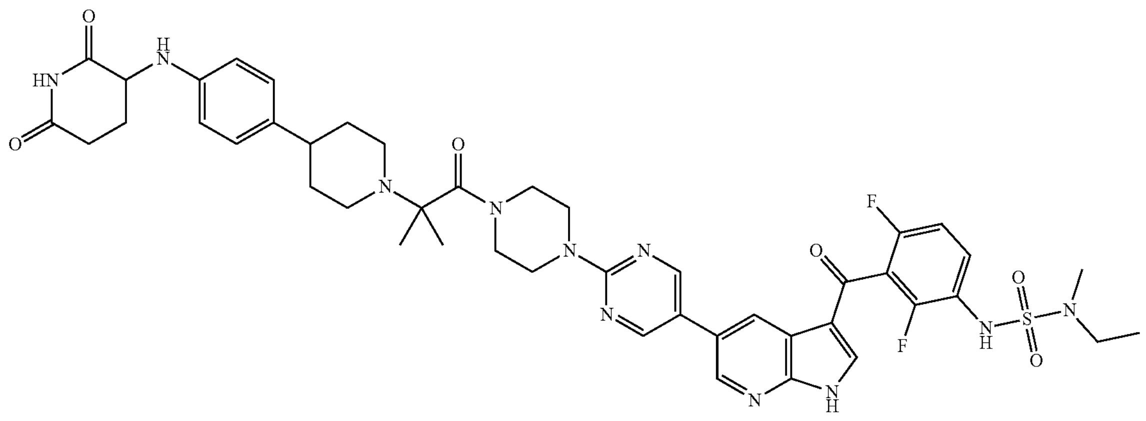 [SMILES: CCN(C)S(=O)(=O)Nc1ccc(F)c(C(=O)c2c[nH]c3ncc(-c4cnc(N5CCN(C(=O)C(C)(C)N6CCC(c7ccc(NC8CCC(=O)NC8=O)cc7)CC6)CC5)nc4)cc23)c1F]

The title compound was obtained as light green solid in 21% yield according to general procedure VIII.

Amine: 3-[3-[[Ethyl(methyl)sulfamoyl]amino]-2,6-difluoro-benzoyl]-5-(2-piperazin-1-ylpyrimidin-5-yl)-1H-pyrrolo[2,3-b]pyridine Acid: 2-[4-[4-[(2,6-dioxo-3-piperidyl)amino]phenyl]-1-piperidyl]-2-methyl-propanoic acid hydrochloride MS m/e: 913 ($[M+H+]^+$)

Example A 56

2-[4-[5-[(2,6-dioxopiperidin-3-yl)amino]pyridin-2-yl]piperidin-1-yl]-N-[1-[4-[3-[3-[[ethyl(methyl)sulfamoyl]amino]-2,6-difluorobenzoyl]-1H-pyrrolo[2,3-b]pyridin-5-yl]phenyl]piperidin-4-yl]acetamide; formic acid

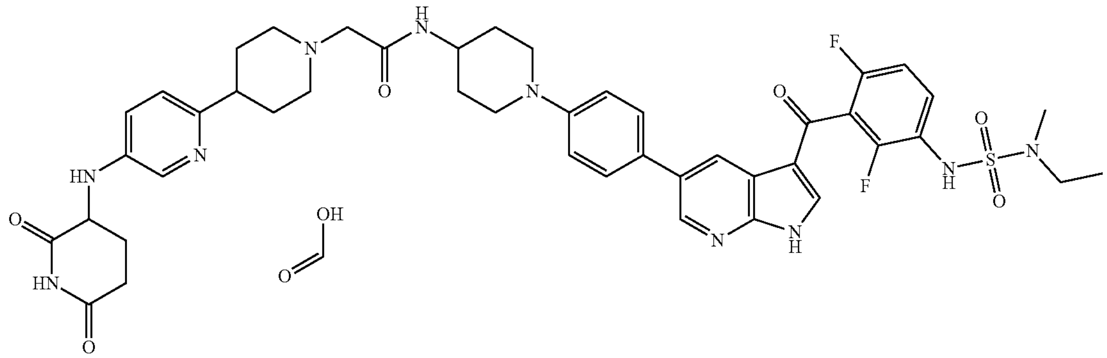 [SMILES: CCN(C)S(=O)(=O)Nc1ccc(F)c(C(=O)c2c[nH]c3ncc(-c4ccc(N5CCC(NC(=O)CN6CCC(c7ccc(NC8CCC(=O)NC8=O)cn7)CC6)CC5)cc4)cc23)c1F ; O=CO]

To a solution of 5-[4-(4-amino-1-piperidyl)phenyl]-3-[3-[[ethyl(methyl)sulfamoyl]amino]-2,6-difluoro-benzoyl]-1H-pyrrolo[2,3-b]pyridine (30.0 mg, 0.05 mmol, 1 eq) in THF (15 mL) was added DIPEA (32.04 mg, 0.25 mmol, 5 eq) and chloroacetyl chloride (5.6 mg, 0.05 mmol, 1 eq) at 0° C. The reaction was stirred at 25° C. for 1 h, then 3-[[6-(4-piperidyl)-3-pyridyl]amino]piperidine-2,6-dione (32.21 mg, 0.1 mmol, 2 eq) and potassium iodide (41.15 mg, 0.25 mmol, 5 eq) was added, the reaction was stirred at 60° C. for 24 h. The reaction mixture was concentrated under reduced pressure to give a residue. The residue was purified by prep-HPLC and lyophilized to give the title compound (7 mg, 0.010 mmol, 14.63% yield) as a light yellow solid. MS m/e: 897.2 ($[M+H+]^+$)

Example A 57

2-[4-[5-[(2,6-dioxopiperidin-3-yl)amino]pyridin-2-yl]piperidin-1-yl]-N-[1-[5-[3-[3-[[ethyl(methyl)sulfamoyl]amino]-2,6-difluorobenzoyl]-1H-pyrrolo[2,3-b]pyridin-5-yl]pyridin-2-yl]piperidin-4-yl]acetamide;formic acid

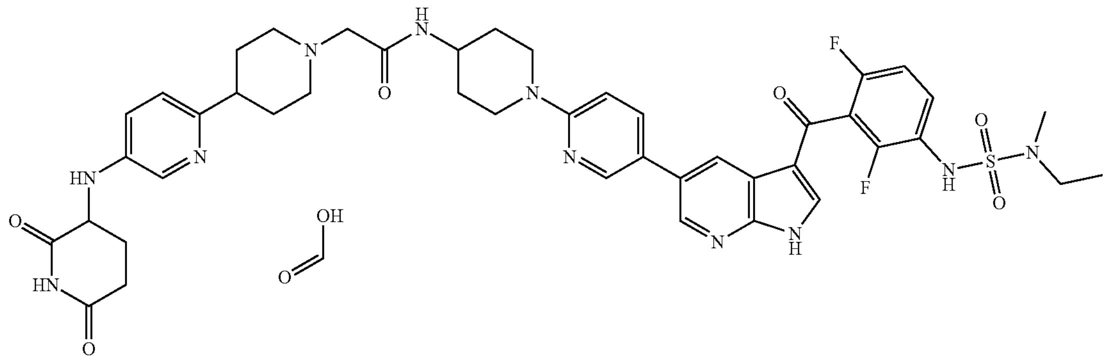

To a solution of 5-[6-(4-amino-1-piperidyl)-3-pyridyl]-3-[3-[[ethyl(methyl)sulfamoyl]amino]-2,6-difluoro-benzoyl]-1H-pyrrolo[2,3-b]pyridine (35.0 mg, 0.05 mmol, 1 eq) in THF (15 mL) was added DIPEA (33.08 mg, 0.26 mmol, 5 eq) and chloroacetyl chloride (5.78 mg, 0.05 mmol, 1 eq) at 0° C. The reaction was stirred at 25° C. for 1 h, then 3-[[6-(4-piperidyl)-3-pyridyl]amino]piperidine-2,6-dione (16.63 mg, 0.05 mmol, 1 eq) and potassium iodide (17.0 mg, 0.1 mmol, 2 eq) was added, the reaction was stirred at 60° C. for 12 h. LCMS showed desired product MS: $[M+H]^+$ =898.1 was detected. The reaction mixture was concentrated under reduced pressure to give a residue. The residue was purified by prep-HPLC and lyophilized to give the title compound (9 mg, 0.010 mmol, 18.62% yield) as a white solid. MS m/e: 898.2 ($[M+H+]^+$)

Example A 58

2-[4-[5-[(2,6-dioxopiperidin-3-yl)amino]pyridin-2-yl]piperidin-1-yl]-N-[1-[5-[3-[3-[[ethyl(methyl)sulfamoyl]amino]-2,6-difluorobenzoyl]-1H-pyrrolo[2,3-b]pyridin-5-yl]pyrimidin-2-yl]piperidin-4-yl]acetamide; formic acid

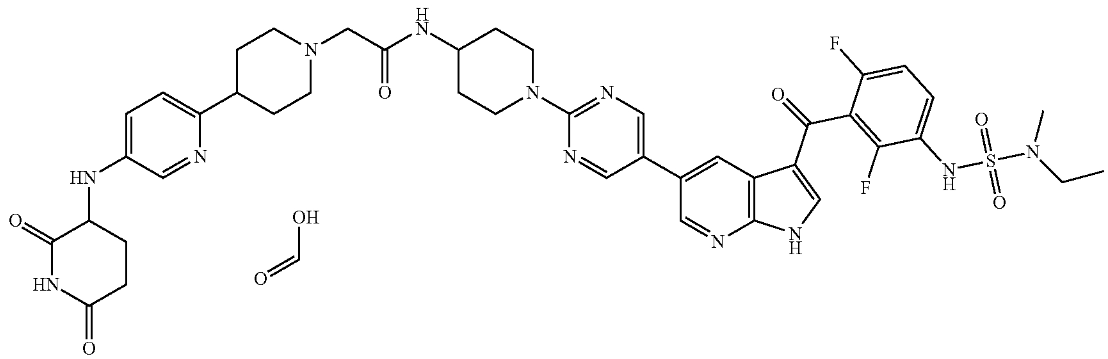 [SMILES: CCN(C)S(=O)(=O)Nc1ccc(F)c(C(=O)c2c[nH]c3ncc(-c4cnc(N5CCC(NC(=O)CN6CCC(c7ccc(NC8CCC(=O)NC8=O)cn7)CC6)CC5)nc4)cc23)c1F ; O=CO]

To a solution of 5-[2-(4-amino-1-piperidyl)pyrimidin-5-yl]-3-[3-[[ethyl(methyl)sulfamoyl]amino]-2,6-difluoro-benzoyl]-1H-pyrrolo[2,3-b]pyridine (30.0 mg, 0.05 mmol, 1 eq) in THF (15 mL) was added DIPEA (31.93 mg, 0.25 mmol, 5 eq) and chloroacetyl chloride (5.58 mg, 0.05 mmol, 1 eq) at 0° C. The reaction was stirred at 25° C. for 1 h, then 3-[[6-(4-piperidyl)-3-pyridyl]amino]piperidine-2,6-dione (32.1 mg, 0.1 mmol, 2 eq) and potassium iodide (41.02 mg, 0.25 mmol, 5 eq) was added, the reaction was stirred at 60° C. for 24 h. The reaction mixture was concentrated under reduced pressure to give a residue. The residue was purified by prep-HPLC and lyophilized to give the title compound (7 mg, 0.010 mmol, 14.51% yield) as a white solid. MS m/e: 899.2 ($[M+H+]^+$)

Example A 59

2-[4-[4-(2,6-Dioxopiperidin-3-yl)oxyphenyl]piperidin-1-yl]-N-[1-[5-[3-[3-[[ethyl(methyl)sulfamoyl]amino]-2,6-difluorobenzoyl]-1H-pyrrolo[2,3-b]pyridin-5-yl]pyrimidin-2-yl]piperidin-4-yl]acetamide; formic acid

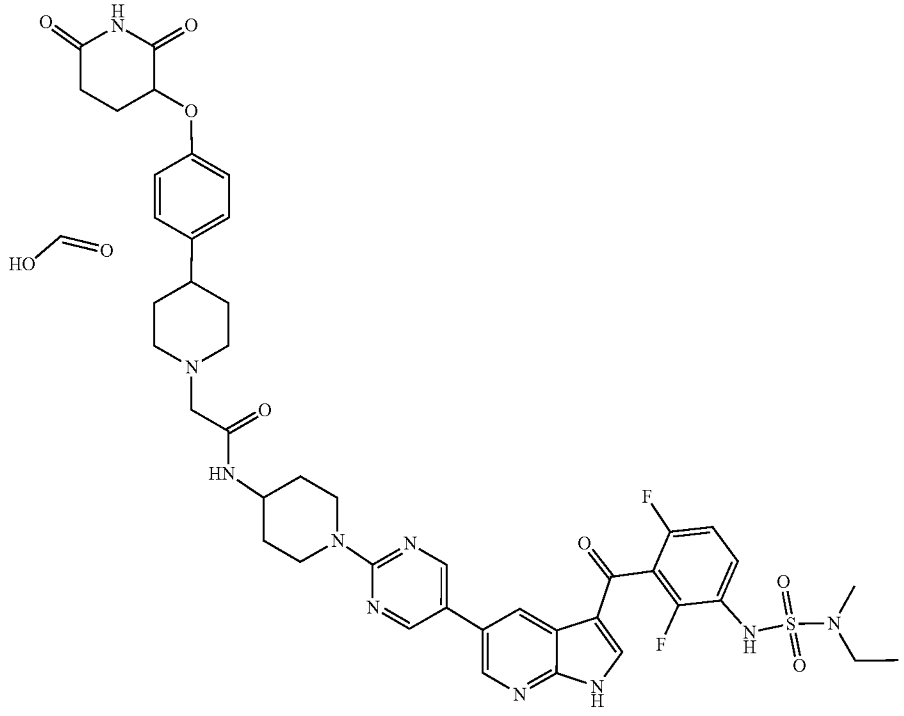

To a solution of 5-[2-(4-amino-1-piperidyl)pyrimidin-5-yl]-3-[3-[[ethyl(methyl)sulfamoyl]amino]-2,6-difluoro-benzoyl]-1H-pyrrolo[2,3-b]pyridine hydrochloride (40.0 mg, 0.070 mmol, 1 eq) in DMF (2 mL) was added DIPEA (35.85 mg, 0.280 mmol, 4.21 eq), 2-[4-[4-[(2,6-dioxo-3-piperidyl)oxy]phenyl]-1-piperidyl]acetic acid (24.02 mg, 0.070 mmol, 1.05 eq) and HATU (26.37 mg, 0.070 mmol, 1.05 eq) at 25° C. Then the reaction was stirred at 25° C. for 2 h. The reaction mixture was concentrated under reduced pressure to give a residue. The residue was purified by prep-HPLC and lyophilized to give the title compound (20 mg, 0.020 mmol, 31.23% yield) as white solid. MS m/e: 899 ([M+H+]$^+$)

Example A 60

2-[4-[5-(2,6-Dioxopiperidin-3-yl)oxypyridin-2-yl]piperidin-1-yl]-N-[1-[5-[3-[3-[[ethyl(methyl)sulfamoyl]amino]-2,6-difluorobenzoyl]-1H-pyrrolo[2,3-b]pyridin-5-yl]pyrimidin-2-yl]piperidin-4-yl]acetamide;formic acid

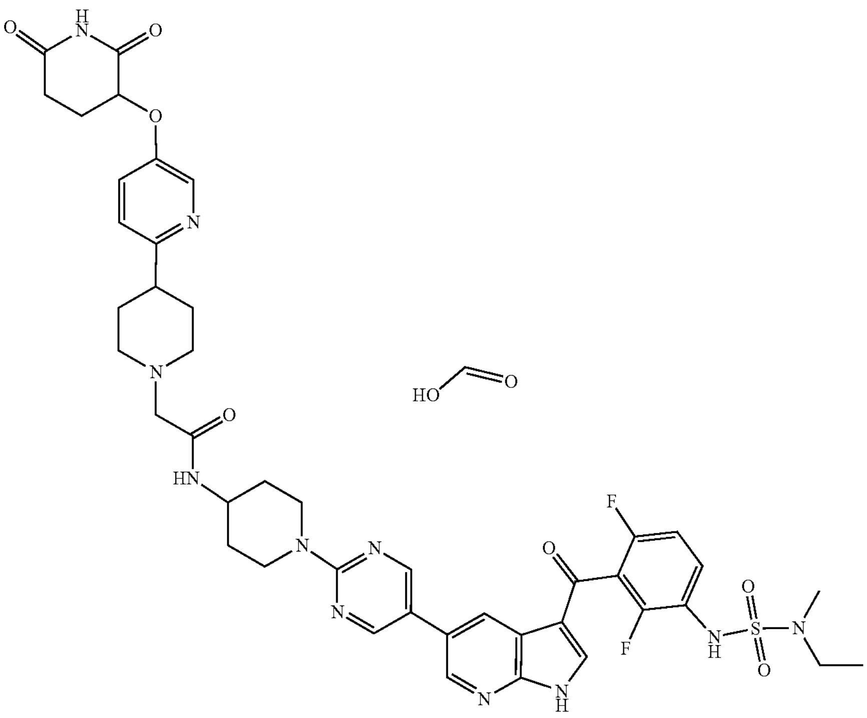 [SMILES: CCN(C)S(=O)(=O)Nc1ccc(F)c(C(=O)c2c[nH]c3ncc(-c4cnc(N5CCC(NC(=O)CN6CCC(c7ccc(OC8CCC(=O)NC8=O)cn7)CC6)CC5)nc4)cc23)c1F ; O=CO]

To a solution of 5-[2-(4-amino-1-piperidyl)pyrimidin-5-yl]-3-[3-[[ethyl(methyl)sulfamoyl]amino]-2,6-difluoro-benzoyl]-1H-pyrrolo[2,3-b]pyridine hydrochloride (40.0 mg, 0.070 mmol, 1 eq) in DMF (2 mL) was added DIPEA (35.85 mg, 0.280 mmol, 4.21 eq), 2-[4-[5-[(2,6-dioxo-3-piperidyl)oxy]-2-pyridyl]-1-piperidyl]acetic acid; 2,2,2-trifluoroacetic acid (32.0 mg, 0.070 mmol, 1.05 eq) and HATU (26.37 mg, 0.070 mmol, 1.05 eq) at 25° C. Then the reaction was stirred at 25° C. for 1 h. The reaction mixture was concentrated under reduced pressure to give a residue. The residue was purified by prep-HPLC and lyophilized to give the title compound (30 mg, 0.030 mmol, 48.13% yield) as white solid. MS m/e: 900.1 ([M+H+]$^+$)

Example A 61

2-[4-[4-(2,6-Dioxopiperidin-3-yl)oxyphenyl]piperidin-1-yl]-N-[1-[5-[3-[3-[[ethyl(methyl)sulfamoyl]amino]-2,6-difluorobenzoyl]-1H-pyrrolo[2,3-b]pyridin-5-yl]pyridin-2-yl]piperidin-4-yl]acetamide; formic acid

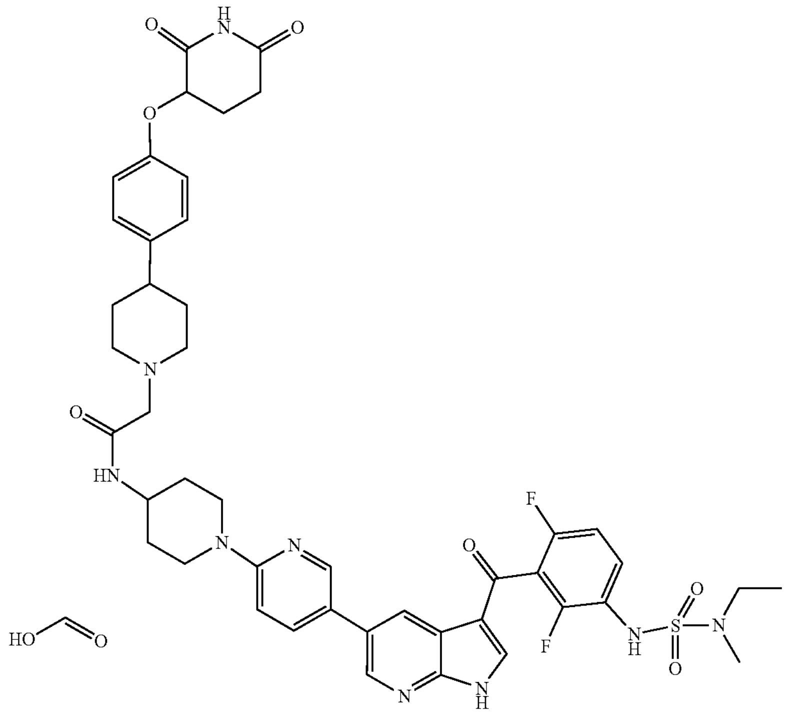 [SMILES: O=CO ; CCN(C)S(=O)(=O)Nc1ccc(F)c(C(=O)c2c[nH]c3ncc(-c4ccc(N5CCC(NC(=O)CN6CCC(c7ccc(OC8CCC(=O)NC8=O)cc7)CC6)CC5)nc4)cc23)c1F]

To a solution of 5-[6-(4-amino-1-piperidyl)-3-pyridyl]-3-[3-[[ethyl(methyl)sulfamoyl]amino]-2,6-difluoro-benzoyl]-1H-pyrrolo[2,3-b]pyridine (30.0 mg, 0.050 mmol, 1 eq) and 2-[4-[4-[(2,6-dioxo-3-piperidyl)oxy]phenyl]-1-piperidyl] acetic acid (20.57 mg, 0.060 mmol, 1.2 eq) in DMF (2 mL) was added DIPEA (0.03 mL, 0.150 mmol, 3 eq) and HATU (41.41 mg, 0.050 mmol, 1.1 eq). The mixture was stirred at 25° C. for 3 h. The reaction mixture was concentrated under reduced pressure to give a residue. The residue was purified by prep-HPLC and lyophilized to give the title compound (24.21 mg, 0.030 mmol, 54.47% yield) as a yellow solid. MS m/e: 898.5 ([M+H+]$^+$)

Example A 62

2-[4-[4-[(2,6-Dioxopiperidin-3-yl)amino]phenyl]piperidin-1-yl]-N-[1-[5-[3-[3-[[ethyl(methyl)sulfamoyl]amino]-2,6-difluorobenzoyl]-1H-pyrrolo[2,3-b]pyridin-5-yl]pyrimidin-2-yl]piperidin-4-yl]acetamide;formic acid

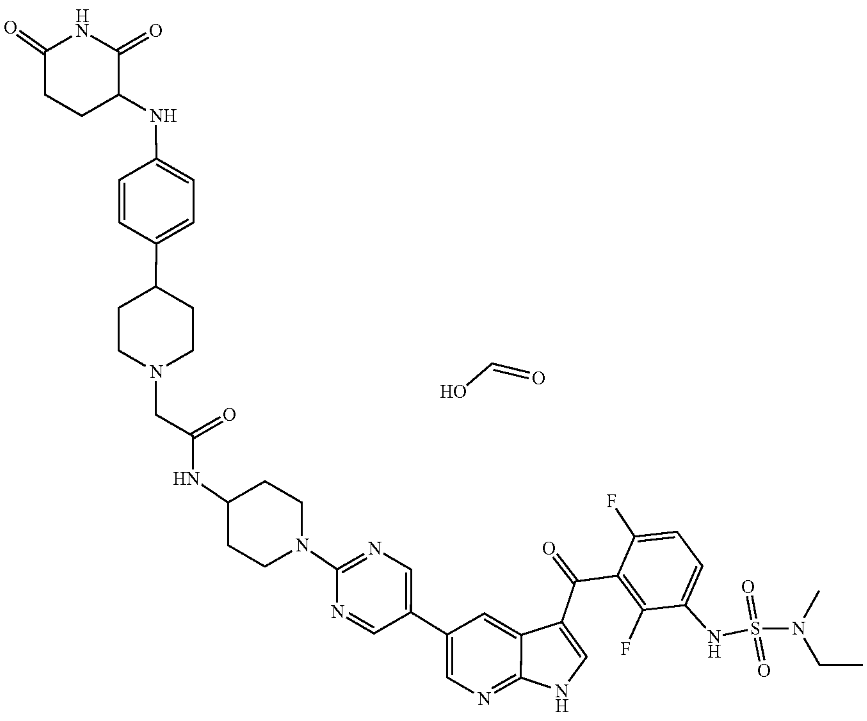 [SMILES: CCN(C)S(=O)(=O)Nc1ccc(F)c(C(=O)c2c[nH]c3ncc(-c4cnc(N5CCC(NC(=O)CN6CCC(c7ccc(NC8CCC(=O)NC8=O)cc7)CC6)CC5)nc4)cc23)c1F ; O=CO]

To a solution of 2-[4-[4-[(2,6-dioxo-3-piperidyl)amino]phenyl]-1-piperidyl]acetic acid; 2,2,2-trifluoroacetic acid (60.54 mg, 0.130 mmol, 2 eq) in DMF (2 mL) was added 5-[2-(4-amino-1-piperidyl)pyrimidin-5-yl]-3-[3-[[ethyl(methyl)sulfamoyl]amino]-2,6-difluoro-benzoyl]-1H-pyrrolo[2,3-b]pyridine hydrochloride (40.0 mg, 0.070 mmol, 1 eq), DIPEA (51.09 mg, 0.400 mmol, 6 eq) and pyBop (36.09 mg, 0.070 mmol, 1.05 eq) at 25° C. Then the reaction was stirred at 25° C. for 1 h. The mixture was purified by prep-HPLC to give the title compound (16 mg, 0.020 mmol, 25.72% yield) as blue solid. MS m/e: 898.1 ([M+H+]$^+$)

Example A 63

2-[4-[4-(2,6-Dioxopiperidin-3-yl)oxyphenyl]piperidin-1-yl]-N-[1-[4-[3-[3-[[ethyl(methyl)sulfamoyl]amino]-2,6-difluorobenzoyl]-1H-pyrrolo[2,3-b]pyridin-5-yl]phenyl]piperidin-4-yl]acetamide;formic acid

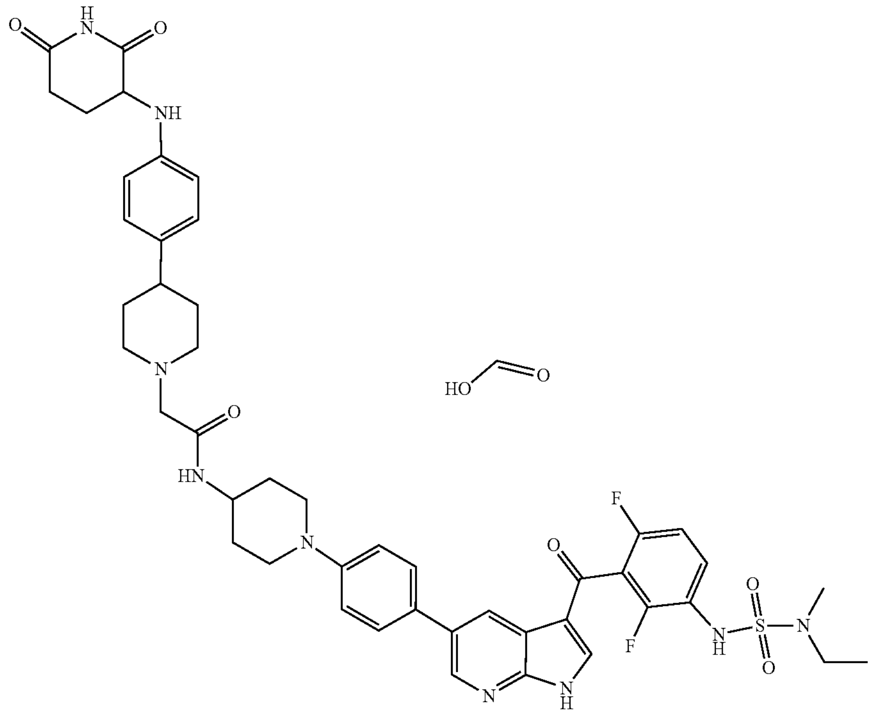 [SMILES: CCN(C)S(=O)(=O)Nc1ccc(F)c(C(=O)c2c[nH]c3ncc(-c4ccc(N5CCC(NC(=O)CN6CCC(c7ccc(NC8CCC(=O)NC8=O)cc7)CC6)CC5)cc4)cc23)c1F ; O=CO]

To a solution of 2-[4-[4-[(2,6-dioxo-3-piperidyl)oxy]phenyl]-1-piperidyl]acetic acid (24.1 mg, 0.070 mmol, 1.05 eq) in DMF (2 mL) was added DIPEA (35.97 mg, 0.280 mmol, 4.21 eq), 5-[4-(4-amino-1-piperidyl)phenyl]-3-[3-[[ethyl (methyl)sulfamoyl]amino]-2,6-difluoro-benzoyl]-1H-pyrrolo[2,3-b]pyridine hydrochloride (40.0 mg, 0.070 mmol, 1 eq) and pyBop (36.21 mg, 0.070 mmol, 1.05 eq) at 25° C. Then the reaction was stirred at 25° C. for 2 h. The mixture was purified by prep-HPLC to give the title compound (20 mg, 0.020 mmol, 32.08% yield) as yellow solid. MS m/e: 897.0 ([M+H-T+]$^{+}$)

Example A 64

2-[4-[5-(2,6-Dioxopiperidin-3-yl)oxypyridin-2-yl]piperidin-1-yl]-N-[1-[4-[3-[3-[[ethyl(methyl)sulfamoyl]amino]-2,6-difluorobenzoyl]-1H-pyrrolo[2,3-b]pyridin-5-yl]phenyl]piperidin-4-yl]acetamide; formic acid

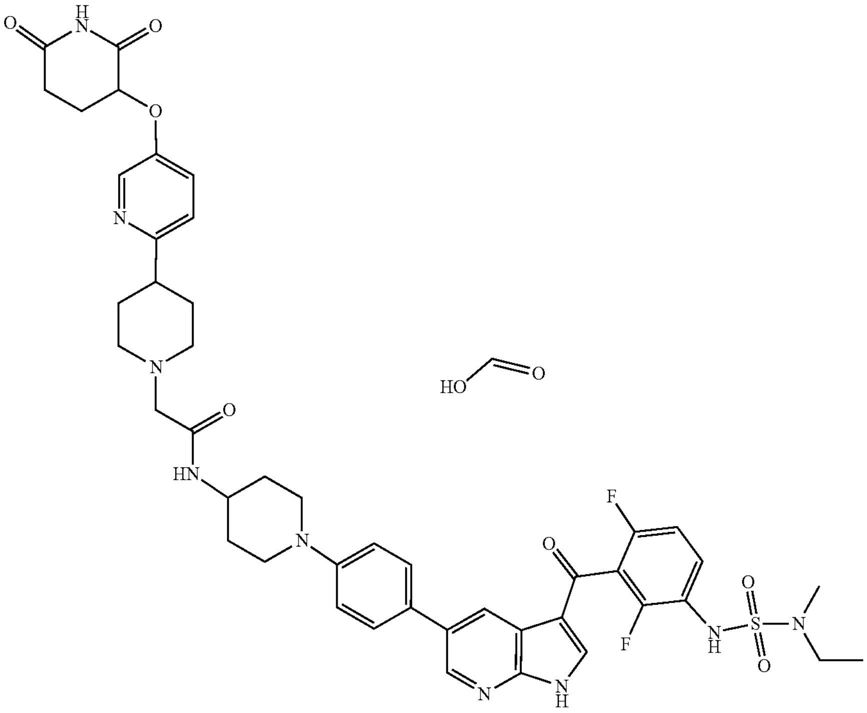 [SMILES: CCN(C)S(=O)(=O)Nc1ccc(F)c(C(=O)c2c[nH]c3ncc(-c4ccc(N5CCC(NC(=O)CN6CCC(c7ccc(OC8CCC(=O)NC8=O)cn7)CC6)CC5)cc4)cc23)c1F ; O=CO]

To a solution of 5-[4-(4-amino-1-piperidyl)phenyl]-3-[3-[[ethyl(methyl)sulfamoyl]amino]-2,6-difluoro-benzoyl]-1H-pyrrolo[2,3-b]pyridine hydrochloride (40.0 mg, 0.070 mmol, 1 eq), 2-[4-[5-[(2,6-dioxo-3-piperidyl)oxy]-2-pyridyl]-1-piperidyl]acetic acid; 2,2,2-trifluoroacetic acid (45.75 mg, 0.100 mmol, 1.5 eq) and DIPEA (35.97 mg, 0.280 mmol, 4.21 eq) in DMF (2 mL) was added pyBop (36.21 mg, 0.070 mmol, 1.05 eq) at 25° C. Then the reaction was stirred at 25° C. for 2 h. The mixture was purified by prep-HPLC to give the title compound (18 mg, 0.020 mmol, 28.84% yield) as yellow solid. MS m/e: 898.1 ([M+H+]$^+$)

Example A 65

2-[4-[5-(2,6-Dioxopiperidin-3-yl)oxypyridin-2-yl]piperidin-1-yl]-N-[1-[5-[3-[3-[[ethyl(methyl)sulfamoyl]amino]-2,6-difluorobenzoyl]-1H-pyrrolo[2,3-b]pyridin-5-yl]pyridin-2-yl]piperidin-4-yl]acetamide;formic acid

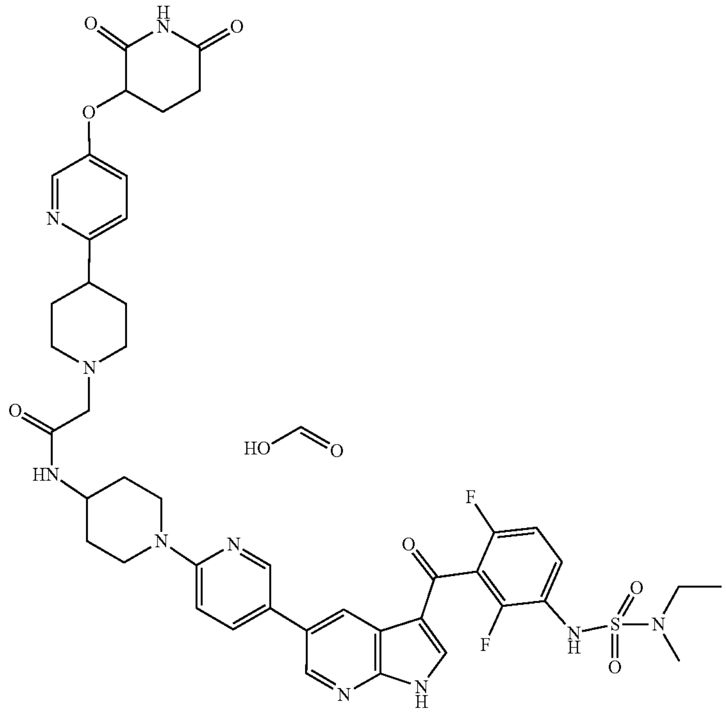 [SMILES: CCN(C)S(=O)(=O)Nc1ccc(F)c(C(=O)c2c[nH]c3ncc(-c4ccc(N5CCC(NC(=O)CN6CCC(c7ccc(OC8CCC(=O)NC8=O)cn7)CC6)CC5)nc4)cc23)c1F ; O=CO]

A solution of 2-[4-[5-[(2,6-dioxo-3-piperidyl)oxy]-2-pyridyl]-1-piperidyl]acetic acid (27.41 mg, 0.060 mmol, 1.2 eq) and 5-[6-(4-amino-1-piperidyl)-3-pyridyl]-3-[3-[[ethyl(methyl)sulfamoyl]amino]-2,6-difluoro-benzoyl]-1H-pyrrolo[2,3-b]pyridine (30.0 mg, 0.050 mmol, 1 eq) in DMF (2 mL) was added DIPEA (0.04 mL, 0.250 mmol, 5 eq) and PyBOP (25.75 mg, 0.050 mmol, 1 eq). The mixture was stirred at 25° C. for 3 h. The mixture was concentrated, purified by prep-HPLC and lyophilized to give the title compound (16.9 mg, 0.020 mmol, 37.98% yield) as a yellow solid. MS m/e: 899.5 ($[M+H+]^+$)

Example A 66

2-[4-[4-[(2,6-Dioxopiperidin-3-yl)amino]phenyl]piperidin-1-yl]-N-[1-[5-[3-[3-[[ethyl(methyl)sulfamoyl]amino]-2,6-difluorobenzoyl]-1H-pyrrolo[2,3-b]pyridin-5-yl]pyridin-2-yl]piperidin-4-yl]acetamide; formic acid

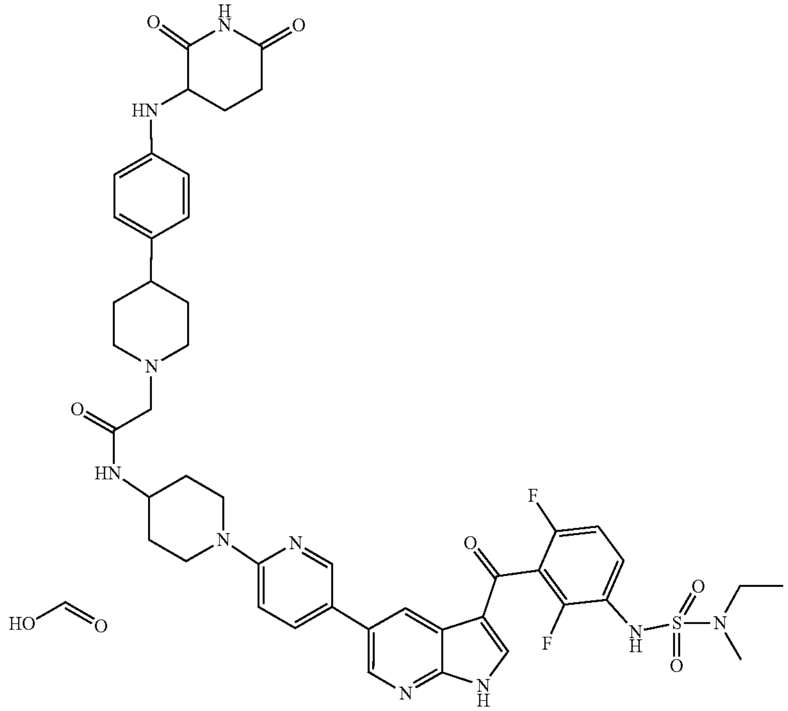 [SMILES: O=CO ; CCN(C)S(=O)(=O)Nc1ccc(F)c(C(=O)c2c[nH]c3ncc(-c4ccc(N5CCC(NC(=O)CN6CCC(c7ccc(NC8CCC(=O)NC8=O)cc7)CC6)CC5)nc4)cc23)c1F]

To a solution of 2-[4-[4-[(2,6-dioxo-3-piperidyl)amino]phenyl]-1-piperidyl]acetic acid (30.0 mg, 0.050 mmol, 1 eq) and 5-[6-(4-amino-1-piperidyl)-3-pyridyl]-3-[3-[[ethyl(methyl)sulfamoyl]amino]-2,6-difluoro-benzoyl]-1H-pyrrolo[2,3]pyridine (45.48 mg, 0.100 mmol, 2 eq) in DMF (2 mL) was added DIPEA (0.04 mL, 0.250 mmol, 5 eq) and PyBOP (25.75 mg, 0.050 mmol, 1 eq). The mixture was stirred at 25° C. for 3 h. The mixture was concentrated, purified by prep-HPLC and lyophilized to give the title compound (23.38 mg, 0.020 mmol, 52.66% yield) as a yellow solid. MS m/e: 897.5 ($[M+H+]^+$)

Example A 67

2-[4-[4-[(2,6-Dioxopiperidin-3-yl)amino]phenyl] piperidin-1-yl]-N-[1-[4-[3-[3-[[ethyl(methyl)sulfamoyl]amino]-2,6-difluorobenzoyl]-1H-pyrrolo[2,3-b]pyridin-5-yl]phenyl]piperidin-4-yl]acetamide; formic acid

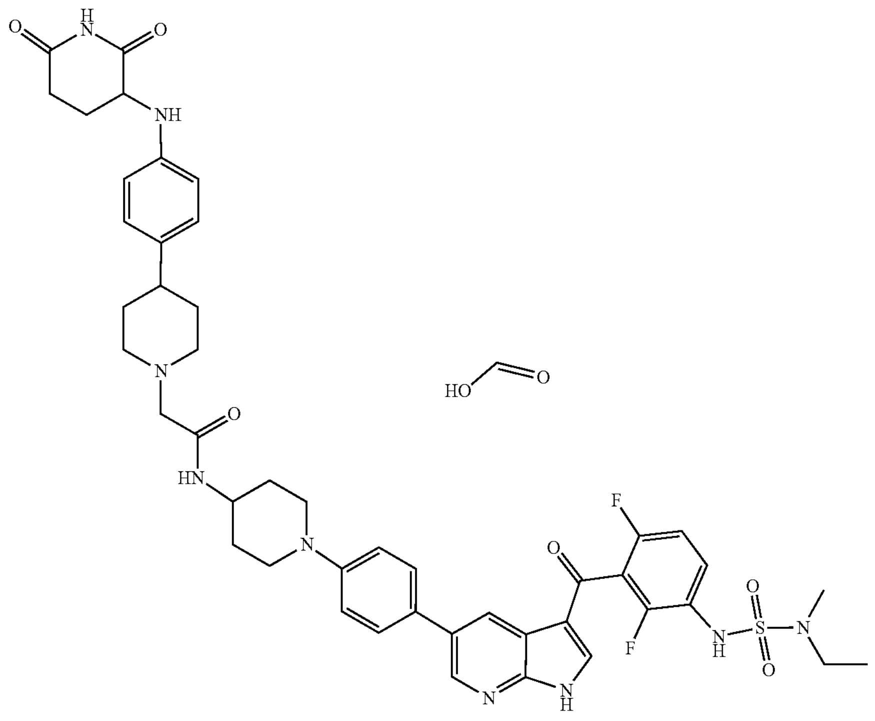 [SMILES: CCN(C)S(=O)(=O)Nc1ccc(F)c(C(=O)c2c[nH]c3ncc(-c4ccc(N5CCC(NC(=O)CN6CCC(c7ccc(NC8CCC(=O)NC8=O)cc7)CC6)CC5)cc4)cc23)c1F ; O=CO]

To a solution of 2-[4-[4-[(2,6-dioxo-3-piperidyl)amino] phenyl]-1-piperidyl]acetic acid; 2,2,2-trifluoroacetic acid (60.74 mg, 0.130 mmol, 2 eq) and 5-[4-(4-amino-1-piperidyl)phenyl]-3-[3-[[ethyl(methyl)sulfamoyl]amino]-2,6-difluoro-benzoyl]-1H-pyrrolo[2,3-b]pyridine hydrochloride (40.0 mg, 0.070 mmol, 1 eq) in DMF (2 mL) was added DIPEA (35.97 mg, 0.280 mmol, 4.21 eq) and PyBOP (36.21 mg, 0.070 mmol, 1.05 eq) at 25° C. Then the reaction was stirred at 25° C. for 2 h. The mixture was purified by prep-HPLC to give the title compound (19 mg, 0.020 mmol, 30.51% yield) as yellow solid. MS m/e: 896.1 ([M+H+]$^+$)

Example A 68

5-[2-[4-[2-[4-[5-(2,6-Dioxopiperidin-3-yl)oxypyridin-2-yl]piperazin-1-yl]acetyl]piperazin-1-yl]pyrimidin-5-yl]-3-[3-[[ethyl(methyl)sulfamoyl]amino]-2,6-difluorobenzoyl]-1H-pyrrolo[2,3-b]pyridine

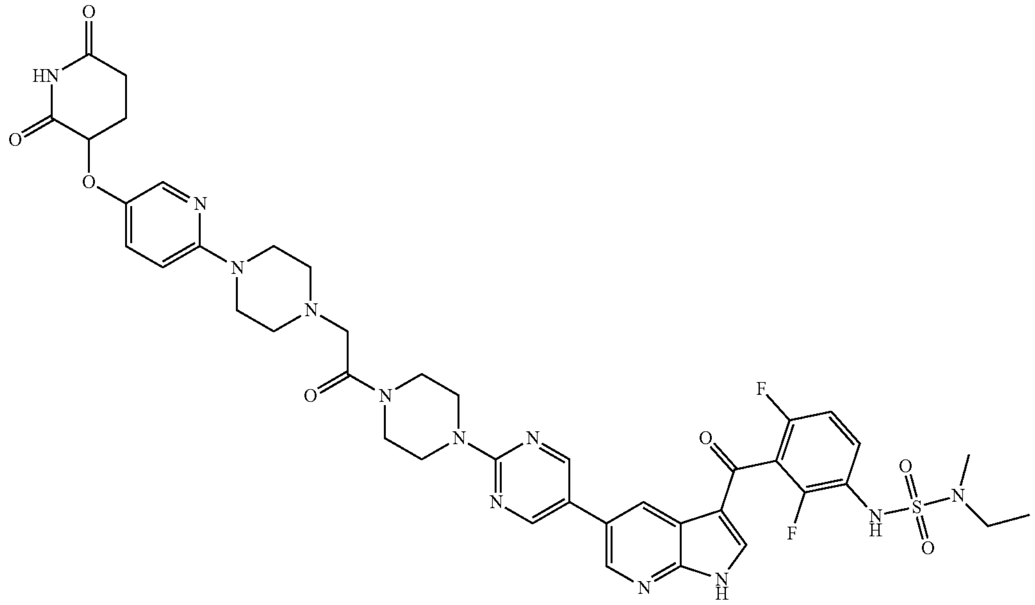 [SMILES: CCN(C)S(=O)(=O)Nc1ccc(F)c(C(=O)c2c[nH]c3ncc(-c4cnc(N5CCN(C(=O)CN6CCN(c7ccc(OC8CCC(=O)NC8=O)cn7)CC6)CC5)nc4)cc23)c1F]

The title compound was obtained as light yellow solid in 65% yield according to general procedure VIII.

Amine: 3-[3-[[Ethyl(methyl)sulfamoyl]amino]-2,6-difluoro-benzoyl]-5-(2-piperazin-1-ylpyrimidin-5-yl)-1H-pyrrolo[2,3-b]pyridine Acid: 2-[4-[5-[(2,6-dioxo-3-piperidyl)oxy]-2-pyridyl]piperazin-1-yl]acetic acid hydrochloride MS m/e: 887.6 ([M+H+]$^+$)

Example A 69

5-[2-[4-[2-[4-[5-[(2,6-Dioxopiperidin-3-yl)amino]pyridin-2-yl]piperidin-1-yl]acetyl]piperazin-1-yl]pyrimidin-5-yl]-3-[3-[[ethyl(methyl)sulfamoyl]amino]-2,6-difluorobenzoyl]-1H-pyrrolo[2,3-b]pyridine

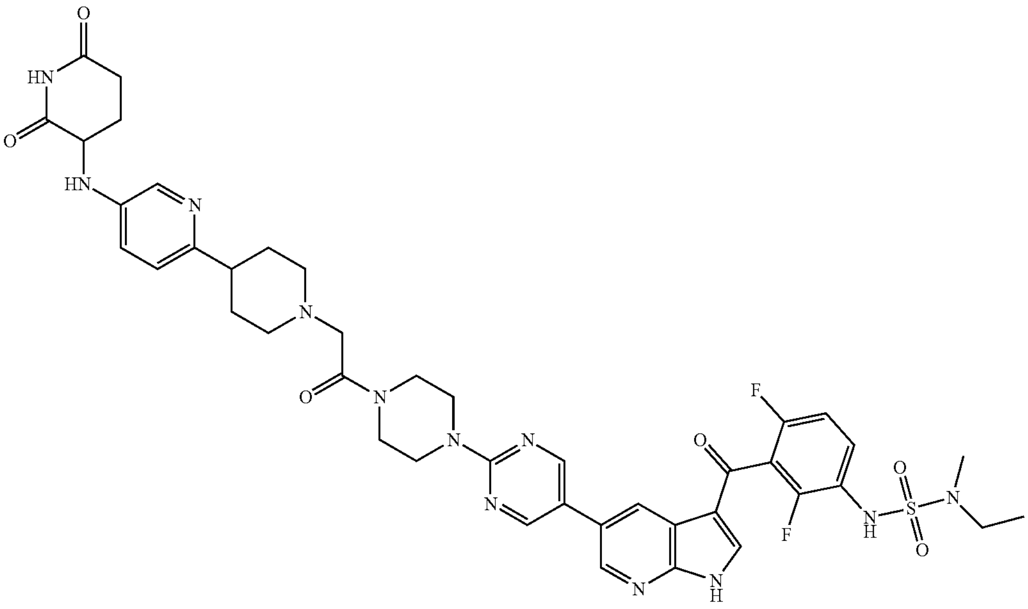 [SMILES: CCN(C)S(=O)(=O)Nc1ccc(F)c(C(=O)c2c[nH]c3ncc(-c4cnc(N5CCN(C(=O)CN6CCC(c7ccc(NC8CCC(=O)NC8=O)cn7)CC6)CC5)nc4)cc23)c1F]

The title compound was obtained as light yellow solid in 54% yield according to general procedure VIII.

Amine: 3-[3-[[Ethyl(methyl)sulfamoyl]amino]-2,6-difluoro-benzoyl]-5-(2-piperazin-1-ylpyrimidin-5-yl)-1H-pyrrolo[2,3-b]pyridine Acid: 2-[4-[5-[(2,6-dioxo-3-piperidyl)amino]-2-pyridyl]-1-piperidyl]acetic acid hydrochloride MS m/e: 885.6 ([M+H+]$^+$)

Example A 70

5-[2-[4-[2-[4-[4-[(2,6-Dioxopiperidin-3-yl)-methyl-amino]phenyl]piperidin-1-yl]acetyl]piperazin-1-yl]pyrimidin-5-yl]-3-[3-[[ethyl(methyl)sulfamoyl]amino]-2,6-difluorobenzoyl]-1H-pyrrolo[2,3-b]pyridine

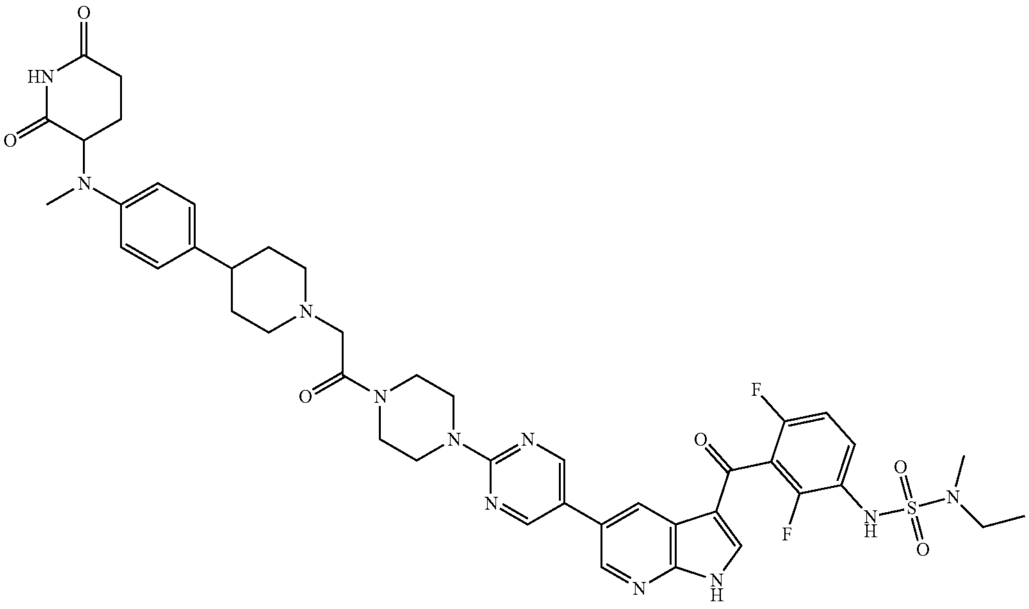 [SMILES: CCN(C)S(=O)(=O)Nc1ccc(F)c(C(=O)c2c[nH]c3ncc(-c4cnc(N5CCN(C(=O)CN6CCC(c7ccc(N(C)C8CCC(=O)NC8=O)cc7)CC6)CC5)nc4)cc23)c1F]

The title compound was obtained as light yellow solid in 53% yield according to general procedure VIII.

Amine: 3-[3-[[Ethyl(methyl)sulfamoyl]amino]-2,6-difluoro-benzoyl]-5-(2-piperazin-1-ylpyrimidin-5-yl)-1H-pyrrolo[2,3-b]pyridine Acid: 2-[4-[4-[(2,6-dioxo-3-piperidyl)-methyl-amino]phenyl]-1-piperidyl]acetic acid hydrochloride MS m/e: 899.7 ([M+H+]$^+$)

Example A 71

3-[3-[[Ethyl(methyl)sulfamoyl]amino]-2,6-difluorobenzoyl]-5-[6-[rac-(1R,5S)-8-[2-[4-[4-[(2,6-dioxopiperidin-3-yl)amino]phenyl]piperidin-1-yl]acetyl]-3,8-diazabicyclo[3.2.1]octan-3-yl]pyridin-3-yl]-1H-pyrrolo[2,3-b]pyridine

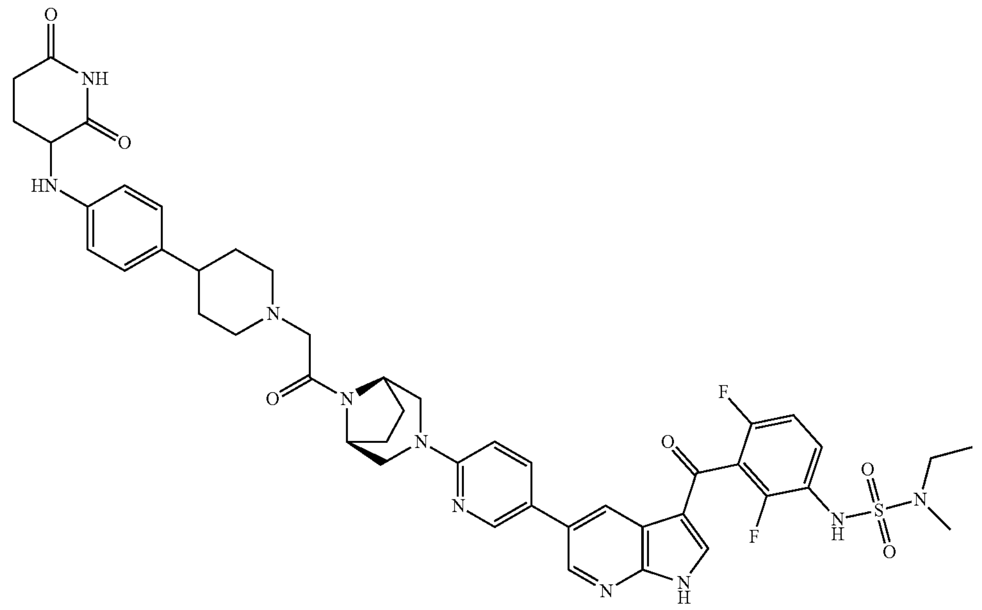 [SMILES: CCN(C)S(=O)(=O)Nc1ccc(F)c(C(=O)c2c[nH]c3ncc(-c4ccc(N5C[C@H]6CC[C@@H](C5)N6C(=O)CN5CCC(c6ccc(NC7CCC(=O)NC7=O)cc6)CC5)nc4)cc23)c1F]

The title compound was obtained according to general procedure VIII.

Amine: 5-[6-(3,8-Diazabicyclo[3.2.1]octan-3-yl)-3-pyridyl]-3-[3-[[ethyl(methyl)sulfamoyl]amino]-2,6-difluoro-benzoyl]-1H-pyrrolo[2,3-b]pyridine 2,2,2-trifluoroacetic acid Acid: 2-[4-[4-[(2,6-dioxo-3-piperidyl)amino]phenyl]-1-piperidyl]acetic acid hydrochloride MS m/e: 909.8 ([M+H+]$^+$)

Example A 72

N-[3-[5-[6-[4-[2-[4-[4-[(2,6-Dioxopiperidin-3-yl)amino]phenyl]piperidin-1-yl]acetyl]piperazin-1-yl]pyridin-3-yl]-1H-pyrrolo[2,3-b]pyridine-3-carbonyl]-2,4-difluorophenyl]pyrrolidine-1-sulfonamide

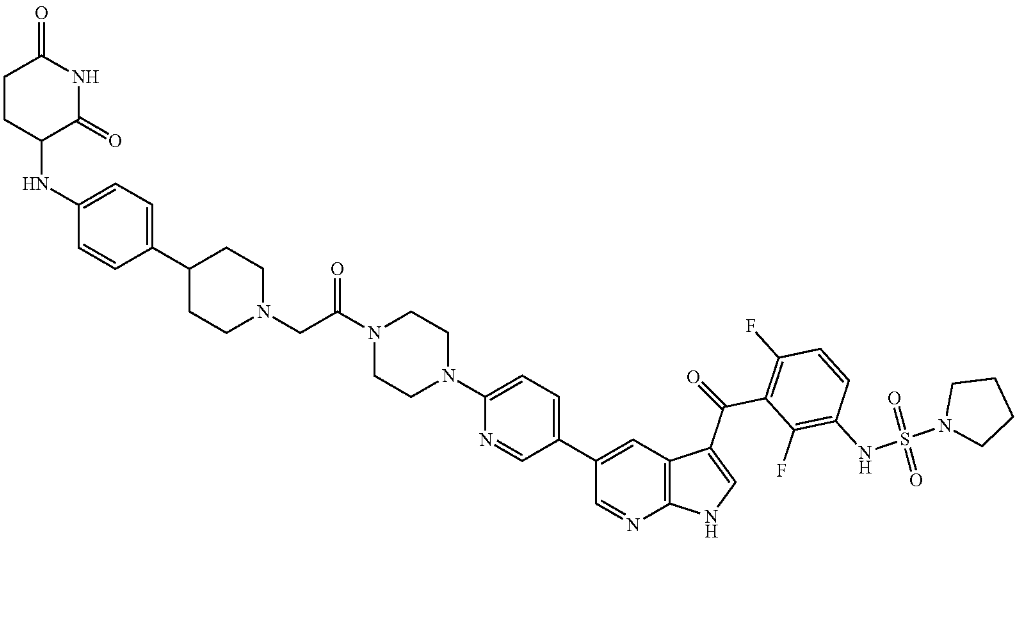 [SMILES: O=C1CCC(Nc2ccc(C3CCN(CC(=O)N4CCN(c5ccc(-c6cnc7[nH]cc(C(=O)c8c(F)ccc(NS(=O)(=O)N9CCCC9)c8F)c7c6)cn5)CC4)CC3)cc2)C(=O)N1]

The title compound was obtained as white powder in 13% yield according to general procedure VIII.

Amine: N-[2,4-difluoro-3-[5-(6-piperazin-1-yl-3-pyridyl)-1H-pyrrolo[2,3-b]pyridine-3-carbonyl]phenyl]pyrrolidine-1-sulfonamide 2,2,2-trifluoroacetic acid Acid: 2-[4-[4-[(2,6-dioxo-3-piperidyl)amino]phenyl]-1-piperidyl]acetic acid hydrochloride MS m/e: 895.4 ([M+H+]$^+$)

Example A 73

N-[3-[5-[6-[4-[2-[4-[4-[(2,6-Dioxopiperidin-3-yl)amino]phenyl]piperazin-1-yl]acetyl]piperazin-1-yl]pyridin-3-yl]-1H-pyrrolo[2,3-b]pyridine-3-carbonyl]-2,4-difluorophenyl]pyrrolidine-1-sulfonamide

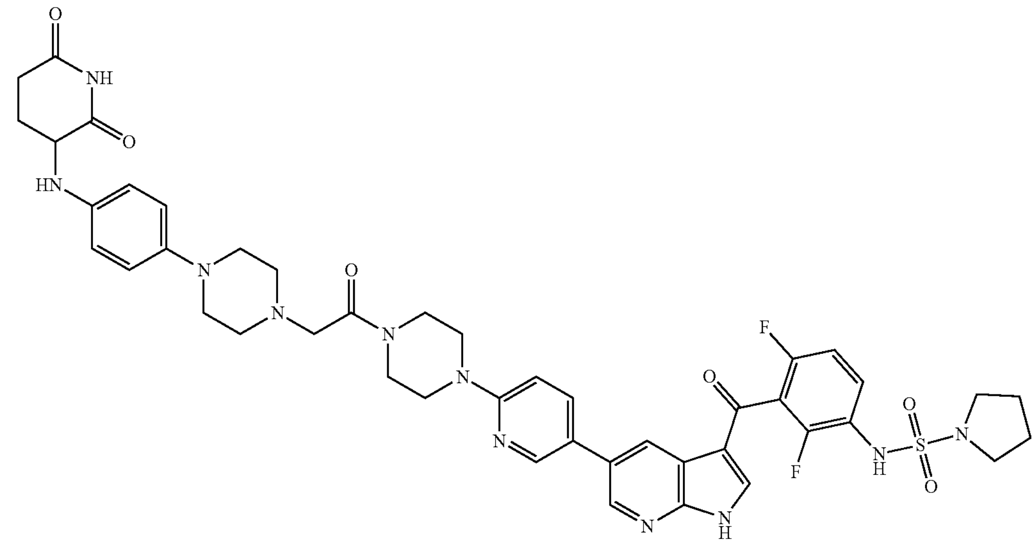 [SMILES: O=C1CCC(Nc2ccc(N3CCN(CC(=O)N4CCN(c5ccc(-c6cnc7[nH]cc(C(=O)c8c(F)ccc(NS(=O)(=O)N9CCCC9)c8F)c7c6)cn5)CC4)CC3)cc2)C(=O)N1]

The title compound was obtained as white powder in 13% yield according to general procedure VIII.

Amine: N-[2,4-difluoro-3-[5-(6-piperazin-1-yl-3-pyridyl)-1H-pyrrolo[2,3-b]pyridine-3-carbonyl]phenyl]pyrrolidine-1-sulfonamide 2,2,2-trifluoroacetic acid Acid: 2-[4-[4-[(2,6-dioxo-3-piperidyl)amino]phenyl]piperazin-1-yl]acetic acid hydrochloride MS m/e: 896.4 ([M+H+]$^+$)

Example A 74

(3R)—N-[3-[5-[4-[4-[2-[4-[4-[(2,6-Dioxopiperidin-3-yl)amino]phenyl]piperazin-1-yl]acetyl]piperazin-1-yl]phenyl]-1H-pyrrolo[2,3-b]pyridine-3-carbonyl]-2,4-difluorophenyl]-3-fluoropyrrolidine-1-sulfonamide

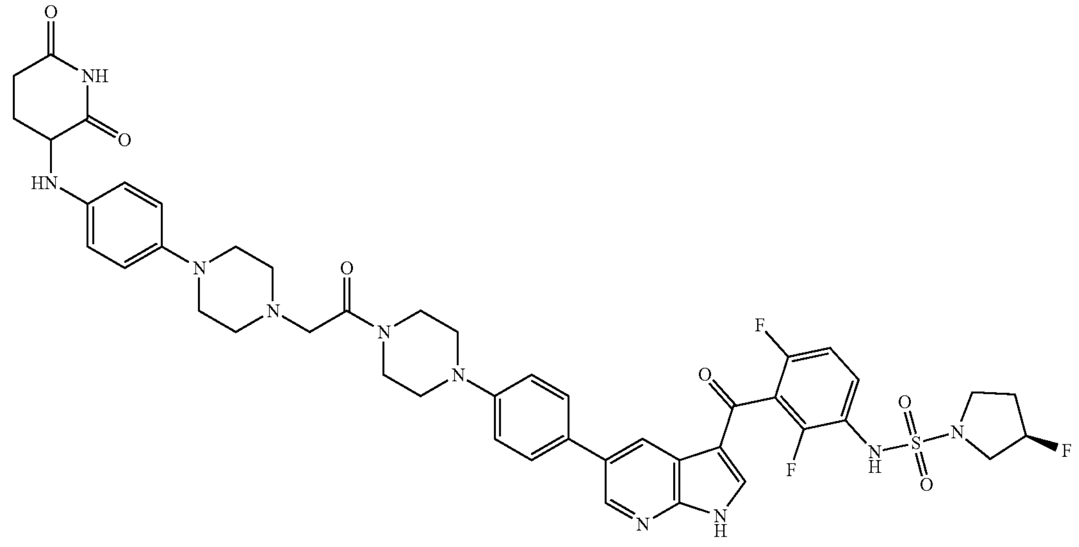 [SMILES: O=C1CCC(Nc2ccc(N3CCN(CC(=O)N4CCN(c5ccc(-c6cnc7[nH]cc(C(=O)c8c(F)ccc(NS(=O)(=O)N9CC[C@@H](F)C9)c8F)c7c6)cc5)CC4)CC3)cc2)C(=O)N1]

The title compound was obtained as white powder in 10% yield according to general procedure VIII.

Amine: (3R)—N-[2,4-Difluoro-3-[5-(4-piperazin-1-ylphenyl)-1H-pyrrolo[2,3-b]pyridine-3-carbonyl]phenyl]-3-fluoro-pyrrolidine-1-sulfonamide trifluoro acetic acid Acid: 2-[4-[4-[(2,6-dioxo-3-piperidyl)amino]phenyl]piperazin-1-yl]acetic acid hydrochloride MS m/e: 913.3 ([M+H+]$^{+}$)

Example A 75

(3R)—N-[3-[5-[4-[4-[2-[4-[4-[(2,6-Dioxopiperidin-3-yl)amino]phenyl]piperidin-1-yl]acetyl]piperazin-1-yl]phenyl]-1H-pyrrolo[2,3-b]pyridine-3-carbonyl]-2,4-difluorophenyl]-3-fluoropyrrolidine-1-sulfonamide

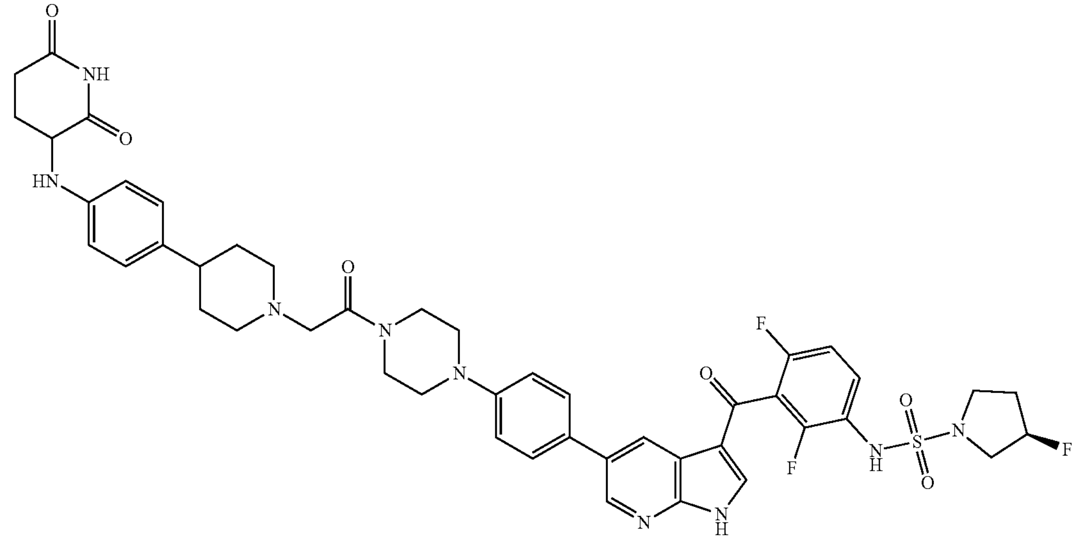 [SMILES: O=C1CCC(Nc2ccc(C3CCN(CC(=O)N4CCN(c5ccc(-c6cnc7[nH]cc(C(=O)c8c(F)ccc(NS(=O)(=O)N9CC[C@@H](F)C9)c8F)c7c6)cc5)CC4)CC3)cc2)C(=O)N1]

The title compound was obtained as white powder in 10% yield according to general procedure VIII.

Amine: (3R)—N-[2,4-Difluoro-3-[5-(4-piperazin-1-ylphenyl)-1H-pyrrolo[2,3-b]pyridine-3-carbonyl]phenyl]-3-fluoro-pyrrolidine-1-sulfonamide trifluoro acetic acid Acid: 2-[4-[4-[(2,6-dioxo-3-piperidyl)amino]phenyl]-1-piperidyl]acetic acid hydrochloride MS m/e: 912.3 ([M+H+]$^+$)

Example A 76

5-[6-[2-[2-[4-[4-[(2,6-dioxopiperidin-3-yl)amino]phenyl]piperidin-1-yl]acetyl]-2,6-diazaspiro[3.3]heptan-6-yl]pyridin-3-yl]-3-[3-[[ethyl(methyl)sulfamoyl]amino]-2,6-difluorobenzoyl]-1H-pyrrolo[2,3-b]pyridine

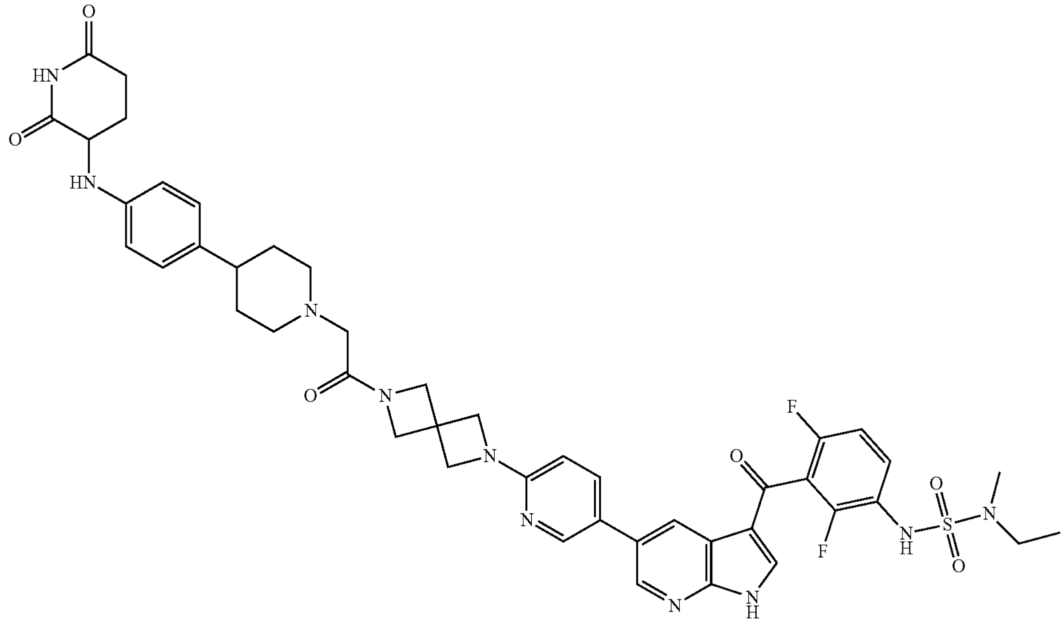 [SMILES: CCN(C)S(=O)(=O)Nc1ccc(F)c(C(=O)c2c[nH]c3ncc(-c4ccc(N5CC6(CN(C(=O)CN7CCC(c8ccc(NC9CCC(=O)NC9=O)cc8)CC7)C6)C5)nc4)cc23)c1F]

The title compound was obtained as white powder in 10% yield according to general procedure VIII.

Amine: 5-[6-(2,6-Diazaspiro[3.3]heptan-2-yl)-3-pyridyl]-3-[3-[[ethyl(methyl)sulfamoyl]amino]-2,6-difluoro-benzoyl]-1H-pyrrolo[2,3-b]pyridine Acid: 2-[4-[4-[(2,6-dioxo-3-piperidyl)amino]phenyl]-1-piperidyl]acetic acid hydrochloride MS m/e: 895.6 ([M+H+]$^+$)

Example A 77

5-[6-[2-[2-[4-[4-[(2,6-Dioxopiperidin-3-yl)amino]phenyl]piperazin-1-yl]acetyl]-2,6-diazaspiro[3.3]heptan-6-yl]pyridin-3-yl]-3-[3-[[ethyl(methyl)sulfamoyl]amino]-2,6-difluorobenzoyl]-1H-pyrrolo[2,3-b]pyridine

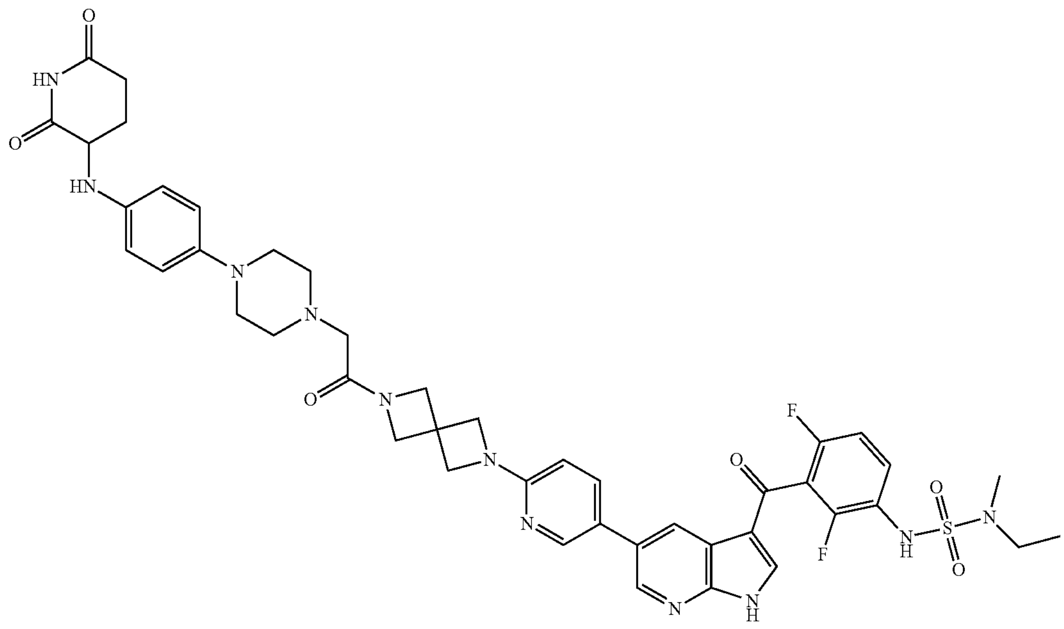 [SMILES: CCN(C)S(=O)(=O)Nc1ccc(F)c(C(=O)c2c[nH]c3ncc(-c4ccc(N5CC6(CN(C(=O)CN7CCN(c8ccc(NC9CCC(=O)NC9=O)cc8)CC7)C6)C5)nc4)cc23)c1F]

The title compound was obtained as white powder in 11% yield according to general procedure VIII.

Amine: 5-[6-(2,6-Diazaspiro[3.3]heptan-2-yl)-3-pyridyl]-3-[3-[[ethyl(methyl)sulfamoyl]amino]-2,6-difluoro-benzoyl]-1H-pyrrolo[2,3-b]pyridine Acid: 2-[4-[4-[(2,6-dioxo-3-piperidyl)amino]phenyl]piperazin-1-yl]acetic acid hydrochloride MS m/e: 896.6 ([M+H+]$^+$)

Example A 78

5-[2-[4-[3-[4-[4-[(2,6-Dioxopiperidin-3-yl)amino]phenyl]piperidin-1-yl]cyclobutanecarbonyl]piperazin-1-yl]pyrimidin-5-yl]-3-[3-[[ethyl(methyl)sulfamoyl]amino]-2,6-difluorobenzoyl]-1H-pyrrolo[2,3-b]pyridine

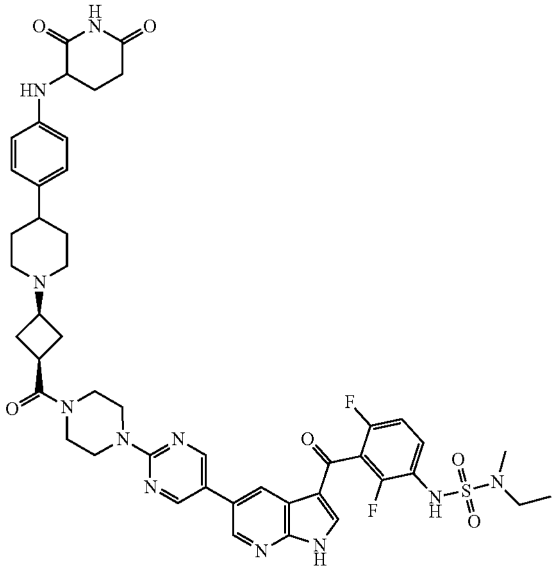 [SMILES: CCN(C)S(=O)(=O)Nc1ccc(F)c(C(=O)c2c[nH]c3ncc(-c4cnc(N5CCN(C(=O)[C@H]6C[C@@H](N7CCC(c8ccc(NC9CCC(=O)NC9=O)cc8)CC7)C6)CC5)nc4)cc23)c1F]

The title compound was obtained as light brown solid in 50% yield according to general procedure VIII.

Amine: 3-[3-[[Ethyl(methyl)sulfamoyl]amino]-2,6-difluoro-benzoyl]-5-(2-piperazin-1-ylpyrimidin-5-yl)-1H-pyrrolo[2,3-b]pyridine Acid: cis-3-[4-[4-[(2,6-Dioxo-3-piperidyl)amino]phenyl]-1-piperidyl]cyclobutanecarboxylic acid MS m/e: 925.4 ($[M+H+]^+$)

Example A 79

5-[2-[4-[2-[4-[4-[(2,6-Dioxopiperidin-3-yl)amino]pyrazol-1-yl]piperidin-1-yl]acetyl]piperazin-1-yl]pyrimidin-5-yl]-3-[3-[[ethyl(methyl)sulfamoyl]amino]-2,6-difluorobenzoyl]-1H-pyrrolo[2,3-b]pyridine

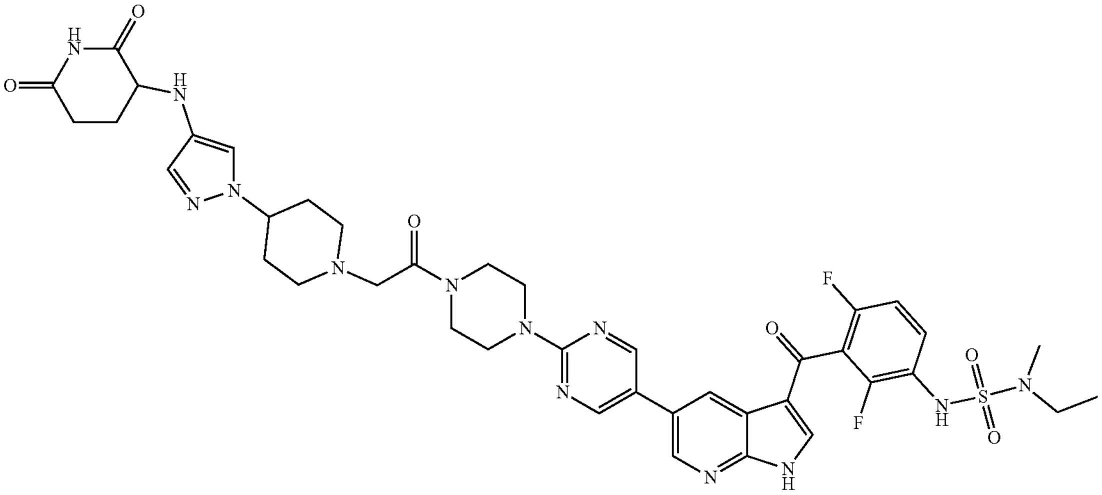 [SMILES: CCN(C)S(=O)(=O)Nc1ccc(F)c(C(=O)c2c[nH]c3ncc(-c4cnc(N5CCN(C(=O)CN6CCC(n7cc(NC8CCC(=O)NC8=O)cn7)CC6)CC5)nc4)cc23)c1F]

The title compound was obtained as green solid in 44% yield according to general procedure VIII.

Amine: 3-[3-[[Ethyl(methyl)sulfamoyl]amino]-2,6-difluoro-benzoyl]-5-(2-piperazin-1-ylpyrimidin-5-yl)-1H-pyrrolo[2,3-b]pyridine Acid: 2-[4-[4-[(2,6-dioxo-3-piperidyl)amino]pyrazol-1-yl]-1-piperidyl]acetic acid hydrochloride MS m/e: 874.7 ([M+H+]$^+$)

Example A 80

5-[4-[4-[2-[4-[4-[(2,6-Dioxopiperidin-3-yl)amino]pyrazol-1-yl]piperidin-1-yl]acetyl]piperazin-1-yl]phenyl]-3-[3-[[ethyl(methyl)sulfamoyl]amino]-2,6-difluorobenzoyl]-1H-pyrrolo[2,3-b]pyridine

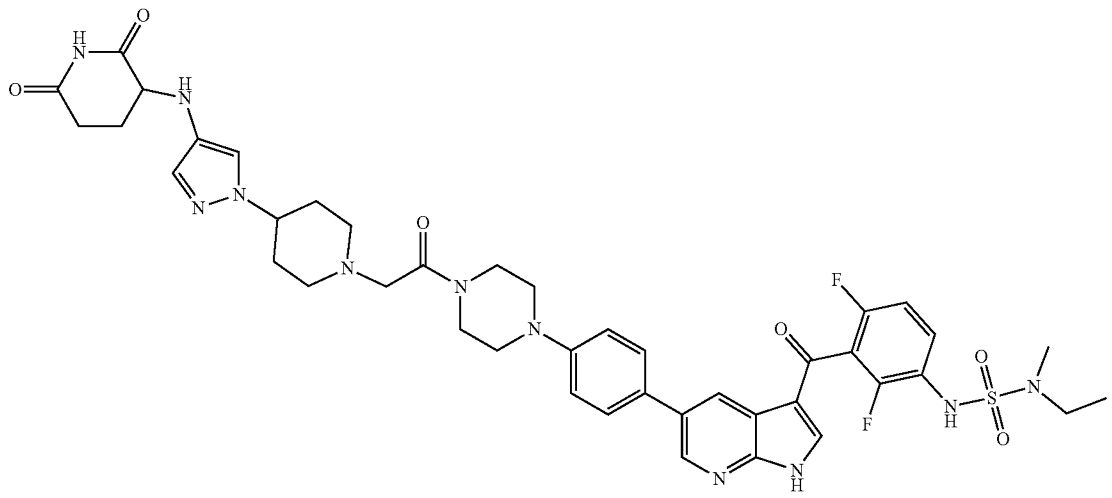 [SMILES: CCN(C)S(=O)(=O)Nc1ccc(F)c(C(=O)c2c[nH]c3ncc(-c4ccc(N5CCN(C(=O)CN6CCC(n7cc(NC8CCC(=O)NC8=O)cn7)CC6)CC5)cc4)cc23)c1F]

The title compound was obtained as green solid in 51% yield according to general procedure VIII.

Amine: 3-[3-[[ethyl(methyl)sulfamoyl]amino]-2,6-difluoro-benzoyl]-5-(4-piperazin-1-ylphenyl)-1H-pyrrolo[2,3-b]pyridine Acid: 2-[4-[4-[(2,6-dioxo-3-piperidyl)amino]pyrazol-1-yl]-1-piperidyl]acetic acid hydrochloride MS m/e: 872.6 ([M+H+]$^+$)

Example A 81

5-[6-[4-[4-[4-[4-(2,6-Dioxopiperidin-3-yl)phenyl]piperidin-1-yl]butanoyl]piperazin-1-yl]pyridin-3-yl]-3-[3-[[ethyl(methyl)sulfamoyl]amino]-2,6-difluorobenzoyl]-1H-pyrrolo[2,3-b]pyridine

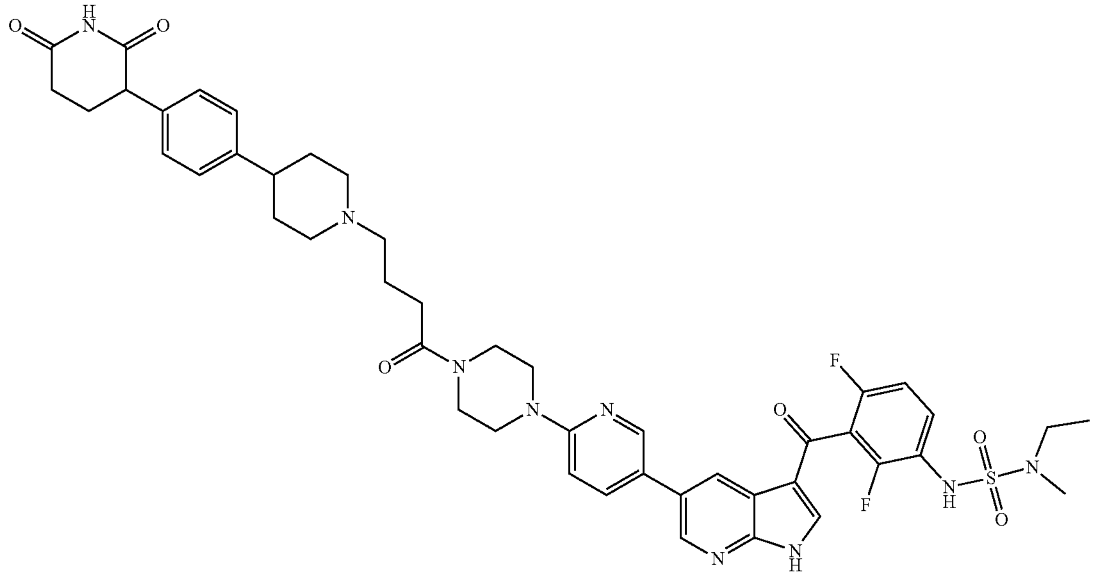 [SMILES: CCN(C)S(=O)(=O)Nc1ccc(F)c(C(=O)c2c[nH]c3ncc(-c4ccc(N5CCN(C(=O)CCCN6CCC(c7ccc(C8CCC(=O)NC8=O)cc7)CC6)CC5)nc4)cc23)c1F]

The title compound was obtained as yellow solid in 27% yield according to general procedure VIII.

Amine: 3-[3-[[ethyl(methyl)sulfamoyl]amino]-2,6-difluoro-benzoyl]-5-(6-piperazin-1-yl-3-pyridyl)-1H-pyrrolo[2,3-b]pyridine Acid: 4-[4-[4-(2,6-Dioxo-3-piperidyl)phenyl]-1-piperidyl]butanoic acid hydrochloride MS m/e: 897.6 ([M+H+]$^+$)

Example A 82

5-[6-[4-[2-[4-[4-(2,6-Dioxopiperidin-3-yl)phenyl]piperidin-1-yl]acetyl]piperazin-1-yl]pyridin-3-yl]-3-[3-[[ethyl(methyl)sulfamoyl]amino]-2,6-difluorobenzoyl]-1H-pyrrolo[2,3-b]pyridine

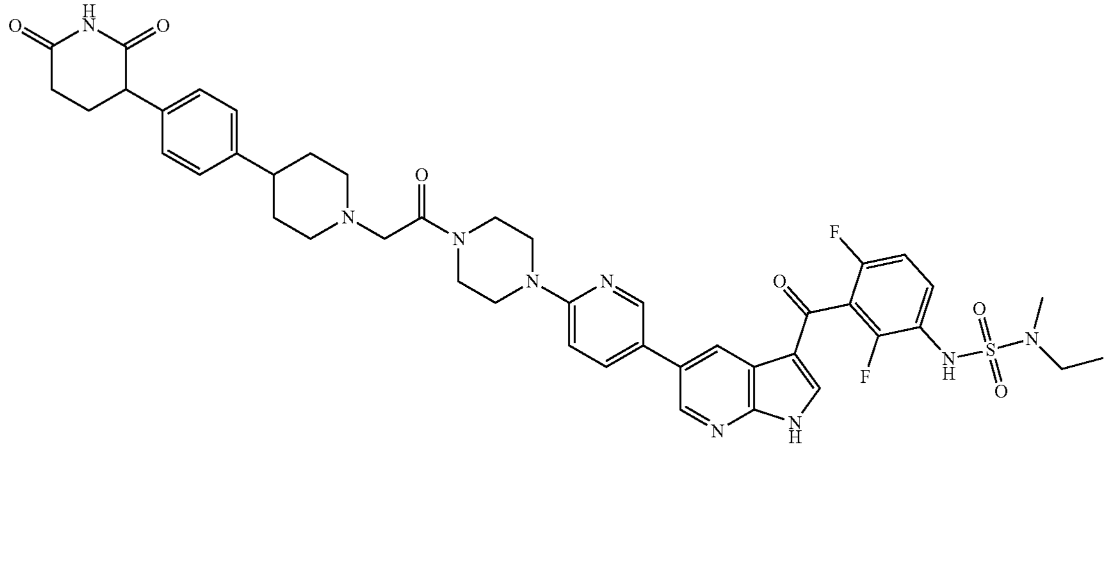 [SMILES: CCN(C)S(=O)(=O)Nc1ccc(F)c(C(=O)c2c[nH]c3ncc(-c4ccc(N5CCN(C(=O)CN6CCC(c7ccc(C8CCC(=O)NC8=O)cc7)CC6)CC5)nc4)cc23)c1F]

The title compound was obtained as light yellow solid in 89% yield according to general procedure VIII.

Amine: 3-[3-[[ethyl(methyl)sulfamoyl]amino]-2,6-difluoro-benzoyl]-5-(6-piperazin-1-yl-3-pyridyl)-1H-pyrrolo[2,3-b]pyridine Acid: 2-[4-[4-(2,6-dioxo-3-piperidyl)phenyl]-1-piperidyl]acetic acid hydrochloride MS m/e: 868.4 ([M+H+]$^+$)

Example A 83

5-[2-[4-[4-[4-[4-[(2,6-Dioxopiperidin-3-yl)amino]phenyl]piperidin-1-yl]piperidine-1-carbonyl]phenyl]ethynyl]-3-[3-[[ethyl(methyl)sulfamoyl]amino]-2,6-difluorobenzoyl]-1H-pyrrolo[2,3-b]pyridine

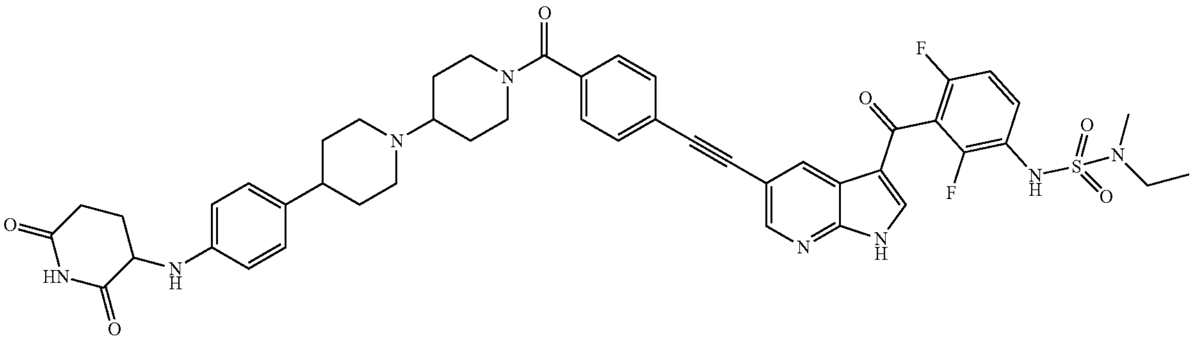 [SMILES: CCN(C)S(=O)(=O)Nc1ccc(F)c(C(=O)c2c[nH]c3ncc(C#Cc4ccc(C(=O)N5CCC(N6CCC(c7ccc(NC8CCC(=O)NC8=O)cc7)CC6)CC5)cc4)cc23)c1F]

The title compound was obtained as orange solid in 31% yield according to general procedure VIII.

Amine: 3-[4-[1-(4-piperidyl)-4-piperidyl]anilino]piperidine-2,6-dione hydrochloride Acid: N-[2-[3-[3-[[ethyl(methyl)sulfamoyl]amino]-2,6-difluoro-benzoyl]-1H-pyrrolo[2,3-b]pyridin-5-yl]ethynyl]benzoic acid MS m/e: 891.5 ([M+H+]$^+$)

Example A 84

N-[2,4-Difluoro-3-[5-[6-[rac-(1R,5S)-9-[2-[4-[4-[(2,6-dioxopiperidin-3-yl)amino]phenyl]piperidin-1-yl]acetyl]-3,9-diazabicyclo[3.3.1]nonan-3-yl]pyridin-3-yl]-1H-pyrrolo[2,3-b]pyridine-3-carbonyl]phenyl]pyrrolidine-1-sulfonamide

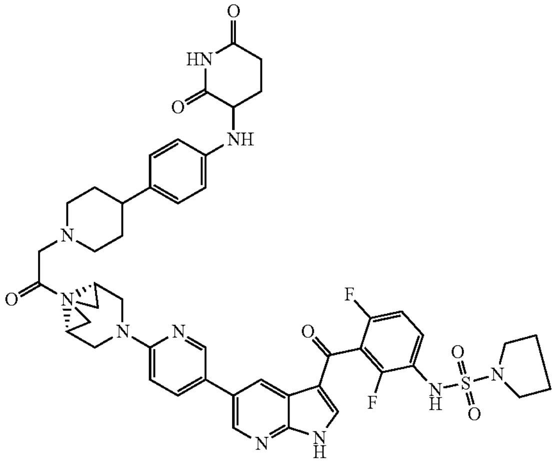

The title compound was obtained as light yellow powder in 15% yield according to general procedure VIII.

Amine: N-[2,4-difluoro-3-[5-[6-[rac-(1S,5R)-3,9-diazabicyclo[3.3.1]nonan-3-yl]-3-pyridyl]-1H-pyrrolo[2,3-b]pyridine-3-carbonyl]phenyl]pyrrolidine-1-sulfonamide 2,2,2-trifluoroacetic acid Acid: 2-[4-[4-[(2,6-dioxo-3-piperidyl)amino]phenyl]piperazin-1-yl]acetic acid hydrochloride MS m/e: 935.4 ([M+H+]$^+$)

Example A 85

N-[3-[5-[4-[4-[2-[4-[4-(2,6-Dioxopiperidin-3-yl)phenyl]piperidin-1-yl]acetyl]piperazin-1-yl]phenyl]-1H-pyrrolo[2,3-b]pyridine-3-carbonyl]-2,4-difluorophenyl]pyrrolidine-1-sulfonamide

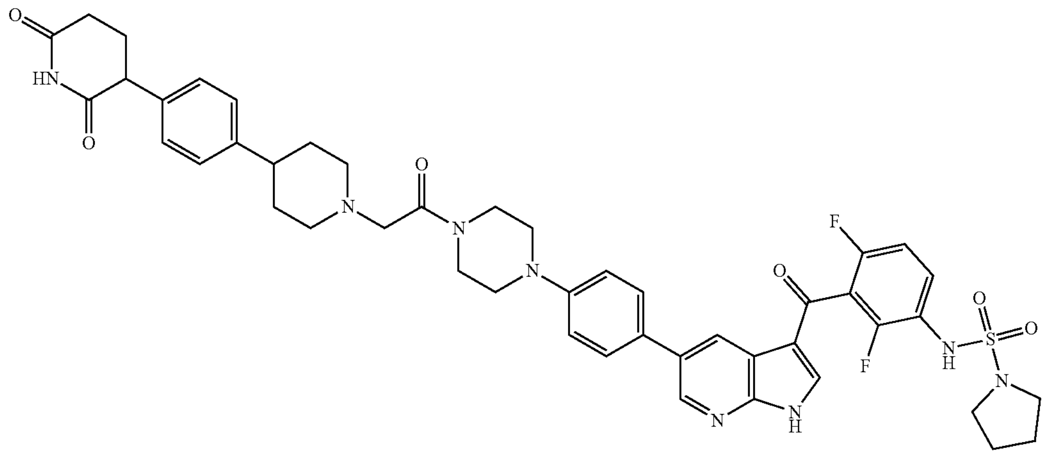 [SMILES: O=C1CCC(c2ccc(C3CCN(CC(=O)N4CCN(c5ccc(-c6cnc7[nH]cc(C(=O)c8c(F)ccc(NS(=O)(=O)N9CCCC9)c8F)c7c6)cc5)CC4)CC3)cc2)C(=O)N1]

The title compound was obtained in 20% yield according to general procedure VIII.

Amine: N-[2,4-difluoro-3-[5-(4-piperazin-1-ylphenyl)-1H-pyrrolo[2,3-b]pyridine-3-carbonyl]phenyl]pyrrolidine-1-sulfonamide 2,2,2-trifluoroacetic acid Acid: 2-[4-[4-(2,6-dioxo-3-piperidyl)phenyl]-1-piperidyl]acetic acid hydrochloride MS m/e: 879.3 ([M+H+]$^+$)

Example A 86

N-[2-[4-[4-[(2,6-Dioxopiperidin-3-yl)amino]phenyl]piperidin-1-yl]ethyl]-4-[2-[3-[3-[[ethyl(methyl)sulfamoyl]amino]-2,6-difluorobenzoyl]-1H-pyrrolo[2,3-b]pyridin-5-yl]ethynyl]benzamide

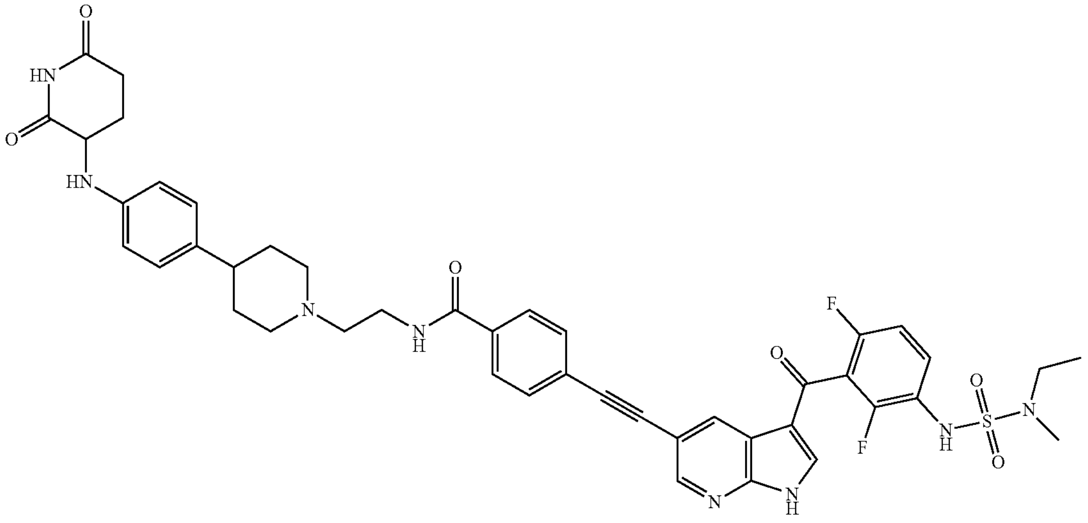 [SMILES: CCN(C)S(=O)(=O)Nc1ccc(F)c(C(=O)c2c[nH]c3ncc(C#Cc4ccc(C(=O)NCCN5CCC(c6ccc(NC7CCC(=O)NC7=O)cc6)CC5)cc4)cc23)c1F]

The title compound was obtained as orange solid in 48% yield according to general procedure VIII.

Amine: 3-[4-[1-(2-aminoethyl)-4-piperidyl]anilino]piperidine-2,6-dione dihydrochloride Acid: 4-[2-[3-[3-[[ethyl(methyl)sulfamoyl]amino]-2,6-difluoro-benzoyl]-1H-pyrrolo[2,3-b]pyridin-5-yl]ethynyl]benzoic acid MS m/e: 851 ([M+H+]$^{+}$)

Example A 87

5-[2-[4-[2-[4-[4-[(2,4-Dioxo-3-azabicyclo[3.1.1]heptan-1-yl)amino]phenyl]piperidin-1-yl]acetyl]piperazin-1-yl]pyrimidin-5-yl]-3-[3-[[ethyl(methyl)sulfamoyl]amino]2,6-difluorobenzoyl]-1H-pyrrolo[2,3-b]pyridine; formic acid

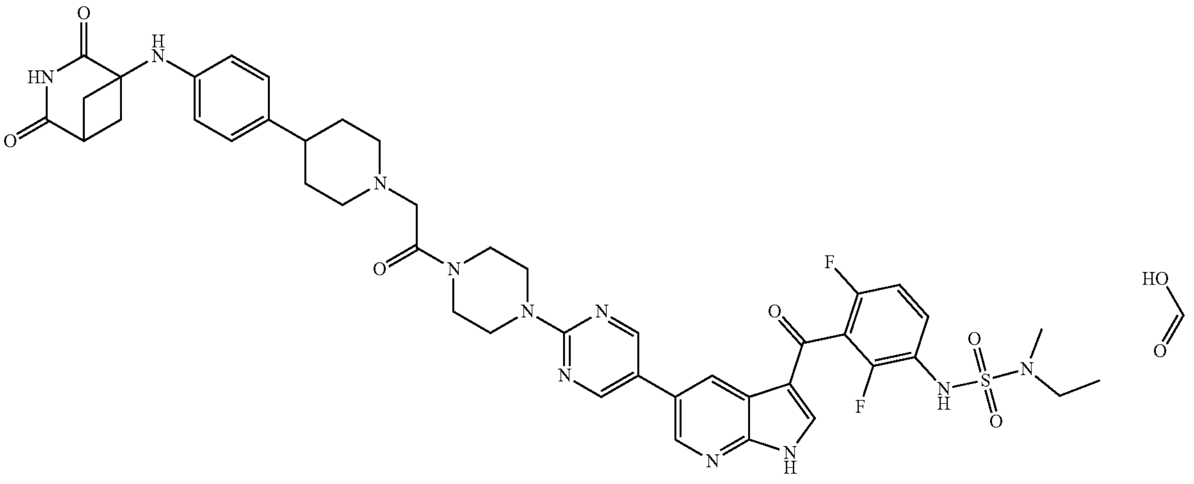 [SMILES: CCN(C)S(=O)(=O)Nc1ccc(F)c(C(=O)c2c[nH]c3ncc(-c4cnc(N5CCN(C(=O)CN6CCC(c7ccc(NC89CC(C8)C(=O)NC9=O)cc7)CC6)CC5)nc4)cc23)c1F ; O=CO]

The title compound was obtained as orange solid in 19% yield according to general procedure VIII.

Amine: 3-[3-[[Ethyl(methyl)sulfamoyl]amino]-2,6-difluoro-benzoyl]-5-(2-piperazin-1-ylpyrimidin-5-yl)-1H-pyrrolo[2,3-b]pyridine Acid: 2-[4-[4-[(2,4-dioxo-3-azabicyclo[3.1.1]heptan-1-yl)amino]phenyl]-1-piperidyl]acetic acid hydrochloride MS m/e: 897.4 ([M+H+]$^{+}$)

Example A 88

N-[3-[5-[4-[4-[2-[4-[3-(2,4-Dioxo-1,3-diazinan-1-yl)phenyl]piperidin-1-yl]acetyl]piperazin-1-yl]phenyl]-1H-pyrrolo[2,3-b]pyridine-3-carbonyl]-2,4-difluoro-phenyl]pyrrolidine-1-sulfonamide

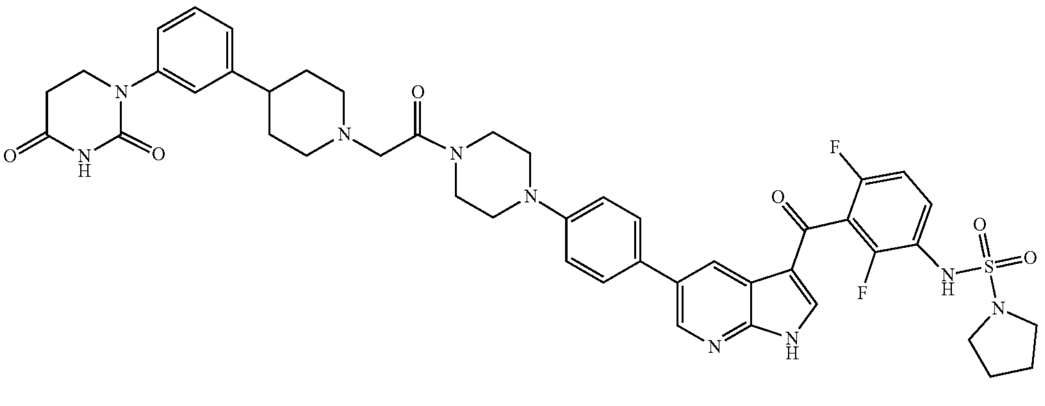 [SMILES: O=C1CCN(c2cccc(C3CCN(CC(=O)N4CCN(c5ccc(-c6cnc7[nH]cc(C(=O)c8c(F)ccc(NS(=O)(=O)N9CCCC9)c8F)c7c6)cc5)CC4)CC3)c2)C(=O)N1]

The title compound was obtained as yellow solid in 22% yield according to general procedure VIII.

Amine: N-[2,4-difluoro-3-[5-(4-piperazin-1-ylphenyl)-1H-pyrrolo[2,3-b]pyridine-3-carbonyl]phenyl]pyrrolidine-1-sulfonamide Acid: 2-[4-[3-(2,4-dioxohexahydropyrimidin-1-yl)phenyl]-1-piperidyl]acetic acid hydrochloride hydrochloride MS m/e: 880.3 ([M+H+]$^+$)

Example A 89

N-[3-[5-[4-[1-[4-[4-[4-[(2,6-dioxopiperidin-3-yl) amino]phenyl]piperidin-1-yl]butanoyl]azetidin-3-yl] phenyl]-1H-pyrrolo[2,3-b]pyridine-3-carbonyl]-2,4-difluorophenyl]pyrrolidine-1-sulfonamide

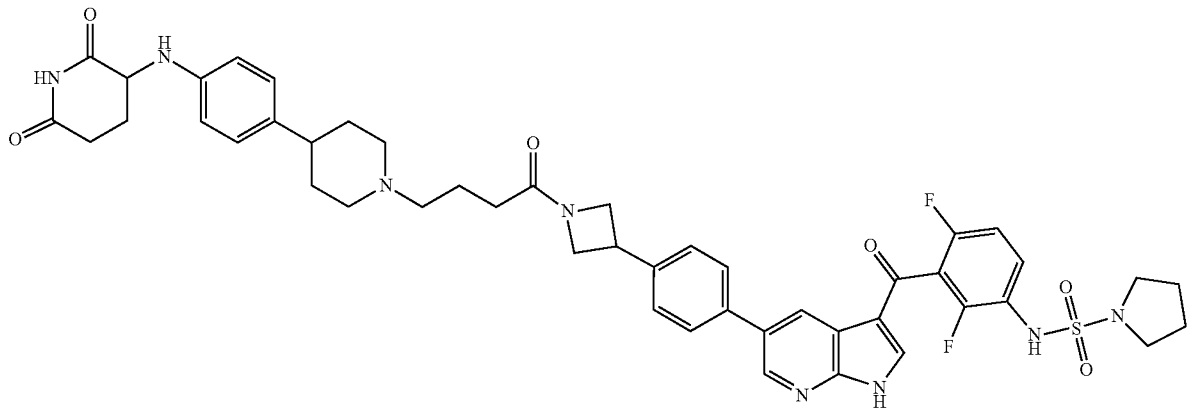 [SMILES: O=C1CCC(Nc2ccc(C3CCN(CCCC(=O)N4CC(c5ccc(-c6cnc7[nH]cc(C(=O)c8c(F)ccc(NS(=O)(=O)N9CCCC9)c8F)c7c6)cc5)C4)CC3)cc2)C(=O)N1]

The title compound was obtained as yellow solid in 25% yield according to general procedure VIII.

Amine: N-[3-[5-[4-(azetidin-3-yl)phenyl]-1H-pyrrolo[2,3-b]pyridine-3-carbonyl]-2,4-difluoro-phenyl]pyrrolidine-1-sulfonamide 2,2,2-trifluoroacetic acid Acid: 4-[4-[4-[(2,6-dioxo-3-piperidyl)amino]phenyl]-1-piperidyl]butanoic acid hydrochloride MS m/e: 893.3 ([M+H+]$^+$)

Example A 90

5-[2-[4-[[2-[4-[5-[(2,6-Dioxopiperidin-3-yl)amino] pyridin-2-yl]piperidin-1-yl]-2-oxoethyl]-methyl-amino]piperidin-1-yl]pyrimidin-5-yl]-3-[3-[[ethyl (methyl)sulfamoyl]amino]-2,6-difluorobenzoyl]-1H-pyrrolo[2,3-b]pyridine;formic acid

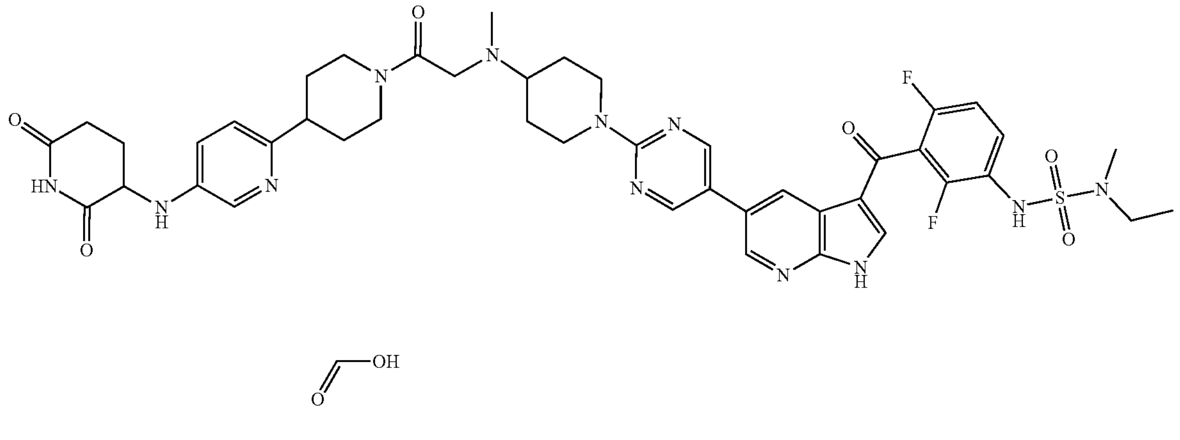 [SMILES: CCN(C)S(=O)(=O)Nc1ccc(F)c(C(=O)c2c[nH]c3ncc(-c4cnc(N5CCC(N(C)CC(=O)N6CCC(c7ccc(NC8CCC(=O)NC8=O)cn7)CC6)CC5)nc4)cc23)c1F ; O=CO]

To a solution of 3-[[6-(4-piperidyl)-3-pyridyl]amino]piperidine-2,6-dione (9.45 mg, 0.030 mmol, 1.1 eq) in DMF (2 mL) was added DIPEA (10.26 mg, 0.080 mmol, 3 eq), 2-[[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]-methyl-amino]acetic acid (17.0 mg, 0.030 mmol, 1 eq) and PyBOP (15.13 mg, 0.030 mmol, 1.1 eq) at 30° C. Then the reaction was stirred at 30° C. for 2 h. The reaction mixture was filtered, the filtrate was purified by prep-HPLC to give the title compound (2.8 mg, 0 mmol, 10.95% yield) as a white solid. MS m/e: 913.1 ([M+H+]$^+$)

Example A 91

5-[2-[4-[2-[4-[4-(2,4-Dioxo-1,3-diazinan-1-yl)phenyl]piperidin-1-yl]acetyl]piperazin-1-yl]pyrimidin-5-yl]-3-[3-[[ethyl(methyl)sulfamoyl]amino]-2,6-difluorobenzoyl]-1H-pyrrolo[2,3-b]pyridine

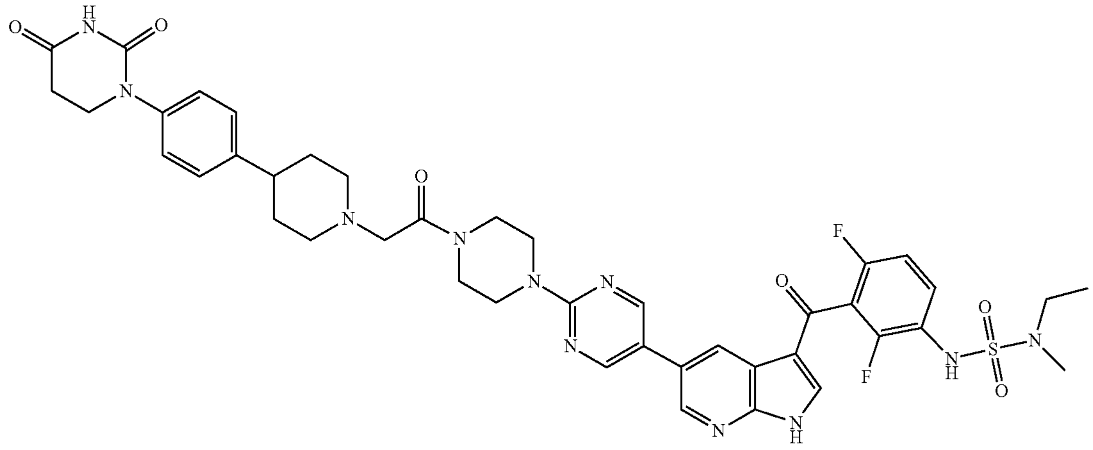 [SMILES: CCN(C)S(=O)(=O)Nc1ccc(F)c(C(=O)c2c[nH]c3ncc(-c4cnc(N5CCN(C(=O)CN6CCC(c7ccc(N8CCC(=O)NC8=O)cc7)CC6)CC5)nc4)cc23)c1F]

The title compound was obtained as light yellow solid in 80% yield according to general procedure VIII.

Amine: 3-[3-[[Ethyl(methyl)sulfamoyl]amino]-2,6-difluoro-benzoyl]-5-(2-piperazin-1-ylpyrimidin-5-yl)-1H-pyrrolo[2,3-b]pyridine Acid: 2-[4-[4-(2,4-dioxohexahydropyrimidin-1-yl)phenyl]-1-piperidyl]acetic acid hydrochloride MS m/e: 870.6 ([M+H+]$^+$)

Example A 92

2-[4-[5-[(2,6-Dioxopiperidin-3-yl)amino]pyridin-2-yl]piperidin-1-yl]-N-[1-[5-[3-[3-[[ethyl(methyl)sulfamoyl]amino]-2,6-difluorobenzoyl]-1H-pyrrolo[2,3-b]pyridin-5-yl]pyrimidin-2-yl]piperidin-4-yl]-N-methylacetamide; formic acid

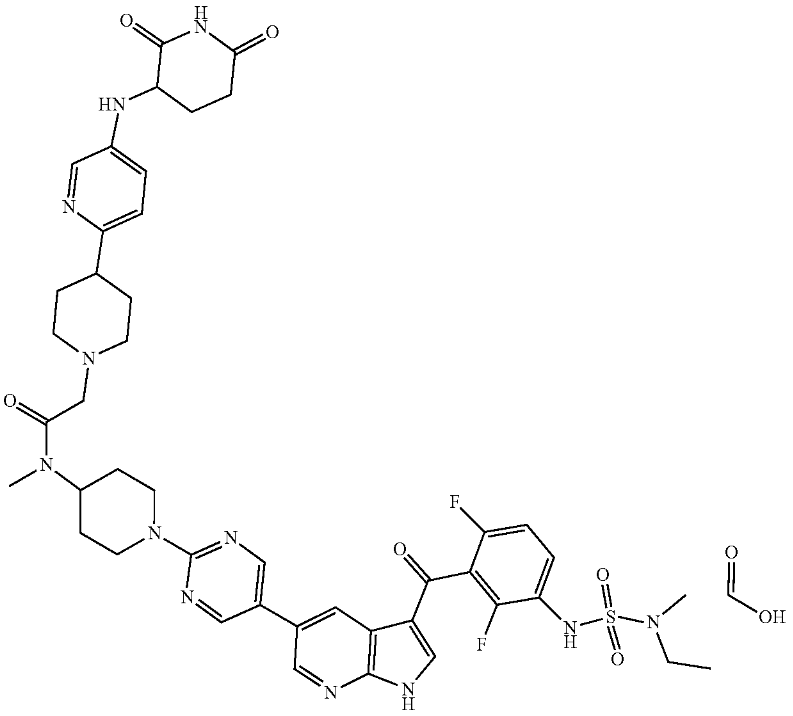

To 3-[3-[[ethyl(methyl)sulfamoyl]amino]-2,6-difluorobenzoyl]-5-[2-[4-(methylamino)-1-piperidyl]pyrimidin-5-yl]-1H-pyrrolo[2,3-b]pyridine hydrochloride (20.0 mg, 0.030 mmol, 1 eq), 2-[4-[5-[(2,6-dioxo-3-piperidyl)amino]-2-pyridyl]-1-piperidyl]acetic acid hydrochloride (13.56 mg, 0.040 mmol, 1.1 eq) and DIPEA (mg, 0.030 mmol, 1 eq) in DMF (4.21 mL) was added PyBOP (18.42 mg, 0.040 mmol, 1.1 eq). The reaction mixture was stirred at 25° C. for 2 h. The reaction mixture was purified by prep-HPLC to give the title compound (10.6 mg, 0.010 mmol, 34.32% yield) as yellow solid. MS m/e: 913.6 ([M+H+]$^+$)

Example A 93

5-[2-[4-[[2-[4-[5-[(2,6-Dioxopiperidin-3-yl)amino]pyridin-2-yl]piperidin-1-yl]-2-oxoethyl]amino]piperidin-1-yl]pyrimidin-5-yl]-3-[3-[[ethyl(methyl)sulfamoyl]amino]-2,6-difluorobenzoyl]-1H-pyrrolo[2,3-b]pyridine;formic acid

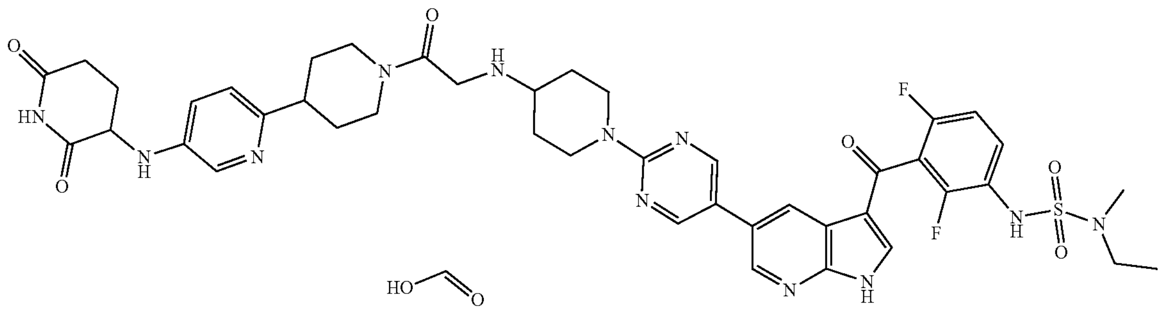 [SMILES: CCN(C)S(=O)(=O)Nc1ccc(F)c(C(=O)c2c[nH]c3ncc(-c4cnc(N5CCC(NCC(=O)N6CCC(c7ccc(NC8CCC(=O)NC8=O)cn7)CC6)CC5)nc4)cc23)c1F ; O=CO]

To a solution of 3-[[6-(4-piperidyl)-3-pyridyl]amino]piperidine-2,6-dione hydrochloride (21.98 mg, 0.070 mmol, 1.5 eq), 2-[[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]amino]acetic acid; 2,2,2-trifluoroacetic acid (33.5 mg, 0.050 mmol, 1 eq) and DIPEA (17.47 mg, 0.140 mmol, 3 eq) in DMF (2 mL) was added PyBOP (25.8 mg, 0.050 mmol, 1.1 eq). The reaction mixture was stirred at 25° C. for 2 h. The reaction mixture was purified by prep-HPLC to give the title compound (13.2 mg, 0.010 mmol, 30.75% yield) as brown solid. MS m/e: 899.6 ($[M+H+]^+$)

Example A 94

5-[2-[4-[4-[4-[(2,6-Dioxopiperidin-3-yl)amino]phenyl]piperidine-1-carbonyl]piperidin-1-yl]pyrimidin-5-yl]-3-[3-[[ethyl(methyl)sulfamoyl]amino]-2,6-difluorobenzoyl]-1H-pyrrolo[2,3-b]pyridine

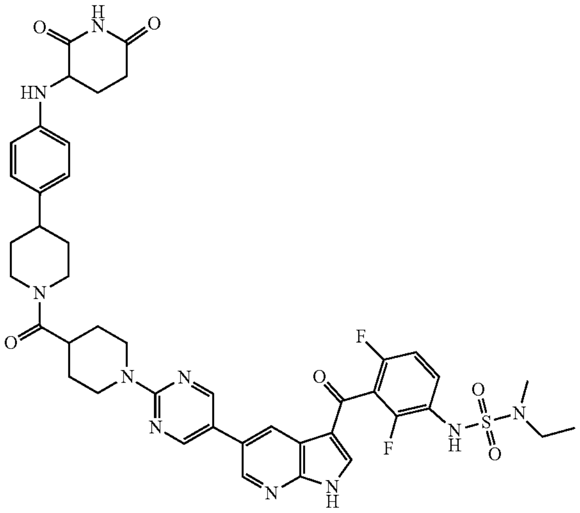 [SMILES: CCN(C)S(=O)(=O)Nc1ccc(F)c(C(=O)c2c[nH]c3ncc(-c4cnc(N5CCC(C(=O)N6CCC(c7ccc(NC8CCC(=O)NC8=O)cc7)CC6)CC5)nc4)cc23)c1F]

The title compound was obtained as light green solid in 53% yield according to general procedure VIII.

Amine: 3-((4-(piperidin-4-yl)phenyl)amino)piperidine-2,6-dione hydrochloride

Acid: 1-(5-(3-(3-((N-ethyl-N-methylsulfamoyl)amino)-2,6-difluorobenzoyl)-1H-pyrrolo[2,3-b]pyridin-5-yl)pyrimidin-2-yl)piperidine-4-carboxylic acid MS m/e: 869.5 ($[M+H+]^+$)

Example A 95

2-[4-[5-[(2,6-Dioxopiperidin-3-yl)amino]pyridin-2-yl]piperidin-1-yl]-N-[1-[5-[3-[3-[[ethyl(methyl)sulfamoyl]amino]-2,6-difluorobenzoyl]-1H-pyrrolo[2,3-b]pyridin-5-yl]pyridin-2-yl]piperidin-4-yl]-N-methylacetamide;hydrochloride

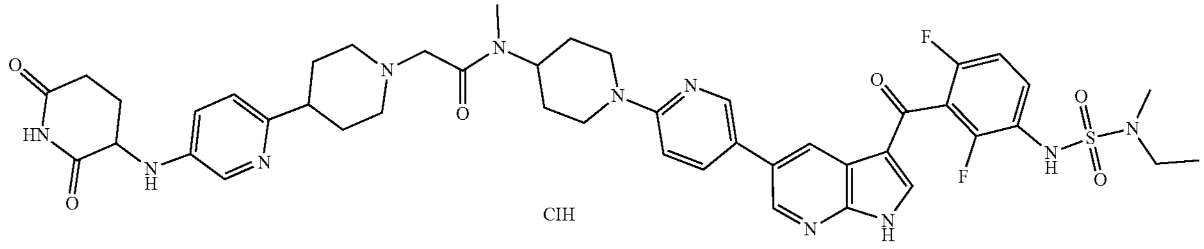 [SMILES: CCN(C)S(=O)(=O)Nc1ccc(F)c(C(=O)c2c[nH]c3ncc(-c4ccc(N5CCC(N(C)C(=O)CN6CCC(c7ccc(NC8CCC(=O)NC8=O)cn7)CC6)CC5)nc4)cc23)c1F ; "CIH"]

To a solution of 3-[3-[[ethyl(methyl)sulfamoyl]amino]-2,6-difluoro-benzoyl]-5-[6-[4-(methylamino)-1-piperidyl]-3-pyridyl]-1H-pyrrolo[2,3-b]pyridine (25.0 mg, 0.040 mmol, 1 eq) and 2-[4-[5-[(2,6-dioxo-3-piperidyl)amino]-2-pyridyl]-1-piperidyl]acetic acid (18.52 mg, 0.050 mmol, 1.2 eq) in DMF (4 mL) was added DIPEA (0.04 mL, 0.200 mmol, 5 eq) and PyBOP (20.97 mg, 0.040 mmol, 1 eq). The mixture was stirred at 25° C. for 3 h. The mixture was concentrated, purified by prep-HPLC and lyophilized to give the title compound (7.4 mg, 0.010 mmol, 19.35% yield) as a yellow solid. MS m/e: 912.6 ([M+H+]$^{+}$)

Example A 96

5-[4-[4-[[2-[4-[5-[(2,6-Dioxopiperidin-3-yl)amino]pyridin-2-yl]piperidin-1-yl]-2-oxoethyl]amino]piperidin-1-yl]phenyl]-3-[3-[[ethyl(methyl)sulfamoyl]amino]-2,6-difluorobenzoyl]-1H-pyrrolo[2,3-b]pyridine; hydrochloride

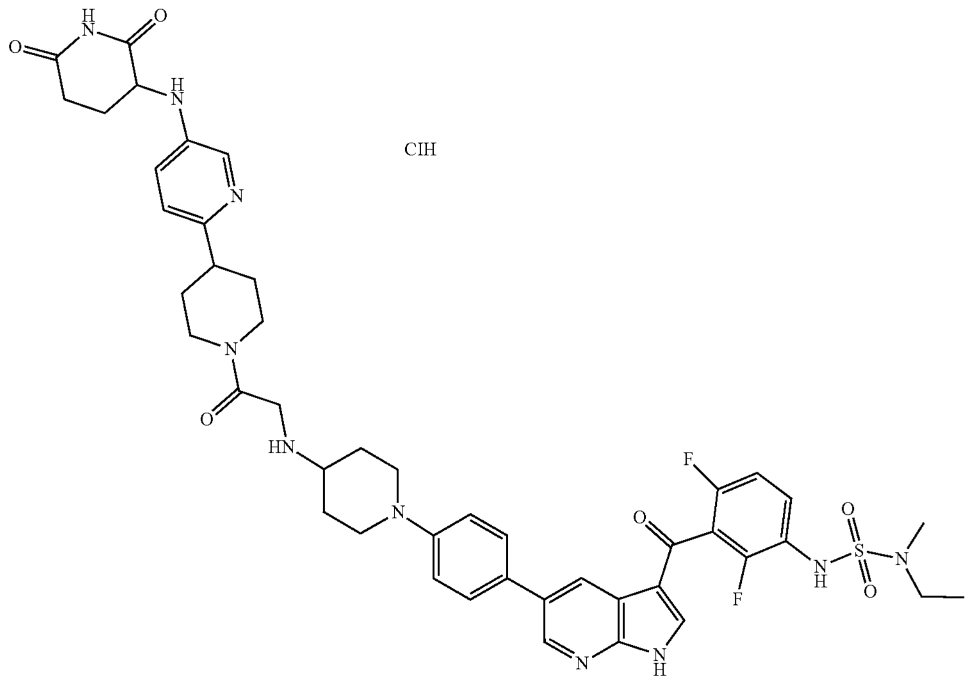 [SMILES: CCN(C)S(=O)(=O)Nc1ccc(F)c(C(=O)c2c[nH]c3ncc(-c4ccc(N5CCC(NCC(=O)N6CCC(c7ccc(NC8CCC(=O)NC8=O)cn7)CC6)CC5)cc4)cc23)c1F ; "CIH"]

To 2-[[1-[4-[3-[3-[[ethyl(methyl)sulfamoyl]amino]-2,6-difluoro-benzoyl]-1H-pyrrolo[2,3-b]pyridin-5-yl]phenyl]-4-piperidyl]amino]acetic acid hydrochloride (25.0 mg, 0.040 mmol, 1 eq) and 3-[[6-(4-piperidyl)-3-pyridyl]amino]piperidine-2,6-dione hydrochloride (18.37 mg, 0.060 mmol, 1.5 eq) in DMF (2.01 mL) was added PyBOP (21.56 mg, 0.040 mmol, 1.1 eq) and DIPEA (14.61 mg, 0.110 mmol, 3 eq). The reaction mixture was stirred at 25° C. for 16 h. The reaction mixture was purified by prep-HPLC and lyophylized to give the title compound (14.5 mg, 0.020 mmol, 42.32% yield) as yellow solid. MS m/e: 897 ([M+H+]$^{+}$)

Example A 97

5-[4-[4-[[2-[4-[5-(2,6-Dioxopiperidin-3-yl)oxypyridin-2-yl]piperidin-1-yl]-2-oxoethyl]amino]piperidin-1-yl]phenyl]-3-[3-[[ethyl(methyl)sulfamoyl]amino]-2,6-difluorobenzoyl]-1H-pyrrolo[2,3-b]pyridine; hydrochloride

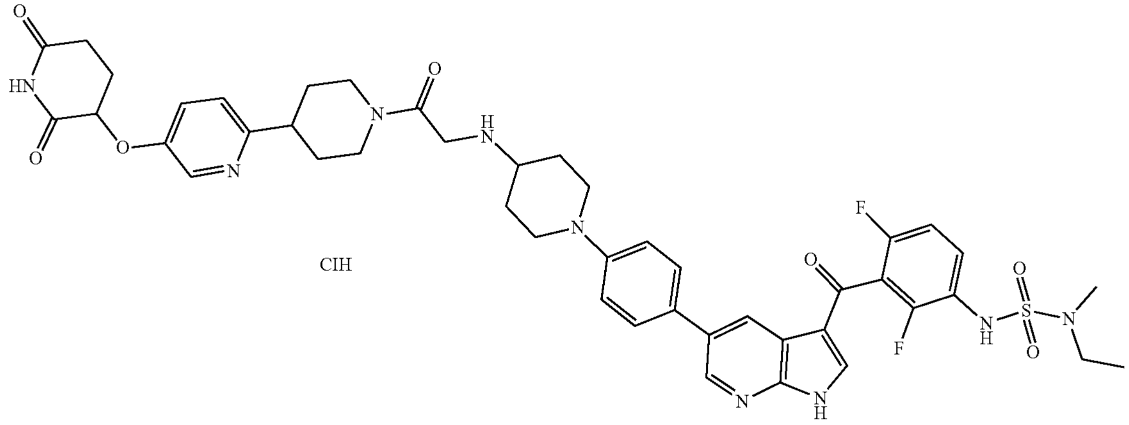 [SMILES: CCN(C)S(=O)(=O)Nc1ccc(F)c(C(=O)c2c[nH]c3ncc(-c4ccc(N5CCC(NCC(=O)N6CCC(c7ccc(OC8CCC(=O)NC8=O)cn7)CC6)CC5)cc4)cc23)c1F ; "CIH"]

To a solution of 3-[[6-(4-piperidyl)-3-pyridyl]oxy]piperidine-2,6-dione hydrochloride (18.42 mg, 0.060 mmol, 1.5 eq) and 2-[[1-[4-[3-[3-[[ethyl(methyl)sulfamoyl]amino]-2,6-difluoro-benzoyl]-1H-pyrrolo[2,3-b]pyridin-5-yl]phenyl]-4-piperidyl]amino]acetic acid hydrochloride (25.0 mg, 0.040 mmol, 1 eq) in DMF (2.01 mL) was added PyBOP (21.56 mg, 0.040 mmol, 1.1 eq) and DIPEA (14.61 mg, 0.110 mmol, 3 eq). The reaction mixture was stirred at 25° C. for 16 h. The reaction mixture was purified by prep-HPLC and lyophylized to give the title compound (18.6 mg, 0.020 mmol, 54.78% yield) as yellow solid. MS m/e: 898 ($[M+H+]^+$)

Example A 98

5-[4-[4-[[2-[4-[4-[(2,6-Dioxopiperidin-3-yl)amino]phenyl]piperidin-1-yl]-2-oxoethyl]amino]piperidin-1-yl]phenyl]-3-[3-[[ethyl(methyl)sulfamoyl]amino]-2,6-difluorobenzoyl]-1H-pyrrolo[2,3-b]pyridine; hydrochloride

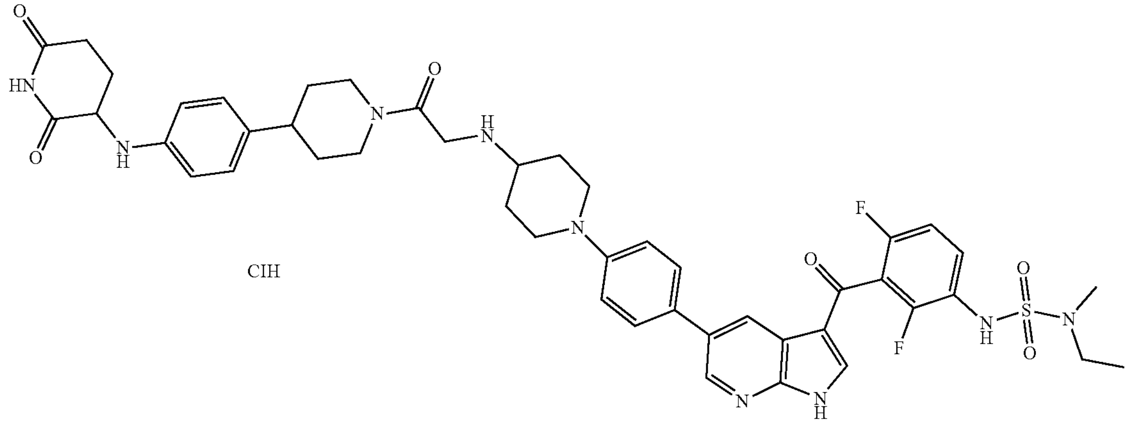 [SMILES: CCN(C)S(=O)(=O)Nc1ccc(F)c(C(=O)c2c[nH]c3ncc(-c4ccc(N5CCC(NCC(=O)N6CCC(c7ccc(NC8CCC(=O)NC8=O)cc7)CC6)CC5)cc4)cc23)c1F ; "CIH"]

To a solution of 3-[4-(4-piperidyl)anilino]piperidine-2,6-dione hydrochloride (18.31 mg, 0.060 mmol, 1.5 eq) and 2-[[1-[4-[3-[3-[[ethyl(methyl)sulfamoyl]amino]-2,6-difluoro-benzoyl]-1H-pyrrolo[2,3-b]pyridin-5-yl]phenyl]-4-piperidyl]amino]acetic acid hydrochloride (25.0 mg, 0.040 mmol, 1 eq) in DMF (2 mL) was added PyBOP (21.56 mg, 0.040 mmol, 1.1 eq) and DIPEA (14.61 mg, 0.110 mmol, 3 eq). The reaction mixture was stirred at 25° C. for 16 h. The reaction mixture was purified by prep-HPLC and lyophylized to give the title compound (21.4 mg, 0.020 mmol, 63.35% yield) as light yellow solid. MS m/e: 896 ([M+H+]$^+$)

Example A 99

5-[4-[4-[[2-[4-[4-(2,6-Dioxopiperidin-3-yl)oxyphenyl]piperidin-1-yl]-2-oxoethyl]amino]piperidin-1-yl]phenyl]-3-[3-[[ethyl(methyl)sulfamoyl]amino]-2,6-difluorobenzoyl]-1H-pyrrolo[2,3-b]pyridine; hydrochloride

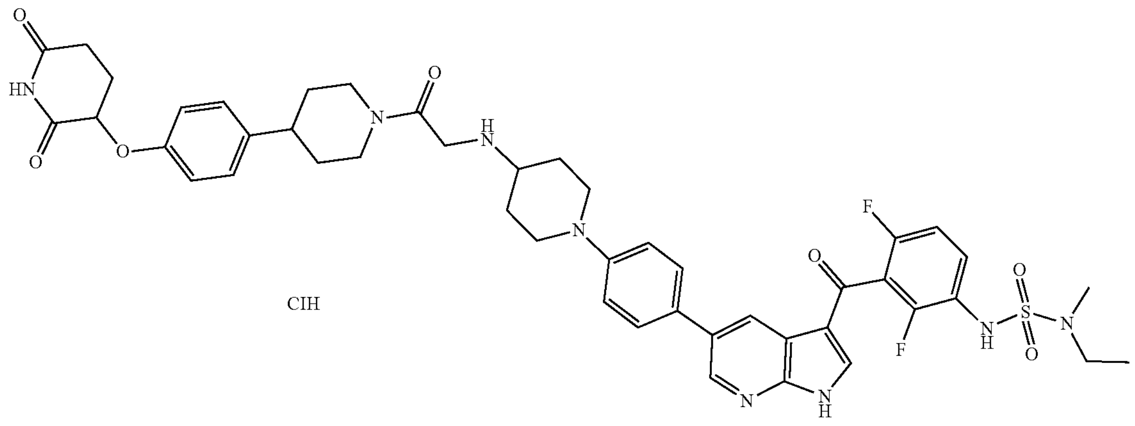 [SMILES: CCN(C)S(=O)(=O)Nc1ccc(F)c(C(=O)c2c[nH]c3ncc(-c4ccc(N5CCC(NCC(=O)N6CCC(c7ccc(OC8CCC(=O)NC8=O)cc7)CC6)CC5)cc4)cc23)c1F ; "CIH"]

To a solution of 3-[4-(4-piperidyl)phenoxy]piperidine-2,6-dione hydrochloride (18.37 mg, 0.060 mmol, 1.5 eq) and 2-[[1-[4-[3-[3-[[ethyl(methyl)sulfamoyl]amino]-2,6-difluoro-benzoyl]-1H-pyrrolo[2,3-b]pyridin-5-yl]phenyl]-4-piperidyl]amino]acetic acid hydrochloride (25.0 mg, 0.040 mmol, 1 eq) in DMF (2.01 mL) was added PyBOP (21.56 mg, 0.040 mmol, 1.1 eq) and DIPEA (14.61 mg, 0.110 mmol, 3 eq). The reaction mixture was stirred at 25° C. for 16 h. The reaction mixture was purified by prep-HPLC and lyophylized to give the title compound (16.25 mg, 0.020 mmol, 47.14% yield) as yellow solid. MS m/e: 897 ([M+H+]$^+$)

Example A 100

5-[2-[4-[[2-[4-[4-[(2,6-Dioxopiperidin-3-yl)amino]phenyl]piperidin-1-yl]-2-oxoethyl]amino]piperidin-1-yl]pyrimidin-5-yl]-3-[3-[[ethyl(methyl)sulfamoyl]amino]-2,6-difluorobenzoyl]-1H-pyrrolo[2,3-b]pyridine;hydrochloride

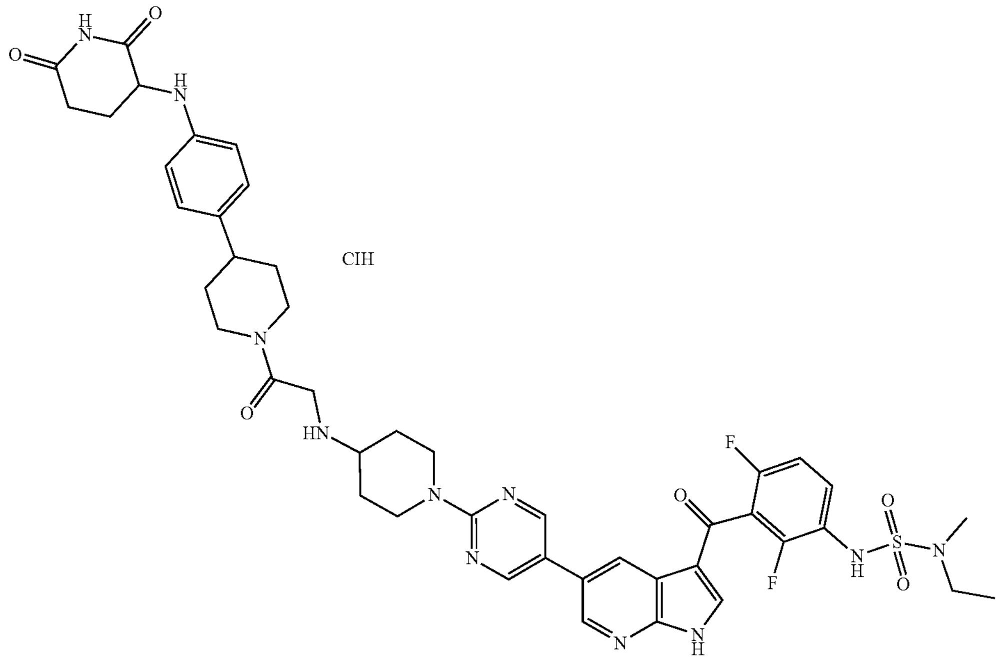

To 2-[[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]amino]acetic acid; 2,2,2-trifluoroacetic acid (50.0 mg, 0.070 mmol, 1 eq), 3-[4-(4-piperidyl)anilino]piperidine-2,6-dione hydrochloride (32.7 mg, 0.100 mmol, 1.5 eq) and DIPEA (26.08 mg, 0.200 mmol, 3 eq) in DMF (3 mL) was added PyBOP (52.51 mg, 0.100 mmol, 1.5 eq). The reaction mixture was stirred at 25° C. for 4 h. The reaction mixture was purified by prep-HPLC to give the title compound (29 mg, 0.030 mmol, 45.36% yield) as brown solid. MS m/e: 898.5 ([M+H+]$^+$)

Example A 101

5-[6-[4-[[2-[4-[5-[(2,6-Dioxopiperidin-3-yl)amino]pyridin-2-yl]piperidin-1-yl]-2-oxoethyl]-methyl-amino]piperidin-1-yl]pyridin-3-yl]-3-[3-[[ethyl(methyl)sulfamoyl]amino]-2,6-difluorobenzoyl]-1H-pyrrolo[2,3-b]pyridine; hydrochloride

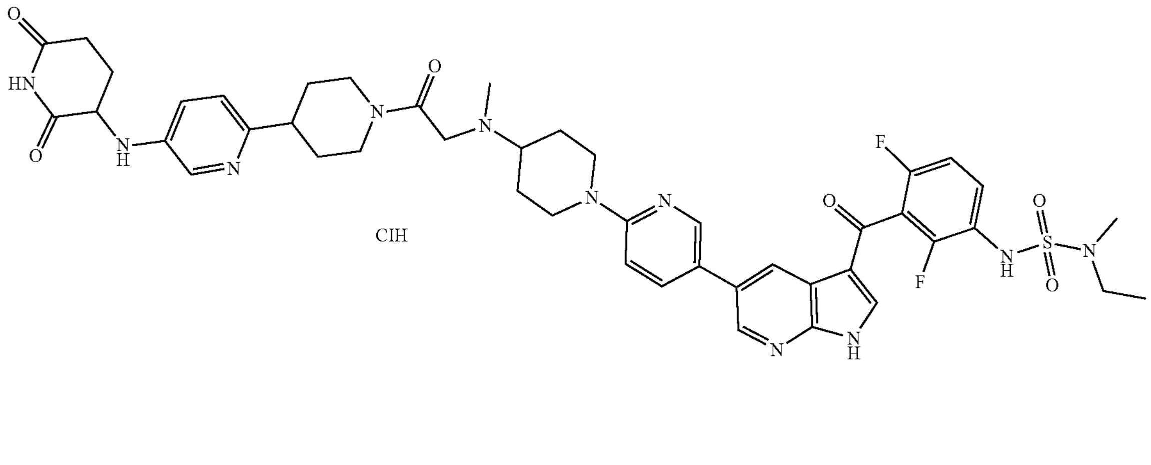 [SMILES: CCN(C)S(=O)(=O)Nc1ccc(F)c(C(=O)c2c[nH]c3ncc(-c4ccc(N5CCC(N(C)CC(=O)N6CCC(c7ccc(NC8CCC(=O)NC8=O)cn7)CC6)CC5)nc4)cc23)c1F ; "CIH"]

To a solution of 2-[[1-[5-[3-[3-[[ethyl(methyl)sulfamoyl]amino]-2,6-difluoro-benzoyl]-1H-pyrrolo[2,3-b]pyridin-5-yl]-2-pyridyl]-4-piperidyl]-methyl-amino]acetic acid; 2,2,2-trifluoroacetic acid (35.0 mg, 0.050 mmol, 1 eq), 3-[[6-(4-piperidyl)-3-pyridyl]amino]piperidine-2,6-dione hydrochloride (22.56 mg, 0.070 mmol, 1.5 eq) and DIPEA (17.94 mg, 0.140 mmol, 3 eq) in DMF (2 mL) was added PyBOP (36.12 mg, 0.070 mmol, 1.5 eq). The reaction mixture was stirred at 25° C. for 4 h. The reaction mixture was purified by prep-HPLC to give the title compound (21 mg, 0.020 mmol, 47.47% yield) as yellow solid. MS m/e: 912.6 ([M+H+]$^+$)

Example A 102

5-[2-[4-[[2-[4-[4-(2,6-Dioxopiperidin-3-yl)oxyphenyl]piperidin-1-yl]-2-oxoethyl]amino]piperidin-1-yl]pyrimidin-5-yl]-3-[3-[[ethyl(methyl)sulfamoyl]amino]-2,6-difluorobenzoyl]-1H-pyrrolo[2,3-b]pyridine;formic acid

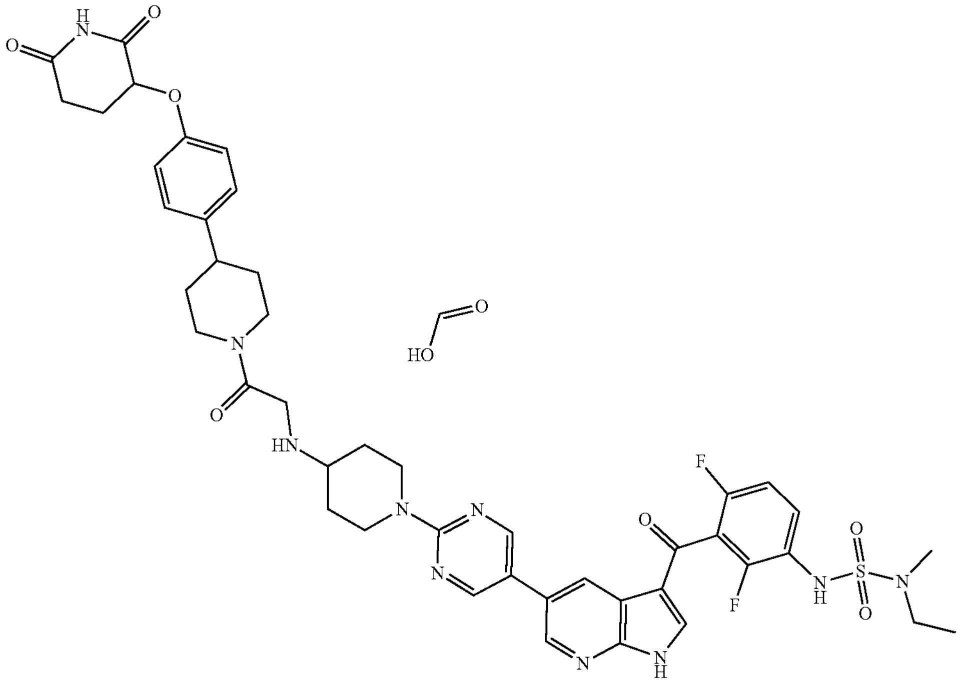 [SMILES: CCN(C)S(=O)(=O)Nc1ccc(F)c(C(=O)c2c[nH]c3ncc(-c4cnc(N5CCC(NCC(=O)N6CCC(c7ccc(OC8CCC(=O)NC8=O)cc7)CC6)CC5)nc4)cc23)c1F ; O=CO]

To a solution of 2-[[1-[5-[3-[3-[[ethyl(methyl)sulfamoyl]amino]-2,6-difluoro-benzoyl]-1H-pyrrolo[2,3-b]pyridin-5-yl]pyrimidin-2-yl]-4-piperidyl]amino]acetic acid; 2,2,2-trifluoroacetic acid (50.0 mg, 0.070 mmol, 1 eq), 3-[4-(4-piperidyl)phenoxy]piperidine-2,6-dione hydrochloride (32.8 mg, 0.100 mmol, 1.5 eq) and DIPEA (26.08 mg, 0.200 mmol, 3 eq) in DMF (2 mL) was added PyBOP (52.51 mg, 0.100 mmol, 1.5 eq). The reaction mixture was stirred at 25° C. for 4 h. The reaction mixture was purified by prep-HPLC to give the title compound (17 mg, 0.020 mmol, 26.61% yield) as yellow solid. MS m/e: 899.5 ([M+H+]$^+$)

Example A 103

5-[2-[4-[2-[4-[4-[[(3R)-2,6-Dioxopiperidin-3-yl]amino]phenyl]piperidin-1-yl]acetyl]piperazin-1-yl]pyrimidin-5-yl]-3-[3-[[ethyl(methyl)sulfamoyl]amino]-2,6-difluorobenzoyl]-1H-pyrrolo[2,3-b]pyridine Chiral

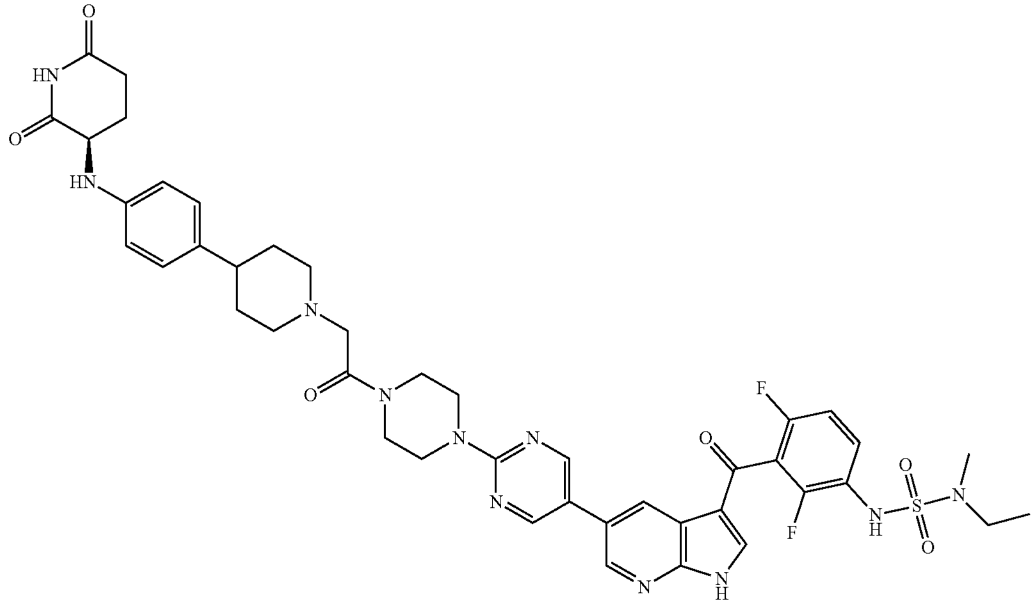

The title compound was obtained as light green solid in 54% yield with a purity of 93% according to general procedure VIII.

Amine: 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine Acid: (R)-2-(4-(4-((2,6-dioxopiperidin-3-yl)amino)phenyl)piperidin-1-yl)acetic acid compound with 2,2,2-trifluoroacetic acid. The stereo center configuration of CRBN is arbitrarily assigned as the (R)—first eluting isomer MS m/e: 884.6 ([M+H+]$^+$). [α]D=−14.933° (c=1.000, MeOH, 20° C.)

Example A 104

5-[6-[4-[2-[4-[4-(2,4-Dioxo-1,3-diazinan-1-yl)phenyl]piperidin-1-yl]acetyl]piperazin-1-yl]pyridin-3-yl]-3-[3-[[ethyl(methyl)sulfamoyl]amino]-2,6-difluorobenzoyl]-1H-pyrrolo[2,3-b]pyridine

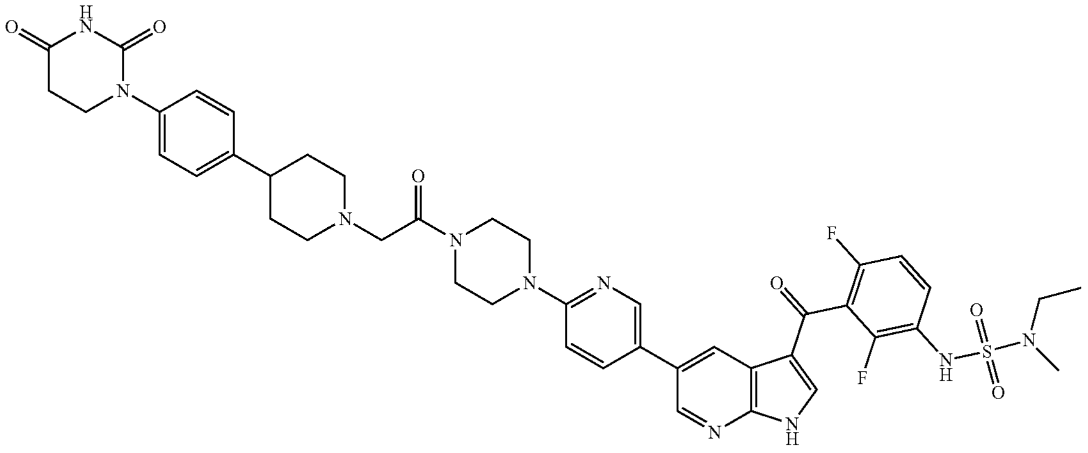 [SMILES: CCN(C)S(=O)(=O)Nc1ccc(F)c(C(=O)c2c[nH]c3ncc(-c4ccc(N5CCN(C(=O)CN6CCC(c7ccc(N8CCC(=O)NC8=O)cc7)CC6)CC5)nc4)cc23)c1F]

The title compound was obtained as light yellow solid in 93% yield according to general procedure VIII.

Amine: 3-[3-[[ethyl(methyl)sulfamoyl]amino]-2,6-difluoro-benzoyl]-5-(6-piperazin-1-yl-3-pyridyl)-1H-pyrrolo[2,3-b]pyridine Acid: 2-(4-(4-(2,4-dioxotetrahydropyrimidin-1(2H)-yl)phenyl)piperidin-1-yl)acetic acid hydrochloride MS m/e: 869.5 ([M+H+]$^+$)

Example A 105

N-[3-[1-[5-[3-[2,6-Difluoro-3-(pyrrolidin-1-ylsulfonylamino)benzoyl]-1H-pyrrolo[2,3-b]pyridin-5-yl]pyridin-2-yl]piperidin-4-yl]oxycyclobutyl]-2-[4-[(2,6-dioxopiperidin-3-yl)amino]phenyl]acetamide

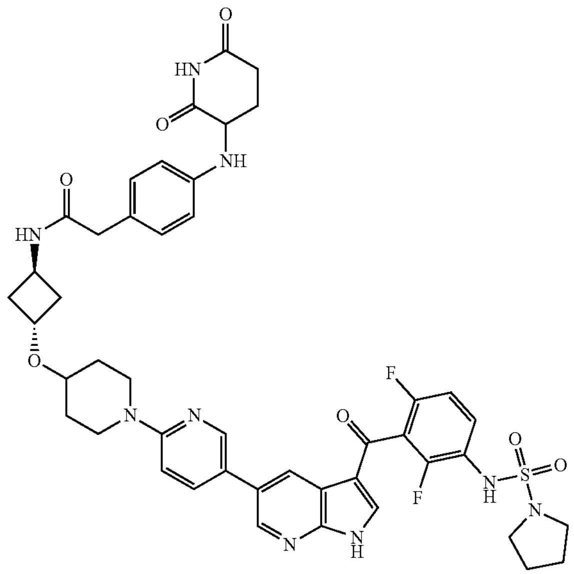 [SMILES: O=C1CCC(Nc2ccc(CC(=O)N[C@H]3C[C@H](OC4CCN(c5ccc(-c6cnc7[nH]cc(C(=O)c8c(F)ccc(NS(=O)(=O)N9CCCC9)c8F)c7c6)cn5)CC4)C3)cc2)C(=O)N1]

The title compound was obtained as white powder in 11% yield according to general procedure VIII.

Amine: N-[3-[5-[6-[4-(3-Aminocyclobutoxy)-1-piperidyl]-3-pyridyl]-1H-pyrrolo[2,3-b]pyridine-3-carbonyl]-2,4-difluoro-phenyl]pyrrolidine-1-sulfonamide;2,2,2-trifluoroacetic acid Acid: 2-[4-[(2,6-dioxo-3-piperidyl)amino]phenyl]acetic acid MS m/e: 896.3 ([M+H+]$^+$)

Example A 106

5-[6-[4-[[2-[4-[5-(2,6-Dioxopiperidin-3-yl)oxypyridin-2-yl]piperidin-1-yl]-2-oxoethyl]amino]piperidin-1-yl]pyridin-3-yl]-3-[3-[[ethyl(methyl)sulfamoyl]amino]-2,6-difluorobenzoyl]-1H-pyrrolo[2,3-b]pyridine;formic acid

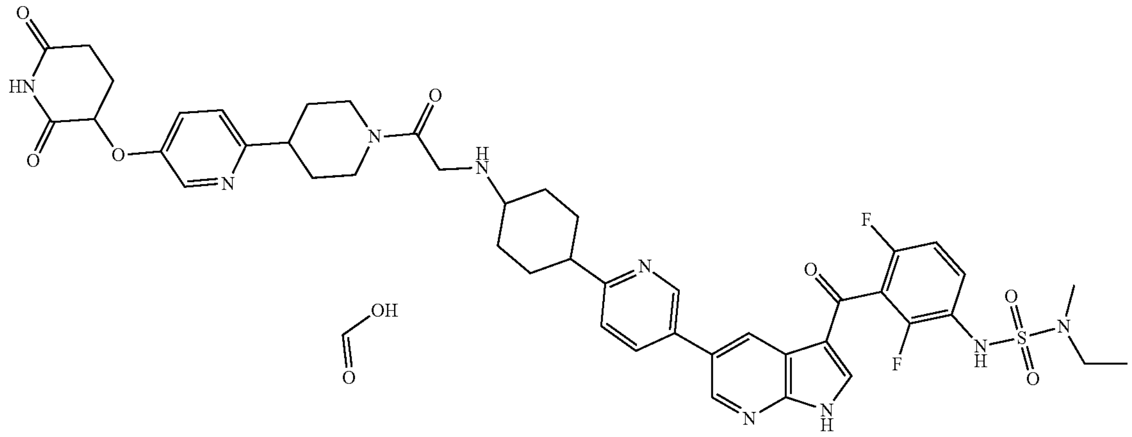 [SMILES: CCN(C)S(=O)(=O)Nc1ccc(F)c(C(=O)c2c[nH]c3ncc(-c4ccc(C5CCC(NCC(=O)N6CCC(c7ccc(OC8CCC(=O)NC8=O)cn7)CC6)CC5)nc4)cc23)c1F ; O=CO]

A solution of 2-[[1-[5-[3-[3-[[ethyl(methyl)sulfamoyl]amino]-2,6-difluoro-benzoyl]-1H-pyrrolo[2,3-b]pyridin-5-yl]-2-pyridyl]-4-piperidyl]amino]acetic acid (22.0 mg, 0.030 mmol, 1 eq) and 3-[[6-(4-piperidyl)-3-pyridyl]oxy]piperidine-2,6-dione (15.96 mg, 0.050 mmol, 1.5 eq) in DMF (2 mL) was added PyBOP (18.68 mg, 0.040 mmol, 1.1 eq) and DIPEA (12.65 mg, 0.100 mmol, 3 eq), the mixture was stirred at 25° C. for 16 h. The mixture was concentrated and purified by prep-HPLC to give the title compound (20.1 mg, 0.020 mmol, 68.47% yield) as a yellow solid. MS: MS m/e: 899.5 ([M+H+]$^+$).

Example A 107

N-[3-[5-[6-[4-[3-[4-[4-[(2,6-Dioxopiperidin-3-yl)amino]phenyl]piperidin-1-yl]cyclobutanecarbonyl]piperazin-1-yl]pyridin-3-yl]-1H-pyrrolo[2,3-b]pyridine-3-carbonyl]-2,4-difluorophenyl]propane-2-sulfonamide

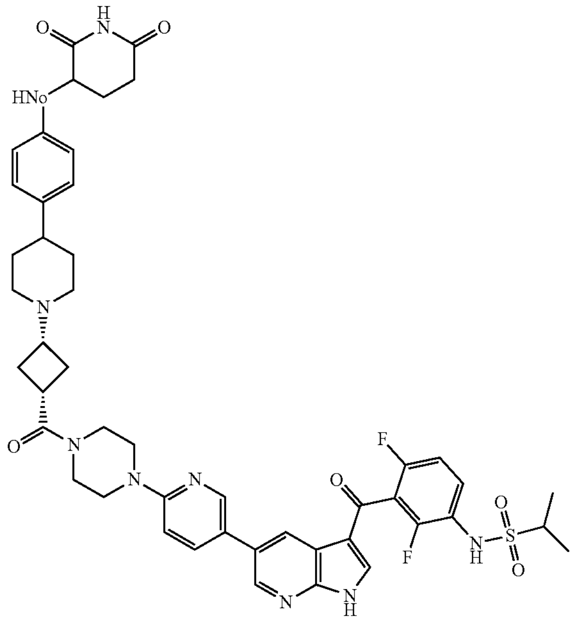

The title compound was obtained as light green solid in 73% yield according to general procedure VIII.

Amine: N-[2,4-difluoro-3-[5-(6-piperazin-1-yl-3-pyridyl)-1H-pyrrolo[2,3-b]pyridine-3-carbonyl]phenyl]propane-2-sulfonamide Acid: cis-3-[4-[4-[(2,6-dioxo-3-piperidyl)amino]phenyl]-1-piperidyl]cyclobutanecarboxylic acid hydrochloride MS m/e: 909.1 ([M+H+]$^+$)

Example A 108

N-[3-[5-[6-[4-[2-[4-[4-(2,4-Dioxo-1,3-diazinan-1-yl)phenyl]piperidin-1-yl]acetyl]piperazin-1-yl]pyridin-3-yl]-1H-pyrrolo[2,3-b]pyridine-3-carbonyl]-2,4-difluorophenyl]propane-2-sulfonamide

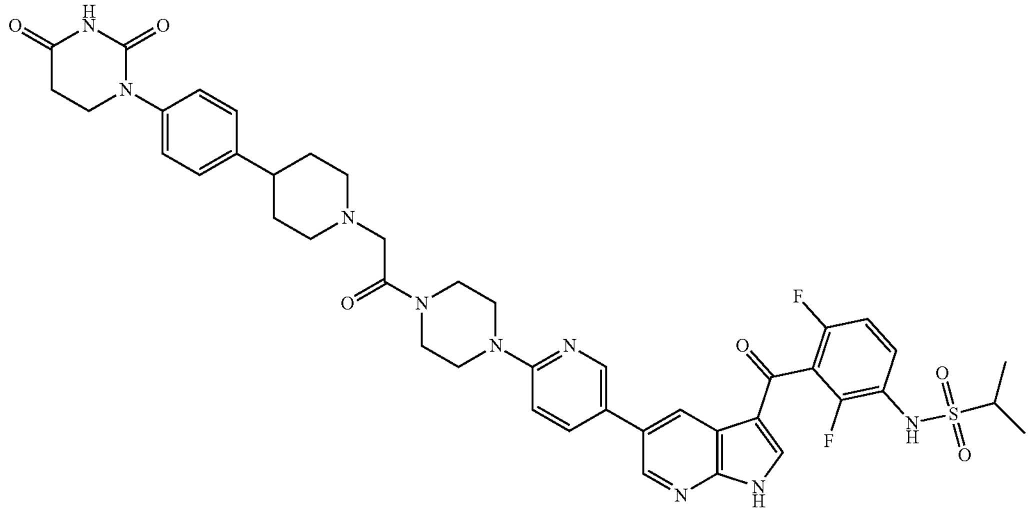 [SMILES: CC(C)S(=O)(=O)Nc1ccc(F)c(C(=O)c2c[nH]c3ncc(-c4ccc(N5CCN(C(=O)CN6CCC(c7ccc(N8CCC(=O)NC8=O)cc7)CC6)CC5)nc4)cc23)c1F]

The title compound was obtained as light yellow solid in 39% yield according to general procedure VIII.

Amine: N-[2,4-difluoro-3-[5-(6-piperazin-1-yl-3-pyridyl)-1H-pyrrolo[2,3-b]pyridine-3-carbonyl]phenyl]propane-2-sulfonamide Acid: 2-[4-[4-(2,4-dioxohexahydropyrimidin-1-yl)phenyl]-1-piperidyl]acetic acid hydrochloride MS m/e: 854.5 ([M+H+]$^+$)

Example A 109

5-[6-[4-[[2-[4-[4-(2,6-Dioxopiperidin-3-yl)oxyphenyl]piperidin-1-yl]-2-oxoethyl]amino]piperidin-1-yl]pyridin-3-yl]-3-[3-[[ethyl(methyl)sulfamoyl]amino]-2,6-difluorobenzoyl]-1H-pyrrolo[2,3-b]pyridine; formic acid

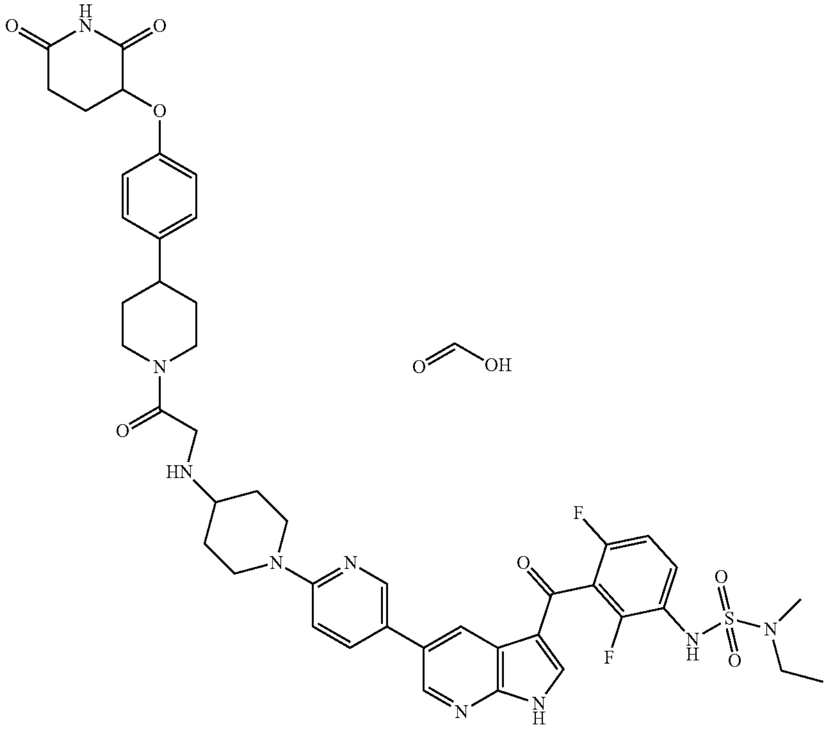 [SMILES: CCN(C)S(=O)(=O)Nc1ccc(F)c(C(=O)c2c[nH]c3ncc(-c4ccc(N5CCC(NCC(=O)N6CCC(c7ccc(OC8CCC(=O)NC8=O)cc7)CC6)CC5)nc4)cc23)c1F ; O=CO]

To a solution of 2-[[1-[5-[3-[3-[[ethyl(methyl)sulfamoyl]amino]-2,6-difluoro-benzoyl]-1H-pyrrolo[2,3-b]pyridin-5-yl]-2-pyridyl]-4-piperidyl]amino]acetic acid (50.0 mg, 0.070 mmol, 1 eq) and 3-[4-(4-piperidyl)phenoxy]piperidine-2,6-dione (21.9 mg, 0.070 mmol, 1 eq) in DMF (2 mL) was added PyBOP (35.06 mg, 0.070 mmol, 1 eq) and DIPEA (26.12 mg, 0.200 mmol, 3 eq), the mixture was stirred at 25° C. for 16 h. The mixture was purified by prep-HPLC to give the title compound (14.5 mg, 0.020 mmol, 23.95% yield) as an off-white solid. MS m/e: 898.5 ([M+H+]$^+$)

Example A 110

5-[6-[4-[[2-[4-[4-[(2,6-Dioxopiperidin-3-yl)amino]phenyl]piperidin-1-yl]-2-oxoethyl]amino]piperidin-1-yl]pyridin-3-yl]-3-[3-[[ethyl(methyl)sulfamoyl]amino]-2,6-difluorobenzoyl]-1H-pyrrolo[2,3-b]pyridine;formic acid

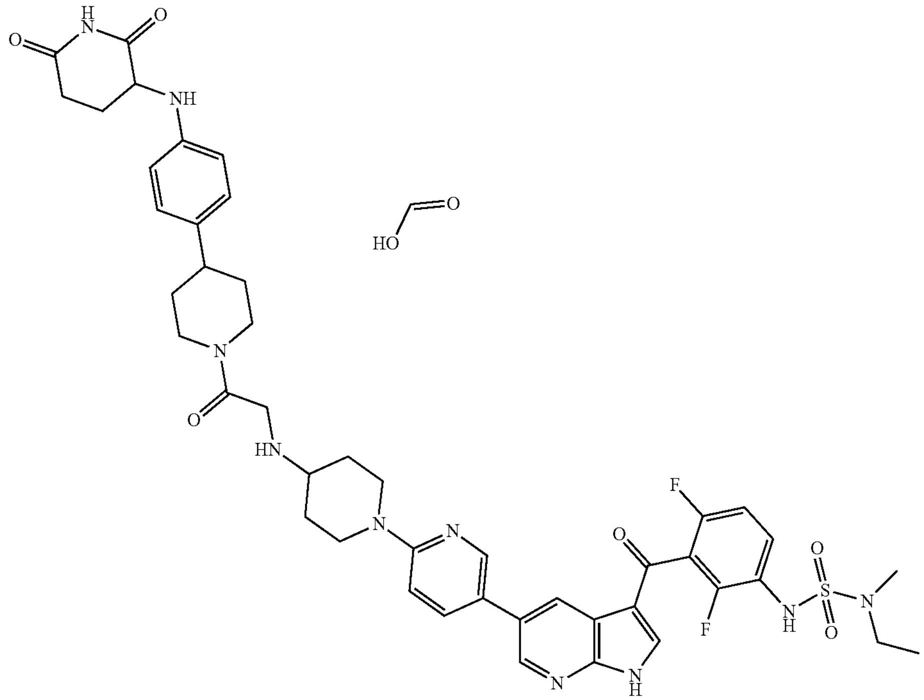 [SMILES: CCN(C)S(=O)(=O)Nc1ccc(F)c(C(=O)c2c[nH]c3ncc(-c4ccc(N5CCC(NCC(=O)N6CCC(c7ccc(NC8CCC(=O)NC8=O)cc7)CC6)CC5)nc4)cc23)c1F ; O=CO]

To a solution of 2-[[1-[5-[3-[3-[[ethyl(methyl)sulfamoyl]amino]-2,6-difluoro-benzoyl]-1H-pyrrolo[2,3-b]pyridin-5-yl]-2-pyridyl]-4-piperidyl]amino]acetic acid (50.0 mg, 0.070 mmol, eq) and 3-[4-(4-piperidyl)anilino]piperidine-2,6-dione (21.83 mg, 0.070 mmol, 1 eq) in DMF (2 mL) was added PyBOP (35.06 mg, 0.070 mmol, 1 eq) and DIPEA (26.12 mg, 0.200 mmol, 3 eq), the mixture was stirred at 25° C. for 2 h. The mixture was purified by prep-HPLC to give the title compound (18.8 mg, 0.020 mmol, 30.39% yield) as an yellow solid. MS m/e: 897.4 ([M+H+]$^+$)

Example A 111

5-[2-[4-[2-[4-[4-[[(3S)-2,6-Dioxopiperidin-3-yl] amino]phenyl]piperidin-1-yl]acetyl]piperazin-1-yl] pyrimidin-5-yl]-3-[3-[[ethyl(methyl)sulfamoyl] amino]-2,6-difluorobenzoyl]-1H-pyrrolo[2,3-b] pyridine

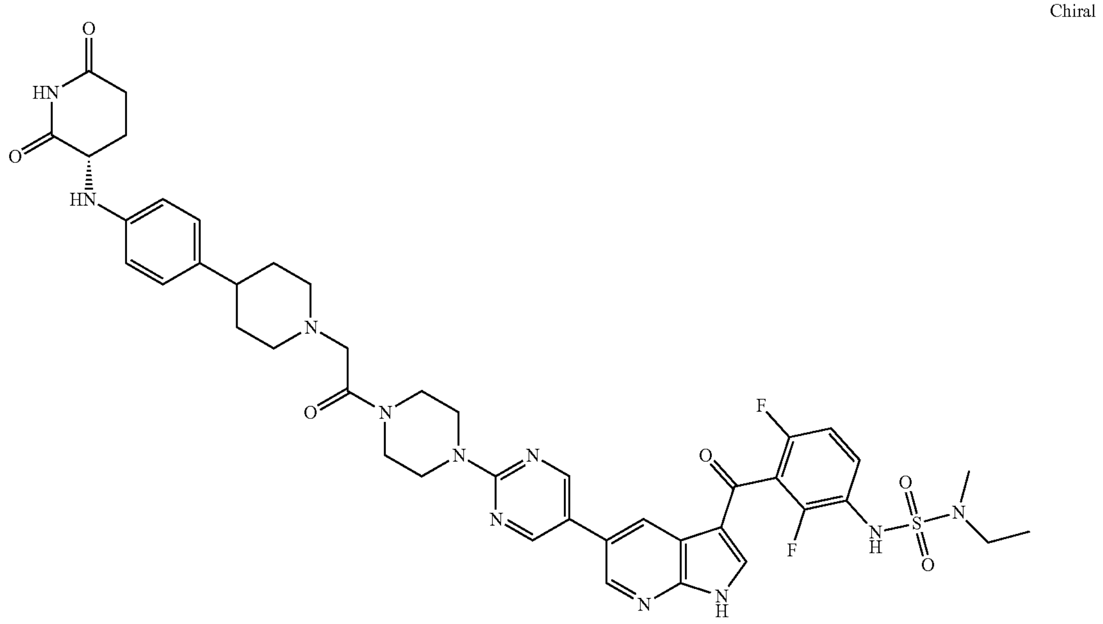 [SMILES: CCN(C)S(=O)(=O)Nc1ccc(F)c(C(=O)c2c[nH]c3ncc(-c4cnc(N5CCN(C(=O)CN6CCC(c7ccc(N[C@H]8CCC(=O)NC8=O)cc7)CC6)CC5)nc4)cc23)c1F]

The title compound was obtained as light green solid in 44% yield according to general procedure VIII.

Amine: 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine Acid: (S)-2-(4-(4-((2,6-dioxopiperidin-3-yl)amino)phenyl)piperidin-1-yl)acetic acid compound with 2,2,2-trifluoroacetic acid. The stereo center configuration of CRBN is arbitrarily assigned as the (S)—second eluting isomer MS m/e: 884.6 ([M+H+]$^+$). [α]D=+19.239 (c=1.000, MeOH, 20.1° C.)

Example A 112

5-[2-[4-[2-[4-[4-[(2,6-Dioxopiperidin-3-yl)amino] phenyl]piperidin-1-yl]-2-oxoethyl]piperidin-1-yl] pyrimidin-5-yl]-3-[3-[[ethyl(methyl)sulfamoyl] amino]-2,6-difluorobenzoyl]-1H-pyrrolo[2,3-b] pyridine

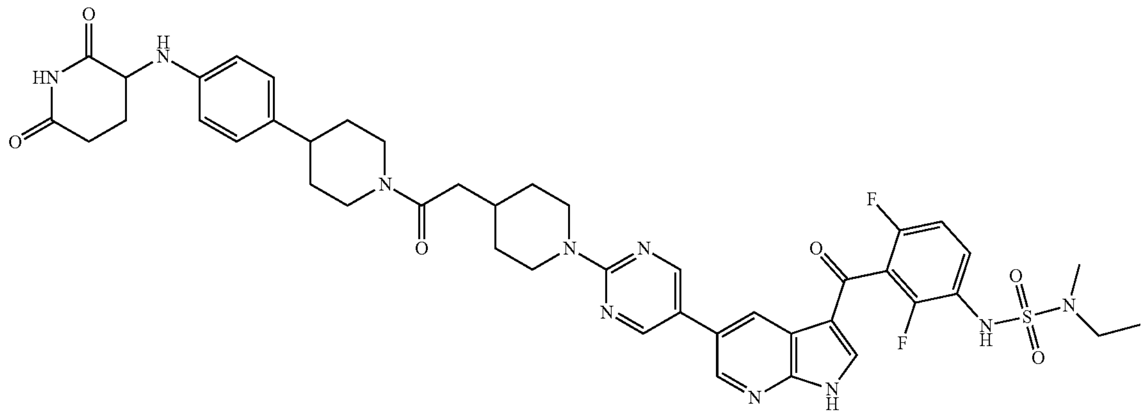 [SMILES: CCN(C)S(=O)(=O)Nc1ccc(F)c(C(=O)c2c[nH]c3ncc(-c4cnc(N5CCC(CC(=O)N6CCC(c7ccc(NC8CCC(=O)NC8=O)cc7)CC6)CC5)nc4)cc23)c1F]

The title compound was obtained as light yellow solid in 71% yield according to general procedure VIII.

Amine: 3-((4-(piperidin-4-yl)phenyl)amino)piperidine-2,6-dione hydrochloride

Acid: 2-(1-(5-(3-(3-((N-ethyl-N-methylsulfamoyl)amino)-2,6-difluorobenzoyl)-1H-pyrrolo[2,3-b]pyridin-5-yl)pyrimidin-2-yl)piperidin-4-yl)acetic acid MS m/e: 883.6 ([M+H+]$^+$).

Example A 113

5-[2-[4-[2-[4-[4-(2,4-Dioxo-1,3-diazinan-1-yl)phenyl]piperidin-1-yl]-2-oxoethyl]piperidin-1-yl]pyrimidin-5-yl]-3-[3-[[ethyl(methyl)sulfamoyl]amino]-2,6-difluorobenzoyl]-1H-pyrrolo[2,3-b]pyridine

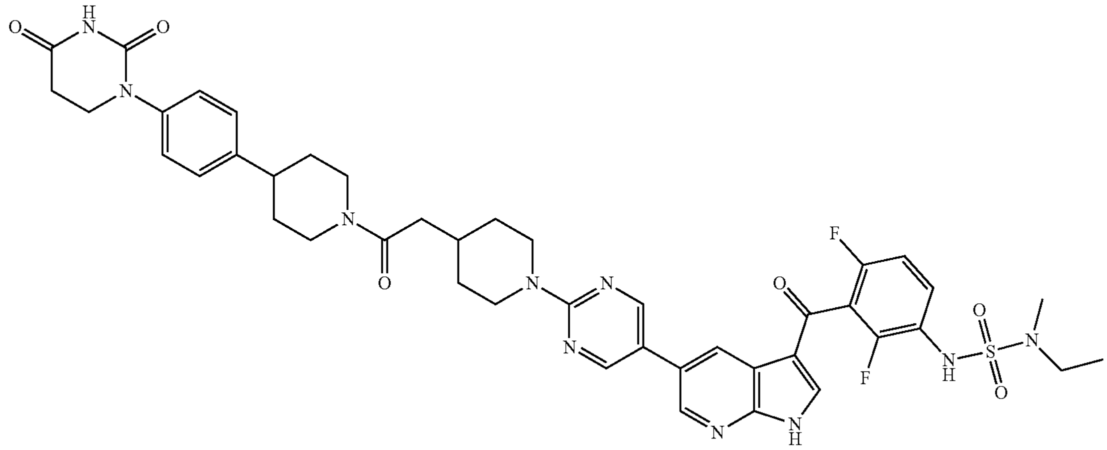 [SMILES: CCN(C)S(=O)(=O)Nc1ccc(F)c(C(=O)c2c[nH]c3ncc(-c4cnc(N5CCC(CC(=O)N6CCC(c7ccc(N8CCC(=O)NC8=O)cc7)CC6)CC5)nc4)cc23)c1F]

The title compound was obtained as yellow solid in 99% yield according to general procedure VIII.

Amine: 1-[4-(4-piperidyl)phenyl]hexahydropyrimidine-2,4-dione hydrochloride

Acid: 2-(1-(5-(3-(3-((N-ethyl-N-methylsulfamoyl)amino)-2,6-difluorobenzoyl)-1H-pyrrolo[2,3-b]pyridin-5-yl)pyrimidin-2-yl)piperidin-4-yl)acetic acid MS m/e: 869.5 ([M+H+]$^+$).

Example A 114

3-[2-Bromo-3-[[ethyl(methyl)sulfamoyl]amino]benzoyl]-5-[6-[4-[2-[4-[4-[(2,6-dioxopiperidin-3-yl)amino]phenyl]piperidin-1-yl]acetyl]piperazin-1-yl]pyridin-3-yl]-1H-pyrrolo[2,3-b]pyridine

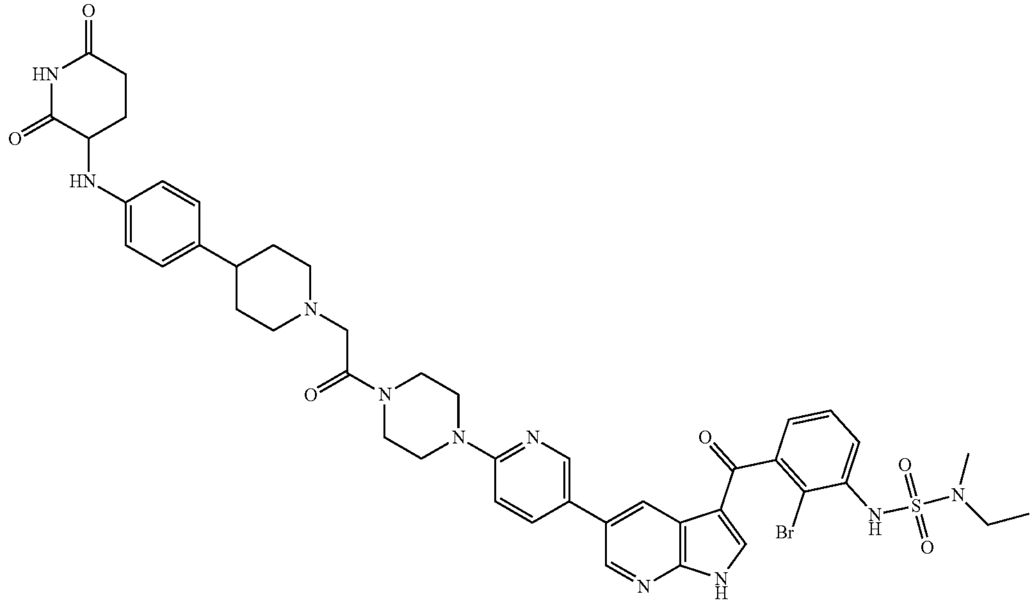 [SMILES: CCN(C)S(=O)(=O)Nc1cccc(C(=O)c2c[nH]c3ncc(-c4ccc(N5CCN(C(=O)CN6CCC(c7ccc(NC8CCC(=O)NC8=O)cc7)CC6)CC5)nc4)cc23)c1Br]

The title compound was obtained as off-white solid in 85% yield with a purity of 95% according to general procedure VIII.

Amine: 3-[2-bromo-3-[[ethyl(methyl)sulfamoyl]amino]benzoyl]-5-(6-piperazin-1-yl-3-pyridyl)-1H-pyrrolo[2,3-b]pyridine Acid: 2-[4-[4-[(2,6-dioxo-3-piperidyl)amino]phenyl]-1-piperidyl]acetic acid hydrochloride MS m/e: 464 ($[M+2H+]^{2+}$).

Example A 115

(3R)—N-[3-[5-[6-[2-[2-[4-[4-(2,6-dioxopiperidin-3-yl)oxyphenyl]piperidin-1-yl]acetyl]-2,6-diazaspiro[3.3]heptan-6-yl]pyridin-3-yl]-1H-pyrrolo[2,3-b]pyridine-3-carbonyl]-2,4-difluorophenyl]-3-fluoropyrrolidine-1-sulfonamide

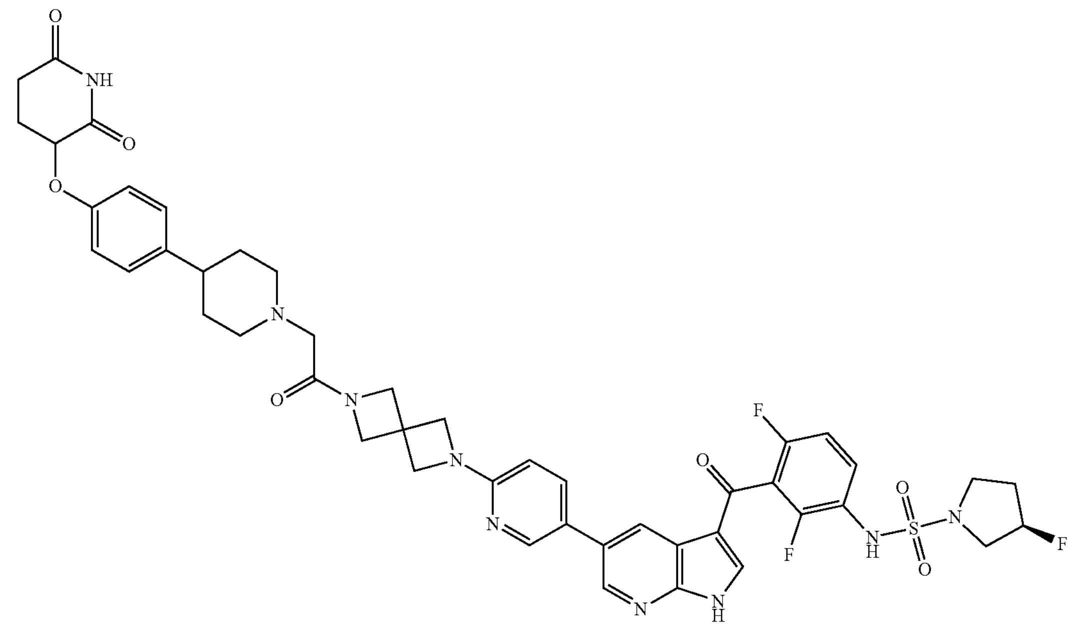 [SMILES: O=C1CCC(Oc2ccc(C3CCN(CC(=O)N4CC5(C4)CN(c4ccc(-c6cnc7[nH]cc(C(=O)c8c(F)ccc(NS(=O)(=O)N9CC[C@@H](F)C9)c8F)c7c6)cn4)C5)CC3)cc2)C(=O)N1]

The title compound was obtained as white solid in 27% yield according to general procedure VIII.

Amine: (3R)—N-[3-[5-[6-(2,6-diazaspiro[3.3]heptan-2-yl)-3-pyridyl]-1H-pyrrolo[2,3-b]pyridine-3-carbonyl]-2,4-difluoro-phenyl]-3-fluoro-pyrrolidine-1-sulfonamide;2,2,2-trifluoroacetic acid Acid: 2-[4-[4-[(2,6-dioxo-3-piperidyl)oxy]phenyl]-1-piperidyl]acetic acid hydrochloride MS m/e: 464 ($[M+2H+]^{2+}$).

Example A 116

N-[3-[5-[4-[2-[2-[4-[4-(2,6-Dioxopiperidin-3-yl)oxyphenyl]piperidin-1-yl]acetyl]-2,6-diazaspiro[3.3]heptan-6-yl]phenyl]-1H-pyrrolo[2,3-b]pyridine-3-carbonyl]-2,4-difluorophenyl]pyrrolidine-1-sulfonamide

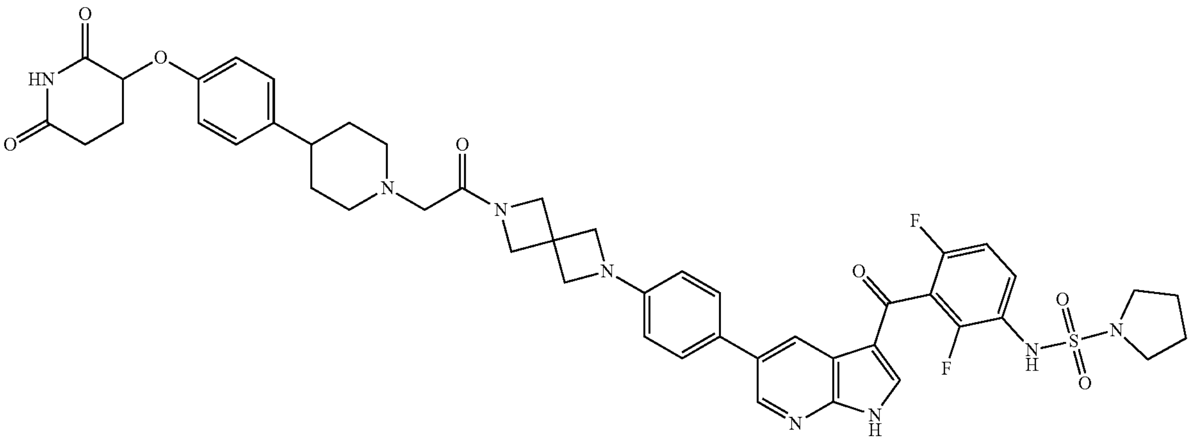

The title compound was obtained as white solid in 5% yield with a purity of 84% according to general procedure VIII.

Amine: N-(3-(5-(4-(2,6-diazaspiro[3.3]heptan-2-yl)phenyl)-1H-pyrrolo[2,3-b]pyridine-3-carbonyl)-2,4-difluorophenyl)pyrrolidine-1-sulfonamide 2,2,2-trifluoroacetate Acid: 2-(4-(4-((2,6-dioxopiperidin-3-yl)oxy)phenyl)piperidin-1-yl)acetic acid hydrochloride MS m/e: 907.3 ([M+H+]$^+$).

Example A 117

N-[3-[5-[4-[2-[2-[4-[4-[(2,4-Dioxo-3-azabicyclo[3.1.1]heptan-1-yl)amino]phenyl]piperidin-1-yl]acetyl]-2,6-diazaspiro[3.3]heptan-6-yl]phenyl]-1H-pyrrolo[2,3-b]pyridine-3-carbonyl]-2,4-difluorophenyl]pyrrolidine-1-sulfonamide

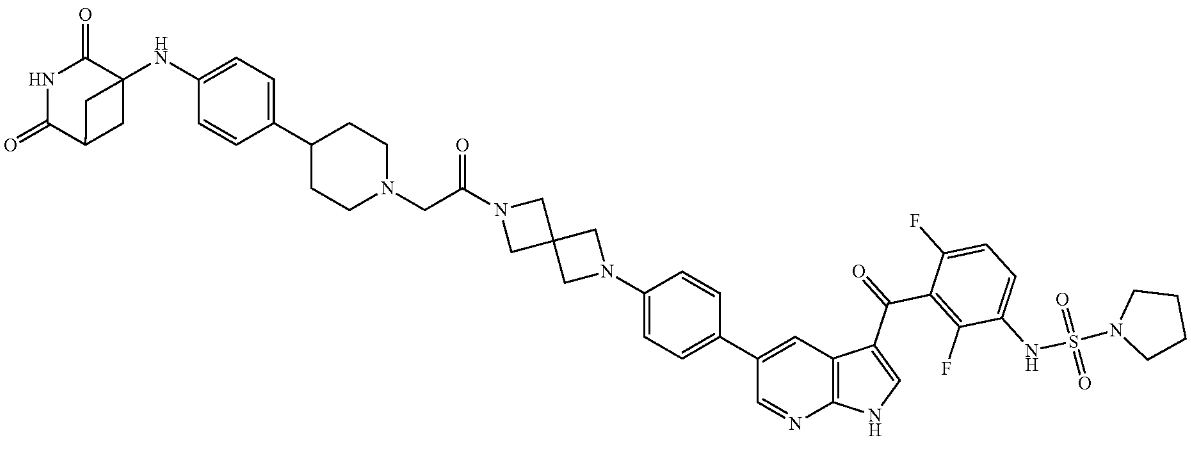 [SMILES: O=C(c1c(F)ccc(NS(=O)(=O)N2CCCC2)c1F)c1c[nH]c2ncc(-c3ccc(N4CC5(CN(C(=O)CN6CCC(c7ccc(NC89CC(C8)C(=O)NC9=O)cc7)CC6)C5)C4)cc3)cc12]

The title compound was obtained as white solid in 11% yield according to general procedure VIII.

Amine: N-(3-(5-(4-(2,6-diazaspiro[3.3]heptan-2-yl)phenyl)-1H-pyrrolo[2,3-b]pyridine-3-carbonyl)-2,4-difluorophenyl)pyrrolidine-1-sulfonamide Acid: 2-(4-(4-((2,4-dioxo-3-azabicyclo[3.1.1]heptan-1-yl)amino)phenyl)piperidin-1-yl)acetic acid hydrochloride MS m/e: 460 ([M+2H+]$^{2+}$).

Example A 118

N-[3-[5-[2-[2-[2-[4-[4-(2,6-Dioxopiperidin-3-yl)phenyl]piperidin-1-yl]acetyl]-2,6-diazaspiro[3.3]heptan-6-yl]pyrimidin-5-yl]-1H-pyrrolo[2,3-b]pyridine-3-carbonyl]-2,4-difluorophenyl]pyrrolidine-1-sulfonamide

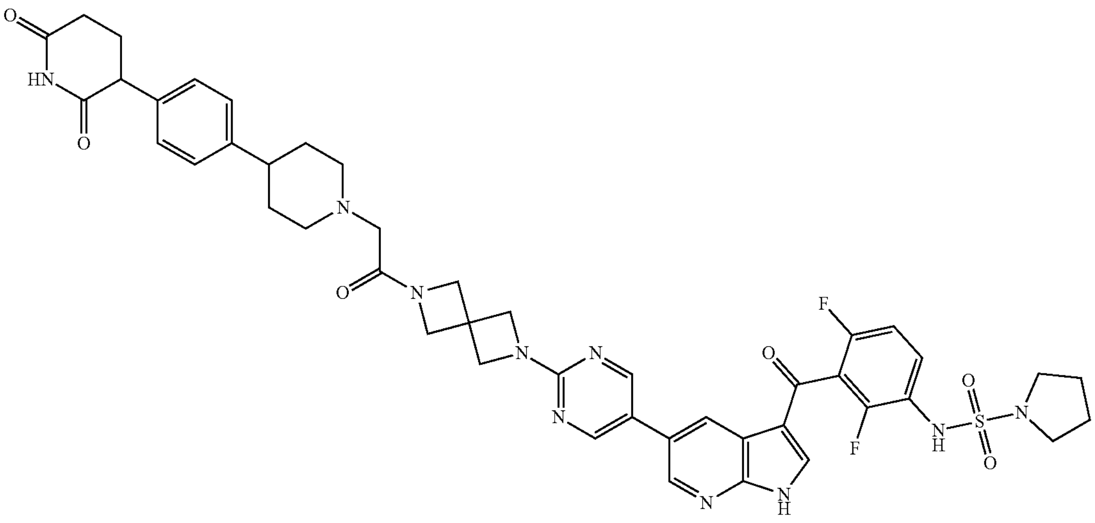 [SMILES: O=C1CCC(c2ccc(C3CCN(CC(=O)N4CC5(C4)CN(c4ncc(-c6cnc7[nH]cc(C(=O)c8c(F)ccc(NS(=O)(=O)N9CCCC9)c8F)c7c6)cn4)C5)CC3)cc2)C(=O)N1]

The title compound was obtained as white solid in 31% yield with a purity of 88% according to general procedure VIII.

Amine: N-(3-(5-(2-(2,6-diazaspiro[3.3]heptan-2-yl)pyrimidin-5-yl)-1H-pyrrolo[2,3-b]pyridine-3-carbonyl)-2,4-difluorophenyl)pyrrolidine-1-sulfonamide 2,2,2-trifluoroacetate Acid: 2-(4-(4-(2,6-dioxopiperidin-3-yl)phenyl)piperidin-1-yl)acetic acid hydrochloride MS m/e: 891.5 ([M+H+]$^{+}$).

Example A 119

N-[3-[5-[2-[2-[2-[4-[4-(2,6-Dioxopiperidin-3-yl)oxyphenyl]piperidin-1-yl]acetyl]-2,6-diazaspiro[3.3]heptan-6-yl]pyrimidin-5-yl]-1H-pyrrolo[2,3-b]pyridine-3-carbonyl]-2,4-difluorophenyl]pyrrolidine-1-sulfonamide

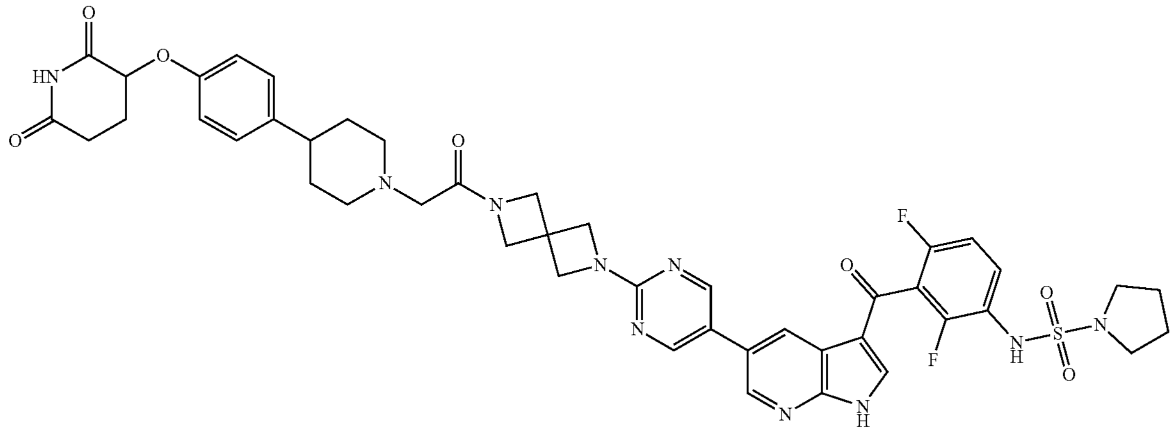 [SMILES: O=C1CCC(Oc2ccc(C3CCN(CC(=O)N4CC5(C4)CN(c4ncc(-c6cnc7[nH]cc(C(=O)c8c(F)ccc(NS(=O)(=O)N9CCCC9)c8F)c7c6)cn4)C5)CC3)cc2)C(=O)N1]

The title compound was obtained as white solid in 37% yield according to general procedure VIII.

Amine: N-(3-(5-(2-(2,6-diazaspiro[3.3]heptan-2-yl)pyrimidin-5-yl)-1H-pyrrolo[2,3-b]pyridine-3-carbonyl)-2,4-difluorophenyl)pyrrolidine-1-sulfonamide 2,2,2-trifluoroacetate Acid: 2-(4-(4-((2,6-dioxopiperidin-3-yl)oxy)phenyl)piperidin-1-yl)acetic acid hydrochloride MS m/e: 455.5 ($[M+2H+]^{2+}$).

Example A 120

N-[3-[5-[2-[2-[2-[4-[4-[(2,6-Dioxopiperidin-3-yl)amino]phenyl]piperidin-1-yl]acetyl]-2,6-diazaspiro[3.3]heptan-6-yl]pyrimidin-5-yl]-1H-pyrrolo[2,3-b]pyridine-3-carbonyl]-2,4-difluorophenyl]pyrrolidine-1-sulfonamide

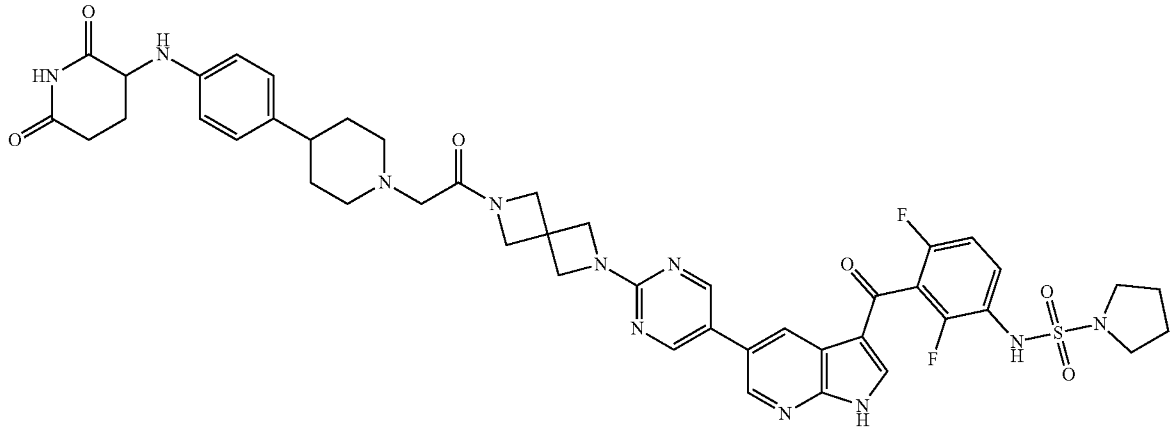 [SMILES: O=C1CCC(Nc2ccc(C3CCN(CC(=O)N4CC5(C4)CN(c4ncc(-c6cnc7[nH]cc(C(=O)c8c(F)ccc(NS(=O)(=O)N9CCCC9)c8F)c7c6)cn4)C5)CC3)cc2)C(=O)N1]

The title compound was obtained as white solid in 2% yield with a purity of 85% according to general procedure VIII.

Amine: N-(3-(5-(2-(2,6-diazaspiro[3.3]heptan-2-yl)pyrimidin-5-yl)-1H-pyrrolo[2,3-b]pyridine-3-carbonyl)-2,4-difluorophenyl)pyrrolidine-1-sulfonamide 2,2,2-trifluoroacetate Acid: 2-(4-(4-((2,6-dioxopiperidin-3-yl)amino)phenyl)piperidin-1-yl)acetic acid hydrochloride MS m/e: 455 ($[M+2H+]^{2+}$).

Example A 121

5-[6-[4-[2-[4-[4-[(3S)-2,6-Dioxopiperidin-3-yl]oxy-phenyl]piperidin-1-yl]acetyl]piperazin-1-yl]pyridin-3-yl]-3-[3-[[ethyl(methyl)sulfamoyl]amino]-2,6-difluorobenzoyl]-1H-pyrrolo[2,3-b]pyridine

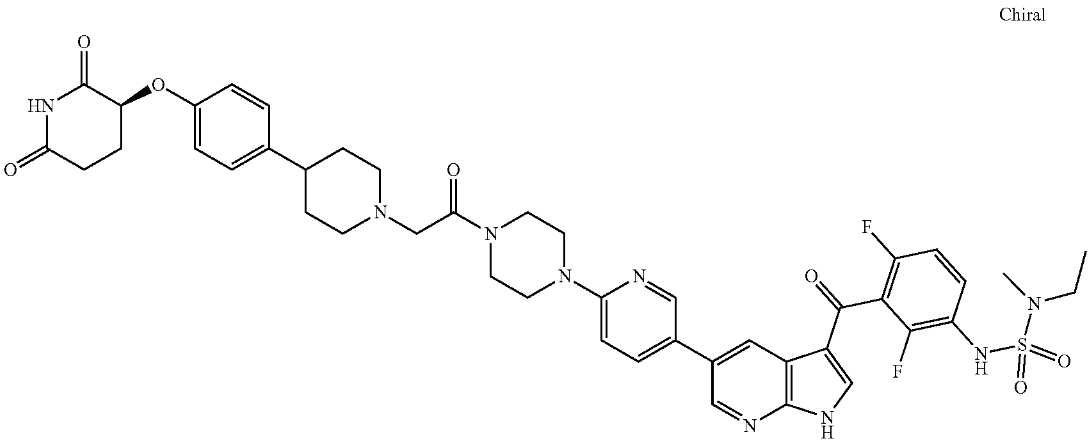 [SMILES: CCN(C)S(=O)(=O)Nc1ccc(F)c(C(=O)c2c[nH]c3ncc(-c4ccc(N5CCN(C(=O)CN6CCC(c7ccc(O[C@H]8CCC(=O)NC8=O)cc7)CC6)CC5)nc4)cc23)c1F]

The title compound was obtained as off white solid with a purity of 94% according to general procedure VIII.

Amine: 3-[3-[[ethyl(methyl)sulfamoyl]amino]-2,6-difluoro-benzoyl]-5-(6-piperazin-1-yl-3-pyridyl)-1H-pyrrolo[2,3-b]pyridine Acid: 2-[4-[4-[[(3S)-2,6-dioxo-3-piperidyl]oxy]phenyl]-1-piperidyl]acetic acid.

MS m/e: 884.4 ([M+H+]$^{2+}$).

Example A 122

5-[6-[4-[2-[4-[4-[(3R)-2,6-Dioxopiperidin-3-yl]oxy-phenyl]piperidin-1-yl]acetyl]piperazin-1-yl]pyridin-3-yl]-3-[3-[[ethyl(methyl)sulfamoyl]amino]-2,6-difluorobenzoyl]-1H-pyrrolo[2,3-b]pyridine

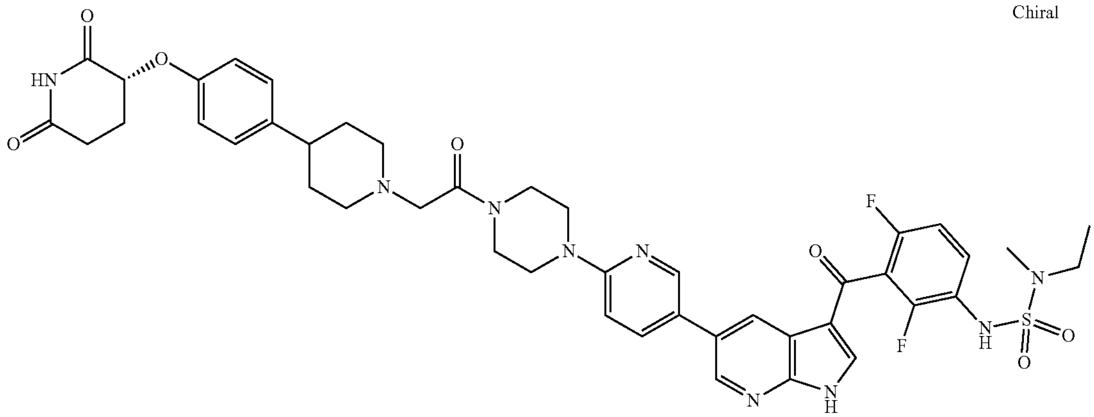 [SMILES: CCN(C)S(=O)(=O)Nc1ccc(F)c(C(=O)c2c[nH]c3ncc(-c4ccc(N5CCN(C(=O)CN6CCC(c7ccc(O[C@@H]8CCC(=O)NC8=O)cc7)CC6)CC5)nc4)cc23)c1F]

The title compound was obtained as off white solid with a purity of 94% according to general procedure VIII.

Amine: 3-[3-[[ethyl(methyl)sulfamoyl]amino]-2,6-difluoro-benzoyl]-5-(6-piperazin-1-yl-3-pyridyl)-1H-pyrrolo[2,3-b]pyridine Acid: 2-[4-[4-[[(3R)-2,6-dioxo-3-piperidyl]oxy]phenyl]-1-piperidyl]acetic acid.

MS m/e: 884.4 ([M+H+]$^{2+}$).

Example A 123

N-[1-[4-[(2,6-Dioxopiperidin-3-yl)amino]-2-fluoro-phenyl]piperidin-4-yl]-4-[5-[3-[3-[[ethyl(methyl) sulfamoyl]amino]-2,6-difluorobenzoyl]-1H-pyrrolo [2,3-b]pyridin-5-yl]pyrimidin-2-yl]piperazine-1-carboxamide; 2,2,2-trifluoroacetic acid

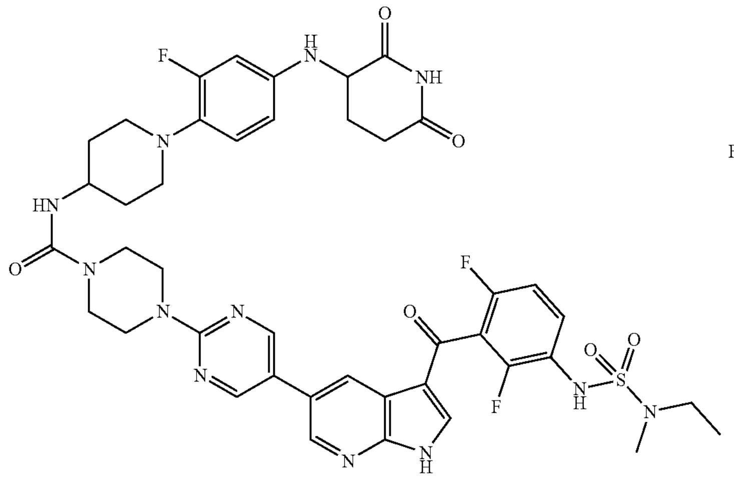

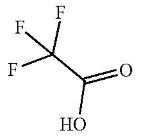

Brought 3-[4-(4-amino-1-piperidyl)-3-fluoro-anilino]piperidine-2,6-dione (21.38 mg, 49.21 umol, 061) up in DCE (431.77 uL) and cooled to 0° C. Added TEA (22.63 mg, 223.68 umol, 31.18 uL) followed by (4-nitrophenyl) carbonochloridate (9.92 mg, 49.21 umol) and let gradually warm to r.t. After 2 hours recooled to 0° C. and added a solution of 3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (30 mg, 44.74 umol, 061) and TEA (22.63 mg, 223.68 umol, 31.18 uL) in NMP (431.77 uL). Let the reaction stir while gradually warming to r.t. O/N. Concentrated off DCE and loaded directly onto a reversed phase isco column for purification (0-100% ACN/water w/TFA) to give the title compound (8 mg, 17%) after lyophilization. MS m/e: 904 ($[M+H]^+$)

Example B 1: Comparitive Efficacy of Encorafenib, Compound 158 and Compound 177 in Mice Female Balb/c nude mice bearing A375 xenograpfts were treated with encorafenib, Compound 158, or Compound 177 as described in the table below and their tumor volume was measured (see FIG. 1).

Study Design

| Group | n | Treatment | Dose (mg/kg) | Dosing Volume (μL/g) | Regimen |
|---|---|---|---|---|---|
| 1 | 6 | Vehicle | — | 10 | p.o., BID × 21 days |
| 2 | 6 | Encorafenib | 6 | 10 | p.o., BID × 27 days |
| 3 | 6 | Compound 177 | 30 | 10 | p.o., BID × 21 days |
| 4 | 6 | Compound 158 | 30 | 10 | p.o., BID × 21 days |

Animals and Housing Condition

Species: Mus Musculus

Strain: Balb/c nude

Age: 6-8 weeks

Sex: Female

Body weight: 18-22 g

Animal supplier: Shanghai Lingchang biological science and technology Co., Ltd.

The mice were kept in individual ventilation 300 mm×180 mm×150 mm polycarbonate cages at constant temperature and humidity with 3 or 4 animals in each cage.

Temperature: 20-26° C.

Humidity: 40-70%.

The mice were provided corn cob bedding which was changed twice per week and free access to irradiated sterilized dry granule food and sterile drinking water.

Innoculation

Each mouse was inoculated subcutaneously at the right flank with A375 tumor cells ($5\times10^6$) in 0.2 mL of PBS supplemented with Matrigel (PBS:Matrigel=1:1) for tumor development. Animals were grouped for the treatment on Day 7 after tumor inoculation when the average tumor volume reached 171 $mm^3$.

Measurements

Prior to the onset of drug treatment, mice were measured for tumor size in two dimensions using a caliper, and the tumor volume ($mm^3$) was calculated using formula $V=0.5\ a\times b^2$ where a and b are the long and short diameters of the tumor in mm, respectively. Mice were randomized into different treatment groups based on the tumor volume. Tumor size was periodically measured during the study.

Example B 2: Comparative Efficacy of Dabrafenib and Compound 89 in Mice

Figure 2:
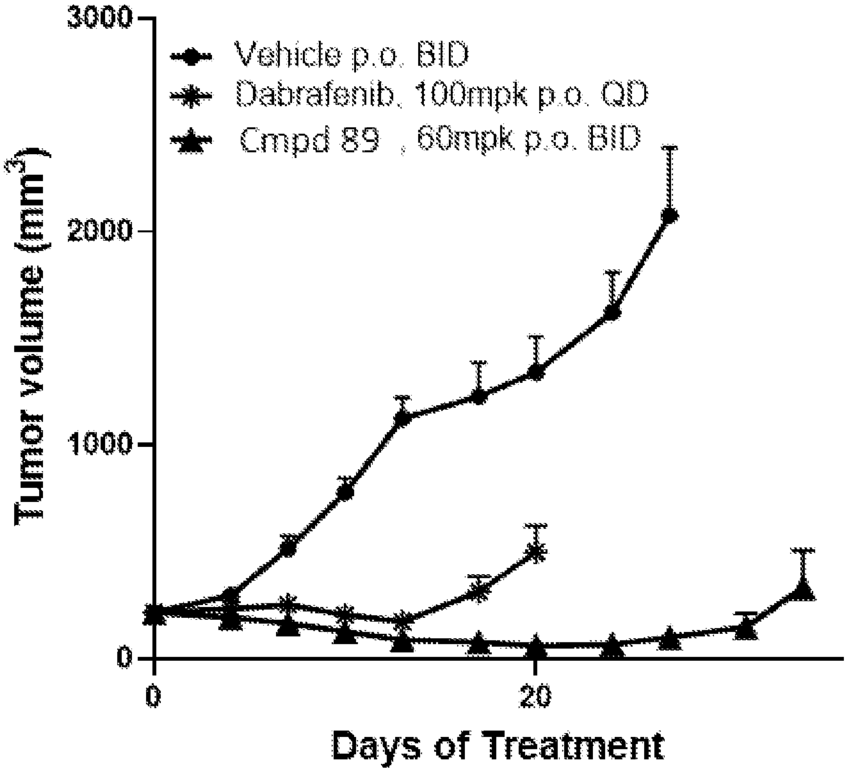
FIG. 2 is a graph comparing tumor volume with no treatment, treatment of 100 mg/kg of dabrafenib p.o. once a day, and treatment of 60 mg/kg of Compound 89 p.o. twice a day. The y-axis is tumor volume measured in $mm^3$ and the x-axis is days of treatment.

Female Balb/c nude mice bearing A375 xenograpfts were treated with dabrafenib or Compound 89 daily for 28 days and their tumor volume was measured (see FIG. 2).

Study Design

| Group | n | Treatment | Dose (mg/kg) | Dosing Volume (μL/g) | Regimen |
|---|---|---|---|---|---|
| 1 | 4 | Vehicle | — | 10 | p.o., BID × 28 days |
| 2 | 4 | Dabrafenib | 100 | 10 | p.o., QD × 28 days |
| 3 | 4 | Compound 89 | 60 | 10 | p.o., BID × 28 days |

Animals and Housing Condition

Species: Mus Musculus

Strain: Balb/c nude

Age: 6-8 weeks

Sex: Female

Body weight: 18-22 g

Animal supplier: Shanghai Lingchang biological science and technology Co., Ltd.

The mice were kept in individual ventilation 300 mm×180 mm×150 mm polycarbonate cages at constant temperature and humidity with 3 or 4 animals in each cage.

Temperature: 20-26° C.

Humidity: 40-70%.

The mice were provided corn cob bedding which was changed twice per week and free access to irradiated sterilized dry granule food and sterile drinking water.

Innoculation

Each mouse was inoculated subcutaneously at the right flank with A375 tumor cells ($5\times10^6$) in 0.2 mL of PBS supplemented with Matrigel (PBS:Matrigel=1:1) for tumor development. Animals were grouped for the treatment on Day 7 after tumor inoculation when the average tumor volume reached 164 $mm^3$.

Measurements

Prior to the onset of drug treatment, mice were measured for tumor size in two dimensions using a caliper, and the tumor volume ($mm^3$) was calculated using formula $V=0.5\ a\times b^2$ where a and b are the long and short diameters of the tumor in mm, respectively. Mice were randomized into different treatment groups based on the tumor volume. Tumor size was periodically measured during the study.

We claim:

1. A compound of Formula I:

(I)

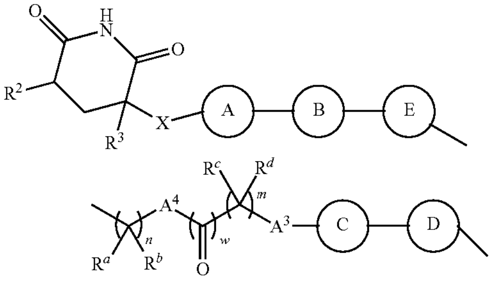

-continued

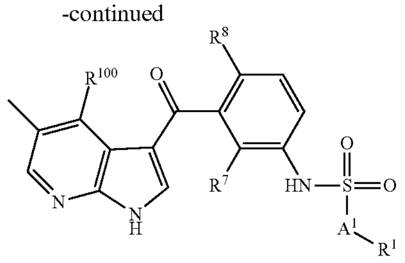

or a pharmaceutically acceptable salt thereof;

wherein $R^2$ and $R^3$ are independently selected from H and $C_{1-6}$-alkyl;

or $R^2$ and $R^3$ together form —$CH_2$—;

X is selected from —$CH_2$—, —$NR^4$—, and —O—;

$R^4$ is selected from H and $C_{1-6}$-alkyl;

A is selected from:

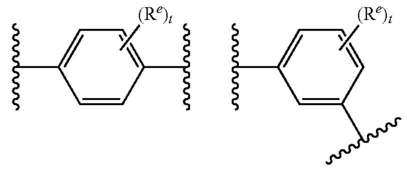

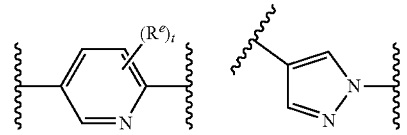

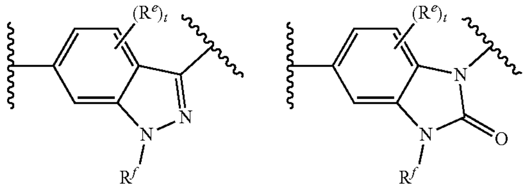

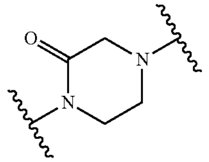

and

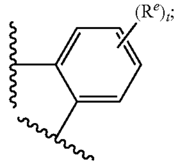

$R^e$ is independently selected from halogen, cyano, and $C_{1-6}$-alkyl;

t is selected from 0, 1, and 2;

$R^f$ is independently selected from H, $C_{3-8}$-cycloalkyl, and $C_{1-6}$-alkyl;

B is absent or selected from:

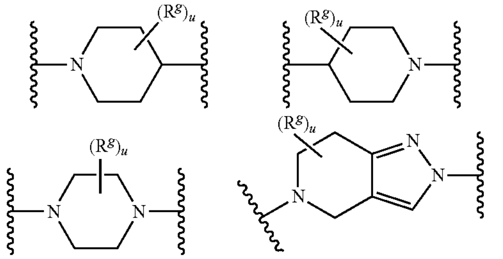

-continued

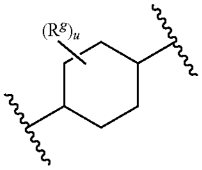 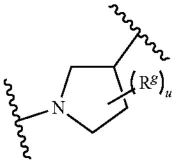

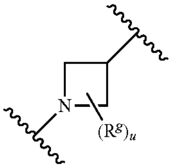 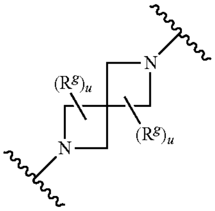

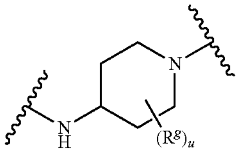 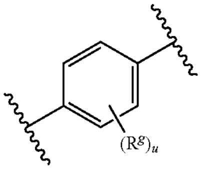

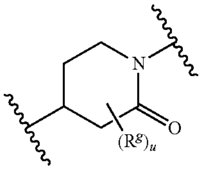 and 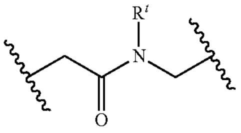 ;

$R^g$ is independently selected from halogen, hydroxy, and $C_{1-6}$-alkyl;

$R^t$ is independently selected from H, $C_{3-8}$-cycloalkyl, and $C_{1-6}$-alkyl;

u is independently selected from 0, 1, and 2;

E is absent or selected from

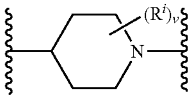 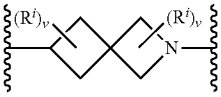

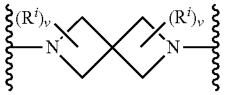 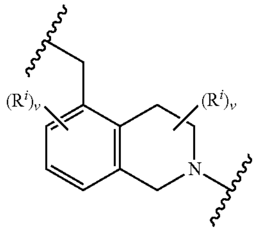 and

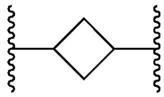

$R^i$ is independently selected from halogen, hydroxy, $C_{3-8}$-cycloalkyl, and $C_{1-6}$-alkyl;

v is independently selected from 0, 1, and 2;

m and n are independently selected from 0, 1, 2, and 3;

$R^a$, $R^b$, $R^c$ and $R^d$ are independently selected from H and $C_{1-6}$-alkyl;

$A^4$ is selected from a bond and —$NR^{101}$—;

$R^{101}$ is selected from H and $C_{1-6}$-alkyl;

w is selected from 0 and 1;

$A^3$ is selected from a bond, —O—, —$NR^{200}$—, and

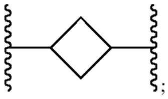;

$R^{200}$ is selected from H and $C_{1-6}$-alkyl;

C is selected from:

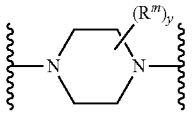 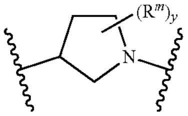

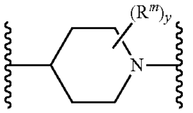 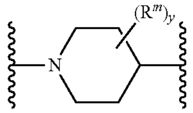

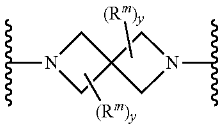 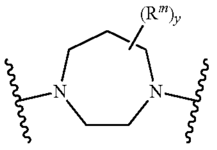

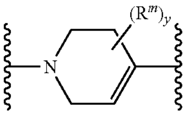 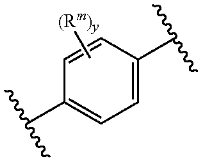

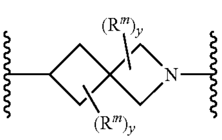 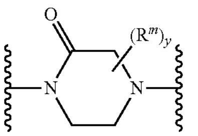

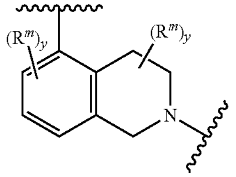 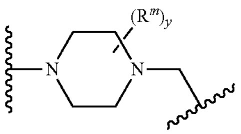

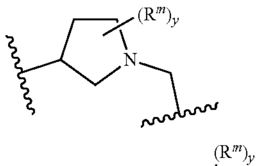 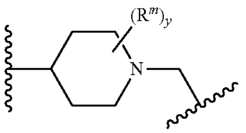

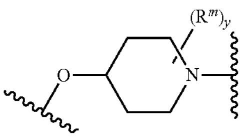 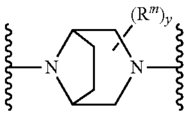

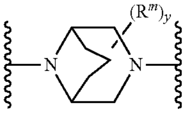 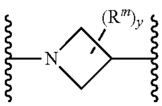 and

-continued

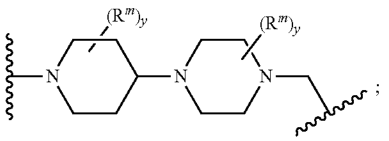

$R^m$ is independently selected from halogen, hydroxy, $C_{3-8}$-cycloalkyl, and $C_{1-6}$-alkyl;

y is independently selected from 0, 1, and 2;

D is selected from:

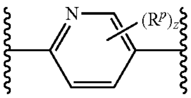
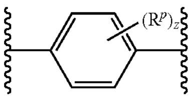

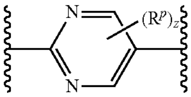
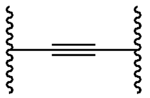

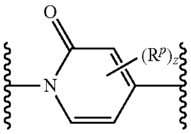
and
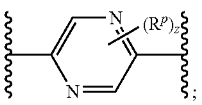

$R^p$ is independently selected from halogen, $C_{3-8}$-cycloalkyl, halo-$C_{1-6}$-alkyl, $C_{1-6}$-alkyl, cyano, $C_{1-6}$-alkyl sulfonyl, and $C_{3-8}$-cycloalkylsulfonyl;

z is independently selected from 0, 1, and 2;

$R^{100}$ is selected from H, halogen, and $C_{1-6}$-alkyl;

$R^7$ and $R^8$ are independently selected from H, $C_{1-6}$-alkyl, and halogen;

$A^1$ is selected from —$NR^5$— and —$CHR^6$—;

$R^5$ is selected from H and $C_{1-6}$-alkyl;

or $R^1$ and $R^5$ together with the nitrogen atom to which they are attached form a heterocycloalkyl optionally substituted by $R^{14}$, $R^{15}$ and $R^{16}$;

$R^6$ is selected from H and $C_{1-6}$-alkyl;

or $R^1$ and $R^6$ together with the carbon atom to which they are attached form a cycloalkyl optionally substituted by $R^{14}$, $R^{15}$ and $R^{16}$;

$R^{14}$, $R^{15}$ and $R^{16}$ are independently selected from $C_{1-6}$-alkyl and halogen; and $R^1$ is selected from $C_{1-6}$-alkyl and $C_{3-8}$-cycloalkyl.

2. The compound of claim 1, wherein $R^2$ and $R^3$ are H.

3. The compound of claim 2, wherein X is —$NR^4$—.

4. The compound of claim 3, wherein A is

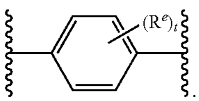

5. The compound of claim 4, wherein $R^e$ is halogen and t is 1.

6. The compound of claim 3, wherein B is

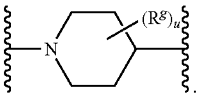

7. The compound of claim 6, wherein $R^g$ is hydroxy and u is 1.

8. The compound of claim 3, wherein E is absent.

9. The compound of claim 3, wherein v is 0 or 1.

10. The compound of claim 1, wherein m is 0 and n is 0.

11. The compound of claim 3, wherein $R^a$ and $R^b$ are H.

12. The compound of claim 3, wherein $R^c$ and $R^d$ are H.

13. The compound of claim 3, wherein C is

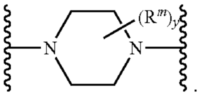

14. The compound of claim 13, wherein y is 0.

15. The compound of claim 3, wherein C is

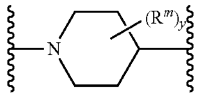
or
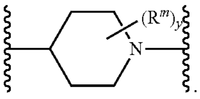

16. The compound of claim 15, wherein $R^m$ is hydroxy.

17. The compound of claim 3, wherein D is

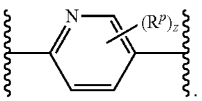

18. The compound of claim 1, wherein the compound is selected from the group consisting of:
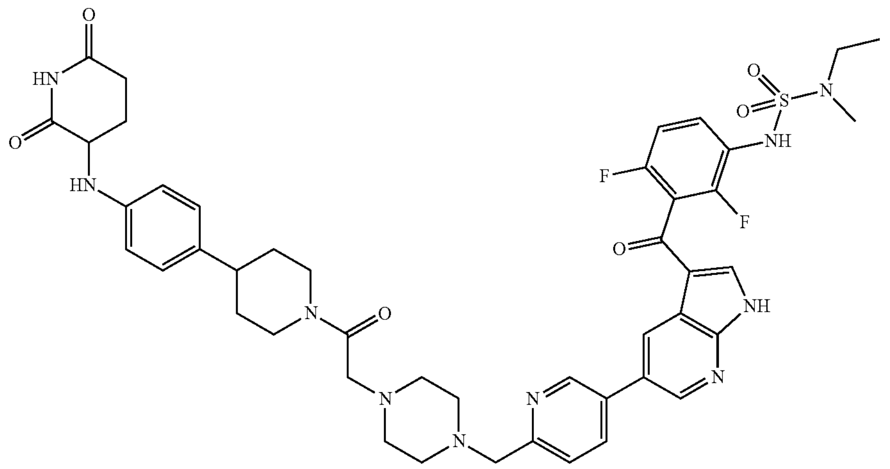
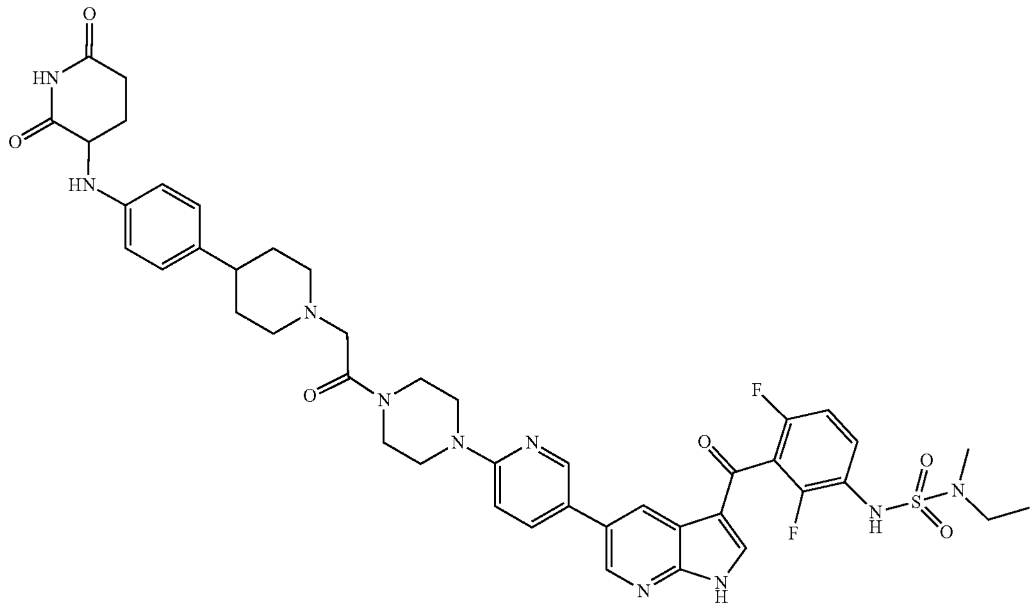
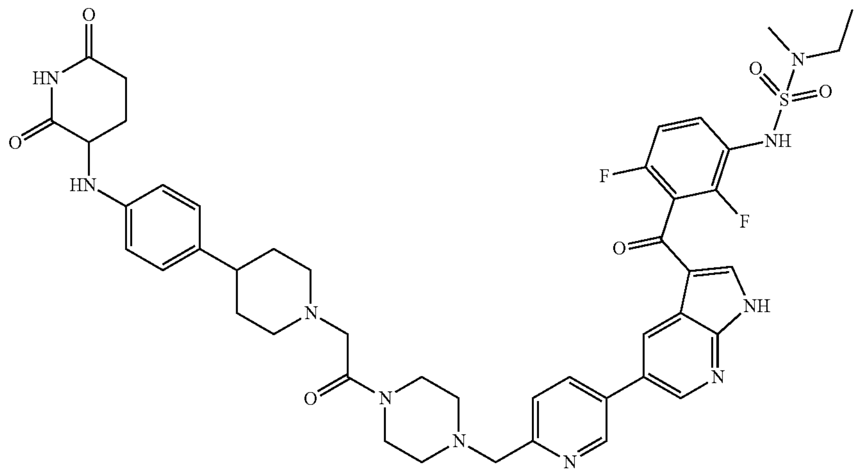

-continued
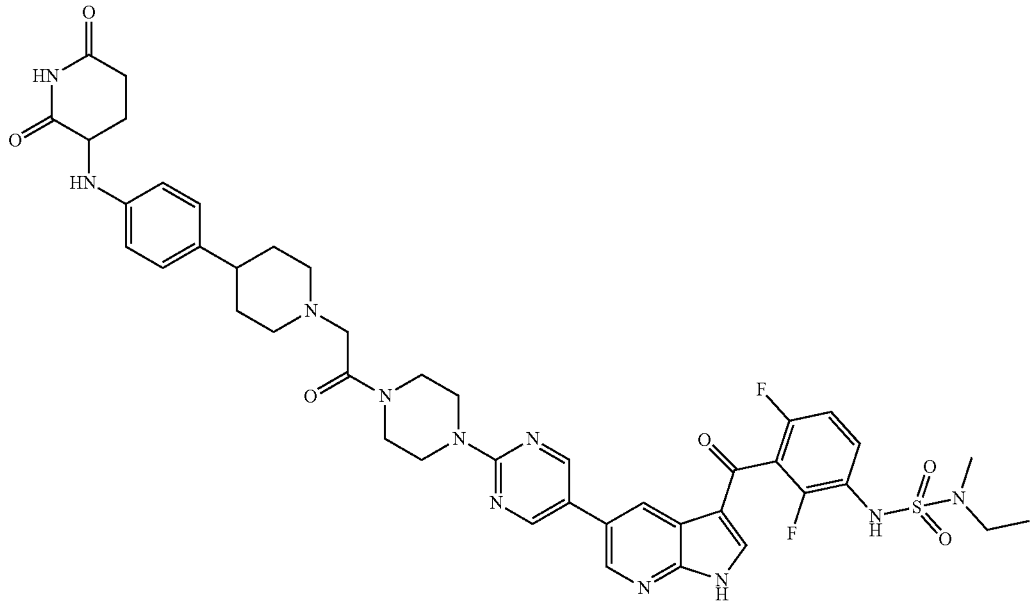
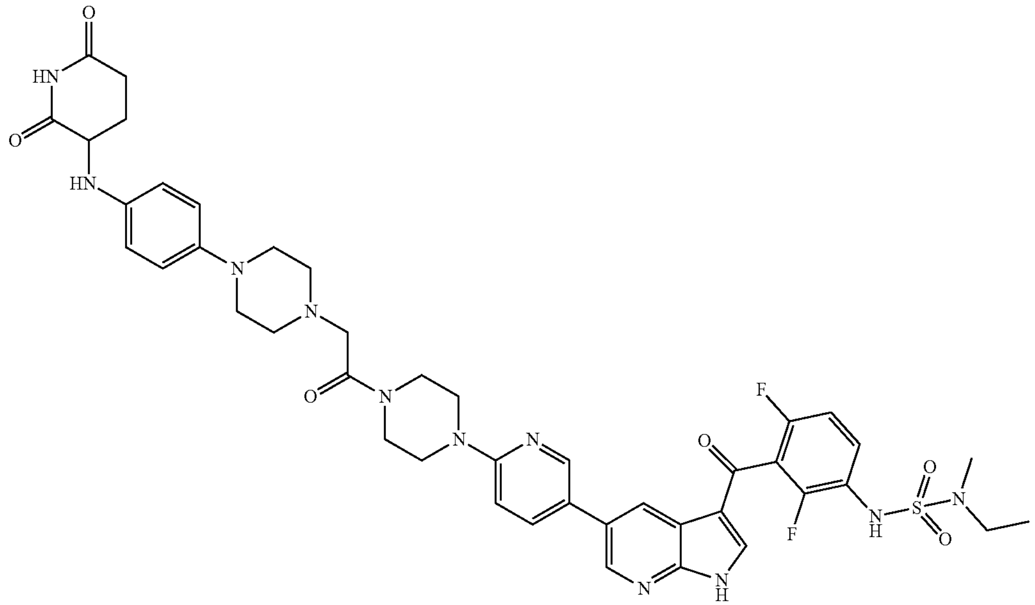
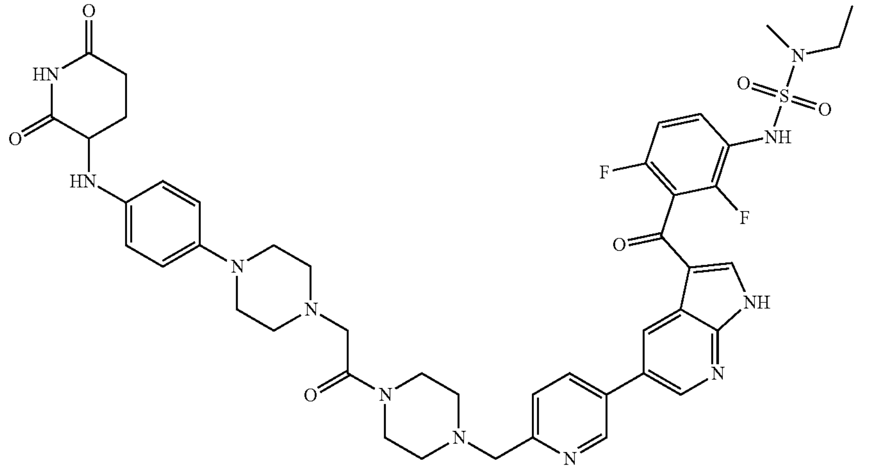

-continued
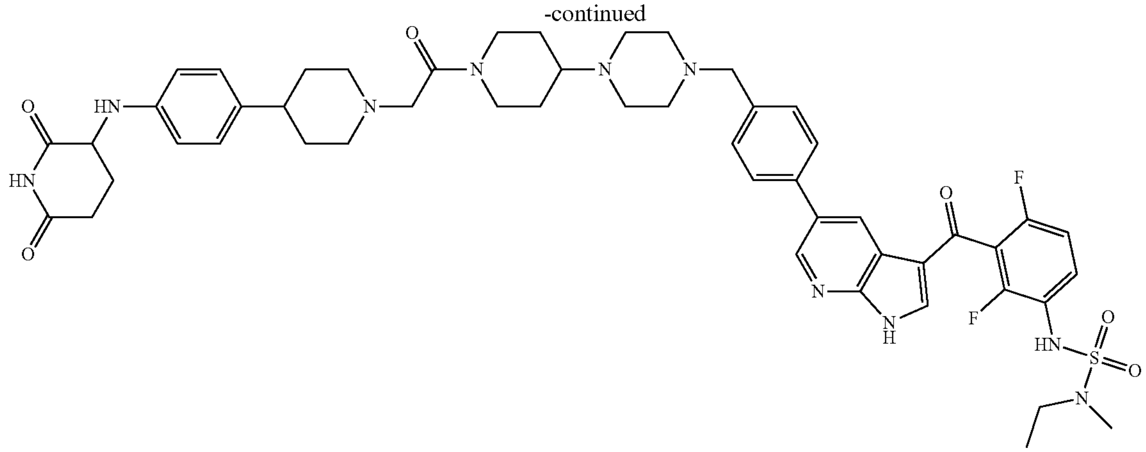
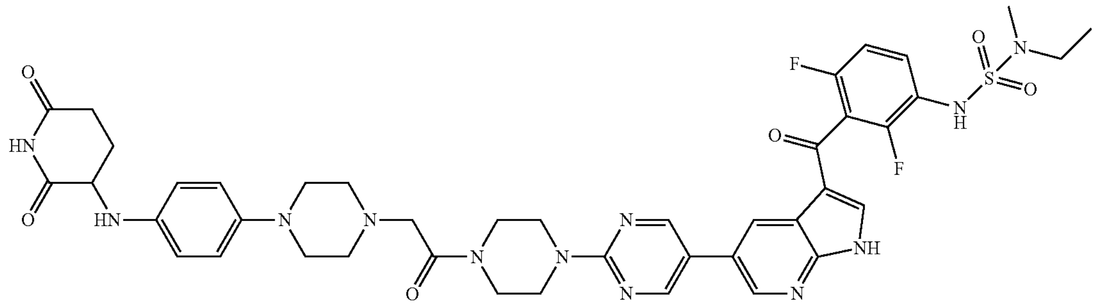
and
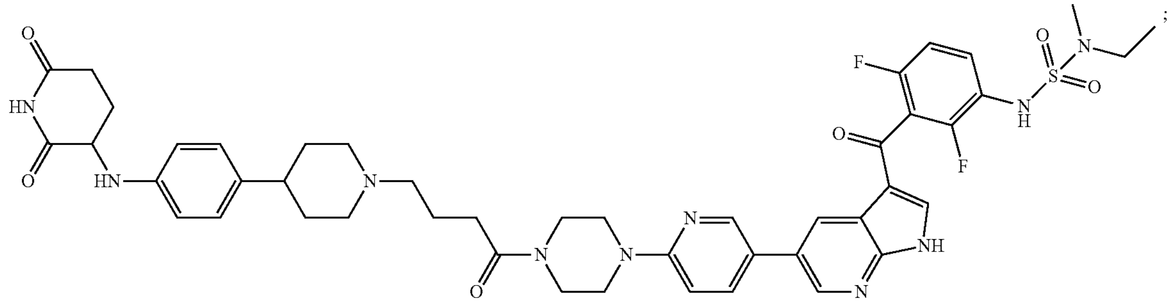
;
or a pharmaceutically acceptable salt thereof.
19. The compound of claim 1, wherein the compound is selected from the group consisting of:
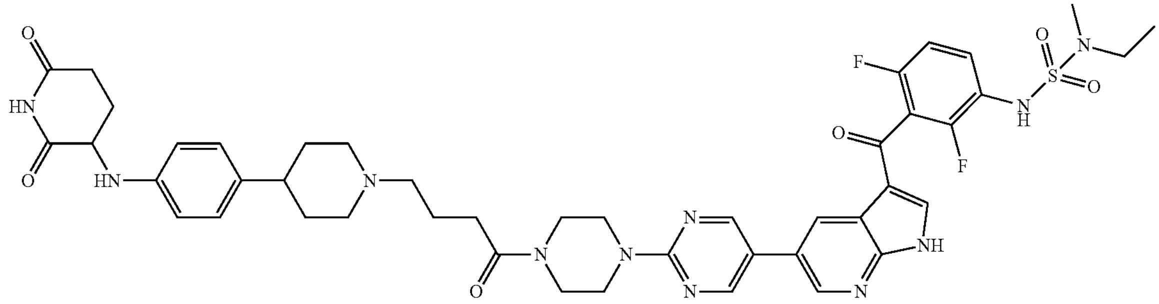

-continued
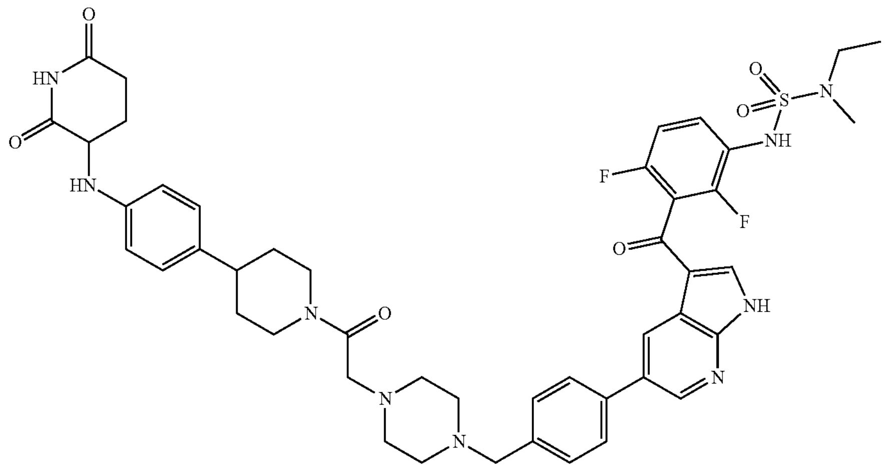
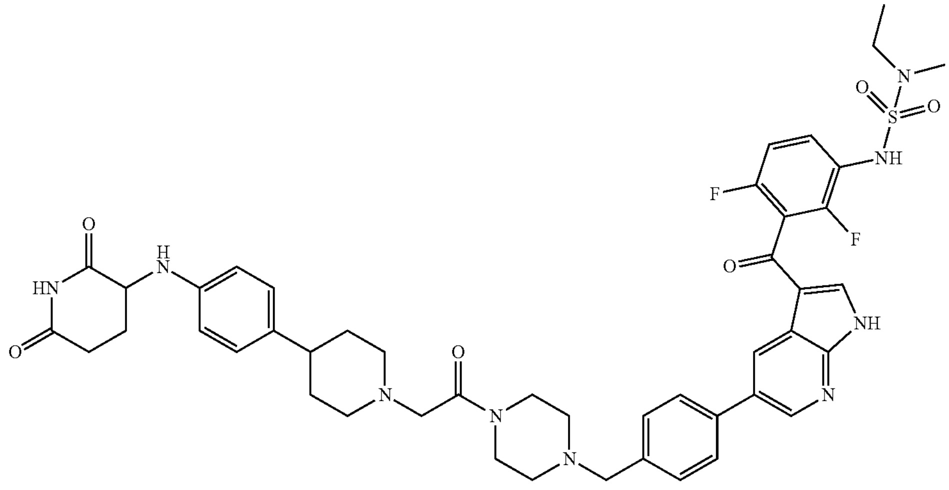
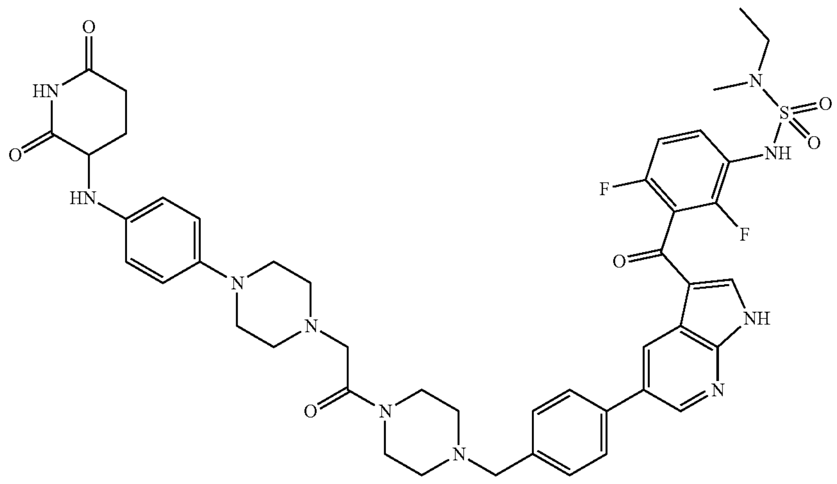

-continued
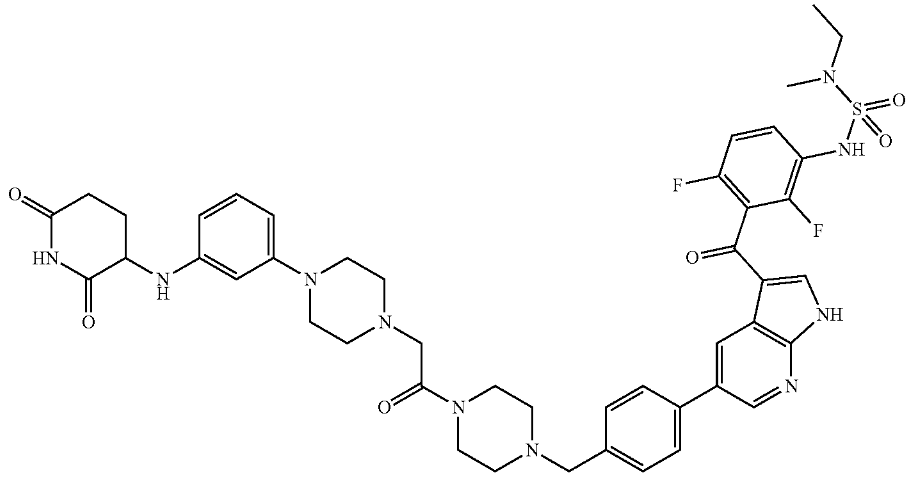
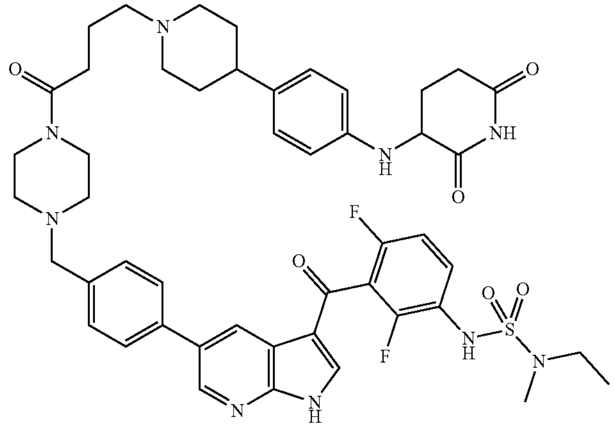
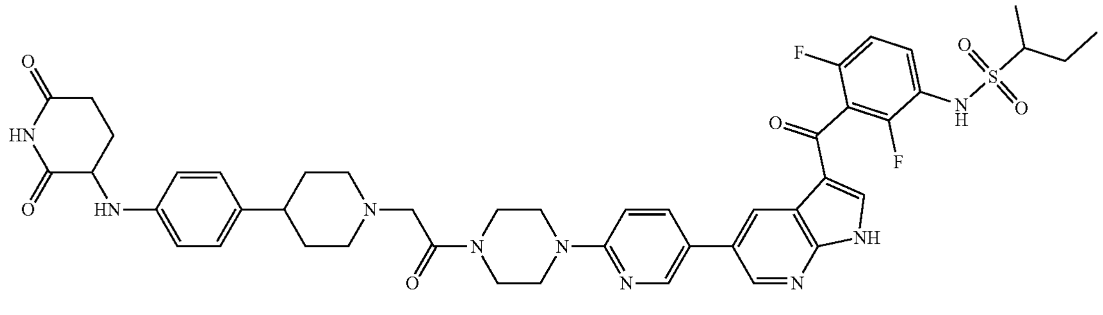
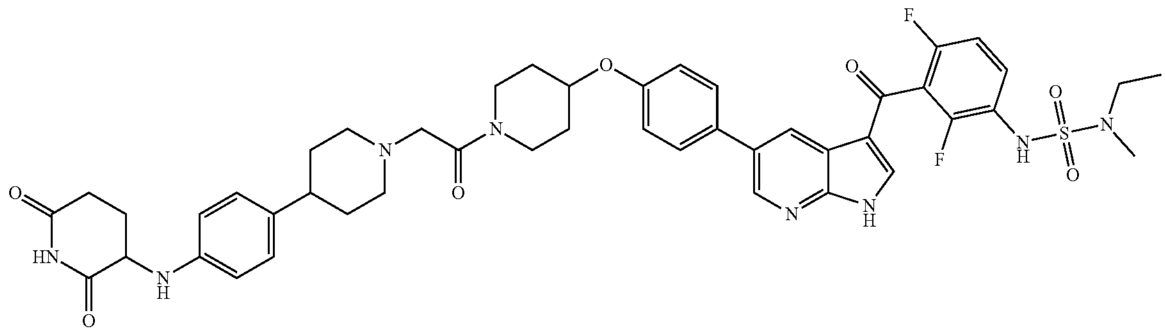

-continued
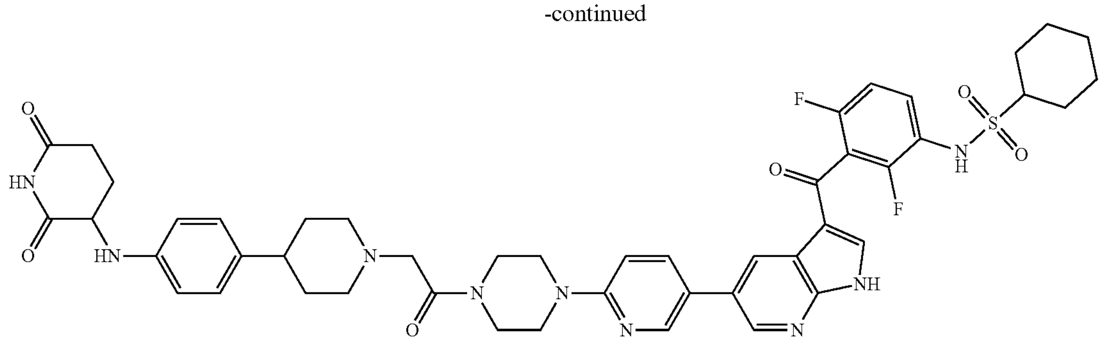
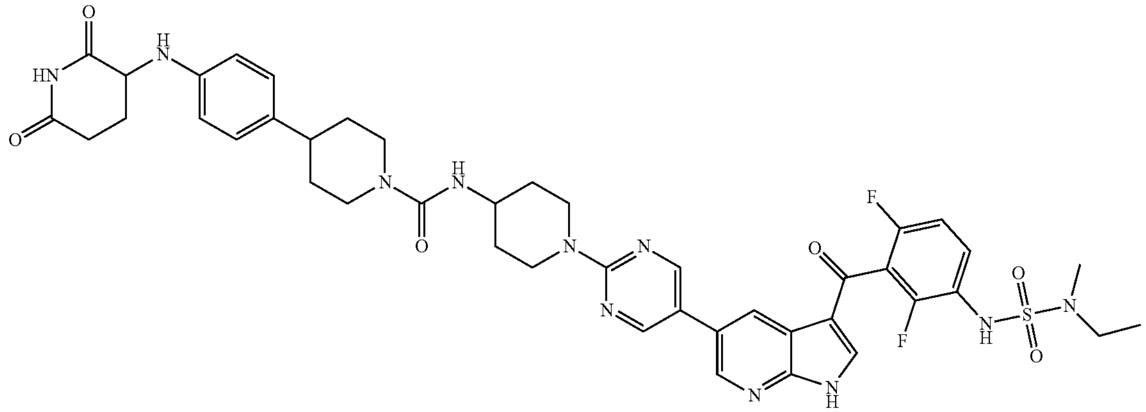
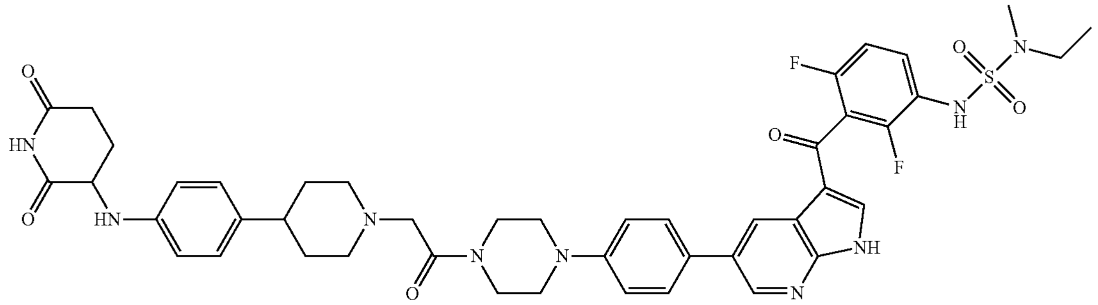
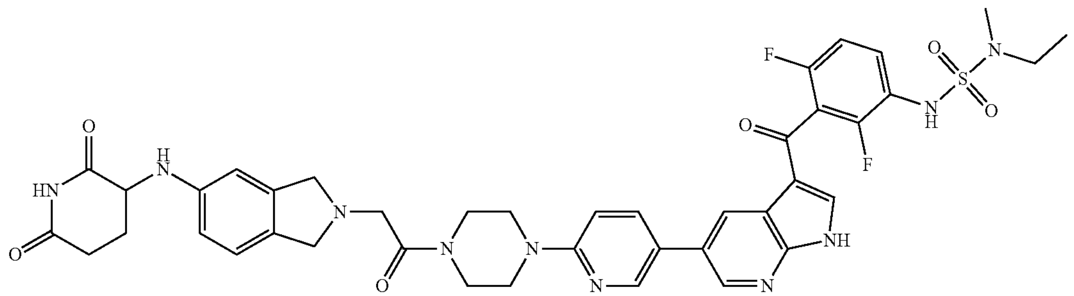
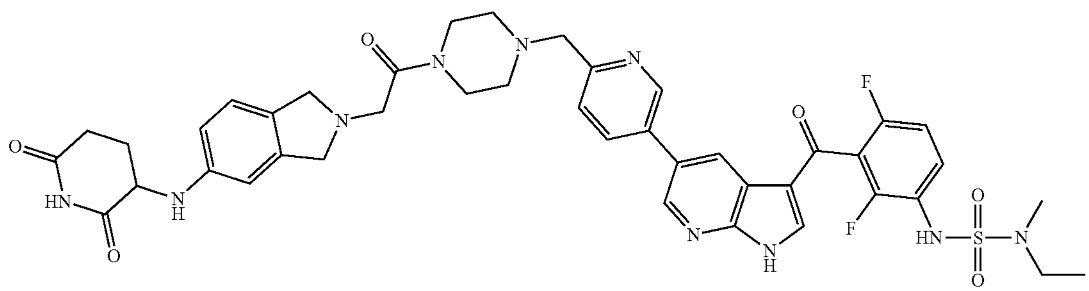

-continued
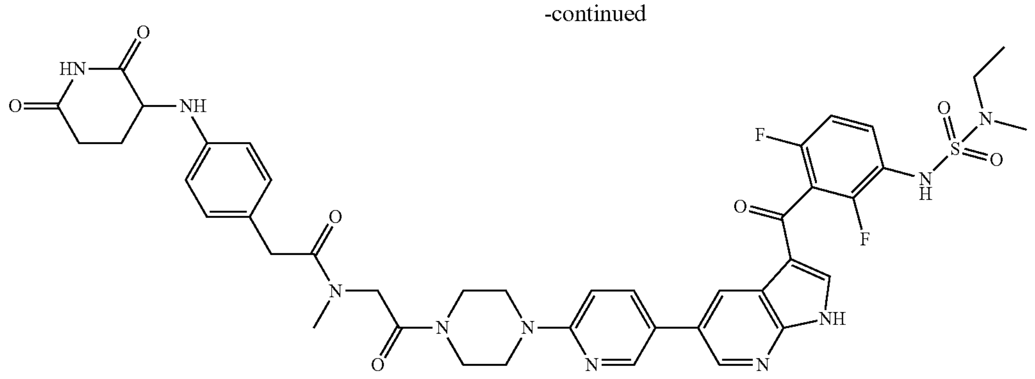
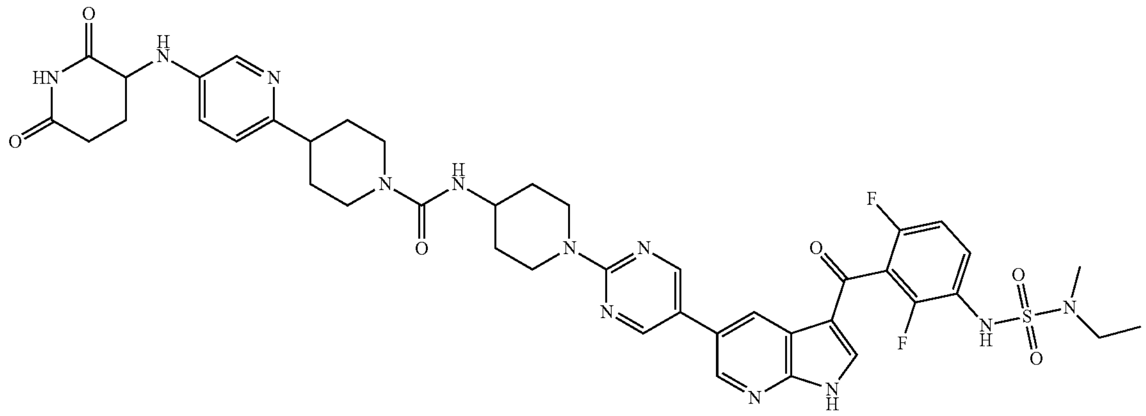
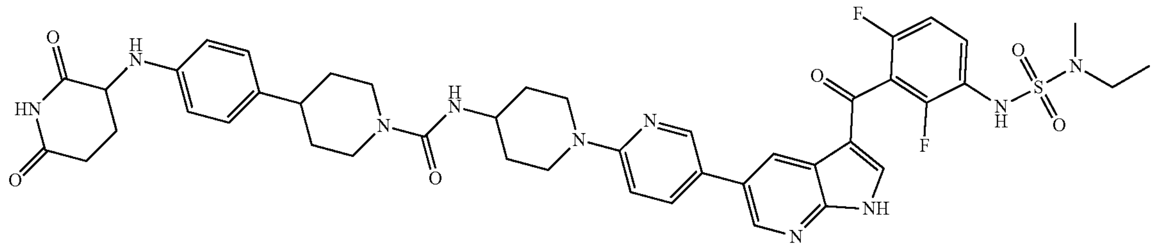
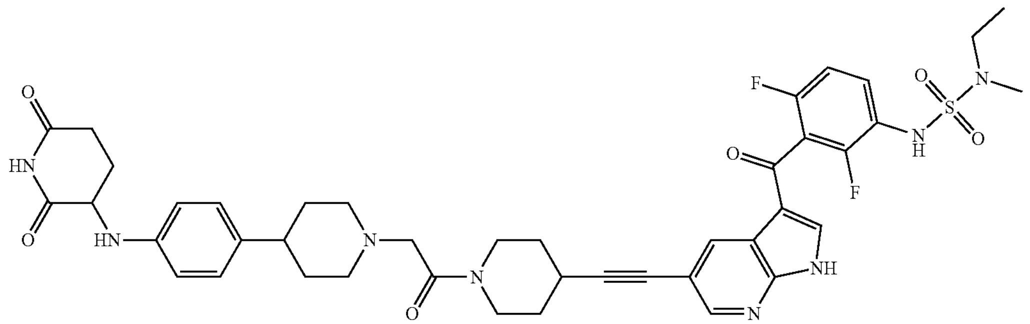
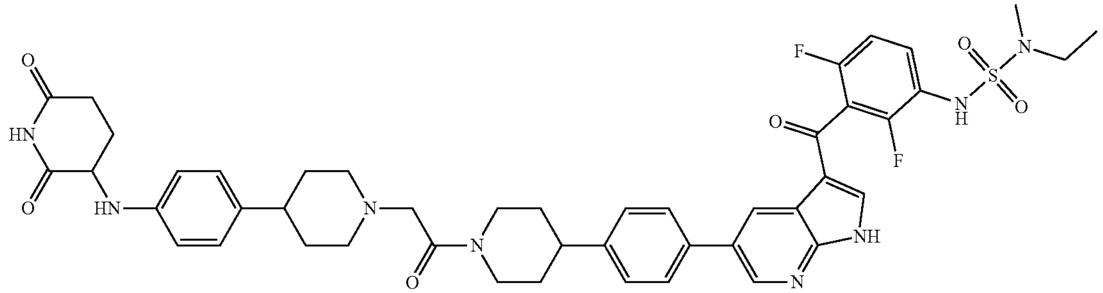

-continued
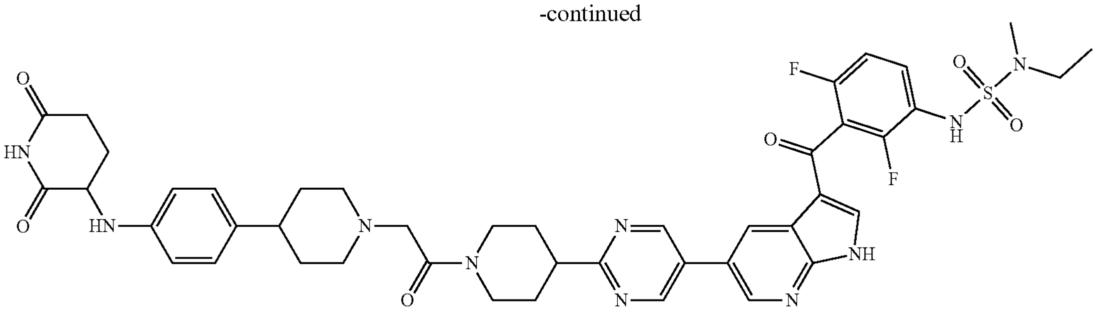
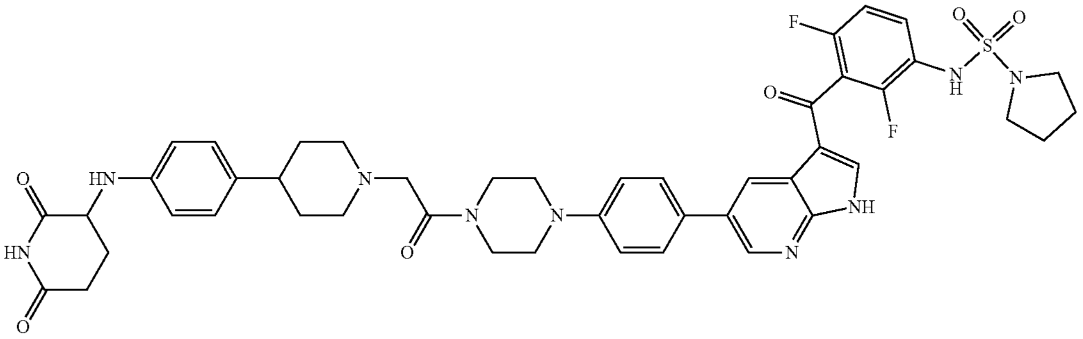
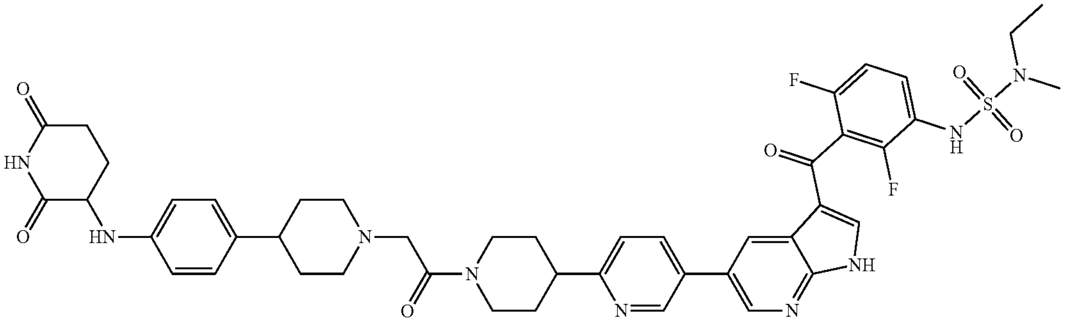
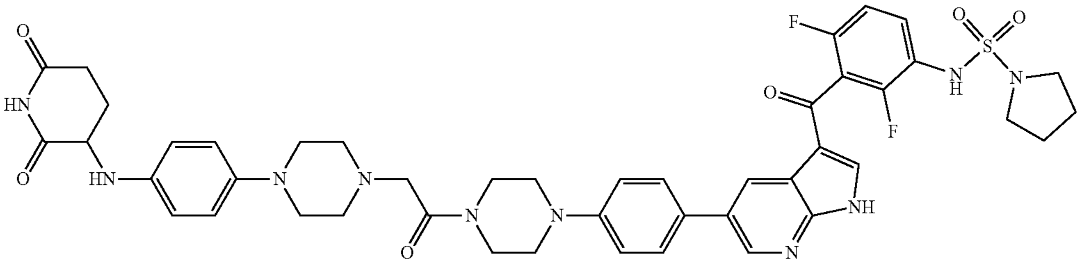
and
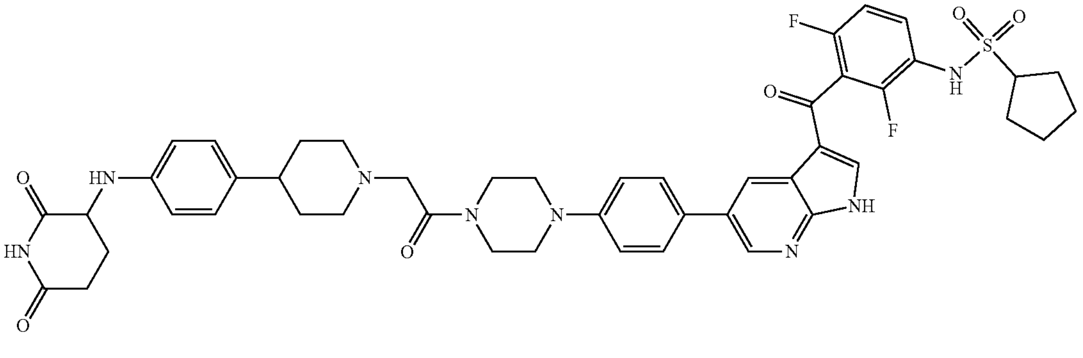
;
or a pharmaceutically acceptable salt thereof.

20. The compound of claim 1, wherein the compound is selected from the group consisting of:
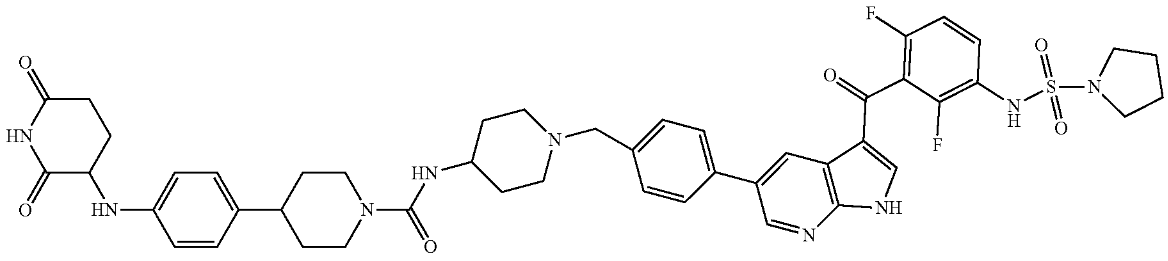
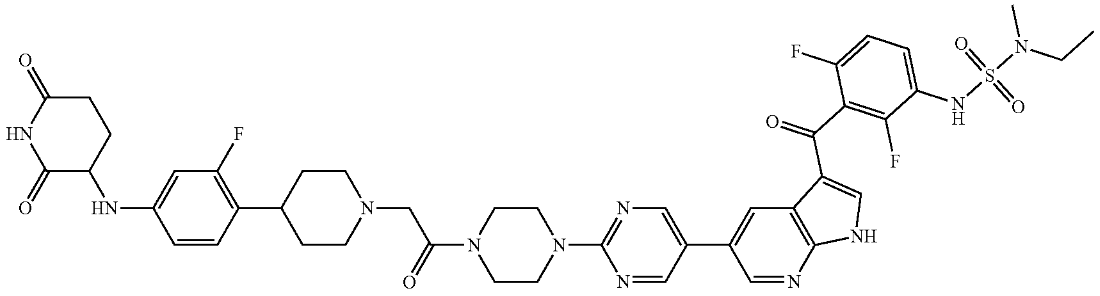
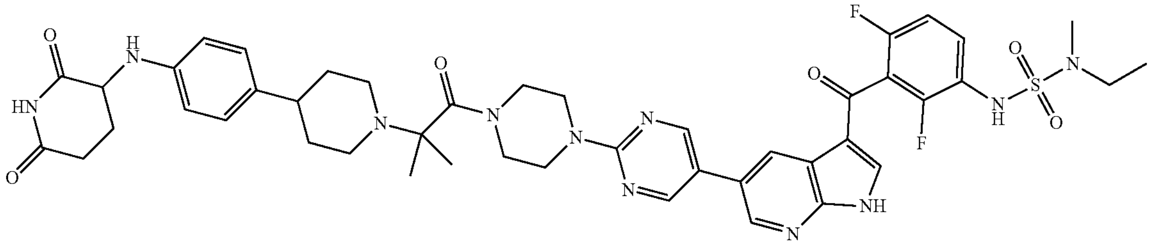
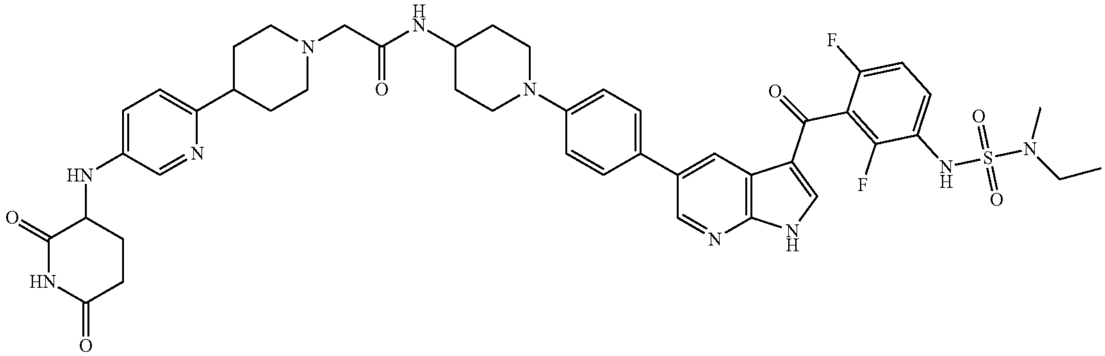
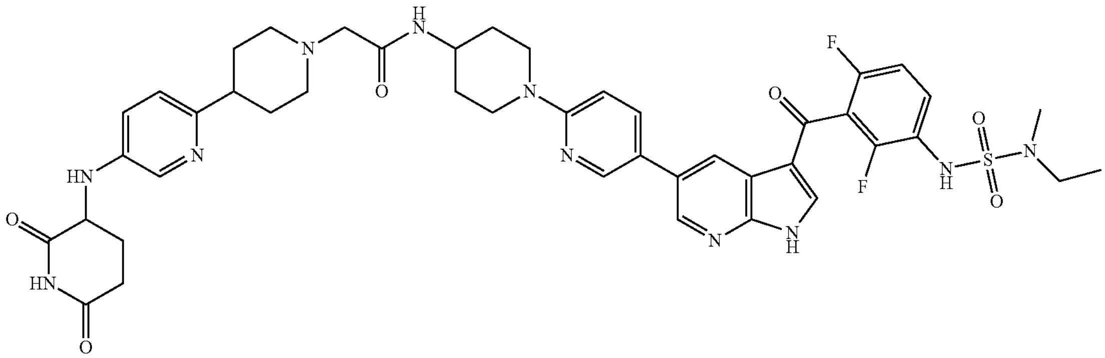

-continued
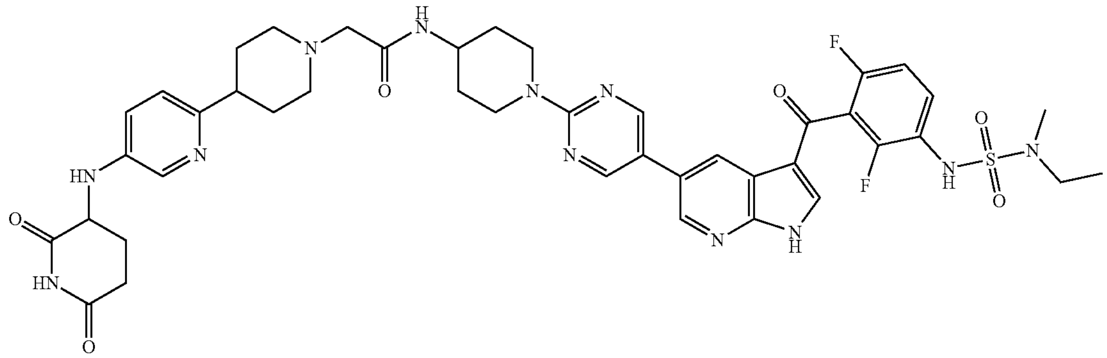
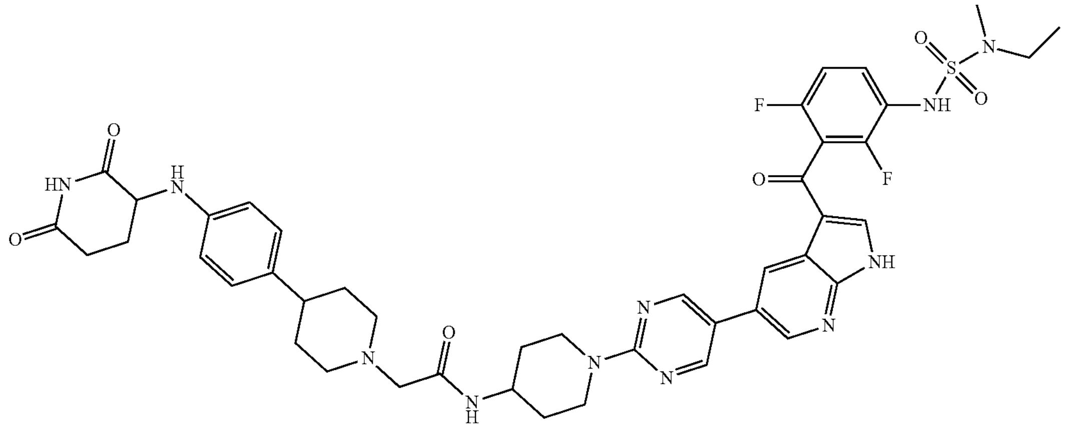
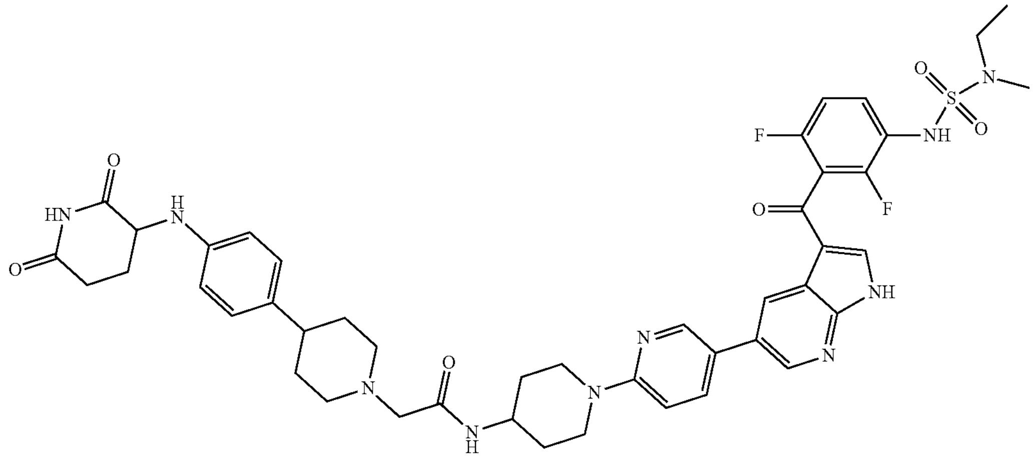
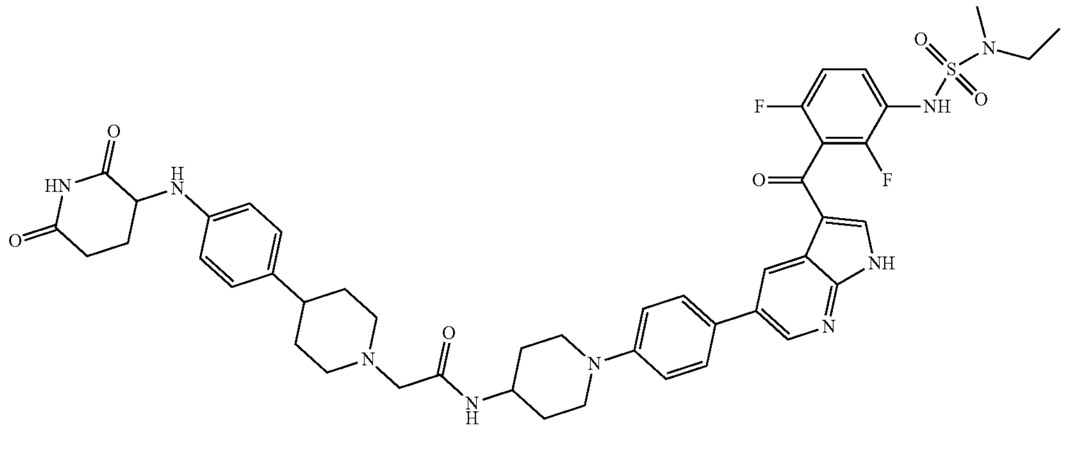

-continued
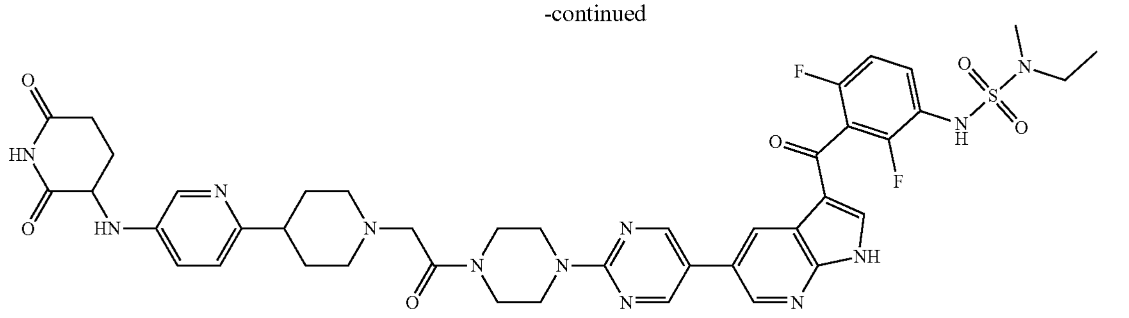
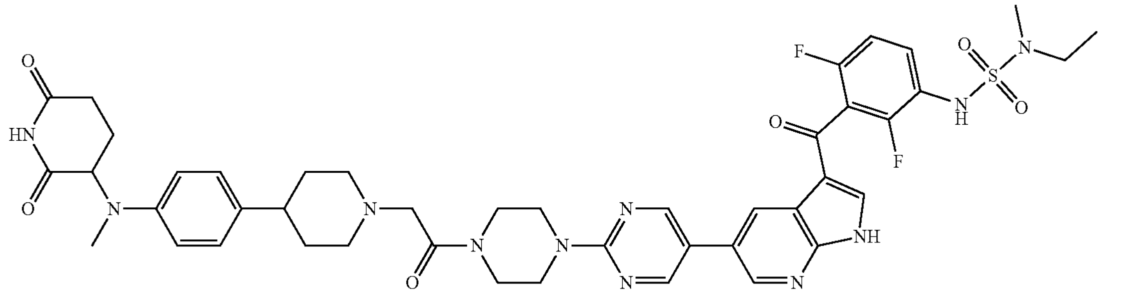
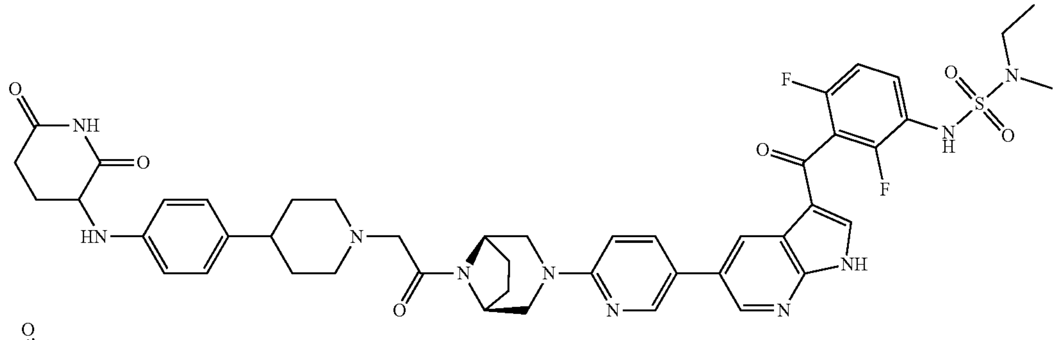
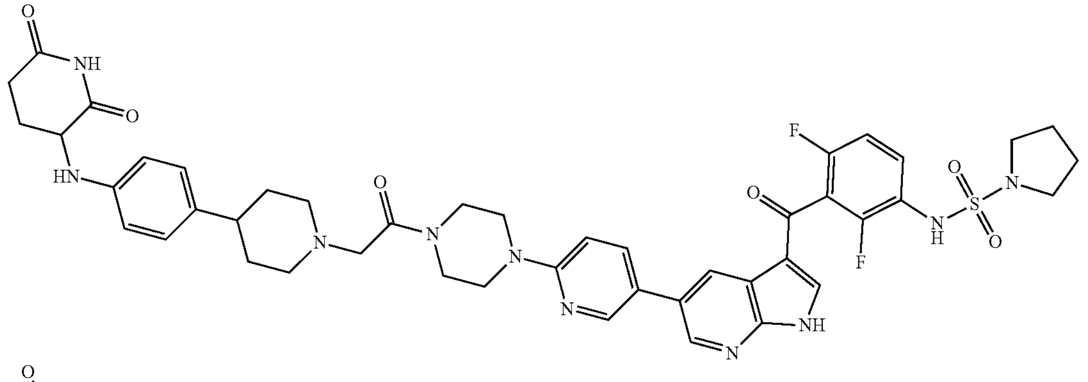
and
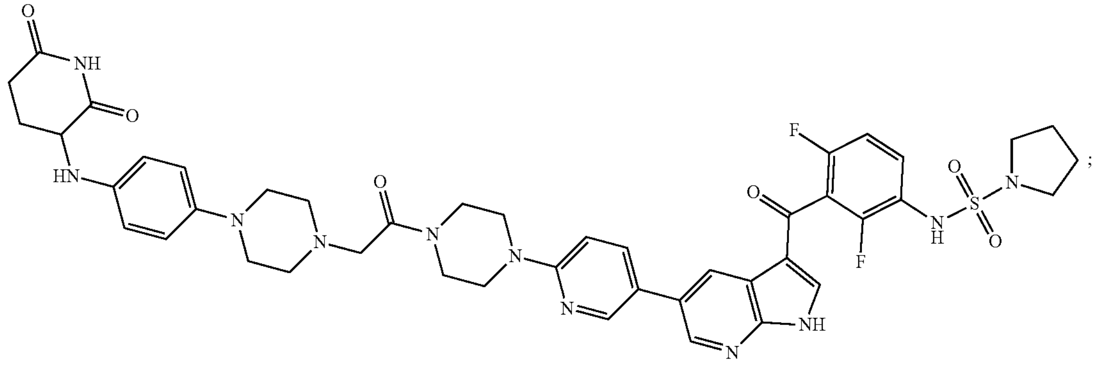
;
or a pharmaceutically acceptable salt thereof.

21. The compound of claim 1, wherein the compound is selected from the group consisting of:
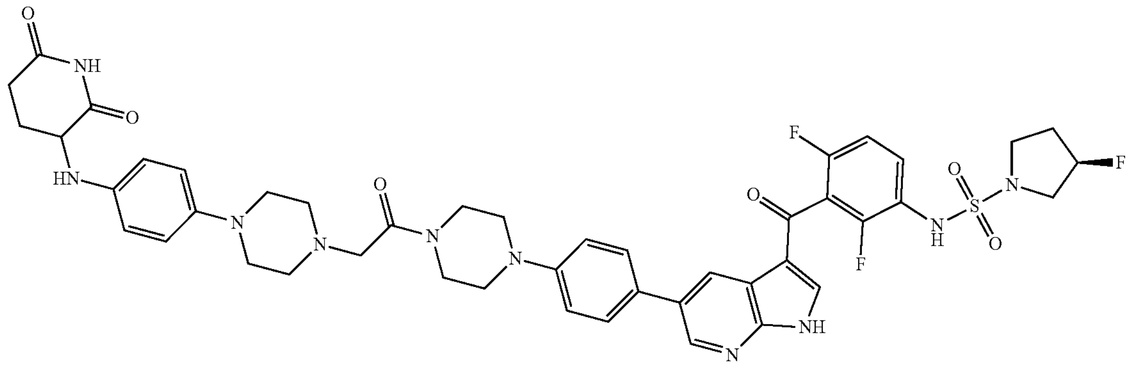
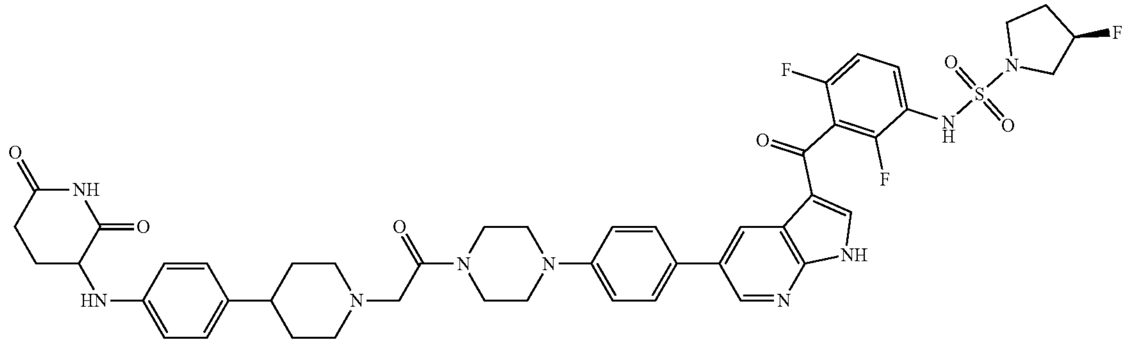
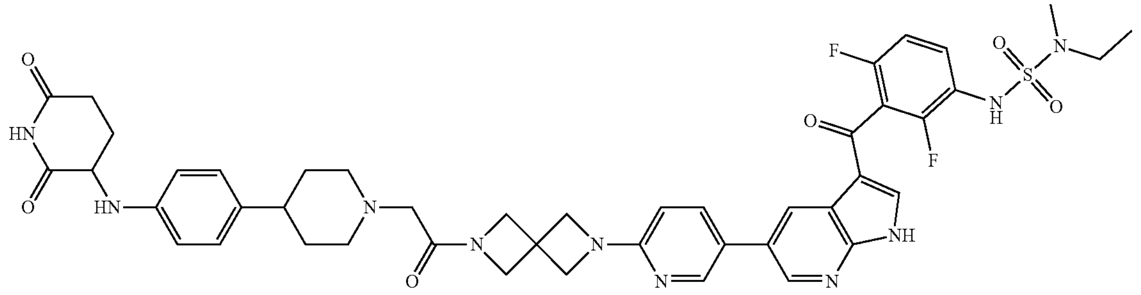
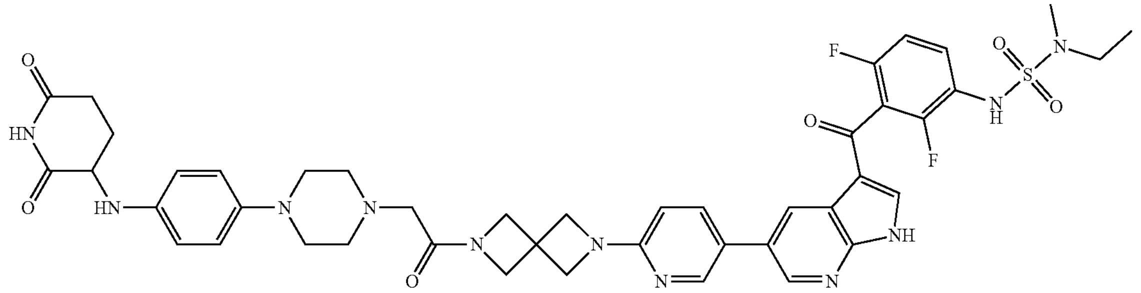
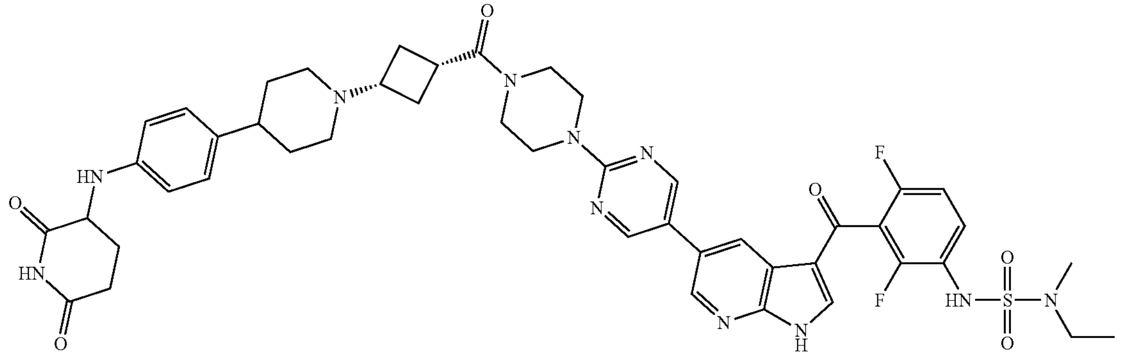

-continued
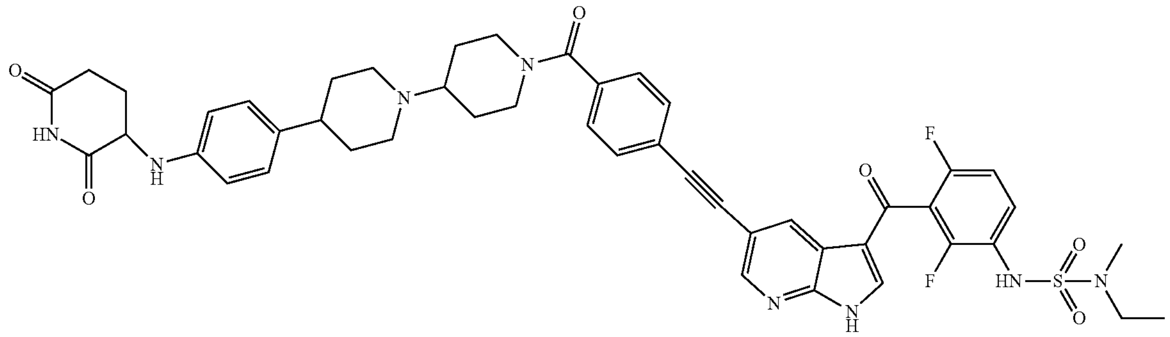
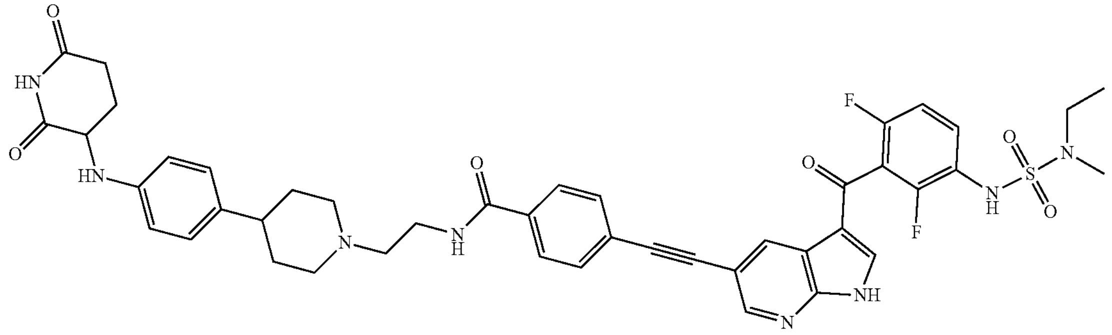
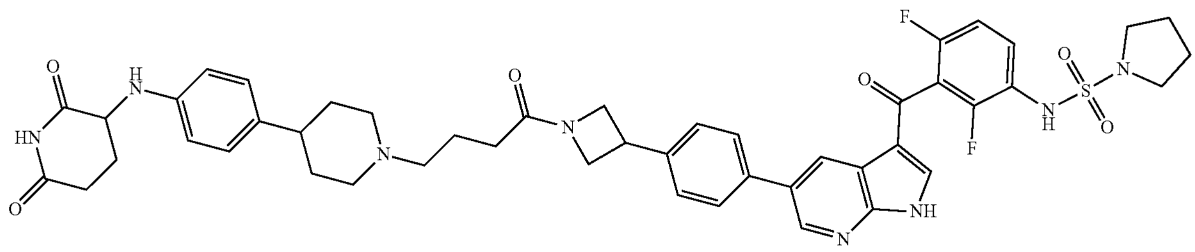
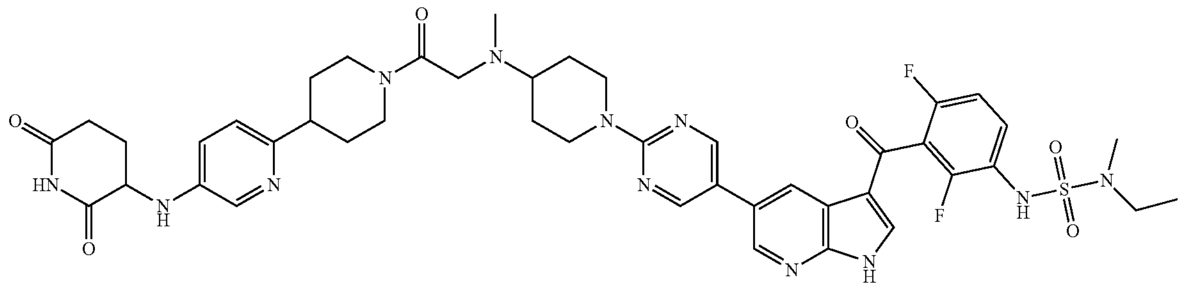
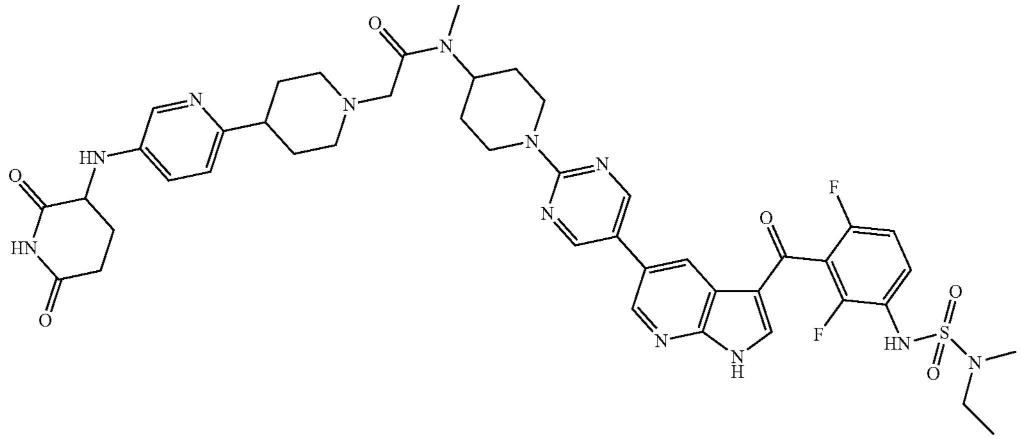

-continued
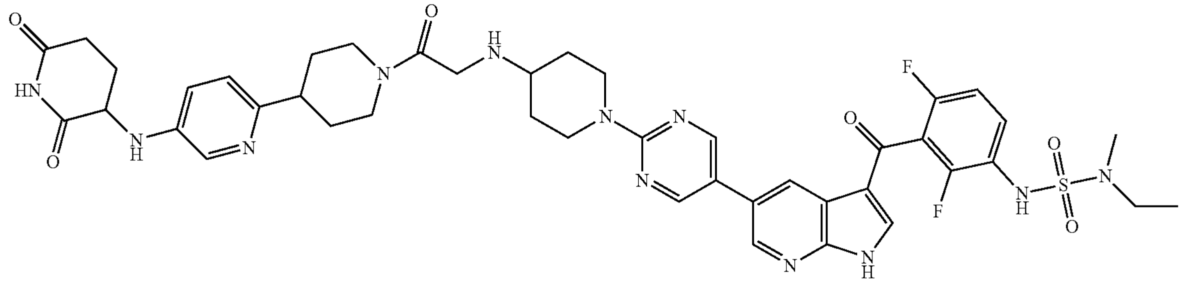
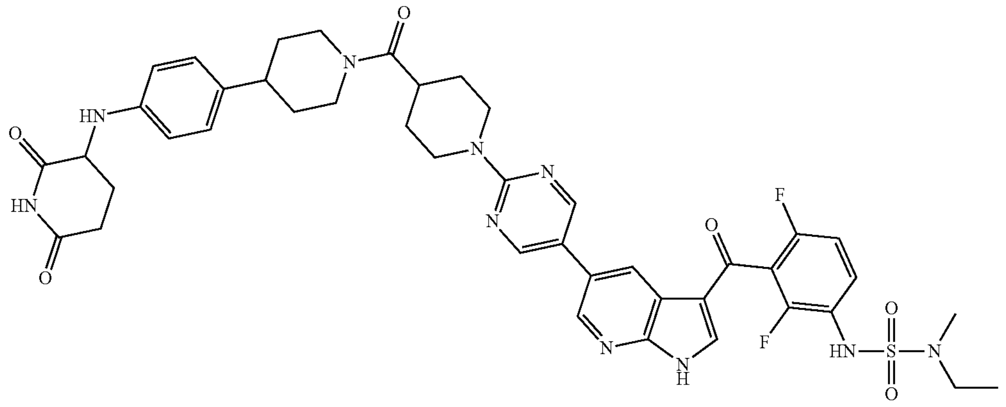
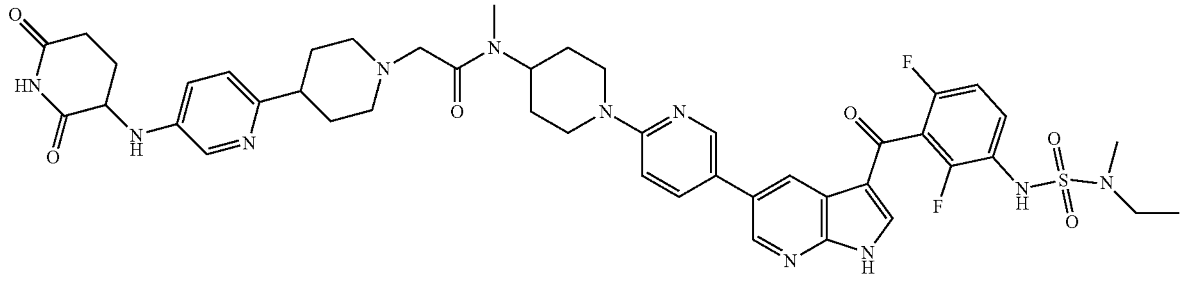
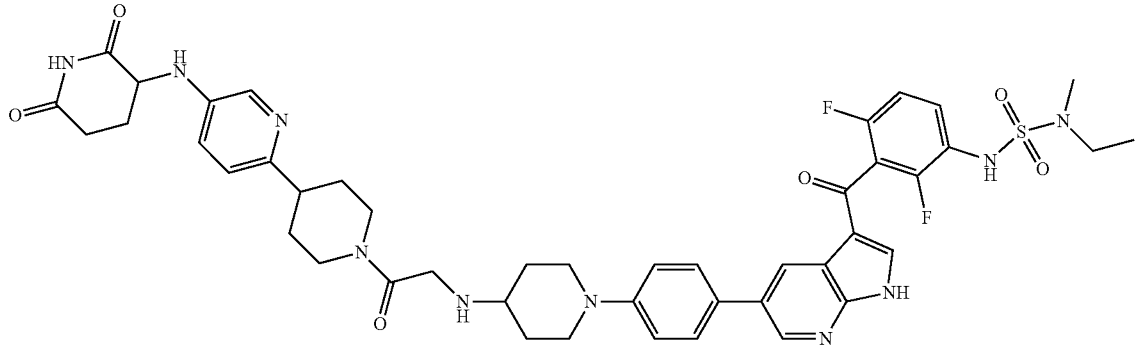
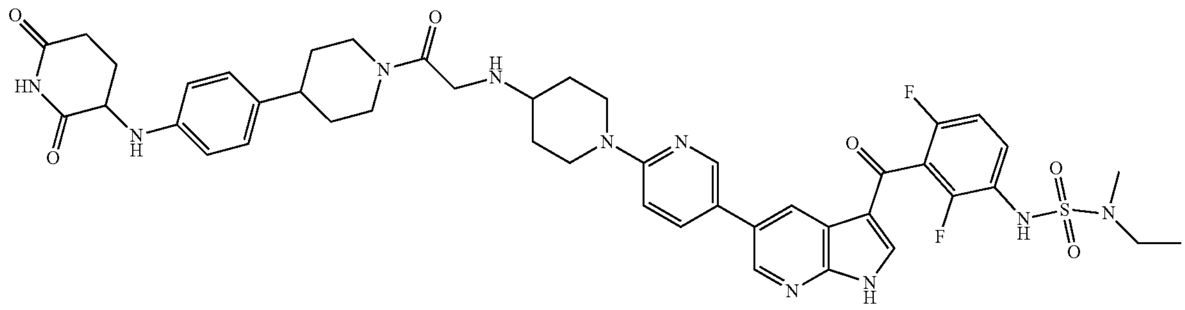

-continued
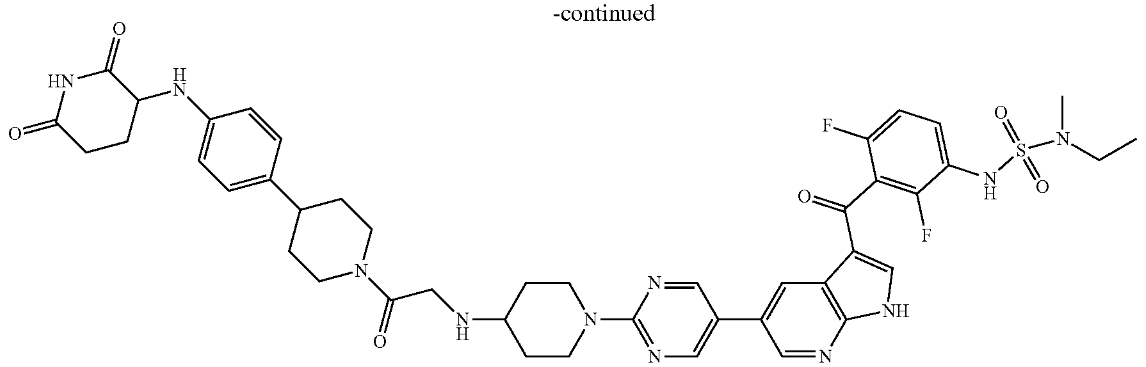
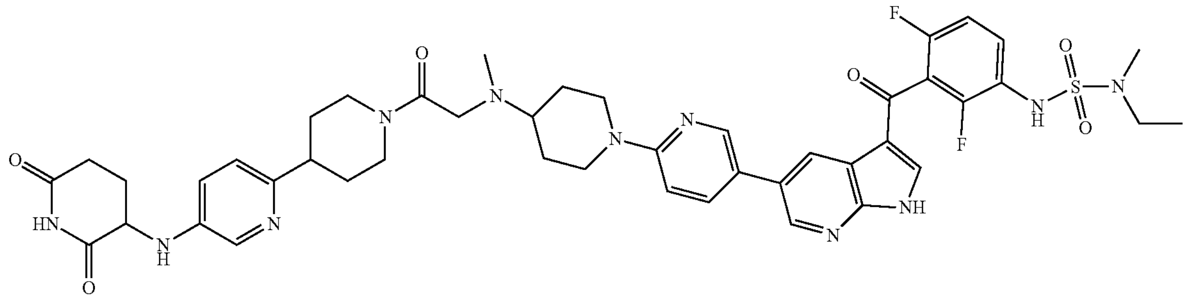
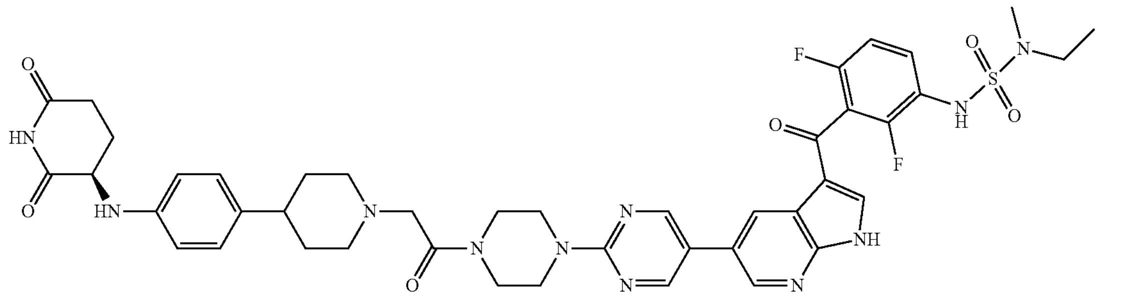
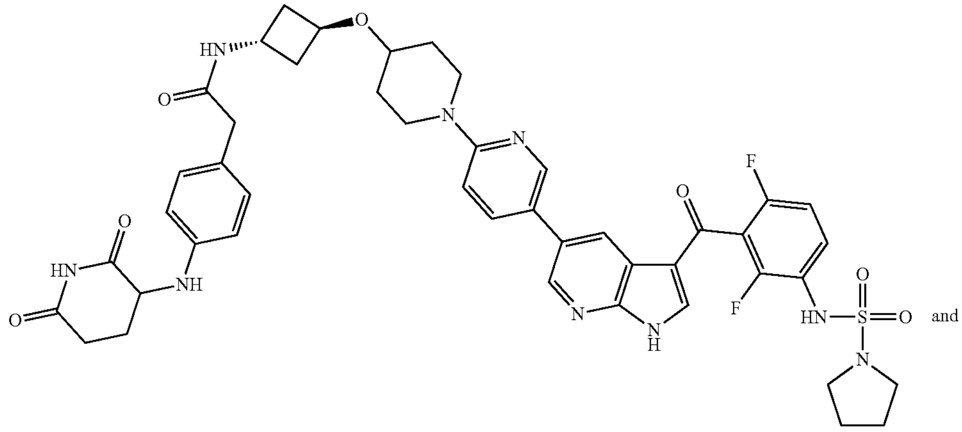
and

-continued
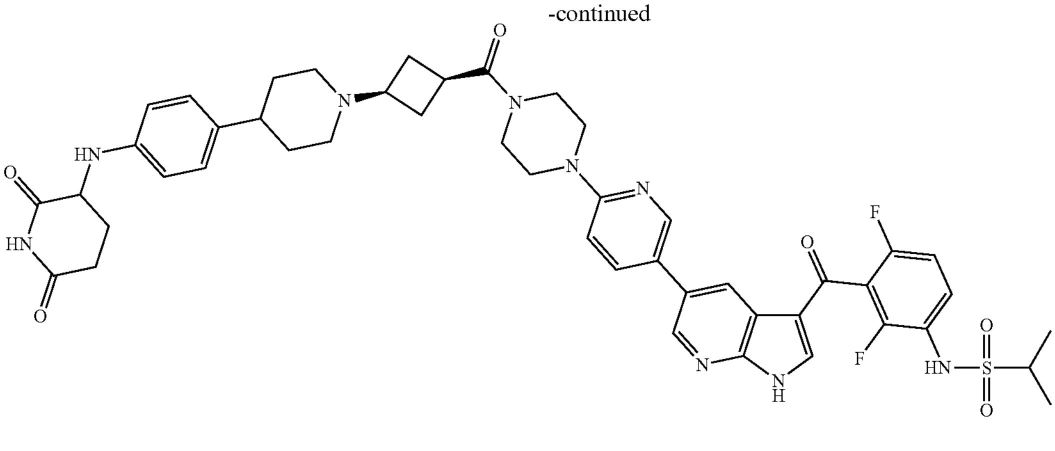
;
or a pharmaceutically acceptable salt thereof.
22. The compound of claim 1, wherein the compound is selected from the group consisting of:
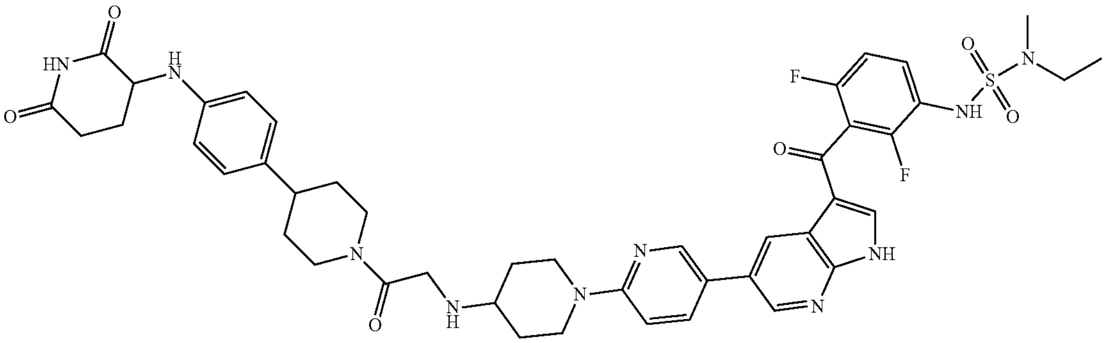
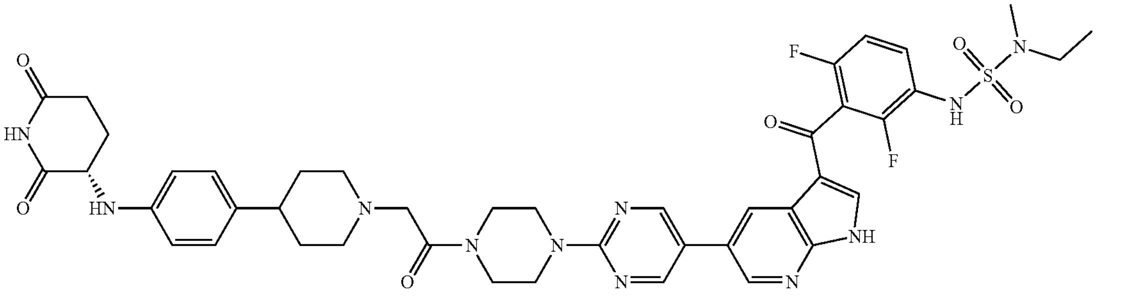
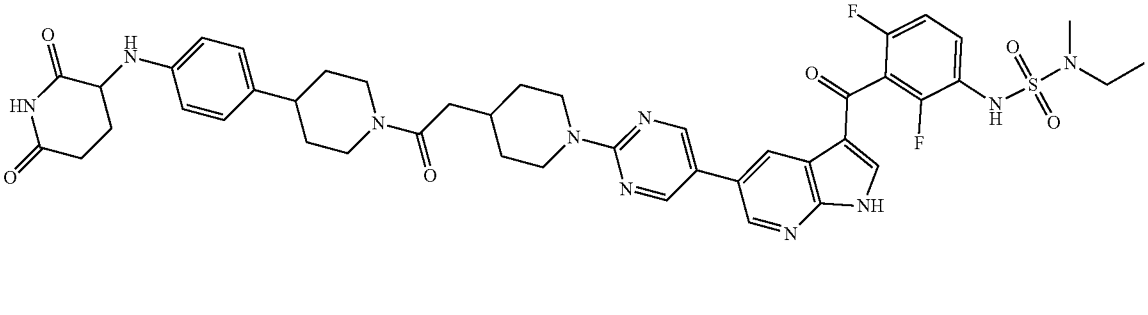

-continued
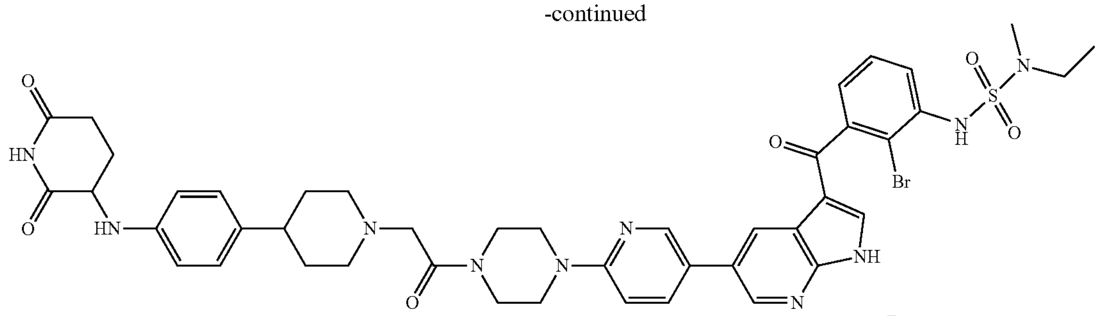
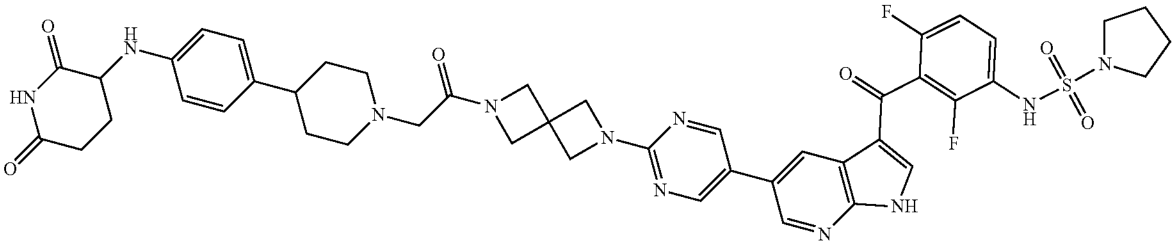
and
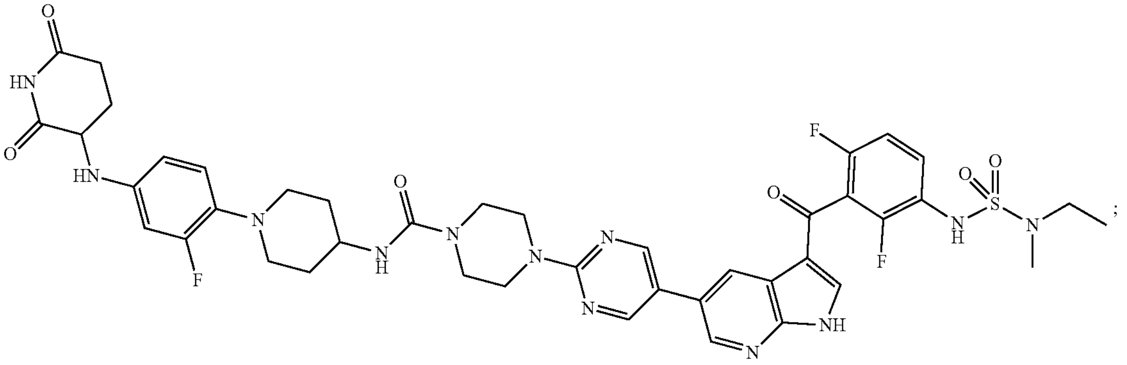
or a pharmaceutically acceptable salt thereof.
23. A pharmaceutical composition comprising a compound of claim 1 or a pharmaceutically acceptable salt thereof, and a pharmaceutically acceptable carrier.
* * * * *